(12) United States Patent
Prakash et al.

(10) Patent No.: US 11,732,265 B2
(45) Date of Patent: Aug. 22, 2023

(54) COMPOSITIONS AND METHODS FOR MODULATING COMPLEMENT FACTOR B EXPRESSION

(71) Applicant: Ionis Pharmaceuticals, Inc., Carlsbad, CA (US)

(72) Inventors: Thazha P. Prakash, Carlsbad, CA (US); Punit P. Seth, Carlsbad, CA (US); Eric E. Swayze, Encinitas, CA (US); Tamar R. Grossman, La Jolla, CA (US); Michael L. McCaleb, La Jolla, CA (US); Andrew T. Watt, San Diego, CA (US); Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 112 days.

(21) Appl. No.: 17/314,537

(22) Filed: May 7, 2021

(65) Prior Publication Data
US 2023/0057718 A1    Feb. 23, 2023

Related U.S. Application Data

(60) Continuation of application No. 16/357,018, filed on Mar. 18, 2019, now abandoned, which is a division of application No. 15/307,526, filed as application No. PCT/US2015/028916 on May 1, 2015, now Pat. No. 10,280,423.

(60) Provisional application No. 62/076,273, filed on Nov. 6, 2014, provisional application No. 61/987,471, filed on May 1, 2014.

(51) Int. Cl.
C12N 15/113     (2010.01)

(52) U.S. Cl.
CPC ........ *C12N 15/1137* (2013.01); *C12N 15/113* (2013.01); *C12Y 304/21047* (2013.01); *C12N 2310/11* (2013.01); *C12N 2310/315* (2013.01); *C12N 2310/321* (2013.01); *C12N 2310/3341* (2013.01); *C12N 2310/341* (2013.01); *C12N 2310/346* (2013.01); *C12N 2310/351* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,751,219 A | 6/1988 | Kempen et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |

(Continued)

FOREIGN PATENT DOCUMENTS

| | | |
|---|---|---|
| WO | WO 1994/002499 | 2/1994 |
| WO | WO 1994/017093 | 8/1994 |

(Continued)

OTHER PUBLICATIONS

Akinc et al., "Targeted Delivery of RNAi Therapeutics with Endogenous and Exogenous Ligand-Based Mechanisms" Molecular Therapy (2010) 18(7): 1357-1364.

Albaek et al., "Analogues of a Locked Nucleic Acid with Three-Carbon 2′,4′-Linkages: Synthesis by Ring-Closing Metathesis and Influence of Nucleic Acid Duplex Stability" J. Org. Chem. (2006) 71:7731-7740.

Allshire, "RNAi and Heterochromatin—a Hushed-Up Affair" Science (2002) 297: 1818-1819.

(Continued)

*Primary Examiner* — Brian Whiteman
(74) *Attorney, Agent, or Firm* — McDonnell Boehnen Hulbert & Berghoff LLP

(57) ABSTRACT

The present embodiments provide methods, compounds, and compositions for treating, preventing, or ameliorating a disease associated with dysregulation of the complement alternative pathway by administering a Complement Factor B (CFB) specific inhibitor to a subject.

28 Claims, No Drawings

Specification includes a Sequence Listing.

(56) References Cited

U.S. PATENT DOCUMENTS

| | | |
|---|---|---|
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'o et al. |
| 5,998,203 A | 12/1999 | Matulic-Adamic |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,300,319 B1 | 10/2001 | Manoharan |
| 6,383,812 B1 | 5/2002 | Chen et al. |
| 6,426,220 B1 | 7/2002 | Bennett et al. |
| 6,525,031 B2 | 2/2003 | Manoharan |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,620,916 B1 | 9/2003 | Takahara et al. |
| 6,660,720 B2 | 12/2003 | Manoharan et al. |
| 6,670,461 B1 | 12/2003 | Wengel et al. |
| 6,673,661 B1 | 1/2004 | Liu et al. |
| 6,770,748 B2 | 8/2004 | Imanishi et al. |
| 6,794,499 B2 | 9/2004 | Wengel et al. |
| 6,906,182 B2 | 6/2005 | Ts'o et al. |
| 6,908,903 B1 | 6/2005 | Theodore et al. |
| 6,964,950 B2 | 11/2005 | Crooke et al. |
| 7,015,315 B1 | 3/2006 | Cook et al. |
| 7,034,133 B2 | 4/2006 | Wengel et al. |
| 7,053,199 B2 | 5/2006 | Imanishi et al. |
| 7,053,207 B2 | 5/2006 | Wengel |
| 7,060,809 B2 | 6/2006 | Wengel et al. |
| 7,101,993 B1 | 9/2006 | Cook et al. |
| 7,217,805 B2 | 5/2007 | Imanishi et al. |
| 7,262,177 B2 | 8/2007 | Ts'o et al. |
| 7,314,923 B2 | 1/2008 | Kaneko et al. |
| 7,399,845 B2 | 7/2008 | Seth et al. |
| 7,427,672 B2 | 9/2008 | Imanishi et al. |
| 7,439,043 B2 | 10/2008 | DeFrees et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,582,744 B2 | 9/2009 | Manoharan et al. |
| 7,666,854 B2 | 2/2010 | Seth et al. |
| 7,696,344 B2 | 4/2010 | Khvorova et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,851,615 B2 | 12/2010 | Manoharan et al. |
| 7,875,733 B2 | 1/2011 | Bhat et al. |
| 7,919,472 B2 | 4/2011 | Monia et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,101,743 B2 | 1/2012 | Brown-Driver et al. |
| 8,106,022 B2 | 1/2012 | Manoharan et al. |
| 8,124,745 B2 | 2/2012 | Allerson et al. |
| 8,137,695 B2 | 3/2012 | Rozema et al. |
| 8,153,365 B2 | 4/2012 | Wengel et al. |
| 8,158,601 B2 | 4/2012 | Chen et al. |
| 8,268,980 B2 | 9/2012 | Seth et al. |
| 8,278,283 B2 | 10/2012 | Seth et al. |
| 8,278,425 B2 | 10/2012 | Prakash et al. |

(56) References Cited

U.S. PATENT DOCUMENTS

| | | |
|---|---|---|
| 8,278,426 B2 | 10/2012 | Seth et al. |
| 8,313,772 B2 | 11/2012 | Rozema et al. |
| 8,344,125 B2 | 1/2013 | Manoharan et al. |
| 8,349,308 B2 | 1/2013 | Yurkovetskiy et al. |
| 8,404,862 B2 | 3/2013 | Manoharan et al. |
| 8,435,491 B2 | 5/2013 | Wang et al. |
| 8,440,803 B2 | 5/2013 | Swayze et al. |
| 8,450,467 B2 | 5/2013 | Manoharan et al. |
| 8,501,805 B2 | 8/2013 | Seth et al. |
| 8,501,930 B2 | 8/2013 | Rozema et al. |
| 8,530,640 B2 | 9/2013 | Seth et al. |
| 8,541,548 B2 | 9/2013 | Rozema |
| 8,546,556 B2 | 10/2013 | Seth et al. |
| 8,552,163 B2 | 10/2013 | Lee et al. |
| 8,575,123 B2 | 11/2013 | Manoharan et al. |
| 8,604,192 B2 | 12/2013 | Seth et al. |
| RE44,779 E | 2/2014 | Imanishi et al. |
| 8,642,752 B2 | 2/2014 | Swayze et al. |
| 8,697,860 B1 | 4/2014 | Monia et al. |
| 8,809,514 B2 | 8/2014 | Yamada et al. |
| 8,828,956 B2 | 9/2014 | Manoharan et al. |
| 8,993,738 B2 | 3/2015 | Prakash et al. |
| 9,005,906 B2 | 4/2015 | Swayze et al. |
| 9,012,421 B2 | 4/2015 | Migawa et al. |
| 9,102,938 B2 | 8/2015 | Rajeev et al. |
| 9,127,276 B2 | 9/2015 | Prakash et al. |
| 9,181,549 B2 | 11/2015 | Prakash et al. |
| 9,290,760 B2 | 3/2016 | Rajeev et al. |
| 10,280,423 B2 | 5/2019 | Prakash et al. |
| 2001/0053519 A1 | 12/2001 | Fodor et al. |
| 2002/0082227 A1 | 6/2002 | Henry et al. |
| 2003/0077829 A1 | 4/2003 | MacLachlan |
| 2003/0082807 A1 | 5/2003 | Wengel |
| 2003/0119724 A1 | 6/2003 | Ts'o et al. |
| 2003/0158403 A1 | 8/2003 | Manoharan et al. |
| 2003/0170249 A1 | 9/2003 | Hakomori et al. |
| 2003/0175906 A1 | 9/2003 | Manoharan et al. |
| 2003/0206887 A1 | 11/2003 | Morrissey et al. |
| 2003/0207841 A1 | 11/2003 | Kaneko et al. |
| 2003/0224377 A1 | 12/2003 | Wengel et al. |
| 2003/0228597 A1 | 12/2003 | Cowsert et al. |
| 2004/0143114 A1 | 7/2004 | Imanishi et al. |
| 2004/0171570 A1 | 9/2004 | Allerson et al. |
| 2004/0192918 A1 | 9/2004 | Imanishi et al. |
| 2004/0203145 A1 | 10/2004 | Zamore et al. |
| 2004/0249178 A1 | 12/2004 | Vargeese et al. |
| 2005/0107319 A1 | 5/2005 | Bansal |
| 2005/0130923 A1 | 6/2005 | Bhat et al. |
| 2005/0164235 A1 | 7/2005 | Manoharan et al. |
| 2005/0244851 A1 | 11/2005 | Blume et al. |
| 2005/0244869 A1 | 11/2005 | Brown-Driver et al. |
| 2006/0148740 A1 | 7/2006 | Platenburg |
| 2006/0183886 A1 | 8/2006 | Tso et al. |
| 2007/0031844 A1 | 2/2007 | Khvorova et al. |
| 2007/0088154 A1 | 4/2007 | Khvorova et al. |
| 2007/0287831 A1 | 12/2007 | Seth et al. |
| 2008/0039618 A1 | 2/2008 | Allerson et al. |
| 2008/0085869 A1 | 4/2008 | Yamada et al. |
| 2008/0108801 A1 | 5/2008 | Manoharan et al. |
| 2008/0206869 A1 | 8/2008 | Smith et al. |
| 2008/0281041 A1 | 11/2008 | Rozema et al. |
| 2008/0281044 A1 | 11/2008 | Manoharan et al. |
| 2009/0012281 A1 | 1/2009 | Swayze et al. |
| 2009/0123928 A1 | 5/2009 | Hopkins |
| 2009/0203132 A1 | 8/2009 | Swayze et al. |
| 2009/0203135 A1 | 8/2009 | Forst et al. |
| 2009/0286973 A1 | 11/2009 | Manoharan et al. |
| 2009/0306005 A1 | 12/2009 | Bhanot et al. |
| 2009/0306179 A1 | 12/2009 | Bhanot et al. |
| 2010/0093085 A1 | 4/2010 | Yamada et al. |
| 2010/0120665 A1 | 5/2010 | Kaleko et al. |
| 2010/0190837 A1 | 7/2010 | Migawa et al. |
| 2010/0197762 A1 | 8/2010 | Swayze et al. |
| 2010/0240730 A1 | 9/2010 | Beigelman et al. |
| 2011/0077386 A1 | 3/2011 | Lee et al. |
| 2011/0097264 A1 | 4/2011 | Wang et al. |
| 2011/0097265 A1 | 4/2011 | Wang et al. |
| 2011/0123520 A1 | 5/2011 | Manoharan et al. |
| 2011/0124853 A1 | 5/2011 | Chen et al. |
| 2011/0201798 A1 | 8/2011 | Manoharan et al. |
| 2011/0207799 A1 | 8/2011 | Rozema et al. |
| 2011/0269814 A1 | 11/2011 | Manoharan et al. |
| 2011/0294868 A1 | 12/2011 | Monia et al. |
| 2012/0035115 A1 | 2/2012 | Manoharan et al. |
| 2012/0052487 A9 | 3/2012 | Dharmacon |
| 2012/0095075 A1 | 4/2012 | Manoharan et al. |
| 2012/0101148 A1 | 4/2012 | Aking et al. |
| 2012/0128760 A1 | 5/2012 | Manoharan et al. |
| 2012/0136042 A1 | 5/2012 | Manoharan et al. |
| 2012/0157509 A1 | 6/2012 | Hadwiger et al. |
| 2012/0165393 A1 | 6/2012 | Rozema et al. |
| 2012/0183602 A1 | 7/2012 | Chen et al. |
| 2012/0225927 A1 | 9/2012 | Sah et al. |
| 2012/0230938 A1 | 9/2012 | Rozema et al. |
| 2013/0004427 A1 | 1/2013 | El-Sayed et al. |
| 2013/0035366 A1 | 2/2013 | Swayze et al. |
| 2013/0109817 A1 | 5/2013 | Yurkovetskiy et al. |
| 2013/0121954 A1 | 5/2013 | Wakefield et al. |
| 2013/0130378 A1 | 5/2013 | Manoharan et al. |
| 2013/0178512 A1 | 7/2013 | Manoharan et al. |
| 2013/0203836 A1 | 8/2013 | Rajeev et al. |
| 2013/0236968 A1 | 9/2013 | Manoharan et al. |
| 2014/0107184 A1 | 4/2014 | Swayze et al. |
| 2014/0107330 A1 | 4/2014 | Freier et al. |
| 2014/0256797 A1 | 9/2014 | Monia et al. |
| 2014/0357701 A1 | 12/2014 | Swayze et al. |
| 2015/0018540 A1 | 1/2015 | Prakash et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |
| 2016/0222389 A1 | 8/2016 | Isis et al. |

FOREIGN PATENT DOCUMENTS

| | | |
|---|---|---|
| WO | WO 1997/020563 | 6/1997 |
| WO | WO 1997/046098 | 12/1997 |
| WO | WO 1998/013381 | 4/1998 |
| WO | WO 1999/014226 | 3/1999 |
| WO | WO 2000/014048 | 3/2000 |
| WO | WO 2000/021559 | 4/2000 |
| WO | WO 2000/063364 | 10/2000 |
| WO | WO 2001/049687 | 7/2001 |
| WO | WO 2002/043771 | 6/2002 |
| WO | WO 2003/004602 | 1/2003 |
| WO | WO 2004/011624 | 2/2004 |
| WO | WO 2004/024757 | 3/2004 |
| WO | WO 2004/035765 | 4/2004 |
| WO | WO 2004/045543 | 6/2004 |
| WO | WO 2004/063208 | 7/2004 |
| WO | WO 2004/101619 | 11/2004 |
| WO | WO 2004/103288 | 12/2004 |
| WO | WO 2004/106356 | 12/2004 |
| WO | WO 2005/021570 | 3/2005 |
| WO | WO 2005/061707 | 7/2005 |
| WO | WO 2005/077417 | 8/2005 |
| WO | WO 2005/097155 | 10/2005 |
| WO | WO 2005/121371 | 12/2005 |
| WO | WO 2006/031461 | 3/2006 |
| WO | WO 2006/047842 | 5/2006 |
| WO | WO 2007/035759 | 3/2007 |
| WO | WO 2007/090071 | 8/2007 |
| WO | WO 2007/134181 | 11/2007 |
| WO | WO 2008/098788 | 8/2008 |
| WO | WO 2008/101157 | 8/2008 |
| WO | WO 2008/106644 | 9/2008 |
| WO | WO 2008/150729 | 12/2008 |
| WO | WO 2008/154401 | 12/2008 |
| WO | WO 2009/003009 | 12/2008 |
| WO | WO 2009/006478 | 1/2009 |
| WO | WO 2009/029293 | 3/2009 |
| WO | WO 2009/073809 | 6/2009 |
| WO | WO 2009/082607 | 7/2009 |
| WO | WO 2009/126933 | 10/2009 |

(56) References Cited

FOREIGN PATENT DOCUMENTS

| | | |
|---|---|---|
| WO | WO 2009/143369 | 11/2009 |
| WO | WO 2010/005310 | 1/2010 |
| WO | WO 2010/017509 | 2/2010 |
| WO | WO 2010/036698 | 4/2010 |
| WO | WO 2010/048549 | 4/2010 |
| WO | WO 2010/048585 | 4/2010 |
| WO | WO 2010/054406 | 5/2010 |
| WO | WO 2010/077578 | 7/2010 |
| WO | WO 2010/088537 | 8/2010 |
| WO | WO 2010/101951 | 9/2010 |
| WO | WO 2010/103204 | 9/2010 |
| WO | WO 2010/129709 | 11/2010 |
| WO | WO 2010/144740 | 12/2010 |
| WO | WO 2011/005860 | 1/2011 |
| WO | WO 2011/005861 | 1/2011 |
| WO | WO 2011/038356 | 3/2011 |
| WO | WO 2011/047312 | 4/2011 |
| WO | WO 2011/100131 | 8/2011 |
| WO | WO 2011/115818 | 9/2011 |
| WO | WO 2011/120053 | 9/2011 |
| WO | WO 2011/133871 | 10/2011 |
| WO | WO 2011/139702 | 10/2011 |
| WO | WO 2011/139917 | 11/2011 |
| WO | WO 2011/163121 | 12/2011 |
| WO | WO 2012/037254 | 3/2012 |
| WO | WO 2012/068187 | 5/2012 |
| WO | WO 2012/083046 | 6/2012 |
| WO | WO 2012/083185 | 6/2012 |
| WO | WO 2012/089352 | 7/2012 |
| WO | WO 2012/089602 | 7/2012 |
| WO | WO 2012/135736 | 10/2012 |
| WO | WO 2012/145674 | 10/2012 |
| WO | WO 2012/145697 | 10/2012 |
| WO | WO 2012/177784 | 12/2012 |
| WO | WO 2012/177947 | 12/2012 |
| WO | WO 2013/033230 | 3/2013 |
| WO | WO 2013/075035 | 5/2013 |
| WO | WO 2013/119979 | 8/2013 |
| WO | WO 2013/165816 | 11/2013 |
| WO | WO 2013/166121 | 11/2013 |
| WO | WO 2013/173789 | 11/2013 |
| WO | WO 2014/076195 | 5/2014 |
| WO | WO 2014/076196 | 5/2014 |
| WO | WO 2014/118267 | 8/2014 |
| WO | WO 2014/118272 | 8/2014 |
| WO | WO 2014/160129 | 10/2014 |
| WO | WO 2014/179620 | 11/2014 |
| WO | WO 2014/179625 | 11/2014 |
| WO | WO 2014/179626 | 11/2014 |
| WO | WO 2014/179627 | 11/2014 |
| WO | WO 2014/179629 | 11/2014 |
| WO | WO 2014/205451 | 12/2014 |
| WO | WO 2014/207232 | 12/2014 |
| WO | WO 2015/006740 | 1/2015 |
| WO | WO 2015/038939 | 3/2015 |
| WO | WO 2015/089368 | 6/2015 |
| WO | WO 2008/036825 | 3/2018 |

OTHER PUBLICATIONS

Altmann et al., "Second generation antisense oligonucleotides—inhibition of PKC-a an c-RAF kinase expression by chimeric oligonucleotides incorporating 5'-substitute carbocyclic nucleosides and 2'-O-ethylene glycol substituted ribonucleosides." Nucleosides Nucleotides (1997) 16(7-9): 917-926.
Altmann et al., "Second Generation of Antisense Oligonucleotides: From Nuclease Resistance to Biological Efficacy in Animals" Chimia (1996) 50: 168-176.
Altmann et al., "Second-generation antisense oligonucleotides: structure-activity relationships and the design of improved signal-transduction inhibitors" Biochem. Soc. Trans. (1996) 24: 630-637.
Andre et al., "Determination of modulation of ligand properties of synthetic complex-type biantennary N-glycans by introduction of bisecting GlcNAc in silico, in vitro and in vivo" Eur. J. Biochem. (2004) 271: 118-134.
Andrews et al., "Spontaneous Murine lupus-like syndromes. Clinical and immunipathological manifestations in several strains." Journal Exp. Med. (1978) 148: 1198-1215.
Asseline et al., "Modification of the 5' Terminus of Oligodeoxyribonucleotides for Conjugation with Ligands" in Current Protocols in Nucleic Acid Chemistry, 2001, Supplement 5, Chapter 4: Unit 4.9 (4.9.1-4.9.28); John Wiley & Sons.
Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem., (1997) 272(18): 11944-12000.
Beaucage et al., "The functionalization of oligonucleotides via phosphoramidate derivatives" Tetrahedron (1993) 49(10): 1925-1963.
Biessen et al., "Novel hepatotrophic prodrugs of the antiviral nucleoside 9-(2-phosphonylmethoxyethyl)adenine with improved pharmacokinetics and antiviral activity" FASEB J. (2000) 14: 1784-1792.
Biessen et al., "Synthesis of Cluster Galactosides with High Affinity for the Hepatic Asialoglycoprotein Receptor" J. Med. Chem. (1995) 38:1538-1546.
Biessen et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852.
Bora et al., "Complement activation via alternative pathway is critical in the development of laser-induced choroidal neovascularization: role of factor B and factor H." Journal of Immunology (2006) 177(3):1872-8.
Braasch et al., "Locked nucleic acid (LNA): fine-tuning the recognition of DNA and RNA" Chem. Biol. (2001) 8:1-7.
Braasch et al., "Novel Antisense and Peptide Nucleic Acid Strategies for Controlling Gene Expression" Biochemistry (2002) 41(14): 4503-4510.
Branch et al., "A good antisense molecule is hard to find," TIBS (1998) 23:45-50.
Branda et al., "Amplification of antibody production by phosphorothioate oligodeoxynucleotides" J Lab Clin Med. (1996) 128(3): 329-338.
Chin "On the Preparation and Utilization of Isolated and Purified Oligonucleotides" Document purportedly located on a CD-ROM and contributed to the public collection of the Katherine R. Everett Law Library of the University of North Carolina (2002).
Choi et al., "Chronic kidney disease, early age-related macular degeneration, and peripheral retinal drusen." Ophthalmic Epidemiology (2011)18(6):259-63.
Coltart et al., "Principles of Mucin Architecture: Structural Studies on Synthetic Glycopeptides Bearing Clustered Mono-, Di-, Tri-, and Hexasaccharide Glycodomains" J. Am. Chem. Soc. (2002) 124: 9833-9844.
Connolly et al., "Binding and Endocytosis of Cluster Glycosides by Rabbit Hepatocytes" J Biol Chem (1982) 257: 939-945.
Costa et al., "Amyloid fibril protein related to prealbumin in familial amyloidotic polyneuropathy" PNAS (1978) 75(9): 4499-4503.
Crooke et al., "Pharmacokinetic Properties of Several Novel Oligonucleotide Analogs in mice" J. Pharmacol. Exp. Ther. (1996) 277(2):923-937.
Crooke et al., "Pharmacological Properties of 2'-O-Methoxyethyl Modified Oligonucleotides" in Antisense a Drug Technology, Chapter 10, pp. 273-303, Crooke, S.T., ed., 2008.
Crooke et al., "Toxicologic Properties of 2-O-Methoxyethyl Chimeric Antisense Inhibitors in Animals and Man" in Antisense a Drug Technology, Chapter 12, pp. 342-351, Crooke, S.T., ed., 2008.
Czech et al. "RNAi-based therapeutic strategies for metabolic disease" Nature Reviews Endocrinology (2011) 7: 473-484.
Dellinger et al., "Solid-Phase Chemical Synthesis of Phosphonoacetate and Thiophosphonoacetate Oligodeoxynucleotides" J. Am .Chem. Soc. (2003) 125: 940-950.

(56) References Cited

OTHER PUBLICATIONS

Dickson et al., "Rat Choroid Plexus Specializes in the Synthesis and the Secretion of Transthyretin" J Biol Chem (1986) 261(8): 3475-3478.
Duff et al., "Intrabody Tissue-Specific Delivery of Antisense Conjugates in Animals: Ligand-Linker-Antisense Oligomer Conjugates" Methods in Enzymology (1999) 313: 297-321.
Dupouy et al., "Watson-Crick Base-Pairing Properties of Nucleic Acid Analogues with Stereocontrolled a and b Torsion Angles (a,b-D-CNAs)" Angew. Chem. Int. Ed. (2006) 45: 3623-3627.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Elayadi et al., "Application of PNA and LNA oligomers to chemotherapy" Curr. Opinion Invens. Drugs (2001) 2:558-561.
Englisch et al., "Chemically Modified Oligonucleotides as Probes and Inhibitors" Agnew Chem. Int. Ed. Engl. (1991) 30:613-629.
Extended European Search Report for Application No. 14844168.6 dated Apr. 4, 2017.
Extended European Search Report for Application No. 15786214.5 dated Aug. 21, 2017.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Gautschi et al., "Activity of a novel bcl-2/bcl-xLbispecific antisense oligonucleotide against tumors of diverse histologic origins" J. Natl. Cancer Inst. (2001) 93:463-471.
Geary et al., "A nonradioisotope biomedical assay for intact oligonucleotide and its chain-shortened metabolites used for determination of exposure and elimination half-life of antisense drugs in tissue." Analytical Biochemistry (1999) 274, 241-248.
Geary et al., "Pharmacokinetic Properties of 2'-O-(2-Methoxyethyl)-Modified Oligonucleotide Analogs in Rats" The Journal of Pharmacology and Experimental Therapeutics (2001) 296:890-897.
GenBank AK130533.1, 2006 National Library of Medicine NCBI.
Grossman et al., "Inhibition of the alternative complement pathway by antisense oligonucleotides targeting complement factor B improves lupus nephritis in mice" Immunobiology (2016) 221(6): 701-708.
Gu et al. "Base Pairing Properties of D- and L-Cyclohexene Nucleic Acids (CeNA)" Oligonucleotides (2003) 13(6): 479-489.
Gu et al., "Enzymatic resolution and base pairing properties of D- and L-cyclohexenyl nucleic acids (CeNA)." Nucleosides, Nucleotides & Nucleic Acids (2005) 24(5-7): 993-998.
Gu et al., "Synthesis of enantiomeric-pure cyclohexenyl nucleoside building blocks for oligonucleotide synthesis" Tetrahedron (2004) 60(9): 2111-2123.
Hall et al., "Establishment and Maintenance of a Heterochromatin Domain" Science (2002) 297: 2232-2237.
Henry et al., "Drug properties of second-generation antisense oligonucleotides: how do they measure up to their predecessors?" Curr Opin Investig Drugs (2001) 2: 1444-1449.
Hoffman et al., "Brain-type N-glycosylation of asialo-transferrin from human cerebrospinal fluid" FEBS Letters (1995) 359: 164-168.
Horn et al., "Chemical synthesis and characterization of branched oligodeoxyribonucleotides (bDNA) for use as signal amplifiers in nucleic acid quantification assays." Nucleic Acids Research (1997) 25: 4842-4849.
Horvath et al., "Stereoselective synthesis of (-)-ara-cyclohexenyl-adenine" Tetrahedron Letters (2007) 48: 3621-3623.
International Search Report for Application PCT/US12/52884 dated Nov. 20, 2012.
International Search Report for Application PCT/US14/36460 dated Oct. 10, 2014.
International Search Report for Application PCT/US14/36462 dated Dec. 23, 2014.
International Search Report for Application PCT/US14/36463 dated Dec. 30, 2014.
International Search Report for Application PCT/US14/36466 dated Dec. 1, 2014.
International Search Report for Application PCT/US14/43731 dated Dec. 10, 2014.
International Search Report for Application PCT/US14/56630 dated Dec. 24, 2014.
Jayaprakash et al., "Non-Nucleoside Building Blocks for Copper-Assisted and Copper-Free Click Chemistry for the Efficient Synthesis of RNA Conjugates" Organic Letters (2010) 12(23): 5410-5413.
Jenuwein "An RNA-Guided Pathway for the Epigenome" Science (2002) 297: 2215-2218.
Jha et al., "The role of complement system in ocular diseases including uveitis and macular degeneration." Molecular Immunology (2007) 44(16): 3901-3908.
Jiang et al., "The Design and Synthesis of Highly Branched and Spherically Symmetric Fluorinated Oils and Amphiles." Tetrahedron (2007) 63(19): 3982-3988.
Jin et al., "Use of α-N,N-bis[Carboxymethyl]lysine-Modified Peroxidase in Immunoassays" Analytical Biochemistry (1995) 229: 54-60.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.
Kanasty et al., "Delivery Materials for siRNA Therapeutics" Nature Materials (2013) 12: 967-977.
Kato et al., "N-acetylgalactosamine incorporation into a peptide containing consecutive threonine residues by UDP-N-acetyl-D-galactosaminide:polypeptide N-acetylgalactosaminyltransferases" Glyobiology (2001) 11: 821-829.
Khorev et al., "Trivalent, Gal/GalNAc-containing ligands designed for the asialoglycoprotein receptor" Bioorganic & Medicinal Chemistry (2008) 16: 5216-5231.
Kim et al., "Oligomeric Glycopeptidomimetics Bearing the Cancer Related TN-Antigen" Tetrahedron Letters (1997) 38(20): 3487-3490.
Kim et al., "Synthesis of Novel Phosphoramidite Building Blocks from Pentaerythritol" Synlett (2003) 12: 1838-1840.
Koller et al., "Mechanisms of single-stranded phosphorothioate modified antisense oligonucleotide accumulation in hepatocytes." Nucleic Acids Res. (2011) 39(11): 4795-4807.
Kornilova et al., "Development of a fluorescence polarization binding assay for asialoglycoprotein receptor" Analytical Biochemistry (2012) 425: 43-46.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Kurosawa et al., "Selective silencing of a mutant transthyretin allele by small interfering RNAs" Biochemical and Biophysical Research Communications (2005) 337 (3): 1012-1018.
Lazaris-Karatzas et al., "Malignant transformation by a eukaryotic initiation factor subunit that binds to mRNA 5' cap" Nature (1990) 345: 544-547.
Lee et al., "Antisense Technology: An Emerging Platform for Cardiovascular Disease Therapeutics" J of Cardiovasc Trans Res (2013) 6: 969-980.
Lee et al., "Facile Synthesis of a High-Affinity Ligand for Mammalian Hepatic Lectin Containing Three Terminal N-Acetylgalactosamine Residues" Bioconjugate Chem. (1997) 8: 762-765.
Lee et al., "New and more efficient multivalent glyco-ligands for asialoglycoprotein receptor of mammalian hepatocytes" Bioorganic & Medicinal Chemistry (2011) 19:2494-2500.

(56) References Cited

OTHER PUBLICATIONS

Lee et al., "New synthetic cluster ligands for galactose/N-acetylgalactosamine-specific lectin of mammalian liver" Biochem (1984) 23: 4255-4261.
Lee et al., "Preparation of Cluster Glycosides of Nacetylgalactosamine That Have Subnanomolar Binding Constants Towards the Mammalian Hepatic Gal/GalNAc-specific Receptor" Glycoconjugate J. (1987) 4: 317-328.
Lee et al., "Protein microarrays to study carbohydrate-recognition events" Bioorg Med Chem Lett (2006) 16(19): 5132-5135.
Lee et al., "Synthesis of multivalent neoglycoconjugates of MUC1 by the conjugation of carbohydrate-centered, triazole-linked glycoclusters to MUC1 peptides using click chemistry." J Org Chem (2012) 77: 7564-7571.
Lee et al., "Synthesis of Peptide-Based Trivalent Scaffold for Preparation of Cluster Glycosides" Methods in Enzymology (2003) 362: 38-43.
Lee et al., "Synthesis of some cluster glycosides suitable for attachment to proteins or solid matrices" Carbohydrate Research (1978) 67: 509-514.
Leeds et al., "Quantitation of phosphorothioate oligonucleotides in human plasma." Analytical Biochemistry (1996) 235, 36-43.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Loyet et al., "Activation of the alternative complement pathway in vitreous is controlled by genetics in age-related macular degeneration." Investigative Ophthalmol & Visual Science (2012) 53(10):6628-37.
Maher et al., "Comparative hybrid arrest by tandem antisense oligodeoxyribonucleotides or oligodeoxyribonucleoside methylphosphonates in a cell-free system" Nucl. Acid. Res. (1998) 16(8):3341-3358.
Maier et al., "Synthesis of Antisense Oligonucleotides Conjugated to a Multivalent Carbohydrate Cluster for Cellular Targeting" Bioconjugate Chem. (2003) 14: 18-29.
Maierhofer et al., "Probing multivalent carbohydrate-lectin interactions by an enzyme-linked lectin assay employing covalently immobilized carbohydrates" Bioorganic & Medicinal Chemistry (2007) 15: 7661-7676.
Manoharan et al., "Chemical Modifications to Improve Uptake and Bioavailability of Antisense Oligonucleotides" Ann. N.Y. Acad. Sci. (1992) 660: 306-309.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids" Tetrahedron Lett. (1995) 36(21):3651-3654.
Manoharan et al., "N-(2-Cyanoethoxycarbonyloxy)succinimide: A New Reagent for Protection of Amino Groups in Oligonucleotides" J. Org. Chem. (1999) 64: 6468-6472.
Manoharan et al., "Oligonucleotide Conjugates: Alteration of the Pharmacokinetic Properties of Antisense Agents" Nucleosides & Nucleotides (1995) 14(3-5):969-973.
Manoharan, "Oligonucleotide Conjugates as Potential Antisense Drugs with Improved Uptake, Biodistribution, Targeted Delivery, and Mechanism of Action" Antisense & Nucleic Acid Drug Development (2002) 12: 103-128.
Marcaurelle et al., "Synthesis of Oxime-Linked Mucin Mimics Containing the Tumor-Related TN and Sialyl TN Antigens" Organic Letters (2001) 3(23): 3691-3694.

Martin, "Ein neuer Zugang zu 2'-O-Alkylribonucleosiden und Eigenscbaften deren Oligonucleotide" Helv. Chim. Acta (1995)78: 486-504.
Merwin et al., "Targeted delivery of DNA using YEE(GalNAcAH)3, a synthetic glycopeptide ligand for the asialoglycoprotein receptor." Bioconjug Chem (1994) 5(6): 612-620.
Mishra et al., "Improved leishmanicidal effect of phosphorotioate antisense oligonucleotides by LDL-mediated delivery" Biochim. Biophys. Acta (1995) 1264:229-237.
Miura et al., "Fluorometric determination of total mRNA with oligo(dT) immobilized on microtiter plates" Clin. Chem. (1996) 42:1758-1764.
Moucari et al., "Early serum HBsAg drop: a strong predictor of sustained virological response to pegylated interferon alfa-2a in HBeAg-negative patients." Hepatology (2009) 49(4): 1151-1157.
Nair et al., "Multivalent N-Acetylgalactosamine-Conjugated siRNA Localizes in Hepatocytes and Elicits Robust RNAi-Mediated Gene Silencing" J. Am. Chem. Soc. (2014) 136(49): 16958-16961.
Nauwelaerts et al., "Cyclohexenyl nucleic acids: conformationally flexible oligonucleotides" Nucleic Acids Research (2005) 33(8): 2452-2463.
Nauwelaerts et al., "Structural Characterization and Biological Evaluation of Small Interfering RNAs Containing Cyclohexenyl Nucleosides" J. Am. Chem. Soc. (2007) 129(30): 9340-9348.
New England Biolabs 1998/99 Catalog (cover page and pp. 121 and 284).
Nitsch et al., "Associations between chronic kidney disease and age-related macular degeneration." Ophthalmic Epidemiology (2009) 16(3):181-186.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Orum et al., "Locked nucleic acids: A promising molecular family for gene-function analysis and antisense drug development" Curr. Opinion Mol. Ther. (2001) 3:239-243.
Ostergaard et al., "Efficient Synthesis and Biological Evaluation of 5'-GalNAc Conjugated Antisense Oligonucleotides" Bioconjug. Chem. (2015) 26(8): 1451-1455.
Pal-Bhadra et al., "Heterochromatic Silencing and HP1 Localization in *Drosophila* Are Dependent on the RNAi Machinery" Science (2004) 303: 669-672.
Park et al., "The asialoglycoprotein receptor clears glycoconjugates terminating with sialic acid a2,6GalNAc" PNAS (2005) 102(47): 17125-17129.
Patel et al., "Age-related macular degeneration: a perspective on genetic studies." Eye (2008) 22(6):768-776.
Pavia et al., "Synthetic TN glycopeptide related to human glycophorin AM. High-field proton and carbon-13 nuclear magnetic resonance study." Int J Pep Protein Res (1983) 22: 539-548.
Pennesi et al., "Animal models of age related macular degeneration." Molecular Apects of Medicine (2012) 33:487-509.
Petrova et al., "Carrier-free cellular uptake and the gene-silencing activity of the lipophilic siRNAs is strongly affected by the length of the linker between siRNA and lipophilic group" Nucleic Acids Research (2012) 40(5): 2330-2344.
Pickering et al., "Spontaneous hemolytic uremic syndrome triggered by complement factor H lacking surface recognition domains" Journal of Experimental Med. (2007) 204: 1249-56.
Pickering et al., "Uncontrolled C3 activation causes membranoproliferative glomerulonephritis in mice deficient in complement factor H." Nature Genetics (2002) 31(4):424-8.
Prakash et al., "Targeted delivery of antisense oligonucleotides to hepatocytes using triantennary N-acetyl galactosamine improves potency 10-fold in mice" Nucleic Acid Research (2014) 42(13): 8796-8807.
Pujol et al., "A Sulfur Tripod Glycoconjugate that Releases a High-Affinity Copper Chelator in Hepatocytes" Angew. Chem. Int. Ed. (2012) 51: 7445-7448.
Rajeev, "Conjugation Strategies for In Vitro siRNA Delivery" 8th Annual Meeting of the Oligonucleotide Therapeutics Society (2012).

(56) References Cited

OTHER PUBLICATIONS

Rajur et al., "Covalent Protein-Oligonucleotide Conjugates for Efficient Delivery of Antisense Molecules" Bioconjugate Chem. (1997) 8: 935-940.
Raouane et al., "Synthesis, Characterization, and in Vivo Delivery of siRNA-Squalene Nanoparticles Targeting Fusion Oncogene in Papillary Thyroid Carcinoma" J. Med. Chem. (2011) 54: 4067-4076.
Rensen et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808.
Rensen et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584.
Rensen et al., "Stimulation of Liver-Directed Cholesterol Flux in Mice by Novel N-Acetylgalactosamine-Terminated Glycolipids With High Affinity for the Asialoglycoprotein Receptor" Arterioscler Thromb Vasc Biol (2006) 26: 169-175.
Reynolds et al., "Rational siRNA design for RNA interference" Nature Biotechnology (2004) 22(3):326-330.
Richards et al., "Inherited complement regulatory protein deficiency predisposes to human disease in acute injury and chronic inflammatory statesthe examples of vascular damage in atypical hemolytic uremic syndrome and debris accumulation in age-related macular degeneration." Advances in Immunology (2007) 96:141-77.
Robeyns et al., "Oligonucleotides with cyclohexene-nucleoside building blocks: crystallization and preliminary X-ray studies of a left-handed sequence GTGT ACAC" Acta Crystallographica, Section F: Structural Biology and Crystallization Communications (2005) F61(6): 585-586.
Robeyns et al., "Structure of the Fully Modified Left-Handed Cyclohexene Nucleic Acid Sequence GTGTACAC" J. Am. Chem. Soc. (2008) 130(6): 1979-1984.
Rohrer et al., "A targeted inhibitor of the alternative complement pathway reduces angiogenesis in a mouse model of age-related macular degeneration." Investigative Ophthalmol Visual Science (2009) 50(7):3056-64.
Rossenberg et al., "Stable polyplexes based on arginine-containing oligopeptides for in vivo gene delivery" Gene Therapy (2004) 11: 457-464.
Rouchaud et al., "A New and Efficient Synthesis of Derivatives of Octahydro-4H-pyrrolo[1,2-c]pyrido[1',2'-a]imidazole" Eur. J. Org. Chem. (2011) 12: 2346-2353.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi et al., "Heterocyclic Base Modifications in Nucleic Acids and Their Applications in Antisense Oligonucleotides" Antisense Research and Applications (1993)273-288.
Sanghvi, Chapter 15, Antisense Research and Applications, Crooke and Lebleu ed., CRC Press (1993).
Sato et al., "Glycoinsulins: Dendritic Sialyloligosaccharide-Displaying Insulins Showing a Prolonged Blood-Sugar-Lowering Activity" J. Am. Chem. Soc. (2004) 126: 14013-14022.
Savige et al., "Retinal abnormalities characteristic of inherited renal disease." Journal of American Society of Nephrol. (2011) 22(8):1403-15.
Seth et al., "Design, Synthesis And Evaluation Of Constrained Methoxyethyl (cMOE) and Constrained Ethyl (cEt) Nucleoside Analogs" Nucleic Acids Symposium Series (2008) 52(1): 553-554.
Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.
Seth et al., "Synthesis and biophysical characterization of R-6'-Me-α-L-LNA modified oligonucleotides." Bioorg. Med. Chem. (2011) 21(4): 1122-1125.

Seth et al., "Synthesis and Biophysical Evaluation of 2',4'-Constrained 2'O-Methoxyethyl and 2',4'-Constrained 2'O-Ethyl Nucleic Acid Analogues" J Org Chem. (2010) 75(5): 1569-1581.
Shchepinov et al., "Oligonucleotide dendrimers: stable nanostructures" Nucleic Acids Research (1999) 27(15): 3035-3041.
Shchepinov et al., "Oligonucleotide dendrimers: synthesis and use as polylabelled DNA probes." Nucleic Acids Research (1997) 25(22): 4447-4454.
Shea et al., "Synthesis, hybridization properties and antiviral activity of lipid-oligodeoxynucleotide conjugates" Nucl. Acids Res. (1990) 18(13):3777-3783.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Sliedregt et al., "Design and Synthesis of Novel Amphiphilic Dendritic Galactosides for Selective Targeting of Liposomes to the Hepatic Asialoglycoprotein Receptor" J. Med. Chem. (1999) 42:609-618.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Swayze et al., "The Medicinal Chemistry of Oligonucleotides" Antisense Drug Technology: Principles, Strategies, and Applications, 2nd ED. (2007) 143-182.
Tober et al., "Self-Metathesis of Polyol Allyl Ethers towards Carbohydrate-Based Oligohydroxy Derivatives" Eur. J. Org. Chem. (2013) 3: 566-577.
Tomiya et al., "Liver-targeting of primaquine-(poly-c-glutamic acid) and its degradation in rat hepatocytes" Bioorganic & Medicinal Chemistry (2013) 21: 5275-5281.
Toyokuni et al., "Synthetic vaccines: I. Synthesis of multivalent Tn antigen cluster-lysyllysine conjugates" Tetrahedron Lett (1990) 31(19): 2673-2676.
Vaculik et al., "Shift of C3 deposition from localization in the glomerulus into the tubulointerstitial compartment in the absence of secreted IgM in immune complex glomerulonephritis." Clinical and Exp Immunology (2007) 151: 146-154.
Valentijn et al., "Solid-phase Synthesis of Lysine-based Cluster Galactosides with High Affinity for the Asialoglycoprotein Receptor" Tetrahedron (1997) 53(2): 759-770.
Van Rossenberg et al., "Stable polyplexes based on arginine-containing oligopeptides for in vivo gene delivery" Gene Ther (2004) 11: 457-464.
Verbeure et al., "RNase H mediated cleavage of RNA by cyclohexene nucleic acid (CeNA)" Nucleic Acids Research (2001) 29(24): 4941-4947.
Verdel et al., "RNAi-Mediated Targeting of Heterochromatin by the RITS Complex" Science (2004) 303: 672-676.
Volpe et al., "Regulation of heterochromatic silencing and histone H3 lysine-9 methylation by RNAi." Science (2002) 297(5588): 1833-1837.
Wahlestedt et al., "Potent and nontoxic antisense oligonucleotide containing locked nucleic acids" Proc. Natl. Acad. Sci. USA (2000) 97: 5633-5638.
Wang et al., "A Straightforward Stereoselective Synthesis of D- and L-5-Hydroxy-4-hydroxymethyl-2-cyclohexenylguanine" Journal of Organic Chem. (2001) 66: 8478-8482.
Wang et al., "Cyclohexene nucleic acids (CeNA) form stable duplexes with RNA and induce RNase H activity." Nucleosides, Nucleotides & Nucleic Acids (2001) 20(4-7) 785-788.
Wang et al., "Cyclohexene Nucleic Acids (CeNA): Serum Stable Oligonucleotides that Activate RNase H and Increase Duplex Stability with Complementary RNA" Journal of American Chem. (2000) 122: 8595-8602.
Wang et al., "Stereocontrolled Synthesis of Ara-Type Cyclohexenyl Nucleosides" Journal of Organic Chem.(2003) 68, 4499-4505.
Weber et al., "Design and synthesis of P2-P1'-linked macrocyclic human renin inhibitors" J. Med. Chem. (1991) 34(9): 2692-2701.

(56) References Cited

OTHER PUBLICATIONS

Westerlind et al., "Ligands of the asialoglycoprotein receptor for targeted gene delivery, part 1: Synthesis of and binding studies with biotinylated cluster glycosides containing N-acetylgalactosamine" Glycoconjugate Journal (2004) 21: 227-241.

Woolf et al., "Specificity of antisense oligonucleotides in vivo" PNAS (1992) 89: 7305-7309.

Wu et al., "A New N-Acetylgalactosamine Containing Peptide as a Targeting Vehicle for Mammalian Hepatocytes Via Asialoglycoprotein Receptor Endocytosis" Current Drug Delivery (2004) 1: 119-127.

Zimmermann et al., "Carbohydrate conjugation to siRNA for liver-specific delivery" Hepatology (2010) 52(1): pp. 587A, Abstract No. 547, Retrieved from STN, Accession No. 0050381852 EMBASE [retrieved on Jun. 25, 2018].

Zhao et al., "Synthesis and preliminary biochemical studies with 5'-deoxy-5'-methylidyne phosphonate linked thymidine oligonucleotides" Tetrahedron Letters (1996) 37(35): 6239-6242.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

Zhou et al., "Proteolytic processing in the secretory pathway." J. Biol. Chem. (1999) 274(30): 20745-20748.

COMPOSITIONS AND METHODS FOR MODULATING COMPLEMENT FACTOR B EXPRESSION

SEQUENCE LISTING

The present application is being filed along with a Sequence Listing in electronic format. The Sequence Listing is provided as a file entitled BIOL0251USC1SEQ_ST25.txt created May 6, 2021, which is 204 kb in size. The information in the electronic format of the sequence listing is incorporated herein by reference in its entirety.

FIELD

The present embodiments provide methods, compounds, and compositions for treating, preventing, or ameliorating a disease associated with dysregulation of the complement alternative pathway by administering a Complement Factor B (CFB) specific inhibitor to a subject.

BACKGROUND

The complement system is part of the host innate immune system involved in lysing foreign cells, enhancing phagocytosis of antigens, clumping antigen-bearing agents, and attracting macrophages and neutrophils. The complement system is divided into three initiation pathways—the classical, lectin, and alternative pathways—that converge at component C3 to generate an enzyme complex known as C3 convertase, which cleaves C3 into C3a and C3b. C3b associates with C3 convertase mediated by CFB and results in generation of C5 convertase, which cleaves C5 into C5a and C5b, which initiates the membrane attack pathway resulting in the formation of the membrane attack complex (MAC) comprising components C5b, C6, C7, C8, and C9. The membrane-attack complex (MAC) forms transmembrane channels and disrupts the phospholipid bilayer of target cells, leading to cell lysis.

In the homeostatic state, the alternative pathway is continuously activated at a low "tickover" level as a result of activation of the alternative pathway by spontaneous hydrolysis of C3 and the production of C3b, which generates C5 convertase.

SUMMARY

The complement system mediates innate immunity and plays an important role in normal inflammatory response to injury, but its dysregulation may cause severe injury. Activation of the alternative complement pathway beyond its constitutive "tickover" level can lead to unrestrained hyperactivity and manifest as diseases of complement dysregulation.

Certain embodiments provided herein relate to methods of treating, preventing, or ameliorating a disease associated with dysregulation of the complement alternative pathway in a subject by administration of a Complement Factor B (CFB) specific inhibitor. Several embodiments provided herein are drawn to a method of inhibiting expression of CFB in a subject having, or at risk of having, a disease associated with dysregulation of the complement alternative pathway by administering a CFB specific inhibitor to the subject. In certain embodiments, a method of reducing or inhibiting accumulation of C3 deposits in the eye of a subject having, or at risk of having, a disease associated with dysregulation of the complement alternative pathway comprises administering a CFB specific inhibitor to the subject. In several embodiments, a method of reducing or inhibiting accumulation of C3 deposits in the kidney of a subject having, or at risk of having, a disease associated with dysregulation of the complement alternative pathway comprises administering a CFB specific inhibitor to the subject.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

"2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

"2'-O-methoxyethyl" (also 2'-MOE and 2'-O(CH$_2$)$_2$—OCH$_3$) refers to an O-methoxy-ethyl modification at the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanosyl ring other than H or OH. In certain embodiments, 2' substituted nucleosides include nucleosides with bicyclic sugar modifications.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5 position. A 5-methylcytosine is a modified nucleobase.

"About" means within ±10% of a value. For example, if it is stated, "the compounds affected at least about 70% inhibition of CFB", it is implied that CFB levels are inhibited within a range of 60% and 80%.

"Administration" or "administering" refers to routes of introducing an antisense compound provided herein to a subject to perform its intended function. An example of a route of administration that can be used includes, but is not limited to parenteral administration, such as subcutaneous, intravenous, or intramuscular injection or infusion.

"Alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms (C1-C12 alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted C1-C12 alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a C1-C12 alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

"Amelioration" refers to a lessening of at least one indicator, sign, or symptom of an associated disease, disorder, or condition. In certain embodiments, amelioration includes a delay or slowing in the progression of one or more indicators of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is is capable of undergoing hybridization to a target nucleic acid through hydrogen bonding Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding region or segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

"Bicyclic nucleic acid" or "BNA" or "BNA nucleosides" means nucleic acid monomers having a bridge connecting two carbon atoms between the 4' and 2' position of the nucleoside sugar unit, thereby forming a bicyclic sugar. Examples of such bicyclic sugar include, but are not limited to A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

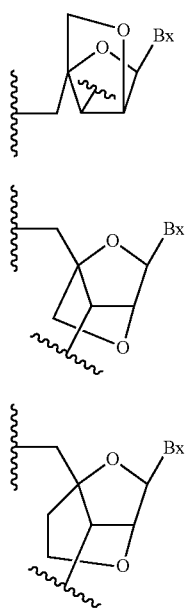

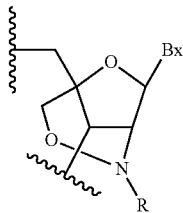

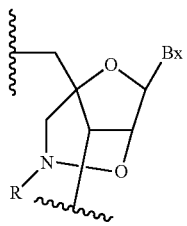

As used herein, LNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —Si(R$_1$)$_2$—, —S(=O)$_x$—, and —N(R$_1$)—; wherein: x is 0, 1, or 2; n is 1, 2, 3, or 4; each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

Examples of 4'-2' bridging groups encompassed within the definition of LNA include, but are not limited to one of formulae: —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$)—. Furthermore, other bridging groups encompassed with the definition of LNA are 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R$_1$)-2' and 4'-CH$_2$—N(R$_1$)—O-2'-bridges, wherein each R$_1$ and R$_2$ is, independently, H, a protecting group or C$_1$-C$_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-CH$_2$—O-2') bridge to form the bicyclic sugar moiety. The bridge can also be a methylene (—CH$_2$—) group connecting the 2' oxygen atom and the 4' carbon atom, for which the term methyleneoxy (4'-CH$_2$—O-2') LNA is used. Furthermore; in the case of the bicyclic sugar moiety having an ethylene bridging group in this position, the term ethyleneoxy (4'-CH$_2$CH$_2$—O-2') LNA is used. α-L-methyleneoxy (4'-CH$_2$—O-2'), an isomer of methyleneoxy (4'-CH$_2$—O-2') LNA is also encompassed within the definition of LNA, as used herein.

"Cap structure" or "terminal cap moiety" means chemical modifications, which have been incorporated at either terminus of an antisense compound.

"Carbohydrate" means a naturally occurring carbohydrate, a modified carbohydrate, or a carbohydrate derivative.

"Carbohydrate cluster" means a compound having one or more carbohydrate residues attached to a scaffold or linker group. (see, e.g., Maier et al., "Synthesis of Antisense Oligonucleotides Conjugated to a Multivalent Carbohydrate Cluster for Cellular Targeting," *Bioconjugate Chemistry*, 2003, (14): 18-29, which is incorporated herein by reference in its entirety, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808, for examples of carbohydrate conjugate clusters).

"Carbohydrate derivative" means any compound which may be synthesized using a carbohydrate as a starting material or intermediate.

"cEt" or "constrained ethyl" means a bicyclic sugar moiety comprising a bridge connecting the 4'-carbon and the 2'-carbon, wherein the bridge has the formula: 4'-CH($CH_3$)—O-2'.

"Chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group that is capable of being split under physiological conditions. In certain embodiments, a cleavable moiety is cleaved inside a cell or sub-cellular compartments, such as a lysosome. In certain embodiments, a cleavable moiety is cleaved by endogenous enzymes, such as nucleases. In certain embodiments, a cleavable moiety comprises a group of atoms having one, two, three, four, or more than four cleavable bonds.

"Conjugate" or "conjugate group" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

"conjugate linker" or "linker" in the context of a conjugate group means a portion of a conjugate group comprising any atom or group of atoms and which covalently link (1) an oligonucleotide to another portion of the conjugate group or (2) two or more portions of the conjugate group.

Conjugate groups are shown herein as radicals, providing a bond for forming covalent attachment to an oligomeric compound such as an antisense oligonucleotide. In certain embodiments, the point of attachment on the oligomeric compound is the 3'-oxygen atom of the 3-hydroxyl group of the 3' terminal nucleoside of the oligomeric compound. In certain embodiments the point of attachment on the oligomeric compound is the 5'-oxygen atom of the 5-hydroxyl group of the 5' terminal nucleoside of the oligomeric compound. In certain embodiments, the bond for forming attachment to the oligomeric compound is a cleavable bond. In certain such embodiments, such cleavable bond constitutes all or part of a cleavable moiety.

In certain embodiments, conjugate groups comprise a cleavable moiety (e.g., a cleavable bond or cleavable nucleoside) and a carbohydrate cluster portion, such as a GalNAc cluster portion. Such carbohydrate cluster portion comprises: a targeting moiety and, optionally, a conjugate linker. In certain embodiments, the carbohydrate cluster portion is identified by the number and identity of the ligand. For example, in certain embodiments, the carbohydrate cluster portion comprises 3 GalNAc groups and is designated "GalNAc3". In certain embodiments, the carbohydrate cluster portion comprises 4 GalNAc groups and is designated "GalNAc4". Specific carbohydrate cluster portions (having specific tether, branching and conjugate linker groups) are described herein and designated by Roman numeral followed by subscript "a". Accordingly "GalNac3-1a" refers to a specific carbohydrate cluster portion of a conjugate group having 3 GalNac groups and specifically identified tether, branching and linking groups. Such carbohydrate cluster fragment is attached to an oligomeric compound via a cleavable moiety, such as a cleavable bond or cleavable nucleoside.

"Conjugate compound" means any atoms, group of atoms, or group of linked atoms suitable for use as a conjugate group. In certain embodiments, conjugate compounds may possess or impart one or more properties, including, but not limited to pharmacodynamic, pharmacokinetic, binding, absorption, cellular distribution, cellular uptake, charge and/or clearance properties.

"Constrained ethyl nucleoside" (also cEt nucleoside) means a nucleoside comprising a bicyclic sugar moiety comprising a 4'-CH($CH_3$)—O-2' bridge.

"Complement Factor B (CFB)" means any nucleic acid or protein of CFB. "CFB nucleic acid" means any nucleic acid encoding CFB. For example, in certain embodiments, a CFB nucleic acid includes a DNA sequence encoding CFB, an RNA sequence transcribed from DNA encoding CFB (including genomic DNA comprising introns and exons), including a non-protein encoding (i.e. non-coding) RNA sequence, and an mRNA sequence encoding CFB. "CFB mRNA" means an mRNA encoding a CFB protein.

"CFB specific inhibitor" refers to any agent capable of specifically inhibiting CFB RNA and/or CFB protein expression or activity at the molecular level. For example, CFB specific inhibitors include nucleic acids (including antisense compounds), peptides, antibodies, small molecules, and other agents capable of inhibiting the expression of CFB RNA and/or CFB protein.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Complementarity" means the capacity for pairing between nucleobases of a first nucleic acid and a second nucleic acid.

"Comprise," "comprises" and "comprising" will be understood to imply the inclusion of a stated step or element or group of steps or elements but not the exclusion of any other step or element or group of steps or elements.

"Contiguous nucleobases" means nucleobases immediately adjacent to each other.

"Deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

"Deoxyribonucleotide" means a nucleotide having a hydrogen at the 2' position of the sugar portion of the nucleotide. Deoxyribonucleotides may be modified with any of a variety of substituents.

"Designing" or "Designed to" refer to the process of designing an oligomeric compound that specifically hybridizes with a selected nucleic acid molecule.

"Differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides.

Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

"Double-stranded" refers to two separate oligomeric compounds that are hybridized to one another. Such double stranded compounds may have one or more or non-hybridizing nucleosides at one or both ends of one or both strands (overhangs) and/or one or more internal non-hybridizing nucleosides (mismatches) provided there is sufficient complementarity to maintain hybridization under physiologically relevant conditions.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Furanosyl" means a structure comprising a 5-membered ring comprising four carbon atoms and one oxygen atom.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Halo" and "halogen," mean an atom selected from fluorine, chlorine, bromine and iodine.

"Heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

"Hybridization" means the annealing of complementary nucleic acid molecules. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Identifying an animal having, or at risk for having, a disease, disorder and/or condition" means identifying an animal having been diagnosed with the disease, disorder and/or condition or identifying an animal predisposed to develop the disease, disorder and/or condition. Such identification may be accomplished by any method including evaluating an individual's medical history and standard clinical tests or assessments.

"Immediately adjacent" means there are no intervening elements between the immediately adjacent elements.

"Individual" means a human or non-human animal selected for treatment or therapy.

"Inhibiting the expression or activity" refers to a reduction, blockade of the expression or activity and does not necessarily indicate a total elimination of expression or activity.

"Internucleoside linkage" refers to the chemical bond between nucleosides.

"Internucleoside neutral linking group" means a neutral linking group that directly links two nucleosides.

"Internucleoside phosphorus linking group" means a phosphorus linking group that directly links two nucleosides.

"Lengthened" antisense oligonucleotides are those that have one or more additional nucleosides relative to an antisense oligonucleotide disclosed herein.

"Linkage motif" means a pattern of linkage modifications in an oligonucleotide or region thereof. The nucleosides of such an oligonucleotide may be modified or unmodified. Unless otherwise indicated, motifs herein describing only linkages are intended to be linkage motifs. Thus, in such instances, the nucleosides are not limited.

"Linked deoxynucleoside" means a nucleic acid base (A, G, C, T, U) substituted by deoxyribose linked by a phosphate ester to form a nucleotide.

"Linked nucleosides" means adjacent nucleosides linked together by an internucleoside linkage.

"Locked nucleic acid nucleoside" or "LNA" means a nucleoside comprising a bicyclic sugar moiety comprising a 4'-CH2-O-2'bridge.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, or modified nucleobase.

"Modified oligonucleotide" means an oligonucleotide comprising at least one modified internucleoside linkage, a modified sugar, and/or a modified nucleobase.

"Modified sugar" means substitution and/or any change from a natural sugar moiety.

"Modulating" refers to changing or adjusting a feature in a cell, tissue, organ or organism. For example, modulating CFB mRNA can mean to increase or decrease the level of CFB mRNA and/or CFB protein in a cell, tissue, organ or organism. A "modulator" effects the change in the cell, tissue, organ or organism. For example, a CFB antisense compound can be a modulator that decreases the amount of CFB mRNA and/or CFB protein in a cell, tissue, organ or organism.

"Monomer" refers to a single unit of an oligomer. Monomers include, but are not limited to, nucleosides and nucleotides, whether naturally occurring or modified.

"Mono or polycyclic ring system" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, hetero-aromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to hetero-cyclic rings as well as rings comprising only C ring atoms which can be present in a mixed motif such as for example benzimidazole wherein one ring has only carbon ring atoms and the fused ring has two nitrogen atoms. The mono or polycyclic ring system can be further substituted with substituent groups such as for example phthalimide which has two =O groups attached to one of the rings. Mono or polycyclic ring systems can be attached to parent molecules using various strategies such as directly through a ring atom, fused through multiple ring atoms, through a substituent group or through a bifunctional linking moiety.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Neutral linking group" means a linking group that is not charged. Neutral linking groups include without limitation phospho-triesters, methylphosphonates, MMI (—CH2-N (CH3)—O—), amide-3 (—CH2-C(=O)—N(H)—), amide-4 (—CH2-N(H)—C(=O)—), formacetal (—O—CH2-O—), and thioformacetal (—S—CH2-O—). Further neutral linking groups include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral linking groups include nonionic linkages comprising mixed N, O, S and CH2 component parts.

"Non-complementary nucleobase" refers to a pair of nucleobases that do not form hydrogen bonds with one another or otherwise support hybridization.

"Non-internucleoside neutral linking group" means a neutral linking group that does not directly link two nucleosides. In certain embodiments, a non-internucleoside neutral linking group links a nucleoside to a group other than a nucleoside. In certain embodiments, a non-internucleoside neutral linking group links two groups, neither of which is a nucleoside.

"Non-internucleoside phosphorus linking group" means a phosphorus linking group that does not directly link two nucleosides. In certain embodiments, a non-internucleoside phosphorus linking group links a nucleoside to a group other than a nucleoside. In certain embodiments, a non-internucleoside phosphorus linking group links two groups, neither of which is a nucleoside.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase modification motif" means a pattern of modifications to nucleobases along an oligonucleotide. Unless otherwise indicated, a nucleobase modification motif is independent of the nucleobase sequence.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleoside motif" means a pattern of nucleoside modifications in an oligonucleotide or a region thereof. The linkages of such an oligonucleotide may be modified or unmodified. Unless otherwise indicated, motifs herein describing only nucleosides are intended to be nucleoside motifs. Thus, in such instances, the linkages are not limited.

"Nucleotide" means a nucleoside having a phosphate group covalently linked to the sugar portion of the nucleoside.

"Oligomeric compound" means a polymer of linked monomeric subunits which is capable of hybridizing to at least a region of a nucleic acid molecule.

"Oligonucleoside" means an oligonucleotide in which the internucleoside linkages do not contain a phosphorus atom.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Phosphorus linking group" means a linking group comprising a phosphorus atom. Phosphorus linking groups include without limitation groups having the formula:

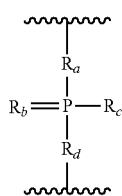

wherein:
$R_a$ and $R_d$ are each, independently, O, S, $CH_2$, NH, or $NJ_1$ wherein $J_1$ is $C_1$-$C_6$ alkyl or substituted $C_1$-$C_6$ alkyl;
$R_b$ is O or S;
$R_c$ is OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and
$J_1$ is $R_b$ is O or S.

Phosphorus linking groups include without limitation, phosphodiester, phosphorothioate, phosphorodithioate, phosphonate, phosphoramidate, phosphorothioamidate, thionoalkylphosphonate, phosphotriesters, thionoalkylphosphotriester and boranophosphate.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound "Prevent" refers to delaying or forestalling the onset, development or progression of a disease, disorder, or condition for a period of time from minutes to indefinitely. Prevent also means reducing the risk of developing a disease, disorder, or condition.

"Prodrug" means an inactive or less active form of a compound which, when administered to a subject, is metabolized to form the active, or more active, compound (e.g., drug).

"Prophylactically effective amount" refers to an amount of a pharmaceutical agent that provides a prophylactic or preventative benefit to an animal.

"Protecting group" means any compound or protecting group known to those having skill in the art. Non-limiting examples of protecting groups may be found in "Protective Groups in Organic Chemistry", T. W. Greene, P. G. M. Wuts, ISBN 0-471-62301-6, John Wiley & Sons, Inc, New York, which is incorporated herein by reference in its entirety.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"RISC based antisense compound" means an antisense compound wherein at least some of the antisense activity of the antisense compound is attributable to the RNA Induced Silencing Complex (RISC).

"RNase H based antisense compound" means an antisense compound wherein at least some of the antisense activity of the antisense compound is attributable to hybridization of the antisense compound to a target nucleic acid and subsequent cleavage of the target nucleic acid by RNase H.

"Segments" are defined as smaller or sub-portions of regions within a target nucleic acid.

"Separate regions" means portions of an oligonucleotide wherein the chemical modifications or the motif of chemical modifications of any neighboring portions include at least one difference to allow the separate regions to be distinguished from one another.

"Sequence motif" means a pattern of nucleobases arranged along an oligonucleotide or portion thereof. Unless otherwise indicated, a sequence motif is independent of chemical modifications and thus may have any combination of chemical modifications, including no chemical modifications.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Sites," as used herein, are defined as unique nucleobase positions within a target nucleic acid.

"Slows progression" means decrease in the development of the said disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unpro¬tected. In certain embodiments, compounds of the present disclosure have substituents at one or at more than one position of the parent compound. Substituents may also be further substituted with other substituent groups and may be attached directly or via a linking group such as an alkyl or hydro¬carbyl group to a parent compound.

Likewise, as used herein, "substituent" in reference to a chemical functional group means an atom or group of atoms that differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C¬(O)¬Raa), carboxyl (—C(O)O-Raa), aliphatic groups, ali-cyclic groups, alkoxy, substituted oxy (—O—Raa), aryl, aralkyl, heterocyclic radical, hetero¬aryl, heteroarylalkyl, amino (N(Rbb)¬(Rcc)), imino(=NRbb), amido (C(O)N¬(Rbb)(Rcc) or N(Rbb)C(O)Raa), azido (—N3), nitro (NO2), cyano (—CN), carbamido (OC(O)N(Rbb)(Rcc) or N(Rbb)¬C(O)¬ORaa), ureido (N(Rbb)C(O)¬N(Rbb)(Rcc)), thioureido (N(Rbb)C¬¬¬(S)N(Rbb)¬(Rcc)), guanidinyl (N(Rbb)¬C(=NRbb)-N(Rbb)(Rcc)), amidinyl (C(=NRbb)¬¬N(Rbb)(Rcc) or N(Rbb)C(=NRbb)(Raa)), thiol (—SRbb), sulfinyl (S(O)Rbb), sulfonyl (—S(O)2Rbb) and sulfonamidyl (—S(O)2N(Rbb)(Rcc) or N(Rbb)¬S¬¬(0)$_2$Rbb). Wherein each Raa, Rbb and Rcc is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and hetero¬aryl¬alkyl. Selected substituents within the compounds described herein are present to a recursive degree.

"Substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

"Sugar moiety" means a naturally occurring sugar moiety or a modified sugar moiety of a nucleoside.

"Sugar motif" means a pattern of sugar modifications in an oligonucleotide or a region thereof.

"Sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

"Target" refers to a protein, the modulation of which is desired.

"Target gene" refers to a gene encoding a target.

"Targeting" means the process of design and selection of an antisense compound that will specifically hybridize to a target nucleic acid and induce a desired effect.

"Target nucleic acid," "target RNA," "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

"Terminal internucleoside linkage" means the linkage between the last two nucleosides of an oligonucleotide or defined region thereof.

"Therapeutically effective amount" means an amount of a pharmaceutical agent that provides a therapeutic benefit to an individual.

"Treat" refers to administering a pharmaceutical composition to an animal in order to effect an alteration or improvement of a disease, disorder, or condition in the animal. In certain embodiments, one or more pharmaceutical compositions can be administered to the animal.

"Unmodified" nucleobases mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods, compounds and compositions for inhibiting Complement Factor B (CFB) expression.

Certain embodiments provide antisense compounds targeted to a CFB nucleic acid. In certain embodiments, the CFB nucleic acid has the sequence set forth in GENBANK Accession No. NM_001710.5 (incorporated herein as SEQ ID NO: 1), GENBANK Accession No. NT_007592.15 truncated from nucleotides 31852000 to U.S. Pat. No. 31,861,000 (incorporated herein as SEQ ID NO: 2), GENBANK Accession No NW_001116486.1 truncated from nucleotides 536000 to 545000 (incorporated herein as SEQ ID NO: 3), GENBANK Accession No. XM_001113553.2 (incorporated herein as SEQ ID NO: 4), or GENBANK Accession No. NM_008198.2 (incorporated herein as SEQ ID NO: 5).

Certain embodiments provide a compound comprising a modified oligonucleotide and a conjugate group, wherein the modified oligonucleotide consists of 10 to 30 linked nucleosides and has a nucleobase sequence comprising at least 8 contiguous nucleobases of any of the nucleobase sequences of SEQ ID NOs: 6-808.

Certain embodiments provide a compound comprising a modified oligonucleotide and a conjugate group, wherein the modified oligonucleotide consists of 10 to 30 linked nucleosides and has a nucleobase sequence comprising at least 9 contiguous nucleobases of any of the nucleobase sequences of SEQ ID NOs: 6-808.

Certain embodiments provide a compound comprising a modified oligonucleotide and a conjugate group, wherein the modified oligonucleotide consists of 10 to 30 linked nucleosides and has a nucleobase sequence comprising at least 10 contiguous nucleobases of any of the nucleobase sequences of SEQ ID NOs: 6-808.

Certain embodiments provide a compound comprising a modified oligonucleotide and a conjugate group, wherein the modified oligonucleotide consists of 10 to 30 linked nucleosides and has a nucleobase sequence comprising at least 11 contiguous nucleobases of any of the nucleobase sequences of SEQ ID NOs: 6-808.

Certain embodiments provide a compound comprising a modified oligonucleotide and a conjugate group, wherein the modified oligonucleotide consists of 10 to 30 linked nucleosides and has a nucleobase sequence comprising at least 12 contiguous nucleobases of any of the nucleobase sequences of SEQ ID NOs: 6-808.

Certain embodiments provide a compound comprising a modified oligonucleotide and a conjugate group, wherein the modified oligonucleotide consists of 10 to 30 linked nucleosides and has a nucleobase sequence comprising the nucleobase sequence of any one of SEQ ID NOs: 6-808.

Certain embodiments provide a compound comprising a modified oligonucleotide and a conjugate group, wherein the modified oligonucleotide consists of the nucleobase sequence of any one of SEQ ID NOs: 6-808.

Certain embodiments provide a compound comprising a modified oligonucleotide and a conjugate group, wherein the modified oligonucleotide consists of 10 to 30 linked nucleosides complementary within nucleobases 30-49, 48-63, 150-169, 151-170, 152-171, 154-169, 154-173, 156-171, 156-175, 157-176, 158-173, 158-177, 480-499, 600-619, 638-657, 644-663, 738-757, 1089-1108, 1135-1154, 1141-1160, 1147-1166, 1150-1169, 1153-1172, 1159-1178, 1162-1181, 1165-1184, 1171-1186, 1171-1190, 1173-1188, 1173-1192, 1175-1190, 1175-1194, 1177-1196, 1183-1202, 1208-1227, 1235-1254, 1298-1317, 1304-1323, 1310-1329, 1316-1335, 1319-1338, 1322-1341, 1328-1347, 1349-1368, 1355-1374, 1393-1412, 1396-1415, 1399-1418, 1405-1424, 1421-1440, 1621-1640, 1646-1665, 1646-1665, 1647-1666, 1689-1708, 1749-1768, 1763-1782, 1912-1931, 2073-2092, 2085-2104, 2166-2185, 2172-2191, 2189-2208, 2191-2210, 2193-2212, 2195-2210, 2195-2214, 2196-2215, 2197-2212, 2197-2216, 2202-2221, 2223-2238, 2223-2242, 2225-2240, 2226-2245, 2227-2242, 2227-2246, 2238-2257, 2241-2260, 2267-2286, 2361-2380, 2388-2407, 2397-2416, 2448-2467, 2453-2472, 2455-2474, 2457-2472, 2457-2476, 2459-2474, 2459-2478, 2461-2476, 2461-2480, 2532-2551, 2550-2569, 2551-2566, 2551-2570, 2552-2568, 2552-2570, 2552-2571, 2553-2568, 2553-2570, 2553-2571, 2553-2572, 2554-2571, 2554-2572, 2554-2573, 2555-2570, 2555-2572, 2555-2574, 2556-2573, 2556-2574, 2556-2575, 2557-2573, 2557-2574, 2557-2575, 2557-2576, 2558-2575, 2558-2576, 2558-2577, 2559-2576, 2559-2577, 2559-2578, 2560-2577, 2560-2578, 2560-2579, 2561-2576, 2561-2578, 2561-2579, 2561-2580, 2562-2577, 2562-2579, 2562-2581, 2563-2578, 2563-2580, 2563-2582, 2564-2581, 2564-2583, 2565-2584, 2566-2583, 2566-2585, 2567-2582, 2567-2584, 2567-2586, 2568-2583, 2568-2585, 2568-2587, 2569-2586, 2569-2588, 2570-2585, 2570-2587, 2570-2589, 2571-2586, 2571-2588, 2571-2590, 2572-2589, 2572-2590, 2572-2591, 2573-2590, 2573-2592, 2574-2590, 2574-2591, 2574-2593, 2575-2590, 2575-2591, 2575-2592, 2575-2594, 2576-2593, 2576-2595, 2577-2594, 2577-2595, 2577-2596, 2578-2594, 2578-2596, 2578-2597, 2579-2598, 2580-2596, 2580-2597, 2580-2598, 2580-2599, 2581-2597, 2581-2598, 2581-2599, 2581-2600, 2582-2598, 2582-2599, 2582-2600, 2582-2601, 2583-2599, 2583-2600, 2583-2601, 2583-2602, 2584-2600, 2584-2601, 2584-2602, 2584-2603, 2585-2601, 2585-2603, 2585-2604, 2586-2601, 2586-2602, 2586-2604, 2586-2605, 2587-2602, 2587-2603, 2587-2605, 2587-2606, 2588-2603, 2588-2604, 2588-2605, 2588-2606, 2588-2607, 2589-2604, 2589-2605, 2589-2606, 2589-2607, 2589-2608, 2590-2605, 2590-2606, 2590-2607, 2590-2608, 2590-2609, 2590-2609, 2591-2607, 2591-2608, 2591-2609, 2591-2610, 2592-2607, 2592-2608, 2592-2609, 2592-2610, 2592-2611, 2593-2608, 2593-2609, 2593-2610, 2593-2612, 2594-2609, 2594-2610, 2594-2611, 2594-2612, 2594-2613, 2595-2610, 2595-2611, 2595-2612, 2595-2613, 2595-2614, 2596-2611, 2596-2612, 2596-2613, 2596-2614, 2596-2615, 2597-2612, 2597-2612, 2597-2613, 2597-2614, 2597-2615, 2597-2616, 2598-2613, 2598-2614, 2598-2615, 2598-2616, 2598-2617, 2599-2614, 2599-2615, 2599-2616, 2599-2617, 2599-2618, 2600-2615, 2600-2616, 2600-2617, 2600-2618, 2600-2619, 2601-2616, 2601-2617, 2601-2618, 2601-2619, 2601-2620, 2602-2617, 2602-2618, 2602-2619, 2602-2620, 2602-2621, 2603-2618, 2603-2619, 2603-2620, 2603-2621, 2603-2622, 2604-2619, 2604-2620, 2604-2621, 2604-2622, 2604-2623, 2605-2620, 2605-2621, 2605-2622, 2605-2623, 2605-2624, 2606-2621, 2606-2622, 2606-2623, 2606-2624, 2606-2625, 2607-2622, 2607-2623, 2607-2624, 2607-2625, 2607-2626, 2608-2623, 2608-2624, 2608-2625, 2608-2626, 2608-2627, 2609-2624, 2609-2625, 2609-2626, 2609-2627, 2609-2628, 2610-2625, 2610-2626, 2610-2627, 2610-2628, 2610-2629, 2611-2626, 2611-2627, 2611-2628, 2611-2629, 2611-2630, 2612-2627, 2612-2628, 2612-2629, 2612-2630, 2612-2631, 2613-2628, 2613-2629, 2613-2630, 2613-2631, 2614-2629, 2614-2630, 2614-2631, 2615-2630, 2615-2631, or 2616-2631 of SEQ ID NO: 1, and wherein said modified oligonucleotide is at least 85%, at least 90%, at least 95%, or 100% complementary to SEQ ID NO: 1.

Certain embodiments provide a compound comprising a modified oligonucleotide and a conjugate group, wherein the modified oligonucleotide consists of 10 to 30 linked nucleosides having a nucleobase sequence comprising a portion of at least 8 contiguous nucleobases complementary to an equal length portion of nucleobases 30-49, 48-63, 150-169, 151-170, 152-171, 154-169, 154-173, 156-171, 156-175, 157-176, 158-173, 158-177, 480-499, 600-619, 638-657, 644-663, 738-757, 1089-1108, 1135-1154, 1141-1160, 1147-1166, 1150-1169, 1153-1172, 1159-1178, 1162-1181, 1165-1184, 1171-1186, 1171-1190, 1173-1188, 1173-1192, 1175-1190, 1175-1194, 1177-1196, 1183-1202, 1208-1227, 1235-1254, 1298-1317, 1304-1323, 1310-1329, 1316-1335, 1319-1338, 1322-1341, 1328-1347, 1349-1368, 1355-1374, 1393-1412, 1396-1415, 1399-1418, 1405-1424, 1421-1440, 1621-1640, 1646-1665, 1646-1665, 1647-1666, 1689-1708, 1749-1768, 1763-1782, 1912-1931, 2073-2092, 2085-2104, 2166-2185, 2172-2191, 2189-2208, 2191-2210, 2193-2212, 2195-2210, 2195-2214, 2196-2215, 2197-2212, 2197-2216, 2202-2221, 2223-2238, 2223-2242, 2225-2240, 2226-2245, 2227-2242, 2227-2246, 2238-2257, 2241-2260, 2267-2286, 2361-2380, 2388-2407, 2397-2416, 2448-2467, 2453-2472, 2455-2474, 2457-2472, 2457-2476, 2459-2474, 2459-2478, 2461-2476, 2461-2480, 2532-2551, 2550-2569, 2551-2566, 2551-2570, 2552-2568, 2552-2570, 2552-2571, 2553-2568, 2553-2570, 2553-2571, 2553-2572, 2554-2571, 2554-2572, 2554-2573, 2555-2570, 2555-2572, 2555-2574, 2556-2573, 2556-2574, 2556-2575, 2557-2573, 2557-2574, 2557-2575, 2557-2576, 2558-2575, 2558-2576, 2558-2577, 2559-2576, 2559-2577, 2559-2578, 2560-2577, 2560-2578, 2560-2579, 2561-2576, 2561-2578, 2561-2579, 2561-2580, 2562-2577, 2562-2579, 2562-2581, 2563-2578, 2563-2580, 2563-2582, 2564-2581, 2564-2583, 2565-2584, 2566-2583, 2566-2585, 2567-2582, 2567-2584, 2567-2586, 2568-2583, 2568-2585, 2568-2587, 2569-2586, 2569-2588, 2570-2585, 2570-2587, 2570-2589, 2571-2586, 2571-2588, 2571-2590, 2572-2589, 2572-2590, 2572-2591, 2573-2590, 2573-2592, 2574-2590, 2574-2591, 2574-2593, 2575-2590, 2575-2591, 2575-2592, 2575-2594, 2576-2593, 2576-2595, 2577-2594, 2577-2595, 2577-2596, 2578-2594, 2578-2596, 2578-2597, 2579-2598, 2580-2596, 2580-2597, 2580-2598, 2580-2599, 2581-2597, 2581-2598, 2581-2599, 2581-2600, 2582-2598, 2582-2599, 2582-2600, 2582-2601, 2583-2599, 2583-2600, 2583-2601, 2584-2600, 2584-2601, 2584-2602, 2584-2603, 2585-2601, 2585-2603, 2585-2604, 2586-2601, 2586-2602, 2586-2604, 2586-2605, 2587-2602, 2587-2603, 2587-2605, 2587-2606, 2588-2603, 2588-2604, 2588-2605, 2588-2606, 2588-2607, 2589-2604, 2589-2605, 2589-2606, 2589-2607, 2589-2608, 2590-2605, 2590-2606, 2590-2607, 2590-2608, 2590-2609, 2591-2607, 2591-2608, 2591-2609, 2591-2610, 2592-2607, 2592-2608, 2592-2609, 2592-2610, 2592-2611, 2593-2608, 2593-2609, 2593-2610, 2593-2612, 2594-2609, 2594-2610, 2594-2611, 2594-2612, 2594-2613, 2595-2610, 2595-2611, 2595-2612, 2595-2613, 2595-2614, 2596-2611, 2596-2612, 2596-2613, 2596-2614, 2596-2615, 2597-2612, 2597-2613, 2597-2614, 2597-2615, 2597-2616, 2598-2613, 2598-2614, 2598-2615, 2598-2616, 2598-2617, 2599-2614, 2599-2615, 2599-2616, 2599-2617, 2599-2618, 2600-2615, 2600-2616, 2600-2617, 2600-2618, 2600-2619, 2601-2616, 2601-2617, 2601-2618, 2601-2619, 2601-2620, 2602-2617, 2602-2618, 2602-2619, 2602-2620, 2602-2621, 2603-2618, 2603-2619, 2603-2620, 2603-2621, 2603-2622, 2604-2619, 2604-2620, 2604-2621, 2604-2622, 2604-2623, 2605-2620, 2605-2621, 2605-2622, 2605-2623, 2605-2624, 2606-2621, 2606-2622, 2606-2623, 2606-2624, 2606-2625, 2607-2622, 2607-2623, 2607-2624, 2607-2625, 2607-2626, 2608-2623, 2608-2624, 2608-2625, 2608-2626, 2608-2627, 2609-2624, 2609-2625, 2609-2626, 2609-2627, 2609-2628, 2610-2625, 2610-2626, 2610-2627, 2610-2628, 2610-2629, 2611-2626, 2611-2627, 2611-2628, 2611-2629, 2611-2630, 2612-2627, 2612-2628, 2612-2629, 2612-2630, 2612-2631, 2613-2628, 2613-2629, 2613-2630, 2613-2631, 2614-2629, 2614-2630, 2614-2631, 2615-2630, 2615-2631, or 2616-2631 of SEQ ID NO:1, and wherein the nucleobase sequence of the modified oligonucleotide is at least 85%, at least 90%, at least 95%, or 100% complementary to SEQ ID NO: 1.

Certain embodiments provide a compound comprising a modified oligonucleotide and a conjugate group, wherein the modified oligonucleotide consists of 10 to 30 linked nucleosides complementary within nucleobases 1608-1627, 1685-1704, 1686-1705, 1751-1770, 1769-1784, 1871-1890, 1872-1891, 1873-1892, 1875-1890, 1875-1894, 1877-1892, 1877-1896, 1878-1897, 1879-1894, 1879-1898, 2288-2307, 2808-2827, 2846-2865, 2852-2871, 2946-2965, 3773-3792, 3819-3838, 3825-3844, 3831-3850, 3834-3853, 3837-3856, 3843-3862, 4151-4166, 4151-4170, 4153-4172, 4159-4178, 4184-4203, 4211-4230, 4609-4628, 4612-4631, 4615-4634, 4621-4640, 4642-4661, 4648-4667, 4686-4705, 4689-4708, 4692-4711, 4698-4717, 4714-4733, 5270-5289, 5295-5314, 5296-5315, 5830-5849, 5890-5909, 5904-5923, 6406-6425, 6662-6681, 6674-6693, 6954-6973, 6960-6979, 6977-6996, 6979-6998, 6981-7000, 6983-6998, 6983-7002, 6984-7003, 6985-7000, 6985-7004, 6990-7009, 7122-7141, 7125-7144, 7151-7170, 7353-7372, 7362-7381, 7683-7702, 7688-7707, 7690-7709, 7692-7707, 7692-7711, 7694-7709, 7694-7713, 7696-7711, 7696-7715, 7767-7786, 7785-7804, 7786-7801, 7787-7803, 7787-7805, 7787-7806, 7788-7803, 7788-7805, 7788-7806, 7788-7807, 7789-7806, 7789-7807, 7789-7808, 7790-7805, 7790-7807, 7790-7809, 7791-7808, 7791-7809, 7791-7810, 7792-7808, 7792-7809, 7792-7810, 7792-7811, 7793-7810, 7793-7811, 7793-7812, 7794-7811, 7794-7812, 7794-7813, 7795-7812, 7795-7813, 7795-7814, 7796-7811, 7796-7813, 7796-7814, 7796-7815, 7797-7812, 7797-7814, 7797-7816, 7798-7813, 7798-7815, 7798-7817, 7799-7816, 7799-7818, 7800-7819, 7801-7818, 7801-7820, 7802-7817, 7802-7819, 7802-7821, 7803-7818, 7803-7820, 7803-7822, 7804-7821, 7804-7823, 7805-7820, 7805-7822, 7805-7824, 7806-7821, 7806-7823, 7806-7825, 7807-7824, 7807-7825, 7807-7826, 7808-7825, 7808-7827, 7809-7825, 7809-7826, 7809-7828, 7810-7825, 7810-7826, 7810-7827, 7810-7829, 7811-7828, 7811-7830, 7812-7829, 7812-7830, 7812-7831, 7813-7829, 7813-7831, 7813-7832, 7814-7833, 7815-7831, 7815-7832, 7815-7833, 7815-7834, 7816-7832, 7816-7833, 7816-7834, 7816-7835, 7817-7833, 7817-7834, 7817-7835, 7817-7836, 7818-7834, 7818-7835, 7818-7836, 7818-7837, 7819-7835, 7819-7836, 7819-7837, 7819-7838, 7820-7836, 7820-7838, 7820-7839, 7821-7836, 7821-7837, 7821-7839, 7821-7840, 7822-7837, 7822-7838, 7822-7840, 7822-7841, 7823-7838, 7823-7839, 7823-7839, 7823-7840, 7823-7841, 7823-7842, 7824-7839, 7824-7840, 7824-7840, 7824-7841, 7824-7842, 7824-7843, 7825-7840, 7825-7841, 7825-7842, 7825-7843, 7825-7844, 7826-7842, 7826-7843, 7826-7844, 7826-7845, 7827-7842, 7827-7843, 7827-7844, 7827-7845, 7827-7846, 7828-7843, 7828-7844, 7828-7845, 7828-7847, 7829-7844, 7829-7845, 7829-7846, 7829-7847, 7829-7848, 7830-7845, 7830-7846, 7830-7847, 7830-7848, 7830-7849, 7831-7846, 7831-7847, 7831-7848, 7831-7849, 7831-7850, 7832-7847, 7832-7848, 7832-7849, 7832-7850, 7832-7851, 7833-7848, 7833-7849, 7833-7850, 7833-7851, 7833-7852, 7834-7849, 7834-7850, 7834-7851, 7834-7852, 7834-7853, 7835-7850, 7835-7851, 7835-7852, 7835-7853, 7835-7854, 7836-7851, 7836-7852, 7836-7853, 7836-7854, 7836-7855, 7837-7852, 7837-7853, 7837-7854, 7837-7855, 7837-7856, 7838-

7853, 7838-7854, 7838-7855, 7838-7856, 7838-7857, 7839-7854, 7839-7855, 7839-7856, 7839-7857, 7839-7858, 7840-7855, 7840-7856, 7840-7857, 7840-7858, 7840-7859, 7841-7856, 7841-7857, 7841-7858, 7841-7859, 7841-7860, 7842-7857, 7842-7858, 7842-7859, 7842-7860, 7842-7861, 7843-7858, 7843-7859, 7843-7860, 7843-7861, 7843-7862, 7844-7859, 7844-7860, 7844-7861, 7844-7862, 7845-7860, 7845-7861, 7845-7862, 7846-7861, or 7846-7862 of SEQ ID NO: 2, and wherein said modified oligonucleotide is at least 85%, at least 90%, at least 95%, or 100% complementary to SEQ ID NO: 2.

Certain embodiments provide a compound comprising a modified oligonucleotide and a conjugate group, wherein the modified oligonucleotide consists of 10 to 30 linked nucleosides having a nucleobase sequence comprising a portion of at least 8 contiguous nucleobases complementary to an equal length portion of nucleobases 1608-1627, 1685-1704, 1686-1705, 1751-1770, 1769-1784, 1871-1890, 1872-1891, 1873-1892, 1875-1890, 1875-1894, 1877-1892, 1877-1896, 1878-1897, 1879-1894, 1879-1898, 2288-2307, 2808-2827, 2846-2865, 2852-2871, 2946-2965, 3773-3792, 3819-3838, 3825-3844, 3831-3850, 3834-3853, 3837-3856, 3843-3862, 4151-4166, 4151-4170, 4153-4172, 4159-4178, 4184-4203, 4211-4230, 4609-4628, 4612-4631, 4615-4634, 4621-4640, 4642-4661, 4648-4667, 4686-4705, 4689-4708, 4692-4711, 4698-4717, 4714-4733, 5270-5289, 5295-5314, 5296-5315, 5830-5849, 5890-5909, 5904-5923, 6406-6425, 6662-6681, 6674-6693, 6954-6973, 6960-6979, 6977-6996, 6979-6998, 6981-7000, 6983-6998, 6983-7002, 6984-7003, 6985-7000, 6985-7004, 6990-7009, 7122-7141, 7125-7144, 7151-7170, 7353-7372, 7362-7381, 7683-7702, 7688-7707, 7690-7709, 7692-7707, 7692-7711, 7694-7709, 7694-7713, 7696-7711, 7696-7715, 7767-7786, 7785-7804, 7786-7801, 7787-7803, 7787-7805, 7787-7806, 7788-7803, 7788-7805, 7788-7806, 7788-7807, 7789-7806, 7789-7807, 7789-7808, 7790-7805, 7790-7807, 7790-7809, 7791-7808, 7791-7809, 7791-7810, 7792-7808, 7792-7809, 7792-7810, 7792-7811, 7793-7810, 7793-7811, 7793-7812, 7794-7811, 7794-7812, 7794-7813, 7795-7812, 7795-7813, 7795-7814, 7796-7811, 7796-7813, 7796-7814, 7796-7815, 7797-7812, 7797-7814, 7797-7816, 7798-7813, 7798-7815, 7798-7817, 7799-7816, 7799-7818, 7800-7819, 7801-7818, 7801-7820, 7802-7817, 7802-7819, 7802-7821, 7803-7818, 7803-7820, 7803-7822, 7804-7821, 7804-7823, 7805-7820, 7805-7822, 7805-7824, 7806-7821, 7806-7823, 7806-7825, 7807-7824, 7807-7825, 7807-7826, 7808-7825, 7808-7827, 7809-7825, 7809-7826, 7809-7828, 7810-7825, 7810-7826, 7810-7827, 7810-7829, 7811-7828, 7811-7830, 7812-7829, 7812-7830, 7812-7831, 7813-7829, 7813-7831, 7813-7832, 7814-7833, 7815-7831, 7815-7832, 7815-7833, 7815-7834, 7816-7832, 7816-7833, 7816-7834, 7816-7835, 7817-7833, 7817-7834, 7817-7835, 7817-7836, 7818-7834, 7818-7835, 7818-7836, 7818-7837, 7819-7835, 7819-7836, 7819-7837, 7819-7838, 7820-7836, 7820-7838, 7820-7839, 7821-7836, 7821-7837, 7821-7839, 7821-7840, 7822-7837, 7822-7838, 7822-7840, 7822-7841, 7823-7838, 7823-7839, 7823-7839, 7823-7840, 7823-7841, 7823-7842, 7824-7839, 7824-7840, 7824-7840, 7824-7841, 7824-7842, 7824-7843, 7825-7840, 7825-7841, 7825-7842, 7825-7843, 7825-7844, 7826-7842, 7826-7843, 7826-7844, 7826-7845, 7827-7842, 7827-7843, 7827-7844, 7827-7845, 7827-7846, 7828-7843, 7828-7844, 7828-7845, 7828-7847, 7829-7844, 7829-7845, 7829-7846, 7829-7847, 7829-7848, 7830-7845, 7830-7846, 7830-7847, 7830-7848, 7830-7849, 7831-7846, 7831-7847, 7831-7848, 7831-7849, 7831-7850, 7832-7847, 7832-7848, 7832-7849, 7832-7850, 7832-7851, 7833-7848, 7833-7849, 7833-7850, 7833-7851, 7833-7852, 7834-7849, 7834-7850, 7834-7851, 7834-7852, 7834-7853, 7835-7850, 7835-7851, 7835-7852, 7835-7853, 7835-7854, 7836-7851, 7836-7852, 7836-7853, 7836-7854, 7836-7855, 7837-7852, 7837-7853, 7837-7854, 7837-7855, 7837-7856, 7838-7853, 7838-7854, 7838-7855, 7838-7856, 7838-7857, 7839-7854, 7839-7855, 7839-7856, 7839-7857, 7839-7858, 7840-7855, 7840-7856, 7840-7857, 7840-7858, 7840-7859, 7841-7856, 7841-7857, 7841-7858, 7841-7859, 7841-7860, 7842-7857, 7842-7858, 7842-7859, 7842-7860, 7842-7861, 7843-7858, 7843-7859, 7843-7860, 7843-7861, 7843-7862, 7844-7859, 7844-7860, 7844-7861, 7844-7862, 7845-7860, 7845-7861, 7845-7862, 7846-7861, and 7846-7862 of SEQ ID NO: 2, and wherein the nucleobase sequence of the modified oligonucleotide is at least 85%, at least 90%, at least 95%, or 100% complementary to SEQ ID NO: 2.

In certain embodiments, antisense compounds or oligonucleotides target a region of a CFB nucleic acid. In certain embodiments, such compounds or oligonucleotides targeted to a region of a CFB nucleic acid have a contiguous nucleobase portion that is complementary to an equal length nucleobase portion of the region. For example, the portion can be at least an 8, 9, 10, 11, 12, 13, 14, 15, or 16 contiguous nucleobase portion complementary to an equal length portion of a region recited herein. In certain embodiments, a compound comprises or consists of a conjugate and a modified oligonucleotide targeting any of the following nucleotide regions of SEQ ID NO: 1: 30-49, 48-63, 150-169, 151-170, 152-171, 154-169, 154-173, 156-171, 156-175, 157-176, 158-173, 158-177, 480-499, 600-619, 638-657, 644-663, 738-757, 1089-1108, 1135-1154, 1141-1160, 1147-1166, 1150-1169, 1153-1172, 1159-1178, 1162-1181, 1165-1184, 1171-1186, 1171-1190, 1173-1188, 1173-1192, 1175-1190, 1175-1194, 1177-1196, 1183-1202, 1208-1227, 1235-1254, 1298-1317, 1304-1323, 1310-1329, 1316-1335, 1319-1338, 1322-1341, 1328-1347, 1349-1368, 1355-1374, 1393-1412, 1396-1415, 1399-1418, 1405-1424, 1421-1440, 1621-1640, 1646-1665, 1646-1665, 1647-1666, 1689-1708, 1749-1768, 1763-1782, 1912-1931, 2073-2092, 2085-2104, 2166-2185, 2172-2191, 2189-2208, 2191-2210, 2193-2212, 2195-2210, 2195-2214, 2196-2215, 2197-2212, 2197-2216, 2202-2221, 2223-2238, 2223-2242, 2225-2240, 2226-2245, 2227-2242, 2227-2246, 2238-2257, 2241-2260, 2267-2286, 2361-2380, 2388-2407, 2397-2416, 2448-2467, 2453-2472, 2455-2474, 2457-2472, 2457-2476, 2459-2474, 2459-2478, 2461-2476, 2461-2480, 2532-2551, 2550-2569, 2551-2566, 2551-2570, 2552-2568, 2552-2570, 2552-2571, 2553-2568, 2553-2570, 2553-2571, 2553-2572, 2554-2571, 2554-2572, 2554-2573, 2555-2570, 2555-2572, 2555-2574, 2556-2573, 2556-2574, 2556-2575, 2557-2573, 2557-2574, 2557-2575, 2557-2576, 2558-2575, 2558-2576, 2558-2577, 2559-2576, 2559-2577, 2559-2578, 2560-2577, 2560-2578, 2560-2579, 2561-2576, 2561-2578, 2561-2579, 2561-2580, 2562-2577, 2562-2579, 2562-2581, 2563-2578, 2563-2580, 2563-2582, 2564-2581, 2564-2583, 2565-2584, 2566-2583, 2566-2585, 2567-2582, 2567-2584, 2567-2586, 2568-2583, 2568-2585, 2568-2587, 2569-2586, 2569-2588, 2570-2585, 2570-2587, 2570-2589, 2571-2586, 2571-2588, 2571-2590, 2572-2589, 2572-2590, 2572-2591, 2573-2590, 2573-2592, 2574-2590, 2574-2591, 2574-2593, 2575-2590, 2575-2591, 2575-2592, 2575-2594, 2576-2593, 2576-2595, 2577-2594, 2577-2595, 2577-2596, 2578-2594, 2578-2596, 2578-2597, 2579-2598, 2580-2596, 2580-2597, 2580-2598, 2580-2599, 2581-2597, 2581-2598, 2581-2599, 2581-2600, 2582-2598, 2582-2599, 2582-2600, 2582-2601, 2583-2599, 2583-2600, 2583-2601, 2583-2602, 2584-2600, 2584-2601, 2584-2602, 2584-2603, 2585-2601, 2585-2603, 2585-2604, 2586-2601, 2586-2602, 2586-2604, 2586-2605, 2587-2602, 2587-2603, 2587-2605, 2587-2606, 2588-2603, 2588-2604, 2588-2605, 2588-2606, 2588-2607, 2589-2604, 2589-2605, 2589-2606, 2589-2607, 2589-2608, 2590-2605, 2590-2606, 2590-2607, 2590-2608, 2590-2609, 2590-2609, 2591-2607, 2591-2608, 2591-2609, 2591-2610, 2592-2607, 2592-2608, 2592-2609, 2592-2610, 2592-2611, 2593-2608, 2593-2609, 2593-2610, 2593-2612, 2594-2609, 2594-2610, 2594-2611, 2594-2612, 2594-2613, 2595-2610, 2595-2611, 2595-2612, 2595-2613, 2595-2614, 2596-2611, 2596-2612, 2596-2613, 2596-2614, 2596-2615, 2597-2612, 2597-2612, 2597-2613, 2597-2614, 2597-2615, 2597-2616, 2598-2613, 2598-2614, 2598-2615, 2598-2616, 2598-2617, 2599-2614, 2599-2615, 2599-2616, 2599-2617, 2599-2618, 2600-2615, 2600-2616, 2600-2617, 2600-2618, 2600-2619, 2601-2616, 2601-2617, 2601-2618, 2601-2619, 2601-2620, 2602-2617, 2602-2618, 2602-2619, 2602-2620, 2602-2621, 2603-2618, 2603-2619, 2603-2620, 2603-2621, 2603-2622, 2604-2619, 2604-2620, 2604-2621, 2604-2622, 2604-2623, 2605-2620, 2605-2621, 2605-2622, 2605-2623, 2605-2624, 2606-2621, 2606-2622, 2606-2623, 2606-2624, 2606-2625, 2607-2622, 2607-2623, 2607-2624, 2607-2625, 2607-2626, 2608-2623, 2608-2624, 2608-2625, 2608-2626, 2608-2627, 2609-2624, 2609-2625, 2609-2626, 2609-2627, 2609-2628, 2610-2625, 2610-2626, 2610-2627, 2610-2628, 2610-2629, 2611-2626, 2611-2627, 2611-2628, 2611-2629, 2611-2630, 2612-2627, 2612-2628, 2612-2629, 2612-2630, 2612-2631, 2613-2628, 2613-2629, 2613-2630, 2613-2631, 2614-2629, 2614-2630, 2614-2631, 2615-2630, 2615-2631, and 2616-2631.

In certain embodiments, antisense compounds or oligonucleotides target a region of a CFB nucleic acid. In certain embodiments, such compounds or oligonucleotides targeted to a region of a CFB nucleic acid have a contiguous nucleobase portion that is complementary to an equal length nucleobase portion of the region. For example, the portion can be at least an 8, 9, 10, 11, 12, 13, 14, 15, or 16 contiguous nucleobase portion complementary to an equal length portion of a region recited herein. In certain embodiments, a compound comprises or consists of a conjugate and a modified oligonucleotide targeting the following nucleotide regions of SEQ ID NO: 2: 1608-1627, 1685-1704, 1686-1705, 1751-1770, 1769-1784, 1871-1890, 1872-1891, 1873-1892, 1875-1890, 1875-1894, 1877-1892, 1877-1896, 1878-1897, 1879-1894, 1879-1898, 2288-2307, 2808-2827, 2846-2865, 2852-2871, 2946-2965, 3773-3792, 3819-3838, 3825-3844, 3831-3850, 3834-3853, 3837-3856, 3843-3862, 4151-4166, 4151-4170, 4153-4172, 4159-4178, 4184-4203, 4211-4230, 4609-4628, 4612-4631, 4615-4634, 4621-4640, 4642-4661, 4648-4667, 4686-4705, 4689-4708, 4692-4711, 4698-4717, 4714-4733, 5270-5289, 5295-5314, 5296-5315, 5830-5849, 5890-5909, 5904-5923, 6406-6425, 6662-6681, 6674-6693, 6954-6973, 6960-6979, 6977-6996, 6979-6998, 6981-7000, 6983-6998, 6983-7002, 6984-7003, 6985-7000, 6985-7004, 6990-7009, 7122-7141, 7125-7144, 7151-7170, 7353-7372, 7362-7381, 7683-7702, 7688-7707, 7690-7709, 7692-7707, 7692-7711, 7694-7709, 7694-7713, 7696-7711, 7696-7715, 7767-7786, 7785-7804, 7786-7801, 7787-7803, 7787-7805, 7787-7806, 7788-7803, 7788-7805, 7788-7806, 7788-7807, 7789-7806, 7789-7807, 7789-7808, 7790-7805, 7790-7807, 7790-7809, 7791-7808, 7791-7809, 7791-7810, 7792-7808, 7792-7809, 7792-7810, 7792-7811, 7793-7810, 7793-7811, 7793-7812, 7794-7811, 7794-7812, 7794-7813, 7795-7812, 7795-7813, 7795-7814, 7796-7811, 7796-7813, 7796-7814, 7796-7815, 7797-7812, 7797-7814, 7797-7816, 7798-7813, 7798-7815, 7798-7817, 7799-7816, 7799-7818, 7800-7819, 7801-7818, 7801-7820, 7802-7817, 7802-7819, 7802-7821, 7803-7818, 7803-7820, 7803-7822, 7804-7821, 7804-7823, 7805-7820, 7805-7822, 7805-7824, 7806-7821, 7806-7823, 7806-7825, 7807-7824, 7807-7825, 7807-7826, 7808-7825, 7808-7827, 7809-7825, 7809-7826, 7809-7828, 7810-7825, 7810-7826, 7810-7827, 7810-7829, 7811-7828, 7811-7830, 7812-7829, 7812-7830, 7812-7831, 7813-7829, 7813-7831, 7813-7832, 7814-7833, 7815-7831, 7815-7832, 7815-7833, 7815-7834, 7816-7832, 7816-7833, 7816-7834, 7816-7835, 7817-7833, 7817-7834, 7817-7835, 7817-7836, 7818-7834, 7818-7835, 7818-7836, 7818-7837, 7819-7835, 7819-7836, 7819-7837, 7819-7838, 7820-7836, 7820-7838, 7820-7839, 7821-7836, 7821-7837, 7821-7839, 7821-7840, 7822-7837, 7822-7838, 7822-7840, 7822-7841, 7823-7838, 7823-7839, 7823-7839, 7823-7840, 7823-7841, 7823-7842, 7824-7839, 7824-7840, 7824-7840, 7824-7841, 7824-7842, 7824-7843, 7825-7840, 7825-7841, 7825-7842, 7825-7843, 7825-7844, 7826-7842, 7826-7843, 7826-7844, 7826-7845, 7827-7842, 7827-7843, 7827-7844, 7827-7845, 7827-7846, 7828-7843, 7828-7844, 7828-7845, 7828-7847, 7829-7844, 7829-7845, 7829-7846, 7829-7847, 7829-7848, 7830-7845, 7830-7846, 7830-7847, 7830-7848, 7830-7849, 7831-7846, 7831-7847, 7831-7848, 7831-7849, 7831-7850, 7832-7847, 7832-7848, 7832-7849, 7832-7850, 7832-7851, 7833-7848, 7833-7849, 7833-7850, 7833-7851, 7833-7852, 7834-7849, 7834-7850, 7834-7851, 7834-7852, 7834-7853, 7835-7850, 7835-7851, 7835-7852, 7835-7853, 7835-7854, 7836-7851, 7836-7852, 7836-7853, 7836-7854, 7836-7855, 7837-7852, 7837-7853, 7837-7854, 7837-7855, 7837-7856, 7838-7853, 7838-7854, 7838-7855, 7838-7856, 7838-7857, 7839-7854, 7839-7855, 7839-7856, 7839-7857, 7839-7858, 7840-7855, 7840-7856, 7840-7857, 7840-7858, 7840-7859, 7841-7856, 7841-7857, 7841-7858, 7841-7859, 7841-7860, 7842-7857, 7842-7858, 7842-7859, 7842-7860, 7842-7861, 7843-7858, 7843-7859, 7843-7860, 7843-7861, 7843-7862, 7844-7859, 7844-7860, 7844-7861, 7844-7862, 7845-7860, 7845-7861, 7845-7862, 7846-7861, and 7846-7862.

In certain embodiments, a compound comprises or consists of a conjugate and a modified oligonucleotide targeting the 3'UTR of a CFB nucleic acid. In certain aspects, the modified oligonucleotide targets within nucleotides 2574-2626 of a CFB nucleic acid having the nucleobase sequence of SEQ ID NO: 1. In certain aspects, the modified oligonucleotide has at least an 8, 9, 10, 11, 12, 13, 14, 15, or 16 contiguous nucleobase portion complementary to an equal length portion within nucleotides 2574-2626 of a CFB nucleic acid having the nucleobase sequence of SEQ ID NO: 1.

In certain embodiments, a compound comprises or consists of a conjugate and a modified oligonucleotide targeting a region of a CFB nucleic acid having the nucleobase sequence of SEQ ID NO: 1 within nucleobases 2457-2631, 2457-2472, 2457-2474, 2457-2476, 2457-2566, 2457-2570, 2457-2571, 2457-2572, 2457-2573, 2457-2574, 2457-2575, 2457-2576, 2457-2577, 2457-2578, 2457-2579, 2457-2580, 2457-2581, 2457-2582, 2457-2583, 2457-2584, 2457-2585, 2457-2586, 2457-2587, 2457-2588, 2457-2589, 2457-2590, 2457-2591, 2457-2592, 2457-2593, 2457-2594, 2457-2595, 2457-2596, 2457-2597, 2457-2598, 2457-2599, 2457-2600, 2457-2601, 2457-2602, 2457-2603, 2457-2604, 2457-2605, 2457-2606, 2457-2607, 2457-2608, 2457-2609, 2457-2610, 2457-2611, 2457-2612, 2457-2613, 2457-2614, 2457-2615, 2457-2616, 2457-2617, 2457-2618, 2457-2619, 2457-2620, 2457-2621, 2457-2622, 2457-2623, 2457-2624, 2457-2625, 2457-2626, 2457-2627, 2457-2628, 2457-2629, 2457-2630, 2457-2631, 2459-2474, 2459-2476, 2459-2566, 2459-2570, 2459-2571, 2459-2572, 2459-2573, 2459-2574, 2459-2575, 2459-2576, 2459-2577, 2459-2578, 2459-2579, 2459-2580, 2459-2581, 2459-2582, 2459-2583, 2459-2584, 2459-2585, 2459-2586, 2459-2587, 2459-2588, 2459-2589, 2459-2590, 2459-2591, 2459-2592, 2459-2593, 2459-2594, 2459-2595, 2459-2596, 2459-2597, 2459-2598, 2459-2599, 2459-2600, 2459-2601, 2459-2602, 2459-2603, 2459-2604, 2459-2605, 2459-2606, 2459-2607, 2459-2608, 2459-2609, 2459-2610, 2459-2611, 2459-2612, 2459-2613, 2459-2614, 2459-2615, 2459-2616, 2459-2617, 2459-2618, 2459-2619, 2459-2620, 2459-2621, 2459-2622, 2459-2623, 2459-2624, 2459-2625, 2459-2626, 2459-2627, 2459-2628, 2459-2629, 2459-2630, 2459-2631, 2461-2476, 2461-2566, 2461-2570, 2461-2571, 2461-2572, 2461-2573, 2461-2574, 2461-2575, 2461-2576, 2461-2577, 2461-2578, 2461-2579, 2461-2580, 2461-2581, 2461-2582, 2461-2583, 2461-2584, 2461-2585, 2461-2586, 2461-2587, 2461-2588, 2461-2589, 2461-2590, 2461-2591, 2461-2592, 2461-2593, 2461-2594, 2461-2595, 2461-2596, 2461-2597, 2461-2598, 2461-2599, 2461-2600, 2461-2601, 2461-2602, 2461-2603, 2461-2604, 2461-2605, 2461-2606, 2461-2607, 2461-2608, 2461-2609, 2461-2610, 2461-2611, 2461-2612, 2461-2613, 2461-2614, 2461-2615, 2461-2616, 2461-2617, 2461-2618, 2461-2619, 2461-2620, 2461-2621, 2461-2622, 2461-2623, 2461-2624, 2461-2625, 2461-2626, 2461-2627, 2461-2628, 2461-2629, 2461-2630, 2461-2631, 2551-2566, 2551-2570, 2551-2571, 2551-2572, 2551-2573, 2551-2574, 2551-2575, 2551-2576, 2551-2577, 2551-2578, 2551-2579, 2551-2580, 2551-2581, 2551-2582, 2551-2583, 2551-2584, 2551-2585, 2551-2586, 2551-2587, 2551-2588, 2551-2589, 2551-2590, 2551-2591, 2551-2592, 2551-2593, 2551-2594, 2551-2595, 2551-2596, 2551-2597, 2551-2598, 2551-2599, 2551-2600, 2551-2601, 2551-2602, 2551-2603, 2551-2604, 2551-2605, 2551-2606, 2551-2607, 2551-2608, 2551-2609, 2551-2610, 2551-2611, 2551-2612, 2551-2613, 2551-2614, 2551-2615, 2551-2616, 2551-2617, 2551-2618, 2551-2619, 2551-2620, 2551-2621, 2551-2622, 2551-2623, 2551-2624, 2551-2625, 2551-2626, 2551-2627, 2551-2628, 2551-2629, 2551-2630, 2551-2631, 2553-2570, 2553-2571, 2553-2572, 2553-2573, 2553-2574, 2553-2575, 2553-2576, 2553-2577, 2553-2578, 2553-2579, 2553-2580, 2553-2581, 2553-2582, 2553-2583, 2553-2584, 2553-2585, 2553-2586, 2553-2587, 2553-2588, 2553-2589, 2553-2590, 2553-2591, 2553-2592, 2553-2593, 2553-2594, 2553-2595, 2553-2596, 2553-2597, 2553-2598, 2553-2599, 2553-2600, 2553-2601, 2553-2602, 2553-2603, 2553-2604, 2553-2605, 2553-2606, 2553-2607, 2553-2608, 2553-2609, 2553-2610, 2553-2611, 2553-2612, 2553-2613, 2553-2614, 2553-2615, 2553-2616, 2553-2617, 2553-2618, 2553-2619, 2553-2620, 2553-2621, 2553-2622, 2553-2623, 2553-2624, 2553-2625, 2553-2626, 2553-2627, 2553-2628, 2553-2629, 2553-2630, 2553-2631, 2554-2573, 2554-2574, 2554-2575, 2554-2576, 2554-2577, 2554-2578, 2554-2579, 2554-2580, 2554-2581, 2554-2582, 2554-2583, 2554-2584, 2554-2585, 2554-2586, 2554-2587, 2554-2588, 2554-2589, 2554-2590, 2554-2591, 2554-2592, 2554-2593, 2554-2594, 2554-2595, 2554-2596, 2554-2597, 2554-2598, 2554-2599, 2554-2600, 2554-2601, 2554-2602, 2554-2603, 2554-2604, 2554-2605, 2554-2606, 2554-2607, 2554-2608, 2554-2609, 2554-2610, 2554-2611, 2554-2612, 2554-2613, 2554-2614, 2554-2615, 2554-2616, 2554-2617, 2554-2618, 2554-2619, 2554-2620, 2554-2621, 2554-2622, 2554-2623, 2554-2624, 2554-2625, 2554-2626, 2554-2627, 2554-2628, 2554-2629, 2554-2630, 2554-2631, 2555-2572, 2555-2573, 2555-2574, 2555-2575, 2555-2576, 2555-2577, 2555-2578, 2555-2579, 2555-2580, 2555-2581, 2555-2582, 2555-2583, 2555-2584, 2555-2585, 2555-2586, 2555-2587, 2555-2588, 2555-2589, 2555-2590, 2555-2591, 2555-2592, 2555-2593, 2555-2594, 2555-2595, 2555-2596, 2555-2597, 2555-2598, 2555-2599, 2555-2600, 2555-2601, 2555-2602, 2555-2603, 2555-2604, 2555-2605, 2555-2606, 2555-2607, 2555-2608, 2555-2609, 2555-2610, 2555-2611, 2555-2612, 2555-2613, 2555-2614, 2555-2615, 2555-2616, 2555-2617, 2555-2618, 2555-2619, 2555-2620, 2555-2621, 2555-2622, 2555-2623, 2555-2624, 2555-2625, 2555-2626, 2555-2627, 2555-2628, 2555-2629, 2555-2630, 2555-2631, 2556-2573, 2556-2574, 2556-2575, 2556-2576, 2556-2577, 2556-2578, 2556-2579, 2556-2580, 2556-2581, 2556-2582, 2556-2583, 2556-2584, 2556-2585, 2556-2586, 2556-2587, 2556-2588, 2556-2589, 2556-2590, 2556-2591, 2556-2592, 2556-2593, 2556-2594, 2556-2595, 2556-2596, 2556-2597, 2556-2598, 2556-2599, 2556-2600, 2556-2601, 2556-2602, 2556-2603, 2556-2604, 2556-2605, 2556-2606, 2556-2607, 2556-2608, 2556-2609, 2556-2610, 2556-2611, 2556-2612, 2556-2613, 2556-2614, 2556-2615, 2556-2616, 2556-2617, 2556-2618, 2556-2619, 2556-2620, 2556-2621, 2556-2622, 2556-2623, 2556-2624, 2556-2625, 2556-2626, 2556-2627, 2556-2628, 2556-2629, 2556-2630, 2556-2631, 2557-2574, 2557-2575, 2557-2576, 2557-2577, 2557-2578, 2557-2579, 2557-2580, 2557-2581, 2557-2582, 2557-2583, 2557-2584, 2557-2585, 2557-2586, 2557-2587, 2557-2588, 2557-2589, 2557-2590, 2557-2591, 2557-2592, 2557-2593, 2557-2594, 2557-2595, 2557-2596, 2557-2597, 2557-2598, 2557-2599, 2557-2600, 2557-2601, 2557-2602, 2557-2603, 2557-2604, 2557-2605, 2557-2606, 2557-2607, 2557-2608, 2557-2609, 2557-2610, 2557-2611, 2557-2612, 2557-2613, 2557-2614, 2557-2615, 2557-2616, 2557-2617, 2557-2618, 2557-2619, 2557-2620, 2557-2621, 2557-2622, 2557-2623, 2557-2624, 2557-2625, 2557-2626, 2557-2627, 2557-2628, 2557-2629, 2557-2630, 2557-2631, 2558-2575, 2558-2576, 2558-2577, 2558-2578, 2558-2579, 2558-2580, 2558-2581, 2558-2582, 2558-2583, 2558-2584, 2558-2585, 2558-2586, 2558-2587, 2558-2588, 2558-2589, 2558-2590, 2558-2591, 2558-2592, 2558-2593, 2558-2594, 2558-2595, 2558-2596, 2558-2597, 2558-2598, 2558-2599, 2558-2600, 2558-2601, 2558-2602, 2558-2603, 2558-2604, 2558-2605, 2558-2606, 2558-2607, 2558-2608, 2558-2609, 2558-2610, 2558-2611, 2558-2612, 2558-2613, 2558-2614, 2558-2615, 2558-2616, 2558-2617, 2558-2618, 2558-2619, 2558-2620, 2558-2621, 2558-2622, 2558-2623, 2558-2624, 2558-2625, 2558-2626, 2558-2627, 2558-2628, 2558-2629, 2558-2630, 2558-2631, 2559-2576, 2559-2577, 2559-2578, 2559-2579, 2559-2580, 2559-2581, 2559-2582, 2559-2583, 2559-2584, 2559-2585, 2559-2586, 2559-2587, 2559-2588, 2559-2589, 2559-2590, 2559-2591, 2559-2592, 2559-2593, 2559-2594, 2559-2595, 2559-2596, 2559-2597, 2559-2598, 2559-2599, 2559-2600, 2559-2601, 2559-2602, 2559-2603, 2559-2604, 2559-2605, 2559-2606, 2559-2607, 2559-2608, 2559-2609, 2559-2610, 2559-2611, 2559-2612, 2559-2613, 2559-2614, 2559-2615, 2559-2616, 2559-2617, 2559-2618, 2559-2619, 2559-2620, 2559-2621, 2559-2622, 2559-2623, 2559-2624, 2559-2625, 2559-2626, 2559-2627, 2559-2628, 2559-2629, 2559-2630, 2559-2631, 2560-2577, 2560-2578, 2560-2579, 2560-2580, 2560-2581, 2560-2582, 2560-2583, 2560-2584, 2560-2585, 2560-2586, 2560-2587, 2560-2588, 2560-2589, 2560-2590, 2560-2591, 2560-2592, 2560-2593, 2560-2594, 2560-2595, 2560-2596, 2560-2597, 2560-2598, 2560-2599, 2560-2600, 2560-2601, 2560-2602, 2560-2603, 2560-2604, 2560-2605, 2560-2606, 2560-2607, 2560-2608, 2560-2609, 2560-2610, 2560-2611, 2560-2612, 2560-2613, 2560-2614, 2560-2615, 2560-2616, 2560-2617, 2560-2618, 2560-2619, 2560-2620, 2560-2621, 2560-2622, 2560-2623, 2560-2624, 2560-2625, 2560-2626, 2560-2627, 2560-2628, 2560-2629, 2560-2630, 2560-2631, 2561-2578, 2561-2579, 2561-2580, 2561-2581, 2561-2582, 2561-2583, 2561-2584, 2561-2585, 2561-2586, 2561-2587, 2561-2588, 2561-2589, 2561-2590, 2561-2591, 2561-2592, 2561-2593, 2561-2594, 2561-2595, 2561-2596, 2561-2597, 2561-2598, 2561-2599, 2561-2600, 2561-2601, 2561-2602, 2561-2603, 2561-2604, 2561-2605, 2561-2606, 2561-2607, 2561-2608, 2561-2609, 2561-2610, 2561-2611, 2561-2612, 2561-2613, 2561-2614, 2561-2615, 2561-2616, 2561-2617, 2561-2618, 2561-2619, 2561-2620, 2561-2621, 2561-2622, 2561-2623, 2561-2624, 2561-2625, 2561-2626, 2561-2627, 2561-2628, 2561-2629, 2561-2630, 2561-2631, 2562-2577, 2562-2578, 2562-2579, 2562-2580, 2562-2581, 2562-2582, 2562-2583, 2562-2584, 2562-2585, 2562-2586, 2562-2587, 2562-2588, 2562-2589, 2562-2590, 2562-2591, 2562-2592, 2562-2593, 2562-2594, 2562-2595, 2562-2596, 2562-2597, 2562-2598, 2562-2599, 2562-2600, 2562-2601, 2562-2602, 2562-2603, 2562-2604, 2562-2605, 2562-2606, 2562-2607, 2562-2608, 2562-2609, 2562-2610, 2562-2611, 2562-2612, 2562-2613, 2562-2614, 2562-2615, 2562-2616, 2562-2617, 2562-2618, 2562-2619, 2562-2620, 2562-2621, 2562-2622, 2562-2623, 2562-2624, 2562-2625, 2562-2626, 2562-2627, 2562-2628, 2562-2629, 2562-2630, 2562-2631, 2563-2580, 2563-2581, 2563-2582, 2563-2583, 2563-2584, 2563-2585, 2563-2586, 2563-2587, 2563-2588, 2563-2589, 2563-2590, 2563-2591, 2563-2592, 2563-2593, 2563-2594, 2563-2595, 2563-2596, 2563-2597, 2563-2598, 2563-2599, 2563-2600, 2563-2601, 2563-2602, 2563-2603, 2563-2604, 2563-2605, 2563-2606, 2563-2607, 2563-2608, 2563-2609, 2563-2610, 2563-2611, 2563-2612, 2563-2613, 2563-2614, 2563-2615, 2563-2616, 2563-2617, 2563-2618, 2563-2619, 2563-2620, 2563-2621, 2563-2622, 2563-2623, 2563-2624, 2563-2625, 2563-2626, 2563-2627, 2563-2628, 2563-2629, 2563-2630, 2563-2631, 2564-2581, 2564-2582, 2564-2583, 2564-2584, 2564-2585, 2564-2586, 2564-2587, 2564-2588, 2564-2589, 2564-2590, 2564-2591, 2564-2592, 2564-2593, 2564-2594, 2564-2595, 2564-2596, 2564-2597, 2564-2598, 2564-2599, 2564-2600, 2564-2601, 2564-2602, 2564-2603, 2564-2604, 2564-2605, 2564-2606, 2564-2607, 2564-2608, 2564-2609, 2564-2610, 2564-2611, 2564-2612, 2564-2613, 2564-2614, 2564-2615, 2564-2616, 2564-2617, 2564-2618, 2564-2619, 2564-2620, 2564-2621, 2564-2622, 2564-2623, 2564-2624, 2564-2625, 2564-2626, 2564-2627, 2564-2628, 2564-2629, 2564-2630, 2564-2631, 2565-2584, 2565-2585, 2565-2586, 2565-2587, 2565-2588, 2565-2589, 2565-2590, 2565-2591, 2565-2592, 2565-2593, 2565-2594, 2565-2595, 2565-2596, 2565-2597, 2565-2598, 2565-2599, 2565-2600, 2565-2601, 2565-2602, 2565-2603, 2565-2604, 2565-2605, 2565-2606, 2565-2607, 2565-2608, 2565-2609, 2565-2610, 2565-2611, 2565-2612, 2565-2613, 2565-2614, 2565-2615, 2565-2616, 2565-2617, 2565-2618, 2565-2619, 2565-2620, 2565-2621, 2565-2622, 2565-2623, 2565-2624, 2565-2625, 2565-2626, 2565-2627, 2565-2628, 2565-2629, 2565-2630, 2565-2631, 2566-2583, 2566-2584, 2566-2585, 2566-2586, 2566-2587, 2566-2588, 2566-2589, 2566-2590, 2566-2591, 2566-2592, 2566-2593, 2566-2594, 2566-2595, 2566-2596, 2566-2597, 2566-2598, 2566-2599, 2566-2600, 2566-2601, 2566-2602, 2566-2603, 2566-2604, 2566-2605, 2566-2606, 2566-2607, 2566-2608, 2566-2609, 2566-2610, 2566-2611, 2566-2612, 2566-2613, 2566-2614, 2566-2615, 2566-2616, 2566-2617, 2566-2618, 2566-2619, 2566-2620, 2566-2621, 2566-2622, 2566-2623, 2566-2624, 2566-2625, 2566-2626, 2566-2627, 2566-2628, 2566-2629, 2566-2630, 2566-2631, 2567-2584, 2567-2585, 2567-2586, 2567-2587, 2567-2588, 2567-2589, 2567-2590, 2567-2591, 2567-2592, 2567-2593, 2567-2594, 2567-2595, 2567-2596, 2567-2597, 2567-2598, 2567-2599, 2567-2600, 2567-2601, 2567-2602, 2567-2603, 2567-2604, 2567-2605, 2567-2606, 2567-2607, 2567-2608, 2567-2609, 2567-2610, 2567-2611, 2567-2612, 2567-2613, 2567-2614, 2567-2615, 2567-2616, 2567-2617, 2567-2618, 2567-2619, 2567-2620, 2567-2621, 2567-2622, 2567-2623, 2567-2624, 2567-2625, 2567-2626, 2567-2627, 2567-2628, 2567-2629, 2567-2630, 2567-2631, 2568-2585, 2568-2586, 2568-2587, 2568-2588, 2568-2589, 2568-2590, 2568-2591, 2568-2592, 2568-2593, 2568-2594, 2568-2595, 2568-2596, 2568-2597, 2568-2598, 2568-2599, 2568-2600, 2568-2601, 2568-2602, 2568-2603, 2568-2604, 2568-2605, 2568-2606, 2568-2607, 2568-2608, 2568-2609, 2568-2610, 2568-2611, 2568-2612, 2568-2613, 2568-2614, 2568-2615, 2568-2616, 2568-2617, 2568-2618, 2568-2619, 2568-2620, 2568-2621, 2568-2622, 2568-2623, 2568-2624, 2568-2625, 2568-2626, 2568-2627, 2568-2628, 2568-2629, 2568-2630, 2568-2631, 2569-2586, 2569-2587, 2569-2588, 2569-2589, 2569-2590, 2569-2591, 2569-2592, 2569-2593, 2569-2594, 2569-2595, 2569-2596, 2569-2597, 2569-2598, 2569-2599, 2569-2600, 2569-2601, 2569-2602, 2569-2603, 2569-2604, 2569-2605, 2569-2606, 2569-2607, 2569-2608, 2569-2609, 2569-2610, 2569-2611, 2569-2612, 2569-2613, 2569-2614, 2569-2615, 2569-2616, 2569-2617, 2569-2618, 2569-2619, 2569-2620, 2569-2621, 2569-2622, 2569-2623, 2569-2624, 2569-2625, 2569-2626, 2569-2627, 2569-2628, 2569-2629, 2569-2630, 2569-2631, 2569-2586, 2569-2587, 2569-2588, 2569-2589, 2569-2590, 2569-2591, 2569-2592, 2569-2593, 2569-2594, 2569-2595, 2569-2596, 2569-2597, 2569-2598, 2569-2599, 2569-2600, 2569-2601, 2569-2602, 2569-2603, 2569-2604, 2569-2605, 2569-2606, 2569-2607, 2569-2608, 2569-2609, 2569-2610, 2569-2611, 2569-2612, 2569-2613, 2569-2614, 2569-2615, 2569-2616, 2569-2617, 2569-2618, 2569-2619, 2569-2620, 2569-2621, 2569-2622, 2569-2623, 2569-2624, 2569-2625, 2569-2626, 2569-2627, 2569-2628, 2569-2629, 2569-2630, 2569-2631, 2571-2588, 2571-2589, 2571-2590, 2571-2591, 2571-2592, 2571-2593, 2571-2594, 2571-2595, 2571-2596, 2571-2597, 2571-2598, 2571-2599, 2571-2600, 2571-2601, 2571-2602, 2571-2603, 2571-2604, 2571-2605, 2571-2606, 2571-2607, 2571-2608, 2571-2609, 2571-2610, 2571-2611, 2571-2612, 2571-2613, 2571-2614, 2571-2615, 2571-2616, 2571-2617, 2571-2618, 2571-2619, 2571-2620, 2571-2621, 2571-2622, 2571-2623, 2571-2624, 2571-2625, 2571-2626, 2571-2627, 2571-2628, 2571-2629, 2571-2630, 2571-2631, 2572-2589, 2572-2590, 2572-2591, 2572-2592, 2572-2593, 2572-2594, 2572-2595, 2572-2596, 2572-2597, 2572-2598, 2572-2599, 2572-2600, 2572-2601, 2572-2602, 2572-2603, 2572-2604, 2572-2605, 2572-2606, 2572-2607, 2572-2608, 2572-2609, 2572-2610, 2572-2611, 2572-2612, 2572-2613, 2572-2614, 2572-2615, 2572-2616, 2572-2617, 2572-2618, 2572-2619, 2572-2620, 2572-2621, 2572-2622, 2572-2623, 2572-2624, 2572-2625, 2572-2626, 2572-2627, 2572-2628, 2572-2629, 2572-2630, 2572-2631, 2573-2590, 2573-2591, 2573-2592, 2573-2593, 2573-2594, 2573-2595, 2573-2596, 2573-2597, 2573-2598, 2573-2599, 2573-2600, 2573-2601, 2573-2602, 2573-2603, 2573-2604, 2573-2605, 2573-2606, 2573-2607, 2573-2608, 2573-2609, 2573-2610, 2573-2611, 2573-2612, 2573-2613, 2573-2614, 2573-2615, 2573-2616, 2573-2617, 2573-2618, 2573-2619, 2573-2620, 2573-2621, 2573-2622, 2573-2623, 2573-2624, 2573-2625, 2573-2626, 2573-2627, 2573-2628, 2573-2629, 2573-2630, 2573-2631, 2574-2591, 2574-2592, 2574-2593, 2574-2594, 2574-2595, 2574-2596, 2574-2597, 2574-2598, 2574-2599, 2574-2600, 2574-2601, 2574-2602, 2574-2603, 2574-2604, 2574-2605, 2574-2606, 2574-2607, 2574-2608, 2574-2609, 2574-2610, 2574-2611, 2574-2612, 2574-2613, 2574-2614, 2574-2615, 2574-2616, 2574-2617, 2574-2618, 2574-2619, 2574-2620, 2574-2621, 2574-2622, 2574-2623, 2574-2624, 2574-2625, 2574-2626, 2574-2627, 2574-2628, 2574-2629, 2574-2630, 2574-2631, 2575-2592, 2575-2593, 2575-2594, 2575-2595, 2575-2596, 2575-2597, 2575-2598, 2575-2599, 2575-2600, 2575-2601, 2575-2602, 2575-2603, 2575-2604, 2575-2605, 2575-2606, 2575-2607, 2575-2608, 2575-2609, 2575-2610, 2575-2611, 2575-2612, 2575-2613, 2575-2614, 2575-2615, 2575-2616, 2575-2617, 2575-2618, 2575-2619, 2575-2620, 2575-2621, 2575-2622, 2575-2623, 2575-2624, 2575-2625, 2575-2626, 2575-2627, 2575-2628, 2575-2629, 2575-2630, 2575-2631, 2576-2593, 2576-2594, 2576-2595, 2576-2596, 2576-2597, 2576-2598, 2576-2599, 2576-2600, 2576-2601, 2576-2602, 2576-2603, 2576-2604, 2576-2605, 2576-2606, 2576-2607, 2576-2608, 2576-2609, 2576-2610, 2576-2611, 2576-2612, 2576-2613, 2576-2614, 2576-2615, 2576-2616, 2576-2617, 2576-2618, 2576-2619, 2576-2620, 2576-2621, 2576-2622, 2576-2623, 2576-2624, 2576-2625, 2576-2626, 2576-2627, 2576-2628, 2576-2629, 2576-2630, 2576-2631, 2577-2594, 2577-2595, 2577-2596, 2577-2597, 2577-2598, 2577-2599, 2577-2600, 2577-2601, 2577-2602, 2577-2603, 2577-2604, 2577-2605, 2577-2606, 2577-2607, 2577-2608, 2577-2609, 2577-2610, 2577-2611, 2577-2612, 2577-2613, 2577-2614, 2577-2615, 2577-2616, 2577-2617, 2577-2618, 2577-2619, 2577-2620, 2577-2621, 2577-2622, 2577-2623, 2577-2624, 2577-2625, 2577-2626, 2577-2627, 2577-2628, 2577-2629, 2577-2630, 2577-2631, 2578-2597, 2578-2598, 2578-2599, 2578-2600, 2578-2601, 2578-2602, 2578-2603, 2578-2604, 2578-2605, 2578-2606, 2578-2607, 2578-2608, 2578-2609, 2578-2610, 2578-2611, 2578-2612, 2578-2613, 2578-2614, 2578-2615, 2578-2616, 2578-2617, 2578-2618, 2578-2619, 2578-2620, 2578-2621, 2578-2622, 2578-2623, 2578-2624, 2578-2625, 2578-2626, 2578-2627, 2578-2628, 2578-2629, 2578-2630, 2578-2631, 2579-2598, 2579-2599, 2579-2600, 2579-2601, 2579-2602, 2579-2603, 2579-2604, 2579-2605, 2579-2606, 2579-2607, 2579-2608, 2579-2609, 2579-2610, 2579-2611, 2579-2612, 2579-2613, 2579-2614, 2579-2615, 2579-2616, 2579-2617, 2579-2618, 2579-2619, 2579-2620, 2579-2621, 2579-2622, 2579-2623, 2579-2624, 2579-2625, 2579-2626, 2579-2627, 2579-2628, 2579-2629, 2579-2630, 2579-2631, 2580-2598, 2580-2599, 2580-2600, 2580-2601, 2580-2602, 2580-2603, 2580-2604, 2580-2605, 2580-2606, 2580-2607, 2580-2608, 2580-2609, 2580-2610, 2580-2611, 2580-2612, 2580-2613, 2580-2614, 2580-2615, 2580-2616, 2580-2617, 2580-2618, 2580-2619, 2580-2620, 2580-2621, 2580-2622, 2580-2623, 2580-2624, 2580-2625, 2580-2626, 2580-2627, 2580-2628, 2580-2629, 2580-2630, 2580-2631, 2581-2597, 2581-2598, 2581-2599, 2581-2600, 2581-2601, 2581-2602, 2581-2603, 2581-2604, 2581-2605, 2581-2606, 2581-2607, 2581-2608, 2581-2609, 2581-2610, 2581-2611, 2581-2612, 2581-2613, 2581-2614, 2581-2615, 2581-2616, 2581-2617, 2581-2618, 2581-2619, 2581-2620, 2581-2621, 2581-2622, 2581-2623, 2581-2624, 2581-2625, 2581-2626, 2581-2627, 2581-2628, 2581-2629, 2581-2630, 2581-2631, 2582-2600, 2582-2601, 2582-2602, 2582-2603, 2582-2604, 2582-2605, 2582-2606, 2582-2607, 2582-2608, 2582-2609, 2582-2610, 2582-2611, 2582-2612, 2582-2613, 2582-2614, 2582-2615, 2582-2616, 2582-2617, 2582-2618, 2582-2619, 2582-2620, 2582-2621, 2582-2622, 2582-2623, 2582-2624, 2582-2625, 2582-2626, 2582-2627, 2582-2628, 2582-2629, 2582-2630, 2582-2631, 2583-2601, 2583-2602, 2583-2603, 2583-2604, 2583-2605, 2583-2606, 2583-2607, 2583-2608, 2583-2609, 2583-2610, 2583-2611, 2583-2612, 2583-2613, 2583-2614, 2583-2615, 2583-2616, 2583-2617, 2583-2618, 2583-2619, 2583-2620, 2583-2621, 2583-2622, 2583-2623, 2583-2624, 2583-2625, 2583-2626, 2583-2627, 2583-2628, 2583-2629, 2583-2630, 2583-2631, 2585-2603, 2585-2604, 2585-2605, 2585-2606, 2585-2607, 2585-2608, 2585-2609, 2585-2610, 2585-2611, 2585-2612, 2585-2613, 2585-2614, 2585-2615, 2585-2616, 2585-2617, 2585-2618, 2585-2619, 2585-2620, 2585-2621, 2585-2622, 2585-2623, 2585-2624, 2585-2625, 2585-2626, 2585-2627, 2585-2628, 2585-2629, 2585-2630, 2585-2631, 2586-2604, 2586-2605, 2586-2606, 2586-2607, 2586-2608, 2586-2609, 2586-2610, 2586-2611, 2586-2612, 2586-2613, 2586-2614, 2586-2615, 2586-2616, 2586-2617, 2586-2618, 2586-2619, 2586-2620, 2586-2621, 2586-2622, 2586-2623, 2586-2624, 2586-2625, 2586-2626, 2586-2627, 2586-2628, 2586-2629, 2586-2630, 2586-2631, 2587-2605, 2587-2606, 2587-2607, 2587-2608, 2587-2609, 2587-2610, 2587-2611, 2587-2612, 2587-2613, 2587-2614, 2587-2615, 2587-2616, 2587-2617, 2587-2618, 2587-2619, 2587-2620, 2587-2621, 2587-2622, 2587-2623, 2587-2624, 2587-2625, 2587-2626, 2587-2627, 2587-2628, 2587-2629, 2587-2630, 2587-2631, 2588-2606, 2588-2607, 2588-2608, 2588-2609, 2588-2610, 2588-2611, 2588-2612, 2588-2613, 2588-2614, 2588-2615, 2588-2616, 2588-2617, 2588-2618, 2588-2619, 2588-2620, 2588-2621, 2588-2622, 2588-2623, 2588-2624, 2588-2625, 2588-2626, 2588-2627, 2588-2628, 2588-2629, 2588-2630, 2588-2631, 2589-2607, 2589-2608, 2589-2609, 2589-2610, 2589-2611, 2589-2612, 2589-2613, 2589-2614, 2589-2615, 2589-2616, 2589-2617, 2589-2618, 2589-2619, 2589-2620, 2589-2621, 2589-2622, 2589-2623, 2589-2624, 2589-2625, 2589-2626, 2589-2627, 2589-2628, 2589-2629, 2589-2630, 2589-2631, 2590-2606, 2590-2607, 2590-2608, 2590-2609, 2590-2610, 2590-2611, 2590-2612, 2590-2613, 2590-2614, 2590-2615, 2590-2616, 2590-2617, 2590-2618, 2590-2619, 2590-2620, 2590-2621, 2590-2622, 2590-2623, 2590-2624, 2590-2625, 2590-2626, 2590-2627, 2590-2628, 2590-2629, 2590-2630, 2590-2631, 2591-2610, 2591-2611, 2591-2612, 2591-2613, 2591-2614, 2591-2615, 2591-2616, 2591-2617, 2591-2618, 2591-2619, 2591-2620, 2591-2621, 2591-2622, 2591-2623, 2591-2624, 2591-2625, 2591-2626, 2591-2627, 2591-2628, 2591-2629, 2591-2630, 2591-2631, 2592-2611, 2592-2612, 2592-2613, 2592-2614, 2592-2615, 2592-2616, 2592-2617, 2592-2618, 2592-2619, 2592-2620, 2592-2621, 2592-2622, 2592-2623, 2592-2624, 2592-2625, 2592-2626, 2592-2627, 2592-2628, 2592-2629, 2592-2630, 2592-2631, 2593-2608, 2593-2612, 2593-2613, 2593-2614, 2593-2615, 2593-2616, 2593-2617, 2593-2618, 2593-2619, 2593-2620, 2593-2621, 2593-2622, 2593-2623, 2593-2624, 2593-2625, 2593-2626, 2593-2627, 2593-2628, 2593-2629, 2593-2630, 2593-2631, 2594-2612, 2594-2613, 2594-2614, 2594-2615, 2594-2616, 2594-2617, 2594-2618, 2594-2619, 2594-2620, 2594-2621, 2594-2622, 2594-2623, 2594-2624, 2594-2625, 2594-2626, 2594-2627, 2594-2628, 2594-2629, 2594-2630, 2594-2631, 2595-2611, 2595-2612, 2595-2613, 2595-2614, 2595-2615, 2595-2616, 2595-2617, 2595-2618, 2595-2619, 2595-2620, 2595-2621, 2595-2622, 2595-2623, 2595-2624, 2595-2625, 2595-2626, 2595-2627, 2595-2628, 2595-2629, 2595-2630, 2595-2631, 2596-2614, 2596-2615, 2596-2616, 2596-2617, 2596-2618, 2596-2619, 2596-2620, 2596-2621, 2596-2622, 2596-2623, 2596-2624, 2596-2625, 2596-2626, 2596-2627, 2596-2628, 2596-2629, 2596-2630, 2596-2631, 2597-2612, 2597-2613, 2597-2614, 2597-2615, 2597-2616, 2597-2617, 2597-2618, 2597-2619, 2597-2620, 2597-2621, 2597-2622, 2597-2623, 2597-2624, 2597-2625, 2597-2626, 2597-2627, 2597-2628, 2597-2629, 2597-2630, 2597-2631, 2598-2613, 2598-2614, 2598-2615, 2598-2616, 2598-2617, 2598-2618, 2598-2619, 2598-2620, 2598-2621, 2598-2622, 2598-2623, 2598-2624, 2598-2625, 2598-2626, 2598-2627, 2598-2628, 2598-2629, 2598-2630, 2598-2631, 2599-2614, 2599-2615, 2599-2616, 2599-2617, 2599-2618, 2599-2619, 2599-2620, 2599-2621, 2599-2622, 2599-2623, 2599-2624, 2599-2625, 2599-2626, 2599-2627, 2599-2628, 2599-2629, 2599-2630, 2599-2631, 2600-2615, 2600-2616, 2600-2617, 2600-2618, 2600-2619, 2600-2620, 2600-2621, 2600-2622, 2600-2623, 2600-2624, 2600-2625, 2600-2626, 2600-2627, 2600-2628, 2600-2629, 2600-2630, 2600-2631, 2601-2616, 2601-2617, 2601-2618, 2601-2619, 2601-2620, 2601-2621, 2601-2622, 2601-2623, 2601-2624, 2601-2625, 2601-2626, 2601-2627, 2601-2628, 2601-2629, 2601-2630, 2601-2631, 2602-2618, 2602-2619, 2602-2620, 2602-2621, 2602-2622, 2602-2623, 2602-2624, 2602-2625, 2602-2626, 2602-2627, 2602-2628, 2602-2629, 2602-2630, 2602-2631, 2603-2620, 2603-2621, 2603-2622, 2603-2623, 2603-2624, 2603-2625, 2603-2626, 2603-2627, 2603-2628, 2603-2629, 2603-2630, 2603-2631, 2604-2619, 2604-2620, 2604-2621, 2604-2622, 2604-2623, 2604-2624, 2604-2625, 2604-2626, 2604-2627, 2604-2628, 2604-2629, 2604-2630, 2604-2631, 2605-2620, 2605-2621, 2605-2622, 2605-2623, 2605-2624, 2605-2625, 2605-2626, 2605-2627, 2605-2628, 2605-2629, 2605-2630, 2605-2631, 2606-2621, 2606-2622, 2606-2623, 2606-2624, 2606-2625, 2606-2626, 2606-2627, 2606-2628, 2606-2629, 2606-2630, 2606-2631, 2607-2622, 2607-2623, 2607-2624, 2607-2625, 2607-2626, 2607-2627, 2607-2628, 2607-2629, 2607-2630, 2607-2631, 2608-2623, 2608-2624, 2608-2625, 2608-2626, 2608-2627, 2608-2628, 2608-2629, 2608-2630, 2608-2631, 2609-2624, 2609-2625, 2609-2626, 2609-2627, 2609-2628, 2609-2629, 2609-2630, 2609-2631, 2610-2625, 2610-2626, 2610-2627, 2610-2628, 2610-2629, 2610-2630, 2610-2631, 2611-2626, 2611-2627, 2611-2628, 2611-2629, 2611-2630, 2611-2631, 2612-2627, 2612-2628, 2612-2629, 2612-2630, 2612-2631, 2613-2628, 2613-2629, 2613-2630, 2613-2631, 2614-2629, 2614-2630, 2614-2631, 2615-2630, 2615-2631, or 2616-2631. In certain aspects, antisense compounds or oligonucleotides target at least an 8, 9, 10, 11, 12, 13, 14, 15, or 16 contiguous nucleobases within the aforementioned nucleobase regions.

In certain embodiments, the following nucleotide regions of SEQ ID NO: 1, when targeted by antisense compounds or oligonucleotides, display at least 50% inhibition: 30-49, 48-63, 150-169, 151-170, 152-171, 154-169, 154-173, 156-171, 156-175, 157-176, 158-173, 158-177, 480-499, 600-619, 638-657, 644-663, 738-757, 1089-1108, 1135-1154, 1141-1160, 1147-1166, 1150-1169, 1153-1172, 1159-1178, 1162-1181, 1165-1184, 1171-1186, 1171-1190, 1173-1188, 1173-1192, 1175-1190, 1175-1194, 1177-1196, 1183-1202, 1208-1227, 1235-1254, 1298-1317, 1304-1323, 1310-1329, 1316-1335, 1319-1338, 1322-1341, 1328-1347, 1349-1368, 1355-1374, 1393-1412, 1396-1415, 1399-1418, 1405-1424, 1421-1440, 1621-1640, 1646-1665, 1646-1665, 1647-1666, 1689-1708, 1749-1768, 1763-1782, 1912-1931, 2073-2092, 2085-2104, 2166-2185, 2172-2191, 2189-2208, 2191-2210, 2193-2212, 2195-2210, 2195-2214, 2196-2215, 2197-2212, 2197-2216, 2202-2221, 2223-2238, 2223-2242, 2225-2240, 2226-2245, 2227-2242, 2227-2246, 2238-2257, 2241-2260, 2267-2286, 2361-2380, 2388-2407, 2397-2416, 2448-2467, 2453-2472, 2455-2474, 2457-2472, 2457-2476, 2459-2474, 2459-2478, 2461-2476, 2461-2480, 2532-2551, 2550-2569, 2551-2566, 2551-2570, 2552-2568, 2552-2570, 2552-2571, 2553-2568, 2553-2570, 2553-2571, 2553-2572, 2554-2571, 2554-2572, 2554-2573, 2555-2570, 2555-2572, 2555-2574, 2556-2573, 2556-2574, 2556-2575, 2557-2573, 2557-2574, 2557-2575, 2557-2576, 2558-2575, 2558-2576, 2558-2577, 2559-2576, 2559-2577, 2559-2578, 2560-2577, 2560-2578, 2560-2579, 2561-2576, 2561-2578, 2561-2579, 2561-2580, 2562-2577, 2562-2579, 2562-2581, 2563-2578, 2563-2580, 2563-2582, 2564-2581, 2564-2583, 2565-2584, 2566-2583, 2566-2585, 2567-2582, 2567-2584, 2567-2586, 2568-2583, 2568-2585, 2568-2587, 2569-2586, 2569-2588, 2570-2585, 2570-2587, 2570-2589, 2571-2586, 2571-2588, 2571-2590, 2572-2589, 2572-2590, 2572-2591, 2573-2590, 2573-2592, 2574-2590, 2574-2591, 2574-2593, 2575-2590, 2575-2591, 2575-2592, 2575-2594, 2576-2593, 2576-2595, 2577-2594, 2577-2595, 2577-2596, 2578-2594, 2578-2596, 2578-2597, 2579-2598, 2580-2596, 2580-2597, 2580-2598, 2580-2599, 2581-2597, 2581-2598, 2581-2599, 2581-2600, 2582-2598, 2582-2599, 2582-2600, 2582-2601, 2583-2599, 2583-2600, 2583-2601, 2583-2602, 2584-2600, 2584-2601, 2584-2602, 2584-2603, 2585-2601, 2585-2603, 2585-2604, 2586-2601, 2586-2602, 2586-2604, 2586-2605, 2587-2602, 2587-2603, 2587-2605, 2587-2606, 2588-2603, 2588-2604, 2588-2605, 2588-2606, 2588-2607, 2589-2604, 2589-2605, 2589-2606, 2589-2607, 2589-2608, 2590-2605, 2590-2606, 2590-2607, 2590-2608, 2590-2609, 2590-2609, 2591-2607, 2591-2608, 2591-2609, 2591-2610, 2592-2607, 2592-2608, 2592-2609, 2592-2610, 2592-2611, 2593-2608, 2593-2609, 2593-2610, 2593-2612, 2594-2609, 2594-2610, 2594-2611, 2594-2612, 2594-2613, 2595-2610, 2595-2611, 2595-2612, 2595-2613, 2595-2614, 2596-2611, 2596-2612, 2596-2613, 2596-2614, 2596-2615, 2597-2612, 2597-2612, 2597-2613, 2597-2614, 2597-2615, 2597-2616, 2598-2613, 2598-2614, 2598-2615, 2598-2616, 2598-2617, 2599-2614, 2599-2615, 2599-2616, 2599-2617, 2599-2618, 2600-2615, 2600-2616, 2600-2617, 2600-2618, 2600-2619, 2601-2616, 2601-2617, 2601-2618, 2601-2619, 2601-2620, 2602-2617, 2602-2618, 2602-2619, 2602-2620, 2602-2621, 2603-2618, 2603-2619, 2603-2620, 2603-2621, 2603-2622, 2604-2619, 2604-2620, 2604-2621, 2604-2622, 2604-2623, 2605-2620, 2605-2621, 2605-2622, 2605-2623, 2605-2624, 2606-2621, 2606-2622, 2606-2623, 2606-2624, 2606-2625, 2607-2622, 2607-2623, 2607-2624, 2607-2625, 2607-2626, 2608-2623, 2608-2624, 2608-2625, 2608-2626, 2608-2627, 2609-2624, 2609-2625, 2609-2626, 2609-2627, 2609-2628, 2610-2625, 2610-2626, 2610-2627, 2610-2628, 2610-2629, 2611-2626, 2611-2627, 2611-2628, 2611-2629, 2611-2630, 2612-2627, 2612-2628, 2612-2629, 2612-2630, 2612-2631, 2613-2628, 2613-2629, 2613-2630, 2613-2631, 2614-2629, 2614-2630, 2614-2631, 2615-2630, 2615-2631, and 2616-2631.

In certain embodiments, the following nucleotide regions of SEQ ID NO: 2, when targeted by antisense compounds or oligonucleotides, display at least 50% inhibition: 1608-1627, 1685-1704, 1686-1705, 1751-1770, 1769-1784, 1871-1890, 1872-1891, 1873-1892, 1875-1890, 1875-1894, 1877-1892, 1877-1896, 1878-1897, 1879-1894, 1879-1898, 2288-2307, 2808-2827, 2846-2865, 2852-2871, 2946-2965, 3773-3792, 3819-3838, 3825-3844, 3831-3850, 3834-3853, 3837-3856, 3843-3862, 4151-4166, 4151-4170, 4153-4172, 4159-4178, 4184-4203, 4211-4230, 4609-4628, 4612-4631, 4615-4634, 4621-4640, 4642-4661, 4648-4667, 4686-4705, 4689-4708, 4692-4711, 4698-4717, 4714-4733, 5270-5289, 5295-5314, 5296-5315, 5830-5849, 5890-5909, 5904-5923, 6406-6425, 6662-6681, 6674-6693, 6954-6973, 6960-6979, 6977-6996, 6979-6998, 6981-7000, 6983-6998, 6983-7002, 6984-7003, 6985-7000, 6985-7004, 6990-7009, 7122-7141, 7125-7144, 7151-7170, 7353-7372, 7362-7381, 7683-7702, 7688-7707, 7690-7709, 7692-7707, 7692-7711, 7694-7709, 7694-7713, 7696-7711, 7696-7715, 7767-7786, 7785-7804, 7786-7801, 7787-7803, 7787-7805, 7787-7806, 7788-7803, 7788-7805, 7788-7806, 7788-7807, 7789-7806, 7789-7807, 7789-7808, 7790-7805, 7790-7807, 7790-7809, 7791-7808, 7791-7809, 7791-7810, 7792-7808, 7792-7809, 7792-7810, 7792-7811, 7793-7810, 7793-7811, 7793-7812, 7794-7811, 7794-7812, 7794-7813, 7795-7812, 7795-7813, 7795-7814, 7796-7811, 7796-7813, 7796-7814, 7796-7815, 7797-7812, 7797-7814, 7797-7816, 7798-7813, 7798-7815, 7798-7817, 7799-7816, 7799-7818, 7800-7819, 7801-7818, 7801-7820, 7802-7817, 7802-7819, 7802-7821, 7803-7818, 7803-7820, 7803-7822, 7804-7821, 7804-7823, 7805-7820, 7805-7822, 7805-7824, 7806-7821, 7806-7823, 7806-7825, 7807-7824, 7807-7825, 7807-7826, 7808-7825, 7808-7827, 7809-7825, 7809-7826, 7809-7828, 7810-7825, 7810-7826, 7810-7827, 7810-7829, 7811-7828, 7811-7830, 7812-7829, 7812-7830, 7812-7831, 7813-7829, 7813-7831, 7813-7832, 7814-7833, 7815-7831, 7815-7832, 7815-7833, 7815-7834, 7816-7832, 7816-7833, 7816-7834, 7816-7835, 7817-7833, 7817-7834, 7817-7835, 7817-7836, 7818-7834, 7818-7835, 7818-7836, 7818-7837, 7819-7835, 7819-7836, 7819-7837, 7819-7838, 7820-7836, 7820-7838, 7820-7839, 7821-7836, 7821-7837, 7821-7839, 7821-7840, 7822-7837, 7822-7838, 7822-7840, 7822-

7841, 7823-7838, 7823-7839, 7823-7839, 7823-7840, 7823-7841, 7823-7842, 7824-7839, 7824-7840, 7824-7840, 7824-7841, 7824-7842, 7824-7843, 7825-7840, 7825-7841, 7825-7842, 7825-7843, 7825-7844, 7826-7842, 7826-7843, 7826-7844, 7826-7845, 7827-7842, 7827-7843, 7827-7844, 7827-7845, 7827-7846, 7828-7843, 7828-7844, 7828-7845, 7828-7847, 7829-7844, 7829-7845, 7829-7846, 7829-7847, 7829-7848, 7830-7845, 7830-7846, 7830-7847, 7830-7848, 7830-7849, 7831-7846, 7831-7847, 7831-7848, 7831-7849, 7831-7850, 7832-7847, 7832-7848, 7832-7849, 7832-7850, 7832-7851, 7833-7848, 7833-7849, 7833-7850, 7833-7851, 7833-7852, 7834-7849, 7834-7850, 7834-7851, 7834-7852, 7834-7853, 7835-7850, 7835-7851, 7835-7852, 7835-7853, 7835-7854, 7836-7851, 7836-7852, 7836-7853, 7836-7854, 7836-7855, 7837-7852, 7837-7853, 7837-7854, 7837-7855, 7837-7856, 7838-7853, 7838-7854, 7838-7855, 7838-7856, 7838-7857, 7839-7854, 7839-7855, 7839-7856, 7839-7857, 7839-7858, 7840-7855, 7840-7856, 7840-7857, 7840-7858, 7840-7859, 7841-7856, 7841-7857, 7841-7858, 7841-7859, 7841-7860, 7842-7857, 7842-7858, 7842-7859, 7842-7860, 7842-7861, 7843-7858, 7843-7859, 7843-7860, 7843-7861, 7843-7862, 7844-7859, 7844-7860, 7844-7861, 7844-7862, 7845-7860, 7845-7861, 7845-7862, 7846-7861, and 7846-7862.

In certain embodiments, the following nucleotide regions of SEQ ID NO: 1, when targeted by antisense compounds or oligonucleotides, display at least 60% inhibition: 48-63, 150-169, 152-171, 154-169, 154-173, 156-171, 156-175, 158-173, 158-177, 600-619, 1135-1154, 1141-1160, 1147-1166, 1153-1172, 1171-1186, 1173-1188, 1175-1190, 1749-1768, 1763-1782, 1763-1782, 1912-1931, 2189-2208, 2191-2210, 2193-2212, 2195-2210, 2195-2214, 2197-2212, 2197-2216, 2223-2238, 2225-2240, 2227-2242, 2238-2257, 2448-2467, 2453-2472, 2455-2474, 2457-2472, 2457-2476, 2459-2474, 2459-2478, 2461-2476, 2461-2480, 2550-2569, 2551-2566, 2552-2571, 2553-2568, 2553-2570, 2553-2571, 2553-2572, 2554-2571, 2554-2572, 2554-2573, 2555-2572, 2555-2574, 2556-2573, 2556-2574, 2556-2575, 2557-2574, 2557-2575, 2557-2576, 2558-2575, 2558-2576, 2558-2577, 2559-2576, 2559-2577, 2559-2578, 2560-2577, 2560-2578, 2560-2579, 2561-2578, 2561-2579, 2561-2580, 2562-2577, 2562-2579, 2562-2581, 2563-2578, 2563-2580, 2563-2582, 2564-2581, 2564-2583, 2565-2584, 2566-2583, 2566-2585, 2567-2582, 2567-2584, 2567-2586, 2568-2583, 2568-2585, 2568-2587, 2569-2586, 2569-2588, 2570-2587, 2570-2589, 2571-2588, 2572-2590, 2572-2591, 2573-2590, 2573-2592, 2574-2591, 2574-2593, 2575-2590, 2575-2592, 2575-2594, 2576-2593, 2576-2595, 2577-2594, 2577-2595, 2577-2596, 2578-2594, 2578-2597, 2579-2598, 2580-2596, 2580-2597, 2580-2598, 2580-2599, 2581-2597, 2581-2598, 2581-2599, 2581-2600, 2582-2598, 2582-2599, 2582-2600, 2582-2601, 2583-2599, 2583-2600, 2583-2601, 2583-2602, 2584-2600, 2584-2602, 2584-2603, 2585-2601, 2585-2603, 2585-2604, 2586-2602, 2586-2604, 2586-2605, 2587-2603, 2587-2605, 2587-2606, 2588-2603, 2588-2604, 2588-2606, 2588-2607, 2589-2605, 2589-2606, 2589-2607, 2589-2608, 2590-2605, 2590-2606, 2590-2607, 2590-2608, 2590-2609, 2591-2607, 2591-2609, 2591-2610, 2592-2608, 2592-2609, 2592-2611, 2593-2608, 2593-2609, 2593-2612, 2594-2609, 2594-2610, 2594-2611, 2594-2612, 2594-2613, 2595-2610, 2595-2611, 2595-2612, 2595-2613, 2595-2614, 2596-2611, 2596-2612, 2596-2613, 2596-2614, 2596-2615, 2597-2612, 2597-2613, 2597-2614, 2597-2615, 2597-2616, 2598-2613, 2598-2614, 2598-2615, 2598-2616, 2598-2617, 2599-2614, 2599-2615, 2599-2616, 2599-2617, 2599-2618, 2600-2615, 2600-2616, 2600-2617, 2600-2618, 2600-2619, 2601-2616, 2601-2617, 2601-2618, 2601-2619, 2601-2620, 2602-2617, 2602-2618, 2602-2619, 2602-2620, 2602-2621, 2603-2618, 2603-2619, 2603-2620, 2603-2621, 2603-2622, 2604-2619, 2604-2620, 2604-2621, 2604-2622, 2604-2623, 2605-2620, 2605-2621, 2605-2622, 2605-2623, 2605-2624, 2606-2621, 2606-2622, 2606-2623, 2606-2624, 2606-2625, 2607-2622, 2607-2623, 2607-2624, 2607-2625, 2607-2626, 2608-2623, 2608-2624, 2608-2625, 2608-2625, 2608-2626, 2608-2627, 2609-2624, 2609-2625, 2609-2626, 2609-2627, 2609-2628, 2610-2625, 2610-2626, 2610-2627, 2610-2628, 2610-2629, 2611-2626, 2611-2626, 2611-2627, 2611-2628, 2611-2629, 2611-2630, 2612-2627, 2612-2628, 2612-2629, 2612-2630, 2612-2631, 2613-2628, 2613-2629, 2613-2630, 2613-2631, 2614-2629, 2614-2630, 2614-2631, 2615-2630, 2615-2630, 2615-2631, 2615-2631, and 2616-2631.

In certain embodiments, the following nucleotide regions of SEQ ID NO: 2, when targeted by antisense compounds or oligonucleotides, display at least 60% inhibition: 1685-1704, 1686-1705, 1769-1784, 1871-1890, 1873-1892, 1875-1890, 1875-1894, 1877-1892, 1877-1896, 1879-1894, 1879-1898, 2808-2827, 3819-3838, 3825-3844, 3831-3850, 3837-3856, 4151-4166, 5890-5909, 5904-5923, 5904-5923, 6406-6425, 6977-6996, 6979-6998, 6981-7000, 6983-6998, 6983-7002, 6985-7000, 6985-7004, 7122-7141, 7683-7702, 7688-7707, 7690-7709, 7692-7707, 7692-7711, 7694-7709, 7696-7711, 7696-7715, 7786-7801, 7787-7806, 7788-7803, 7788-7805, 7788-7806, 7788-7807, 7789-7806, 7789-7807, 7789-7808, 7790-7807, 7790-7809, 7791-7808, 7791-7809, 7791-7810, 7792-7809, 7792-7810, 7792-7811, 7793-7810, 7793-7811, 7793-7812, 7794-7811, 7794-7812, 7794-7813, 7795-7812, 7795-7813, 7795-7814, 7796-7813, 7796-7814, 7796-7815, 7797-7812, 7797-7814, 7797-7816, 7798-7813, 7798-7815, 7798-7817, 7799-7816, 7799-7818, 7800-7819, 7801-7818, 7801-7820, 7802-7817, 7802-7819, 7802-7821, 7803-7818, 7803-7820, 7803-7822, 7804-7821, 7804-7823, 7805-7822, 7805-7824, 7806-7823, 7806-7825, 7807-7824, 7807-7825, 7807-7826, 7808-7825, 7808-7827, 7809-7826, 7809-7828, 7810-7825, 7810-7827, 7810-7829, 7811-7828, 7811-7830, 7812-7829, 7812-7830, 7812-7831, 7813-7829, 7813-7832, 7814-7833, 7815-7831, 7815-7832, 7815-7833, 7815-7834, 7816-7832, 7816-7833, 7816-7834, 7816-7835, 7817-7833, 7817-7834, 7817-7835, 7817-7836, 7818-7834, 7818-7835, 7818-7836, 7818-7837, 7819-7835, 7819-7837, 7819-7838, 7820-7836, 7820-7838, 7820-7839, 7821-7837, 7821-7839, 7821-7840, 7822-7838, 7822-7840, 7822-7841, 7823-7838, 7823-7839, 7823-7841, 7823-7842, 7824-7840, 7824-7841, 7824-7842, 7824-7843, 7825-7840, 7825-7841, 7825-7842, 7825-7843, 7825-7844, 7826-7842, 7826-7844, 7826-7845, 7827-7843, 7827-7844, 7827-7846, 7828-7843, 7828-7844, 7828-7847, 7829-7844, 7829-7845, 7829-7846, 7829-7847, 7829-7848, 7830-7845, 7830-7846, 7830-7847, 7830-7848, 7830-7849, 7831-7846, 7831-7847, 7831-7848, 7831-7849, 7831-7850, 7832-7847, 7832-7848, 7832-7849, 7832-7850, 7832-7851, 7833-7848, 7833-7849, 7833-7850, 7833-7851, 7833-7852, 7834-7849, 7834-7850, 7834-7851, 7834-7852, 7834-7853, 7835-7850, 7835-7851, 7835-7852, 7835-7853, 7835-7854, 7836-7851, 7836-7852, 7836-7853, 7836-7854, 7836-7855, 7837-7852, 7837-7853, 7837-7854, 7837-7855, 7837-7856, 7838-7853, 7838-7854, 7838-7855, 7838-7856, 7838-7857, 7839-7854, 7839-7855, 7839-7856, 7839-7857, 7839-7858, 7840-7855, 7840-7856, 7840-7857, 7840-7858, 7840-7859, 7841-7856, 7841-7857, 7841-7858, 7841-7859, 7841-7860, 7842-7857, 7842-7858, 7842-7859, 7842-7860, 7842-7861, 7843-7858, 7843-7859, 7843-7860, 7843-7861, 7843-7862, 7844-7859, 7844-7860, 7844-7861, 7844-7862, 7845-7860, 7845-7861, 7845-7862, 7846-7861, 7846-7862, and 7847-7862.

In certain embodiments, the following nucleotide regions of SEQ ID NO: 1, when targeted by antisense compounds or oligonucleotides, display at least 70% inhibition: 48-63, 150-169, 152-171, 154-169, 154-173, 156-171, 156-175, 158-173, 158-177, 1135-1154, 1141-1160, 1147-1166, 1171-1186, 1173-1188, 1175-1190, 1749-1768, 1763-1782, 1912-1931, 2193-2212, 2195-2210, 2195-2214, 2197-2212, 2197-2216, 2223-2238, 2225-2240, 2227-2242, 2453-2472, 2455-2474, 2457-2472, 2457-2476, 2459-2474, 2461-2476, 2461-2480, 2550-2569, 2551-2566, 2552-2571, 2553-2570, 2553-2571, 2553-2572, 2554-2571, 2554-2572, 2554-2573, 2554-2573, 2555-2572, 2555-2574, 2555-2574, 2556-2573, 2556-2574, 2556-2575, 2557-2574, 2557-2576, 2558-2575, 2558-2576, 2558-2577, 2559-2576, 2559-2577, 2559-2578, 2560-2577, 2560-2578, 2560-2579, 2561-2578, 2561-2579, 2561-2580, 2562-2577, 2562-2579, 2562-2581, 2563-2578, 2563-2580, 2563-2582, 2564-2581, 2564-2583, 2565-2584, 2566-2583, 2566-2585, 2567-2582, 2567-2584, 2567-2586, 2568-2585, 2568-2587, 2569-2586, 2569-2588, 2570-2587, 2570-2589, 2571-2588, 2571-2590, 2572-2589, 2572-2591, 2573-2590, 2573-2592, 2574-2591, 2574-2593, 2575-2592, 2575-2594, 2576-2593, 2576-2595, 2577-2594, 2577-2596, 2578-2597, 2579-2598, 2580-2596, 2580-2598, 2580-2599, 2581-2597, 2581-2600, 2582-2598, 2582-2600, 2582-2601, 2583-2599, 2583-2601, 2583-2602, 2584-2600, 2584-2602, 2584-2603, 2585-2601, 2585-2603, 2585-2604, 2586-2605, 2587-2606, 2588-2604, 2588-2606, 2588-2607, 2589-2605, 2589-2606, 2589-2607, 2589-2608, 2590-2605, 2590-2606, 2590-2607, 2590-2609, 2591-2607, 2591-2610, 2592-2611, 2593-2608, 2593-2612, 2594-2609, 2594-2610, 2594-2612, 2594-2613, 2595-2610, 2595-2611, 2595-2612, 2595-2613, 2595-2614, 2596-2611, 2596-2614, 2596-2615, 2597-2612, 2597-2613, 2597-2614, 2597-2615, 2597-2616, 2598-2613, 2598-2614, 2598-2615, 2598-2616, 2598-2617, 2599-2614, 2599-2615, 2599-2616, 2599-2617, 2599-2618, 2600-2615, 2600-2616, 2600-2617, 2600-2618, 2600-2619, 2601-2616, 2601-2617, 2601-2618, 2601-2619, 2601-2620, 2602-2617, 2602-2618, 2602-2619, 2602-2620, 2602-2621, 2603-2619, 2603-2620, 2603-2621, 2603-2622, 2604-2619, 2604-2620, 2604-2621, 2604-2622, 2604-2623, 2605-2620, 2605-2621, 2605-2622, 2605-2623, 2605-2624, 2606-2621, 2606-2622, 2606-2623, 2606-2624, 2606-2625, 2607-2622, 2607-2623, 2607-2624, 2607-2625, 2607-2626, 2608-2623, 2608-2624, 2608-2625, 2608-2626, 2608-2627, 2609-2624, 2609-2625, 2609-2626, 2609-2627, 2609-2628, 2610-2625, 2610-2626, 2610-2627, 2610-2628, 2610-2629, 2611-2626, 2611-2627, 2611-2629, 2611-2630, 2612-2627, 2612-2628, 2612-2629, 2612-2630, 2612-2631, 2613-2628, 2613-2629, 2613-2630, 2613-2631, 2614-2629, 2614-2630, 2614-2631, 2615-2630, 2615-2630, 2615-2631, and 2616-2631.

In certain embodiments, the following nucleotide regions of SEQ ID NO: 2, when targeted by antisense compounds or oligonucleotides, display at least 70% inhibition: 1685-1704, 1686-1705, 1769-1784, 1871-1890, 1873-1892, 1875-1890, 1875-1894, 1877-1892, 1877-1896, 1879-1894, 1879-1898, 3819-3838, 3825-3844, 3831-3850, 4151-4166, 5890-5909, 5904-5923, 5904-5923, 6406-6425, 6983-6998, 6983-7002, 6985-7000, 6985-7004, 7688-7707, 7690-7709, 7692-7707, 7692-7711, 7694-7709, 7696-7711, 7696-7715, 7786-7801, 7787-7806, 7788-7805, 7788-7806, 7788-7807, 7789-7806, 7789-7807, 7789-7808, 7790-7807, 7790-7809, 7791-7808, 7791-7809, 7791-7810, 7792-7809, 7792-7811, 7793-7810, 7793-7811, 7793-7812, 7794-7811, 7794-7812, 7794-7813, 7795-7812, 7795-7813, 7795-7814, 7796-7813, 7796-7814, 7796-7815, 7797-7812, 7797-7814, 7797-7816, 7798-7813, 7798-7815, 7798-7817, 7799-7816, 7799-7818, 7800-7819, 7801-7818, 7801-7820, 7802-7817, 7802-7819, 7802-7821, 7803-7820, 7803-7822, 7804-7821, 7804-7823, 7805-7822, 7805-7824, 7806-7823, 7806-7825, 7807-7824, 7807-7826, 7808-7825, 7808-7827, 7809-7826, 7809-7828, 7810-7827, 7811-7828, 7811-7830, 7812-7829, 7812-7831, 7813-7832, 7814-7833, 7815-7831, 7815-7833, 7815-7834, 7816-7832, 7816-7835, 7817-7833, 7817-7835, 7817-7836, 7818-7834, 7818-7836, 7818-7837, 7819-7835, 7819-7837, 7819-7838, 7820-7836, 7820-7838, 7820-7839, 7821-7840, 7822-7841, 7823-7839, 7823-7841, 7823-7842, 7824-7840, 7824-7841, 7824-7842, 7824-7843, 7825-7840, 7825-7841, 7825-7842, 7825-7844, 7826-7842, 7826-7845, 7827-7846, 7828-7843, 7828-7847, 7829-7844, 7829-7845, 7829-7847, 7829-7848, 7830-7845, 7830-7846, 7830-7847, 7830-7848, 7830-7849, 7831-7846, 7831-7849, 7831-7850, 7832-7847, 7832-7848, 7832-7849, 7832-7850, 7832-7851, 7833-7848, 7833-7849, 7833-7850, 7833-7851, 7833-7852, 7834-7849, 7834-7850, 7834-7851, 7834-7852, 7834-7853, 7835-7850, 7835-7851, 7835-7852, 7835-7853, 7835-7854, 7836-7851, 7836-7852, 7836-7853, 7836-7854, 7836-7855, 7837-7852, 7837-7853, 7837-7854, 7837-7855, 7837-7856, 7838-7854, 7838-7855, 7838-7856, 7838-7857, 7839-7854, 7839-7855, 7839-7856, 7839-7857, 7839-7858, 7840-7855, 7840-7856, 7840-7857, 7840-7858, 7840-7859, 7841-7856, 7841-7857, 7841-7858, 7841-7859, 7841-7860, 7842-7857, 7842-7858, 7842-7859, 7842-7860, 7842-7861, 7843-7858, 7843-7859, 7843-7860, 7843-7861, 7843-7862, 7844-7859, 7844-7860, 7844-7861, 7844-7862, 7845-7860, 7845-7861, 7845-7862, 7846-7861, 7846-7862, and 7847-7862.

In certain embodiments, the following nucleotide regions of SEQ ID NO: 1, when targeted by antisense compounds or oligonucleotides, display at least 80% inhibition: 152-171, 154-169, 156-171, 158-173, 1135-1154, 1171-1186, 1173-1188, 1175-1190, 1763-1782, 1912-1931, 2197-2212, 2223-2238, 2225-2240, 2227-2242, 2457-2472, 2459-2474, 2461-2476, 2551-2566, 2553-2570, 2553-2571, 2553-2572, 2554-2573, 2555-2572, 2555-2574, 2556-2573, 2556-2574, 2556-2575, 2557-2574, 2557-2576, 2558-2575, 2558-2576, 2559-2577, 2559-2578, 2560-2577, 2560-2578, 2560-2579, 2561-2578, 2561-2579, 2561-2580, 2562-2577, 2562-2579, 2562-2581, 2563-2580, 2563-2582, 2564-2581, 2564-2583, 2565-2584, 2566-2583, 2567-2584, 2567-2586, 2568-2585, 2568-2587, 2569-2586, 2569-2588, 2570-2587, 2571-2588, 2571-2590, 2572-2589, 2572-2591, 2573-2590, 2573-2592, 2574-2591, 2574-2593, 2575-2592, 2576-2593, 2576-2595, 2577-2594, 2577-2596, 2578-2597, 2580-2598, 2580-2599, 2581-2597, 2581-2600, 2582-2598, 2583-2602, 2584-2603, 2585-2604, 2586-2587-2606, 2588-2607, 2589-2608, 2590-2606, 2590-2607, 2590-2609, 2591-2610, 2592-2611, 2593-2608, 2593-2612, 2594-2613, 2595-2611, 2595-2614, 2596-2615, 2597-2612, 2597-2613, 2597-2614, 2597-2615, 2597-2616, 2598-2613, 2598-2613, 2598-2614, 2598-2615, 2598-2616, 2598-2617, 2599-2614, 2599-2617, 2599-2618, 2600-2615, 2600-2617, 2600-2618, 2600-2619, 2601-2616, 2601-2617, 2601-2619, 2601-2620, 2602-2618, 2602-2621, 2603-2620, 2603-2621, 2603-2622, 2604-2619, 2604-2620, 2604-2621, 2604-2622, 2604-2623, 2605-2620, 2605-2621, 2605-2622, 2605-2623, 2605-2624, 2606-2621, 2606-2622, 2606-2623, 2606-2624, 2606-2625, 2607-2622, 2607-2623, 2607-2624, 2607-2625, 2607-2626, 2608-2623, 2608-2624, 2608-2625, 2608-2627, 2609-2624, 2609-2626, 2609-2627, 2609-2628, 2610-2625, 2610-2626, 2610-2628, 2610-2629, 2611-2626, 2611-2627, 2611-2629, 2611-2630, 2612-2627, 2612-2628, 2612-2630, 2612-2631, 2613-2628, 2613-2629, 2613-2631, 2614-2629, 2614-2630, 2614-2631, 2615-2630, and 2616-2631.

In certain embodiments, the following nucleotide regions of SEQ ID NO: 2, when targeted by antisense compounds or oligonucleotides, display at least 80% inhibition: 1685-1704, 1686-1705, 1873-1892, 1875-1890, 1877-1892, 1879-

1894, 3819-3838, 4151-4166, 5904-5923, 6406-6425, 6985-7000, 7692-7707, 7694-7709, 7696-7711, 7786-7801, 7788-7805, 7788-7806, 7788-7807, 7789-7808, 7790-7807, 7790-7809, 7791-7808, 7791-7809, 7791-7810, 7792-7809, 7792-7811, 7793-7810, 7793-7811, 7794-7812, 7794-7813, 7795-7812, 7795-7813, 7795-7814, 7796-7813, 7796-7814, 7796-7815, 7797-7812, 7797-7814, 7797-7816, 7798-7815, 7798-7817, 7799-7816, 7799-7818, 7800-7819, 7801-7818, 7802-7819, 7802-7821, 7803-7820, 7803-7822, 7804-7821, 7804-7823, 7805-7822, 7806-7823, 7806-7825, 7807-7824, 7807-7826, 7808-7825, 7808-7827, 7809-7826, 7809-7828, 7810-7827, 7811-7828, 7812-7829, 7812-7831, 7813-7832, 7814-7833, 7815-7834, 7816-7832, 7816-7835, 7817-7836, 7818-7837, 7819-7838, 7820-7839, 7821-7840, 7822-7841, 7823-7842, 7824-7843, 7825-7841, 7825-7842, 7825-7844, 7826-7845, 7827-7846, 7828-7843, 7828-7847, 7829-7848, 7830-7846, 7830-7849, 7831-7850, 7832-7847, 7832-7848, 7832-7849, 7832-7850, 7832-7851, 7833-7848, 7833-7849, 7833-7850, 7833-7851, 7833-7852, 7834-7849, 7834-7852, 7834-7853, 7835-7850, 7835-7852, 7835-7853, 7835-7854, 7836-7851, 7836-7852, 7836-7854, 7836-7855, 7837-7853, 7837-7856, 7838-7855, 7838-7856, 7838-7857, 7839-7854, 7839-7855, 7839-7856, 7839-7857, 7839-7858, 7840-7855, 7840-7856, 7840-7857, 7840-7858, 7840-7859, 7841-7856, 7841-7857, 7841-7858, 7841-7859, 7841-7860, 7842-7857, 7842-7858, 7842-7859, 7842-7860, 7842-7861, 7843-7858, 7843-7859, 7843-7860, 7843-7862, 7844-7859, 7844-7861, 7844-7862, 7845-7860, 7845-7861, 7846-7862, and 7847-7862.

In certain embodiments, the following nucleotide regions of SEQ ID NO: 1, when targeted by antisense compounds or oligonucleotides, display at least 90% inhibition: 154-169, 156-171, 158-173, 1135-1154, 1171-1186, 1173-1188, 1763-1782, 1912-1931, 2223-2238, 2227-2242, 2459-2474, 2461-2476, 2554-2573, 2555-2574, 2560-2577, 2561-2578, 2561-2579, 2562-2581, 2563-2580, 2563-2582, 2564-2581, 2566-2583, 2567-2584, 2568-2585, 2568-2587, 2569-2586, 2570-2587, 2576-2593, 2577-2594, 2577-2596, 2578-2597, 2580-2599, 2581-2600, 2582-2601, 2583-2602, 2584-2603, 2586-2605, 2587-2605, 2587-2606, 2588-2607, 2589-2608, 2590-2607, 2590-2609, 2592-2611, 2595-2614, 2596-2615, 2597-2612, 2597-2613, 2597-2615, 2597-2616, 2598-2613, 2598-2613, 2598-2617, 2599-2614, 2599-2618, 2600-2615, 2600-2619, 2601-2617, 2601-2620, 2602-2621, 2603-2622, 2604-2623, 2605-2621, 2605-2622, 2605-2624, 2606-2625, 2607-2626, 2608-2623, 2608-2625, 2609-2628, 2611-2627, 2611-2630, 2612-2628, 2612-2631, 2613-2629, 2614-2629, 2615-2630, and 2616-2631.

In certain embodiments, the following nucleotide regions of SEQ ID NO: 2, when targeted by antisense compounds or oligonucleotides, display at least 90% inhibition: 1685-1704, 1686-1705, 1875-1890, 1877-1892, 1879-1894, 3819-3838, 5904-5923, 6406-6425, 7694-7709, 7696-7711, 7789-7808, 7790-7809, 7795-7812, 7795-7813, 7796-7813, 7796-7814, 7797-7814, 7797-7816, 7798-7815, 7798-7817, 7799-7816, 7801-7818, 7802-7819, 7803-7820, 7803-7822, 7804-7821, 7805-7822, 7811-7828, 7812-7829, 7812-7831, 7813-7832, 7815-7834, 7818-7837, 7819-7838, 7821-7840, 7822-7840, 7822-7841, 7825-7842, 7832-7847, 7832-7848, 7832-7850, 7833-7848, 7833-7852, 7834-7849, 7834-7853, 7835-7850, 7836-7852, 7836-7855, 7837-7856, 7838-7856, 7839-7857, 7839-7858, 7840-7856, 7840-7857, 7840-7859, 7843-7858, 7843-7860, and 7846-7862.

In certain embodiments, the following antisense compounds or oligonucleotides target a region of a CFB nucleic acid and effect at least a 50% inhibition of a CFB mRNA, ISIS NOs: 516350, 532614, 532632, 532635, 532638, 532639, 532686, 532687, 532688, 532689, 532690, 532691, 532692, 532692, 532693, 532694, 532695, 532696, 532697, 532698, 532699, 532700, 532701, 532702, 532703, 532704, 532705, 532706, 532707, 532770, 532775, 532778, 532780, 532791, 532800, 532809, 532810, 532811, 532917, 532952, 588509, 588510, 588511, 588512, 588513, 588514, 588515, 588516, 588517, 588518, 588519, 588520, 588522, 588523, 588524, 588525, 588527, 588528, 588529, 588530, 588531, 588532, 588533, 588534, 588535, 588536, 588537, 588538, 588539, 588540, 588541, 588542, 588543, 588544, 588545, 588546, 588547, 588548, 588549, 588550, 588551, 588552, 588553, 588554, 588555, 588556, 588557, 588558, 588559, 588560, 588561, 588562, 588563, 588564, 588565, 588566, 588567, 588568, 588569, 588570, 588571, 588572, 588573, 588574, 588575, 588576, 588577, 588580, 588581, 588585, 588586, 588589, 588590, 588599, 588603, 588606, 588608, 588610, 588614, 588616, 588628, 588631, 588632, 588634, 588636, 588638, 588640, 588645, 588646, 588654, 588656, 588658, 588660, 588662, 588664, 588670, 588672, 588676, 588682, 588688, 588696, 588698, 588807, 588808, 588809, 588813, 588814, 588815, 588819, 588820, 588822, 588823, 588838, 588839, 588840, 588841, 588842, 588846, 588847, 588848, 588849, 588850, 588851, 588852, 588853, 588854, 588855, 588856, 588857, 588858, 588859, 588860, 588861, 588862, 588863, 588864, 588865, 588866, 588867, 588868, 588870, 588871, 588872, 588873, 588874, 588875, 588876, 588877, 588878, 588879, 588880, 588881, 588882, 588883, 588884, 598999, 599000, 599001, 599002, 599003, 599004, 599005, 599006, 599007, 599008, 599009, 599010, 599011, 599012, 599013, 599014, 599015, 599018, 599019, 599023, 599024, 599025, 599026, 599027, 599028, 599029, 599030, 599031, 599032, 599033, 599034, 599035, 599058, 599062, 599063, 599064, 599065, 599070, 599071, 599072, 599073, 599074, 599076, 599077, 599078, 599079, 599080, 599081, 599082, 599083, 599084, 599085, 599086, 599087, 599088, 599089, 599090, 599091, 599092, 599093, 599094, 599095, 599096, 599097, 599098, 599102, 599119, 599123, 599124, 599125, 599126, 599127, 599128, 599132, 599133, 599134, 599135, 599136, 599137, 599138, 599139, 599140, 599141, 599142, 599143, 599144, 599145, 599147, 599148, 599149, 599150, 599151, 599152, 599153, 599154, 599155, 599156, 599157, 599158, 599159, 599178, 599179, 599180, 599181, 599182, 599186, 599187, 599188, 599189, 599190, 599191, 599192, 599193, 599194, 599195, 599196, 599197, 599198, 599199, 599200, 599201, 599202, 599203, 599204, 599205, 599206, 599207, 599208, 599209, 599210, 599211, 599212, 599213, 599214, 599215, 599216, 599217, 599218, 599219, 599220, 599221, 599221, 599222, 599223, 599224, 599225, 599226, 599227, 599228, 599229, 599230, 599231, 599232, 599233, 599234, 599235, 599236, 599241, 599247, 599248, 599249, 599255, 599256, 599257, 599258, 599260, 599261, 599262, 599263, 599264, 599265, 599266, 599267, 599268, 599269, 599270, 599271, 599272, 599273, 599274, 599275, 599276, 599277, 599278, 599279, 599280, 599297, 599299, 599306, 599307, 599308, 599309, 599311, 599312, 599313, 599314, 599315, 599316, 599317, 599318, 599319, 599320, 599321, 599322, 599323, 599324, 599325, 599326, 599327, 599328, 599329, 599330, 599338, 599349, 599353, 599354, 599355, 599356, 599357, 599358, 599359, 599360, 599361, 599362, 599363, 599364, 599369, 599371, 599372, 599373, 599376, 599378, 599379, 599382, 599383, 599384, 599385, 599386, 599387, 599388, 599389, 599390, 599391, 599392, 599393, 599394, 599395, 599396, 599397, 599398, 599399, 599400, 599401, 599402, 599403, 599404, 599405, 599406, 599407, 599408, 599409, 599410, 599412, 599413, 599414, 599415, 599416, 599417, 599418, 599419, 599420, 599421, 599422, 599423, 599424, 599425, 599426, 599433, 599434, 599435, 599436, 599437, 599438, 599439, 599440, 599441, 599442, 599443, 599444, 599445, 599446, 599447, 599448, 599450, 599454, 599455, 599456, 599467, 599468, 599469, 599471, 599472, 599473, 599474, 599475, 599476, 599477, 599478, 599479, 599480, 599481, 599482, 599483, 599484, 599485, 599486, 599487, 599488, 599489, 599490, 599491, 599492, 599493, 599494, 599495, 599496, 599497, 599498, 599499, 599500, 599501, 599502, 599503, 599504, 599505, 599506, 599507, 599508, 599509, 599512, 599515, 599518, 599531, 599541, 599541, 599546, 599547, 599548, 599549, 599550, 599552, 599553, 599554, 599555, 599557, 599558, 599561, 599562, 599563, 599564, 599565, 599566, 599567, 599568, 599569, 599570, 599577, 599578, 599579, 599580, 599581, 599581, 599582, 599584, 599585, 599586, 599587, 599588, 599589, 599590, 599591, 599592, 599593, 599594, 599595, 601321, 601322, 601323, 601325, 601327, 601328, 601329, 601330, 601332, 601333, 601334, 601335, 601336, 601337, 601338, 601339, 601341, 601342, 601343, 601344, 601345, 601346, 601347, 601348, 601349, 601362, 601367, 601368, 601369, 601371, 601372, 601373, 601374, 601375, 601377, 601378, 601380, 601381, 601382, 601383, 601384, 601385, 601386, 601387, and 601388.

In certain embodiments, the following antisense compounds or oligonucleotides target a region of a CFB nucleic acid and effect at least a 50% inhibition of a CFB mRNA, SEQ ID NOs: 12, 30, 33, 36, 37, 84, 85, 86, 87, 88, 89, 90, 90, 91, 92, 93, 94, 95, 96, 97, 98, 99, 100, 101, 102, 103, 104, 105, 198, 203, 206, 208, 219, 228, 237, 238, 239, 317, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 468, 472, 473, 475, 478, 479, 488, 492, 494, 495, 498, 499, 500, 502, 503, 509, 510, 511, 512, 513, 514, 515, 517, 518, 522, 523, 524, 525, 529, 530, 531, 534, 535, 537, 540, 541, 542, 543, 544, 545, 546, 547, 549, 550, 551, 552, 553, 554, 555, 556, 557, 558, 559, 563, 564, 565, 569, 570, 572, 573, 577, 588, 589, 590, 591, 592, 594, 595, 596, 597, 598, 599, 600, 601, 602, 603, 604, 605, 606, 607, 608, 609, 610, 611, 612, 613, 614, 615, 616, 617, 618, 619, 623, 640, 641, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 700, 704, 705, 706, 707, 708, 709, 711, 712, 713, 714, 715, 716, 717, 718, 720, 721, 722, 723, 724, 725, 726, 727, 728, 729, 730, 731, 732, 733, 734, 735, 736, 737, 738, 739, 740, 741, 742, 743, 744, 745, 745, 746, 747, 748, 749, 750, 751, 752, 753, 754, 755, 756, 758, 759, 760, 761, 762, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 813, 833, 834, 841, 846, 849, 850, 867, and 873.

In certain embodiments, the following antisense compounds or oligonucleotides target a region of a CFB nucleic acid and effect at least a 60% inhibition of a CFB mRNA, ISIS NOs: 516350, 532614, 532635, 532686, 532687, 532688, 532689, 532770, 532800, 532809, 532810, 532811, 532917, 532952, 588512, 588513, 588514, 588515, 588516, 588517, 588518, 588519, 588522, 588523, 588524, 588525, 588527, 588528, 588529, 588530, 588531, 588532, 588533, 588534, 588535, 588536, 588537, 588538, 588539, 588540, 588541, 588542, 588543, 588544, 588545, 588546, 588547, 588548, 588549, 588550, 588551, 588552, 588553, 588554, 588555, 588556, 588557, 588558, 588559, 588560, 588561, 588562, 588563, 588564, 588565, 588566, 588567, 588568, 588569, 588570, 588571, 588572, 588573, 588574, 588575, 588576, 588577, 588636, 588638, 588640, 588664, 588676, 588696, 588698, 588807, 588808, 588814, 588815, 588819, 588820, 588840, 588842, 588846, 588847, 588848, 588849, 588850, 588851, 588852, 588853, 588854, 588855, 588856, 588857, 588858, 588859, 588860, 588861, 588862, 588863, 588864, 588866, 588867, 588868, 588870, 588871, 588872, 588873, 588874, 588875, 588876, 588877, 588878, 588879, 588880, 588881, 588882, 588883, 588884, 598999, 599000, 599001, 599002, 599003, 599004, 599005, 599006, 599007, 599008, 599009, 599010, 599011, 599012, 599013, 599014, 599015, 599019, 599024, 599025, 599026, 599027, 599028, 599029, 599030, 599031, 599032, 599033, 599034, 599035, 599064, 599065, 599071, 599072, 599077, 599078, 599079, 599080, 599083, 599084, 599085, 599086, 599087, 599088, 599089, 599090, 599091, 599092, 599093, 599094, 599095, 599096, 599097, 599125, 599126, 599127, 599133, 599134, 599135, 599136, 599138, 599139, 599140, 599141, 599142, 599148, 599149, 599150, 599151, 599152, 599154, 599155, 599156, 599157, 599158, 599159, 599178, 599179, 599180, 599181, 599187, 599188, 599190, 599192, 599193, 599194, 599195, 599196, 599197, 599198, 599199, 599200, 599201, 599202, 599203, 599204, 599205, 599206, 599207, 599208, 599209, 599210, 599211, 599212, 599213, 599214, 599215, 599216, 599217, 599218, 599219, 599220, 599221, 599222, 599223, 599224, 599225, 599226, 599227, 599228, 599229, 599230, 599231, 599232, 599233, 599234, 599235, 599236, 599247, 599255, 599256, 599257, 599263, 599264, 599265, 599266, 599270, 599271, 599272, 599273, 599274, 599275, 599276, 599277, 599278, 599279, 599280, 599306, 599307, 599308, 599311, 599312, 599313, 599314, 599315, 599316, 599317, 599318, 599319, 599320, 599321, 599322, 599323, 599324, 599325, 599327, 599328, 599329, 599330, 599349, 599353, 599355, 599356, 599357, 599358, 599359, 599360, 599361, 599362, 599363, 599364, 599369, 599371, 599372, 599373, 599376, 599378, 599379, 599382, 599384, 599386, 599387, 599388, 599389, 599390, 599391, 599392, 599393, 599394, 599395, 599396, 599397, 599398, 599399, 599400, 599401, 599402, 599403, 599404, 599405, 599406, 599407, 599408, 599409, 599410, 599412, 599413, 599414, 599415, 599416, 599417, 599418, 599419, 599420, 599421, 599422, 599423, 599424, 599425, 599433, 599434, 599435, 599436, 599437, 599438, 599439, 599440, 599441, 599442, 599443, 599444, 599445, 599446, 599447, 599448, 599456, 599467, 599468, 599471, 599472, 599473, 599474, 599475, 599476, 599477, 599478, 599479, 599480, 599481, 599482, 599483, 599484, 599485, 599486, 599487, 599488, 599489, 599490, 599491, 599492, 599493, 599494, 599495, 599496, 599497, 599498, 599499, 599500, 599501, 599502, 599503, 599504, 599505, 599506, 599507, 599508, 599512, 599531, 599547, 599548, 599549, 599552, 599553, 599554, 599555, 599557, 599558, 599562, 599563, 599564, 599565, 599566, 599567, 599568, 599569, 599570, 599577, 599578, 599579, 599580, 599581, 599582, 599584, 599585, 599586, 599587, 599588, 599589, 599590, 599591, 599592, 599593, 599594, 599595, 601323, 601327, 601329, 601332, 601333, 601333, 601334, 601335, 601336, 601338, 601339, 601341, 601342, 601343, 601344, 601345, 601346, 601347, 601348, 601349, 601368, 601369, 601371, 601372, 601374, 601375, 601377, 601378, 601380, 601381, 601382, 601383, 601384, 601385, 601386, 601387, and 601388.

In certain embodiments, the following antisense compounds or oligonucleotides target a region of a CFB nucleic acid and effect at least a 60% inhibition of a CFB mRNA, SEQ ID NOs: 12, 33, 84, 85, 86, 87, 198, 228, 237, 238, 239, 317, 395, 396, 397, 398, 399, 400, 401, 402, 403, 404, 405, 406, 407, 408, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 472, 473, 513, 514, 515, 531, 537, 541, 542, 543, 544, 545, 546, 547, 549, 550, 551, 552, 553, 554, 555, 556, 557, 558, 564, 565, 569, 570, 577, 590, 592, 595, 596, 597, 598, 599, 600, 601, 602, 603, 604, 605, 606, 607, 608, 609, 610, 611, 612, 613, 614, 615, 616, 617, 618, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 682, 683, 684, 685, 686, 687, 688, 689, 700, 704, 706, 707, 708, 709, 711, 712, 713, 714, 715, 716, 717, 720, 721, 722, 723, 724, 725, 726, 727, 727, 728, 729, 730, 731, 732, 733, 734, 736, 737, 738, 739, 740, 741, 742, 743, 744, 745, 745, 746, 747, 748, 749, 750, 751, 752, 753, 754, 755, 756, 758, 759, 760, 761, 767, 768, 770, 772, 773, 774, 775, 775, 776, 776, 777, 777, 778, 779, 780, 781, 782, 783, 783, 784, 784, 785, 786, 787, 788, 789, 790, 791, 792, 793, 794, 795, 796, 797, 798, 799, 813, 833, 834, 841, 846, 849, and 850.

In certain embodiments, the following antisense compounds or oligonucleotides target a region of a CFB nucleic acid and effect at least a 70% inhibition of a CFB mRNA, ISIS NOs: 516350, 532614, 532686, 532687, 532688, 532770, 532800, 532809, 532810, 532811, 532917, 532952, 588512, 588513, 588514, 588515, 588516, 588517, 588518, 588524, 588529, 588530, 588531, 588532, 588533, 588534, 588535, 588536, 588537, 588538, 588539, 588540, 588541, 588542, 588543, 588544, 588545, 588546, 588547, 588548, 588549, 588550, 588551, 588552, 588553, 588554, 588555, 588556, 588557, 588558, 588559, 588560, 588561, 588562, 588563, 588564, 588565, 588568, 588569, 588570, 588571, 588572, 588573, 588574, 588575, 588577, 588636, 588638, 588640, 588696, 588698, 588807, 588814, 588815, 588819, 588842, 588847, 588848, 588849, 588850, 588851, 588852, 588853, 588856, 588857, 588858, 588859, 588860, 588861, 588862, 588863, 588866, 588867, 588870, 588871, 588872, 588873, 588874, 588875, 588876, 588877, 588878, 588879, 588880, 588881, 588882, 588883, 588884, 599000, 599001, 599003, 599004, 599005, 599008, 599009, 599010, 599011, 599014, 599015, 599024, 599025, 599027, 599028, 599029, 599030, 599031, 599032, 599033, 599034, 599072, 599077, 599080, 599085, 599086, 599087, 599088, 599089, 599090, 599091, 599093, 599094, 599095, 599096, 599097, 599125, 599126, 599134, 599138, 599139, 599148, 599149, 599150, 599151, 599152, 599154, 599155, 599156, 599157, 599158, 599187, 599188, 599193, 599195, 599196, 599197, 599198, 599199, 599200, 599201, 599202, 599203, 599204, 599205, 599206, 599207, 599208, 599210, 599211, 599212, 599213, 599214, 599215, 599216, 599217, 599218, 599219, 599220, 599221, 599222, 599223, 599224, 599225, 599226, 599227, 599228, 599229, 599230, 599231, 599232, 599233, 599234, 599235, 599236, 599266, 599272, 599272, 599273, 599274, 599275, 599277, 599278, 599279, 599280, 599280, 599306, 599311, 599312, 599313, 599314, 599315, 599316, 599317, 599318, 599319, 599320, 599321, 599322, 599323, 599325, 599327, 599328, 599329, 599330, 599355, 599357, 599358, 599359, 599360, 599361, 599362, 599363, 599364, 599369, 599371, 599372, 599373, 599378, 599379, 599382, 599384, 599386, 599387, 599388, 599389, 599390, 599391, 599392, 599393, 599394, 599395, 599396, 599397, 599398, 599399, 599400, 599401, 599402, 599403, 599404, 599405, 599406, 599407, 599408, 599409, 599410, 599413, 599414, 599415, 599416, 599417, 599418, 599419, 599420, 599421, 599422, 599423, 599424, 599433, 599434, 599435, 599436, 599437, 599438, 599439, 599440, 599441, 599442, 599443, 599445, 599446, 599447, 599448, 599472, 599473, 599474, 599475, 599476, 599477, 599478, 599479, 599480, 599481, 599482, 599483, 599484, 599485, 599486, 599487, 599488, 599489, 599490, 599491, 599492, 599493, 599494, 599495, 599496, 599497, 599498, 599499, 599500, 599501, 599502, 599503, 599504, 599505, 599506, 599507, 599508, 599512, 599547, 599548, 599552, 599553, 599554, 599555, 599558, 599562, 599563, 599564, 599566, 599567, 599568, 599569, 599570, 599577, 599578, 599579, 599580, 599581, 599582, 599585, 599586, 599587, 599588, 599589, 599590, 599591, 599592, 599593, 599594, 599595, 601332, 601335, 601341, 601343, 601344, 601345, 601346, 601347, 601348, 601349, 601371, 601372, 601380, 601382, 601383, 601384, 601385, 601386, and 601387.

In certain embodiments, the following antisense compounds or oligonucleotides target a region of a CFB nucleic acid and effect at least a 70% inhibition of a CFB mRNA, SEQ ID NOs: 12, 84, 85, 86, 198, 228, 237, 238, 239, 317, 395, 396, 397, 398, 399, 402, 403, 404, 405, 407, 408, 410, 411, 412, 412, 413, 414, 415, 416, 417, 418, 419, 420, 421, 422, 423, 424, 425, 426, 427, 428, 429, 430, 431, 432, 433, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 464, 465, 472, 473, 513, 514, 515, 541, 542, 543, 544, 545, 546, 547, 549, 550, 551, 552, 553, 554, 555, 556, 557, 564, 565, 569, 592, 595, 596, 597, 598, 599, 600, 601, 602, 603, 604, 606, 607, 608, 609, 610, 611, 612, 613, 614, 615, 616, 617, 618, 645, 646, 647, 648, 649, 650, 653, 654, 655, 656, 659, 660, 662, 663, 664, 665, 666, 668, 669, 670, 671, 672, 673, 674, 675, 676, 677, 677, 678, 679, 680, 682, 683, 684, 686, 687, 688, 689, 706, 708, 709, 711, 712, 713, 714, 715, 720, 721, 722, 723, 724, 725, 726, 727, 728, 729, 730, 731, 732, 733, 734, 736, 737, 738, 739, 740, 741, 742, 743, 744, 745, 746, 747, 748, 749, 750, 751, 752, 753, 754, 755, 756, 767, 768, 773, 775, 776, 777, 778, 779, 780, 781, 782, 783, 784, 785, 786, 787, 788, 789, 790, 791, 792, 793, 793, 794, 795, 797, 798, 799, 813, 833, 834, 841, 846, 849, 867, and 873.

In certain embodiments, the following antisense compounds or oligonucleotides target a region of a CFB nucleic acid and effect at least an 80% inhibition of a CFB mRNA, ISIS NOs: 532686, 532809, 532810, 532811, 532917, 532952, 588512, 588517, 588518, 588533, 588534, 588535, 588536, 588537, 588538, 588539, 588540, 588542, 588543, 588544, 588545, 588546, 588547, 588548, 588549, 588550, 588551, 588552, 588553, 588554, 588555, 588556, 588557, 588558, 588559, 588560, 588561, 588562, 588563, 588564, 588565, 588571, 588638, 588640, 588696, 588698, 588807, 588814, 588849, 588850, 588851, 588853, 588857, 588858, 588859, 588860, 588861, 588862, 588863, 588866, 588867, 588871, 588872, 588873, 588874, 588875, 588876, 588877, 588878, 588879, 588880, 588881, 588882, 588883, 599001, 599024, 599025, 599033, 599086, 599087, 599088, 599089, 599093, 599094, 599095, 599096, 599134, 599139, 599148, 599149, 599151, 599154, 599155, 599156, 599158, 599188, 599195, 599196, 599198, 599201, 599202, 599203, 599204, 599205, 599206, 599207, 599212, 599213, 599215, 599216, 599217, 599218, 599219, 599220, 599221, 599222, 599223, 599224, 599225, 599226, 599227, 599228, 599229, 599230, 599231, 599232, 599233, 599234, 599235, 599236, 599272, 599273, 599275, 599277, 599278, 599279, 599280, 599311, 599313, 599314, 599316, 599317, 599318, 599320, 599321, 599322, 599323, 599327, 599328, 599329, 599330, 599355, 599357, 599358, 599359, 599360, 599361, 599362, 599363, 599364, 599371, 599372, 599373, 599378, 599379, 599382, 599384, 599386, 599387, 599388, 599389, 599390, 599391, 599392, 599393, 599397, 599398, 599399, 599400, 599401, 599403, 599404, 599405, 599407, 599408, 599409, 599410, 599413, 599414, 599415, 599416, 599417, 599418, 599419, 599420, 599421, 599422, 599423, 599424, 599433, 599434, 599435, 599436, 599437, 599438, 599439, 599440, 599441, 599445, 599446, 599447, 599448, 599474, 599476, 599477, 599479, 599481, 599482, 599483, 599485, 599486, 599487, 599488, 599489, 599490, 599491, 599492, 599494, 599495, 599496, 599497, 599498, 599499, 599500, 599502, 599503, 599504, 599505, 599506, 599507, 599508, 599547, 599552, 599553, 599554, 599558, 599563, 599567, 599568, 599569, 599570, 599577, 599578, 599581, 599582, 599585, 599587, 599588, 599590, 599591, 599592, 599593, 599594, 601332, 601344, 601345, 601382, 601383, and 601385.

In certain embodiments, the following antisense compounds or oligonucleotides target a region of a CFB nucleic acid and effect at least a 80% inhibition of a CFB mRNA, SEQ ID NOs: 84, 237, 238, 239, 317, 395, 397, 411, 412, 413, 414, 415, 417, 418, 419, 420, 421, 422, 423, 425, 426, 427, 429, 430, 431, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 472, 473, 514, 515, 542, 543, 544, 545, 546, 547, 550, 551, 552, 553, 554, 555, 556, 557, 564, 595, 599, 600, 601, 602, 603, 606, 607, 608, 609, 610, 611, 612, 613, 614, 615, 616, 617, 618, 646, 655, 660, 662, 663, 666, 669, 670, 671, 672, 673, 675, 676, 677, 678, 679, 682, 684, 686, 687, 688, 689, 706, 708, 709, 711, 712, 713, 714, 715, 720, 722, 723, 724, 725, 726, 727, 729, 730, 731, 732, 733, 736, 737, 738, 739, 740, 741, 742, 743, 744, 745, 746, 747, 748, 749, 750, 751, 752, 753, 754, 755, 756, 768, 775, 776, 778, 781, 782, 783, 784, 785, 787, 788, 789, 790, 791, 792, 793, 794, 799, 813, 833, 834, 841, 849, 867, and 873.

In certain embodiments, the following antisense compounds or oligonucleotides target a region of a CFB nucleic acid and effect at least a 90% inhibition of a CFB mRNA, ISIS NOs: 532686, 532811, 532917, 588536, 588537, 588538, 588539, 588544, 588545, 588546, 588548, 588551, 588552, 588553, 588554, 588555, 588556, 588557, 588558, 588559, 588560, 588561, 588562, 588564, 588638, 588640, 588696, 588698, 588849, 588850, 588851, 588860, 588866, 588867, 588872, 588873, 588874, 588876, 588877, 588878, 588879, 588881, 588883, 599149, 599188, 599203, 599206, 599220, 599221, 599222, 599223, 599224, 599225, 599226, 599227, 599228, 599229, 599235, 599236, 599279, 599280, 599314, 599321, 599362, 599378, 599390, 599391, 599398, 599399, 599404, 599413, 599414, 599416, 599419, 599420, 599422, 599435, 599437, 599438, 599441, 599483, 599494, 599508, 599552, 599553, 599554, 599568, 599570, 599577, 599581, 599591, 599592, and 599593.

In certain embodiments, the following antisense compounds or oligonucleotides target a region of a CFB nucleic acid and effect at least a 90% inhibition of a CFB mRNA, SEQ ID NOs: 84, 238, 239, 317, 412, 413, 420, 421, 426, 434, 436, 437, 438, 439, 440, 442, 443, 444, 445, 446, 448, 451, 452, 453, 454, 455, 456, 457, 458, 459, 460, 461, 462, 464, 465, 472, 473, 514, 515, 542, 543, 544, 545, 546, 551, 553, 555, 556, 599, 600, 601, 602, 610, 616, 617, 618, 662, 666, 670, 676, 677, 678, 688, 689, 713, 723, 729, 730, 740, 741, 742, 743, 744, 745, 746, 747, 748, 749, 755, 756, 768, 783, 793, 833, and 867.

In certain embodiments, a compound can comprise or consist of any oligonucleotide targeted to CFB described herein and a conjugate group.

In certain embodiments, a compound comprises a modified oligonucleotide and a conjugate group, wherein the modified oligonucleotide consists of 10 to 30 linked nucleosides complementary within nucleotides 2193-2212, 2195-2210, 2457-2476, 2571-2590, 2584-2603, 2588-2607, 2592-2611, 2594-2613, 2597-2616, 2600-2619, or 2596-2611 of SEQ ID NO: 1.

In certain embodiments, a compound comprises a modified oligonucleotide and a conjugate group, wherein the modified oligonucleotide consists of 10 to 30 linked nucleosides having a nucleobase sequence comprising any one of SEQ ID NOs: 198, 228, 237, 440, 444, 448, 450, 453, 455, 549, and 598.

In certain embodiments, a compound comprises a modified oligonucleotide and a conjugate group, wherein the modified oligonucleotide has a nucleobase sequence consisting of any one of SEQ ID NOs: 198, 228, 237, 440, 444, 448, 450, 453, 455, 549, and 598.

In certain embodiments, any of the foregoing compounds or oligonucleotides can comprise at least one modified internucleoside linkage, at least one modified sugar, and/or at least one modified nucleobase.

In certain aspects, any of the foregoing compounds or oligonucleotides can comprise at least one modified sugar. In certain aspects, at least one modified sugar comprises a 2'-O-methoxyethyl group. In certain aspects, at least one modified sugar is a bicyclic sugar, such as a 4'-CH(CH$_3$)—O-2' group, a 4'-CH$_2$—O-2' group, or a 4'-(CH$_2$)$_2$—O-2'group.

In certain aspects, the modified oligonucleotide comprises at least one modified internucleoside linkage, such as a phosphorothioate internucleoside linkage.

In certain embodiments, the modified oligonucleotide comprises at least 1, 2, 3, 4, 5, 6, or 7 phosphodiester internucleoside linkages.

In certain embodiments, each internucleoside linkage of the modified oligonucleotide is selected from a phosphodiester internucleoside linkage and a phosphorothioate internucleoside linkage.

In certain embodiments, each internucleoside linkage of the modified oligonucleotide is a phosphorothioate linkage.

In certain embodiments, any of the foregoing compounds or oligonucleotides comprises at least one modified nucleobase, such as 5-methylcytosine.

In certain embodiments, a compound comprises a conjugate group and a modified oligonucleotide comprising:

a gap segment consisting of linked deoxynucleosides;
a 5' wing segment consisting of linked nucleosides; and
a 3' wing segment consisting of linked nucleosides;
wherein the gap segment is positioned between the 5' wing segment and the 3' wing segment and wherein each nucleoside of each wing segment comprises a modified sugar. In certain embodiments, the oligonucleotide consists of 10 to 30 linked nucleosides having a nucleobase sequence comprising the sequence recited in SEQ ID NO: 198, 228, 237, 440, 444, 448, 450, 453, 455, 549, or 598.

In certain embodiments, the modified oligonucleotide has a nucleobase sequence comprising or consisting of the sequence recited in SEQ ID NO: 198, 228, 237, 440, 444, 448, 450, 453, or 455, wherein the modified oligonucleotide comprises:

a gap segment consisting of ten linked deoxynucleosides;
a 5' wing segment consisting of five linked nucleosides; and
a 3' wing segment consisting of five linked nucleosides;
wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage and wherein each cytosine is a 5-methylcytosine.

In certain embodiments, a compound comprises or consists of a single-stranded modified oligonucleotide and a conjugate group, wherein the modified oligonucleotide consists of 20 linked nucleosides having a nucleobase sequence consisting of the sequence recited in SEQ ID NO: 198, 228, 237, 440, 444, 448, 450, 453, or 455, wherein the oligonucleotide comprises:

a gap segment consisting of ten linked deoxynucleosides;
a 5' wing segment consisting of five linked nucleosides; and
a 3' wing segment consisting of five linked nucleosides;
wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage; and wherein each cytosine is a 5-methylcytosine.

In certain embodiments, a compound comprises or consists of ISIS 588540 and a conjugate group. In certain embodiments, ISIS 588540 has the following chemical structure:

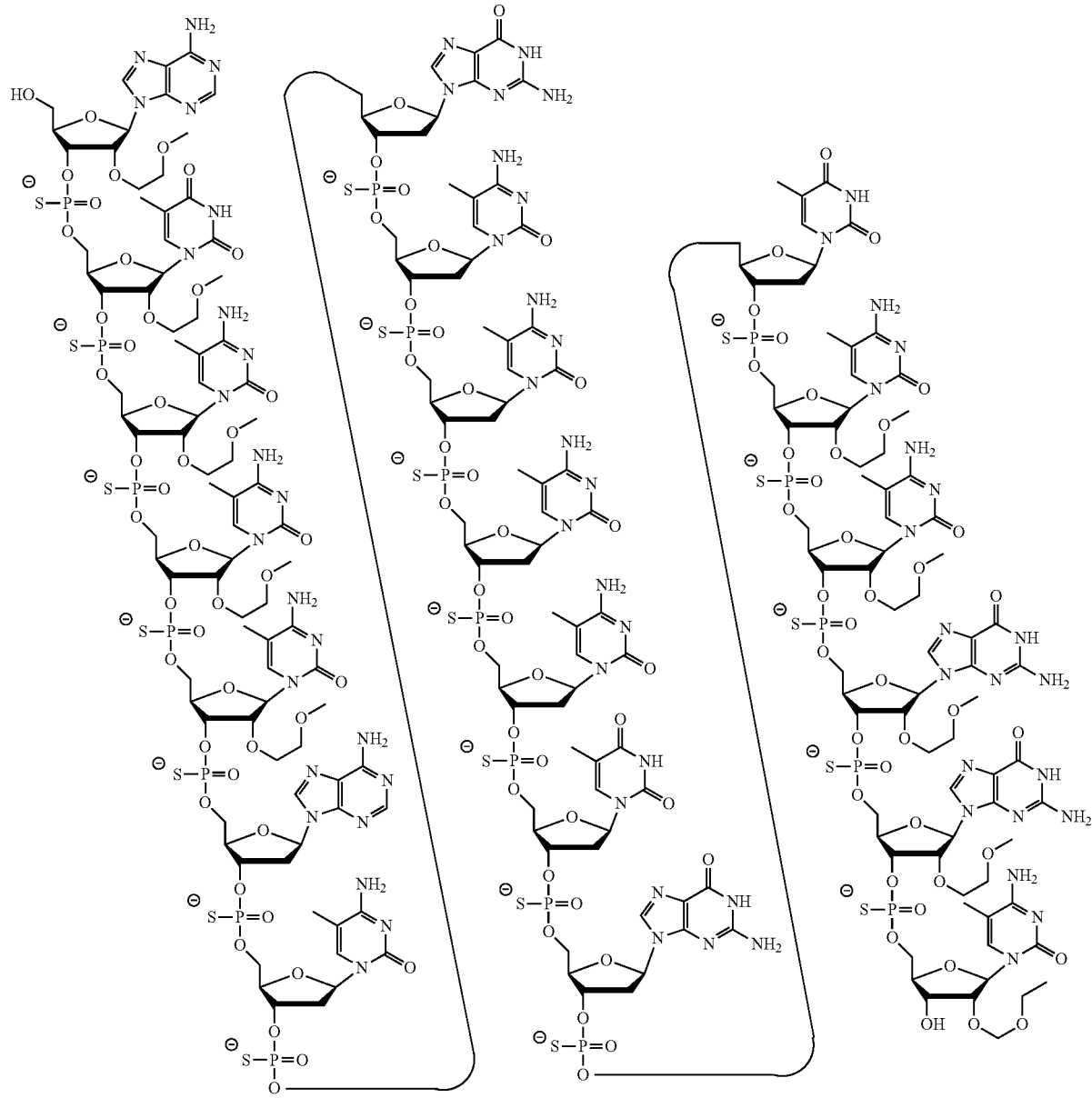

In certain embodiments, the modified oligonucleotide has a nucleobase sequence comprising or consisting of the sequence recited in SEQ ID NO: 549, wherein the modified oligonucleotide comprises
a gap segment consisting of ten linked deoxynucleosides;
a 5' wing segment consisting of three linked nucleosides; and
a 3' wing segment consisting of three linked nucleosides;
wherein the gap segment is positioned between the 5' wing segment and the 3' wing segment; wherein each nucleoside of each wing segment comprises a cEt sugar; wherein each internucleoside linkage is a phosphorothioate linkage; and wherein each cytosine is a 5-methylcytosine.

In certain aspects, the modified oligonucleotide has a nucleobase sequence comprising or consisting of the sequence recited in SEQ ID NO: 598, wherein the modified oligonucleotide comprises a gap segment consisting of ten linked deoxynucleosides;

a 5' wing segment consisting of three linked nucleosides; and a 3' wing segment consisting of three linked nucleosides;

wherein the gap segment is positioned between the 5' wing segment and the 3' wing segment; wherein the 5' wing segment comprises a 2'-O-methoxyethyl sugar, 2'-O-methoxyethyl sugar, and cEt sugar in the 5' to 3' direction; wherein the 3' wing segment comprises a cEt sugar, cEt sugar, and 2'-O-methoxyethyl sugar in the 5' to 3' direction; wherein each internucleoside linkage is a phosphorothioate linkage; and wherein each cytosine is a 5-methylcytosine.

In any of the foregoing embodiments, the compound or oligonucleotide can be at least 85%, at least 90%, at least 95%, at least 98%, at least 99%, or 100% complementary to a nucleic acid encoding CFB.

In any of the foregoing embodiments, the compound or oligonucleotide can be single-stranded.

In certain embodiments, the conjugate group is linked to the modified oligonucleotide at the 5' end of the modified oligonucleotide. In certain embodiments, the conjugate group is linked to the modified oligonucleotide at the 3' end of the modified oligonucleotide. In certain embodiments, the conjugate group comprises at least one N-Acetylgalactosamine (GalNAc), at least two N-Acetylgalactosamines (GalNAcs), or at least three N-Acetylgalactosamines (GalNAcs).

In certain embodiments, a compound having the following chemical structure comprises or consists of ISIS 588540 with a 5'-X, wherein X is a conjugate group comprising GalNAc as described herein:

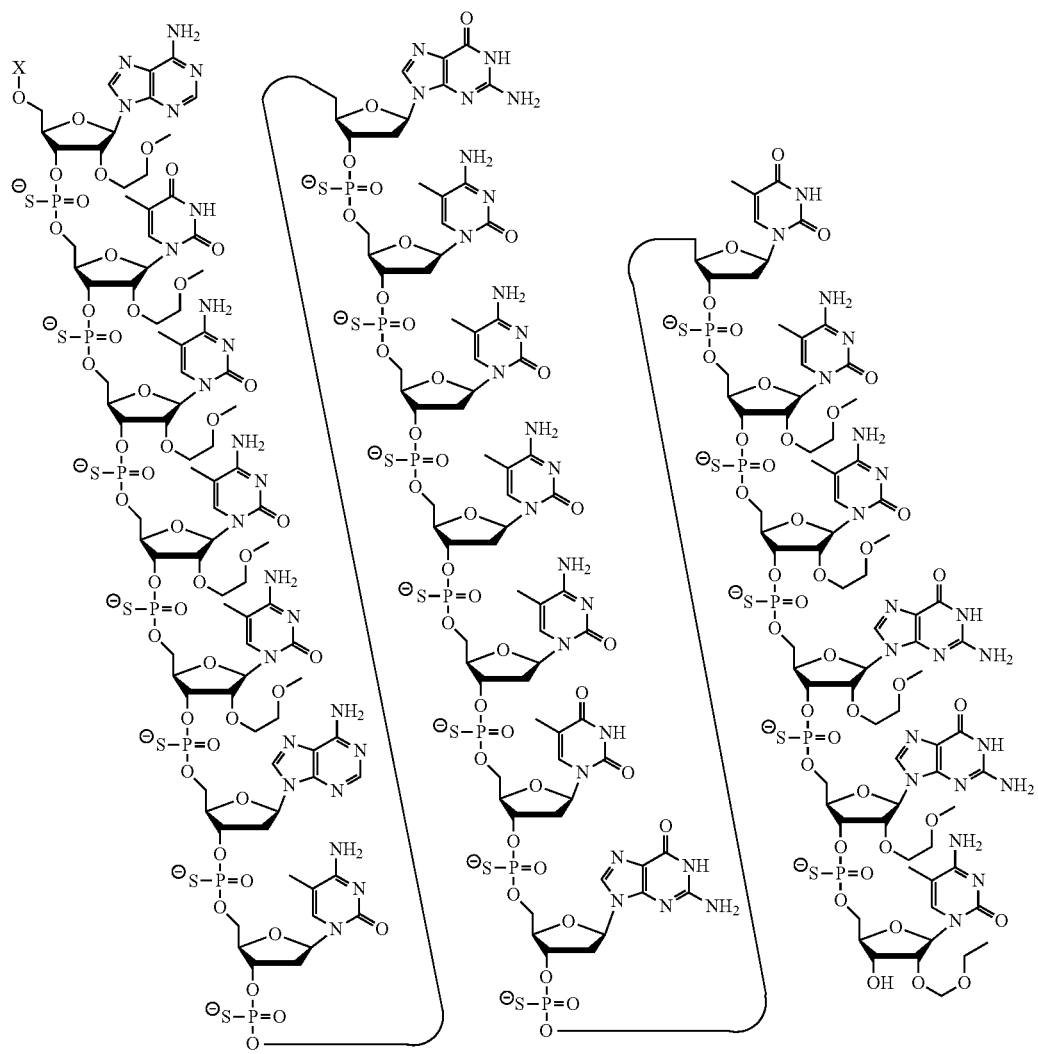

In certain embodiments, a compound comprises or consists of SEQ ID NO: 440, 5'-GalNAc, and chemical modifications as represented by the following chemical structure:

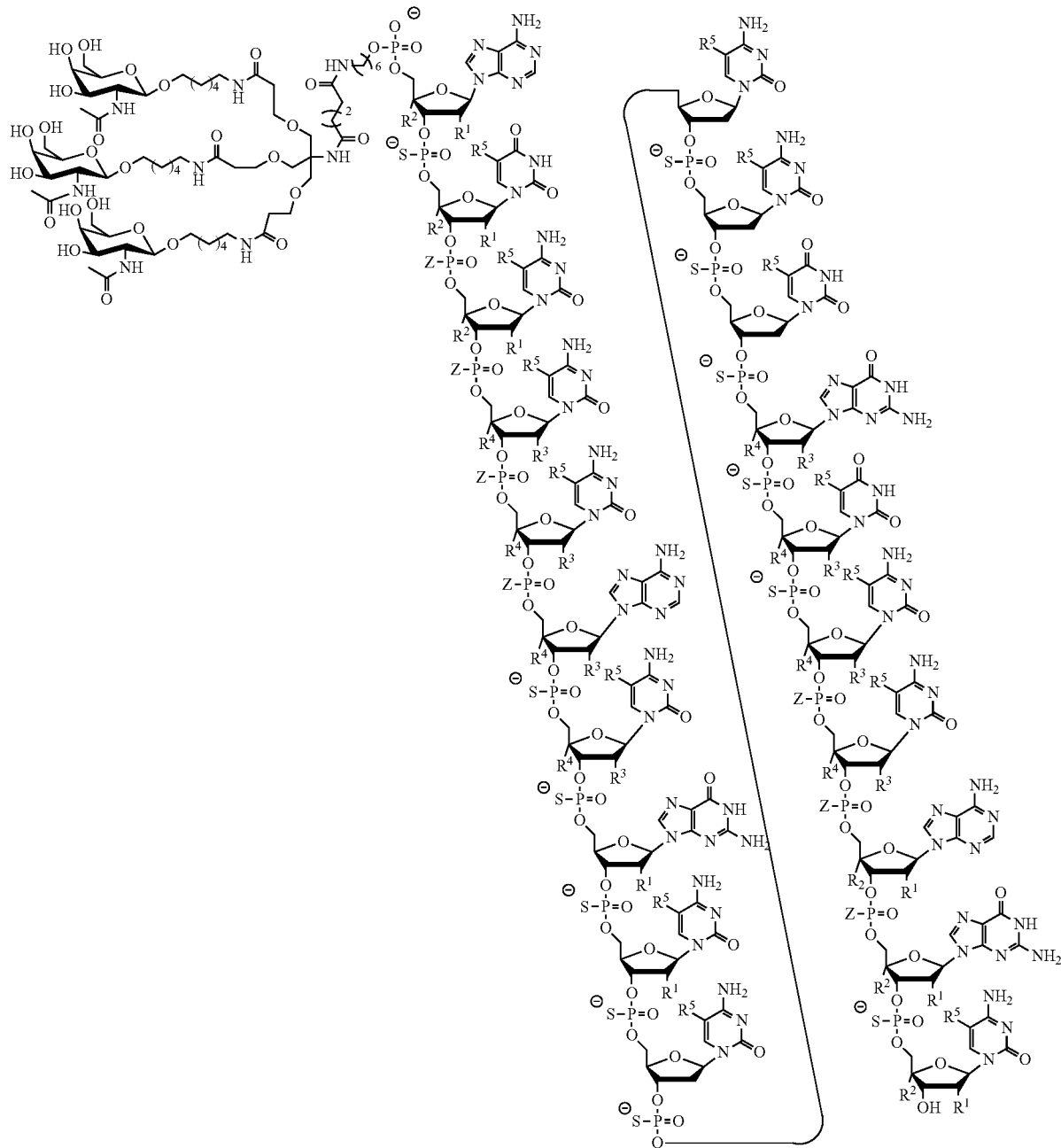

wherein either $R^1$ is —OCH$_2$CH$_2$OCH$_3$ (MOE) and $R^2$ is H; or $R^1$ and $R^2$ together form a bridge, wherein $R^1$ is —O— and $R^2$ is —CH$_2$—, —CH(CH$_3$)—, or —CH$_2$CH$_2$—, and $R^1$ and $R^2$ are directly connected such that the resulting bridge is selected from: —O—CH$_2$—, —O—CH(CH$_3$)—, and —O—CH$_2$CH$_2$—;

And for each pair of $R^3$ and $R^4$ on the same ring, independently for each ring: either $R^3$ is selected from H and —OCH$_2$CH$_2$OCH$_3$ and $R^4$ is H; or $R^3$ and $R^4$ together form a bridge, wherein $R^3$ is —O—, and $R^4$ is —CH$_2$—, —CH(CH$_3$)—, or —CH$_2$CH$_2$— and $R^3$ and $R^4$ are directly connected such that the resulting bridge is selected from: —O—CH$_2$—, —O—CH(CH$_3$)—, and —O—CH$_2$CH$_2$—;

And $R^5$ is selected from H and —CH$_3$;

And Z is selected from S$^-$ and O$^-$.

In certain embodiments, a compound comprises ISIS 696844. In certain embodiments, a compound consists of ISIS 696844. In certain embodiments, ISIS 696844 has the following chemical structure:
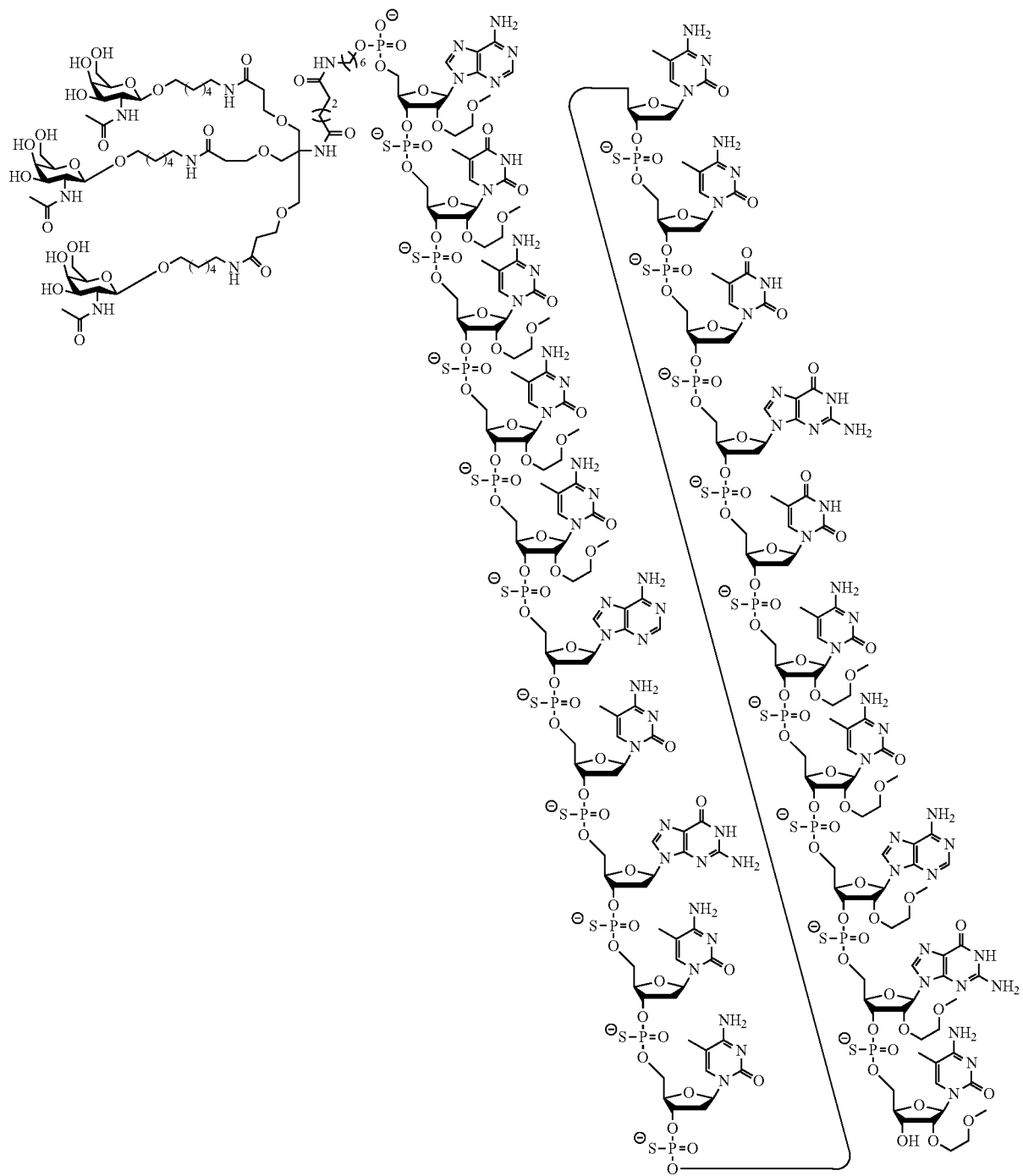

In certain embodiments, a compound comprises ISIS 696845. In certain embodiments, a compound consists of ISIS 696845. In certain embodiments, ISIS 696845 has the following chemical structure:
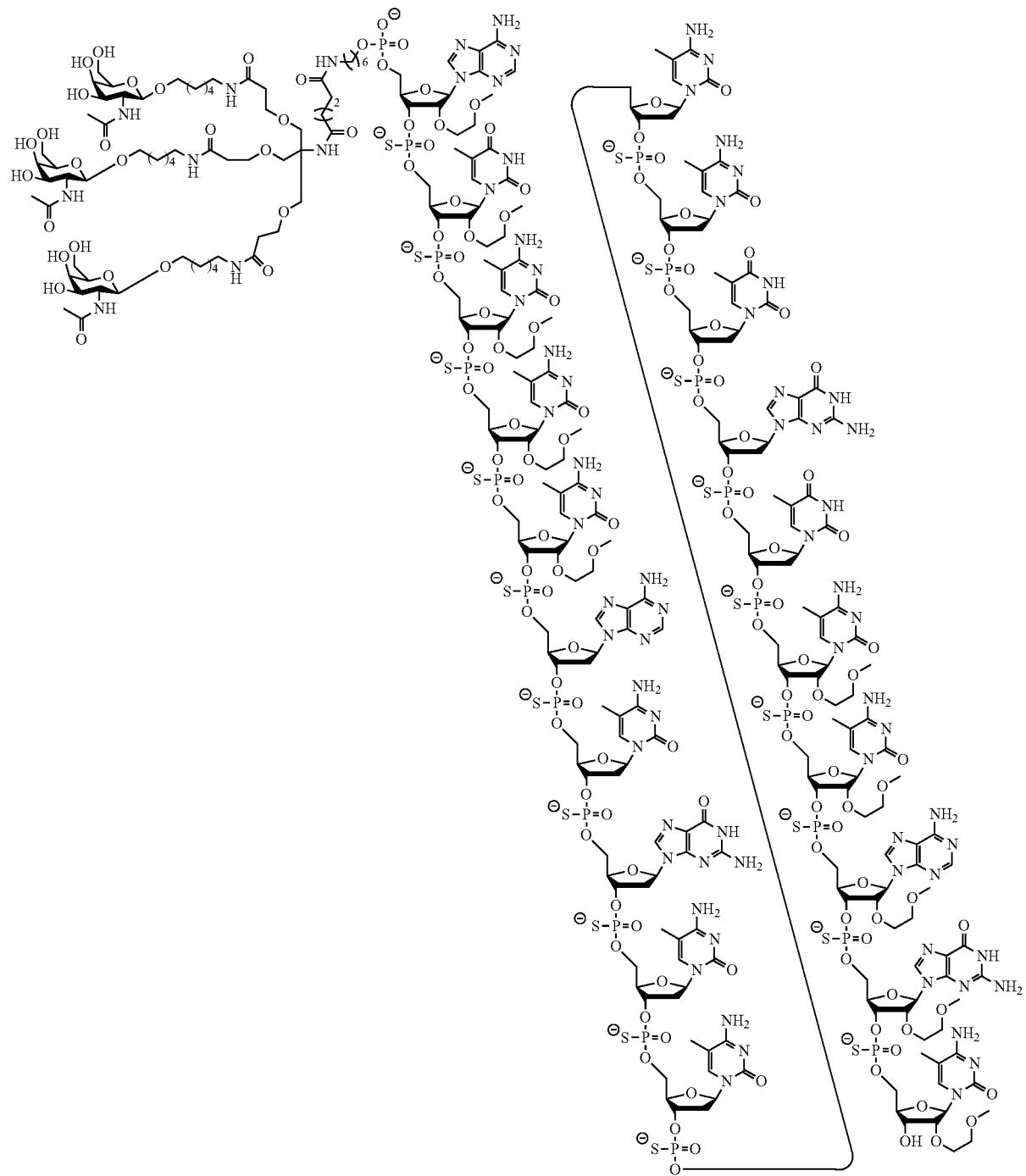

In certain embodiments, a compound comprises ISIS 698969. In certain embodiments, a compound consists of ISIS 698969. In certain embodiments, ISIS 698969 has the following chemical structure:
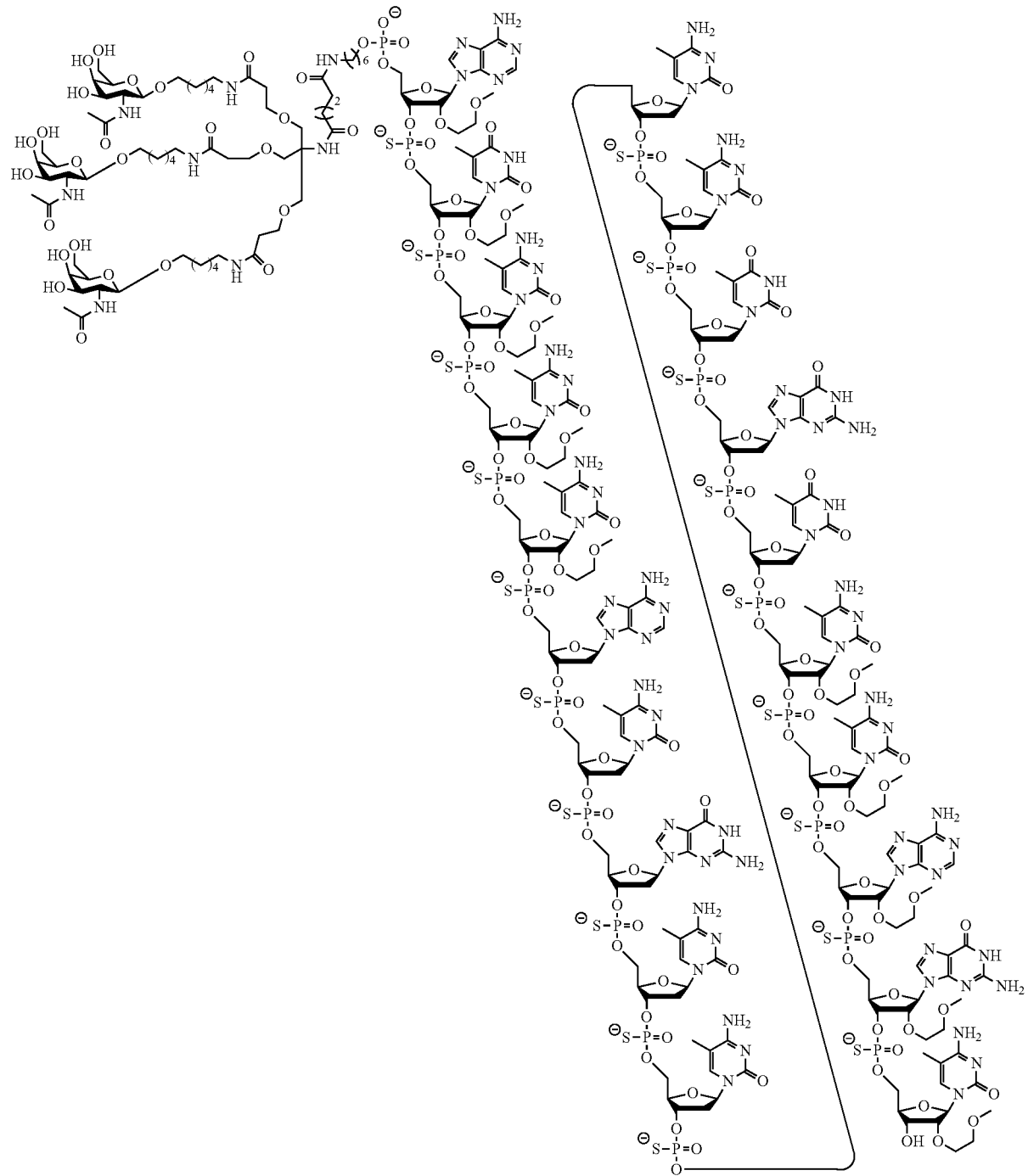

In certain embodiments, a compound comprises ISIS 698970. In certain embodiments, a compound consists of ISIS 698970. In certain embodiments, ISIS 698970 has the following chemical structure:

least one of an in vitro $IC_{50}$ of less than 250 nM, less than 200 nM, less than 150 nM, less than 100 nM, less than 90 nM, less than 80 nM, less than 70 nM, less than 65 nM, less than 60 nM, less than 55 nM, less than 50 nM, less than 45

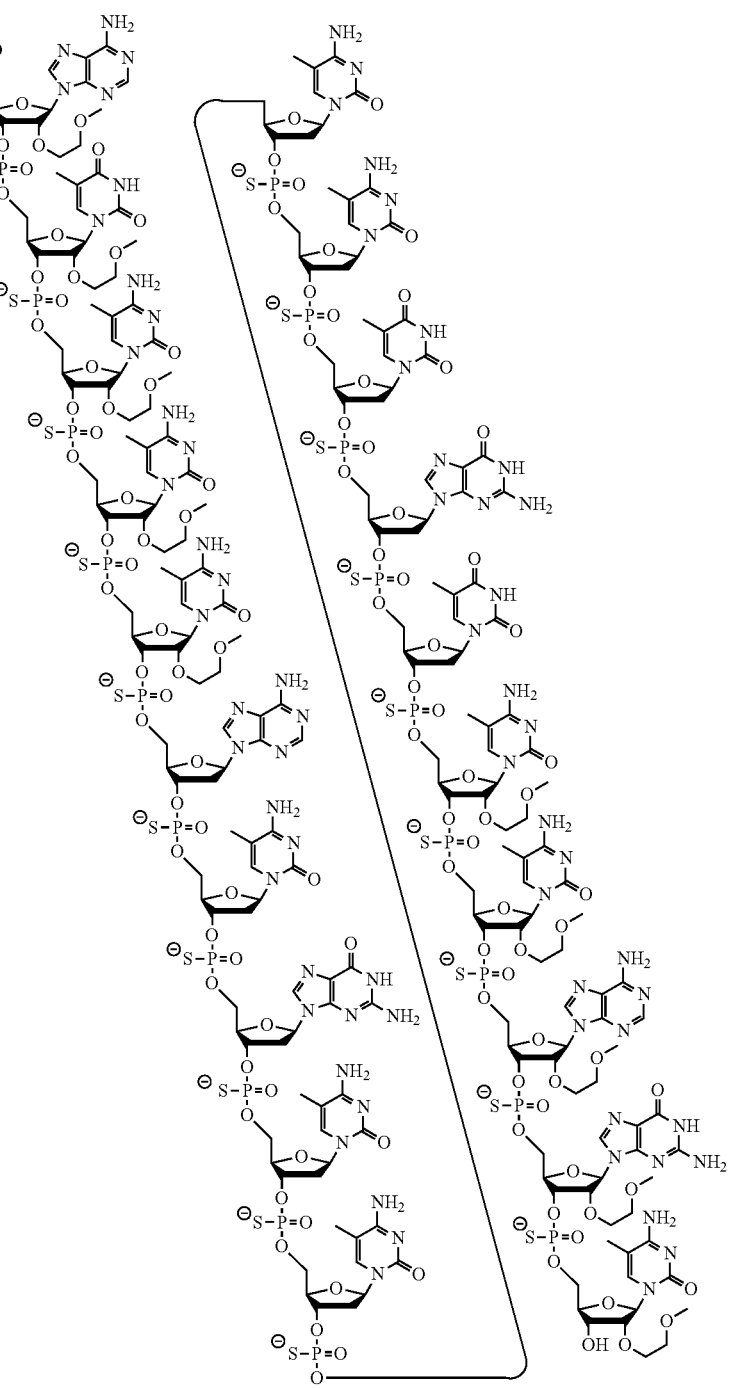

Certain embodiments provide compositions comprising any of the compounds comprising or consisting of a modified oligonucleotide targeted to CFB or salt thereof and a conjugate group, and at least one of a pharmaceutically acceptable carrier or diluent.

In certain embodiments, the compounds or compositions as described herein are efficacious by virtue of having at nM, less than 40 nM, less than 35 nM, less than 30 nM, less than 25 nM, or less than 20 nM.

In certain embodiments, the compounds or compositions as described herein are highly tolerable as demonstrated by having at least one of an increase an ALT or AST value of no more than 4 fold, 3 fold, or 2 fold over saline treated animals or an increase in liver, spleen, or kidney weight of no more than 30%, 20%, 15%, 12%, 10%, 5%, or 2%. In certain embodiments, the compounds or compositions as described herein are highly tolerable as demonstrated by having no increase of ALT or AST over saline treated animals. In certain embodiments, the compounds or compositions as described herein are highly tolerable as demonstrated by having no increase in liver, spleen, or kidney weight over saline treated animals.

Certain embodiments provide a composition comprising the compound of any of the aforementioned embodiments or salt thereof and at least one of a pharmaceutically acceptable carrier or diluent. In certain aspects, the composition has a viscosity less than about 40 centipoise (cP), less than about 30 centipose (cP), less than about 20 centipose (cP), less than about 15 centipose (cP), or less than about 10 centipose (cP). In certain aspects, the composition having any of the aforementioned viscosities comprises a compound provided herein at a concentration of about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL. In certain aspects, the composition having any of the aforementioned viscosities and/or compound concentrations has a temperature of room temperature or about 20° C., about 21° C., about 22° C., about 23° C., about 24° C., about 25° C., about 26° C., about 27° C., about 28° C., about 29° C., or about 30° C.

In certain embodiments, a method of treating, preventing, or ameliorating a disease associated with dysregulation of the complement alternative pathway in a subject comprises administering to the subject a compound or composition described herein, thereby treating, preventing, or ameliorating the disease. In certain aspects, the complement alternative pathway is activated greater than normal. In certain embodiments, a method of treating, preventing, or ameliorating a disease associated with dysregulation of the complement alternative pathway in a subject comprises administering to the subject a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 6-808. In certain embodiments, a method of treating, preventing, or ameliorating a disease associated with dysregulation of the complement alternative pathway in a subject comprises administering to the subject a compound comprising or consisting of a modified oligonucleotide and a conjugate group, wherein the modified oligonucleotide consists of 10 to 30 linked nucleosides having a nucleobase sequence comprising any one of SEQ ID NOs: 198, 228, 237, 440, 444, 448, 450, 453, 455, 549, and 598. In certain embodiments, a method of treating, preventing, or ameliorating a disease associated with dysregulation of the complement alternative pathway in a subject comprises administering to the subject a compound comprising or consisting of ISIS 696844, ISIS 696845, ISIS 698969, or ISIS 698970.

In certain embodiments, a method of treating, preventing, or ameliorating macular degeneration, such as age-related macular degeneration (AMD) in a subject comprises administering to the subject a compound or composition described herein, thereby treating, preventing, or ameliorating AMD. In certain aspects, the complement alternative pathway is activated greater than normal. In certain aspects, the AMD is wet AMD. In certain aspects, the AMD is dry AMD, such as Geographic Atrophy. In certain embodiments, a method of treating, preventing, or ameliorating macular degeneration in a subject, such as age-related macular degeneration (AMD), wet AMD, dry AMD, or Geographic Atrophy comprises administering to the subject a a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 6-808. In certain embodiments, a method of treating, preventing, or ameliorating macular degeneration, such as age-related macular degeneration (AMD), wet AMD, dry AMD, or Geographic Atrophy in a subject comprises administering to the subject a comprises administering to the subject a compound comprising or consisting of a modified oligonucleotide and a conjugate group, wherein the modified oligonucleotide consists of 10 to 30 linked nucleosides having a nucleobase sequence comprising any one of SEQ ID NOs: 198, 228, 237, 440, 444, 448, 450, 453, 455, 549, and 598. In certain embodiments, a method of treating, preventing, or ameliorating macular degeneration, such as age-related macular degeneration (AMD), wet AMD, dry AMD, or Geographic Atrophy in a subject comprises administering to the subject a compound comprising or consisting of ISIS 696844, ISIS 696845, ISIS 698969, or ISIS 698970. In certain aspects, the compound or composition is administered to the subject parenterally.

In certain embodiments, a method of treating, preventing, or ameliorating a kidney disease associated with dysregulation of the complement alternative pathway in a subject comprises administering to the subject a compound or composition described herein, thereby treating, preventing, or ameliorating the kidney disease. In certain embodiments, a method of treating, preventing, or ameliorating a kidney disease associated with dysregulation of the complement alternative pathway in a subject comprises administering to the subject a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 6-808. In certain embodiments, a method of treating, preventing, or ameliorating a kidney disease associated with dysregulation of the complement alternative pathway in a subject comprises administering to the subject a compound comprising or consisting of a modified oligonucleotide and a conjugate group, wherein the modified oligonucleotide consists of 10 to 30 linked nucleosides having a nucleobase sequence comprising any one of SEQ ID NOs: 198, 228, 237, 440, 444, 448, 450, 453, 455, 549, and 598. In certain embodiments, a method of treating, preventing, or ameliorating a kidney disease associated with dysregulation of the complement alternative pathway in a subject comprises administering to the subject a compound comprising or consisting of ISIS 696844, ISIS 696845, ISIS 698969, or ISIS 698970. In certain aspects, the complement alternative pathway is activated greater than normal. In certain aspects, the kidney disease is lupus nephritis, systemic lupus erythematosus (SLE), dense deposit disease (DDD), C3 glomerulonephritis (C3GN), CFHR5 nephropathy, or atypical hemolytic uremic syndrome (aHUS), or any combination thereof. In certain aspects, the kidney disease is associated with C3 deposits, such as C3 deposits in the glomerulus. In certain aspects, the kidney disease is associated with lower than normal circulating C3 levels, such as serum or plasma C3 levels. In certain aspects, administering the compound or composition reduces or inhibits accumulation of ocular C3 levels, such as C3 protein levels. In certain aspects, administering the compound or composition reduces the level of ocular C3 deposits or inhibits accumulation of ocular C3 deposits. In certain aspects, the compound or composition is administered to the subject parenterally. In certain aspects, administering the compound or composition reduces or inhibits accumulation of C3 levels in the kidney, such as C3 protein levels. In certain aspects, administering the compound or composition reduces the level of kidney C3 deposits or inhibits accumulation of kidney C3 deposits, such as C3 levels in the glomerulus. In certain aspects, the subject is identified as having or at risk of having a disease associated with dysregulation of the complement alternative pathway, for example by detecting complement levels or membrane-attack complex levels in the subject's blood and/or performing a genetic test for gene mutations of complement factors associated with the disease.

In certain embodiments, a method of inhibiting expression of Complement Factor B (CFB) in a subject having, or at risk of having, a disease associated with dysregulation of the complement alternative pathway comprises administering a compound or composition described herein to the subject, thereby inhibiting expression of CFB in the subject. In certain embodiments, a method of inhibiting expression of Complement Factor B (CFB) in a subject having, or at risk of having, a disease associated with dysregulation of the complement alternative pathway comprises administering to the subject a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 6-808. In certain embodiments, a method of inhibiting expression of Complement Factor B (CFB) in a subject having, or at risk of having, a disease associated with dysregulation of the complement alternative pathway comprises administering to the subject a compound comprising or consisting of a modified oligonucleotide and a conjugate group, wherein the modified oligonucleotide consists of 10 to 30 linked nucleosides having a nucleobase sequence comprising any one of SEQ ID NOs: 198, 228, 237, 440, 444, 448, 450, 453, 455, 549, and 598. In certain embodiments, a method of inhibiting expression of Complement Factor B (CFB) in a subject having, or at risk of having, a disease associated with dysregulation of the complement alternative pathway comprises administering to the subject a compound comprising or consisting of ISIS 696844, ISIS 696845, ISIS 698969, or ISIS 698970. In certain aspects, administering the compound or composition inhibits expression of CFB in the eye. In certain aspects, the subject has, or is at risk of having, age related macular degeneration (AMD), such as wet AMD and dry AMD. In certain aspects, dry AMD can be Geographic Atrophy. Geographic Atrophy is considered an advanced form of dry AMD involving degeneration of the retina. In certain aspects, administering the compound or composition inhibits expression of CFB in the kidney, such as in the glomerulus. In certain aspects, the subject has, or is at risk of having, lupus nephritis, systemic lupus erythematosus (SLE), dense deposit disease (DDD), C3 glomerulonephritis (C3GN), CFHR5 nephropathy, or atypical hemolytic uremic syndrome (aHUS), or any combination thereof.

In certain embodiments, a method of reducing or inhibiting accumulation of C3 deposits in the eye of a subject having, or at risk of having, a disease associated with dysregulation of the complement alternative pathway comprises administering a compound or composition described herein to the subject, thereby reducing or inhibiting accumulation of C3 deposits in the eye of the subject. In certain embodiments, a method of reducing or inhibiting accumulation of C3 deposits in the eye of a subject having, or at risk of having, a disease associated with dysregulation of the complement alternative pathway comprises administering to the subject a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 6-808. In certain embodiments, a method of reducing or inhibiting accumulation of C3 deposits in the eye of a subject having, or at risk of having, a disease associated with dysregulation of the complement alternative pathway comprises administering to the subject a compound comprising or consisting of a modified oligonucleotide and a conjugate group, wherein the modified oligonucleotide consists of 10 to 30 linked nucleosides having a nucleobase sequence comprising any one of SEQ ID NOs: 198, 228, 237, 440, 444, 448, 450, 453, 455, 549, and 598. In certain embodiments, a method of reducing or inhibiting accumulation of C3 deposits in the eye of a subject having, or at risk of having, a disease associated with dysregulation of the complement alternative pathway comprises administering to the subject a compound comprising or consisting of ISIS 696844, ISIS 696845, ISIS 698969, or ISIS 698970. In certain aspects, the subject has, or is at risk of having, age related macular degeneration (AMD), such as wet AMD and dry AMD. In certain aspects, dry AMD can be Geographic Atrophy. In certain aspects, the compound or composition is administered to the subject parenterally.

In certain embodiments, a method of reducing or inhibiting accumulation of C3 deposits in the kidney of a subject having, or at risk of having, a disease associated with dysregulation of the complement alternative pathway comprises administering a compound or composition described herein to the subject, thereby reducing or inhibiting accumulation of C3 deposits in the kidney of the subject. In certain embodiments, a method of reducing or inhibiting accumulation of C3 deposits in the kidney of a subject having, or at risk of having, a disease associated with dysregulation of the complement alternative pathway comprises administering to the subject a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 6-808. In certain embodiments, a method of reducing or inhibiting accumulation of C3 deposits in the kidney of a subject having, or at risk of having, a disease associated with dysregulation of the complement alternative pathway comprises administering to the subject a compound comprising or consisting of a modified oligonucleotide and a conjugate group, wherein the modified oligonucleotide consists of 10 to 30 linked nucleosides having a nucleobase sequence comprising any one of SEQ ID NOs: 198, 228, 237, 440, 444, 448, 450, 453, 455, 549, and 598. In certain embodiments, a method of reducing or inhibiting accumulation of C3 deposits in the kidney of a subject having, or at risk of having, a disease associated with dysregulation of the complement alternative pathway comprises administering to the subject a compound comprising or consisting of ISIS 696844, ISIS 696845, ISIS 698969, or ISIS 698970. In certain aspects, the subject has, or is at risk of having, lupus nephritis, systemic lupus erythematosus (SLE), dense deposit disease (DDD), C3 glomerulonephritis (C3GN), CFHR5 nephropathy, or atypical hemolytic uremic syndrome (aHUS), or any combination thereof. In certain aspects, the compound or composition is administered to the subject parenterally.

Certain embodiments are drawn to use of a compound or composition described herein for treating a disease associated with dysregulation of the complement alternative pathway. Certain embodiments are drawn to use of a compound comprising or consisting of a modified oligonucleotide and a conjugate group, wherein the modified oligonucleotide consists of 10 to 30 linked nucleosides and has a nucleobase sequence comprising the nucleobase sequence of any one of SEQ ID NOs: 6-808, for treating a disease associated with dysregulation of the complement alternative pathway. Certain embodiments are drawn to use of a compound comprising or consisting of a modified oligonucleotide and a conjugate group, wherein the modified oligonucleotide consists of 10 to 30 linked nucleosides having a nucleobase sequence comprising any one of SEQ ID NOs: 198, 228, 237, 440, 444, 448, 450, 453, 455, 549, and 598, for treating a disease associated with dysregulation of the complement alternative pathway. Certain embodiments are drawn to use of a compound comprising or consisting of ISIS 696844, ISIS 696845, ISIS 698969, or ISIS 698970 for treating a disease associated with dysregulation of the complement alternative pathway. In certain aspects, the complement alternative pathway is activated greater than normal. In certain aspects, the disease is macular degeneration, such as age related macular degeneration (AMD), which can be wet AMD or dry AMD. In certain aspects, dry AMD can be Geographic Atrophy. In certain aspects, the disease is a kidney disease such as lupus nephritis, systemic lupus erythematosus (SLE), dense deposit disease (DDD), C3 glomerulonephritis (C3GN), CFHR5 nephropathy, or atypical hemolytic uremic syndrome (aHUS), or any combination thereof. In certain aspects, the compound or composition is administered to the subject parenterally.

In certain embodiments, a compound or composition described herein is administered parenterally. For example, in certain embodiments the compound or composition can be administered through injection or infusion. Parenteral administration includes subcutaneous administration, intravenous administration, intramuscular administration, intraarterial administration, intraperitoneal administration, or intracranial administration, e.g. intrathecal or intracerebroventricular administration.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted.

In certain embodiments, an antisense compound is 10 to 30 subunits in length. In certain embodiments, an antisense compound is 12 to 30 subunits in length. In certain embodiments, an antisense compound is 12 to 22 subunits in length. In certain embodiments, an antisense compound is 14 to 30 subunits in length. In certain embodiments, an antisense compound is 14 to 20 subunits in length. In certain embodiments, an antisense compound is 15 to 30 subunits in length. In certain embodiments, an antisense compound is 15 to 20 subunits in length. In certain embodiments, an antisense compound is 16 to 30 subunits in length. In certain embodiments, an antisense compound is 16 to 20 subunits in length. In certain embodiments, an antisense compound is 17 to 30 subunits in length. In certain embodiments, an antisense compound is 17 to 20 subunits in length. In certain embodiments, an antisense compound is 18 to 30 subunits in length. In certain embodiments, an antisense compound is 18 to 21 subunits in length. In certain embodiments, an antisense compound is 18 to 20 subunits in length. In certain embodiments, an antisense compound is 20 to 30 subunits in length. In other words, such antisense compounds are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, an antisense compound is 14 subunits in length. In certain embodiments, an antisense compound is 16 subunits in length. In certain embodiments, an antisense compound is 17 subunits in length. In certain embodiments, an antisense compound is 18 subunits in length. In certain embodiments, an antisense compound is 19 subunits in length. In certain embodiments, an antisense compound is 20 subunits in length. In other embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In certain embodiments antisense oligonucleotides may be shortened or truncated. For example, a single subunit may be deleted from the 5' end (5' truncation), or alternatively from the 3' end (3' truncation). A shortened or truncated antisense compound targeted to an CFB nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (*J. Natl. Cancer Inst.* 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (*Nuc. Acid. Res.* 16:3341-3358,1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Certain Antisense Compound Motifs and Mechanisms

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the RISC pathway and include, without limitation, siRNA, ssRNA and microRNA mechanisms; and occupancy based mechanisms. Certain antisense compounds may act through more than one such mechanism and/or through additional mechanisms.

RNase H-Mediated Antisense

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2-modified nucleosides (such 2'-modified nucleosides may include 2'-MOE and 2'-O—$CH_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X—Y—Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X—Y—Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound targeted to a CFB nucleic acid has a gapmer motif in which the gap consists of 6, 7, 8, 9, 10, 11, 12, 13, 14, 15, or 16 linked nucleosides.

In certain embodiments, the antisense oligonucleotide has a sugar motif described by Formula A as follows:

$(J)_m$-$(B)_n$-$(J)_p$-$(B)_r$-$(A)_t$-$(D)_g$-$(A)_v$-$(B)_w$-$(J)_x$-$(B)_y$-$(J)_z$ wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6-14; provided that:
at least one of m, n, and r is other than 0;
at least one of w and y is other than 0;
the sum of m, n, p, r, and t is from 2 to 5; and
the sum of v, w, x, y, and z is from 2 to 5.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIc:

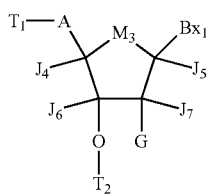

IIc wherein:
$T_1$ is an optionally protected phosphorus moiety;
$T_2$ is an internucleoside linking group linking the compound of Formula IIc to the oligomeric compound;
A has one of the formulas:

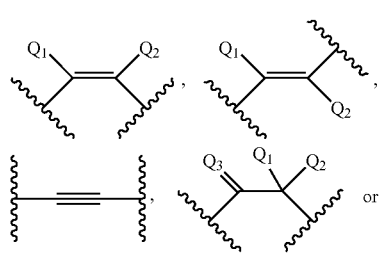

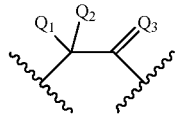

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;
$Q_3$ is O, S, $N(R_5)$ or $C(R_6)(R_7)$;
each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;
$M_3$ is O, S, $NR_{14}$, $C(R_{15})(R_{16})$, $C(R_{15})(R_{16})C(R_{17})(R_{18})$, $C(R_{15})$=$C(R_{17})$, $OC(R_{15})(R_{16})$ or $OC(R_{15})(Bx_2)$;
$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$Bx_1$ is a heterocyclic base moiety;
or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})$=$C(R_{21})$, $C[$=$C(R_{20})(R_{21})]$ and $C($=$O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
G is H, OH, halogen or O—$[C(R_8)(R_9)]_n$—$[(C$=$O)_m$—$X_1]_j$—Z;
each $R_8$ and $R_9$ is, independently, H, halogen, $C_1$-$C_6$ alkyl or substituted $C_1$-$C_6$ alkyl;
$X_1$ is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, =$NJ_1$, $SJ_1$, $N_3$, CN, $OC($=$X_2)J_1$, $OC($=$X_2)N(J_1)(J_2)$ and $C($=$X_2)N(J_1)(J_2)$;
$X_2$ is O, S or $NJ_3$;
each $J_1$, $J_2$ and $J_3$ is, independently, H or $C_1$-$C_6$ alkyl;
when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH=CH, $OCH_2$ or OC(H)($Bx_2$). In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

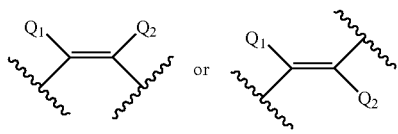

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

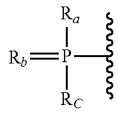

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—N($R_{10}$)($R_1$), $O(CH_2)_2$—ON($R_{10}$)($R_1$), $O(CH_2)_2$—O($CH_2)_2$—N($R_{10}$) ($R_1$), $OCH_2C$(=O)—N($R_{10}$)($R_1$), $OCH_2C$(=O)—N ($R_{12}$)—($CH_2)_2$—N($R_{10}$)($R_1$) or $O(CH_2)_2$—N($R_{12}$)—C (=$NR_{13}$)[N($R_{10}$)($R_{11}$)] wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—N($CH_3)_2$, $OCH_2C$(=O)—N(H)$CH_3$, $OCH_2C$(=O)—N (H)—($CH_2)_2$—N($CH_3)_2$ or $OCH_2$—N(H)—C(=NH)$NH_2$. In certain embodiments, G is F, $OCH_3$ or $O(CH_2)_2$—$OCH_3$. In certain embodiments, G is $O(CH_2)_2$—$OCH_3$.

In certain embodiments, the 5-terminal nucleoside has Formula IIe:

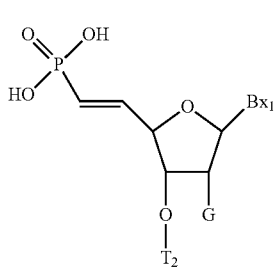

IIe

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$ wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:
AABBAA;
ABBABB;
AABAAB;
ABBABAABB;
ABABAA;
AABABAB;
ABABAA;
ABBAABBABABAA;

BABBAABBABABAA; or
ABABBAABBABABAA;

wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif Such regions comprises the following motif:

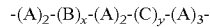

wherein: A is a first type of modified nucleoside;
B and C, are nucleosides that are differently modified than A, however, B and C may have the same or different modifications as one another;
x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

wherein:
Q is a nucleoside comprising a stabilized phosphate moiety. In certain embodiments, Q is a nucleoside having Formula IIc or IIe;
A is a first type of modified nucleoside;
B is a second type of modified nucleoside;
D is a modified nucleoside comprising a modification different from the nucleoside adjacent to it.

Thus, if y is 0, then D must be differently modified than B and if y is 1, then D must be differently modified than A. In certain embodiments, D differs from both A and B.

X is 5-15;
Y is 0 or 1;
Z is 0-4.

In certain embodiments, oligonucleosides have the following sugar motif:

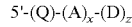

wherein:
Q is a nucleoside comprising a stabilized phosphate moiety. In certain embodiments, Q is a nucleoside having Formula IIc or IIe;
A is a first type of modified nucleoside;
D is a modified nucleoside comprising a modification different from A.
X is 11-30;
Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
| --- | --- | --- |
| PS | Alternating PO/PS | 6 PS |
| PS | Alternating PO/PS | 7 PS |
| PS | Alternating PO/PS | 8 PS | ii. siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In some embodiments, the target nucleic acid is CFB. In certain embodiment, the degradation of the targeted CFB is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfil a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target CFB by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

Target Nucleic Acids, Target Regions and Nucleotide Sequences

Nucleotide sequences that encode Complement Factor B (CFB) include, without limitation, the following: GENBANK Accession No. NM_001710.5 (incorporated herein as SEQ ID NO: 1), GENBANK Accession No. NT_007592.15 truncated from nucleotides 31852000 to U.S. Pat. No. 31,861,000 (incorporated herein as SEQ ID NO: 2), GENBANK Accession No NW_001116486.1 truncated from nucleotides 536000 to 545000 (incorporated herein as SEQ ID NO: 3), GENBANK Accession No. XM_001113553.2 (incorporated herein as SEQ ID NO: 4), or GENBANK Accession No. NM_008198.2 (incorporated herein as SEQ ID NO: 5).

Hybridization

In some embodiments, hybridization occurs between an antisense compound disclosed herein and a CFB nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a CFB nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a CFB nucleic acid).

Non-complementary nucleobases between an antisense compound and a CFB nucleic acid may be tolerated provided that the antisense compound remains able to specifically hybridize to a target nucleic acid. Moreover, an antisense compound may hybridize over one or more segments of a CFB nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a CFB nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to a CFB nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a CFB nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a CFB nucleic acid, or specified portion thereof.

The antisense compounds provided also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds are complementary to at least an 11 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a CFB nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide.

In certain such embodiments, at least one such block is located within 3 nucleosides of the 3' end of the oligonucleotide.

In certain embodiments, oligonucleotides comprise one or more methylphosponate linkages. In certain embodiments, oligonucleotides having a gapmer nucleoside motif comprise a linkage motif comprising all phosphorothioate linkages except for one or two methylphosponate linkages. In certain embodiments, one methylphosponate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

Modified Sugar Moieties Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)—N(R)—(CH$_2$)$_2$—N(R$_m$)(R$_n$), where each R$_l$, R$_m$ and R$_n$ is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleosides include without limitation nucleosides comprising abridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' (also referred to as constrained ethyl or cEt) and 4'-CH (CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO 2009/006478, published Jan. 8, 2009); 4'-CH$_2$—N (OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Zhou et al., *J. Org. Chem.*, 2009, 74, 118-134); and 4'-CH$_2$—C(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; 8,530,640; and 7,696,345; U.S. Patent Publication No. US2008-0039618; US2009-0012281; U.S. Patent Ser. Nos. 61/026,995 and 61/097,787; Published PCT International applications; WO 2009/067647; WO 2011/017521; WO 2010/036698 WO 1999/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C (R$_b$)—, —C(R$_a$)=N—, —C(=O)—, —C(=NR$_a$)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a$)($R_b$)]$_n$—, —[C($R_a$)($R_b$)]$_n$O—C($R_aR_b$)—N(R)—O— or —C($R_aR_b$)—O—N(R)—. In certain embodiments, the bridge is 4'-$CH_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA and (K) vinyl BNA as depicted below:

(A)

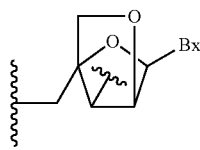

(B)

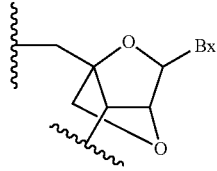

(C)

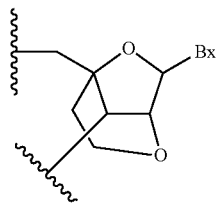

(D)

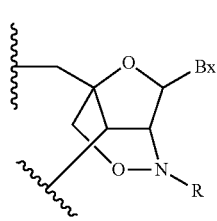

-continued (E)

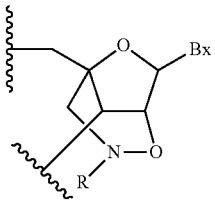

(F)

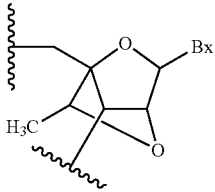

(G)

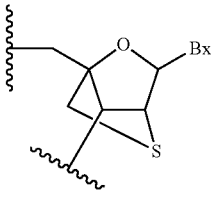

(H)

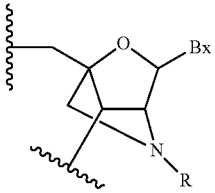

(I)

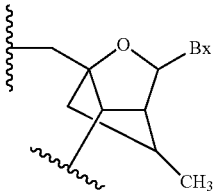

(J)

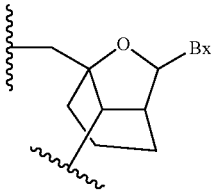

(K)

wherein Bx is the base moiety and R is independently H, a protecting group, $C_1$-$C_{12}$ alkyl or $C_1$-$C_{12}$ alkoxy.

In certain embodiments, bicyclic nucleosides are provided having Formula I:

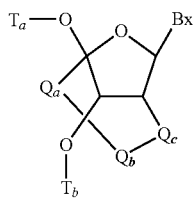

I wherein:

Bx is a heterocyclic base moiety;

$-Q_a-Q_b-Q_c-$ is $-CH_2-N(R_c)-CH_2-$, $-C(=O)-N(R_c)-CH_2-$, $-CH_2-O-N(R_c)-$, $-CH_2-N(R_c)-O-$ or $-N(R_c)-O-CH_2$;

$R_c$ is $C_1-C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

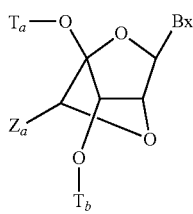

II wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1-C_6$ alkyl, $C_2-C_6$ alkenyl, $C_2-C_6$ alkynyl, substituted $C_1-C_6$ alkyl, substituted $C_2-C_6$ alkenyl, substituted $C_2-C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_b$, $SJ_c$, $N_3$, $OC(=X)J_c$, and $NJ_eC(=X)NJ_cJ_a$, wherein each $J_c$, $J_a$ and $J_e$ is, independently, H, $C_1-C_6$ alkyl, or substituted $C_1-C_6$ alkyl and X is O or $NJ_c$.

In certain embodiments, bicyclic nucleosides are provided having Formula III:

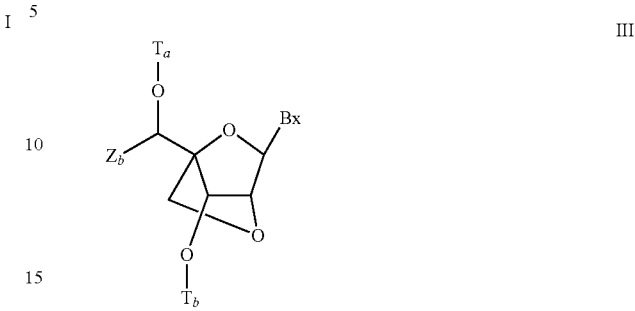

III wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1-C_6$ alkyl, $C_2-C_6$ alkenyl, $C_2-C_6$ alkynyl, substituted $C_1-C_6$ alkyl, substituted $C_2-C_6$ alkenyl, substituted $C_2-C_6$ alkynyl or substituted acyl (C(=O)—).

In certain embodiments, bicyclic nucleosides are provided having Formula IV:

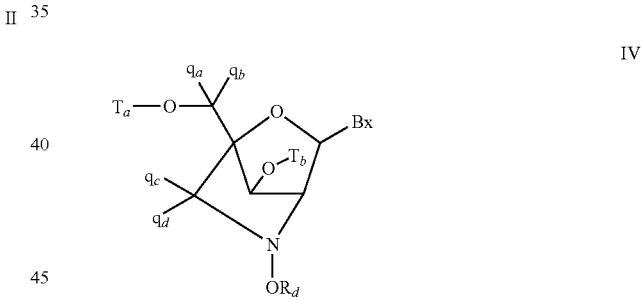

IV wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1-C_6$ alkyl, substituted $C_1-C_6$ alkyl, $C_2-C_6$ alkenyl, substituted $C_2-C_6$ alkenyl, $C_2-C_6$ alkynyl or substituted $C_2-C_6$ alkynyl;

each $q_a$, $q_b$, $q_c$ and $q_d$ is, independently, H, halogen, $C_1-C_6$ alkyl, substituted $C_1-C_6$ alkyl, $C_2-C_6$ alkenyl, substituted $C_2-C_6$ alkenyl, $C_2-C_6$ alkynyl or substituted $C_2-C_6$ alkynyl, $C_1-C_6$ alkoxyl, substituted $C_1-C_6$ alkoxyl, acyl, substituted acyl, $C_1-C_6$ aminoalkyl or substituted $C_1-C_6$ aminoalkyl;

In certain embodiments, bicyclic nucleosides are provided having Formula V:

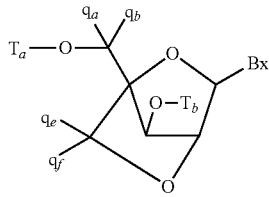

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

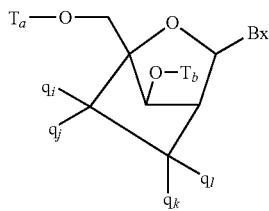

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-($CH_2$)$_3$-2' bridge and the alkenyl analog bridge 4'-CH=CH—$CH_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[($CH_2$)$_n$O]$_m$$CH_3$, O($CH_2$)$_n$$NH_2$, O($CH_2$)$_n$$CH_3$, O($CH_2$)$_n$F, O($CH_2$)$_n$$ONH_2$, OCH$_2$C(=O)N(H)$CH_3$, and O($CH_2$)$_n$ON[($CH_2$)$_n$$CH_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., Chimia, 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.,* 2002, 10, 841-854) or fluoro HNA (F-HNA) having a tetrahydropyran ring system as illustrated below:

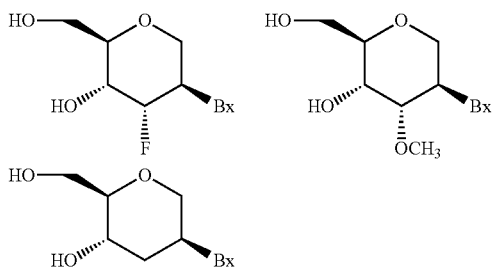

In certain embodiments, sugar surrogates are selected having Formula VII:

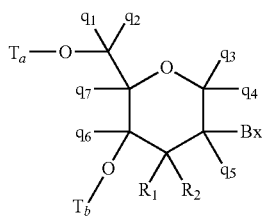

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H.

In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomenc compounds has been reported (see for example: Braasch et al., *Biochemistry,* 2002, 41, 4503-4510; and U.S. Pat. Nos. 5,698,685; 5,166, 315; 5,185,444; and 5,034,506). As used here, the term "morpholino" means a sugar surrogate having the following formula:

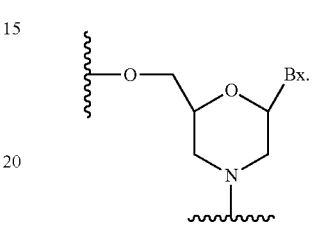

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J Am. Chem. Soc.,* 2008, 130(6), 1979-1984; Horváth et al., *Tetrahedron Letters,* 2007, 48, 3621-3623; Nauwelaerts et al., *J. Am. Chem. Soc.,* 2007, 129(30), 9340-9348; Gu et al., *Nucleosides, Nucleotides & Nucleic Acids,* 2005, 24(5-7), 993-998; Nauwelaerts et al., *Nucleic Acids Research,* 2005, 33(8), 2452-2463; Robeyns et al., *Acta Crystallographica, Section F: Structural Biology and Crystallization Communications,* 2005, F61(6), 585-586; Gu et al., *Tetrahedron,* 2004, 60(9), 2111-2123; Gu et al., *Oligonucleotides,* 2003, 13(6), 479-489; Wang et al., *J Org. Chem.,* 2003, 68, 4499-4505; Verbeure et al., *Nucleic Acids Research,* 2001, 29(24), 4941-4947; Wang et al., *J. Org. Chem.,* 2001, 66, 8478-82; Wang et al., *Nucleosides, Nucleotides & Nucleic Acids,* 2001, 20(4-7), 785-788; Wang et al., *J. Am. Chem. Acids,* 2000, 122, 8595-8602; Published PCT application, WO 06/047842; and Published PCT Application WO 01/049687;

the text of each is incorporated by reference herein, in their entirety). Certain modified cyclohexenyl nucleosides have Formula X.

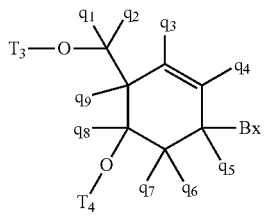

wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$O—$CH_3$, 2'-O$(CH_2)_2$S$CH_3$, O—$(CH_2)_2$—O—N$(R_m)(R_n)$, or O—$CH_2$—C(=O)—N$(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854). Such ring systems can undergo various additional substitutions to enhance activity.

Methods for the preparations of modified sugars are well known to those skilled in the art. Some representative U.S. patents that teach the preparation of such modified sugars include without limitation, U.S.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4'-CH($CH_3$)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a CFB nucleic acid comprise one or more modified nucleobases. In certain embodiments, shortened or gap-widened antisense oligonucleotides targeted to a CFB nucleic acid comprise one or more modified nucleobases. In certain embodiments, the modified nucleobase is 5-methylcytosine. In certain embodiments, each cytosine is a 5-methylcytosine.

Conjugated Antisense Compounds

In certain embodiments, the present disclosure provides conjugated antisense compounds. In certain embodiments, the present disclosure provides conjugated antisense compounds comprising an antisense oligonucleotide complementary to a nucleic acid transcript. In certain embodiments, the present disclosure provides methods comprising contacting a cell with a conjugated antisense compound comprising an antisense oligonucleotide complementary to a nucleic acid transcript. In certain embodiments, the present disclosure provides methods comprising contacting a cell with a conjugated antisense compound comprising an antisense oligonucleotide and reducing the amount or activity of a nucleic acid transcript in a cell.

The asialoglycoprotein receptor (ASGP-R) has been described previously. See e.g., Park et al., *PNAS* vol. 102, No. 47, pp 17125-17129 (2005). Such receptors are expressed on liver cells, particularly hepatocytes. Further, it has been shown that compounds comprising clusters of three N-acetylgalactosamine (GalNAc) ligands are capable of binding to the ASGP-R, resulting in uptake of the compound into the cell. See e.g., Khorev et al., Bioorganic and Medicinal Chemistry, 16, 9, pp 5216-5231 (May 2008). Accordingly, conjugates comprising such GalNAc clusters have been used to facilitate uptake of certain compounds into liver cells, specifically hepatocytes. For example it has been shown that certain GalNAc-containing conjugates increase activity of duplex siRNA compounds in liver cells in vivo. In such instances, the GalNAc-containing conjugate is typically attached to the sense strand of the siRNA duplex. Since the sense strand is discarded before the antisense strand ultimately hybridizes with the target nucleic acid, there is little concern that the conjugate will interfere with activity. Typically, the conjugate is attached to the 3' end of the sense strand of the siRNA. See e.g., U.S. Pat. No. 8,106,022. Certain conjugate groups described herein are more active and/or easier to synthesize than conjugate groups previously described.

In certain embodiments of the present invention, conjugates are attached to single-stranded antisense compounds, including, but not limited to RNase H based antisense compounds and antisense compounds that alter splicing of a pre-mRNA target nucleic acid. In such embodiments, the conjugate should remain attached to the antisense compound long enough to provide benefit (improved uptake into cells) but then should either be cleaved, or otherwise not interfere with the subsequent steps necessary for activity, such as hybridization to a target nucleic acid and interaction with RNase H or enzymes associated with splicing or splice modulation. This balance of properties is more important in the setting of single-stranded antisense compounds than in siRNA compounds, where the conjugate may simply be attached to the sense strand. Disclosed herein are conjugated single-stranded antisense compounds having improved potency in liver cells in vivo compared with the same antisense compound lacking the conjugate. Given the required balance of properties for these compounds such improved potency is surprising.

In certain embodiments, conjugate groups herein comprise a cleavable moiety. As noted, without wishing to be bound by mechanism, it is logical that the conjugate should remain on the compound long enough to provide enhancement in uptake, but after that, it is desirable for some portion or, ideally, all of the conjugate to be cleaved, releasing the parent compound (e.g., antisense compound) in its most active form. In certain embodiments, the cleavable moiety is a cleavable nucleoside. Such embodiments take advantage of endogenous nucleases in the cell by attaching the rest of the conjugate (the cluster) to the antisense oligonucleotide through a nucleoside via one or more cleavable bonds, such as those of a phosphodiester linkage. In certain embodiments, the cluster is bound to the cleavable nucleoside through a phosphodiester linkage. In certain embodiments, the cleavable nucleoside is attached to the antisense oligonucleotide (antisense compound) by a phosphodiester linkage. In certain embodiments, the conjugate group may comprise two or three cleavable nucleosides. In such embodiments, such cleavable nucleosides are linked to one another, to the antisense compound and/or to the cluster via cleavable bonds (such as those of a phosphodiester linkage). Certain conjugates herein do not comprise a cleavable nucleoside and instead comprise a cleavable bond. It is shown that that sufficient cleavage of the conjugate from the oligonucleotide is provided by at least one bond that is vulnerable to cleavage in the cell (a cleavable bond).

In certain embodiments, conjugated antisense compounds are prodrugs. Such prodrugs are administered to an animal and are ultimately metabolized to a more active form. For example, conjugated antisense compounds are cleaved to remove all or part of the conjugate resulting in the active (or more active) form of the antisense compound lacking all or some of the conjugate.

In certain embodiments, conjugates are attached at the 5' end of an oligonucleotide. Certain such 5'-conjugates are cleaved more efficiently than counterparts having a similar conjugate group attached at the 3' end. In certain embodiments, improved activity may correlate with improved cleavage. In certain embodiments, oligonucleotides comprising a conjugate at the 5' end have greater efficacy than oligonucleotides comprising a conjugate at the 3' end (see, for example, Examples 56, 81, 83, and 84). Further, 5'-attachment allows simpler oligonucleotide synthesis. Typically, oligonucleotides are synthesized on a solid support in the 3' to 5' direction. To make a 3'-conjugated oligonucleotide, typically one attaches a pre-conjugated 3' nucleoside to the solid support and then builds the oligonucleotide as usual. However, attaching that conjugated nucleoside to the solid support adds complication to the synthesis. Further, using that approach, the conjugate is then present throughout the synthesis of the oligonucleotide and can become degraded during subsequent steps or may limit the sorts of reactions and reagents that can be used. Using the structures and techniques described herein for 5'-conjugated oligonucleotides, one can synthesize the oligonucleotide using standard automated techniques and introduce the conjugate with the final (5'-most) nucleoside or after the oligonucleotide has been cleaved from the solid support.

In view of the art and the present disclosure, one of ordinary skill can easily make any of the conjugates and conjugated oligonucleotides herein. Moreover, synthesis of certain such conjugates and conjugated oligonucleotides disclosed herein is easier and/or requires few steps, and is therefore less expensive than that of conjugates previously disclosed, providing advantages in manufacturing. For example, the synthesis of certain conjugate groups consists of fewer synthetic steps, resulting in increased yield, relative to conjugate groups previously described. Conjugate groups such as GalNAc3-10 in Example 46 and GalNAc3-7 in Example 48 are much simpler than previously described conjugates such as those described in U.S. Pat. No. 8,106,022 or U.S. Pat. No. 7,262,177 that require assembly of more chemical intermediates. Accordingly, these and other conjugates described herein have advantages over previously described compounds for use with any oligonucleotide, including single-stranded oligonucleotides and either strand of double-stranded oligonucleotides (e.g., siRNA).

Similarly, disclosed herein are conjugate groups having only one or two GalNAc ligands. As shown, such conjugates groups improve activity of antisense compounds. Such compounds are much easier to prepare than conjugates comprising three GalNAc ligands. Conjugate groups comprising one or two GalNAc ligands may be attached to any antisense compounds, including single-stranded oligonucleotides and either strand of double-stranded oligonucleotides (e.g., siRNA).

In certain embodiments, the conjugates herein do not substantially alter certain measures of tolerability. For example, it is shown herein that conjugated antisense compounds are not more immunogenic than unconjugated parent compounds. Since potency is improved, embodiments in which tolerability remains the same (or indeed even if tolerability worsens only slightly compared to the gains in potency) have improved properties for therapy.

In certain embodiments, conjugation allows one to alter antisense compounds in ways that have less attractive consequences in the absence of conjugation. For example, in certain embodiments, replacing one or more phosphorothioate linkages of a fully phosphorothioate antisense compound with phosphodiester linkages results in improvement in some measures of tolerability. For example, in certain instances, such antisense compounds having one or more phosphodiester are less immunogenic than the same compound in which each linkage is a phosphorothioate. However, in certain instances, as shown in Example 26, that same replacement of one or more phosphorothioate linkages with phosphodiester linkages also results in reduced cellular uptake and/or loss in potency. In certain embodiments, conjugated antisense compounds described herein tolerate such change in linkages with little or no loss in uptake and potency when compared to the conjugated full-phosphorothioate counterpart. In fact, in certain embodiments, for example, in Examples 44, 57, 59, and 86, oligonucleotides comprising a conjugate and at least one phosphodiester internucleoside linkage actually exhibit increased potency in vivo even relative to a full phosphorothioate counterpart also comprising the same conjugate. Moreover, since conjugation results in substantial increases in uptake/potency a small loss in that substantial gain may be acceptable to achieve improved tolerability. Accordingly, in certain embodiments, conjugated antisense compounds comprise at least one phosphodiester linkage.

In certain embodiments, conjugation of antisense compounds herein results in increased delivery, uptake and activity in hepatocytes. Thus, more compound is delivered to liver tissue. However, in certain embodiments, that increased delivery alone does not explain the entire increase in activity. In certain such embodiments, more compound enters hepatocytes. In certain embodiments, even that increased hepatocyte uptake does not explain the entire increase in activity. In such embodiments, productive uptake of the conjugated compound is increased. For example, as shown in Example 102, certain embodiments of GalNAc-containing conjugates increase enrichment of antisense oligonucleotides in hepatocytes versus non-parenchymal cells. This enrichment is beneficial for oligonucleotides that target genes that are expressed in hepatocytes.

In certain embodiments, conjugated antisense compounds herein result in reduced kidney exposure. For example, as shown in Example 20, the concentrations of antisense oligonucleotides comprising certain embodiments of GalNAc-containing conjugates are lower in the kidney than that of antisense oligonucleotides lacking a GalNAc-containing conjugate. This has several beneficial therapeutic implications. For therapeutic indications where activity in the kidney is not sought, exposure to kidney risks kidney toxicity without corresponding benefit. Moreover, high concentration in kidney typically results in loss of compound to the urine resulting in faster clearance. Accordingly for non-kidney targets, kidney accumulation is undesired.

In certain embodiments, the present disclosure provides conjugated antisense compounds represented by the formula:

wherein

A is the antisense oligonucleotide;

B is the cleavable moiety

C is the conjugate linker

D is the branching group each E is a tether;

each F is a ligand; and q is an integer between 1 and 5.

In the above diagram and in similar diagrams herein, the branching group "D" branches as many times as is necessary to accommodate the number of (E-F) groups as indicated by "q". Thus, where q=1, the formula is:

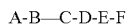

where q=2, the formula is:

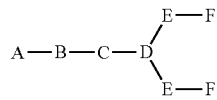

where q=3, the formula is:

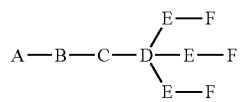

where q=4, the formula is:

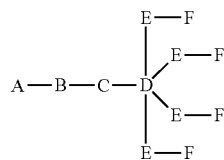

where q=5, the formula is:
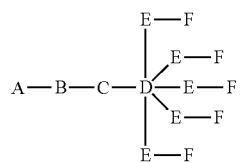
In certain embodiments, conjugated antisense compounds are provided having the structure:
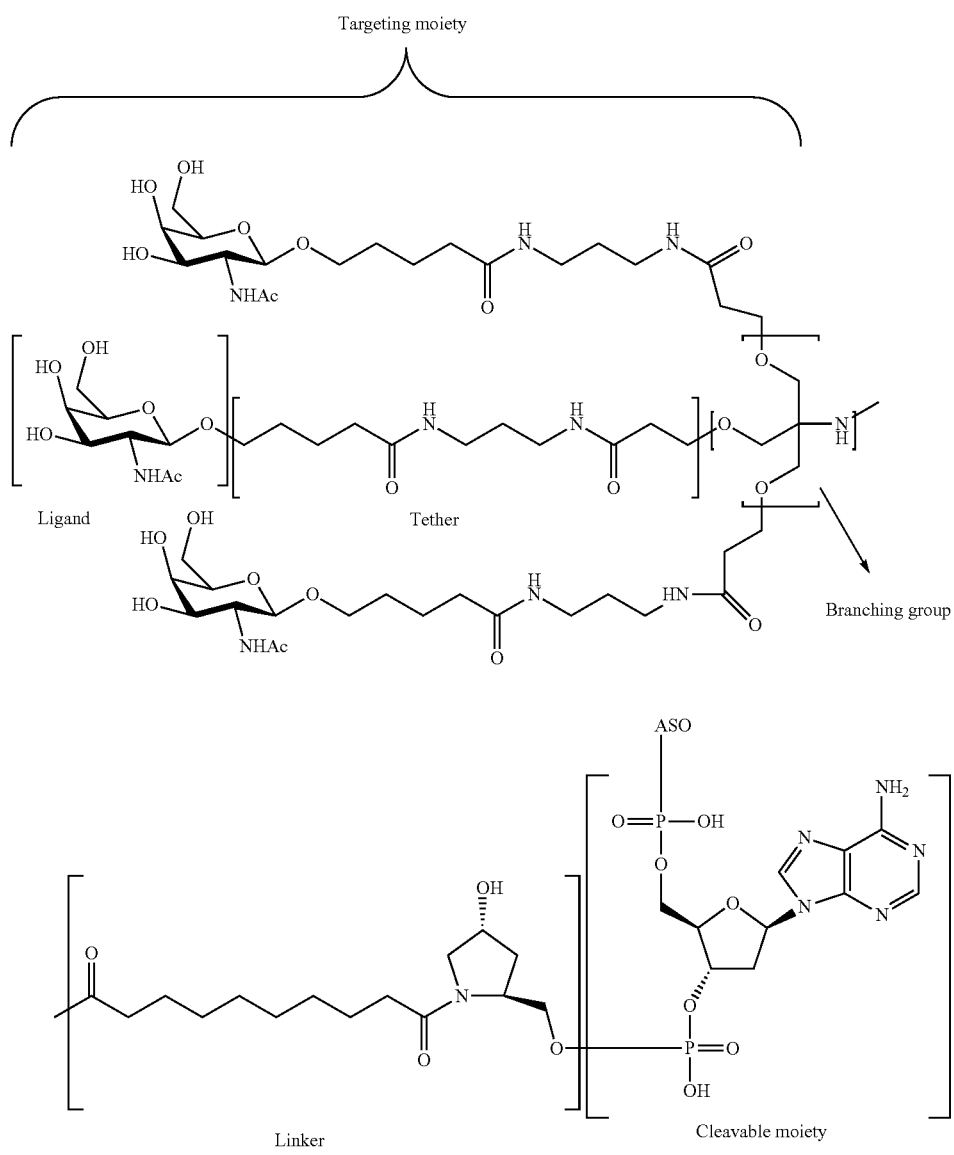

In certain embodiments, conjugated antisense compounds are provided having the structure:
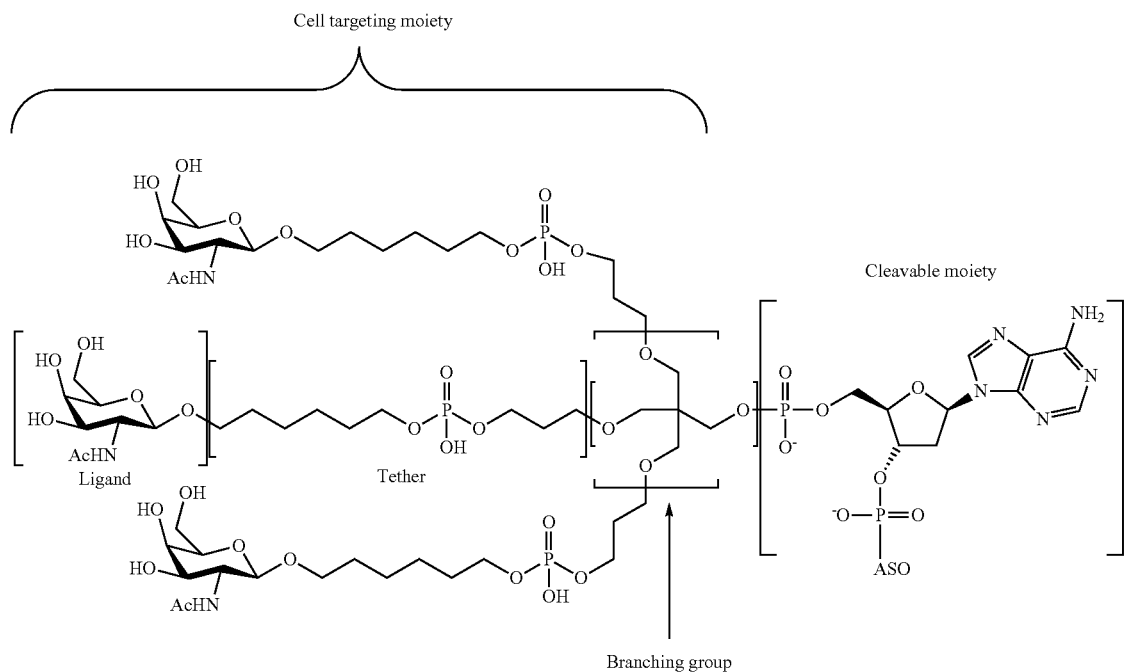
In certain embodiments, conjugated antisense compounds are provided having the structure:
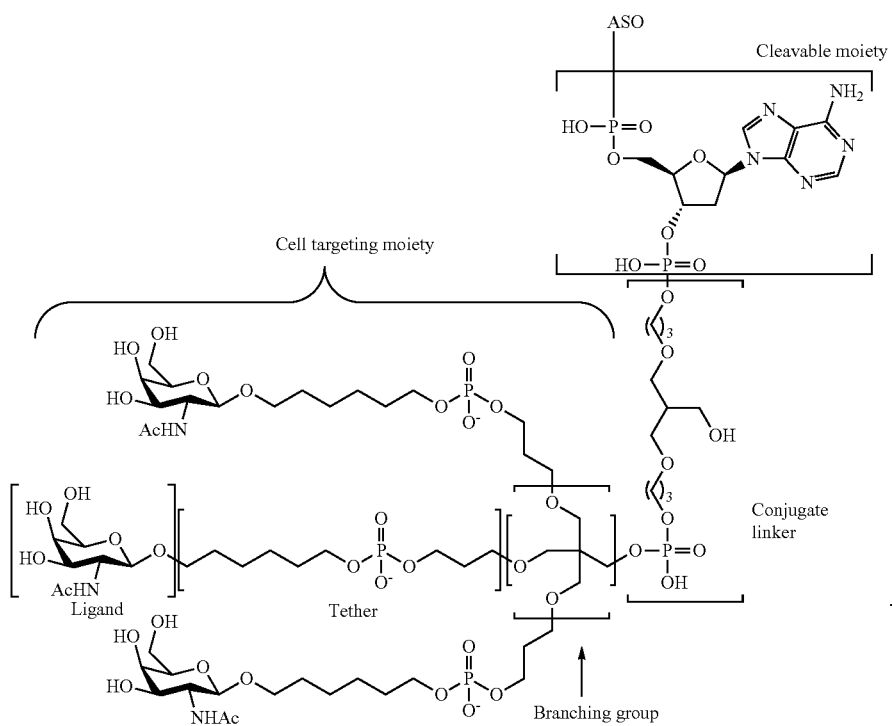

In certain embodiments, conjugated antisense compounds are provided having the structure:

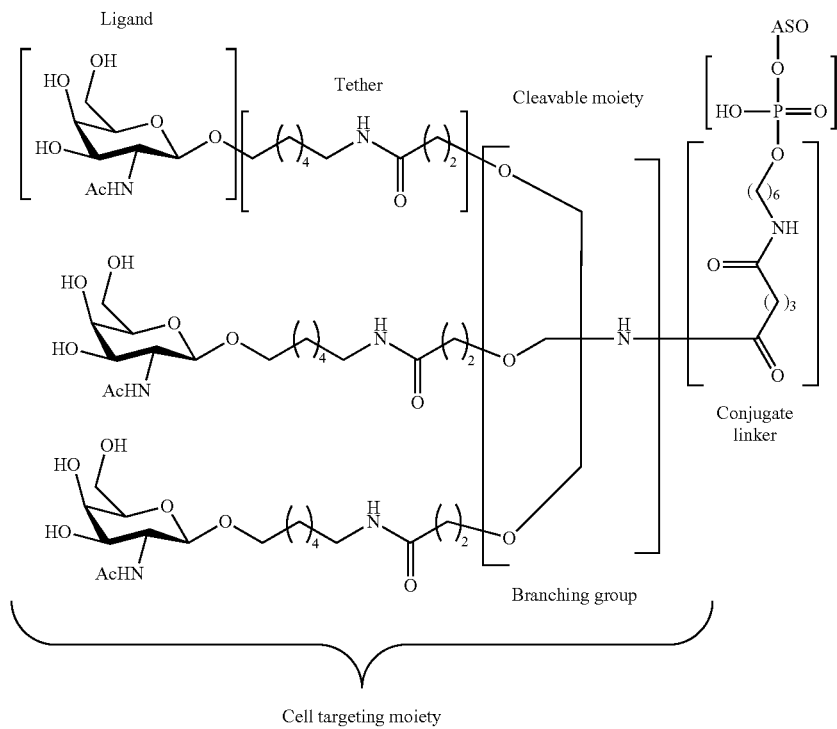

The present disclosure provides the following non-limiting numbered embodiments:

Embodiment 1. The conjugated antisense compound of any of embodiments 1179 to 1182, wherein the tether has a structure selected from among:

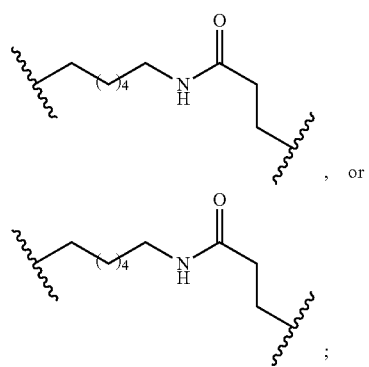

wherein each n is independently, 0, 1, 2, 3, 4, 5, 6, or 7.

Embodiment 2. The conjugated antisense compound of any of embodiments 1179 to 1182, wherein the tether has the structure:

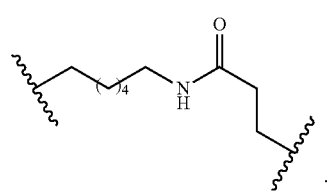

Embodiment 3. The conjugated antisense compound of any of embodiments 1179 to 1182 or 1688 to 1689, wherein the linker has a structure selected from among:

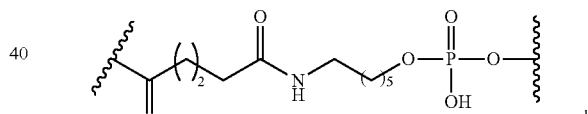

and

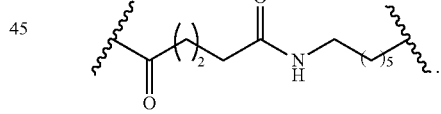

Embodiment 4. The conjugated antisense compound of any of embodiments 1179 to 1182 or 1688 to 1689, wherein the linker has a structure selected from among:

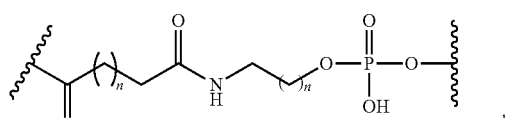

and

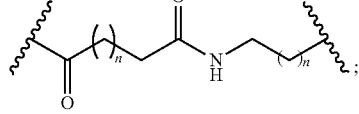

wherein each n is independently, 0, 1, 2, 3, 4, 5, 6, or 7.

Embodiment 5. The conjugated antisense compound of any of embodiments 1179 to 1182 or 1688 to 1689, wherein the linker has the structure:

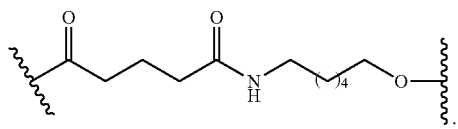

In embodiments having more than one of a particular variable (e.g., more than one "m" or "n"), unless otherwise indicated, each such particular variable is selected independently. Thus, for a structure having more than one n, each n is selected independently, so they may or may not be the same as one another.

i. Certain Cleavable Moieties

In certain embodiments, a cleavable moiety is a cleavable bond. In certain embodiments, a cleavable moiety comprises a cleavable bond. In certain embodiments, the conjugate group comprises a cleavable moiety. In certain such embodiments, the cleavable moiety attaches to the antisense oligonucleotide. In certain such embodiments, the cleavable moiety attaches directly to the cell-targeting moiety. In certain such embodiments, the cleavable moiety attaches to the conjugate linker. In certain embodiments, the cleavable moiety comprises a phosphate or phosphodiester. In certain embodiments, the cleavable moiety is a cleavable nucleoside or nucleoside analog. In certain embodiments, the nucleoside or nucleoside analog comprises an optionally protected heterocyclic base selected from a purine, substituted purine, pyrimidine or substituted pyrimidine. In certain embodiments, the cleavable moiety is a nucleoside comprising an optionally protected heterocyclic base selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. In certain embodiments, the cleavable moiety is 2'-deoxy nucleoside that is attached to the 3' position of the antisense oligonucleotide by a phosphodiester linkage and is attached to the linker by a phosphodiester or phosphorothioate linkage. In certain embodiments, the cleavable moiety is 2'-deoxy adenosine that is attached to the 3' position of the antisense oligonucleotide by a phosphodiester linkage and is attached to the linker by a phosphodiester or phosphorothioate linkage. In certain embodiments, the cleavable moiety is 2'-deoxy adenosine that is attached to the 3' position of the antisense oligonucleotide by a phosphodiester linkage and is attached to the linker by a phosphodiester linkage.

In certain embodiments, the cleavable moiety is attached to the 3' position of the antisense oligonucleotide. In certain embodiments, the cleavable moiety is attached to the 5' position of the antisense oligonucleotide. In certain embodiments, the cleavable moiety is attached to a 2' position of the antisense oligonucleotide. In certain embodiments, the cleavable moiety is attached to the antisense oligonucleotide by a phosphodiester linkage. In certain embodiments, the cleavable moiety is attached to the linker by either a phosphodiester or a phosphorothioate linkage. In certain embodiments, the cleavable moiety is attached to the linker by a phosphodiester linkage. In certain embodiments, the conjugate group does not include a cleavable moiety.

In certain embodiments, the cleavable moiety is cleaved after the complex has been administered to an animal only after being internalized by a targeted cell. Inside the cell the cleavable moiety is cleaved thereby releasing the active antisense oligonucleotide. While not wanting to be bound by theory it is believed that the cleavable moiety is cleaved by one or more nucleases within the cell. In certain embodiments, the one or more nucleases cleave the phosphodiester linkage between the cleavable moiety and the linker. In certain embodiments, the cleavable moiety has a structure selected from among the following:

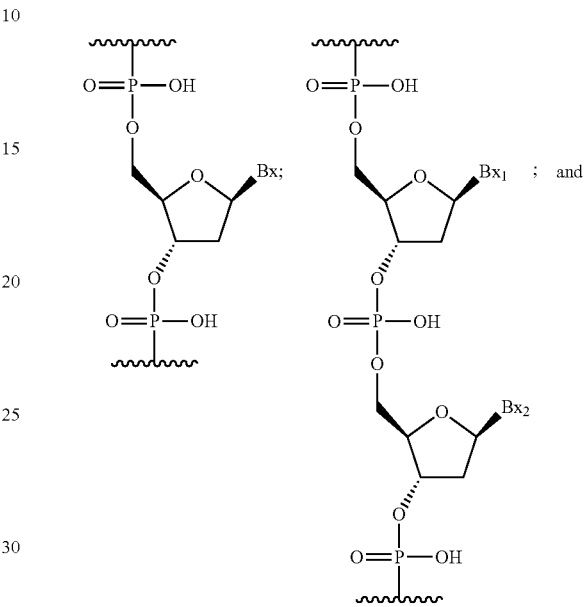

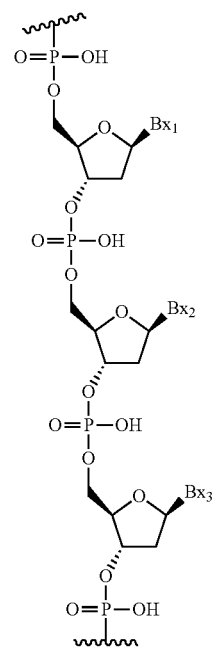

wherein each of Bx, Bx$_1$, Bx$_2$, and Bx$_3$ is independently a heterocyclic base moiety. In certain embodiments, the cleavable moiety has a structure selected from among the following:

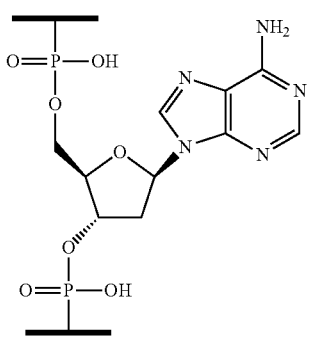

ii. Certain Linkers

In certain embodiments, the conjugate groups comprise a linker. In certain such embodiments, the linker is covalently bound to the cleavable moiety. In certain such embodiments, the linker is covalently bound to the antisense oligonucleotide. In certain embodiments, the linker is covalently bound to a cell-targeting moiety. In certain embodiments, the linker further comprises a covalent attachment to a solid support. In certain embodiments, the linker further comprises a covalent attachment to a protein binding moiety. In certain embodiments, the linker further comprises a covalent attachment to a solid support and further comprises a covalent attachment to a protein binding moiety. In certain embodiments, the linker includes multiple positions for attachment of tethered ligands. In certain embodiments, the linker includes multiple positions for attachment of tethered ligands and is not attached to a branching group. In certain embodiments, the linker further comprises one or more cleavable bond. In certain embodiments, the conjugate group does not include a linker.

In certain embodiments, the linker includes at least a linear group comprising groups selected from alkyl, amide, disulfide, polyethylene glycol, ether, thioether (—S—) and hydroxylamino (—O—N(H)—) groups. In certain embodiments, the linear group comprises groups selected from alkyl, amide and ether groups. In certain embodiments, the linear group comprises groups selected from alkyl and ether groups. In certain embodiments, the linear group comprises at least one phosphorus linking group. In certain embodiments, the linear group comprises at least one phosphodiester group. In certain embodiments, the linear group includes at least one neutral linking group. In certain embodiments, the linear group is covalently attached to the cell-targeting moiety and the cleavable moiety. In certain embodiments, the linear group is covalently attached to the cell-targeting moiety and the antisense oligonucleotide. In certain embodiments, the linear group is covalently attached to the cell-targeting moiety, the cleavable moiety and a solid support. In certain embodiments, the linear group is covalently attached to the cell-targeting moiety, the cleavable moiety, a solid support and a protein binding moiety. In certain embodiments, the linear group includes one or more cleavable bond.

In certain embodiments, the linker includes the linear group covalently attached to a scaffold group. In certain embodiments, the scaffold includes a branched aliphatic group comprising groups selected from alkyl, amide, disulfide, polyethylene glycol, ether, thioether and hydroxylamino groups. In certain embodiments, the scaffold includes a branched aliphatic group comprising groups selected from alkyl, amide and ether groups. In certain embodiments, the scaffold includes at least one mono or polycyclic ring system. In certain embodiments, the scaffold includes at least two mono or polycyclic ring systems. In certain embodiments, the linear group is covalently attached to the scaffold group and the scaffold group is covalently attached to the cleavable moiety and the linker. In certain embodiments, the linear group is covalently attached to the scaffold group and the scaffold group is covalently attached to the cleavable moiety, the linker and a solid support. In certain embodiments, the linear group is covalently attached to the scaffold group and the scaffold group is covalently attached to the cleavable moiety, the linker and a protein binding moiety. In certain embodiments, the linear group is covalently attached to the scaffold group and the scaffold group is covalently attached to the cleavable moiety, the linker, a protein binding moiety and a solid support. In certain embodiments, the scaffold group includes one or more cleavable bond.

In certain embodiments, the linker includes a protein binding moiety. In certain embodiments, the protein binding moiety is a lipid such as for example including but not limited to cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, friedelin, epifriedelanol derivatized lithocholic acid), or a cationic lipid. In certain embodiments, the protein binding moiety is a C16 to C22 long chain saturated or unsaturated fatty acid, cholesterol, cholic acid, vitamin E, adamantane or 1-pentafluoropropyl.

In certain embodiments, a linker has a structure selected from among:

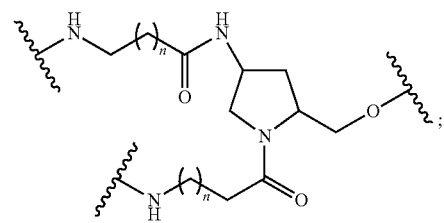

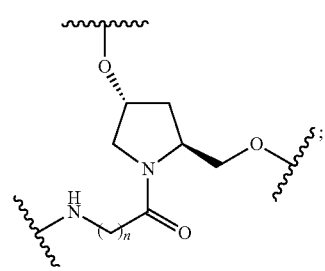

107
-continued
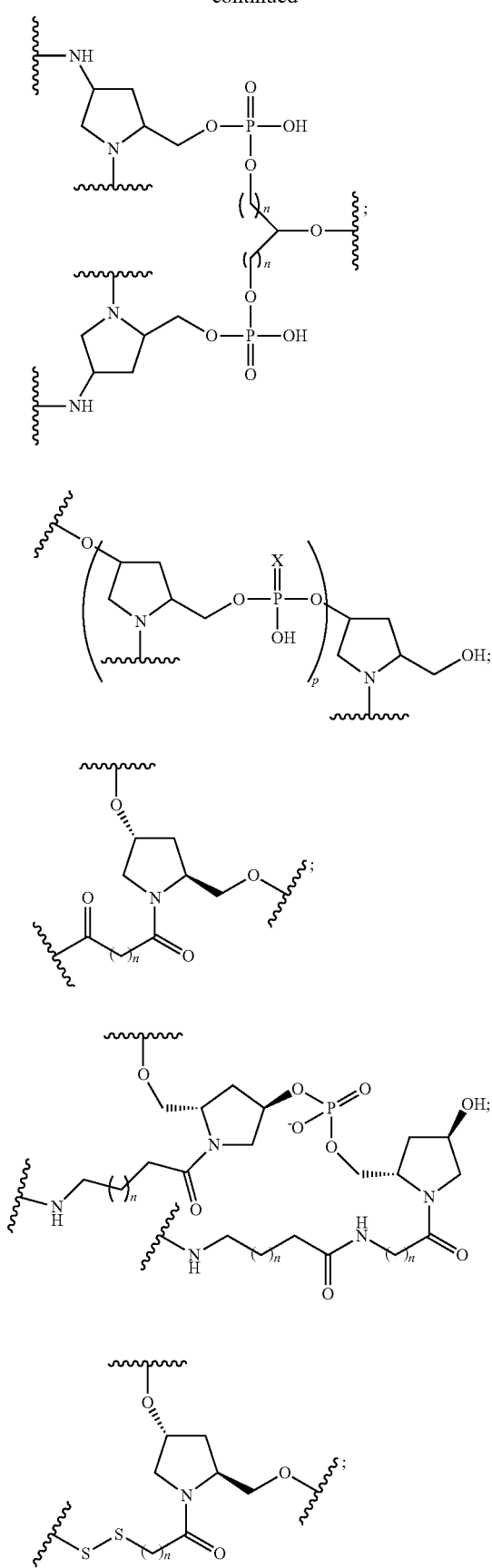
108
-continued
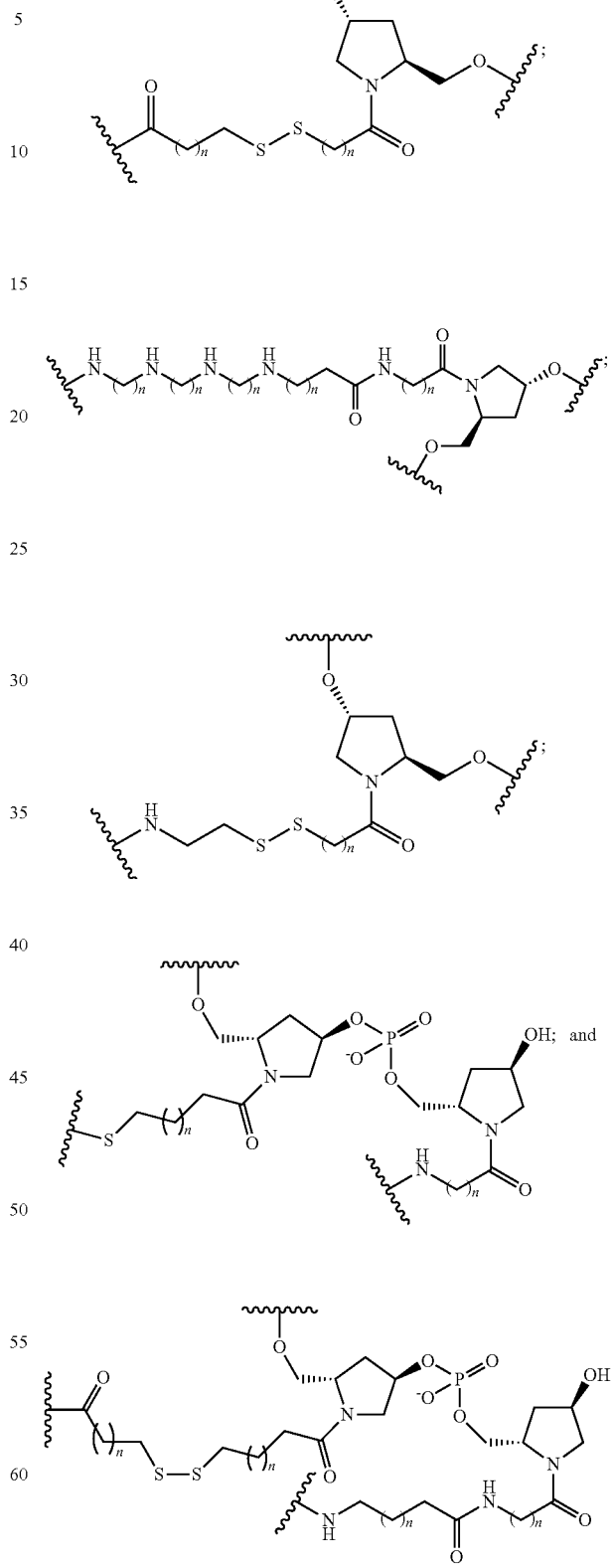
wherein each n is, independently, from 1 to 20; and p is from 1 to 6.

In certain embodiments, a linker has a structure selected from among:
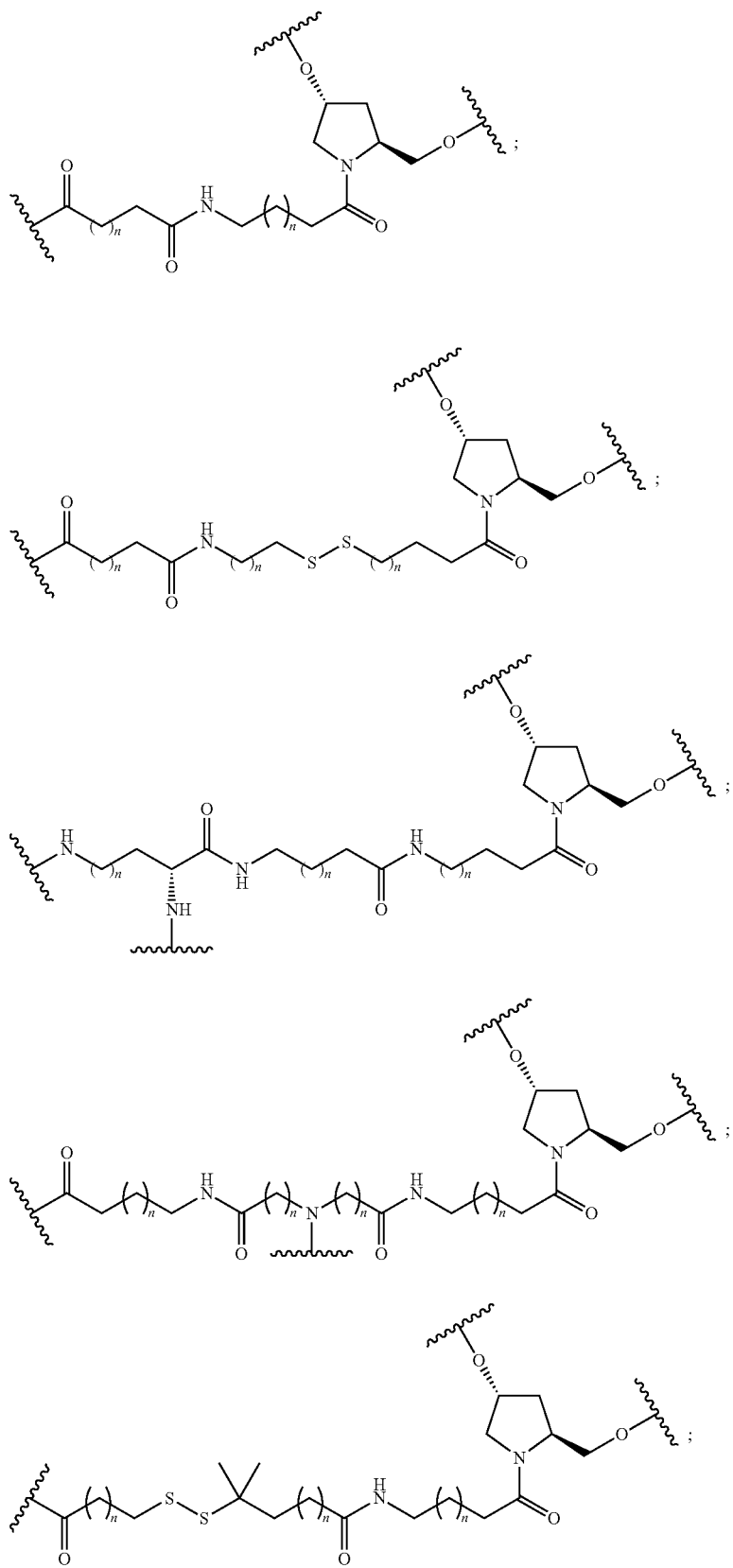

-continued
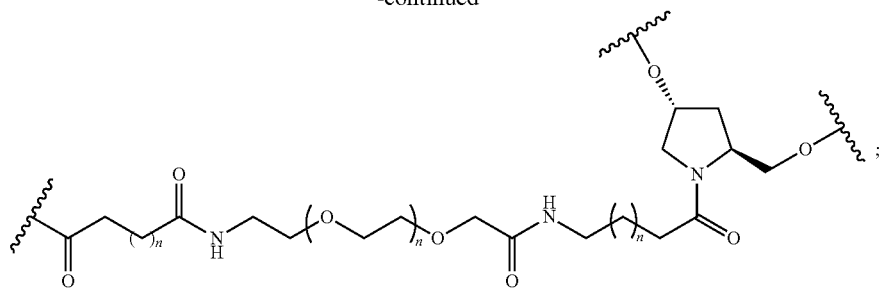
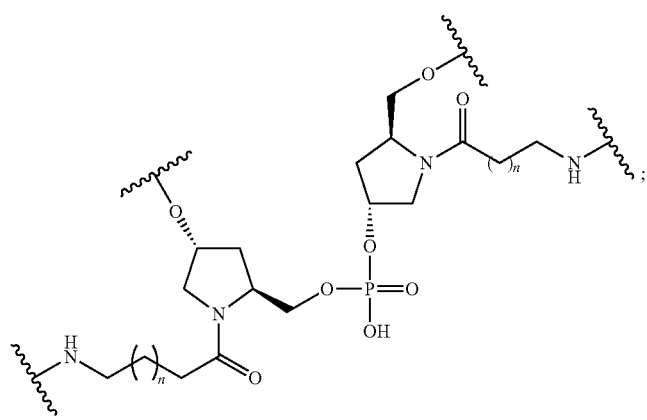
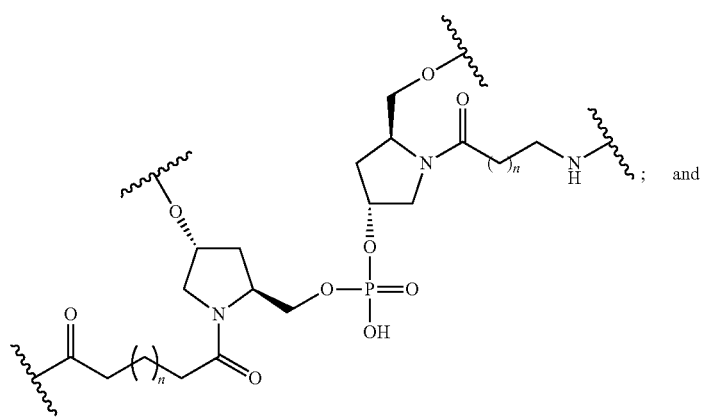
and
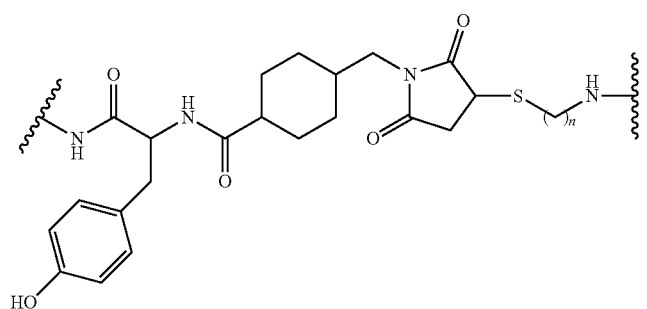
wherein each n is, independently, from 1 to 20.

In certain embodiments, a linker has a structure selected from among:
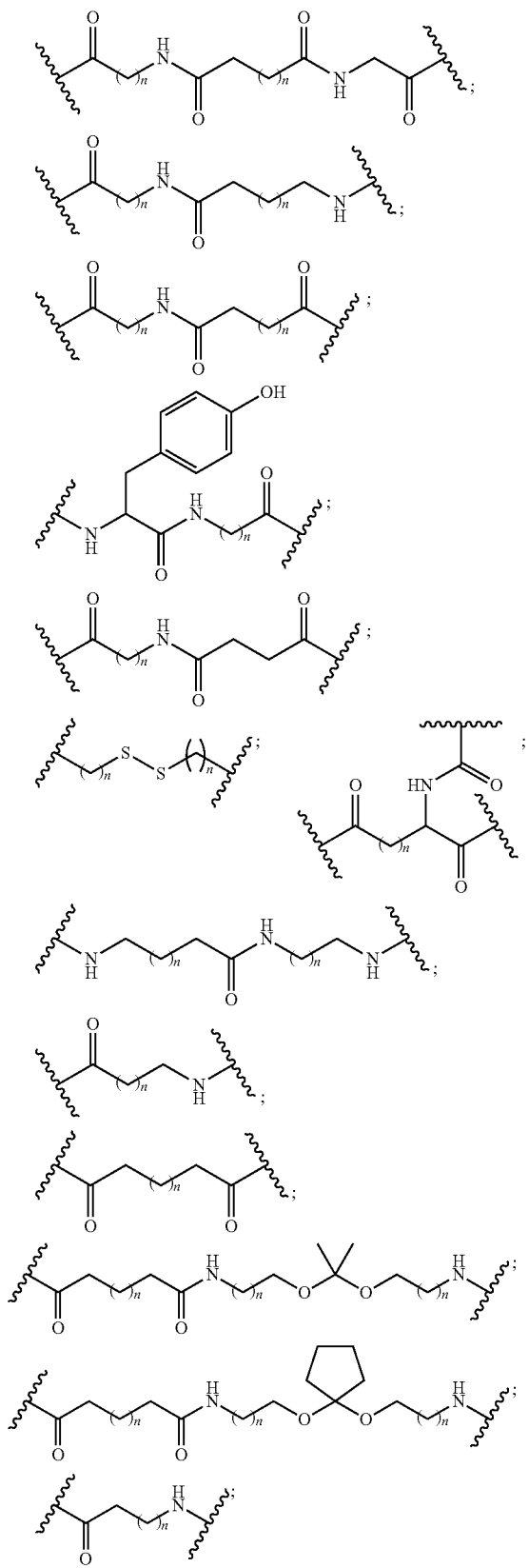
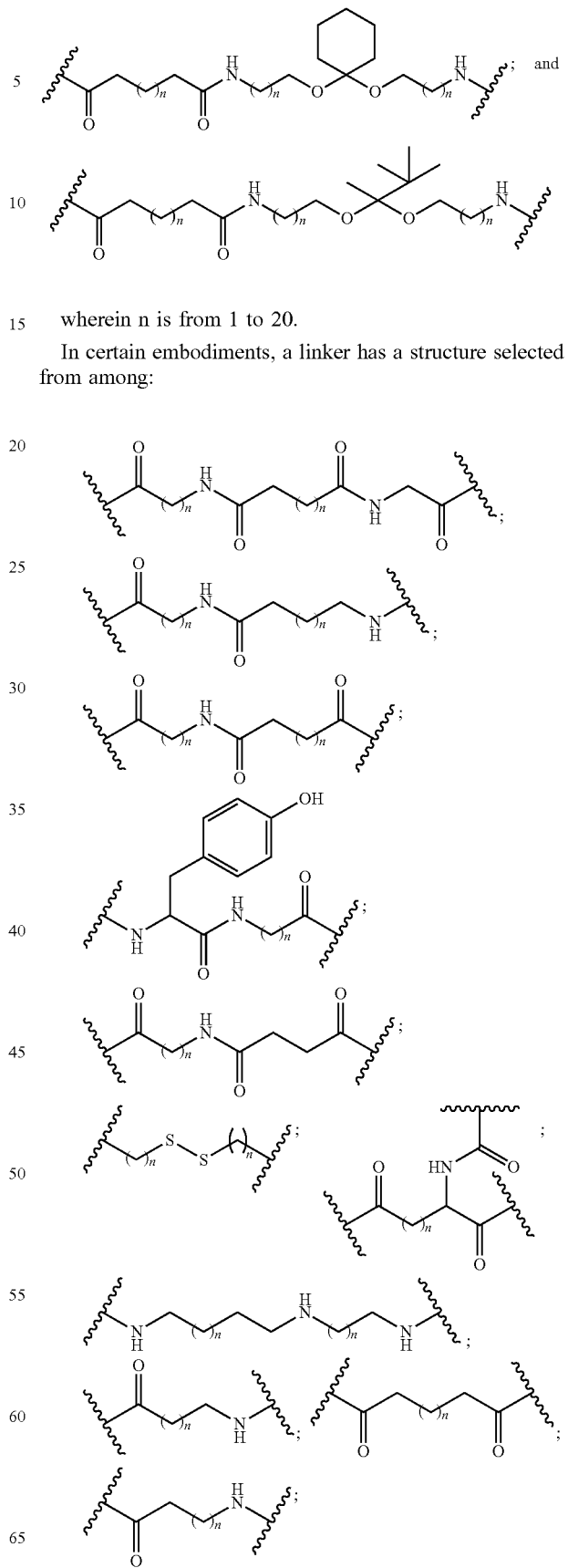
wherein n is from 1 to 20.
In certain embodiments, a linker has a structure selected from among:

115
-continued
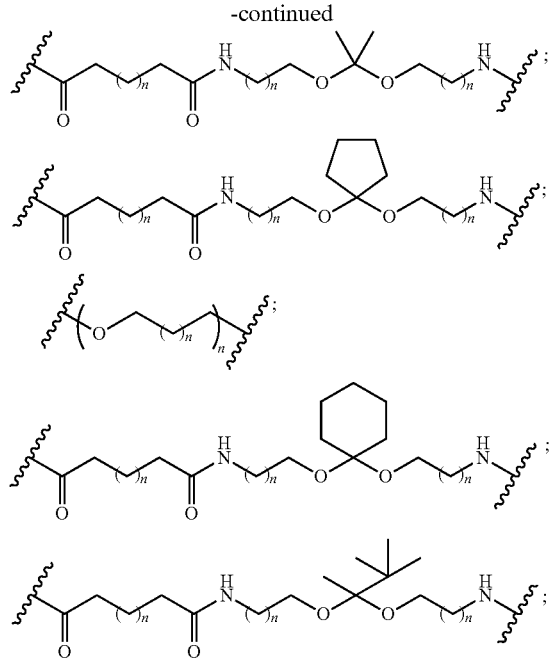
116
-continued
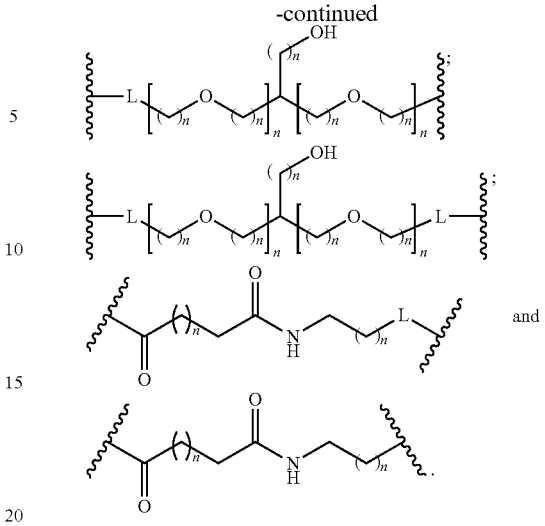
wherein each L is, independently, a phosphorus linking group or a neutral linking group; and
each n is, independently, from 1 to 20.
In certain embodiments, a linker has a structure selected from among:
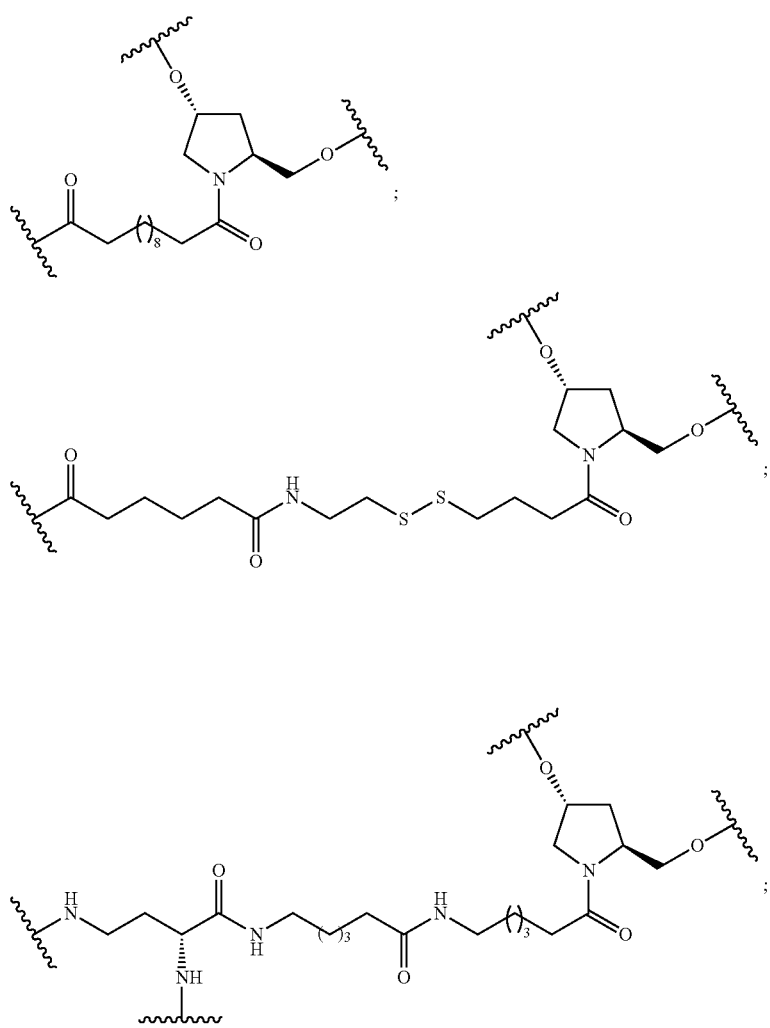

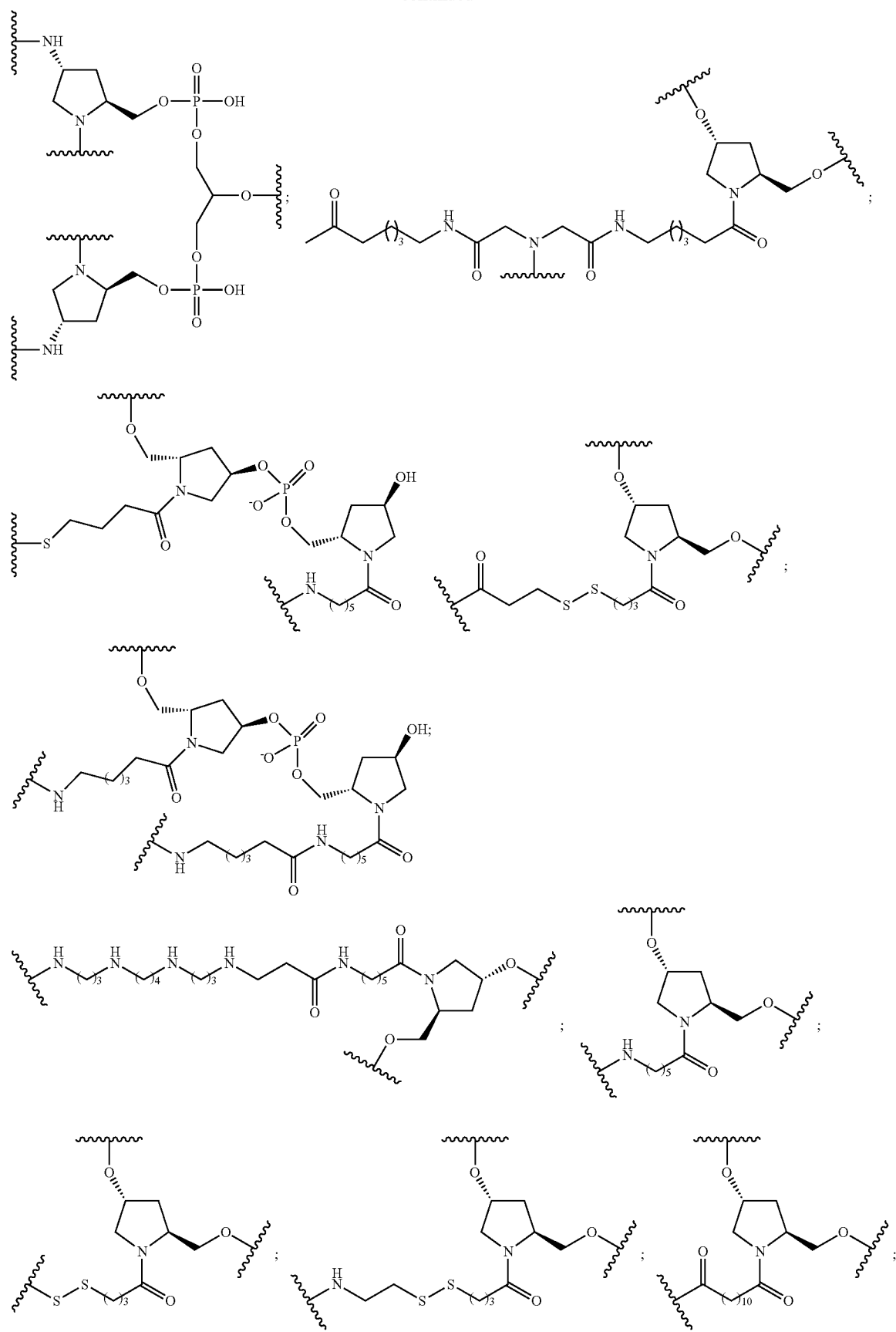

-continued
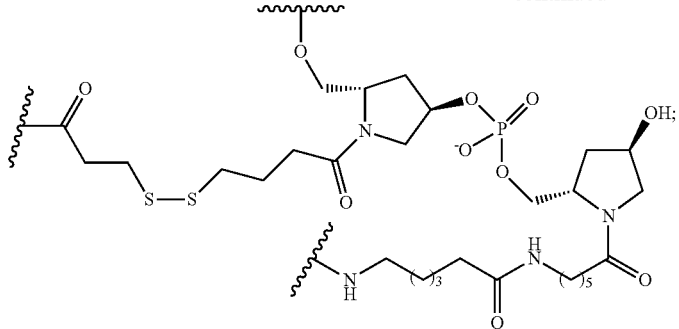
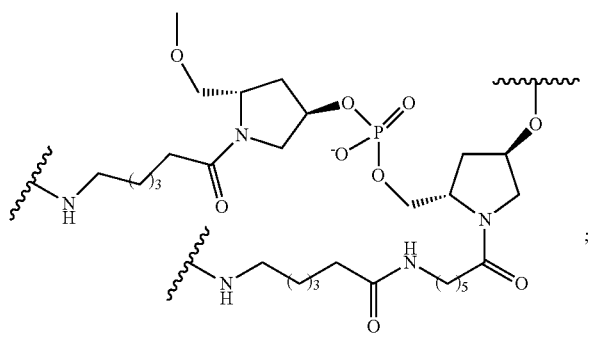
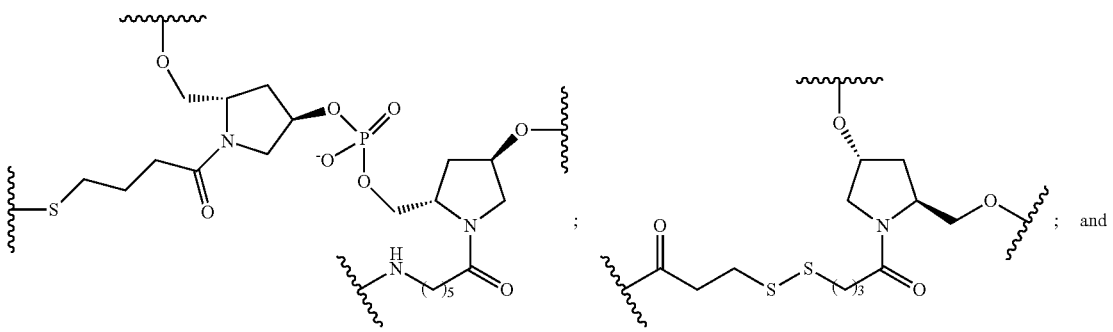
; and
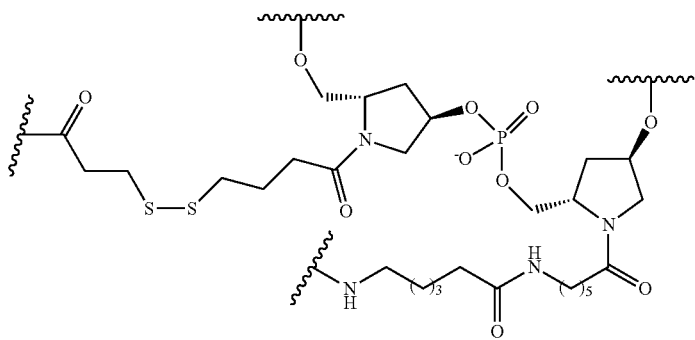

In certain embodiments, a linker has a structure selected from among:
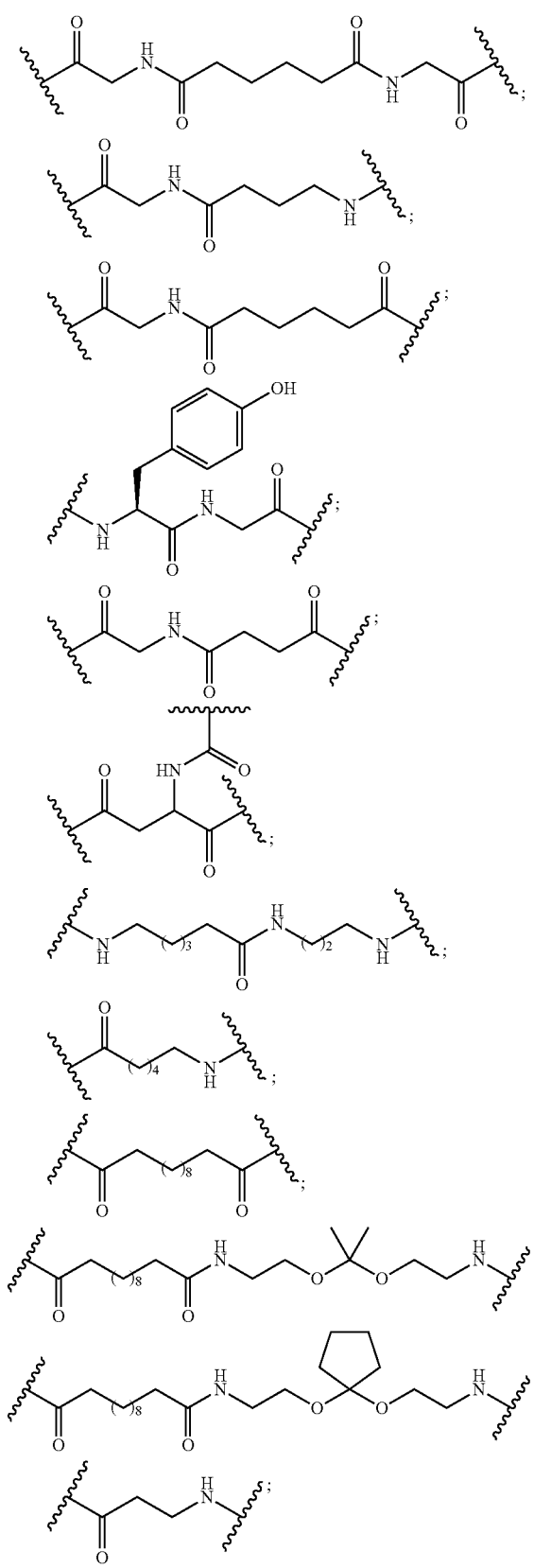
In certain embodiments, a linker has a structure selected from among:
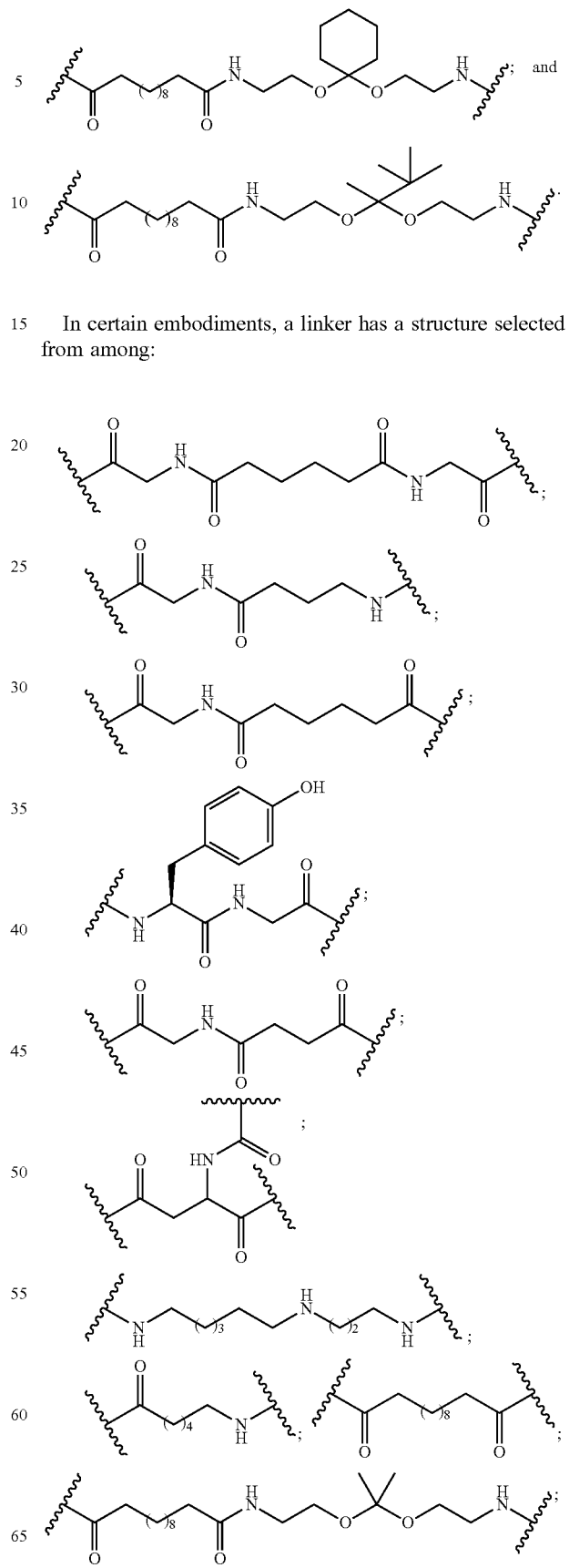

-continued
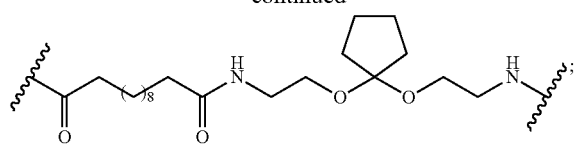
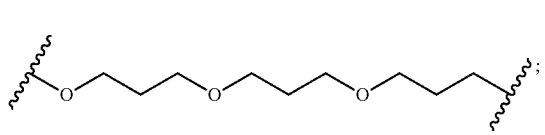
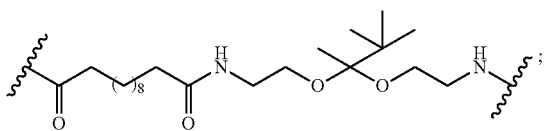
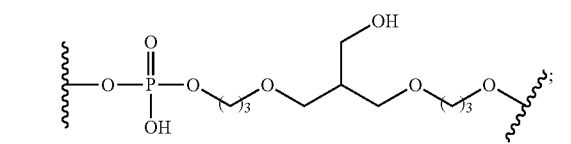
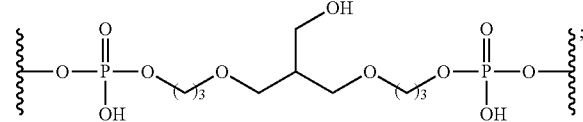
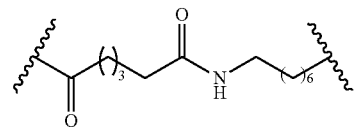
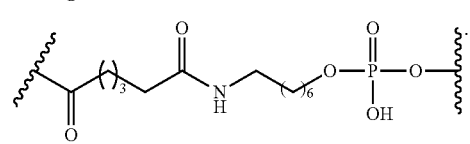
In certain embodiments, a linker has a structure selected from among:
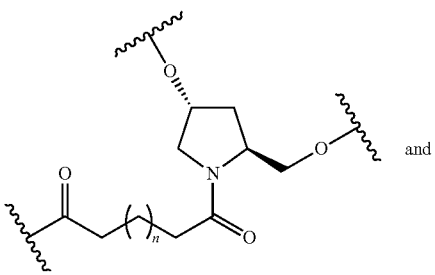 and
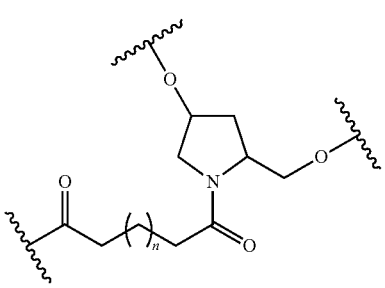
wherein n is from 1 to 20.
In certain embodiments, a linker has a structure selected from among:
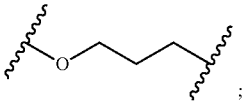
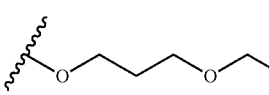 and
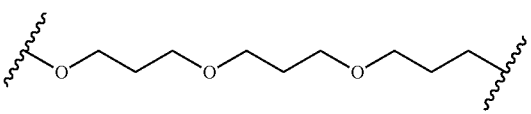
In certain embodiments, a linker has a structure selected from among:
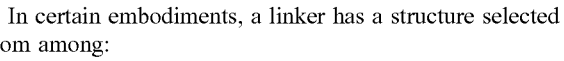 and
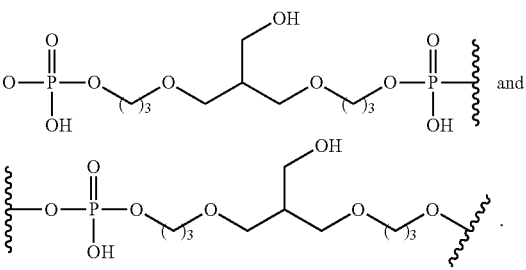

In certain embodiments, a linker has a structure selected from among:

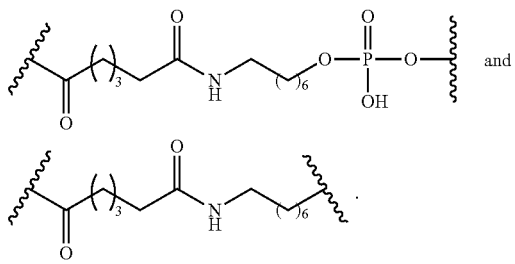

In certain embodiments, the conjugate linker has the structure:

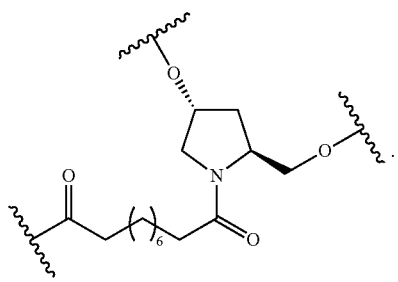

In certain embodiments, the conjugate linker has the structure:

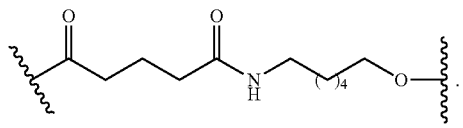

In certain embodiments, a linker has a structure selected from among:

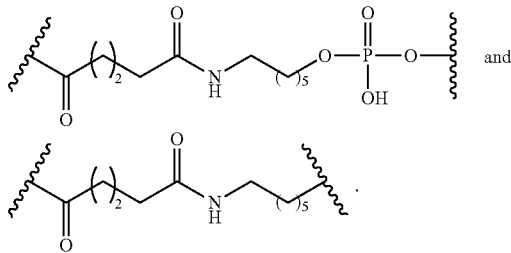

In certain embodiments, a linker has a structure selected from among:

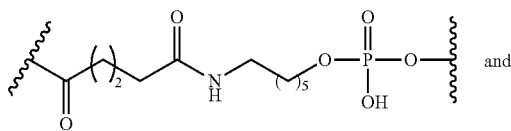

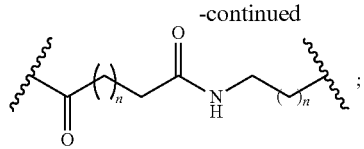

wherein each n is independently, 0, 1, 2, 3, 4, 5, 6, or 7.

iii. Certain Cell-Targeting Moieties

In certain embodiments, conjugate groups comprise cell-targeting moieties. Certain such cell-targeting moieties increase cellular uptake of antisense compounds. In certain embodiments, cell-targeting moieties comprise a branching group, one or more tether, and one or more ligand. In certain embodiments, cell-targeting moieties comprise a branching group, one or more tether, one or more ligand and one or more cleavable bond.

1. Certain Branching Groups

In certain embodiments, the conjugate groups comprise a targeting moiety comprising a branching group and at least two tethered ligands. In certain embodiments, the branching group attaches the conjugate linker. In certain embodiments, the branching group attaches the cleavable moiety. In certain embodiments, the branching group attaches the antisense oligonucleotide. In certain embodiments, the branching group is covalently attached to the linker and each of the tethered ligands. In certain embodiments, the branching group comprises a branched aliphatic group comprising groups selected from alkyl, amide, disulfide, polyethylene glycol, ether, thioether and hydroxylamino groups. In certain embodiments, the branching group comprises groups selected from alkyl, amide and ether groups. In certain embodiments, the branching group comprises groups selected from alkyl and ether groups. In certain embodiments, the branching group comprises a mono or polycyclic ring system. In certain embodiments, the branching group comprises one or more cleavable bond. In certain embodiments, the conjugate group does not include a branching group.

In certain embodiments, a branching group has a structure selected from among:

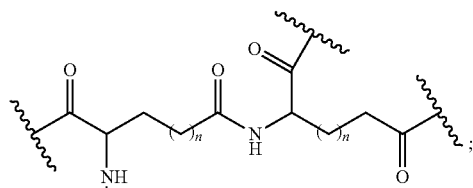

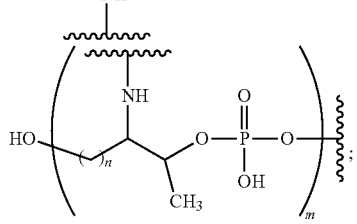

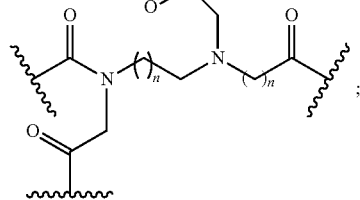

127
-continued
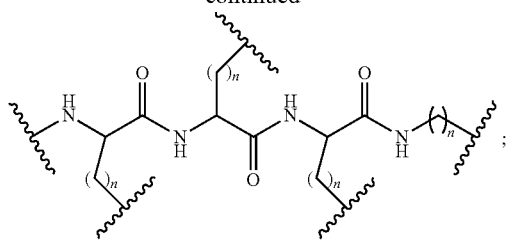
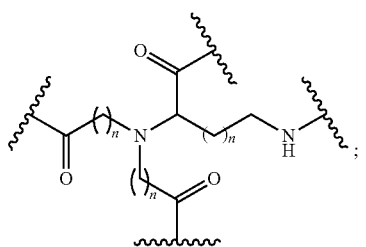
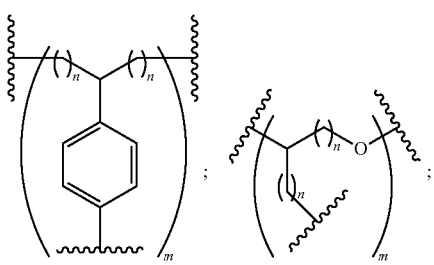
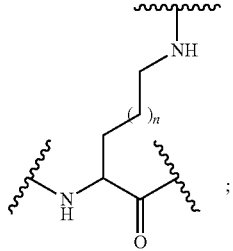
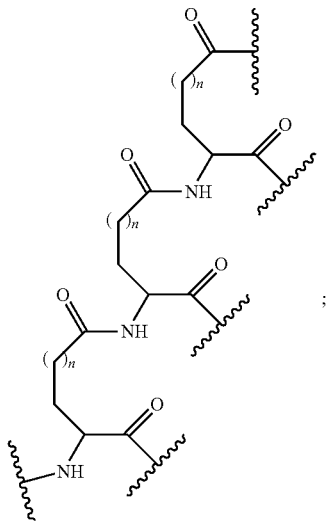
128
-continued
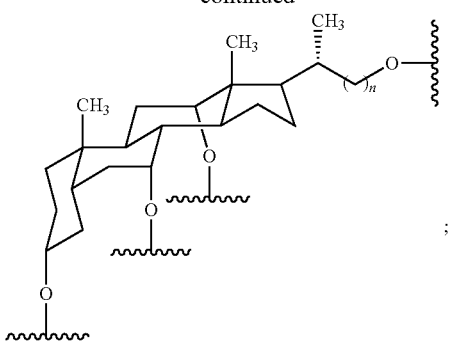
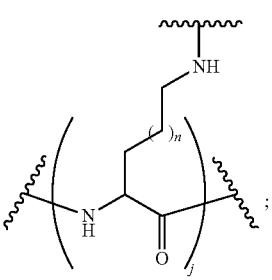
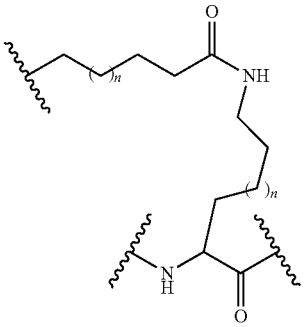
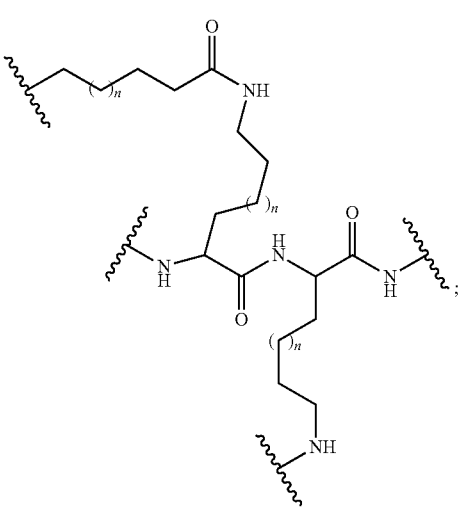

129
-continued
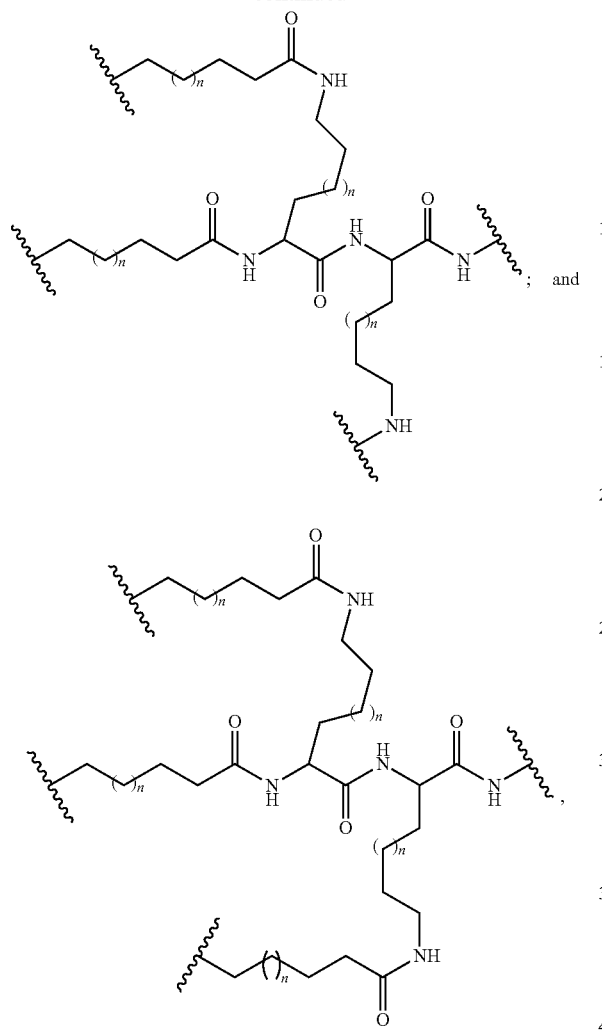
130
-continued
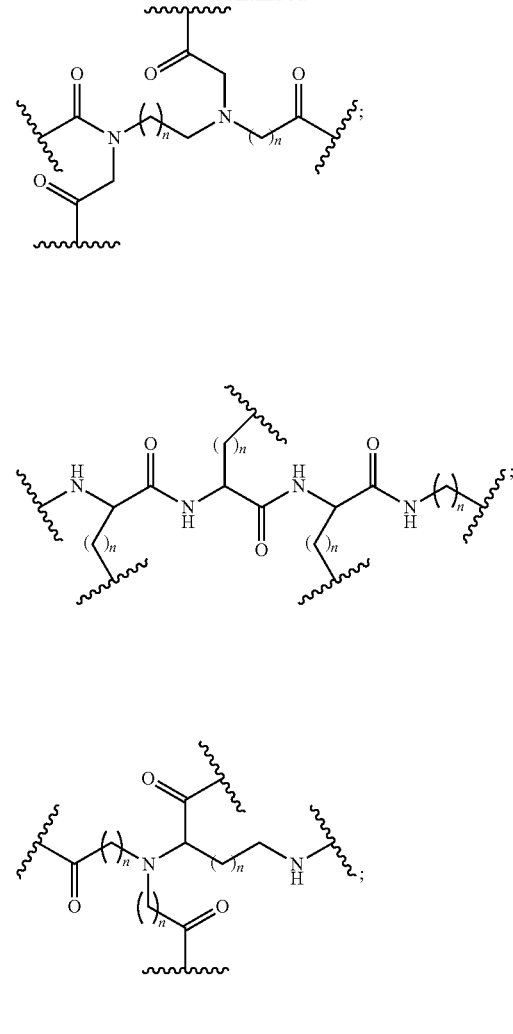
wherein each n is, independently, from 1 to 20;
j is from 1 to 3; and
m is from 2 to 6.
In certain embodiments, a branching group has a structure selected from among:
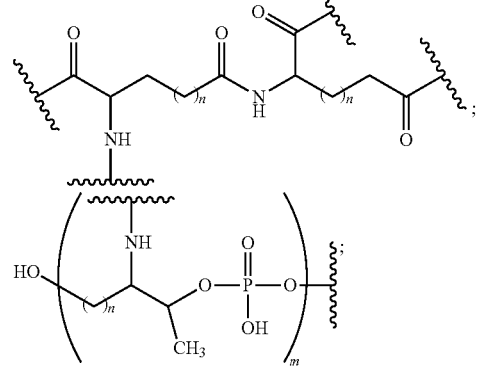
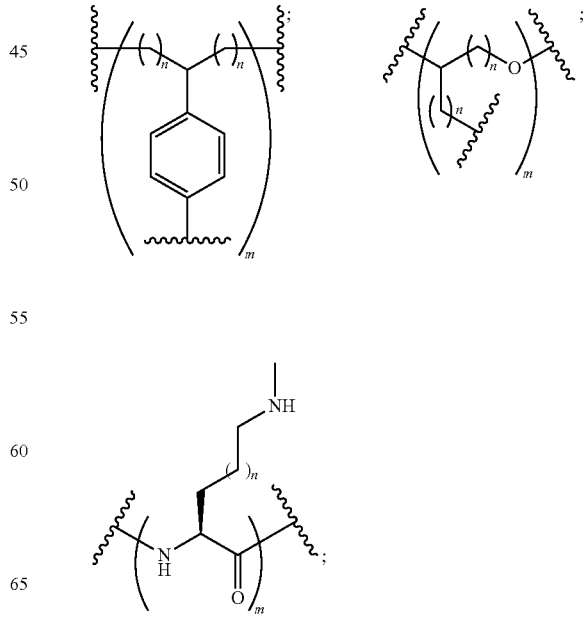

131
-continued
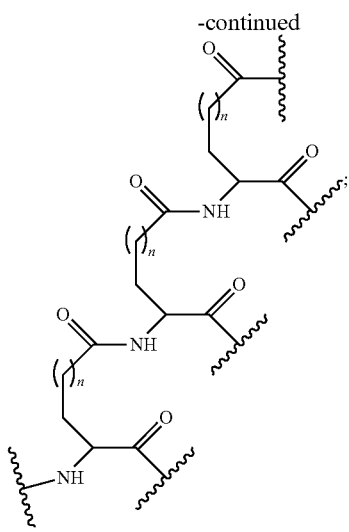
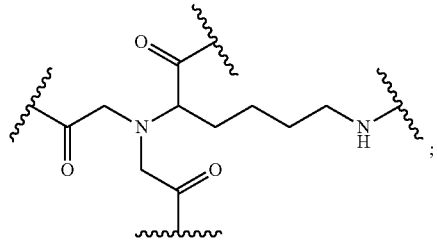
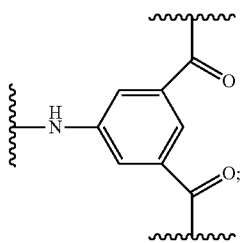
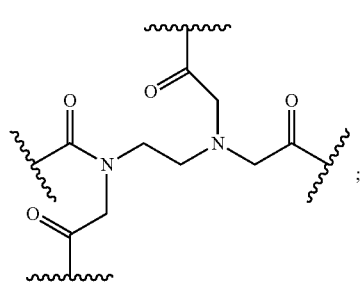
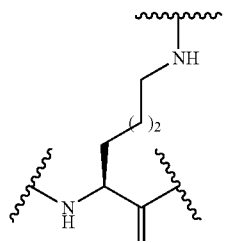
wherein each n is, independently, from 1 to 20; and m is from 2 to 6.
In certain embodiments, a branching group has a structure selected from among:
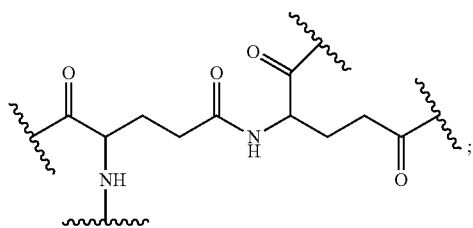
132
-continued
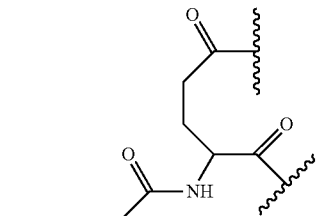
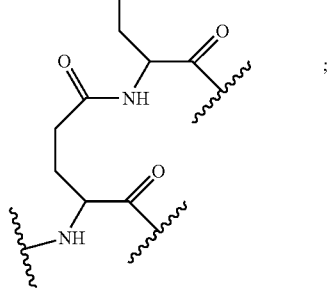

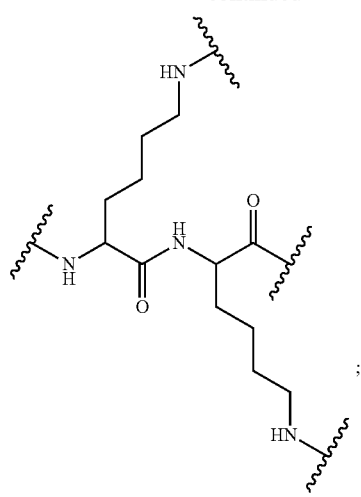
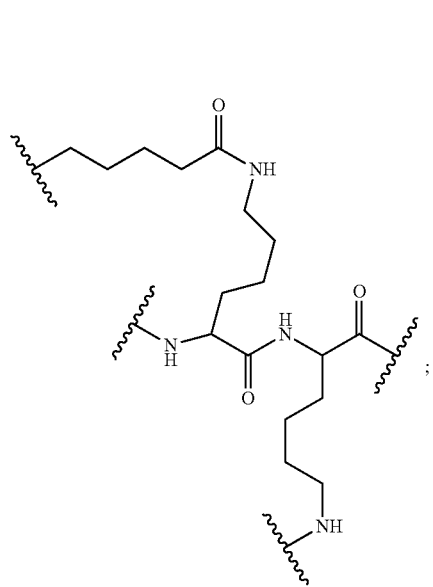
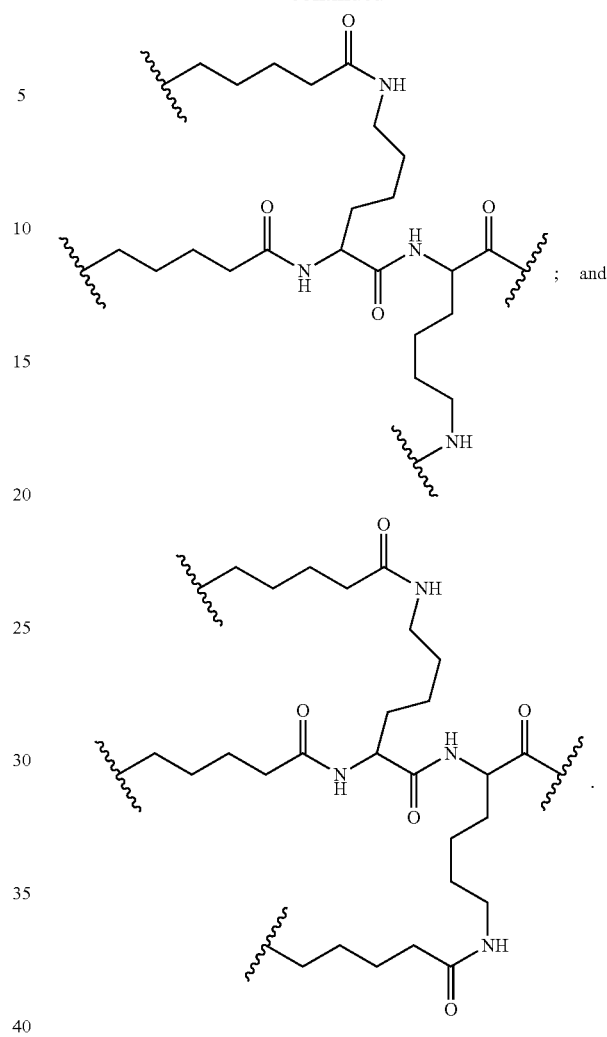
In certain embodiments, a branching group has a structure selected from among:
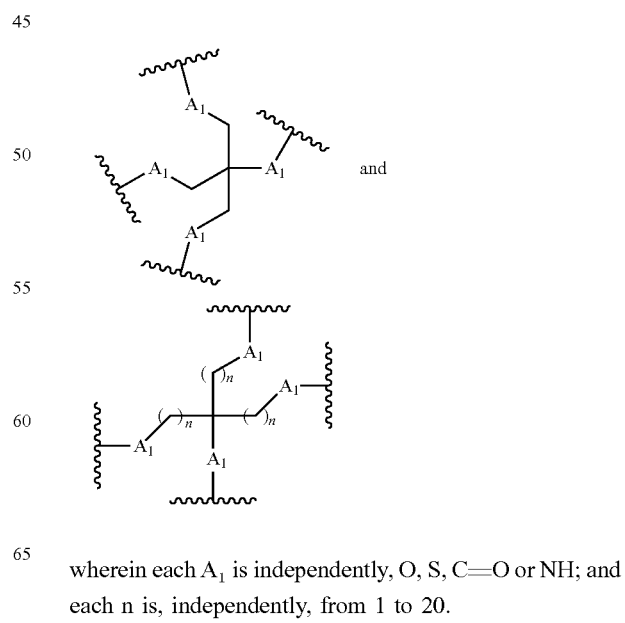
wherein each $A_1$ is independently, O, S, C=O or NH; and each n is, independently, from 1 to 20.

In certain embodiments, a branching group has a structure selected from among:

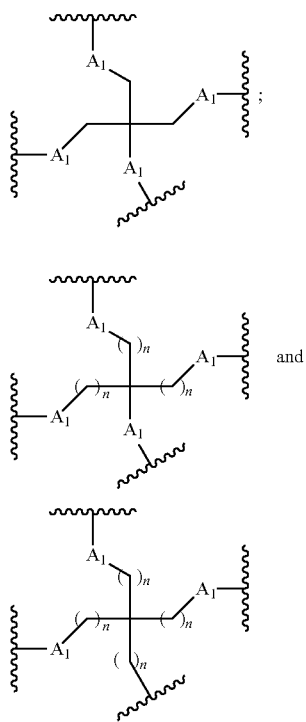

wherein each $A_1$ is independently, O, S, C=O or NH; and each n is, independently, from 1 to 20.

In certain embodiments, a branching group has a structure selected from among:

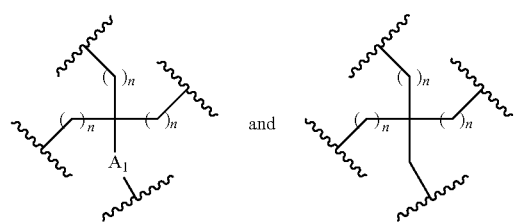

wherein $A_1$ is O, S, C=O or NH; and each n is, independently, from 1 to 20.

In certain embodiments, a branching group has a structure selected from among:

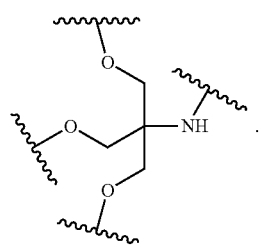 [SMILES: *NC(CO*)(CO*)CO*]

In certain embodiments, a branching group has a structure selected from among:

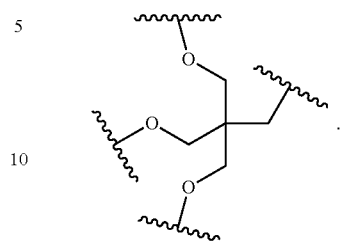

In certain embodiments, a branching group has a structure selected from among:

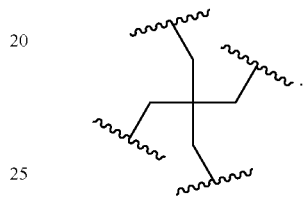

2. Certain Tethers

In certain embodiments, conjugate groups comprise one or more tethers covalently attached to the branching group. In certain embodiments, conjugate groups comprise one or more tethers covalently attached to the linking group. In certain embodiments, each tether is a linear aliphatic group comprising one or more groups selected from alkyl, ether, thioether, disulfide, amide and polyethylene glycol groups in any combination. In certain embodiments, each tether is a linear aliphatic group comprising one or more groups selected from alkyl, substituted alkyl, ether, thioether, disulfide, amide, phosphodiester and polyethylene glycol groups in any combination. In certain embodiments, each tether is a linear aliphatic group comprising one or more groups selected from alkyl, ether and amide groups in any combination. In certain embodiments, each tether is a linear aliphatic group comprising one or more groups selected from alkyl, substituted alkyl, phosphodiester, ether and amide groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, the tether includes one or more cleavable bond. In certain embodiments, the tether is attached to the branching group through either an amide or an ether group. In certain embodiments, the tether is attached to the branching group through a phosphodiester group. In certain embodiments, the tether is attached to the branching group through a phosphorus linking group or neutral linking group. In certain embodiments, the tether is attached to the branching group through an ether group. In certain embodiments, the tether is attached to the ligand through either an amide or an ether group. In certain embodiments, the tether is attached to the ligand through an ether group. In certain embodiments, the tether is attached to the ligand through either an amide or an ether group. In certain embodiments, the tether is attached to the ligand through an ether group.

In certain embodiments, each tether comprises from about 8 to about 20 atoms in chain length between the ligand and the branching group. In certain embodiments, each tether group comprises from about 10 to about 18 atoms in chain length between the ligand and the branching group. In certain embodiments, each tether group comprises about 13 atoms in chain length.

In certain embodiments, a tether has a structure selected from among:

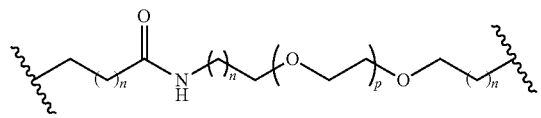

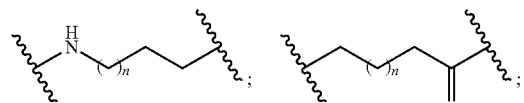

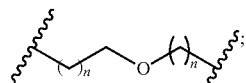

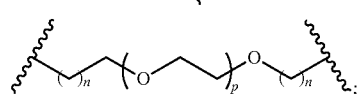

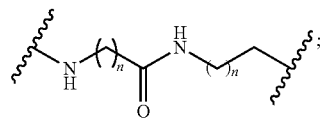

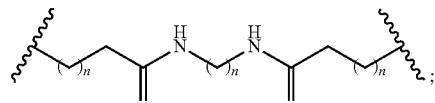

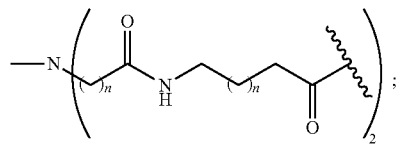

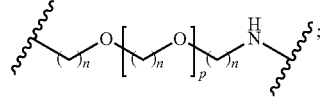

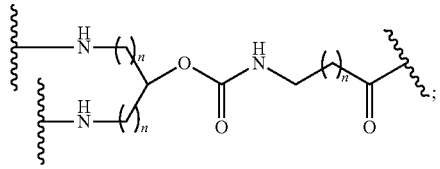

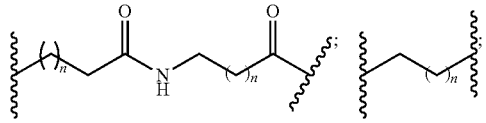

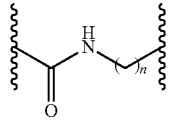

wherein each n is, independently, from 1 to 20; and each p is from 1 to about 6.

In certain embodiments, a tether has a structure selected from among:

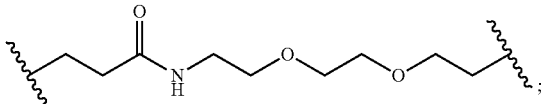

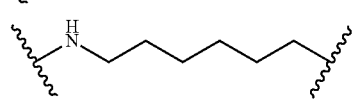

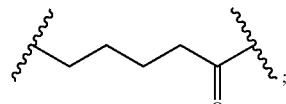

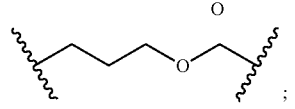

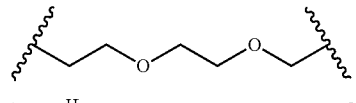

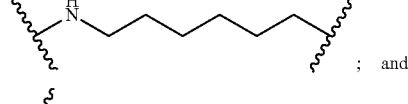

; and

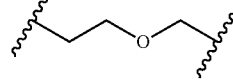

In certain embodiments, a tether has a structure selected from among:

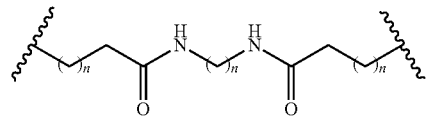

wherein each n is, independently, from 1 to 20.

In certain embodiments, a tether has a structure selected from among:

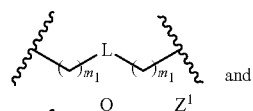

and

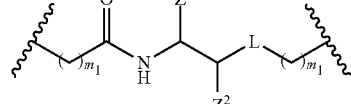

wherein L is either a phosphorus linking group or a neutral linking group;

$Z_1$ is C(=O)O—$R_2$;

$Z_2$ is H, $C_1$-$C_6$ alkyl or substituted $C_1$-$C_6$ alky;

$R_2$ is H, $C_1$-$C_6$ alkyl or substituted $C_1$-$C_6$ alky; and each $m_1$ is, independently, from 0 to 20 wherein at least one $m_1$ is greater than 0 for each tether.

In certain embodiments, a tether has a structure selected from among:

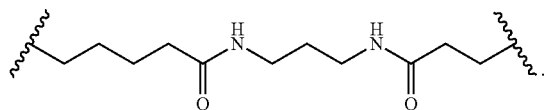 [SMILES: *CCCCC(=O)NCCCNC(=O)CC*]

In certain embodiments, a tether has a structure selected from among:

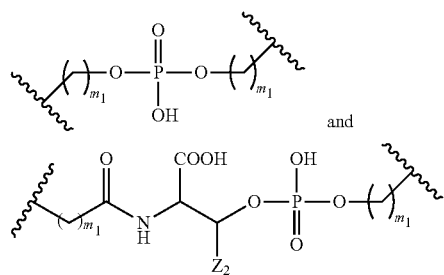

wherein $Z_2$ is H or $CH_3$; and
each $m_1$ is, independently, from 0 to 20 wherein at least one $m_1$ is greater than 0 for each tether.

In certain embodiments, a tether has a structure selected from among:

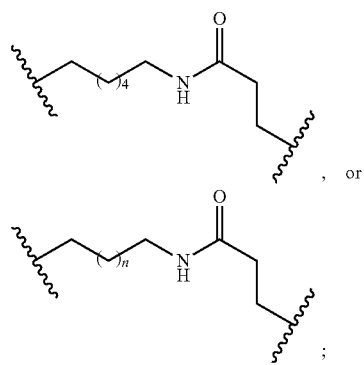

wherein each n is independently, 0, 1, 2, 3, 4, 5, 6, or 7.

In certain embodiments, a tether comprises a phosphorus linking group. In certain embodiments, a tether does not comprise any amide bonds. In certain embodiments, a tether comprises a phosphorus linking group and does not comprise any amide bonds.

3. Certain Ligands

In certain embodiments, the present disclosure provides ligands wherein each ligand is covalently attached to a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamone and fucose. In certain embodiments, each ligand is N-acetyl galactoseamine (GalNAc). In certain embodiments, the targeting moiety comprises 2 to 6 ligands. In certain embodiments, the targeting moiety comprises 3 ligands. In certain embodiments, the targeting moiety comprises 3 N-acetyl galactoseamine ligands.

In certain embodiments, the ligand is a carbohydrate, carbohydrate derivative, modified carbohydrate, multivalent carbohydrate cluster, polysaccharide, modified polysaccharide, or polysaccharide derivative. In certain embodiments, the ligand is an amino sugar or a thio sugar. For example, amino sugars may be selected from any number of compounds known in the art, for example glucosamine, sialic acid, α-D-galactosamine, N-Acetylgalactosamine, 2-acetamido-2-deoxy-D-galactopyranose (GalNAc), 2-Amino-3-O—[(R)-1-carboxyethyl]-2-deoxy-β-D-glucopyranose (β-muramic acid), 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose and N-sulfo-D-glucosamine, and N-Glycoloyl-α-neuraminic acid. For example, thio sugars may be selected from the group consisting of 5-Thio-β-D-glucopyranose, Methyl 2,3,4-tri-O-acetyl-1-thio-6-O-trityl-α-D-glucopyranoside, 4-Thio-β-D-galactopyranose, and ethyl 3,4,6,7-tetra-O-acetyl-2-deoxy-1,5-dithio-α-D-gluco-heptopyranoside.

In certain embodiments, "GalNac" or "Gal-NAc" refers to 2-(Acetylamino)-2-deoxy-D-galactopyranose, commonly referred to in the literature as N-acetyl galactosamine. In certain embodiments, "N-acetyl galactosamine" refers to 2-(Acetylamino)-2-deoxy-D-galactopyranose. In certain embodiments, "GalNac" or "Gal-NAc" refers to 2-(Acetylamino)-2-deoxy-D-galactopyranose. In certain embodiments, "GalNac" or "Gal-NAc" refers to 2-(Acetylamino)-2-deoxy-D-galactopyranose, which includes both the β-form: 2-(Acetylamino)-2-deoxy-β-D-galactopyranose and α-form: 2-(Acetylamino)-2-deoxy-D-galactopyranose. In certain embodiments, both the β-form: 2-(Acetylamino)-2-deoxy-β-D-galactopyranose and α-form: 2-(Acetylamino)-2-deoxy-D-galactopyranose may be used interchangeably. Accordingly, in structures in which one form is depicted, these structures are intended to include the other form as well. For example, where the structure for an α-form: 2-(Acetylamino)-2-deoxy-D-galactopyranose is shown, this structure is intended to include the other form as well. In certain embodiments, In certain preferred embodiments, the β-form 2-(Acetylamino)-2-deoxy-D-galactopyranose is the preferred embodiment.

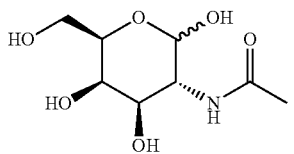

2-(Acetylamino)-2-deoxy-D-galactopyranose

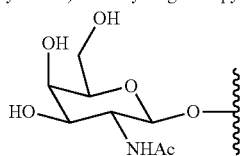

2-(Acetylamino)-2-deoxy-β-D-galactopyranose

-continued

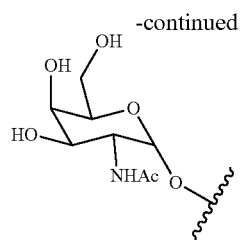

2-(Acetylamino)-2-deoxy-α-D-galactopyranose

In certain embodiments one or more ligand has a structure selected from among:

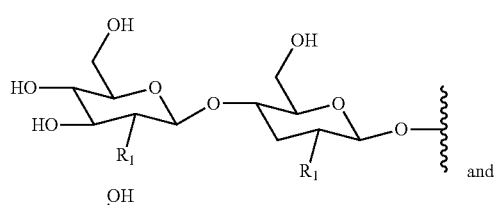 and

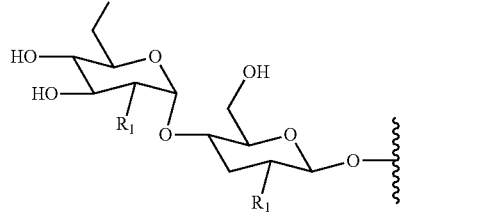

wherein each R₁ is selected from OH and NHCOOH.

In certain embodiments one or more ligand has a structure selected from among:

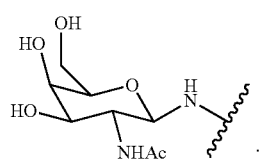

In certain embodiments one or more ligand has a structure selected from among:

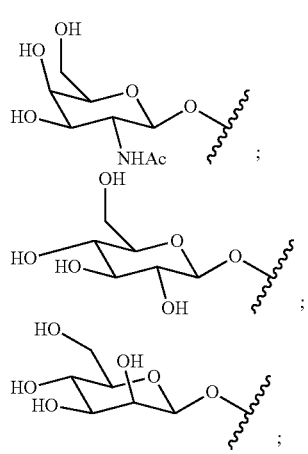

-continued

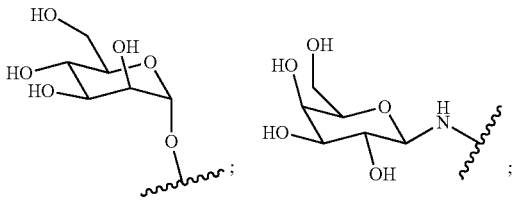

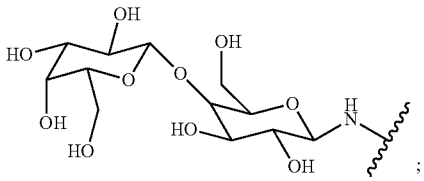

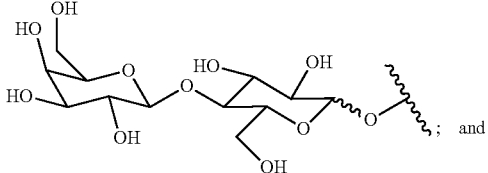 and

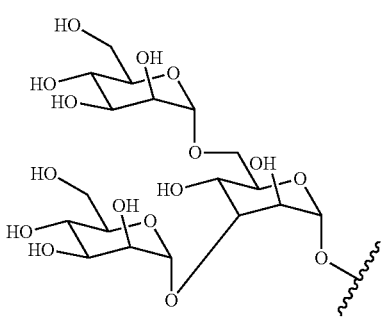

In certain embodiments one or more ligand has a structure selected from among:

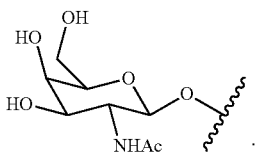 [SMILES: *OC1OC(CO)C(O)C(O)C1NC(C)=O]

i. Certain Conjugates
In certain embodiments, conjugate groups comprise the structural features above. In certain such embodiments, conjugate groups have the following structure:
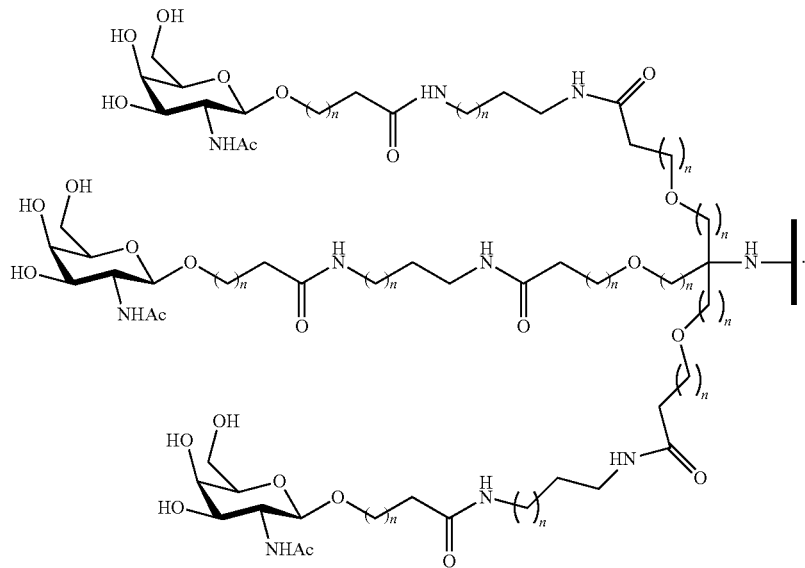
wherein each n is, independently, from 1 to 20.
In certain such embodiments, conjugate groups have the following structure:
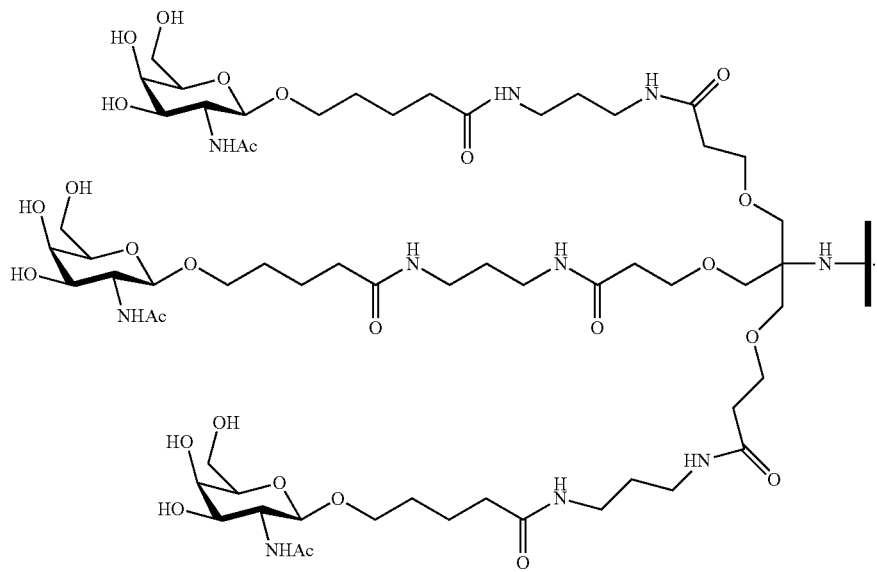

In certain such embodiments, conjugate groups have the following structure:
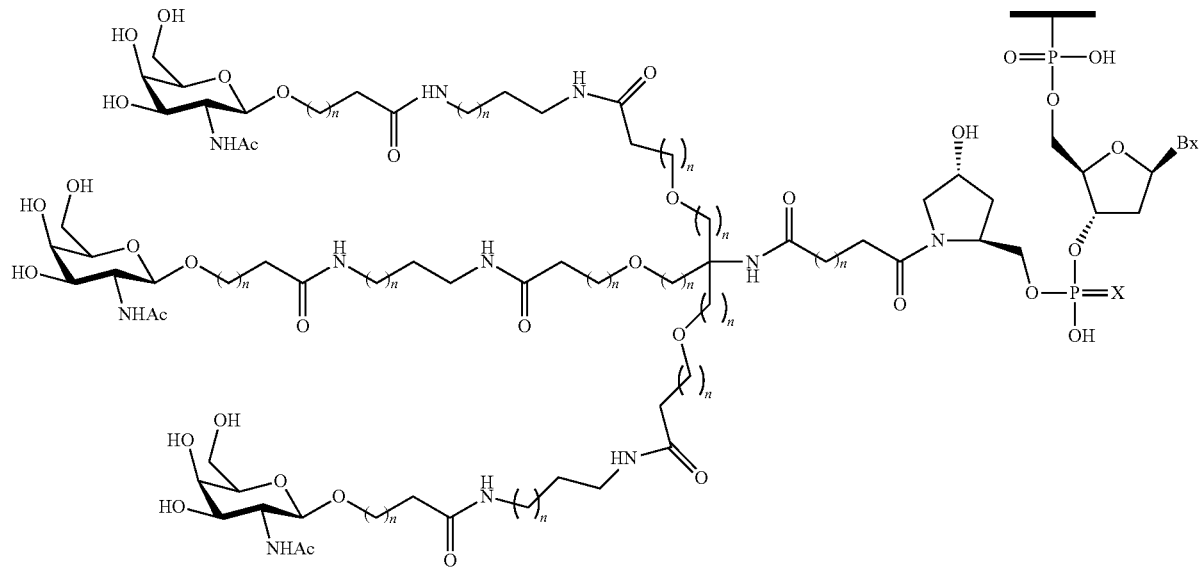
wherein each n is, independently, from 1 to 20;
Z is H or a linked solid support;
Q is an antisense compound;
X is O or S; and
Bx is a heterocyclic base moiety.
In certain such embodiments, conjugate groups have the following structure:
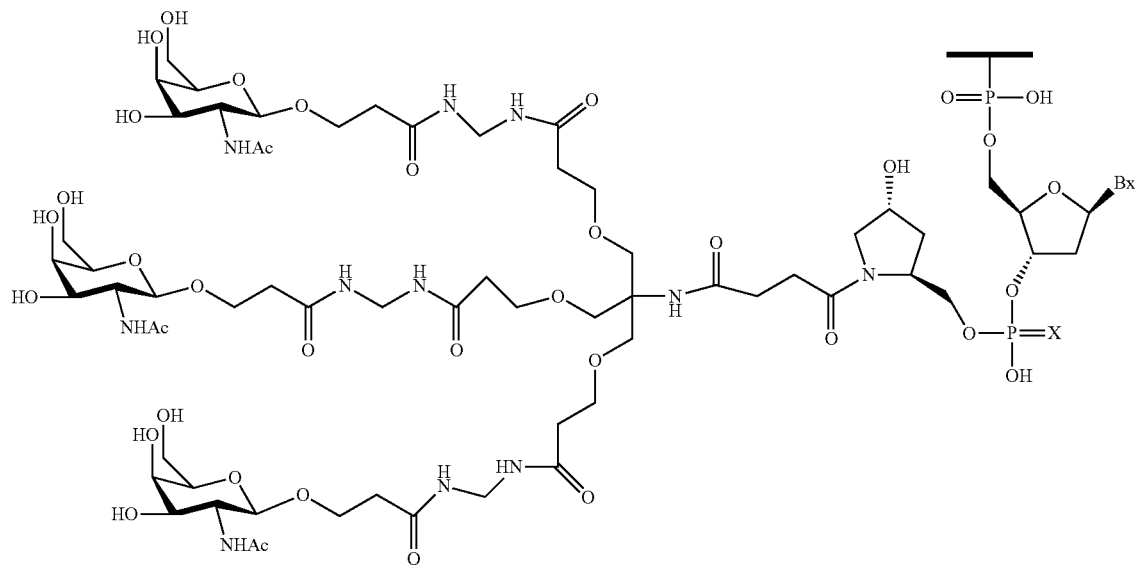

In certain such embodiments, conjugate groups have the following structure:
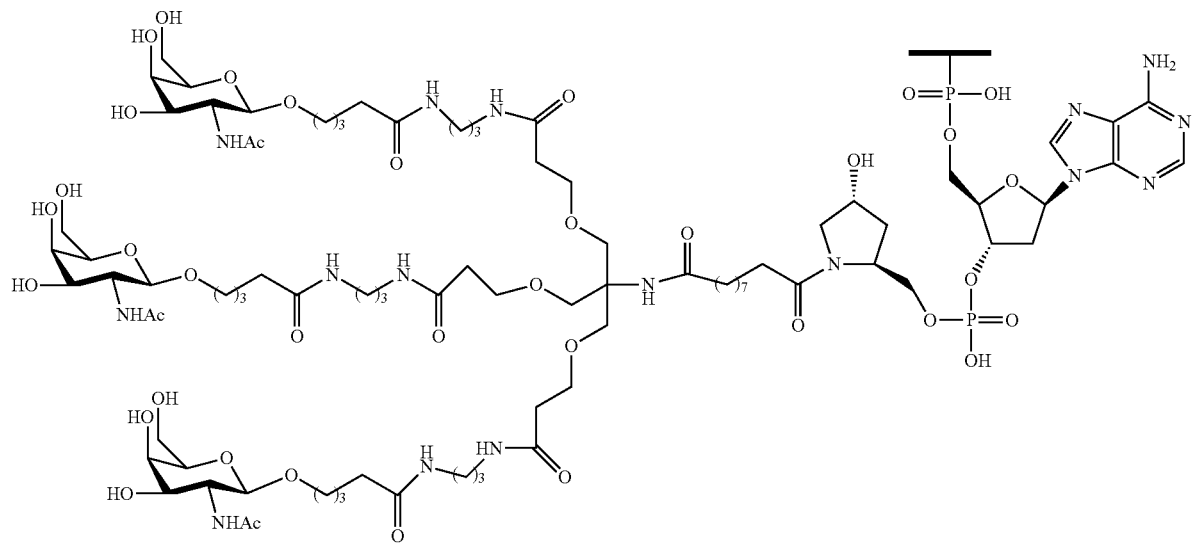
In certain such embodiments, conjugate groups have the following structure:
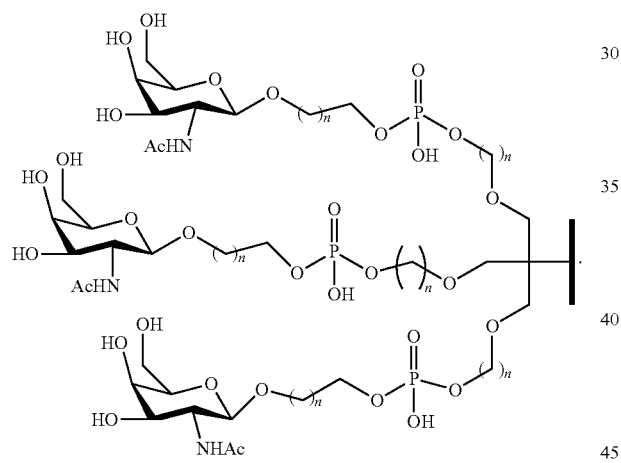
In certain such embodiments, conjugate groups have the following structure:
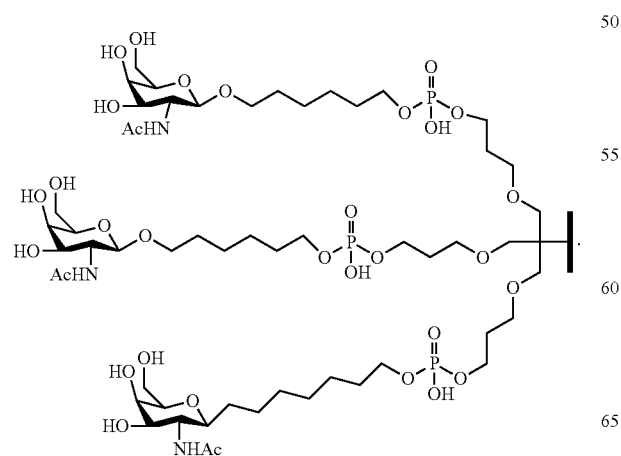

In certain such embodiments, conjugate groups have the following structure:
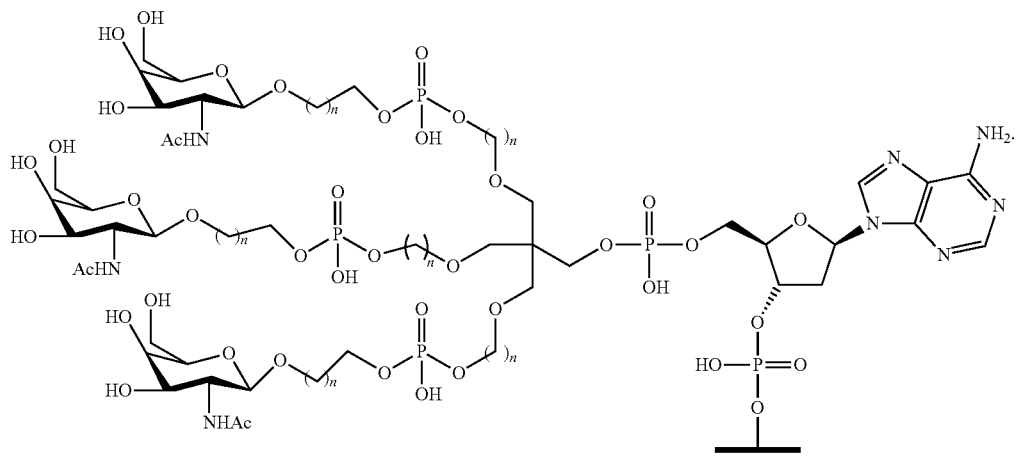
In certain such embodiments, conjugate groups have the following structure:
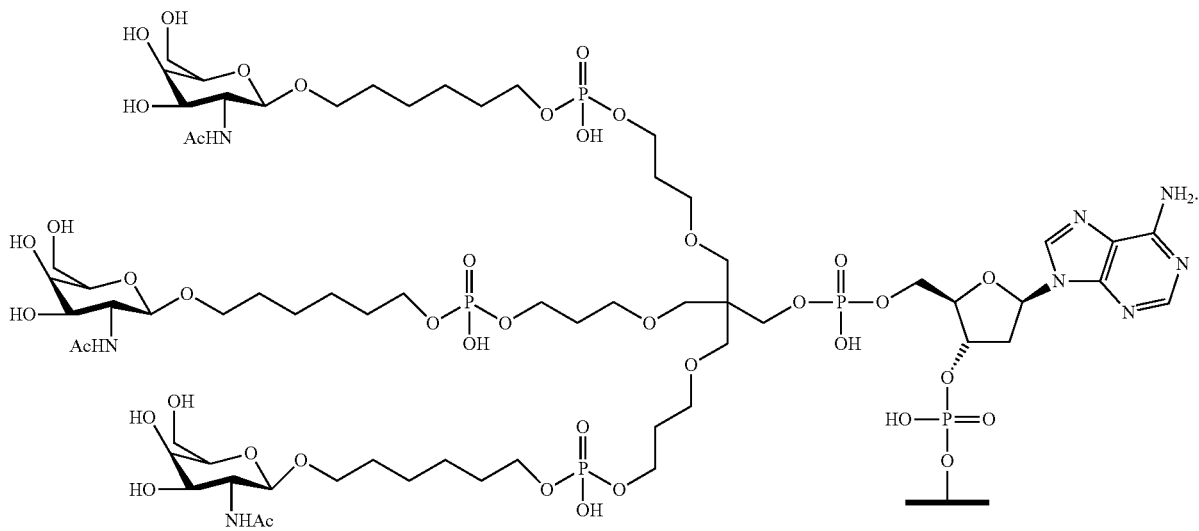
In certain such embodiments, conjugate groups have the following structure:
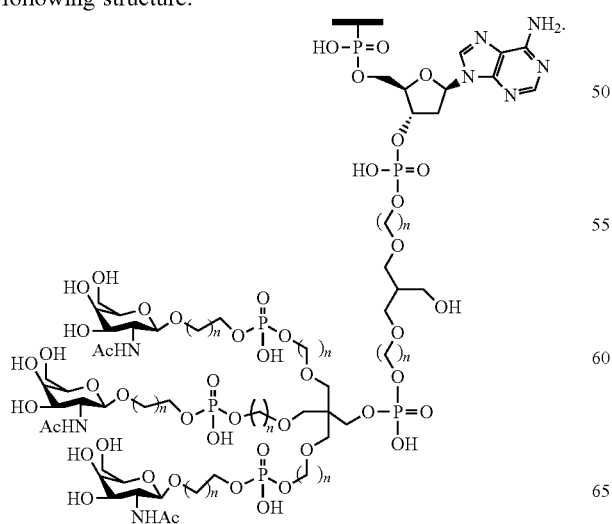

In certain such embodiments, conjugate groups have the following structure:
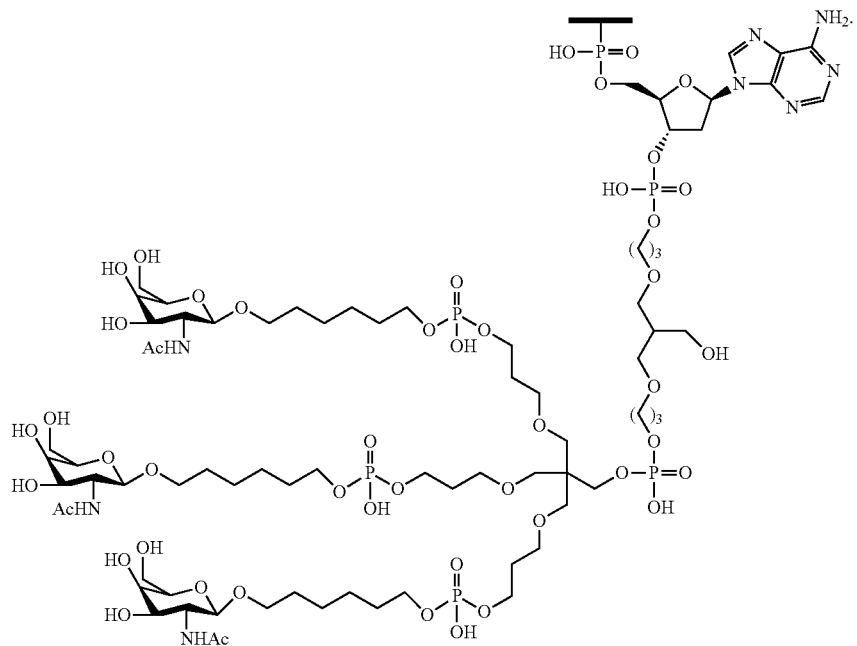
In certain embodiments, conjugates do not comprise a pyrrolidine.
In certain such embodiments, conjugate groups have the following structure:
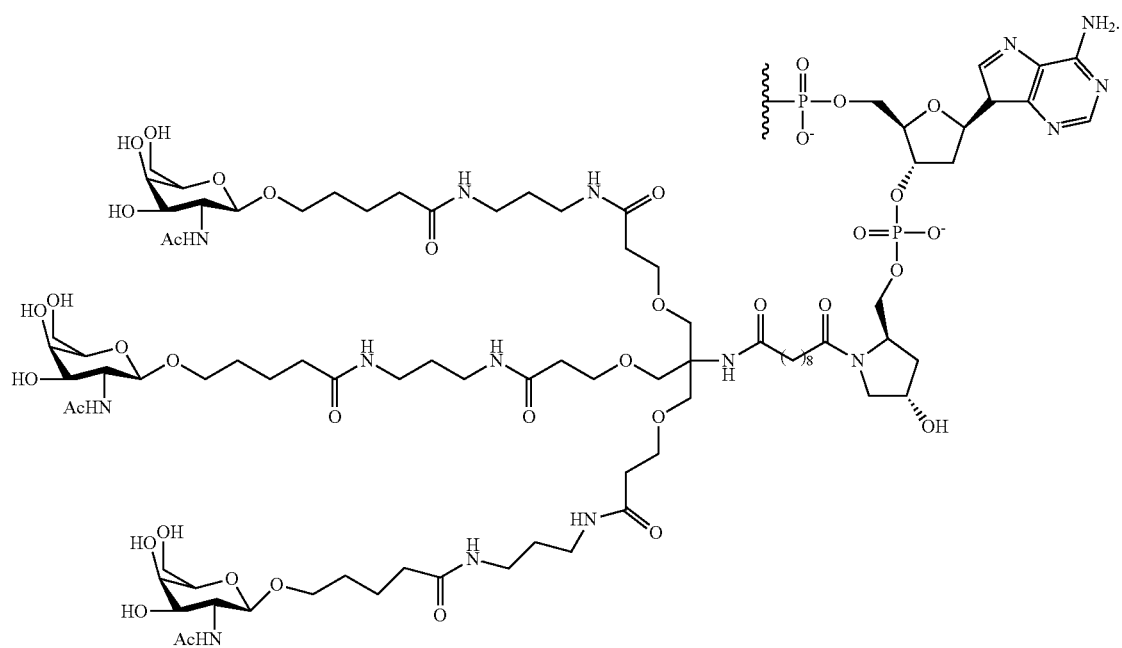

In certain such embodiments, conjugate groups have the following structure:
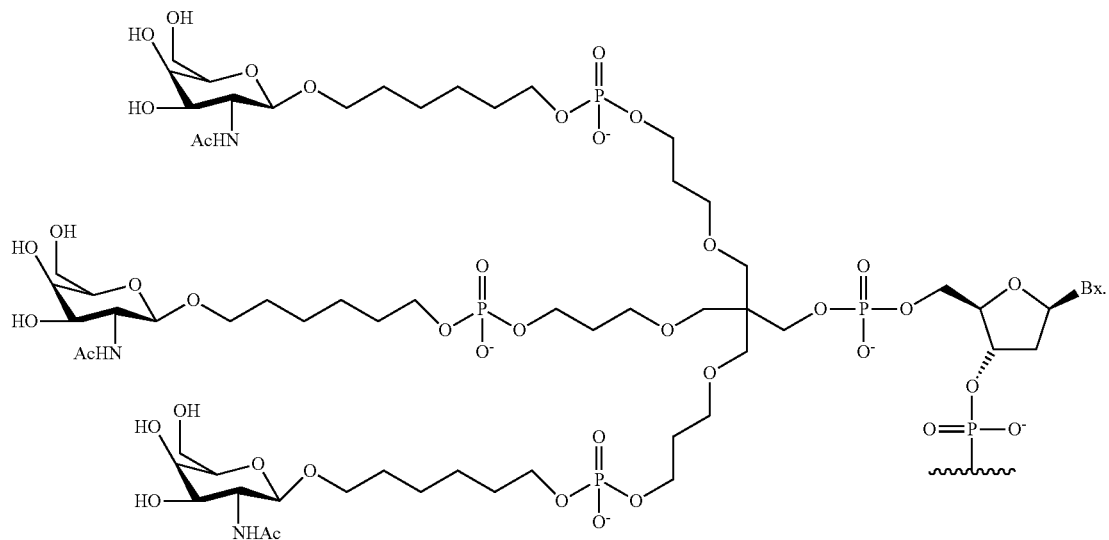
In certain such embodiments, conjugate groups have the following structure:
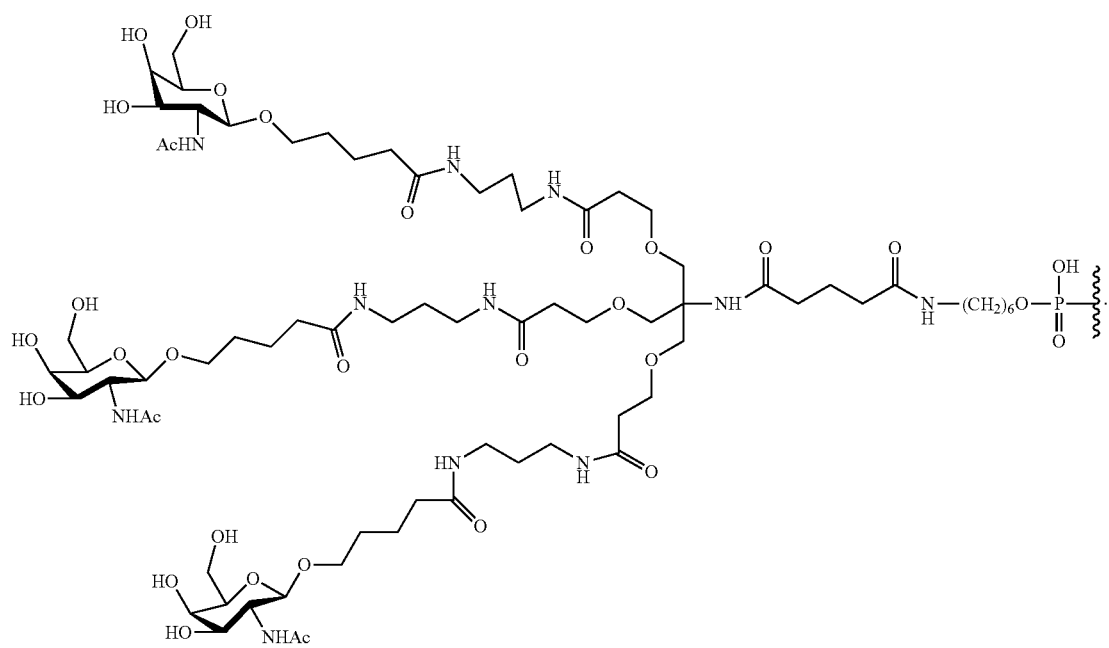

In certain such embodiments, conjugate groups have the following structure:
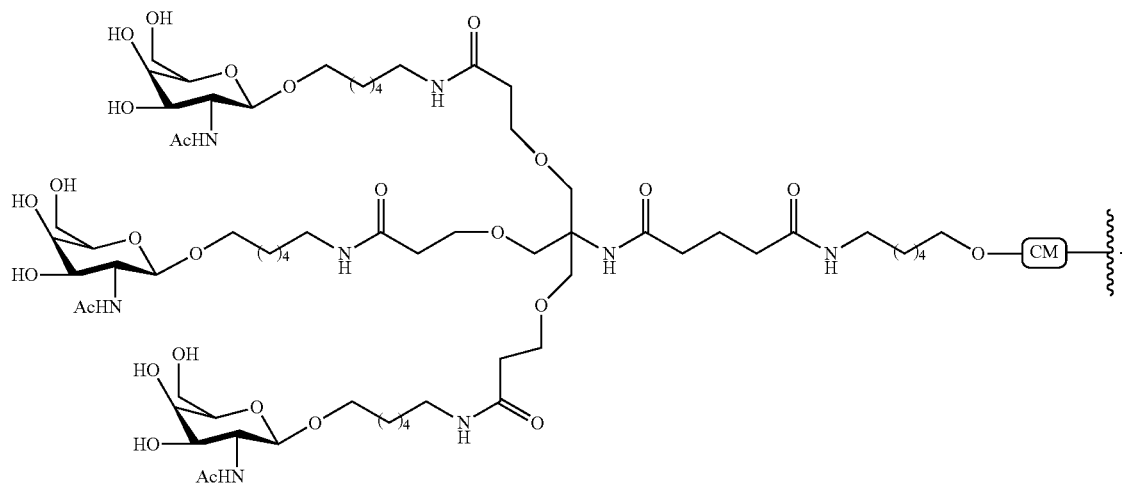
In certain such embodiments, conjugate groups have the following structure:
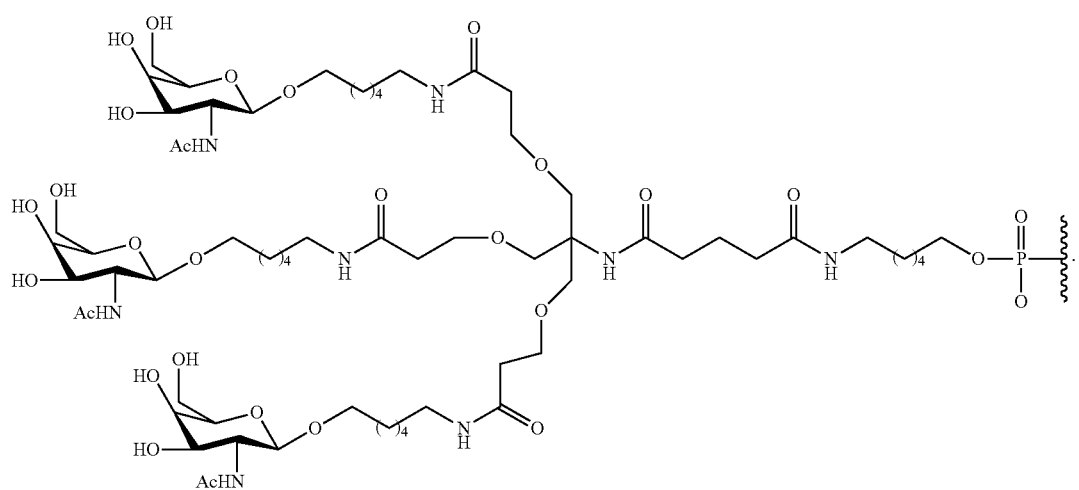
In certain such embodiments conjugate groups have the following structure:
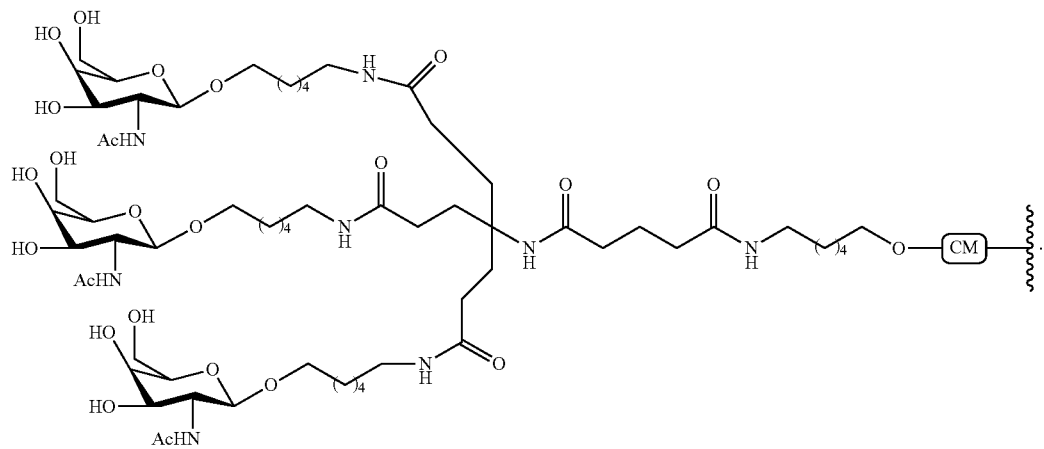

In certain such embodiments, conjugate groups have the following structure:
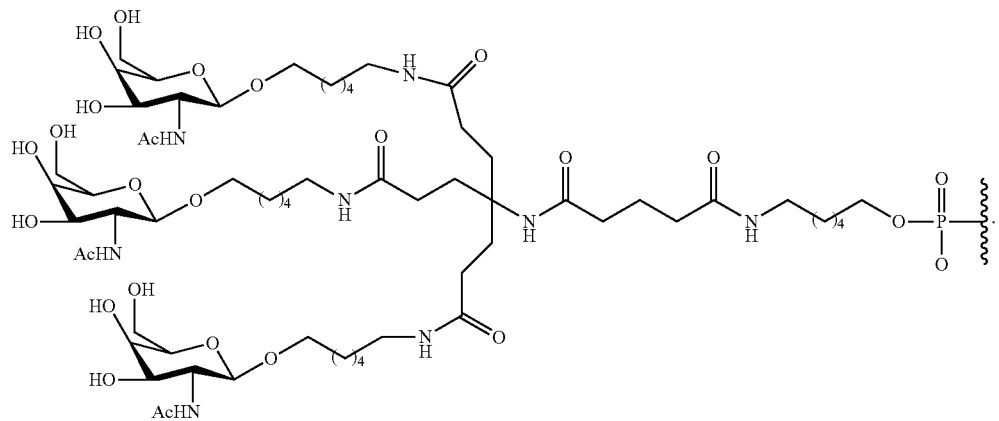
In certain such embodiments, conjugate groups have the following structure:
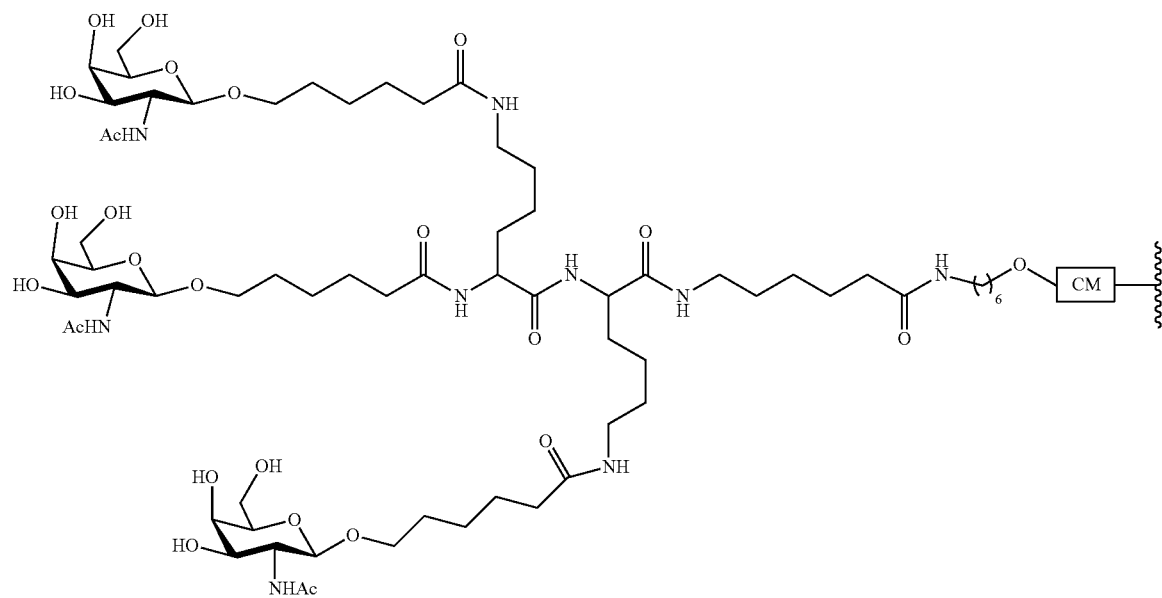

In certain such embodiments, conjugate groups have the following structure:
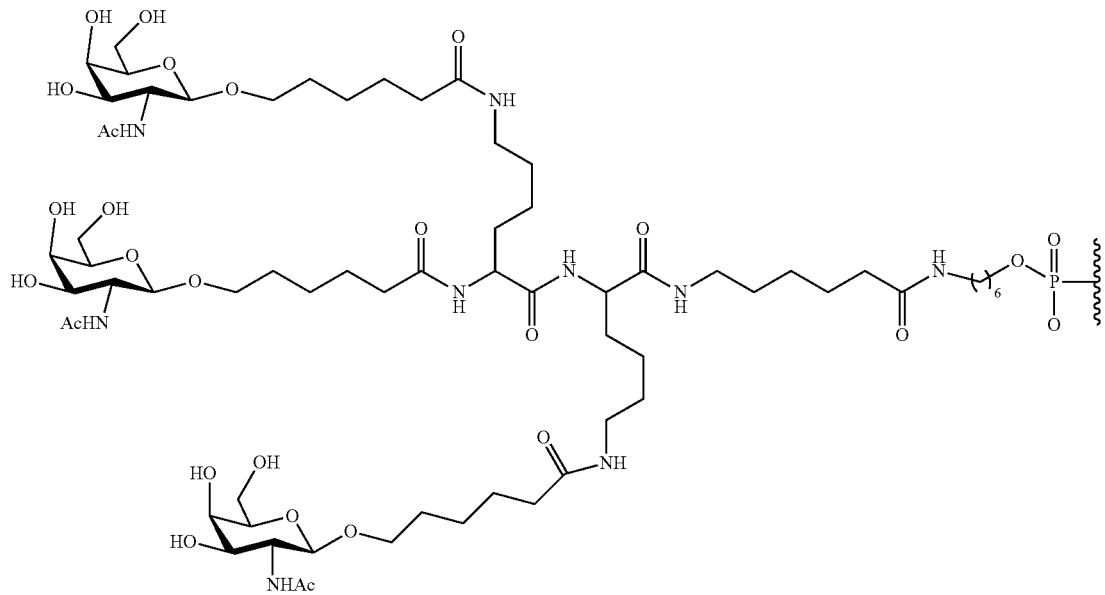
In certain such embodiments, conjugate groups have the following structure:
In certain such embodiments, conjugate groups have the following structure:
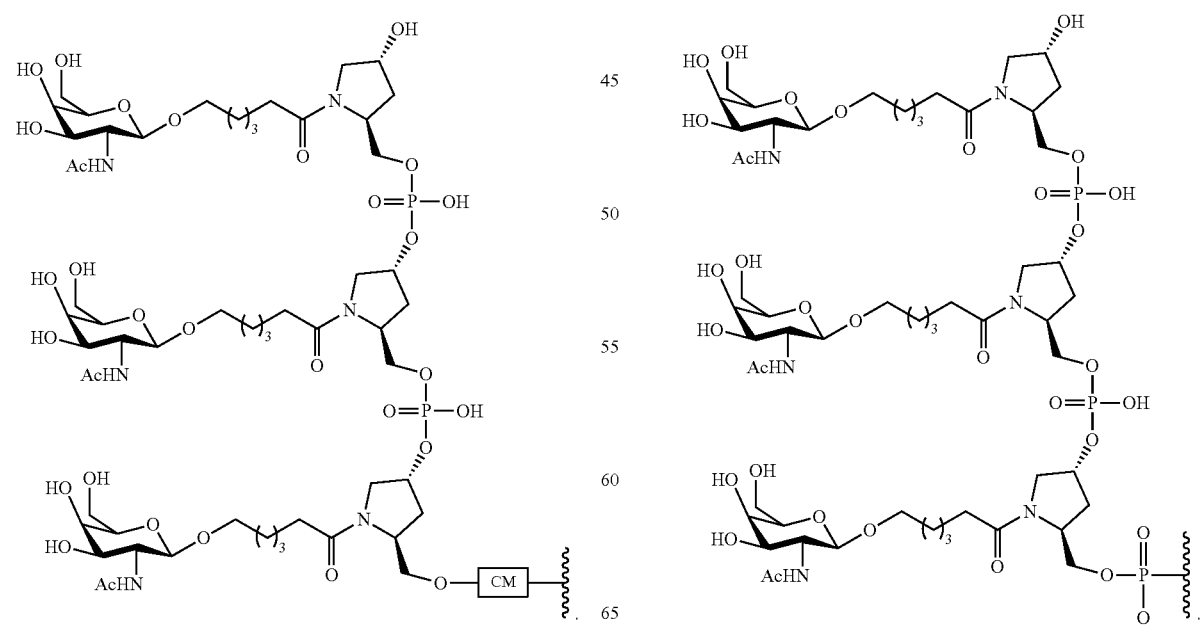

In certain embodiments, the cell-targeting moiety of the conjugate group has the following structure:

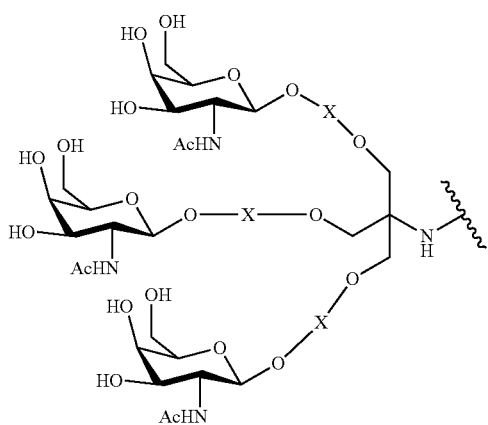

wherein X is a substituted or unsubstituted tether of six to eleven consecutively bonded atoms.

In certain embodiments, the cell-targeting moiety of the conjugate group has the following structure:

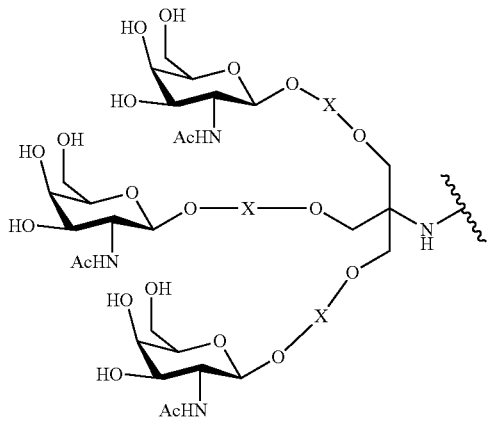

wherein X is a substituted or unsubstituted tether of ten consecutively bonded atoms.

In certain embodiments, the cell-targeting moiety of the conjugate group has the following structure:

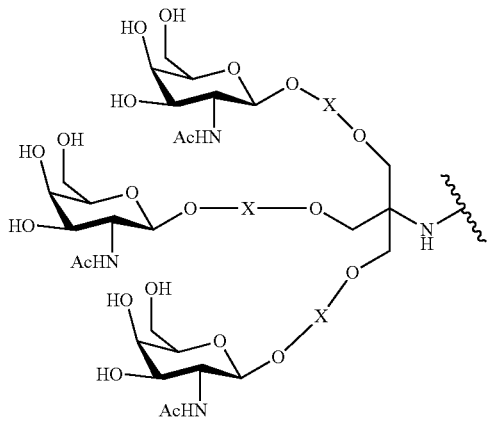

wherein X is a substituted or unsubstituted tether of four to eleven consecutively bonded atoms and wherein the tether comprises exactly one amide bond.

In certain embodiments, the cell-targeting moiety of the conjugate group has the following structure:

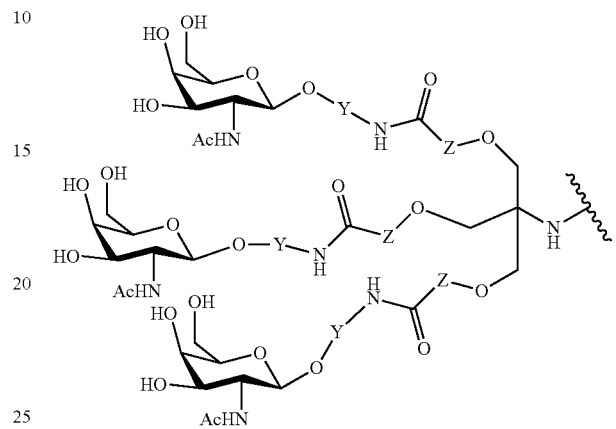

wherein Y and Z are independently selected from a $C_1$-$C_{12}$ substituted or unsubstituted alkyl, alkenyl, or alkynyl group, or a group comprising an ether, a ketone, an amide, an ester, a carbamate, an amine, a piperidine, a phosphate, a phosphodiester, a phosphorothioate, a triazole, a pyrrolidine, a disulfide, or a thioether.

In certain such embodiments, the cell-targeting moiety of the conjugate group has the following structure:

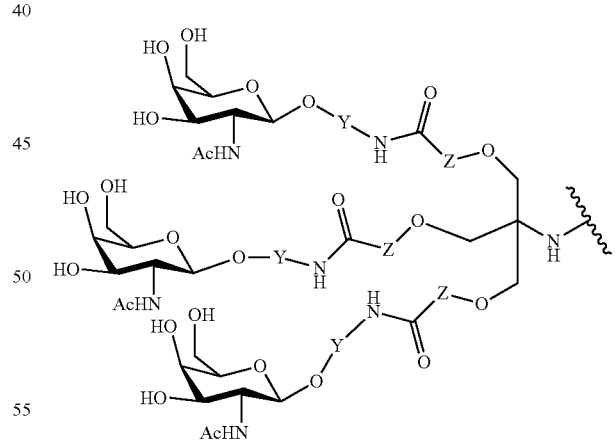

wherein Y and Z are independently selected from a $C_1$-$C_{12}$ substituted or unsubstituted alkyl group, or a group comprising exactly one ether or exactly two ethers, an amide, an amine, a piperidine, a phosphate, a phosphodiester, or a phosphorothioate.

In certain such embodiments, the cell-targeting moiety of the conjugate group has the following structure:

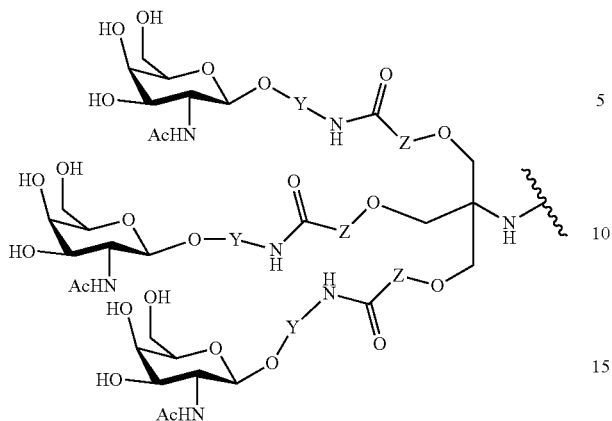

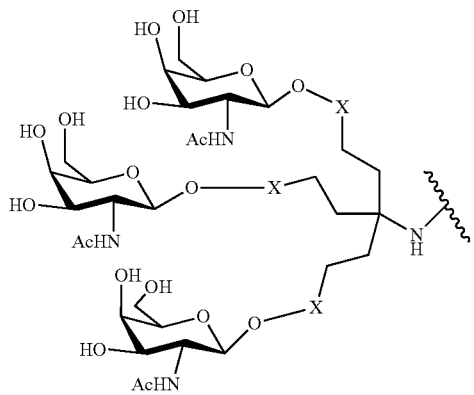

wherein Y and Z are independently selected from a $C_1$-$C_{12}$ substituted or unsubstituted alkyl group.

In certain such embodiments, the cell-targeting moiety of the conjugate group has the following structure:

wherein X is a substituted or unsubstituted tether of four to thirteen consecutively bonded atoms, and wherein X does not comprise an ether group.

In certain embodiments, the cell-targeting moiety of the conjugate group has the following structure:

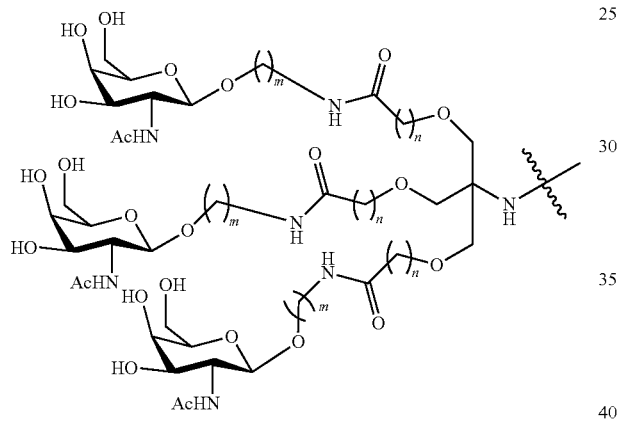

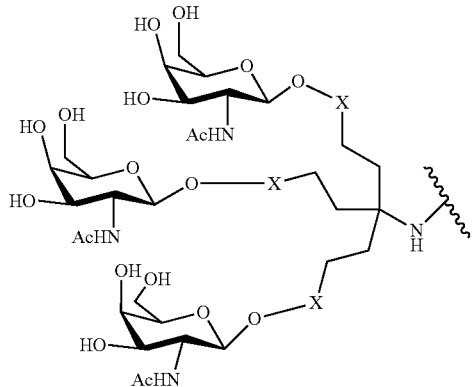

wherein m and n are independently selected from 1, 2, 3, 4, 5, 6, 7, 8, 9, 10, 11, and 12.

In certain such embodiments, the cell-targeting moiety of the conjugate group has the following structure:

wherein X is a substituted or unsubstituted tether of eight consecutively bonded atoms, and wherein X does not comprise an ether group.

In certain embodiments, the cell-targeting moiety of the conjugate group has the following structure:

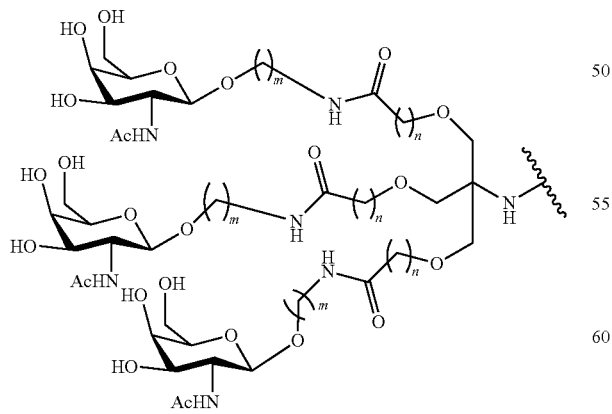

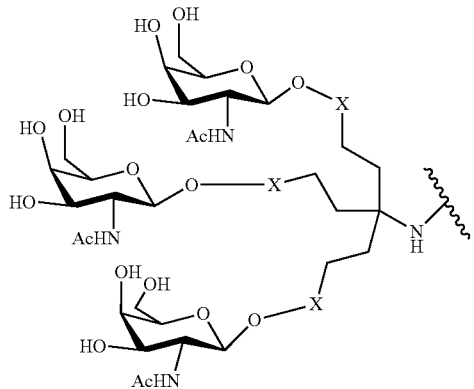

wherein m is 4, 5, 6, 7, or 8, and n is 1, 2, 3, or 4.

In certain embodiments, the cell-targeting moiety of the conjugate group has the following structure:

wherein X is a substituted or unsubstituted tether of four to thirteen consecutively bonded atoms, and wherein the tether comprises exactly one amide bond, and wherein X does not comprise an ether group.

In certain embodiments, the cell-targeting moiety of the conjugate group has the following structure:

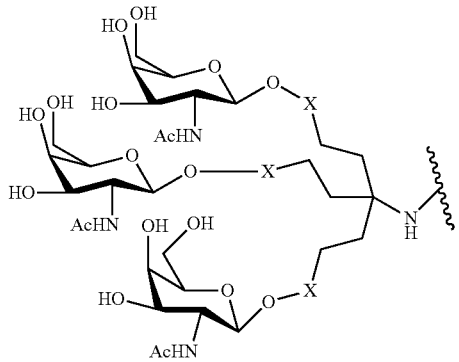

wherein X is a substituted or unsubstituted tether of four to thirteen consecutively bonded atoms and wherein the tether consists of an amide bond and a substituted or unsubstituted $C_2$-$C_{11}$ alkyl group.

In certain embodiments, the cell-targeting moiety of the conjugate group has the following structure:

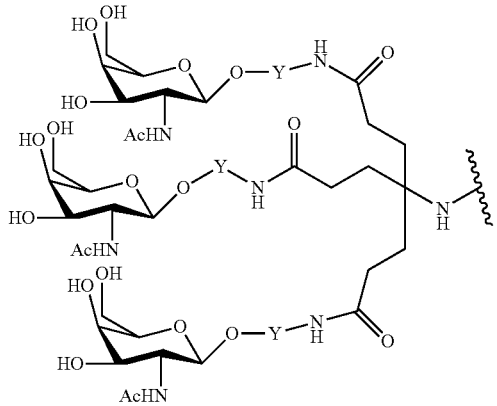

wherein Y is selected from a $C_1$-$C_{12}$ substituted or unsubstituted alkyl, alkenyl, or alkynyl group, or a group comprising an ether, a ketone, an amide, an ester, a carbamate, an amine, a piperidine, a phosphate, a phosphodiester, a phosphorothioate, a triazole, a pyrrolidine, a disulfide, or a thioether.

In certain such embodiments, the cell-targeting moiety of the conjugate group has the following structure:

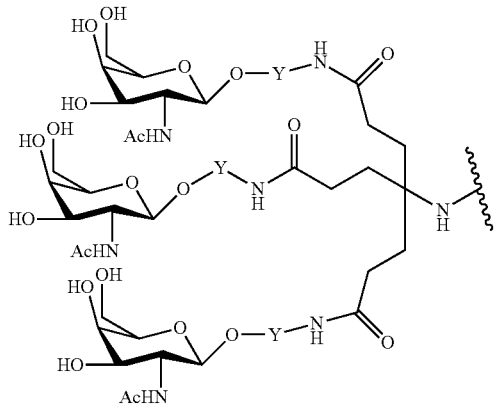

wherein Y is selected from a $C_1$-$C_{12}$ substituted or unsubstituted alkyl group, or a group comprising an ether, an amine, a piperidine, a phosphate, a phosphodiester, or a phosphorothioate.

In certain such embodiments, the cell-targeting moiety of the conjugate group has the following structure:

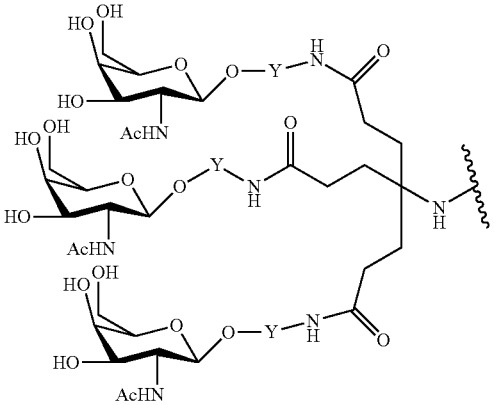

wherein Y is selected from a $C_1$-$C_{12}$ substituted or unsubstituted alkyl group.

In certain such embodiments, the cell-targeting moiety of the conjugate group has the following structure:

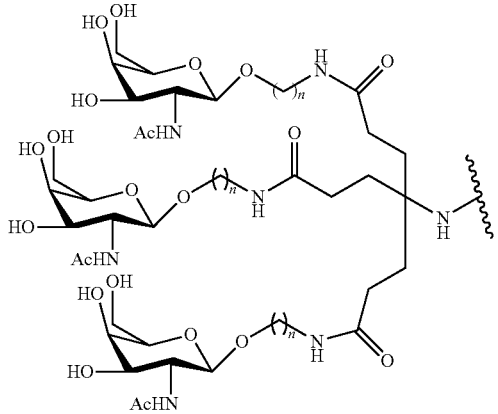

Wherein n is 1, 2, 3, 4, 5, 6, 7, 8, 9, 10, 11, or 12.

In certain such embodiments, the cell-targeting moiety of the conjugate group has the following structure:

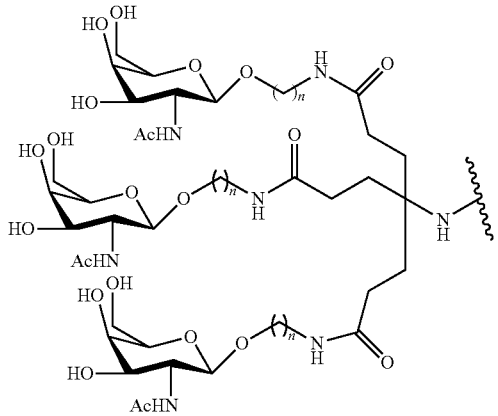

wherein n is 4, 5, 6, 7, or 8.

In certain embodiments, conjugates do not comprise a pyrrolidine.

a Certain Conjugated Antisense Compounds

In certain embodiments, the conjugates are bound to a nucleoside of the antisense oligonucleotide at the 2', 3', of 5' position of the nucleoside. In certain embodiments, a conjugated antisense compound has the following structure:

wherein
A is the antisense oligonucleotide;
B is the cleavable moiety
C is the conjugate linker
D is the branching group
each E is a tether;
each F is a ligand; and
q is an integer between 1 and 5.

In certain embodiments, a conjugated antisense compound has the following structure:

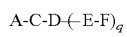

wherein
A is the antisense oligonucleotide;
C is the conjugate linker
D is the branching group
each E is a tether;
each F is a ligand; and
q is an integer between 1 and 5.

In certain such embodiments, the conjugate linker comprises at least one cleavable bond.

In certain such embodiments, the branching group comprises at least one cleavable bond.

In certain embodiments each tether comprises at least one cleavable bond.

In certain embodiments, the conjugates are bound to a nucleoside of the antisense oligonucleotide at the 2', 3', of 5' position of the nucleoside.

In certain embodiments, a conjugated antisense compound has the following structure:

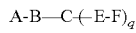

wherein
A is the antisense oligonucleotide;
B is the cleavable moiety
C is the conjugate linker
each E is a tether;
each F is a ligand; and
q is an integer between 1 and 5.

In certain embodiments, the conjugates are bound to a nucleoside of the antisense oligonucleotide at the 2', 3', of 5' position of the nucleoside. In certain embodiments, a conjugated antisense compound has the following structure:

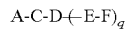

wherein
A is the antisense oligonucleotide;
C is the conjugate linker
each E is a tether;
each F is a ligand; and
q is an integer between 1 and 5.

In certain embodiments, a conjugated antisense compound has the following structure:

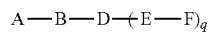

wherein
A is the antisense oligonucleotide;
B is the cleavable moiety
D is the branching group
each E is a tether;
each F is a ligand; and
q is an integer between 1 and 5.

In certain embodiments, a conjugated antisense compound has the following structure:

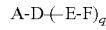

wherein
A is the antisense oligonucleotide;
D is the branching group
each E is a tether;
each F is a ligand; and
q is an integer between 1 and 5.

In certain such embodiments, the conjugate linker comprises at least one cleavable bond.

In certain embodiments each tether comprises at least one cleavable bond.

In certain embodiments, a conjugated antisense compound has a structure selected from among the following:

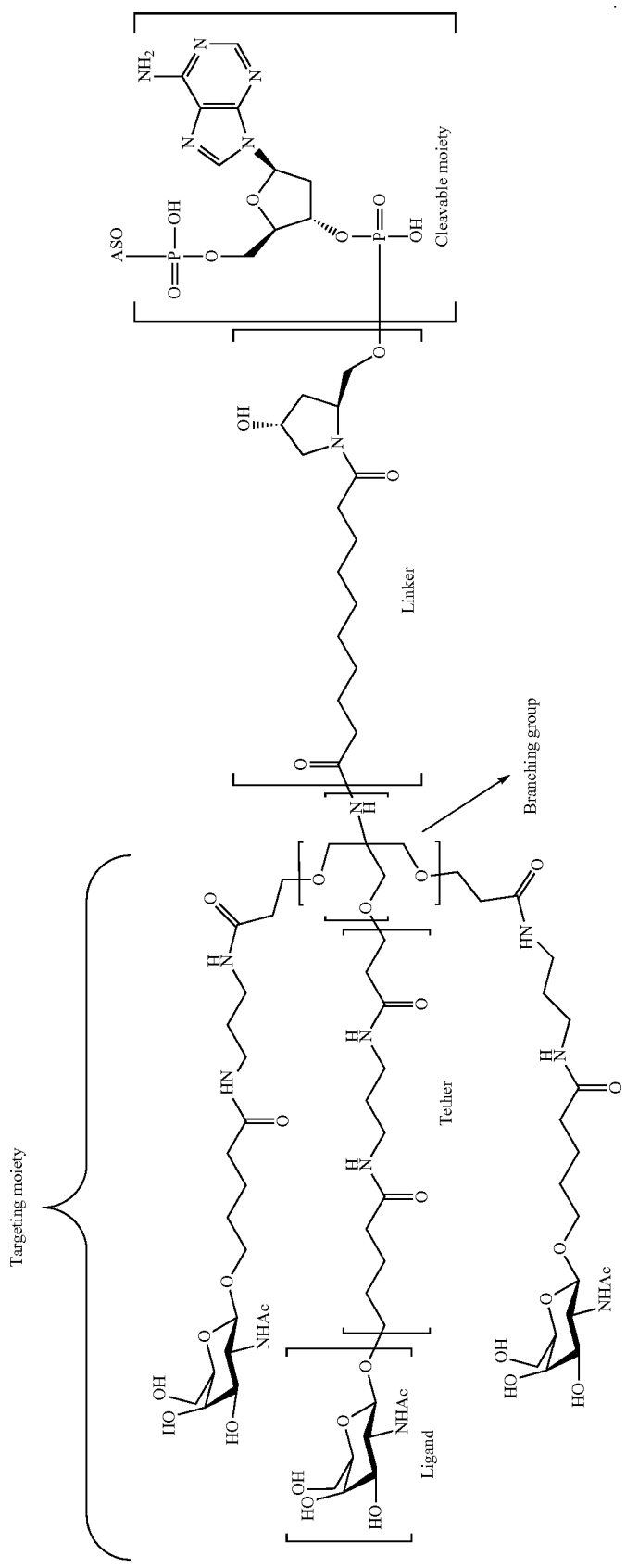

In certain embodiments, a conjugated antisense compound has a structure selected from among the following:

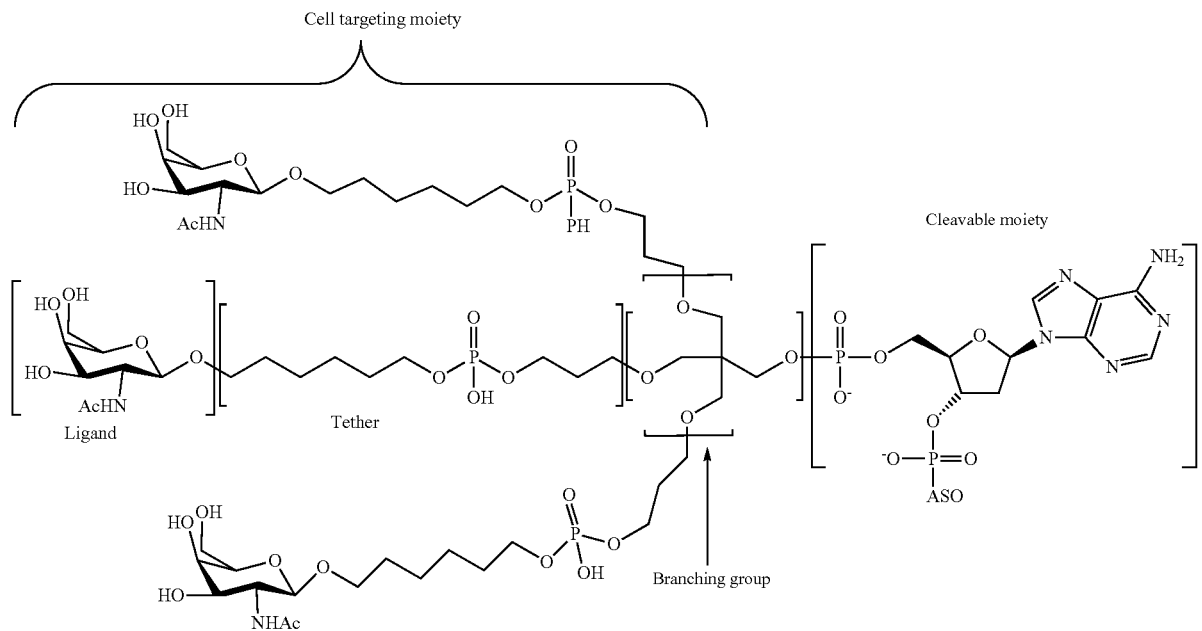

In certain embodiments, a conjugated antisense compound has a structure selected from among the following:

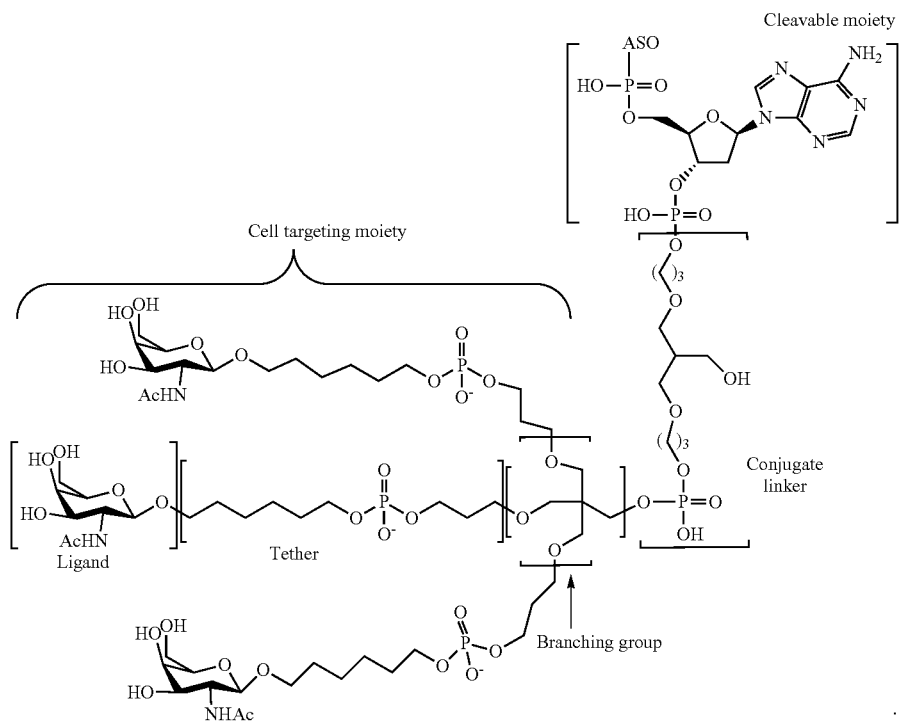

Representative United States patents, United States patent application publications, and international patent application publications that teach the preparation of certain of the above noted conjugates, conjugated antisense compounds, tethers, linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, US 2006/

0148740, US 2011/0123520, WO 2013/033230 and WO 2012/037254, each of which is incorporated by reference herein in its entirety.

Representative publications that teach the preparation of certain of the above noted conjugates, conjugated antisense compounds, tethers, linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem. (1995) 38:1538-1546, LEE et al., "New and more efficient multivalent glyco-ligands for asialoglycoprotein receptor of mammalian hepatocytes" Bioorganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584, RENSEN et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808, SLIEDREGT et al., "Design and Synthesis of Novel Amphiphilic Dendritic Galactosides for Selective Targeting of Liposomes to the Hepatic Asialoglycoprotein Receptor" J. Med. Chem. (1999) 42:609-618, and Valentijn et al., "Solid-phase synthesis of lysine-based cluster galactosides with high affinity for the Asialoglycoprotein Receptor" Tetrahedron, 1997, 53(2), 759-770, each of which is incorporated by reference herein in its entirety.

In certain embodiments, conjugated antisense compounds comprise an RNase H based oligonucleotide (such as a gapmer) or a splice modulating oligonucleotide (such as a fully modified oligonucleotide) and any conjugate group comprising at least one, two, or three GalNAc groups. In certain embodiments a conjugated antisense compound comprises any conjugate group found in any of the following references: Lee, Carbohydr Res, 1978, 67, 509-514; Connolly et al., J Biol Chem, 1982, 257, 939-945; Pavia et al., Int J Pep Protein Res, 1983, 22, 539-548; Lee et al., Biochem, 1984, 23, 4255-4261; Lee et al., Glycoconjugate J, 1987, 4, 317-328; Toyokuni et al., Tetrahedron Lett, 1990, 31, 2673-2676; Biessen et al., J Med Chem, 1995, 38, 1538-1546; Valentijn et al., Tetrahedron, 1997, 53, 759-770; Kim et al., Tetrahedron Lett, 1997, 38, 3487-3490; Lee et al., Bioconjug Chem, 1997, 8, 762-765; Kato et al., Glycobiol, 2001, 11, 821-829; Rensen et al., J Biol Chem, 2001, 276, 37577-37584; Lee et al., Methods Enzymol, 2003, 362, 38-43; Westerlind et al., Glycoconj J, 2004, 21, 227-241; Lee et al., Bioorg Med Chem Lett, 2006, 16(19), 5132-5135; Maierhofer et al., Bioorg Med Chem, 2007, 15, 7661-7676; Khorev et al., Bioorg Med Chem, 2008, 16, 5216-5231; Lee et al., Bioorg Med Chem, 2011, 19, 2494-2500; Kornilova et al., Analyt Biochem, 2012, 425, 43-46; Pujol et al., Angew Chemie Int Ed Engl, 2012, 51, 7445-7448; Biessen et al., J Med Chem, 1995, 38, 1846-1852; Sliedregt et al., J Med Chem, 1999, 42, 609-618; Rensen et al., J Med Chem, 2004, 47, 5798-5808; Rensen et al., Arterioscler Thromb Vasc Biol, 2006, 26, 169-175; van Rossenberg et al., Gene Ther, 2004, 11, 457-464; Sato et al., J Am Chem Soc, 2004, 126, 14013-14022; Lee et al., J Org Chem, 2012, 77, 7564-7571; Biessen et al., FASEB J, 2000, 14, 1784-1792; Rajur et al., Bioconjug Chem, 1997, 8, 935-940; Duff et al., Methods Enzymol, 2000, 313, 297-321; Maier et al., Bioconjug Chem, 2003, 14, 18-29; Jayaprakash et al., Org Lett, 2010, 12, 5410-5413; Manoharan, Antisense Nucleic Acid Drug Dev, 2002, 12, 103-128; Merwin et al., Bioconjug Chem, 1994, 5, 612-620; Tomiya et al., Bioorg Med Chem, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132; each of which is incorporated by reference in its entirety.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Yet another technique used to introduce antisense oligonucleotides into cultured cells includes free uptake of the oligonucleotides by the cells.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Certain Indications

Certain embodiments provided herein relate to methods of treating, preventing, or ameliorating a disease associated with dysregulation of the complement alternative pathway in a subject by administration of a CFB specific inhibitor, such as an antisense compound targeted to CFB.

Examples of renal diseases associated with dysregulation of the complement alternative pathway treatable, preventable, and/or ameliorable with the methods provided herein include C3 glomerulopathy, atypical hemolytic uremic syndrome (aHUS), dense deposit disease (DDD; also known as MPGN Type II or C3Neph), and CFHR5 nephropathy.

Additional renal diseases associated with dysregulation of the complement alternative pathway treatable, preventable, and/or ameliorable with the methods provided herein include IgA nephropathy; mesangiocapillary (membranoproliferative) glomerulonephritis (MPGN); autoimmune disorders including lupus nephritis and systemic lupus erythematosus (SLE); infection-induced glomerulonephritis (also known as Postinfectious glomerulonephritis); and renal ischemia-reperfusion injury, for example post-transplant renal ischemia-reperfusion injury.

Examples of non-renal disorders associated with dysregulation of the complement alternative pathway treatable and/or preventable with the methods provided herein include ocular diseases such as macular degeneration, for example age-related macular degeneration (AMD), including wet AMD and dry AMD, such as Geographic Atrophy; neuromyelitis optica; corneal disease, such as corneal inflammation; autoimmune uveitis; and diabetic retinopathy. It has been reported that complement system is involved in ocular diseases. Jha P, et al., *Mol Immunol* (2007) 44(16): 3901-3908. Additional examples of non-renal disorders associated with dysregulation of the complement alternative pathway treatable and/or preventable with the methods provided herein include ANCA-assocaited vasculitis, antiphospholipid syndrome (also known as antiphospholipid antibody syndrome (APS)), asthma, rheumatoid arthritis, Myasthenia Gravis, and multiple sclerosis.

Certain embodiments provided herein relate to methods of treating, preventing, or ameliorating a renal disease associated with dysregulation of the complement alternative pathway in a subject by administration of a CFB specific inhibitor, such as an antisense compound targeted to CFB. In certain aspects, the renal disease is lupus nephritis, systemic lupus erythematosus (SLE), dense deposit disease (DDD), $C_3$ glomerulonephritis ($C_3$GN), CFHR5 nephropathy, or atypical hemolytic uremic syndrome (aHUS), or any combination thereof.

Certain embodiments provided herein relate to methods of treating, preventing, or ameliorating macular degeneration, such as age-related macular degeneration (AMD), in a subject by administration of a CFB specific inhibitor, such as an antisense compound targeted to CFB. In certain aspects, the AMD is wet AMD or dry AMD. In certain aspects, dry AMD can be Geographic Atrophy. Studies have demonstrated the association of complement alternative pathway dysregulation and AMD. Complement components are common constituents of ocular drusen, the extracellular material that accumulates in the macula of AMD patients. Furthermore, it has been reported that CFH and CFB variants account for nearly 75% of AMD cases in northern Europe and North America. It has also been found that a specific CFB polymorphism confers protection against AMD. Patel, N. et al., *Eye* (2008) 22(6):768-76. Additionally, CFB homozygous null mice have lower complement pathway activity, exhibit smaller ocular lesions, and choroidal neovascularization (CNV) after laser photocoagulation. Rohrer, B. et al., *Invest Ophthalmol Vis Sci.* (2009) 50(7):3056-64. Furthermore, CFB siRNA treatment protects mice from laser induced CNV. Bora, N S et al., *J Immunol.* (2006) 177(3): 1872-8. Studies have also shown that the kidney and eye share developmental pathways and structural features including basement membrane collagen IV protomer composition and vascularity. Savige et al., *J Am Soc Nephrol.* (2011) 22(8):1403-15. There is evidence that the complement pathway is involved in renal and ocular diseases. For instance, inherited complement regulatory protein deficiency causes predisposition to atypical hemolytic uremic syndrome and AMD. Richards A et al., *Adv Immunol.* (2007) 96:141-77. Additionally, chronic kidney disease has been associated with AMD. Nitsch, D. et al., *Ophthalmic Epidemiol.* (2009) 16(3):181-6; Choi, J. et al, *Ophthalmic Epidemiol.* (2011) 18(6):259-63. Dense deposit disease (DDD), a kidney disease associated with dysregulated complement alternative pathway, is characterized by acute nephritic syndrome and ocular drusen. Cruz and Smith, *GeneReviews* (2007) Jul. 20. Moreover, mice harboring genetic deletion of a component of the complement alternative pathway have coexisting renal and ocular disease phenotypes. It has been reported that CFH homozygous null mice develop DDD and present retinal abnormalities and visual dysfunction. Pickering et al., *Nat Genet.* (2002) 31(4):424-8. Mouse models of renal diseases associated with dysregulation of the complement alternative pathway are also accepted as models of AMD. Pennesi M E et al., *Mol Aspects Med* (2012) 33:487-509. CFH null mice, for example, are an accepted model for renal diseases, such as DDD, and AMD. Furthermore, it has been reported that AMD is associated with the systemic source of complement factors, which accumulate locally in the eye to drive alternative pathway complement activation. Loyet et al., *Invest Ophthalmol Vis Sci.* (2012) 53(10):6628-37.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif And, for example, where a particular high-affinity modification appears at a particular position, other high-affinity modifications at the same position are considered suitable, unless otherwise indicated.

Example 1: General Method for the Preparation of Phosphoramidites, Compounds 1, 1a and 2

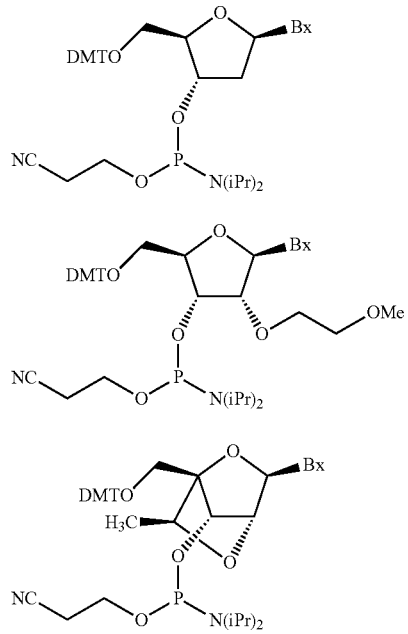

Bx is a heterocyclic base;

Compounds 1, 1a and 2 were prepared as per the procedures well known in the art as described in the specification herein (see Seth et al., Bioorg. Med. Chem., 2011, 21(4), 1122-1125, J. Org. Chem., 2010, 75(5), 1569-1581, Nucleic Acids Symposium Series, 2008, 52(1), 553-554); and also see published PCT International Applications (WO 2011/115818, WO 2010/077578, WO2010/036698, WO2009/143369, WO 2009/006478, and WO 2007/090071), and U.S. Pat. No. 7,569,686).

Example 2: Preparation of Compound 7

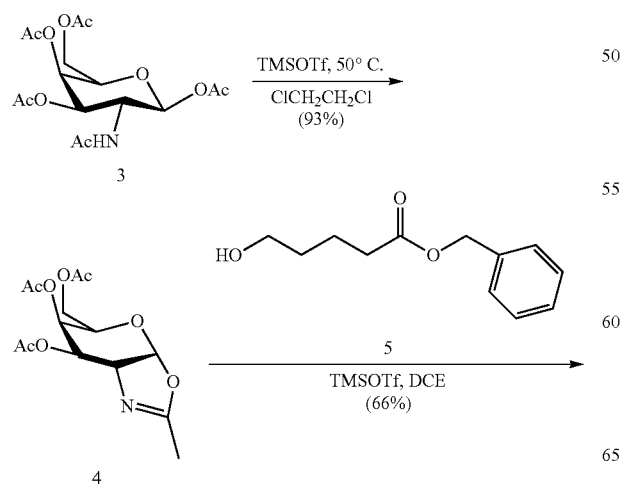

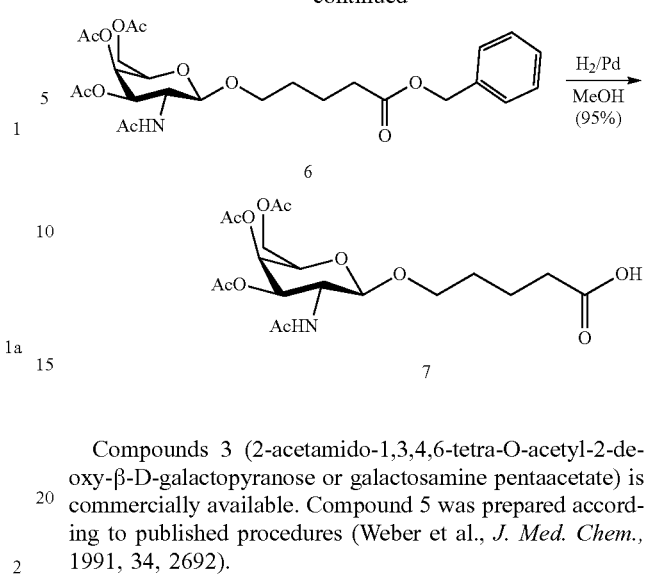

Compounds 3 (2-acetamido-1,3,4,6-tetra-O-acetyl-2-deoxy-β-D-galactopyranose or galactosamine pentaacetate) is commercially available. Compound 5 was prepared according to published procedures (Weber et al., *J. Med. Chem.*, 1991, 34, 2692).

Example 3: Preparation of Compound 11

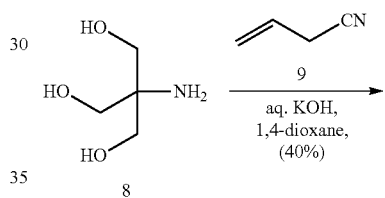

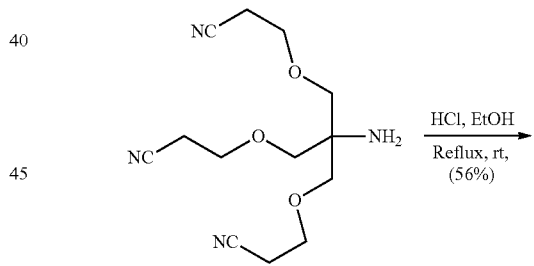

Compounds 8 and 9 are commercially available.

Example 4: Preparation of Compound 18
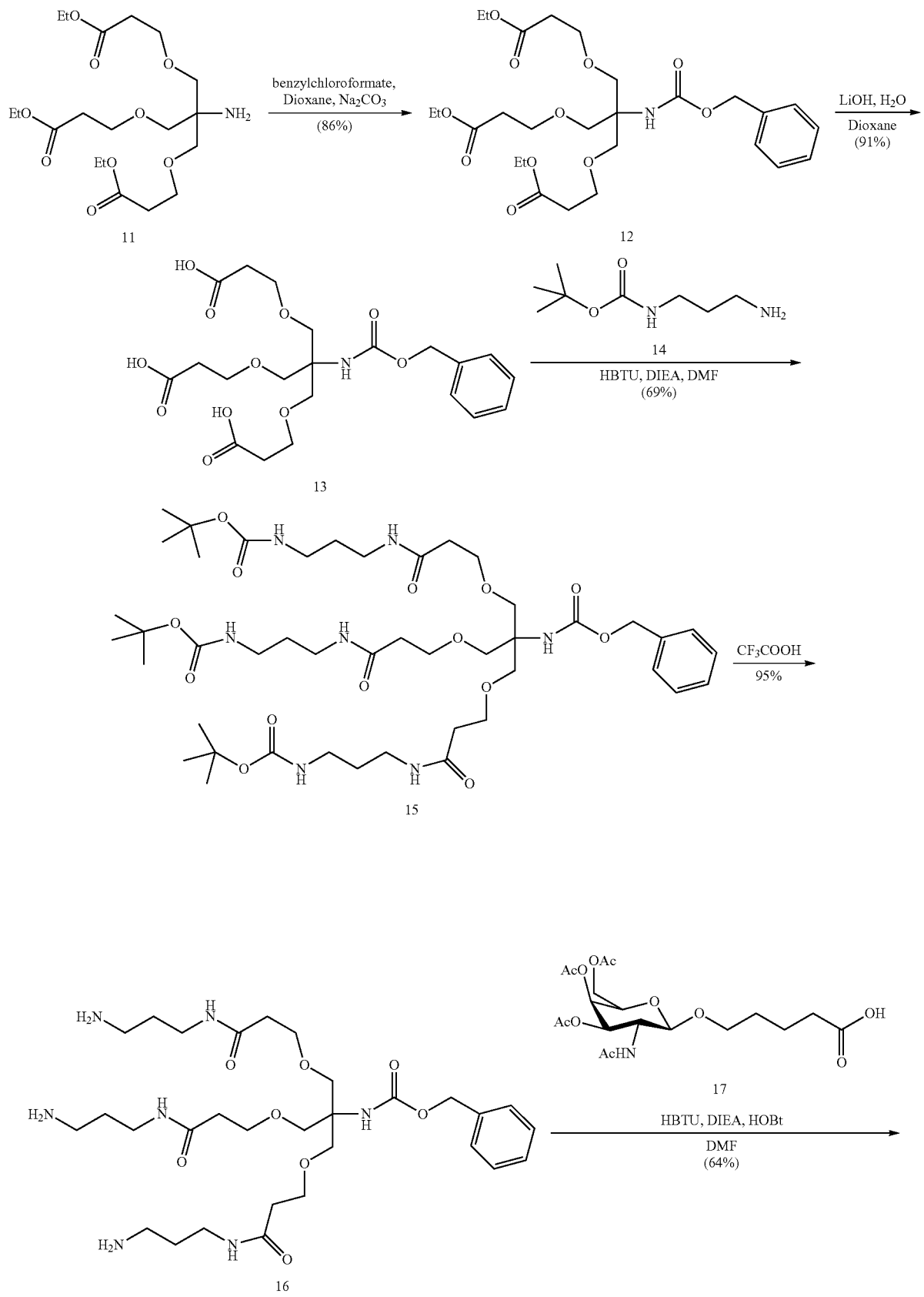

-continued
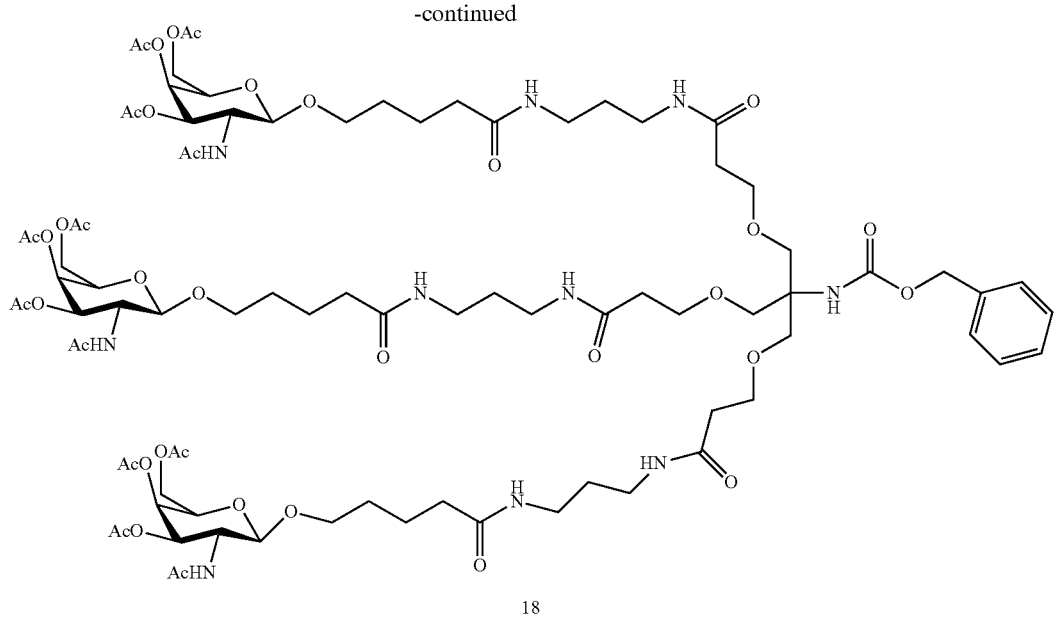
18
Compound 11 was prepared as per the procedures illustrated in Example 3. Compound 14 is commercially available. Compound 17 was prepared using similar procedures reported by Rensen et al., *J. Med. Chem.*, 2004, 47, 5798-5808.
Example 5: Preparation of Compound 23
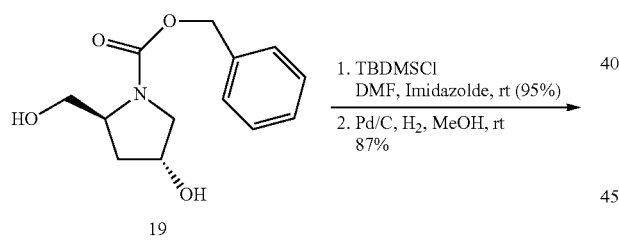
19
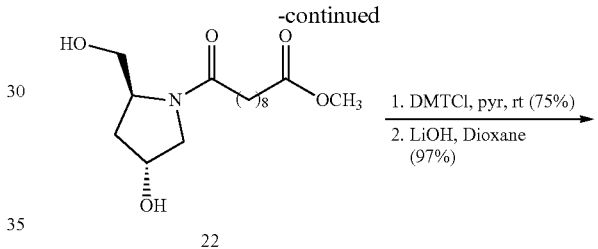
22
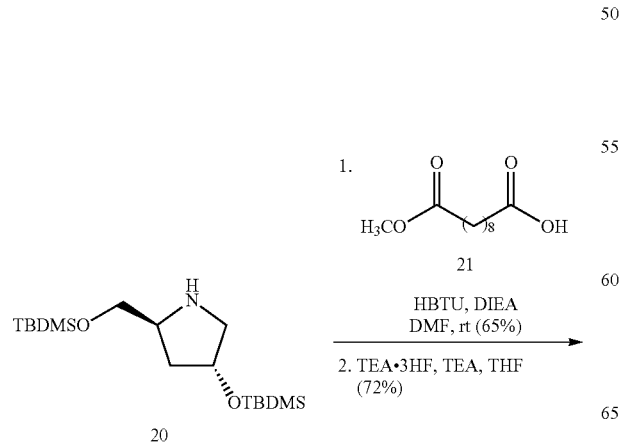
20
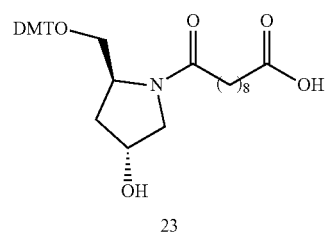
23
Compounds 19 and 21 are commercially available.

Example 6: Preparation of Compound 24
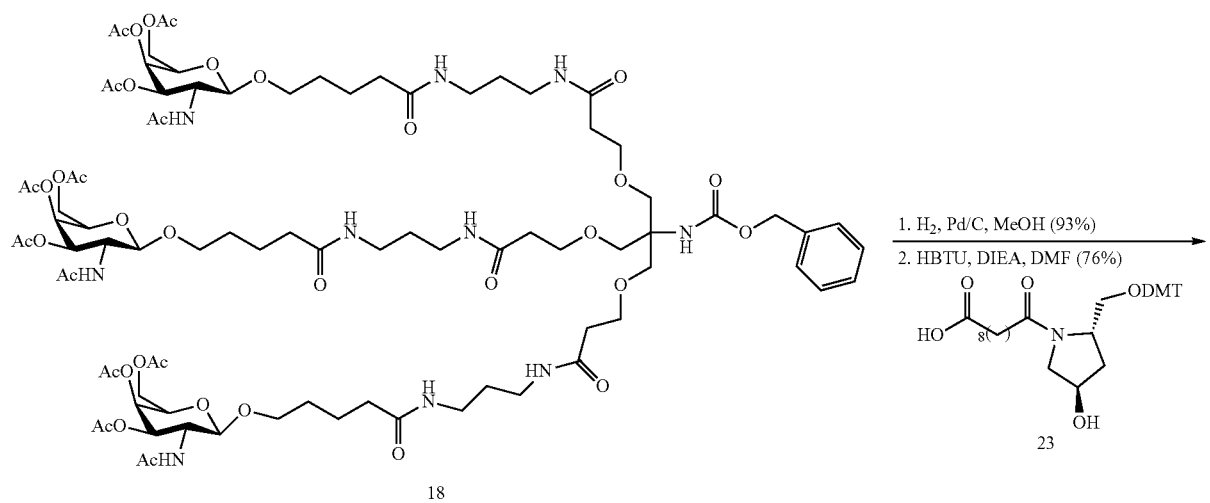
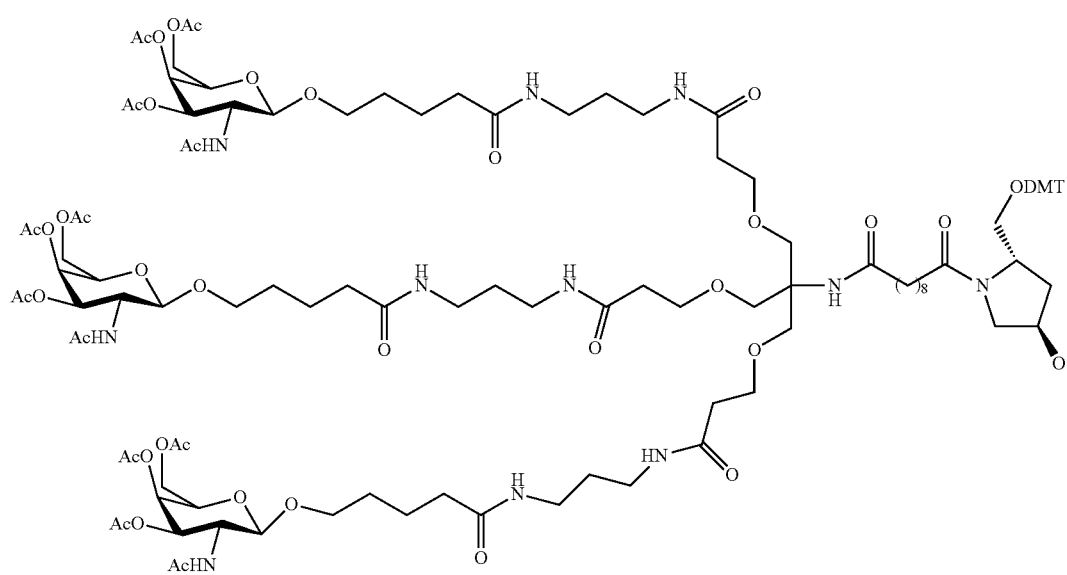
Compounds 18 and 23 were prepared as per the procedures illustrated in Examples 4 and 5.

Example 7: Preparation of Compound 25
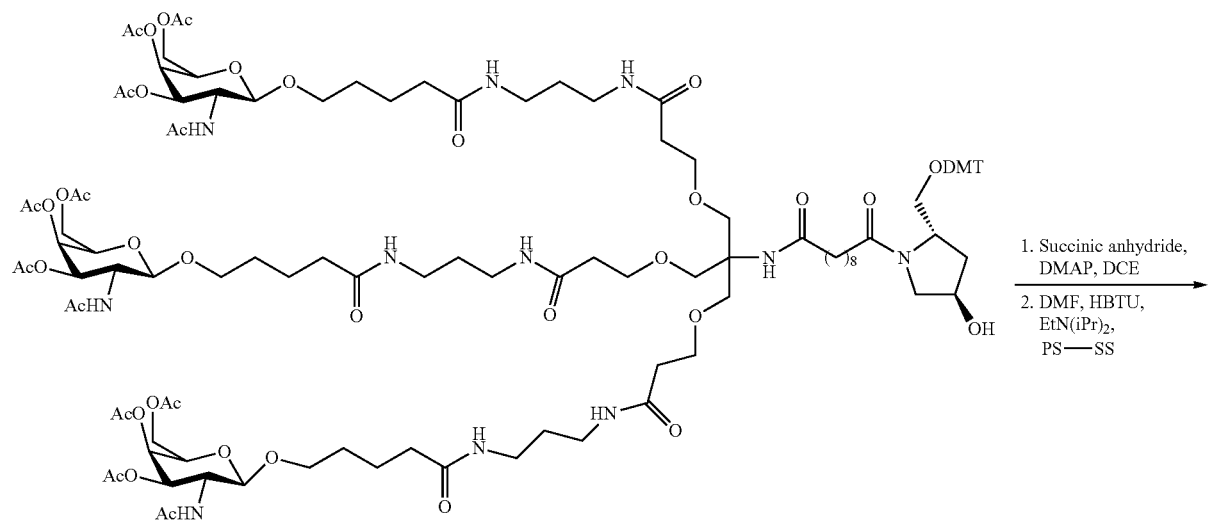
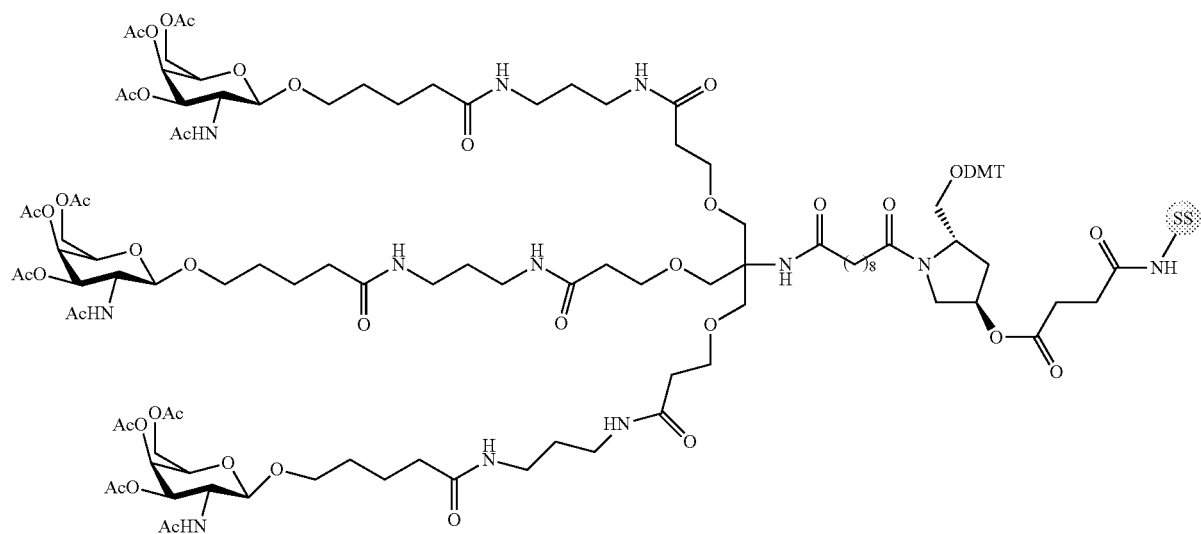
Compound 24 was prepared as per the procedures illustrated in Example 6.

Example 8: Preparation of Compound 26
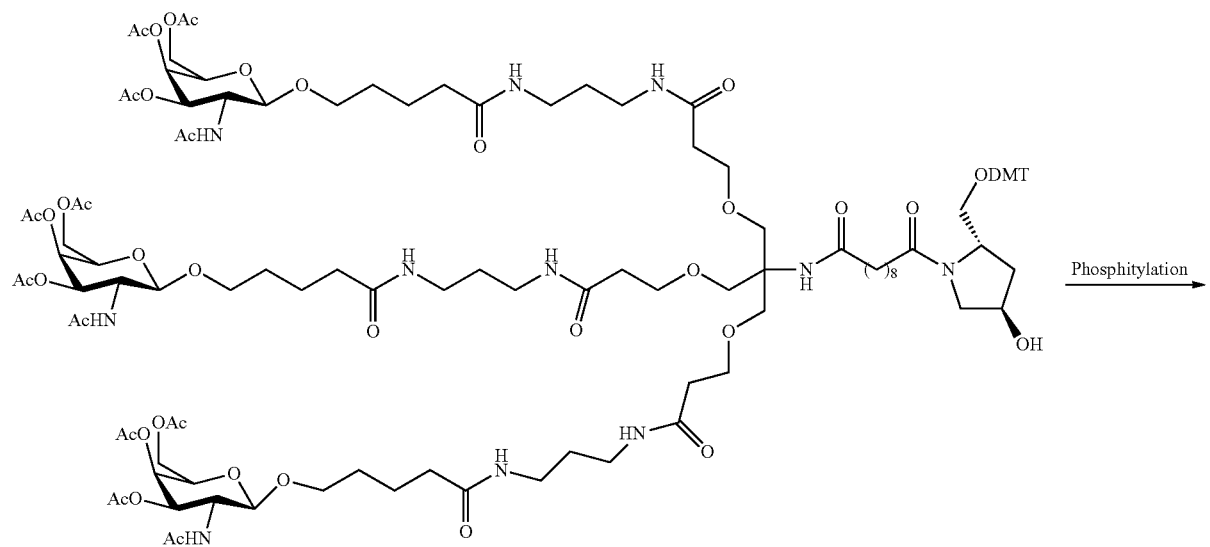
24
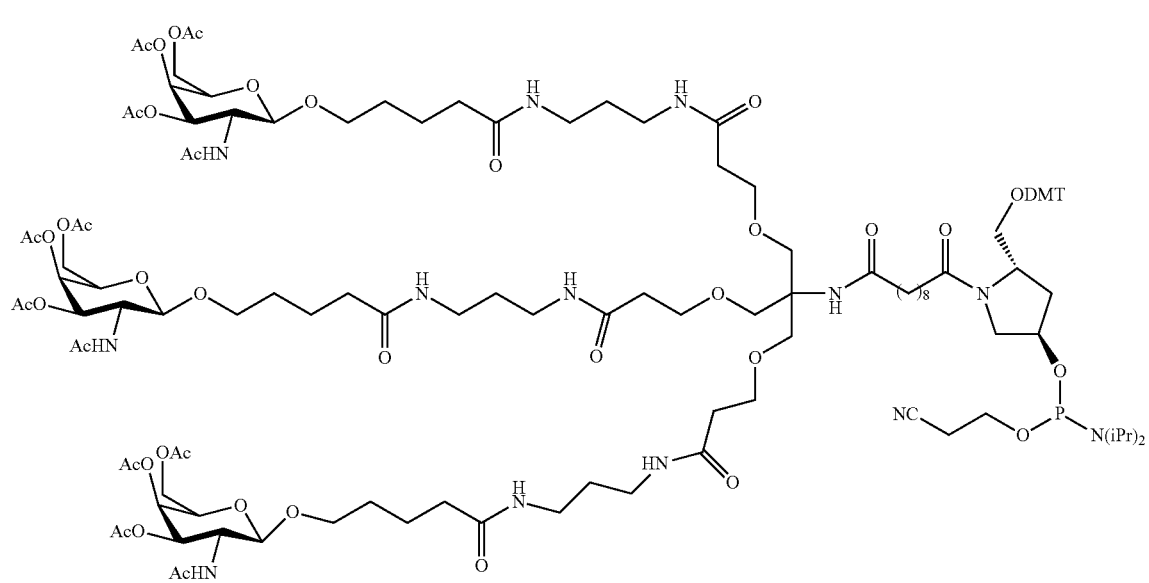
26
Compound 24 is prepared as per the procedures illustrated in Example 6.

Example 9: General Preparation of Conjugated ASOs Comprising GalNAc₃-1 at the 3' Terminus, Compound 29
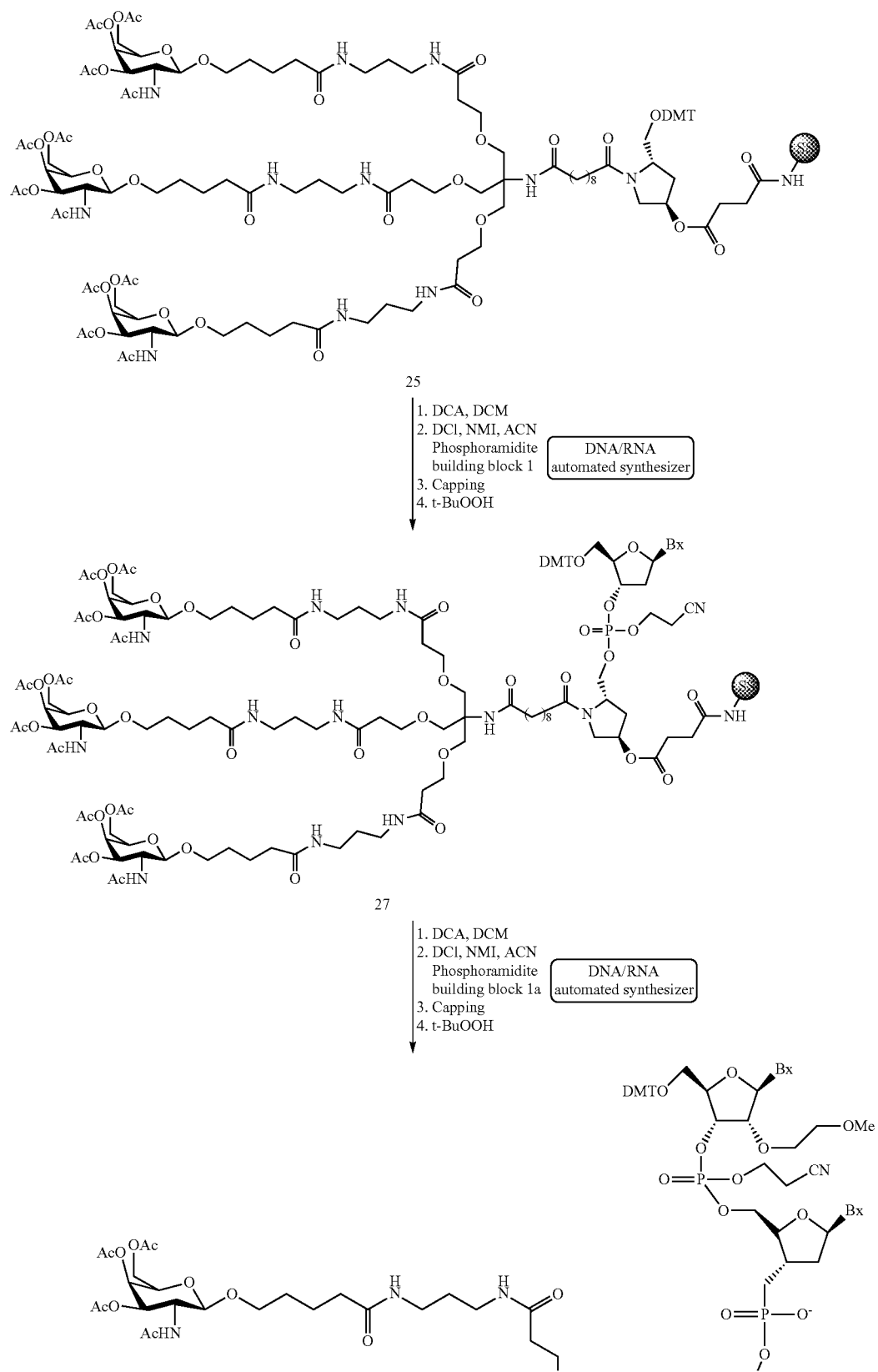

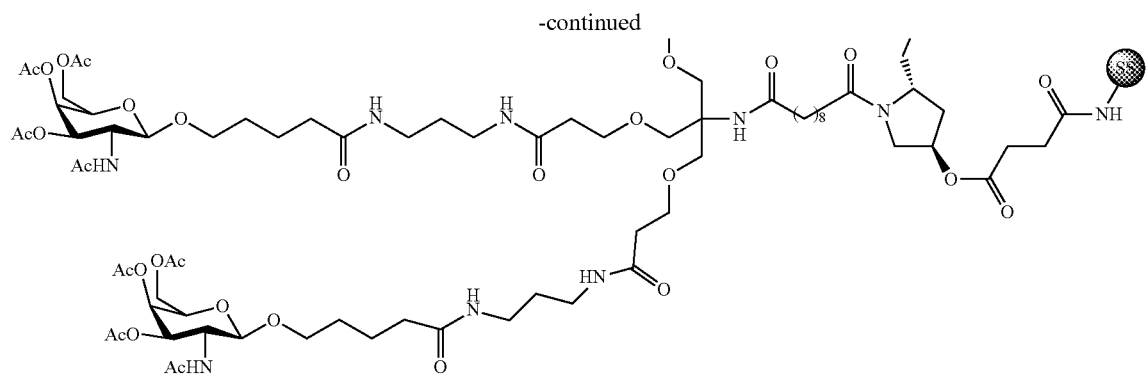
1. DCA, DCM
2. DCl, NMI, ACN
   Phosphoramidite building blocks — DNA/RNA automated synthesizer
3. Capping
4. xanthane hydride or t-BuOOH
5. Et₃N/CH₃CN (1:1)
6. Aqueous NH₃ (cleavage)
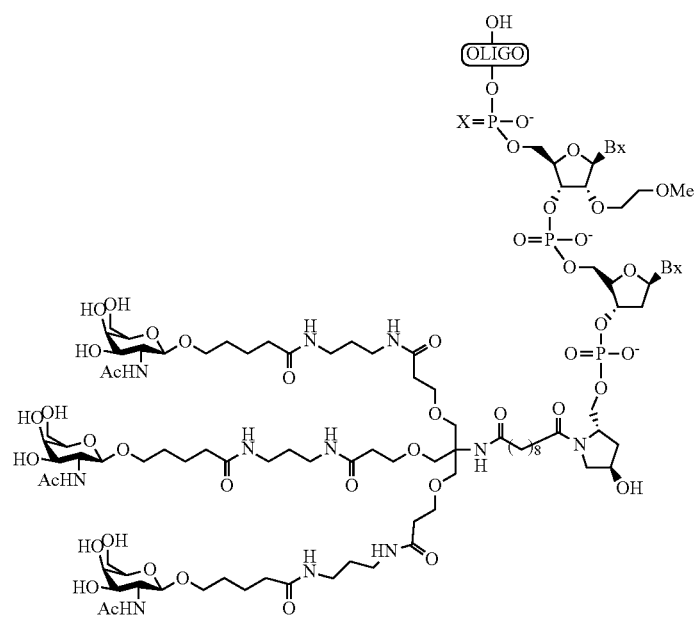
Bx = Heterocyclic base
X = O or S Wherein the protected GalNAc$_3$-1 has the structure:

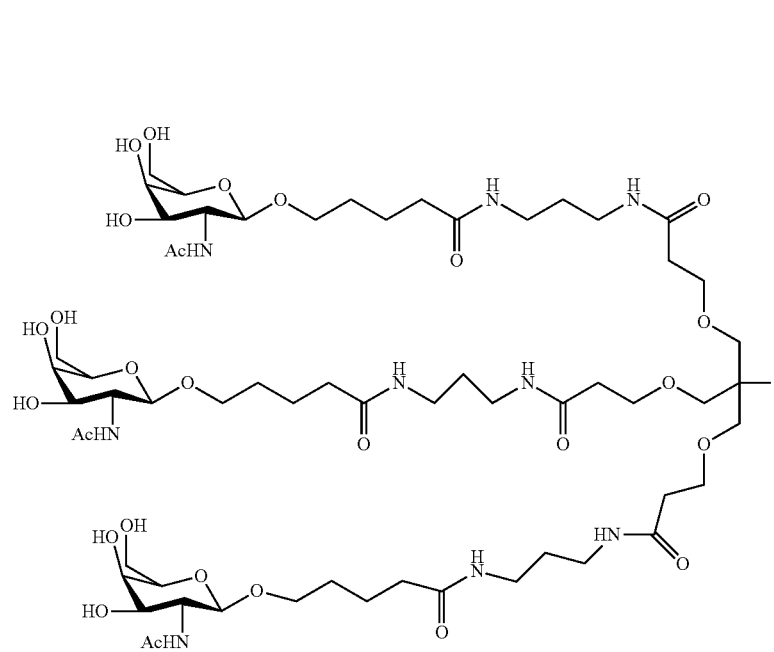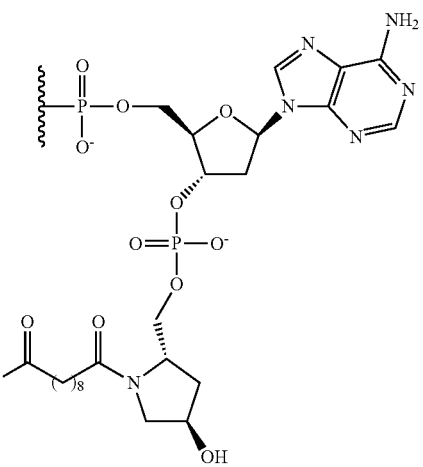

The GalNAc$_3$ cluster portion of the conjugate group GalNAc$_3$-1 (GalNAc$_3$-1$_a$) can be combined with any cleavable moiety to provide a variety of conjugate groups. Wherein GalNAc$_3$-1$_a$ has the formula:

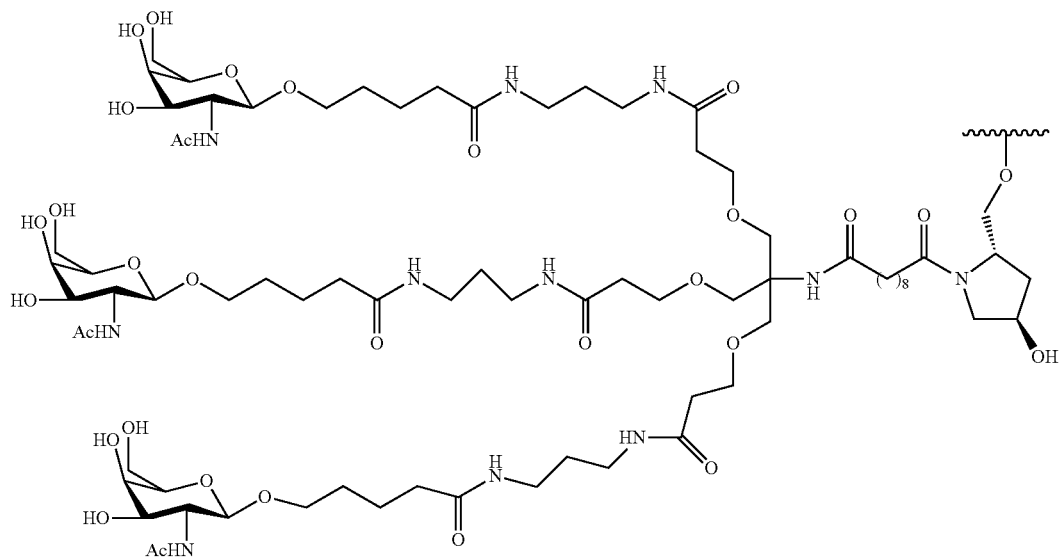

The solid support bound protected GalNAc$_3$-1, Compound 25, was prepared as per the procedures illustrated in Example 7. Oligomeric Compound 29 comprising GalNAc$_3$-1 at the 3' terminus was prepared using standard procedures in automated DNA/RNA synthesis (see Dupouy et al., *Angew. Chem. Int. Ed.*, 2006, 45, 3623-3627). Phosphoramidite building blocks, Compounds 1 and 1a were prepared as per the procedures illustrated in Example 1. The phosphoramidites illustrated are meant to be representative and not intended to be limiting as other phosphoramidite building blocks can be used to prepare oligomeric compounds having a predetermined sequence and composition. The order and quantity of phosphoramidites added to the solid support can be adjusted to prepare gapped oligomeric compounds as described herein. Such gapped oligomeric compounds can have predetermined composition and base sequence as dictated by any given target.

Example 10: General Preparation Conjugated ASOs Comprising GalNAc$_3$-1 at the 5' Terminus, Compound 34
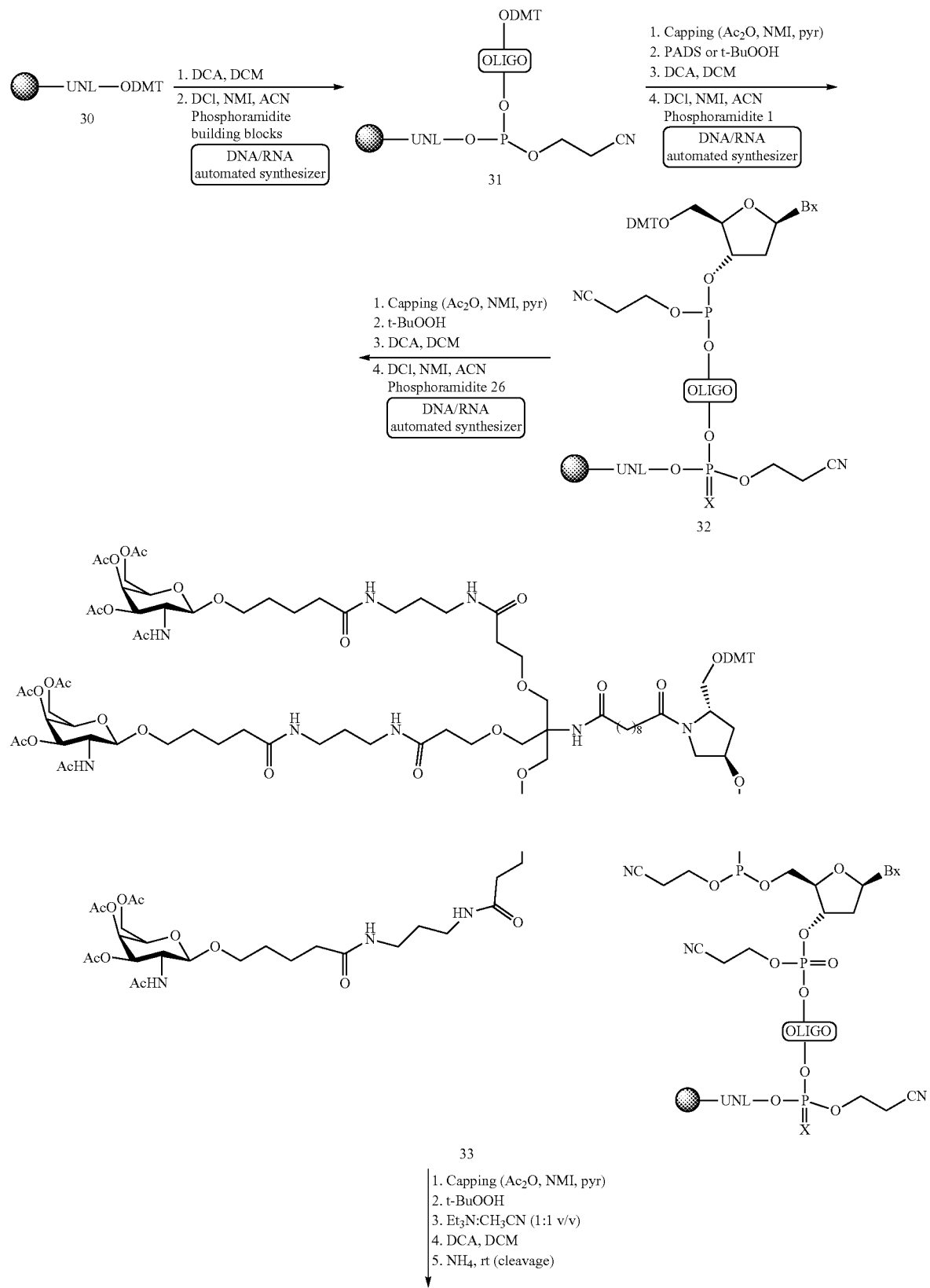

-continued

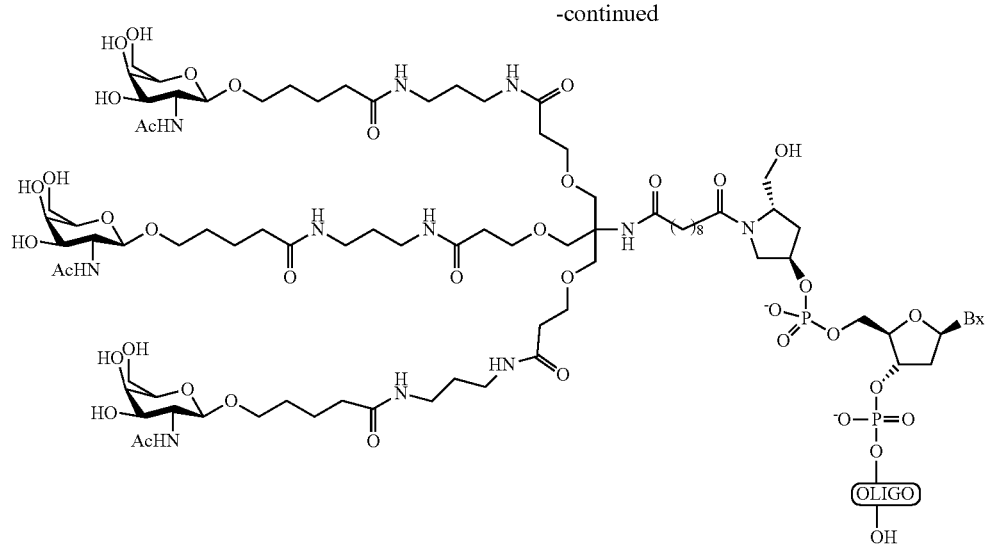

34

X = O, or S
Bx = Heterocylic base

The Unylinker™ 30 is commercially available. Oligomeric Compound 34 comprising a GalNAc$_3$-1 cluster at the 5' terminus is prepared using standard procedures in automated DNA/RNA synthesis (see Dupouy et al., *Angew. Chem. Int. Ed.*, 2006, 45, 3623-3627). Phosphoramidite building blocks, Compounds 1 and 1a were prepared as per the procedures illustrated in Example 1. The phosphoramidites illustrated are meant to be representative and not intended to be limiting as other phosphoramidite building blocks can be used to prepare an oligomeric compound having a predetermined sequence and composition. The order and quantity of phosphoramidites added to the solid support can be adjusted to prepare gapped oligomeric compounds as described herein. Such gapped oligomeric compounds can have predetermined composition and base sequence as dictated by any given target.

Example 11: Preparation of Compound 39

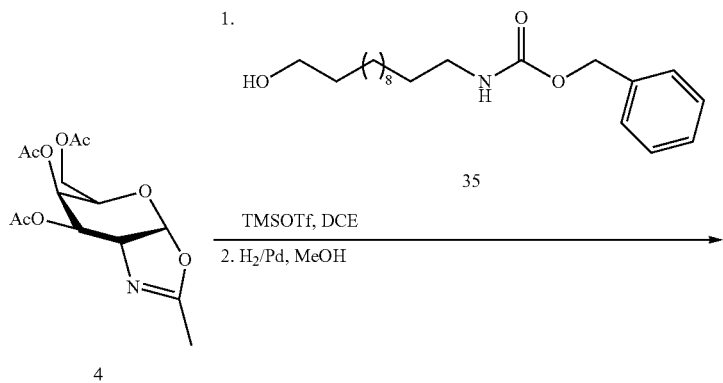

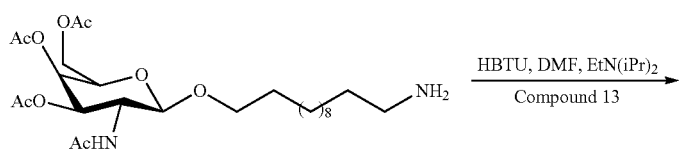

-continued
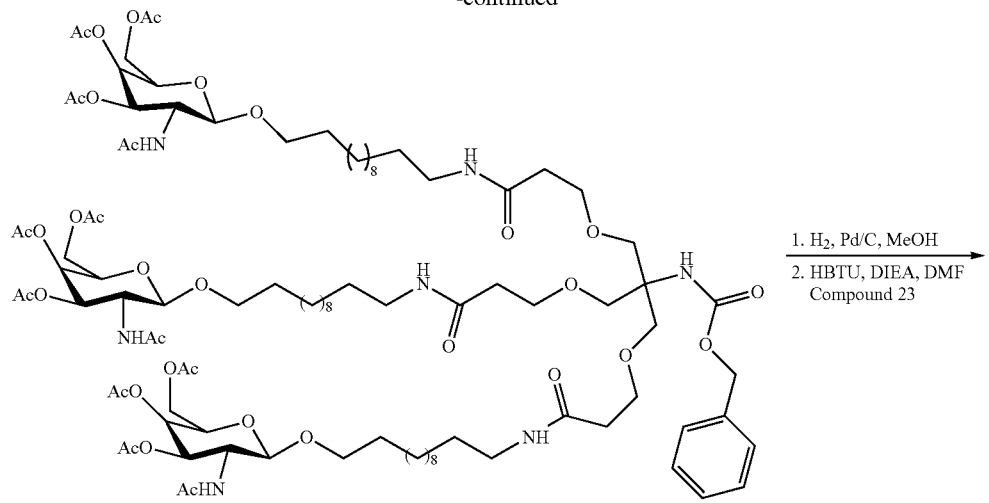
37
1. H₂, Pd/C, MeOH
2. HBTU, DIEA, DMF
Compound 23
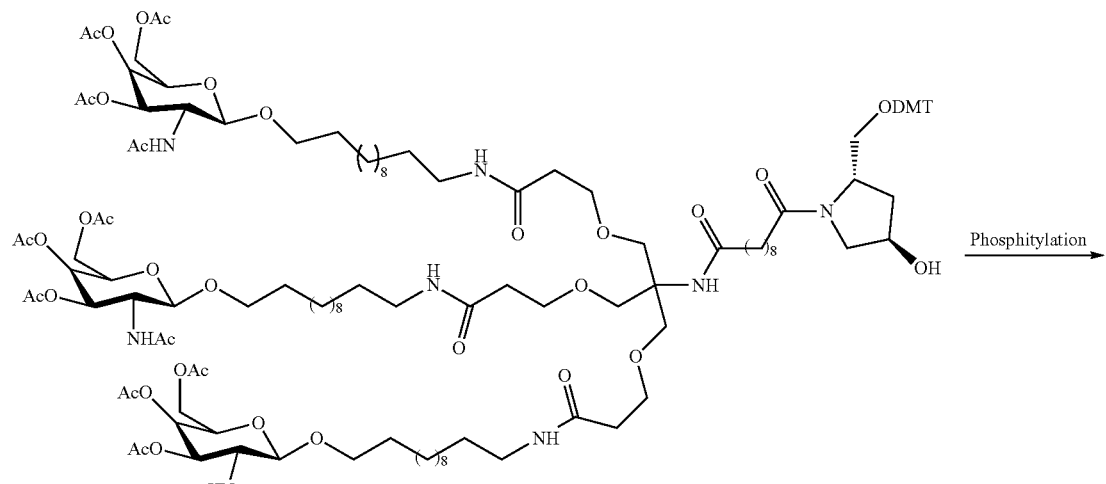
38
Phosphitylation
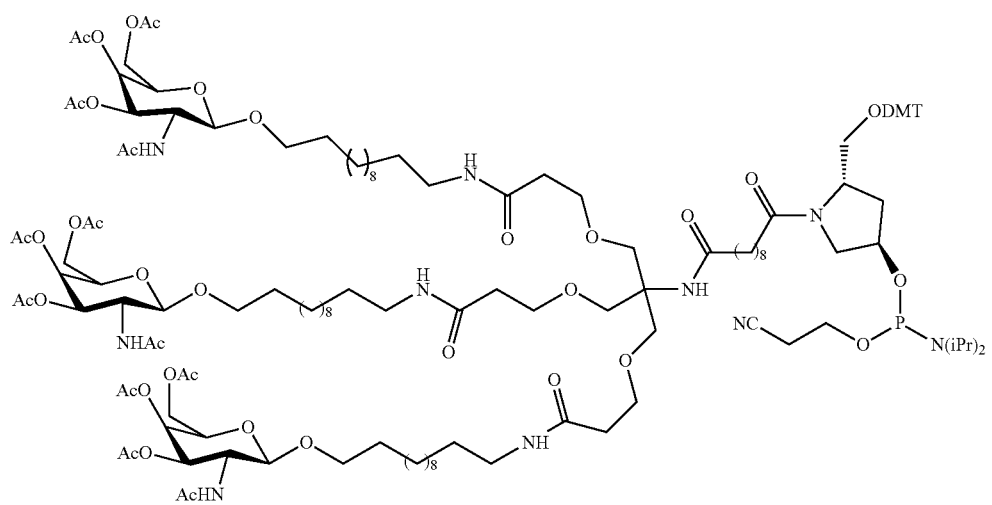
39

Compounds 4, 13 and 23 were prepared as per the procedures illustrated in Examples 2, 4, and 5. Compound 35 is prepared using similar procedures published in Rouchaud et al., *Eur. J Org. Chem.,* 2011, 12, 2346-2353.
Example 12: Preparation of Compound 40
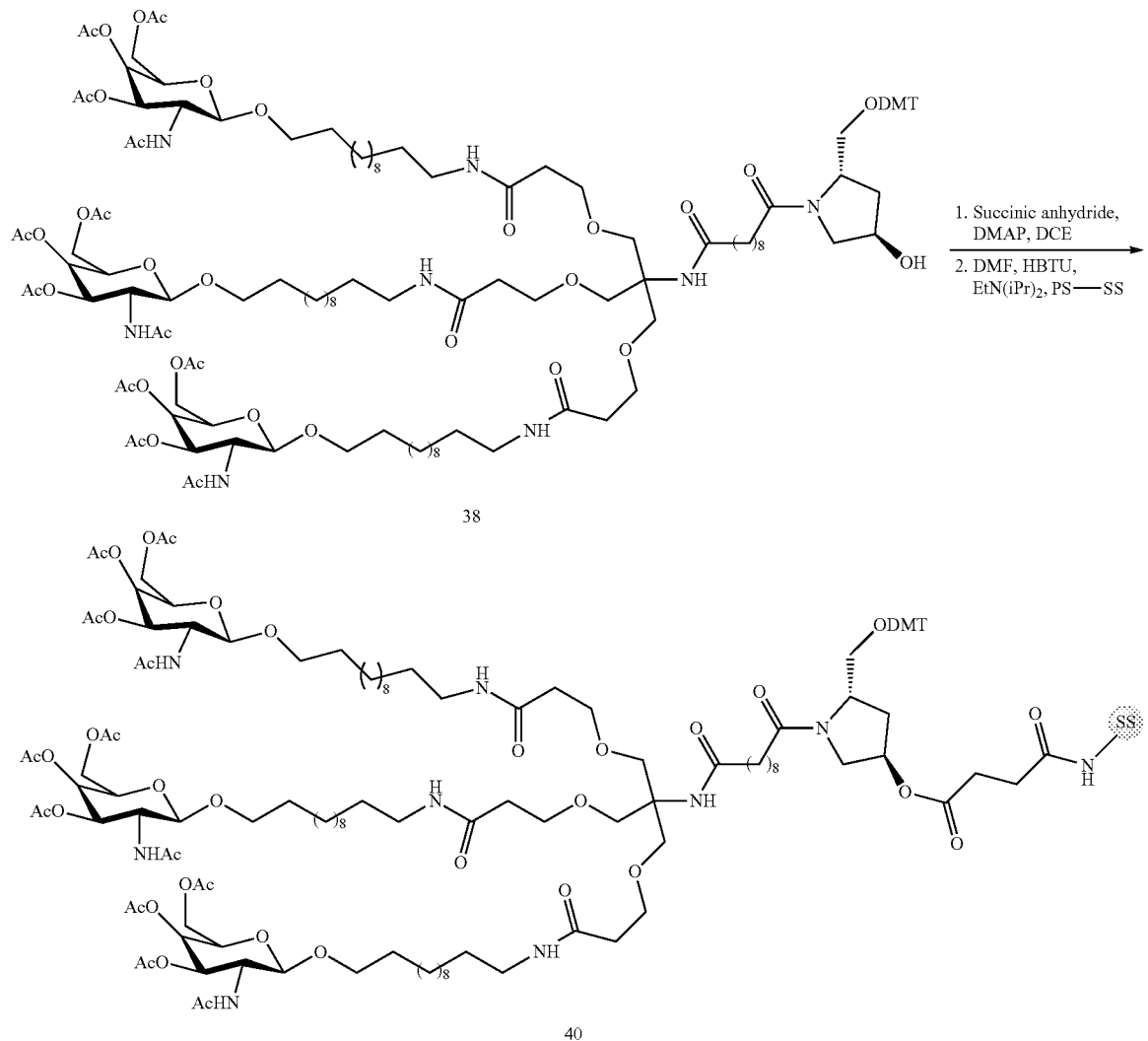
Compound 38 is prepared as per the procedures illustrated in Example 11.
Example 13: Preparation of Compound 44
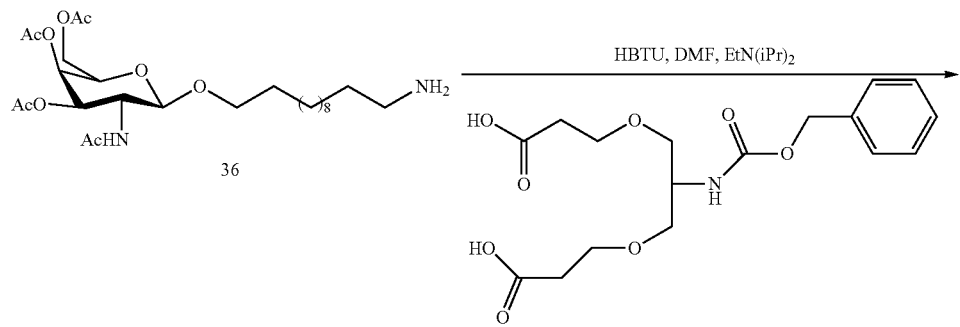

-continued
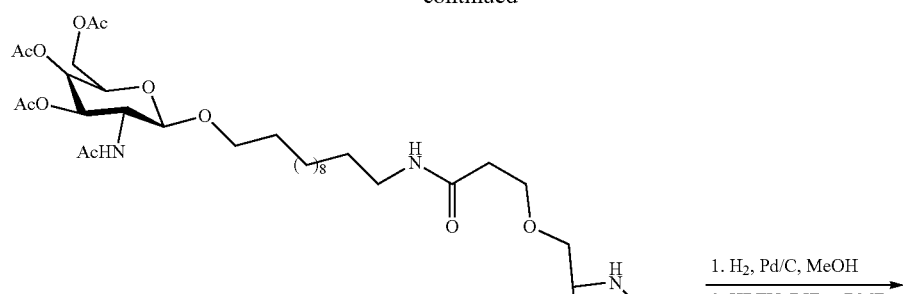
42
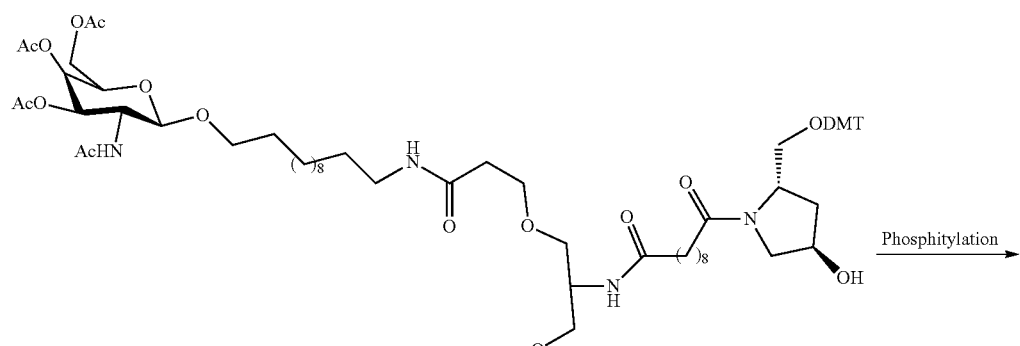
43
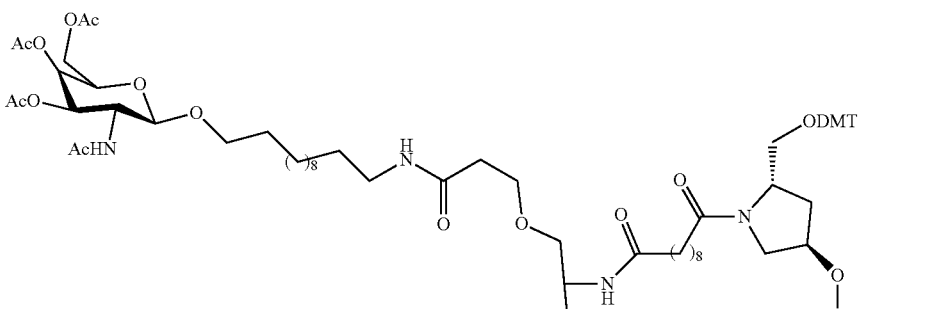
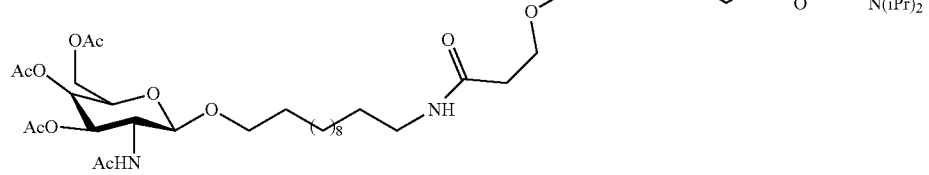
44

Compounds 23 and 36 are prepared as per the procedures illustrated in Examples 5 and 11. Compound 41 is prepared using similar procedures published in WO 2009082607.
Example 14: Preparation of Compound 45
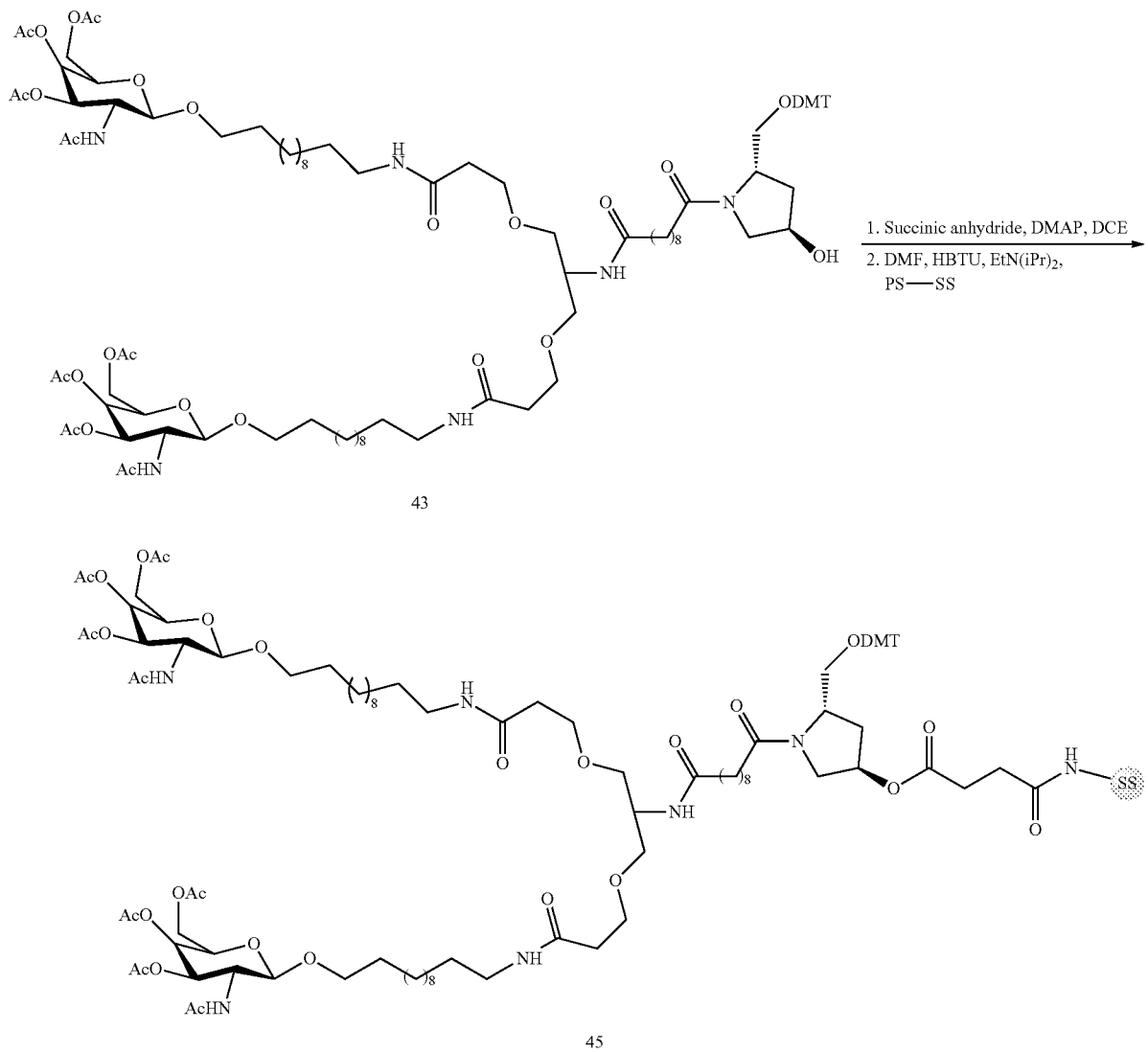
Compound 43 is prepared as per the procedures illustrated in Example 13.
Example 15: Preparation of Compound 47
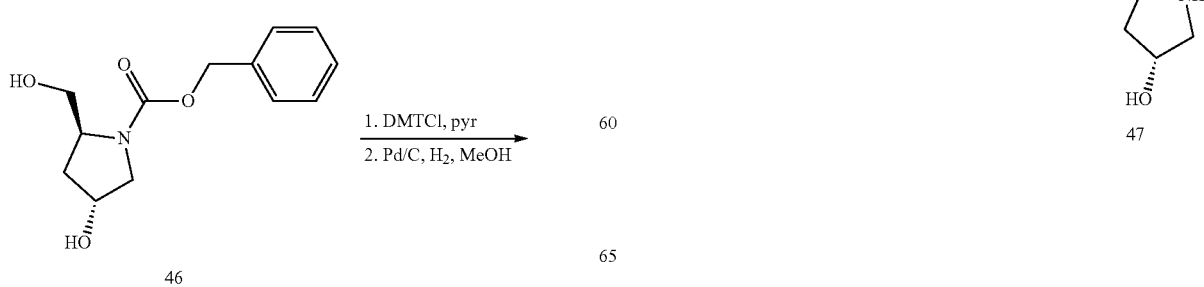
Compound 46 is commercially available.

Example 16: Preparation of Compound 53
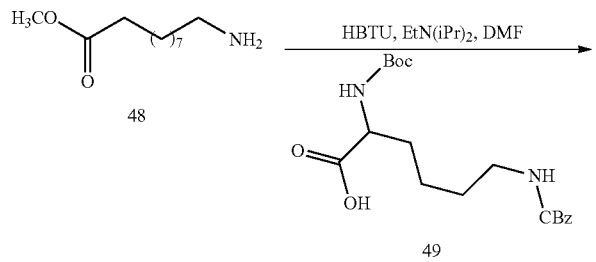
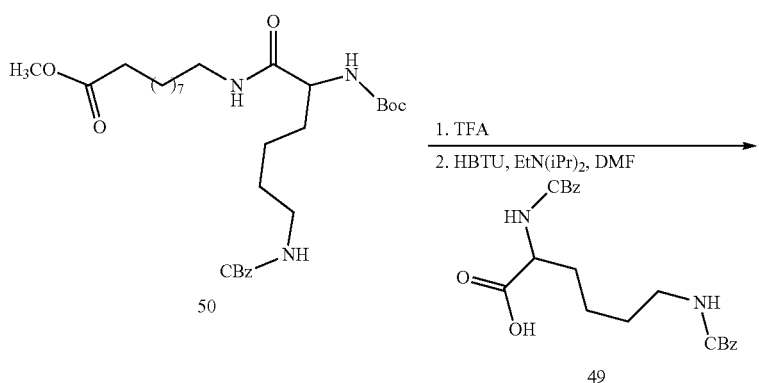
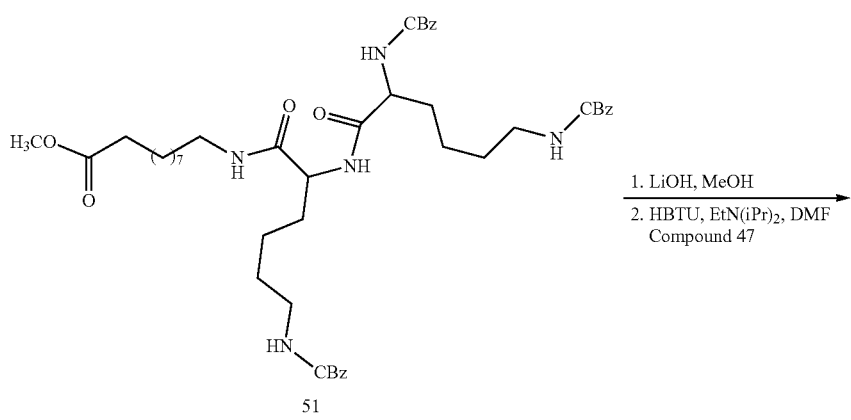

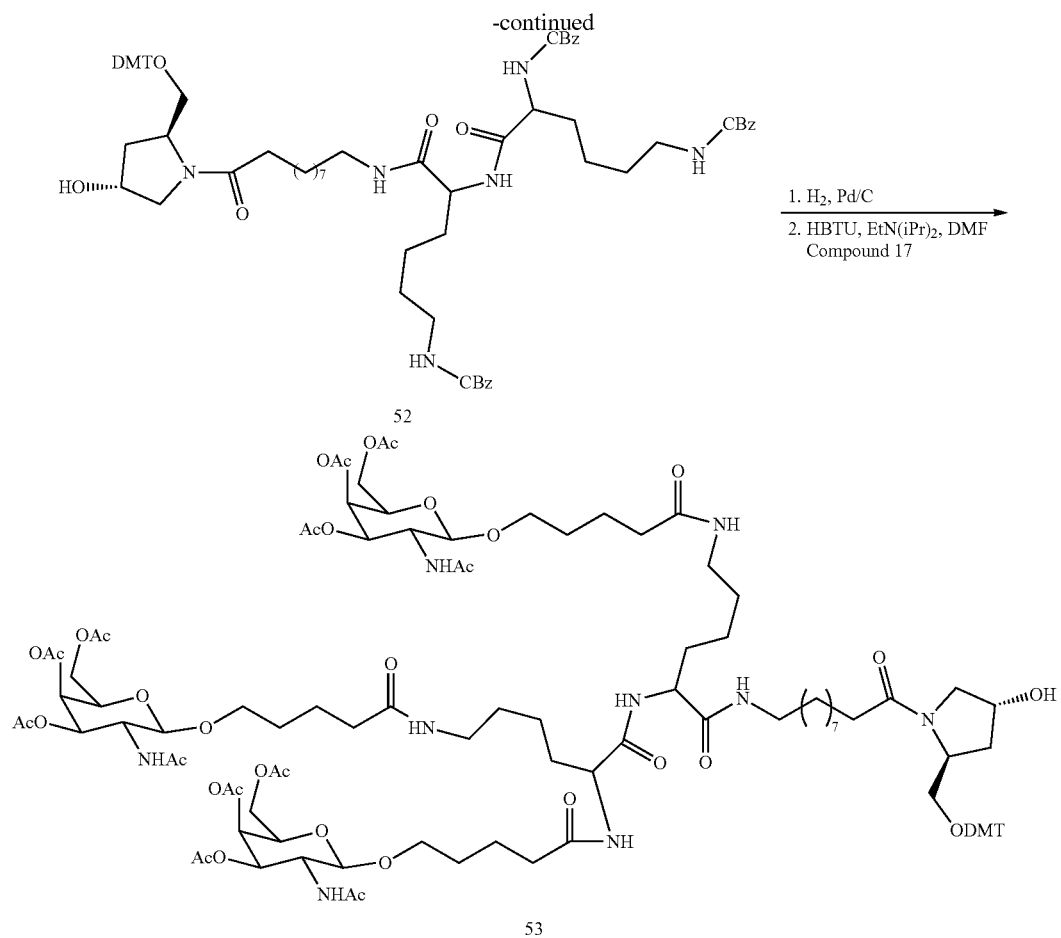
Compounds 48 and 49 are commercially available. Compounds 17 and 47 are prepared as per the procedures illustrated in Examples 4 and 15.
Example 17: Preparation of Compound 54
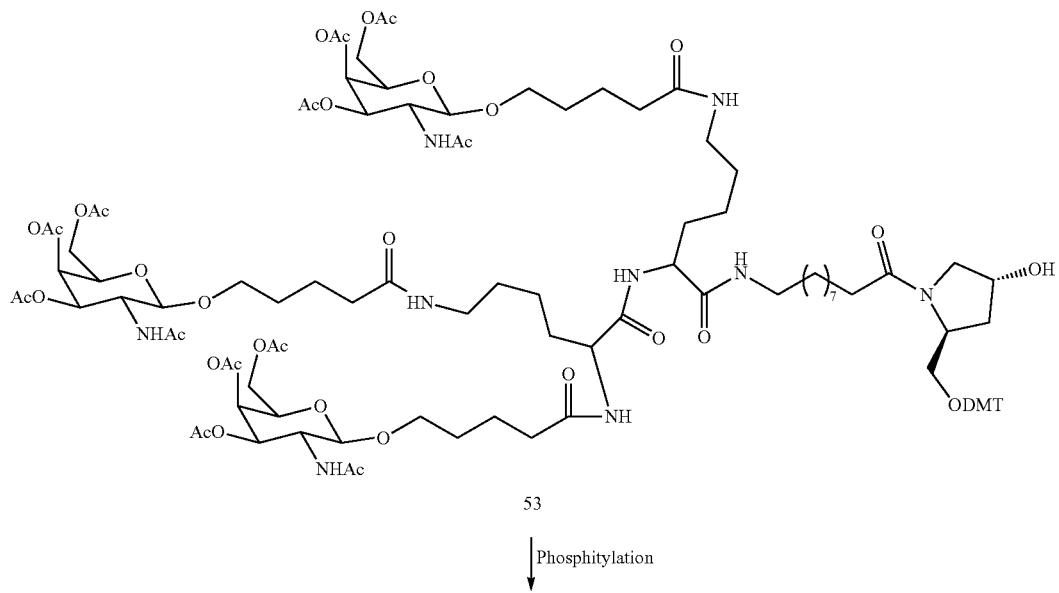

-continued
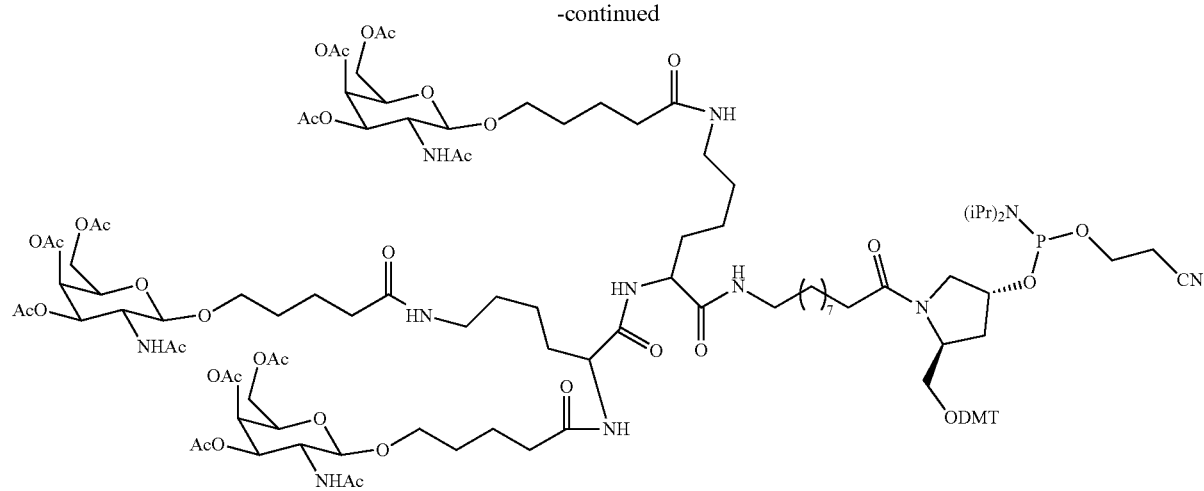
54
Compound 53 is prepared as per the procedures illustrated in Example 16.
Example 18: Preparation of Compound 55
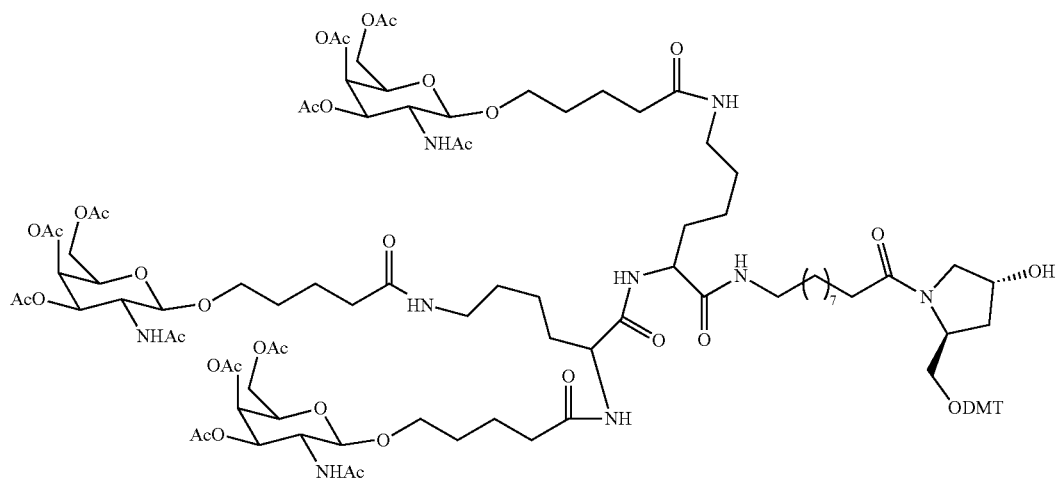
53
1. Succinic anhydride, DMAP, DCE
2. DMF, HBTU, EtN(iPr)₂, PS—SS

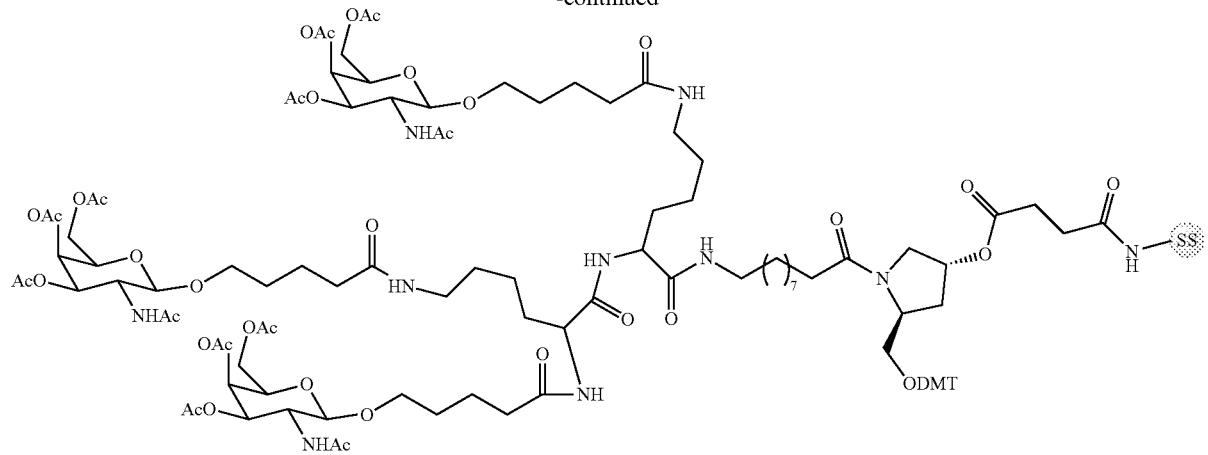

Compound 53 is prepared as per the procedures illustrated in Example 16.

Example 19: General Method for the Preparation of Conjugated ASOs Comprising GalNAc$_3$-1 at the 3' Position Via Solid Phase Techniques (Preparation of ISIS 647535, 647536 and 651900)

Unless otherwise stated, all reagents and solutions used for the synthesis of oligomeric compounds are purchased from commercial sources. Standard phosphoramidite building blocks and solid support are used for incorporation nucleoside residues which include for example T, A, G, and $^m$C residues. A 0.1 M solution of phosphoramidite in anhydrous acetonitrile was used for β-D-2'-deoxyribonucleoside and 2'-MOE.

The ASO syntheses were performed on ABI 394 synthesizer (1-2 μmol scale) or on GE Healthcare Bioscience ÄKTA oligopilot synthesizer (40-200 μmol scale) by the phosphoramidite coupling method on an GalNAc$_3$-1 loaded VIMAD solid support (110 μmol/g, Guzaev et al., 2003) packed in the column. For the coupling step, the phosphoramidites were delivered 4 fold excess over the loading on the solid support and phosphoramidite condensation was carried out for 10 min. All other steps followed standard protocols supplied by the manufacturer. A solution of 6% dichloroacetic acid in toluene was used for removing dimethoxytrityl (DMT) group from 5'-hydroxyl group of the nucleotide. 4,5-Dicyanoimidazole (0.7 M) in anhydrous CH$_3$CN was used as activator during coupling step. Phosphorothioate linkages were introduced by sulfurization with 0.1 M solution of xanthane hydride in 1:1 pyridine/CH$_3$CN for a contact time of 3 minutes. A solution of 20% tert-butylhydroperoxide in CH$_3$CN containing 6% water was used as an oxidizing agent to provide phosphodiester internucleoside linkages with a contact time of 12 minutes.

After the desired sequence was assembled, the cyanoethyl phosphate protecting groups were deprotected using a 1:1 (v/v) mixture of triethylamine and acetonitrile with a contact time of 45 minutes. The solid-support bound ASOs were suspended in aqueous ammonia (28-30 wt %) and heated at 55° C. for 6 h.

The unbound ASOs were then filtered and the ammonia was boiled off. The residue was purified by high pressure liquid chromatography on a strong anion exchange column (GE Healthcare Bioscience, Source 30Q, 30 μm, 2.54×8 cm, A=100 mM ammonium acetate in 30% aqueous CH$_3$CN, B=1.5 M NaBr in A, 0-40% of B in 60 min, flow 14 mL min-1, λ=260 nm). The residue was desalted by HPLC on a reverse phase column to yield the desired ASOs in an isolated yield of 15-30% based on the initial loading on the solid support. The ASOs were characterized by ion-pair-HPLC coupled MS analysis with Agilent 1100 MSD system.

Antisense oligonucleotides not comprising a conjugate were synthesized using standard oligonucleotide synthesis procedures well known in the art.

Using these methods, three separate antisense compounds targeting ApoC III were prepared. As summarized in Table 17, below, each of the three antisense compounds targeting ApoC III had the same nucleobase sequence; ISIS 304801 is a 5-10-5 MOE gapmer having all phosphorothioate linkages; ISIS 647535 is the same as ISIS 304801, except that it had a GalNAc$_3$-1 conjugated at its 3'end; and ISIS 647536 is the same as ISIS 647535 except that certain internucleoside linkages of that compound are phosphodiester linkages. As further summarized in Table 17, two separate antisense compounds targeting SRB-1 were synthesized. ISIS 440762 was a 2-10-2 cEt gapmer with all phosphorothioate internucleoside linkages; ISIS 651900 is the same as ISIS 440762, except that it included a GalNAc$_3$-1 at its 3'-end.

TABLE 17

Modified ASO targeting ApoC III and SRB-1

| ASO | Sequence (5' to 3') | Target | CalCd Mass | Observed Mass | SEQ ID No. |
|---|---|---|---|---|---|
| ISIS 304801 | A$_{es}$G$_{es}$$^m$C$_{es}$T$_{es}$T$_{es}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$ T$_{es}$T$_{es}$T$_{es}$A$_{es}$T$_e$ | ApoC III | 7165.4 | 7164.4 | 821 |

TABLE 17-continued

Modified ASO targeting ApoC III and SRB-1

| ASO | Sequence (5' to 3') | Target | CalCd Mass | Observed Mass | SEQ ID No. |
|---|---|---|---|---|---|
| ISIS 647535 | $A_{es}G_{es}{}^mC_{es}T_{es}T_{es}{}^mC_{ds}T_{ds}T_{ds}G_{ds}T_{ds}{}^mC_{ds}{}^mC_{ds}A_{ds}G_{ds}{}^mC_{ds}T_{es}T_{es}T_{es}A_{es}T_{eo}A_{do'}$-GalNAc$_3$-1$_a$ | ApoC III | 9239.5 | 9237.8 | 822 |
| ISIS 647536 | $A_{es}G_{eo}{}^mC_{eo}T_{eo}T_{eo}{}^mC_{ds}T_{ds}T_{ds}G_{ds}T_{ds}{}^mC_{ds}{}^mC_{ds}A_{ds}G_{ds}{}^mC_{ds}T_{eo}T_{eo}T_{es}A_{es}T_{eo}A_{do'}$-GalNAc$_3$-1$_a$ | ApoC III | 9142.9 | 9140.8 | 822 |
| ISIS 440762 | $T_{ks}{}^mC_{ks}A_{ds}G_{ds}T_{ds}{}^mC_{ds}A_{ds}T_{ds}G_{ds}A_{ds}{}^mC_{ds}T_{ds}T_{ks}{}^mC_k$ | SRB-1 | 4647.0 | 4646.4 | 823 |
| ISIS 651900 | $T_{ks}{}^mC_{ks}A_{ds}G_{ds}T_{ds}{}^mC_{ds}A_{ds}T_{ds}G_{ds}A_{ds}{}^mC_{ds}T_{ds}T_{ks}{}^mC_{ko}A_{do'}$-GalNAc$_3$-1$_a$ | SRB-1 | 6721.1 | 6719.4 | 824 |

Subscripts: "e" indicates 2'-MOE modified nucleoside; "d" indicates β-D-2'-deoxyribonucleoside; "k" indicates 6'-(S)—CH$_3$ bicyclic nucleoside (e.g. cEt); "s" indicates phosphorothioate internucleoside linkages (PS); "o" indicates phosphodiester internucleoside linkages (PO); and "o'" indicates —O—P(=O)(OH)—. Superscript "m" indicates 5-methylcytosines. "GalNAc$_3$-1" indicates a conjugate group having the structure shown previously in Example 9. Note that GalNAc$_3$-1 comprises a cleavable adenosine which links the ASO to remainder of the conjugate, which is designated "GalNAc$_3$-1$_a$." This nomenclature is used in the above table to show the full nucleobase sequence, including the adenosine, which is part of the conjugate. Thus, in the above table, the sequences could also be listed as ending with "GalNAc$_3$-1" with the "$A_{do'}$" omitted. This convention of using the subscript "a" to indicate the portion of a conjugate group lacking a cleavable nucleoside or cleavable moiety is used throughout these Examples. This portion of a conjugate group lacking the cleavable moiety is referred to herein as a "cluster" or "conjugate cluster" or "GalNAc$_3$ cluster." In certain instances it is convenient to describe a conjugate group by separately providing its cluster and its cleavable moiety.

Example 20: Dose-Dependent Antisense Inhibition of Human ApoC III in huApoC III Transgenic Mice ISIS 304801 and ISIS 647535, each targeting human ApoC III and described above, were separately tested and evaluated in a dose-dependent study for their ability to inhibit human ApoC III in human ApoC III transgenic mice.

Treatment

Human ApoCIII transgenic mice were maintained on a 12-hour light/dark cycle and fed ad libitum Teklad lab chow. Animals were acclimated for at least 7 days in the research facility before initiation of the experiment. ASOs were prepared in PBS and sterilized by filtering through a 0.2 micron filter. ASOs were dissolved in 0.9% PBS for injection.

Human ApoC III transgenic mice were injected intraperitoneally once a week for two weeks with ISIS 304801 or 647535 at 0.08, 0.25. 0.75, 2.25 or 6.75 μmol/kg or with PBS as a control. Each treatment group consisted of 4 animals. Forty-eight hours after the administration of the last dose, blood was drawn from each mouse and the mice were sacrificed and tissues were collected.

ApoC III mRNA Analysis

ApoC III mRNA levels in the mice's livers were determined using real-time PCR and RIBOGREEN® RNA quantification reagent (Molecular Probes, Inc. Eugene, Oreg.) according to standard protocols. ApoC III mRNA levels were determined relative to total RNA (using Ribogreen), prior to normalization to PBS-treated control. The results below are presented as the average percent of ApoC III mRNA levels for each treatment group, normalized to PBS-treated control and are denoted as "% PBS". The half maximal effective dosage ($ED_{50}$) of each ASO is also presented in Table 18, below.

As illustrated, both antisense compounds reduced ApoC III RNA relative to the PBS control. Further, the antisense compound conjugated to GalNAc$_3$-1 (ISIS 647535) was substantially more potent than the antisense compound lacking the GalNAc$_3$-1 conjugate (ISIS 304801).

TABLE 18

Effect of ASO treatment on ApoC III mRNA levels in human ApoC III transgenic mice

| ASO | Dose (μmol/kg) | % PBS | $ED_{50}$ (μmol/kg) | 3' Conjugate | Internucleoside linkage/Length | SEQ ID No. |
|---|---|---|---|---|---|---|
| PBS | 0 | 100 | — | — | — | |
| ISIS 304801 | 0.08 | 95 | 0.77 | None | PS/20 | 821 |
| | 0.75 | 42 | | | | |
| | 2.25 | 32 | | | | |
| | 6.75 | 19 | | | | |
| ISIS 647535 | 0.08 | 50 | 0.074 | GalNAc$_3$-1 | PS/20 | 822 |
| | 0.75 | 15 | | | | |
| | 2.25 | 17 | | | | |
| | 6.75 | 8 | | | | |

ApoC III Protein Analysis (Turbidometric Assay)

Plasma ApoC III protein analysis was determined using procedures reported by Graham et al, *Circulation Research*, published online before print Mar. 29, 2013.

Approximately 100 μl of plasma isolated from mice was analyzed without dilution using an Olympus Clinical Analyzer and a commercially available turbidometric ApoC III assay (Kamiya, Cat #KAI-006, Kamiya Biomedical, Seattle, Wash.). The assay protocol was performed as described by the vendor.

As shown in the Table 19 below, both antisense compounds reduced ApoC III protein relative to the PBS control. Further, the antisense compound conjugated to GalNAc$_3$-1 (ISIS 647535) was substantially more potent than the antisense compound lacking the GalNAc$_3$-1 conjugate (ISIS 304801).

TABLE 19

Effect of ASO treatment on ApoC III plasma protein levels in human ApoC III transgenic mice

| ASO | Dose (μmol/kg) | % PBS | ED$_{50}$ (μmol/kg) | 3' Conjugate | Internucleoside Linkage/Length | SEQ ID No. |
|---|---|---|---|---|---|---|
| PBS | 0 | 100 | — | — | — | |
| ISIS 304801 | 0.08 | 86 | 0.73 | None | PS/20 | 821 |
| | 0.75 | 51 | | | | |
| | 2.25 | 23 | | | | |
| | 6.75 | 13 | | | | |
| ISIS 647535 | 0.08 | 72 | 0.19 | GalNAc$_3$-1 | PS/20 | 822 |
| | 0.75 | 14 | | | | |
| | 2.25 | 12 | | | | |
| | 6.75 | 11 | | | | |

Plasma triglycerides and cholesterol were extracted by the method of Bligh and Dyer (Bligh, E. G. and Dyer, W. J. *Can. J. Biochem. Physiol.* 37: 911-917, 1959)(Bligh, E and Dyer, W, *Can J Biochem Physiol*, 37, 911-917, 1959)(Bligh, E and Dyer, W, *Can J Biochem Physiol*, 37, 911-917, 1959) and measured by using a Beckmann Coulter clinical analyzer and commercially available reagents.

The triglyceride levels were measured relative to PBS injected mice and are denoted as "% PBS". Results are presented in Table 20. As illustrated, both antisense compounds lowered triglyceride levels. Further, the antisense compound conjugated to GalNAc$_3$-1 (ISIS 647535) was substantially more potent than the antisense compound lacking the GalNAc$_3$-1 conjugate (ISIS 304801).

TABLE 20

Effect of ASO treatment on triglyceride levels in transgenic mice

| ASO | Dose (μmol/kg) | % PBS | ED$_{50}$ (μmol/kg) | 3' Conjugate | Internucleoside Linkage/Length | SEQ ID No. |
|---|---|---|---|---|---|---|
| PBS | 0 | 100 | — | — | — | |
| ISIS 304801 | 0.08 | 87 | 0.63 | None | PS/20 | 821 |
| | 0.75 | 46 | | | | |
| | 2.25 | 21 | | | | |
| | 6.75 | 12 | | | | |
| ISIS 647535 | 0.08 | 65 | 0.13 | GalNAc$_3$-1 | PS/20 | 822 |
| | 0.75 | 9 | | | | |
| | 2.25 | 8 | | | | |
| | 6.75 | 9 | | | | |

Plasma samples were analyzed by HPLC to determine the amount of total cholesterol and of different fractions of cholesterol (HDL and LDL). Results are presented in Tables 21 and 22. As illustrated, both antisense compounds lowered total cholesterol levels; both lowered LDL; and both raised HDL. Further, the antisense compound conjugated to GalNAc$_3$-1 (ISIS 647535) was substantially more potent than the antisense compound lacking the GalNAc$_3$-1 conjugate (ISIS 304801). An increase in HDL and a decrease in LDL levels is a cardiovascular beneficial effect of antisense inhibition of ApoC III.

TABLE 21

Effect of ASO treatment on total cholesterol levels in transgenic mice

| ASO | Dose (μmol/kg) | Total Cholesterol (mg/dL) | 3' Conjugate | Internucleoside Linkage/Length | SEQ ID No. |
|---|---|---|---|---|---|
| PBS | 0 | 257 | — | — | |
| ISIS 304801 | 0.08 | 226 | None | PS/20 | 821 |
|  | 0.75 | 164 | | | |
|  | 2.25 | 110 | | | |
|  | 6.75 | 82 | | | |
| ISIS 647535 | 0.08 | 230 | GalNAc$_3$-1 | PS/20 | 822 |
|  | 0.75 | 82 | | | |
|  | 2.25 | 86 | | | |
|  | 6.75 | 99 | | | |

TABLE 22

Effect of ASO treatment on HDL and LDL cholesterol levels in transgenic mice

| ASO | Dose (μmol/kg) | HDL (mg/dL) | LDL (mg/dL) | 3' Conjugate | Internucleoside Linkage/Length | SEQ ID No. |
|---|---|---|---|---|---|---|
| PBS | 0 | 17 | 28 | — | — | |
| ISIS 304801 | 0.08 | 17 | 23 | None | PS/20 | 821 |
|  | 0.75 | 27 | 12 | | | |
|  | 2.25 | 50 | 4 | | | |
|  | 6.75 | 45 | 2 | | | |
| ISIS 647535 | 0.08 | 21 | 21 | GalNAc$_3$-1 | PS/20 | 822 |
|  | 0.75 | 44 | 2 | | | |
|  | 2.25 | 50 | 2 | | | |
|  | 6.75 | 58 | 2 | | | |

Pharmacokinetics Analysis (PK)

The PK of the ASOs was also evaluated. Liver and kidney samples were minced and extracted using standard protocols. Samples were analyzed on MSD1 utilizing IP-HPLC-MS. The tissue level (μg/g) of full-length ISIS 304801 and 647535 was measured and the results are provided in Table 23. As illustrated, liver concentrations of total full-length antisense compounds were similar for the two antisense compounds. Thus, even though the GalNAc$_3$-1-conjugated antisense compound is more active in the liver (as demonstrated by the RNA and protein data above), it is not present at substantially higher concentration in the liver. Indeed, the calculated EC$_{50}$ (provided in Table 23) confirms that the observed increase in potency of the conjugated compound cannot be entirely attributed to increased accumulation. This result suggests that the conjugate improved potency by a mechanism other than liver accumulation alone, possibly by improving the productive uptake of the antisense compound into cells.

The results also show that the concentration of GalNAc$_3$-1 conjugated antisense compound in the kidney is lower than that of antisense compound lacking the GalNAc conjugate. This has several beneficial therapeutic implications. For therapeutic indications where activity in the kidney is not sought, exposure to kidney risks kidney toxicity without corresponding benefit. Moreover, high concentration in kidney typically results in loss of compound to the urine resulting in faster clearance. Accordingly, for non-kidney targets, kidney accumulation is undesired. These data suggest that GalNAc$_3$-1 conjugation reduces kidney accumulation.

TABLE 23

PK analysis of ASO treatment in transgenic mice

| ASO | Dose (μmol/kg) | Liver (μg/g) | Kidney (μg/g) | Liver EC$_{50}$ (μg/g) | 3' Conjugate | Internucleoside Linkage/Length | SEQ ID No. |
|---|---|---|---|---|---|---|---|
| ISIS 304801 | 0.1 | 5.2 | 2.1 | 53 | None | PS/20 | 821 |
|  | 0.8 | 62.8 | 119.6 |  |  |  |  |
|  | 2.3 | 142.3 | 191.5 |  |  |  |  |
|  | 6.8 | 202.3 | 337.7 |  |  |  |  |
| ISIS 647535 | 0.1 | 3.8 | 0.7 | 3.8 | GalNAc$_3$-1 | PS/20 | 822 |
|  | 0.8 | 72.7 | 34.3 |  |  |  |  |
|  | 2.3 | 106.8 | 111.4 |  |  |  |  |
|  | 6.8 | 237.2 | 179.3 |  |  |  |  |

Metabolites of ISIS 647535 were also identified and their masses were confirmed by high resolution mass spectrometry analysis. The cleavage sites and structures of the observed metabolites are shown below. The relative 00 of full length ASO was calculated using standard procedures and the results are presented in Table 23a. The major metabolite of ISIS 647535 was full-length ASO lacking the entire conjugate (i.e. ISIS 304801), which results from cleavage at cleavage site A, shown below. Further, additional metabolites resulting from other cleavage sites were also observed. These results suggest that introducing other cleabable bonds such as esters, peptides, disulfides, phosphoramidates or acyl-hydrazones between the GalNAc$_3$-1 sugar and the ASO, which can be cleaved by enzymes inside the cell, or which may cleave in the reductive environment of the cytosol, or which are labile to the acidic pH inside endosomes and lyzosomes, can also be useful.

TABLE 23a

Observed full length metabolites of ISIS 647535

| Metabolite | ASO | Cleavage site | Relative % |
|---|---|---|---|
| 1 | ISIS 304801 | A | 36.1 |
| 2 | ISIS 304801 + dA | B | 10.5 |
| 3 | ISIS 647535 minus [3 GalNAc] | C | 16.1 |
| 4 | ISIS 647535 minus [3 GalNAc + 1 5-hydroxy-pentanoic acid tether] | D | 17.6 |
| 5 | ISIS 647535 minus [2 GalNAc + 2 5-hydroxy-pentanoic acid tether] | D | 9.9 |
| 6 | ISIS 647535 minus [3 GalNAc + 3 5-hydroxy-pentanoic acid tether] | D | 9.8 |

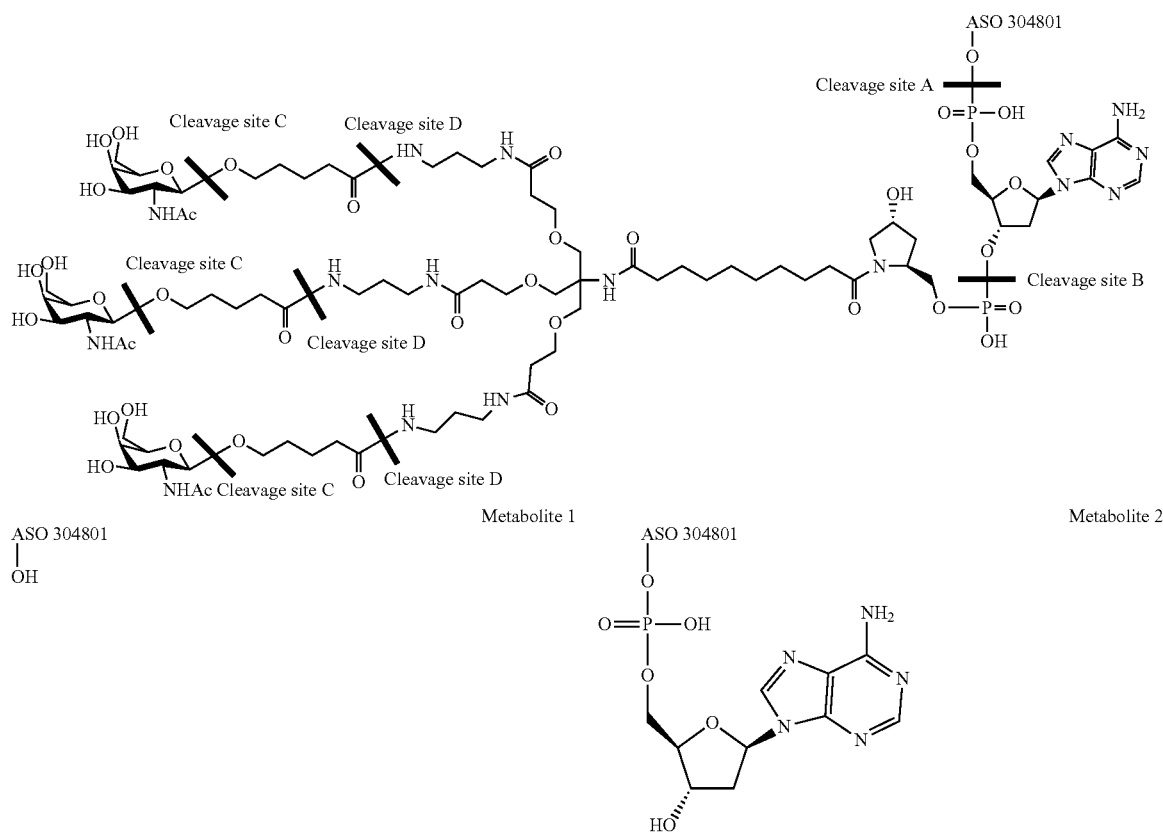

Cleavage Sties

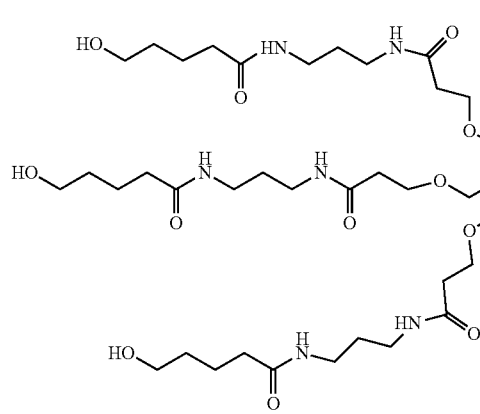
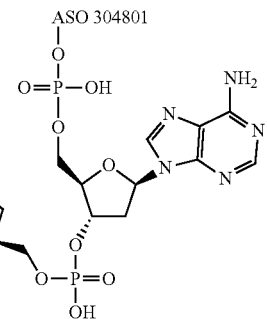
Metabolite 3
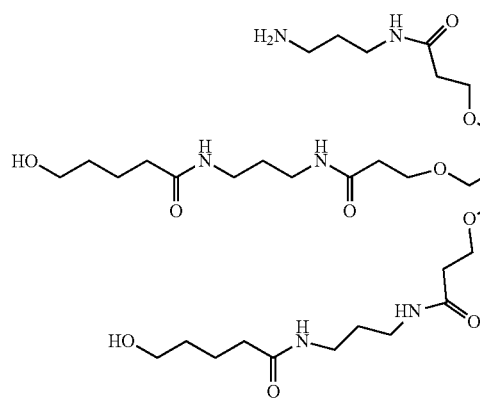
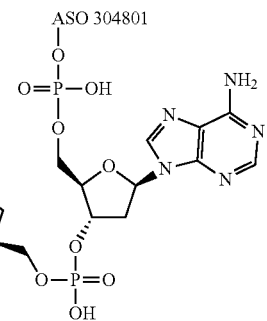
Metabolite 4
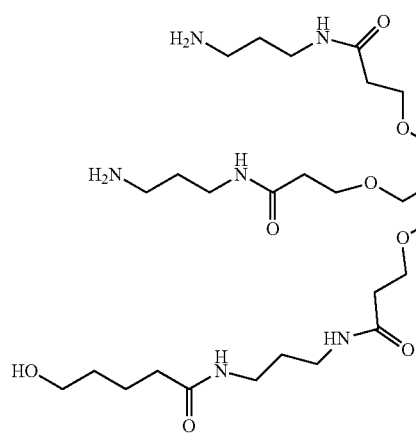
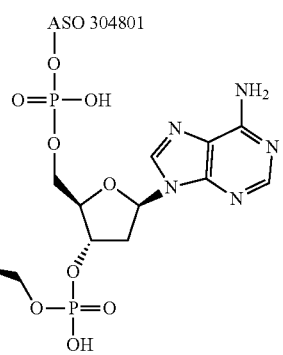
Metabolite 5

Metabolite 6

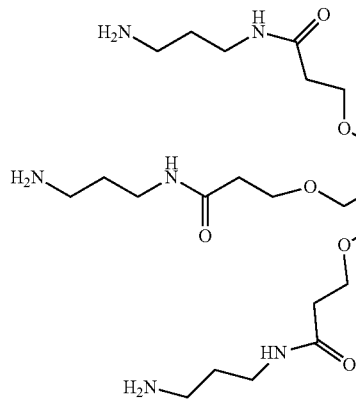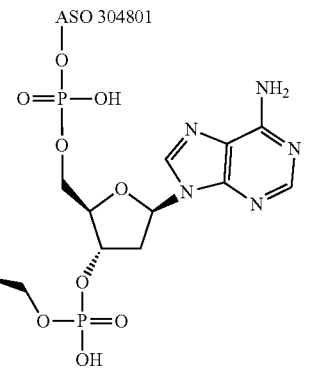

Example 21: Antisense Inhibition of Human ApoC III in Human ApoC III Transgenic Mice in Single Administration Study ISIS 304801, 647535 and 647536 each targeting human ApoC III and described in Table 17, were further evaluated in a single administration study for their ability to inhibit human ApoC III in human ApoC III transgenic mice.

Treatment

Human ApoCIII transgenic mice were maintained on a 12-hour light/dark cycle and fed ad libitum Teklad lab chow. Animals were acclimated for at least 7 days in the research facility before initiation of the experiment. ASOs were prepared in PBS and sterilized by filtering through a 0.2 micron filter. ASOs were dissolved in 0.9% PBS for injection.

Human ApoC III transgenic mice were injected intraperitoneally once at the dosage shown below with ISIS 304801, 647535 or 647536 (described above) or with PBS treated control. The treatment group consisted of 3 animals and the control group consisted of 4 animals. Prior to the treatment as well as after the last dose, blood was drawn from each mouse and plasma samples were analyzed. The mice were sacrificed 72 hours following the last administration.

Samples were collected and analyzed to determine the ApoC III mRNA and protein levels in the liver; plasma triglycerides; and cholesterol, including HDL and LDL fractions were assessed as described above (Example 20). Data from those analyses are presented in Tables 24-28, below. Liver transaminase levels, alanine aminotransferase (ALT) and aspartate aminotransferase (AST), in serum were measured relative to saline injected mice using standard protocols. The ALT and AST levels showed that the antisense compounds were well tolerated at all administered doses.

These results show improvement in potency for antisense compounds comprising a GalNAc$_3$-1 conjugate at the 3' terminus (ISIS 647535 and 647536) compared to the antisense compound lacking a GalNAc$_3$-1 conjugate (ISIS 304801). Further, ISIS 647536, which comprises a GalNAc$_3$-1 conjugate and some phosphodiester linkages was as potent as ISIS 647535, which comprises the same conjugate and all internucleoside linkages within the ASO are phosphorothioate.

TABLE 24

Effect of ASO treatment on ApoC III mRNA levels in human ApoC III transgenic mice

| ASO | Dose (mg/kg) | % PBS | ED$_{50}$ (mg/kg) | 3' Conjugate | Internucleoside linkage/Length | SEQ ID No. |
|---|---|---|---|---|---|---|
| PBS | 0 | 99 | — | — | — | |
| ISIS 304801 | 1 | 104 | 13.2 | None | PS/20 | 821 |
| | 3 | 92 | | | | |
| | 10 | 71 | | | | |
| | 30 | 40 | | | | |
| ISIS 647535 | 0.3 | 98 | 1.9 | GalNAc$_3$-1 | PS/20 | 822 |
| | 1 | 70 | | | | |
| | 3 | 33 | | | | |
| | 10 | 20 | | | | |
| ISIS 647536 | 0.3 | 103 | 1.7 | GalNAc$_3$-1 | PS/PO/20 | 822 |
| | 1 | 60 | | | | |
| | 3 | 31 | | | | |
| | 10 | 21 | | | | |

TABLE 25

Effect of ASO treatment on ApoC III plasma protein levels in human ApoC III transgenic mice

| ASO | Dose (mg/kg) | % PBS | ED$_{50}$ (mg/kg) | 3' Conjugate | Internucleoside Linkage/Length | SEQ ID No. |
|---|---|---|---|---|---|---|
| PBS | 0 | 99 | — | — | — | |
| ISIS 304801 | 1 | 104 | 23.2 | None | PS/20 | 821 |
| | 3 | 92 | | | | |
| | 10 | 71 | | | | |
| | 30 | 40 | | | | |
| ISIS 647535 | 0.3 | 98 | 2.1 | GalNAc$_3$-1 | PS/20 | 822 |
| | 1 | 70 | | | | |
| | 3 | 33 | | | | |
| | 10 | 20 | | | | |
| ISIS 647536 | 0.3 | 103 | 1.8 | GalNAc$_3$-1 | PS/PO/20 | 822 |
| | 1 | 60 | | | | |
| | 3 | 31 | | | | |
| | 10 | 21 | | | | |

TABLE 26

Effect of ASO treatment on triglyceride levels in transgenic mice

| ASO | Dose (mg/kg) | % PBS | ED$_{50}$ (mg/kg) | 3' Conjugate | Internucleoside Linkage/Length | SEQ ID No. |
|---|---|---|---|---|---|---|
| PBS | 0 | 98 | — | — | — | |
| ISIS 304801 | 1 | 80 | 29.1 | None | PS/20 | 821 |
| | 3 | 92 | | | | |
| | 10 | 70 | | | | |
| | 30 | 47 | | | | |
| ISIS 647535 | 0.3 | 100 | 2.2 | GalNAc$_3$-1 | PS/20 | 822 |
| | 1 | 70 | | | | |
| | 3 | 34 | | | | |
| | 10 | 23 | | | | |
| ISIS 647536 | 0.3 | 95 | 1.9 | GalNAc$_3$-1 | PS/PO/20 | 822 |
| | 1 | 66 | | | | |
| | 3 | 31 | | | | |
| | 10 | 23 | | | | |

TABLE 27

Effect of ASO treatment on total cholesterol levels in transgenic mice

| ASO | Dose (mg/kg) | % PBS | 3' Conjugate | Internucleoside Linkage/Length | SEQ ID No. |
|---|---|---|---|---|---|
| PBS | 0 | 96 | — | — | |
| ISIS 304801 | 1 | 104 | None | PS/20 | 821 |
| | 3 | 96 | | | |
| | 10 | 86 | | | |
| | 30 | 72 | | | |
| ISIS 647535 | 0.3 | 93 | GalNAc$_3$-1 | PS/20 | 822 |
| | 1 | 85 | | | |
| | 3 | 61 | | | |
| | 10 | 53 | | | |
| ISIS 647536 | 0.3 | 115 | GalNAc$_3$-1 | PS/PO/20 | 822 |
| | 1 | 79 | | | |
| | 3 | 51 | | | |
| | 10 | 54 | | | |

TABLE 28

Effect of ASO treatment on HDL and LDL cholesterol levels in transgenic mice

| ASO | Dose (mg/kg) | HDL % PBS | LDL % PBS | 3' Conjugate | Internucleoside Linkage/Length | SEQ ID No. |
|---|---|---|---|---|---|---|
| PBS | 0 | 131 | 90 | — | — | |
| ISIS 304801 | 1 | 130 | 72 | None | PS/20 | 821 |
| | 3 | 186 | 79 | | | |
| | 10 | 226 | 63 | | | |
| | 30 | 240 | 46 | | | |
| ISIS 647535 | 0.3 | 98 | 86 | GalNAc$_3$-1 | PS/20 | 822 |
| | 1 | 214 | 67 | | | |
| | 3 | 212 | 39 | | | |
| | 10 | 218 | 35 | | | |

TABLE 28-continued

Effect of ASO treatment on HDL and LDL cholesterol levels in transgenic mice

| ASO | Dose (mg/kg) | HDL % PBS | LDL % PBS | 3' Conjugate | Internucleoside Linkage/Length | SEQ ID No. |
|---|---|---|---|---|---|---|
| ISIS 647536 | 0.3 | 143 | 89 | GalNAc$_3$-1 | PS/PO/20 | 822 |
|  | 1 | 187 | 56 |  |  |  |
|  | 3 | 213 | 33 |  |  |  |
|  | 10 | 221 | 34 |  |  |  |

These results confirm that the GalNAc$_3$-1 conjugate improves potency of an antisense compound. The results also show equal potency of a GalNAc$_3$-1 conjugated antisense compounds where the antisense oligonucleotides have mixed linkages (ISIS 647536 which has six phosphodiester linkages) and a full phosphorothioate version of the same antisense compound (ISIS 647535).

Phosphorothioate linkages provide several properties to antisense compounds. For example, they resist nuclease digestion and they bind proteins resulting in accumulation of compound in the liver, rather than in the kidney/urine. These are desirable properties, particularly when treating an indication in the liver. However, phosphorothioate linkages have also been associated with an inflammatory response. Accordingly, reducing the number of phosphorothioate linkages in a compound is expected to reduce the risk of inflammation, but also lower concentration of the compound in liver, increase concentration in the kidney and urine, decrease stability in the presence of nucleases, and lower overall potency. The present results show that a GalNAc$_3$-1 conjugated antisense compound where certain phosphorothioate linkages have been replaced with phosphodiester linkages is as potent against a target in the liver as a counterpart having full phosphorothioate linkages. Such compounds are expected to be less proinflammatory (See Example 24 describing an experiment showing reduction of PS results in reduced inflammatory effect).

Example 22: Effect of GalNAc$_3$-1 Conjugated Modified ASO Targeting SRB-1 In Vivo ISIS 440762 and 651900, each targeting SRB-1 and described in Table 17, were evaluated in a dose-dependent study for their ability to inhibit SRB-1 in Balb/c mice.
Treatment Six week old male Balb/c mice (Jackson Laboratory, Bar Harbor, Me.) were injected subcutaneously once at the dosage shown below with ISIS 440762, 651900 or with PBS treated control. Each treatment group consisted of 4 animals. The mice were sacrificed 48 hours following the final administration to determine the SRB-1 mRNA levels in liver using real-time PCR and RIBOGREEN® RNA quantification reagent (Molecular Probes, Inc. Eugene, Oreg.) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS".

As illustrated in Table 29, both antisense compounds lowered SRB-1 mRNA levels. Further, the antisense compound comprising the GalNAc$_3$-1 conjugate (ISIS 651900) was substantially more potent than the antisense compound lacking the GalNAc$_3$-1 conjugate (ISIS 440762). These results demonstrate that the potency benefit of GalNAc$_3$-1 conjugates are observed using antisense oligonucleotides complementary to a different target and having different chemically modified nucleosides, in this instance modified nucleosides comprise constrained ethyl sugar moieties (a bicyclic sugar moiety).

TABLE 29

Effect of ASO treatment on SRB-1 mRNA levels in Balb/c mice

| ASO | Dose (mg/kg) | Liver % PBS | ED$_{50}$ (mg/kg) | 3' Conjugate | Internucleoside linkage/Length | SEQ ID No. |
|---|---|---|---|---|---|---|
| PBS | 0 | 100 | — | — | — |  |
| ISIS 440762 | 0.7 | 85 | 2.2 | None | PS/14 | 823 |
|  | 2 | 55 |  |  |  |  |
|  | 7 | 12 |  |  |  |  |
|  | 20 | 3 |  |  |  |  |
| ISIS 651900 | 0.07 | 98 | 0.3 | GalNAc$_3$-1 | PS/14 | 824 |
|  | 0.2 | 63 |  |  |  |  |
|  | 0.7 | 20 |  |  |  |  |
|  | 2 | 6 |  |  |  |  |
|  | 7 | 5 |  |  |  |  |

Example 23: Human Peripheral Blood Mononuclear Cells (hPBMC) Assay Protocol

The hPBMC assay was performed using BD Vautainer CPT tube method. A sample of whole blood from volunteered donors with informed consent at US HealthWorks clinic (Faraday & El Camino Real, Carlsbad) was obtained and collected in 4-15 BD Vacutainer CPT 8 ml tubes (VWR Cat. #BD362753). The approximate starting total whole blood volume in the CPT tubes for each donor was recorded using the PBMC assay data sheet.

The blood sample was remixed immediately prior to centrifugation by gently inverting tubes 8-10 times. CPT tubes were centrifuged at rt (18-25° C.) in a horizontal (swing-out) rotor for 30 min. at 1500-1800 RCF with brake off (2700 RPM Beckman Allegra 6R). The cells were retrieved from the buffy coat interface (between Ficoll and polymer gel layers); transferred to a sterile 50 ml conical tube and pooled up to 5 CPT tubes/50 ml conical tube/donor. The cells were then washed twice with PBS ($Ca^{++}$, $Mg^{++}$ free; GIBCO). The tubes were topped up to 50 ml and mixed by inverting several times. The sample was then centrifuged at 330×g for 15 minutes at rt (1215 RPM in Beckman Allegra 6R) and aspirated as much supernatant as possible without disturbing pellet. The cell pellet was dislodged by gently swirling tube and resuspended cells in RPMI+10% FBS+pen/strep (~1 ml/10 ml starting whole blood volume). A 60 µl sample was pipette into a sample vial (Beckman Coulter) with 600 µl VersaLyse reagent (Beckman Coulter Cat #A09777) and was gently vortexed for 10-15 sec. The sample was allowed to incubate for 10 min. at rt and being mixed again before counting. The cell suspension was counted on Vicell XR cell viability analyzer (Beckman Coulter) using PBMC cell type (dilution factor of 1:11 was stored with other parameters). The live cell/ml and viability were recorded. The cell suspension was diluted to $1 \times 10^7$ live PBMC/ml in RPMI+10% FBS+pen/strep.

The cells were plated at $5 \times 10^5$ in 50 µl/well of 96-well tissue culture plate (Falcon Microtest). 50 µl/well of 2× concentration oligos/controls diluted in RPMI+10% FBS+pen/strep. was added according to experiment template (100 µl/well total). Plates were placed on the shaker and allowed to mix for approx. 1 min. After being incubated for 24 hrs at 37° C.; 5% $CO_2$, the plates were centrifuged at 400×g for 10 minutes before removing the supernatant for MSD cytokine assay (i.e. human IL-6, IL-10, IL-8 and MCP-1).

Example 24: Evaluation of Proinflammatory Effects in hPBMC Assay for $GalNAc_3$-1 Conjugated ASOs The antisense oligonucleotides (ASOs) listed in Table 30 were evaluated for proinflammatory effect in hPBMC assay using the protocol described in Example 23. ISIS 353512 is an internal standard known to be a high responder for IL-6 release in the assay. The hPBMCs were isolated from fresh, volunteered donors and were treated with ASOs at 0, 0.0128, 0.064, 0.32, 1.6, 8, 40 and 200 µM concentrations. After a 24 hr treatment, the cytokine levels were measured.

The levels of IL-6 were used as the primary readout. The $EC_{50}$ and $E_{max}$ was calculated using standard procedures. Results are expressed as the average ratio of $E_{max}/EC_{50}$ from two donors and is denoted as "$E_{max}/EC_{50}$." The lower ratio indicates a relative decrease in the proinflammatory response and the higher ratio indicates a relative increase in the proinflammatory response.

With regard to the test compounds, the least proinflammatory compound was the PS/PO linked ASO (ISIS 616468). The $GalNAc_3$-1 conjugated ASO, ISIS 647535 was slightly less proinflammatory than its non-conjugated counterpart ISIS 304801. These results indicate that incorporation of some PO linkages reduces proinflammatory reaction and addition of a $GalNAc_3$-1 conjugate does not make a compound more proinflammatory and may reduce proinflammatory response. Accordingly, one would expect that an antisense compound comprising both mixed PS/PO linkages and a $GalNAc_3$-1 conjugate would produce lower proinflammatory responses relative to full PS linked antisense compound with or without a $GalNAc_3$-1 conjugate. These results show that $GalNAc_3$-1 conjugated antisense compounds, particularly those having reduced PS content are less proinflammatory.

Together, these results suggest that a $GalNAc_3$-1 conjugated compound, particularly one with reduced PS content, can be administered at a higher dose than a counterpart full PS antisense compound lacking a $GalNAc_3$-1 conjugate. Since half-life is not expected to be substantially different for these compounds, such higher administration would result in less frequent dosing. Indeed such administration could be even less frequent, because the $GalNAc_3$-1 conjugated compounds are more potent (See Examples 20-22) and re-dosing is necessary once the concentration of a compound has dropped below a desired level, where such desired level is based on potency.

TABLE 30

Modified ASOs

| ASO | Sequence (5' to 3') | Target | SEQ ID No. |
|---|---|---|---|
| ISIS 104838 | $G_{es}{}^mC_{es}T_{es}G_{es}A_{es}T_{ds}T_{ds}A_{ds}G_{ds}A_{ds}G_{ds}A_{ds}G_{ds}A_{ds}G_{ds}G_{es}T_{es}{}^mC_{es}{}^mC_{es}{}^mC_e$ | TNFα | 825 |
| ISIS 353512 | $T_{es}{}^mC_{es}{}^mC_{es}{}^mC_{ds}A_{ds}T_{ds}T_{ds}T_{ds}{}^mC_{ds}A_{ds}G_{ds}G_{ds}A_{ds}G_{ds}A_{ds}{}^mC_{ds}{}^mC_{ds}T_{es}G_{es}G_e$ | CRP | 826 |
| ISIS 304801 | $A_{es}G_{es}{}^mC_{es}T_{es}T_{es}{}^mC_{ds}T_{ds}T_{ds}G_{ds}T_{ds}{}^mC_{ds}{}^mC_{ds}A_{ds}G_{ds}{}^mC_{ds}T_{es}T_{es}T_{es}A_{es}T_e$ | ApoC III | 821 |
| ISIS 647535 | $A_{es}G_{es}{}^mC_{es}T_{es}T_{es}{}^mC_{ds}T_{ds}T_{ds}G_{ds}T_{ds}{}^mC_{ds}{}^mC_{ds}A_{ds}G_{ds}{}^mC_{ds}T_{es}T_{es}T_{es}A_{es}T_{eo}\text{-}A_{do'}\text{-}\textbf{GalNAc}_3\textbf{-1}_a$ | ApoC III | 822 |
| ISIS 616468 | $A_{es}G_{eo}{}^mC_{eo}T_{eo}T_{eo}{}^mC_{ds}T_{ds}T_{ds}G_{ds}T_{ds}{}^mC_{ds}{}^mC_{ds}A_{ds}G_{ds}{}^mC_{ds}T_{eo}T_{eo}T_{es}A_{es}T_e$ | ApoC III | 821 |

Subscripts: "e" indicates 2'-MOE modified nucleoside; "d" indicates β-D-2'-deoxyribonucleoside; "k" indicates 6'-(S)—$CH_3$ bicyclic nucleoside (e.g. cEt); "s" indicates phosphorothioate internucleoside linkages (PS); "o" indicates phosphodiester internucleoside linkages (PO); and "o'" indicates —O—P(=O)(OH)—. Superscript "m" indicates 5-methylcytosines. "$A_{do'}$-$GalNAc_3$-$1_a$" indicates a conjugate having the structure $GalNAc_3$-1 shown in Example 9 attached to the 3'-end of the antisense oligonucleotide, as indicated.

TABLE 31

| ASO | $EC_{50}$ (µM) | $E_{max}$ (µM) | $E_{max}/EC_{50}$ | 3' Conjugate | Internucleoside Linkage/Length | SEQ ID No. |
|---|---|---|---|---|---|---|
| ISIS 353512 (high responder) | 0.01 | 265.9 | 26,590 | None | PS/20 | 826 |
| ISIS 304801 | 0.07 | 106.55 | 1,522 | None | PS/20 | 821 |
| ISIS 647535 | 0.12 | 138 | 1,150 | $GalNAc_3$-1 | PS/20 | 822 |
| ISIS 616468 | 0.32 | 71.52 | 224 | None | PS/PO/20 | 821 |

Proinflammatory Effect of ASOs targeting ApoC III in hPBMC assay

Example 25: Effect of GalNAc$_3$-1 Conjugated Modified ASO Targeting Human ApoC III In Vitro ISIS 304801 and 647535 described above were tested in vitro. Primary hepatocyte cells from transgenic mice at a density of 25,000 cells per well were treated with 0.03, 0.08, 0.24, 0.74, 2.22, 6.67 and 20 µM concentrations of modified oligonucleotides. After a treatment period of approximately 16 hours, RNA was isolated from the cells and mRNA levels were measured by quantitative real-time PCR and the hApoC III mRNA levels were adjusted according to total RNA content, as measured by RIBOGREEN.

The IC$_{50}$ was calculated using the standard methods and the results are presented in Table 32. As illustrated, comparable potency was observed in cells treated with ISIS 647535 as compared to the control, ISIS 304801.

TABLE 32

Modified ASO targeting human ApoC III in primary hepatocytes

| ASO | IC$_{50}$ (µM) | 3' Conjugate | Internucleoside linkage/Length | SEQ ID No. |
|---|---|---|---|---|
| ISIS 304801 | 0.44 | None | PS/20 | 821 |
| ISIS 647535 | 0.31 | GalNAc$_3$-1 | PS/20 | 822 |

In this experiment, the large potency benefits of GalNAc$_3$-1 conjugation that are observed in vivo were not observed in vitro. Subsequent free uptake experiments in primary hepatocytes in vitro did show increased potency of oligonucleotides comprising various GalNAc conjugates relative to oligonucleotides that lacking the GalNAc conjugate. (see Examples 60, 82, and 92)

Example 26: Effect of PO/PS Linkages on ApoC III ASO Activity

Human ApoC III transgenic mice were injected intraperitoneally once at 25 mg/kg of ISIS 304801, or ISIS 616468 (both described above) or with PBS treated control once per week for two weeks. The treatment group consisted of 3 animals and the control group consisted of 4 animals. Prior to the treatment as well as after the last dose, blood was drawn from each mouse and plasma samples were analyzed. The mice were sacrificed 72 hours following the last administration.

Samples were collected and analyzed to determine the ApoC III protein levels in the liver as described above (Example 20). Data from those analyses are presented in Table 33, below.

These results show reduction in potency for antisense compounds with PO/PS (ISIS 616468) in the wings relative to full PS (ISIS 304801).

TABLE 33

Effect of ASO treatment on ApoC III protein levels in human ApoC III transgenic mice

| ASO | Dose (mg/kg) | % PBS | 3' Conjugate | Internucleoside linkage/Length | SEQ ID No. |
|---|---|---|---|---|---|
| PBS | 0 | 99 | — | — | |
| ISIS 304801 | 25 mg/kg/wk for 2 wks | 24 | None | Full PS | 821 |
| ISIS 616468 | 25 mg/kg/wk for 2 wks | 40 | None | 14 PS/6 PO | 821 |

Example 27: Compound 56

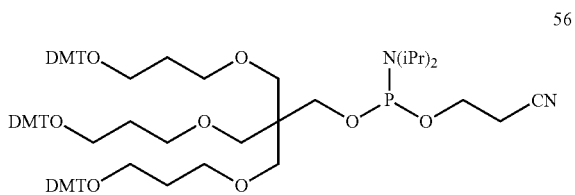

Compound 56 is commercially available from Glen Research or may be prepared according to published procedures reported by Shchepinov et al., *Nucleic Acids Research*, 1997, 25(22), 4447-4454.

Example 28: Preparation of Compound 60

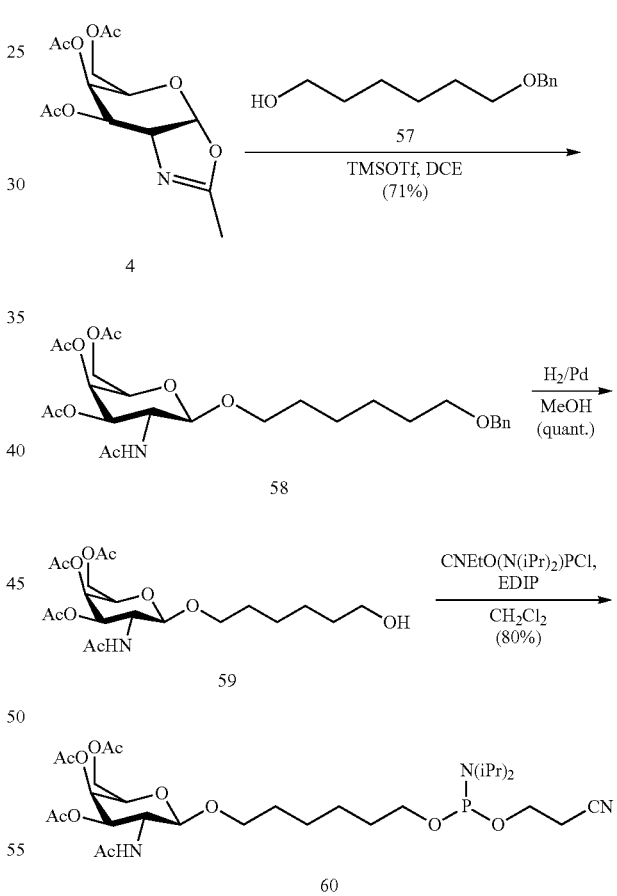

Compound 4 was prepared as per the procedures illustrated in Example 2. Compound 57 is commercially available. Compound 60 was confirmed by structural analysis.

Compound 57 is meant to be representative and not intended to be limiting as other mono-protected substituted or unsubstituted alkyl diols including but not limited to those presented in the specification herein can be used to prepare phosphoramidites having a predetermined composition.

Example 29: Preparation of Compound 63

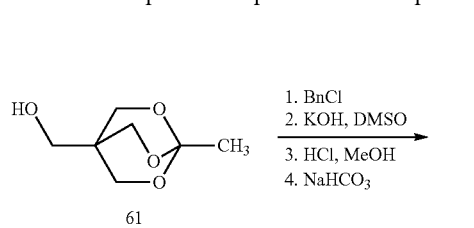

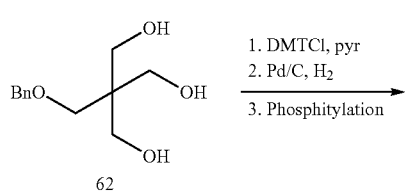

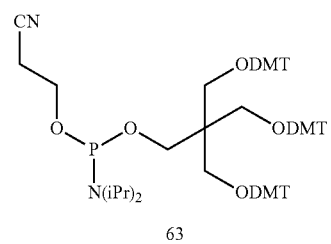

Compounds 61 and 62 are prepared using procedures similar to those reported by Tober et al., *Eur. J. Org. Chem.*, 2013, 3, 566-577; and Jiang et al., *Tetrahedron*, 2007, 63(19), 3982-3988.

Alternatively, Compound 63 is prepared using procedures similar to those reported in scientific and patent literature by Kim et al., *Synlett*, 2003, 12, 1838-1840; and Kim et al., published PCT International Application, WO 2004063208.

Example 30: Preparation of Compound 63b

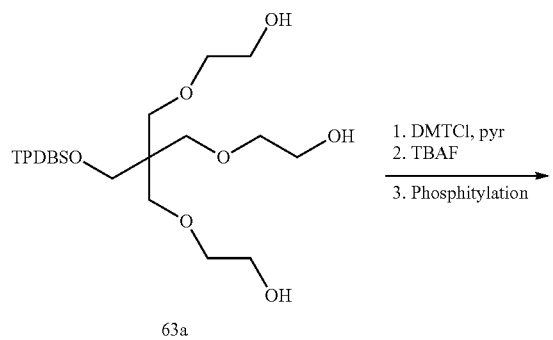

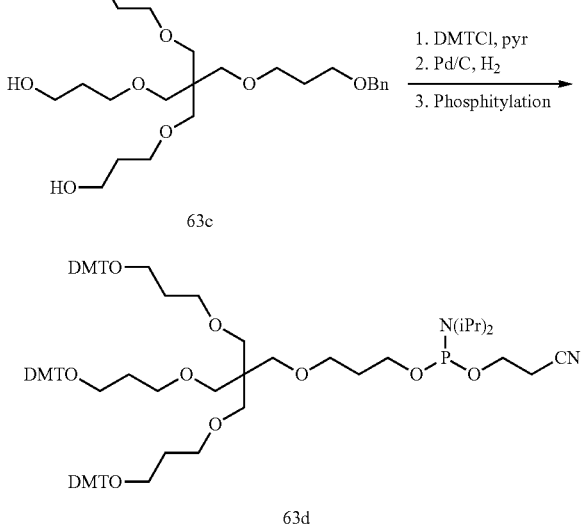

Compound 63a is prepared using procedures similar to those reported by Hanessian et al., *Canadian Journal of Chemistry*, 1996, 74(9), 1731-1737.

Example 31: Preparation of Compound 63d

Compound 63c is prepared using procedures similar to those reported by Chen et al., *Chinese Chemical Letters*, 1998, 9(5), 451-453.

Example 32: Preparation of Compound 67

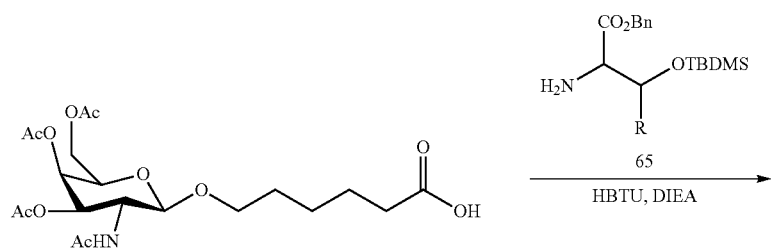

-continued

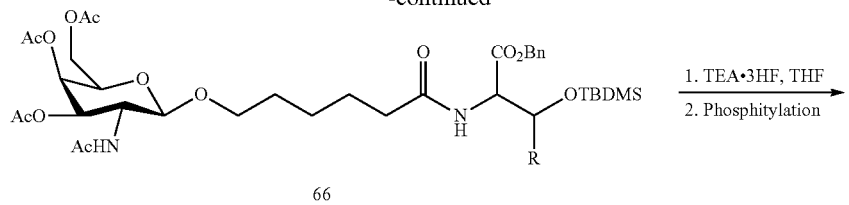

66

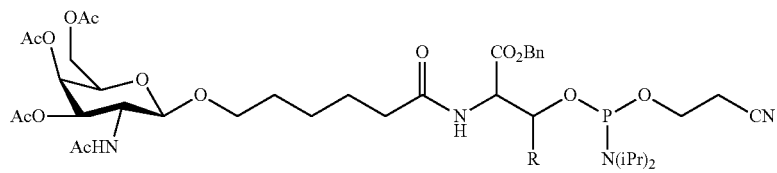

67

R = H or CH₃

Compound 64 was prepared as per the procedures illustrated in Example 2. Compound 65 is prepared using procedures similar to those reported by Or et al., published PCT International Application, WO 2009003009. The protecting groups used for Compound 65 are meant to be representative and not intended to be limiting as other protecting groups including but not limited to those presented in the specification herein can be used.

Example 33: Preparation of Compound 70

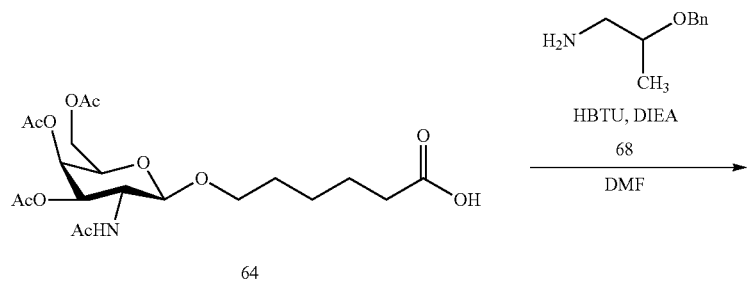

64

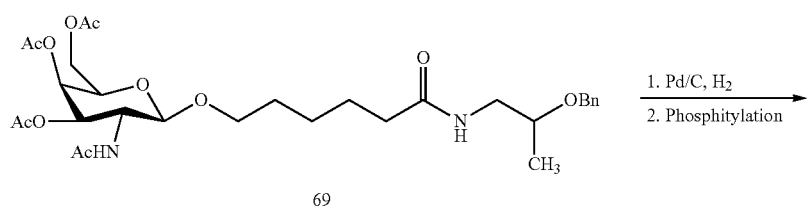

69

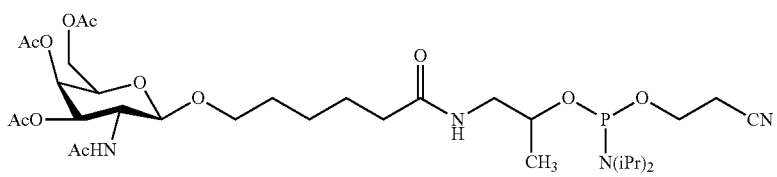

70

Compound 64 was prepared as per the procedures illustrated in Example 2. Compound 68 is commercially available. The protecting group used for Compound 68 is meant to be representative and not intended to be limiting as other protecting groups including but not limited to those presented in the specification herein can be used.

Example 34: Preparation of Compound 75a

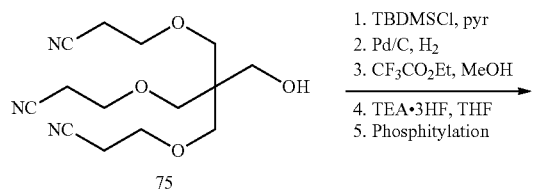

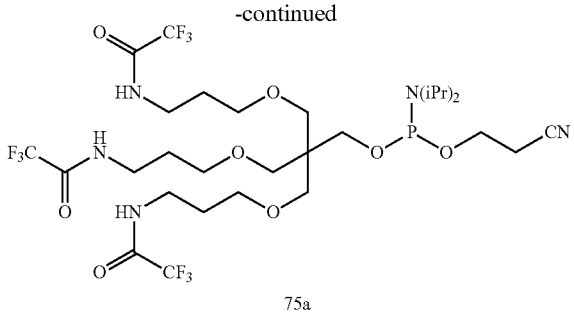

Compound 75 is prepared according to published procedures reported by Shchepinov et al., *Nucleic Acids Research*, 1997, 25(22), 4447-4454.

Example 35: Preparation of Compound 79

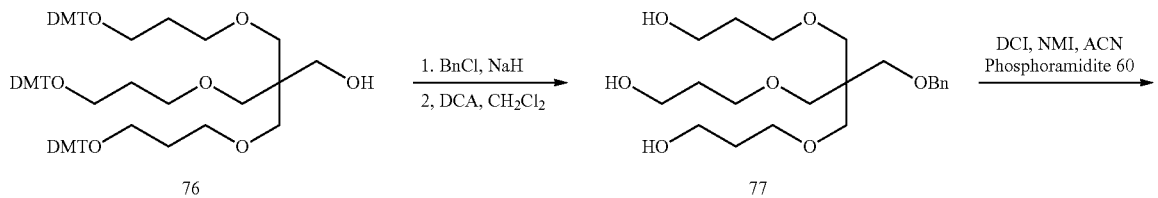

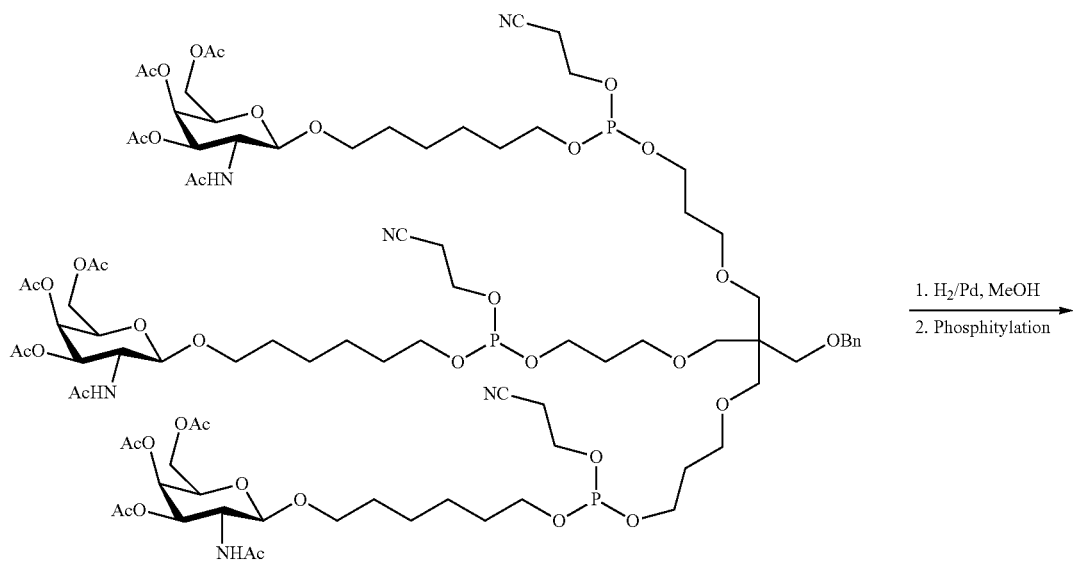

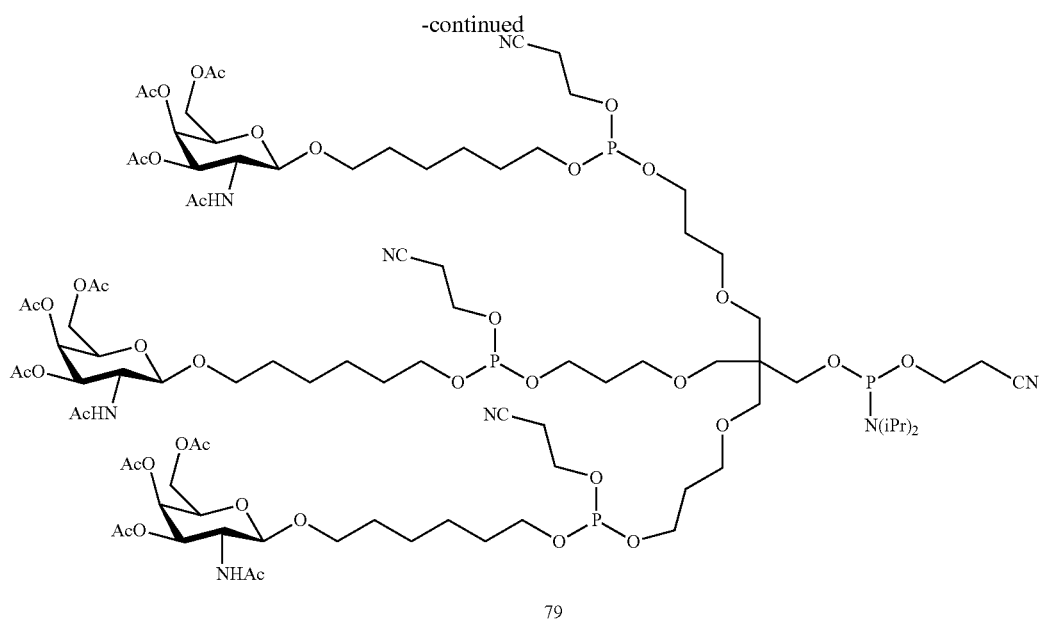

79

Compound 76 was prepared according to published procedures reported by Shchepinov et al., *Nucleic Acids Research*, 1997, 25(22), 4447-4454.

Example 36: Preparation of Compound 79a

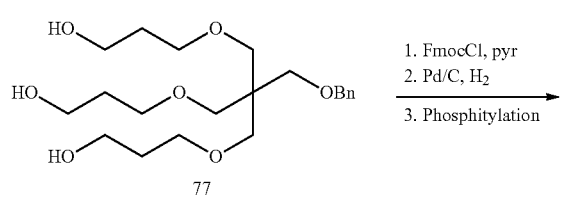

Compound 77 is prepared as per the procedures illustrated in Example 35.

Example 37: General Method for the Preparation of Conjugated Oligomeric Compound 82 Comprising a Phosphodiester Linked GalNAc$_3$-2 Conjugate at 5' Terminus Via Solid Support (Method I)

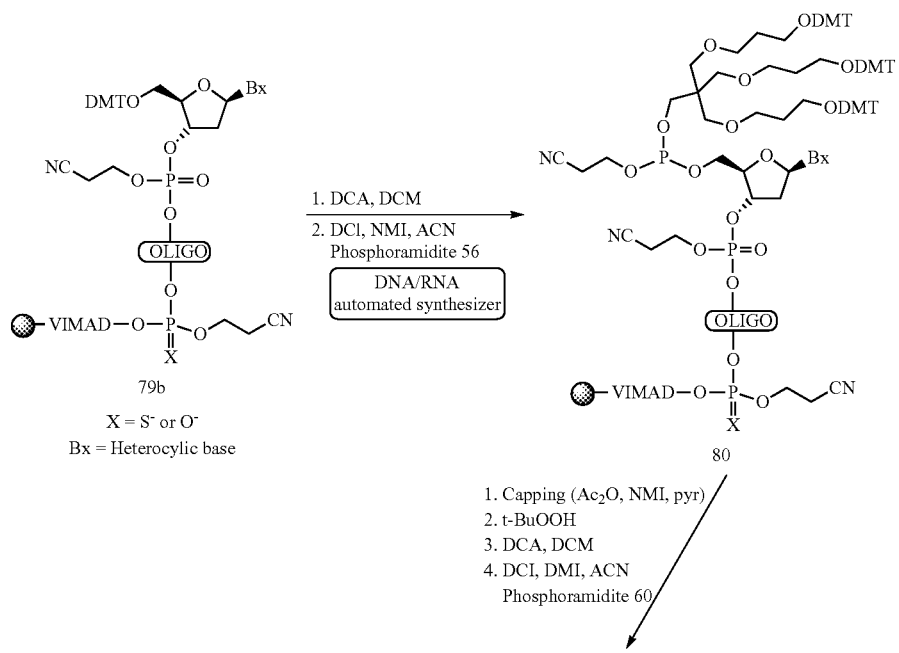

-continued
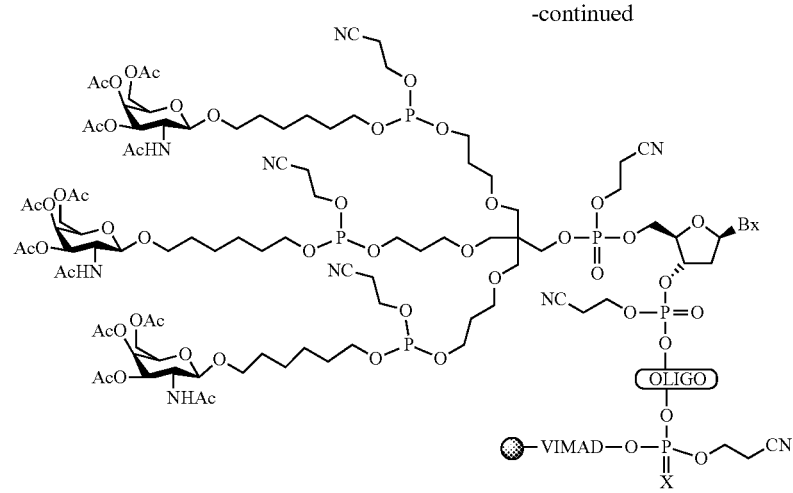
81
1. Capping (Ac₂O, NMI, pyr)
2. t-BuOOH
3. 20% Et₂NH in Toluene (v/v)
4. NH₄, 55° C.,
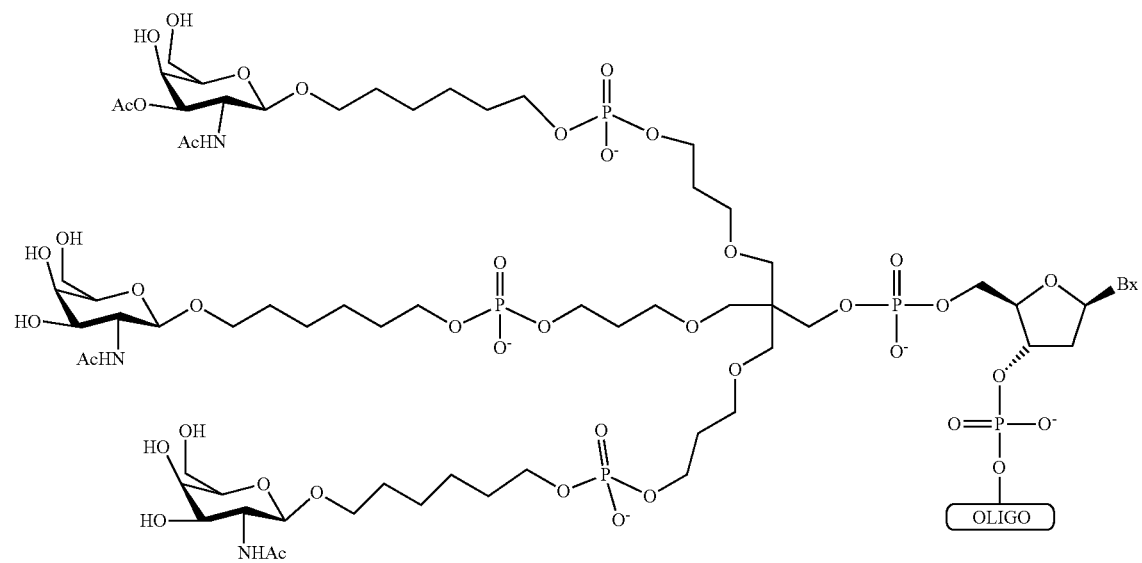
82 wherein GalNAc$_3$-2 has the structure:

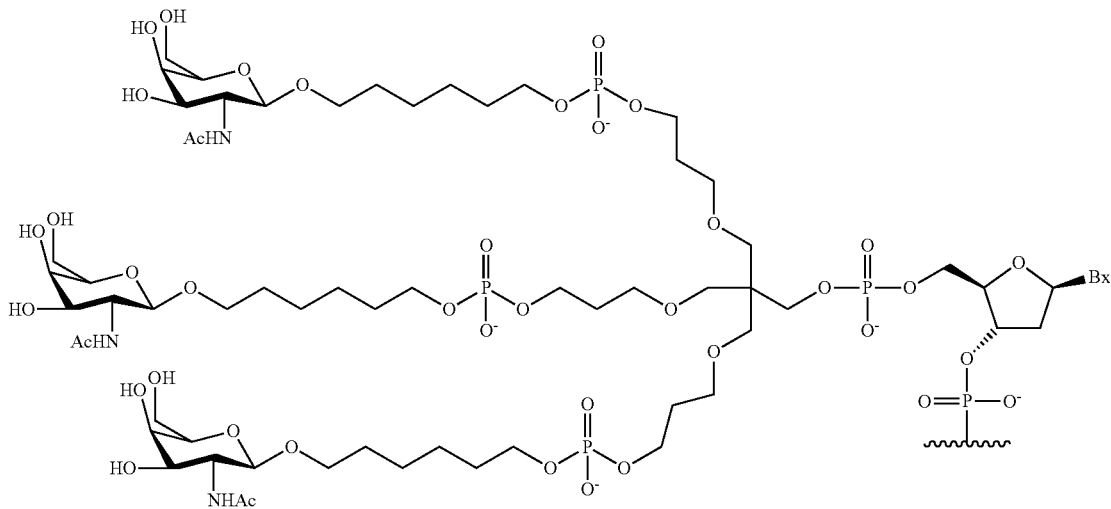

The GalNAc$_3$ cluster portion of the conjugate group GalNAc$_3$-2 (GalNAc$_3$-2$_a$) can be combined with any cleavable moiety to provide a variety of conjugate groups. Wherein GalNAc$_3$-2$_a$ has the formula:

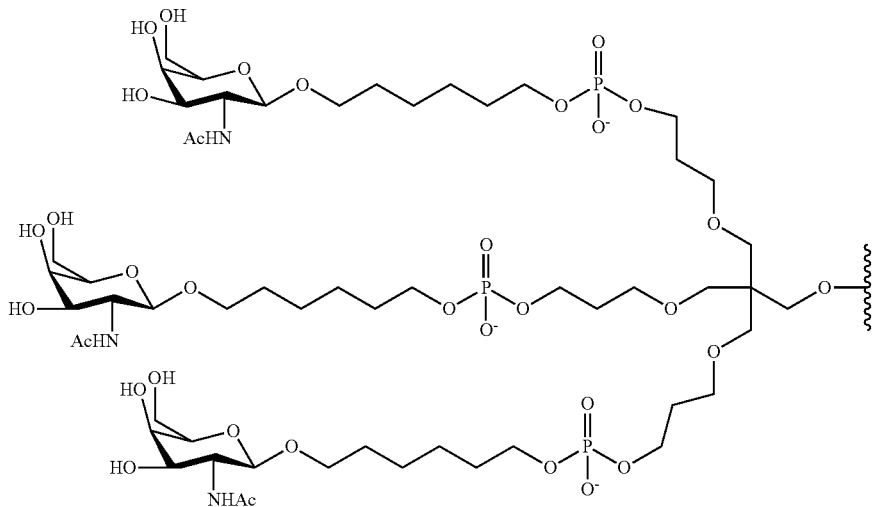

The VIMAD-bound oligomeric compound 79b was prepared using standard procedures for automated DNA/RNA synthesis (see Dupouy et al., *Angew. Chem. Int. Ed.*, 2006, 45, 3623-3627). The phosphoramidite Compounds 56 and 60 were prepared as per the procedures illustrated in Examples 27 and 28, respectively. The phosphoramidites illustrated are meant to be representative and not intended to be limiting as other phosphoramidite building blocks including but not limited those presented in the specification herein can be used to prepare an oligomeric compound having a phosphodiester linked conjugate group at the 5' terminus. The order and quantity of phosphoramidites added to the solid support can be adjusted to prepare the oligomeric compounds as described herein having any predetermined sequence and composition.

Example 38: Alternative Method for the Preparation of Oligomeric Compound 82 Comprising a Phosphodiester Linked GalNAc₃-2 Conjugate at 5' Terminus (Method II)

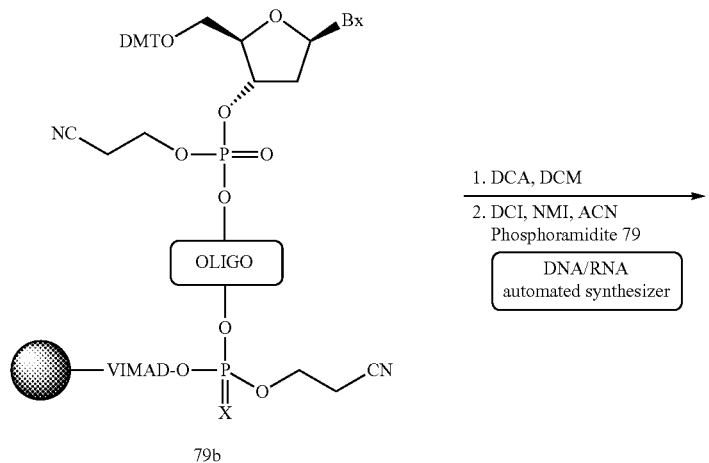

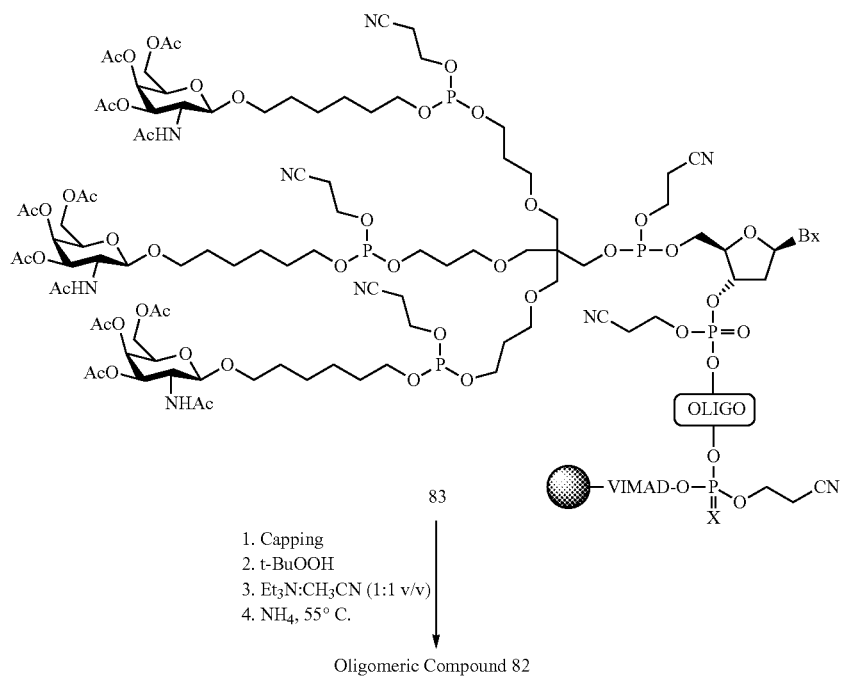

X = S⁻ or O⁻
Bx = Heterocyclic base

The VIMAD-bound oligomeric compound 79b was prepared using standard procedures for automated DNA/RNA synthesis (see Dupouy et al., *Angew. Chem. Int. Ed.,* 2006, 45, 3623-3627). The GalNAc₃-2 cluster phosphoramidite, Compound 79 was prepared as per the procedures illustrated in Example 35. This alternative method allows a one-step installation of the phosphodiester linked GalNAc₃-2 conjugate to the oligomeric compound at the final step of the synthesis. The phosphoramidites illustrated are meant to be representative and not intended to be limiting, as other phosphoramidite building blocks including but not limited to those presented in the specification herein can be used to prepare oligomeric compounds having a phosphodiester conjugate at the 5' terminus. The order and quantity of phosphoramidites added to the solid support can be adjusted to prepare the oligomeric compounds as described herein having any predetermined sequence and composition.

Example 39: General Method for the Preparation of Oligomeric Compound 83h Comprising a GalNAc₃-3 Conjugate at the 5' Terminus (GalNAc₃-1 Modified for 5' End Attachment) Via Solid Support
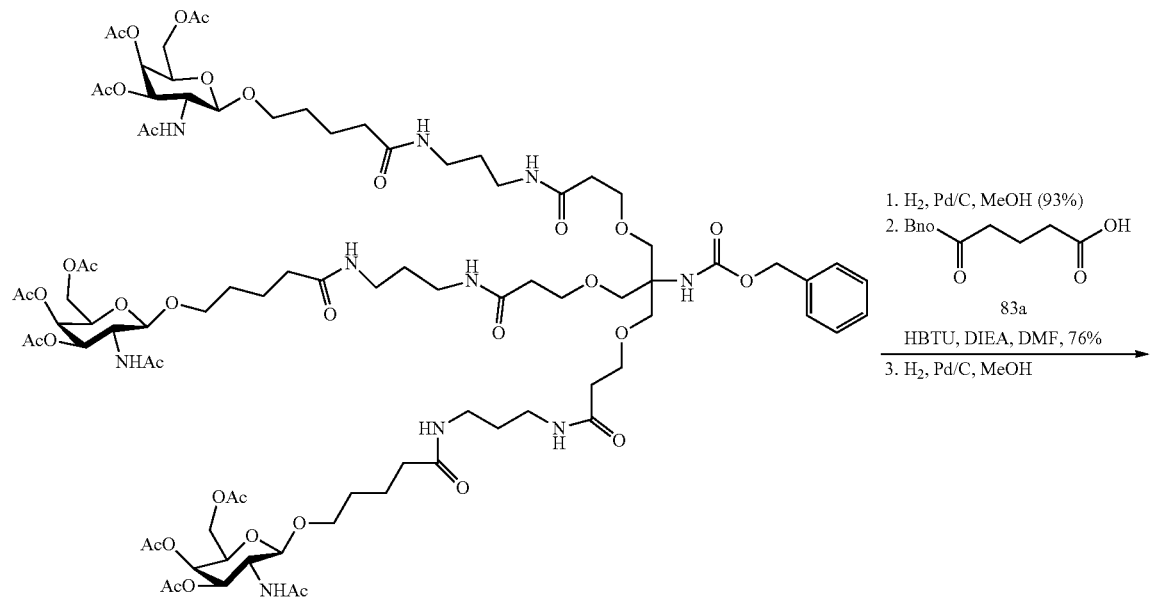
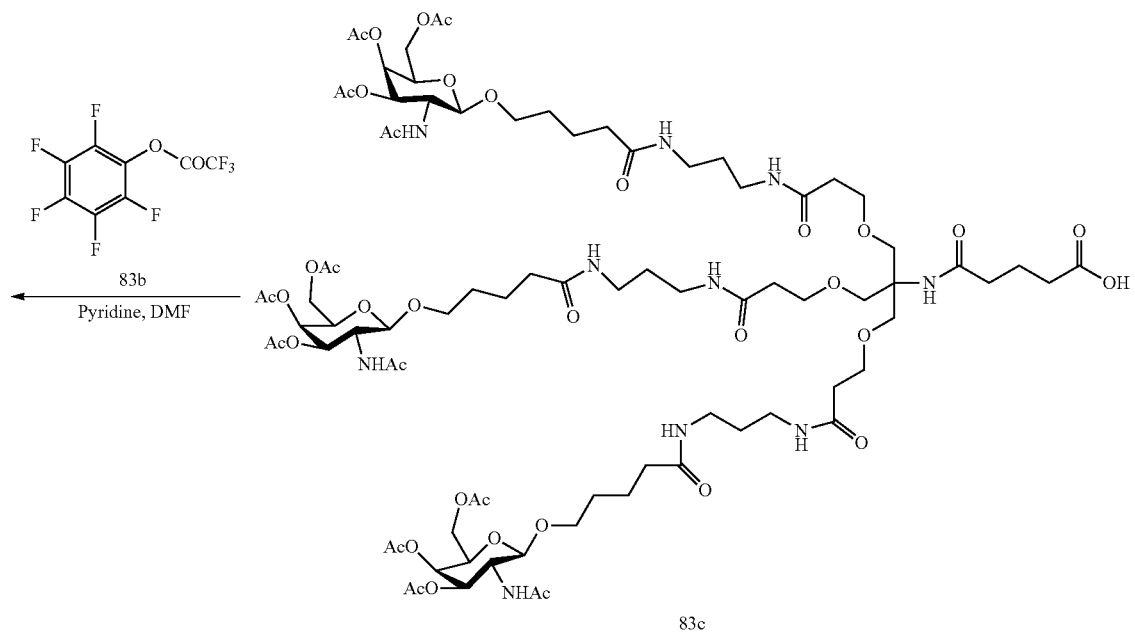

-continued
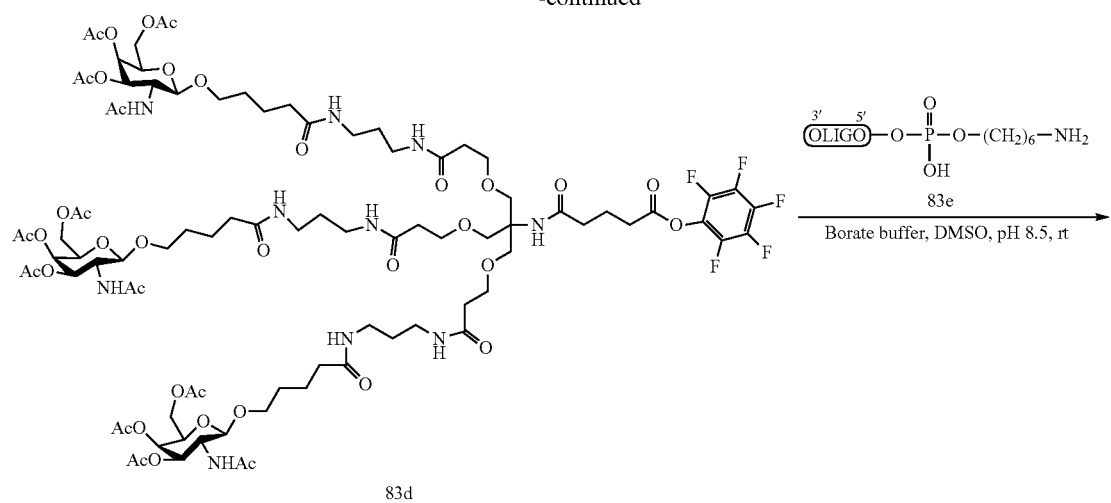
83d
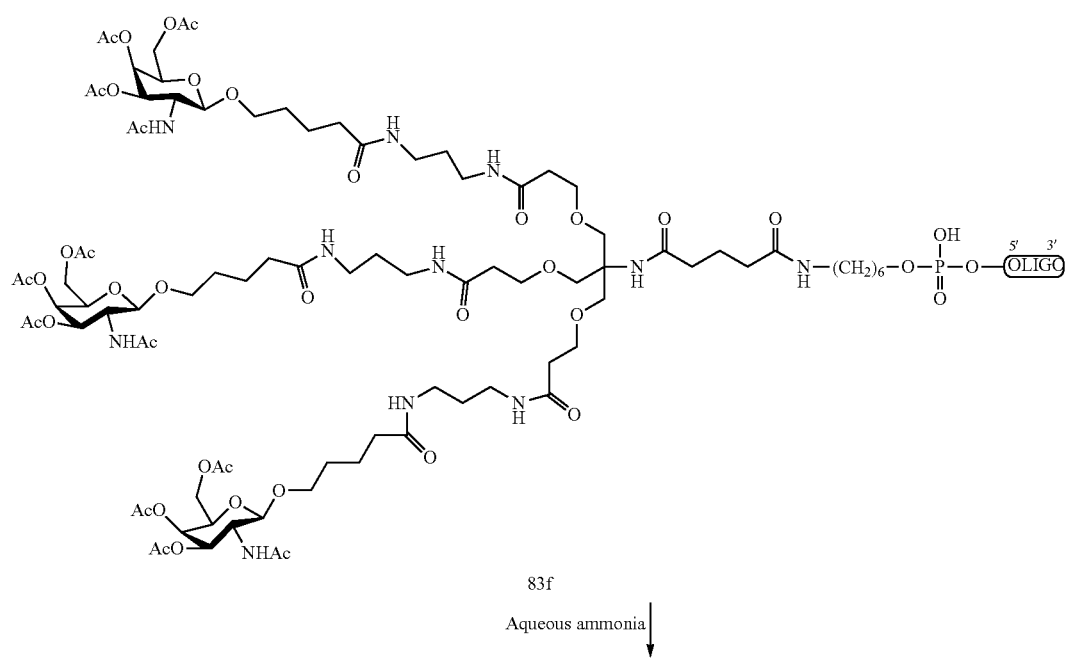
83f
Aqueous ammonia

-continued

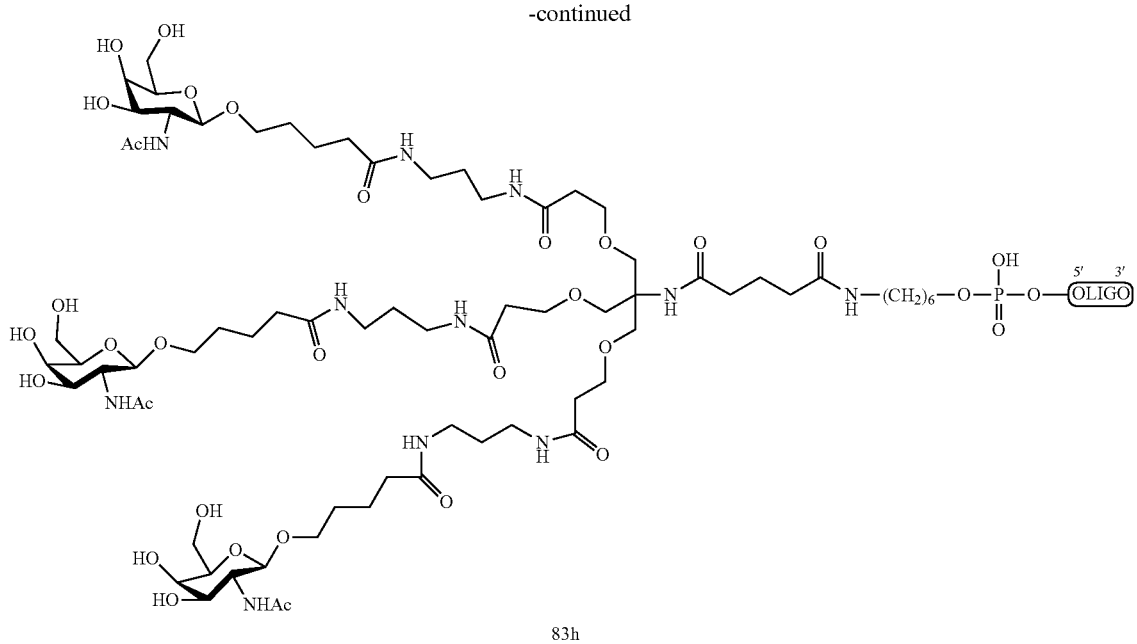

83h

Compound 18 was prepared as per the procedures illustrated in Example 4. Compounds 83a and 83b are commercially available. Oligomeric Compound 83e comprising a phosphodiester linked hexylamine was prepared using standard oligonucleotide synthesis procedures. Treatment of the protected oligomeric compound with aqueous ammonia provided the 5'-GalNAc$_3$-3 conjugated oligomeric compound (83h).

Wherein GalNAc$_3$-3 has the structure:

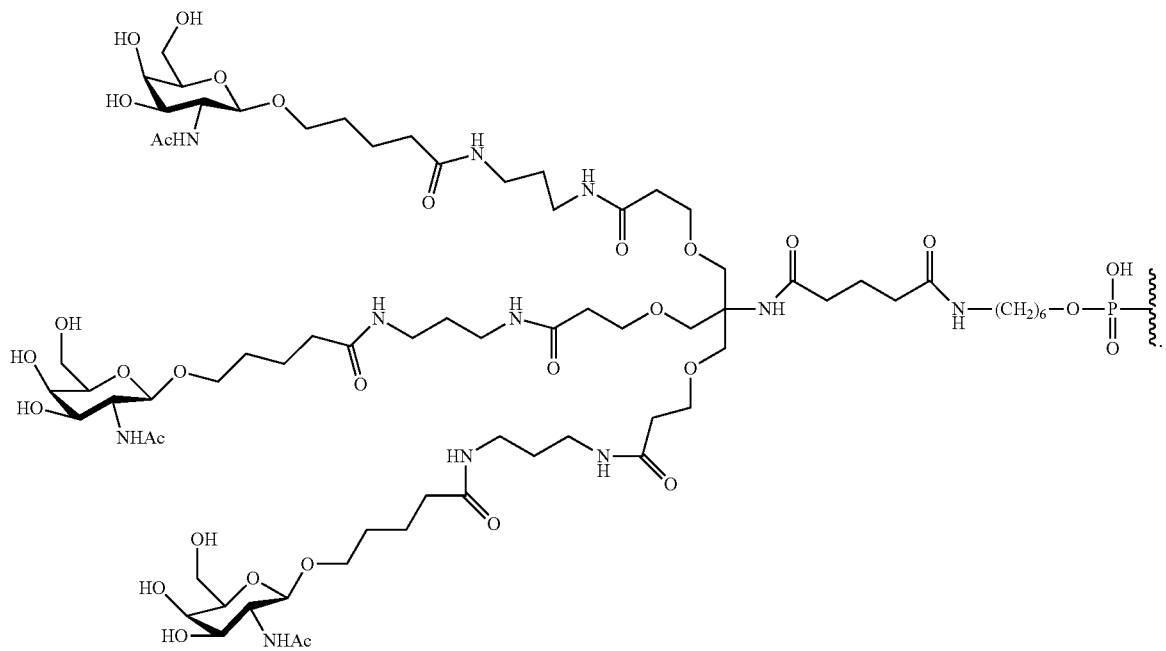

The GalNAc$_3$ cluster portion of the conjugate group GalNAc$_3$-3 (GalNAc$_3$-3$_a$) can be combined with any cleavable moiety to provide a variety of conjugate groups. Wherein GalNAc$_3$-3$_a$ has the formula:

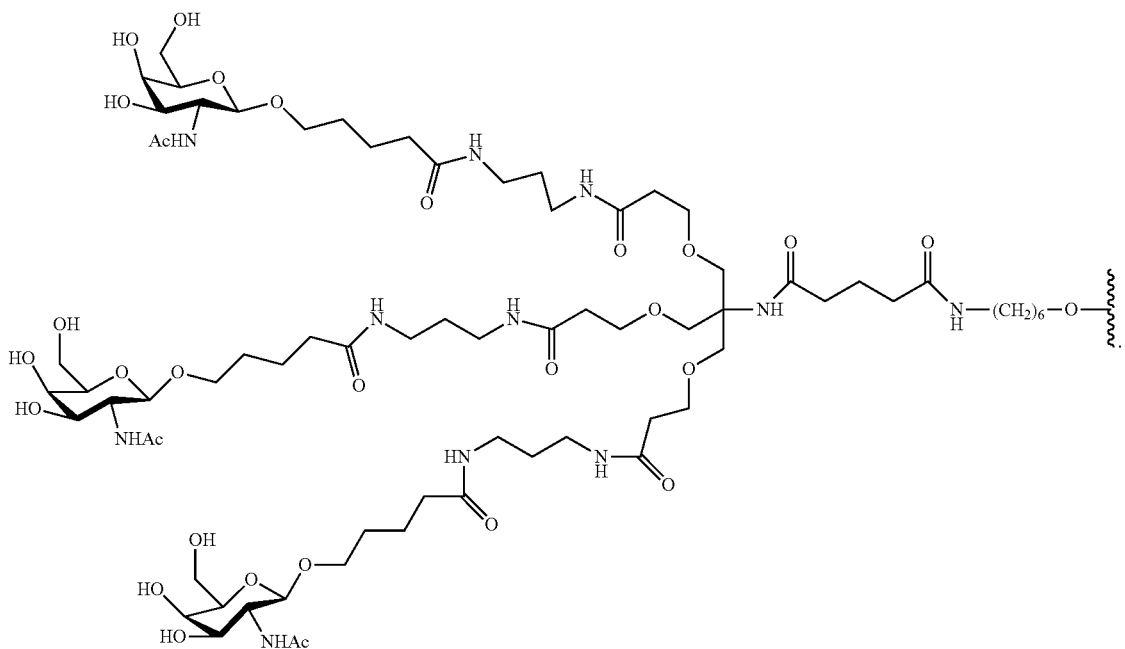
Example 40: General Method for the Preparation of Oligomeric Compound 89 Comprising a Phosphodiester Linked GalNAc$_3$-4 Conjugate at the 3' Terminus Via Solid Support
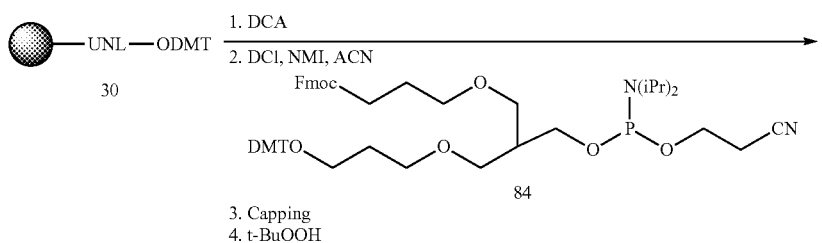
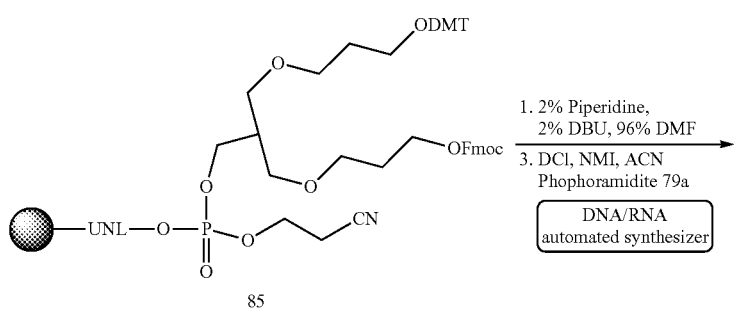

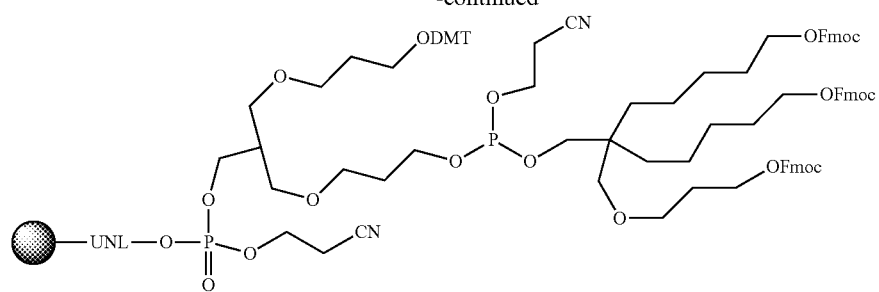
86
1. Capping
2. t-BuOOH
3. 2% Piperidine, 2% DBU, 96% DMF
4. DCl, NMI, ACN
   Phosphoramidite 60
   DNA/RNA automated synthesizer
5. Capping
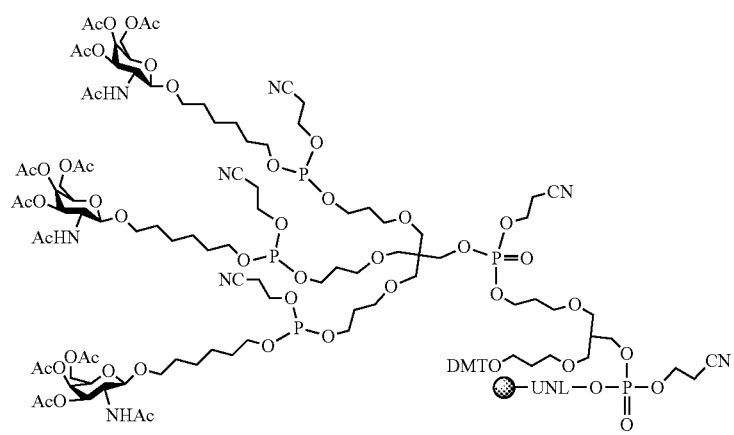
87
1. t-BuOOH
2. DCM
3. Oligo synthesis (DNA/RNA automated synthesizer)
4. Capping
5. Oxidation
6. Et$_3$N:CH$_3$CN (1:1, v/v)

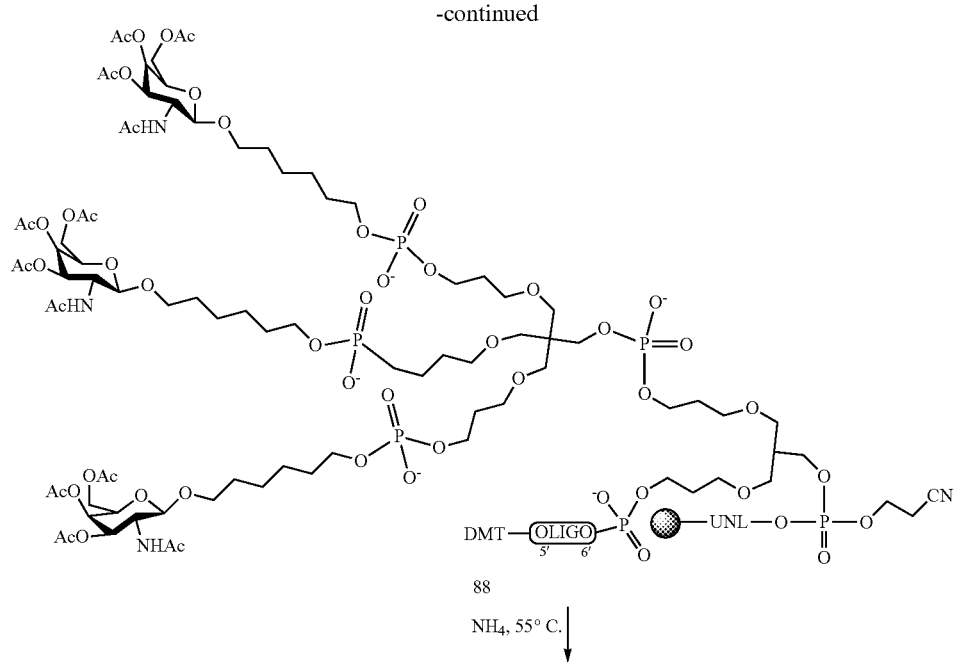
88
NH₄, 55° C.
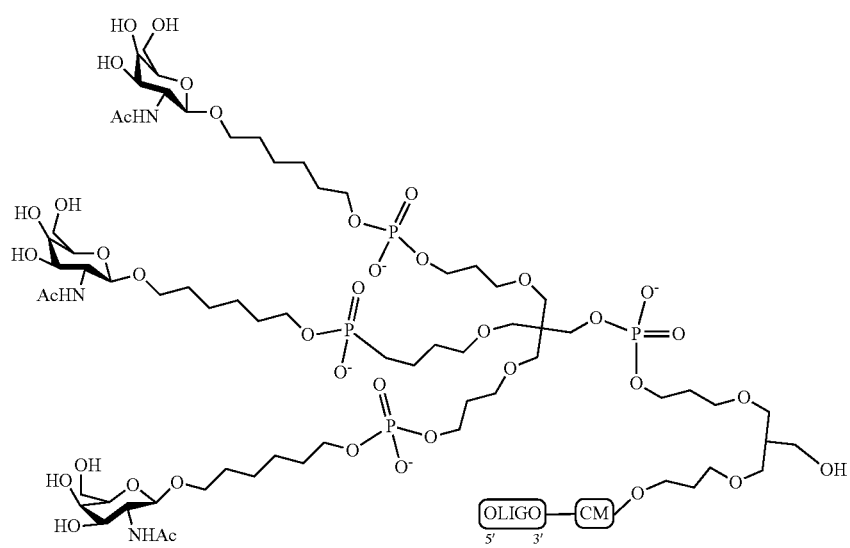
89

Wherein GalNAc₃-4 has the structure:
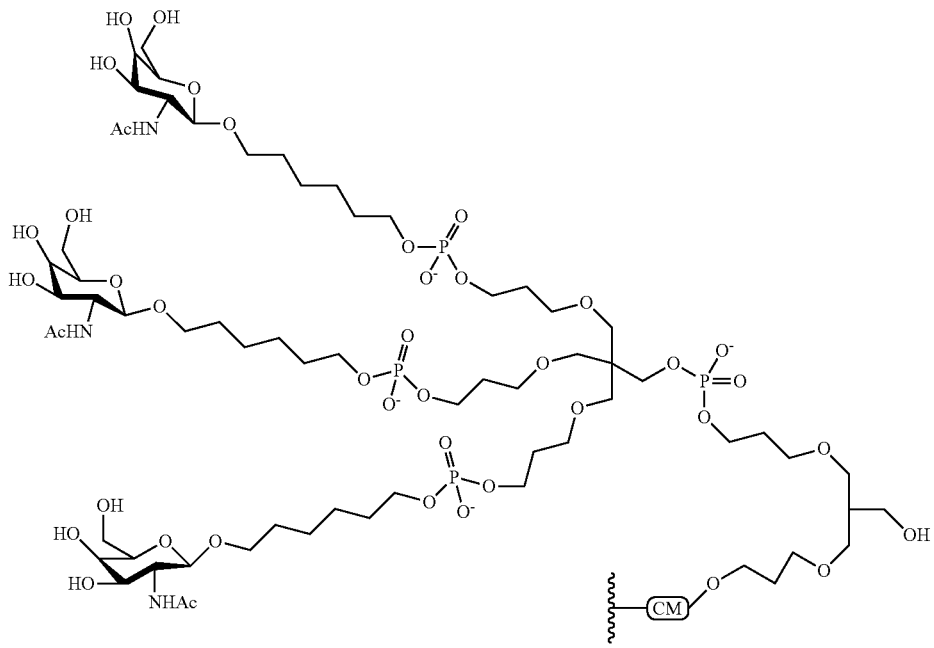
Wherein CM is a cleavable moiety. In certain embodiments, cleavable moiety is:
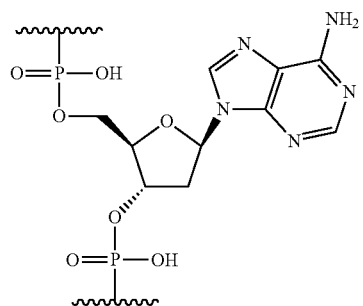 [SMILES: *P(=O)(O)OC[C@H]1O[C@@H](n2cnc3c(N)ncnc32)C[C@@H]1OP(*)(=O)O]
The GalNAc₃ cluster portion of the conjugate group GalNAc₃-4 (GalNAc₃-4ₐ) can be combined with any cleavable moiety to provide a variety of conjugate groups. Wherein GalNAc₃-4ₐ has the formula:

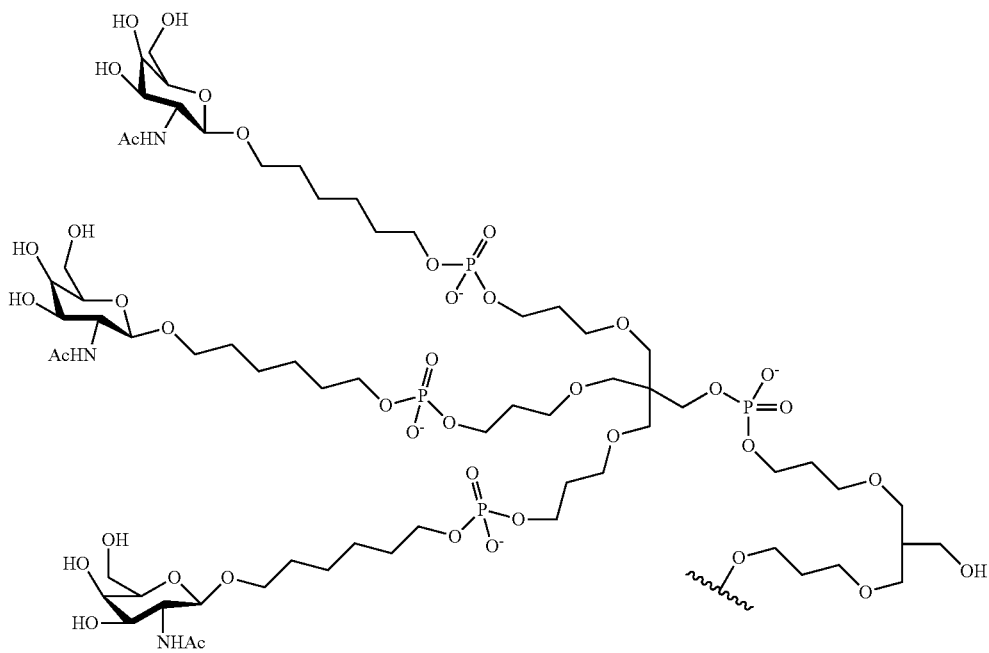

The protected Unylinker functionalized solid support Compound 30 is commercially available. Compound 84 is prepared using procedures similar to those reported in the literature (see Shchepinov et al., *Nucleic Acids Research*, 1997, 25(22), 4447-4454; Shchepinov et al., *Nucleic Acids Research*, 1999, 27, 3035-3041; and Hornet et al., *Nucleic Acids Research*, 1997, 25, 4842-4849).

The phosphoramidite building blocks, Compounds 60 and 79a are prepared as per the procedures illustrated in Examples 28 and 36. The phosphoramidites illustrated are meant to be representative and not intended to be limiting as other phosphoramidite building blocks can be used to prepare an oligomeric compound having a phosphodiester linked conjugate at the 3' terminus with a predetermined sequence and composition. The order and quantity of phosphoramidites added to the solid support can be adjusted to prepare the oligomeric compounds as described herein having any predetermined sequence and composition.

Example 41: General Method for the Preparation of ASOs Comprising a Phosphodiester Linked GalNAc$_3$-2 (See Example 37, Bx is Adenine) Conjugate at the 5' Position Via Solid Phase Techniques (Preparation of ISIS 661134)

Unless otherwise stated, all reagents and solutions used for the synthesis of oligomeric compounds are purchased from commercial sources. Standard phosphoramidite building blocks and solid support are used for incorporation nucleoside residues which include for example T, A, G, and $^m$C residues. Phosphoramidite compounds 56 and 60 were used to synthesize the phosphodiester linked GalNAc$_3$-2 conjugate at the 5' terminus. A 0.1 M solution of phosphoramidite in anhydrous acetonitrile was used for β-D-2'-deoxyribonucleoside and 2'-MOE.

The ASO syntheses were performed on ABI 394 synthesizer (1-2 μmol scale) or on GE Healthcare Bioscience ÄKTA oligopilot synthesizer (40-200 μmol scale) by the phosphoramidite coupling method on VIMAD solid support (110 μmol/g, Guzaev et al., 2003) packed in the column. For the coupling step, the phosphoramidites were delivered at a 4 fold excess over the initial loading of the solid support and phosphoramidite coupling was carried out for 10 min. All other steps followed standard protocols supplied by the manufacturer. A solution of 6% dichloroacetic acid in toluene was used for removing the dimethoxytrityl (DMT) groups from 5'-hydroxyl groups of the nucleotide. 4,5-Dicyanoimidazole (0.7 M) in anhydrous CH$_3$CN was used as activator during the coupling step. Phosphorothioate linkages were introduced by sulfurization with 0.1 M solution of xanthane hydride in 1:1 pyridine/CH$_3$CN for a contact time of 3 minutes. A solution of 20% tert-butylhydroperoxide in CH$_3$CN containing 6% water was used as an oxidizing agent to provide phosphodiester internucleoside linkages with a contact time of 12 minutes.

After the desired sequence was assembled, the cyanoethyl phosphate protecting groups were deprotected using a 20% diethylamine in toluene (v/v) with a contact time of 45 minutes. The solid-support bound ASOs were suspended in aqueous ammonia (28-30 wt %) and heated at 55° C. for 6 h. The unbound ASOs were then filtered and the ammonia was boiled off. The residue was purified by high pressure liquid chromatography on a strong anion exchange column (GE Healthcare Bioscience, Source 30Q, 30 μm, 2.54×8 cm, A=100 mM ammonium acetate in 30% aqueous CH$_3$CN, B=1.5 M NaBr in A, 0-40% of B in 60 min, flow 14 mL min-1, λ=260 nm). The residue was desalted by HPLC on a reverse phase column to yield the desired ASOs in an isolated yield of 15-30% based on the initial loading on the solid support. The ASOs were characterized by ion-pair-HPLC coupled MS analysis with Agilent 1100 MSD system.

TABLE 34

ASO comprising a phosphodiester linked GalNAc$_3$-2 conjugate at the 5' position targeting SRB-1

| ISIS No. | Sequence (5' to 3') | CalCd Mass | Observed Mass | SEQ ID No. |
|---|---|---|---|---|
| 661134 | GalNAc$_3$-2$_a$-$_o$,  A$_{do}$T$_{ks}$$^m$C$_{ks}$A$_{ds}$G$_{ds}$T$_{ds}$$^m$C$_{ds}$A$_{ds}$T$_{ds}$G$_{ds}$ A$_{ds}$$^m$C$_{ds}$T$_{ds}$T$_{ks}$$^m$C$_k$ | 6482.2 | 6481.6 | 827 |

Subscripts: "e" indicates 2'-MOE modified nucleoside; "d" indicates β-D-2'-deoxyribonucleoside; "k" indicates 6'-(S)—CH$_3$ bicyclic nucleoside (e.g. cEt); "s" indicates phosphorothioate internucleoside linkages (PS); "o" indicates phosphodiester internucleoside linkages (PO); and "o'" indicates —O—P(=O)(OH)—. Superscript "m" indicates 5-methylcytosines. The structure of GalNAc$_3$-2$_a$ is shown in Example 37.

Example 42: General Method for the Preparation of ASOs Comprising a GalNAc$_3$-3 Conjugate at the 5' Position Via Solid Phase Techniques (Preparation of ISIS 661166)

The synthesis for ISIS 661166 was performed using similar procedures as illustrated in Examples 39 and 41.

ISIS 661166 is a 5-10-5 MOE gapmer, wherein the 5' position comprises a GalNAc$_3$-3 conjugate. The ASO was characterized by ion-pair-HPLC coupled MS analysis with Agilent 1100 MSD system.

TABLE 34a

ASO comprising a GalNAc$_3$-3 conjugate at the 5' position via a hexylamino phosphodiester linkage targeting Malat-1

| ISIS No. | Sequence (5' to 3') | Conjugate | Calcd Mass | Observed Mass | SEQ ID No. |
|---|---|---|---|---|---|
| 661166 | 5'-GalNAc$_3$-3$_a$-$_o$,$^m$C$_{es}$G$_{es}$G$_{es}$T$_{es}$G$_{es}$ $^m$C$_{ds}$A$_{ds}$A$_{ds}$G$_{ds}$G$_{ds}$$^m$C$_{ds}$T$_{ds}$T$_{ds}$A$_{ds}$G$_{ds}$ G$_{es}$A$_{es}$A$_{es}$T$_{es}$T$_e$ | 5'-GalNAc$_3$-3 | 8992.16 | 8990.51 | 828 |

Subscripts: "e" indicates 2'-MOE modified nucleoside; "d" indicates β-D-2'-deoxyribonucleoside; "s" indicates phosphorothioate internucleoside linkages (PS); "o" indicates phosphodiester internucleoside linkages (PO); and "o'" indicates —O—P(=O)(OH)—. Superscript "m" indicates 5-methylcytosines. The structure of "5'-GalNAc$_3$-3a" is shown in Example 39.

Example 43: Dose-Dependent Study of Phosphodiester Linked GalNAc$_3$-2 (See Examples 37 and 41, Bx is Adenine) at the 5' Terminus Targeting SRB-1 In Vivo ISIS 661134 (see Example 41) comprising a phosphodiester linked GalNAc$_3$-2 conjugate at the 5' terminus was tested in a dose-dependent study for antisense inhibition of SRB-1 in mice. Unconjugated ISIS 440762 and 651900 (GalNAc$_3$-1 conjugate at 3' terminus, see Example 9) were included in the study for comparison and are described previously in Table 17.

Treatment

Six week old male Balb/c mice (Jackson Laboratory, Bar Harbor, Me.) were injected subcutaneously once at the dosage shown below with ISIS 440762, 651900, 661134 or with PBS treated control. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, Oreg.) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS". The ED$_{50}$s were measured using similar methods as described previously and are presented below.

As illustrated in Table 35, treatment with antisense oligonucleotides lowered SRB-1 mRNA levels in a dose-dependent manner. Indeed, the antisense oligonucleotides comprising the phosphodiester linked GalNAc$_3$-2 conjugate at the 5' terminus (ISIS 661134) or the GalNAc$_3$-1 conjugate linked at the 3' terminus (ISIS 651900) showed substantial improvement in potency compared to the unconjugated antisense oligonucleotide (ISIS 440762). Further, ISIS 661134, which comprises the phosphodiester linked GalNAc$_3$-2 conjugate at the 5' terminus was equipotent compared to ISIS 651900, which comprises the GalNAc$_3$-1 conjugate at the 3' terminus.

TABLE 35

ASOs containing GalNAc$_3$-1 or GalNAc$_3$-2 targeting SRB-1

| ISIS No. | Dosage (mg/kg) | SRB-1 mRNA levels (% PBS) | ED$_{50}$ (mg/kg) | Conjugate | SEQ ID No. |
|---|---|---|---|---|---|
| PBS | 0 | 100 | — | — | |
| 440762 | 0.2 | 116 | 2.58 | No conjugate | 823 |
|  | 0.7 | 91 | | | |
|  | 2 | 69 | | | |
|  | 7 | 22 | | | |
|  | 20 | 5 | | | |
| 651900 | 0.07 | 95 | 0.26 | 3' GalNAc$_3$-1 | 824 |
|  | 0.2 | 77 | | | |
|  | 0.7 | 28 | | | |
|  | 2 | 11 | | | |
|  | 7 | 8 | | | |

TABLE 35-continued

ASOs containing GalNAc₃-1 or GalNAc₃-2 targeting SRB-1

| ISIS No. | Dosage (mg/kg) | SRB-1 mRNA levels (% PBS) | ED$_{50}$ (mg/kg) | Conjugate | SEQ ID No. |
|---|---|---|---|---|---|
| 661134 | 0.07 | 107 | 0.25 | 5' GalNAc₃-2 | 827 |
|  | 0.2 | 86 |  |  |  |
|  | 0.7 | 28 |  |  |  |
|  | 2 | 10 |  |  |  |
|  | 7 | 6 |  |  |  |

Structures for 3' GalNAc₃-1 and 5' GalNAc₃-2 were described previously in Examples 9 and 37.

Pharmacokinetics Analysis (PK)

The PK of the ASOs from the high dose group (7 mg/kg) was examined and evaluated in the same manner as illustrated in Example 20. Liver sample was minced and extracted using standard protocols. The full length metabolites of 661134 (5' GalNAc₃-2) and ISIS 651900 (3' GalNAc₃-1) were identified and their masses were confirmed by high resolution mass spectrometry analysis. The results showed that the major metabolite detected for the ASO comprising a phosphodiester linked GalNAc₃-2 conjugate at the 5' terminus (ISIS 661134) was ISIS 440762 (data not shown). No additional metabolites, at a detectable level, were observed. Unlike its counterpart, additional metabolites similar to those reported previously in Table 23a were observed for the ASO having the GalNAc₃-1 conjugate at the 3' terminus (ISIS 651900). These results suggest that having the phosphodiester linked GalNAc₃-1 or GalNAc₃-2 conjugate may improve the PK profile of ASOs without compromising their potency.

Example 44: Effect of PO/PS Linkages on Antisense Inhibition of ASOs Comprising GalNAc₃-1 Conjugate (See Example 9) at the 3' Terminus Targeting SRB-1

ISIS 655861 and 655862 comprising a GalNAc₃-1 conjugate at the 3' terminus each targeting SRB-1 were tested in a single administration study for their ability to inhibit SRB-1 in mice. The parent unconjugated compound, ISIS 353382 was included in the study for comparison.

The ASOs are 5-10-5 MOE gapmers, wherein the gap region comprises ten 2'-deoxyribonucleosides and each wing region comprises five 2'-MOE modified nucleosides. The ASOs were prepared using similar methods as illustrated previously in Example 19 and are described Table 36, below.

TABLE 36

Modified ASOs comprising GalNAc₃-1 conjugate at the 3' terminus targeting SRB-1

| ISIS No. | Sequence (5' to 3') | Chemistry | SEQ ID No. |
|---|---|---|---|
| 353382 (parent) | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{es}$$^m$C$_{es}$$^m$C$_{es}$T$_{es}$T$_{e}$ | Full PS no conjugate | 829 |
| 655861 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{es}$$^m$C$_{es}$$^m$C$_{es}$T$_{es}$T$_{eo}$A$_{do'}$-GalNAc₃-1$_a$ | Full PS with GalNAc₃-1 conjugate | 830 |
| 655862 | G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{eo}$$^m$C$_{eo}$$^m$C$_{es}$T$_{es}$T$_{eo}$A$_{do'}$-GalNAc₃-1$_a$ | Mixed PS/PO with GalNAc₃-1 conjugate | 830 |

Subscripts: "e" indicates 2'-MOE modified nucleoside; "d" indicates β-D-2'-deoxyribonucleoside; "s" indicates phosphorothioate internucleoside linkages (PS); "o" indicates phosphodiester internucleoside linkages (PO); and "o'" indicates —O—P(=O)(OH)—. Superscript "m" indicates 5-methylcytosines. The structure of "GalNAc₃-1" is shown in Example 9.

Treatment

Six week old male Balb/c mice (Jackson Laboratory, Bar Harbor, Me.) were injected subcutaneously once at the dosage shown below with ISIS 353382, 655861, 655862 or with PBS treated control. Each treatment group consisted of 4 animals. Prior to the treatment as well as after the last dose, blood was drawn from each mouse and plasma samples were analyzed. The mice were sacrificed 72 hours following the final administration to determine the liver SRB-1 mRNA levels using real-time PCR and RIBOGREEN® RNA quantification reagent (Molecular Probes, Inc. Eugene, Oreg.) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS". The ED$_{50}$s were measured using similar methods as described previously and are reported below.

As illustrated in Table 37, treatment with antisense oligonucleotides lowered SRB-1 mRNA levels in a dose-dependent manner compared to PBS treated control. Indeed, the antisense oligonucleotides comprising the GalNAc₃-1 conjugate at the 3' terminus (ISIS 655861 and 655862) showed substantial improvement in potency comparing to the unconjugated antisense oligonucleotide (ISIS 353382). Further, ISIS 655862 with mixed PS/PO linkages showed an improvement in potency relative to full PS (ISIS 655861).

TABLE 37

Effect of PO/PS linkages on antisense inhibition of ASOs comprising GalNAc₃-1 conjugate at 3' terminus targeting SRB-1

| ISIS No. | Dosage (mg/kg) | SRB-1 mRNA levels (% PBS) | ED₅₀ (mg/kg) | Chemistry | SEQ ID No. |
|---|---|---|---|---|---|
| PBS | 0 | 100 | — | — | |
| 353382 (parent) | 3 | 76.65 | 10.4 | Full PS without conjugate | 829 |
| | 10 | 52.40 | | | |
| | 30 | 24.95 | | | |
| 655861 | 0.5 | 81.22 | 2.2 | Full PS with GalNAc₃-1 conjugate | 830 |
| | 1.5 | 63.51 | | | |
| | 5 | 24.61 | | | |
| | 15 | 14.80 | | | |
| 655862 | 0.5 | 69.57 | 1.3 | Mixed PS/PO with GalNAc₃-1 conjugate | 830 |
| | 1.5 | 45.78 | | | |
| | 5 | 19.70 | | | |
| | 15 | 12.90 | | | |

Liver transaminase levels, alanine aminotransferase (ALT) and aspartate aminotransferase (AST), in serum were measured relative to saline injected mice using standard protocols. Organ weights were also evaluated. The results demonstrated that no elevation in transaminase levels (Table 38) or organ weights (data not shown) were observed in mice treated with ASOs compared to PBS control. Further, the ASO with mixed PS/PO linkages (ISIS 655862) showed similar transaminase levels compared to full PS (ISIS 655861).

TABLE 38

Effect of PO/PS linkages on transaminase levels of ASOs comprising GalNAc₃-1 conjugate at 3' terminus targeting SRB-1

| ISIS No. | Dosage (mg/kg) | ALT (U/L) | AST (U/L) | Chemistry | SEQ ID No. |
|---|---|---|---|---|---|
| PBS | 0 | 28.5 | 65 | — | |
| 353382 (parent) | 3 | 50.25 | 89 | Full PS without conjugate | 829 |
| | 10 | 27.5 | 79.3 | | |
| | 30 | 27.3 | 97 | | |
| 655861 | 0.5 | 28 | 55.7 | Full PS with GalNAc₃-1 | 830 |
| | 1.5 | 30 | 78 | | |
| | 5 | 29 | 63.5 | | |
| | 15 | 28.8 | 67.8 | | |
| 655862 | 0.5 | 50 | 75.5 | Mixed PS/PO with GalNAc₃-1 | 830 |
| | 1.5 | 21.7 | 58.5 | | |
| | 5 | 29.3 | 69 | | |
| | 15 | 22 | 61 | | |

Example 45: Preparation of PFP Ester, Compound 110a

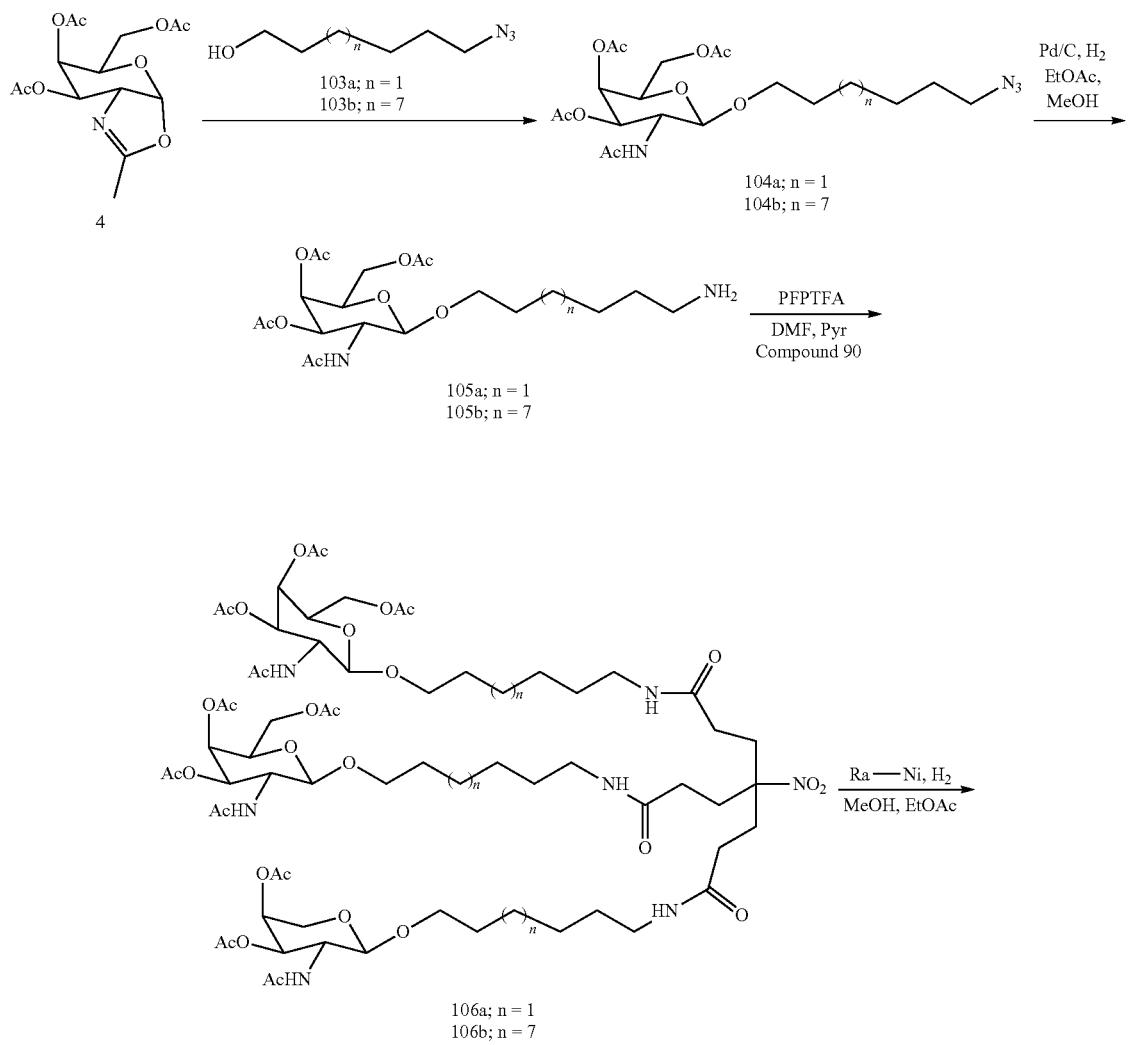

-continued
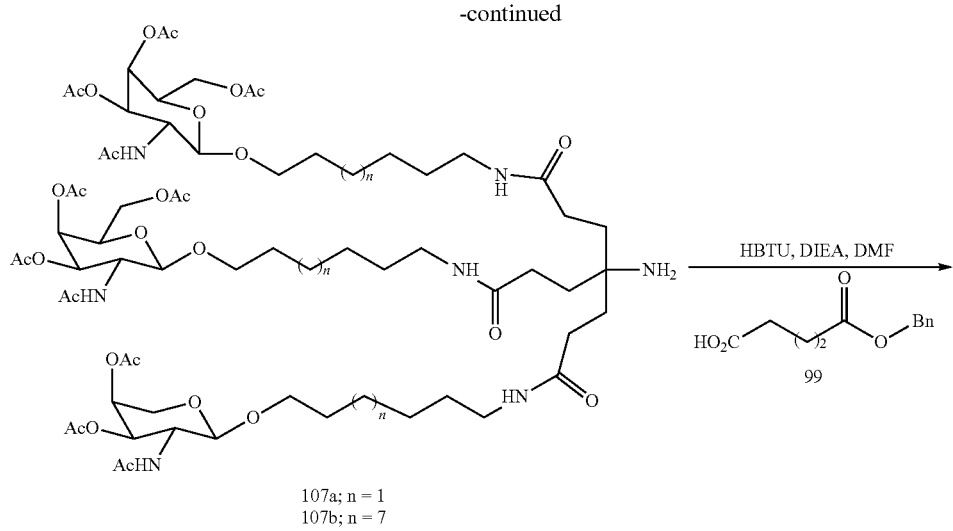
107a; n = 1
107b; n = 7
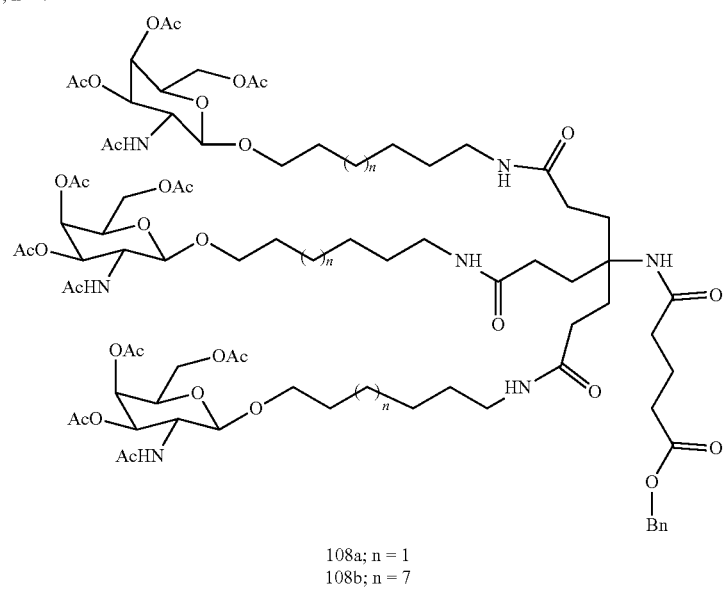
108a; n = 1
108b; n = 7
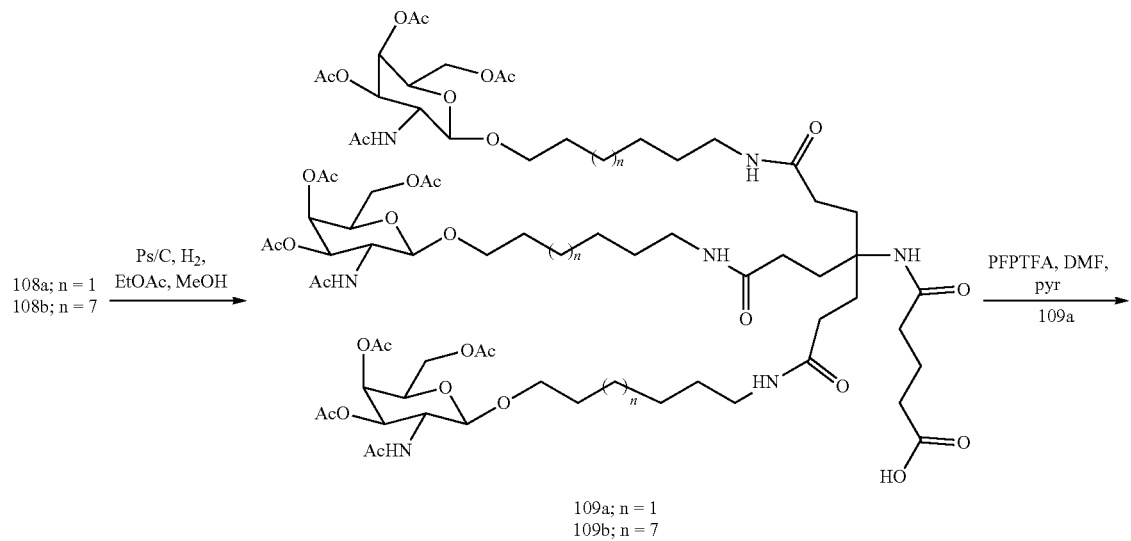
109a; n = 1
109b; n = 7

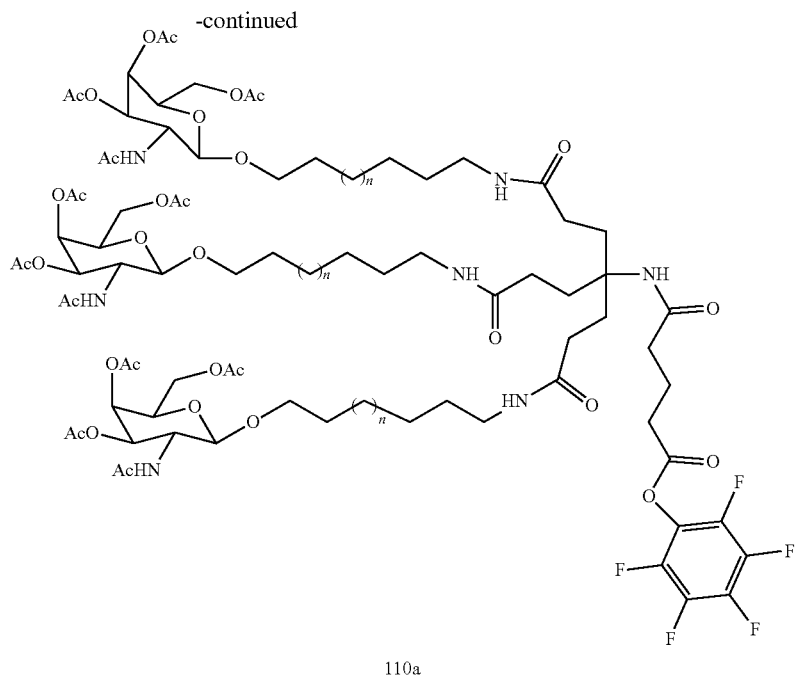

110a

Compound 4 (9.5 g, 28.8 mmoles) was treated with compound 103a or 103b (38 mmoles), individually, and TMSOTf (0.5 eq.) and molecular sieves in dichloromethane (200 mL), and stirred for 16 hours at room temperature. At that time, the organic layer was filtered thru celite, then washed with sodium bicarbonate, water and brine. The organic layer was then separated and dried over sodium sulfate, filtered and reduced under reduced pressure. The resultant oil was purified by silica gel chromatography (2%→10% methanol/dichloromethane) to give compounds 104a and 104b in >80% yield. LCMS and proton NMR was consistent with the structure.

Compounds 104a and 104b were treated to the same conditions as for compounds 100a-d (Example 47), to give compounds 105a and 105b in >90% yield. LCMS and proton NMR was consistent with the structure.

Compounds 105a and 105b were treated, individually, with compound 90 under the same conditions as for compounds 901a-d, to give compounds 106a (80%) and 106b (20%). LCMS and proton NMR was consistent with the structure.

Compounds 106a and 106b were treated to the same conditions as for compounds 96a-d (Example 47), to give 107a (60%) and 107b (20%). LCMS and proton NMR was consistent with the structure.

Compounds 107a and 107b were treated to the same conditions as for compounds 97a-d (Example 47), to give compounds 108a and 108b in 40-60% yield. LCMS and proton NMR was consistent with the structure.

Compounds 108a (60%) and 108b (40%) were treated to the same conditions as for compounds 100a-d (Example 47), to give compounds 109a and 109b in >80% yields. LCMS and proton NMR was consistent with the structure.

Compound 109a was treated to the same conditions as for compounds 101a-d (Example 47), to give Compound 110a in 30-60% yield. LCMS and proton NMR was consistent with the structure. Alternatively, Compound 110b can be prepared in a similar manner starting with Compound 109b.

Example 46: General Procedure for Conjugation with PFP Esters (Oligonucleotide 111); Preparation of ISIS 666881 (GalNAc$_3$-10)

A 5'-hexylamino modified oligonucleotide was synthesized and purified using standard solid-phase oligonucleotide procedures. The 5'-hexylamino modified oligonucleotide was dissolved in 0.1 M sodium tetraborate, pH 8.5 (200 μL) and 3 equivalents of a selected PFP esterified GalNAc$_3$ cluster dissolved in DMSO (50 μL) was added. If the PFP ester precipitated upon addition to the ASO solution DMSO was added until all PFP ester was in solution. The reaction was complete after about 16 h of mixing at room temperature. The resulting solution was diluted with water to 12 mL and then spun down at 3000 rpm in a spin filter with a mass cut off of 3000 Da. This process was repeated twice to remove small molecule impurities. The solution was then lyophilized to dryness and redissolved in concentrated aqueous ammonia and mixed at room temperature for 2.5 h followed by concentration in vacuo to remove most of the ammonia. The conjugated oligonucleotide was purified and desalted by RP-HPLC and lyophilized to provide the GalNAc$_3$ conjugated oligonucleotide.

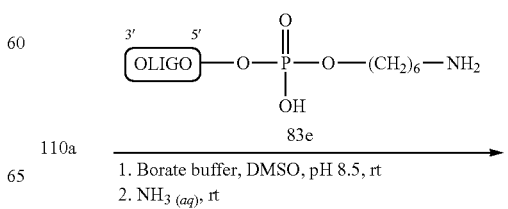

110a
83e
1. Borate buffer, DMSO, pH 8.5, rt
2. NH$_3$ $(aq)$, rt

-continued

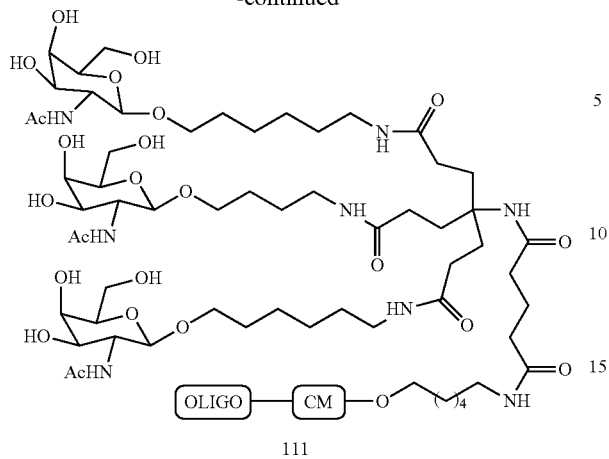

111

Oligonucleotide 111 is conjugated with GalNAc$_3$-10. The GalNAc$_3$ cluster portion of the conjugate group GalNAc$_3$-10 (GalNAc$_3$-10$_a$) can be combined with any cleavable moiety to provide a variety of conjugate groups. In certain embodiments, the cleavable moiety is —P(=O)(OH)-A$_d$-P(=O)(OH)— as shown in the oligonucleotide (ISIS 666881) synthesized with GalNAc$_3$-10 below. The structure of GalNAc$_3$-10 (GalNAc$_3$-10$_a$-CM-) is shown below:

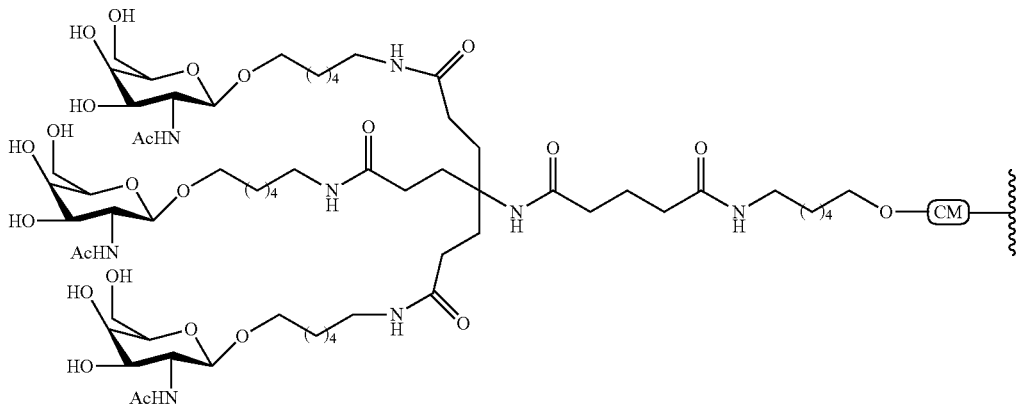

Following this general procedure ISIS 666881 was prepared. 5'-hexylamino modified oligonucleotide, ISIS 660254, was synthesized and purified using standard solid-phase oligonucleotide procedures. ISIS 660254 (40 mg, 5.2 μmol) was dissolved in 0.1 M sodium tetraborate, pH 8.5 (200 μL) and 3 equivalents PFP ester (Compound 110a) dissolved in DMSO (50 μL) was added. The PFP ester precipitated upon addition to the ASO solution requiring additional DMSO (600 μL) to fully dissolve the PFP ester. The reaction was complete after 16 h of mixing at room temperature. The solution was diluted with water to 12 mL total volume and spun down at 3000 rpm in a spin filter with a mass cut off of 3000 Da. This process was repeated twice to remove small molecule impurities. The solution was lyophilized to dryness and redissolved in concentrated aqueous ammonia with mixing at room temperature for 2.5 h followed by concentration in vacuo to remove most of the ammonia. The conjugated oligonucleotide was purified and desalted by RP-HPLC and lyophilized to give ISIS 666881 in 90% yield by weight (42 mg, 4.7 μmol).

| | GalNAc$_3$-10 conjugated oligonucleotide | | |
|---|---|---|---|
| ASO | Sequence (5' to 3') | 5' group | SEQ ID No. |
| ISIS 660254 | NH$_2$(CH$_2$)$_6$-$_o$ A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | Hexylamine | 831 |
| ISIS 666881 | GalNAc$_3$-10$_a$-$_o$, A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_3$-10 | 831 |

Capital letters indicate the nucleobase for each nucleoside and $^{m}C$ indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

Example 47: Preparation of Oligonucleotide 102 Comprising GalNAc$_3$-8

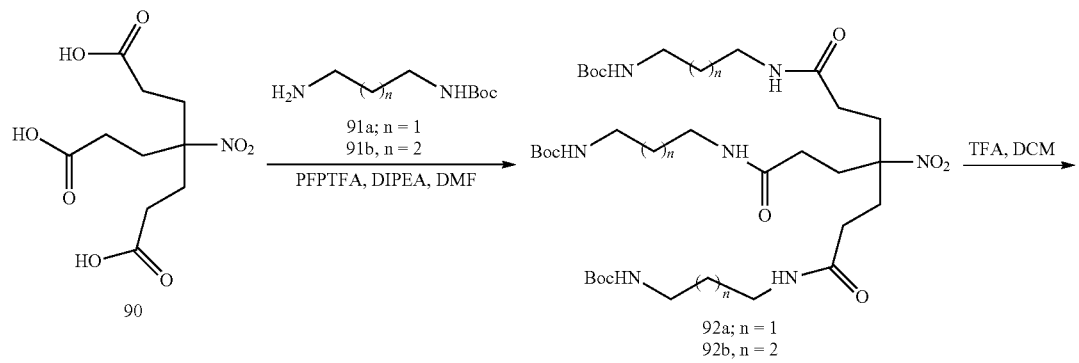

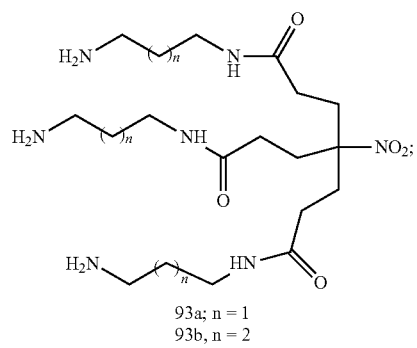

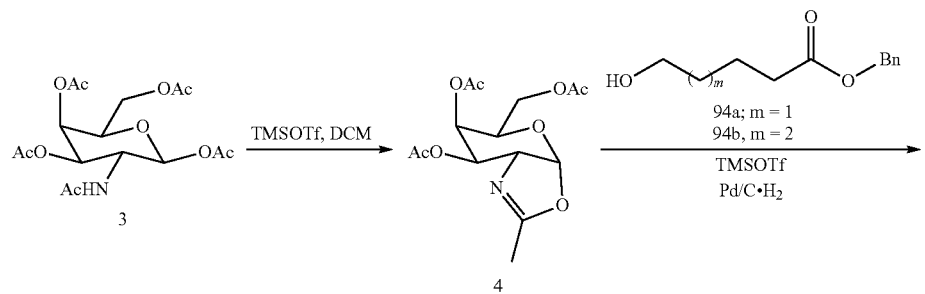

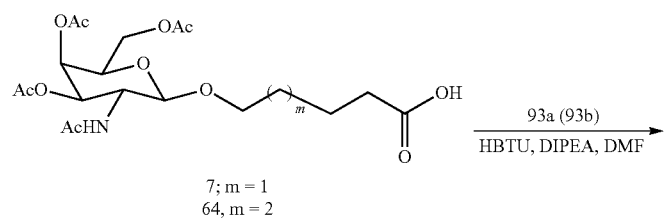

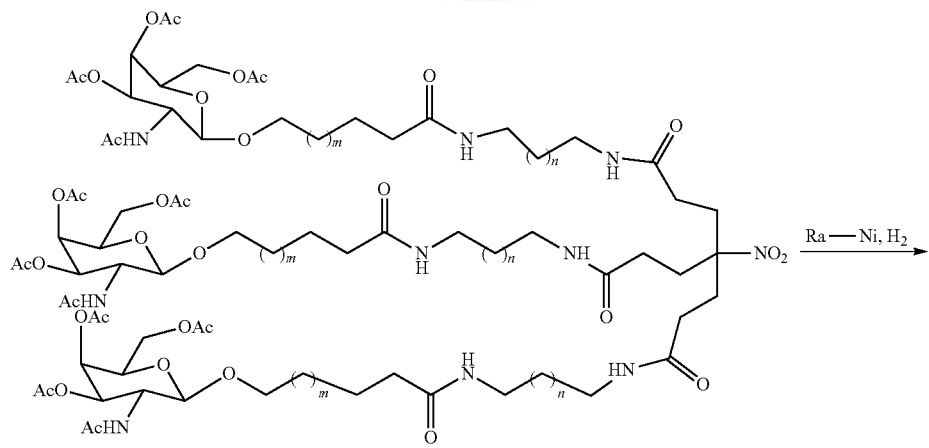
96a; n = 1, m = 1
96b; n = 7, m = 2
96c; n = 2, m = 1
96d; n = 2, m = 2
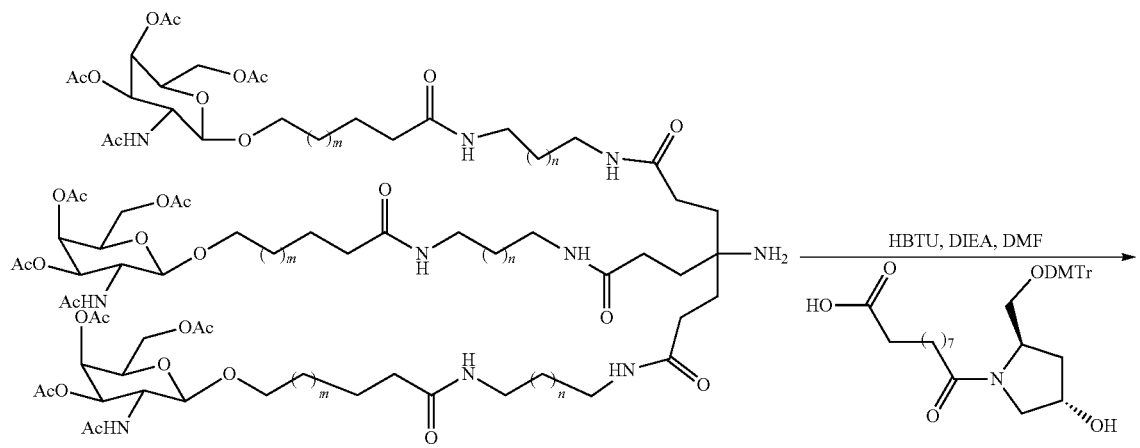
97a; n = 1, m = 1
97b; n = 7, m = 2
97c; n = 2, m = 1
97d; n = 2, m = 2
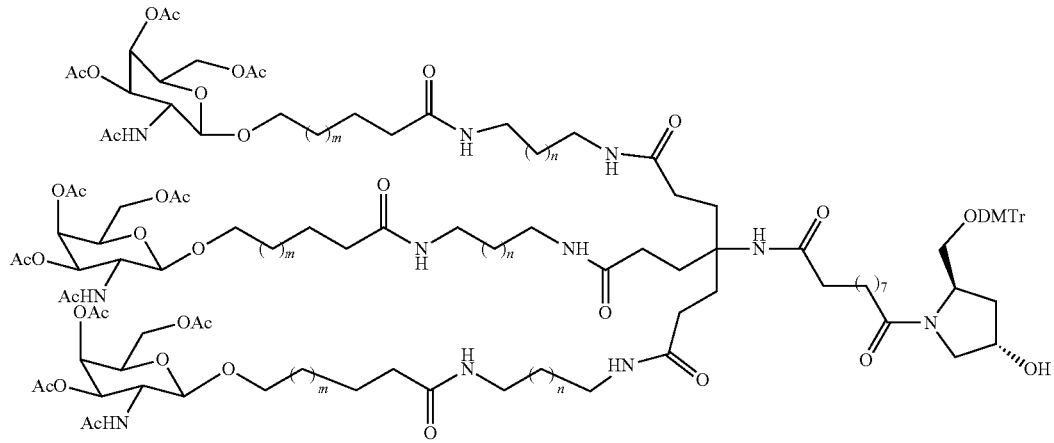
98a; n = 1, m = 1
98b; n = 7, m = 2
98c; n = 2, m = 1
98d; n = 2, m = 2

-continued
97a; n = 1, m = 1
97b; n = 7, m = 2
97c; n = 2, m = 1
97d; n = 2, m = 2
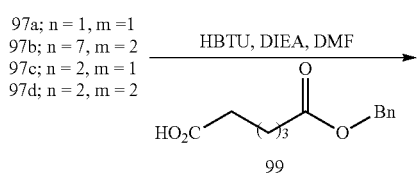
HBTU, DIEA, DMF
→
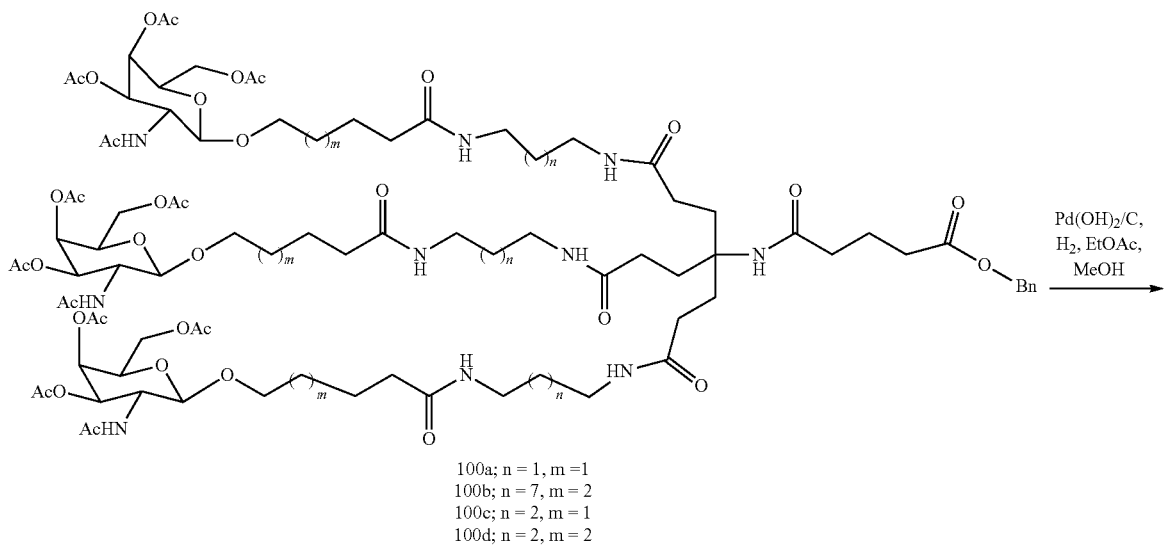
100a; n = 1, m = 1
100b; n = 7, m = 2
100c; n = 2, m = 1
100d; n = 2, m = 2
Pd(OH)$_2$/C, H$_2$, EtOAc, MeOH →
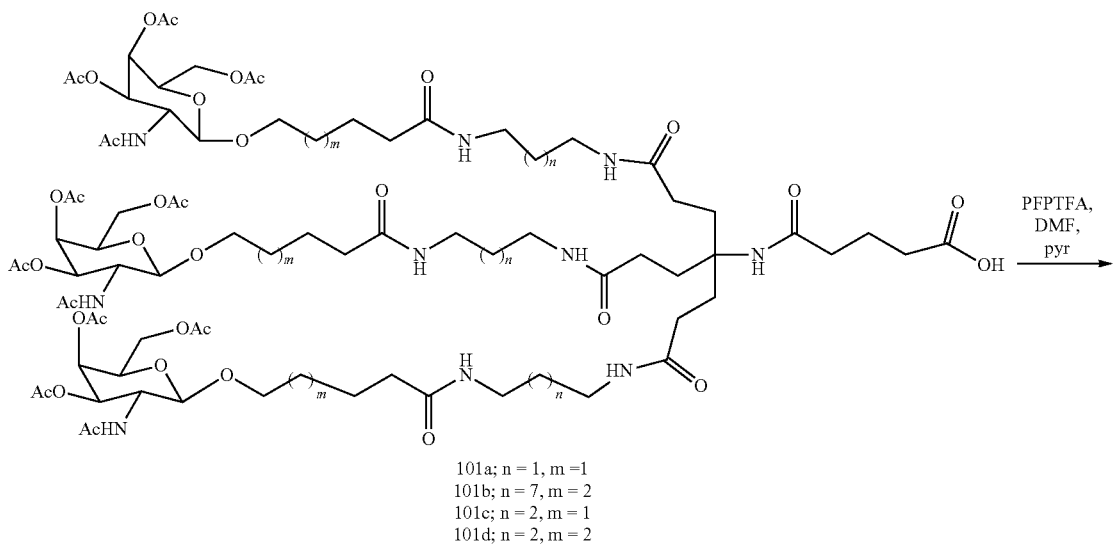
101a; n = 1, m = 1
101b; n = 7, m = 2
101c; n = 2, m = 1
101d; n = 2, m = 2
PFPTFA, DMF, pyr →

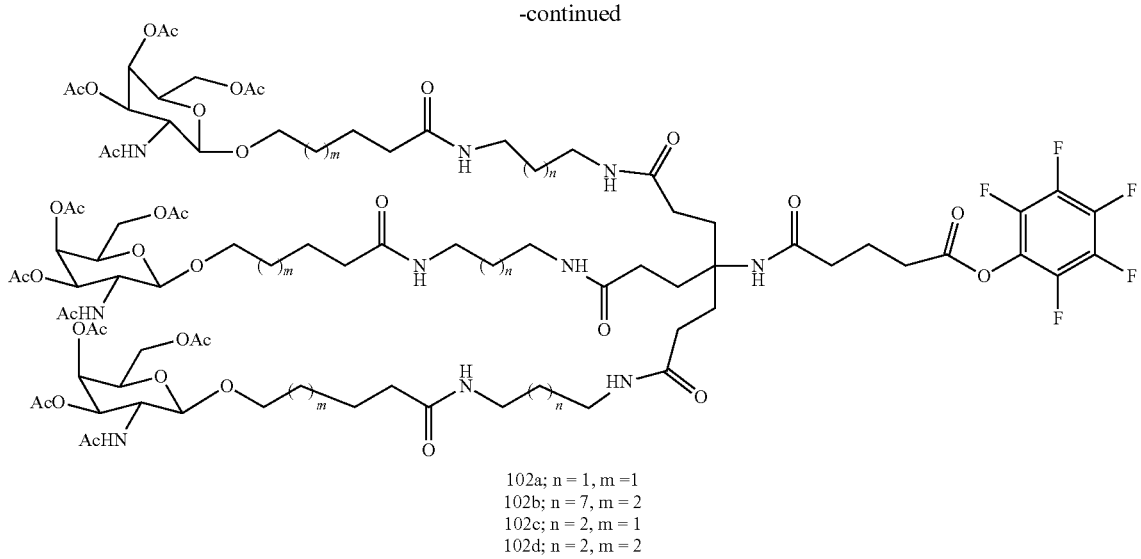

102a; n = 1, m = 1
102b; n = 7, m = 2
102c; n = 2, m = 1
102d; n = 2, m = 2

The triacid 90 (4 g, 14.43 mmol) was dissolved in DMF (120 mL) and N,N-Diisopropylethylamine (12.35 mL, 72 mmoles). Pentafluorophenyl trifluoroacetate (8.9 mL, 52 mmoles) was added dropwise, under argon, and the reaction was allowed to stir at room temperature for 30 minutes. Boc-diamine 91a or 91b (68.87 mmol) was added, along with N,N-Diisopropylethylamine (12.35 mL, 72 mmoles), and the reaction was allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→10% methanol/dichloromethane) to give compounds 92a and 92b in an approximate 80% yield. LCMS and proton NMR were consistent with the structure.

Compound 92a or 92b (6.7 mmoles) was treated with 20 mL of dichloromethane and 20 mL of trifluoroacetic acid at room temperature for 16 hours. The resultant solution was evaporated and then dissolved in methanol and treated with DOWEX-OH resin for 30 minutes. The resultant solution was filtered and reduced to an oil under reduced pressure to give 85-90% yield of compounds 93a and 93b.

Compounds 7 or 64 (9.6 mmoles) were treated with HBTU (3.7 g, 9.6 mmoles) and N,N-Diisopropylethylamine (5 mL) in DMF (20 mL) for 15 minutes. To this was added either compounds 93a or 93b (3 mmoles), and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (5%→20% methanol/dichloromethane) to give compounds 96a-d in 20-40% yield. LCMS and proton NMR was consistent with the structure.

Compounds 96a-d (0.75 mmoles), individually, were hydrogenated over Raney Nickel for 3 hours in Ethanol (75 mL). At that time, the catalyst was removed by filtration thru celite, and the ethanol removed under reduced pressure to give compounds 97a-d in 80-90% yield. LCMS and proton NMR were consistent with the structure.

Compound 23 (0.32 g, 0.53 mmoles) was treated with HBTU (0.2 g, 0.53 mmoles) and N,N-Diisopropylethylamine (0.19 mL, 1.14 mmoles) in DMF (30 mL) for 15 minutes. To this was added compounds 97a-d (0.38 mmoles), individually, and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→20% methanol/dichloromethane) to give compounds 98a-d in 30-40% yield. LCMS and proton NMR was consistent with the structure.

Compound 99 (0.17 g, 0.76 mmoles) was treated with HBTU (0.29 g, 0.76 mmoles) and N,N-Diisopropylethylamine (0.35 mL, 2.0 mmoles) in DMF (50 mL) for 15 minutes. To this was added compounds 97a-d (0.51 mmoles), individually, and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (5%→20% methanol/dichloromethane) to give compounds 100a-d in 40-60% yield. LCMS and proton NMR was consistent with the structure.

Compounds 100a-d (0.16 mmoles), individually, were hydrogenated over 10% Pd(OH)$_2$/C for 3 hours in methanol/ethyl acetate (1:1, 50 mL). At that time, the catalyst was removed by filtration thru celite, and the organics removed under reduced pressure to give compounds 101a-d in 80-90% yield. LCMS and proton NMR was consistent with the structure.

Compounds 101a-d (0.15 mmoles), individually, were dissolved in DMF (15 mL) and pyridine (0.016 mL, 0.2 mmoles). Pentafluorophenyl trifluoroacetate (0.034 mL, 0.2 mmoles) was added dropwise, under argon, and the reaction was allowed to stir at room temperature for 30 minutes. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→5% methanol/ dichloromethane) to give compounds 102a-d in an approximate 80% yield. LCMS and proton NMR were consistent with the structure.

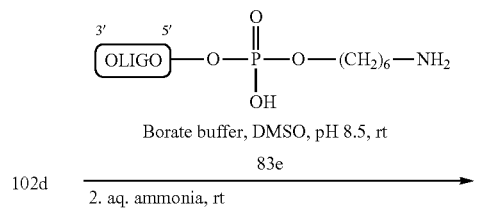

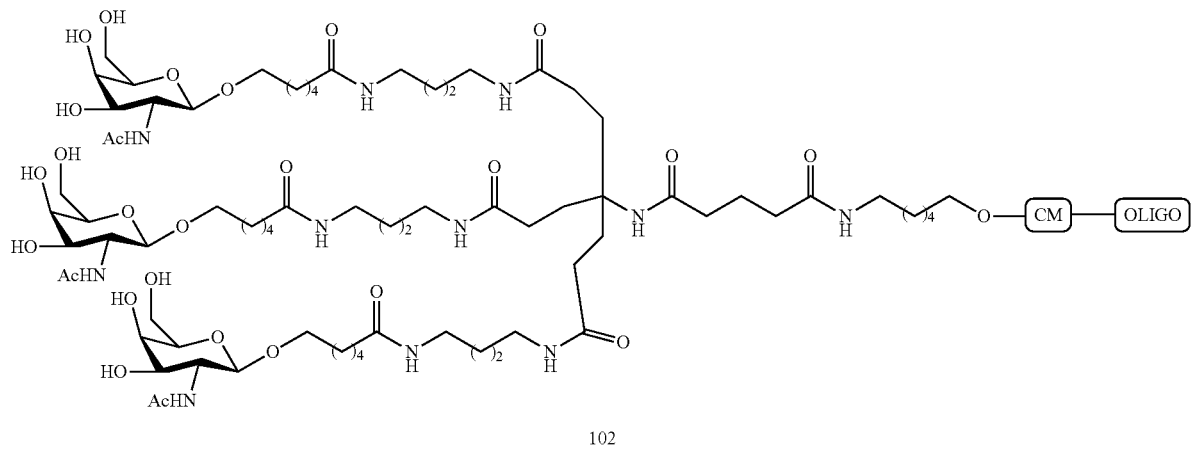

102

Oligomeric Compound 102, comprising a GalNAc$_3$-8 conjugate group, was prepared using the general procedures illustrated in Example 46. The GalNAc$_3$ cluster portion of the conjugate group GalNAc$_3$-8 (GalNAc$_3$-8$_a$) can be combined with any cleavable moiety to provide a variety of conjugate groups. In a preferred embodiment, the cleavable moiety is —P(=O)(OH)-A$_d$-P(=O)(OH)—.

The structure of GalNAc$_3$-8 (GalNAc$_3$-8$_a$-CM-) is shown below:

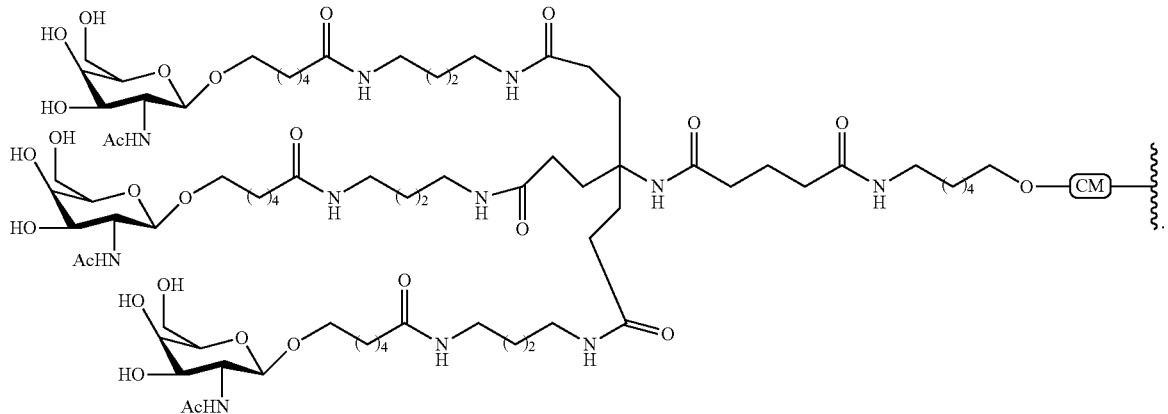

Example 48: Preparation of Oligonucleotide 119 Comprising GalNAc₃-7
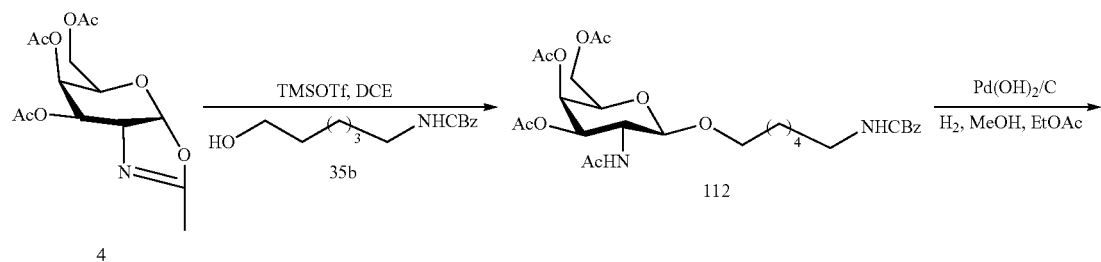
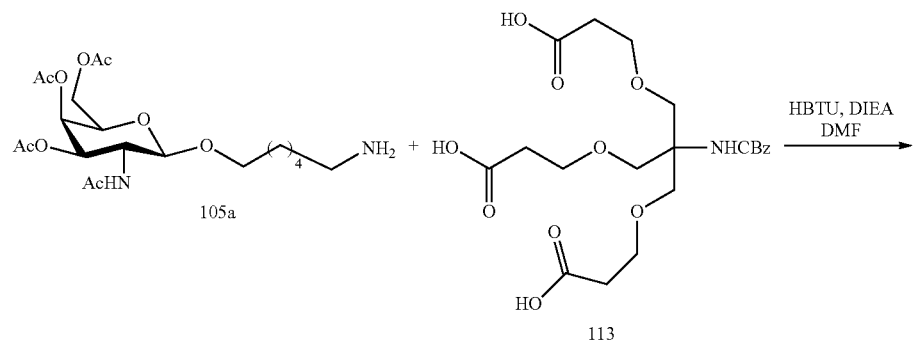
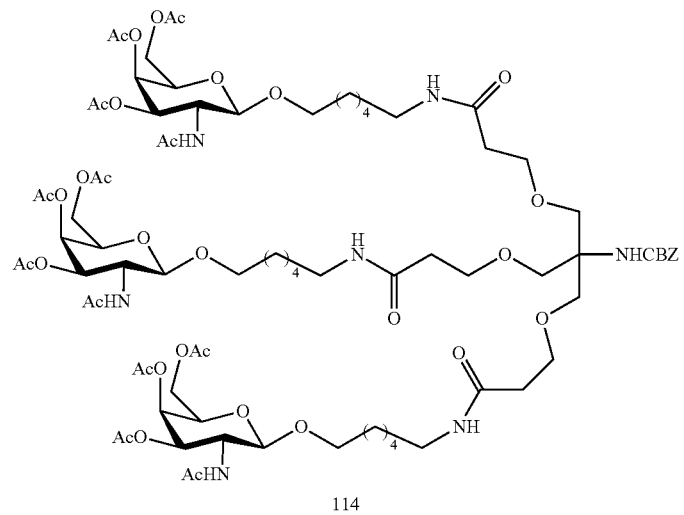
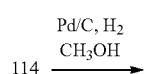

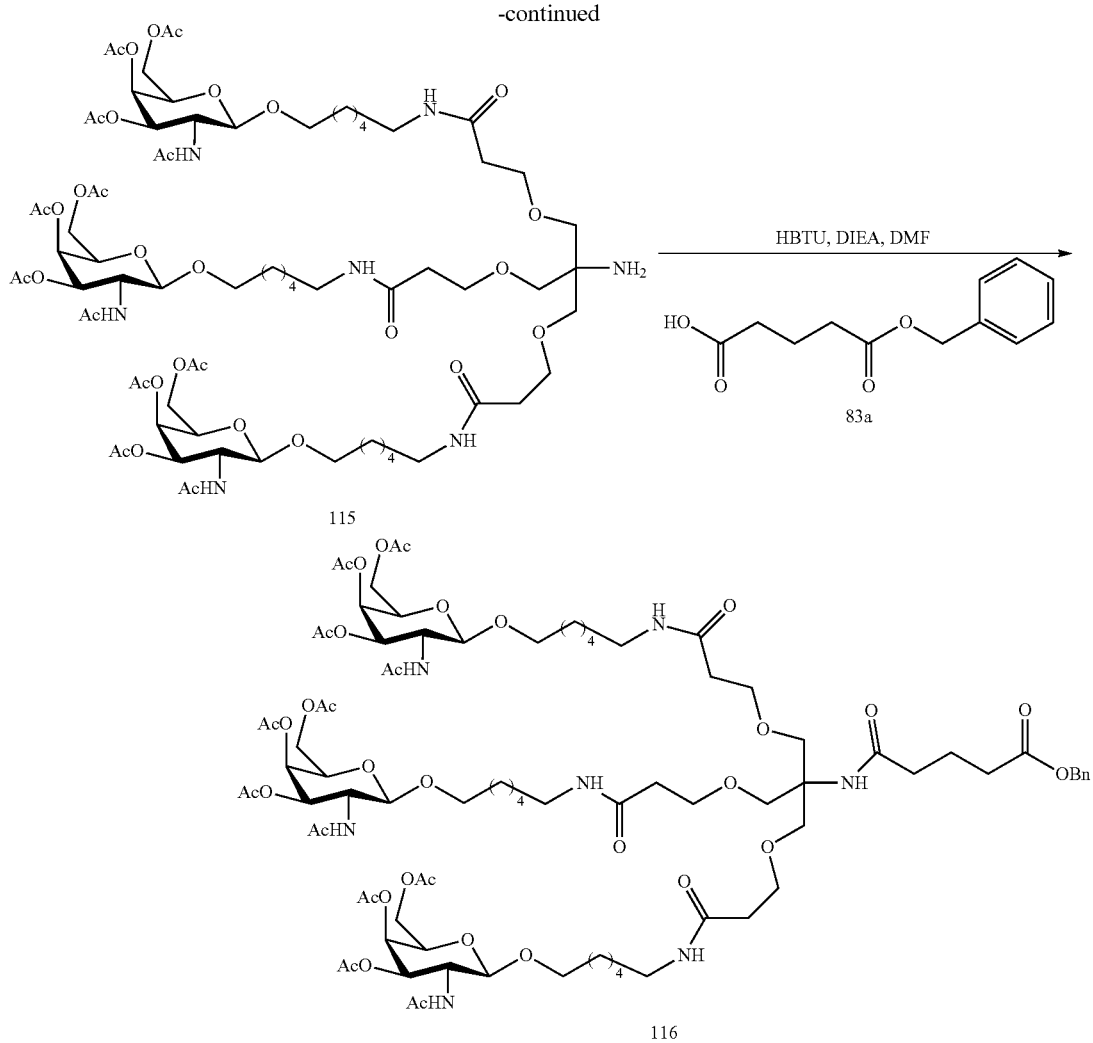

Compound 112 was synthesized following the procedure described in the literature (*J. Med. Chem.* 2004, 47, 5798-5808).

Compound 112 (5 g, 8.6 mmol) was dissolved in 1:1 methanol/ethyl acetate (22 mL/22 mL). Palladium hydroxide on carbon (0.5 g) was added. The reaction mixture was stirred at room temperature under hydrogen for 12 h. The reaction mixture was filtered through a pad of celite and washed the pad with 1:1 methanol/ethyl acetate. The filtrate and the washings were combined and concentrated to dryness to yield Compound 105a (quantitative). The structure was confirmed by LCMS.

Compound 113 (1.25 g, 2.7 mmol), HBTU (3.2 g, 8.4 mmol) and DIEA (2.8 mL, 16.2 mmol) were dissolved in anhydrous DMF (17 mL) and the reaction mixture was stirred at room temperature for 5 min. To this a solution of Compound 105a (3.77 g, 8.4 mmol) in anhydrous DMF (20 mL) was added. The reaction was stirred at room temperature for 6 h. Solvent was removed under reduced pressure to get an oil. The residue was dissolved in $CH_2Cl_2$ (100 mL) and washed with aqueous saturated $NaHCO_3$ solution (100 mL) and brine (100 mL). The organic phase was separated, dried ($Na_2SO_4$), filtered and evaporated. The residue was purified by silica gel column chromatography and eluted with 10 to 20% MeOH in dichloromethane to yield Compound 114 (1.45 g, 30%). The structure was confirmed by LCMS and $^1H$ NMR analysis.

Compound 114 (1.43 g, 0.8 mmol) was dissolved in 1:1 methanol/ethyl acetate (4 mL/4 mL). Palladium on carbon (wet, 0.14 g) was added. The reaction mixture was flushed with hydrogen and stirred at room temperature under hydrogen for 12 h. The reaction mixture was filtered through a pad of celite. The celite pad was washed with methanol/ethyl acetate (1:1). The filtrate and the washings were combined together and evaporated under reduced pressure to yield Compound 115 (quantitative). The structure was confirmed by LCMS and $^1H$ NMR analysis.

Compound 83a (0.17 g, 0.75 mmol), HBTU (0.31 g, 0.83 mmol) and DIEA (0.26 mL, 1.5 mmol) were dissolved in anhydrous DMF (5 mL) and the reaction mixture was stirred at room temperature for 5 min. To this a solution of Compound 115 (1.22 g, 0.75 mmol) in anhydrous DMF was added and the reaction was stirred at room temperature for 6 h. The solvent was removed under reduced pressure and the residue was dissolved in $CH_2C_2$. The organic layer was washed aqueous saturated $NaHCO_3$ solution and brine and dried over anhydrous $Na_2SO_4$ and filtered. The organic layer was concentrated to dryness and the residue obtained was purified by silica gel column chromatography and eluted with 3 to 15% MeOH in dichloromethane to yield Compound 116 (0.84 g, 61%). The structure was confirmed by LC MS and $^1H$ NMR analysis.

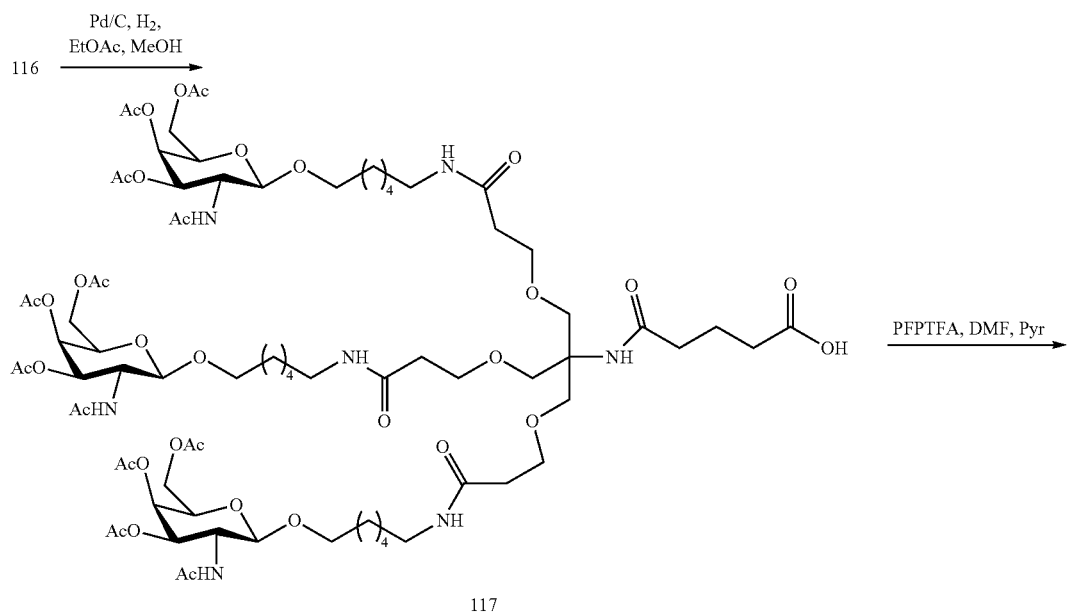

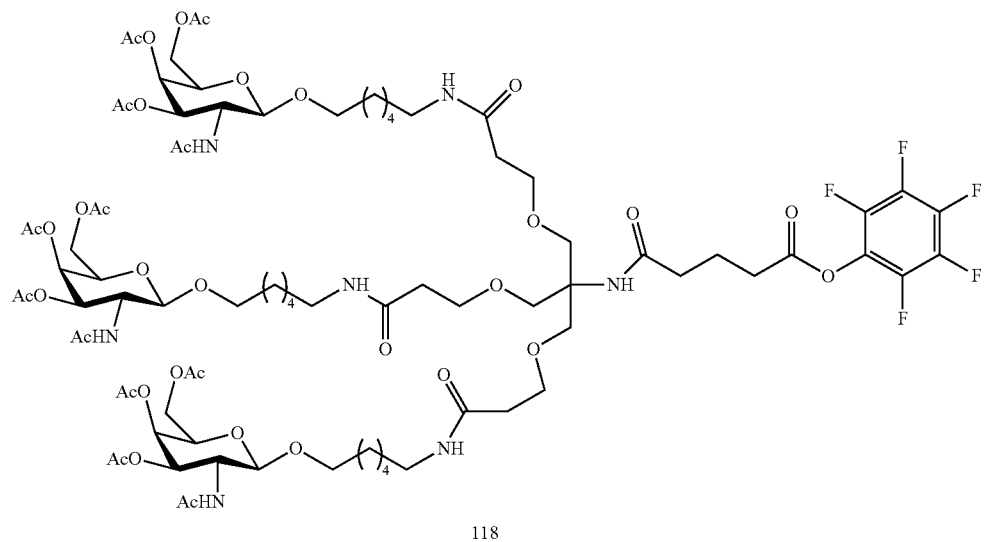

Compound 116 (0.74 g, 0.4 mmol) was dissolved in 1:1 methanol/ethyl acetate (5 mL/5 mL). Palladium on carbon (wet, 0.074 g) was added. The reaction mixture was flushed with hydrogen and stirred at room temperature under hydrogen for 12 h. The reaction mixture was filtered through a pad of celite. The celite pad was washed with methanol/ethyl acetate (1:1). The filtrate and the washings were combined together and evaporated under reduced pressure to yield compound 117 (0.73 g, 98%). The structure was confirmed by LCMS and $^1$H NMR analysis.

Compound 117 (0.63 g, 0.36 mmol) was dissolved in anhydrous DMF (3 mL). To this solution N,N-Diisopropylethylamine (70 μL, 0.4 mmol) and pentafluorophenyl trifluoroacetate (72 μL, 0.42 mmol) were added. The reaction mixture was stirred at room temperature for 12 h and poured into a aqueous saturated NaHCO$_3$ solution. The mixture was extracted with dichloromethane, washed with brine and dried over anhydrous Na$_2$SO$_4$. The dichloromethane solution was concentrated to dryness and purified with silica gel column chromatography and eluted with 5 to 10% MeOH in dichloromethane to yield compound 118 (0.51 g, 79%). The structure was confirmed by LCMS and $^1$H and $^1$H and $^{19}$F NMR.

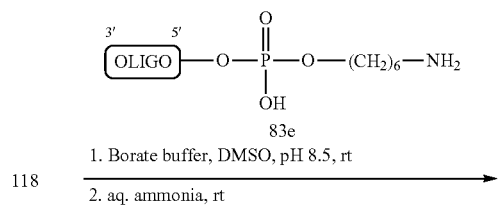

118    1. Borate buffer, DMSO, pH 8.5, rt
2. aq. ammonia, rt

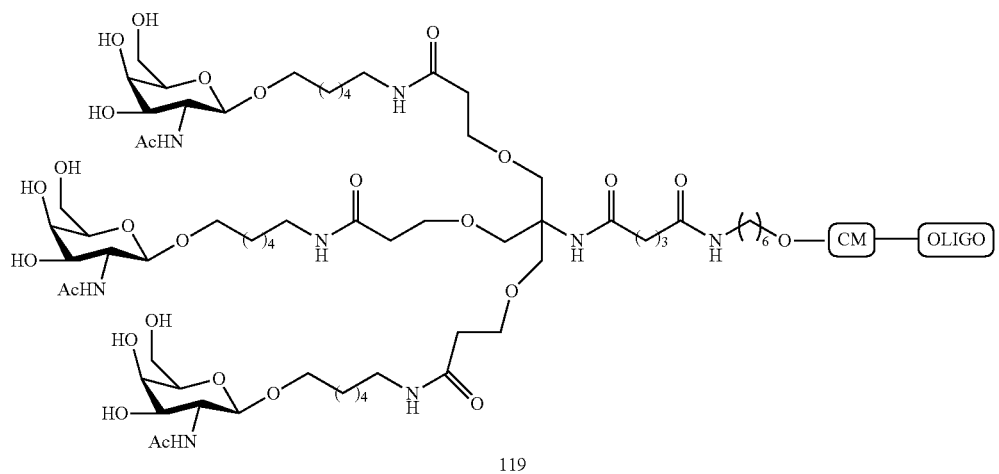

119

Oligomeric Compound 119, comprising a GalNAc$_3$-7 conjugate group, was prepared using the general procedures illustrated in Example 46. The GalNAc$_3$ cluster portion of the conjugate group GalNAc$_3$-7 (GalNAc$_3$-7$_a$) can be combined with any cleavable moiety to provide a variety of conjugate groups. In certain embodiments, the cleavable moiety is —P(=O)(OH)-A$_d$-P(=O)(OH)—.

The structure of GalNAc$_3$-7 (GalNAc$_3$-7$_a$-CM-) is shown below:

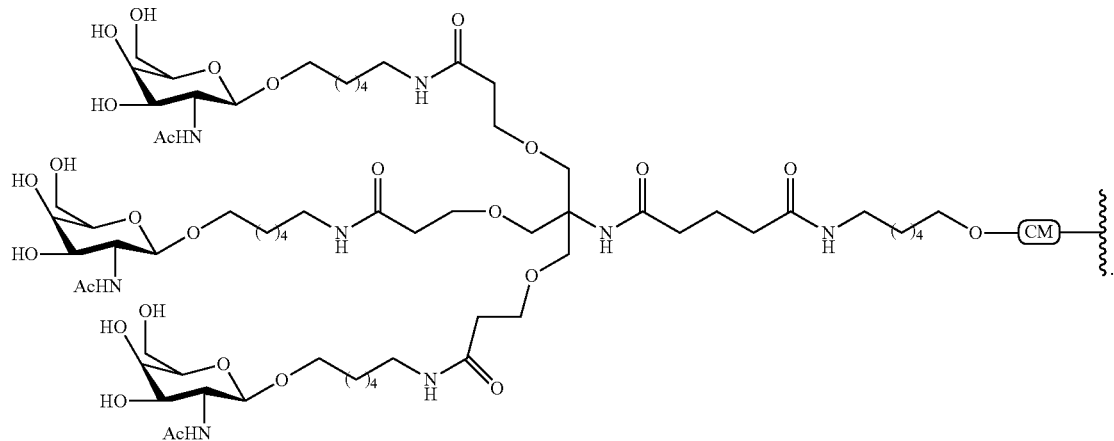

Example 49: Preparation of Oligonucleotide 132 Comprising GalNAc₃-5

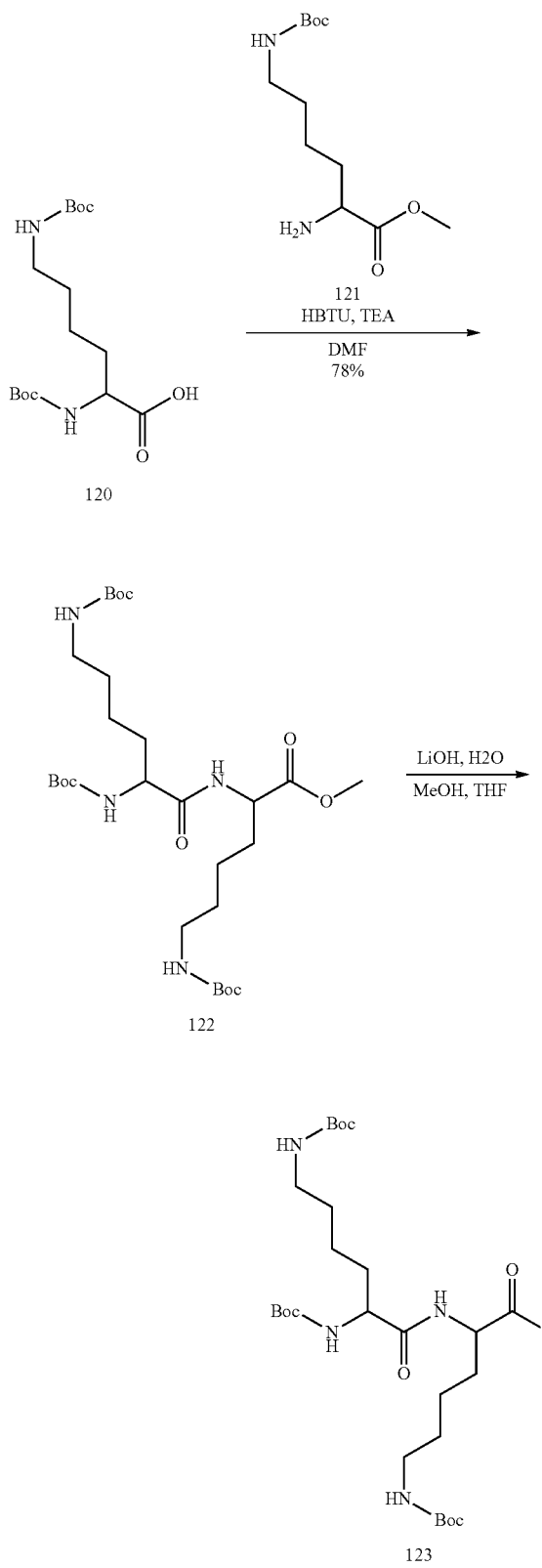

Compound 120 (14.01 g, 40 mmol) and HBTU (14.06 g, 37 mmol) were dissolved in anhydrous DMF (80 mL). Triethylamine (11.2 mL, 80.35 mmol) was added and stirred for 5 min. The reaction mixture was cooled in an ice bath and a solution of compound 121 (10 g, mmol) in anhydrous DMF (20 mL) was added. Additional triethylamine (4.5 mL, 32.28 mmol) was added and the reaction mixture was stirred for 18 h under an argon atmosphere. The reaction was monitored by TLC (ethyl acetate:hexane; 1:1; Rf=0.47). The solvent was removed under reduced pressure. The residue was taken up in EtOAc (300 mL) and washed with 1M NaHSO₄ (3×150 mL), aqueous saturated NaHCO₃ solution (3×150 mL) and brine (2×100 mL). Organic layer was dried with Na₂SO₄. Drying agent was removed by filtration and organic layer was concentrated by rotary evaporation. Crude mixture was purified by silica gel column chromatography and eluted by using 35-50% EtOAc in hexane to yield a compound 122 (15.50 g, 78.13%). The structure was confirmed by LCMS and ¹H NMR analysis. Mass m z 589.3 [M+H]⁺.

A solution of LiOH (92.15 mmol) in water (20 mL) and THF (10 mL) was added to a cooled solution of Compound 122 (7.75 g, 13.16 mmol) dissolved in methanol (15 mL). The reaction mixture was stirred at room temperature for 45 min. and monitored by TLC (EtOAc:hexane; 1:1). The reaction mixture was concentrated to half the volume under reduced pressure. The remaining solution was cooled an ice bath and neutralized by adding concentrated HCl. The reaction mixture was diluted, extracted with EtOAc (120 mL) and washed with brine (100 mL). An emulsion formed and cleared upon standing overnight. The organic layer was separated dried (Na₂SO₄), filtered and evaporated to yield Compound 123 (8.42 g). Residual salt is the likely cause of excess mass. LCMS is consistent with structure. Product was used without any further purification. M.W. cal: 574.36; M.W. fd: 575.3 [M+H]⁺.

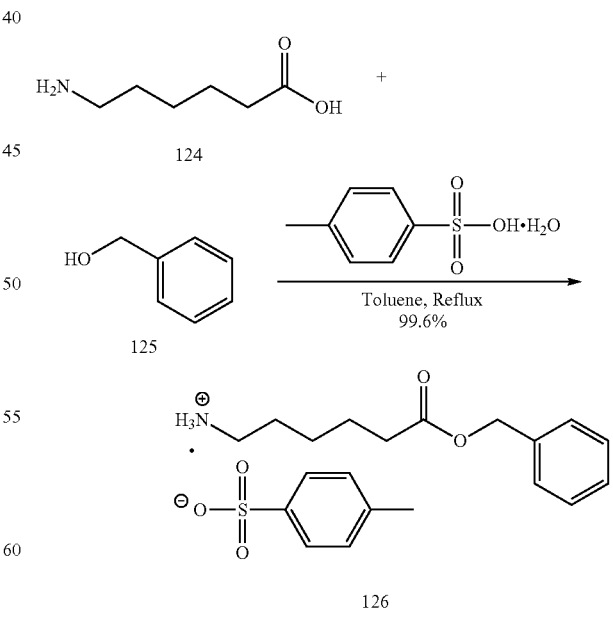

Compound 126 was synthesized following the procedure described in the literature (*J. Am. Chem. Soc.* 2011, 133, 958-963).

297 298
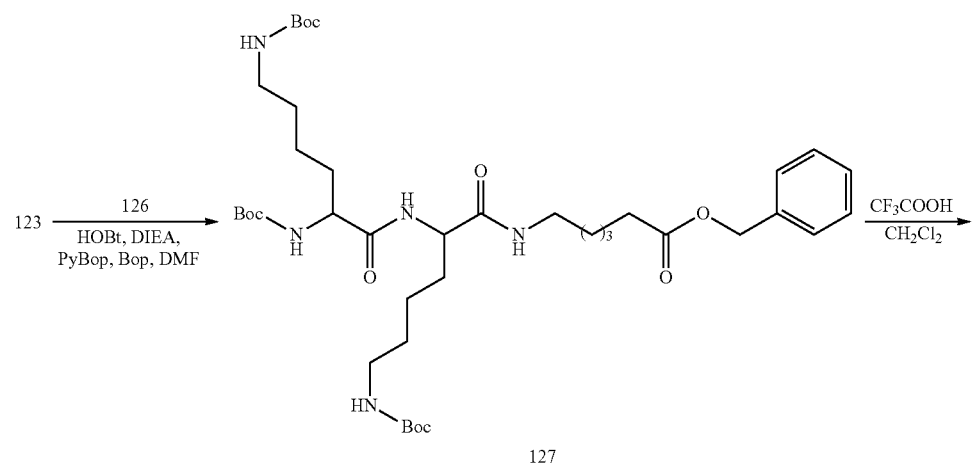
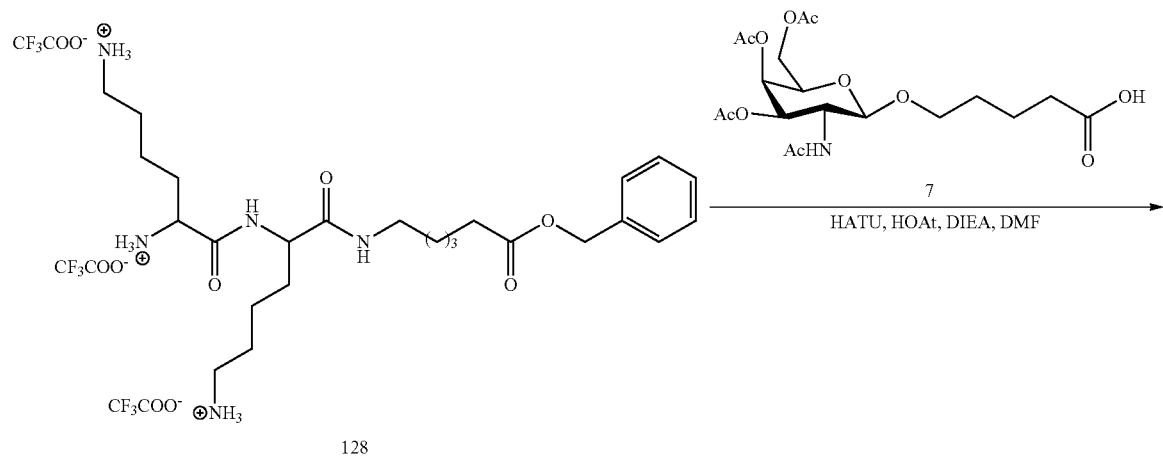
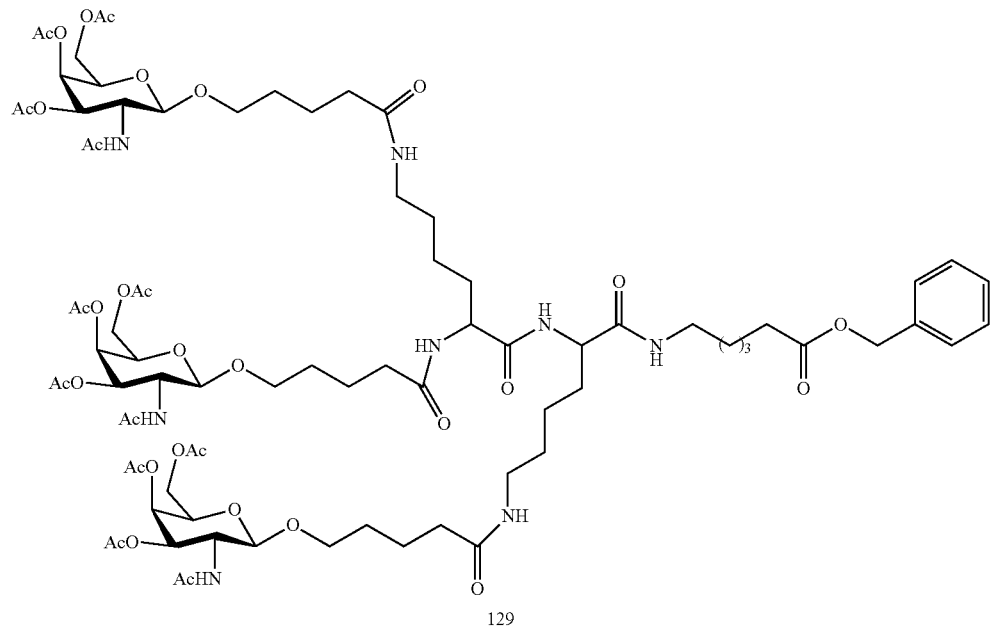

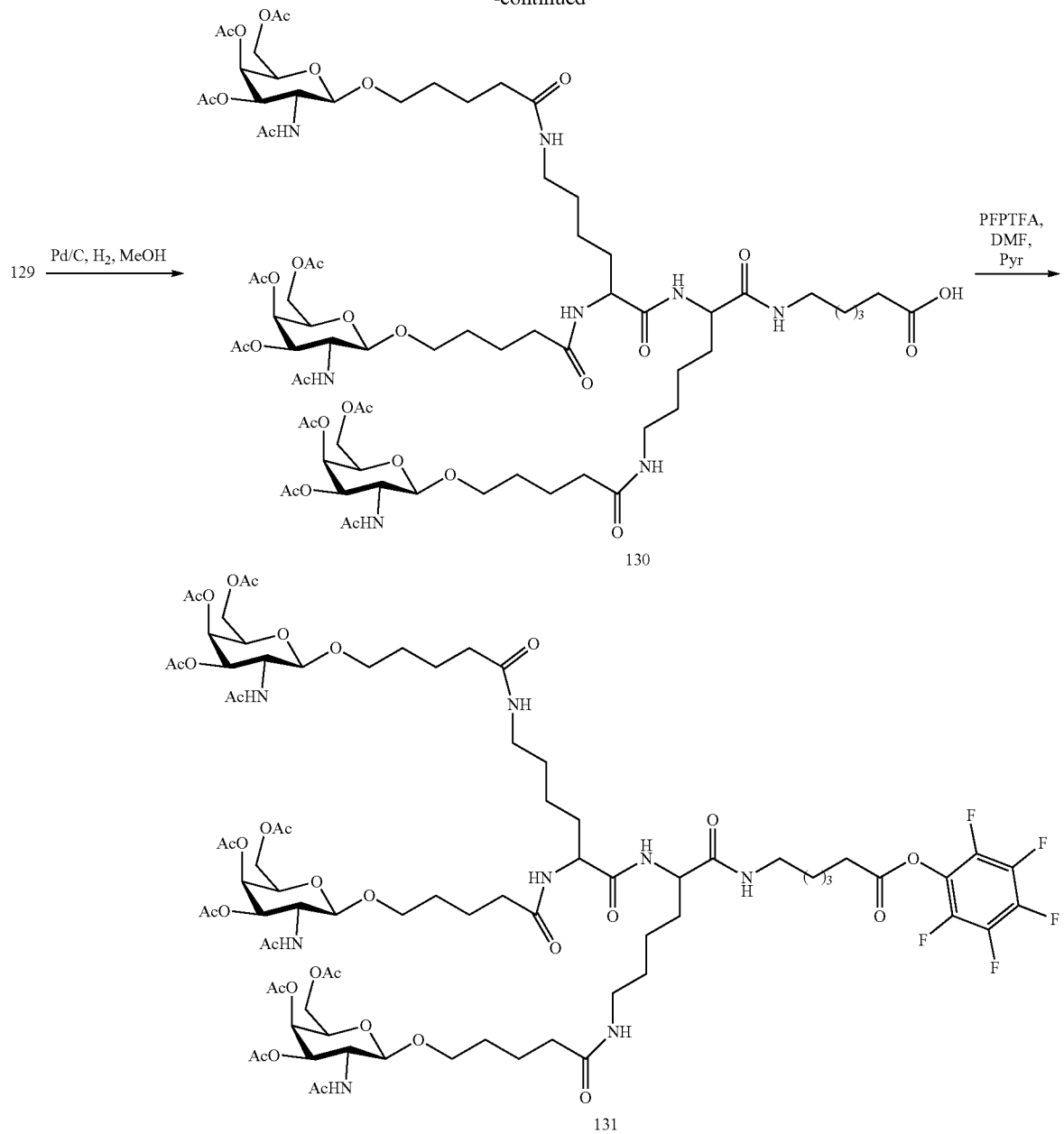

Compound 123 (7.419 g, 12.91 mmol), HOBt (3.49 g, 25.82 mmol) and compound 126 (6.33 g, 16.14 mmol) were dissolved in and DMF (40 mL) and the resulting reaction mixture was cooled in an ice bath. To this N,N-Diisopropylethylamine (4.42 mL, 25.82 mmol), PyBop (8.7 g, 16.7 mmol) followed by Bop coupling reagent (1.17 g, 2.66 mmol) were added under an argon atmosphere. The ice bath was removed and the solution was allowed to warm to room temperature. The reaction was completed after 1 h as determined by TLC (DCM:MeOH:AA; 89:10:1). The reaction mixture was concentrated under reduced pressure. The residue was dissolved in EtOAc (200 mL) and washed with 1 M NaHSO$_4$ (3×100 mL), aqueous saturated NaHCO$_3$ (3×100 mL) and brine (2×100 mL). The organic phase separated dried (Na$_2$SO$_4$), filtered and concentrated. The residue was purified by silica gel column chromatography with a gradient of 50% hexanes/EtOAC to 100% EtOAc to yield Compound 127 (9.4 g) as a white foam. LCMS and $^1$H NMR were consistent with structure. Mass m z 778.4 [M+H]$^+$.

Trifluoroacetic acid (12 mL) was added to a solution of compound 127 (1.57 g, 2.02 mmol) in dichloromethane (12 mL) and stirred at room temperature for 1 h. The reaction mixture was co-evaporated with toluene (30 mL) under reduced pressure to dryness. The residue obtained was co-evaporated twice with acetonitrile (30 mL) and toluene (40 mL) to yield Compound 128 (1.67 g) as trifluoro acetate salt and used for next step without further purification. LCMS and $^1$H NMR were consistent with structure. Mass m z 478.2 [M+H]$^+$.

Compound 7 (0.43 g, 0.963 mmol), HATU (0.35 g, 0.91 mmol), and HOAt (0.035 g, 0.26 mmol) were combined together and dried for 4 h over P$_2$O$_5$ under reduced pressure in a round bottom flask and then dissolved in anhydrous DMF (1 mL) and stirred for 5 min. To this a solution of compound 128 (0.20 g, 0.26 mmol) in anhydrous DMF (0.2 mL) and N,N-Diisopropylethylamine (0.2 mL) was added. The reaction mixture was stirred at room temperature under an argon atmosphere. The reaction was complete after 30 min as determined by LCMS and TLC (7% MeOH/DCM). The reaction mixture was concentrated under reduced pressure. The residue was dissolved in DCM (30 mL) and washed with 1 M NaHSO$_4$ (3×20 mL), aqueous saturated NaHCO$_3$ (3×20 mL) and brine (3×20 mL). The organic phase was separated, dried over Na$_2$SO$_4$, filtered and concentrated. The residue was purified by silica gel column chromatography using 5-15% MeOH in dichloromethane to yield Compound 129 (96.6 mg). LC MS and $^1$H NMR are consistent with structure. Mass m/z 883.4 [M+2H]$^+$.

Compound 129 (0.09 g, 0.051 mmol) was dissolved in methanol (5 mL) in 20 mL scintillation vial. To this was added a small amount of 10% Pd/C (0.015 mg) and the reaction vessel was flushed with H$_2$ gas. The reaction mixture was stirred at room temperature under H$_2$ atmosphere for 18 h. The reaction mixture was filtered through a pad of Celite and the Celite pad was washed with methanol. The filtrate washings were pooled together and concentrated under reduced pressure to yield Compound 130 (0.08 g). LCMS and $^1$H NMR were consistent with structure. The product was used without further purification. Mass m z 838.3 [M+2H]$^+$.

To a 10 mL pointed round bottom flask were added compound 130 (75.8 mg, 0.046 mmol), 0.37 M pyridine/DMF (200 µL) and a stir bar. To this solution was added 0.7 M pentafluorophenyl trifluoroacetate/DMF (100 µL) drop wise with stirring. The reaction was completed after 1 h as determined by LC MS. The solvent was removed under reduced pressure and the residue was dissolved in CHCl$_3$ (~10 mL). The organic layer was partitioned against NaHSO$_4$ (1 M, 10 mL), aqueous saturated NaHCO$_3$ (10 mL) and brine (10 mL) three times each. The organic phase separated and dried over Na$_2$SO$_4$, filtered and concentrated to yield Compound 131 (77.7 mg). LCMS is consistent with structure. Used without further purification. Mass m z 921.3 [M+2H]$^+$.

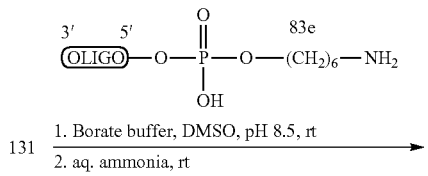

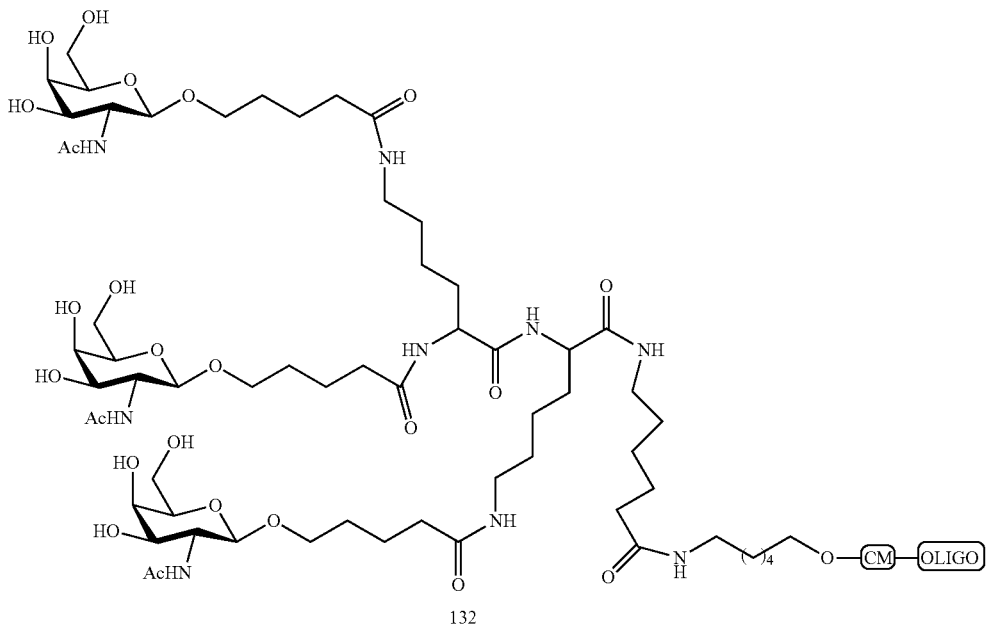

Oligomeric Compound 132, comprising a GalNAc$_3$-5 conjugate group, was prepared using the general procedures illustrated in Example 46. The GalNAc$_3$ cluster portion of the conjugate group GalNAc$_3$-5 (GalNAc$_3$-5$_a$) can be combined with any cleavable moiety to provide a variety of conjugate groups. In certain embodiments, the cleavable moiety is —P(=O)(OH)-A$_d$-P(=O)(OH)—.

The structure of GalNAc$_3$-5 (GalNAc$_3$-5$_a$-CM-) is shown below:

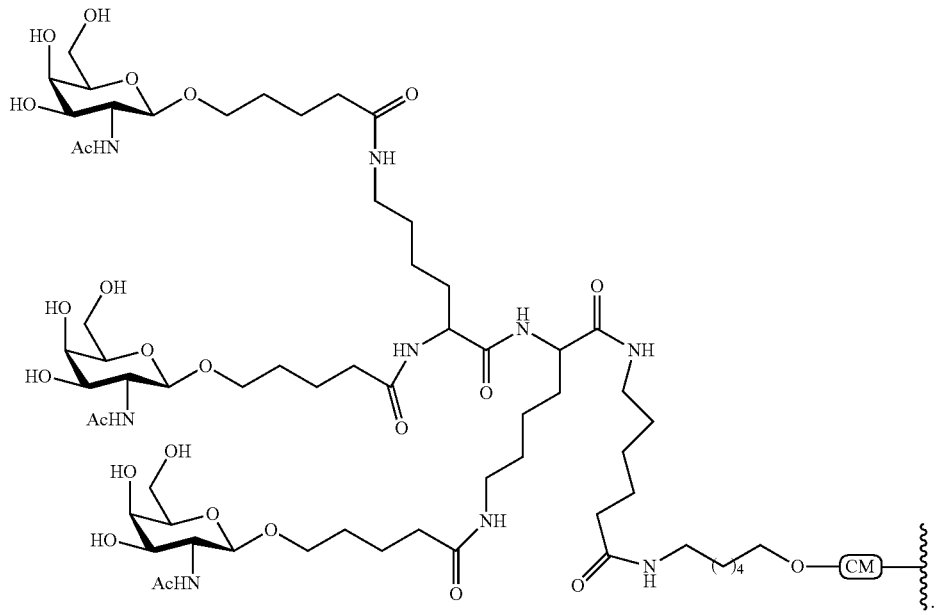

Example 50: Preparation of Oligonucleotide 144 Comprising GalNAc$_4$-11

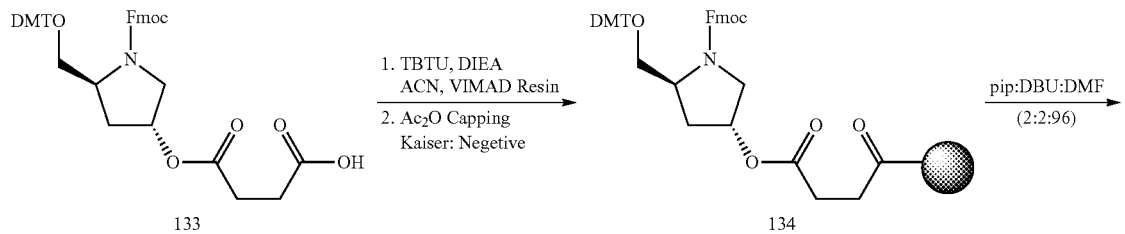

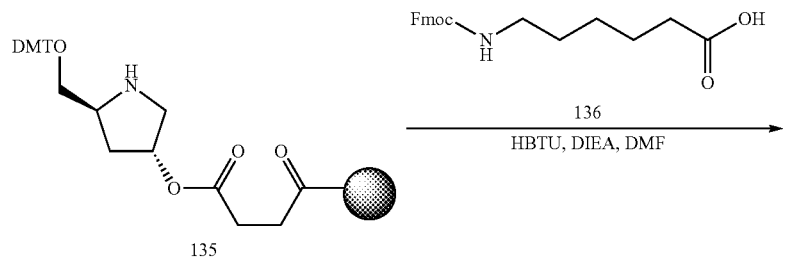

-continued
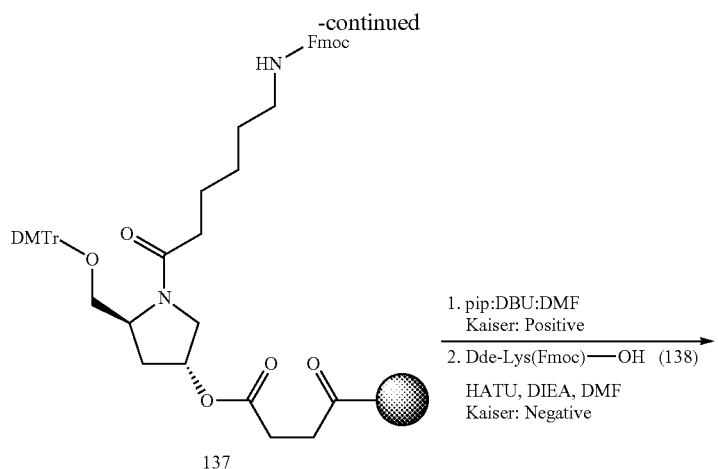
137
1. pip:DBU:DMF
   Kaiser: Positive
2. Dde-Lys(Fmoc)—OH (138)
   HATU, DIEA, DMF
   Kaiser: Negative
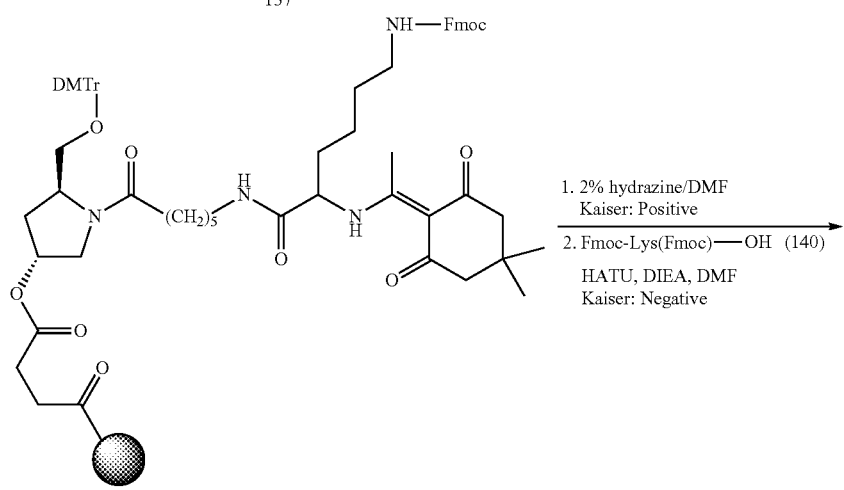
139
1. 2% hydrazine/DMF
   Kaiser: Positive
2. Fmoc-Lys(Fmoc)—OH (140)
   HATU, DIEA, DMF
   Kaiser: Negative
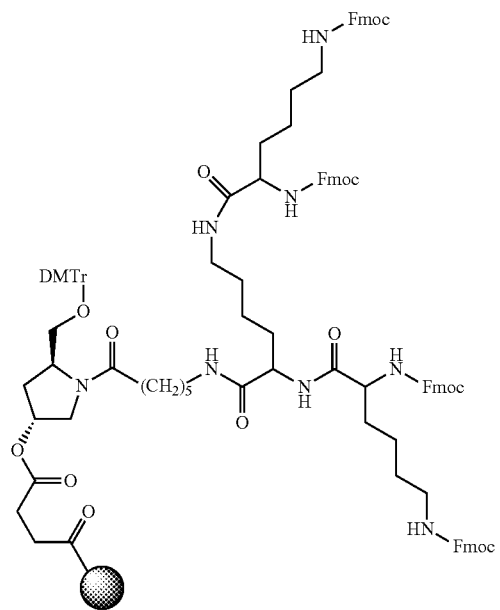
141

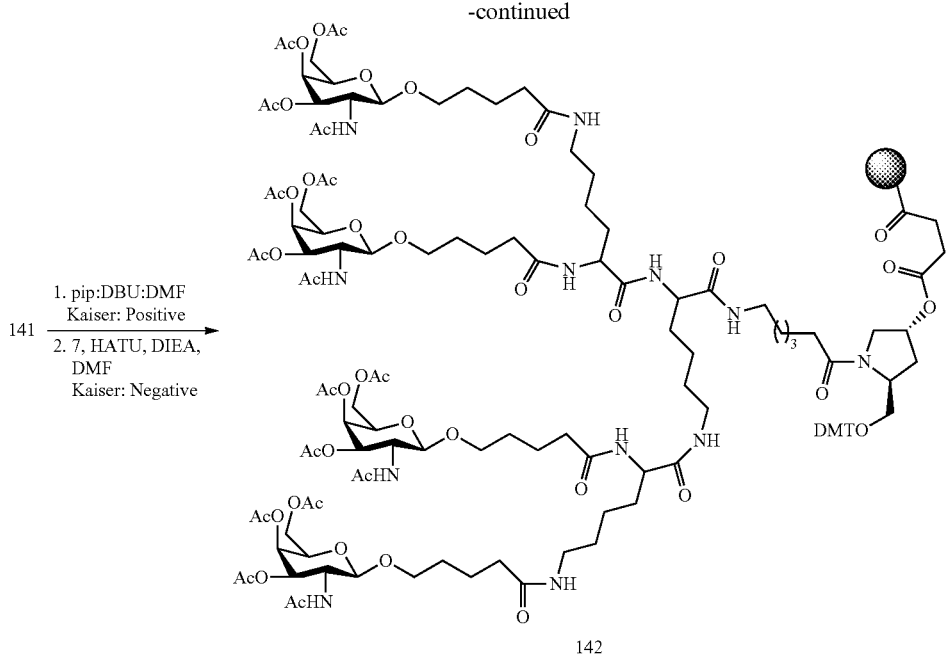

Synthesis of Compound 134. To a Merrifield flask was added aminomethyl VIMAD resin (2.5 g, 450 μmol/g) that was washed with acetonitrile, dimethylformamide, dichloromethane and acetonitrile. The resin was swelled in acetonitrile (4 mL). Compound 133 was pre-activated in a 100 mL round bottom flask by adding 20 (1.0 mmol, 0.747 g), TBTU (1.0 mmol, 0.321 g), acetonitrile (5 mL) and DIEA (3.0 mmol, 0.5 mL). This solution was allowed to stir for 5 min and was then added to the Merrifield flask with shaking. The suspension was allowed to shake for 3 h. The reaction mixture was drained and the resin was washed with acetonitrile, DMF and DCM. New resin loading was quantitated by measuring the absorbance of the DMT cation at 500 nm (extinction coefficient=76000) in DCM and determined to be 238 μmol/g. The resin was capped by suspending in an acetic anhydride solution for ten minutes three times.

The solid support bound compound 141 was synthesized using iterative Fmoc-based solid phase peptide synthesis methods. A small amount of solid support was withdrawn and suspended in aqueous ammonia (28-30 wt %) for 6 h. The cleaved compound was analyzed by LC-MS and the observed mass was consistent with structure. Mass m z 1063.8 [M+2H]*.

The solid support bound compound 142 was synthesized using solid phase peptide synthesis methods.

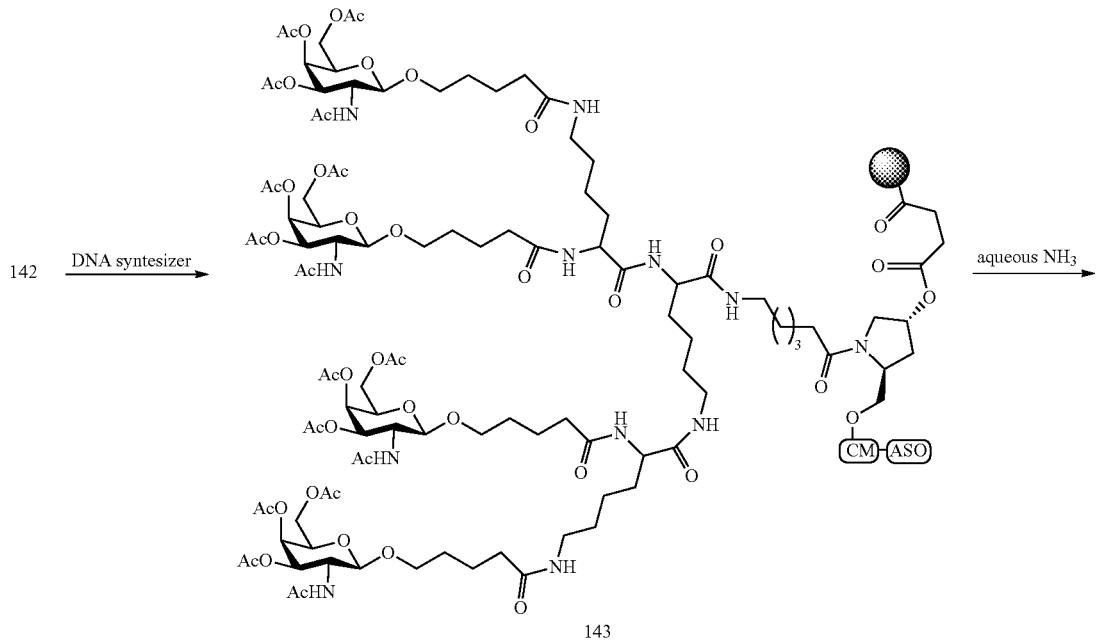

-continued

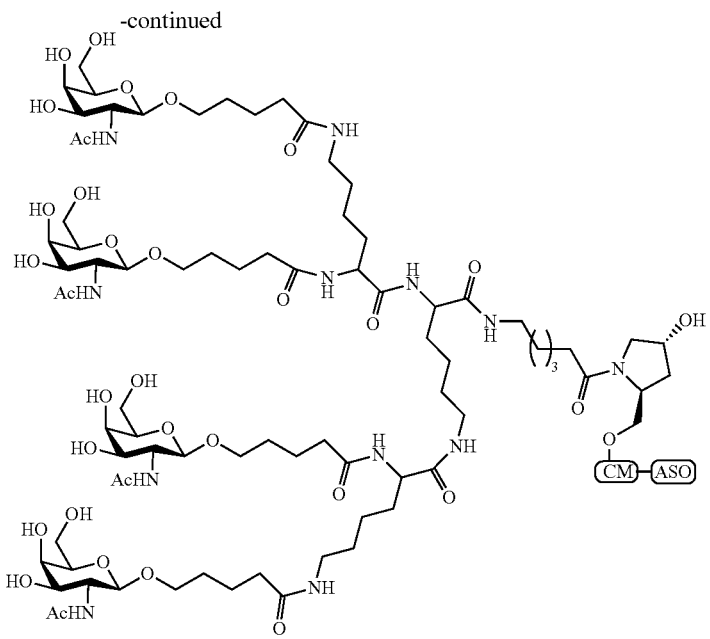

144

The solid support bound compound 143 was synthesized using standard solid phase synthesis on a DNA synthesizer.

The solid support bound compound 143 was suspended in aqueous ammonia (28-30 wt %) and heated at 55° C. for 16 h. The solution was cooled and the solid support was filtered. The filtrate was concentrated and the residue dissolved in water and purified by HPLC on a strong anion exchange column. The fractions containing full length compound 144 were pooled together and desalted. The resulting GalNAc$_4$-11 conjugated oligomeric compound was analyzed by LC-MS and the observed mass was consistent with structure.

The GalNAc$_4$ cluster portion of the conjugate group GalNAc$_4$-11 (GalNAc$_4$-11$_a$) can be combined with any cleavable moiety to provide a variety of conjugate groups. In certain embodiments, the cleavable moiety is —P(=O)(OH)-A$_d$-P(=O)(OH)—.

The structure of GalNAc$_4$-11 (GalNAc$_4$-11$_a$-CM) is shown below:

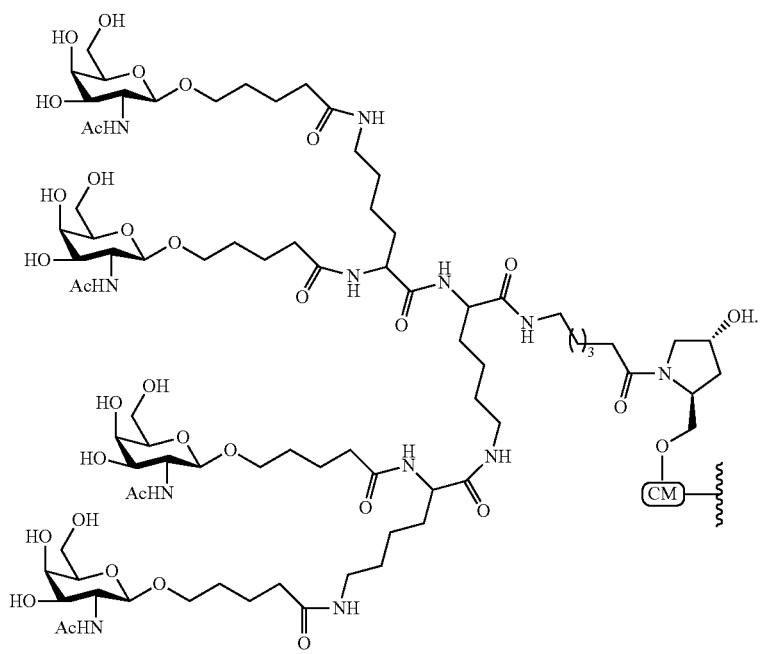

Example 51: Preparation of Oligonucleotide 155 Comprising GalNAc$_3$-6
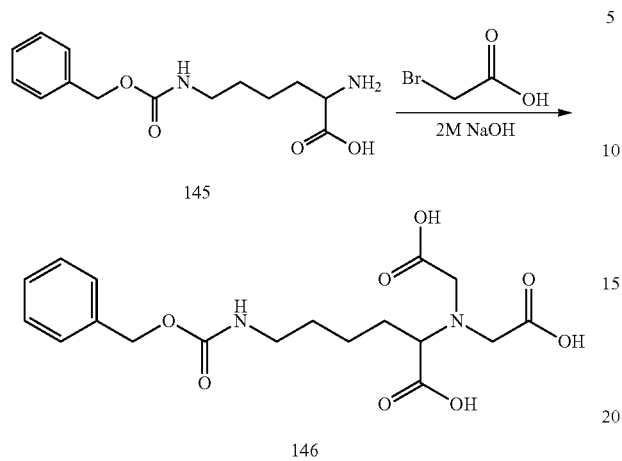
Compound 146 was synthesized as described in the literature (*Analytical Biochemistry* 1995, 229, 54-60).
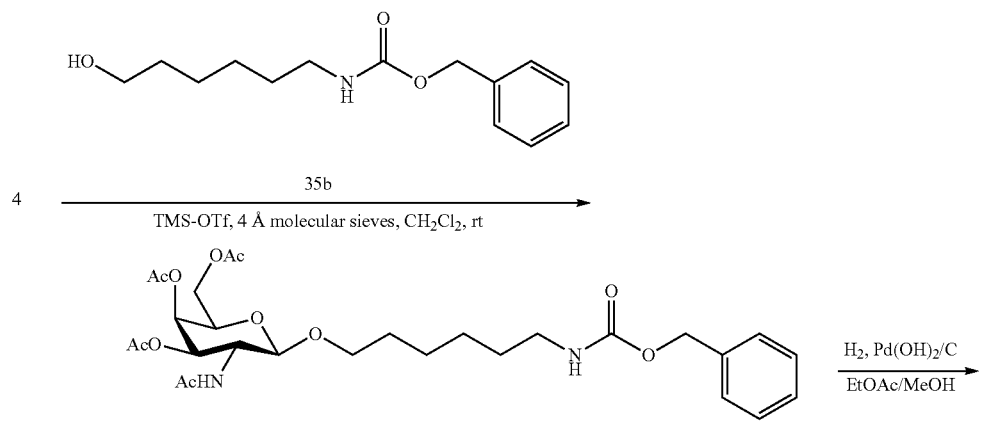
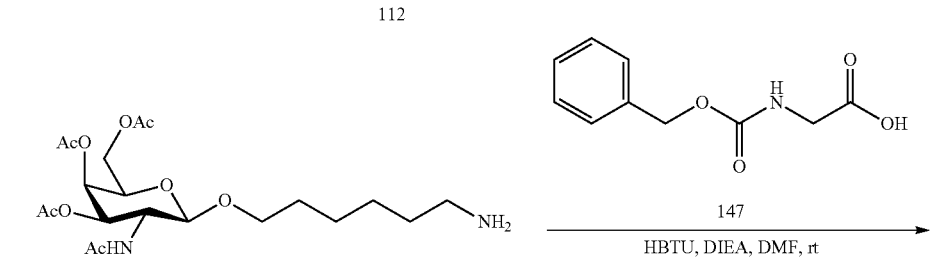
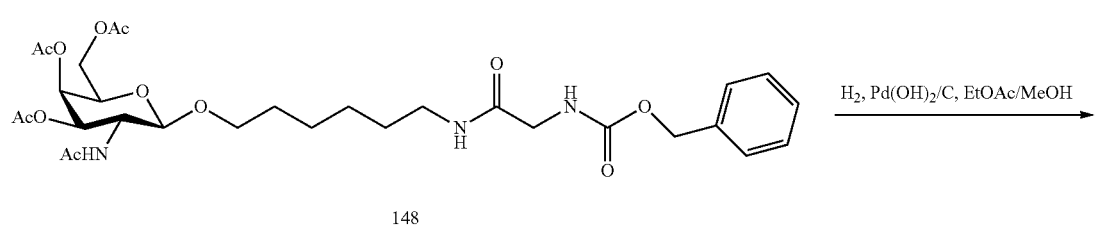

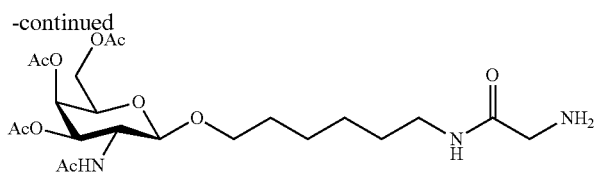

149

Compound 4 (15 g, 45.55 mmol) and compound 35b (14.3 grams, 57 mmol) were dissolved in CH$_2$Cl$_2$ (200 ml). Activated molecular sieves (4 Å. 2 g, powdered) were added, and the reaction was allowed to stir for 30 minutes under nitrogen atmosphere. TMS-OTf was added (4.1 ml, 22.77 mmol) and the reaction was allowed to stir at room temp overnight. Upon completion, the reaction was quenched by pouring into solution of saturated aqueous NaHCO$_3$ (500 ml) and crushed ice (~150 g). The organic layer was separated, washed with brine, dried over MgSO$_4$, filtered, and was concentrated to an orange oil under reduced pressure. The crude material was purified by silica gel column chromatography and eluted with 2-10% MeOH in CH$_2$Cl$_2$ to yield Compound 112 (16.53 g, 63%). LCMS and $^1$H NMR were consistent with the expected compound.

Compound 112 (4.27 g, 7.35 mmol) was dissolved in 1:1 MeOH/EtOAc (40 ml). The reaction mixture was purged by bubbling a stream of argon through the solution for 15 minutes. Pearlman's catalyst (palladium hydroxide on carbon, 400 mg) was added, and hydrogen gas was bubbled through the solution for 30 minutes. Upon completion (TLC 10% MeOH in CH$_2$Cl$_2$, and LCMS), the catalyst was removed by filtration through a pad of celite. The filtrate was concentrated by rotary evaporation, and was dried briefly under high vacuum to yield Compound 105a (3.28 g). LCMS and 1H NMR were consistent with desired product.

Compound 147 (2.31 g, 11 mmol) was dissolved in anhydrous DMF (100 mL). N,N-Diisopropylethylamine (DIEA, 3.9 mL, 22 mmol) was added, followed by HBTU (4 g, 10.5 mmol). The reaction mixture was allowed to stir for ~15 minutes under nitrogen. To this a solution of compound 105a (3.3 g, 7.4 mmol) in dry DMF was added and stirred for 2 h under nitrogen atmosphere. The reaction was diluted with EtOAc and washed with saturated aqueous NaHCO$_3$ and brine. The organics phase was separated, dried (MgSO$_4$), filtered, and concentrated to an orange syrup. The crude material was purified by column chromatography 2-5% MeOH in CH$_2$Cl$_2$ to yield Compound 148 (3.44 g, 73%). LCMS and $^1$H NMR were consistent with the expected product.

Compound 148 (3.3 g, 5.2 mmol) was dissolved in 1:1 MeOH/EtOAc (75 ml). The reaction mixture was purged by bubbling a stream of argon through the solution for 15 minutes. Pearlman's catalyst (palladium hydroxide on carbon) was added (350 mg). Hydrogen gas was bubbled through the solution for 30 minutes. Upon completion (TLC 10% MeOH in DCM, and LCMS), the catalyst was removed by filtration through a pad of celite. The filtrate was concentrated by rotary evaporation, and was dried briefly under high vacuum to yield Compound 149 (2.6 g). LCMS was consistent with desired product. The residue was dissolved in dry DMF (10 ml) was used immediately in the next step.

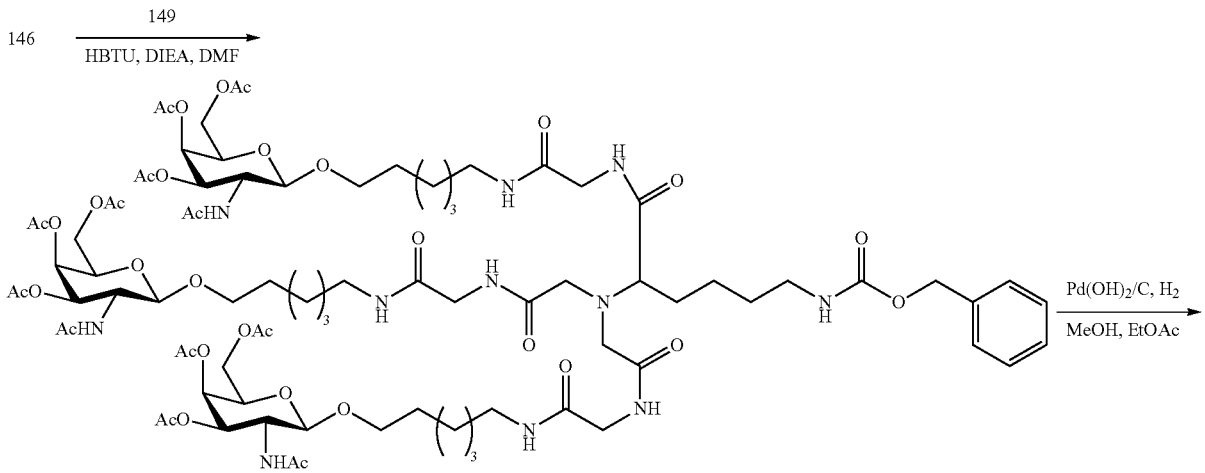

-continued

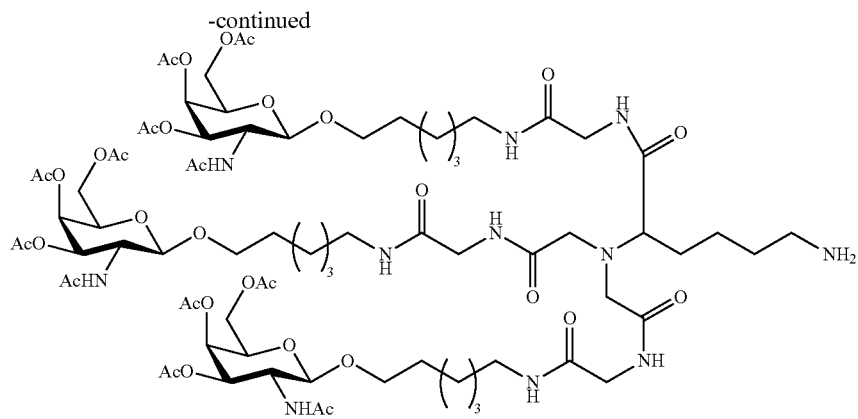

151

Compound 146 (0.68 g, 1.73 mmol) was dissolved in dry DMF (20 ml). To this DIEA (450 µL, 2.6 mmol, 1.5 eq.) and HBTU (1.96 g, 0.5.2 mmol) were added. The reaction mixture was allowed to stir for 15 minutes at room temperature under nitrogen. A solution of compound 149 (2.6 g) in anhydrous DMF (10 mL) was added. The pH of the reaction was adjusted to pH=9-10 by addition of DIEA (if necessary). The reaction was allowed to stir at room temperature under nitrogen for 2 h. Upon completion the reaction was diluted with EtOAc (100 mL), and washed with aqueous saturated aqueous NaHCO$_3$, followed by brine. The organic phase was separated, dried over MgSO$_4$, filtered, and concentrated. The residue was purified by silica gel column chromatography and eluted with 2-10% MeOH in CH$_2$C$_2$ to yield Compound 150 (0.62 g, 20%). LCMS and $^1$H NMR were consistent with the desired product.

Compound 150 (0.62 g) was dissolved in 1:1 MeOH/EtOAc (5 L). The reaction mixture was purged by bubbling a stream of argon through the solution for 15 minutes. Pearlman's catalyst (palladium hydroxide on carbon) was added (60 mg). Hydrogen gas was bubbled through the solution for 30 minutes. Upon completion (TLC 10% MeOH in DCM, and LCMS), the catalyst was removed by filtration (syringe-tip Teflon filter, 0.45 µm). The filtrate was concentrated by rotary evaporation, and was dried briefly under high vacuum to yield Compound 151 (0.57 g). The LCMS was consistent with the desired product. The product was dissolved in 4 mL dry DMF and was used immediately in the next step.

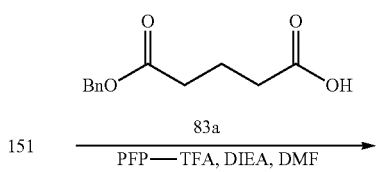

151 $\xrightarrow[\text{PFP—TFA, DIEA, DMF}]{\text{83a}}$

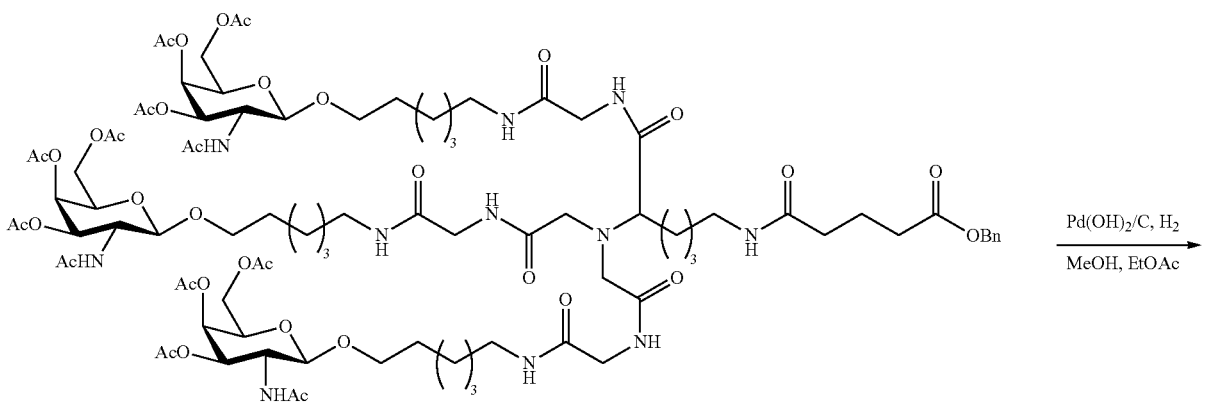

152

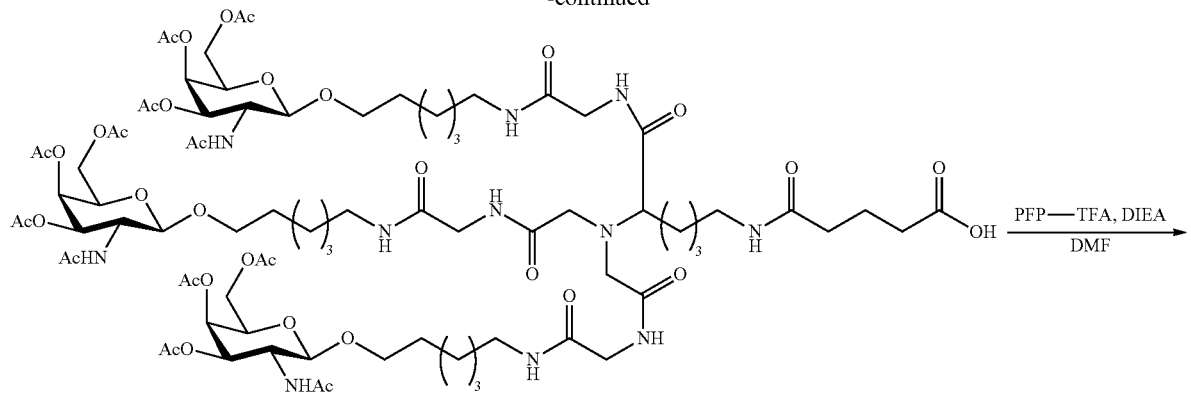

153

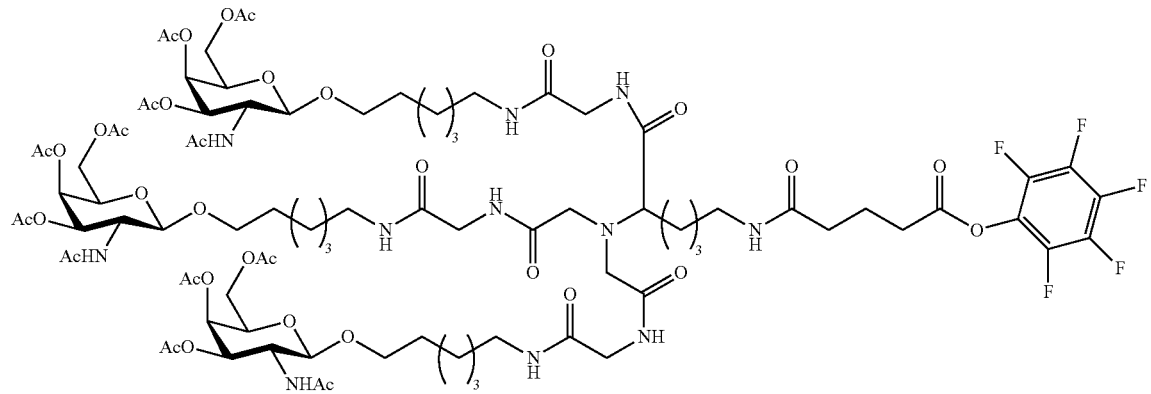

154

Compound 83a (0.11 g, 0.33 mmol) was dissolved in anhydrous DMF (5 mL) and N,N-Diisopropylethylamine (75 µL, 1 mmol) and PFP-TFA (90 µL, 0.76 mmol) were added. The reaction mixture turned magenta upon contact, and gradually turned orange over the next 30 minutes. Progress of reaction was monitored by TLC and LCMS. Upon completion (formation of the PFP ester), a solution of compound 151 (0.57 g, 0.33 mmol) in DMF was added. The pH of the reaction was adjusted to pH=9-10 by addition of N,N-Diisopropylethylamine (if necessary). The reaction mixture was stirred under nitrogen for ~30 min. Upon completion, the majority of the solvent was removed under reduced pressure. The residue was diluted with $CH_2Cl_2$ and washed with aqueous saturated $NaHCO_3$, followed by brine. The organic phase separated, dried over $MgSO_4$, filtered, and concentrated to an orange syrup. The residue was purified by silica gel column chromatography (2-10% MeOH in $CH_2Cl_2$) to yield Compound 152 (0.35 g, 55%). LCMS and $^1H$ NMR were consistent with the desired product.

Compound 152 (0.35 g, 0.182 mmol) was dissolved in 1:1 MeOH/EtOAc (10 mL). The reaction mixture was purged by bubbling a stream of argon thru the solution for 15 minutes. Pearlman's catalyst (palladium hydroxide on carbon) was added (35 mg). Hydrogen gas was bubbled thru the solution for 30 minutes. Upon completion (TLC 10% MeOH in DCM, and LCMS), the catalyst was removed by filtration (syringe-tip Teflon filter, 0.45 µm). The filtrate was concentrated by rotary evaporation, and was dried briefly under high vacuum to yield Compound 153 (0.33 g, quantitative). The LCMS was consistent with desired product.

Compound 153 (0.33 g, 0.18 mmol) was dissolved in anhydrous DMF (5 mL) with stirring under nitrogen. To this N,N-Diisopropylethylamine (65 µL, 0.37 mmol) and PFP-TFA (35 µL, 0.28 mmol) were added. The reaction mixture was stirred under nitrogen for ~30 min. The reaction mixture turned magenta upon contact, and gradually turned orange. The pH of the reaction mixture was maintained at pH=9-10 by adding more N,-Diisopropylethylamine. The progress of the reaction was monitored by TLC and LCMS. Upon completion, the majority of the solvent was removed under reduced pressure. The residue was diluted with $CH_2C_2$ (50 mL), and washed with saturated aqueous $NaHCO_3$, followed by brine. The organic layer was dried over $MgSO_4$, filtered, and concentrated to an orange syrup. The residue was purified by column chromatography and eluted with 2-10% MeOH in $CH_2Cl_2$ to yield Compound 154 (0.29 g, 79%). LCMS and $^1H$ NMR were consistent with the desired product.

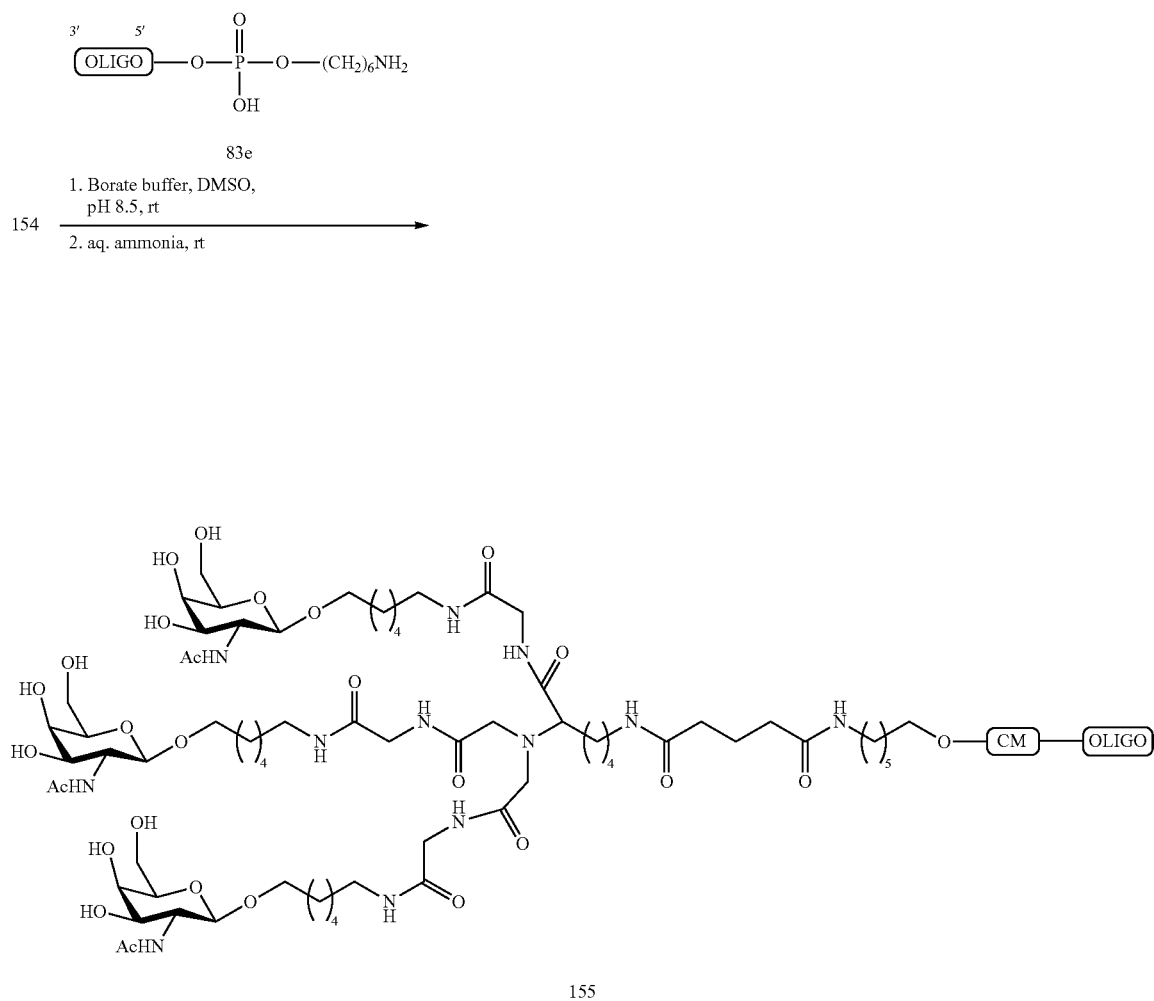

Oligomeric Compound 155, comprising a GalNAc$_3$-6 conjugate group, was prepared using the general procedures illustrated in Example 46. The GalNAc$_3$ cluster portion of the conjugate group GalNAc$_3$-6 (GalNAc$_3$-6$_a$) can be combined with any cleavable moiety to provide a variety of conjugate groups. In certain embodiments, the cleavable moiety is —P(=O)(OH)-A$_d$-P(=O)(OH)—.

The structure of GalNAc$_3$-6 (GalNAc$_3$-6$_a$-CM-) is shown below:

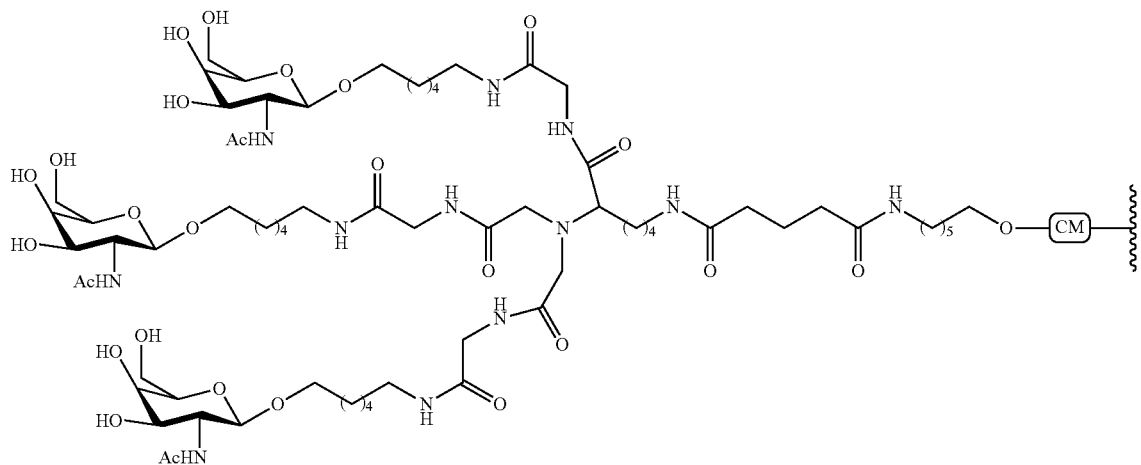

Example 52: Preparation of Oligonucleotide 160 Comprising GalNAc₃-9

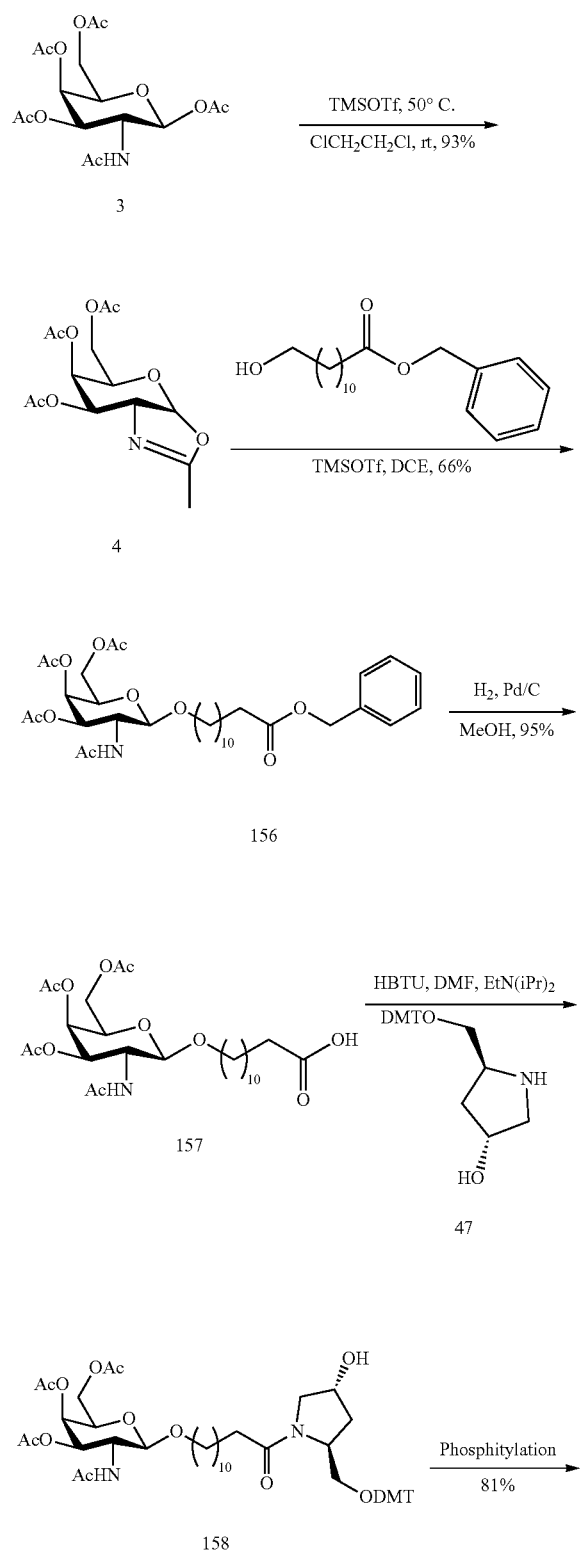

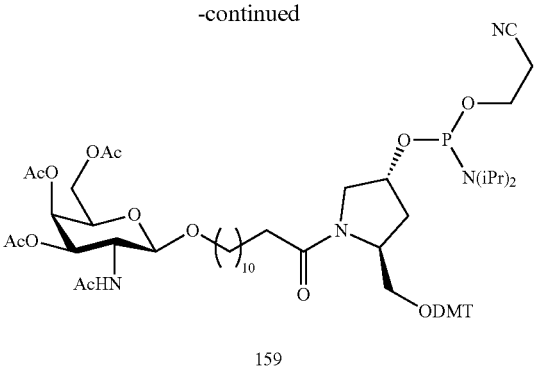

Compound 156 was synthesized following the procedure described in the literature (*J. Med. Chem.* 2004, 47, 5798-5808).

Compound 156, (18.60 g, 29.28 mmol) was dissolved in methanol (200 mL). Palladium on carbon (6.15 g, 10 wt %, loading (dry basis), matrix carbon powder, wet) was added. The reaction mixture was stirred at room temperature under hydrogen for 18 h. The reaction mixture was filtered through a pad of celite and the celite pad was washed thoroughly with methanol. The combined filtrate was washed and concentrated to dryness. The residue was purified by silica gel column chromatography and eluted with 5-10% methanol in dichloromethane to yield Compound 157 (14.26 g, 89%). Mass m z 544.1 [M–H]⁻.

Compound 157 (5 g, 9.17 mmol) was dissolved in anhydrous DMF (30 mL). HBTU (3.65 g, 9.61 mmol) and N,N-Diisopropylethylamine (13.73 mL, 78.81 mmol) were added and the reaction mixture was stirred at room temperature for 5 minutes. To this a solution of compound 47 (2.96 g, 7.04 mmol) was added. The reaction was stirred at room temperature for 8 h. The reaction mixture was poured into a saturated NaHCO₃ aqueous solution. The mixture was extracted with ethyl acetate and the organic layer was washed with brine and dried (Na₂SO₄), filtered and evaporated. The residue obtained was purified by silica gel column chromatography and eluted with 50% ethyl acetate in hexane to yield compound 158 (8.25 g, 73.3%). The structure was confirmed by MS and ¹H NMR analysis.

Compound 158 (7.2 g, 7.61 mmol) was dried over P₂O₅ under reduced pressure. The dried compound was dissolved in anhydrous DMF (50 mL). To this 1H-tetrazole (0.43 g, 6.09 mmol) and N-methylimidazole (0.3 mL, 3.81 mmol) and 2-cyanoethyl-N,N,N',N'-tetraisopropyl phosphorodiamidite (3.65 mL, 11.50 mmol) were added. The reaction mixture was stirred t under an argon atmosphere for 4 h. The reaction mixture was diluted with ethyl acetate (200 mL). The reaction mixture was washed with saturated NaHCO₃ and brine. The organic phase was separated, dried (Na₂SO₄), filtered and evaporated. The residue was purified by silica gel column chromatography and eluted with 50-90% ethyl acetate in hexane to yield Compound 159 (7.82 g, 80.5%). The structure was confirmed by LCMS and ³¹P NMR analysis.

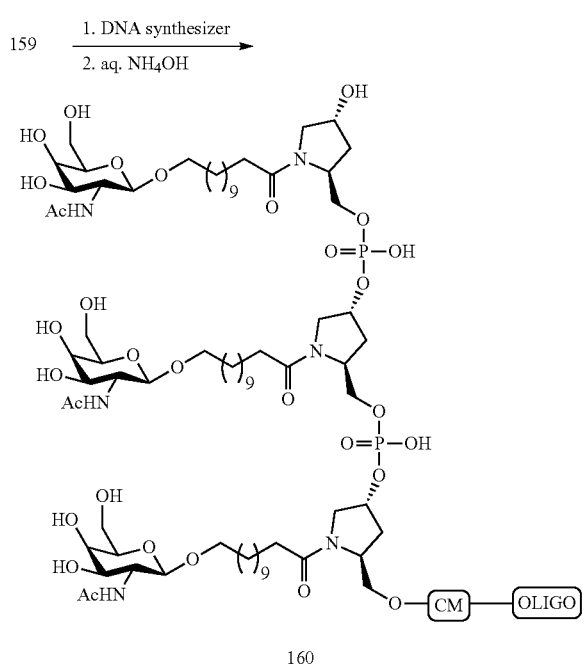

Oligomeric Compound 160, comprising a GalNAc₃-9 conjugate group, was prepared using standard oligonucleotide synthesis procedures. Three units of compound 159 were coupled to the solid support, followed by nucleotide phosphoramidites. Treatment of the protected oligomeric compound with aqueous ammonia yielded compound 160. The GalNAc₃ cluster portion of the conjugate group GalNAc₃-9 (GalNAc₃-9$_a$) can be combined with any cleavable moiety to provide a variety of conjugate groups. In certain embodiments, the cleavable moiety is —P(=O)(OH)-A$_d$-P(=O)(OH)—. The structure of GalNAc₃-9 (GalNAc₃-9$_a$-CM) is shown below:

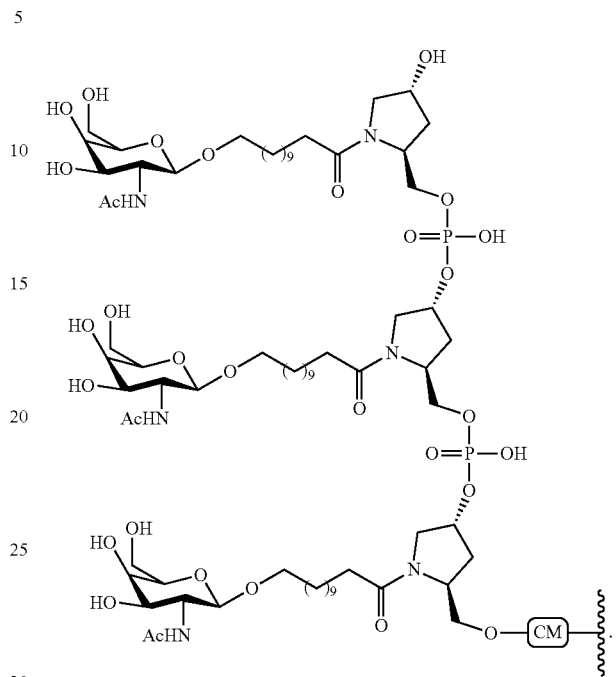

Example 53: Alternate Procedure for Preparation of Compound 18 (GalNAc₃-1a and GalNAc₃-3a)

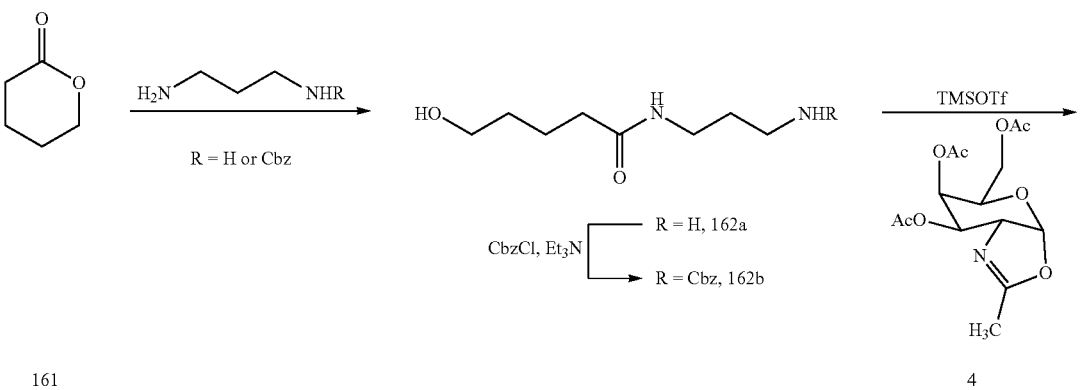

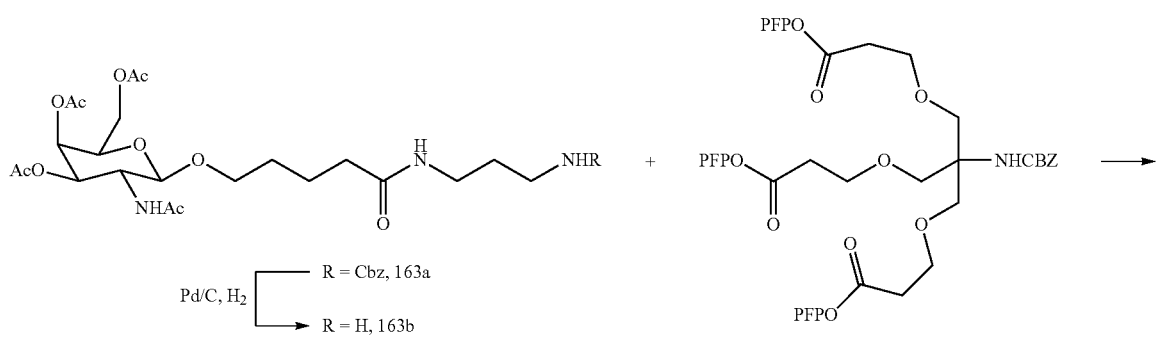

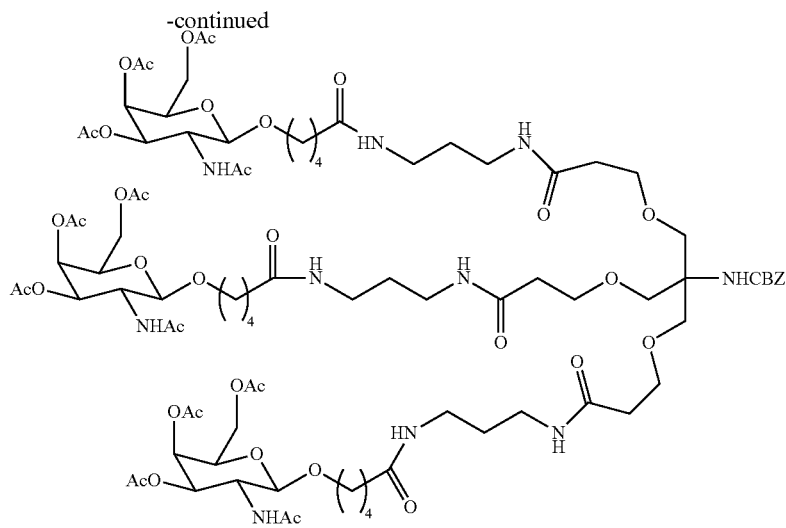

18

Lactone 161 was reacted with diamino propane (3-5 eq) or Mono-Boc protected diamino propane (1 eq) to provide alcohol 162a or 162b. When unprotected propanediamine was used for the above reaction, the excess diamine was removed by evaporation under high vacuum and the free amino group in 162a was protected using CbzCl to provide 162b as a white solid after purification by column chromatography. Alcohol 162b was further reacted with compound 4 in the presence of TMSOTf to provide 163a which was converted to 163b by removal of the Cbz group using catalytic hydrogenation. The pentafluorophenyl (PFP) ester 164 was prepared by reacting triacid 113 (see Example 48) with PFPTFA (3.5 eq) and pyridine (3.5 eq) in DMF (0.1 to 0.5 M). The triester 164 was directly reacted with the amine 163b (3-4 eq) and DIPEA (3-4 eq) to provide Compound 18. The above method greatly facilitates purification of intermediates and minimizes the formation of byproducts which are formed using the procedure described in Example 4.

Example 54: Alternate Procedure for Preparation of Compound 18 (GalNAc$_3$-1a and GalNAc$_3$-3a)

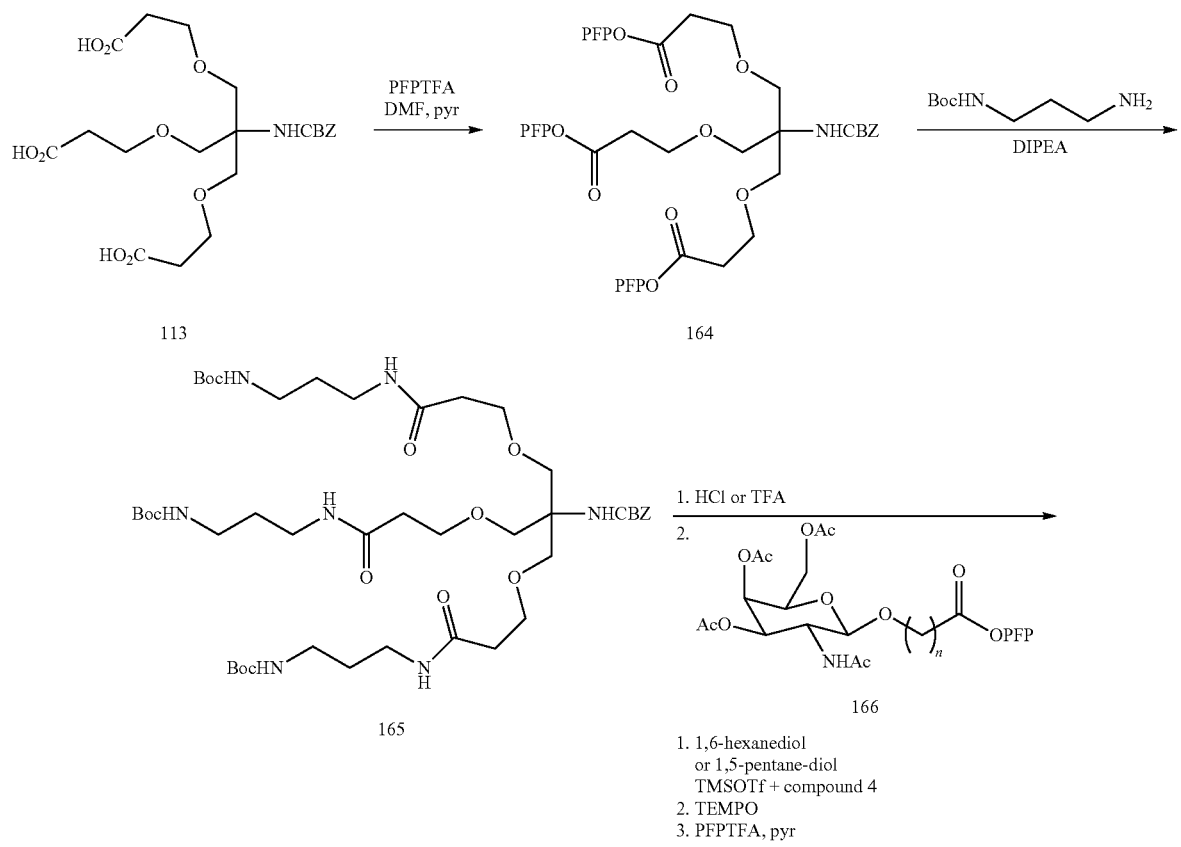

-continued

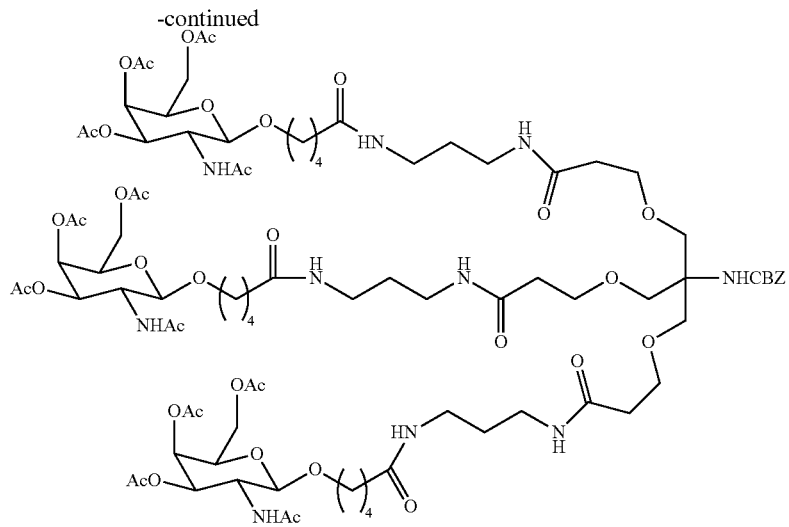

18

The triPFP ester 164 was prepared from acid 113 using the procedure outlined in example 53 above and reacted with mono-Boc protected diamine to provide 165 in essentially quantitative yield. The Boc groups were removed with hydrochloric acid or trifluoroacetic acid to provide the triamine which was reacted with the PFP activated acid 166 in the presence of a suitable base such as DIPEA to provide Compound 18.

The PFP protected Gal-NAc acid 166 was prepared from the corresponding acid by treatment with PFPTFA (1-1.2 eq) and pyridine (1-1.2 eq) in DMF. The precursor acid in turn was prepared from the corresponding alcohol by oxidation using TEMPO (0.2 eq) and BAIB in acetonitrile and water. The precursor alcohol was prepared from sugar intermediate 4 by reaction with 1,6-hexanediol (or 1,5-pentanediol or other diol for other n values) (2-4 eq) and TMSOTf using conditions described previously in example 47.

Example 55: Dose-Dependent Study of Oligonucleotides Comprising Either a 3' or 5'-Conjugate Group (Comparison of GalNAc$_3$-1, 3, 8 and 9) Targeting SRB-1 In Vivo The oligonucleotides listed below were tested in a dose-dependent study for antisense inhibition of SRB-1 in mice. Unconjugated ISIS 353382 was included as a standard. Each of the various GalNAc$_3$ conjugate groups was attached at either the 3' or 5' terminus of the respective oligonucleotide by a phosphodiester linked 2'-deoxyadenosine nucleoside (cleavable moiety).

TABLE 39

Modified ASO targeting SRB-1

| ASO | Sequence (5' to 3') | Motif | Conjugate | SEQ ID No. |
|---|---|---|---|---|
| ISIS 353382 (parent) | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | 5/10/5 | none | 829 |
| ISIS 655861 | $G_{es}{}^mC_{es}T_{es}T_{es}{}^mC_{es}A_{ds}G_{ds}T_{ds}{}^mC_{ds}A_{ds}T_{ds}G_{ds}A_{ds}$ $^mC_{ds}T_{ds}T_{es}{}^mC_{es}{}^mC_{es}T_{es}T_{eo}A_{do}$'-GalNAc$_3$-1$_a$ | 5/10/5 | GalNAc$_3$-1 | 830 |
| ISIS 664078 | $G_{es}{}^mC_{es}T_{es}T_{es}{}^mC_{es}A_{ds}G_{ds}T_{ds}{}^mC_{ds}A_{ds}T_{ds}G_{ds}A_{ds}$ $^mC_{ds}T_{ds}T_{es}{}^mC_{es}{}^mC_{es}T_{es}T_{eo}A_{do}$'-GalNAc$_3$-9$_a$ | 5/10/5 | GalNAc$_3$-9 | 830 |
| ISIS 661161 | GalNAc$_3$-3$_a$-$_o$,A$_{do}$ $G_{es}{}^mC_{es}T_{es}T_{es}{}^mC_{es}A_{ds}G_{ds}T_{ds}{}^mC_{ds}A_{ds}T_{ds}G_{ds}A_{ds}$ $^mC_{ds}T_{ds}T_{es}{}^mC_{es}{}^mC_{es}T_{es}T_e$ | 5/10/5 | GalNAc$_3$-3 | 831 |
| ISIS 665001 | GalNAc$_3$-8$_a$-$_o$,A$_{do}$ $G_{es}{}^mC_{es}T_{es}T_{es}{}^mC_{es}A_{ds}G_{ds}T_{ds}{}^mC_{ds}A_{ds}T_{ds}G_{ds}A_{ds}$ $^mC_{ds}T_{ds}T_{es}{}^mC_{es}{}^mC_{es}T_{es}T_e$ | 5/10/5 | GalNAc$_3$-8 | 831 |

Capital letters indicate the nucleobase for each nucleoside and $^mC$ indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-1$_a$ was shown previously in Example 9. The structure of GalNAc$_3$-9 was shown previously in Example 52. The structure of GalNAc$_3$-3 was shown previously in Example 39. The structure of GalNAc$_3$-8 was shown previously in Example 47.

Treatment

Six week old male Balb/c mice (Jackson Laboratory, Bar Harbor, Me.) were injected subcutaneously once at the dosage shown below with ISIS 353382, 655861, 664078, 661161, 665001 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, Oreg.) according to standard protocols. The results below are presented as the average percent of SRB-1 mRNA levels for each treatment group, normalized to the saline control.

As illustrated in Table 40, treatment with antisense oligonucleotides lowered SRB-1 mRNA levels in a dose-dependent manner. Indeed, the antisense oligonucleotides comprising the phosphodiester linked GalNAc$_3$-1 and GalNAc$_3$-9 conjugates at the 3' terminus (ISIS 655861 and ISIS 664078) and the GalNAc$_3$-3 and GalNAc$_3$-8 conjugates linked at the 5' terminus (ISIS 661161 and ISIS 665001) showed substantial improvement in potency compared to the unconjugated antisense oligonucleotide (ISIS 353382). Furthermore, ISIS 664078, comprising a GalNAc$_3$-9 conjugate at the 3' terminus was essentially equipotent compared to ISIS 655861, which comprises a GalNAc$_3$-1 conjugate at the 3' terminus. The 5' conjugated antisense oligonucleotides, ISIS 661161 and ISIS 665001, comprising a GalNAc$_3$-3 or GalNAc$_3$-9, respectively, had increased potency compared to the 3' conjugated antisense oligonucleotides (ISIS 655861 and ISIS 664078).

TABLE 40

ASOs containing GalNAc$_3$-1, 3, 8 or 9 targeting SRB-1

| ISIS No. | Dosage (mg/kg) | SRB-1 mRNA (% Saline) | Conjugate |
|---|---|---|---|
| Saline | n/a | 100 | |
| 353382 | 3 | 88 | none |
|  | 10 | 68 | |
|  | 30 | 36 | |
| 655861 | 0.5 | 98 | GalNac$_3$-1 (3') |
|  | 1.5 | 76 | |
|  | 5 | 31 | |
|  | 15 | 20 | |
| 664078 | 0.5 | 88 | GalNac$_3$-9 (3') |
|  | 1.5 | 85 | |
|  | 5 | 46 | |
|  | 15 | 20 | |
| 661161 | 0.5 | 92 | GalNac$_3$-3 (5') |
|  | 1.5 | 59 | |
|  | 5 | 19 | |
|  | 15 | 11 | |
| 665001 | 0.5 | 100 | GalNac$_3$-8 (5') |
|  | 1.5 | 73 | |
|  | 5 | 29 | |
|  | 15 | 13 | |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in the table below.

TABLE 41

| ISIS No. | Dosage mg/kg | ALT | AST | Total Bilirubin | BUN | Conjugate |
|---|---|---|---|---|---|---|
| Saline | | 24 | 59 | 0.1 | 37.52 | |
| 353382 | 3 | 21 | 66 | 0.2 | 34.65 | none |
|  | 10 | 22 | 54 | 0.2 | 34.2 | |
|  | 30 | 22 | 49 | 0.2 | 33.72 | |
| 655861 | 0.5 | 25 | 62 | 0.2 | 30.65 | GalNac$_3$-1 (3') |
|  | 1.5 | 23 | 48 | 0.2 | 30.97 | |
|  | 5 | 28 | 49 | 0.1 | 32.92 | |
|  | 15 | 40 | 97 | 0.1 | 31.62 | |
| 664078 | 0.5 | 40 | 74 | 0.1 | 35.3 | GalNac$_3$-9 (3') |
|  | 1.5 | 47 | 104 | 0.1 | 32.75 | |
|  | 5 | 20 | 43 | 0.1 | 30.62 | |
|  | 15 | 38 | 92 | 0.1 | 26.2 | |
| 661161 | 0.5 | 101 | 162 | 0.1 | 34.17 | GalNac$_3$-3 (5') |
|  | 1.5 g | 42 | 100 | 0.1 | 33.37 | |
|  | 5 g | 23 | 99 | 0.1 | 34.97 | |
|  | 15 | 53 | 83 | 0.1 | 34.8 | |
| 665001 | 0.5 | 28 | 54 | 0.1 | 31.32 | GalNac$_3$-8 (5') |
|  | 1.5 | 42 | 75 | 0.1 | 32.32 | |
|  | 5 | 24 | 42 | 0.1 | 31.85 | |
|  | 15 | 32 | 67 | 0.1 | 31. | |

Example 56: Dose-Dependent Study of Oligonucleotides Comprising Either a 3' or 5'-Conjugate Group (Comparison of GalNAc$_3$-1, 2, 3, 5, 6, 7 and 10) Targeting SRB-1 In Vivo The oligonucleotides listed below were tested in a dose-dependent study for antisense inhibition of SRB-1 in mice. Unconjugated ISIS 353382 was included as a standard. Each of the various GalNAc$_3$ conjugate groups was attached at the 5' terminus of the respective oligonucleotide by a phosphodiester linked 2'-deoxyadenosine nucleoside (cleavable moiety) except for ISIS 655861 which had the GalNAc$_3$ conjugate group attached at the 3' terminus.

TABLE 42

Modified ASO targeting SRB-1

| ASO | Sequence (5' to 3') | Motif | Conjugate | SEQ ID No. |
|---|---|---|---|---|
| ISIS 353382 (parent) | $G_{es}{}^mC_{es}T_{es}T_{es}{}^mC_{es}A_{ds}G_{ds}T_{ds}{}^mC_{ds}A_{ds}T_{ds}G_{ds}A_{ds}$ ${}^mC_{ds}T_{ds}T_{es}{}^mC_{es}{}^mC_{es}T_{es}T_e$ | 5/10/5 | no conjugate | 829 |
| ISIS 655861 | $G_{es}{}^mC_{es}T_{es}T_{es}{}^mC_{es}A_{ds}G_{ds}T_{ds}{}^mC_{ds}A_{ds}T_{ds}G_{ds}A_{ds}$ ${}^mC_{ds}T_{ds}T_{es}{}^mC_{es}{}^mC_{es}T_{es}T_{eo}A_{do}$'-GalNAc$_3$-1$_a$ | 5/10/5 | GalNAc$_3$-1 | 830 |
| ISIS 664507 | GalNAc$_3$-2$_a$-$_o$' $A_{do}G_{es}{}^mC_{es}T_{es}T_{es}{}^mC_{es}A_{ds}G_{ds}T_{ds}$ ${}^mC_{ds}A_{ds}T_{ds}G_{ds}A_{ds}{}^mC_{ds}T_{ds}T_{es}{}^mC_{es}{}^mC_{es}T_{es}T_e$ | 5/10/5 | GalNAc$_3$-2 | 831 |
| ISIS 661161 | GalNAc$_3$-3$_a$-$_o$,A$_{do}$ $G_{es}{}^mC_{es}T_{es}T_{es}{}^mC_{es}A_{ds}G_{ds}T_{ds}{}^mC_{ds}A_{ds}T_{ds}G_{ds}A_{ds}$ ${}^mC_{ds}T_{ds}T_{es}{}^mC_{es}{}^mC_{es}T_{es}T_e$ | 5/10/5 | GalNAc$_3$-3 | 831 |
| ISIS 666224 | GalNAc$_3$-5$_a$-$_o$' $A_{do}G_{es}{}^mC_{es}T_{es}T_{es}{}^mC_{es}A_{ds}G_{ds}T_{ds}$ ${}^mC_{ds}A_{ds}T_{ds}G_{ds}A_{ds}{}^mC_{ds}T_{ds}T_{es}{}^mC_{es}{}^mC_{es}T_{es}T_e$ | 5/10/5 | GalNAc$_3$-5 | 831 |
| ISIS 666961 | GalNAc$_3$-6$_a$-$_o$' $A_{do}G_{es}{}^mC_{es}T_{es}T_{es}{}^mC_{es}A_{ds}G_{ds}T_{ds}$ ${}^mC_{ds}A_{ds}T_{ds}G_{ds}A_{ds}{}^mC_{ds}T_{ds}T_{es}{}^mC_{es}{}^mC_{es}T_{es}T_e$ | 5/10/5 | GalNAc$_3$-6 | 831 |
| ISIS 666981 | GalNAc$_3$-7$_a$-$_o$' $A_{do}G_{es}{}^mC_{es}T_{es}T_{es}{}^mC_{es}A_{ds}G_{ds}T_{ds}$ ${}^mC_{ds}A_{ds}T_{ds}G_{ds}A_{ds}{}^mC_{ds}T_{ds}T_{es}{}^mC_{es}{}^mC_{es}T_{es}T_e$ | 5/10/5 | GalNAc$_3$-7 | 831 |
| ISIS 666881 | GalNAc$_3$-10$_a$-$_o$' $A_{do}G_{es}{}^mC_{es}T_{es}T_{es}{}^mC_{es}A_{ds}G_{ds}T_{ds}$ ${}^mC_{ds}A_{ds}T_{ds}G_{ds}A_{ds}{}^mC_{ds}T_{ds}T_{es}{}^mC_{es}{}^mC_{es}T_{es}T_e$ | 5/10/5 | GalNAc$_3$-10 | 831 |

Capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-1$_a$ was shown previously in Example 9. The structure of GalNAc$_3$-2$_a$ was shown previously in Example 37. The structure of GalNAc$_3$-3$_a$ was shown previously in Example 39. The structure of GalNAc$_3$-5$_a$ was shown previously in Example 49. The structure of GalNAc$_3$-6$_a$ was shown previously in Example 51. The structure of GalNAc$_3$-7$_a$ was shown previously in Example 48. The structure of GalNAc$_3$-10$_a$ was shown previously in Example 46.

Treatment

Six week old male Balb/c mice (Jackson Laboratory, Bar Harbor, Me.) were injected subcutaneously once at the dosage shown below with ISIS 353382, 655861, 664507, 661161, 666224, 666961, 666981, 666881 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, Oreg.) according to standard protocols. The results below are presented as the average percent of SRB-1 mRNA levels for each treatment group, normalized to the saline control.

As illustrated in Table 43, treatment with antisense oligonucleotides lowered SRB-1 mRNA levels in a dose-dependent manner. Indeed, the conjugated antisense oligonucleotides showed substantial improvement in potency compared to the unconjugated antisense oligonucleotide (ISIS 353382). The 5' conjugated antisense oligonucleotides showed a slight increase in potency compared to the 3' conjugated antisense oligonucleotide.

TABLE 43

| ISIS No. | Dosage (mg/kg) | SRB-1 mRNA (% Saline) | Conjugate |
|---|---|---|---|
| Saline | n/a | 100.0 | |
| 353382 | 3 | 96.0 | none |
| | 10 | 73.1 | |
| | 30 | 36.1 | |
| 655861 | 0.5 | 99.4 | GalNac$_3$-1 (3') |
| | 1.5 | 81.2 | |
| | 5 | 33.9 | |
| | 15 | 15.2 | |
| 664507 | 0.5 | 102.0 | GalNAc$_3$-2 (5') |
| | 1.5 | 73.2 | |
| | 5 | 31.3 | |
| | 15 | 10.8 | |
| 661161 | 0.5 | 90.7 | GalNAc$_3$-3 (5') |
| | 1.5 | 67.6 | |
| | 5 | 24.3 | |
| | 15 | 11.5 | |
| 666224 | 0.5 | 96.1 | GalNAc$_3$-5 (5') |
| | 1.5 | 61.6 | |
| | 5 | 25.6 | |
| | 15 | 11.7 | |
| 666961 | 0.5 | 85.5 | GalNAc$_3$-6 (5') |
| | 1.5 | 56.3 | |
| | 5 | 34.2 | |
| | 15 | 13.1 | |
| 666981 | 0.5 | 84.7 | GalNAc$_3$-7 (5') |
| | 1.5 | 59.9 | |
| | 5 | 24.9 | |
| | 15 | 8.5 | |
| 666881 | 0.5 | 100.0 | GalNAc$_3$-10 (5') |
| | 1.5 | 65.8 | |
| | 5 | 26.0 | |
| | 15 | 13.0 | |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in Table 44 below.

TABLE 44

| ISIS No. | Dosage mg/kg | ALT | AST | Total Bilirubin | BUN | Conjugate |
|---|---|---|---|---|---|---|
| Saline |  | 26 | 57 | 0.2 | 27 |  |
| 353382 | 3 | 25 | 92 | 0.2 | 27 | none |
|  | 10 | 23 | 40 | 0.2 | 25 |  |
|  | 30 | 29 | 54 | 0.1 | 28 |  |
| 655861 | 0.5 | 25 | 71 | 0.2 | 34 | GalNac$_3$-1 (3') |
|  | 1.5 | 28 | 60 | 0.2 | 26 |  |
|  | 5 | 26 | 63 | 0.2 | 28 |  |
|  | 15 | 25 | 61 | 0.2 | 28 |  |
| 664507 | 0.5 | 25 | 62 | 0.2 | 25 | GalNac$_3$-2 (5') |
|  | 1.5 | 24 | 49 | 0.2 | 26 |  |
|  | 5 | 21 | 50 | 0.2 | 26 |  |
|  | 15 | 59 | 84 | 0.1 | 22 |  |
| 661161 | 0.5 | 20 | 42 | 0.2 | 29 | GalNac$_3$-3 (5') |
|  | 1.5 g | 37 | 74 | 0.2 | 25 |  |
|  | 5 g | 28 | 61 | 0.2 | 29 |  |
|  | 15 | 21 | 41 | 0.2 | 25 |  |

TABLE 44-continued

| ISIS No. | Dosage mg/kg | ALT | AST | Total Bilirubin | BUN | Conjugate |
|---|---|---|---|---|---|---|
| 666224 | 0.5 | 34 | 48 | 0.2 | 21 | GalNac$_3$-5 (5') |
|  | 1.5 | 23 | 46 | 0.2 | 26 |  |
|  | 5 | 24 | 47 | 0.2 | 23 |  |
|  | 15 | 32 | 49 | 0.1 | 26 |  |
| 666961 | 0.5 | 17 | 63 | 0.2 | 26 | GalNAc$_3$-6 (5') |
|  | 1.5 | 23 | 68 | 0.2 | 26 |  |
|  | 5 | 25 | 66 | 0.2 | 26 |  |
|  | 15 | 29 | 107 | 0.2 | 28 |  |
| 666981 | 0.5 | 24 | 48 | 0.2 | 26 | GalNAc$_3$-7 (5') |
|  | 1.5 | 30 | 55 | 0.2 | 24 |  |
|  | 5 | 46 | 74 | 0.1 | 24 |  |
|  | 15 | 29 | 58 | 0.1 | 26 |  |
| 666881 | 0.5 | 20 | 65 | 0.2 | 27 | GalNAc$_3$-10 (5') |
|  | 1.5 | 23 | 59 | 0.2 | 24 |  |
|  | 5 | 45 | 70 | 0.2 | 26 |  |
|  | 15 | 21 | 57 | 0.2 | 24 |  |

Example 57: Duration of Action Study of Oligonucleotides Comprising a 3'-Conjugate Group Targeting ApoC III In Vivo Mice were injected once with the doses indicated below and monitored over the course of 42 days for ApoC-III and plasma triglycerides (Plasma TG) levels. The study was performed using 3 transgenic mice that express human APOC-III in each group.

TABLE 45

Modified ASO targeting ApoC III

| ASO | Sequence (5' to 3') | Linkages | SEQ ID No. |
|---|---|---|---|
| ISIS 304801 | A$_{es}$G$_{es}$$^m$C$_{es}$T$_{es}$T$_{es}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{es}$T$_{es}$A$_{es}$T$_{e}$ | PS | 821 |
| ISIS 647535 | A$_{es}$G$_{es}$$^m$C$_{es}$T$_{es}$T$_{es}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{es}$T$_{es}$T$_{es}$A$_{es}$T$_{eo}$A$_{do}$,-GalNAc$_3$-1$_a$ | PS | 822 |
| ISIS 647536 | A$_{es}$G$_{eo}$$^m$C$_{eo}$T$_{eo}$T$_{eo}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{eo}$T$_{eo}$T$_{es}$A$_{es}$T$_{eo}$A$_{do}$,-GalNAc$_3$-1$_a$ | PO/PS | 822 |

Capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-1$_a$ was shown previously in Example 9.

TABLE 46

ApoC III mRNA (% Saline on Day 1) and Plasma TG Levels (% Saline on Day 1)

| ASO | Dose | Target | Day 3 | Day 7 | Day 14 | Day 35 | Day 42 |
|---|---|---|---|---|---|---|---|
| Saline | 0 mg/kg | ApoC-III | 98 | 100 | 100 | 95 | 116 |
| ISIS 304801 | 30 mg/kg | ApoC-III | 28 | 30 | 41 | 65 | 74 |
| ISIS 647535 | 10 mg/kg | ApoC-III | 16 | 19 | 25 | 74 | 94 |
| ISIS 647536 | 10 mg/kg | ApoC-III | 18 | 16 | 17 | 35 | 51 |
| Saline | 0 mg/kg | Plasma TG | 121 | 130 | 123 | 105 | 109 |
| ISIS 304801 | 30 mg/kg | Plasma TG | 34 | 37 | 50 | 69 | 69 |
| ISIS 647535 | 10 mg/kg | Plasma TG | 18 | 14 | 24 | 18 | 71 |
| ISIS 647536 | 10 mg/kg | Plasma TG | 21 | 19 | 15 | 32 | 35 |

As can be seen in the table above the duration of action increased with addition of the 3'-conjugate group compared to the unconjugated oligonucleotide. There was a further increase in the duration of action for the conjugated mixed PO/PS oligonucleotide 647536 as compared to the conjugated full PS oligonucleotide 647535.

Example 58: Dose-Dependent Study of Oligonucleotides Comprising a 3'-Conjugate Group (Comparison of GalNAc$_3$-1 and GalNAc$_4$-11) Targeting SRB-1 In Vivo The oligonucleotides listed below were tested in a dose-dependent study for antisense inhibition of SRB-1 in mice. Unconjugated ISIS 440762 was included as an unconjugated standard. Each of the conjugate groups were attached at the 3' terminus of the respective oligonucleotide by a phosphodiester linked 2'-deoxyadenosine nucleoside cleavable moiety.

The structure of GalNAc$_3$-1$_a$ was shown previously in Example 9. The structure of GalNAc$_3$-11$_a$ was shown previously in Example 50.

Treatment

Six week old male Balb/c mice (Jackson Laboratory, Bar Harbor, Me.) were injected subcutaneously once at the dosage shown below with ISIS 440762, 651900, 663748 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, Oreg.) according to standard protocols. The results below are presented as the average percent of SRB-1 mRNA levels for each treatment group, normalized to the saline control.

As illustrated in Table 47, treatment with antisense oligonucleotides lowered SRB-1 mRNA levels in a dose-dependent manner. The antisense oligonucleotides comprising the phosphodiester linked GalNAc$_3$-1 and GalNAc$_4$-11 conjugates at the 3' terminus (ISIS 651900 and ISIS 663748) showed substantial improvement in potency compared to the unconjugated antisense oligonucleotide (ISIS 440762). The two conjugated oligonucleotides, GalNAc$_3$-1 and GalNAc$_4$-11, were equipotent.

Capital letters indicate the nucleobase for each nucleoside and $^m$C indicates a 5-methyl cytosine. Subscripts: "e" indicates a 2'-MOE modified nucleoside; "k" indicates 6'-(S)—CH$_3$ bicyclic nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in Table 48 below.

TABLE 48

| ISIS No. | Dosage mg/kg | ALT | AST | Total Bilirubin | BUN | Conjugate |
|---|---|---|---|---|---|---|
| Saline | | 30 | 76 | 0.2 | 40 | |
| 440762 | 0.60 | 32 | 70 | 0.1 | 35 | none |
| | 2 | 26 | 57 | 0.1 | 35 | |
| | 6 | 31 | 48 | 0.1 | 39 | |
| 651900 | 0.2 | 32 | 115 | 0.2 | 39 | GalNac$_3$-1 (3') |
| | 0.6 | 33 | 61 | 0.1 | 35 | |
| | 2 | 30 | 50 | 0.1 | 37 | |
| | 6 | 34 | 52 | 0.1 | 36 | |
| 663748 | 0.2 | 28 | 56 | 0.2 | 36 | GalNac$_4$-11 (3') |
| | 0.6 | 34 | 60 | 0.1 | 35 | |
| | 2 | 44 | 62 | 0.1 | 36 | |
| | 6 | 38 | 71 | 0.1 | 33 | |

Example 59: Effects of GalNAc$_3$-1 Conjugated ASOs Targeting FXI In Vivo

The oligonucleotides listed below were tested in a multiple dose study for antisense inhibition of FXI in mice. ISIS 404071 was included as an unconjugated standard. Each of the conjugate groups was attached at the 3' terminus of the respective oligonucleotide by a phosphodiester linked 2'-deoxyadenosine nucleoside cleavable moiety.

TABLE 47

Modified ASO targeting SRB-1

| ASO | Sequence (5' to 3') | Dose mg/kg | % Saline control | SEQ ID No. |
|---|---|---|---|---|
| Saline | | | 100 | |
| ISIS 440762 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_{k}$ | 0.6 | 73.45 | 823 |
| | | 2 | 59.66 | |
| | | 6 | 23.50 | |
| ISIS 651900 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_{ko}$A$_{do}$,-GalNAc$_3$-1$_a$ | 0.2 | 62.75 | 824 |
| | | 0.6 | 29.14 | |
| | | 2 | 8.61 | |
| | | 6 | 5.62 | |
| ISIS 663748 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_{ko}$A$_{do}$,-GalNAc$_4$-11$_a$ | 0.2 | 63.99 | 824 |
| | | 0.6 | 33.53 | |
| | | 2 | 7.58 | |
| | | 6 | 5.52 | |

TABLE 49

Modified ASOs targeting FXI

| ASO | Sequence (5' to 3') | Linkages | SEQ ID No. |
|---|---|---|---|
| ISIS 404071 | T$_{es}$G$_{es}$G$_{es}$T$_{es}$A$_{es}$A$_{ds}$T$_{ds}$$^m$C$_{ds}$$^m$C$_{ds}$A$_{ds}$$^m$C$_{ds}$T$_{ds}$T$_{ds}$T$_{ds}$$^m$C$_{ds}$A$_{es}$G$_{es}$A$_{es}$G$_{es}$G$_{e}$ | PS | 832 |
| ISIS 656172 | T$_{es}$G$_{es}$G$_{es}$T$_{es}$A$_{es}$A$_{ds}$T$_{ds}$$^m$C$_{ds}$$^m$C$_{ds}$A$_{ds}$$^m$C$_{ds}$T$_{ds}$T$_{ds}$T$_{ds}$$^m$C$_{ds}$A$_{es}$G$_{es}$A$_{es}$G$_{es}$G$_{eo}$A$_{do'}$-GalNAc$_3$-1$_a$ | PS | 833 |
| ISIS 656173 | T$_{es}$G$_{eo}$G$_{eo}$T$_{eo}$A$_{eo}$A$_{ds}$T$_{ds}$$^m$C$_{ds}$$^m$C$_{ds}$A$_{ds}$$^m$C$_{ds}$T$_{ds}$T$_{ds}$T$_{ds}$$^m$C$_{ds}$A$_{eo}$G$_{eo}$A$_{es}$G$_{es}$G$_{eo}$A$_{do'}$-GalNAc$_3$-1$_a$ | PO/PS | 833 |

Capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-1$_a$ was shown previously in Example 9.

Treatment

Six week old male Balb/c mice (Jackson Laboratory, Bar Harbor, Me.) were injected subcutaneously twice a week for 3 weeks at the dosage shown below with ISIS 404071, 656172, 656173 or with PBS treated control. Each treatment group consisted of 4 animals. The mice were sacrificed 72 hours following the final administration to determine the liver FXI mRNA levels using real-time PCR and RIBOGREEN® RNA quantification reagent (Molecular Probes, Inc. Eugene, Oreg.) according to standard protocols. Plasma FXI protein levels were also measured using ELISA. FXI mRNA levels were determined relative to total RNA (using RIBOGREEN®), prior to normalization to PBS-treated control. The results below are presented as the average percent of FXI mRNA levels for each treatment group. The data was normalized to PBS-treated control and is denoted as "% PBS". The ED$_{50}$s were measured using similar methods as described previously and are presented below.

TABLE 50

Factor XI mRNA (% Saline)

| ASO | Dose mg/kg | % Control | Conjugate | Linkages |
|---|---|---|---|---|
| Saline | | 100 | none | |
| ISIS 404071 | 3 | 92 | none | PS |
| | 10 | 40 | | |
| | 30 | 15 | | |
| ISIS 656172 | 0.7 | 74 | GalNAc$_3$-1 | PS |
| | 2 | 33 | | |
| | 6 | 9 | | |
| ISIS 656173 | 0.7 | 49 | GalNAc$_3$-1 | PO/PS |
| | 2 | 22 | | |
| | 6 | 1 | | |

As illustrated in Table 50, treatment with antisense oligonucleotides lowered FXI mRNA levels in a dose-dependent manner. The oligonucleotides comprising a 3'-GalNAc$_3$-1 conjugate group showed substantial improvement in potency compared to the unconjugated antisense oligonucleotide (ISIS 404071). Between the two conjugated oligonucleotides an improvement in potency was further provided by substituting some of the PS linkages with PO (ISIS 656173).

As illustrated in Table 50a, treatment with antisense oligonucleotides lowered FXI protein levels in a dose-dependent manner. The oligonucleotides comprising a 3'-GalNAc$_3$-1 conjugate group showed substantial improvement in potency compared to the unconjugated antisense oligonucleotide (ISIS 404071). Between the two conjugated oligonucleotides an improvement in potency was further provided by substituting some of the PS linkages with PO (ISIS 656173).

TABLE 50a

Factor XI protein (% Saline)

| ASO | Dose mg/kg | Protein (% Control) | Conjugate | Linkages |
|---|---|---|---|---|
| Saline | | 100 | none | |
| ISIS 404071 | 3 | 127 | none | PS |
| | 10 | 32 | | |
| | 30 | 3 | | |
| ISIS 656172 | 0.7 | 70 | GalNAc$_3$-1 | PS |
| | 2 | 23 | | |
| | 6 | 1 | | |
| ISIS 656173 | 0.7 | 45 | GalNAc$_3$-1 | PO/PS |
| | 2 | 6 | | |
| | 6 | 0 | | |

Liver transaminase levels, alanine aminotransferase (ALT) and aspartate aminotransferase (AST), in serum were measured relative to saline injected mice using standard protocols. Total bilirubin, total albumin, CRE and BUN were also evaluated. The change in body weights was evaluated with no significant change from the saline group. ALTs, ASTs, total bilirubin and BUN values are shown in the table below.

TABLE 51

| ISIS No. | Dosage mg/kg | ALT | AST | Total Albumin | Total Bilirubin | CRE | BUN | Conjugate |
|---|---|---|---|---|---|---|---|---|
| Saline | | 71.8 | 84.0 | 3.1 | 0.2 | 0.2 | 22.9 | |
| 404071 | 3 | 152.8 | 176.0 | 3.1 | 0.3 | 0.2 | 23.0 | none |
| | 10 | 73.3 | 121.5 | 3.0 | 0.2 | 0.2 | 21.4 | |
| | 30 | 82.5 | 92.3 | 3.0 | 0.2 | 0.2 | 23.0 | |
| 656172 | 0.7 | 62.5 | 111.5 | 3.1 | 0.2 | 0.2 | 23.8 | GalNac$_3$-1 (3') |
| | 2 | 33.0 | 51.8 | 2.9 | 0.2 | 0.2 | 22.0 | |
| | 6 | 65.0 | 71.5 | 3.2 | 0.2 | 0.2 | 23.9 | |

TABLE 51-continued

| ISIS No. | Dosage mg/kg | ALT | AST | Total Albumin | Total Bilirubin | CRE | BUN | Conjugate |
|---|---|---|---|---|---|---|---|---|
| 656173 | 0.7 | 54.8 | 90.5 | 3.0 | 0.2 | 0.2 | 24.9 | GalNac$_3$-1 (3') |
|  | 2 | 85.8 | 71.5 | 3.2 | 0.2 | 0.2 | 21.0 |  |
|  | 6 | 114.0 | 101.8 | 3.3 | 0.2 | 0.2 | 22.7 |  |

Example 60: Effects of Conjugated ASOs Targeting SRB-1 in Vitro

The oligonucleotides listed below were tested in a multiple dose study for antisense inhibition of SRB-1 in primary mouse hepatocytes. ISIS 353382 was included as an unconjugated standard. Each of the conjugate groups were attached at the 3' or 5' terminus of the respective oligonucleotide by a phosphodiester linked 2'-deoxyadenosine nucleoside cleavable moiety.

shown previously in Example 47. The structure of GalNAc$_3$-9a was shown previously in Example 52. The structure of GalNAc$_3$-6a was shown previously in Example 51. The structure of GalNAc$_3$-2a was shown previously in Example 37. The structure of GalNAc$_3$-10a was shown previously in Example 46. The structure of GalNAc$_3$-5a was shown previously in Example 49. The structure of GalNAc$_3$-7a was shown previously in Example 48.

TABLE 52

Modified ASO targeting SRB-1

| ASO | Sequence (5' to 3') | Motif | Conjugate | SEQ ID No. |
|---|---|---|---|---|
| ISIS 353382 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | 5/10/5 | none | 829 |
| ISIS 655861 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{eo}$A$_{do'}$-GalNAc$_3$-1a | 5/10/5 | GalNAc$_3$-1 | 830 |
| ISIS 655862 | G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{eo}$$^m$C$_{es}$T$_{es}$T$_{eo}$A$_{do'}$-GalNAc$_3$-1a | 5/10/5 | GalNAc$_3$-1 | 830 |
| ISIS 661161 | GalNAc$_3$-3$_{a-o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | 5/10/5 | GalNAc$_3$-3 | 831 |
| ISIS 665001 | GalNAc$_3$-8$_{a-o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | 5/10/5 | GalNAc$_3$-8 | 831 |
| ISIS 664078 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{eo}$A$_{do'}$-GalNAc$_3$-9$_a$ | 5/10/5 | GalNAc$_3$-9 | 830 |
| ISIS 666961 | GalNAc$_3$-6$_{a-o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | 5/10/5 | GalNAc$_3$-6 | 831 |
| ISIS 664507 | GalNAc$_3$-2$_{a-o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | 5/10/5 | GalNAc$_3$-2 | 831 |
| ISIS 666881 | GalNAc$_3$-10$_{a-o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | 5/10/5 | GalNAc$_3$-10 | 831 |
| ISIS 666224 | GalNAc$_3$-5$_{a-o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | 5/10/5 | GalNAc$_3$-5 | 831 |
| ISIS 666981 | GalNAc$_3$-7$_{a-o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | 5/10/5 | GalNAc$_3$-7 | 831 |

Capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—. Conjugate groups are in bold.

The structure of GalNAc$_3$-1$_a$ was shown previously in Example 9. The structure of GalNAc$_3$-3a was shown previously in Example 39. The structure of GalNAc$_3$-8a was Treatment The oligonucleotides listed above were tested in vitro in primary mouse hepatocyte cells plated at a density of 25,000 cells per well and treated with 0.03, 0.08, 0.24, 0.74, 2.22, 6.67 or 20 nM modified oligonucleotide. After a treatment period of approximately 16 hours, RNA was isolated from the cells and mRNA levels were measured by quantitative real-time PCR and the SRB-1 mRNA levels were adjusted according to total RNA content, as measured by RIBOGREEN®.

The IC$_{50}$ was calculated using standard methods and the results are presented in Table 53. The results show that, under free uptake conditions in which no reagents or electroporation techniques are used to artificially promote entry of the oligonucleotides into cells, the oligonucleotides comprising a GalNAc conjugate were significantly more potent in hepatocytes than the parent oligonucleotide (ISIS 353382) that does not comprise a GalNAc conjugate.

TABLE 53

| ASO | IC$_{50}$ (nM) | Internucleoside linkages | Conjugate | SEQ ID No. |
|---|---|---|---|---|
| ISIS 353382 | 190[a] | PS | none | 829 |
| ISIS 655861 | 11[a] | PS | GalNAc$_3$-1 | 830 |

TABLE 53-continued

| ASO | IC$_{50}$ (nM) | Internucleoside linkages | Conjugate | SEQ ID No. |
|---|---|---|---|---|
| ISIS 655862 | 3 | PO/PS | GalNAc$_3$-1 | 830 |
| ISIS 661161 | 15[a] | PS | GalNAc$_3$-3 | 831 |
| ISIS 665001 | 20 | PS | GalNAc$_3$-8 | 831 |
| ISIS 664078 | 55 | PS | GalNAc$_3$-9 | 830 |
| ISIS 666961 | 22[a] | PS | GalNAc$_3$-6 | 831 |
| ISIS 664507 | 30 | PS | GalNAc$_3$-2 | 831 |
| ISIS 666881 | 30 | PS | GalNAc$_3$-10 | 831 |
| ISIS 666224 | 30[a] | PS | GalNAc$_3$-5 | 831 |
| ISIS 666981 | 40 | PS | GalNAc$_3$-7 | 831 |

[a]Average of multiple runs.

Example 61: Preparation of Oligomeric Compound 175 Comprising GalNAc$_3$-12

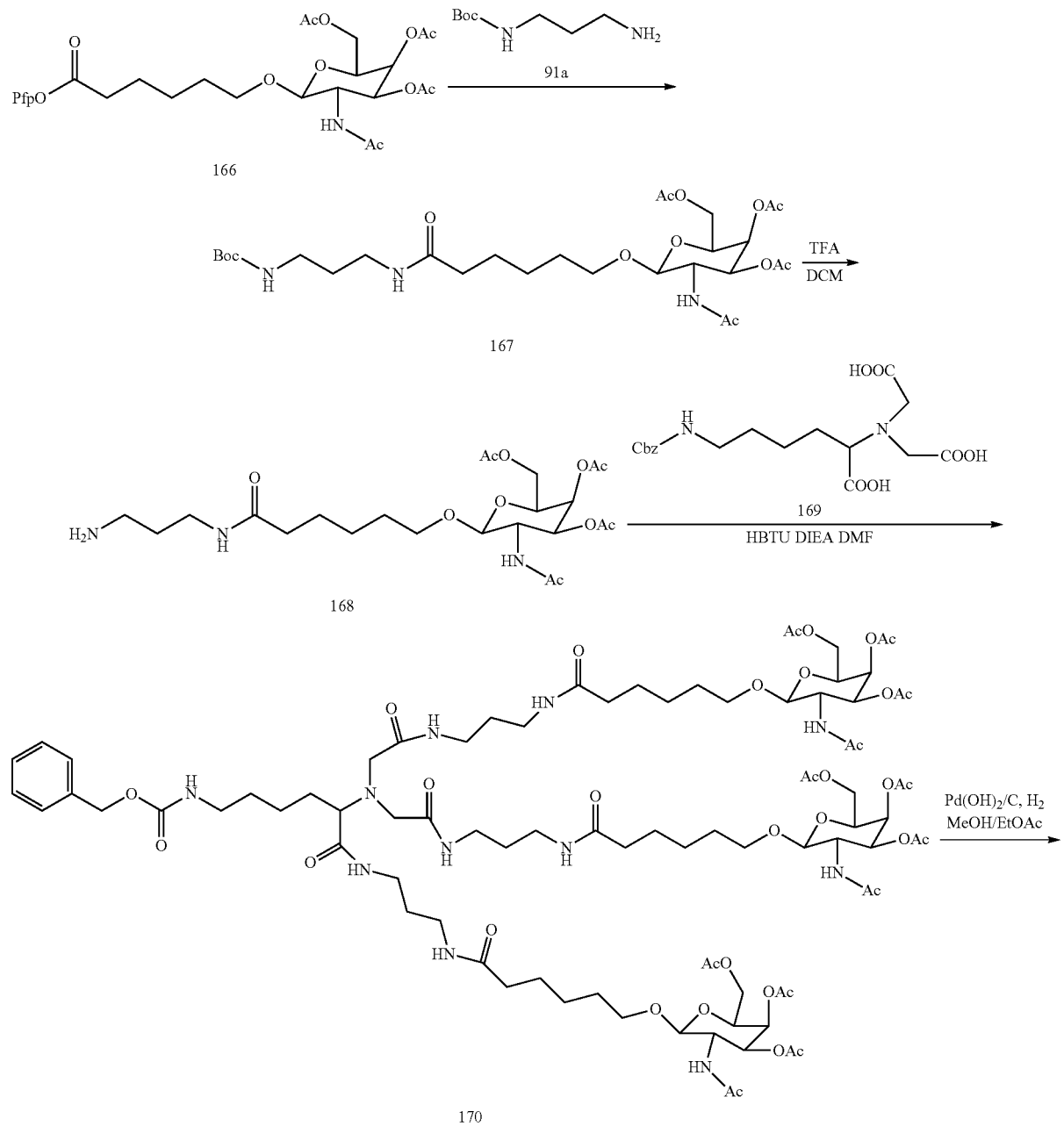

343
-continued
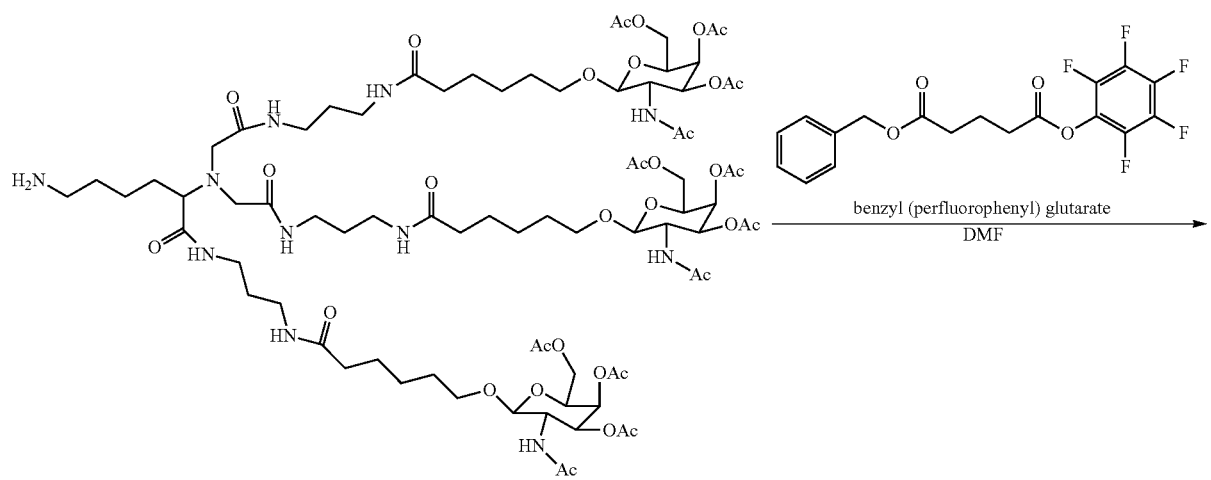
171
344
benzyl (perfluorophenyl) glutarate
DMF
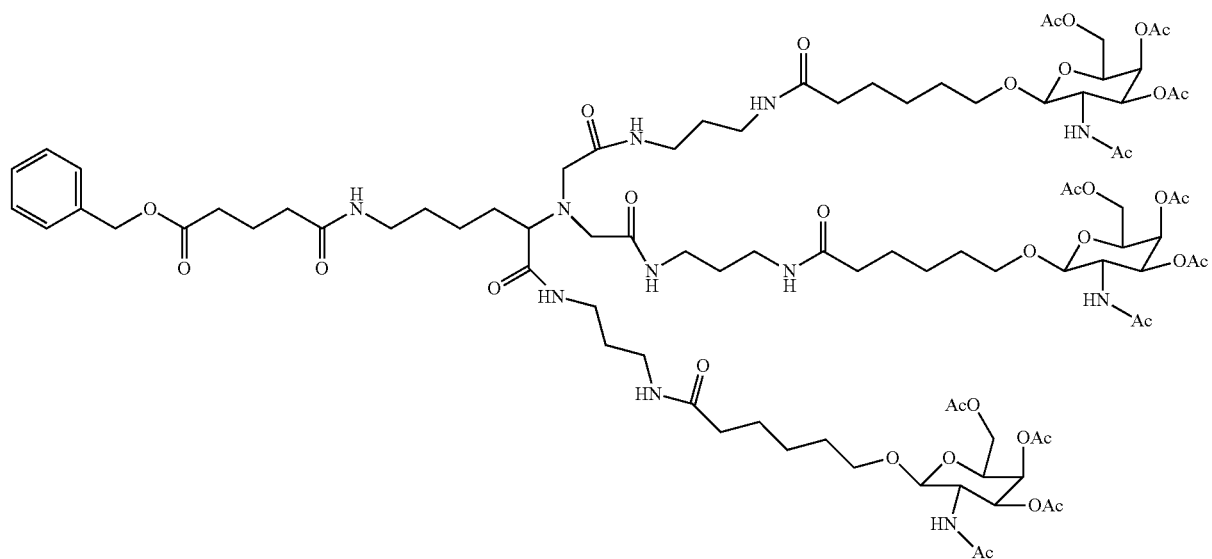
172
172 —Pd(OH)₂C, H₂ / MeOH/EtOAc→

-continued
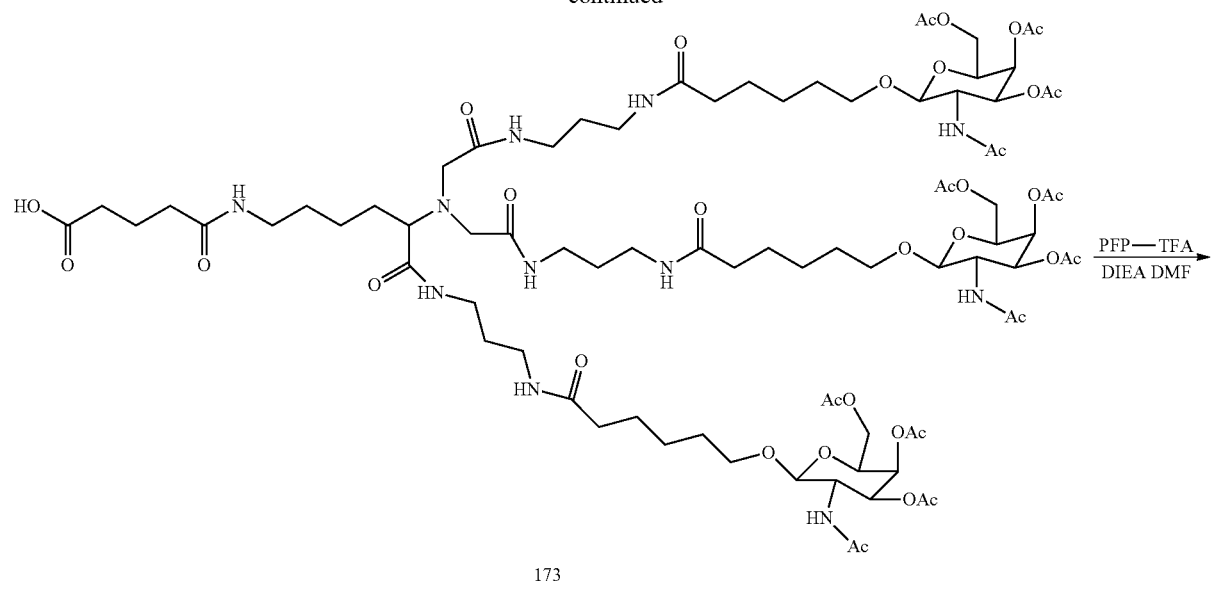
173
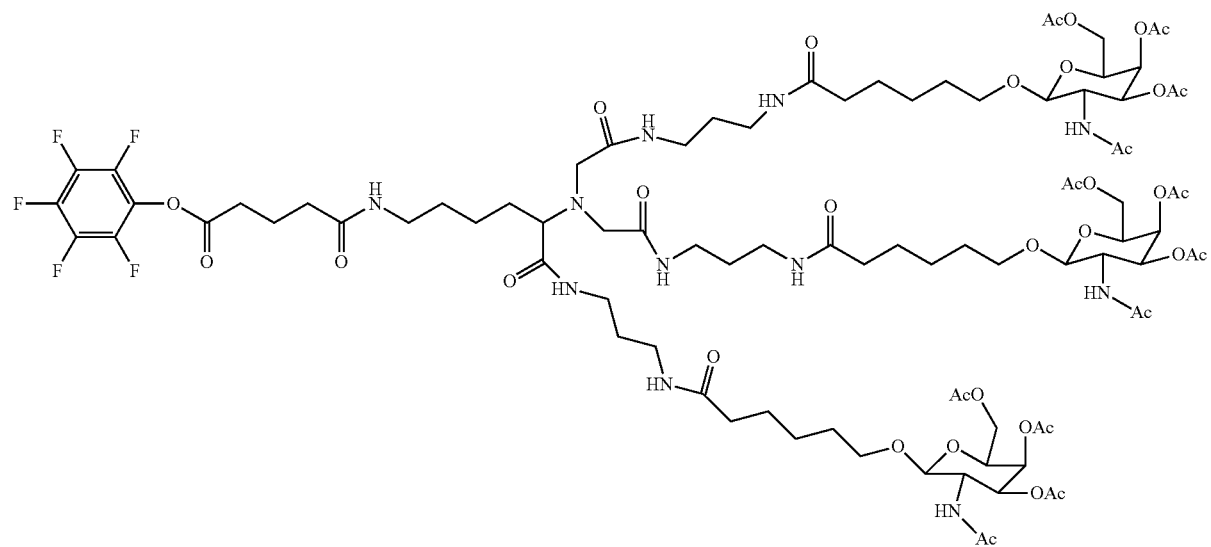
174
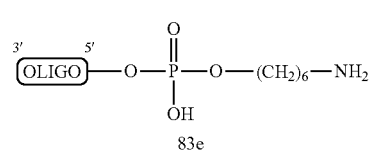
83e
174 →
1. Borate buffer, DMSO, pH 8.5, rt
2. aq. ammonia, rt -continued

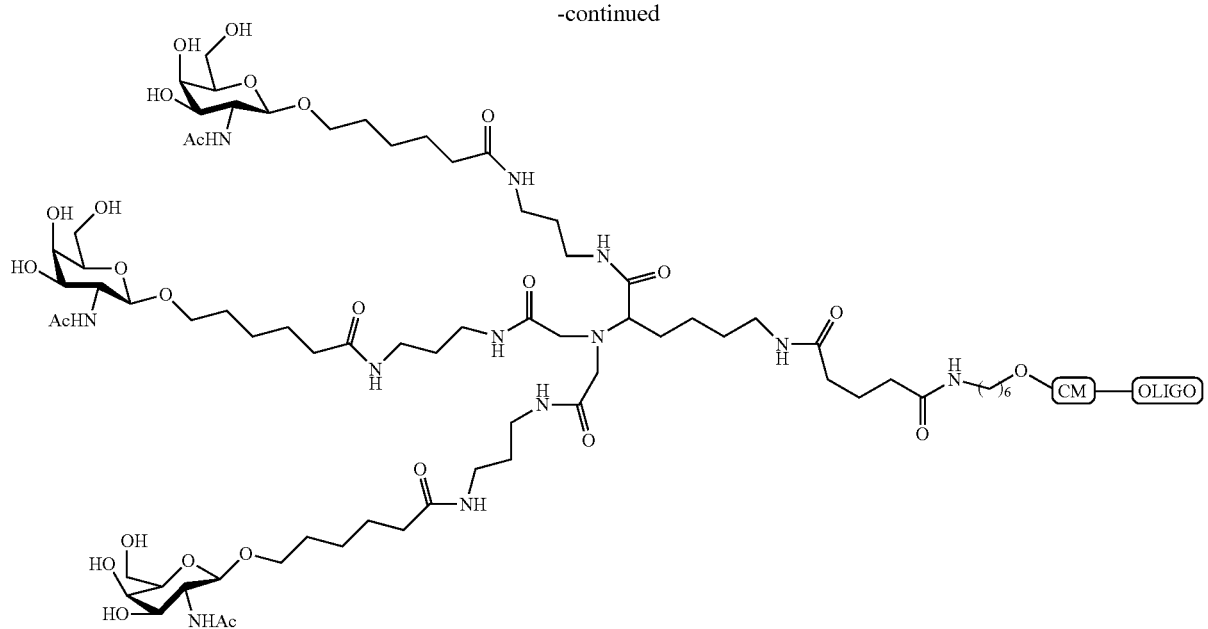

175

Compound 169 is commercially available. Compound 172 was prepared by addition of benzyl (perfluorophenyl) glutarate to compound 171. The benzyl (perfluorophenyl) glutarate was prepared by adding PFP-TFA and DIEA to 5-(benzyloxy)-5-oxopentanoic acid in DMF. Oligomeric compound 175, comprising a GalNAc$_3$-12 conjugate group, was prepared from compound 174 using the general procedures illustrated in Example 46. The GalNAc$_3$ cluster portion of the conjugate group GalNAc$_3$-12 (GalNAc$_3$-12$_a$) can be combined with any cleavable moiety to provide a variety of conjugate groups. In a certain embodiments, the cleavable moiety is —P(=O)(OH)-A$_d$-P(=O)(OH)—. The structure of GalNAc$_3$-12 (GalNAc$_3$-12$_a$-CM-) is shown below:

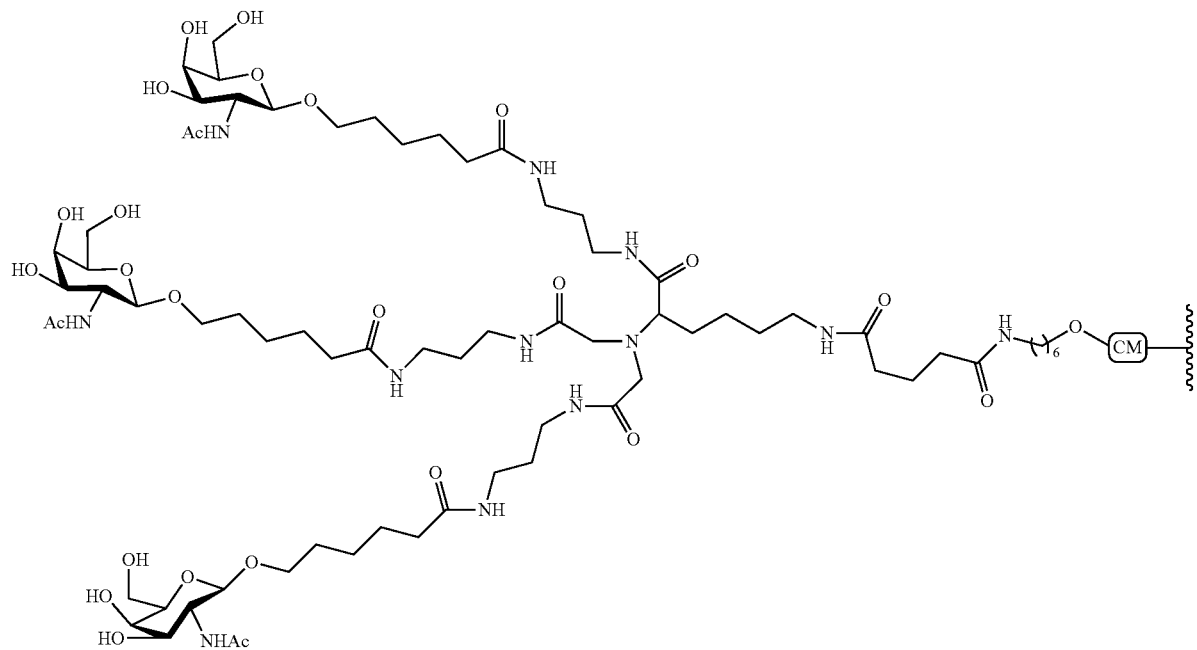

Example 62: Preparation of Oligomeric Compound 180 Comprising GalNAc$_3$-13
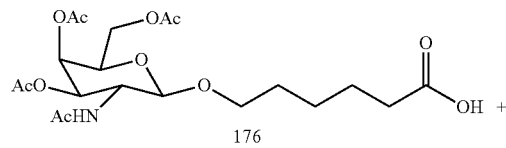
176
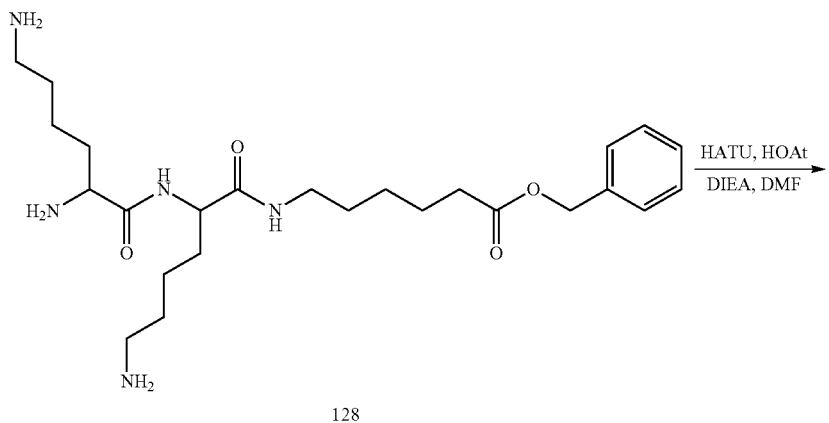
128
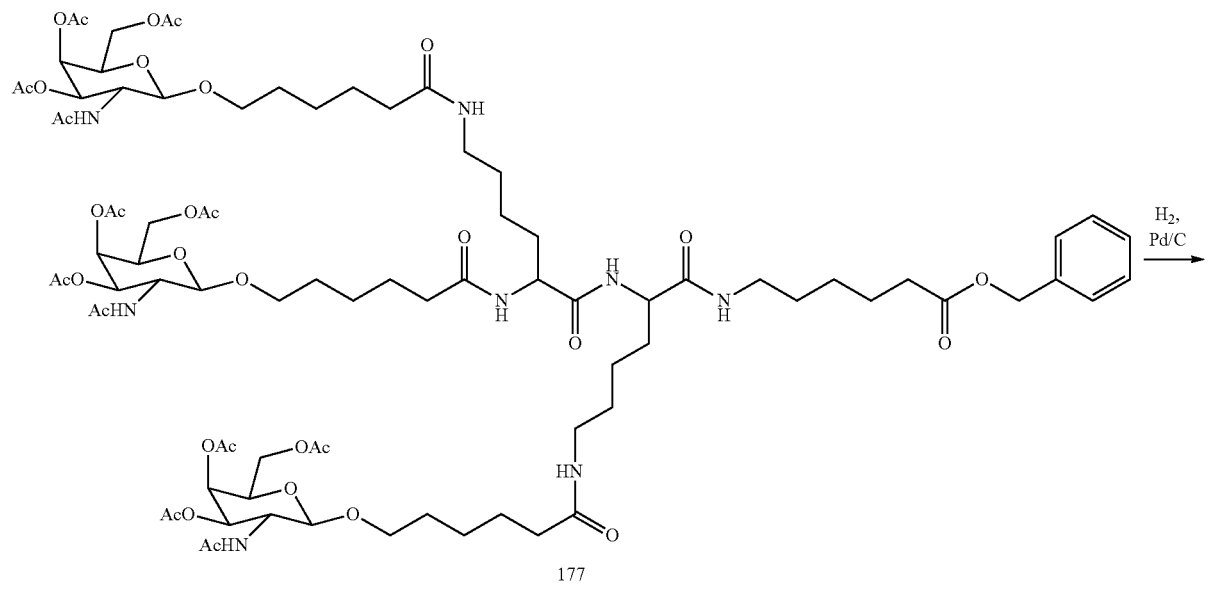
177

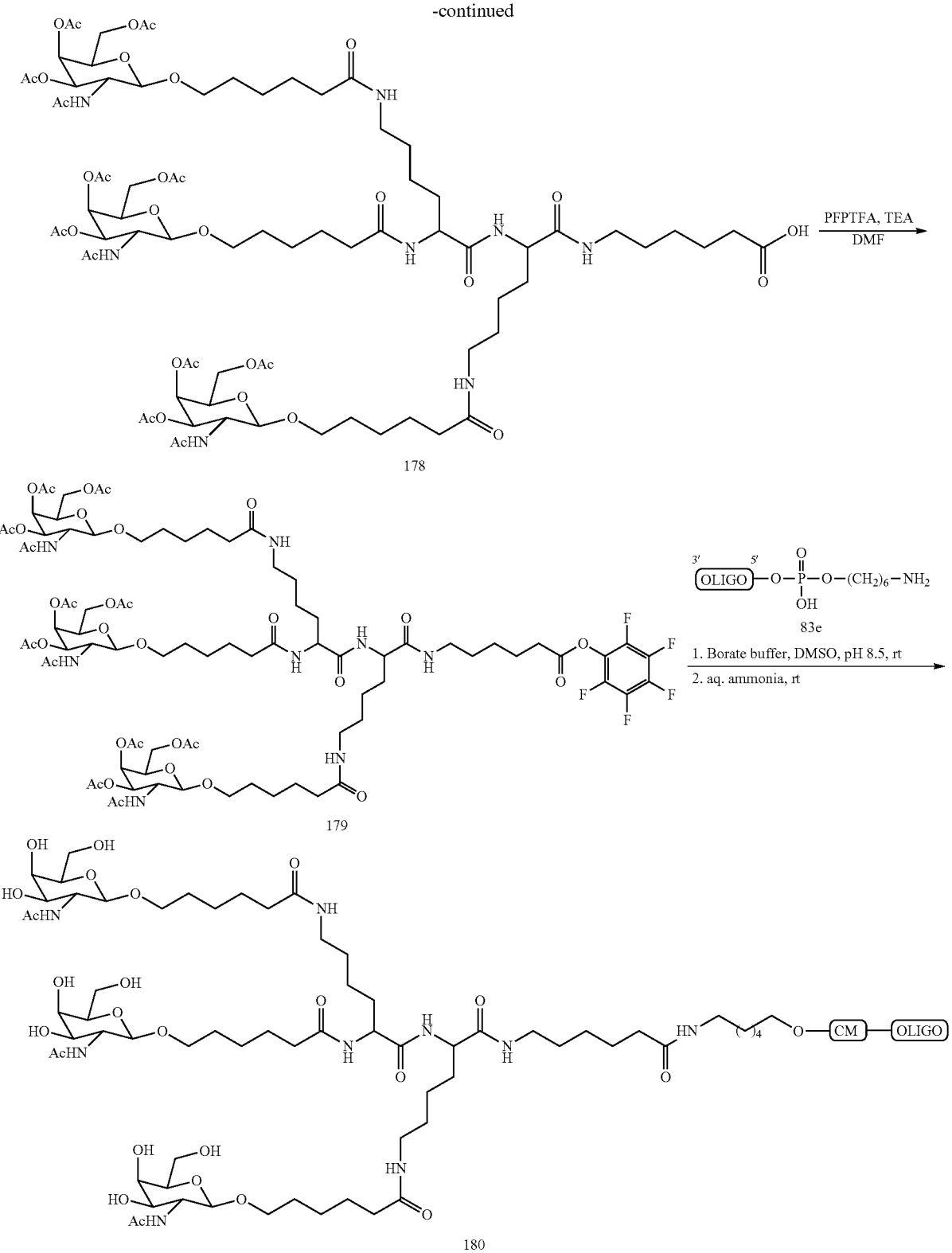

Compound 176 was prepared using the general procedure shown in Example 2. Oligomeric compound 180, comprising a GalNAc$_3$-13 conjugate group, was prepared from compound 177 using the general procedures illustrated in Example 49. The GalNAc$_3$ cluster portion of the conjugate group GalNAc$_3$-13 (GalNAc$_3$-13$_a$) can be combined with any cleavable moiety to provide a variety of conjugate groups. In a certain embodiments, the cleavable moiety is —P(=O)(OH)-A$_d$-P(=O)(OH)—. The structure of GalNAc$_3$-13 (GalNAc$_3$-13$_a$-CM-) is shown below:

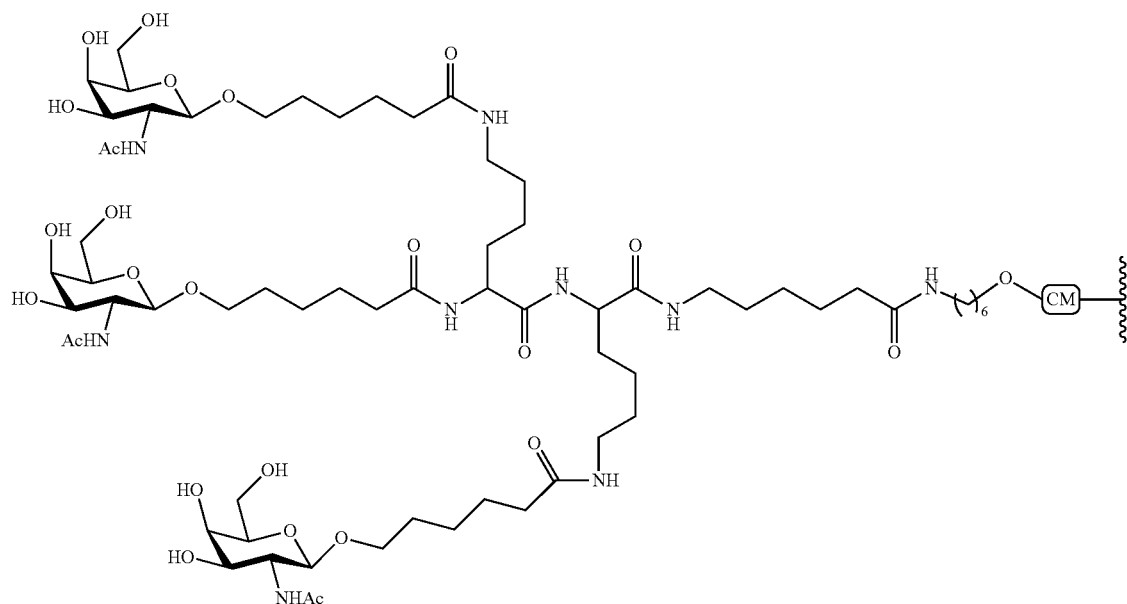
Example 63: Preparation of Oligomeric Compound 188 Comprising GalNAc$_3$-14
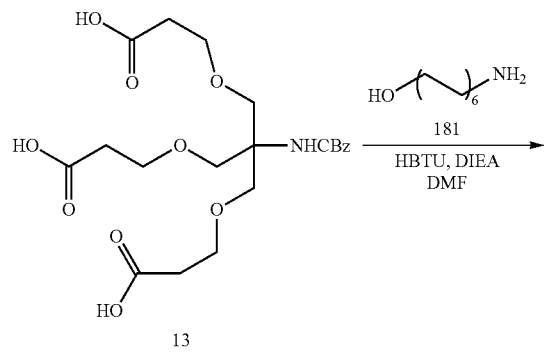
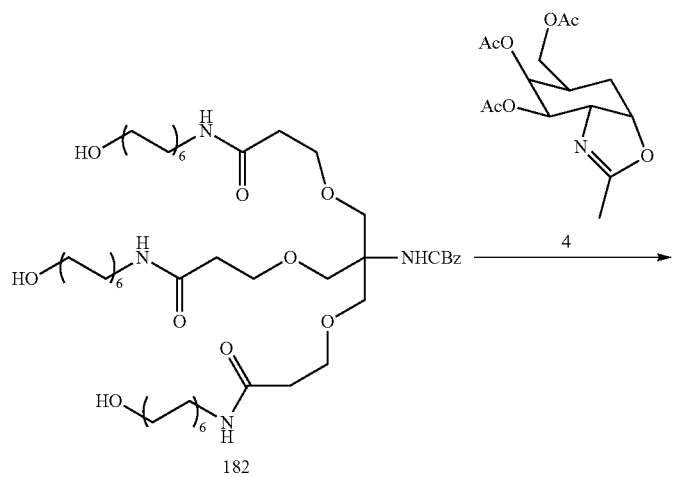

-continued
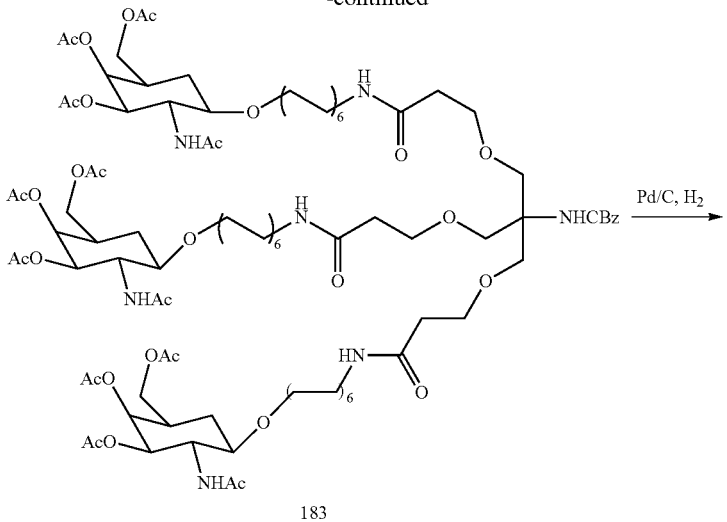
183
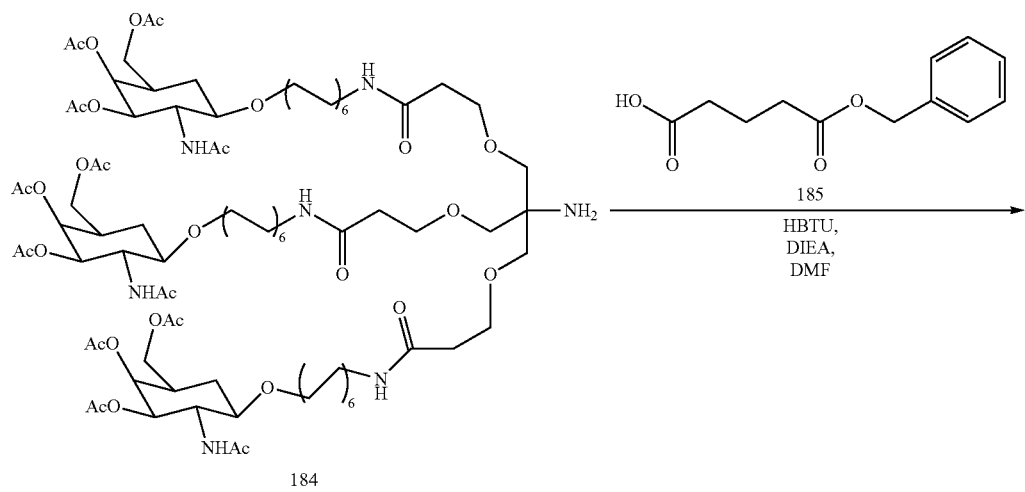
184
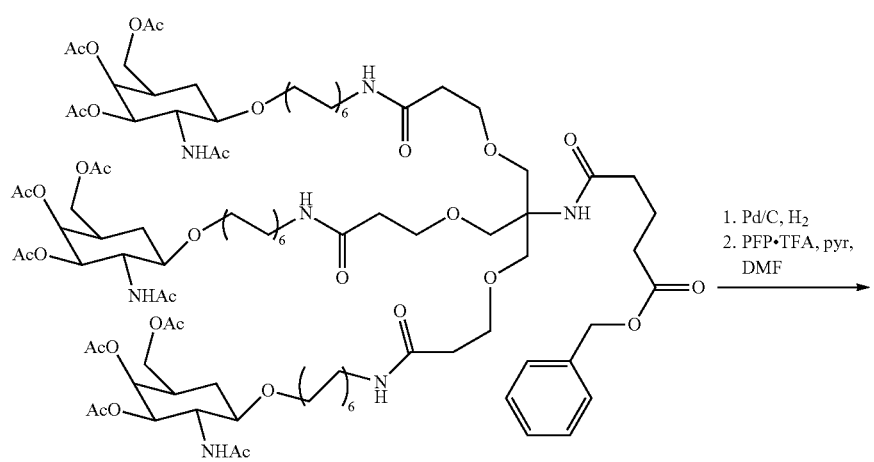
186

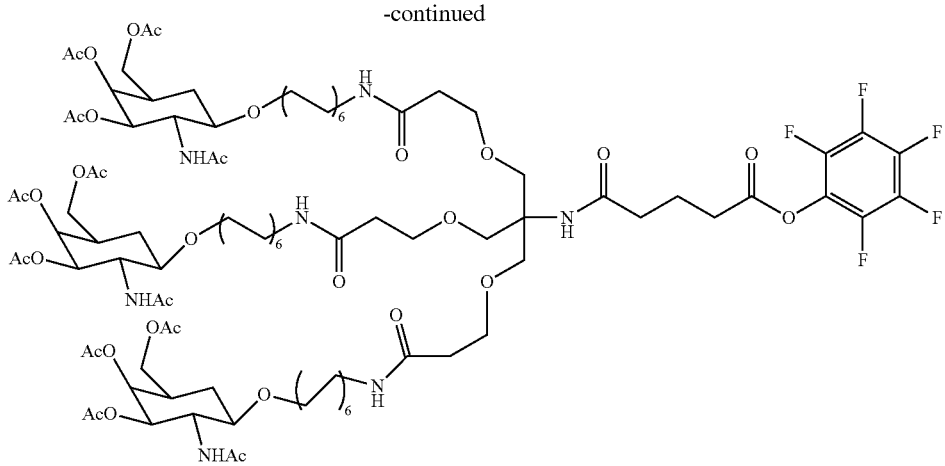

187

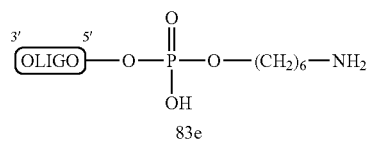

83e

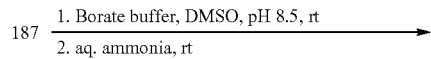

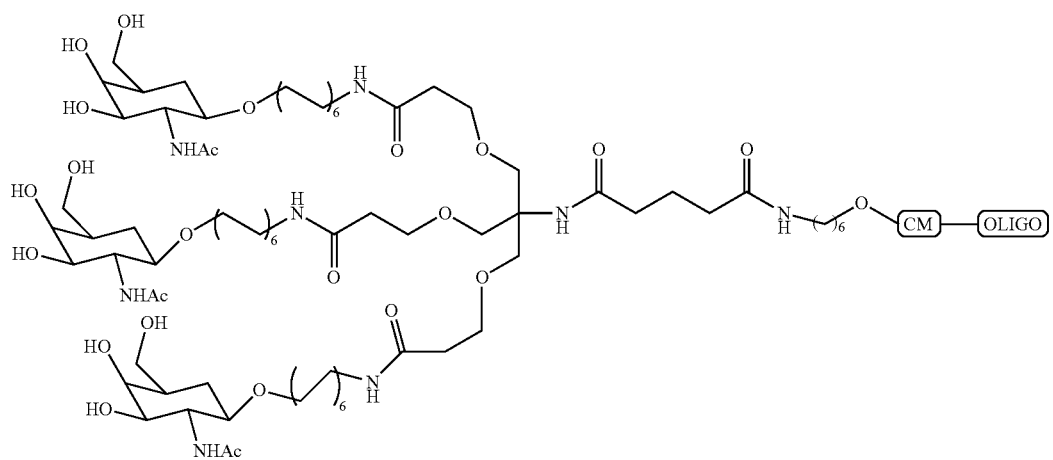

188

Compounds 181 and 185 are commercially available. Oligomeric compound 188, comprising a GalNAc$_3$-14 conjugate group, was prepared from compound 187 using the general procedures illustrated in Example 46. The GalNAc$_3$ cluster portion of the conjugate group GalNAc$_3$-14 (GalNAc$_3$-14$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-14 (GalNAc$_3$-14$_a$-CM-) is shown below:

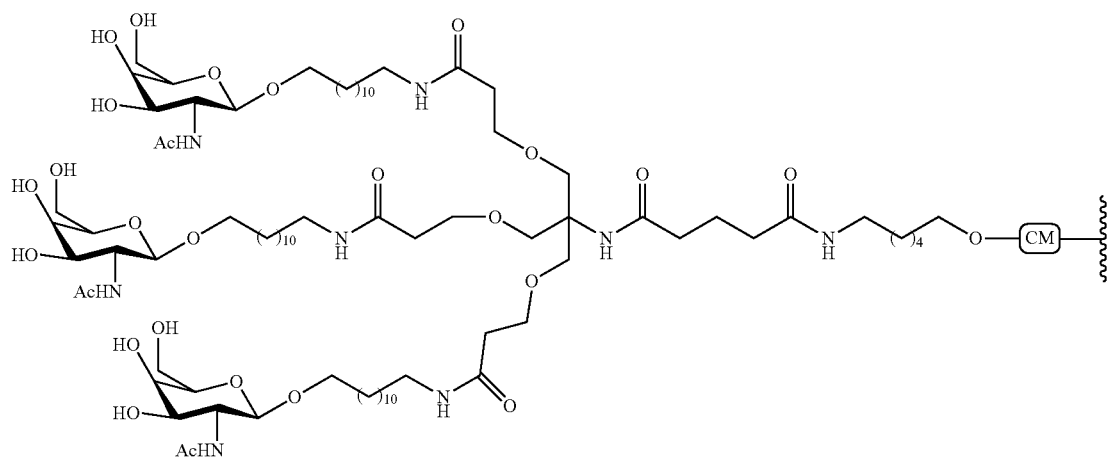
Example 64: Preparation of Oligomeric Compound 197 Comprising GalNAc₃-15
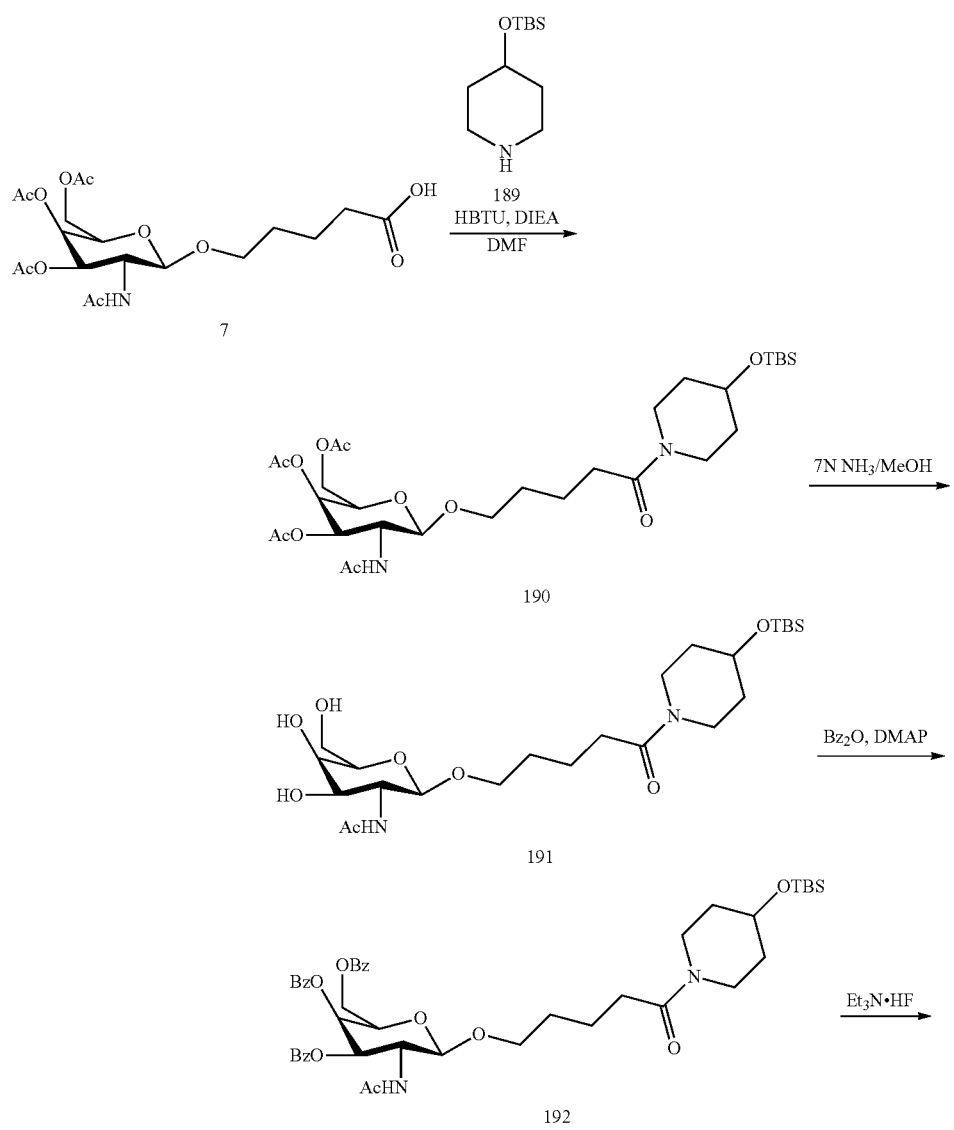

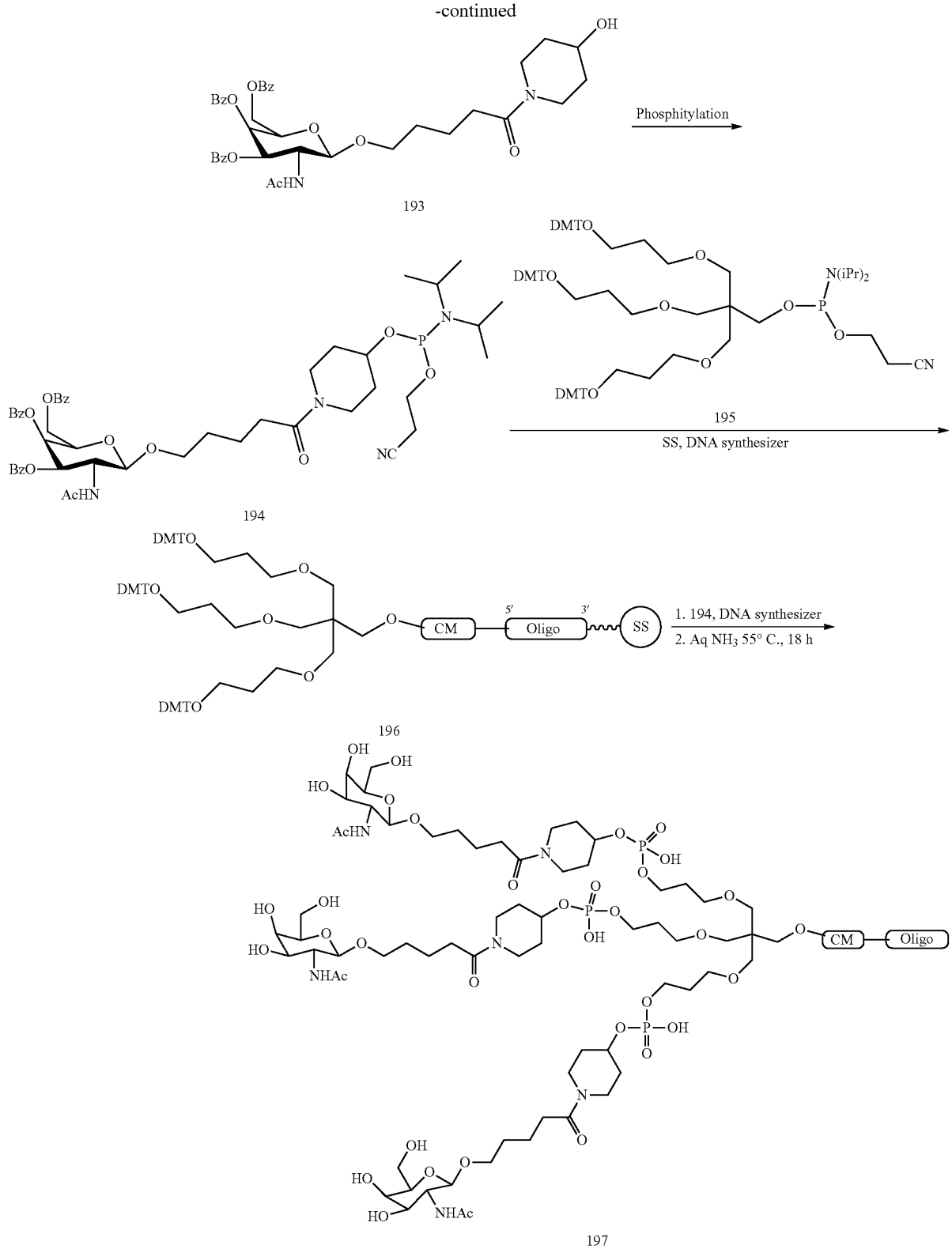

Compound 189 is commercially available. Compound 195 was prepared using the general procedure shown in Example 31. Oligomeric compound 197, comprising a GalNAc₃-15 conjugate group, was prepared from compounds 194 and 195 using standard oligonucleotide synthesis procedures.

The GalNAc₃ cluster portion of the conjugate group Gal-NAc₃-15 (GalNAc₃-15$_a$) can be combined with any cleavable moiety to provide a variety of conjugate groups. In certain embodiments, the cleavable moiety is —P(=O)(OH)-A$_d$-P(=O)(OH)—. The structure of GalNAc₃-15 (GalNAc₃-15$_a$-CM-) is shown below:

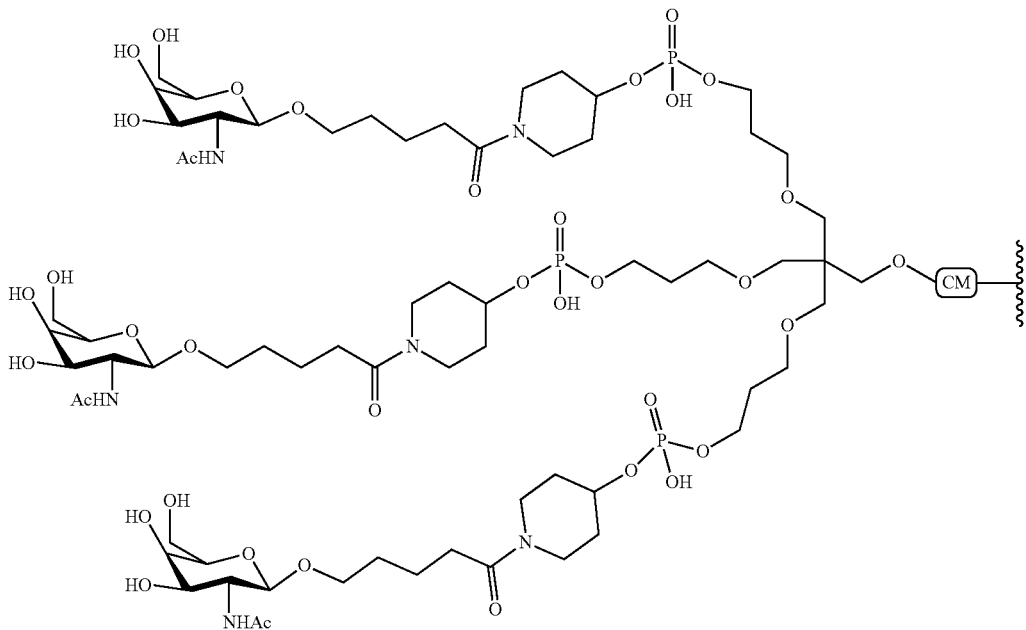

Example 65: Dose-Dependent Study of Oligonucleotides Comprising a 5'-Conjugate Group (Comparison of GalNAc$_3$-3, 12, 13, 14, and 15) Targeting SRB-1 In Vivo The oligonucleotides listed below were tested in a dose-dependent study for antisense inhibition of SRB-1 in mice. Unconjugated ISIS 353382 was included as a standard. Each of the GalNAc$_3$ conjugate groups was attached at the 5' terminus of the respective oligonucleotide by a phosphodiester linked 2-deoxyadenosine nucleoside (cleavable moiety).

TABLE 54

Modified ASOs targeting SRB-1

| ISIS No. | Sequences (5' to 3') | Conjugate | SEQ ID No. |
|---|---|---|---|
| 353382 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | none | 829 |
| 661161 | GalNAc$_3$-3$_a$-$_o$, A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_3$-3 | 831 |
| 671144 | GalNAc$_3$-12$_a$-$_o$, A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_3$-12 | 831 |
| 670061 | GalNAc$_3$-13$_a$-$_o$, A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_3$-13 | 831 |
| 671261 | GalNAc$_3$-14$_a$-$_o$, A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_3$-14 | 831 |
| 671262 | GalNAc$_3$-15$_a$-$_o$, A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_3$-15 | 831 |

Capital letters indicate the nucleobase for each nucleoside and $^mC$ indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-3$_a$ was shown previously in Example 39. The structure of GalNAc$_3$-12a was shown previously in Example 61. The structure of GalNAc$_3$-13a was shown previously in Example 62. The structure of GalNAc$_3$-14a was shown previously in Example 63. The structure of GalNAc$_3$-15a was shown previously in Example 64.

Treatment

Six to eight week old C57bl6 mice (Jackson Laboratory, Bar Harbor, Me.) were injected subcutaneously once or twice at the dosage shown below with ISIS 353382, 661161, 671144, 670061, 671261, 671262, or with saline. Mice that were dosed twice received the second dose three days after the first dose. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, Oreg.) according to standard protocols. The results below are presented as the average percent of SRB-1 mRNA levels for each treatment group, normalized to the saline control.

As illustrated in Table 55, treatment with antisense oligonucleotides lowered SRB-1 mRNA levels in a dose-dependent manner. No significant differences in target knockdown were observed between animals that received a single dose and animals that received two doses (see ISIS 353382 dosages 30 and 2×15 mg/kg; and ISIS 661161 dosages 5 and 2×2.5 mg/kg). The antisense oligonucleotides comprising the phosphodiester linked GalNAc$_3$-3, 12, 13, 14, and 15 conjugates showed substantial improvement in potency compared to the unconjugated antisense oligonucleotide (ISIS 335382).

TABLE 55

SRB-1 mRNA (% Saline)

| ISIS No. | Dosage (mg/kg) | SRB-1 mRNA (% Saline) | ED$_{50}$ (mg/kg) | Conjugate |
|---|---|---|---|---|
| Saline | n/a | 100.0 | n/a | n/a |
| 353382 | 3 | 85.0 | 22.4 | none |
|  | 10 | 69.2 |  |  |
|  | 30 | 34.2 |  |  |
|  | 2 × 15 | 36.0 |  |  |
| 661161 | 0.5 | 87.4 | 2.2 | GalNAc$_3$-3 |
|  | 1.5 | 59.0 |  |  |
|  | 5 | 25.6 |  |  |
|  | 2 × 2.5 | 27.5 |  |  |
|  | 15 | 17.4 |  |  |
| 671144 | 0.5 | 101.2 | 3.4 | GalNAc$_3$-12 |
|  | 1.5 | 76.1 |  |  |
|  | 5 | 32.0 |  |  |
|  | 15 | 17.6 |  |  |
| 670061 | 0.5 | 94.8 | 2.1 | GalNAc$_3$-13 |
|  | 1.5 | 57.8 |  |  |
|  | 5 | 20.7 |  |  |
|  | 15 | 13.3 |  |  |
| 671261 | 0.5 | 110.7 | 4.1 | GalNAc$_3$-14 |
|  | 1.5 | 81.9 |  |  |
|  | 5 | 39.8 |  |  |
|  | 15 | 14.1 |  |  |
| 671262 | 0.5 | 109.4 | 9.8 | GalNAc$_3$-15 |
|  | 1.5 | 99.5 |  |  |
|  | 5 | 69.2 |  |  |
|  | 15 | 36.1 |  |  |

Liver transaminase levels, alanine aminotransferase (ALT) and aspartate aminotransferase (AST), in serum were measured relative to saline injected mice using standard protocols. Total bilirubin and BUN were also evaluated. The changes in body weights were evaluated with no significant differences from the saline group (data not shown). ALTs, ASTs, total bilirubin and BUN values are shown in Table 56 below.

TABLE 56

| ISIS No. | Dosage (mg/kg) | ALT (U/L) | AST (U/L) | Total Bilirubin (mg/dL) | BUN (mg/dL) | Conjugate |
|---|---|---|---|---|---|---|
| Saline | n/a | 28 | 60 | 0.1 | 39 | n/a |
| 353382 | 3 | 30 | 77 | 0.2 | 36 | none |
|  | 10 | 25 | 78 | 0.2 | 36 |  |
|  | 30 | 28 | 62 | 0.2 | 35 |  |
|  | 2 × 15 | 22 | 59 | 0.2 | 33 |  |
| 661161 | 0.5 | 39 | 72 | 0.2 | 34 | GalNAc$_3$-3 |
|  | 1.5 | 26 | 50 | 0.2 | 33 |  |
|  | 5 | 41 | 80 | 0.2 | 32 |  |
|  | 2 × 2.5 | 24 | 72 | 0.2 | 28 |  |
|  | 15 | 32 | 69 | 0.2 | 36 |  |
| 671144 | 0.5 | 25 | 39 | 0.2 | 34 | GalNAc$_3$-12 |
|  | 1.5 | 26 | 55 | 0.2 | 28 |  |
|  | 5 | 48 | 82 | 0.2 | 34 |  |
|  | 15 | 23 | 46 | 0.2 | 32 |  |
| 670061 | 0.5 | 27 | 53 | 0.2 | 33 | GalNAc$_3$-13 |
|  | 1.5 | 24 | 45 | 0.2 | 35 |  |
|  | 5 | 23 | 58 | 0.1 | 34 |  |
|  | 15 | 24 | 72 | 0.1 | 31 |  |
| 671261 | 0.5 | 69 | 99 | 0.1 | 33 | GalNAc$_3$-14 |
|  | 1.5 | 34 | 62 | 0.1 | 33 |  |
|  | 5 | 43 | 73 | 0.1 | 32 |  |
|  | 15 | 32 | 53 | 0.2 | 30 |  |
| 671262 | 0.5 | 24 | 51 | 0.2 | 29 | GalNAc$_3$-15 |
|  | 1.5 | 32 | 62 | 0.1 | 31 |  |
|  | 5 | 30 | 76 | 0.2 | 32 |  |
|  | 15 | 31 | 64 | 0.1 | 32 |  |

Example 66: Effect of Various Cleavable Moieties on Antisense Inhibition In Vivo by Oligonucleotides Targeting SRB-1 Comprising a 5'-GalNAc$_3$ Cluster The oligonucleotides listed below were tested in a dose-dependent study for antisense inhibition of SRB-1 in mice. Each of the GalNAc$_3$ conjugate groups was attached at the 5' terminus of the respective oligonucleotide by a phosphodiester linked nucleoside (cleavable moiety (CM)).

TABLE 57

Modified ASOs targeting SRB-1

| ISIS No. | Sequences (5' to 3') | GalNAc$_3$ Cluster | CM | SEQ ID No. |
|---|---|---|---|---|
| 661161 | GalNAc$_3$-3$_a$-$_o$.A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{es}$$^m$C$_{es}$$^m$C$_{es}$T$_{es}$T$_e$ | GalNAc$_3$-3a | A$_d$ | 831 |
| 670699 | GalNAc$_3$-3$_a$-$_o$.T$_{do}$G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{eo}$$^m$C$_{eo}$$^m$C$_{es}$T$_{es}$T$_e$ | GalNAc$_3$-3a | T$_d$ | 834 |
| 670700 | GalNAc$_3$-3$_a$-$_o$.A$_{eo}$G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{eo}$$^m$C$_{eo}$$^m$C$_{es}$T$_{es}$T$_e$ | GalNAc$_3$-3a | A$_e$ | 831 |
| 670701 | GalNAc$_3$-3$_a$-o'T$_{eo}$G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{eo}$$^m$C$_{eo}$$^m$C$_{es}$T$_{es}$T$_e$ | GalNAc$_3$-3a | T$_e$ | 834 |
| 671165 | GalNAc$_3$-13$_a$-o'A$_{do}$G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{eo}$$^m$C$_{eo}$$^m$C$_{es}$T$_{es}$T$_e$ | GalNAc$_3$-13a | A$_d$ | 831 |

Capital letters indicate the nucleobase for each nucleoside and $^m$C indicates a 5-methyl cytosine Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—. Conjugate groups are in bold.

The structure of GalNAc$_3$-3$_a$ was shown previously in Example 39. The structure of GalNAc$_3$-13a was shown previously in Example 62.

Treatment

Six to eight week old C57bl6 mice (Jackson Laboratory, Bar Harbor, MVE) were injected subcutaneously once at the dosage shown below with ISIS 661161, 670699, 670700, 670701, 671165, or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, Oreg.) according to standard protocols. The results below are presented as the average percent of SRB-1 mRNA levels for each treatment group, normalized to the saline control.

As illustrated in Table 58, treatment with antisense oligonucleotides lowered SRB-1 mRNA levels in a dose-dependent manner. The antisense oligonucleotides comprising various cleavable moieties all showed similar potencies.

TABLE 58

SRB-1 mRNA (% Saline)

| ISIS No. | Dosage (mg/kg) | SRB-1 mRNA (% Saline) | GalNAc$_3$ Cluster | CM |
|---|---|---|---|---|
| Saline | n/a | 100.0 | n/a | n/a |
| 661161 | 0.5 | 87.8 | GalNAc$_3$-3a | A$_d$ |
|  | 1.5 | 61.3 |  |  |
|  | 5 | 33.8 |  |  |
|  | 15 | 14.0 |  |  |
| 670699 | 0.5 | 89.4 | GalNAc$_3$-3a | T$_d$ |
|  | 1.5 | 59.4 |  |  |
|  | 5 | 31.3 |  |  |
|  | 15 | 17.1 |  |  |
| 670700 | 0.5 | 79.0 | GalNAc$_3$-3a | A$_e$ |
|  | 1.5 | 63.3 |  |  |
|  | 5 | 32.8 |  |  |
|  | 15 | 17.9 |  |  |
| 670701 | 0.5 | 79.1 | GalNAc$_3$-3a | T$_e$ |
|  | 1.5 | 59.2 |  |  |
|  | 5 | 35.8 |  |  |
|  | 15 | 17.7 |  |  |
| 671165 | 0.5 | 76.4 | GalNAc$_3$-13a | A$_d$ |
|  | 1.5 | 43.2 |  |  |
|  | 5 | 22.6 |  |  |
|  | 15 | 10.0 |  |  |

Liver transaminase levels, alanine aminotransferase (ALT) and aspartate aminotransferase (AST), in serum were measured relative to saline injected mice using standard protocols. Total bilirubin and BUN were also evaluated. The changes in body weights were evaluated with no significant differences from the saline group (data not shown). ALTs, ASTs, total bilirubin and BUN values are shown in Table 56 below.

TABLE 59

| ISIS No. | Dosage (mg/kg) | ALT (U/L) | AST (U/L) | Total Bilirubin (mg/dL) | BUN (mg/dL) | GalNAc$_3$ Cluster | CM |
|---|---|---|---|---|---|---|---|
| Saline | n/a | 24 | 64 | 0.2 | 31 | n/a | n/a |
| 661161 | 0.5 | 25 | 64 | 0.2 | 31 | GalNAc$_3$-3a | A$_d$ |
|  | 1.5 | 24 | 50 | 0.2 | 32 |  |  |
|  | 5 | 26 | 55 | 0.2 | 28 |  |  |
|  | 15 | 27 | 52 | 0.2 | 31 |  |  |
| 670699 | 0.5 | 42 | 83 | 0.2 | 31 | GalNAc$_3$-3a | T$_d$ |
|  | 1.5 | 33 | 58 | 0.2 | 32 |  |  |
|  | 5 | 26 | 70 | 0.2 | 29 |  |  |
|  | 15 | 25 | 67 | 0.2 | 29 |  |  |

TABLE 59-continued
| ISIS No. | Dosage (mg/kg) | ALT (U/L) | AST (U/L) | Total Bilirubin (mg/dL) | BUN (mg/dL) | GalNAc₃ Cluster | CM |
|---|---|---|---|---|---|---|---|
| 670700 | 0.5 | 40 | 74 | 0.2 | 27 | GalNAc₃-3a | $A_e$ |
|  | 1.5 | 23 | 62 | 0.2 | 27 |  |  |
|  | 5 | 24 | 49 | 0.2 | 29 |  |  |
|  | 15 | 25 | 87 | 0.1 | 25 |  |  |
| 670701 | 0.5 | 30 | 77 | 0.2 | 27 | GalNAc₃-3a | $T_e$ |
|  | 1.5 | 22 | 55 | 0.2 | 30 |  |  |
|  | 5 | 81 | 101 | 0.2 | 25 |  |  |
|  | 15 | 31 | 82 | 0.2 | 24 |  |  |
| 671165 | 0.5 | 44 | 84 | 0.2 | 26 | GalNAc₃-13a | $A_d$ |
|  | 1.5 | 47 | 71 | 0.1 | 24 |  |  |
|  | 5 | 33 | 91 | 0.2 | 26 |  |  |
|  | 15 | 33 | 56 | 0.2 | 29 |  |  |
Example 67: Preparation of Oligomeric Compound 199 Comprising GalNAc₃-16
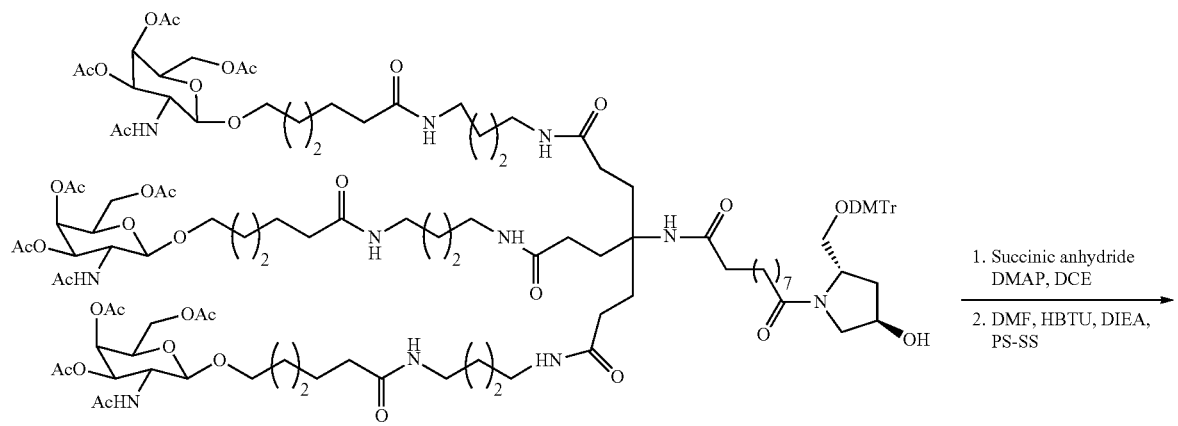
98d
1. Succinic anhydride DMAP, DCE
2. DMF, HBTU, DIEA, PS-SS
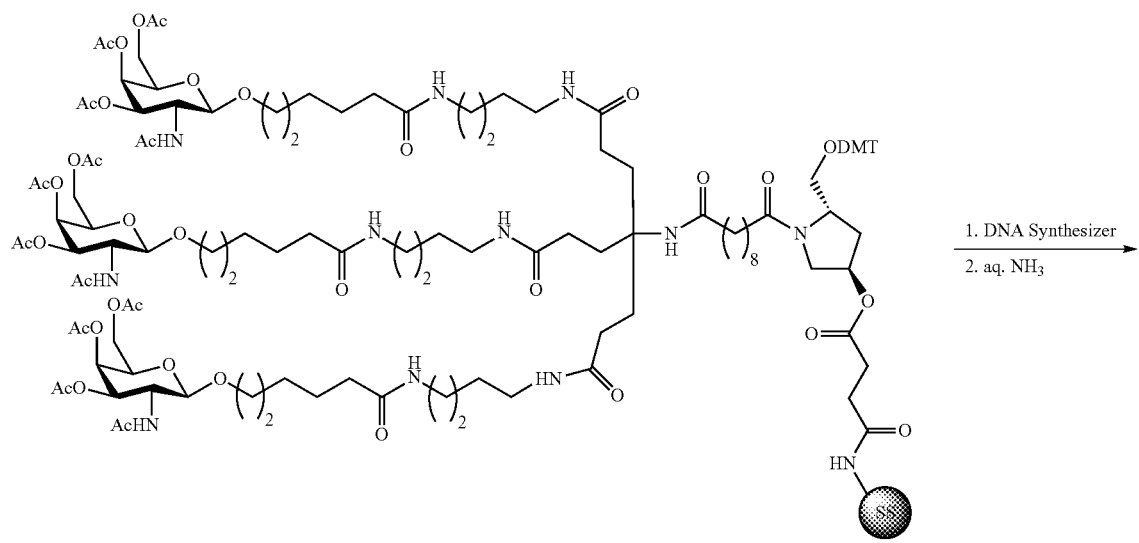
1. DNA Synthesizer
2. aq. NH₃
198

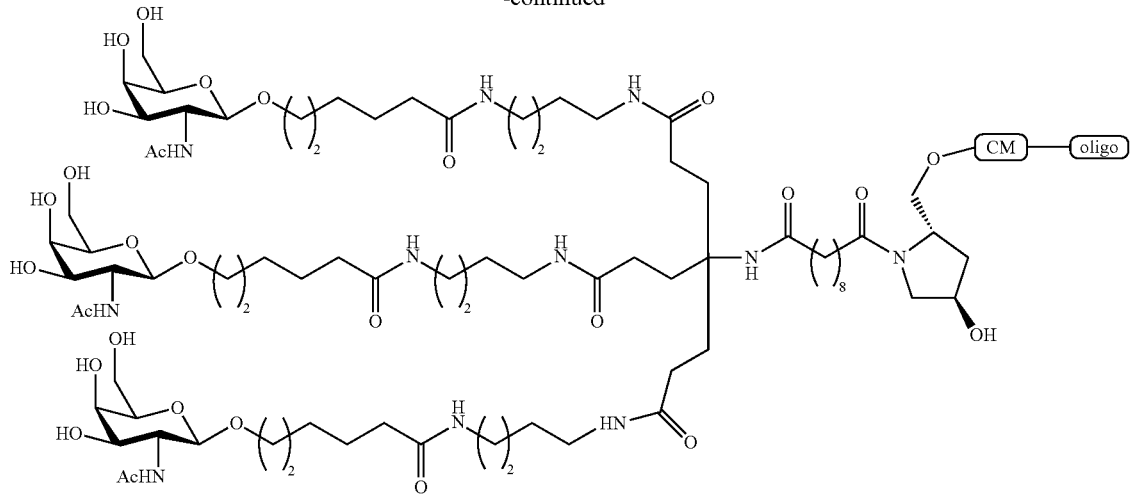

199

Oligomeric compound 199, comprising a GalNAc₃-16 conjugate group, is prepared using the general procedures illustrated in Examples 7 and 9. The GalNAc₃ cluster portion of the conjugate group GalNAc₃-16 (GalNAc₃-16$_a$) can be combined with any cleavable moiety to provide a variety of conjugate groups. In certain embodiments, the cleavable moiety is —P(=O)(OH)-A$_d$-P(=O)(OH)—. The structure of GalNAc₃-16 (GalNAc₃-16$_a$-CM-) is shown below:

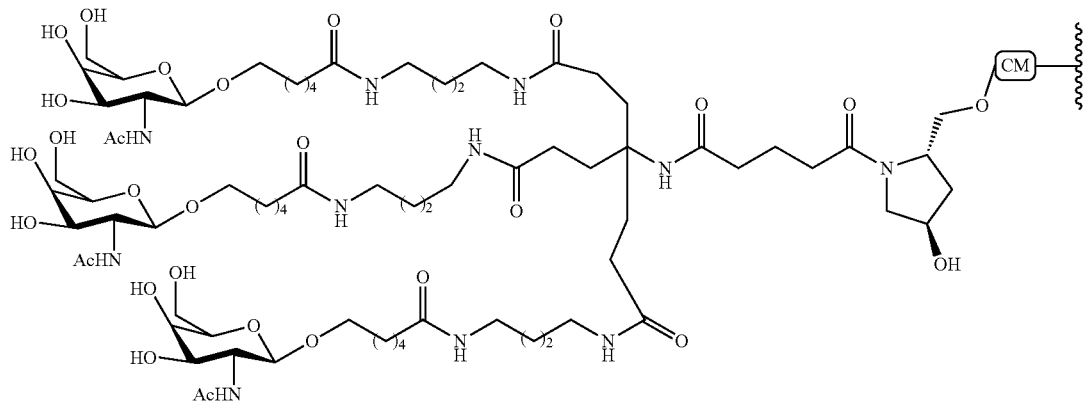

Example 68: Preparation of Oligomeric Compound 200 Comprising GalNAc₃-17

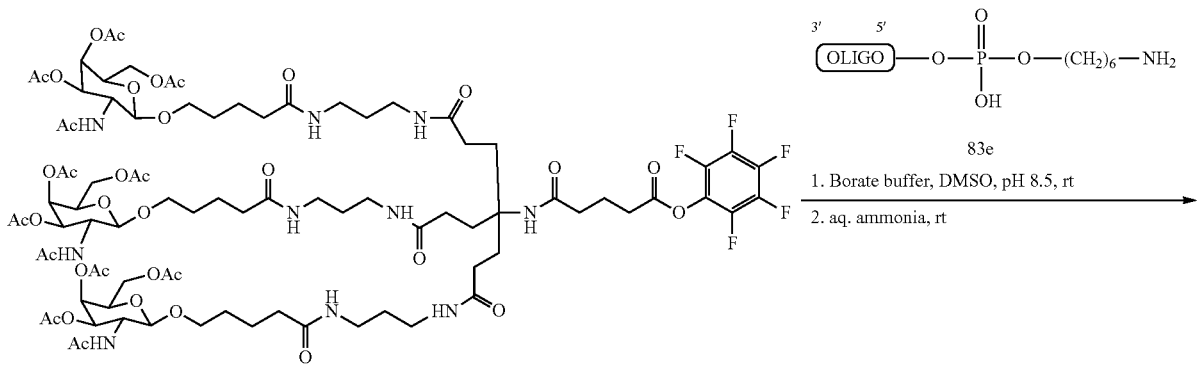

102a

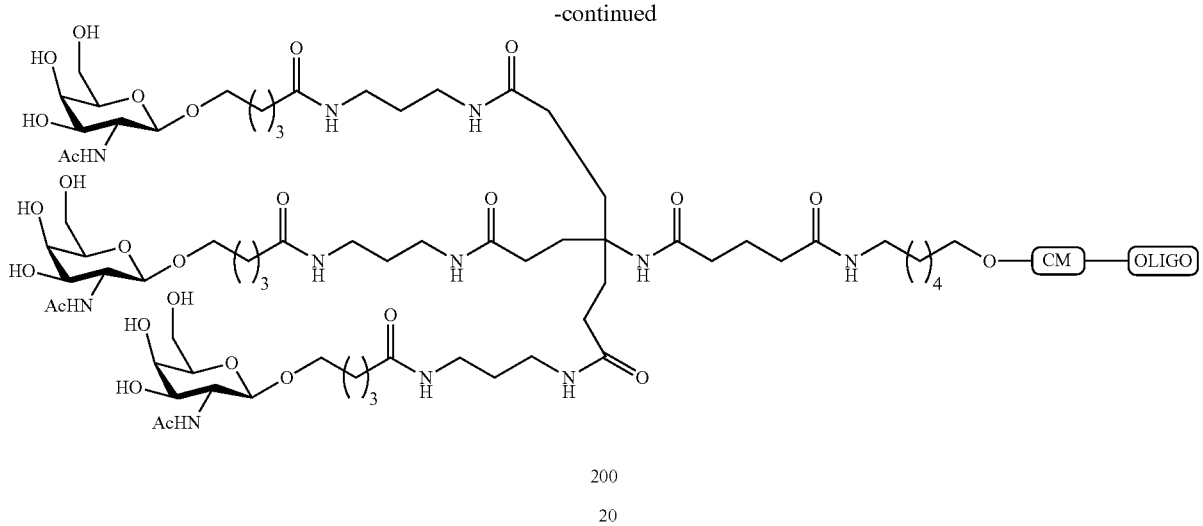

200

Oligomeric compound 200, comprising a GalNAc$_3$-17 conjugate group, was prepared using the general procedures illustrated in Example 46. The GalNAc$_3$ cluster portion of the conjugate group GalNAc$_3$-17 (GalNAc$_3$-17$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-17 (GalNAc$_3$-17$_a$-CM-) is shown below:

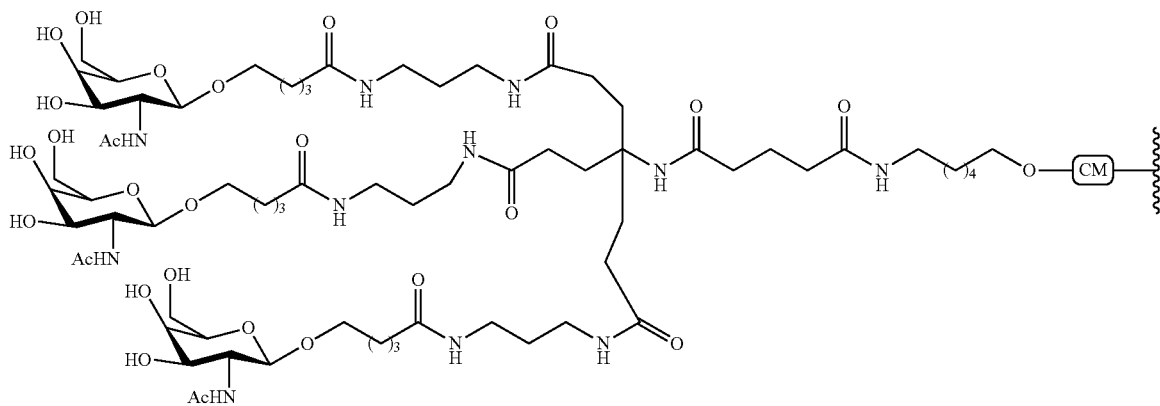

Example 69: Preparation of Oligomeric Compound 201 Comprising GalNAc$_3$-18

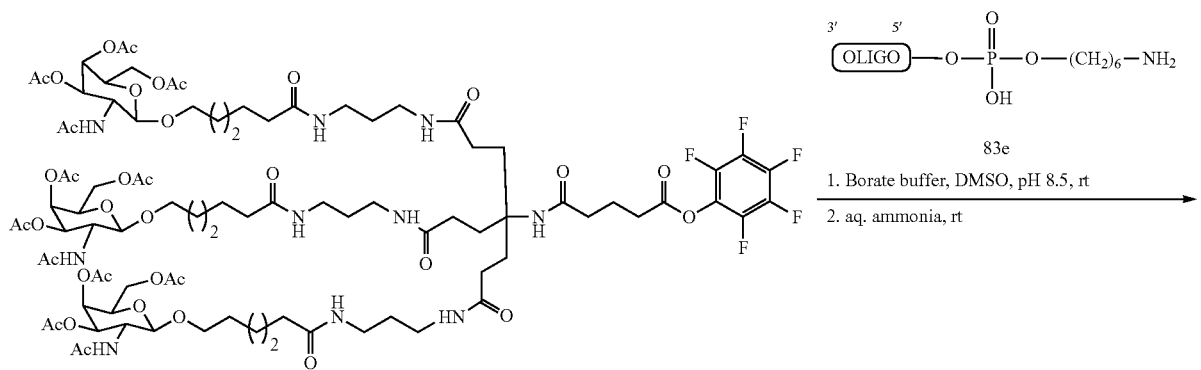

102b

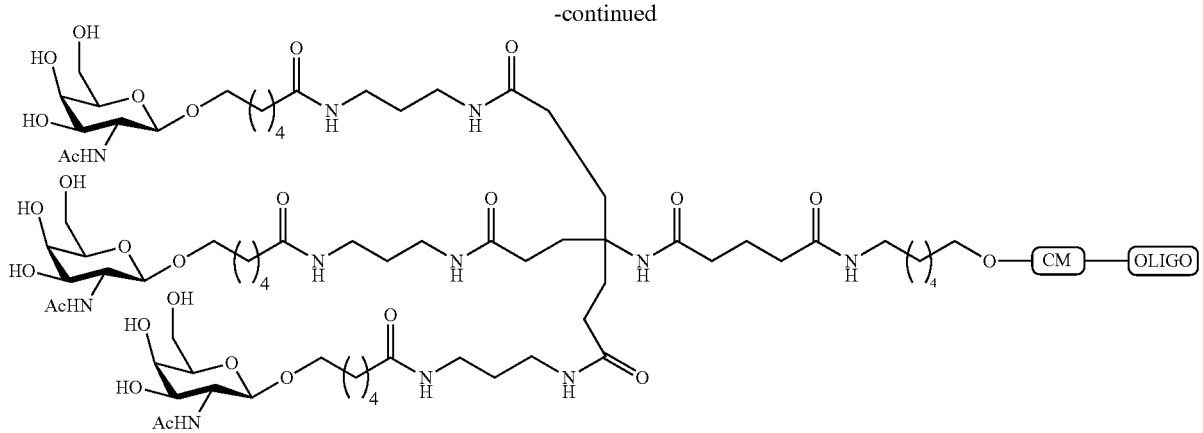

201

Oligomeric compound 201, comprising a GalNAc$_3$-18 conjugate group, was prepared using the general procedures illustrated in Example 46. The GalNAc$_3$ cluster portion of the conjugate group GalNAc$_3$-18 (GalNAc$_3$-18$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-18 (GalNAc$_3$-18$_a$-CM-) is shown below:

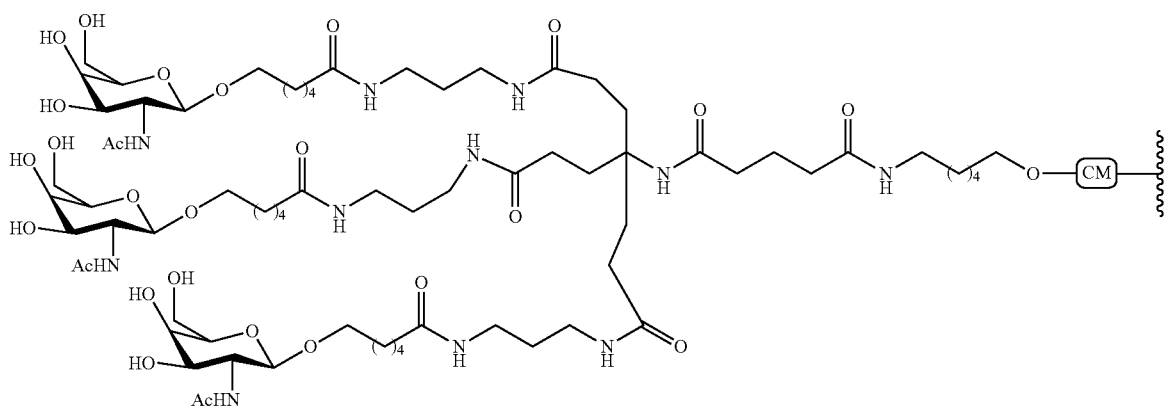

Example 70: Preparation of Oligomeric Compound 204 Comprising GalNAc$_3$-19

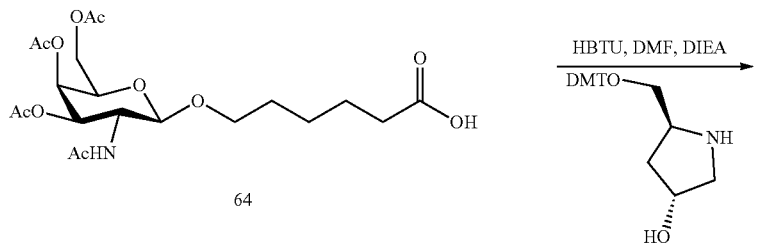

-continued
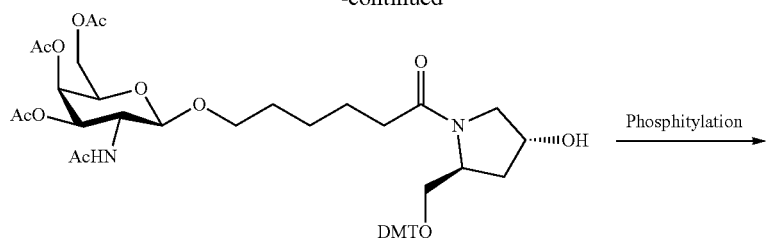
202
Phosphitylation →
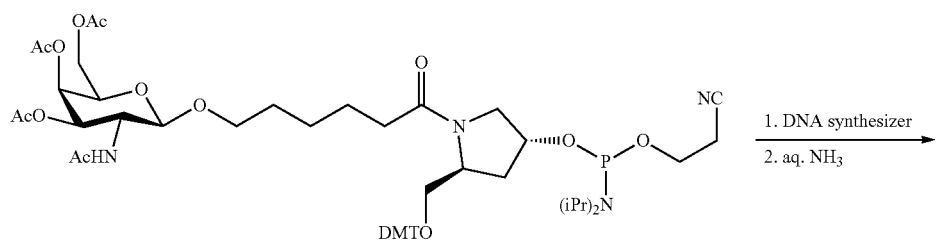
203
1. DNA synthesizer
2. aq. NH₃
→
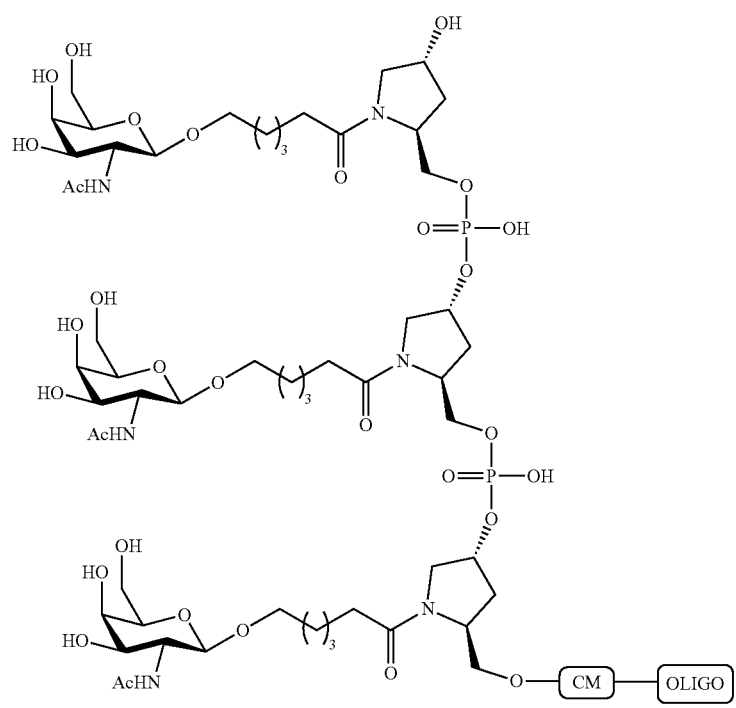
204

Oligomeric compound 204, comprising a GalNAc$_3$-19 conjugate group, was prepared from compound 64 using the general procedures illustrated in Example 52. The GalNAc$_3$ cluster portion of the conjugate group GalNAc$_3$-19 (GalNAc$_3$-19$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-19 (GalNAc$_3$-19$_a$-CM-) is shown below:

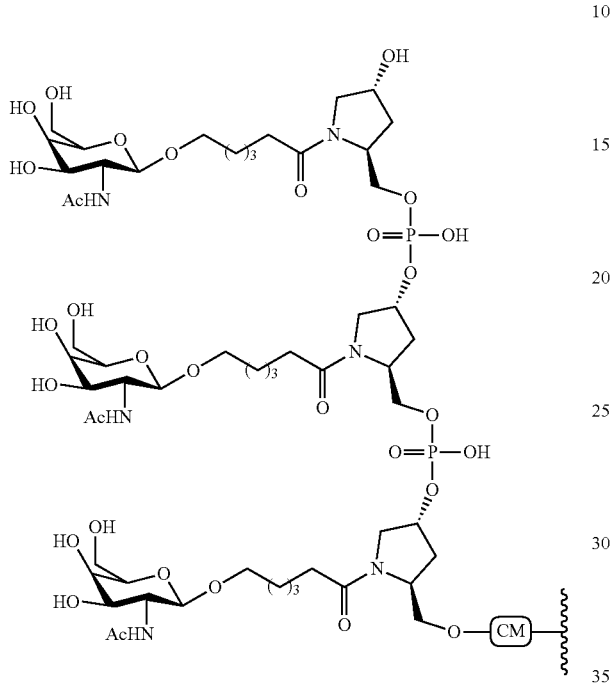

Example 71: Preparation of Oligomeric Compound 210 Comprising GalNAc$_3$-20

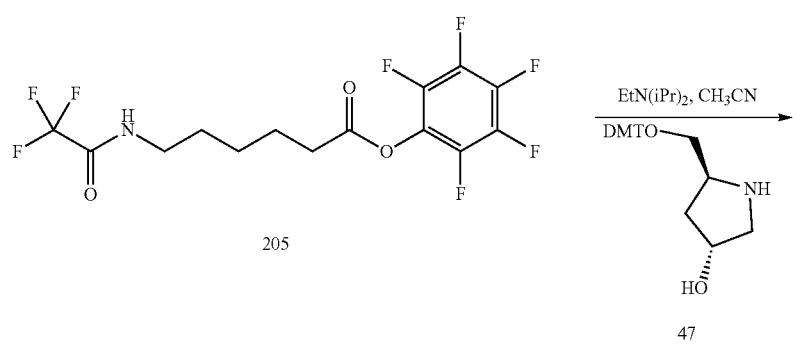

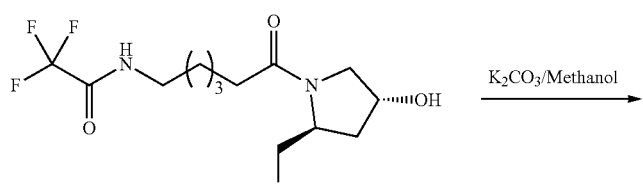

-continued
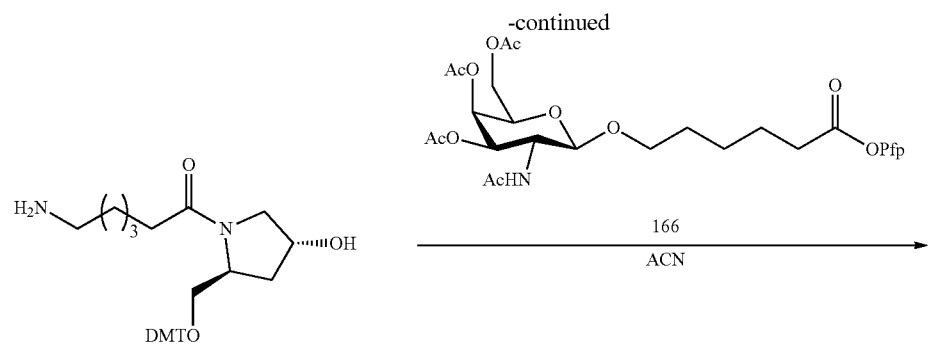
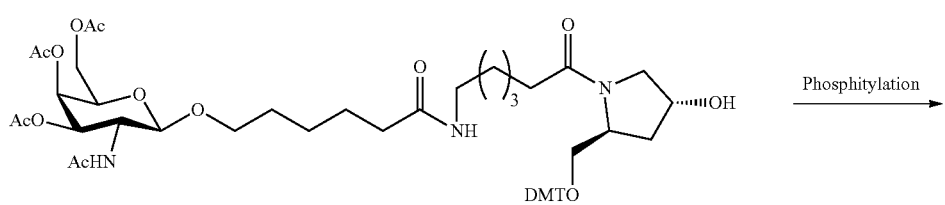
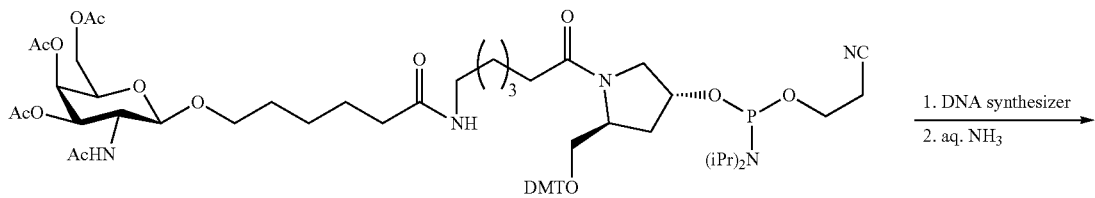
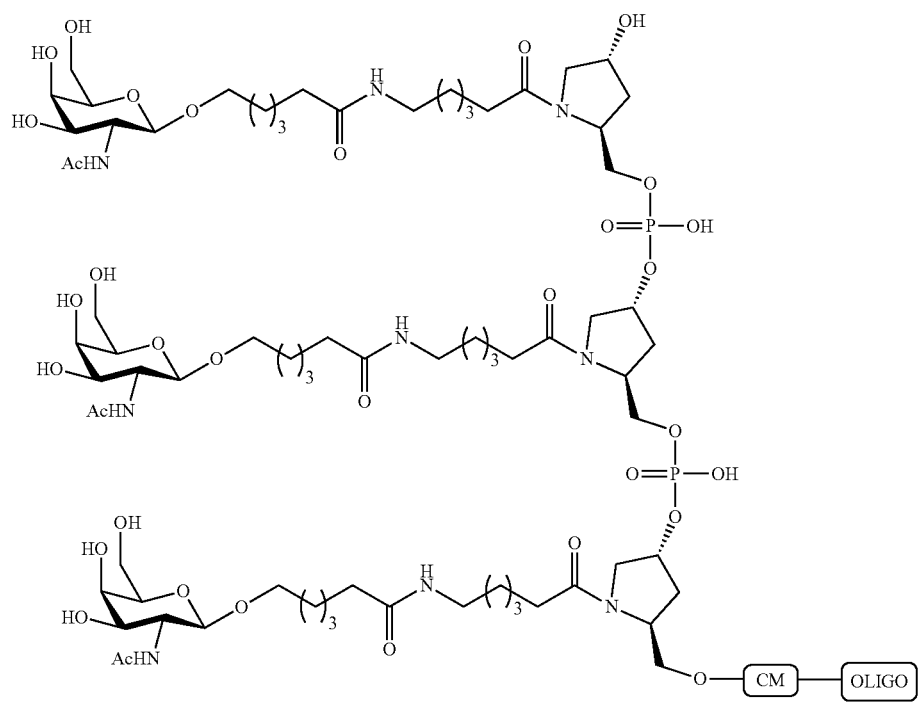

Compound 205 was prepared by adding PFP-TFA and DIEA to 6-(2,2,2-trifluoroacetamido)hexanoic acid in acetonitrile, which was prepared by adding triflic anhydride to 6-aminohexanoic acid. The reaction mixture was heated to 80° C., then lowered to rt. Oligomeric compound 210, comprising a GalNAc$_3$-20 conjugate group, was prepared from compound 208 using the general procedures illustrated in Example 52.

The GalNAc$_3$ cluster portion of the conjugate group GalNAc$_3$-20 (GalNAc$_3$-20$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-20 (GalNAc$_3$-20$_a$-CM-) is shown below:

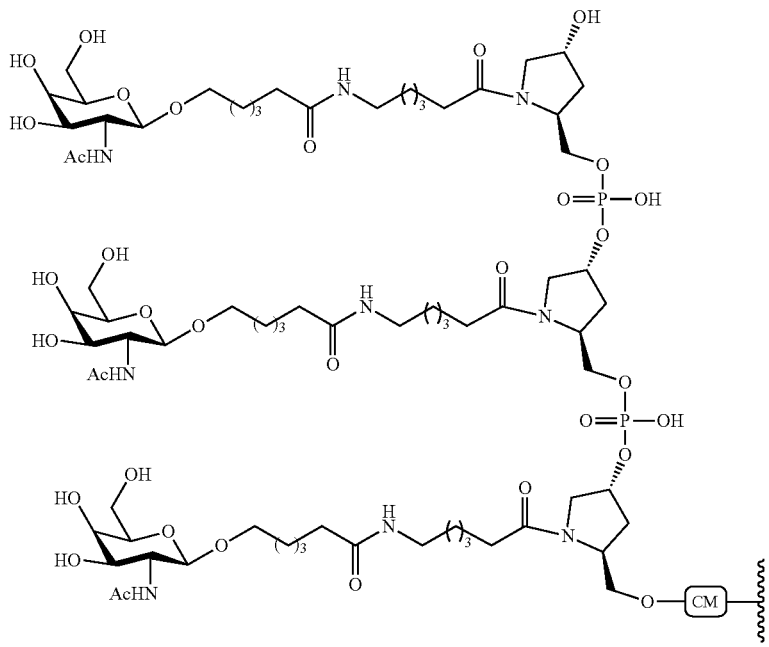

Example 72: Preparation of Oligomeric Compound 215 Comprising GalNAc$_3$-21

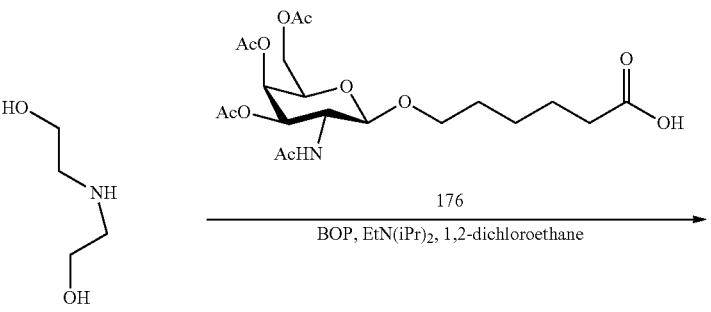

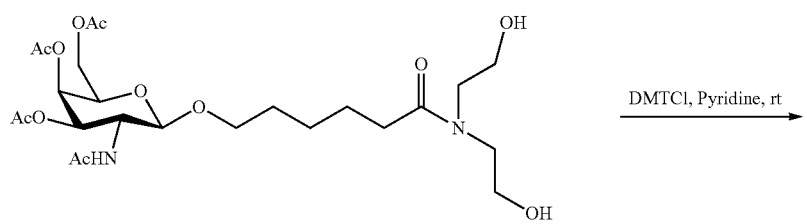

-continued

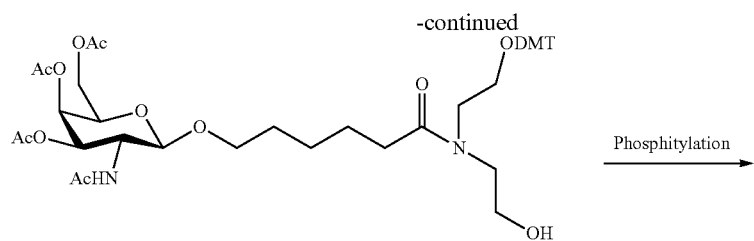

213

Phosphitylation →

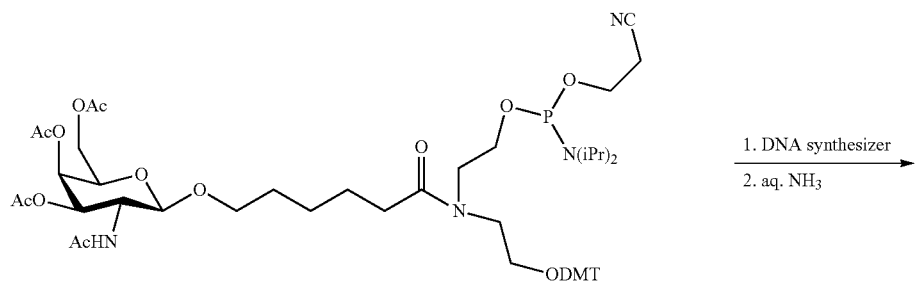

214

1. DNA synthesizer
2. aq. NH₃
→

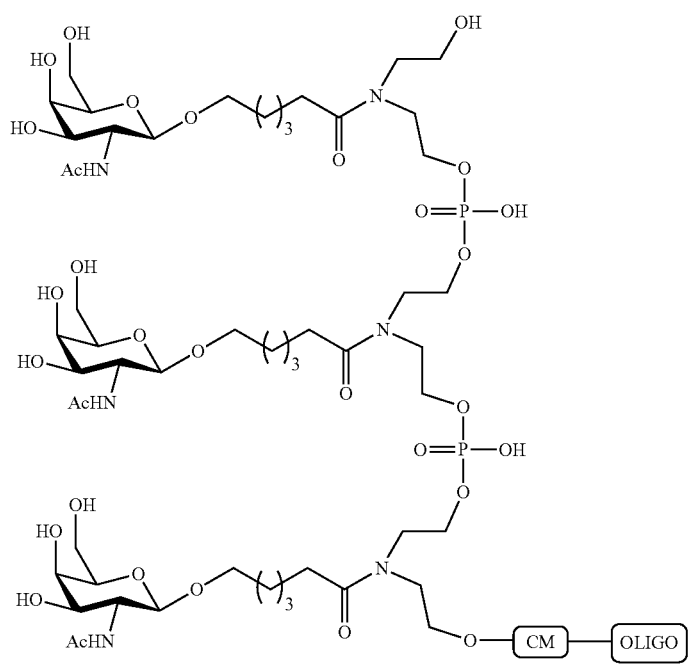

215

Compound 211 is commercially available. Oligomeric compound 215, comprising a GalNAc₃-21 conjugate group, was prepared from compound 213 using the general procedures illustrated in Example 52. The GalNAc₃ cluster portion of the conjugate group GalNAc₃-21 (GalNAc₃-21$_a$) can be combined with any cleavable moiety to provide a variety of conjugate groups. In certain embodiments, the cleavable moiety is —P(=O)(OH)-A$_d$-P(=O)(OH)—. The structure of GalNAc₃-21 (GalNAc₃-21$_a$-CM-) is shown below:

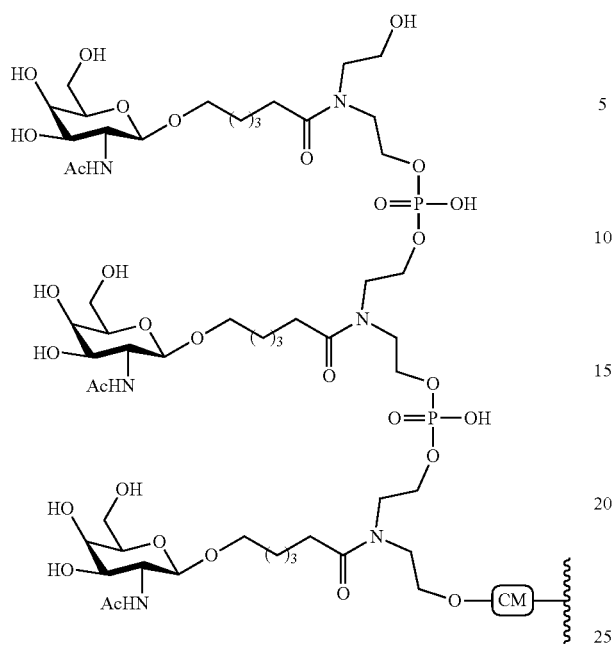
Example 73: Preparation of Oligomeric Compound 221 Comprising GalNAc₃-22
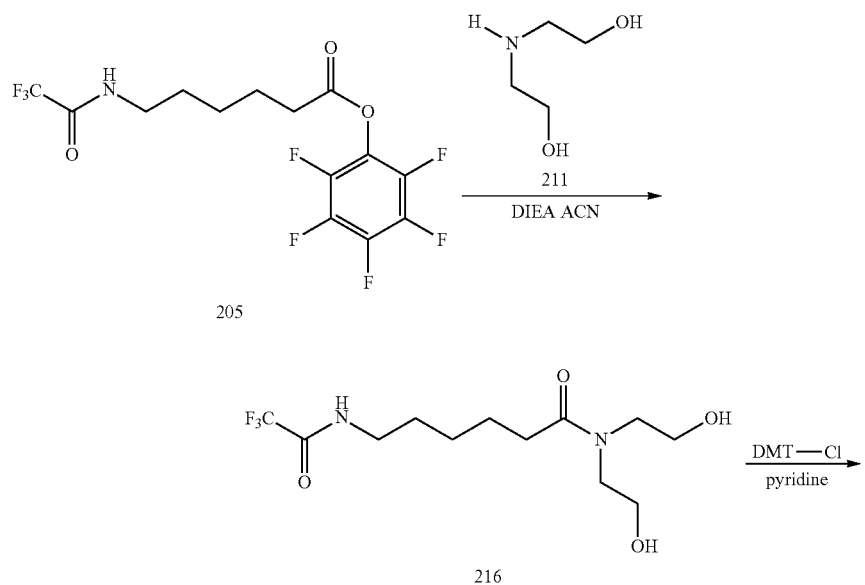
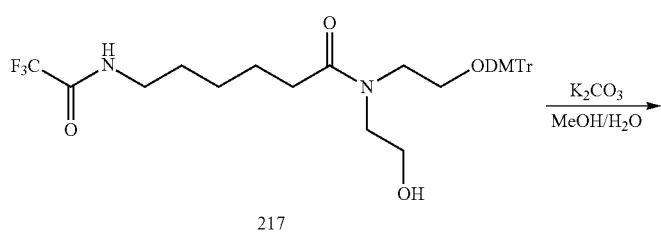

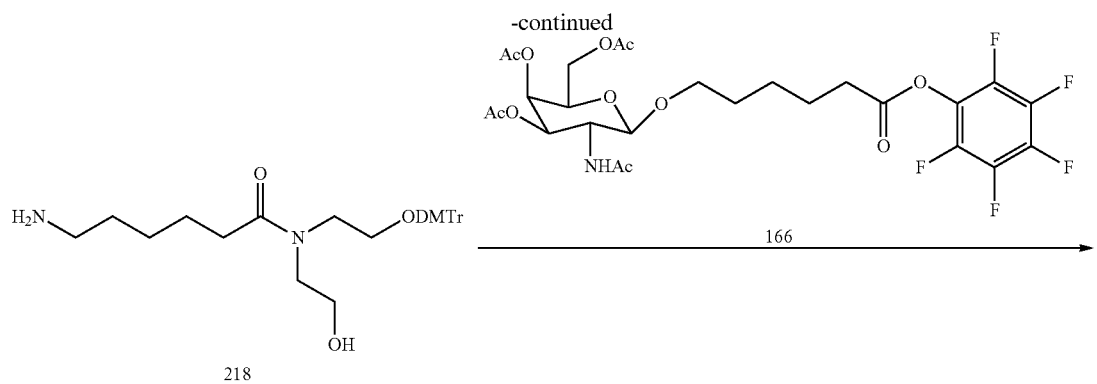

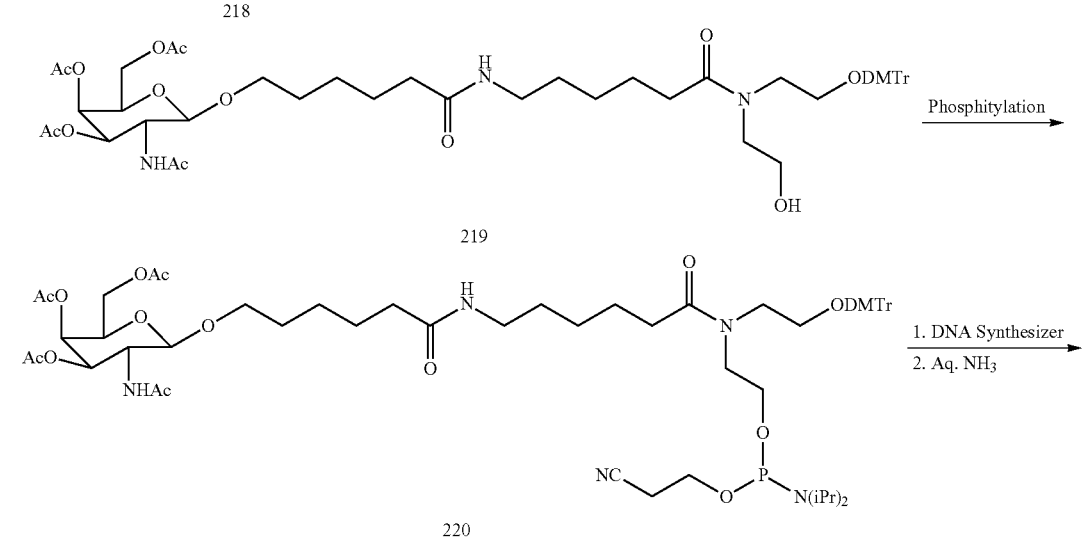

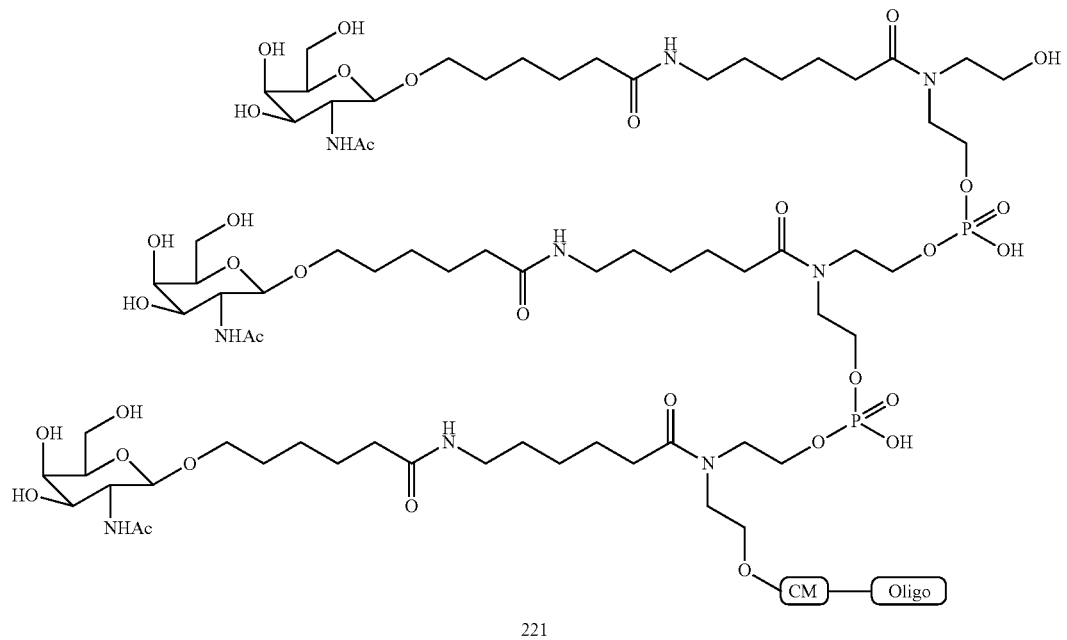

Compound 220 was prepared from compound 219 using diisopropylammonium tetrazolide. Oligomeric compound 221, comprising a GalNAc$_3$-21 conjugate group, is prepared from compound 220 using the general procedure illustrated in Example 52. The GalNAc$_3$ cluster portion of the conjugate group GalNAc$_3$-22 (GalNAc$_3$-22$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-22 (GalNAc$_3$-22$_a$-CM-) is shown below:

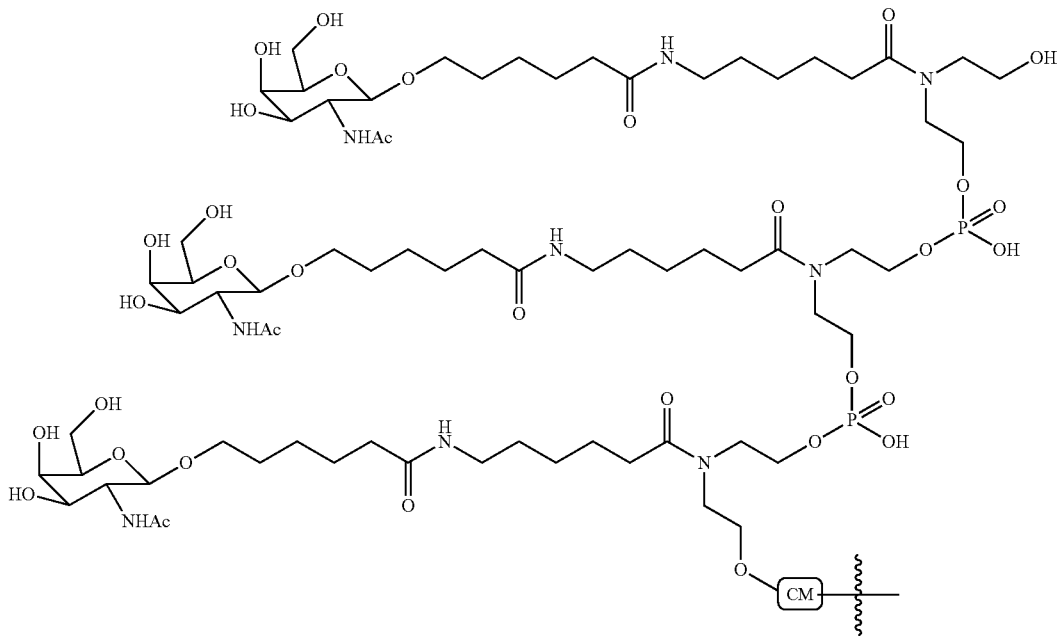

Example 74: Effect of Various Cleavable Moieties on Antisense Inhibition In Vivo by Oligonucleotides Targeting SRB-1 Comprising a 5'-GalNAc₃ Conjugate The oligonucleotides listed below were tested in a dose-dependent study for antisense inhibition of SRB-1 in mice. Each of the GalNAc₃ conjugate groups was attached at the 5' terminus of the respective oligonucleotide.

Treatment

Six to eight week old C57BL/6 mice (Jackson Laboratory, Bar Harbor, Me.) were injected subcutaneously once at the dosage shown below with an oligonucleotide listed in Table 60 or with saline. Each treatment group consisted of 4 animals. The mice were sacrificed 72 hours following the final administration to determine the SRB-1 mRNA levels using real-time PCR and RIBOGREEN® RNA quantification reagent (Molecular Probes, Inc. Eugene, Oreg.) accord-

TABLE 60

Modified ASOs targeting SRB-1

| ISIS No. | Sequences (5' to 3') | GalNAc₃ Cluster | CM | SEQ ID No. |
|---|---|---|---|---|
| 353382 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | n/a | n/a | 829 |
| 661161 | GalNAc₃-3$_a$-$_o$,A$_{do}$$G_{es}{}^mC_{es}T_{es}T_{es}{}^mC_{es}A_{ds}G_{ds}T_{ds}{}^mC_{ds}A_{ds}T_{ds}$$G_{ds}A_{ds}{}^mC_{ds}T_{ds}T_{es}{}^mC_{es}{}^mC_{es}T_{es}T_e$ | GalNAc₃-3a | A$_d$ | 831 |
| 666904 | GalNAc₃-3$_a$-$_o$,$G_{es}{}^mC_{es}T_{es}T_{es}{}^mC_{es}A_{ds}G_{ds}T_{ds}{}^mC_{ds}A_{ds}T_{ds}$$G_{ds}A_{ds}{}^mC_{ds}T_{ds}T_{es}{}^mC_{es}{}^mC_{es}T_{es}T_e$ | GalNAc₃-3a | PO | 829 |
| 675441 | GalNAc₃-17$_a$-$_o$,A$_{do}$$G_{es}{}^mC_{es}T_{es}T_{es}{}^mC_{es}A_{ds}G_{ds}T_{ds}{}^mC_{ds}A_{ds}T_{ds}$$G_{ds}A_{ds}{}^mC_{ds}T_{ds}T_{es}{}^mC_{es}{}^mC_{es}T_{es}T_e$ | GalNAc₃-17a | A$_d$ | 831 |
| 675442 | GalNAc₃-18$_a$-$_o$,A$_{do}$$G_{es}{}^mC_{es}T_{es}T_{es}{}^mC_{es}A_{ds}G_{ds}T_{ds}{}^mC_{ds}A_{ds}T_{ds}$$G_{ds}A_{ds}{}^mC_{ds}T_{ds}T_{es}{}^mC_{es}{}^mC_{es}T_{es}T_e$ | GalNAc₃-18a | A$_d$ | 831 |

In all tables, capital letters indicate the nucleobase for each nucleoside and $^mC$ indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc₃-3$_a$ was shown previously in Example 39. The structure of GalNAc₃-17a was shown previously in Example 68, and the structure of GalNAc₃-18a was shown in Example 69.

ing to standard protocols. The results below are presented as the average percent of SRB-1 mRNA levels for each treatment group, normalized to the saline control.

As illustrated in Table 61, treatment with antisense oligonucleotides lowered SRB-1 mRNA levels in a dose-dependent manner. The antisense oligonucleotides comprising a GalNAc conjugate showed similar potencies and were significantly more potent than the parent oligonucleotide lacking a GalNac conjugate.

TABLE 61

SRB-1 mRNA (% Saline)

| ISIS No. | Dosage (mg/kg) | SRB-1 mRNA (% Saline) | GalNAc$_3$ Cluster | CM |
|---|---|---|---|---|
| Saline | n/a | 100.0 | n/a | n/a |
| 353382 | 3 | 79.38 | n/a | n/a |
|  | 10 | 68.67 |  |  |
|  | 30 | 40.70 |  |  |
| 661161 | 0.5 | 79.18 | GalNAc$_3$-3a | A$_d$ |
|  | 1.5 | 75.96 |  |  |
|  | 5 | 30.53 |  |  |
|  | 15 | 12.52 |  |  |
| 666904 | 0.5 | 91.30 | GalNAc$_3$-3a | PO |
|  | 1.5 | 57.88 |  |  |
|  | 5 | 21.22 |  |  |
|  | 15 | 16.49 |  |  |
| 675441 | 0.5 | 76.71 | GalNAc$_3$-17a | A$_d$ |
|  | 1.5 | 63.63 |  |  |
|  | 5 | 29.57 |  |  |
|  | 15 | 13.49 |  |  |
| 675442 | 0.5 | 95.03 | GalNAc$_3$-18a | A$_d$ |
|  | 1.5 | 60.06 |  |  |
|  | 5 | 31.04 |  |  |
|  | 15 | 19.40 |  |  |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group (data not shown). ALTs, ASTs, total bilirubin and BUN values are shown in Table 62 below.

TABLE 62

| ISIS No. | Dosage (mg/kg) | ALT (U/L) | AST (U/L) | Total Bilirubin (mg/dL) | BUN (mg/dL) | GalNAc$_3$ Cluster | CM |
|---|---|---|---|---|---|---|---|
| Saline | n/a | 26 | 59 | 0.16 | 42 | n/a | n/a |
| 353382 | 3 | 23 | 58 | 0.18 | 39 | n/a | n/a |
|  | 10 | 28 | 58 | 0.16 | 43 |  |  |
|  | 30 | 20 | 48 | 0.12 | 34 |  |  |
| 661161 | 0.5 | 30 | 47 | 0.13 | 35 | GalNAc$_3$-3a | A$_d$ |
|  | 1.5 | 23 | 53 | 0.14 | 37 |  |  |
|  | 5 | 26 | 48 | 0.15 | 39 |  |  |
|  | 15 | 32 | 57 | 0.15 | 42 |  |  |
| 666904 | 0.5 | 24 | 73 | 0.13 | 36 | GalNAc$_3$-3a | PO |
|  | 1.5 | 21 | 48 | 0.12 | 32 |  |  |
|  | 5 | 19 | 49 | 0.14 | 33 |  |  |
|  | 15 | 20 | 52 | 0.15 | 26 |  |  |
| 675441 | 0.5 | 42 | 148 | 0.21 | 36 | GalNAc$_3$-17a | A$_d$ |
|  | 1.5 | 60 | 95 | 0.16 | 34 |  |  |
|  | 5 | 27 | 75 | 0.14 | 37 |  |  |
|  | 15 | 24 | 61 | 0.14 | 36 |  |  |
| 675442 | 0.5 | 26 | 65 | 0.15 | 37 | GalNAc$_3$-18a | A$_d$ |
|  | 1.5 | 25 | 64 | 0.15 | 43 |  |  |
|  | 5 | 27 | 69 | 0.15 | 37 |  |  |
|  | 15 | 30 | 84 | 0.14 | 37 |  |  |

Example 75: Pharmacokinetic Analysis of Oligonucleotides Comprising a 5'-Conjugate Group The PK of the ASOs in Tables 54, 57 and 60 above was evaluated using liver samples that were obtained following the treatment procedures described in Examples 65, 66, and 74. The liver samples were minced and extracted using standard protocols and analyzed by IP-HPLC-MS alongside an internal standard. The combined tissue level (μg/g) of all metabolites was measured by integrating the appropriate UV peaks, and the tissue level of the full-length ASO missing the conjugate ("parent," which is Isis No. 353382 in this case) was measured using the appropriate extracted ion chromatograms (EIC).

TABLE 63

PK Analysis in Liver

| ISIS No. | Dosage (mg/kg) | Total Tissue Level by UV (μg/g) | Parent ASO Tissue Level by EIC (μg/g) | GalNAc$_3$ Cluster | CM |
|---|---|---|---|---|---|
| 353382 | 3 | 8.9 | 8.6 | n/a | n/a |
|  | 10 | 22.4 | 21.0 |  |  |
|  | 30 | 54.2 | 44.2 |  |  |
| 661161 | 5 | 32.4 | 20.7 | GalNAc$_3$-3a | A$_d$ |
|  | 15 | 63.2 | 44.1 |  |  |
| 671144 | 5 | 20.5 | 19.2 | GalNAc$_3$-12a | A$_d$ |
|  | 15 | 48.6 | 41.5 |  |  |
| 670061 | 5 | 31.6 | 28.0 | GalNAc$_3$-13a | A$_d$ |
|  | 15 | 67.6 | 55.5 |  |  |
| 671261 | 5 | 19.8 | 16.8 | GalNAc$_3$-14a | A$_d$ |
|  | 15 | 64.7 | 49.1 |  |  |
| 671262 | 5 | 18.5 | 7.4 | GalNAc$_3$-15a | A$_d$ |
|  | 15 | 52.3 | 24.2 |  |  |
| 670699 | 5 | 16.4 | 10.4 | GalNAc$_3$-3a | T$_d$ |
|  | 15 | 31.5 | 22.5 |  |  |
| 670700 | 5 | 19.3 | 10.9 | GalNAc$_3$-3a | A$_e$ |
|  | 15 | 38.1 | 20.0 |  |  |
| 670701 | 5 | 21.8 | 8.8 | GalNAc$_3$-3a | T$_e$ |
|  | 15 | 35.2 | 16.1 |  |  |
| 671165 | 5 | 27.1 | 26.5 | GalNAc$_3$-13a | A$_d$ |
|  | 15 | 48.3 | 44.3 |  |  |
| 666904 | 5 | 30.8 | 24.0 | GalNAc$_3$-3a | PO |
|  | 15 | 52.6 | 37.6 |  |  |
| 675441 | 5 | 25.4 | 19.0 | GalNAc$_3$-17a | A$_d$ |
|  | 15 | 54.2 | 42.1 |  |  |
| 675442 | 5 | 22.2 | 20.7 | GalNAc$_3$-18a | A$_d$ |
|  | 15 | 39.6 | 29.0 |  |  |

The results in Table 63 above show that there were greater liver tissue levels of the oligonucleotides comprising a GalNAc₃ conjugate group than of the parent oligonucleotide that does not comprise a GalNAc₃ conjugate group (ISIS 353382) 72 hours following oligonucleotide administration, particularly when taking into consideration the differences in dosing between the oligonucleotides with and without a GalNAc₃ conjugate group. Furthermore, by 72 hours, 40-98% of each oligonucleotide comprising a GalNAc₃ conjugate group was metabolized to the parent compound, indicating that the GalNAc₃ conjugate groups were cleaved from the oligonucleotides.

Example 76: Preparation of Oligomeric Compound 230 Comprising GalNAc₃-23

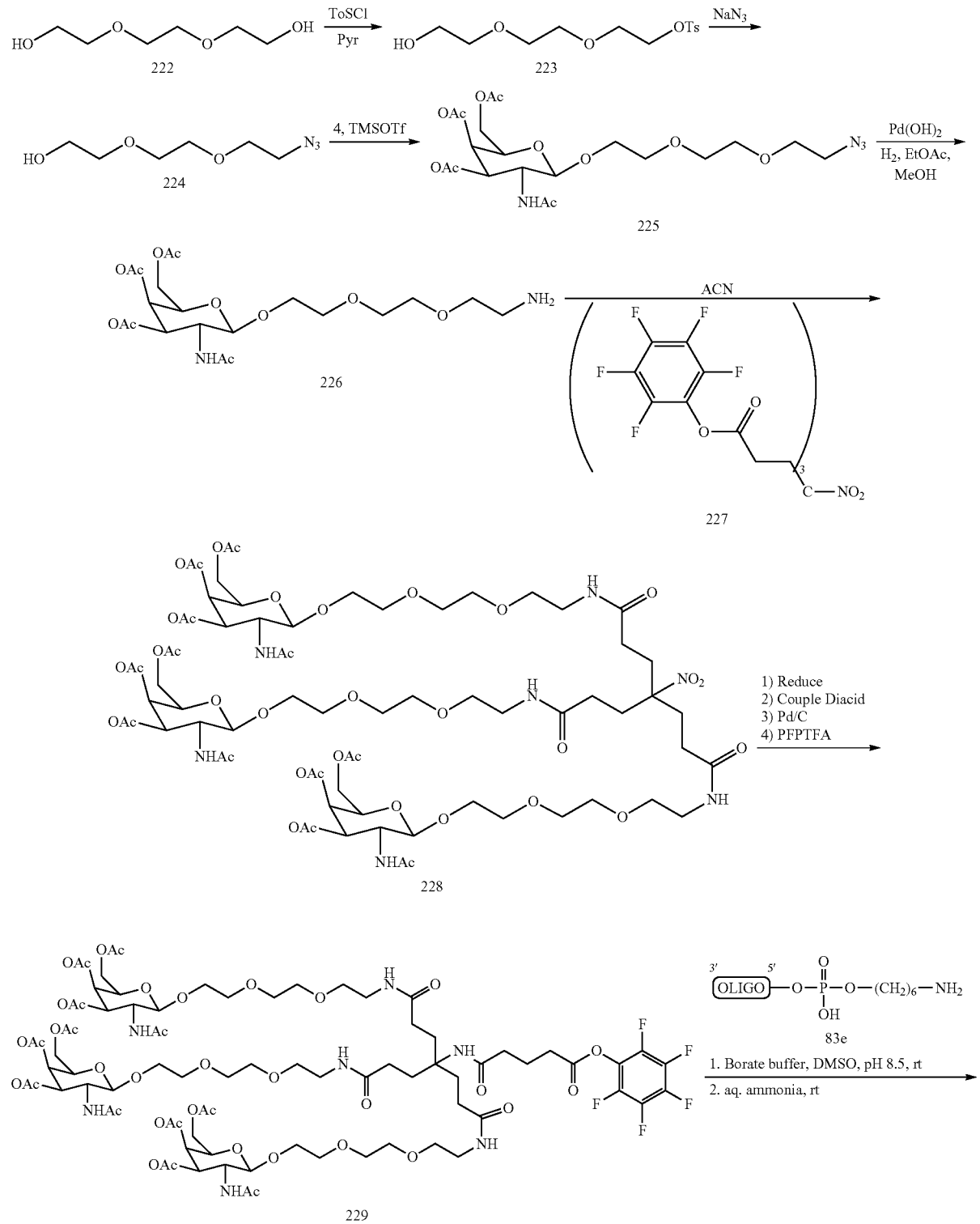

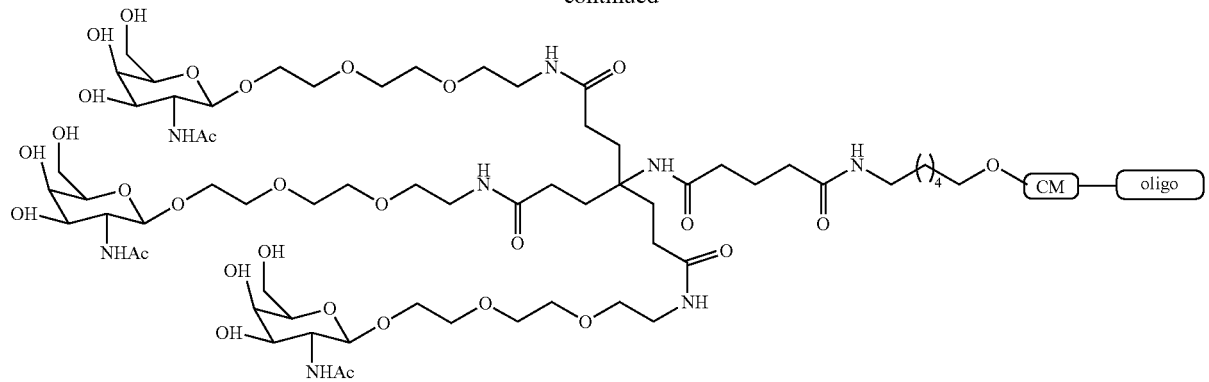

230

Compound 222 is commercially available. 44.48 ml (0.33 mol) of compound 222 was treated with tosyl chloride (25.39 g, 0.13 mol) in pyridine (500 mL) for 16 hours. The reaction was then evaporated to an oil, dissolved in EtOAc and washed with water, sat. NaHCO$_3$, brine, and dried over Na$_2$SO$_4$. The ethyl acetate was concentrated to dryness and purified by column chromatography, eluted with EtOAc/hexanes (1:1) followed by 10% methanol in CH$_2$Cl$_2$ to give compound 223 as a colorless oil. LCMS and NMR were consistent with the structure. 10 g (32.86 mmol) of 1-Tosyltriethylene glycol (compound 223) was treated with sodium azide (10.68 g, 164.28 mmol) in DMSO (100 mL) at room temperature for 17 hours. The reaction mixture was then poured onto water, and extracted with EtOAc. The organic layer was washed with water three times and dried over Na$_2$SO$_4$. The organic layer was concentrated to dryness to give 5.3 g of compound 224 (92%). LCMS and NMR were consistent with the structure. 1-Azidotriethylene glycol (compound 224, 5.53 g, 23.69 mmol) and compound 4 (6 g, 18.22 mmol) were treated with 4A molecular sieves (5 g), and TMSOTf (1.65 ml, 9.11 mmol) in dichloromethane (100 mL) under an inert atmosphere. After 14 hours, the reaction was filtered to remove the sieves, and the organic layer was washed with sat. NaHCO$_3$, water, brine, and dried over Na$_2$SO$_4$. The organic layer was concentrated to dryness and purified by column chromatography, eluted with a gradient of 2 to 4% methanol in dichloromethane to give compound 225. LCMS and NMR were consistent with the structure. Compound 225 (11.9 g, 23.59 mmol) was hydrogenated in EtOAc/Methanol (4:1, 250 mL) over Pearlman's catalyst. After 8 hours, the catalyst was removed by filtration and the solvents removed to dryness to give compound 226. LCMS and NMR were consistent with the structure.

In order to generate compound 227, a solution of nitromethanetrispropionic acid (4.17 g, 15.04 mmol) and Hunig's base (10.3 ml, 60.17 mmol) in DMF (100 mL) were treated dropwise with pentaflourotrifluoro acetate (9.05 ml, 52.65 mmol). After 30 minutes, the reaction was poured onto ice water and extracted with EtOAc. The organic layer was washed with water, brine, and dried over Na$_2$SO$_4$. The organic layer was concentrated to dryness and then recrystallized from heptane to give compound 227 as a white solid. LCMS and NMR were consistent with the structure. Compound 227 (1.5 g, 1.93 mmol) and compound 226 (3.7 g, 7.74 mmol) were stirred at room temperature in acetonitrile (15 mL) for 2 hours. The reaction was then evaporated to dryness and purified by column chromatography, eluting with a gradient of 2 to 10% methanol in dichloromethane to give compound 228. LCMS and NMR were consistent with the structure. Compound 228 (1.7 g, 1.02 mmol) was treated with Raney Nickel (about 2 g wet) in ethanol (100 mL) in an atmosphere of hydrogen. After 12 hours, the catalyst was removed by filtration and the organic layer was evaporated to a solid that was used directly in the next step. LCMS and NMR were consistent with the structure. This solid (0.87 g, 0.53 mmol) was treated with benzylglutaric acid (0.18 g, 0.8 mmol), HBTU (0.3 g, 0.8 mmol) and DIEA (273.7 µl, 1.6 mmol) in DMF (5 mL). After 16 hours, the DMF was removed under reduced pressure at 65° C. to an oil, and the oil was dissolved in dichloromethane. The organic layer was washed with sat. NaHCO$_3$, brine, and dried over Na$_2$SO$_4$. After evaporation of the organic layer, the compound was purified by column chromatography and eluted with a gradient of 2 to 20% methanol in dichloromethane to give the coupled product. LCMS and NMR were consistent with the structure. The benzyl ester was deprotected with Pearlman's catalyst under a hydrogen atmosphere for 1 hour. The catalyst was them removed by filtration and the solvents removed to dryness to give the acid. LCMS and NMR were consistent with the structure. The acid (486 mg, 0.27 mmol) was dissolved in dry DMF (3 mL). Pyridine (53.61 µl, 0.66 mmol) was added and the reaction was purged with argon. Pentaflourotriflouro acetate (46.39 µl, 0.4 mmol) was slowly added to the reaction mixture. The color of the reaction changed from pale yellow to burgundy, and gave off a light smoke which was blown away with a stream of argon. The reaction was allowed to stir at room temperature for one hour (completion of reaction was confirmed by LCMS). The solvent was removed under reduced pressure (rotovap) at 70° C. The residue was diluted with DCM and washed with 1N NaHSO$_4$, brine, saturated sodium bicarbonate and brine again. The organics were dried over Na$_2$SO$_4$, filtered, and were concentrated to dryness to give 225 mg of compound 229 as a brittle yellow foam. LCMS and NMR were consistent with the structure.

Oligomeric compound 230, comprising a GalNAc$_3$-23 conjugate group, was prepared from compound 229 using the general procedure illustrated in Example 46. The GalNAc$_3$ cluster portion of the GalNAc$_3$-23 conjugate group (GalNAc$_3$-23$_a$) can be combined with any cleavable moiety to provide a variety of conjugate groups. The structure of GalNAc$_3$-23 (GalNAc$_3$-23$_a$-CM) is shown below:

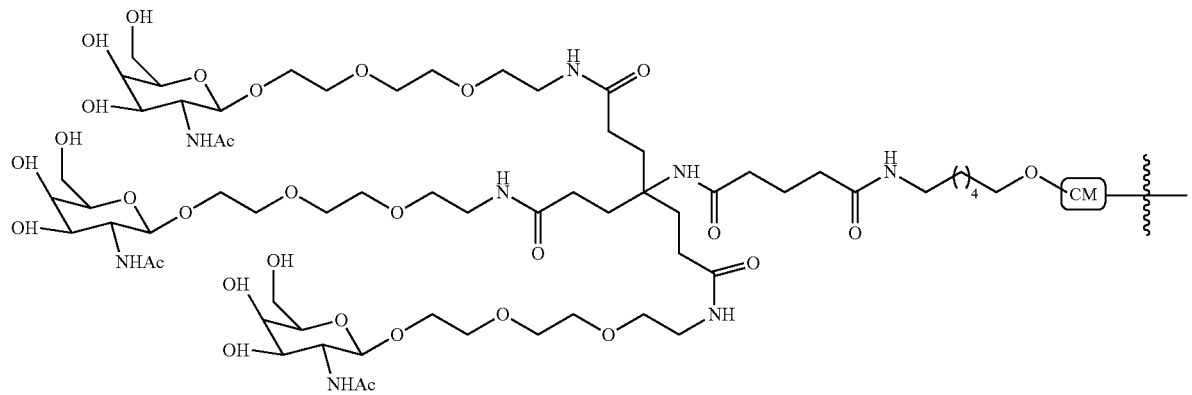

Example 77: Antisense Inhibition In Vivo by Oligonucleotides Targeting SRB-1 Comprising a GalNAc₃ Conjugate The oligonucleotides listed below were tested in a dose-dependent study for antisense inhibition of SRB-1 in mice.

TABLE 64

Modified ASOs targeting SRB-1

| ISIS No. | Sequences (5' to 3') | GalNAc₃ Cluster | CM | SEQ ID No. |
|---|---|---|---|---|
| 661161 | GalNAc₃-3$_a$-$_o$,$A_{do}G_{es}{}^mC_{es}T_{es}T_{es}{}^mC_{es}A_{ds}G_{ds}T_{ds}{}^mC_{ds}A_{ds}T_{ds}$ $G_{ds}A_{ds}{}^mC_{ds}T_{ds}T_{es}{}^mC_{es}{}^mC_{es}T_{es}T_e$ | GalNAc₃-3a | $A_d$ | 831 |
| 666904 | GalNAc₃-3$_a$-$_o$,$G_{es}{}^mC_{es}T_{es}T_{es}{}^mC_{es}A_{ds}G_{ds}T_{ds}{}^mC_{ds}A_{ds}T_{ds}$ $G_{ds}A_{ds}{}^mC_{ds}T_{ds}T_{es}{}^mC_{es}{}^mC_{es}T_{es}T_e$ | GalNAc₃-3a | PO | 829 |
| 673502 | GalNAc₃-10$_a$-$_o$,$A_{do}G_{es}{}^mC_{eo}T_{eo}T_{eo}{}^mC_{eo}A_{ds}G_{ds}T_{ds}{}^mC_{ds}A_{d}T_{ds}$ $G_{ds}A_{ds}{}^mC_{ds}T_{ds}T_{eo}{}^mC_{eo}{}^mC_{es}T_{es}T_e$ | GalNAc₃-10a | $A_d$ | 831 |
| 677844 | GalNAc₃-9$_a$-$_o$,$A_{do}G_{es}{}^mC_{es}T_{es}T_{es}{}^mC_{es}A_{ds}G_{ds}T_{ds}{}^mC_{ds}A_{ds}T_{ds}$ $G_{ds}A_{ds}{}^mC_{ds}T_{ds}T_{es}{}^mC_{es}{}^mC_{es}T_{es}T_e$ | GalNAc₃-9a | $A_d$ | 831 |
| 677843 | GalNAc₃-23$_a$-$_o$,$A_{do}G_{es}{}^mC_{es}T_{es}T_{es}{}^mC_{es}A_{ds}G_{ds}T_{ds}{}^mC_{ds}A_{ds}T_{ds}$ $G_{ds}A_{ds}{}^mC_{ds}T_{ds}T_{es}{}^mC_{es}{}^mC_{es}T_{es}T_e$ | GalNAc₃-23a | $A_d$ | 831 |
| 655861 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}$ ${}^mC_{es}T_{es}T_{eo}A_{do}$,-GalNAc₃-1$_a$ | GalNAc₃-1a | $A_d$ | 830 |
| 677841 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}$ ${}^mC_{es}T_{es}T_{eo}A_{do}$,-GalNAc₃-19$_a$ | GalNAc₃-19a | $A_d$ | 830 |
| 677842 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}$ ${}^mC_{es}T_{es}T_{eo}A_{do}$,-GalNAc₃-20$_a$ | GalNAc₃-20a | $A_d$ | 830 |

The structure of GalNAc₃-1$_a$ was shown previously in Example 9, GalNAc₃-3$_a$ was shown in Example 39, GalNAc₃-9$_a$ was shown in Example 52, GalNAc₃-10$_a$ was shown in Example 46, GalNAc₃-19$_a$ was shown in Example 70, GalNAc₃-20$_a$ was shown in Example 71, and GalNAc₃-23$_a$ was shown in Example 76.

Treatment

Six to eight week old C57BL/6 mice (Jackson Laboratory, Bar Harbor, Me.) were each injected subcutaneously once at a dosage shown below with an oligonucleotide listed in Table 64 or with saline. Each treatment group consisted of 4 animals. The mice were sacrificed 72 hours following the final administration to determine the SRB-1 mRNA levels using real-time PCR and RIBOGREEN® RNA quantification reagent (Molecular Probes, Inc. Eugene, Oreg.) according to standard protocols. The results below are presented as the average percent of SRB-1 mRNA levels for each treatment group, normalized to the saline control.

As illustrated in Table 65, treatment with antisense oligonucleotides lowered SRB-1 mRNA levels in a dose-dependent manner.

TABLE 65

| ISIS No. | Dosage (mg/kg) | SRB-1 mRNA (% Saline) | GalNAc₃ Cluster | CM |
|---|---|---|---|---|
| Saline | n/a | 100.0 | n/a | n/a |
| 661161 | 0.5 | 89.18 | GalNAc₃-3a | $A_d$ |
|  | 1.5 | 77.02 |  |  |
|  | 5 | 29.10 |  |  |
|  | 15 | 12.64 |  |  |

TABLE 65-continued

SRB-1 mRNA (% Saline)

| ISIS No. | Dosage (mg/kg) | SRB-1 mRNA (% Saline) | GalNAc$_3$ Cluster | CM |
|---|---|---|---|---|
| 666904 | 0.5 | 93.11 | GalNAc$_3$-3a | PO |
|  | 1.5 | 55.85 |  |  |
|  | 5 | 21.29 |  |  |
|  | 15 | 13.43 |  |  |
| 673502 | 0.5 | 77.75 | GalNAc$_3$-10a | A$_d$ |
|  | 1.5 | 41.05 |  |  |
|  | 5 | 19.27 |  |  |
|  | 15 | 14.41 |  |  |
| 677844 | 0.5 | 87.65 | GalNAc$_3$-9a | A$_d$ |
|  | 1.5 | 93.04 |  |  |
|  | 5 | 40.77 |  |  |
|  | 15 | 16.95 |  |  |
| 677843 | 0.5 | 102.28 | GalNAc$_3$-23a | A$_d$ |
|  | 1.5 | 70.51 |  |  |
|  | 5 | 30.68 |  |  |
|  | 15 | 13.26 |  |  |
| 655861 | 0.5 | 79.72 | GalNAc$_3$-1a | A$_d$ |
|  | 1.5 | 55.48 |  |  |
|  | 5 | 26.99 |  |  |
|  | 15 | 17.58 |  |  |
| 677841 | 0.5 | 67.43 | GalNAc$_3$-19a | A$_d$ |
|  | 1.5 | 45.13 |  |  |
|  | 5 | 27.02 |  |  |
|  | 15 | 12.41 |  |  |
| 677842 | 0.5 | 64.13 | GalNAc$_3$-20a | A$_d$ |
|  | 1.5 | 53.56 |  |  |
|  | 5 | 20.47 |  |  |
|  | 15 | 10.23 |  |  |

Liver transaminase levels, alanine aminotransferase (ALT) and aspartate aminotransferase (AST), in serum were also measured using standard protocols. Total bilirubin and BUN were also evaluated. Changes in body weights were evaluated, with no significant change from the saline group (data not shown). ALTs, ASTs, total bilirubin and BUN values are shown in Table 66 below.

TABLE 66

| ISIS No. | Dosage (mg/kg) | ALT (U/L) | AST (U/L) | Total Bilirubin (mg/dL) | BUN (mg/dL) | GalNAc$_3$ Cluster | CM |
|---|---|---|---|---|---|---|---|
| Saline | n/a | 21 | 45 | 0.13 | 34 | n/a | n/a |
| 661161 | 0.5 | 28 | 51 | 0.14 | 39 | GalNAc$_3$-3a | A$_d$ |
|  | 1.5 | 23 | 42 | 0.13 | 39 |  |  |
|  | 5 | 22 | 59 | 0.13 | 37 |  |  |
|  | 15 | 21 | 56 | 0.15 | 35 |  |  |
| 666904 | 0.5 | 24 | 56 | 0.14 | 37 | GalNAc$_3$-3a | PO |
|  | 1.5 | 26 | 68 | 0.15 | 35 |  |  |
|  | 5 | 23 | 77 | 0.14 | 34 |  |  |
|  | 15 | 24 | 60 | 0.13 | 35 |  |  |
| 673502 | 0.5 | 24 | 59 | 0.16 | 34 | GalNAc$_3$-10a | A$_d$ |
|  | 1.5 | 20 | 46 | 0.17 | 32 |  |  |
|  | 5 | 24 | 45 | 0.12 | 31 |  |  |
|  | 15 | 24 | 47 | 0.13 | 34 |  |  |
| 677844 | 0.5 | 25 | 61 | 0.14 | 37 | GalNAc$_3$-9a | A$_d$ |
|  | 1.5 | 23 | 64 | 0.17 | 33 |  |  |
|  | 5 | 25 | 58 | 0.13 | 35 |  |  |
|  | 15 | 22 | 65 | 0.14 | 34 |  |  |
| 677843 | 0.5 | 53 | 53 | 0.13 | 35 | GalNAc$_3$-23a | A$_d$ |
|  | 1.5 | 25 | 54 | 0.13 | 34 |  |  |
|  | 5 | 21 | 60 | 0.15 | 34 |  |  |
|  | 15 | 22 | 43 | 0.12 | 38 |  |  |
| 655861 | 0.5 | 21 | 48 | 0.15 | 33 | GalNAc$_3$-1a | A$_d$ |
|  | 1.5 | 28 | 54 | 0.12 | 35 |  |  |
|  | 5 | 22 | 60 | 0.13 | 36 |  |  |
|  | 15 | 21 | 55 | 0.17 | 30 |  |  |
| 677841 | 0.5 | 32 | 54 | 0.13 | 34 | GalNAc$_3$-19a | A$_d$ |
|  | 1.5 | 24 | 56 | 0.14 | 34 |  |  |
|  | 5 | 23 | 92 | 0.18 | 31 |  |  |
|  | 15 | 24 | 58 | 0.15 | 31 |  |  |
| 677842 | 0.5 | 23 | 61 | 0.15 | 35 | GalNAc$_3$-20a | A$_d$ |
|  | 1.5 | 24 | 57 | 0.14 | 34 |  |  |
|  | 5 | 41 | 62 | 0.15 | 35 |  |  |
|  | 15 | 24 | 37 | 0.14 | 32 |  |  |

Example 78: Antisense Inhibition In Vivo by Oligonucleotides Targeting Angiotensinogen Comprising a GalNAc$_3$ Conjugate The oligonucleotides listed below were tested in a dose-dependent study for antisense inhibition of Angiotensinogen (AGT) in normotensive Sprague Dawley rats.

TABLE 67

Modified ASOs targeting AGT

| ISIS No. | Sequences (5' to 3') | GalNAc$_3$ Cluster | CM | SEQ ID No. |
|---|---|---|---|---|
| 552668 | $^mC_{es}A_{es}{}^mC_{es}T_{es}G_{es}A_{ds}T_{ds}T_{ds}T_{ds}T_{ds}T_{ds}G_{ds}{}^mC_{ds}{}^mC_{ds}{}^mC_{ds}A_{es}G_{es}G_{es}A_{es}T_e$ | n/a | n/a | 835 |
| 669509 | $^mC_{es}A_{es}{}^mC_{es}T_{es}G_{es}A_{ds}T_{ds}T_{ds}T_{ds}T_{ds}T_{ds}G_{ds}{}^mC_{ds}{}^mC_{ds}{}^mC_{ds}A_{es}G_{es}G_{es}A_{es}T_{eo}A_{do'}$-GalNAC$_3$-1$_a$ | GalNAc$_3$-1$_a$ | A$_d$ | 836 |

The structure of GalNAc$_3$-1$_a$ was shown previously in Example 9.

Treatment

Six week old, male Sprague Dawley rats were each injected subcutaneously once per week at a dosage shown below, for a total of three doses, with an oligonucleotide listed in Table 67 or with PBS. Each treatment group consisted of 4 animals. The rats were sacrificed 72 hours following the final dose. AGT liver mRNA levels were measured using real-time PCR and RIBOGREEN® RNA quantification reagent (Molecular Probes, Inc. Eugene, Oreg.) according to standard protocols. AGT plasma protein levels were measured using the Total Angiotensinogen ELISA (Catalog #JP27412, IBL International, Toronto, ON) with plasma diluted 1:20,000. The results below are presented as the average percent of AGT mRNA levels in liver or AGT protein levels in plasma for each treatment group, normalized to the PBS control.

As illustrated in Table 68, treatment with antisense oligonucleotides lowered AGT liver mRNA and plasma protein levels in a dose-dependent manner, and the oligonucleotide comprising a GalNAc conjugate was significantly more potent than the parent oligonucleotide lacking a GalNAc conjugate.

TABLE 68

AGT liver mRNA and plasma protein levels

| ISIS No. | Dosage (mg/kg) | AGT liver mRNA (% PBS) | AGT plasma protein (% PBS) | GalNAc$_3$ Cluster | CM |
|---|---|---|---|---|---|
| PBS | n/a | 100 | 100 | n/a | n/a |
| 552668 | 3 | 95 | 122 | n/a | n/a |
|  | 10 | 85 | 97 |  |  |
|  | 30 | 46 | 79 |  |  |
|  | 90 | 8 | 11 |  |  |
| 669509 | 0.3 | 95 | 70 | GalNAc$_3$-1a | A$_d$ |
|  | 1 | 95 | 129 |  |  |
|  | 3 | 62 | 97 |  |  |
|  | 10 | 9 | 23 |  |  |

Liver transaminase levels, alanine aminotransferase (ALT) and aspartate aminotransferase (AST), in plasma and body weights were also measured at time of sacrifice using standard protocols. The results are shown in Table 69 below.

TABLE 69

Liver transaminase levels and rat body weights

| ISIS No. | Dosage (mg/kg) | ALT (U/L) | AST (U/L) | Body Weight (% of baseline) | GalNAc$_3$ Cluster | CM |
|---|---|---|---|---|---|---|
| PBS | n/a | 51 | 81 | 186 | n/a | n/a |
| 552668 | 3 | 54 | 93 | 183 | n/a | n/a |
|  | 10 | 51 | 93 | 194 |  |  |
|  | 30 | 59 | 99 | 182 |  |  |
|  | 90 | 56 | 78 | 170 |  |  |
| 669509 | 0.3 | 53 | 90 | 190 | GalNAc$_3$-1a | A$_d$ |
|  | 1 | 51 | 93 | 192 |  |  |
|  | 3 | 48 | 85 | 189 |  |  |
|  | 10 | 56 | 95 | 189 |  |  |

Example 79: Duration of Action In Vivo of Oligonucleotides Targeting APOC-II Comprising a GalNAc$_3$ Conjugate The oligonucleotides listed in Table 70 below were tested in a single dose study for duration of action in mice.

TABLE 70

Modified ASOs targeting APOC-III

| ISIS No. | Sequences (5' to 3') | GalNAc$_3$ Cluster | CM | SEQ ID No. |
|---|---|---|---|---|
| 304801 | $A_{es}G_{es}{}^mC_{es}T_{es}T_{es}{}^mC_{ds}T_{ds}T_{ds}G_{ds}T_{ds}{}^mC_{ds}{}^mC_{ds}A_{ds}G_{ds}{}^mC_{ds}T_{es}T_{es}T_{es}A_{es}T_e$ | n/a | n/a | 821 |

TABLE 70-continued

Modified ASOs targeting APOC-III

| ISIS No. | Sequences (5' to 3') | GalNAc₃ Cluster | CM | SEQ ID No. |
|---|---|---|---|---|
| 647535 | $A_{es}G_{es}{}^mC_{es}T_{es}T_{es}{}^mC_{ds}T_{ds}T_{ds}G_{ds}T_{ds}{}^mC_{ds}{}^mC_{ds}A_{ds}G_{ds}{}^mC_{ds}T_{es}T_{es}T_{es}A_{es}T_{eo}A_{do}$,-GalNAc₃-1$_a$ | GalNAc₃-1a | $A_d$ | 822 |
| 663083 | GalNAc3-3$_a$-$_o$,$A_{do}A_{es}G_{es}{}^mC_{es}T_{es}T_{es}{}^mC_{ds}T_{ds}T_{ds}G_{ds}T_{ds}{}^mC_{ds}$ ${}^mC_{ds}A_{ds}G_{ds}{}^mC_{ds}T_{es}T_{es}T_{es}A_{es}T_e$ | GalNAc₃-3a | $A_d$ | 837 |
| 674449 | GalNAC₃-7$_a$-$_o$,$A_{do}A_{es}G_{es}{}^mC_{es}T_{es}T_{es}{}^mC_{ds}T_{ds}T_{ds}G_{ds}T_{ds}{}^mC_{ds}$ ${}^mC_{ds}A_{ds}G_{ds}{}^mC_{ds}T_{es}T_{es}T_{es}A_{es}T_e$ | GalNAc₃-7a | $A_d$ | 837 |
| 674450 | GalNAc₃-10$_a$-$_o$,$A_{do}A_{es}G_{es}{}^mC_{es}T_{es}T_{es}{}^mC_{ds}T_{ds}T_{ds}G_{ds}T_{ds}{}^mC_{ds}$ ${}^mC_{ds}A_{ds}G_{ds}{}^mC_{ds}T_{es}T_{es}T_{es}A_{es}T_e$ | GalNAc₃-10a | $A_d$ | 837 |
| 674451 | GalNAc₃-13$_a$-$_o$,$A_{do}A_{es}G_{es}{}^mC_{es}T_{es}T_{es}{}^mC_{ds}T_{ds}T_{ds}G_{ds}T_{ds}{}^mC_{ds}$ ${}^mC_{ds}A_{ds}G_{ds}{}^mC_{ds}T_{es}T_{es}T_{es}A_{es}T_e$ | GalNAc₃-13a | $A_d$ | 837 |

The structure of GalNAc₃-1$_a$ was shown previously in Example 9, GalNAc₃-3$_a$ was shown in Example 39, GalNAc₃-7$_a$ was shown in Example 48, GalNAc₃-10$_a$ was shown in Example 46, and GalNAc₃-13$_a$ was shown in Example 62.

Treatment

Six to eight week old transgenic mice that express human APOC-III were each injected subcutaneously once with an oligonucleotide listed in Table 70 or with PBS. Each treatment group consisted of 3 animals. Blood was drawn before dosing to determine baseline and at 72 hours, 1 week, 2 weeks, 3 weeks, 4 weeks, 5 weeks, and 6 weeks following the dose. Plasma triglyceride and APOC-III protein levels were measured as described in Example 20. The results below are presented as the average percent of plasma triglyceride and APOC-II levels for each treatment group, normalized to baseline levels, showing that the oligonucleotides comprising a GalNAc conjugate group exhibited a longer duration of action than the parent oligonucleotide without a conjugate group (ISIS 304801) even though the dosage of the parent was three times the dosage of the oligonucleotides comprising a GalNAc conjugate group.

TABLE 71

Plasma triglyceride and APOC-III protein levels in transgenic mice

| ISIS No. | Dosage (mg/kg) | Time point (days post-dose) | Triglycerides (% baseline) | APOC-III protein (% baseline) | GalNAc₃ Cluster | CM |
|---|---|---|---|---|---|---|
| PBS | n/a | 3 | 97 | 102 | n/a | n/a |
| | | 7 | 101 | 98 | | |
| | | 14 | 108 | 98 | | |
| | | 21 | 107 | 107 | | |
| | | 28 | 94 | 91 | | |
| | | 35 | 88 | 90 | | |
| | | 42 | 91 | 105 | | |
| 304801 | 30 | 3 | 40 | 34 | n/a | n/a |
| | | 7 | 41 | 37 | | |
| | | 14 | 50 | 57 | | |
| | | 21 | 50 | 50 | | |
| | | 28 | 57 | 73 | | |
| | | 35 | 68 | 70 | | |
| | | 42 | 75 | 93 | | |
| 647535 | 10 | 3 | 36 | 37 | GalNAc₃-1a | $A_d$ |
| | | 7 | 39 | 47 | | |
| | | 14 | 40 | 45 | | |
| | | 21 | 41 | 41 | | |
| | | 28 | 42 | 62 | | |
| | | 35 | 69 | 69 | | |
| | | 42 | 85 | 102 | | |
| 663083 | 10 | 3 | 24 | 18 | GalNAc₃-3a | $A_d$ |
| | | 7 | 28 | 23 | | |
| | | 14 | 25 | 27 | | |
| | | 21 | 28 | 28 | | |
| | | 28 | 37 | 44 | | |
| | | 35 | 55 | 57 | | |
| | | 42 | 60 | 78 | | |
| 674449 | 10 | 3 | 29 | 26 | GalNAc₃-7a | $A_d$ |
| | | 7 | 32 | 31 | | |
| | | 14 | 38 | 41 | | |
| | | 21 | 44 | 44 | | |
| | | 28 | 53 | 63 | | |
| | | 35 | 69 | 77 | | |
| | | 42 | 78 | 99 | | |

TABLE 71-continued

Plasma triglyceride and APOC-III protein levels in transgenic mice

| ISIS No. | Dosage (mg/kg) | Time point (days post-dose) | Triglycerides (% baseline) | APOC-III protein (% baseline) | GalNAc$_3$ Cluster | CM |
|---|---|---|---|---|---|---|
| 674450 | 10 | 3 | 33 | 30 | GalNAc$_3$-10a | A$_d$ |
|  |  | 7 | 35 | 34 |  |  |
|  |  | 14 | 31 | 34 |  |  |
|  |  | 21 | 44 | 44 |  |  |
|  |  | 28 | 56 | 61 |  |  |
|  |  | 35 | 68 | 70 |  |  |
|  |  | 42 | 83 | 95 |  |  |
| 674451 | 10 | 3 | 35 | 33 | GalNAc$_3$-13a | A$_d$ |
|  |  | 7 | 24 | 32 |  |  |
|  |  | 14 | 40 | 34 |  |  |
|  |  | 21 | 48 | 48 |  |  |
|  |  | 28 | 54 | 67 |  |  |
|  |  | 35 | 65 | 75 |  |  |
|  |  | 42 | 74 | 97 |  |  |

Example 80: Antisense Inhibition In Vivo by Oligonucleotides Targeting Alpha-1 Antitrypsin (A1AT) Comprising a GalNAc$_3$ Conjugate The oligonucleotides listed in Table 72 below were tested in a study for dose-dependent inhibition of A1AT in mice.

TABLE 72

Modified ASOs targeting A1AT

| ISIS No. | Sequences (5' to 3') | GalNAc$_3$ Cluster | CM | SEQ ID No. |
|---|---|---|---|---|
| 476366 | A$_{es}$$^m$C$_{es}$$^m$C$_{es}$$^m$C$_{es}$A$_{es}$A$_{ds}$T$_{ds}$T$_{ds}$$^m$C$_{ds}$A$_{ds}$G$_{ds}$A$_{ds}$A$_{ds}$G$_{ds}$G$_{ds}$A$_{es}$A$_{es}$G$_{es}$G$_{es}$A$_e$ | n/a | n/a | 838 |
| 656326 | A$_{es}$$^m$C$_{es}$$^m$C$_{es}$$^m$C$_{es}$A$_{es}$A$_{ds}$T$_{ds}$T$_{ds}$$^m$C$_{ds}$A$_{ds}$G$_{ds}$A$_{ds}$A$_{ds}$G$_{ds}$G$_{ds}$A$_{es}$A$_{es}$G$_{es}$G$_{es}$A$_{eo}$A$_{do}$'-GalNAc$_3$-1$_a$ | GalNAc$_3$-1a | A$_d$ | 839 |
| 678381 | GalNAc$_3$-3$_a$-$_o$'A$_{do}$A$_{es}$$^m$C$_{es}$$^m$C$_{es}$$^m$C$_{es}$A$_{es}$A$_{ds}$T$_{ds}$T$_{ds}$$^m$C$_{ds}$A$_{ds}$G$_{ds}$A$_{ds}$A$_{ds}$G$_{ds}$G$_{ds}$A$_{es}$A$_{es}$G$_{es}$G$_{es}$A$_e$ | GalNAc$_3$-3a | A$_d$ | 840 |
| 678382 | GalNAC$_3$-7$_a$-$_o$'A$_{do}$A$_{es}$$^m$C$_{es}$$^m$C$_{es}$$^m$C$_{es}$A$_{es}$A$_{ds}$T$_{ds}$T$_{ds}$$^m$C$_{ds}$A$_{ds}$G$_{ds}$A$_{ds}$A$_{ds}$G$_{ds}$G$_{ds}$A$_{es}$A$_{es}$G$_{es}$G$_{es}$A$_e$ | GalNAc$_3$-7a | A$_d$ | 840 |
| 678383 | GalNAc$_3$-10$_a$-$_o$'A$_{do}$A$_{es}$$^m$C$_{es}$$^m$C$_{es}$$^m$C$_{es}$A$_{es}$A$_{ds}$T$_{ds}$T$_{ds}$$^m$C$_{ds}$A$_{ds}$G$_{ds}$A$_{ds}$A$_{ds}$G$_{ds}$G$_{ds}$A$_{es}$A$_{es}$G$_{es}$G$_{es}$A$_e$ | GalNAc$_3$-10a | A$_d$ | 840 |
| 678384 | GalNAc$_3$-13$_a$-$_o$'A$_{do}$A$_{es}$$^m$C$_{es}$$^m$C$_{es}$$^m$C$_{es}$A$_{es}$A$_{ds}$T$_{ds}$T$_{ds}$$^m$C$_{ds}$A$_{ds}$G$_{ds}$A$_{ds}$A$_{ds}$G$_{ds}$G$_{ds}$A$_{es}$A$_{es}$G$_{es}$G$_{es}$A$_e$ | GalNAc$_3$-13a | A$_d$ | 840 |

The structure of GalNAc$_3$-1$_a$ was shown previously in Example 9, GalNAc$_3$-3$_a$ was shown in Example 39, GalNAc$_3$-7$_a$ was shown in Example 48, GalNAc$_3$-10$_a$ was shown in Example 46, and GalNAc$_3$-13$_a$ was shown in Example 62.

Treatment

Six week old, male C57BL/6 mice (Jackson Laboratory, Bar Harbor, Me.) were each injected subcutaneously once per week at a dosage shown below, for a total of three doses, with an oligonucleotide listed in Table 72 or with PBS. Each treatment group consisted of 4 animals. The mice were sacrificed 72 hours following the final administration. AAT liver mRNA levels were determined using real-time PCR and RIBOGREEN® RNA quantification reagent (Molecular Probes, Inc. Eugene, Oreg.) according to standard protocols. AAT plasma protein levels were determined using the Mouse Alpha 1-Antitrypsin ELISA (catalog #41-A1AMS-E01, Alpco, Salem, NH). The results below are presented as the average percent of A1AT liver mRNA and plasma protein levels for each treatment group, normalized to the PBS control.

As illustrated in Table 73, treatment with antisense oligonucleotides lowered A1AT liver mRNA and A1AT plasma protein levels in a dose-dependent manner. The oligonucleotides comprising a GalNAc conjugate were significantly more potent than the parent (ISIS 476366).

TABLE 73

A1AT liver mRNA and plasma protein levels

| ISIS No. | Dosage (mg/kg) | A1AT liver mRNA (% PBS) | A1AT plasma protein (% PBS) | GalNAc$_3$ Cluster | CM |
|---|---|---|---|---|---|
| PBS | n/a | 100 | 100 | n/a | n/a |
| 476366 | 5 | 86 | 78 | n/a | n/a |
|  | 15 | 73 | 61 |  |  |
|  | 45 | 30 | 38 |  |  |

TABLE 73-continued

A1AT liver mRNA and plasma protein levels

| ISIS No. | Dosage (mg/kg) | A1AT liver mRNA (% PBS) | A1AT plasma protein (% PBS) | GalNAc₃ Cluster | CM |
|---|---|---|---|---|---|
| 656326 | 0.6 | 99 | 90 | GalNAc₃-1a | $A_d$ |
| | 2 | 61 | 70 | | |
| | 6 | 15 | 30 | | |
| | 18 | 6 | 10 | | |
| 678381 | 0.6 | 105 | 90 | GalNAc₃-3a | $A_d$ |
| | 2 | 53 | 60 | | |
| | 6 | 16 | 20 | | |
| | 18 | 7 | 13 | | |
| 678382 | 0.6 | 90 | 79 | GalNAc₃-7a | $A_d$ |
| | 2 | 49 | 57 | | |
| | 6 | 21 | 27 | | |
| | 18 | 8 | 11 | | |
| 678383 | 0.6 | 94 | 84 | GalNAc₃-10a | $A_d$ |
| | 2 | 44 | 53 | | |
| | 6 | 13 | 24 | | |
| | 18 | 6 | 10 | | |
| 678384 | 0.6 | 106 | 91 | GalNAc₃-13a | $A_d$ |
| | 2 | 65 | 59 | | |
| | 6 | 26 | 31 | | |
| | 18 | 11 | 15 | | |

Liver transaminase and BUN levels in plasma were measured at time of sacrifice using standard protocols. Body weights and organ weights were also measured. The results are shown in Table 74 below. Body weight is shown as 0% relative to baseline. Organ weights are shown as 0% of body weight relative to the PBS control group.

TABLE 74

| ISIS No. | Dosage (mg/kg) | ALT (U/L) | AST (U/L) | BUN (mg/dL) | Body weight (% baseline) | Liver weight (Rel % BW) | Kidney weight (Rel % BW) | Spleen weight (Rel % BW) |
|---|---|---|---|---|---|---|---|---|
| PBS | n/a | 25 | 51 | 37 | 119 | 100 | 100 | 100 |
| 476366 | 5 | 34 | 68 | 35 | 116 | 91 | 98 | 106 |
| | 15 | 37 | 74 | 30 | 122 | 92 | 101 | 128 |
| | 45 | 30 | 47 | 31 | 118 | 99 | 108 | 123 |
| 656326 | 0.6 | 29 | 57 | 40 | 123 | 100 | 103 | 119 |
| | 2 | 36 | 75 | 39 | 114 | 98 | 111 | 106 |
| | 6 | 32 | 67 | 39 | 125 | 99 | 97 | 122 |
| | 18 | 46 | 77 | 36 | 116 | 102 | 109 | 101 |
| 678381 | 0.6 | 26 | 57 | 32 | 117 | 93 | 109 | 110 |
| | 2 | 26 | 52 | 33 | 121 | 96 | 106 | 125 |
| | 6 | 40 | 78 | 32 | 124 | 92 | 106 | 126 |
| | 18 | 31 | 54 | 28 | 118 | 94 | 103 | 120 |
| 678382 | 0.6 | 26 | 42 | 35 | 114 | 100 | 103 | 103 |
| | 2 | 25 | 50 | 31 | 117 | 91 | 104 | 117 |
| | 6 | 30 | 79 | 29 | 117 | 89 | 102 | 107 |
| | 18 | 65 | 112 | 31 | 120 | 89 | 104 | 113 |
| 678383 | 0.6 | 30 | 67 | 38 | 121 | 91 | 100 | 123 |
| | 2 | 33 | 53 | 33 | 118 | 98 | 102 | 121 |
| | 6 | 32 | 63 | 32 | 117 | 97 | 105 | 105 |
| | 18 | 36 | 68 | 31 | 118 | 99 | 103 | 108 |
| 678384 | 0.6 | 36 | 63 | 31 | 118 | 98 | 103 | 98 |
| | 2 | 32 | 61 | 32 | 119 | 93 | 102 | 114 |
| | 6 | 34 | 69 | 34 | 122 | 100 | 100 | 96 |
| | 18 | 28 | 54 | 30 | 117 | 98 | 101 | 104 |

Example 81: Duration of Action In Vivo of Oligonucleotides Targeting A1AT Comprising a GalNAc₃ Cluster The oligonucleotides listed in Table 72 were tested in a single dose study for duration of action in mice.
Treatment Six week old, male C57BL/6 mice were each injected subcutaneously once with an oligonucleotide listed in Table 72 or with PBS. Each treatment group consisted of 4 animals. Blood was drawn the day before dosing to determine baseline and at 5, 12, 19, and 25 days following the dose. Plasma A1AT protein levels were measured via ELISA (see Example 80). The results below are presented as the average percent of plasma A1AT protein levels for each treatment group, normalized to baseline levels. The results show that the oligonucleotides comprising a GalNAc conjugate were more potent and had longer duration of action than the parent lacking a GalNAc conjugate (ISIS 476366). Furthermore, the oligonucleotides comprising a 5'-GalNAc conjugate (ISIS 678381, 678382, 678383, and 678384) were generally even more potent with even longer duration of action than the oligonucleotide comprising a 3'-GalNAc conjugate (ISIS 656326).

TABLE 75

Plasma A1AT protein levels in mice

| ISIS No. | Dosage (mg/kg) | Time point (days post-dose) | A1AT (% baseline) | GalNAc₃ Cluster | CM |
|---|---|---|---|---|---|
| PBS | n/a | 5 | 93 | n/a | n/a |
| | | 12 | 93 | | |
| | | 19 | 90 | | |
| | | 25 | 97 | | |
| 476366 | 100 | 5 | 38 | n/a | n/a |
| | | 12 | 46 | | |
| | | 19 | 62 | | |
| | | 25 | 77 | | |
| 656326 | 18 | 5 | 33 | GalNAc₃-1a | $A_d$ |
| | | 12 | 36 | | |
| | | 19 | 51 | | |
| | | 25 | 72 | | |

TABLE 75-continued

Plasma A1AT protein levels in mice

| ISIS No. | Dosage (mg/kg) | Time point (days post-dose) | A1AT (% baseline) | GalNAc₃ Cluster | CM |
|---|---|---|---|---|---|
| 678381 | 18 | 5 | 21 | GalNAc₃-3a | $A_d$ |
| | | 12 | 21 | | |
| | | 19 | 35 | | |
| | | 25 | 48 | | |

TABLE 75-continued

Plasma A1AT protein levels in mice

| ISIS No. | Dosage (mg/kg) | Time point (days post-dose) | A1AT (% baseline) | GalNAc$_3$ Cluster | CM |
|---|---|---|---|---|---|
| 678382 | 18 | 5 | 21 | GalNAc$_3$-7a | A$_d$ |
|  |  | 12 | 21 |  |  |
|  |  | 19 | 39 |  |  |
|  |  | 25 | 60 |  |  |
| 678383 | 18 | 5 | 24 | GalNAc$_3$-10a | A$_d$ |
|  |  | 12 | 21 |  |  |
|  |  | 19 | 45 |  |  |
|  |  | 25 | 73 |  |  |
| 678384 | 18 | 5 | 29 | GalNAc$_3$-13a | A$_d$ |
|  |  | 12 | 34 |  |  |
|  |  | 19 | 57 |  |  |
|  |  | 25 | 76 |  |  |

Example 82: Antisense Inhibition In Vitro by Oligonucleotides Targeting SRB-1 Comprising a GalNAc$_3$ Conjugate Primary mouse liver hepatocytes were seeded in 96 well plates at 15,000 cells/well 2 hours prior to treatment. The oligonucleotides listed in Table 76 were added at 2, 10, 50, or 250 nM in Williams E medium and cells were incubated overnight at 37° C. in 500 $CO_2$. Cells were lysed 16 hours following oligonucleotide addition, and total RNA was purified using RNease 3000 BioRobot (Qiagen). SRB-1 mRNA levels were determined using real-time PCR and RIBOGREEN® RNA quantification reagent (Molecular Probes, Inc. Eugene, Oreg.) according to standard protocols. $IC_{50}$ values were determined using Prism 4 software (GraphPad). The results show that oligonucleotides comprising a variety of different GalNAc conjugate groups and a variety of different cleavable moieties are significantly more potent in an in vitro free uptake experiment than the parent oligonucleotides lacking a GalNAc conjugate group (ISIS 353382 and 666841).

TABLE 76

Inhibition of SRB-1 expression in vitro

| ISIS No. | Sequences (5' to 3') | Linkages | GalNAc Cluster | CM | IC$_{50}$ (nM) | SEQ ID No. |
|---|---|---|---|---|---|---|
| 353382 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$ A$_{ds}$$^m$C$_{ds}$T$_{ds}$T$_{es}$$^m$C$_{es}$$^m$C$_{es}$T$_{es}$T$_e$ | PS | n/a | n/a | 250 | 829 |
| 655861 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$ A$_{ds}$$^m$C$_{ds}$T$_{ds}$T$_{es}$$^m$C$_{es}$$^m$C$_{es}$T$_{es}$T$_{eo}$A$_{do'}$-GalNAc$_3$-1$_a$ | PS | GalNAc$_3$-1$_a$ | A$_d$ | 40 | 830 |
| 661161 | GalNAc$_3$-3$_a$-$_{o'}$A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-3$_a$ | A$_d$ | 40 | 831 |
| 661162 | GalNAc$_3$-3$_a$-$_{o'}$A$_{do}$G$_{es}$$^m$C$_{eo}$T$_{eo}$T$_{eo}$$^m$T$_{eo}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T$_e$ | PO/PS | GalNAc$_3$-3$_a$ | A$_d$ | 8 | 831 |
| 664078 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$ A$_{ds}$$^m$C$_{ds}$T$_{ds}$T$_{es}$$^m$C$_{es}$$^m$C$_{es}$T$_{es}$T$_{eo}$A$_{do'}$-GalNAc$_3$-9$_a$ | PS | GalNAc$_3$-9$_a$ | A$_d$ | 20 | 830 |
| 665001 | GalNAc$_3$-8$_a$-$_{o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$-A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-8$_a$ | A$_d$ | 70 | 831 |
| 666224 | GalNAc$_3$-5$_a$-$_{o'}$A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-5$_a$ | A$_d$ | 80 | 831 |
| 666841 | G$_{es}$$^m$C$_{eo}$T$_{eo}$T$_{eo}$$^m$C$_{es}$A$_{ds}$G$_{ds}$T$_{ds}$$^m$C$_{ds}$A$_{ds}$T$_{ds}$G$_{ds}$ A$_{ds}$$^m$C$_{ds}$T$_{ds}$T$_{eo}$$^m$C$_{eo}$$^m$C$_{es}$T$_{es}$T$_e$ | PO/PS | n/a | n/a | >250 | 829 |
| 666881 | GalNAc$_3$-10$_a$-$_{o'}$A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-10$_a$ | A$_d$ | 30 | 831 |
| 666904 | GalNAc$_3$-3$_a$-$_{o'}$G$_{es}$$^m$C$_{es}$T$_{es}$T$_{es}$$^m$C$_{es}$A$_{ds}$G$_{ds}$T$_{ds}$$^m$C$_{ds}$ A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-3$_a$ | PO | 9 | 829 |
| 666924 | GalNAc$_3$-3$_a$-$_{o'}$T$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-3$_a$ | T$_d$ | 15 | 834 |
| 666961 | GalNAc$_3$-6$_a$-$_{o'}$A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-6$_a$ | A$_d$ | 150 | 831 |
| 666981 | GalNAc$_3$-7$_a$-$_{o'}$A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-7$_a$ | A$_d$ | 20 | 831 |

TABLE 76-continued

Inhibition of SRB-1 expression in vitro

| ISIS No. | Sequences (5' to 3') | Linkages | GalNAc Cluster | CM | IC$_{50}$ (nM) | SEQ ID No. |
|---|---|---|---|---|---|---|
| 670061 | GalNAc$_3$-13$_a$-$_{o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-13$_a$ | A$_d$ | 30 | 831 |
| 670699 | GalNAc$_3$-3$_a$-$_{o'}$T$_{do}$G$_{es}$$^m$C$_{eo}$T$_{eo}$T$_{eo}$$^m$T$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T$_e$ | PO/PS | GalNAc$_3$-3$_a$ | T$_d$ | 15 | 834 |
| 670700 | GalNAc3-3$_a$-$_{o'}$A$_{eo}$G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T | PO/PS | GalNAc$_3$-3$_a$ | A$_e$ | 30 | 831 |
| 670701 | GalNAc$_3$-3$_a$-$_{o'}$T$_{eo}$G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T$_e$ | PO/PS | GalNAc$_3$-3$_a$ | T$_e$ | 25 | 834 |
| 671144 | GalNAc$_3$-12$_a$-$_{o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-12$_a$ | A$_d$ | 40 | 831 |
| 671165 | GalNAc$_3$-13$_a$-$_{o'}$A$_{do}$G$_{es}$$^m$C$_{eo}$T$_{eo}$T$_{eo}$$^m$T$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T | PO/PS | GalNAc$_3$-13$_a$ | A$_d$ | 8 | 831 |
| 671261 | GalNAc$_3$-14$_a$-$_{o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-14$_a$ | A$_d$ | >250 | 831 |
| 671262 | GalNAc$_3$-15$_a$-$_{o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-15$_a$ | A$_d$ | >250 | 831 |
| 673501 | GalNAc$_3$-7$_a$-$_{o'}$A$_{do}$G$_{es}$$^m$C$_{eo}$T$_{eo}$T$_{eo}$$^m$T$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T$_e$ | PO/PS | GalNAc$_3$-7$_a$ | A$_d$ | 30 | 831 |
| 673502 | GalNAc$_3$-10$_a$-$_{o'}$A$_{do}$G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T$_e$ | PO/PS | GalNAc$_3$-10$_a$ | A$_d$ | 8 | 831 |
| 675441 | GalNAc$_3$-17$_a$-$_{o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-17$_a$ | A$_d$ | 30 | 831 |
| 675442 | GalNAc$_3$-18$_a$-$_{o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-18$_a$ | A$_d$ | 20 | 831 |
| 677841 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{eo}$A$_{do'}$-GalNAc$_3$-19$_a$ | PS | GalNAc$_3$-19$_a$ | A$_d$ | 40 | 830 |
| 677842 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$ $^m$CasTasT$_{es}$$^m$C$_{es}$$^m$C$_{es}$T$_{es}$T$_{eo}$A$_{do'}$-GalNAc$_3$-20$_a$ | PS | GalNAc$_3$-20$_a$ | A$_d$ | 30 | 830 |
| 677843 | GalNAc$_3$-23$_a$-$_{o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-23$_a$ | A$_d$ | 40 | 831 |

The structure of GalNAc$_3$-1$_a$ was shown previously in Example 9, GalNAc$_3$-3$_a$ was shown in Example 39, GalNAc$_3$-5$_a$ was shown in Example 49, GalNAc$_3$-6$_a$ was shown in Example 51, GalNAc$_3$-7$_a$ was shown in Example 48, GalNAc$_3$-8$_a$ was shown in Example 47, GalNAc$_3$-9$_a$ was shown in Example 52, GalNAc$_3$-10$_a$ was shown in Example 46, GalNAc$_3$-12$_a$ was shown in Example 61, GalNAc$_3$-13$_a$ was shown in Example 62, GalNAc$_3$-14$_a$ was shown in Example 63, GalNAc$_3$-15$_a$ was shown in Example 64, GalNAc$_3$-17$_a$ was shown in Example 68, GalNAc$_3$-18$_a$ was shown in Example 69, GalNAc$_3$-19$_a$ was shown in Example 70, GalNAc$_3$-20$_a$ was shown in Example 71, and GalNAc$_3$-23$_a$ was shown in Example 76.

Example 83: Antisense Inhibition In Vivo by Oligonucleotides Targeting Factor XI Comprising a GalNAc$_3$ Cluster The oligonucleotides listed in Table 77 below were tested in a study for dose-dependent inhibition of Factor XI in mice.

TABLE 77

Modified oligonucleotides targeting Factor XI

| ISIS No. | Sequences (5' to 3') | GalNAc Cluster | CM | SEQ ID No. |
|---|---|---|---|---|
| 404071 | $T_{es}G_{es}G_{es}T_{es}A_{es}A_{ds}T_{ds}{}^mC_{ds}{}^mC_{ds}A_{ds}{}^mC_{ds}T_{ds}T_{ds}T_{ds}{}^mC_{ds}A_{es}G_{es}A_{es}G_{es}G_{e}$ | n/a | n/a | 832 |
| 656173 | $T_{es}G_{es}G_{eo}T_{eo}A_{eo}A_{ds}T_{ds}{}^mC_{ds}{}^mC_{ds}A_{ds}{}^mC_{ds}T_{ds}T_{ds}T_{ds}{}^mC_{ds}A_{eo}G_{eo}A_{es}G_{es}G_{eo}A_{do'}$-GalNAc$_3$-1$_a$ | GalNAc$_3$-1$_a$ | $A_d$ | 833 |
| 663086 | GalNAc$_3$-3$_a$-$_{o'}A_{do}T_{es}G_{eo}G_{eo}T_{eo}A_{eo}A_{ds}T_{ds}{}^mC_{ds}{}^mC_{ds}A_{ds}{}^mC_{ds}T_{ds}T_{ds}T_{ds}{}^mC_{ds}A_{eo}G_{eo}A_{es}G_{es}G_{e}$ | GalNAc$_3$-3$_a$ | $A_d$ | 841 |
| 678347 | GalNAc$_3$-7$_a$-$_{o'}A_{do}T_{es}G_{eo}G_{eo}T_{eo}A_{eo}A_{ds}T_{ds}{}^mC_{ds}{}^mC_{ds}A_{ds}{}^mC_{ds}T_{ds}T_{ds}T_{ds}{}^mC_{ds}A_{eo}G_{eo}A_{es}G_{es}G_{e}$ | GalNAc$_3$-7$_a$ | $A_d$ | 841 |
| 678348 | GalNAc$_3$-10$_a$-$_{o'}A_{do}T_{es}G_{eo}G_{eo}T_{eo}A_{eo}A_{ds}T_{ds}{}^mC_{ds}{}^mC_{ds}A_{ds}{}^mC_{ds}T_{ds}T_{ds}T_{ds}{}^mC_{ds}A_{eo}G_{eo}A_{es}G_{es}G_{e}$ | GalNAc$_3$-10$_a$ | $A_d$ | 841 |
| 678349 | GalNAc$_3$-13$_a$-$_{o'}A_{do}T_{es}G_{eo}G_{eo}T_{eo}A_{eo}A_{ds}T_{ds}{}^mC_{ds}{}^mC_{ds}A_{ds}{}^mC_{ds}T_{ds}T_{ds}T_{ds}{}^mC_{ds}A_{eo}G_{eo}A_{es}G_{es}G_{e}$ | GalNAc$_3$-13$_a$ | $A_d$ | 841 |

The structure of GalNAc$_3$-1$_a$ was shown previously in Example 9, GalNAc$_3$-3$_a$ was shown in Example 39, GalNAc$_3$-7$_a$ was shown in Example 48, GalNAc$_3$-10$_a$ was shown in Example 46, and GalNAc$_3$-13$_a$ was shown in Example 62.

Treatment

Six to eight week old mice were each injected subcutaneously once per week at a dosage shown below, for a total of three doses, with an oligonucleotide listed below or with PBS. Each treatment group consisted of 4 animals. The mice were sacrificed 72 hours following the final dose. Factor XI liver mRNA levels were measured using real-time PCR and normalized to cyclophilin according to standard protocols. Liver transaminases, BUN, and bilirubin were also measured. The results below are presented as the average percent for each treatment group, normalized to the PBS control.

As illustrated in Table 78, treatment with antisense oligonucleotides lowered Factor XI liver mRNA in a dose-dependent manner. The results show (that the oligonucleotides comprising a GalNAc conjugate were more potent than the parent lacking a GalNAc conjugate (ISIS 404071). Furthermore, the oligonucleotides comprising a 5'-GalNAc conjugate (ISIS 663086, 678347, 678348, and 678349) were even more potent than the oligonucleotide comprising a 3'-GalNAc conjugate (ISIS 656173).

TABLE 78

Factor XI liver mRNA, liver transaminase, BUN, and bilirubin levels

| ISIS No. | Dosage (mg/kg) | Factor XI mRNA (% PBS) | ALT (U/L) | AST (U/L) | BUN (mg/dL) | Bilirubin (mg/dL) | GalNAc$_3$ Cluster | SEQ ID No. |
|---|---|---|---|---|---|---|---|---|
| PBS | n/a | 100 | 63 | 70 | 21 | 0.18 | n/a | n/a |
| 404071 | 3 | 65 | 41 | 58 | 21 | 0.15 | n/a | 832 |
|  | 10 | 33 | 49 | 53 | 23 | 0.15 |  |  |
|  | 30 | 17 | 43 | 57 | 22 | 0.14 |  |  |
| 656173 | 0.7 | 43 | 90 | 89 | 21 | 0.16 | GalNAc$_3$-1a | 833 |
|  | 2 | 9 | 36 | 58 | 26 | 0.17 |  |  |
|  | 6 | 3 | 50 | 63 | 25 | 0.15 |  |  |
| 663086 | 0.7 | 33 | 91 | 169 | 25 | 0.16 | GalNAc$_3$-3a | 841 |
|  | 2 | 7 | 38 | 55 | 21 | 0.16 |  |  |
|  | 6 | 1 | 34 | 40 | 23 | 0.14 |  |  |
| 678347 | 0.7 | 35 | 28 | 49 | 20 | 0.14 | GalNAc$_3$-7a | 841 |
|  | 2 | 10 | 180 | 149 | 21 | 0.18 |  |  |
|  | 6 | 1 | 44 | 76 | 19 | 0.15 |  |  |
| 678348 | 0.7 | 39 | 43 | 54 | 21 | 0.16 | GalNAc$_3$-10a | 841 |
|  | 2 | 5 | 38 | 55 | 22 | 0.17 |  |  |
|  | 6 | 2 | 25 | 38 | 20 | 0.14 |  |  |
| 678349 | 0.7 | 34 | 39 | 46 | 20 | 0.16 | GalNAc$_3$-13a | 841 |
|  | 2 | 8 | 43 | 63 | 21 | 0.14 |  |  |
|  | 6 | 2 | 28 | 41 | 20 | 0.14 |  |  |

Example 84: Duration of Action In Vivo of Oligonucleotides Targeting Factor XI Comprising a GalNAc₃ Conjugate The oligonucleotides listed in Table 77 were tested in a single dose study for duration of action in mice.

Treatment

Six to eight week old mice were each injected subcutaneously once with an oligonucleotide listed in Table 77 or with PBS. Each treatment group consisted of 4 animals. Blood was drawn by tail bleeds the day before dosing to determine baseline and at 3, 10, and 17 days following the dose. Plasma Factor XI protein levels were measured by ELISA using Factor XI capture and biotinylated detection antibodies from R & D Systems, Minneapolis, Minn. (catalog #AF2460 and #BAF2460, respectively) and the OptEIA Reagent Set B (Catalog #550534, BD Biosciences, San Jose, Calif.). The results below are presented as the average percent of plasma Factor XI protein levels for each treatment group, normalized to baseline levels. The results show that the oligonucleotides comprising a GalNAc conjugate were more potent with longer duration of action than the parent lacking a GalNAc conjugate (ISIS 404071). Furthermore, the oligonucleotides comprising a 5'-GalNAc conjugate (ISIS 663086, 678347, 678348, and 678349) were even more potent with an even longer duration of action than the oligonucleotide comprising a 3'-GalNAc conjugate (ISIS 656173).

TABLE 79

Plasma Factor XI protein levels in mice

| ISIS No. | Dosage (mg/kg) | Time point (days post-dose) | Factor XI (% baseline) | GalNAc₃ Cluster | CM | SEQ ID No. |
|---|---|---|---|---|---|---|
| PBS | n/a | 3 | 123 | n/a | n/a | n/a |
| | | 10 | 56 | | | |
| | | 17 | 100 | | | |
| 404071 | 30 | 3 | 11 | n/a | n/a | 832 |
| | | 10 | 47 | | | |
| | | 17 | 52 | | | |
| 656173 | 6 | 3 | 1 | GalNAc₃-1a | A_d | 833 |
| | | 10 | 3 | | | |
| | | 17 | 21 | | | |
| 663086 | 6 | 3 | 1 | GalNAc₃-3a | A_d | 841 |
| | | 10 | 2 | | | |
| | | 17 | 9 | | | |
| 678347 | 6 | 3 | 1 | GalNAc₃-7a | A_d | 841 |
| | | 10 | 1 | | | |
| | | 17 | 8 | | | |
| 678348 | 6 | 3 | 1 | GalNAc₃-10a | A_d | 841 |
| | | 10 | 1 | | | |
| | | 17 | 6 | | | |
| 678349 | 6 | 3 | 1 | GalNAc₃-13a | A_d | 841 |
| | | 10 | 1 | | | |
| | | 17 | 5 | | | |

Example 85: Antisense Inhibition In Vivo by Oligonucleotides Targeting SRB-1 Comprising a GalNAc₃ Conjugate Oligonucleotides listed in Table 76 were tested in a dose-dependent study for antisense inhibition of SRB-1 in mice.

Treatment

Six to eight week old C57BL/6 mice were each injected subcutaneously once per week at a dosage shown below, for a total of three doses, with an oligonucleotide listed in Table 76 or with saline. Each treatment group consisted of 4 animals. The mice were sacrificed 48 hours following the final administration to determine the SRB-1 mRNA levels using real-time PCR and RIBOGREEN® RNA quantification reagent (Molecular Probes, Inc. Eugene, Oreg.) according to standard protocols. The results below are presented as the average percent of liver SRB-1 mRNA levels for each treatment group, normalized to the saline control.

As illustrated in Tables 80 and 81, treatment with antisense oligonucleotides lowered SRB-1 mRNA levels in a dose-dependent manner.

TABLE 80

SRB-1 mRNA in liver

| ISIS No. | Dosage (mg/kg) | SRB-1 mRNA (% Saline) | GalNAc₃ Cluster | CM |
|---|---|---|---|---|
| Saline | n/a | 100 | n/a | n/a |
| 655861 | 0.1 | 94 | GalNAc₃-1a | A_d |
| | 0.3 | 119 | | |
| | 1 | 68 | | |
| | 3 | 32 | | |
| 661161 | 0.1 | 120 | GalNAc₃-3a | A_d |
| | 0.3 | 107 | | |
| | 1 | 68 | | |
| | 3 | 26 | | |
| 666881 | 0.1 | 107 | GalNAc₃-10a | A_d |
| | 0.3 | 107 | | |
| | 1 | 69 | | |
| | 3 | 27 | | |

TABLE 80-continued

SRB-1 mRNA in liver

| ISIS No. | Dosage (mg/kg) | SRB-1 mRNA (% Saline) | GalNAc₃ Cluster | CM |
|---|---|---|---|---|
| 666981 | 0.1 | 120 | GalNAc₃-7a | A_d |
| | 0.3 | 103 | | |
| | 1 | 54 | | |
| | 3 | 21 | | |
| 670061 | 0.1 | 118 | GalNAc₃-13a | A_d |
| | 0.3 | 89 | | |

TABLE 80-continued

SRB-1 mRNA in liver

| ISIS No. | Dosage (mg/kg) | SRB-1 mRNA (% Saline) | GalNAc$_3$ Cluster | CM |
|---|---|---|---|---|
| | 1 | 52 | | |
| | 3 | 18 | | |
| 677842 | 0.1 | 119 | GalNAc$_3$-20a | A$_d$ |
| | 0.3 | 96 | | |
| | 1 | 65 | | |
| | 3 | 23 | | |

TABLE 81

SRB-1 mRNA in liver

| ISIS No. | Dosage (mg/kg) | SRB-1 mRNA (% Saline) | GalNAc$_3$ Cluster | CM |
|---|---|---|---|---|
| 661161 | 0.1 | 107 | GalNAc$_3$-3a | A$_d$ |
| | 0.3 | 95 | | |
| | 1 | 53 | | |
| | 3 | 18 | | |
| 677841 | 0.1 | 110 | GalNAc$_3$-19a | A$_d$ |
| | 0.3 | 88 | | |
| | 1 | 52 | | |
| | 3 | 25 | | |

Liver transaminase levels, total bilirubin, BUN, and body weights were also measured using standard protocols. Average values for each treatment group are shown in Table 82 below.

TABLE 82

| ISIS No. | Dosage (mg/kg) | ALT (U/L) | AST (U/L) | Bilirubin (mg/dL) | BUN (mg/dL) | Body Weight (% baseline) | GalNAc$_3$ Cluster | CM |
|---|---|---|---|---|---|---|---|---|
| Saline | n/a | 19 | 39 | 0.17 | 26 | 118 | n/a | n/a |
| 655861 | 0.1 | 25 | 47 | 0.17 | 27 | 114 | GalNAc$_3$-1a | A$_d$ |
| | 0.3 | 29 | 56 | 0.15 | 27 | 118 | | |
| | 1 | 20 | 32 | 0.14 | 24 | 112 | | |
| | 3 | 27 | 54 | 0.14 | 24 | 115 | | |
| 661161 | 0.1 | 35 | 83 | 0.13 | 24 | 113 | GalNAc$_3$-3a | A$_d$ |
| | 0.3 | 42 | 61 | 0.15 | 23 | 117 | | |
| | 1 | 34 | 60 | 0.18 | 22 | 116 | | |
| | 3 | 29 | 52 | 0.13 | 25 | 117 | | |
| 666881 | 0.1 | 30 | 51 | 0.15 | 23 | 118 | GalNAc$_3$-10a | A$_d$ |
| | 0.3 | 49 | 82 | 0.16 | 25 | 119 | | |
| | 1 | 23 | 45 | 0.14 | 24 | 117 | | |
| | 3 | 20 | 38 | 0.15 | 21 | 112 | | |
| 666981 | 0.1 | 21 | 41 | 0.14 | 22 | 113 | GalNAc$_3$-7a | A$_d$ |
| | 0.3 | 29 | 49 | 0.16 | 24 | 112 | | |
| | 1 | 19 | 34 | 0.15 | 22 | 111 | | |
| | 3 | 77 | 78 | 0.18 | 25 | 115 | | |
| 670061 | 0.1 | 20 | 63 | 0.18 | 24 | 111 | GalNAc$_3$-13a | A$_d$ |
| | 0.3 | 20 | 57 | 0.15 | 21 | 115 | | |
| | 1 | 20 | 35 | 0.14 | 20 | 115 | | |
| | 3 | 27 | 42 | 0.12 | 20 | 116 | | |
| 677842 | 0.1 | 20 | 38 | 0.17 | 24 | 114 | GalNAc$_3$-20a | A$_d$ |
| | 0.3 | 31 | 46 | 0.17 | 21 | 117 | | |
| | 1 | 22 | 34 | 0.15 | 21 | 119 | | |
| | 3 | 41 | 57 | 0.14 | 23 | 118 | | |

Example 86: Antisense Inhibition In Vivo by Oligonucleotides Targeting TTR Comprising a GalNAc$_3$ Cluster Oligonucleotides listed in Table 83 below were tested in a dose-dependent study for antisense inhibition of human transthyretin (TTR) in transgenic mice that express the human TTR gene.

Treatment

Eight week old TTR transgenic mice were each injected subcutaneously once per week for three weeks, for a total of three doses, with an oligonucleotide and dosage listed in the tables below or with PBS. Each treatment group consisted of 4 animals. The mice were sacrificed 72 hours following the final administration. Tail bleeds were performed at various time points throughout the experiment, and plasma TTR protein, ALT, and AST levels were measured and reported in Tables 85-87. After the animals were sacrificed, plasma ALT, AST, and human TTR levels were measured, as were body weights, organ weights, and liver human TTR mRNA levels. TTR protein levels were measured using a clinical analyzer (AU480, Beckman Coulter, Calif.). Real-time PCR and RIBOGREEN® RNA quantification reagent (Molecular Probes, Inc. Eugene, Oreg.) were used according to standard protocols to determine liver human TTR mRNA levels. The results presented in Tables 84-87 are the average values for each treatment group. The mRNA levels are the average values relative to the average for the PBS group. Plasma protein levels are the average values relative to the average value for the PBS group at baseline. Body weights are the average percent weight change from baseline until sacrifice for each individual treatment group. Organ weights shown are normalized to the animal's body weight, and the average normalized organ weight for each treatment group is then presented relative to the average normalized organ weight for the PBS group.

In Tables 84-87, "BL" indicates baseline, measurements that were taken just prior to the first dose. As illustrated in Tables 84 and 85, treatment with antisense oligonucleotides lowered TTR expression levels in a dose-dependent manner. The oligonucleotides comprising a GalNAc conjugate were more potent than the parent lacking a GalNAc conjugate (ISIS 420915). Furthermore, the oligonucleotides comprising a GalNAc conjugate and mixed PS/PG internucleoside linkages were even more potent than the oligonucleotide comprising a GalNAc conjugate and full PS linkages.

TABLE 83

Oligonucleotides targeting human TTR

| ISIS No. | Sequences (5' to 3') | Linkages | GalNAc Cluster | CM | SEQ ID No. |
|---|---|---|---|---|---|
| 420915 | $T_{es}{}^mC_{es}T_{es}T_{es}G_{es}G_{ds}T_{ds}T_{ds}A_{ds}{}^mC_{ds}A_{ds}T_{ds}G_{ds}A_{ds}A_{ds}A_{es}T_{es}{}^mC_{es}{}^mC_{es}{}^mC_e$ | PS | n/a | n/a | 842 |
| 660261 | $T_{es}{}^mC_{es}T_{es}T_{es}G_{es}G_{ds}T_{ds}T_{ds}A_{ds}{}^mC_{ds}A_{ds}T_{ds}G_{ds}A_{ds}A_{ds}A_{es}T_{es}{}^mC_{es}{}^mC_{es}{}^mC_{eo}A_{do'}$-GalNAc$_3$-1$_a$ | PS | GalNAc$_3$-1a | A$_d$ | 843 |
| 682883 | GalNAc$_3$-3$_a$-$_{o'}T_{es}{}^mC_{eo}T_{eo}T_{eo}G_{eo}G_{ds}T_{ds}T_{ds}A_{ds}{}^mC_{ds}A_{ds}T_{ds}G_{ds}A_{ds}A_{ds}A_{eo}T_{eo}{}^mC_{es}{}^mC_{es}{}^mC_e$ | PS/PO | GalNAc$_3$-3a | PO | 842 |
| 682884 | GalNAc$_3$-7$_a$-$_{o'}T_{es}{}^mC_{eo}T_{eo}T_{eo}G_{eo}G_{ds}T_{ds}T_{ds}A_{ds}{}^mC_{ds}A_{ds}T_{ds}G_{ds}A_{ds}A_{ds}A_{eo}T_{eo}{}^mC_{es}{}^mC_{es}{}^mC_e$ | PS/PO | GalNAc$_3$-7a | PO | 842 |
| 682885 | GalNAc$_3$-10$_a$-$_{o'}T_{es}{}^mC_{eo}T_{eo}T_{eo}G_{eo}G_{ds}T_{ds}T_{ds}A_{ds}{}^mC_{ds}A_{ds}T_{ds}G_{ds}A_{ds}A_{ds}A_{eo}T_{eo}{}^mC_{es}{}^mC_{es}{}^mC_e$ | PS/PO | GalNAc$_3$-10a | PO | 842 |
| 682886 | GalNAc$_3$-13$_a$-$_{o'}T_{es}{}^mC_{eo}T_{eo}T_{eo}G_{eo}G_{ds}T_{ds}T_{ds}A_{ds}{}^mC_{ds}A_{ds}T_{ds}G_{ds}A_{ds}A_{ds}A_{eo}T_{eo}{}^mC_{es}{}^mC_{es}{}^mC_e$ | PS/PO | GalNAc$_3$-13a | PO | 842 |
| 684057 | $T_{es}{}^mC_{eo}T_{eo}T_{eo}G_{eo}G_{ds}T_{ds}T_{ds}A_{ds}{}^mC_{ds}A_{ds}T_{ds}G_{ds}A_{ds}A_{ds}A_{eo}T_{eo}{}^mC_{es}{}^mC_{es}{}^mC_{eo}A_{do'}$-GalNAc$_3$-19$_a$ | PS/PO | GalNAc$_3$-19a | A$_d$ | 843 |

The legend for Table 85 can be found in Example 74. The structure of GalNAc$_3$-1 was shown in Example 9. The structure of GalNAc$_3$-3$_a$ was shown in Example 39. The structure of GalNAc$_3$-7$_a$ was shown in Example 48. The structure of GalNAc$_3$-10$_a$ was shown in Example 46. The structure of GalNAc$_3$-13$_a$ was shown in Example 62. The structure of GalNAc$_3$-19$_a$ was shown in Example 70.

TABLE 84

Antisense inhibition of human TTR in vivo

| Isis No. | Dosage (mg/kg) | TTR mRNA (% PBS) | Plasma TTR protein (% PBS) | GalNAc cluster | CM | SEQ ID No. |
|---|---|---|---|---|---|---|
| PBS | n/a | 100 | 100 | n/a | n/a | |
| 420915 | 6 | 99 | 95 | n/a | n/a | 842 |
|  | 20 | 48 | 65 | | | |
|  | 60 | 18 | 28 | | | |
| 660261 | 0.6 | 113 | 87 | GalNAc$_3$-1a | A$_d$ | 843 |
|  | 2 | 40 | 56 | | | |
|  | 6 | 20 | 27 | | | |
|  | 20 | 9 | 11 | | | |

TABLE 85

Antisense inhibition of human TTR in vivo

| Isis No. | Dosage (mg/kg) | TTR mRNA (% PBS) | Plasma TTR protein (% PBS at BL) | | | Day 17 (After sac) | GalNAc cluster | CM | SEQ ID No. |
|---|---|---|---|---|---|---|---|---|---|
| | | | BL | Day 3 | Day 10 | | | | |
| PBS | n/a | 100 | 100 | 96 | 90 | 114 | n/a | n/a | |
| 420915 | 6 | 74 | 106 | 86 | 76 | 83 | n/a | n/a | 842 |
|  | 20 | 43 | 102 | 66 | 61 | 58 | | | |
|  | 60 | 24 | 92 | 43 | 29 | 32 | | | |
| 682883 | 0.6 | 60 | 88 | 73 | 63 | 68 | GalNAc$_3$-3a | PO | 842 |
|  | 2 | 18 | 75 | 38 | 23 | 23 | | | |
|  | 6 | 10 | 80 | 35 | 11 | 9 | | | |

TABLE 85-continued

Antisense inhibition of human TTR in vivo

| Isis No. | Dosage (mg/kg) | TTR mRNA (% PBS) | Plasma TTR protein (% PBS at BL) | | | Day 17 (After sac) | GalNAc cluster | CM | SEQ ID No. |
|---|---|---|---|---|---|---|---|---|---|
| | | | BL | Day 3 | Day 10 | | | | |
| 682884 | 0.6 | 56 | 88 | 78 | 63 | 67 | GalNAc$_3$-7a | PO | 842 |
| | 2 | 19 | 76 | 44 | 25 | 23 | | | |
| | 6 | 15 | 82 | 35 | 21 | 24 | | | |
| 682885 | 0.6 | 60 | 92 | 77 | 68 | 76 | GalNAc$_3$-10a | PO | 842 |
| | 2 | 22 | 93 | 58 | 32 | 32 | | | |
| | 6 | 17 | 85 | 37 | 25 | 20 | | | |
| 682886 | 0.6 | 57 | 91 | 70 | 64 | 69 | GalNAc$_3$-13a | PO | 842 |
| | 2 | 21 | 89 | 50 | 31 | 30 | | | |
| | 6 | 18 | 102 | 41 | 24 | 27 | | | |
| 684057 | 0.6 | 53 | 80 | 69 | 56 | 62 | GalNAc$_3$-19a | A$_d$ | 843 |
| | 2 | 21 | 92 | 55 | 34 | 30 | | | |
| | 6 | 11 | 82 | 50 | 18 | 13 | | | |

TABLE 86

Transaminase levels, body weight changes, and relative organ weights

| Isis No. | Dosage (mg/kg) | ALT (U/L) | | | | AST (U/L) | | | | Body (% BL) | Liver (% PBS) | Spleen (% PBS) | Kidney (% PBS) | SEQ ID No. |
|---|---|---|---|---|---|---|---|---|---|---|---|---|---|---|
| | | BL | Day 3 | Day 10 | Day 17 | BL | Day 3 | Day 10 | Day 17 | | | | | |
| PBS | n/a | 33 | 34 | 33 | 24 | 58 | 62 | 67 | 52 | 105 | 100 | 100 | 100 | n/a |
| 420915 | 6 | 34 | 33 | 27 | 21 | 64 | 59 | 73 | 47 | 115 | 99 | 89 | 91 | 842 |
| | 20 | 34 | 30 | 28 | 19 | 64 | 54 | 56 | 42 | 111 | 97 | 83 | 89 | |
| | 60 | 34 | 35 | 31 | 24 | 61 | 58 | 71 | 58 | 113 | 102 | 98 | 95 | |
| 660261 | 0.6 | 33 | 38 | 28 | 26 | 70 | 71 | 63 | 59 | 111 | 96 | 99 | 92 | 843 |
| | 2 | 29 | 32 | 31 | 34 | 61 | 60 | 68 | 61 | 118 | 100 | 92 | 90 | |
| | 6 | 29 | 29 | 28 | 34 | 58 | 59 | 70 | 90 | 114 | 99 | 97 | 95 | |
| | 20 | 33 | 32 | 28 | 33 | 64 | 54 | 68 | 95 | 114 | 101 | 106 | 92 | |

TABLE 87

Transaminase levels, body weight changes, and relative organ weights

| Isis No. | Dosage (mg/kg) | ALT (U/L) | | | | AST (U/L) | | | | Body (% BL) | Liver (% PBS) | Spleen (% PBS) | Kidney (% PBS) | SEQ ID No. |
|---|---|---|---|---|---|---|---|---|---|---|---|---|---|---|
| | | BL | Day 3 | Day 10 | Day 17 | BL | Day 3 | Day 10 | Day 17 | | | | | |
| PBS | n/a | 32 | 34 | 37 | 41 | 62 | 78 | 76 | 77 | 104 | 100 | 100 | 100 | n/a |
| 420915 | 6 | 32 | 30 | 34 | 34 | 61 | 71 | 72 | 66 | 102 | 103 | 102 | 105 | 842 |
| | 20 | 41 | 34 | 37 | 33 | 80 | 76 | 63 | 54 | 106 | 107 | 135 | 101 | |
| | 60 | 36 | 30 | 32 | 34 | 58 | 81 | 57 | 60 | 106 | 105 | 104 | 99 | |
| 682883 | 0.6 | 32 | 35 | 38 | 40 | 53 | 81 | 74 | 76 | 104 | 101 | 112 | 95 | 842 |
| | 2 | 38 | 39 | 42 | 43 | 71 | 84 | 70 | 77 | 107 | 98 | 116 | 99 | |
| | 6 | 35 | 35 | 41 | 38 | 62 | 79 | 103 | 65 | 105 | 103 | 143 | 97 | |
| 682884 | 0.6 | 33 | 32 | 35 | 34 | 70 | 74 | 75 | 67 | 101 | 100 | 130 | 99 | 842 |
| | 2 | 31 | 32 | 38 | 38 | 63 | 77 | 66 | 55 | 104 | 103 | 122 | 100 | |
| | 6 | 38 | 32 | 36 | 34 | 65 | 85 | 80 | 62 | 99 | 105 | 129 | 95 | |
| 682885 | 0.6 | 39 | 26 | 37 | 35 | 63 | 63 | 77 | 59 | 100 | 109 | 109 | 112 | 842 |
| | 2 | 30 | 26 | 38 | 40 | 54 | 56 | 71 | 72 | 102 | 98 | 111 | 102 | |
| | 6 | 27 | 27 | 34 | 35 | 46 | 52 | 56 | 64 | 102 | 98 | 113 | 96 | |
| 682886 | 0.6 | 30 | 40 | 34 | 36 | 58 | 87 | 54 | 61 | 104 | 99 | 120 | 101 | 842 |
| | 2 | 27 | 26 | 34 | 36 | 51 | 55 | 55 | 69 | 103 | 91 | 105 | 92 | |
| | 6 | 40 | 28 | 34 | 37 | 107 | 54 | 61 | 69 | 109 | 100 | 102 | 99 | |
| 684057 | 0.6 | 35 | 26 | 33 | 39 | 56 | 51 | 51 | 69 | 104 | 99 | 110 | 102 | 843 |
| | 2 | 33 | 32 | 31 | 40 | 54 | 57 | 56 | 87 | 103 | 100 | 112 | 97 | |
| | 6 | 39 | 33 | 35 | 40 | 67 | 52 | 55 | 92 | 98 | 104 | 121 | 108 | |

Example 87: Duration of Action In Vivo by Single Doses of Oligonucleotides Targeting TTR Comprising a GalNAc$_3$ Cluster ISIS numbers 420915 and 660261 (see Table 83) were tested in a single dose study for duration of action in mice. ISIS numbers 420915, 682883, and 682885 (see Table 83) were also tested in a single dose study for duration of action in mice.

Treatment

Eight week old, male transgenic mice that express human TTR were each injected subcutaneously once with 100 mg/kg ISIS No. 420915 or 13.5 mg/kg ISIS No. 660261. Each treatment group consisted of 4 animals. Tail bleeds were performed before dosing to determine baseline and at days 3, 7, 10, 17, 24, and 39 following the dose. Plasma TTR protein levels were measured as described in Example 86. The results below are presented as the average percent of plasma TTR levels for each treatment group, normalized to baseline levels.

TABLE 88

Plasma TTR protein levels

| ISIS No. | Dosage (mg/kg) | Time point (days post-dose) | TTR (% baseline) | GalNAc$_3$ Cluster | CM | SEQ ID No. |
|---|---|---|---|---|---|---|
| 420915 | 100 | 3 | 30 | n/a | n/a | 842 |
|  |  | 7 | 23 |  |  |  |
|  |  | 10 | 35 |  |  |  |
|  |  | 17 | 53 |  |  |  |
|  |  | 24 | 75 |  |  |  |
|  |  | 39 | 100 |  |  |  |
| 660261 | 13.5 | 3 | 27 | GalNAc$_3$-1a | A$_d$ | 843 |
|  |  | 7 | 21 |  |  |  |
|  |  | 10 | 22 |  |  |  |
|  |  | 17 | 36 |  |  |  |
|  |  | 24 | 48 |  |  |  |
|  |  | 39 | 69 |  |  |  |

Treatment

Female transgenic mice that express human TTR were each injected subcutaneously once with 100 mg/kg ISIS No. 420915, 10.0 mg/kg ISIS No. 682883, or 10.0 mg/kg 682885. Each treatment group consisted of 4 animals. Tail bleeds were performed before dosing to determine baseline and at days 3, 7, 10, 17, 24, and 39 following the dose. Plasma TTR protein levels were measured as described in Example 86. The results below are presented as the average percent of plasma TTR levels for each treatment group, normalized to baseline levels.

TABLE 89

Plasma TTR protein levels

| ISIS No. | Dosage (mg/kg) | Time point (days post-dose) | TTR (% baseline) | GalNAc$_3$ Cluster | CM | SEQ ID No. |
|---|---|---|---|---|---|---|
| 420915 | 100 | 3 | 48 | n/a | n/a | 842 |
|  |  | 7 | 48 |  |  |  |
|  |  | 10 | 48 |  |  |  |
|  |  | 17 | 66 |  |  |  |
|  |  | 31 | 80 |  |  |  |
| 682883 | 10.0 | 3 | 45 | GalNAc$_3$-3a | PO | 842 |
|  |  | 7 | 37 |  |  |  |
|  |  | 10 | 38 |  |  |  |
|  |  | 17 | 42 |  |  |  |
|  |  | 31 | 65 |  |  |  |
| 682885 | 10.0 | 3 | 40 | GalNAc$_3$-10a | PO | 842 |
|  |  | 7 | 33 |  |  |  |
|  |  | 10 | 34 |  |  |  |
|  |  | 17 | 40 |  |  |  |
|  |  | 31 | 64 |  |  |  |

The results in Tables 88 and 89 show that the oligonucleotides comprising a GalNAc conjugate are more potent with a longer duration of action than the parent oligonucleotide lacking a conjugate (ISIS 420915).

Example 88: Splicing Modulation In Vivo by Oligonucleotides Targeting SMN Comprising a GalNAc$_3$ Conjugate The oligonucleotides listed in Table 90 were tested for splicing modulation of human survival of motor neuron (SMN) in mice.

TABLE 90

Modified ASOs targeting SMN

| ISIS No. | Sequences (5' to 3') | GalNAc$_3$ Cluster | CM | SEQ ID No. |
|---|---|---|---|---|
| 387954 | $A_{es}T_{es}T_{es}{}^mC_{es}A_{es}{}^mC_{es}T_{es}T_{es}T_{es}{}^mC_{es}A_{es}T_{es}A_{es}A_{es}T_{es}G_{es}{}^mC_{es}T_{es}G_{es}G_e$ | n/a | n/a | 844 |
| 699819 | GalNAc$_3$-7$_a$-$_o$,$A_{es}T_{es}T_{es}{}^mC_{es}A_{es}{}^mC_{es}T_{es}T_{es}T_{es}{}^mC_{es}A_{es}T_{es}A_{es}A_{es}T_{es}G_{es}{}^mC_{es}T_{es}G_{es}G_e$ | GalNAc$_3$-7a | PO | 844 |
| 699821 | GalNAc$_3$-7$_a$-$_o$,$A_{es}T_{eo}T_{eo}{}^mC_{eo}A_{eo}{}^mC_{eo}T_{eo}T_{eo}T_{eo}{}^mC_{eo}A_{eo}T_{eo}A_{eo}A_{eo}T_{eo}G_{eo}{}^mC_{eo}T_{es}G_{es}G_e$ | GalNAc$_3$-7a | PO | 844 |
| 700000 | $A_{es}T_{es}T_{es}{}^mC_{es}A_{es}{}^mC_{es}T_{es}T_{es}T_{es}{}^mC_{es}A_{es}T_{es}A_{es}A_{es}T_{es}G_{es}{}^mC_{es}T_{es}G_{es}G_{eo}A_{do'}$-GalNAc$_3$-1$_a$ | GalNAc$_3$-1a | $A_d$ | 845 |
| 703421 | X-ATT$^m$CA$^m$CTTT$^m$CATAATG$^m$CTGG | n/a | n/a | 844 |
| 703422 | GalNAc$_3$-7$_b$-X-ATT$^m$CA$^m$CTTT$^m$CATAATG$^m$CTGG | GalNAc$_3$-7b | n/a | 844 |

The structure of GalNAc$_3$-7$_a$ was shown previously in Example 48. "X" indicates a 5' primary amine generated by Gene Tools (Philomath, Oreg.), and GalNAc$_3$-7$_b$ indicates the structure of GalNAc$_3$-7$_a$ lacking the —NH—C$_6$—O portion of the linker as shown below:

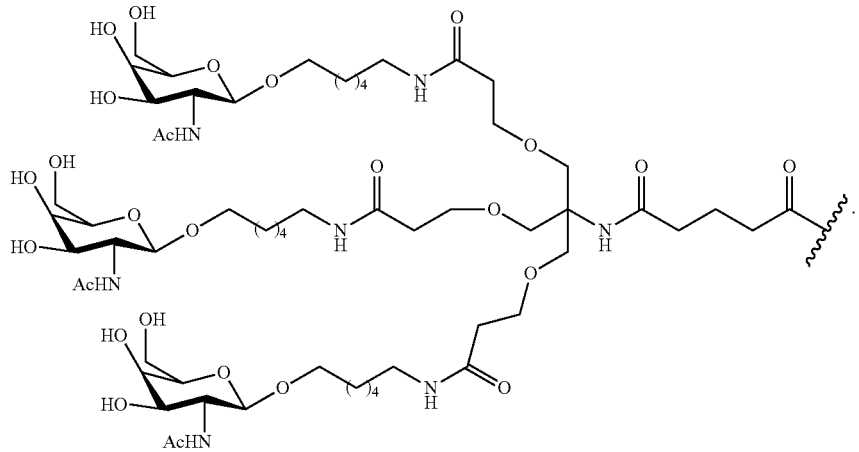

ISIS numbers 703421 and 703422 are morphlino oligonucleotides, wherein each nucleotide of the two oligonucleotides is a morpholino nucleotide.

Treatment

Six week old transgenic mice that express human SMN were injected subcutaneously once with an oligonucleotide listed in Table 91 or with saline. Each treatment group consisted of 2 males and 2 females. The mice were sacrificed 3 days following the dose to determine the liver human SMN mRNA levels both with and without exon 7 using real-time PCR according to standard protocols. Total RNA was measured using Ribogreen reagent. The SMN mRNA levels were normalized to total mRNA, and further normalized to the averages for the saline treatment group. The resulting average ratios of SMN mRNA including exon 7 to SMN mRNA missing exon 7 are shown in Table 91. The results show that fully modified oligonucleotides that modulate splicing and comprise a GalNAc conjugate are significantly more potent in altering splicing in the liver than the parent oligonucleotides lacking a GlaNAc conjugate. Furthermore, this trend is maintained for multiple modification chemistries, including 2'-MOE and morpholino modified oligonucleotides.

TABLE 91

Effect of oligonucleotides targeting human SMN in vivo

| ISIS No. | Dose (mg/kg) | +Exon 7/−Exon 7 | GalNAc$_3$ Cluster | CM | SEQ ID No. |
|---|---|---|---|---|---|
| Saline | n/a | 1.00 | n/a | n/a | n/a |
| 387954 | 32 | 1.65 | n/a | n/a | 844 |
| 387954 | 288 | 5.00 | n/a | n/a | 844 |
| 699819 | 32 | 7.84 | GalNAc$_3$-7a | PO | 844 |
| 699821 | 32 | 7.22 | GalNAc$_3$-7a | PO | 844 |
| 700000 | 32 | 6.91 | GalNAc$_3$-1a | A$_d$ | 845 |
| 703421 | 32 | 1.27 | n/a | n/a | 844 |
| 703422 | 32 | 4.12 | GalNAc$_3$-7b | n/a | 844 |

Example 89: Antisense Inhibition In Vivo by Oligonucleotides Targeting Apolipoprotein a (Apo(a)) Comprising a GalNAc$_3$ Conjugate The oligonucleotides listed in Table 92 below were tested in a study for dose-dependent inhibition of Apo(a) in transgenic mice.

TABLE 92

Modified ASOs targeting Apo(a)

| ISIS No. | Sequences (5' to 3') | GalNAc$_3$ Cluster | CM | SEQ ID No. |
|---|---|---|---|---|
| 494372 | T$_{es}$G$_{es}$$^m$C$_{es}$T$_{es}$$^m$C$_{es}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{es}$G$_{es}$T$_{es}$T$_{es}$$^m$C$_e$ | n/a | n/a | 847 |
| 681257 | GalNAc$_3$-7$_a$-$_o$,T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{eo}$G$_{eo}$T$_{es}$T$_{es}$$^m$C$_e$ | GalNAc$_3$-7a | PO | 847 |

The structure of GalNAc$_3$-7$_a$ was shown in Example 48.

Treatment

Eight week old, female C57BL/6 mice (Jackson Laboratory, Bar Harbor, Me.) were each injected subcutaneously once per week at a dosage shown below, for a total of six doses, with an oligonucleotide listed in Table 92 or with PBS. Each treatment group consisted of 3-4 animals. Tail bleeds were performed the day before the first dose and weekly following each dose to determine plasma Apo(a) protein levels. The mice were sacrificed two days following the final administration. Apo(a) liver mRNA levels were determined using real-time PCR and RIBOGREEN® RNA quantification reagent (Molecular Probes, Inc. Eugene, Oreg.) according to standard protocols. Apo(a) plasma protein levels were determined using ELISA, and liver transaminase levels were determined. The mRNA and plasma protein results in Table 93 are presented as the treatment group average percent relative to the PBS treated group. Plasma protein levels were further normalized to the baseline (BL) value for the PBS group. Average absolute transaminase levels and body weights (% relative to baseline averages) are reported in Table 94.

As illustrated in Table 93, treatment with the oligonucleotides lowered Apo(a) liver mRNA and plasma protein levels in a dose-dependent manner. Furthermore, the oligonucleotide comprising the GalNAc conjugate was significantly more potent with a longer duration of action than the parent oligonucleotide lacking a GalNAc conjugate. As illustrated in Table 94, transaminase levels and body weights were unaffected by the oligonucleotides, indicating that the oligonucleotides were well tolerated.

TABLE 93

Apo(a) liver mRNA and plasma protein levels

| ISIS No. | Dosage (mg/kg) | Apo(a) mRNA (% PBS) | Apo(a) plasma protein (% PBS) | | | | | |
|---|---|---|---|---|---|---|---|---|
| | | | BL | Week 1 | Week 2 | Week 3 | Week 4 | Week 5 | Week 6 |
| PBS | n/a | 100 | 100 | 120 | 119 | 113 | 88 | 121 | 97 |
| 494372 | 3 | 80 | 84 | 89 | 91 | 98 | 87 | 87 | 79 |
| | 10 | 30 | 87 | 72 | 76 | 71 | 57 | 59 | 46 |
| | 30 | 5 | 92 | 54 | 28 | 10 | 7 | 9 | 7 |
| 681257 | 0.3 | 75 | 79 | 76 | 89 | 98 | 71 | 94 | 78 |
| | 1 | 19 | 79 | 88 | 66 | 60 | 54 | 32 | 24 |
| | 3 | 2 | 82 | 52 | 17 | 7 | 4 | 6 | 5 |
| | 10 | 2 | 79 | 17 | 6 | 3 | 2 | 4 | 5 |

TABLE 94

| ISIS No. | Dosage (mg/kg) | ALT (U/L) | AST (U/L) | Body weight (% baseline) |
|---|---|---|---|---|
| PBS | n/a | 37 | 54 | 103 |
| 494372 | 3 | 28 | 68 | 106 |
|  | 10 | 22 | 55 | 102 |
|  | 30 | 19 | 48 | 103 |
| 681257 | 0.3 | 30 | 80 | 104 |
|  | 1 | 26 | 47 | 105 |
|  | 3 | 29 | 62 | 102 |
|  | 10 | 21 | 52 | 107 | levels are the average values relative to the average value for the PBS group at baseline. "BL" indicates baseline, measurements that were taken just prior to the first dose. As illustrated in Table 96, treatment with antisense oligonucleotides lowered TTR expression levels in a dose-dependent manner. The oligonucleotides comprising a GalNAc conjugate were more potent than the parent lacking a GalNAc conjugate (ISIS 420915), and oligonucleotides comprising a phosphodiester or deoxyadenosine cleavable moiety showed significant improvements in potency compared to the parent lacking a conjugate (see ISIS numbers 682883 and 666943 vs 420915 and see Examples 86 and 87).

TABLE 95

Oligonucleotides targeting human TTR

| ISIS No. | Sequences (5' to 3') | Linkages | GalNAc$_3$ Cluster | CM | SEQ ID No. |
|---|---|---|---|---|---|
| 420915 | T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_{e}$ | PS | n/a | n/a | 842 |
| 682883 | GalNAc$_3$-3$_a$-$_o$'T$_{es}$$^m$C$_{eo}$T$_{eo}$T$_{eo}$G$_{eo}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{eo}$T$_{eo}$$^m$C$_{es}$$^m$C$_{es}$$^m$C$_{e}$ | PS/PO | GalNAc$_3$-3a | PO | 842 |
| 666943 | GalNAc$_3$-3$_a$-$_o$'A$_{do}$T$_{es}$$^m$C$_{eo}$T$_{eo}$G$_{eo}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{eo}$T$_{eo}$$^m$C$_{es}$$^m$C$_{es}$$^m$C$_{e}$ | PS/PO | GalNAc$_3$-3a | A$_d$ | 846 |
| 682887 | GalNAc$_3$-7$_a$-$_o$'A$_{do}$T$_{es}$$^m$C$_{eo}$T$_{eo}$G$_{eo}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{eo}$T$_{eo}$$^m$C$_{es}$$^m$C$_{es}$$^m$C$_{e}$ | PS/PO | GalNAc$_3$-7a | A$_d$ | 846 |
| 682888 | GalNAc$_3$-10$_a$-$_o$'A$_{do}$T$_{es}$$^m$C$_{eo}$T$_{eo}$G$_{eo}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{eo}$T$_{eo}$$^m$C$_{es}$$^m$C$_{es}$$^m$C$_{e}$ | PS/PO | GalNAc$_3$-10a | A$_d$ | 846 |
| 682889 | GalNAc$_3$-13$_a$-$_o$'A$_{do}$T$_{es}$$^m$C$_{eo}$T$_{eo}$G$_{eo}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{eo}$T$_{eo}$$^m$C$_{es}$$^m$C$_{es}$$^m$C$_{e}$ | PS/PO | GalNAc$_3$-13a | A$_d$ | 846 |

Example 90: Antisense Inhibition In Vivo by Oligonucleotides Targeting TTR Comprising a GalNAc$_3$ Cluster Oligonucleotides listed in Table 95 below were tested in a dose-dependent study for antisense inhibition of human transthyretin (TTR) in transgenic mice that express the human TTR gene.

Treatment

TTR transgenic mice were each injected subcutaneously once per week for three weeks, for a total of three doses, with an oligonucleotide and dosage listed in Table 96 or with PBS. Each treatment group consisted of 4 animals. Prior to the first dose, a tail bleed was performed to determine plasma TTR protein levels at baseline (BL). The mice were sacrificed 72 hours following the final administration. TTR protein levels were measured using a clinical analyzer (AU480, Beckman Coulter, Calif.). Real-time PCR and RIBOGREEN® RNA quantification reagent (Molecular Probes, Inc. Eugene, Oreg.) were used according to standard protocols to determine liver human TTR mRNA levels. The results presented in Table 96 are the average values for each treatment group. The mRNA levels are the average values relative to the average for the PBS group. Plasma protein The legend for Table 95 can be found in Example 74. The structure of GalNAc$_3$-3$_a$ was shown in Example 39. The structure of GalNAc$_3$-7$_a$ was shown in Example 48. The structure of GalNAc$_3$-10$_a$ was shown in Example 46. The structure of GalNAc$_3$-13$_a$ was shown in Example 62.

TABLE 96

Antisense inhibition of human TTR in vivo

| Isis No. | Dosage (mg/kg) | TTR mRNA (% PBS) | TTR protein (% BL) | GalNAc cluster | CM |
|---|---|---|---|---|---|
| PBS | n/a | 100 | 124 | n/a | n/a |
| 420915 | 6 | 69 | 114 | n/a | n/a |
|  | 20 | 71 | 86 |  |  |
|  | 60 | 21 | 36 |  |  |
| 682883 | 0.6 | 61 | 73 | GalNAc$_3$-3a | PO |
|  | 2 | 23 | 36 |  |  |
|  | 6 | 18 | 23 |  |  |
| 666943 | 0.6 | 74 | 93 | GalNAc$_3$-3a | A$_d$ |
|  | 2 | 33 | 57 |  |  |
|  | 6 | 17 | 22 |  |  |
| 682887 | 0.6 | 60 | 97 | GalNAc$_3$-7a | A$_d$ |
|  | 2 | 36 | 49 |  |  |
|  | 6 | 12 | 19 |  |  |
| 682888 | 0.6 | 65 | 92 | GalNAc$_3$-10a | A$_d$ |
|  | 2 | 32 | 46 |  |  |
|  | 6 | 17 | 22 |  |  |

TABLE 96-continued

Antisense inhibition of human TTR in vivo

| Isis No. | Dosage (mg/kg) | TTR mRNA (% PBS) | TTR protein (% BL) | GalNAc cluster | CM |
|---|---|---|---|---|---|
| 682889 | 0.6 | 72 | 74 | GalNAc$_3$-13a | A$_d$ |
|  | 2 | 38 | 45 |  |  |
|  | 6 | 16 | 18 |  |  |

Example 91: Antisense Inhibition In Vivo by Oligonucleotides Targeting Factor VII Comprising a GalNAc$_3$ Conjugate in Non-Human Primates Oligonucleotides listed in Table 97 below were tested in a non-terminal, dose escalation study for antisense inhibition of Factor VII in monkeys.

Treatment

Non-naïve monkeys were each injected subcutaneously on days 0, 15, and 29 with escalating doses of an oligonucleotide listed in Table 97 or with PBS. Each treatment group consisted of 4 males and 1 female. Prior to the first dose and at various time points thereafter, blood draws were performed to determine plasma Factor VII protein levels. Factor VII protein levels were measured by ELISA. The results presented in Table 98 are the average values for each treatment group relative to the average value for the PBS group at baseline (BL), the measurements taken just prior to the first dose. As illustrated in Table 98, treatment with antisense oligonucleotides lowered Factor VII expression levels in a dose-dependent manner, and the oligonucleotide comprising the GalNAc conjugate was significantly more potent in monkeys compared to the oligonucleotide lacking a GalNAc conjugate.

TABLE 97

Oligonucleotides targeting Factor VII

| ISIS No. | Sequences (5' to 3') | Linkages | GalNAc$_3$ Cluster | CM | SEQ ID No. |
|---|---|---|---|---|---|
| 407935 | A$_{es}$T$_{es}$G$_{es}$$^m$C$_{es}$A$_{es}$T$_{ds}$G$_{ds}$G$_{ds}$T$_{ds}$G$_{ds}$A$_{ds}$T$_{ds}$G$_{ds}$ $^m$C$_{ds}$T$_{ds}$T$_{es}$$^m$C$_{es}$T$_{es}$G$_{es}$A$_e$ | PS | n/a | n/a | 848 |
| 686892 | GalNAc$_3$-10$_a$-$_o$,A$_{es}$T$_{es}$G$_{es}$$^m$C$_{es}$A$_{es}$T$_{ds}$G$_{ds}$G$_{ds}$T$_{ds}$G$_{ds}$ A$_{ds}$T$_{ds}$G$_{ds}$$^m$C$_{ds}$T$_{ds}$T$_{es}$$^m$C$_{es}$T$_{es}$G$_{es}$A$_e$ | PS | GalNAc$_3$-10a | PO | 848 |

The legend for Table 97 can be found in Example 74. The structure of GalNAc$_3$-10$_a$ was shown in Example 46.

TABLE 98

Factor VII plasma protein levels

| ISIS No. | Day | Dose (mg/kg) | Factor VII (% BL) |
|---|---|---|---|
| 407935 | 0 | n/a | 100 |
|  | 15 | 10 | 87 |
|  | 22 | n/a | 92 |
|  | 29 | 30 | 77 |
|  | 36 | n/a | 46 |
|  | 43 | n/a | 43 |
| 686892 | 0 | 3 | 100 |
|  | 15 | 10 | 56 |
|  | 22 | n/a | 29 |
|  | 29 | 30 | 19 |
|  | 36 | n/a | 15 |
|  | 43 | n/a | 11 |

Example 92: Antisense Inhibition in Primary Hepatocytes by Antisense Oligonucleotides Targeting Apo-CIII Comprising a GalNAc$_3$ Conjugate Primary mouse hepatocytes were seeded in 96-well plates at 15,000 cells per well, and the oligonucleotides listed in Table 99, targeting mouse ApoC-II, were added at 0.46, 1.37, 4.12, or 12.35, 37.04, 111.11, or 333.33 nM or 1.00 µM. After incubation with the oligonucleotides for 24 hours, the cells were lysed and total RNA was purified using RNeasy (Qiagen). ApoC-II mRNA levels were determined using real-time PCR and RIBOGREEN® RNA quantification reagent (Molecular Probes, Inc.) according to standard protocols. IC$_{50}$ values were determined using Prism 4 software (GraphPad). The results show that regardless of whether the cleavable moiety was a phosphodiester or a phosphodiester-linked deoxyadensoine, the oligonucleotides comprising a GalNAc conjugate were significantly more potent than the parent oligonucleotide lacking a conjugate.

TABLE 99

Inhibition of mouse APOC-III expression in mouse primary hepatocytes

| ISIS No. | Sequences (5' to 3') | CM | IC$_{50}$ (nM) | SEQ ID No. |
|---|---|---|---|---|
| 440670 | $^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}$ $^mC_{es}A_e$ | n/a | 13.20 | 849 |
| 661180 | $^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}$ $A_{es}G_{es}{}^mC_{es}A_{eo}A_{do'}$-GalNAc$_3$-1$_a$ | A$_d$ | 1.40 | 850 |
| 680771 | GalNAc$_3$-3$_a$- $_{o'}{}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}$ $A_{es}G_{es}{}^mC_{es}A_e$ | PO | 0.70 | 849 |
| 680772 | GalNAc$_3$-7$_a$- $_{o'}{}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}$ $A_{es}G_{es}{}^mC_{es}A_e$ | PO | 1.70 | 849 |
| 680773 | GalNAc$_3$-10$_a$- $_{o'}{}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}$ $A_{es}G_{es}{}^mC_{es}A_e$ | PO | 2.00 | 849 |
| 680774 | GalNAc$_3$-13$_a$- $_{o'}{}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}$ $A_{es}G_{es}{}^mC_{es}A_e$ | PO | 1.50 | 849 |
| 681272 | GalNAc$_3$-3$_a$- $_{o'}{}^mC_{es}A_{eo}G_{eo}{}^mC_{eo}T_{eo}T_{ds}T_{ds}A_{ds}T_{ds}T_{ds}A_{ds}G_{ds}G_{ds}G_{ds}A_{ds}{}^mC_{eo}$ $A_{eo}G_{es}{}^mC_{es}A_e$ | PO | <0.46 | 849 |
| 681273 | GalNAc$_3$-3$_a$- $_{o'}$Ado$^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}$ $^mC_{es}A_{es}G_{es}{}^mC_{es}A_e$ | A$_d$ | 1.10 | 851 |
| 683733 | $^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}$ $A_{es}G_{es}{}^mC_{es}A_{eo}A_{do'}$-GalNAc$_3$-19$_a$ | A$_d$ | 2.50 | 850 |

The structure of GalNAc$_3$-1$_a$ was shown previously in Example 9, GalNAc$_3$-3$_a$ was shown in Example 39, GalNAc$_3$-7$_a$ was shown in Example 48, GalNAc$_3$-10$_a$ was shown in Example 46, GalNAc$_3$-13$_a$ was shown in Example 62, and GalNAc$_3$-19$_a$ was shown in Example 70.

Example 93: Antisense Inhibition In Vivo by Oligonucleotides Targeting SRB-1 Comprising Mixed Wings and a 5'-GalNAc$_3$ Conjugate The oligonucleotides listed in Table 100 were tested in a dose-dependent study for antisense inhibition of SRB-1 in mice.

TABLE 100

Modified ASOs targeting SRB-1

| ISIS No. | Sequences (5' to 3') | GalNAc$_3$ Cluster | CM | SEQ ID No. |
|---|---|---|---|---|
| 449093 | $T_{ks}T_{ks}{}^mC_{ks}A_{ds}G_{ds}T_{ds}{}^mC_{ds}A_{ds}T_{ds}G_{ds}A_{ds}{}^mC_{ds}T_{ds}T_{ks}{}^mC_{ks}{}^mC_k$ | n/a | n/a | 852 |
| 699806 | GalNAc$_3$-3$_a$-$_{o'}T_{ks}T_{ks}{}^mC_{ks}A_{ds}G_{ds}T_{ds}{}^mC_{ds}A_{ds}T_{ds}G_{ds}A_{ds}{}^mC_{ds}$ $T_{ds}T_{ks}{}^mC_{ks}{}^mC_k$ | GalNAc$_3$-3a | PO | 852 |
| 699807 | GalNAc$_3$-7$_a$-$_{o'}T_{ks}T_{ks}{}^mC_{ks}A_{ds}G_{ds}T_{ds}{}^mC_{ds}A_{ds}T_{ds}G_{ds}A_{ds}{}^mC_{ds}$ $T_{ds}T_{ks}{}^mC_{ks}{}^mC_k$ | GalNAc$_3$-7a | PO | 852 |
| 699809 | GalNAc$_3$-7$_a$-$_{o'}T_{ks}T_{ks}{}^mC_{ks}A_{ds}G_{ds}T_{ds}{}^mC_{ds}A_{ds}T_{ds}G_{ds}A_{ds}{}^mC_{ds}$ $T_{ds}T_{es}{}^mC_{es}{}^mC_e$ | GalNAc$_3$-7a | PO | 852 |
| 699811 | GalNAc$_3$-7$_a$-$_{o'}T_{es}T_{es}{}^mC_{es}A_{ds}G_{ds}T_{ds}{}^mC_{ds}A_{ds}T_{ds}G_{ds}A_{ds}{}^mC_{ds}$ $T_{ds}T_{ks}{}^mC_{ks}{}^mC_k$ | GalNAc$_3$-7a | PO | 852 |
| 699813 | GalNAc$_3$-7$_a$-$_{o'}T_{ks}T_{ds}{}^mC_{ks}A_{ds}G_{ds}T_{ds}{}^mC_{ds}A_{ds}T_{ds}G_{ds}A_{ds}{}^mC_{ds}$ $T_{ds}T_{ks}{}^mC_{ds}{}^mC_k$ | GalNAc$_3$-7a | PO | 852 |

TABLE 100-continued

Modified ASOs targeting SRB-1

| ISIS No. | Sequences (5' to 3') | GalNAc$_3$ Cluster | CM | SEQ ID No. |
|---|---|---|---|---|
| 699815 | GalNAc$_3$-7$_a$-$_o$,T$_{es}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$ T$_{ds}$T$_{ks}$$^m$C$_{ks}$$^m$C$_e$ | GalNAc$_3$-7a | PO | 852 |

The structure of GalNAc$_3$-3$_a$ was shown previously in Example 39, and the structure of GalNAc$_3$-7$_a$ was shown previously in Example 48. Subscripts: "e" indicates 2'-MOE modified nucleoside; "d" indicates β-D-2'-deoxyribonucleoside; "k" indicates 6'-(S)—CH$_3$ bicyclic nucleoside (cEt); "s" indicates phosphorothioate internucleoside linkages (PS); "o" indicates phosphodiester internucleoside linkages (PO). Superscript "m" indicates 5-methylcytosines.

Treatment

Six to eight week old C57BL/6 mice (Jackson Laboratory, Bar Harbor, Me.) were injected subcutaneously once at the dosage shown below with an oligonucleotide listed in Table 100 or with saline. Each treatment group consisted of 4 animals. The mice were sacrificed 72 hours following the final administration. Liver SRB-1 mRNA levels were measured using real-time PCR. SRB-1 mRNA levels were normalized to cyclophilin mRNA levels according to standard protocols. The results are presented as the average percent of SRB-1 mRNA levels for each treatment group relative to the saline control group. As illustrated in Table 101, treatment with antisense oligonucleotides lowered SRB-1 mRNA levels in a dose-dependent manner, and the gapmer oligonucleotides comprising a GalNAc conjugate and having wings that were either full cEt or mixed sugar modifications were significantly more potent than the parent oligonucleotide lacking a conjugate and comprising full cEt modified wings.

Body weights, liver transaminases, total bilirubin, and BUN were also measured, and the average values for each treatment group are shown in Table 101. Body weight is shown as the average percent body weight relative to the baseline body weight (% BL) measured just prior to the oligonucleotide dose.

TABLE 101

SRB-1 mRNA, ALT, AST, BUN, and total bilirubin levels and body weights

| ISIS No. | Dosage (mg/kg) | SRB-1 mRNA (% PBS) | ALT (U/L) | AST (U/L) | Bil | BUN | Body weight (% BL) |
|---|---|---|---|---|---|---|---|
| PBS | n/a | 100 | 31 | 84 | 0.15 | 28 | 102 |
| 449093 | 1 | 111 | 18 | 48 | 0.17 | 31 | 104 |
|  | 3 | 94 | 20 | 43 | 0.15 | 26 | 103 |
|  | 10 | 36 | 19 | 50 | 0.12 | 29 | 104 |
| 699806 | 0.1 | 114 | 23 | 58 | 0.13 | 26 | 107 |
|  | 0.3 | 59 | 21 | 45 | 0.12 | 27 | 108 |
|  | 1 | 25 | 30 | 61 | 0.12 | 30 | 104 |
| 699807 | 0.1 | 121 | 19 | 41 | 0.14 | 25 | 100 |
|  | 0.3 | 73 | 23 | 56 | 0.13 | 26 | 105 |
|  | 1 | 24 | 22 | 69 | 0.14 | 25 | 102 |
| 699809 | 0.1 | 125 | 23 | 57 | 0.14 | 26 | 104 |
|  | 0.3 | 70 | 20 | 49 | 0.10 | 25 | 105 |
|  | 1 | 33 | 34 | 62 | 0.17 | 25 | 107 |
| 699811 | 0.1 | 123 | 48 | 77 | 0.14 | 24 | 106 |
|  | 0.3 | 94 | 20 | 45 | 0.13 | 25 | 101 |
|  | 1 | 66 | 57 | 104 | 0.14 | 24 | 107 |
| 699813 | 0.1 | 95 | 20 | 58 | 0.13 | 28 | 104 |
|  | 0.3 | 98 | 22 | 61 | 0.17 | 28 | 105 |
|  | 1 | 49 | 19 | 47 | 0.11 | 27 | 106 |
| 699815 | 0.1 | 93 | 30 | 79 | 0.17 | 25 | 105 |
|  | 0.3 | 64 | 30 | 61 | 0.12 | 26 | 105 |
|  | 1 | 24 | 18 | 41 | 0.14 | 25 | 106 |

Example 94: Antisense Inhibition In Vivo by Oligonucleotides Targeting SRB-1 Comprising 2'-Sugar Modifications and a 5'-GalNAc$_3$ Conjugate The oligonucleotides listed in Table 102 were tested in a dose-dependent study for antisense inhibition of SRB-1 in mice.

TABLE 102

Modified ASOs targeting SRB-1

| ISIS No. | Sequences (5' to 3') | GalNAc$_3$ Cluster | CM | SEQ ID No. |
|---|---|---|---|---|
| 353382 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | n/a | n/a | 829 |
| 700989 | G$_{ms}$C$_{ms}$U$_{ms}$U$_{ms}$C$_{ms}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$U$_{ms}$C$_{ms}$C$_{ms}$U$_{ms}$U$_m$ | n/a | n/a | 853 |
| 666904 | GalNAc$_3$-3$_a$-$_o$,G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{es}$$^m$C$_{es}$$^m$C$_{es}$T$_{es}$T$_e$ | GalNAc$_3$-3a | PO | 829 |
| 700991 | GalNAc$_3$-7$_a$-$_o$,G$_{ms}$C$_{ms}$U$_{ms}$U$_{ms}$C$_{ms}$A$_{ds}$G$_{ds}$T$_{ds}$$^m$C$_{ds}$A$_{ds}$T$_{ds}$G$_{ds}$ A$_{ds}$$^m$C$_{ds}$T$_{ds}$U$_{ms}$C$_{ms}$C$_{ms}$U$_{ms}$U$_m$ | GalNAc$_3$-7a | PO | 853 |

Subscript "m" indicates a 2'-O-methyl modified nucleoside. See Example 74 for complete table legend. The structure of GalNAc$_3$-3$_a$ was shown previously in Example 39, and the structure of GalNAc$_3$-7$_a$ was shown previously in Example 48.

Treatment

The study was completed using the protocol described in Example 93. Results are shown in Table 103 below and show that both the 2'-MOE and 2'-OMe modified oligonucleotides comprising a GalNAc conjugate were significantly more potent than the respective parent oligonucleotides lacking a conjugate. The results of the body weights, liver transaminases, total bilirubin, and BUN measurements indicated that the compounds were all well tolerated.

TABLE 103

SRB-1 mRNA

| ISIS No. | Dosage (mg/kg) | SRB-1 mRNA (% PBS) |
|---|---|---|
| PBS | n/a | 100 |
| 353382 | 5 | 116 |
|  | 15 | 58 |
|  | 45 | 27 |
| 700989 | 5 | 120 |
|  | 15 | 92 |
|  | 45 | 46 |
| 666904 | 1 | 98 |
|  | 3 | 45 |
|  | 10 | 17 |
| 700991 | 1 | 118 |
|  | 3 | 63 |
|  | 10 | 14 |

Example 95: Antisense Inhibition In Vivo by Oligonucleotides Targeting SRB-1 Comprising Bicyclic Nucleosides and a 5'-GalNAc$_3$ Conjugate The oligonucleotides listed in Table 104 were tested in a dose-dependent study for antisense inhibition of SRB-1 in mice.

Treatment

The study was completed using the protocol described in Example 93. Results are shown in Table 105 below and show that oligonucleotides comprising a GalNAc conjugate and various bicyclic nucleoside modifications were significantly more potent than the parent oligonucleotide lacking a conjugate and comprising bicyclic nucleoside modifications. Furthermore, the oligonucleotide comprising a GalNAc conjugate and fluoro-HNA modifications was significantly more potent than the parent lacking a conjugate and comprising fluoro-HNA modifications. The results of the body weights, liver transaminases, total bilirubin, and BUN measurements indicated that the compounds were all well tolerated.

TABLE 105

SRB-1 mRNA, ALT, AST, BUN, and total bilirubin levels and body weights

| ISIS No. | Dosage (mg/kg) | SRB-1 mRNA (% PBS) |
|---|---|---|
| PBS | n/a | 100 |
| 440762 | 1 | 104 |
|  | 3 | 65 |
|  | 10 | 35 |
| 666905 | 0.1 | 105 |
|  | 0.3 | 56 |
|  | 1 | 18 |
| 699782 | 0.1 | 93 |
|  | 0.3 | 63 |
|  | 1 | 15 |
| 699783 | 0.1 | 105 |
|  | 0.3 | 53 |
|  | 1 | 12 |
| 653621 | 0.1 | 109 |
|  | 0.3 | 82 |
|  | 1 | 27 |
| 439879 | 1 | 96 |
|  | 3 | 77 |
|  | 10 | 37 |
| 699789 | 0.1 | 82 |
|  | 0.3 | 69 |
|  | 1 | 26 |

TABLE 104

Modified ASOs targeting SRB-1

| ISIS No. | Sequences (5' to 3') | GalNAc$_3$ Cluster | CM | SEQ ID No |
|---|---|---|---|---|
| 440762 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | n/a | n/a | 823 |
| 666905 | GalNAc$_3$-3$_a$-$_o$,T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | GalNAc$_3$-3$_a$ | PO | 823 |
| 699782 | GalNAc$_3$-7$_a$-$_o$,T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | GalNAc$_3$-7$_a$ | PO | 823 |
| 699783 | GalNAc$_3$-3$_a$-$_o$,T$_{ls}$$^m$C$_{ls}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ls}$$^m$C$_l$ | GalNAc$_3$-3$_a$ | PO | 823 |
| 653621 | T$_{ls}$$^m$C$_{ls}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{lsm}$C$_{lo}$A$_{do}$'-GalNAC$_3$-1$_a$ | GalNAc$_3$-1$_a$ | A$_d$ | 824 |
| 439879 | T$_{gs}$$^m$C$_{gs}$A$_{ds}$G$_{ds}$T$_{ds}$$^m$C$_{ds}$A$_{ds}$T$_d$G$_{ds}$A$_{ds}$$^m$C$_{ds}$T$_{ds}$T$_{gs}$$^m$C$_g$ | n/a | n/a | 823 |
| 699789 | GalNAc$_3$-3$_a$-$_o$,T$_{gs}$$^m$C$_{gs}$A$_{ds}$G$_{ds}$T$_{ds}$$^m$C$_{ds}$A$_{ds}$T$_d$G$_{ds}$A$_{ds}$$^m$C$_{ds}$T$_{ds}$T$_{gs}$$^m$C$_g$ | GalNAc$_3$-3$_a$ | PO | 823 |

Subscript "g" indicates a fluoro-HNA nucleoside, subscript "l" indicates a locked nucleoside comprising a 2'-O—CH$_2$-4' bridge. See the Example 74 table legend for other abbreviations. The structure of GalNAc$_3$-1$_a$ was shown previously in Example 9, the structure of GalNAc$_3$-3$_a$ was shown previously in Example 39, and the structure of GalNAc$_3$-7$_a$ was shown previously in Example 48.

Example 96: Plasma Protein Binding of Antisense Oligonucleotides Comprising a GalNAc$_3$ Conjugate Group Oligonucleotides listed in Table 70 targeting ApoC-II and oligonucleotides in Table 106 targeting Apo(a) were tested in an ultra-filtration assay in order to assess plasma protein binding.

TABLE 106

Modified oligonucleotides targeting Apo(a)

| ISIS No. | Sequences (5' to 3') | GalNAc$_3$ Cluster | CM | SEQ ID No |
|---|---|---|---|---|
| 494372 | T$_{es}$G$_{es}$$^m$C$_{es}$T$_{es}$$^m$C$_{es}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{es}$G$_{es}$T$_{es}$T$_{es}$$^m$C$_e$ | n/a | n/a | 847 |
| 693401 | T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{eo}$G$_{eo}$T$_{es}$T$_{es}$$^m$C$_e$ | n/a | n/a | 847 |
| 681251 | GalNAc$_3$-7$_a$-$_o$'T$_{es}$G$_{es}$$^m$C$_{es}$T$_{es}$$^m$C$_{es}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{es}$G$_{es}$T$_{es}$T$_{es}$$^m$C$_e$ | GalNAc$_3$-7$_a$ | PO | 847 |
| 681257 | GalNAC$_3$-7$_a$-$_o$'T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{eo}$G$_{eo}$T$_{es}$T$_{es}$$^m$C$_e$ | GalNAc$_3$-7$_a$ | PO | 847 |

See the Example 74 for table legend. The structure of GalNAc$_3$-7$_a$ was shown previously in Example 48.

Ultrafree-MC ultrafiltration units (30,000 NMWL, low-binding regenerated cellulose membrane, Millipore, Bedford, Mass.) were pre-conditioned with 300 µL of 0.500 Tween 80 and centrifuged at 2000 g for 10 minutes, then with 300 µL of a 300 µg/mL solution of a control oligonucleotide in H$_2$O and centrifuged at 2000 g for 16 minutes. In order to assess non-specific binding to the filters of each test oligonucleotide from Tables 70 and 106 to be used in the studies, 300 µL of a 250 ng/mL solution of oligonucleotide in H$_2$O at pH 7.4 was placed in the pre-conditioned filters and centrifuged at 2000 g for 16 minutes. The unfiltered and filtered samples were analyzed by an ELISA assay to determine the oligonucleotide concentrations. Three replicates were used to obtain an average concentration for each sample. The average concentration of the filtered sample relative to the unfiltered sample is used to determine the percent of oligonucleotide that is recovered through the filter in the absence of plasma (% recovery).

Frozen whole plasma samples collected in K3-EDTA from normal, drug-free human volunteers, cynomolgus monkeys, and CD-1 mice, were purchased from Bioreclamation LLC (Westbury, N.Y.). The test oligonucleotides were added to 1.2 mL aliquots of plasma at two concentrations (5 and 150 µg/mL). An aliquot (300 µL) of each spiked plasma sample was placed in a pre-conditioned filter unit and incubated at 37° C. for 30 minutes, immediately followed by centrifugation at 2000 g for 16 minutes. Aliquots of filtered and unfiltered spiked plasma samples were analyzed by an ELISA to determine the oligonucleotide concentration in each sample. Three replicates per concentration were used to determine the average percentage of bound and unbound oligonucleotide in each sample. The average concentration of the filtered sample relative to the concentration of the unfiltered sample is used to determine the percent of oligonucleotide in the plasma that is not bound to plasma proteins (% unbound). The final unbound oligonucleotide values are corrected for non-specific binding by dividing the % unbound by the % recovery for each oligonucleotide. The final % bound oligonucleotide values are determined by subtracting the final % unbound values from 100. The results are shown in Table 107 for the two concentrations of oligonucleotide tested (5 and 150 µg/mL) in each species of plasma. The results show that GalNAc conjugate groups do not have a significant impact on plasma protein binding. Furthermore, oligonucleotides with full PS internucleoside linkages and mixed PO/PS linkages both bind plasma proteins, and those with full PS linkages bind plasma proteins to a somewhat greater extent than those with mixed PO/PS linkages.

TABLE 107

Percent of modified oligonucleotide bound to plasma proteins

| ISIS No. | Human plasma | | Monkey plasma | | Mouse plasma | |
|---|---|---|---|---|---|---|
| | 5 µg/mL | 150 µg/mL | 5 µg/mL | 150 µg/mL | 5 µg/mL | 150 µg/mL |
| 304801 | 99.2 | 98.0 | 99.8 | 99.5 | 98.1 | 97.2 |
| 663083 | 97.8 | 90.9 | 99.3 | 99.3 | 96.5 | 93.0 |
| 674450 | 96.2 | 97.0 | 98.6 | 94.4 | 94.6 | 89.3 |
| 494372 | 94.1 | 89.3 | 98.9 | 97.5 | 97.2 | 93.6 |
| 693401 | 93.6 | 89.9 | 96.7 | 92.0 | 94.6 | 90.2 |
| 681251 | 95.4 | 93.9 | 99.1 | 98.2 | 97.8 | 96.1 |
| 681257 | 93.4 | 90.5 | 97.6 | 93.7 | 95.6 | 92.7 |

Example 97: Modified Oligonucleotides Targeting TTR Comprising a GalNAc$_3$ Conjugate Group The oligonucleotides shown in Table 108 comprising a GalNAc conjugate were designed to target TTR.

TABLE 108

Modified oligonucleotides targeting TTR

| ISIS No. | Sequences (5' to 3') | GalNAc$_3$ Cluster | CM | SEQ ID No |
|---|---|---|---|---|
| 666941 | GalNAC$_3$-3$_a$-$_o$'A$_{do}$T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc$_3$-3 | A$_d$ | 846 |
| 666942 | T$_{es}$$^m$C$_{eo}$T$_{eo}$T$_{eo}$G$_{eo}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{eo}$T$_{eo}$$^m$C$_{es}$$^m$C$_{es}$$^m$C$_{eo}$A$_{do}$'-GalNAc$_3$-3$_a$ | GalNAc$_3$-1 | A$_d$ | 843 |
| 682876 | GalNAC$_3$-3$_a$-$_o$'T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc$_3$-3 | PO | 842 |

TABLE 108-continued

Modified oligonucleotides targeting TTR

| ISIS No. | Sequences (5' to 3') | GalNAc$_3$ Cluster | CM | SEQ ID No |
|---|---|---|---|---|
| 682877 | GalNAc$_3$-7$_a$-$_o$,T$_{es}$$^m$C$_{es}$T$_{es}$T$_{es}$G$_{es}$G$_{ds}$T$_{ds}$T$_{ds}$A$_{ds}$$^m$C$_{ds}$ A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc$_3$-7 | PO | 842 |
| 682878 | GalNAc$_3$-10$_a$-$_o$,T$_{es}$$^m$C$_{es}$T$_{es}$T$_{es}$G$_{es}$G$_{ds}$T$_{ds}$T$_{ds}$A$_{ds}$$^m$C$_{ds}$ A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc$_3$-10 | PO | 842 |
| 682879 | GalNAc$_3$-13$_a$-$_o$,T$_{es}$$^m$C$_{es}$T$_{es}$T$_{es}$G$_{es}$G$_{ds}$T$_{ds}$T$_{ds}$A$_{ds}$$^m$C$_{ds}$ A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc$_3$-13 | PO | 842 |
| 682880 | GalNAc$_3$-7$_a$-$_o$,A$_{do}$T$_{es}$$^m$C$_{es}$T$_{es}$T$_{es}$G$_{es}$G$_{ds}$T$_{ds}$T$_{ds}$A$_{ds}$ $^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc$_3$-7 | A$_d$ | 846 |
| 682881 | GalNAc$_3$-10$_a$-$_o$,A$_{do}$T$_{es}$$^m$C$_{es}$T$_{es}$T$_{es}$G$_{es}$G$_{ds}$T$_{ds}$T$_{ds}$A$_{ds}$ $^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc$_3$-10 | A$_d$ | 846 |
| 682882 | GalNAc$_3$-13$_a$-$_o$,A$_{do}$T$_{es}$$^m$C$_{es}$T$_{es}$T$_{es}$G$_{es}$G$_{ds}$T$_{ds}$T$_{ds}$A$_{ds}$ $^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc$_3$-13 | A$_d$ | 846 |
| 684056 | T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$ A$_{ds}$A$_{es}$T$_{es}$$^m$C$_{es}$$^m$C$_{es}$$^m$C$_e$C$_{eo}$A$_{do}$,-GalNAc$_3$-19$_a$ | GalNAc$_3$-19 | A$_d$ | 846 |

The legend for Table 108 can be found in Example 74. The structure of GalNAc$_3$-1 was shown in Example 9. The structure of GalNAc$_3$-3$_a$ was shown in Example 39. The structure of GalNAc$_3$-7$_a$ was shown in Example 48. The structure of GalNAc$_3$-10$_a$ was shown in Example 46. The structure of GalNAc$_3$-13$_a$ was shown in Example 62. The structure of GalNAc$_3$-19$_a$ was shown in Example 70.

Example 98: Evaluation of Pro-Inflammatory Effects of Oligonucleotides Comprising a GalNAc Conjugate in hPMBC Assay The oligonucleotides listed in Table 109 and were tested for pro-inflammatory effects in an hPMBC assay as described in Examples 23 and 24. (See Tables 30, 83, 95, and 108 for descriptions of the oligonucleotides.) ISIS 353512 is a high responder used as a positive control, and the other oligonucleotides are described in Tables 83, 95, and 108. The results shown in Table 109 were obtained using blood from one volunteer donor. The results show that the oligonucleotides comprising mixed PO/PS internucleoside linkages produced significantly lower pro-inflammatory responses compared to the same oligonucleotides having full PS linkages. Furthermore, the GalNAc conjugate group did not have a significant effect in this assay.

TABLE 109

| ISIS No. | E$_{max}$/EC$_{50}$ | GalNAc$_3$ cluster | Linkages | CM |
|---|---|---|---|---|
| 353512 | 3630 | n/a | PS | n/a |
| 420915 | 802 | n/a | PS | n/a |
| 682881 | 1311 | GalNAc$_3$-10 | PS | A$_d$ |
| 682888 | 0.26 | GalNAc$_3$-10 | PO/PS | A$_d$ |
| 684057 | 1.03 | GalNAc$_3$-19 | PO/PS | A$_d$ |

Example 99: Binding Affinities of Oligonucleotides Comprising a GalNAc Conjugate for the Asialoglycoprotein Receptor The binding affinities of the oligonucleotides listed in Table 110 (see Table 76 for descriptions of the oligonucleotides) for the asialoglycoprotein receptor were tested in a competitive receptor binding assay. The competitor ligand, α1-acid glycoprotein (AGP), was incubated in 50 mM sodium acetate buffer (pH 5) with 1 U neuraminidase-agarose for 16 hours at 37° C., and >90% desialylation was confirmed by either sialic acid assay or size exclusion chromatography (SEC). Iodine monochloride was used to iodinate the AGP according to the procedure by Atsma et al. (see J Lipid Res. 1991 January; 32(1):173-81.) In this method, desialylated α1-acid glycoprotein (de-AGP) was added to 10 mM iodine chloride, Na$^{125}$I, and 1 M glycine in 0.25 M NaOH. After incubation for 10 minutes at room temperature, $^{125}$I-labeled de-AGP was separated from free $^{125}$I by concentrating the mixture twice utilizing a 3 KDMWCO spin column. The protein was tested for labeling efficiency and purity on a HPLC system equipped with an Agilent SEC-3 column (7.8×300 mm) and a ß-RAM counter. Competition experiments utilizing $^{125}$I-labeled de-AGP and various GalNAc-cluster containing ASOs were performed as follows. Human HepG2 cells (10$^6$ cells/ml) were plated on 6-well plates in 2 ml of appropriate growth media. MEM media supplemented with 10% fetal bovine serum (FBS), 2 mM L-Glutamine and 10 mM HEPES was used. Cells were incubated 16-20 hours @ 37° C. with 5% and 10% CO$_2$ respectively. Cells were washed with media without FBS prior to the experiment. Cells were incubated for 30 min @37° C. with 1 ml competition mix containing appropriate growth media with 2% FBS, 10$^{-8}$ M $^{125}$I-labeled de-AGP and GalNAc-cluster containing ASOs at concentrations ranging from 10$^{-11}$ to 10$^{-5}$ M. Non-specific binding was determined in the presence of 10$^{-2}$ M GalNAc sugar. Cells were washed twice with media without FBS to remove unbound $^{125}$I-labeled de-AGP and competitor GalNAc ASO. Cells were lysed using Qiagen's RLT buffer containing 1% ß-mercaptoethanol. Lysates were transferred to round bottom assay tubes after a brief 10 min freeze/thaw cycle and assayed on a γ-counter. Non-specific binding was subtracted before dividing $^{125}$I protein counts by the value of the lowest GalNAc-ASO concentration counts. The inhibition curves were fitted according to a single site competition binding equation using a nonlinear regression algorithm to calculate the binding affinities (K$_D$'s).

The results in Table 110 were obtained from experiments performed on five different days. Results for oligonucleotides marked with superscript "a" are the average of experiments run on two different days. The results show that the oligonucleotides comprising a GalNAc conjugate group on the 5'-end bound the asialoglycoprotein receptor on human HepG2 cells with 1.5 to 16-fold greater affinity than the oligonucleotides comprising a GalNAc conjugate group on the 3'-end.

TABLE 110

Asialoglycoprotein receptor binding assay results

| ISIS No. | GalNAc conjugate | Oligonucleotide end to which GalNAc conjugate is attached | $K_D$ (nM) |
|---|---|---|---|
| 661161$^a$ | GalNAc$_3$-3 | 5' | 3.7 |
| 666881$^a$ | GalNAc$_3$-10 | 5' | 7.6 |
| 666981 | GalNAc$_3$-7 | 5' | 6.0 |
| 670061 | GalNAc$_3$-13 | 5' | 7.4 |
| 655861$^a$ | GalNAc$_3$-1 | 3' | 11.6 |
| 677841$^a$ | GalNAc$_3$-19 | 3' | 60.8 |

Example 100: Antisense Inhibition In Vivo by Oligonucleotides Comprising a GalNAc Conjugate Group Targeting Apo(a) In Vivo The oligonucleotides listed in Table 111a below were tested in a single dose study for duration of action in mice.

TABLE 111a

Modified ASOs targeting APO(a)

| ISIS No. | Sequences (5' to 3') | GalNAc$_3$ Cluster | CM | SEQ ID No. |
|---|---|---|---|---|
| 681251 | GalNAC$_3$-7$_a$-$_o$,T$_{es}$G$_{es}$$^m$C$_{es}$T$_{es}$$^m$C$_{es}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{es}$G$_{es}$T$_{es}$T$_{es}$$^m$C$_e$ | GalNAc$_3$-7a | PO | 847 |
| 681257 | GalNAC$_3$-7$_a$-$_o$,T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{eo}$G$_{eo}$T$_{es}$T$_{es}$$^m$C$_e$ | GalNAc$_3$-7a | PO | 847 |

The structure of GalNAc$_3$-7$_a$ was shown in Example 48.

Treatment

Female transgenic mice that express human Apo(a) were each injected subcutaneously once per week, for a total of 6 doses, with an oligonucleotide and dosage listed in Table 111b or with PBS. Each treatment group consisted of 3 animals. Blood was drawn the day before dosing to determine baseline levels of Apo(a) protein in plasma and at 72 hours, 1 week, and 2 weeks following the first dose. Additional blood draws will occur at 3 weeks, 4 weeks, 5 weeks, and 6 weeks following the first dose. Plasma Apo(a) protein levels were measured using an ELISA. The results in Table 111b are presented as the average percent of plasma Apo(a) protein levels for each treatment group, normalized to baseline levels (% BL), The results show that the oligonucleotides comprising a GalNAc conjugate group exhibited potent reduction in Apo(a) expression. This potent effect was observed for the oligonucleotide that comprises full PS internucleoside linkages and the oligonucleotide that comprises mixed PO and PS linkages.

TABLE 111b

Apo(a) plasma protein levels

| ISIS No. | Dosage (mg/kg) | Apo(a) at 72 hours (% BL) | Apo(a) at 1 week (% BL) | Apo(a) at 3 weeks (% BL) |
|---|---|---|---|---|
| PBS | n/a | 116 | 104 | 107 |
| 681251 | 0.3 | 97 | 108 | 93 |
| | 1.0 | 85 | 77 | 57 |
| | 3.0 | 54 | 49 | 11 |
| | 10.0 | 23 | 15 | 4 |
| 681257 | 0.3 | 114 | 138 | 104 |
| | 1.0 | 91 | 98 | 54 |
| | 3.0 | 69 | 40 | 6 |
| | 10.0 | 30 | 21 | 4 |

Example 101: Antisense Inhibition by Oligonucleotides Comprising a GalNAc Cluster Linked Via a Stable Moiety The oligonucleotides listed in Table 112 were tested for inhibition of mouse APOC-III expression in vivo. C57B1/6 mice were each injected subcutaneously once with an oligonucleotide listed in Table 112 or with PBS. Each treatment group consisted of 4 animals. Each mouse treated with ISIS 440670 received a dose of 2, 6, 20, or 60 mg/kg. Each mouse treated with ISIS 680772 or 696847 received 0.6, 2, 6, or 20 mg/kg. The GalNAc conjugate group of ISIS 696847 is linked via a stable moiety, a phosphorothioate linkage instead of a readily cleavable phosphodiester containing linkage. The animals were sacrificed 72 hours after the dose. Liver APOC-III mRNA levels were measured using realtime PCR. APOC-III mRNA levels were normalized to cyclophilin mRNA levels according to standard protocols. The results are presented in Table 112 as the average percent of APOC-III mRNA levels for each treatment group relative to the saline control group. The results show that the oligonucleotides comprising a GalNAc conjugate group were significantly more potent than the oligonucleotide lacking a conjugate group. Furthermore, the oligonucleotide comprising a GalNAc conjugate group linked to the oligonucleotide via a cleavable moiety (ISIS 680772) was even more potent than the oligonucleotide comprising a GalNAc conjugate group linked to the oligonucleotide via a stable moiety (ISIS 696847).

TABLE 112

Modified oligonucleotides targeting mouse APOC-III

| ISIS No. | Sequences (5' to 3') | CM | Dosage (mg/kg) | APOC-III mRNA (% PBS) | SEQ ID No. |
|---|---|---|---|---|---|
| 440670 | $^mC_{es}A_{es}G_{es}{}^mC_{es}T_{es}T_{ds}T_{ds}A_{ds}T_{ds}T_{ds}A_{ds}$ $G_{ds}G_{ds}G_{ds}A_{ds}{}^mC_{es}A_{es}G_{es}{}^mC_{es}A_{e}$ | n/a | 2 | 92 | 849 |
| | | | 6 | 86 | |
| | | | 20 | 59 | |
| | | | 60 | 37 | |
| 680772 | GalNAC$_3$-7$_a$-$_o$,$^mC_{es}A_{es}G_{es}{}^mC_{es}T_{es}T_{ds}T_{ds}A_{ds}$ $T_{ds}T_{ds}A_{ds}G_{ds}G_{ds}G_{ds}A_{ds}{}^mC_{es}A_{es}G_{es}{}^mC_{es}A_{e}$ | PO | 0.6 | 79 | 849 |
| | | | 2 | 58 | |
| | | | 6 | 31 | |
| | | | 20 | 13 | |
| 696847 | GalNAC$_3$-7$_a$-$_s$,$^mC_{es}A_{es}G_{es}{}^mC_{es}T_{es}T_{ds}T_{ds}A_{ds}T_{ds}$ $T_{ds}A_{ds}G_{ds}G_{ds}G_{ds}A_{ds}{}^mC_{es}A_{es}G_{es}{}^mC_{es}A_{e}$ | n/a (PS) | 0.6 | 83 | 849 |
| | | | 2 | 73 | |
| | | | 6 | 40 | |
| | | | 20 | 28 | |

The structure of GalNAc$_3$-7$_a$ was shown in Example 48.

Example 102: Distribution in Liver of Antisense Oligonucleotides Comprising a GalNAc Conjugate The liver distribution of ISIS 353382 (see Table 36) that does not comprise a GalNAc conjugate and ISIS 655861 (see Table 36) that does comprise a GalNAc conjugate was evaluated. Male balb/c mice were subcutaneously injected once with ISIS 353382 or 655861 at a dosage listed in Table 113. Each treatment group consisted of 3 animals except for the 18 mg/kg group for ISIS 655861, which consisted of 2 animals. The animals were sacrificed 48 hours following the dose to determine the liver distribution of the oligonucleotides. In order to measure the number of antisense oligonucleotide molecules per cell, a Ruthenium (II) tris-bipyridine tag (MSD TAG, Meso Scale Discovery) was conjugated to an oligonucleotide probe used to detect the antisense oligonucleotides. The results presented in Table 113 are the average concentrations of oligonucleotide for each treatment group in units of millions of oligonucleotide molecules per cell. The results show that at equivalent doses, the oligonucleotide comprising a GalNAc conjugate was present at higher concentrations in the total liver and in hepatocytes than the oligonucleotide that does not comprise a GalNAc conjugate. Furthermore, the oligonucleotide comprising a GalNAc conjugate was present at lower concentrations in non-parenchymal liver cells than the oligonucleotide that does not comprise a GalNAc conjugate. And while the concentrations of ISIS 655861 in hepatocytes and non-parenchymal liver cells were similar per cell, the liver is approximately 80% hepatocytes by volume. Thus, the majority of the ISIS 655861 oligonucleotide that was present in the liver was found in hepatocytes, whereas the majority of the ISIS 353382 oligonucleotide that was present in the liver was found in non-parenchymal liver cells.

TABLE 113

| ISIS No. | Dosage (mg/kg) | Concentration in whole liver (molecules*10^6 per cell) | Concentration in hepatocytes (molecules*10^6 per cell) | Concentration in non-parenchymal liver cells (molecules*10^6 per cell) |
|---|---|---|---|---|
| 353382 | 3 | 9.7 | 1.2 | 37.2 |
| | 10 | 17.3 | 4.5 | 34.0 |
| | 20 | 23.6 | 6.6 | 65.6 |
| | 30 | 29.1 | 11.7 | 80.0 |
| | 60 | 73.4 | 14.8 | 98.0 |
| | 90 | 89.6 | 18.5 | 119.9 |
| 655861 | 0.5 | 2.6 | 2.9 | 3.2 |
| | 1 | 6.2 | 7.0 | 8.8 |
| | 3 | 19.1 | 25.1 | 28.5 |
| | 6 | 44.1 | 48.7 | 55.0 |
| | 18 | 76.6 | 82.3 | 77.1 |

Example 103: Duration of Action In Vivo of Oligonucleotides Targeting APOC-III Comprising a GalNAc$_3$ Conjugate The oligonucleotides listed in Table 114 below were tested in a single dose study for duration of action in mice.

TABLE 114

Modified ASOs targeting APOC-III

| ISIS No. | Sequences (5' to 3') | GalNAc$_3$ Cluster | CM | SEQ ID No. |
|---|---|---|---|---|
| 304801 | $A_{es}G_{es}{}^mC_{es}T_{es}T_{es}{}^mC_{ds}T_{ds}T_{ds}G_{ds}T_{ds}{}^mC_{ds}{}^mC_{ds}A_{ds}G_{ds}{}^mC_{ds}T_{es}T_{es}T_{es}A_{es}T_{e}$ | n/a | n/a | 821 |
| 663084 | GalNAC$_3$-3$_a$-$_o$,$A_{do}A_{es}G_{eo}{}^mC_{eo}T_{eo}T_{eo}{}^mC_{ds}T_{ds}T_{ds}G_{ds}T_{ds}{}^mC_{ds}$ $^mC_{ds}A_{ds}G_{ds}{}^mC_{ds}T_{eo}T_{eo}T_{es}A_{es}T_{e}$ | GalNAc$_3$-3a | A$_d$ | 837 |
| 679241 | $A_{es}G_{eo}{}^mC_{eo}T_{eo}T_{eo}{}^mC_{ds}T_{ds}T_{ds}G_{ds}T_{ds}{}^mC_{ds}{}^mC_{ds}A_{ds}G_{ds}{}^mC_{ds}T_{eo}T_{eo}$ $T_{es}A_{es}T_{eo}A_{do}$,-GalNAc$_3$-19$_a$ | GalNAc$_3$-19a | A$_d$ | 822 |

The structure of GalNAc$_3$-3$_a$ was shown in Example 39, and GalNAc$_3$-19$_a$ was shown in Example 70.

Treatment

Female transgenic mice that express human APOC-III were each injected subcutaneously once with an oligonucleotide listed in Table 114 or with PBS. Each treatment group consisted of 3 animals. Blood was drawn before dosing to determine baseline and at 3, 7, 14, 21, 28, 35, and 42 days following the dose. Plasma triglyceride and APOC-III protein levels were measured as described in Example 20. The results in Table 115 are presented as the average percent of plasma triglyceride and APOC-III levels for each treatment group, normalized to baseline levels. A comparison of the results in Table 71 of example 79 with the results in Table 115 below show that oligonucleotides comprising a mixture of phosphodiester and phosphorothioate internucleoside linkages exhibited increased duration of action than equivalent oligonucleotides comprising only phosphorothioate internucleoside linkages.

TABLE 115

Plasma triglyceride and APOC-III protein levels in transgenic mice

| ISIS No. | Dosage (mg/kg) | Time point (days post-dose) | Triglycerides (% baseline) | APOC-III protein (% baseline) | GalNAc$_3$ Cluster | CM |
|---|---|---|---|---|---|---|
| PBS | n/a | 3 | 96 | 101 | n/a | n/a |
|  |  | 7 | 88 | 98 |  |  |
|  |  | 14 | 91 | 103 |  |  |
|  |  | 21 | 69 | 92 |  |  |
|  |  | 28 | 83 | 81 |  |  |
|  |  | 35 | 65 | 86 |  |  |
|  |  | 42 | 72 | 88 |  |  |
| 304801 | 30 | 3 | 42 | 46 | n/a | n/a |
|  |  | 7 | 42 | 51 |  |  |
|  |  | 14 | 59 | 69 |  |  |
|  |  | 21 | 67 | 81 |  |  |
|  |  | 28 | 79 | 76 |  |  |
|  |  | 35 | 72 | 95 |  |  |
|  |  | 42 | 82 | 92 |  |  |
| 663084 | 10 | 3 | 35 | 28 | GalNAc$_3$-3a | A$_d$ |
|  |  | 7 | 23 | 24 |  |  |
|  |  | 14 | 23 | 26 |  |  |
|  |  | 21 | 23 | 29 |  |  |
|  |  | 28 | 30 | 22 |  |  |
|  |  | 35 | 32 | 36 |  |  |
|  |  | 42 | 37 | 47 |  |  |
| 679241 | 10 | 3 | 38 | 30 | GalNAc$_3$-19a | A$_d$ |
|  |  | 7 | 31 | 28 |  |  |
|  |  | 14 | 30 | 22 |  |  |
|  |  | 21 | 36 | 34 |  |  |
|  |  | 28 | 48 | 34 |  |  |
|  |  | 35 | 50 | 45 |  |  |
|  |  | 42 | 72 | 64 |  |  |

Example 104: Synthesis of Oligonucleotides Comprising a 5'-GalNAc$_2$ Conjugate

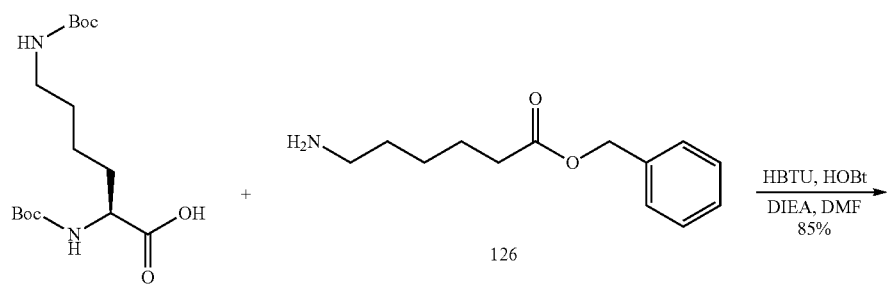

-continued
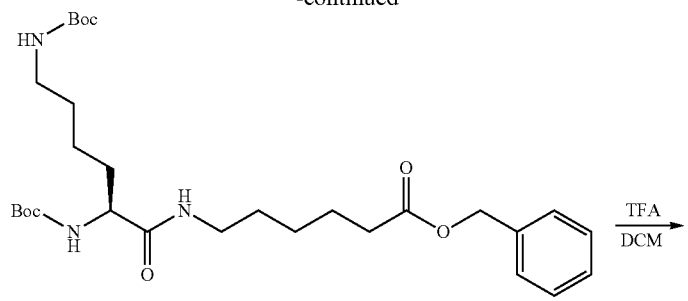
231
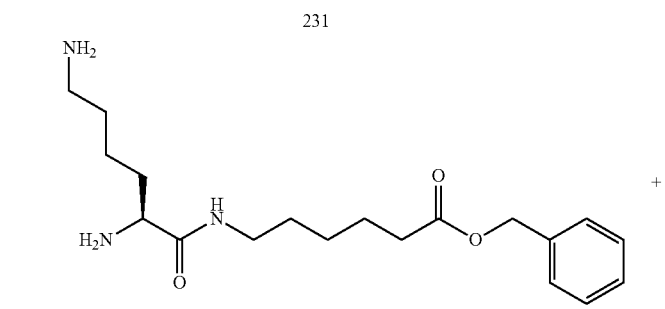
232
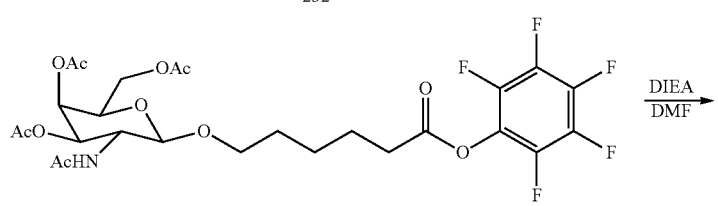
166
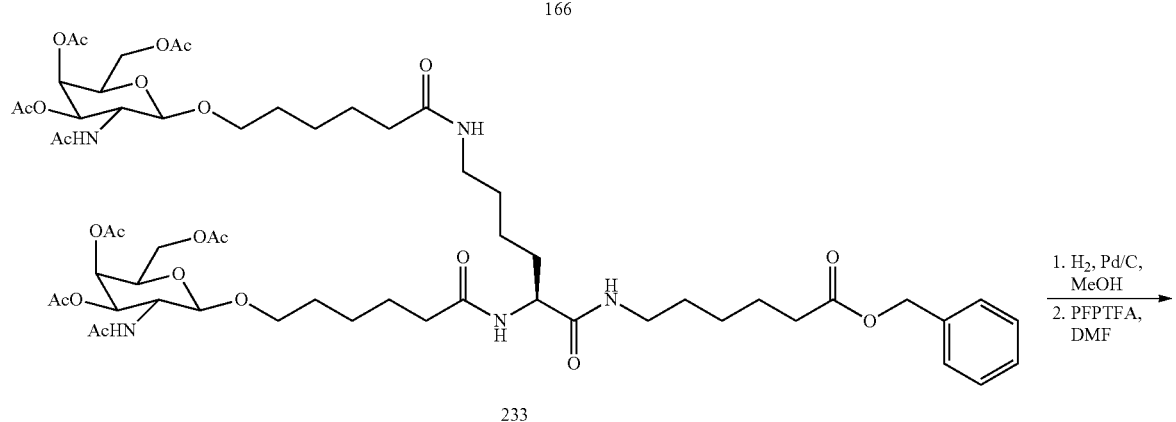
233
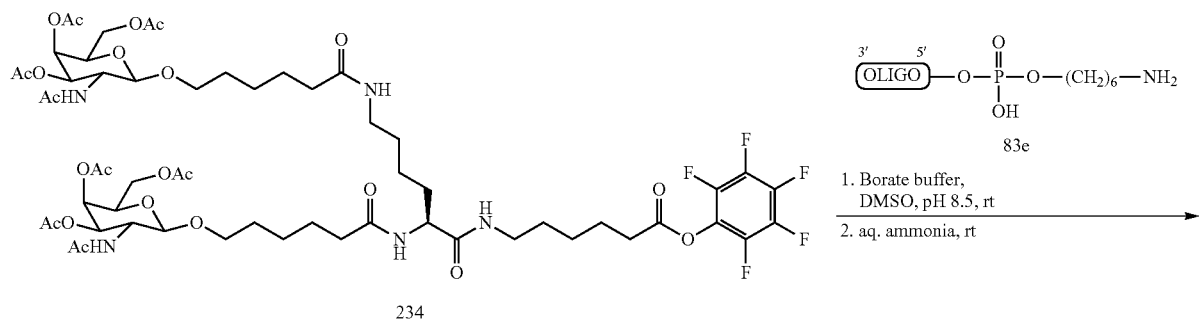
234

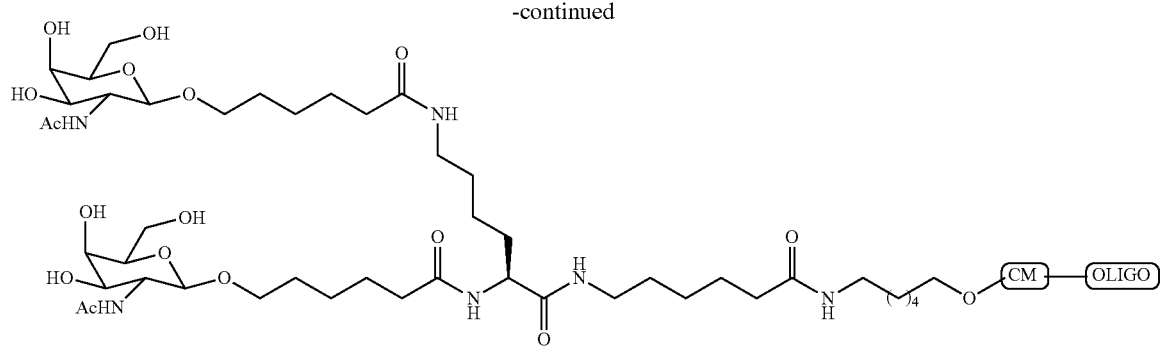

235

Compound 120 is commercially available, and the synthesis of compound 126 is described in Example 49. Compound 120 (1 g, 2.89 mmol), HBTU (0.39 g, 2.89 mmol), and HOBt (1.64 g, 4.33 mmol) were dissolved in DMF (10 mL. and N,N-diisopropylethylamine (1.75 mL, 10.1 mmol) were added. After about 5 min, aminohexanoic acid benzyl ester (1.36 g, 3.46 mmol) was added to the reaction. After 3 h, the reaction mixture was poured into 100 mL of 1 M NaHSO₄ and extracted with 2×50 mL ethyl acetate. Organic layers were combined and washed with 3×40 mL sat NaHCO₃ and 2× brine, dried with Na₂SO₄, filtered and concentrated. The product was purified by silica gel column chromatography (DCM:EA:Hex, 1:1:1) to yield compound 231. LCMS and NMR were consistent with the structure. Compounds 231 (1.34 g, 2.438 mmol) was dissolved in dichloromethane (10 mL) and trifluoracetic acid (10 mL) was added. After stirring at room temperature for 2 h, the reaction mixture was concentrated under reduced pressure and co-evaporated with toluene (3×10 mL). The residue was dried under reduced pressure to yield compound 232 as the trifuloracetate salt. The synthesis of compound 166 is described in Example 54. Compound 166 (3.39 g, 5.40 mmol) was dissolved in DMF (3 mL). A solution of compound 232 (1.3 g, 2.25 mmol) was dissolved in DMF (3 mL) and N,N-diisopropylethylamine (1.55 mL) was added. The reaction was stirred at room temperature for 30 minutes, then poured into water (80 mL) and the aqueous layer was extracted with EtOAc (2×100 mL). The organic phase was separated and washed with sat. aqueous NaHCO₃ (3×80 mL), 1 M NaHSO₄ (3×80 mL) and brine (2×80 mL), then dried (Na₂SO₄), filtered, and concentrated. The residue was purified by silica gel column chromatography to yield compound 233. LCMS and NMR were consistent with the structure. Compound 233 (0.59 g, 0.48 mmol) was dissolved in methanol (2.2 mL) and ethyl acetate (2.2 mL). Palladium on carbon (10 wt % Pd/C, wet, 0.07 g) was added, and the reaction mixture was stirred under hydrogen atmosphere for 3 h. The reaction mixture was filtered through a pad of Celite and concentrated to yield the carboxylic acid. The carboxylic acid (1.32 g, 1.15 mmol, cluster free acid) was dissolved in DMF (3.2 mL). To this N,N-diisopropylehtylamine (0.3 mL, 1.73 mmol) and PFPTFA (0.30 mL, 1.73 mmol) were added. After 30 min stirring at room temperature the reaction mixture was poured into water (40 mL) and extracted with EtOAc (2×50 mL). A standard work-up was completed as described above to yield compound 234. LCMS and NMR were consistent with the structure. Oligonucleotide 235 was prepared using the general procedure described in Example 46. The GalNAc2 cluster portion (GalNAc2-24$_a$) of the conjugate group GalNAc2-24 can be combined with any cleavable moiety present on the oligonucleotide to provide a variety of conjugate groups. The structure of GalNAc2-24 (GalNAc2-24$_a$-CM) is shown below:

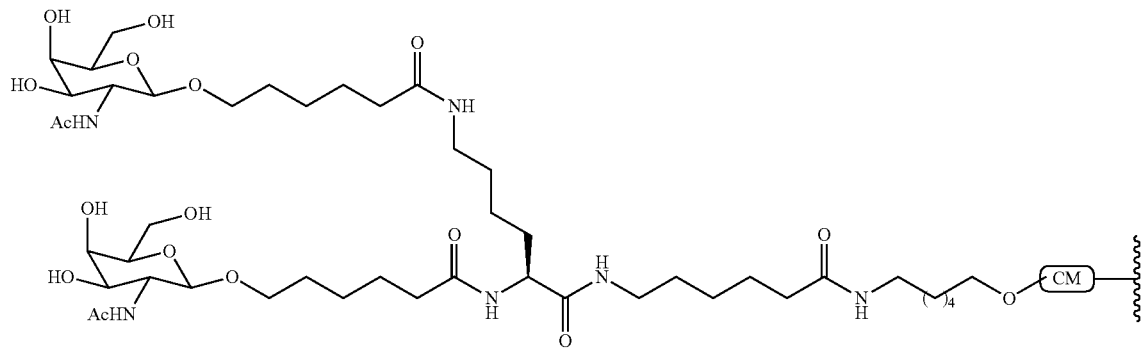

Example 105: Synthesis of Oligonucleotides Comprising a GalNAc$_1$-25 Conjugate

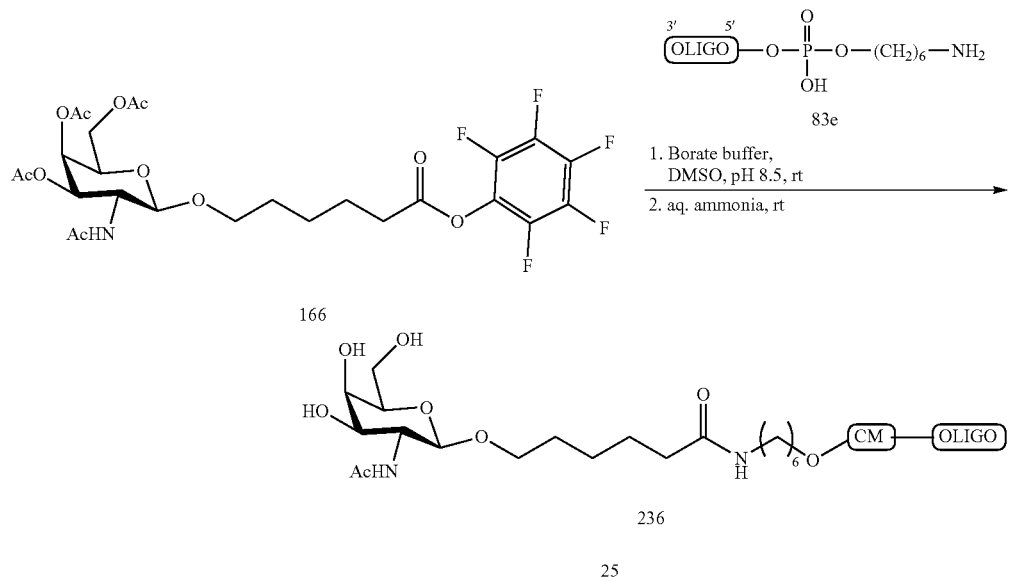

The synthesis of compound 166 is described in Example 54. Oligonucleotide 236 was prepared using the general procedure described in Example 46.

Alternatively, oligonucleotide 236 was synthesized using the scheme shown below, and compound 238 was used to form the oligonucleotide 236 using procedures described in Example 10.

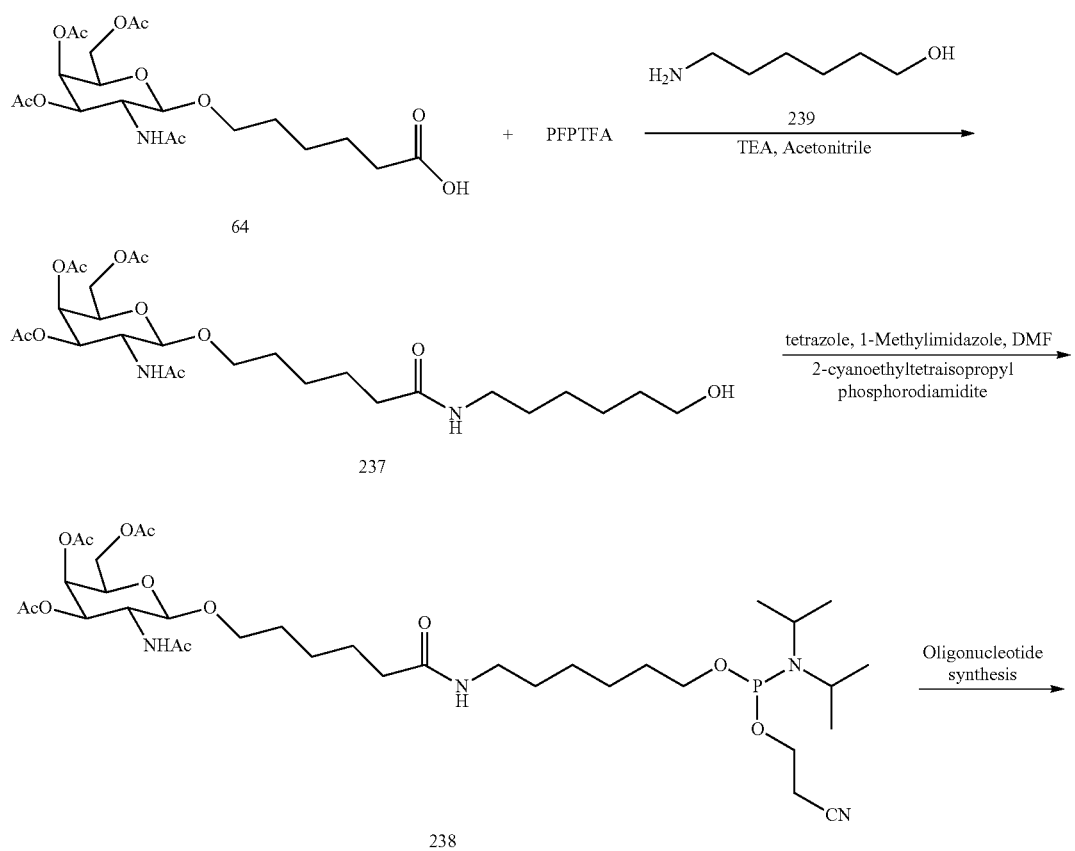

-continued

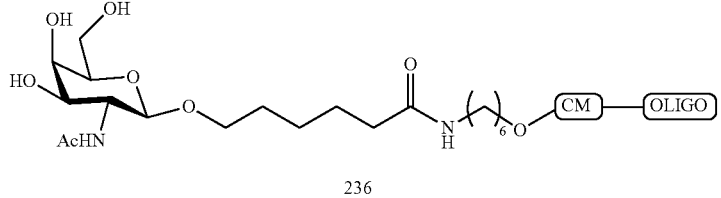

236

The GalNAc$_1$ cluster portion (GalNAc$_1$-25$_a$) of the conjugate group GalNAc$_1$-25 can be combined with any cleavable moiety present on the oligonucleotide to provide a variety of conjugate groups. The structure of GalNAc$_1$-25 (GalNAc$_1$-25$_a$-CM) is shown below:

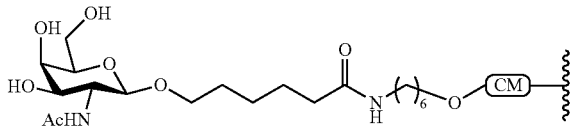

Example 106: Antisense Inhibition In Vivo by Oligonucleotides Targeting SRB-1 Comprising a 5'-GalNAc$_2$ or a 5'-GalNAc$_3$ Conjugate Oligonucleotides listed in Tables 116 and 117 were tested in dose-dependent studies for antisense inhibition of SRB-1 in mice.

Treatment

Six to week old, male C57BL/6 mice (Jackson Laboratory, Bar Harbor, Me.) were injected subcutaneously once with 2, 7, or 20 mg/kg of ISIS No. 440762; or with 0.2, 0.6, 2, 6, or 20 mg/kg of ISIS No. 686221, 686222, or 708561; or with saline. Each treatment group consisted of 4 animals. The mice were sacrificed 72 hours following the final administration. Liver SRB-1 mRNA levels were measured using real-time PCR. SRB-1 mRNA levels were normalized to cyclophilin mRNA levels according to standard protocols. The antisense oligonucleotides lowered SRB-1 mRNA levels in a dose-dependent manner, and the ED$_{50}$ results are presented in Tables 116 and 117. Although previous studies showed that trivalent GalNAc-conjugated oligonucleotides were significantly more potent than divalent GalNAc-conjugated oligonucleotides, which were in turn significantly more potent than monovalent GalNAc conjugated oligonucleotides (see, e.g., Khorev et al., Bioorg. & Med. Chem., Vol. 16, 5216-5231 (2008)), treatment with antisense oligonucleotides comprising monovalent, divalent, and trivalent GalNAc clusters lowered SRB-1 mRNA levels with similar potencies as shown in Tables 116 and 117.

TABLE 116

Modified oligonucleotides targeting SRB-1

| ISIS No. | Sequences (5' to 3') | GalNAc Cluster | ED$_{50}$ (mg/kg) | SEQ ID No |
|---|---|---|---|---|
| 440762 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | n/a | 4.7 | 823 |
| 686221 | GalNAc$_2$-24$_a$-$_o$,A$_{do}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | GalNAc$_2$-24$_a$ | 0.39 | 827 |
| 686222 | GalNAc$_3$-13$_a$-$_o$,A$_{do}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | GalNAc$_3$-13$_a$ | 0.41 | 827 |

See Example 93 for table legend. The structure of GalNAc$_3$-13a was shown in Example 62, and the structure of GalNAc2-24a was shown in Example 104.

TABLE 117

Modified oligonucleotides targeting SRB-1

| ISIS No. | Sequences (5' to 3') | GalNAc Cluster | ED$_{50}$ (mg/kg) | SEQ ID No |
|---|---|---|---|---|
| 440762 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | n/a | 5 | 823 |
| 708561 | GalNAc$_1$-25$_a$-$_o$,T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | GalNAc$_1$-25$_a$ | 0.4 | 823 |

See Example 93 for table legend. The structure of GalNAc$_1$-25$_a$ was shown in Example 105.

The concentrations of the oligonucleotides in Tables 116 and 117 in liver were also assessed, using procedures described in Example 75. The results shown in Tables 117a and 117b below are the average total antisense oligonucleotide tissues levels for each treatment group, as measured by UV in units of μg oligonucleotide per gram of liver tissue. The results show that the oligonucleotides comprising a GalNAc conjugate group accumulated in the liver at significantly higher levels than the same dose of the oligonucleotide lacking a GalNAc conjugate group. Furthermore, the antisense oligonucleotides comprising one, two, or three GalNAc ligands in their respective conjugate groups all accumulated in the liver at similar levels. This result is surprising in view of the Khorev et al. literature reference cited above and is consistent with the activity data shown in Tables 116 and 117 above.

TABLE 117a

Liver concentrations of oligonucleotides comprising a GalNAc$_2$ or GalNAc$_3$ conjugate group

| ISIS No. | Dosage (mg/kg) | [Antisense oligonucleotide] (μg/g) | GalNAc cluster | CM |
|---|---|---|---|---|
| 440762 | 2 | 2.1 | n/a | n/a |
| | 7 | 13.1 | | |
| | 20 | 31.1 | | |
| 686221 | 0.2 | 0.9 | GalNAc$_2$-24a | A$_d$ |
| | 0.6 | 2.7 | | |
| | 2 | 12.0 | | |
| | 6 | 26.5 | | |

TABLE 117a-continued

Liver concentrations of oligonucleotides comprising a GalNAc$_2$ or GalNAc$_3$ conjugate group

| ISIS No. | Dosage (mg/kg) | [Antisense oligonucleotide] (μg/g) | GalNAc cluster | CM |
|---|---|---|---|---|
| 686222 | 0.2 | 0.5 | GalNAc$_3$-13a | A$_d$ |
| | 0.6 | 1.6 | | |
| | 2 | 11.6 | | |
| | 6 | 19.8 | | |

TABLE 117b

Liver concentrations of oligonucleotides comprising a GalNAc$_1$ conjugate group

| ISIS No. | Dosage (mg/kg) | [Antisense oligonucleotide] (μg/g) | GalNAc cluster | CM |
|---|---|---|---|---|
| 440762 | 2 | 2.3 | n/a | n/a |
| | 7 | 8.9 | | |
| | 20 | 23.7 | | |
| 708561 | 0.2 | 0.4 | GalNAc$_1$-25$_a$ | PO |
| | 0.6 | 1.1 | | |
| | 2 | 5.9 | | |
| | 6 | 23.7 | | |
| | 20 | 53.9 | | |

Example 107: Synthesis of Oligonucleotides Comprising a GalNAc$_1$-26 or GalNAc$_1$-27 Conjugate

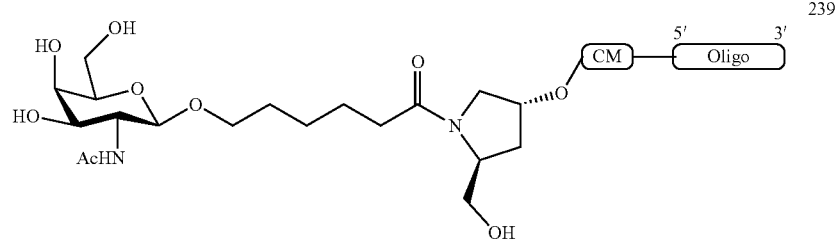

239

Oligonucleotide 239 is synthesized via coupling of compound 47 (see Example 15) to acid 64 (see Example 32) using HBTU and DIEA in DMF. The resulting amide containing compound is phosphitylated, then added to the 5'-end of an oligonucleotide using procedures described in Example 10. The GalNAc$_1$ cluster portion (GalNAc$_1$-26$_a$) of the conjugate group GalNAc$_1$-26 can be combined with any cleavable moiety present on the oligonucleotide to provide a variety of conjugate groups. The structure of GalNAc$_1$-26 (GalNAc$_1$-26$_a$-CM) is shown below:

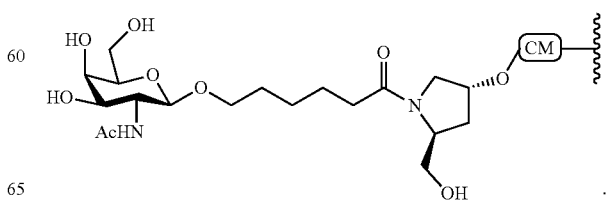

In order to add the GalNAc$_1$ conjugate group to the 3'-end of an oligonucleotide, the amide formed from the reaction of compounds 47 and 64 is added to a solid support using procedures described in Example 7. The oligonucleotide synthesis is then completed using procedures described in Example 9 in order to form oligonucleotide 240.

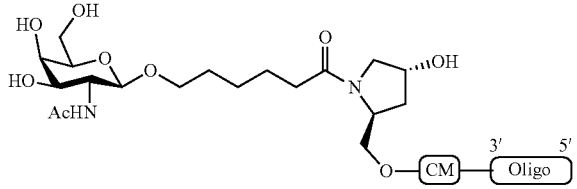

240

The GalNAc$_1$ cluster portion (GalNAc$_1$-27$_a$) of the conjugate group GalNAc$_1$-27 can be combined with any cleavable moiety present on the oligonucleotide to provide a variety of conjugate groups. The structure of GalNAc$_1$-27 (GalNAc$_1$-27$_a$-CM) is shown below:

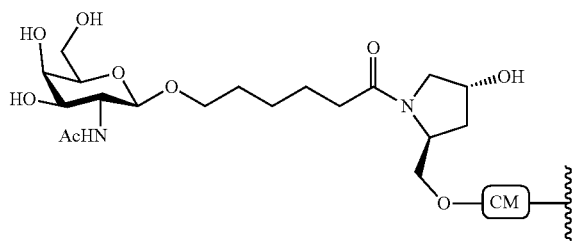

Example 108: Antisense Inhibition In Vivo by Oligonucleotides Comprising a GalNAc Conjugate Group Targeting Apo(a) In Vivo The oligonucleotides listed in Table 118 below were tested in a single dose study in mice.

The structure of GalNAc$_3$-7$_a$ was shown in Example 48.

Treatment

Male transgenic mice that express human Apo(a) were each injected subcutaneously once with an oligonucleotide and dosage listed in Table 119 or with PBS. Each treatment group consisted of 4 animals. Blood was drawn the day before dosing to determine baseline levels of Apo(a) protein in plasma and at 1 week following the first dose. Additional blood draws will occur weekly for approximately 8 weeks. Plasma Apo(a) protein levels were measured using an ELISA. The results in Table 119 are presented as the average percent of plasma Apo(a) protein levels for each treatment group, normalized to baseline levels (% BL). The results show that the antisense oligonucleotides reduced Apo(a) protein expression. Furthermore, the oligonucleotides comprising a GalNAc conjugate group exhibited even more potent reduction in Apo(a) expression than the oligonucleotide that does not comprise a conjugate group.

TABLE 119

| Apo(a) plasma protein levels | | |
|---|---|---|
| ISIS No. | Dosage (mg/kg) | Apo(a) at 1 week (% BL) |
| PBS | n/a | 143 |
| 494372 | 50 | 58 |
| 681251 | 10 | 15 |
| 681255 | 10 | 14 |
| 681256 | 10 | 17 |
| 681257 | 10 | 24 |
| 681258 | 10 | 22 |
| 681260 | 10 | 26 |

TABLE 118

Modified ASOs targeting APO(a)

| ISIS No. | Sequences (5' to 3') | GalNAc$_3$ Cluster | CM | SEQ ID No. |
|---|---|---|---|---|
| 494372 | T$_{es}$G$_{es}$$^m$C$_{es}$T$_{es}$$^m$C$_{es}$$^m$C$_{ds}$G$_{ds}$T$_{ds}$T$_{ds}$G$_{ds}$G$_{ds}$T$_{ds}$G$_{ds}$$^m$C$_{ds}$ T$_{ds}$T$_{es}$G$_{es}$T$_{es}$T$_{es}$$^m$C$_e$ | n/a | n/a | 847 |
| 681251 | GalNAc$_3$-7$_a$-$_o$,T$_{es}$G$_{es}$$^m$C$_{es}$T$_{es}$$^m$C$_{es}$$^m$C$_{ds}$G$_{ds}$T$_{ds}$T$_{ds}$G$_{ds}$G$_{ds}$ T$_{ds}$G$_{ds}$$^m$C$_{ds}$T$_{ds}$T$_{es}$G$_{es}$T$_{es}$T$_{es}$$^m$C$_e$ | GalNAc$_3$-7a | PO | 847 |
| 681255 | GalNAc$_3$-3$_a$-$_o$,T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$ T$_{ds}$G$_{ds}$$^m$C$_{ds}$T$_{ds}$T$_{eo}$G$_{eo}$T$_{es}$T$_{es}$$^m$C$_e$ | GalNAc$_3$-3a | PO | 847 |
| 681256 | GalNAc$_3$-10$_a$-$_o$,T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$ T$_{ds}$G$_{ds}$$^m$C$_{ds}$T$_{ds}$T$_{eo}$G$_{eo}$T$_{es}$T$_{es}$$^m$C$_e$ | GalNAc$_3$-10a | PO | 847 |
| 681257 | GalNAc$_3$-7$_a$-$_o$,T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$ T$_{ds}$G$_{ds}$$^m$C$_{ds}$T$_{ds}$T$_{eo}$G$_{eo}$T$_{es}$T$_{es}$$^m$C$_e$ | GalNAc$_3$-7a | PO | 847 |
| 681258 | GalNAc$_3$-13$_a$-$_o$,T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$ T$_{ds}$G$_{ds}$$^m$C$_{ds}$T$_{ds}$T$_{eo}$G$_{eo}$T$_{es}$T$_{es}$$^m$C$_e$ | GalNAc$_3$-13a | PO | 847 |
| 681260 | T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{eo}$G$_{eo}$ T$_{es}$T$_{es}$$^m$C$_{eo}$A$_{do}$,-GalNAc$_3$-19 | GalNAc$_3$-19a | A$_d$ | 854 |

Example 109: Synthesis of Oligonucleotides Comprising a GalNAc$_1$-28 or GalNAc$_1$-29 Conjugate

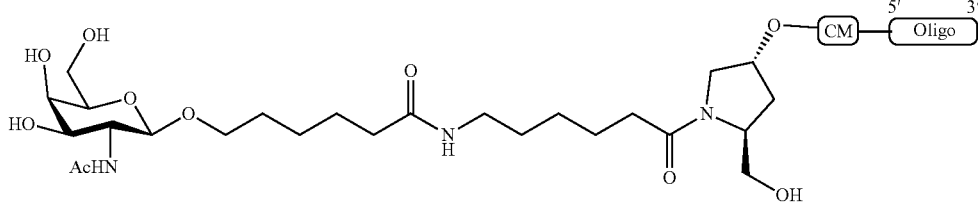

241

Oligonucleotide 241 is synthesized using procedures similar to those described in Example 71 to form the phosphoramidite intermediate, followed by procedures described in Example 10 to synthesize the oligonucleotide. The GalNAc$_1$ cluster portion (GalNAc$_1$-28$_a$) of the conjugate group GalNAc$_1$-28 can be combined with any cleavable moiety present on the oligonucleotide to provide a variety of conjugate groups. The structure of GalNAc$_1$-28 (GalNAc$_1$-28$_a$-CM) is shown below:

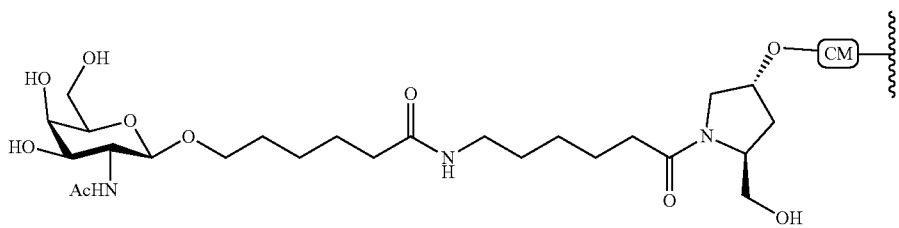

In order to a the GalNAc$_1$ conjugate group to t e 3'-end of an oligonucleotide, procedures similar to those described in Example 71 are used to form the hydroxyl intermediate, which is then added to the solid support using procedures described in Example 7. The oligonucleotide synthesis is then completed using procedures described in Example 9 in order to form oligonucleotide 242.

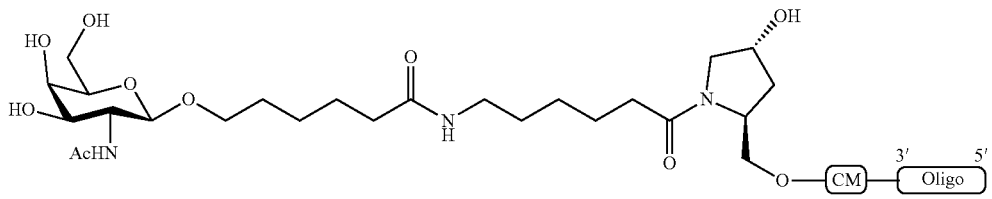

242

The GalNAc$_1$ cluster portion (GalNAc$_1$-29$_a$) of the conjugate group GalNAc$_1$-29 can be combined with any cleavable moiety present on the oligonucleotide to provide a variety of conjugate groups. The structure of GalNAc$_1$-29 (GalNAc$_1$-29$_a$-CM) is shown below:

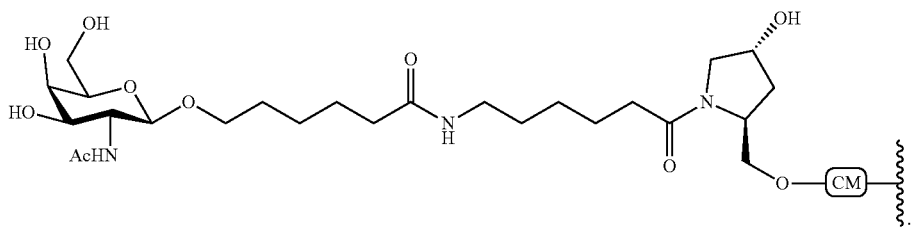

Example 110: Synthesis of Oligonucleotides Comprising a GalNAc$_1$-30 Conjugate

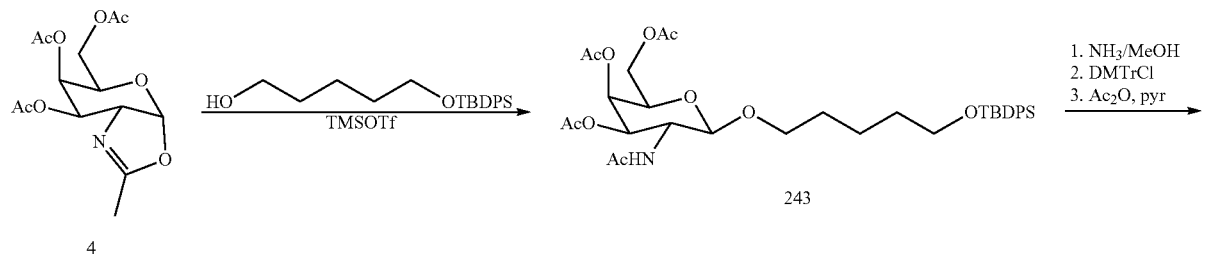

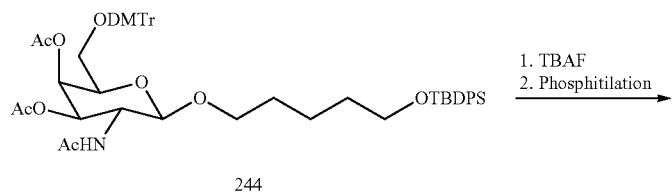

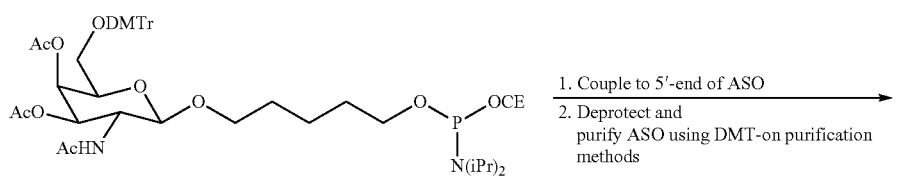

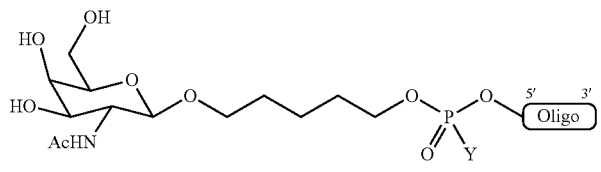

Oligonucleotide 246 comprising a GalNAc$_1$-30 conjugate group, wherein Y is selected from O, S, a substituted or unsubstituted C$_1$-C$_{10}$ alkyl, amino, substituted amino, azido, alkenyl or alkynyl, is synthesized as shown above. The GalNAc$_1$ cluster portion (GalNAc$_1$-30$_a$) of the conjugate group GalNAc$_1$-30 can be combined with any cleavable moiety to provide a variety of conjugate groups. In certain embodiments, Y is part of the cleavable moiety. In certain embodiments, Y is part of a stable moiety, and the cleavable moiety is present on the oligonucleotide. The structure of GalNAc$_1$-30$_a$ is shown below:

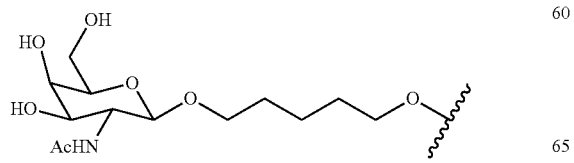

Example 111: Synthesis of Oligonucleotides Comprising a GalNAc$_2$-31 or GalNAc$_2$-32 Conjugate

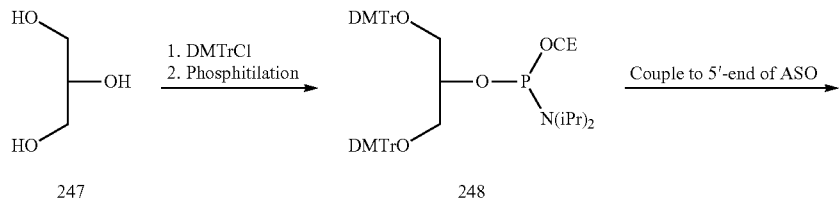

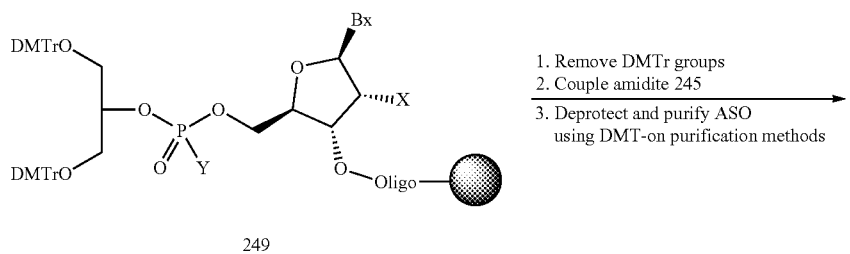

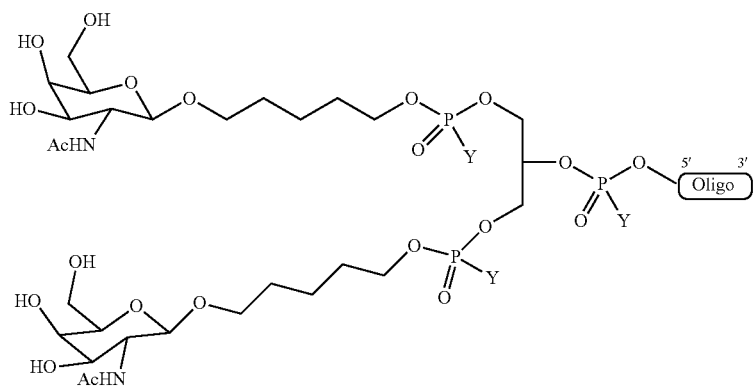

Oligonucleotide 250 comprising a GalNAc2-31 conjugate group, wherein Y is selected from O, S, a substituted or unsubstituted $C_1$-$C_{10}$ alkyl, amino, substituted amino, azido, alkenyl or alkynyl, is synthesized as shown above. The GalNAc2 cluster portion (GalNAc2-31$_a$) of the conjugate group GalNAc2-31 can be combined with any cleavable moiety to provide a variety of conjugate groups. In certain embodiments, the Y-containing group directly adjacent to the 5'-end of the oligonucleotide is part of the cleavable moiety. In certain embodiments, the Y-containing group directly adjacent to the 5'-end of the oligonucleotide is part of a stable moiety, and the cleavable moiety is present on the oligonucleotide. The structure of GalNAc2-31$_a$ is shown below:

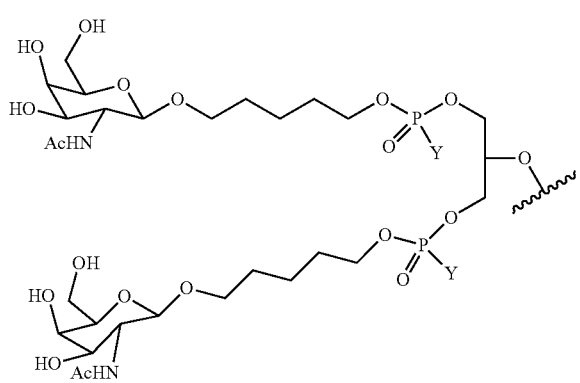

The synthesis of an oligonucleotide comprising a GalNAc2-32 conjugate is shown below.

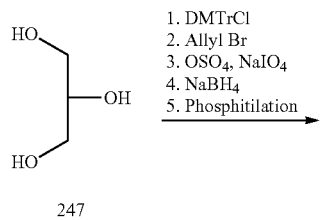
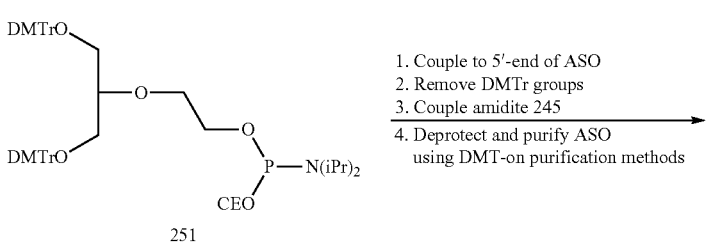

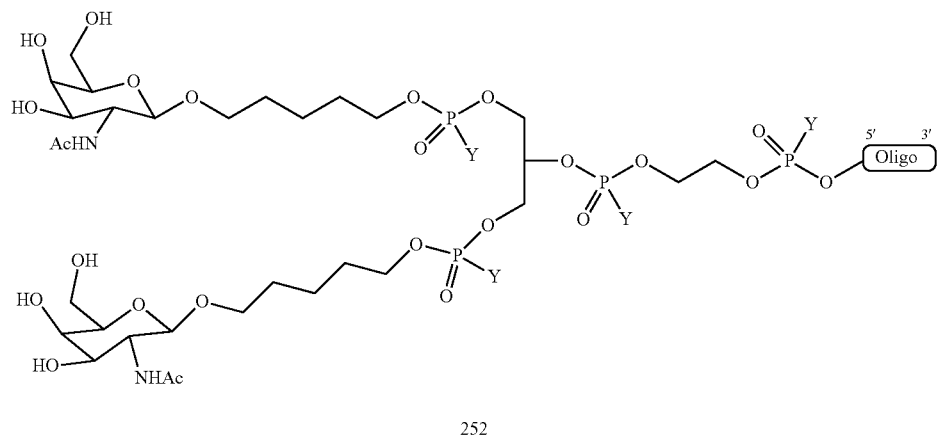

Oligonucleotide 252 comprising a GalNAc2-32 conjugate group, wherein Y is selected from O, S, a substituted or unsubstituted $C_1$-$C_{10}$ alkyl, amino, substituted amino, azido, alkenyl or alkynyl, is synthesized as shown above. The GalNAc2 cluster portion (GalNAc2-$32_a$) of the conjugate group GalNAc2-32 can be combined with any cleavable moiety to provide a variety of conjugate groups. In certain embodiments, the Y-containing group directly adjacent to the 5'-end of the oligonucleotide is part of the cleavable moiety. In certain embodiments, the Y-containing group directly adjacent to the 5'-end of the oligonucleotide is part of a stable moiety, and the cleavable moiety is present on the oligonucleotide. The structure of GalNAc2-$32_a$ is shown below:

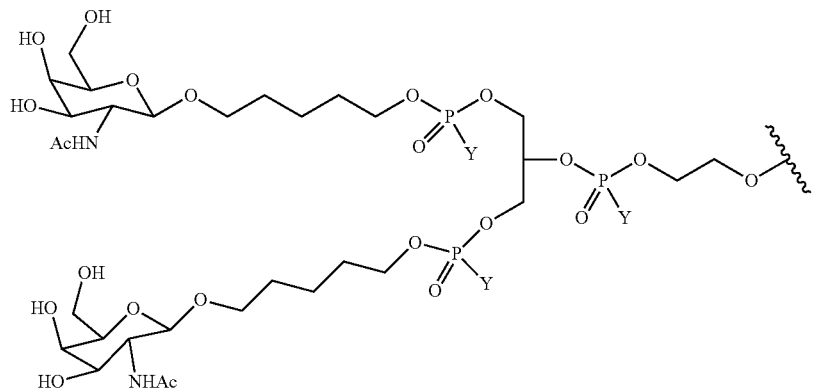

Example 112: Modified Oligonucleotides Comprising a GalNAc$_1$ Conjugate

The oligonucleotides in Table 120 targeting SRB-1 were synthesized with a GalNAc$_1$ conjugate group in order to further test the potency of oligonucleotides comprising conjugate groups that contain one GalNAc ligand.

TABLE 120

| ISIS No. | Sequences (5' to 3') | GalNAc Cluster | CM | SEQ ID No. |
|---|---|---|---|---|
| 711461 | GalNAc$_1$-25$_a$-$_o$,A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_1$-25$_a$ | A$_d$ | 831 |
| 711462 | GalNAc$_1$-25$_a$-$_o$,G$_{es}$$^m$C$_{es}$T$_{es}$T$_{es}$$^m$C$_{es}$A$_{ds}$G$_{ds}$T$_{ds}$$^m$C$_{ds}$ A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_1$-25$_a$ | PO | 829 |
| 711463 | GalNAc$_1$-25$_a$-$_o$,G$_{es}$$^m$C$_{eo}$T$_{eo}$T$_{eo}$$^m$C$_{eo}$A$_{ds}$G$_{ds}$T$_{ds}$$^m$C$_{ds}$ A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T$_e$ | GalNAc$_1$-25$_a$ | PO | 829 |
| 711465 | GalNAc$_1$-26$_a$-$_o$,A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_1$-26$_a$ | A$_d$ | 831 |
| 711466 | GalNAc$_1$-26$_a$-$_o$,G$_{es}$$^m$C$_{es}$T$_{es}$T$_{es}$$^m$C$_{es}$A$_{ds}$G$_{ds}$T$_{ds}$$^m$C$_{ds}$ A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_1$-26$_a$ | PO | 829 |
| 711467 | GalNAc$_1$-26$_a$-$_o$,G$_{es}$$^m$C$_{eo}$T$_{eo}$T$_{eo}$$^m$C$_{eo}$A$_{ds}$G$_{ds}$T$_{ds}$$^m$C$_{ds}$ A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T$_e$ | GalNAc$_1$-26$_a$ | PO | 829 |
| 711468 | GalNAc$_1$-28$_a$-$_o$,A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_1$-28$_a$ | A$_d$ | 831 |
| 711469 | GalNAc$_1$-28$_a$-$_o$,G$_{es}$$^m$C$_{es}$T$_{es}$T$_{es}$$^m$C$_{es}$A$_{ds}$G$_{ds}$T$_{ds}$$^m$C$_{ds}$ A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_1$-28$_a$ | PO | 829 |
| 711470 | GalNAc$_1$-28$_a$-$_o$,G$_{es}$$^m$C$_{eo}$T$_{eo}$T$_{eo}$$^m$C$_{eo}$A$_{ds}$G$_{ds}$T$_{ds}$$^m$C$_{ds}$ A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T$_e$ | GalNAc$_1$-28$_a$ | PO | 829 |
| 713844 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{es}$$^m$C$_{es}$$^m$C$_{es}$T$_{es}$T$_{eo}$,-GalNAc$_1$-27$_a$ | GalNAc$_1$-27$_a$ | PO | 829 |
| 713845 | G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{eo}$$^m$C$_{eo}$$^m$C$_{es}$T$_{es}$T$_{eo}$,-GalNAc$_1$-27$_a$ | GalNAc$_1$-27$_a$ | PO | 829 |
| 713846 | G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{eo}$$^m$C$_{eo}$$^m$C$_{es}$T$_{es}$T$_{eo}$A$_{do}$,-GalNAc$_1$-27$_a$ | GalNAc$_1$-27$_a$ | A$_d$ | 830 |
| 713847 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{es}$$^m$C$_{es}$$^m$C$_{es}$T$_{es}$T$_{eo}$,-GalNAc$_1$-29$_a$ | GalNAc$_1$-29$_a$ | PO | 829 |
| 713848 | G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{eo}$$^m$C$_{eo}$$^m$C$_{es}$T$_{es}$T$_{eo}$,-GalNAc$_1$-29$_a$ | GalNAc$_1$-29$_a$ | PO | 829 |
| 713849 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{es}$$^m$C$_{es}$$^m$C$_{es}$T$_{es}$T$_{eo}$A$_{do}$,-GalNAc$_1$-29$_a$ | GalNAc$_1$-29$_a$ | A$_d$ | 830 |
| 713850 | G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{eo}$$^m$C$_{eo}$$^m$C$_{es}$T$_{es}$T$_{eo}$A$_{do}$,-GalNAc$_1$-29$_a$ | GalNAc$_1$-29$_a$ | A$_d$ | 830 |

Example 113: Antisense Inhibition In Vivo by Oligonucleotides Targeting CFB

The oligonucleotides listed in Table 121 were tested in a dose-dependent study for antisense inhibition of human Complement Factor B (CFB) in mice.

TABLE 121

Modified ASOs targeting CFB

| ISIS No. | Sequences (5' to 3') | GalNAc$_3$ Cluster | CM | SEQ ID No. |
|---|---|---|---|---|
| 588540 | A$_{es}$T$_{es}$$^m$C$_{es}$$^m$C$_{es}$$^m$C$_{es}$A$_{ds}$$^m$C$_{ds}$G$_{ds}$$^m$C$_{ds}$$^m$C$_{ds}$$^m$C$_{ds}$ $^m$C$_{ds}$T$_{ds}$G$_{ds}$T$_{ds}$$^m$C$_{es}$$^m$C$_{es}$A$_{es}$G$_{es}$$^m$Ce | n/a | n/a | 440 |

TABLE 121-continued

Modified ASOs targeting CFB

| ISIS No. | Sequences (5' to 3') | GalNAc$_3$ Cluster | CM | SEQ ID No. |
|---|---|---|---|---|
| 687301 | GalNAc$_3$-3$_a$-$_o$,A$_{es}$T$_{es}$$^m$C$_{es}$$^m$C$_{es}$$^m$C$_{es}$A$_{ds}$$^m$C$_{ds}$G$_{ds}$ $^m$C$_{ds}$$^m$C$_{ds}$$^m$C$_{ds}$$^m$C$_{ds}$T$_{ds}$G$_{ds}$T$_{ds}$$^m$C$_{es}$$^m$C$_{es}$A$_{es}$G$_{es}$$^m$C$_e$ | GalNAc$_3$-3a | PO | 440 |

The structure of GalNAc$_3$-3$_a$ was shown previously in Example 39.

Treatment

Transgenic mice that express human CFB (Jackson Laboratory, Bar Harbor, Me.) were injected subcutaneously once per week for 3 weeks (a total of 4 doses) with an oligonucleotide listed in Table 122 or with saline. The four treatment groups that received ISIS No. 588540 were given 6, 12, 25, or 50 mg/kg per dose. The four treatment groups that received ISIS No. 687301 were given 0.25, 0.5, 2, or 6 mg/kg per dose. Each treatment group consisted of 4 animals. The mice were sacrificed 2 days following the final administration to determine the liver and kidney human CFB and cyclophilin mRNA levels using real-time PCR according to standard protocols. The CFB mRNA levels were normalized to the cyclophilin levels, and the averages for each treatment group were used to determine the dose that achieved 50% inhibition of the human CFB transcript expression (ED$_{50}$). The results are the averages of four experiments completed with two different primer probe sets and are shown in Table 122.

TABLE 122

Potencies of oligonucleotides targeting human CFB in vivo

| ISIS No. | ED$_{50}$ in liver (mg/kg) | ED$_{50}$ in kidney (mg/kg) | GalNAc$_3$ Cluster | CM |
|---|---|---|---|---|
| 588540 | 7.9 | 11.7 | n/a | n/a |
| 687301 | 0.49 | 0.35 | GalNAc$_3$-3a | PO |

Liver transaminase levels, alanine aminotransferase (ALT) and aspartate aminotransferase (AST), in serum were measured relative to saline injected mice using standard protocols. Total bilirubin, BUN, and body weights were also evaluated. The results show that there were no significant changes in any of the treatment groups relative to the saline treated group (data not shown), indicating that both oligonucleotides were very well tolerated.

Example 114: Antisense Inhibition In Vivo by Oligonucleotides Targeting CFB

The oligonucleotides listed in Table 123 were tested in a dose-dependent study for antisense inhibition of human CFB in mice.

Treatment

Transgenic mice that express human CFB (Jackson Laboratory, Bar Harbor, Me.) were injected subcutaneously once with 0.6, 1, 6, or 18 mg/kg of an oligonucleotide listed in Table 123 or with saline. Each treatment group consisted of 4 or 5 animals. The mice were sacrificed 72 hours following the dose to determine the liver human CFB and cyclophilin mRNA levels using real-time PCR according to standard protocols. The CFB mRNA levels were normalized to the cyclophilin levels, and the averages for each treatment group were used to determine the dose that achieved 50% inhibition of the human CFB transcript expression (ED$_{50}$). The results are shown in Table 123.

TABLE 123

Modified ASOs targeting CFB

| ISIS No. | Sequences (5' to 3') | GalNAc$_3$ Cluster | CM | ED$_{50}$ in liver (mg/kg) | SEQ ID No. |
|---|---|---|---|---|---|
| 696844 | GalNAc$_3$-7$_a$-$_o$,A$_{es}$T$_{es}$$^m$C$_{es}$$^m$C$_{es}$$^m$C$_{es}$A$_{ds}$$^m$C$_{ds}$G$_{ds}$ $^m$C$_{ds}$$^m$C$_{ds}$$^m$C$_{ds}$$^m$C$_{ds}$T$_{ds}$G$_{ds}$T$_{ds}$$^m$C$_{es}$$^m$C$_{es}$A$_{es}$G$_{es}$$^m$C$_e$ | GalNAc$_3$-7a | PO | 0.86 | 440 |
| 696845 | GalNAc$_3$-7$_a$-$_o$,A$_{es}$T$_{eo}$$^m$C$_{eo}$$^m$C$_{eo}$$^m$C$_{eo}$A$_{ds}$$^m$C$_{ds}$G$_{ds}$ $^m$C$_{ds}$$^m$C$_{ds}$$^m$C$_{ds}$$^m$C$_{ds}$T$_{ds}$G$_{ds}$T$_{ds}$$^m$C$_{eo}$$^m$C$_{eo}$A$_{e}$G$_{es}$$^m$C$_e$ | GalNAc$_3$-7a | PO | 0.71 | 440 |
| 698969 | GalNAc$_3$-7$_a$-$_o$,A$_{es}$T$_{eo}$$^m$C$_{eo}$$^m$C$_{eo}$$^m$C$_{es}$A$_{ds}$$^m$C$_{ds}$G$_{ds}$ $^m$C$_{ds}$$^m$C$_{ds}$$^m$C$_{ds}$$^m$C$_{ds}$T$_{ds}$G$_{ds}$T$_{ds}$$^m$C$_{eo}$$^m$C$_{eo}$A$_{es}$G$_{es}$$^m$C$_e$ | GalNAc$_3$-7a | PO | 0.51 | 440 |
| 698970 | GalNAc$_3$-7$_a$-$_o$,A$_{es}$T$_{es}$$^m$C$_{eo}$$^m$C$_{eo}$$^m$C$_{eo}$A$_{ds}$$^m$C$_{ds}$G$_{ds}$ $^m$C$_{ds}$$^m$C$_{ds}$$^m$C$_{ds}$$^m$C$_{ds}$T$_{ds}$G$_{ds}$T$_{ds}$$^m$C$_{eo}$$^m$C$_{eo}$A$_{es}$G$_{es}$$^m$C$_e$ | GalNAc$_3$-7a | PO | 0.55 | 440 |

The structure of GalNAc$_3$-7$_a$ was shown previously in Example 48.

Example 115: Antisense Inhibition of Human Complement Factor B (CFB) in HepG2 Cells by MOE Gapmers Antisense oligonucleotides were designed targeting human Complement Factor B (CFB) nucleic acid and were tested for their effects on CFB mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 4,500 nM antisense oligonucleotide. After a treatment period of approximately 24 hours, RNA was isolated from the cells and CFB mRNA levels were measured by quantitative real-time PCR. Human primer probe set RTS3459 (forward sequence AGTCTCTGTGGCATGGTTTGG, designated herein as SEQ ID NO: 810; reverse sequence GGGCGAATGACTGAGATCTTG, designated herein as SEQ ID NO: 811; probe sequence TACCGATTACCACAAGCAACCATGGCA, designated herein as SEQ ID NO: 812) was used to measure mRNA levels. CFB mRNA levels were adjusted according to total RNA content, as measured by RIBOGREEN®. Results are presented as percent inhibition of CFB, relative to untreated control cells.

The newly designed chimeric antisense oligonucleotides in the Tables below were designed as 5-10-5 MOE gapmers. The 5-10-5 MOE gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human CFB mRNA, designated herein as SEQ ID NO: 1 (GENBANK Accession No. NM_001710.5) or the human CFB genomic sequence, designated herein as SEQ ID NO: 2 (GENBANK Accession No. NT_007592.15 truncated from nucleotides 31852000 to 31861000), or both. 'n/a' indicates that the antisense oligonucleotide does not target that particular gene sequence with 100% complementarity.

TABLE 124

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532608 | 20 | 39 | Exon 1 | GCTGAGCTGCCAGTCAAGGA | 36 | 1741 | 1760 | 6 |
| 532609 | 26 | 45 | Exon 1 | GGCCCCGCTGAGCTGCCAGT | 16 | 1747 | 1766 | 7 |
| 532610 | 45 | 64 | Exon 1 | CGGAACATCCAAGCGGGAGG | 11 | 1766 | 1785 | 8 |
| 532611 | 51 | 70 | Exon 1 | CTTTCCCGGAACATCCAAGC | 26 | 1772 | 1791 | 9 |
| 532612 | 100 | 119 | Exon 1 | ATCTGTGTTCTGGCACCTGC | 25 | 1821 | 1840 | 10 |
| 532613 | 148 | 167 | Exon 1 | GTCACATTCCCTTCCCCTGC | 39 | 1869 | 1888 | 11 |
| 532614 | 154 | 173 | Exon 1 | GACCTGGTCACATTCCCTTC | 71 | 1875 | 1894 | 12 |
| 532615 | 160 | 179 | Exon 1 | GACCTAGACCTGGTCACATT | 35 | 1881 | 1900 | 13 |
| 532616 | 166 | 185 | Exon 1 | ACTCCAGACCTAGACCTGGT | 39 | 1887 | 1906 | 14 |
| 532617 | 172 | 191 | Exon 1 | GCTGAAACTCCAGACCTAGA | 27 | 1893 | 1912 | 15 |
| 532618 | 178 | 197 | Exon 1 | GTCCAAGCTGAAACTCCAGA | 29 | 1899 | 1918 | 16 |
| 532619 | 184 | 203 | Exon 1 | CTCAGTGTCCAAGCTGAAAC | 21 | 1905 | 1924 | 17 |
| 532620 | 246 | 265 | Exon 1 | AGGAGAGAAGCTGGGCCTGG | 31 | 1967 | 1986 | 18 |
| 532621 | 252 | 271 | Exon 1 | GAAGGCAGGAGAGAAGCTGG | 25 | 1973 | 1992 | 19 |
| 532622 | 336 | 355 | Exon 1-2 Junction | GTGGTGGTCACACCTCCAGA | 28 | n/a | n/a | 20 |
| 532623 | 381 | 400 | Exon 2 | CCCTCCAGAGAGCAGGATCC | 22 | 2189 | 2208 | 21 |
| 532624 | 387 | 406 | Exon 2 | TCTACCCCTCCAGAGAGCA | 37 | 2195 | 2214 | 22 |
| 532625 | 393 | 412 | Exon 2 | TTGATCTCTACCCCTCCAG | 30 | 2201 | 2220 | 23 |
| 532626 | 417 | 436 | Exon 2 | TGGAGAAGTCGGAAGGAGCC | 35 | 2225 | 2244 | 24 |
| 532627 | 423 | 442 | Exon 2 | CCCTCTTGGAGAAGTCGGAA | 37 | 2231 | 2250 | 25 |
| 532628 | 429 | 448 | Exon 2 | GCCTGGCCCTCTTGGAGAAG | 0 | 2237 | 2256 | 26 |
| 532629 | 435 | 454 | Exon 2 | TCCAGTGCCTGGCCCTCTTG | 26 | 2243 | 2262 | 27 |
| 532630 | 458 | 477 | Exon 2 | AGAAGCCAGAAGGACACACG | 30 | 2266 | 2285 | 28 |
| 532631 | 464 | 483 | Exon 2 | ACGGGTAGAAGCCAGAAGGA | 43 | 2272 | 2291 | 29 |
| 532632 | 480 | 499 | Exon 2 | CGTGTCTGCACAGGGTACGG | 57 | 2288 | 2307 | 30 |

TABLE 124-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532633 | 513 | 532 | Exon 2 | AGGGTGCTCCAGGACCCCGT | 27 | 2321 | 2340 | 31 |
| 532634 | 560 | 579 | Exon 2-3 Junction | TTGCTCTGCACTCTGCCTTC | 41 | n/a | n/a | 32 |
| 532635 | 600 | 619 | Exon 3 | TATTCCCCGTTCTCGAAGTC | 67 | 2808 | 2827 | 33 |
| 532636 | 626 | 645 | Exon 3 | CATTGTAGTAGGGAGACCGG | 24 | 2834 | 2853 | 34 |
| 532637 | 632 | 651 | Exon 3 | CACTCACATTGTAGTAGGGA | 49 | 2840 | 2859 | 35 |
| 532638 | 638 | 657 | Exon 3 | TCTCATCACTCACATTGTAG | 50 | 2846 | 2865 | 36 |
| 532639 | 644 | 663 | Exon 3 | AAGAGATCTCATCACTCACA | 52 | 2852 | 2871 | 37 |
| 532640 | 650 | 669 | Exon 3 | AGTGGAAAGAGATCTCATCA | 34 | 2858 | 2877 | 38 |
| 532641 | 656 | 675 | Exon 3 | CATAGCAGTGGAAAGAGATC | 32 | 2864 | 2883 | 39 |
| 532642 | 662 | 681 | Exon 3 | AACCGTCATAGCAGTGGAAA | 45 | 2870 | 2889 | 40 |
| 532643 | 668 | 687 | Exon 3 | GAGTGTAACCGTCATAGCAG | 36 | 2876 | 2895 | 41 |
| 532644 | 674 | 693 | Exon 3 | CCCGGAGAGTGTAACCGTCA | 30 | 2882 | 2901 | 42 |
| 532645 | 680 | 699 | Exon 3 | CAGAGCCCCGGAGAGTGTAA | 27 | 2888 | 2907 | 43 |
| 532646 | 686 | 705 | Exon 3 | GATTGGCAGAGCCCCGGAGA | 20 | 2894 | 2913 | 44 |
| 532647 | 692 | 711 | Exon 3 | AGGTGCGATTGGCAGAGCCC | 28 | 2900 | 2919 | 45 |
| 532648 | 698 | 717 | Exon 3 | CTTGGCAGGTGCGATTGGCA | 24 | 2906 | 2925 | 46 |
| 532649 | 704 | 723 | Exon 3 | CATTCACTTGGCAGGTGCGA | 28 | 2912 | 2931 | 47 |
| 532650 | 729 | 748 | Exon 3 | ATCGCTGTCTGCCCACTCCA | 44 | 2937 | 2956 | 48 |
| 532651 | 735 | 754 | Exon 3 | TCACAGATCGCTGTCTGCCC | 44 | 2943 | 2962 | 49 |
| 532652 | 741 | 760 | Exon 3 | CCGTTGTCACAGATCGCTGT | 27 | 2949 | 2968 | 50 |
| 532653 | 747 | 766 | Exon 3-4 Junction | CCCGCTCCGTTGTCACAGAT | 28 | n/a | n/a | 51 |
| 532654 | 753 | 772 | Exon 3-4 Junction | CAGTACCCCGCTCCGTTGTC | 13 | n/a | n/a | 52 |
| 532655 | 759 | 778 | Exon 3-4 Junction | TTGGAGCAGTACCCCGCTCC | 8 | n/a | n/a | 53 |
| 532656 | 789 | 808 | Exon 4 | ACCTTCCTTGTGCCAATGGG | 40 | 3152 | 3171 | 54 |
| 532657 | 795 | 814 | Exon 4 | CTGCCCACCTTCCTTGTGCC | 41 | 3158 | 3177 | 55 |
| 532658 | 818 | 837 | Exon 4 | CGCTGTCTTCAAGGCGGTAC | 33 | 3181 | 3200 | 56 |
| 532659 | 835 | 854 | Exon 4 | GCTGCAGTGGTAGGTGACGC | 32 | 3198 | 3217 | 57 |
| 532660 | 841 | 860 | Exon 4 | CCCCCGGCTGCAGTGGTAGG | 17 | 3204 | 3223 | 58 |
| 532661 | 847 | 866 | Exon 4 | GGTAAGCCCCGGCTGCAGT | 28 | 3210 | 3229 | 59 |
| 532662 | 853 | 872 | Exon 4 | ACGCAGGGTAAGCCCCGGC | 13 | 3216 | 3235 | 60 |
| 532663 | 859 | 878 | Exon 4 | GGAGCCACGCAGGGTAAGCC | 33 | 3222 | 3241 | 61 |
| 532664 | 866 | 885 | Exon 4 | GCCGCTGGGAGCCACGCAGG | 10 | 3229 | 3248 | 62 |
| 532665 | 891 | 910 | Exon 4 | CAAGAGCCACCTTCCTGACA | 17 | 3254 | 3273 | 63 |
| 532666 | 897 | 916 | Exon 4 | CCGCTCCAAGAGCCACCTTC | 25 | 3260 | 3279 | 64 |
| 532667 | 903 | 922 | Exon 4 | TCCGTCCCGCTCCAAGAGCC | 29 | 3266 | 3285 | 65 |

TABLE 124-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532668 | 909 | 928 | Exon 4 | GAAGGCTCCGTCCCGCTCCA | 14 | 3272 | 3291 | 66 |
| 532669 | 915 | 934 | Exon 4 | TGGCAGGAAGGCTCCGTCCC | 18 | 3278 | 3297 | 67 |
| 532670 | 921 | 940 | Exon 4-5 Junction | GAGTCTTGGCAGGAAGGCTC | 20 | n/a | n/a | 68 |
| 532671 | 927 | 946 | Exon 4-5 Junction | ATGAAGGAGTCTTGGCAGGA | 14 | n/a | n/a | 69 |
| 532672 | 956 | 975 | Exon 5 | CTTCGGCCACCTCTTGAGGG | 45 | 3539 | 3558 | 70 |
| 532673 | 962 | 981 | Exon 5 | GGAAAGCTTCGGCCACCTCT | 37 | 3545 | 3564 | 71 |
| 532674 | 968 | 987 | Exon 5 | AAGACAGGAAAGCTTCGGCC | 28 | 3551 | 3570 | 72 |
| 532675 | 974 | 993 | Exon 5 | TCAGGGAAGACAGGAAAGCT | 16 | 3557 | 3576 | 73 |
| 532676 | 996 | 1015 | Exon 5 | TCGACTCCTTCTATGGTCTC | 31 | 3579 | 3598 | 74 |
| 532677 | 1033 | 1052 | Exon 5-6 Junction | CTTCTGTTGTTCCCCTGGGC | 36 | n/a | n/a | 75 |
| 532678 | 1068 | 1087 | Exon 6 | TTCATGGAGCCTGAAGGGTC | 19 | 3752 | 3771 | 76 |
| 532679 | 1074 | 1093 | Exon 6 | TAGATGTTCATGGAGCCTGA | 24 | 3758 | 3777 | 77 |
| 532680 | 1080 | 1099 | Exon 6 | ACCAGGTAGATGTTCATGGA | 13 | 3764 | 3783 | 78 |
| 532681 | 1086 | 1105 | Exon 6 | TCTAGCACCAGGTAGATGTT | 20 | 3770 | 3789 | 79 |
| 532682 | 1092 | 1111 | Exon 6 | GATCCATCTAGCACCAGGTA | 33 | 3776 | 3795 | 80 |
| 532683 | 1098 | 1117 | Exon 6 | CTGTCTGATCCATCTAGCAC | 44 | 3782 | 3801 | 81 |
| 532684 | 1104 | 1123 | Exon 6 | CCAATGCTGTCTGATCCATC | 29 | 3788 | 3807 | 82 |
| 532685 | 1129 | 1148 | Exon 6 | TTTGGCTCCTGTGAAGTTGC | 40 | 3813 | 3832 | 83 |

TABLE 125

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532686 | 1135 | 1154 | Exon 6 | ACACTTTTTGGCTCCTGTGA | 91 | 3819 | 3838 | 84 |
| 532687 | 1141 | 1160 | Exon 6 | GACTAGACACTTTTTGGCTC | 77 | 3825 | 3844 | 85 |
| 532688 | 1147 | 1166 | Exon 6 | TAAGTTGACTAGACACTTTT | 70 | 3831 | 3850 | 86 |
| 532689 | 1153 | 1172 | Exon 6 | CTCAATTAAGTTGACTAGAC | 61 | 3837 | 3856 | 87 |
| 532690 | 1159 | 1178 | Exon 6-7 Junction | CACCTTCTCAATTAAGTTGA | 57 | 3843 | 3862 | 88 |
| 532691 | 1165 | 1184 | Exon 6-7 Junction | ACTTGCCACCTTCTCAATTA | 56 | n/a | n/a | 89 |
| 532692 | 1171 | 1190 | Exon 6-7 Junction | ACCATAACTTGCCACCTTCT | 56 | n/a | n/a | 90 |
| 532693 | 1177 | 1196 | Exon 7 | CTTCACACCATAACTTGCCA | 56 | 4153 | 4172 | 91 |
| 532694 | 1183 | 1202 | Exon 7 | TCTTGGCTTCACACCATAAC | 55 | 4159 | 4178 | 92 |

TABLE 125-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532695 | 1208 | 1227 | Exon 7 | ATGTGGCATATGTCACTAGA | 55 | 4184 | 4203 | 93 |
| 532696 | 1235 | 1254 | Exon 7 | CAGACACTTTGACCCAAATT | 55 | 4211 | 4230 | 94 |
| 532697 | 1298 | 1317 | Exon 7-8 Junction | GGTCTTCATAATTGATTTCA | 53 | n/a | n/a | 95 |
| 532698 | 1304 | 1323 | Exon 7-8 Junction | ACTTGTGGTCTTCATAATTG | 53 | n/a | n/a | 96 |
| 532699 | 1310 | 1329 | Exon 7-8 Junction | ACTTCAACTTGTGGTCTTCA | 52 | n/a | n/a | 97 |
| 532700 | 1316 | 1335 | Exon 8 | TCCCTGACTTCAACTTGTGG | 52 | 4609 | 4628 | 98 |
| 532701 | 1322 | 1341 | Exon 8 | TGTTAGTCCCTGACTTCAAC | 52 | 4615 | 4634 | 99 |
| 532702 | 1328 | 1347 | Exon 8 | TCTTGGTGTTAGTCCCTGAC | 51 | 4621 | 4640 | 100 |
| 532703 | 1349 | 1368 | Exon 8 | TGTACACTGCCTGGAGGGCC | 51 | 4642 | 4661 | 101 |
| 532704 | 1355 | 1374 | Exon 8 | TCATGCTGTACACTGCCTGG | 51 | 4648 | 4667 | 102 |
| 532705 | 1393 | 1412 | Exon 8 | GTTCCAGCCTTCAGGAGGGA | 50 | 4686 | 4705 | 103 |
| 532706 | 1399 | 1418 | Exon 8 | GGTGCGGTTCCAGCCTTCAG | 50 | 4692 | 4711 | 104 |
| 532707 | 1405 | 1424 | Exon 8 | ATGGCGGGTGCGGTTCCAGC | 50 | 4698 | 4717 | 105 |
| 532708 | 1411 | 1430 | Exon 8 | GATGACATGGCGGGTGCGGT | 49 | 4704 | 4723 | 106 |
| 532709 | 1417 | 1436 | Exon 8 | GAGGATGATGACATGGCGGG | 49 | 4710 | 4729 | 107 |
| 532710 | 1443 | 1462 | Exon 8-9 Junction | CCCATGTTGTGCAATCCATC | 48 | n/a | n/a | 108 |
| 532711 | 1449 | 1468 | Exon 9 | TCCCCGCCCATGTTGTGCAA | 48 | 5023 | 5042 | 109 |
| 532712 | 1455 | 1474 | Exon 9 | ATTGGGTCCCCGCCCATGTT | 48 | 5029 | 5048 | 110 |
| 532713 | 1461 | 1480 | Exon 9 | ACAGTAATTGGGTCCCCGCC | 48 | 5035 | 5054 | 111 |
| 532714 | 1467 | 1486 | Exon 9 | TCAATGACAGTAATTGGGTC | 47 | 5041 | 5060 | 112 |
| 532715 | 1473 | 1492 | Exon 9 | ATCTCATCAATGACAGTAAT | 47 | 5047 | 5066 | 113 |
| 532716 | 1479 | 1498 | Exon 9 | TCCCGGATCTCATCAATGAC | 46 | 5053 | 5072 | 114 |
| 532717 | 1533 | 1552 | Exon 9-10 Junction | ACATCCAGATAATCCTCCCT | 46 | n/a | n/a | 115 |
| 532718 | 1539 | 1558 | Exon 9-10 Junction | ACATAGACATCCAGATAATC | 46 | n/a | n/a | 116 |
| 532719 | 1545 | 1564 | Exon 9-10 Junction | CCAAACACATAGACATCCAG | 46 | n/a | n/a | 117 |
| 532720 | 1582 | 1601 | Exon 10 | AGCATTGATGTTCACTTGGT | 46 | 5231 | 5250 | 118 |
| 532721 | 1588 | 1607 | Exon 10 | AGCCAAAGCATTGATGTTCA | 45 | 5237 | 5256 | 119 |
| 532722 | 1594 | 1613 | Exon 10 | CTTGGAAGCCAAAGCATTGA | 45 | 5243 | 5262 | 120 |
| 532723 | 1600 | 1619 | Exon 10 | GTCTTTCTTGGAAGCCAAAG | 45 | 5249 | 5268 | 121 |
| 532724 | 1606 | 1625 | Exon 10 | CTCATTGTCTTTCTTGGAAG | 44 | 5255 | 5274 | 122 |
| 532725 | 1612 | 1631 | Exon 10 | ATGTTGCTCATTGTCTTTCT | 44 | 5261 | 5280 | 123 |
| 532726 | 1618 | 1637 | Exon 10 | GAACACATGTTGCTCATTGT | 44 | 5267 | 5286 | 124 |
| 532727 | 1624 | 1643 | Exon 10 | GACTTTGAACACATGTTGCT | 43 | 5273 | 5292 | 125 |

TABLE 125-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhi- bition | SEQ ID NO: 2 start site | SEQ ID NO: 2 stop site | SEQ ID NO: |
|---|---|---|---|---|---|---|---|---|
| 532728 | 1630 | 1649 | Exon 10 | ATCCTTGACTTTGAACACAT | 43 | 5279 | 5298 | 126 |
| 532729 | 1636 | 1655 | Exon 10 | TTCCATATCCTTGACTTTGA | 43 | 5285 | 5304 | 127 |
| 532730 | 1642 | 1661 | Exon 10 | CAGGTTTTCCATATCCTTGA | 42 | 5291 | 5310 | 128 |
| 532731 | 1686 | 1705 | Exon 11 | CTCAGAGACTGGCTTTCATC | 42 | 5827 | 5846 | 129 |
| 532732 | 1692 | 1711 | Exon 11 | CAGAGACTCAGAGACTGGCT | 42 | 5833 | 5852 | 130 |
| 516252 | 1698 | 1717 | Exon 11 | ATGCCACAGAGACTCAGAGA | 42 | 5839 | 5858 | 131 |
| 532733 | 1704 | 1723 | Exon 11 | CAAACCATGCCACAGAGACT | 41 | 5845 | 5864 | 132 |
| 532734 | 1710 | 1729 | Exon 11 | TGTTCCCAAACCATGCCACA | 41 | 5851 | 5870 | 133 |
| 532735 | 1734 | 1753 | Exon 11 | TTGTGGTAATCGGTACCCTT | 41 | 5875 | 5894 | 134 |
| 532736 | 1740 | 1759 | Exon 11 | GGTTGCTTGTGGTAATCGGT | 40 | 5881 | 5900 | 135 |
| 532737 | 1746 | 1765 | Exon 11 | TGCCATGGTTGCTTGTGGTA | 40 | 5887 | 5906 | 136 |
| 532738 | 1752 | 1771 | Exon 11 | TTGGCCTGCCATGGTTGCTT | 40 | 5893 | 5912 | 137 |
| 532739 | 1758 | 1777 | Exon 11 | GAGATCTTGGCCTGCCATGG | 38 | 5899 | 5918 | 138 |
| 532740 | 1803 | 1822 | Exon 12 | ACAGCCCCCATACAGCTCTC | 38 | 6082 | 6101 | 139 |
| 532741 | 1809 | 1828 | Exon 12 | GACACCACAGCCCCCATACA | 38 | 6088 | 6107 | 140 |
| 532742 | 1815 | 1834 | Exon 12 | TACTCAGACACCACAGCCCC | 38 | 6094 | 6113 | 141 |
| 532743 | 1821 | 1840 | Exon 12 | ACAAAGTACTCAGACACCAC | 37 | 6100 | 6119 | 142 |
| 532744 | 1827 | 1846 | Exon 12 | GTCAGCACAAAGTACTCAGA | 37 | 6106 | 6125 | 143 |
| 532745 | 1872 | 1891 | Exon 12 | TTGATTGAGTGTTCCTTGTC | 36 | 6151 | 6170 | 144 |
| 532746 | 1878 | 1897 | Exon 12 | CTGACCTTGATTGAGTGTTC | 35 | 6157 | 6176 | 145 |
| 532747 | 1909 | 1928 | Exon 13 | TATCTCCAGGTCCCGCTTCT | 35 | 6403 | 6422 | 146 |
| 532748 | 1967 | 1986 | Exon 13 | GAATTCCTGCTTCTTTTTTC | 32 | 6461 | 6480 | 147 |
| 532749 | 1973 | 1992 | Exon 13 | ATTCAGGAATTCCTGCTTCT | 32 | 6467 | 6486 | 148 |
| 532750 | 1979 | 1998 | Exon 13 | CATAAAATTCAGGAATTCCT | 32 | 6473 | 6492 | 149 |
| 532751 | 1985 | 2004 | Exon 13 | CATAGTCATAAAATTCAGGA | 31 | 6479 | 6498 | 150 |
| 532752 | 2006 | 2025 | Exon 13 | TGAGCTTGATCAGGGCAACG | 30 | 6500 | 6519 | 151 |
| 532753 | 2012 | 2031 | Exon 13 | TATTCTTGAGCTTGATCAGG | 30 | 6506 | 6525 | 152 |
| 532754 | 2048 | 2067 | Exon 13-14 Junction | GACAAATGGGCCTGATAGTC | 30 | n/a | n/a | 153 |
| 532755 | 2070 | 2089 | Exon 14 | GTTGTTCCCTCGGTGCAGGG | 29 | 6659 | 6678 | 154 |
| 532756 | 2076 | 2095 | Exon 14 | GCTCGAGTTGTTCCCTCGGT | 28 | 6665 | 6684 | 155 |
| 532757 | 2082 | 2101 | Exon 14 | CTCAAAGCTCGAGTTGTTCC | 28 | 6671 | 6690 | 156 |
| 532758 | 2088 | 2107 | Exon 14 | GGAAGCCTCAAAGCTCGAGT | 25 | 6677 | 6696 | 157 |
| 532759 | 2094 | 2113 | Exon 14 | GTTGGAGGAAGCCTCAAAGC | 23 | 6683 | 6702 | 158 |
| 532760 | 2100 | 2119 | Exon 14 | GTGGTAGTTGGAGGAAGCCT | 23 | 6689 | 6708 | 159 |
| 532761 | 2106 | 2125 | Exon 14 | TGGCAAGTGGTAGTTGGAGG | 18 | 6695 | 6714 | 160 |
| 532762 | 2112 | 2131 | Exon 14 | TGTTGCTGGCAAGTGGTAGT | 14 | 6701 | 6720 | 161 |

TABLE 126

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532812 | n/a | n/a | Exon 1 | TCCAGCTCACTCCCCTGTTG | 19 | 1593 | 1612 | 162 |
| 532813 | n/a | n/a | Exon 1 | TAAGGATCCAGCTCACTCCC | 40 | 1599 | 1618 | 163 |
| 532814 | n/a | n/a | Exon 1 | CAGAAATAAGGATCCAGCTC | 39 | 1605 | 1624 | 164 |
| 532815 | n/a | n/a | Exon 1 | AGGGACCAGAAATAAGGATC | 0 | 1611 | 1630 | 165 |
| 532816 | n/a | n/a | Exon 1 | CCACTTAGGGACCAGAAATA | 27 | 1617 | 1636 | 166 |
| 532817 | n/a | n/a | Exon 1 | TCCAGGACTCTCCCCTTCAG | 39 | 1682 | 1701 | 167 |
| 532818 | n/a | n/a | Exon 1 | AAGTCCCACCCTTTGCTGCC | 15 | 1707 | 1726 | 168 |
| 532819 | n/a | n/a | Exon 1 | CTGCAGAAGTCCCACCCTTT | 26 | 1713 | 1732 | 169 |
| 532820 | n/a | n/a | Exon 1 | CAGAAACTGCAGAAGTCCCA | 8 | 1719 | 1738 | 170 |
| 532821 | n/a | n/a | Exon 2-Intron 2 | AACCTCTGCACTCTGCCTTC | 39 | 2368 | 2387 | 171 |
| 532822 | n/a | n/a | Exon 2-Intron 2 | CCCTCAAACCTCTGCACTCT | 3 | 2374 | 2393 | 172 |
| 532823 | n/a | n/a | Exon 2-Intron 2 | TCATTGCCCTCAAACCTCTG | 19 | 2380 | 2399 | 173 |
| 532824 | n/a | n/a | Intron 2 | CCACACTCATTGCCCTCAAA | 37 | 2386 | 2405 | 174 |
| 532825 | n/a | n/a | Intron 2 | CACTGCCCACACTCATTGCC | 23 | 2392 | 2411 | 175 |
| 532826 | n/a | n/a | Intron 2 | TTAGGCCACTGCCCACACTC | 15 | 2398 | 2417 | 176 |
| 532827 | n/a | n/a | Intron 2 | CTAGTCCTGACCTTGCTGCC | 28 | 2436 | 2455 | 177 |
| 532828 | n/a | n/a | Intron 2 | CTCATCCTAGTCCTGACCTT | 25 | 2442 | 2461 | 178 |
| 532829 | n/a | n/a | Intron 2 | CCTAGTCTCATCCTAGTCCT | 23 | 2448 | 2467 | 179 |
| 532830 | n/a | n/a | Intron 2 | ACCCTGCCTAGTCTCATCCT | 30 | 2454 | 2473 | 180 |
| 532831 | n/a | n/a | Intron 2 | CTTGTCACCCTGCCTAGTCT | 34 | 2460 | 2479 | 181 |
| 532832 | n/a | n/a | Intron 2 | GCCCACCTTGTCACCCTGCC | 36 | 2466 | 2485 | 182 |
| 532833 | n/a | n/a | Intron 2 | CCTAAAACTGCTCCTACTCC | 9 | 2492 | 2511 | 183 |
| 532834 | n/a | n/a | Intron 4 | GAGTCAGAAATGAGGTCAAA | 19 | 3494 | 3513 | 184 |
| 532835 | n/a | n/a | Intron 11 | CCCTACTCCCATTTCACCTT | 16 | 5971 | 5990 | 185 |
| 532836 | n/a | n/a | Intron 8-Exon 9 | TGTTGTGCAATCCTGCAGAA | 25 | 5013 | 5032 | 186 |
| 532837 | n/a | n/a | Intron 1 | AAAGGCTGATGAAGCCTGGC | 18 | 2123 | 2142 | 187 |
| 532838 | n/a | n/a | Intron 7 | CCTTTGACCACAAAGTGGCC | 21 | 4461 | 4480 | 188 |
| 532839 | n/a | n/a | Intron 12 | AGGTACCACCTCTTTGTGGG | 29 | 6362 | 6381 | 189 |
| 532840 | n/a | n/a | Intron 1-Exon 2 | TGGTGGTCACACCTGAAGAG | 34 | 2143 | 2162 | 190 |
| 532763 | 2133 | 2152 | Exon 14-15 Junction | GCAGGGAGCAGCTCTTCCTT | 40 | n/a | n/a | 191 |

TABLE 126-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532764 | 2139 | 2158 | Exon 15 | TCCTGTGCAGGGAGCAGCTC | 28 | 6927 | 6946 | 192 |
| 532765 | 2145 | 2164 | Exon 15 | TTGATATCCTGTGCAGGGAG | 41 | 6933 | 6952 | 193 |
| 532766 | 2151 | 2170 | Exon 15 | AGAGCTTTGATATCCTGTGC | 36 | 6939 | 6958 | 194 |
| 532767 | 2157 | 2176 | Exon 15 | ACAAACAGAGCTTTGATATC | 33 | 6945 | 6964 | 195 |
| 532768 | 2163 | 2182 | Exon 15 | TCAGACACAAACAGAGCTTT | 41 | 6951 | 6970 | 196 |
| 532769 | 2169 | 2188 | Exon 15 | TCCTCCTCAGACACAAACAG | 49 | 6957 | 6976 | 197 |
| 532770 | 2193 | 2212 | Exon 15 | ACCTCCTTCCGAGTCAGCTT | 61 | 6981 | 7000 | 198 |
| 532771 | 2199 | 2218 | Exon 15 | ATGTAGACCTCCTTCCGAGT | 39 | 6987 | 7006 | 199 |
| 532772 | 2205 | 2224 | Exon 15 | TTCTTGATGTAGACCTCCTT | 30 | 6993 | 7012 | 200 |
| 532773 | 2211 | 2230 | Exon 15 | TCCCCATTCTTGATGTAGAC | 31 | 6999 | 7018 | 201 |
| 532774 | 2217 | 2236 | Exon 15-16 Junction | TTCTTATCCCCATTCTTGAT | 36 | n/a | n/a | 202 |
| 532775 | 2223 | 2242 | Exon 15-16 Junction | CTGCCTTTCTTATCCCCATT | 56 | n/a | n/a | 203 |
| 532776 | 2229 | 2248 | Exon 15-16 Junction | TCACAGCTGCCTTTCTTATC | 33 | n/a | n/a | 204 |
| 532777 | 2235 | 2254 | Exon 16 | TCTCTCTCACAGCTGCCTTT | 38 | 7119 | 7138 | 205 |
| 532778 | 2241 | 2260 | Exon 16 | TGAGCATCTCTCTCACAGCT | 51 | 7125 | 7144 | 206 |
| 532779 | 2247 | 2266 | Exon 16 | GCATATTGAGCATCTCTCTC | 39 | 7131 | 7150 | 207 |
| 532780 | 2267 | 2286 | Exon 16 | TGACTTTGTCATAGCCTGGG | 56 | 7151 | 7170 | 208 |
| 532781 | 2273 | 2292 | Exon 16 | TGTCCTTGACTTTGTCATAG | 36 | 7157 | 7176 | 209 |
| 532782 | 2309 | 2328 | Exon 16 | CAGTACAAAGGAACCGAGGG | 30 | 7193 | 7212 | 210 |
| 532783 | 2315 | 2334 | Exon 16 | CTCCTCCAGTACAAAGGAAC | 21 | 7199 | 7218 | 211 |
| 532784 | 2321 | 2340 | Exon 16 | GACTCACTCCTCCAGTACAA | 31 | 7205 | 7224 | 212 |
| 532785 | 2327 | 2346 | Exon 16 | CATAGGGACTCACTCCTCCA | 30 | 7211 | 7230 | 213 |
| 532786 | 2333 | 2352 | Exon 16 | GGTCAGCATAGGGACTCACT | 31 | 7217 | 7236 | 214 |
| 532787 | 2352 | 2371 | Exon 16-17 Junction | TCACCTCTGCAAGTATTGGG | 42 | 7236 | 7255 | 215 |
| 532788 | 2358 | 2377 | Exon 16-17 Junction | CCAGAATCACCTCTGCAAGT | 32 | n/a | n/a | 216 |
| 532789 | 2364 | 2383 | Exon 16-17 Junction | GGGCCGCCAGAATCACCTCT | 35 | n/a | n/a | 217 |
| 532790 | 2382 | 2401 | Exon 17 | CTCTTGTGAACTATCAAGGG | 33 | 7347 | 7366 | 218 |
| 532791 | 2388 | 2407 | Exon 17 | CGACTTCTCTTGTGAACTAT | 52 | 7353 | 7372 | 219 |
| 532792 | 2394 | 2413 | Exon 17 | ATGAAACGACTTCTCTTGTG | 16 | 7359 | 7378 | 220 |

TABLE 126-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532793 | 2400 | 2419 | Exon 17-18 Junction | ACTTGAATGAAACGACTTCT | 45 | 7365 | 7384 | 221 |
| 532794 | 2406 | 2425 | Exon 17-18 Junction | ACACCAACTTGAATGAAACG | 18 | n/a | n/a | 222 |
| 532795 | 2427 | 2446 | Exon 18 | TCCACTACTCCCCAGCTGAT | 30 | 7662 | 7681 | 223 |
| 532796 | 2433 | 2452 | Exon 18 | CAGACATCCACTACTCCCCA | 38 | 7668 | 7687 | 224 |
| 532797 | 2439 | 2458 | Exon 18 | TTTTTGCAGACATCCACTAC | 35 | 7674 | 7693 | 225 |
| 532798 | 2445 | 2464 | Exon 18 | TTCTGGTTTTGCAGACATC | 45 | 7680 | 7699 | 226 |
| 532799 | 2451 | 2470 | Exon 18 | TGCCGCTTCTGGTTTTGCA | 47 | 7686 | 7705 | 227 |
| 532800 | 2457 | 2476 | Exon 18 | TGCTTTTGCCGCTTCTGGTT | 61 | 7692 | 7711 | 228 |
| 532801 | 2463 | 2482 | Exon 18 | GGTACCTGCTTTTGCCGCTT | 47 | 7698 | 7717 | 229 |
| 532802 | 2469 | 2488 | Exon 18 | TGAGCAGGTACCTGCTTTTG | 31 | 7704 | 7723 | 230 |
| 532803 | 2517 | 2536 | Exon 18 | TTCAGCCAGGGCAGCACTTG | 41 | 7752 | 7771 | 231 |
| 532804 | 2523 | 2542 | Exon 18 | TTCTCCTTCAGCCAGGGCAG | 44 | 7758 | 7777 | 232 |
| 532805 | 2529 | 2548 | Exon 18 | TGGAGTTTCTCCTTCAGCCA | 46 | 7764 | 7783 | 233 |
| 532806 | 2535 | 2554 | Exon 18 | TCATCTTGGAGTTTCTCCTT | 49 | 7770 | 7789 | 234 |
| 532807 | 2541 | 2560 | Exon 18 | AAATCCTCATCTTGGAGTTT | 30 | 7776 | 7795 | 235 |
| 532808 | 2547 | 2566 | Exon 18 | AAACCCAAATCCTCATCTTG | 20 | 7782 | 7801 | 236 |
| 532809 | 2571 | 2590 | Exon 18 | GTCCAGCAGGAAACCCCTTA | 65 | 7806 | 7825 | 237 |
| 532810 | 2577 | 2596 | Exon 18 | GCCCCTGTCCAGCAGGAAAC | 74 | 7812 | 7831 | 238 |
| 532811 | 2599 | 2618 | Exon 18 | AGCTGTTTTAATTCAATCCC | 96 | 7834 | 7853 | 239 |

TABLE 127

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532841 | n/a | n/a | Intron 6-Exon 7 | AACTTGCCACCTGTGGGTGA | 41 | 4142 | 4161 | 240 |
| 532842 | n/a | n/a | Exon 15-Intron 15 | TCACCTTATCCCCATTCTTG | 42 | 7007 | 7026 | 241 |
| 532843 | n/a | n/a | Intron 11 | TCAACTTTCACAAACCACCA | 16 | 6015 | 6034 | 242 |
| 532844 | n/a | n/a | Intron 16-Exon 17 | CCGCCAGAATCACCTGCAAG | 33 | 7326 | 7345 | 243 |
| 532845 | n/a | n/a | Intron 10 | AGGAGGAATGAAGAAGGCTT | 29 | 5431 | 5450 | 244 |
| 532846 | n/a | n/a | Intron 13 | GCCTTTCCTCAGGGATCTGG | 26 | 6561 | 6580 | 245 |
| 532847 | n/a | n/a | Intron 4 | AAATGTCTGGGAGTGTCAGG | 18 | 3477 | 3496 | 246 |
| 532848 | n/a | n/a | Intron 15 | GCCTAGAGTGCCTCCTTAGG | 20 | 7038 | 7057 | 247 |

TABLE 127-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532849 | n/a | n/a | Intron 17 | GGCATCTCCCCAGATAGGAA | 7396 | 7415 | 16 | 248 |
| 532850 | n/a | n/a | Intron 6 | AGGGAGCTAGTCCTGGAAGA | 3906 | 3925 | 14 | 249 |
| 532851 | n/a | n/a | Intron 1-Exon 2 | ACACCTGAAGAGAAAGGCTG | 2135 | 2154 | 6 | 250 |
| 532852 | n/a | n/a | Intron 7 | CCCTTTGACCACAAAGTGGC | 4462 | 4481 | 25 | 251 |
| 532853 | n/a | n/a | Intron 7 | GCCCTCAAGGTAGTCTCATG | 4354 | 4373 | 26 | 252 |
| 532854 | n/a | n/a | Intron 6 | AAGGGAAGGAGGACAGAATA | 3977 | 3996 | 18 | 253 |
| 532855 | n/a | n/a | Intron 1 | AAAGGCCAAGGAGGGATGCT | 2099 | 2118 | 9 | 254 |
| 532856 | n/a | n/a | Exon 8-Intron 8 | AGAGGTCCCTTCTGACCATC | 4736 | 4755 | 4 | 255 |
| 532857 | n/a | n/a | Intron 8 | GCTGGGACAGGAGAGAGGTC | 4749 | 4768 | 0 | 256 |
| 532858 | n/a | n/a | Intron 4 | TCAAATGTCTGGGAGTGTCA | 3479 | 3498 | 13 | 257 |
| 532859 | n/a | n/a | Intron 10 | AGAAGGAGAATGTGCTGAAA | 5801 | 5820 | 20 | 258 |
| 532860 | n/a | n/a | Intron 17 | TGCTGACCACTTGGCATCTC | 7408 | 7427 | 20 | 259 |
| 532861 | n/a | n/a | Intron 11 | CAACTTTCACAAACCACCAT | 6014 | 6033 | 18 | 260 |
| 532862 | n/a | n/a | Intron 10 | AGCTCTGTGATTCTAAGGTT | 5497 | 5516 | 15 | 261 |
| 532863 | n/a | n/a | Intron 6-Exon 7 | CCACCTGTGGGTGAGGAGAA | 4136 | 4155 | 16 | 262 |
| 532864 | n/a | n/a | Exon 17-Intron 17 | GAGGACTCACTTGAATGAAA | 7373 | 7392 | 21 | 263 |
| 532865 | n/a | n/a | Intron 6 | TGGAATGATCAGGGAGCTAG | 3916 | 3935 | 30 | 264 |
| 532866 | n/a | n/a | Intron 5 | GTCCCTTCTCCATTTTCCCC | 3659 | 3678 | 26 | 265 |
| 532867 | n/a | n/a | Intron 7 | TCAACTTTTTAAGTTAATCA | 4497 | 4516 | 14 | 266 |
| 532868 | n/a | n/a | Intron 6 | GGGTGAGGAGAACAAGGCGC | 4128 | 4147 | 21 | 267 |
| 532869 | n/a | n/a | Intron 7 | CTTCCAAGCCATCTTTTAAC | 4553 | 4572 | 5 | 268 |
| 532870 | n/a | n/a | Exon 17-Intron 17 | AGGACTCACTTGAATGAAAC | 7372 | 7391 | 18 | 269 |
| 532871 | n/a | n/a | Intron 10 | TTCCAGGCAACTAGAGCTTC | 5412 | 5431 | 15 | 270 |
| 532872 | n/a | n/a | Exon 1 | CAGAGTCCAGCCACTGTTTG | 1557 | 1576 | 13 | 271 |
| 532873 | n/a | n/a | Intron 17-Exon 18 | CCAACCTGCAGAGGCAGTGG | 7638 | 7657 | 23 | 272 |
| 532874 | n/a | n/a | Intron 16 | TGCAAGGAGAGGAGAAGCTG | 7312 | 7331 | 10 | 273 |
| 532875 | n/a | n/a | Exon 9-Intron 9 | CTAGGCAGGTTACTCACCCA | 5120 | 5139 | 21 | 274 |
| 532876 | n/a | n/a | Intron 6-Exon 7 | CACCATAACTTGCCACCTGT | 4148 | 4167 | 41 | 275 |
| 532877 | n/a | n/a | Intron 12 | TAGGTACCACCTCTTTGTGG | 6363 | 6382 | 27 | 276 |
| 532878 | n/a | n/a | Intron 11 | CTTGACCTCACCTCCCCCAA | 5954 | 5973 | 13 | 277 |
| 532879 | n/a | n/a | Intron 12 | CCACCTCTTTGTGGGCAGCT | 6357 | 6376 | 33 | 278 |
| 532880 | n/a | n/a | Intron 11 | TTCACAAACCACCATCTCTT | 6009 | 6028 | 8 | 279 |

TABLE 127-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532881 | n/a | n/a | Exon 3-Intron 3 | TTCTCACCTCCGTTGTCACA | 2958 | 2977 | 17 | 280 |
| 532882 | n/a | n/a | Intron 12 | GAAAGTGGGAGGTGTTGCCT | 6225 | 6244 | 19 | 281 |
| 532883 | n/a | n/a | Intron 1 | ACAGCAGGAAGGGAAGGTTA | 2075 | 2094 | 34 | 282 |
| 532884 | n/a | n/a | Intron 17 | CATGCTGACCACTTGGCATC | 7410 | 7429 | 18 | 283 |
| 532885 | n/a | n/a | Exon 4-Intron 4 | GGTCACCTTGGCAGGAAGGC | 3286 | 3305 | 0 | 284 |
| 532886 | n/a | n/a | Intron 8 | GTATAGTGTTACAAGTGGAC | 4804 | 4823 | 13 | 285 |
| 532887 | n/a | n/a | Intron 7 | GGACTTCCCTTTGACCACAA | 4468 | 4487 | 18 | 286 |
| 532888 | n/a | n/a | Intron 11 | TCACCTTGACCTCACCTCCC | 5958 | 5977 | 20 | 287 |
| 532889 | n/a | n/a | Intron 15 | TAGAGTGCCTCCTTAGGATG | 7035 | 7054 | 27 | 288 |
| 532890 | n/a | n/a | Intron 7 | TGACTTCAACTTGTGGTCTG | 4605 | 4624 | 16 | 289 |
| 532891 | n/a | n/a | Intron 10 | CAGAGAAGGAGAATGTGCTG | 5804 | 5823 | 25 | 290 |
| 532892 | n/a | n/a | Intron 14-Exon 15 | AGGGAGCAGCTCTTCCTCTG | 6919 | 6938 | 47 | 291 |
| 532893 | n/a | n/a | Intron 5-Exon 6 | TGTTCCCCTGGGTGCCAGGA | 3710 | 3729 | 24 | 292 |
| 532894 | n/a | n/a | Intron 10 | GGCCTGGCTGTTTTCAAGCC | 5612 | 5631 | 15 | 293 |
| 532895 | n/a | n/a | Intron 10-Exon 11 | GACTGGCTTTCATCTGGCAG | 5821 | 5840 | 25 | 294 |
| 532896 | n/a | n/a | Intron 10 | GAAGGCTTTCCAGGCAACTA | 5419 | 5438 | 19 | 295 |
| 532897 | n/a | n/a | Exon 17-Intron 17 | TCACTTGAATGAAACGACTT | 7367 | 7386 | 11 | 296 |
| 532898 | n/a | n/a | Intron 1 | GGCCCCAAAAGGCCAAGGAG | 2106 | 2125 | 5 | 297 |
| 532899 | n/a | n/a | Intron 16-Exon 17 | AATCACCTGCAAGGAGAGGA | 7319 | 7338 | 19 | 298 |
| 532900 | n/a | n/a | Intron 12 | GACCTTCAGTTGCATCCTTA | 6183 | 6202 | 25 | 299 |
| 532901 | n/a | n/a | Intron 1 | TGATGAAGCCTGGCCCCAAA | 2117 | 2136 | 0 | 300 |
| 532902 | n/a | n/a | Intron 12 | TAGAAAGTGGGAGGTGTTGC | 6227 | 6246 | 0 | 301 |
| 532903 | n/a | n/a | Target 12 | CCCATCCCTGACTGGTCTGG | 6295 | 6314 | 14 | 302 |
| 532904 | n/a | n/a | Intron 8 | CCATGGGTATAGTGTTACAA | 4810 | 4829 | 13 | 303 |
| 532905 | n/a | n/a | Intron 2 | GTGTTCTCTTGACTTCCAGG | 2586 | 2605 | 23 | 304 |
| 532906 | n/a | n/a | Intron 13 | GGCCTGCTCCTCACCCCAGT | 6597 | 6616 | 27 | 305 |
| 532907 | n/a | n/a | Intron 10 | GAGGCCTGGCTGTTTTCAAG | 5614 | 5633 | 32 | 306 |
| 532908 | n/a | n/a | Exon 1 | GACTCTCCCCTTCAGTACCT | 1677 | 1696 | 16 | 307 |
| 532909 | n/a | n/a | Intron 8 | CATGGGTATAGTGTTACAAG | 4809 | 4828 | 10 | 308 |
| 532910 | n/a | n/a | Intron 10 | GAAGGAGAATGTGCTGAAAA | 5800 | 5819 | 0 | 309 |
| 532911 | n/a | n/a | Intron 7 | TCACCTGGTCTTCCAAGCCA | 4562 | 4581 | 0 | 310 |
| 532912 | n/a | n/a | Intron 17 | CTCCCCAGATAGGAAAGGGA | 7391 | 7410 | 0 | 311 |
| 532913 | n/a | n/a | Exon 17-Intron 17 | GGACTCACTTGAATGAAACG | 7371 | 7390 | 0 | 312 |

TABLE 127-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532914 | n/a | n/a | Intron 16-Exon 17 | GGCCGCCAGAATCACCTGCA | 7328 | 7347 | 30 | 313 |
| 532915 | n/a | n/a | Exon 17-Intron 17 | CTCACTTGAATGAAACGACT | 7368 | 7387 | 22 | 314 |
| 532916 | n/a | n/a | Intron 13 | CTTTCCCAGCCTTTCCTCAG | 6569 | 6588 | 28 | 315 |
| 532918 | n/a | n/a | Intron 12 | AGAAAGTGGGAGGTGTTGCC | 6226 | 6245 | 3 | 316 |
| 532917 | 2604 | 2623 | Exon 18 | GTCGCAGCTGTTTTAATTCA | 7839 | 7858 | 90 | 317 |

TABLE 128

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532919 | n/a | n/a | Exon 1 | CCAGGACTCTCCCCTTCAGT | 1681 | 1700 | 4 | 318 |
| 532920 | n/a | n/a | Intron 6 | AGGGAAGGAGGACAGAATAG | 3976 | 3995 | 25 | 319 |
| 532921 | n/a | n/a | Intron 4 | GAAATGAGGTCAAATGTCTG | 3488 | 3507 | 30 | 320 |
| 532922 | n/a | n/a | Intron 4 | GGAGAGTCAGAAATGAGGTC | 3497 | 3516 | 25 | 321 |
| 532923 | n/a | n/a | Intron 12 | GTAGAAAGTGGGAGGTGTTG | 6228 | 6247 | 26 | 322 |
| 532924 | n/a | n/a | Intron 10 | TAGAAAGATCTCTGAAGTGC | 5521 | 5540 | 24 | 323 |
| 532925 | n/a | n/a | Intron 13 | CTGCTCCTCACCCCAGTCCT | 6594 | 6613 | 26 | 324 |
| 532926 | n/a | n/a | Intron 11 | CTACTGGGATTCTGTGCTTA | 5927 | 5946 | 30 | 325 |
| 532927 | n/a | n/a | Intron 1 | CCCAAAAGGCCAAGGAGGGA | 2103 | 2122 | 13 | 326 |
| 532928 | n/a | n/a | Intron 17 | TGACCACTTGGCATCTCCCC | 7405 | 7424 | 27 | 327 |
| 532929 | n/a | n/a | Intron 16-Exon 17 | CCTGCAAGGAGAGGAGAAGC | 7314 | 7333 | 29 | 328 |
| 532930 | n/a | n/a | Exon 16-Intron 16 | CTCTCACCTCTGCAAGTATT | 7239 | 7258 | 44 | 329 |
| 532931 | n/a | n/a | Intron 1 | CCCCAAAAGGCCAAGGAGGG | 2104 | 2123 | 21 | 330 |
| 532932 | n/a | n/a | Intron 7 | GTCTTCCAAGCCATCTTTTA | 4555 | 4574 | 20 | 331 |
| 532933 | n/a | n/a | Intron 8 | GTTACAAGTGGACTTAAGGG | 4797 | 4816 | 30 | 332 |
| 532934 | n/a | n/a | Intron 8-Exon 9 | CCCATGTTGTGCAATCCTGC | 5017 | 5036 | 30 | 333 |
| 532935 | n/a | n/a | Intron 15 | GAGGTGGGAAGCATGGAGAA | 7091 | 7110 | 17 | 334 |
| 532936 | n/a | n/a | Intron 14 | TGCTCCCACCACTGTCATCT | 6874 | 6893 | 21 | 335 |
| 532937 | n/a | n/a | Exon 9-Intron 9 | AGGCAGGTTACTCACCCAGA | 5118 | 5137 | 18 | 336 |
| 532938 | n/a | n/a | Intron 11 | TACTGGGATTCTGTGCTTAC | 5926 | 5945 | 15 | 337 |
| 532939 | n/a | n/a | Intron 13 | GCCTTTCCCAGCCTTTCCTC | 6571 | 6590 | 27 | 338 |
| 532940 | n/a | n/a | Intron 8-Exon 9 | GTGCAATCCTGCAGAAGAGA | 5009 | 5028 | 21 | 339 |

TABLE 128-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | SEQ ID NO: 2 start site | SEQ ID NO: 2 stop site | % inhibition | SEQ ID NO: |
|---|---|---|---|---|---|---|---|---|
| 532941 | n/a | n/a | Intron 8 | ACAGGAGAGAGGTCCCTTCT | 4743 | 4762 | 20 | 340 |
| 532942 | n/a | n/a | Intron 10 | CCCAAAAGGAGAAAGGGAAA | 5717 | 5736 | 14 | 341 |
| 532943 | n/a | n/a | Intron 2 | AAGCCCAGGGTAAATGCTTA | 2557 | 2576 | 32 | 342 |
| 532944 | n/a | n/a | Intron 1 | GATGAAGCCTGGCCCCAAAA | 2116 | 2135 | 22 | 343 |
| 532945 | n/a | n/a | Intron 10 | TGGCAGAGAAGGAGAATGTG | 5807 | 5826 | 22 | 344 |
| 532946 | n/a | n/a | Intron 13 | TTCCCAGCCTTTCCTCAGGG | 6567 | 6586 | 35 | 345 |
| 532947 | n/a | n/a | Intron 10 | GGCAGAGAAGGAGAATGTGC | 5806 | 5825 | 30 | 346 |
| 532948 | n/a | n/a | Intron 10 | ACAGTGCCAGGAAACAAGAA | 5471 | 5490 | 25 | 347 |
| 532949 | n/a | n/a | Exon 9-Intron 9 | TAGGCAGGTTACTCACCCAG | 5119 | 5138 | 22 | 348 |
| 532950 | n/a | n/a | Intron 2 | TTCTCTTGACTTCCAGGGCT | 2583 | 2602 | 22 | 349 |
| 532951 | n/a | n/a | Intron 13 | CCTGCTCCTCACCCCAGTCC | 6595 | 6614 | 16 | 350 |
| 532953 | n/a | n/a | Intron 7 | TCCCACTAACCTCCATTGCC | 4422 | 4441 | 14 | 351 |
| 532954 | n/a | n/a | Intron 7 | TTCCCTTTGACCACAAAGTG | 4464 | 4483 | 16 | 352 |
| 532955 | n/a | n/a | Intron 9 | CTGGGTCCTAGGCAGGTTAC | 5127 | 5146 | 30 | 353 |
| 532956 | n/a | n/a | Intron 10 | TCCAGGCAACTAGAGCTTCA | 5411 | 5430 | 20 | 354 |
| 532957 | n/a | n/a | Intron 8-Exon 9 | GCCCATGTTGTGCAATCCTG | 5018 | 5037 | 45 | 355 |
| 532958 | n/a | n/a | Intron 7 | GGTTCCCACTAACCTCCATT | 4425 | 4444 | 18 | 356 |
| 532959 | n/a | n/a | Intron 3 | AGGTAGAGAGCAAGAGTTAC | 3052 | 3071 | 26 | 357 |
| 532960 | n/a | n/a | Intron 7 | CCACTAACCTCCATTGCCCA | 4420 | 4439 | 10 | 358 |
| 532961 | n/a | n/a | Intron 11 | TCACAAACCACCATCTCTTA | 6008 | 6027 | 40 | 359 |
| 532962 | n/a | n/a | Exon 9-Intron 9 | TACTCACCCAGATAATCCTC | 5110 | 5129 | 27 | 360 |
| 532963 | n/a | n/a | Intron 13 | TGCTCCTCACCCCAGTCCTC | 6593 | 6612 | 24 | 361 |
| 532964 | n/a | n/a | Intron 15-Exon 16 | TCTCACAGCTGCCTTTCTGT | 7115 | 7134 | 25 | 362 |
| 532965 | n/a | n/a | Exon 17-Intron 17 | GAAAGGGAGGACTCACTTGA | 7379 | 7398 | 11 | 363 |
| 532966 | n/a | n/a | Intron 7 | CCATCTTTTAACCCCAGAGA | 4545 | 4564 | 18 | 364 |
| 532967 | n/a | n/a | Intron 13 | TCCTCACCCCAGTCCTCCAG | 6590 | 6609 | 27 | 365 |
| 532968 | n/a | n/a | Intron 10 | CTGGCAGAGAAGGAGAATGT | 5808 | 5827 | 15 | 366 |
| 532969 | n/a | n/a | Intron 17 | TCTCCCCAGATAGGAAAGGG | 7392 | 7411 | 23 | 367 |
| 532970 | n/a | n/a | Intron 14 | ACTTCAGCTGCTCCCACCAC | 6882 | 6901 | 18 | 368 |
| 532971 | n/a | n/a | Intron 1 | GACAGCAGGAAGGGAAGGTT | 2076 | 2095 | 13 | 369 |
| 532972 | n/a | n/a | Intron 13-Exon 14 | GGAGACAAATGGGCCTATAA | 6640 | 6659 | 33 | 370 |
| 532973 | n/a | n/a | Intron 14 | CTGCTCCCACCACTGTCATC | 6875 | 6894 | 11 | 371 |
| 532974 | n/a | n/a | Intron 10 | AGGAATGAAGAAGGCTTTCC | 5428 | 5447 | 21 | 372 |

TABLE 128-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532975 | n/a | n/a | Intron 14 | GGGATCTCATCCTTATCCTC | 6741 | 6760 | 31 | 373 |
| 532976 | n/a | n/a | Intron 9 | GTGCTGGGTCCTAGGCAGGT | 5130 | 5149 | 16 | 374 |
| 532977 | n/a | n/a | Intron 1 | CAAAAGGCCAAGGAGGGATG | 2101 | 2120 | 14 | 375 |
| 532978 | n/a | n/a | Intron 17 | CCATGCTGACCACTTGGCAT | 7411 | 7430 | 20 | 376 |
| 532979 | n/a | n/a | Intron 8 | GGAGGCTGGGACAGGAGAGA | 4753 | 4772 | 25 | 377 |
| 532980 | n/a | n/a | Intron 14-Exon 15 | GGAGCAGCTCTTCCTCTGGA | 6917 | 6936 | 36 | 378 |
| 532981 | n/a | n/a | Exon 3-Intron 3 | TCTCACCTCCGTTGTCACAG | 2957 | 2976 | 20 | 379 |
| 532982 | n/a | n/a | Intron 13 | CAGTCCTCCAGCCTTTCCCA | 6581 | 6600 | 21 | 380 |
| 532983 | n/a | n/a | Intron 13 | AGTCCTCCAGCCTTTCCCAG | 6580 | 6599 | 22 | 381 |
| 532984 | n/a | n/a | Intron 4-Exon 5 | TGAAGGAGTCTGGGAGAGTC | 3509 | 3528 | 12 | 382 |
| 532985 | n/a | n/a | Intron 16-Exon 17 | CAGAATCACCTGCAAGGAGA | 7322 | 7341 | 20 | 383 |
| 532986 | n/a | n/a | Exon 17-Intron 17 | TAGGAAAGGGAGGACTCACT | 7382 | 7401 | 3 | 384 |
| 532987 | n/a | n/a | Exon 4-Intron 4 | ACCTTGGCAGGAAGGCTCCG | 3282 | 3301 | 12 | 385 |
| 532988 | n/a | n/a | Intron 13-Exon 14 | GAGACAAATGGGCCTATAAA | 6639 | 6658 | 15 | 386 |
| 532989 | n/a | n/a | Intron 1 | CTGAAGAGAAAGGCTGATGA | 2131 | 2150 | 17 | 387 |
| 532990 | n/a | n/a | Intron 6 | AATGATCAGGGAGCTAGTCC | 3913 | 3932 | 30 | 388 |
| 532991 | n/a | n/a | Intron 17 | CTTAGCTGACCTAAAGGAAT | 7557 | 7576 | 22 | 389 |
| 532992 | n/a | n/a | Intron 8 | TGGGTATAGTGTTACAAGTG | 4807 | 4826 | 17 | 390 |
| 532993 | n/a | n/a | Intron 1 | TGAAGAGAAAGGCTGATGAA | 2130 | 2149 | 19 | 391 |
| 532994 | n/a | n/a | Intron 8 | GTGTTACAAGTGGACTTAAG | 4799 | 4818 | 25 | 392 |
| 532995 | n/a | n/a | Intron 6 | ACCTGTGGGTGAGGAGAACA | 4134 | 4153 | 24 | 393 |
| 532996 | n/a | n/a | Exon 9-Intron 9 | TCACCCAGATAATCCTCCCT | 5107 | 5126 | 36 | 394 |
| 532952 | 2608 | 2627 | Exon 18 | TGTTGTCGCAGCTGTTTTAA | 7843 | 7862 | 90 | 395 |

Example 116: Antisense Inhibition of Human Complement Factor B (CFB) in HepG2 Cells by MOE Gapmers Additional antisense oligonucleotides were designed targeting human Complement Factor B (CFB) nucleic acid and were tested for their effects on CFB mRNA in vitro. Cultured HepG2 cells at a density of 20,000 cells per well were transfected using electroporation with 4,500 nM antisense oligonucleotide. After a treatment period of approximately 24 hours, RNA was isolated from the cells and CFB mRNA levels were measured by quantitative real-time PCR. Human primer probe set RTS3460_MGB (forward sequence CGAAGCAGCTCAATGAAATCAA, designated herein as SEQ ID NO: 813; reverse sequence TGCCTG-GAGGGCCTTCTT, designated herein as SEQ ID NO: 814; probe sequence AGACCACAAGTTGAAGTC, designated herein as SEQ ID NO: 815) was used to measure mRNA levels. CFB mRNA levels were adjusted according to total RNA content, as measured by RIBOGREEN®. Results are presented as percent inhibition of CFB, relative to untreated control cells.

The newly designed chimeric antisense oligonucleotides in the Tables below were designed as 5-10-5 MOE gapmers. The 5-10-5 MOE gapmers are 20 nucleosides in length, wherein the central gap segment comprises of ten 2'-deoxy-nucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human CFB mRNA, designated herein as SEQ ID NO: 1 (GENBANK Accession No. NM_001710.5) or the human CFB genomic sequence, designated herein as SEQ ID NO: 2 (GENBANK Accession No. NT_007592.15 truncated from nucleotides 31852000 to 31861000), or both. 'n/a' indicates that the antisense oligonucleotide does not target that particular gene sequence with 10000 complementarity.

TABLE 129

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532686 | 1135 | 1154 | Exon 6 | ACACTTTTTGGCTCCTGTGA | 48 | 3819 | 3838 | 84 |
| 532687 | 1141 | 1160 | Exon 6 | GACTAGACACTTTTTGGCTC | 63 | 3825 | 3844 | 85 |
| 532688 | 1147 | 1166 | Exon 6 | TAAGTTGACTAGACACTTTT | 47 | 3831 | 3850 | 86 |
| 532689 | 1153 | 1172 | Exon 6 | CTCAATTAAGTTGACTAGAC | 57 | 3837 | 3856 | 87 |
| 532690 | 1159 | 1178 | Exon 6-7 Junction | CACCTTCTCAATTAAGTTGA | 49 | 3843 | 3862 | 88 |
| 532691 | 1165 | 1184 | Exon 6-7 Junction | ACTTGCCACCTTCTCAATTA | 33 | n/a | n/a | 89 |
| 532692 | 1171 | 1190 | Exon 6-7 Junction | ACCATAACTTGCCACCTTCT | 67 | n/a | n/a | 90 |
| 532693 | 1177 | 1196 | Exon 7 | CTTCACACCATAACTTGCCA | 56 | 4153 | 4172 | 91 |
| 532694 | 1183 | 1202 | Exon 7 | TCTTGGCTTCACACCATAAC | 50 | 4159 | 4178 | 92 |
| 532695 | 1208 | 1227 | Exon 7 | ATGTGGCATATGTCACTAGA | 53 | 4184 | 4203 | 93 |
| 532696 | 1235 | 1254 | Exon 7 | CAGACACTTTGACCCAAATT | 52 | 4211 | 4230 | 94 |
| 532697 | 1298 | 1317 | Exon 7-8 Juncion | GGTCTTCATAATTGATTTCA | 59 | n/a | n/a | 95 |
| 532698 | 1304 | 1323 | Exon 7-8 Juncion | ACTTGTGGTCTTCATAATTG | 52 | n/a | n/a | 96 |
| 532699 | 1310 | 1329 | Exon 7-8 Juncion | ACTTCAACTTGTGGTCTTCA | 85 | n/a | n/a | 97 |
| 532700 | 1316 | 1335 | Exon 8 | TCCCTGACTTCAACTTGTGG | 96 | 4609 | 4628 | 98 |
| 532701 | 1322 | 1341 | Exon 8 | TGTTAGTCCCTGACTTCAAC | 56 | 4615 | 4634 | 99 |
| 532702 | 1328 | 1347 | Exon 8 | TCTTGGTGTTAGTCCCTGAC | 86 | 4621 | 4640 | 100 |
| 532703 | 1349 | 1368 | Exon 8 | TGTACACTGCCTGGAGGGCC | 35 | 4642 | 4661 | 101 |
| 532704 | 1355 | 1374 | Exon 8 | TCATGCTGTACACTGCCTGG | 12 | 4648 | 4667 | 102 |
| 532705 | 1393 | 1412 | Exon 8 | GTTCCAGCCTTCAGGAGGGA | 27 | 4686 | 4705 | 103 |
| 532706 | 1399 | 1418 | Exon 8 | GGTGCGGTTCCAGCCTTCAG | 67 | 4692 | 4711 | 104 |
| 532707 | 1405 | 1424 | Exon 8 | ATGGCGGGTGCGGTTCCAGC | 26 | 4698 | 4717 | 105 |
| 532708 | 1411 | 1430 | Exon 8 | GATGACATGGCGGGTGCGGT | 28 | 4704 | 4723 | 106 |
| 532709 | 1417 | 1436 | Exon 8 | GAGGATGATGACATGGCGGG | 6 | 4710 | 4729 | 107 |
| 532710 | 1443 | 1462 | Exon 8-9 Junction | CCCATGTTGTGCAATCCATC | 35 | n/a | n/a | 108 |
| 532711 | 1449 | 1468 | Exon 9 | TCCCCGCCCATGTTGTGCAA | 28 | 5023 | 5042 | 109 |
| 532712 | 1455 | 1474 | Exon 9 | ATTGGGTCCCCGCCCATGTT | 19 | 5029 | 5048 | 110 |
| 532713 | 1461 | 1480 | Exon 9 | ACAGTAATTGGGTCCCCGCC | 29 | 5035 | 5054 | 111 |

TABLE 129-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532714 | 1467 | 1486 | Exon 9 | TCAATGACAGTAATTGGGTC | 49 | 5041 | 5060 | 112 |
| 532715 | 1473 | 1492 | Exon 9 | ATCTCATCAATGACAGTAAT | 45 | 5047 | 5066 | 113 |
| 532716 | 1479 | 1498 | Exon 9 | TCCCGGATCTCATCAATGAC | 54 | 5053 | 5072 | 114 |
| 532717 | 1533 | 1552 | Exon 9-10 Junction | ACATCCAGATAATCCTCCCT | 22 | n/a | n/a | 115 |
| 532718 | 1539 | 1558 | Exon 9-10 Junction | ACATAGACATCCAGATAATC | 8 | n/a | n/a | 116 |
| 532719 | 1545 | 1564 | Exon 9-10 Junction | CCAAACACATAGACATCCAG | 30 | n/a | n/a | 117 |
| 532720 | 1582 | 1601 | Exon 10 | AGCATTGATGTTCACTTGGT | 62 | 5231 | 5250 | 118 |
| 532721 | 1588 | 1607 | Exon 10 | AGCCAAAGCATTGATGTTCA | 46 | 5237 | 5256 | 119 |
| 532722 | 1594 | 1613 | Exon 10 | CTTGGAAGCCAAAGCATTGA | 35 | 5243 | 5262 | 120 |
| 532723 | 1600 | 1619 | Exon 10 | GTCTTTCTTGGAAGCCAAAG | 43 | 5249 | 5268 | 121 |
| 532724 | 1606 | 1625 | Exon 10 | CTCATTGTCTTTCTTGGAAG | 40 | 5255 | 5274 | 122 |
| 532725 | 1612 | 1631 | Exon 10 | ATGTTGCTCATTGTCTTTCT | 49 | 5261 | 5280 | 123 |
| 532726 | 1618 | 1637 | Exon 10 | GAACACATGTTGCTCATTGT | 68 | 5267 | 5286 | 124 |
| 532727 | 1624 | 1643 | Exon 10 | GACTTTGAACACATGTTGCT | 54 | 5273 | 5292 | 125 |
| 532728 | 1630 | 1649 | Exon 10 | ATCCTTGACTTTGAACACAT | 61 | 5279 | 5298 | 126 |
| 532729 | 1636 | 1655 | Exon 10 | TTCCATATCCTTGACTTTGA | 55 | 5285 | 5304 | 127 |
| 532730 | 1642 | 1661 | Exon 10 | CAGGTTTTCCATATCCTTGA | 51 | 5291 | 5310 | 440 |
| 532731 | 1686 | 1705 | Exon 10-11 Junction | CTCAGAGACTGGCTTTCATC | 41 | 5827 | 5846 | 129 |
| 532732 | 1692 | 1711 | Exon 11 | CAGAGACTCAGAGACTGGCT | 59 | 5833 | 5852 | 130 |
| 516252 | 1698 | 1717 | Exon 11 | ATGCCACAGAGACTCAGAGA | 57 | 5839 | 5858 | 131 |
| 532733 | 1704 | 1723 | Exon 11 | CAAACCATGCCACAGAGACT | 34 | 5845 | 5864 | 132 |
| 532734 | 1710 | 1729 | Exon 11 | TGTTCCCAAACCATGCCACA | 51 | 5851 | 5870 | 133 |
| 532735 | 1734 | 1753 | Exon 11 | TTGTGGTAATCGGTACCCTT | 50 | 5875 | 5894 | 134 |
| 532736 | 1740 | 1759 | Exon 11 | GGTTGCTTGTGGTAATCGGT | 64 | 5881 | 5900 | 135 |
| 532737 | 1746 | 1765 | Exon 11 | TGCCATGGTTGCTTGTGGTA | 40 | 5887 | 5906 | 136 |
| 532738 | 1752 | 1771 | Exon 11 | TTGGCCTGCCATGGTTGCTT | 49 | 5893 | 5912 | 137 |
| 532739 | 1758 | 1777 | Exon 11 | GAGATCTTGGCCTGCCATGG | 47 | 5899 | 5918 | 138 |
| 532740 | 1803 | 1822 | Exon 12 | ACAGCCCCATACAGCTCTC | 48 | 6082 | 6101 | 139 |
| 532741 | 1809 | 1828 | Exon 12 | GACACCACAGCCCCATACA | 40 | 6088 | 6107 | 140 |
| 532742 | 1815 | 1834 | Exon 12 | TACTCAGACACCACAGCCCC | 33 | 6094 | 6113 | 141 |
| 532743 | 1821 | 1840 | Exon 12 | ACAAAGTACTCAGACACCAC | 39 | 6100 | 6119 | 142 |
| 532744 | 1827 | 1846 | Exon 12 | GTCAGCACAAAGTACTCAGA | 45 | 6106 | 6125 | 143 |

TABLE 129-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532745 | 1872 | 1891 | Exon 12 | TTGATTGAGTGTTCCTTGTC | 42 | 6151 | 6170 | 144 |
| 532746 | 1878 | 1897 | Exon 12 | CTGACCTTGATTGAGTGTTC | 53 | 6157 | 6176 | 145 |
| 532747 | 1909 | 1928 | Exon 13 | TATCTCCAGGTCCCGCTTCT | 31 | 6403 | 6422 | 146 |
| 532748 | 1967 | 1986 | Exon 13 | GAATTCCTGCTTCTTTTTTC | 30 | 6461 | 6480 | 147 |
| 532749 | 1973 | 1992 | Exon 13 | ATTCAGGAATTCCTGCTTCT | 40 | 6467 | 6486 | 148 |
| 532750 | 1979 | 1998 | Exon 13 | CATAAAATTCAGGAATTCCT | 45 | 6473 | 6492 | 149 |
| 532751 | 1985 | 2004 | Exon 13 | CATAGTCATAAAATTCAGGA | 43 | 6479 | 6498 | 150 |
| 532752 | 2006 | 2025 | Exon 13 | TGAGCTTGATCAGGGCAACG | 61 | 6500 | 6519 | 151 |
| 532753 | 2012 | 2031 | Exon 13 | TATTCTTGAGCTTGATCAGG | 47 | 6506 | 6525 | 152 |
| 532754 | 2048 | 2067 | Exon 13-14 Junction | GACAAATGGGCCTGATAGTC | 35 | n/a | n/a | 153 |
| 532755 | 2070 | 2089 | Exon 14 | GTTGTTCCCTCGGTGCAGGG | 43 | 6659 | 6678 | 154 |
| 532756 | 2076 | 2095 | Exon 14 | GCTCGAGTTGTTCCCTCGGT | 51 | 6665 | 6684 | 155 |
| 532757 | 2082 | 2101 | Exon 14 | CTCAAAGCTCGAGTTGTTCC | 36 | 6671 | 6690 | 156 |
| 532758 | 2088 | 2107 | Exon 14 | GGAAGCCTCAAAGCTCGAGT | 54 | 6677 | 6696 | 157 |
| 532759 | 2094 | 2113 | Exon 14 | GTTGGAGGAAGCCTCAAAGC | 52 | 6683 | 6702 | 158 |
| 532760 | 2100 | 2119 | Exon 14 | GTGGTAGTTGGAGGAAGCCT | 22 | 6689 | 6708 | 159 |
| 532761 | 2106 | 2125 | Exon 14 | TGGCAAGTGGTAGTTGGAGG | 34 | 6695 | 6714 | 160 |
| 532762 | 2112 | 2131 | Exon 14 | TGTTGCTGGCAAGTGGTAGT | 52 | 6701 | 6720 | 161 |

Example 117: Antisense Inhibition of Human Complement Factor B (CFB) in HepG2 Cells by MOE Gapmers Additional antisense oligonucleotides were designed targeting human Complement Factor B (CFB) nucleic acid and were tested for their effects on CFB mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 5,000 nM antisense oligonucleotide. After a treatment period of approximately 24 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The newly designed chimeric antisense oligonucleotides in the Tables below were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human CFB mRNA, designated herein as SEQ ID NO: 1 (GENBANK Accession No. NM_001710.5) or the human CFB genomic sequence, designated herein as SEQ ID NO: 2 (GENBANK Accession No. NT_007592.15 truncated from nucleotides 31852000 to 31861000), or both. 'n/a' indicates that the antisense oligonucleotide does not target that particular gene sequence with 100% complementarity. In case the sequence alignment for a target gene in a particular table is not shown, it is understood that none of the oligonucleotides presented in that table align with 100% complementarity with that target gene.

TABLE 130

Inhibition of CFB mRNA by 5-10-5 MOE gapmers targeting SEQ ID NO: 1

| ISIS NO | SEQ ID NO: 1 start site | SEQ ID NO: 1 stop site | Target Region | Sequence | % inhibition | SEQ ID NO: |
|---|---|---|---|---|---|---|
| 588570 | 150 | 169 | Exon 1 | TGGTCACATTCCCTTCCCCT | 54 | 396 |
| 588571 | 152 | 171 | Exon 1 | CCTGGTCACATTCCCTTCCC | 63 | 397 |
| 532614 | 154 | 173 | Exon 1 | GACCTGGTCACATTCCCTTC | 64 | 12 |
| 588572 | 156 | 175 | Exon 1 | TAGACCTGGTCACATTCCCT | 62 | 398 |
| 588573 | 158 | 177 | Exon 1 | CCTAGACCTGGTCACATTCC | 53 | 399 |
| 588566 | 2189 | 2208 | Exon 15 | CCTTCCGAGTCAGCTTTTTC | 60 | 400 |
| 588567 | 2191 | 2210 | Exon 15 | CTCCTTCCGAGTCAGCTTTT | 61 | 401 |
| 532770 | 2193 | 2212 | Exon 15 | ACCTCCTTCCGAGTCAGCTT | 77 | 198 |
| 588568 | 2195 | 2214 | Exon 15 | AGACCTCCTTCCGAGTCAGC | 72 | 402 |
| 588569 | 2197 | 2216 | Exon 15 | GTAGACCTCCTTCCGAGTCA | 46 | 403 |
| 588574 | 2453 | 2472 | Exon 18 | TTTGCCGCTTCTGGTTTTTG | 46 | 404 |
| 588575 | 2455 | 2474 | Exon 18 | CTTTTGCCGCTTCTGGTTTT | 41 | 405 |
| 532800 | 2457 | 2476 | Exon 18 | TGCTTTTGCCGCTTCTGGTT | 69 | 228 |
| 588576 | 2459 | 2478 | Exon 18 | CCTGCTTTTGCCGCTTCTGG | 61 | 406 |
| 588577 | 2461 | 2480 | Exon 18 | TACCTGCTTTTGCCGCTTCT | 51 | 407 |
| 516350 | 2550 | 2569 | Exon 18 | AGAAAACCCAAATCCTCATC | 71 | 408 |
| 588509 | 2551 | 2570 | Exon 18 | TAGAAAACCCAAATCCTCAT | 58 | 409 |
| 588510 | 2552 | 2571 | Exon 18 | ATAGAAAACCCAAATCCTCA | 57 | 410 |
| 588511 | 2553 | 2572 | Exon 18 | TATAGAAAACCCAAATCCTC | 57 | 411 |
| 588512 | 2554 | 2573 | Exon 18 | TTATAGAAAACCCAAATCCT | 44 | 412 |
| 588513 | 2555 | 2574 | Exon 18 | CTTATAGAAAACCCAAATCC | 37 | 413 |
| 588514 | 2556 | 2575 | Exon 18 | CCTTATAGAAAACCCAAATC | 50 | 414 |
| 588515 | 2557 | 2576 | Exon 18 | CCCTTATAGAAAACCCAAAT | 45 | 415 |
| 588516 | 2558 | 2577 | Exon 18 | CCCCTTATAGAAAACCCAAA | 60 | 416 |
| 588517 | 2559 | 2578 | Exon 18 | ACCCCTTATAGAAAACCCAA | 67 | 417 |
| 588518 | 2560 | 2579 | Exon 18 | AACCCCTTATAGAAAACCCA | 57 | 418 |
| 588519 | 2561 | 2580 | Exon 18 | AAACCCCTTATAGAAAACCC | 61 | 419 |
| 588520 | 2562 | 2581 | Exon 18 | GAAACCCCTTATAGAAAACC | 27 | 420 |
| 588521 | 2563 | 2582 | Exon 18 | GGAAACCCCTTATAGAAAAC | 25 | 421 |
| 588522 | 2564 | 2583 | Exon 18 | AGGAAACCCCTTATAGAAAA | 36 | 422 |
| 588523 | 2565 | 2584 | Exon 18 | CAGGAAACCCCTTATAGAAA | 36 | 423 |
| 588524 | 2566 | 2585 | Exon 18 | GCAGGAAACCCCTTATAGAA | 46 | 424 |
| 588525 | 2567 | 2586 | Exon 18 | AGCAGGAAACCCCTTATAGA | 38 | 425 |
| 588526 | 2568 | 2587 | Exon 18 | CAGCAGGAAACCCCTTATAG | 47 | 426 |
| 588527 | 2569 | 2588 | Exon 18 | CCAGCAGGAAACCCCTTATA | 68 | 427 |
| 588528 | 2570 | 2589 | Exon 18 | TCCAGCAGGAAACCCCTTAT | 63 | 428 |
| 532809 | 2571 | 2590 | Exon 18 | GTCCAGCAGGAAACCCCTTA | 85 | 237 |

TABLE 130-continued

Inhibition of CFB mRNA by 5-10-5 MOE gapmers targeting SEQ ID NO: 1

| ISIS NO | SEQ ID NO: 1 start site | SEQ ID NO: 1 stop site | Target Region | Sequence | % inhibition | SEQ ID NO: |
|---|---|---|---|---|---|---|
| 588529 | 2572 | 2591 | Exon 18 | TGTCCAGCAGGAAACCCCTT | 76 | 429 |
| 588530 | 2573 | 2592 | Exon 18 | CTGTCCAGCAGGAAACCCCT | 74 | 430 |
| 588531 | 2574 | 2593 | Exon 18 | CCTGTCCAGCAGGAAACCCC | 75 | 431 |
| 588532 | 2575 | 2594 | Exon 18 | CCCTGTCCAGCAGGAAACCC | 73 | 432 |
| 588533 | 2576 | 2595 | Exon 18 | CCCCTGTCCAGCAGGAAACC | 82 | 433 |
| 532810 | 2577 | 2596 | Exon 18 | GCCCCTGTCCAGCAGGAAAC | 88 | 238 |
| 588534 | 2578 | 2597 | Exon 18 | CGCCCCTGTCCAGCAGGAAA | 86 | 434 |
| 588535 | 2579 | 2598 | Exon 18 | ACGCCCCTGTCCAGCAGGAA | 86 | 435 |
| 588536 | 2580 | 2599 | Exon 18 | CACGCCCCTGTCCAGCAGGA | 93 | 436 |
| 588537 | 2581 | 2600 | Exon 18 | CCACGCCCCTGTCCAGCAGG | 92 | 437 |
| 588538 | 2582 | 2601 | Exon 18 | CCCACGCCCCTGTCCAGCAG | 94 | 438 |
| 588539 | 2583 | 2602 | Exon 18 | TCCCACGCCCCTGTCCAGCA | 96 | 439 |
| 588540 | 2584 | 2603 | Exon 18 | ATCCCACGCCCCTGTCCAGC | 88 | 440 |
| 588541 | 2585 | 2604 | Exon 18 | AATCCCACGCCCCTGTCCAG | 79 | 441 |
| 588542 | 2586 | 2605 | Exon 18 | CAATCCCACGCCCCTGTCCA | 83 | 442 |
| 588543 | 2587 | 2606 | Exon 18 | TCAATCCCACGCCCCTGTCC | 86 | 443 |
| 588544 | 2588 | 2607 | Exon 18 | TTCAATCCCACGCCCCTGTC | 90 | 444 |
| 588545 | 2589 | 2608 | Exon 18 | ATTCAATCCCACGCCCCTGT | 92 | 445 |
| 588546 | 2590 | 2609 | Exon 18 | AATTCAATCCCACGCCCCTG | 92 | 446 |
| 588547 | 2591 | 2610 | Exon 18 | TAATTCAATCCCACGCCCCT | 88 | 447 |
| 588548 | 2592 | 2611 | Exon 18 | TTAATTCAATCCCACGCCCC | 93 | 448 |
| 588549 | 2593 | 2612 | Exon 18 | TTTAATTCAATCCCACGCCC | 88 | 449 |
| 588550 | 2594 | 2613 | Exon 18 | TTTTAATTCAATCCCACGCC | 89 | 450 |
| 588551 | 2595 | 2614 | Exon 18 | GTTTTAATTCAATCCCACGC | 94 | 451 |
| 588552 | 2596 | 2615 | Exon 18 | TGTTTTAATTCAATCCCACG | 93 | 452 |
| 588553 | 2597 | 2616 | Exon 18 | CTGTTTTAATTCAATCCCAC | 96 | 453 |
| 588554 | 2598 | 2617 | Exon 18 | GCTGTTTTAATTCAATCCCA | 98 | 454 |
| 532811 | 2599 | 2618 | Exon 18 | AGCTGTTTTAATTCAATCCC | 97 | 239 |
| 532811 | 2599 | 2618 | Exon 18 | AGCTGTTTTAATTCAATCCC | 95 | 239 |
| 588555 | 2600 | 2619 | Exon 18 | CAGCTGTTTTAATTCAATCC | 93 | 455 |
| 588556 | 2601 | 2620 | Exon 18 | GCAGCTGTTTTAATTCAATC | 96 | 456 |
| 588557 | 2602 | 2621 | Exon 18 | CGCAGCTGTTTTAATTCAAT | 98 | 457 |
| 588558 | 2603 | 2622 | Exon 18 | TCGCAGCTGTTTTAATTCAA | 95 | 458 |
| 532917 | 2604 | 2623 | Exon 18 | GTCGCAGCTGTTTTAATTCA | 97 | 317 |
| 588559 | 2605 | 2624 | Exon 18 | TGTCGCAGCTGTTTTAATTC | 95 | 459 |
| 588560 | 2606 | 2625 | Exon 18 | TTGTCGCAGCTGTTTTAATT | 92 | 460 |

TABLE 130-continued

Inhibition of CFB mRNA by 5-10-5 MOE gapmers targeting SEQ ID NO: 1

| ISIS NO | SEQ ID NO: 1 start site | SEQ ID NO: 1 stop site | Target Region | Sequence | % inhibition | SEQ ID NO: |
|---|---|---|---|---|---|---|
| 588561 | 2607 | 2626 | Exon 18 | GTTGTCGCAGCTGTTTTAAT | 93 | 461 |
| 532952 | 2608 | 2627 | Exon 18 | TGTTGTCGCAGCTGTTTTAA | 88 | 395 |
| 588562 | 2609 | 2628 | Exon 18/ Repeat | TTGTTGTCGCAGCTGTTTTA | 90 | 462 |
| 588563 | 2610 | 2629 | Exon 18/ Repeat | TTTGTTGTCGCAGCTGTTTT | 89 | 463 |
| 588564 | 2611 | 2630 | Exon 18/ Repeat | TTTTGTTGTCGCAGCTGTTT | 92 | 464 |
| 588565 | 2612 | 2631 | Exon 18/ Repeat | TTTTTGTTGTCGCAGCTGTT | 88 | 465 |

TABLE 131

Inhibition of CFB mRNA by 5-10-5 MOE gapmers targeting SEQ ID NO: 1 or SEQ ID NO: 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 588685 | n/a | n/a | Exon 1 | GGATCCAGCTCACTCCCCTG | 48 | 1596 | 1615 | 466 |
| 588686 | n/a | n/a | Exon 1 | AAATAAGGATCCAGCTCACT | 29 | 1602 | n/a | 467 |
| 588688 | n/a | n/a | Exon 1 | GACCAGAAATAAGGATCCAG | 58 | 1608 | 1627 | 468 |
| 588690 | n/a | n/a | Exon 1 | CTTAGGGACCAGAAATAAGG | 45 | 1614 | 1633 | 469 |
| 588692 | n/a | n/a | Exon 1 | CACCCACTTAGGGACCAGAA | 36 | 1620 | 1639 | 470 |
| 588694 | n/a | n/a | Exon 1 | ACCACCCACTTAGGGACCAG | 47 | 1622 | 1641 | 471 |
| 588696 | n/a | n/a | Exon 1 | AGGTCCAGGACTCTCCCCTT | 96 | 1685 | 1704 | 472 |
| 588698 | n/a | n/a | Exon 1 | AAGGTCCAGGACTCTCCCCT | 96 | 1686 | 1705 | 473 |
| 588700 | n/a | n/a | Exon 1 | AAACTGCAGAAGTCCCACCC | 2 | 1716 | 1735 | 474 |
| 588586 | 30 | 49 | Exon 1 | GGAGGGCCCCGCTGAGCTGC | 59 | 1751 | 1770 | 475 |
| 588587 | 48 | 67 | Exon 1 | TCCCGGAACATCCAAGCGGG | 45 | 1769 | 1788 | 476 |
| 588588 | 56 | 75 | Exon 1 | CATCACTTTCCCGGAACATC | 39 | 1777 | n/a | 477 |
| 588589 | 151 | 170 | Exon 1 | CTGGTCACATTCCCTTCCCC | 29 | 1872 | 1891 | 478 |
| 588590 | 157 | 176 | Exon 1 | CTAGACCTGGTCACATTCCC | 47 | 1878 | 1897 | 479 |
| 588591 | 339 | 358 | Exon 1-2 Junction | GGAGTGGTGGTCACACCTCC | 44 | n/a | n/a | 480 |
| 588592 | 384 | 403 | Exon 2 | ACCCCCTCCAGAGAGCAGGA | 43 | 2192 | 2211 | 481 |
| 588593 | 390 | 409 | Exon 2 | ATCTCTACCCCCTCCAGAGA | 34 | 2198 | 2217 | 482 |
| 588594 | 467 | 486 | Exon 2 | GGTACGGGTAGAAGCCAGAA | 17 | 2275 | 2294 | 483 |
| 588595 | 671 | 690 | Exon 3 | GGAGAGTGTAACCGTCATAG | 37 | 2879 | 2898 | 484 |
| 588596 | 689 | 708 | Exon 3 | TGCGATTGGCAGAGCCCCGG | 18 | 2897 | 2916 | 485 |
| 588597 | 695 | 714 | Exon 3 | GGCAGGTGCGATTGGCAGAG | 32 | 2903 | 2922 | 486 |
| 588598 | 707 | 726 | Exon 3 | GGCCATTCACTTGGCAGGTG | 45 | 2915 | 2934 | 487 |

TABLE 131-continued

Inhibition of CFB mRNA by 5-10-5 MOE gapmers targeting SEQ ID NO: 1 or SEQ ID NO: 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 588599 | 738 | 757 | Exon 3 | TTGTCACAGATCGCTGTCTG | 52 | 2946 | 2965 | 488 |
| 588600 | 924 | 943 | Exon 4-5 Junction | AAGGAGTCTTGGCAGGAAGG | 39 | n/a | n/a | 489 |
| 588601 | 931 | 950 | Exon 4-5 Junction | GTACATGAAGGAGTCTTGGC | 37 | n/a | n/a | 490 |
| 588602 | 959 | 978 | Exon 5 | AAGCTTCGGCCACCTCTTGA | 21 | 3542 | 3561 | 491 |
| 588603 | 1089 | 1108 | Exon 6 | CCATCTAGCACCAGGTAGAT | 22 | 3773 | 3792 | 492 |
| 588604 | 1108 | 1127 | Exon 6 | GGCCCCAATGCTGTCTGATC | 21 | 3792 | 3811 | 493 |
| 588606 | 1150 | 1169 | Exon 6 | AATTAAGTTGACTAGACACT | 56 | 3834 | 3853 | 494 |
| 588608 | 1162 | 1181 | Exon 6-7 Junction | TGCCACCTTCTCAATTAAGT | 50 | | 19 | 495 |
| 588578 | 1167 | 1186 | Exon 6-7 Junction | TAACTTGCCACCTTCTCAAT | 23 | n/a | n/a | 496 |
| 588579 | 1169 | 1188 | Exon 6-7 Junction | CATAACTTGCCACCTTCTCA | 23 | n/a | n/a | 497 |
| 532692 | 1171 | 1190 | Exon 6-7 Junction | ACCATAACTTGCCACCTTCT | 15 | n/a | n/a | 90 |
| 588580 | 1173 | 1192 | Exon 6-7 Junction | ACACCATAACTTGCCACCTT | 16 | n/a | n/a | 498 |
| 588581 | 1175 | 1194 | Exon 6-7 Junction | TCACACCATAACTTGCCACC | 14 | 4151 | 4170 | 499 |
| 588610 | 1319 | 1338 | Exon 8 | TAGTCCCTGACTTCAACTTG | 50 | 4612 | 4631 | 500 |
| 588612 | 1325 | 1344 | Exon 8 | TGGTGTTAGTCCCTGACTTC | 47 | 4618 | 4637 | 501 |
| 588614 | 1396 | 1415 | Exon 8 | GCGGTTCCAGCCTTCAGGAG | 47 | 4689 | 4708 | 502 |
| 588616 | 1421 | 1440 | Exon 8 | TCATGAGGATGATGACATGG | 51 | 4714 | 4733 | 503 |
| 588618 | 1446 | 1465 | Exon 9 | CCGCCCATGTTGTGCAATCC | 18 | 5020 | 5039 | 504 |
| 588620 | 1458 | 1477 | Exon 9 | GTAATTGGGTCCCCGCCCAT | 40 | 5032 | 5051 | 505 |
| 588623 | 1482 | 1501 | Exon 9 | AAGTCCCGGATCTCATCAAT | 40 | 5056 | 5075 | 506 |
| 588624 | 1542 | 1561 | Exon 9-10 Junction | AACACATAGACATCCAGATA | 45 | n/a | n/a | 507 |
| 588626 | 1585 | 1604 | Exon 10 | CAAAGCATTGATGTTCACTT | 43 | 5234 | 5253 | 508 |
| 588628 | 1621 | 1640 | Exon 10 | TTTGAACACATGTTGCTCAT | 45 | 5270 | 5289 | 509 |
| 588631 | 1646 | 1665 | Exon 10 | CTTCCAGGTTTTCCATATCC | 53 | 5295 | 5314 | 510 |
| 588632 | 1647 | 1666 | Exon 10 | TCTTCCAGGTTTTCCATATC | 56 | 5296 | 5315 | 511 |
| 588634 | 1689 | 1708 | Exon 11 | AGACTCAGAGACTGGCTTTC | 35 | 5830 | 5849 | 512 |
| 588636 | 1749 | 1768 | Exon 11 | GCCTGCCATGGTTGCTTGTG | 55 | 5890 | 5909 | 513 |
| 588638 | 1763 | 1782 | Exon 11 | TGACTGAGATCTTGGCCTGC | 78 | 5904 | 5923 | 514 |
| 588640 | 1912 | 1931 | Exon 13 | TTCTATCTCCAGGTCCCGCT | 95 | 6406 | 6425 | 515 |
| 588642 | 1982 | 2001 | Exon 13 | AGTCATAAAATTCAGGAATT | 44 | 6476 | 6495 | 516 |
| 588645 | 2073 | 2092 | Exon 14 | CGAGTTGTTCCCTCGGTGCA | 40 | 6662 | 6681 | 517 |

TABLE 131-continued

Inhibition of CFB mRNA by 5-10-5 MOE gapmers targeting SEQ ID NO: 1 or SEQ ID NO: 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 588646 | 2085 | 2104 | Exon 14 | AGCCTCAAAGCTCGAGTTGT | 57 | 6674 | 6693 | 518 |
| 588648 | 2091 | 2110 | Exon 14 | GGAGGAAGCCTCAAAGCTCG | 48 | 6680 | 6699 | 519 |
| 588651 | 2097 | 2116 | Exon 14 | GTAGTTGGAGGAAGCCTCAA | 40 | 6686 | 6705 | 520 |
| 588652 | 2103 | 2122 | Exon 14 | CAAGTGGTAGTTGGAGGAAG | 43 | 6692 | 6711 | 521 |
| 588654 | 2166 | 2185 | Exon 15 | TCCTCAGACACAAACAGAGC | 13 | 6954 | 6973 | 522 |
| 588656 | 2172 | 2191 | Exon 15 | TTCTCCTCCTCAGACACAAA | 55 | 6960 | 6979 | 523 |
| 588658 | 2196 | 2215 | Exon 15 | TAGACCTCCTTCCGAGTCAG | 44 | 6984 | 7003 | 524 |
| 588660 | 2202 | 2221 | Exon 15 | TTGATGTAGACCTCCTTCCG | 50 | 6990 | 7009 | 525 |
| 588582 | 2219 | 2238 | Exon 15-16 Junction | CTTTCTTATCCCCATTCTTG | 19 | n/a | n/a | 526 |
| 588583 | 2221 | 2240 | Exon 15-16 Junction | GCCTTTCTTATCCCCATTCT | 14 | n/a | n/a | 527 |
| 532775 | 2223 | 2242 | Exon 15-16 Junction | CTGCCTTTCTTATCCCCATT | 3 | n/a | n/a | 203 |
| 588584 | 2225 | 2244 | Exon 15-16 Junction | AGCTGCCTTTCTTATCCCCA | 18 | n/a | n/a | 528 |
| 588662 | 2226 | 2245 | Exon 15-16 Junction | CAGCTGCCTTTCTTATCCCC | 27 | n/a | n/a | 529 |
| 588585 | 2227 | 2246 | Exon 15-16 Junction | ACAGCTGCCTTTCTTATCCC | 59 | n/a | n/a | 530 |
| 588664 | 2238 | 2257 | Exon 16 | GCATCTCTCTCACAGCTGCC | 49 | 7122 | 7141 | 531 |
| 588666 | 2276 | 2295 | Exon 16 | AGATGTCCTTGACTTTGTCA | 41 | 7160 | 7179 | 532 |
| 588668 | 2330 | 2349 | Exon 16 | CAGCATAGGGACTCACTCCT | 41 | 7214 | 7233 | 533 |
| 588670 | 2361 | 2380 | Exon 16-17 Junction | CCGCCAGAATCACCTCTGCA | 43 | n/a | n/a | 534 |
| 588672 | 2397 | 2416 | Exon 17 | TGAATGAAACGACTTCTCTT | 52 | 7362 | 7381 | 535 |
| 588674 | 2430 | 2449 | Exon 18 | ACATCCACTACTCCCCAGCT | 39 | 7665 | 7684 | 536 |
| 588676 | 2448 | 2467 | Exon 18 | CGCTTCTGGTTTTGCAGAC | 69 | 7683 | 7702 | 537 |
| 588678 | 2454 | 2473 | Exon 18 | TTTTGCCGCTTCTGGTTTTT | 46 | 7689 | 7708 | 538 |
| 588680 | 2466 | 2485 | Exon 18 | GCAGGTACCTGCTTTTGCCG | 47 | 7701 | 7720 | 539 |
| 588682 | 2532 | 2551 | Exon 18 | TCTTGGAGTTTCTCCTTCAG | 58 | 7767 | 7786 | 540 |
| 532811 | 2599 | 2618 | Exon 18 | AGCTGTTTTAATTCAATCCC | 10 | 7834 | 7853 | 239 |
| 532917 | 2604 | 2623 | Exon 18 | GTCGCAGCTGTTTTAATTCA | 11 | 7839 | 7858 | 317 |

Example 118: Antisense Inhibition of Human Complement Factor B (CFB) in HepG2 Cells by MOE Gapmers Antisense oligonucleotides were designed targeting human Complement Factor B (CFB) nucleic acid and were tested for their effects on CFB mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 3,000 nM antisense oligonucleotide. After a treatment period of approximately 24 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The newly designed chimeric antisense oligonucleotides in the Tables below were designed as 4-8-5 MOE, 5-9-5 MOE, 5-10-5 MOE, 3-10-4 MOE, 3-10-7 MOE, 6-7-6-MOE, 6-8-6 MOE, or 5-7-5 MOE gapmers, or as deoxy, MOE, and (S)-cEt oligonucleotides.

The 4-8-5 MOE gapmers are 17 nucleosides in length, wherein the central gap segment comprises of eight 2'-deoxynucleosides and is flanked by wing segments on the 5' direction and the 3' direction comprising four and five nucleosides respectively. The 5-9-5 MOE gapmers are 19 nucleosides in length, wherein the central gap segment comprises of nine 2'-deoxynucleosides and is flanked by wing segments on the 5' direction and the 3' direction comprising five nucleosides each. The 5-10-5 MOE gapmers are 20 nucleosides in length, wherein the central gap segment comprises of ten 2'-deoxynucleosides and is flanked by wing segments on the 5' direction and the 3' direction comprising five nucleosides each. The 5-7-5 MOE gapmers are 17 nucleosides in length, wherein the central gap segment comprises of seven 2'-deoxynucleosides and is flanked by wing segments on the 5' direction and the 3' direction comprising five nucleosides each. The 3-10-4 MOE gapmers are 17 nucleosides in length, wherein the central gap segment comprises of ten 2'-deoxynucleosides and is flanked by wing segments on the 5' direction and the 3' direction comprising three and four nucleosides respectively. The 3-10-7 MOE gapmers are 20 nucleosides in length, wherein the central gap segment comprises of ten 2'-deoxynucleosides and is flanked by wing segments on the 5' direction and the 3' direction comprising three and seven nucleosides respectively. The 6-7-6 MOE gapmers are 19 nucleosides in length, wherein the central gap segment comprises of seven 2'-deoxynucleosides and is flanked by wing segments on the 5' direction and the 3' direction comprising six nucleosides each. The 6-8-6 MOE gapmers are 20 nucleosides in length, wherein the central gap segment comprises of eight 2'-deoxynucleosides and is flanked by wing segments on the 5' direction and the 3' direction comprising six nucleosides each. The internucleoside linkages throughout each gapmer are phosphorothioate (P=S) linkages. All cytosine residues throughout each gapmer are 5-methylcytosines.

The deoxy, MOE and (S)-cEt oligonucleotides are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; 'd' indicates deoxyribose; and 'e' indicates a MOE modification.

"Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human CFB mRNA, designated herein as SEQ ID NO: 1 (GENBANK Accession No. NM_001710.5) or the human CFB genomic sequence, designated herein as SEQ ID NO: 2 (GENBANK Accession No. NT_007592.15 truncated from nucleotides 31852000 to 31861000), or both. 'n/a' indicates that the antisense oligonucleotide does not target that particular gene sequence with 100% complementarity.

TABLE 132

Inhibition of CFB mRNA by deoxy, MOE and (S)-cEt oligonucleotides targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 532811 | 2599 | 2618 | Exon 18 | AGCTGTTTTAATTCAATCCC | 10 | 7834 | 7853 | eeeeedddddddddeeeee | 239 |
| 588884 | 48 | 63 | Exon 1 | GGAACATCCAAGCGGG | 79 | 1769 | 1784 | eekddddddddddke | 541 |
| 588872 | 154 | 169 | Exon 1 | TGGTCACATTCCCTTC | 91 | 1875 | 1890 | eekddddddddddke | 542 |
| 588873 | 156 | 171 | Exon 1 | CCTGGTCACATTCCCT | 91 | 1877 | 1892 | eekddddddddddke | 543 |
| 588874 | 158 | 173 | Exon 1 | GACCTGGTCACATTCC | 91 | 1879 | 1894 | eekddddddddddke | 544 |
| 588878 | 1171 | 1186 | Exon 6-7 Junction | TAACTTGCCACCTTCT | 92 | n/a | n/a | eekddddddddddke | 545 |
| 588879 | 1173 | 1188 | Exon 6-7 Junction | CATAACTTGCCACCTT | 94 | n/a | n/a | eekddddddddddke | 546 |
| 588880 | 1175 | 1190 | Exon 6-7 Junction | ACCATAACTTGCCACC | 89 | 4151 | 4166 | eekddddddddddke | 547 |
| 588869 | 2193 | 2208 | Exon 15 | CCTTCCGAGTCAGCTT | 17 | 6981 | 6996 | eekddddddddddke | 548 |
| 588870 | 2195 | 2210 | Exon 15 | CTCCTTCCGAGTCAGC | 78 | 6983 | 6998 | eekddddddddddke | 549 |
| 588871 | 2197 | 2212 | Exon 15 | ACCTCCTTCCGAGTCA | 80 | 6985 | 7000 | eekddddddddddke | 550 |
| 588881 | 2223 | 2238 | Exon 15-16 Junction | CTTTCTTATCCCCATT | 93 | n/a | n/a | eekddddddddddke | 551 |
| 588882 | 2225 | 2240 | Exon 15-16 Junction | GCCTTTCTTATCCCCA | 88 | n/a | n/a | eekddddddddddke | 552 |

TABLE 132-continued

Inhibition of CFB mRNA by deoxy, MOE and (S)-cEt oligonucleotides targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 588883 | 2227 | 2242 | Exon 15-16 Junction | CTGCCTTTCTTATCCC | 90 | n/a | n/a | eekddddddddddke | 553 |
| 588875 | 2457 | 2472 | Exon 18 | TTTGCCGCTTCTGGTT | 81 | 7692 | 7707 | eekddddddddddke | 554 |
| 588876 | 2459 | 2474 | Exon 18 | CTTTTGCCGCTTCTGG | 95 | 7694 | 7709 | eekddddddddddke | 555 |
| 588877 | 2461 | 2476 | Exon 18 | TGCTTTTGCCGCTTCT | 91 | 7696 | 7711 | eekddddddddddke | 556 |
| 588807 | 2551 | 2566 | Exon 18 | AAACCCAAATCCTCAT | 82 | 7786 | 7801 | eekddddddddddke | 557 |
| 588808 | 2553 | 2568 | Exon 18 | GAAACCCAAATCCTC | 69 | 7788 | 7803 | eekddddddddddke | 558 |
| 588809 | 2555 | 2570 | Exon 18 | TAGAAACCCAAATCC | 51 | 7790 | 7805 | eekddddddddddke | 559 |
| 588810 | 2556 | 2571 | Exon 18 | ATAGAAACCCAAATC | 23 | 7791 | 7806 | eekddddddddddke | 560 |
| 588811 | 2559 | 2574 | Exon 18 | CTTATAGAAACCCAA | 13 | 7794 | 7809 | eekddddddddddke | 561 |
| 588812 | 2560 | 2575 | Exon 18 | CCTTATAGAAAACCCA | 29 | 7795 | 7810 | eekddddddddddke | 562 |
| 588813 | 2561 | 2576 | Exon 18 | CCCTTATAGAAAACCC | 53 | 7796 | 7811 | eekddddddddddke | 563 |
| 588814 | 2562 | 2577 | Exon 18 | CCCCTTATAGAAAACC | 86 | 7797 | 7812 | eekddddddddddke | 564 |
| 588815 | 2563 | 2578 | Exon 18 | ACCCCTTATAGAAAAC | 76 | 7798 | 7813 | eekddddddddddke | 565 |
| 588816 | 2564 | 2579 | Exon 18 | AACCCCTTATAGAAAA | 33 | 7799 | 7814 | eekddddddddddke | 566 |
| 588817 | 2565 | 2580 | Exon 18 | AAACCCCTTATAGAAA | 48 | 7800 | 7815 | eekddddddddddke | 567 |
| 588818 | 2566 | 2581 | Exon 18 | GAAACCCCTTATAGAA | 44 | 7801 | 7816 | eekddddddddddke | 568 |
| 588819 | 2567 | 2582 | Exon 18 | GGAAACCCCTTATAGA | 74 | 7802 | 7817 | eekddddddddddke | 569 |
| 588820 | 2568 | 2583 | Exon 18 | AGGAAACCCCTTATAG | 68 | 7803 | 7818 | eekddddddddddke | 570 |
| 588821 | 2569 | 2584 | Exon 18 | CAGGAAACCCCTTATA | 45 | 7804 | 7819 | eekddddddddddke | 571 |
| 588822 | 2570 | 2585 | Exon 18 | GCAGGAAACCCCTTAT | 50 | 7805 | 7820 | eekddddddddddke | 572 |
| 588823 | 2571 | 2586 | Exon 18 | AGCAGGAAACCCCTTA | 54 | 7806 | 7821 | eekddddddddddke | 573 |
| 588824 | 2572 | 2587 | Exon 18 | CAGCAGGAAACCCCTT | 35 | 7807 | 7822 | eekddddddddddke | 574 |
| 588825 | 2573 | 2588 | Exon 18 | CCAGCAGGAAACCCCT | 11 | 7808 | 7823 | eekddddddddddke | 575 |
| 588826 | 2574 | 2589 | Exon 18 | TCCAGCAGGAAACCCC | 19 | 7809 | 7824 | eekddddddddddke | 576 |
| 588827 | 2575 | 2590 | Exon 18 | GTCCAGCAGGAAACCC | 42 | 7810 | 7825 | eekddddddddddke | 577 |
| 588828 | 2576 | 2591 | Exon 18 | TGTCCAGCAGGAAACC | 0 | 7811 | 7826 | eekddddddddddke | 578 |
| 588829 | 2577 | 2592 | Exon 18 | CTGTCCAGCAGGAAAC | 49 | 7812 | 7827 | eekddddddddddke | 579 |
| 588830 | 2578 | 2593 | Exon 18 | CCTGTCCAGCAGGAAA | 11 | 7813 | 7828 | eekddddddddddke | 580 |
| 588831 | 2579 | 2594 | Exon 18 | CCCTGTCCAGCAGGAA | 20 | 7814 | 7829 | eekddddddddddke | 581 |
| 588832 | 2580 | 2595 | Exon 18 | CCCCTGTCCAGCAGGA | 19 | 7815 | 7830 | eekddddddddddke | 582 |
| 588833 | 2581 | 2596 | Exon 18 | GCCCCTGTCCAGCAGG | 12 | 7816 | 7831 | eekddddddddddke | 583 |
| 588834 | 2582 | 2597 | Exon 18 | CGCCCCTGTCCAGCAG | 10 | 7817 | 7832 | eekddddddddddke | 584 |
| 588835 | 2583 | 2598 | Exon 18 | ACGCCCCTGTCCAGCA | 13 | 7818 | 7833 | eekddddddddddke | 585 |
| 588836 | 2584 | 2599 | Exon 18 | CACGCCCCTGTCCAGC | 13 | 7819 | 7834 | eekddddddddddke | 586 |
| 588837 | 2585 | 2600 | Exon 18 | CCACGCCCCTGTCCAG | 39 | 7820 | 7835 | eekddddddddddke | 587 |

TABLE 132-continued

Inhibition of CFB mRNA by deoxy, MOE and (S)-cEt oligonucleotides targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 588838 | 2586 | 2601 | Exon 18 | CCCACGCCCCTGTCCA | 54 | 7821 | 7836 | eekddddddddddke | 588 |
| 588839 | 2587 | 2602 | Exon 18 | TCCCACGCCCCTGTCC | 51 | 7822 | 7837 | eekddddddddddke | 589 |
| 588840 | 2588 | 2603 | Exon 18 | ATCCCACGCCCCTGTC | 65 | 7823 | 7838 | eekddddddddddke | 590 |
| 588841 | 2589 | 2604 | Exon 18 | AATCCCACGCCCCTGT | 59 | 7824 | 7839 | eekddddddddddke | 591 |
| 588842 | 2590 | 2605 | Exon 18 | CAATCCCACGCCCCTG | 70 | 7825 | 7840 | eekddddddddddke | 592 |
| 588843 | 2591 | 2606 | Exon 18 | TCAATCCCACGCCCCT | 0 | 7826 | 7841 | eekddddddddddke | 593 |
| 588844 | 2592 | 2607 | Exon 18 | TTCAATCCCACGCCCC | 48 | 7827 | 7842 | eekddddddddddke | 594 |
| 588845 | 2593 | 2608 | Exon 18 | ATTCAATCCCACGCCC | 46 | 7828 | 7843 | eekddddddddddke | 595 |
| 588846 | 2594 | 2609 | Exon 18 | AATTCAATCCCACGCC | 67 | 7829 | 7844 | eekddddddddddke | 596 |
| 588847 | 2595 | 2610 | Exon 18 | TAATTCAATCCCACGC | 75 | 7830 | 7845 | eekddddddddddke | 597 |
| 588848 | 2596 | 2611 | Exon 18 | TTAATTCAATCCCACG | 76 | 7831 | 7846 | eekddddddddddke | 598 |
| 588849 | 2597 | 2612 | Exon 18 | TTTAATTCAATCCCAC | 94 | 7832 | 7847 | eekddddddddddke | 599 |
| 588850 | 2598 | 2613 | Exon 18 | TTTTAATTCAATCCCA | 91 | 7833 | 7848 | eekddddddddddke | 600 |
| 588851 | 2599 | 2614 | Exon 18 | GTTTTAATTCAATCCC | 91 | 7834 | 7849 | eekddddddddddke | 601 |
| 588852 | 2600 | 2615 | Exon 18 | TGTTTTAATTCAATCC | 78 | 7835 | 7850 | eekddddddddddke | 602 |
| 588853 | 2601 | 2616 | Exon 18 | CTGTTTTAATTCAATC | 81 | 7836 | 7851 | eekddddddddddke | 603 |
| 588854 | 2602 | 2617 | Exon 18 | GCTGTTTTAATTCAAT | 63 | 7837 | 7852 | eekddddddddddke | 604 |
| 588855 | 2603 | 2618 | Exon 18 | AGCTGTTTTAATTCAA | 65 | 7838 | 7853 | eekddddddddddke | 605 |
| 588856 | 2604 | 2619 | Exon 18 | CAGCTGTTTTAATTCA | 76 | 7839 | 7854 | eekddddddddddke | 606 |
| 588857 | 2605 | 2620 | Exon 18 | GCAGCTGTTTTAATTC | 89 | 7840 | 7855 | eekddddddddddke | 607 |
| 588858 | 2606 | 2621 | Exon 18 | CGCAGCTGTTTTAATT | 89 | 7841 | 7856 | eekddddddddddke | 608 |
| 588859 | 2607 | 2622 | Exon 18 | TCGCAGCTGTTTTAAT | 89 | 7842 | 7857 | eekddddddddddke | 609 |
| 588860 | 2608 | 2623 | Exon 18 | GTCGCAGCTGTTTTAA | 76 | 7843 | 7858 | eekddddddddddke | 610 |
| 588861 | 2609 | 2624 | Exon 18 | TGTCGCAGCTGTTTTA | 87 | 7844 | 7859 | eekddddddddddke | 611 |
| 588862 | 2610 | 2625 | Exon 18 | TTGTCGCAGCTGTTTT | 85 | 7845 | 7860 | eekddddddddddke | 612 |
| 588863 | 2611 | 2626 | Exon 18 | GTTGTCGCAGCTGTTT | 87 | 7846 | 7861 | eekddddddddddke | 613 |
| 588864 | 2612 | 2627 | Exon 18 | TGTTGTCGCAGCTGTT | 67 | 7847 | 7862 | eekddddddddddke | 614 |
| 588865 | 2613 | 2628 | Exon 18 | TTGTTGTCGCAGCTGT | 51 | n/a | n/a | eekddddddddddke | 615 |
| 588866 | 2614 | 2629 | Exon 18 | TTTGTTGTCGCAGCTG | 95 | n/a | n/a | eekddddddddddke | 616 |
| 588867 | 2615 | 2630 | Exon 18 | TTTTGTTGTCGCAGCT | 92 | n/a | n/a | eekddddddddddke | 617 |
| 588868 | 2616 | 2631 | Exon 18 | TTTTTGTTGTCGCAGC | 66 | n/a | n/a | eekddddddddddke | 618 |

TABLE 133

Inhibition of CFB mRNA by 5-10-5 MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | SEQ ID NO: |
|---|---|---|---|---|---|---|---|---|
| 588685 | n/a | n/a | Exon 1 | GGATCCAGCTCACTCCCCTG | 14 | 1596 | 1615 | 466 |
| 588686 | n/a | n/a | Exon 1 | AAATAAGGATCCAGCTCACT | 2 | 1602 | 1621 | 467 |
| 588688 | n/a | n/a | Exon 1 | GACCAGAAATAAGGATCCAG | 3 | 1608 | 1627 | 468 |
| 588690 | n/a | n/a | Exon 1 | CTTAGGGACCAGAAATAAGG | 10 | 1614 | 1633 | 469 |
| 588692 | n/a | n/a | Exon 1 | CACCCACTTAGGGACCAGAA | 23 | 1620 | 1639 | 470 |
| 588694 | n/a | n/a | Exon 1 | ACCACCCACTTAGGGACCAG | 23 | 1622 | 1641 | 471 |
| 588696 | n/a | n/a | Exon 1 | AGGTCCAGGACTCTCCCCTT | 15 | 1685 | 1704 | 472 |
| 588698 | n/a | n/a | Exon 1 | AAGGTCCAGGACTCTCCCCT | 19 | 1686 | 1705 | 473 |
| 588700 | n/a | n/a | Exon 1 | AAACTGCAGAAGTCCCACCC | 16 | 1716 | 1735 | 474 |
| 588586 | 30 | 49 | Exon 1 | GGAGGGCCCCGCTGAGCTGC | 11 | 1751 | 1770 | 475 |
| 588587 | 48 | 67 | Exon 1 | TCCCGGAACATCCAAGCGGG | 14 | 1769 | 1788 | 476 |
| 588588 | 56 | 75 | Exon 1 | CATCACTTTCCCGGAACATC | 18 | 1777 | 1796 | 477 |
| 588589 | 151 | 170 | Exon 1 | CTGGTCACATTCCCTTCCCC | 59 | 1872 | 1891 | 478 |
| 588590 | 157 | 176 | Exon 1 | CTAGACCTGGTCACATTCCC | 59 | 1878 | 1897 | 479 |
| 588591 | 339 | 358 | Exon 1-2 Junction | GGAGTGGTGGTCACACCTCC | 45 | n/a | n/a | 480 |
| 588592 | 384 | 403 | Exon 2 | ACCCCCTCCAGAGAGCAGGA | 39 | 2192 | 2211 | 481 |
| 588593 | 390 | 409 | Exon 2 | ATCTCTACCCCCTCCAGAGA | 29 | 2198 | 2217 | 482 |
| 588594 | 467 | 486 | Exon 2 | GGTACGGGTAGAAGCCAGAA | 47 | 2275 | 2294 | 483 |
| 588595 | 671 | 690 | Exon 3 | GGAGAGTGTAACCGTCATAG | 44 | 2879 | 2898 | 484 |
| 588596 | 689 | 708 | Exon 3 | TGCGATTGGCAGAGCCCCGG | 43 | 2897 | 2916 | 638 |
| 588597 | 695 | 714 | Exon 3 | GGCAGGTGCGATTGGCAGAG | 34 | 2903 | 2922 | 486 |
| 588598 | 707 | 726 | Exon 3 | GGCCATTCACTTGGCAGGTG | 17 | 2915 | 2934 | 487 |
| 588599 | 738 | 757 | Exon 3 | TTGTCACAGATCGCTGTCTG | 37 | 2946 | 2965 | 488 |
| 588600 | 924 | 943 | Exon 3-4 Junction | AAGGAGTCTTGGCAGGAAGG | 18 | n/a | n/a | 489 |
| 588601 | 931 | 950 | Exon 3-4 Junction | GTACATGAAGGAGTCTTGGC | 32 | n/a | n/a | 490 |
| 588602 | 959 | 978 | Exon 5 | AAGCTTCGGCCACCTCTTGA | 45 | 3542 | 3561 | 491 |
| 588603 | 1089 | 1108 | Exon 6 | CCATCTAGCACCAGGTAGAT | 52 | 3773 | 3792 | 492 |
| 588604 | 1108 | 1127 | Exon 6 | GGCCCCAATGCTGTCTGATC | 39 | 3792 | 3811 | 493 |
| 588606 | 1150 | 1169 | Exon 6 | AATTAAGTTGACTAGACACT | 37 | 3834 | 3853 | 494 |
| 588608 | 1162 | 1181 | Exon 6-7 Junction | TGCCACCTTCTCAATTAAGT | 21 | n/a | n/a | 648 |
| 588578 | 1167 | 1186 | Exon 6-7 Junction | TAACTTGCCACCTTCTCAAT | 22 | n/a | n/a | 496 |
| 588579 | 1169 | 1188 | Exon 6-7 Junction | CATAACTTGCCACCTTCTCA | 21 | n/a | n/a | 497 |
| 532692 | 1171 | 1190 | Exon 6-7 Junction | ACCATAACTTGCCACCTTCT | 56 | n/a | n/a | 90 |

TABLE 133-continued

Inhibition of CFB mRNA by 5-10-5 MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | SEQ ID NO: |
|---|---|---|---|---|---|---|---|---|
| 588580 | 1173 | 1192 | Exon 6-7 Junction | ACACCATAACTTGCCACCTT | 50 | n/a | n/a | 498 |
| 588581 | 1175 | 1194 | Exon 7 | TCACACCATAACTTGCCACC | 50 | 4151 | 4170 | 499 |
| 588610 | 1319 | 1338 | Exon 8 | TAGTCCCTGACTTCAACTTG | 47 | 4612 | 4631 | 500 |
| 588612 | 1325 | 1344 | Exon 8 | TGGTGTTAGTCCCTGACTTC | 47 | 4618 | 4637 | 501 |
| 588614 | 1396 | 1415 | Exon 8 | GCGGTTCCAGCCTTCAGGAG | 51 | 4689 | 4708 | 502 |
| 588616 | 1421 | 1440 | Exon 8 | TCATGAGGATGATGACATGG | 18 | 4714 | 4733 | 503 |
| 588618 | 1446 | 1465 | Exon 9 | CCGCCCATGTTGTGCAATCC | 40 | 5020 | 5039 | 504 |
| 588620 | 1458 | 1477 | Exon 9 | GTAATTGGGTCCCCGCCCAT | 40 | 5032 | 5051 | 505 |
| 588623 | 1482 | 1501 | Exon 9 | AAGTCCCGGATCTCATCAAT | 45 | 5056 | 5075 | 506 |
| 588624 | 1542 | 1561 | Exon 9-10 Junction | AACACATAGACATCCAGATA | 43 | n/a | n/a | 507 |
| 588626 | 1585 | 1604 | Exon 10 | CAAAGCATTGATGTTCACTT | 45 | 5234 | 5253 | 508 |
| 588628 | 1621 | 1640 | Exon 10 | TTTGAACACATGTTGCTCAT | 53 | 5270 | 5289 | 509 |
| 588631 | 1646 | 1665 | Exon 10 | CTTCCAGGTTTTCCATATCC | 56 | 5295 | 5314 | 510 |
| 588632 | 1647 | 1666 | Exon 10 | TCTTCCAGGTTTTCCATATC | 35 | 5296 | 5315 | 511 |
| 588634 | 1689 | 1708 | Exon 11 | AGACTCAGAGACTGGCTTTC | 55 | 5830 | 5849 | 512 |
| 588636 | 1749 | 1768 | Exon 11 | GCCTGCCATGGTTGCTTGTG | 78 | 5890 | 5909 | 513 |
| 588638 | 1763 | 1782 | Exon 11 | TGACTGAGATCTTGGCCTGC | 95 | 5904 | 5923 | 514 |
| 588640 | 1912 | 1931 | Exon 13 | TTCTATCTCCAGGTCCCGCT | 44 | 6406 | 6425 | 515 |
| 588642 | 1982 | 2001 | Exon 13 | AGTCATAAAATTCAGGAATT | 40 | 6476 | 6495 | 516 |
| 588645 | 2073 | 2092 | Exon 14 | CGAGTTGTTCCCTCGGTGCA | 57 | 6662 | 6681 | 517 |
| 588646 | 2085 | 2104 | Exon 14 | AGCCTCAAAGCTCGAGTTGT | 48 | 6674 | 6693 | 518 |
| 588648 | 2091 | 2110 | Exon 14 | GGAGGAAGCCTCAAAGCTCG | 40 | 6680 | 6699 | 519 |
| 588651 | 2097 | 2116 | Exon 14 | GTAGTTGGAGGAAGCCTCAA | 43 | 6686 | 6705 | 520 |
| 588652 | 2103 | 2122 | Exon 14 | CAAGTGGTAGTTGGAGGAAG | 13 | 6692 | 6711 | 521 |
| 588654 | 2166 | 2185 | Exon 15 | TCCTCAGACACAAACAGAGC | 55 | 6954 | 6973 | 522 |
| 588656 | 2172 | 2191 | Exon 15 | TTCTCCTCCTCAGACACAAA | 44 | 6960 | 6979 | 523 |
| 588658 | 2196 | 2215 | Exon 15 | TAGACCTCCTTCCGAGTCAG | 50 | 6984 | 7003 | 524 |
| 588660 | 2202 | 2221 | Exon 15 | TTGATGTAGACCTCCTTCCG | 27 | 6990 | 7009 | 525 |
| 588582 | 2219 | 2238 | Exon 15-16 Junction | CTTTCTTATCCCCATTCTTG | 49 | n/a | n/a | 526 |
| 588583 | 2221 | 2240 | Exon 15-16 Junction | GCCTTTCTTATCCCCATTCT | 41 | n/a | n/a | 527 |
| 532775 | 2223 | 2242 | Exon 15-16 Junction | CTGCCTTTCTTATCCCCATT | 41 | n/a | n/a | 203 |

TABLE 133-continued

Inhibition of CFB mRNA by 5-10-5 MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | SEQ ID NO: |
|---|---|---|---|---|---|---|---|---|
| 588584 | 2225 | 2244 | Exon 15-16 Junction | AGCTGCCTTTCTTATCCCCA | 43 | n/a | n/a | 528 |
| 588662 | 2226 | 2245 | Exon 15-16 Junction | CAGCTGCCTTTCTTATCCCC | 52 | n/a | n/a | 529 |
| 588585 | 2227 | 2246 | Exon 15-16 Junction | ACAGCTGCCTTTCTTATCCC | 39 | n/a | n/a | 530 |
| 588664 | 2238 | 2257 | Exon 16 | GCATCTCTCTCACAGCTGCC | 69 | 7122 | 7141 | 531 |
| 588666 | 2276 | 2295 | Exon 16 | AGATGTCCTTGACTTTGTCA | 46 | 7160 | 7179 | 532 |
| 588668 | 2330 | 2349 | Exon 16 | CAGCATAGGGACTCACTCCT | 47 | 7214 | 7233 | 533 |
| 588670 | 2361 | 2380 | Exon 16-17 Junction | CCGCCAGAATCACCTCTGCA | 58 | n/a | n/a | 534 |
| 588672 | 2397 | 2416 | Exon 17 | TGAATGAAACGACTTCTCTT | 48 | 7362 | 7381 | 535 |
| 588674 | 2430 | 2449 | Exon 18 | ACATCCACTACTCCCCAGCT | 29 | 7665 | 7684 | 536 |
| 588676 | 2448 | 2467 | Exon 18 | CGCTTCTGGTTTTTGCAGAC | 58 | 7683 | 7702 | 537 |
| 588678 | 2454 | 2473 | Exon 18 | TTTTGCCGCTTCTGGTTTTT | 45 | 7689 | 7708 | 538 |
| 588680 | 2466 | 2485 | Exon 18 | GCAGGTACCTGCTTTTGCCG | 36 | 7701 | 7720 | 539 |
| 588682 | 2532 | 2551 | Exon 18 | TCTTGGAGTTTCTCCTTCAG | 47 | 7767 | 7786 | 540 |
| 532811 | 2599 | 2618 | Exon 18 | AGCTGTTTTAATTCAATCCC | 96 | 7834 | 7853 | 239 |
| 532917 | 2604 | 2623 | Exon 18 | GTCGCAGCTGTTTTAATTCA | 96 | 7839 | 7858 | 317 |

TABLE 134

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 598973 | 2552 | 2568 | Exon 18 | GAAAACCCAAATCCTCA | 40 | 7787 | 7803 | 3-10-4 | 619 |
| 599036 | 2552 | 2568 | Exon 18 | GAAAACCCAAATCCTCA | 18 | 7787 | 7803 | 5-7-5 | 619 |
| 598974 | 2553 | 2569 | Exon 18 | AGAAAACCCAAATCCTC | 28 | 7788 | 7804 | 3-10-4 | 620 |
| 599037 | 2553 | 2569 | Exon 18 | AGAAAACCCAAATCCTC | 19 | 7788 | 7804 | 5-7-5 | 620 |
| 598975 | 2554 | 2570 | Exon 18 | TAGAAAACCCAAATCCT | 15 | 7789 | 7805 | 3-10-4 | 621 |
| 599038 | 2554 | 2570 | Exon 18 | TAGAAAACCCAAATCCT | 32 | 7789 | 7805 | 5-7-5 | 621 |
| 598976 | 2555 | 2571 | Exon 18 | ATAGAAAACCCAAATCC | 12 | 7790 | 7806 | 3-10-4 | 622 |
| 599039 | 2555 | 2571 | Exon 18 | ATAGAAAACCCAAATCC | 7 | 7790 | 7806 | 5-7-5 | 622 |
| 598977 | 2557 | 2573 | Exon 18 | TTATAGAAAACCCAAAT | 13 | 7792 | 7808 | 3-10-4 | 623 |
| 599040 | 2557 | 2573 | Exon 18 | TTATAGAAAACCCAAAT | 13 | 7792 | 7808 | 5-7-5 | 623 |
| 598978 | 2558 | 2574 | Exon 18 | CTTATAGAAACCCAAA | 0 | 7793 | 7809 | 3-10-4 | 624 |

TABLE 134-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599041 | 2558 | 2574 | Exon 18 | CTTATAGAAAACCCAAA | 0 | 7793 | 7809 | 5-7-5 | 624 |
| 598979 | 2559 | 2575 | Exon 18 | CCTTATAGAAAACCCAA | 8 | 7794 | 7810 | 3-10-4 | 625 |
| 599042 | 2559 | 2575 | Exon 18 | CCTTATAGAAAACCCAA | 19 | 7794 | 7810 | 5-7-5 | 625 |
| 598980 | 2560 | 2576 | Exon 18 | CCCTTATAGAAAACCCA | 42 | 7795 | 7811 | 3-10-4 | 626 |
| 599043 | 2560 | 2576 | Exon 18 | CCCTTATAGAAAACCCA | 10 | 7795 | 7811 | 5-7-5 | 626 |
| 598981 | 2561 | 2577 | Exon 18 | CCCCTTATAGAAAACCC | 20 | 7796 | 7812 | 3-10-4 | 627 |
| 599044 | 2561 | 2577 | Exon 18 | CCCCTTATAGAAAACCC | 12 | 7796 | 7812 | 5-7-5 | 627 |
| 598982 | 2562 | 2578 | Exon 18 | ACCCCTTATAGAAAACC | 10 | 7797 | 7813 | 3-10-4 | 628 |
| 599045 | 2562 | 2578 | Exon 18 | ACCCCTTATAGAAAACC | 3 | 7797 | 7813 | 5-7-5 | 628 |
| 598983 | 2563 | 2579 | Exon 18 | AACCCCTTATAGAAAAC | 0 | 7798 | 7814 | 3-10-4 | 629 |
| 599046 | 2563 | 2579 | Exon 18 | AACCCCTTATAGAAAAC | 18 | 7798 | 7814 | 5-7-5 | 629 |
| 598984 | 2564 | 2580 | Exon 18 | AAACCCCTTATAGAAAA | 0 | 7799 | 7815 | 3-10-4 | 630 |
| 599047 | 2564 | 2580 | Exon 18 | AAACCCCTTATAGAAAA | 7 | 7799 | 7815 | 5-7-5 | 630 |
| 598985 | 2565 | 2581 | Exon 18 | GAAACCCCTTATAGAAA | 0 | 7800 | 7816 | 3-10-4 | 631 |
| 599048 | 2565 | 2581 | Exon 18 | GAAACCCCTTATAGAAA | 9 | 7800 | 7816 | 5-7-5 | 631 |
| 598986 | 2566 | 2582 | Exon 18 | GGAAACCCCTTATAGAA | 0 | 7801 | 7817 | 3-10-4 | 632 |
| 599049 | 2566 | 2582 | Exon 18 | GGAAACCCCTTATAGAA | 18 | 7801 | 7817 | 5-7-5 | 632 |
| 598988 | 2567 | 2583 | Exon 18 | AGGAAACCCCTTATAGA | 0 | 7802 | 7818 | 3-10-4 | 633 |
| 599050 | 2567 | 2583 | Exon 18 | AGGAAACCCCTTATAGA | 8 | 7802 | 7818 | 5-7-5 | 633 |
| 598989 | 2568 | 2584 | Exon 18 | CAGGAAACCCCTTATAG | 0 | 7803 | 7819 | 3-10-4 | 634 |
| 598990 | 2569 | 2585 | Exon 18 | GCAGGAAACCCCTTATA | 8 | 7804 | 7820 | 3-10-4 | 635 |
| 598991 | 2570 | 2586 | Exon 18 | AGCAGGAAACCCCTTAT | 25 | 7805 | 7821 | 3-10-4 | 636 |
| 598992 | 2571 | 2587 | Exon 18 | CAGCAGGAAACCCCTTA | 12 | 7806 | 7822 | 3-10-4 | 637 |
| 598993 | 2572 | 2588 | Exon 18 | CCAGCAGGAAACCCCTT | 37 | 7807 | 7823 | 3-10-4 | 638 |
| 598994 | 2573 | 2589 | Exon 18 | TCCAGCAGGAAACCCCT | 29 | 7808 | 7824 | 3-10-4 | 639 |
| 598995 | 2574 | 2590 | Exon 18 | GTCCAGCAGGAAACCCC | 42 | 7809 | 7825 | 3-10-4 | 640 |
| 598996 | 2575 | 2591 | Exon 18 | TGTCCAGCAGGAAACCC | 36 | 7810 | 7826 | 3-10-4 | 641 |
| 598997 | 2576 | 2592 | Exon 18 | CTGTCCAGCAGGAAACC | 18 | 7811 | 7827 | 3-10-4 | 642 |
| 598998 | 2577 | 2593 | Exon 18 | CCTGTCCAGCAGGAAAC | 27 | 7812 | 7828 | 3-10-4 | 643 |
| 598999 | 2578 | 2594 | Exon 18 | CCCTGTCCAGCAGGAAA | 61 | 7813 | 7829 | 3-10-4 | 644 |
| 599000 | 2580 | 2596 | Exon 18 | GCCCTGTCCAGCAGGA | 71 | 7815 | 7831 | 3-10-4 | 645 |
| 599001 | 2581 | 2597 | Exon 18 | CGCCCCTGTCCAGCAGG | 80 | 7816 | 7832 | 3-10-4 | 646 |
| 599002 | 2582 | 2598 | Exon 18 | ACGCCCCTGTCCAGCAG | 68 | 7817 | 7833 | 3-10-4 | 647 |
| 599003 | 2583 | 2599 | Exon 18 | CACGCCCCTGTCCAGCA | 71 | 7818 | 7834 | 3-10-4 | 648 |
| 599004 | 2584 | 2600 | Exon 18 | CCACGCCCCTGTCCAGC | 76 | 7819 | 7835 | 3-10-4 | 649 |
| 599005 | 2585 | 2601 | Exon 18 | CCCACGCCCCTGTCCAG | 70 | 7820 | 7836 | 3-10-4 | 650 |

TABLE 134-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599006 | 2586 | 2602 | Exon 18 | TCCCACGCCCCTGTCCA | 65 | 7821 | 7837 | 3-10-4 | 651 |
| 599007 | 2587 | 2603 | Exon 18 | ATCCCACGCCCCTGTCC | 60 | 7822 | 7838 | 3-10-4 | 652 |
| 599008 | 2588 | 2604 | Exon 18 | AATCCCACGCCCCTGTC | 72 | 7823 | 7839 | 3-10-4 | 653 |
| 599009 | 2589 | 2605 | Exon 18 | CAATCCCACGCCCCTGT | 79 | 7824 | 7840 | 3-10-4 | 654 |
| 599010 | 2590 | 2606 | Exon 18 | TCAATCCCACGCCCCTG | 73 | 7825 | 7841 | 3-10-4 | 655 |
| 599011 | 2591 | 2607 | Exon 18 | TTCAATCCCACGCCCCT | 79 | 7826 | 7842 | 3-10-4 | 656 |
| 599012 | 2592 | 2608 | Exon 18 | ATTCAATCCCACGCCCC | 67 | 7827 | 7843 | 3-10-4 | 657 |
| 599013 | 2593 | 2609 | Exon 18 | AATTCAATCCCACGCCC | 65 | 7828 | 7844 | 3-10-4 | 658 |
| 599014 | 2594 | 2610 | Exon 18 | TAATTCAATCCCACGCC | 74 | 7829 | 7845 | 3-10-4 | 659 |
| 599015 | 2595 | 2611 | Exon 18 | TTAATTCAATCCCACGC | 71 | 7830 | 7846 | 3-10-4 | 660 |
| 599016 | 2596 | 2612 | Exon 18 | TTTAATTCAATCCCACG | 48 | 7831 | 7847 | 3-10-4 | 661 |
| 599017 | 2597 | 2613 | Exon 18 | TTTTAATTCAATCCCAC | 34 | 7832 | 7848 | 3-10-4 | 662 |
| 599018 | 2598 | 2614 | Exon 18 | GTTTTAATTCAATCCCA | 56 | 7833 | 7849 | 3-10-4 | 663 |
| 599019 | 2599 | 2615 | Exon 18 | TGTTTTAATTCAATCCC | 60 | 7834 | 7850 | 3-10-4 | 664 |
| 599020 | 2600 | 2616 | Exon 18 | CTGTTTTAATTCAATCC | 0 | 7835 | 7851 | 3-10-4 | 665 |
| 599021 | 2601 | 2617 | Exon 18 | GCTGTTTTAATTCAATC | 33 | 7836 | 7852 | 3-10-4 | 666 |
| 599022 | 2602 | 2618 | Exon 18 | AGCTGTTTTAATTCAAT | 17 | 7837 | 7853 | 3-10-4 | 667 |
| 599023 | 2603 | 2619 | Exon 18 | CAGCTGTTTTAATTCAA | 52 | 7838 | 7854 | 3-10-4 | 668 |
| 532917 | 2604 | 2623 | Exon 18 | GTCGCAGCTGTTTTAATTCA | 86 | 7839 | 7858 | 5-10-5 | 317 |
| 599024 | 2604 | 2620 | Exon 18 | GCAGCTGTTTTAATTCA | 88 | 7839 | 7855 | 3-10-4 | 669 |
| 599025 | 2605 | 2621 | Exon 18 | CGCAGCTGTTTTAATTC | 85 | 7840 | 7856 | 3-10-4 | 670 |
| 599026 | 2606 | 2622 | Exon 18 | TCGCAGCTGTTTTAATT | 69 | 7841 | 7857 | 3-10-4 | 671 |
| 599027 | 2607 | 2623 | Exon 18 | GTCGCAGCTGTTTTAAT | 77 | 7842 | 7858 | 3-10-4 | 672 |
| 599028 | 2608 | 2624 | Exon 18 | TGTCGCAGCTGTTTTAA | 73 | 7843 | 7859 | 3-10-4 | 673 |
| 599029 | 2609 | 2625 | Exon 18 | TTGTCGCAGCTGTTTTA | 78 | 7844 | 7860 | 3-10-4 | 674 |
| 599030 | 2610 | 2626 | Exon 18 | GTTGTCGCAGCTGTTTT | 75 | 7845 | 7861 | 3-10-4 | 675 |
| 599031 | 2611 | 2627 | Exon 18 | TGTTGTCGCAGCTGTTT | 77 | 7846 | 7862 | 3-10-4 | 676 |
| 599032 | 2612 | 2628 | Exon 18/ Repeat | TTGTTGTCGCAGCTGTT | 79 | n/a | n/a | 3-10-4 | 677 |
| 599033 | 2613 | 2629 | Exon 18/ Repeat | TTTGTTGTCGCAGCTGT | 80 | n/a | n/a | 3-10-4 | 678 |
| 599034 | 2614 | 2630 | Exon 18/ Repeat | TTTTGTTGTCGCAGCTG | 78 | n/a | n/a | 3-10-4 | 679 |
| 599035 | 2615 | 2631 | Exon 18/ Repeat | TTTTTGTTGTCGCAGCT | 63 | n/a | n/a | 3-10-4 | 680 |

TABLE 135

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599098 | 2552 | 2568 | Exon 18 | GAAAACCCAAATCCTCA | 57 | 7787 | 7803 | 4-8-5 | 619 |
| 599099 | 2553 | 2569 | Exon 18 | AGAAAACCCAAATCCTC | 33 | 7788 | 7804 | 4-8-5 | 620 |
| 599100 | 2554 | 2570 | Exon 18 | TAGAAAACCCAAATCCT | 32 | 7789 | 7805 | 4-8-5 | 621 |
| 599101 | 2555 | 2571 | Exon 18 | ATAGAAAACCCAAATCC | 47 | 7790 | 7806 | 4-8-5 | 622 |
| 599102 | 2557 | 2573 | Exon 18 | TTATAGAAAACCCAAAT | 59 | 7792 | 7808 | 4-8-5 | 623 |
| 599103 | 2558 | 2574 | Exon 18 | CTTATAGAAAACCCAAA | 10 | 7793 | 7809 | 4-8-5 | 624 |
| 599104 | 2559 | 2575 | Exon 18 | CCTTATAGAAAACCCAA | 3 | 7794 | 7810 | 4-8-5 | 625 |
| 599105 | 2560 | 2576 | Exon 18 | CCCTTATAGAAAACCCA | 45 | 7795 | 7811 | 4-8-5 | 626 |
| 599106 | 2561 | 2577 | Exon 18 | CCCCTTATAGAAAACCC | 49 | 7796 | 7812 | 4-8-5 | 627 |
| 599107 | 2562 | 2578 | Exon 18 | ACCCCTTATAGAAAACC | 35 | 7797 | 7813 | 4-8-5 | 628 |
| 599108 | 2563 | 2579 | Exon 18 | AACCCCTTATAGAAAAC | 17 | 7798 | 7814 | 4-8-5 | 629 |
| 599109 | 2564 | 2580 | Exon 18 | AAACCCCTTATAGAAAA | 36 | 7799 | 7815 | 4-8-5 | 630 |
| 599110 | 2565 | 2581 | Exon 18 | GAAACCCCTTATAGAAA | 20 | 7800 | 7816 | 4-8-5 | 631 |
| 599111 | 2566 | 2582 | Exon 18 | GGAAACCCCTTATAGAA | 20 | 7801 | 7817 | 4-8-5 | 632 |
| 599112 | 2567 | 2583 | Exon 18 | AGGAAACCCCTTATAGA | 15 | 7802 | 7818 | 4-8-5 | 633 |
| 599113 | 2568 | 2584 | Exon 18 | CAGGAAACCCCTTATAG | 19 | 7803 | 7819 | 4-8-5 | 634 |
| 599051 | 2568 | 2584 | Exon 18 | CAGGAAACCCCTTATAG | 26 | 7803 | 7819 | 5-7-5 | 634 |
| 599114 | 2569 | 2585 | Exon 18 | GCAGGAAACCCCTTATA | 18 | 7804 | 7820 | 4-8-5 | 635 |
| 599052 | 2569 | 2585 | Exon 18 | GCAGGAAACCCCTTATA | 21 | 7804 | 7820 | 5-7-5 | 635 |
| 599115 | 2570 | 2586 | Exon 18 | AGCAGGAAACCCCTTAT | 31 | 7805 | 7821 | 4-8-5 | 636 |
| 599053 | 2570 | 2586 | Exon 18 | AGCAGGAAACCCCTTAT | 25 | 7805 | 7821 | 5-7-5 | 636 |
| 599116 | 2571 | 2587 | Exon 18 | CAGCAGGAAACCCCTTA | 39 | 7806 | 7822 | 4-8-5 | 637 |
| 599054 | 2571 | 2587 | Exon 18 | CAGCAGGAAACCCCTTA | 36 | 7806 | 7822 | 5-7-5 | 637 |
| 599117 | 2572 | 2588 | Exon 18 | CCAGCAGGAAACCCCTT | 46 | 7807 | 7823 | 4-8-5 | 638 |
| 599055 | 2572 | 2588 | Exon 18 | CCAGCAGGAAACCCCTT | 22 | 7807 | 7823 | 5-7-5 | 638 |
| 599118 | 2573 | 2589 | Exon 18 | TCCAGCAGGAAACCCCT | 40 | 7808 | 7824 | 4-8-5 | 639 |
| 599056 | 2573 | 2589 | Exon 18 | TCCAGCAGGAAACCCCT | 32 | 7808 | 7824 | 5-7-5 | 639 |
| 599119 | 2574 | 2590 | Exon 18 | GTCCAGCAGGAAACCCC | 50 | 7809 | 7825 | 4-8-5 | 640 |
| 599057 | 2574 | 2590 | Exon 18 | GTCCAGCAGGAAACCCC | 46 | 7809 | 7825 | 5-7-5 | 640 |
| 599120 | 2575 | 2591 | Exon 18 | TGTCCAGCAGGAAACCC | 30 | 7810 | 7826 | 4-8-5 | 641 |
| 599058 | 2575 | 2591 | Exon 18 | TGTCCAGCAGGAAACCC | 52 | 7810 | 7826 | 5-7-5 | 641 |
| 599121 | 2576 | 2592 | Exon 18 | CTGTCCAGCAGGAAACC | 31 | 7811 | 7827 | 4-8-5 | 642 |
| 599059 | 2576 | 2592 | Exon 18 | CTGTCCAGCAGGAAACC | 24 | 7811 | 7827 | 5-7-5 | 642 |
| 599122 | 2577 | 2593 | Exon 18 | CCTGTCCAGCAGGAAAC | 23 | 7812 | 7828 | 4-8-5 | 643 |
| 599060 | 2577 | 2593 | Exon 18 | CCTGTCCAGCAGGAAAC | 37 | 7812 | 7828 | 5-7-5 | 643 |
| 599123 | 2578 | 2594 | Exon 18 | CCCTGTCCAGCAGGAAA | 51 | 7813 | 7829 | 4-8-5 | 644 |

TABLE 135-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599061 | 2578 | 2594 | Exon 18 | CCCTGTCCAGCAGGAAA | 34 | 7813 | 7829 | 5-7-5 | 644 |
| 599124 | 2580 | 2596 | Exon 18 | GCCCCTGTCCAGCAGGA | 56 | 7815 | 7831 | 4-8-5 | 645 |
| 599062 | 2580 | 2596 | Exon 18 | GCCCCTGTCCAGCAGGA | 51 | 7815 | 7831 | 5-7-5 | 645 |
| 599125 | 2581 | 2597 | Exon 18 | CGCCCCTGTCCAGCAGG | 70 | 7816 | 7832 | 4-8-5 | 646 |
| 599063 | 2581 | 2597 | Exon 18 | CGCCCCTGTCCAGCAGG | 56 | 7816 | 7832 | 5-7-5 | 646 |
| 599126 | 2582 | 2598 | Exon 18 | ACGCCCCTGTCCAGCAG | 76 | 7817 | 7833 | 4-8-5 | 647 |
| 599064 | 2582 | 2598 | Exon 18 | ACGCCCCTGTCCAGCAG | 61 | 7817 | 7833 | 5-7-5 | 647 |
| 599127 | 2583 | 2599 | Exon 18 | CACGCCCCTGTCCAGCA | 67 | 7818 | 7834 | 4-8-5 | 648 |
| 599065 | 2583 | 2599 | Exon 18 | CACGCCCCTGTCCAGCA | 64 | 7818 | 7834 | 5-7-5 | 648 |
| 599066 | 2584 | 2600 | Exon 18 | CCACGCCCCTGTCCAGC | 40 | 7819 | 7835 | 5-7-5 | 649 |
| 599067 | 2585 | 2601 | Exon 18 | CCCACGCCCCTGTCCAG | 37 | 7820 | 7836 | 5-7-5 | 650 |
| 599068 | 2586 | 2602 | Exon 18 | TCCCACGCCCCTGTCCA | 31 | 7821 | 7837 | 5-7-5 | 651 |
| 599069 | 2587 | 2603 | Exon 18 | ATCCCACGCCCCTGTCC | 39 | 7822 | 7838 | 5-7-5 | 652 |
| 599070 | 2588 | 2604 | Exon 18 | AATCCCACGCCCCTGTC | 59 | 7823 | 7839 | 5-7-5 | 653 |
| 599071 | 2589 | 2605 | Exon 18 | CAATCCCACGCCCCTGT | 63 | 7824 | 7840 | 5-7-5 | 657 |
| 599072 | 2590 | 2606 | Exon 18 | TCAATCCCACGCCCCTG | 74 | 7825 | 7841 | 5-7-5 | 655 |
| 599073 | 2591 | 2607 | Exon 18 | TTCAATCCCACGCCCCT | 53 | 7826 | 7842 | 5-7-5 | 656 |
| 599074 | 2592 | 2608 | Exon 18 | ATTCAATCCCACGCCCC | 56 | 7827 | 7843 | 5-7-5 | 657 |
| 599075 | 2593 | 2609 | Exon 18 | AATTCAATCCCACGCCC | 49 | 7828 | 7844 | 5-7-5 | 658 |
| 599076 | 2594 | 2610 | Exon 18 | TAATTCAATCCCACGCC | 54 | 7829 | 7845 | 5-7-5 | 659 |
| 599077 | 2595 | 2611 | Exon 18 | TTAATTCAATCCCACGC | 79 | 7830 | 7846 | 5-7-5 | 660 |
| 599078 | 2596 | 2612 | Exon 18 | TTTAATTCAATCCCACG | 67 | 7831 | 7847 | 5-7-5 | 661 |
| 599079 | 2597 | 2613 | Exon 18 | TTTTAATTCAATCCCAC | 69 | 7832 | 7848 | 5-7-5 | 662 |
| 599080 | 2598 | 2614 | Exon 18 | GTTTTAATTCAATCCCA | 79 | 7833 | 7849 | 5-7-5 | 663 |
| 599081 | 2599 | 2615 | Exon 18 | TGTTTTAATTCAATCCC | 57 | 7834 | 7850 | 5-7-5 | 664 |
| 599082 | 2600 | 2616 | Exon 18 | CTGTTTTAATTCAATCC | 50 | 7835 | 7851 | 5-7-5 | 665 |
| 599083 | 2601 | 2617 | Exon 18 | GCTGTTTTAATTCAATC | 67 | 7836 | 7852 | 5-7-5 | 666 |
| 599084 | 2602 | 2618 | Exon 18 | AGCTGTTTTAATTCAAT | 60 | 7837 | 7853 | 5-7-5 | 667 |
| 599085 | 2603 | 2619 | Exon 18 | CAGCTGTTTTAATTCAA | 71 | 7838 | 7854 | 5-7-5 | 668 |
| 532917 | 2604 | 2623 | Exon 18 | GTCGCAGCTGTTTTAATTCA | 82 | 7839 | 7858 | 5-10-5 | 317 |
| 599086 | 2604 | 2620 | Exon 18 | GCAGCTGTTTTAATTCA | 81 | 7839 | 7855 | 5-7-5 | 669 |
| 599087 | 2605 | 2621 | Exon 18 | CGCAGCTGTTTTAATTC | 88 | 7840 | 7856 | 5-7-5 | 670 |
| 599088 | 2606 | 2622 | Exon 18 | TCGCAGCTGTTTTAATT | 84 | 7841 | 7857 | 5-7-5 | 671 |
| 599089 | 2607 | 2623 | Exon 18 | GTCGCAGCTGTTTTAAT | 81 | 7842 | 7858 | 5-7-5 | 672 |
| 599090 | 2608 | 2624 | Exon 18 | TGTCGCAGCTGTTTTAA | 77 | 7843 | 7859 | 5-7-5 | 673 |
| 599091 | 2609 | 2625 | Exon 18 | TTGTCGCAGCTGTTTTA | 74 | 7844 | 7860 | 5-7-5 | 674 |

TABLE 135-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599092 | 2610 | 2626 | Exon 18 | GTTGTCGCAGCTGTTTT | 66 | 7845 | 7861 | 5-7-5 | 675 |
| 599093 | 2611 | 2627 | Exon 18 | TGTTGTCGCAGCTGTTT | 89 | 7846 | 7862 | 5-7-5 | 676 |
| 599094 | 2612 | 2628 | Exon 18/Repeat | TTGTTGTCGCAGCTGTT | 82 | n/a | n/a | 5-7-5 | 677 |
| 599095 | 2613 | 2629 | Exon 18/Repeat | TTTGTTGTCGCAGCTGT | 87 | n/a | n/a | 5-7-5 | 678 |
| 599096 | 2614 | 2630 | Exon 18/Repeat | TTTTGTTGTCGCAGCTG | 85 | n/a | n/a | 5-7-5 | 679 |
| 599097 | 2615 | 2631 | Exon 18/Repeat | TTTTTGTTGTCGCAGCT | 78 | n/a | n/a | 5-7-5 | 680 |

TABLE 136

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599510 | 2552 | 2570 | Exon 18 | TAGAAAACCCAAATCCTCA | 45 | 7787 | 7805 | 5-9-5 | 681 |
| 599331 | 2553 | 2571 | Exon 18 | ATAGAAAACCCAAATCCTC | 46 | 7788 | 7806 | 5-9-5 | 682 |
| 599332 | 2554 | 2572 | Exon 18 | TATAGAAAACCCAAATCCT | 38 | 7789 | 7807 | 5-9-5 | 683 |
| 599333 | 2556 | 2574 | Exon 18 | CTTATAGAAAACCCAAATC | 1 | 7791 | 7809 | 5-9-5 | 684 |
| 599334 | 2557 | 2575 | Exon 18 | CCTTATAGAAAACCCAAAT | 5 | 7792 | 7810 | 5-9-5 | 685 |
| 599335 | 2558 | 2576 | Exon 18 | CCCTTATAGAAAACCCAAA | 34 | 7793 | 7811 | 5-9-5 | 686 |
| 599336 | 2559 | 2577 | Exon 18 | CCCCTTATAGAAAACCCAA | 40 | 7794 | 7812 | 5-9-5 | 687 |
| 599337 | 2560 | 2578 | Exon 18 | ACCCCTTATAGAAAACCCA | 39 | 7795 | 7813 | 5-9-5 | 688 |
| 599338 | 2561 | 2579 | Exon 18 | AACCCCTTATAGAAAACCC | 57 | 7796 | 7814 | 5-9-5 | 689 |
| 599339 | 2562 | 2580 | Exon 18 | AAACCCCTTATAGAAAACC | 26 | 7797 | 7815 | 5-9-5 | 690 |
| 599281 | 2562 | 2580 | Exon 18 | AAACCCCTTATAGAAAACC | 15 | 7797 | 7815 | 6-7-6 | 690 |
| 599340 | 2563 | 2581 | Exon 18 | GAAACCCCTTATAGAAAAC | 17 | 7798 | 7816 | 5-9-5 | 691 |
| 599282 | 2563 | 2581 | Exon 18 | GAAACCCCTTATAGAAAAC | 12 | 7798 | 7816 | 6-7-6 | 691 |
| 599341 | 2564 | 2582 | Exon 18 | GGAAACCCCTTATAGAAAA | 23 | 7799 | 7817 | 5-9-5 | 692 |
| 599283 | 2564 | 2582 | Exon 18 | GGAAACCCCTTATAGAAAA | 18 | 7799 | 7817 | 6-7-6 | 692 |
| 599342 | 2565 | 2583 | Exon 18 | AGGAAACCCCTTATAGAAA | 10 | 7800 | 7818 | 5-9-5 | 693 |
| 599284 | 2565 | 2583 | Exon 18 | AGGAAACCCCTTATAGAAA | 14 | 7800 | 7818 | 6-7-6 | 693 |
| 599343 | 2566 | 2584 | Exon 18 | CAGGAAACCCCTTATAGAA | 10 | 7801 | 7819 | 5-9-5 | 694 |
| 599285 | 2566 | 2584 | Exon 18 | CAGGAAACCCCTTATAGAA | 13 | 7801 | 7819 | 6-7-6 | 694 |
| 599344 | 2567 | 2585 | Exon 18 | GCAGGAAACCCCTTATAGA | 22 | 7802 | 7820 | 5-9-5 | 695 |
| 599286 | 2567 | 2585 | Exon 18 | GCAGGAAACCCCTTATAGA | 31 | 7802 | 7820 | 6-7-6 | 695 |
| 599345 | 2568 | 2586 | Exon 18 | AGCAGGAAACCCCTTATAG | 19 | 7803 | 7821 | 5-9-5 | 696 |

TABLE 136-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599287 | 2568 | 2586 | Exon 18 | AGCAGGAAACCCCTTATAG | 12 | 7803 | 7821 | 6-7-6 | 696 |
| 599346 | 2569 | 2587 | Exon 18 | CAGCAGGAAACCCCTTATA | 30 | 7804 | 7822 | 5-9-5 | 697 |
| 599288 | 2569 | 2587 | Exon 18 | CAGCAGGAAACCCCTTATA | 28 | 7804 | 7822 | 6-7-6 | 697 |
| 599347 | 2570 | 2588 | Exon 18 | CCAGCAGGAAACCCCTTAT | 46 | 7805 | 7823 | 5-9-5 | 698 |
| 599289 | 2570 | 2588 | Exon 18 | CCAGCAGGAAACCCCTTAT | 32 | 7805 | 7823 | 6-7-6 | 698 |
| 599348 | 2571 | 2589 | Exon 18 | TCCAGCAGGAAACCCCTTA | 44 | 7806 | 7824 | 5-9-5 | 699 |
| 599290 | 2571 | 2589 | Exon 18 | TCCAGCAGGAAACCCCTTA | 24 | 7806 | 7824 | 6-7-6 | 699 |
| 599349 | 2572 | 2590 | Exon 18 | GTCCAGCAGGAAACCCCTT | 60 | 7807 | 7825 | 5-9-5 | 700 |
| 599291 | 2572 | 2590 | Exon 18 | GTCCAGCAGGAAACCCCTT | 38 | 7807 | 7825 | 6-7-6 | 700 |
| 599350 | 2573 | 2591 | Exon 18 | TGTCCAGCAGGAAACCCCT | 49 | 7808 | 7826 | 5-9-5 | 701 |
| 599292 | 2573 | 2591 | Exon 18 | TGTCCAGCAGGAAACCCCT | 35 | 7808 | 7826 | 6-7-6 | 701 |
| 599351 | 2575 | 2593 | Exon 18 | CCTGTCCAGCAGGAAACCC | 46 | 7810 | 7828 | 5-9-5 | 702 |
| 599293 | 2575 | 2593 | Exon 18 | CCTGTCCAGCAGGAAACCC | 12 | 7810 | 7828 | 6-7-6 | 702 |
| 599352 | 2576 | 2594 | Exon 18 | CCCTGTCCAGCAGGAAACC | 49 | 7811 | 7829 | 5-9-5 | 703 |
| 599294 | 2576 | 2594 | Exon 18 | CCCTGTCCAGCAGGAAACC | 38 | 7811 | 7829 | 6-7-6 | 703 |
| 599353 | 2577 | 2595 | Exon 18 | CCCCTGTCCAGCAGGAAAC | 64 | 7812 | 7830 | 5-9-5 | 704 |
| 599295 | 2577 | 2595 | Exon 18 | CCCCTGTCCAGCAGGAAAC | 33 | 7812 | 7830 | 6-7-6 | 704 |
| 599354 | 2578 | 2596 | Exon 18 | GCCCCTGTCCAGCAGGAAA | 56 | 7813 | 7831 | 5-9-5 | 705 |
| 599296 | 2578 | 2596 | Exon 18 | GCCCCTGTCCAGCAGGAAA | 13 | 7813 | 7831 | 6-7-6 | 705 |
| 599355 | 2580 | 2598 | Exon 18 | ACGCCCTGTCCAGCAGGA | 81 | 7815 | 7833 | 5-9-5 | 706 |
| 599297 | 2580 | 2598 | Exon 18 | ACGCCCTGTCCAGCAGGA | 57 | 7815 | 7833 | 6-7-6 | 706 |
| 599356 | 2581 | 2599 | Exon 18 | CACGCCCCTGTCCAGCAGG | 64 | 7816 | 7834 | 5-9-5 | 707 |
| 599298 | 2581 | 2599 | Exon 18 | CACGCCCCTGTCCAGCAGG | 39 | 7816 | 7834 | 6-7-6 | 707 |
| 599299 | 2582 | 2600 | Exon 18 | CCACGCCCCTGTCCAGCAG | 55 | 7817 | 7835 | 6-7-6 | 708 |
| 599300 | 2583 | 2601 | Exon 18 | CCCACGCCCCTGTCCAGCA | 45 | 7818 | 7836 | 6-7-6 | 709 |
| 599301 | 2584 | 2602 | Exon 18 | TCCCACGCCCCTGTCCAGC | 39 | 7819 | 7837 | 6-7-6 | 710 |
| 599302 | 2585 | 2603 | Exon 18 | ATCCCACGCCCCTGTCCAG | 27 | 7820 | 7838 | 6-7-6 | 711 |
| 599303 | 2586 | 2604 | Exon 18 | AATCCCACGCCCCTGTCCA | 35 | 7821 | 7839 | 6-7-6 | 712 |
| 599304 | 2587 | 2605 | Exon 18 | CAATCCCACGCCCCTGTCC | 16 | 7822 | 7840 | 6-7-6 | 713 |
| 599305 | 2588 | 2606 | Exon 18 | TCAATCCCACGCCCCTGTC | 41 | 7823 | 7841 | 6-7-6 | 714 |
| 599306 | 2589 | 2607 | Exon 18 | TTCAATCCCACGCCCCTGT | 70 | 7824 | 7842 | 6-7-6 | 715 |
| 599307 | 2590 | 2608 | Exon 18 | ATTCAATCCCACGCCCCTG | 66 | 7825 | 7843 | 6-7-6 | 716 |
| 599308 | 2591 | 2609 | Exon 18 | AATTCAATCCCACGCCCCT | 68 | 7826 | 7844 | 6-7-6 | 717 |
| 599309 | 2592 | 2610 | Exon 18 | TAATTCAATCCCACGCCCC | 52 | 7827 | 7845 | 6-7-6 | 718 |
| 599310 | 2593 | 2611 | Exon 18 | TTAATTCAATCCCACGCCC | 39 | 7828 | 7846 | 6-7-6 | 719 |
| 599311 | 2594 | 2612 | Exon 18 | TTTAATTCAATCCCACGCC | 83 | 7829 | 7847 | 6-7-6 | 720 |

TABLE 136-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599312 | 2595 | 2613 | Exon 18 | TTTTAATTCAATCCCACGC | 72 | 7830 | 7848 | 6-7-6 | 721 |
| 599313 | 2596 | 2614 | Exon 18 | GTTTTAATTCAATCCCACG | 86 | 7831 | 7849 | 6-7-6 | 722 |
| 599314 | 2597 | 2615 | Exon 18 | TGTTTTAATTCAATCCCAC | 91 | 7832 | 7850 | 6-7-6 | 723 |
| 599315 | 2598 | 2616 | Exon 18 | CTGTTTTAATTCAATCCCA | 71 | 7833 | 7851 | 6-7-6 | 724 |
| 599316 | 2599 | 2617 | Exon 18 | GCTGTTTTAATTCAATCCC | 89 | 7834 | 7852 | 6-7-6 | 725 |
| 599317 | 2600 | 2618 | Exon 18 | AGCTGTTTTAATTCAATCC | 87 | 7835 | 7853 | 6-7-6 | 726 |
| 599318 | 2601 | 2619 | Exon 18 | CAGCTGTTTTAATTCAATC | 81 | 7836 | 7854 | 6-7-6 | 727 |
| 599319 | 2602 | 2620 | Exon 18 | GCAGCTGTTTTAATTCAAT | 75 | 7837 | 7855 | 6-7-6 | 728 |
| 599320 | 2603 | 2621 | Exon 18 | CGCAGCTGTTTTAATTCAA | 84 | 7838 | 7856 | 6-7-6 | 729 |
| 532917 | 2604 | 2623 | Exon 18 | GTCGCAGCTGTTTTAATTCA | 92 | 7839 | 7858 | 5-10-5 | 317 |
| 599321 | 2604 | 2622 | Exon 18 | TCGCAGCTGTTTTAATTCA | 90 | 7839 | 7857 | 6-7-6 | 730 |
| 599322 | 2605 | 2623 | Exon 18 | GTCGCAGCTGTTTTAATTC | 89 | 7840 | 7858 | 6-7-6 | 731 |
| 599323 | 2606 | 2624 | Exon 18 | TGTCGCAGCTGTTTTAATT | 81 | 7841 | 7859 | 6-7-6 | 732 |
| 599324 | 2607 | 2625 | Exon 18 | TTGTCGCAGCTGTTTTAAT | 68 | 7842 | 7860 | 6-7-6 | 733 |
| 599325 | 2608 | 2626 | Exon 18 | GTTGTCGCAGCTGTTTTAA | 71 | 7843 | 7861 | 6-7-6 | 734 |
| 599326 | 2609 | 2627 | Exon 18 | TGTTGTCGCAGCTGTTTTA | 52 | 7844 | 7862 | 6-7-6 | 735 |
| 599327 | 2610 | 2628 | Exon 18/ Repeat | TTGTTGTCGCAGCTGTTTT | 88 | n/a | n/a | 6-7-6 | 736 |
| 599328 | 2611 | 2629 | Exon 18/ Repeat | TTTGTTGTCGCAGCTGTTT | 87 | n/a | n/a | 6-7-6 | 737 |
| 599329 | 2612 | 2630 | Exon 18/ Repeat | TTTTGTTGTCGCAGCTGTT | 84 | n/a | n/a | 6-7-6 | 738 |
| 599330 | 2613 | 2631 | Exon 18/ Repeat | TTTTTGTTGTCGCAGCTGT | 87 | n/a | n/a | 6-7-6 | 739 |

TABLE 137

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599512 | 2552 | 2571 | Exon 18 | ATAGAAAACCCAAATCCTCA | 74 | 7787 | 7806 | 3-10-7 | 410 |
| 599449 | 2553 | 2572 | Exon 18 | TATAGAAAACCCAAATCCTC | 43 | 7788 | 7807 | 3-10-7 | 411 |
| 599450 | 2554 | 2573 | Exon 18 | TTATAGAAAACCCAAATCCT | 51 | 7789 | 7808 | 3-10-7 | 412 |
| 599451 | 2555 | 2574 | Exon 18 | CTTATAGAAAACCCAAATCC | 35 | 7790 | 7809 | 3-10-7 | 413 |
| 599452 | 2556 | 2575 | Exon 18 | CCTTATAGAAAACCCAAATC | 34 | 7791 | 7810 | 3-10-7 | 414 |
| 599453 | 2557 | 2576 | Exon 18 | CCCTTATAGAAAACCCAAAT | 44 | 7792 | 7811 | 3-10-7 | 415 |
| 599454 | 2558 | 2577 | Exon 18 | CCCCTTATAGAAAACCCAAA | 54 | 7793 | 7812 | 3-10-7 | 416 |

TABLE 137-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599455 | 2559 | 2578 | Exon 18 | ACCCCTTATAGAAAACCCAA | 53 | 7794 | 7813 | 3-10-7 | 417 |
| 599456 | 2560 | 2579 | Exon 18 | AACCCCTTATAGAAAACCCA | 69 | 7795 | 7814 | 3-10-7 | 418 |
| 599457 | 2561 | 2580 | Exon 18 | AAACCCCTTATAGAAAACCC | 46 | 7796 | 7815 | 3-10-7 | 419 |
| 599458 | 2562 | 2581 | Exon 18 | GAAACCCCTTATAGAAAACC | 0 | 7797 | 7816 | 3-10-7 | 420 |
| 599459 | 2563 | 2582 | Exon 18 | GGAAACCCCTTATAGAAAAC | 12 | 7798 | 7817 | 3-10-7 | 421 |
| 599460 | 2564 | 2583 | Exon 18 | AGGAAACCCCTTATAGAAAA | 17 | 7799 | 7818 | 3-10-7 | 422 |
| 599461 | 2565 | 2584 | Exon 18 | CAGGAAACCCCTTATAGAAA | 24 | 7800 | 7819 | 3-10-7 | 423 |
| 599462 | 2566 | 2585 | Exon 18 | GCAGGAAACCCCTTATAGAA | 33 | 7801 | 7820 | 3-10-7 | 424 |
| 599463 | 2567 | 2586 | Exon 18 | AGCAGGAAACCCCTTATAGA | 38 | 7802 | 7821 | 3-10-7 | 425 |
| 599464 | 2568 | 2587 | Exon 18 | CAGCAGGAAACCCCTTATAG | 33 | 7803 | 7822 | 3-10-7 | 426 |
| 599465 | 2569 | 2588 | Exon 18 | CCAGCAGGAAACCCCTTATA | 49 | 7804 | 7823 | 3-10-7 | 427 |
| 599466 | 2570 | 2589 | Exon 18 | TCCAGCAGGAAACCCCTTAT | 45 | 7805 | 7824 | 3-10-7 | 428 |
| 599467 | 2571 | 2590 | Exon 18 | GTCCAGCAGGAAACCCCTTA | 60 | 7806 | 7825 | 3-10-7 | 237 |
| 599468 | 2572 | 2591 | Exon 18 | TGTCCAGCAGGAAACCCCTT | 61 | 7807 | 7826 | 3-10-7 | 429 |
| 599469 | 2573 | 2592 | Exon 18 | CTGTCCAGCAGGAAACCCCT | 52 | 7808 | 7827 | 3-10-7 | 430 |
| 599470 | 2574 | 2593 | Exon 18 | CCTGTCCAGCAGGAAACCCC | 45 | 7809 | 7828 | 3-10-7 | 431 |
| 599471 | 2575 | 2594 | Exon 18 | CCCTGTCCAGCAGGAAACCC | 67 | 7810 | 7829 | 3-10-7 | 432 |
| 599472 | 2576 | 2595 | Exon 18 | CCCCTGTCCAGCAGGAAACC | 79 | 7811 | 7830 | 3-10-7 | 433 |
| 599473 | 2577 | 2596 | Exon 18 | GCCCCTGTCCAGCAGGAAAC | 72 | 7812 | 7831 | 3-10-7 | 238 |
| 599474 | 2578 | 2597 | Exon 18 | CGCCCCTGTCCAGCAGGAAA | 87 | 7813 | 7832 | 3-10-7 | 434 |
| 599475 | 2579 | 2598 | Exon 18 | ACGCCCCTGTCCAGCAGGAA | 76 | 7814 | 7833 | 3-10-7 | 435 |
| 599476 | 2580 | 2599 | Exon 18 | CACGCCCCTGTCCAGCAGGA | 81 | 7815 | 7834 | 3-10-7 | 436 |
| 599477 | 2581 | 2600 | Exon 18 | CCACGCCCCTGTCCAGCAGG | 83 | 7816 | 7835 | 3-10-7 | 437 |
| 599478 | 2582 | 2601 | Exon 18 | CCCACGCCCCTGTCCAGCAG | 72 | 7817 | 7836 | 3-10-7 | 438 |
| 599479 | 2583 | 2602 | Exon 18 | TCCCACGCCCCTGTCCAGCA | 81 | 7818 | 7837 | 3-10-7 | 439 |
| 599480 | 2584 | 2603 | Exon 18 | ATCCCACGCCCCTGTCCAGC | 77 | 7819 | 7838 | 3-10-7 | 440 |
| 599481 | 2585 | 2604 | Exon 18 | AATCCCACGCCCCTGTCCAG | 83 | 7820 | 7839 | 3-10-7 | 441 |
| 599482 | 2586 | 2605 | Exon 18 | CAATCCCACGCCCCTGTCCA | 87 | 7821 | 7840 | 3-10-7 | 442 |
| 599483 | 2587 | 2606 | Exon 18 | TCAATCCCACGCCCCTGTCC | 90 | 7822 | 7841 | 3-10-7 | 443 |
| 599484 | 2588 | 2607 | Exon 18 | TTCAATCCCACGCCCCTGTC | 72 | 7823 | 7842 | 3-10-7 | 444 |
| 599485 | 2589 | 2608 | Exon 18 | ATTCAATCCCACGCCCCTGT | 82 | 7824 | 7843 | 3-10-7 | 445 |
| 599486 | 2590 | 2609 | Exon 18 | AATTCAATCCCACGCCCCTG | 84 | 7825 | 7844 | 3-10-7 | 446 |
| 599487 | 2591 | 2610 | Exon 18 | TAATTCAATCCCACGCCCCT | 84 | 7826 | 7845 | 3-10-7 | 447 |
| 599488 | 2592 | 2611 | Exon 18 | TTAATTCAATCCCACGCCCC | 87 | 7827 | 7846 | 3-10-7 | 448 |
| 599489 | 2593 | 2612 | Exon 18 | TTTAATTCAATCCCACGCCC | 87 | 7828 | 7847 | 3-10-7 | 449 |
| 599490 | 2594 | 2613 | Exon 18 | TTTTAATTCAATCCCACGCC | 86 | 7829 | 7848 | 3-10-7 | 450 |

TABLE 137-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhi-bition | SEQ ID NO: 2 Start site | SEQ ID NO: 2 Stop site | Motif | SEQ ID NO: |
|---|---|---|---|---|---|---|---|---|---|
| 599491 | 2595 | 2614 | Exon 18 | GTTTTAATTCAATCCCACGC | 87 | 7830 | 7849 | 3-10-7 | 451 |
| 599492 | 2596 | 2615 | Exon 18 | TGTTTTAATTCAATCCCACG | 88 | 7831 | 7850 | 3-10-7 | 452 |
| 599493 | 2597 | 2616 | Exon 18 | CTGTTTTAATTCAATCCCAC | 75 | 7832 | 7851 | 3-10-7 | 453 |
| 599433 | 2597 | 2616 | Exon 18 | CTGTTTTAATTCAATCCCAC | 89 | 7832 | 7851 | 6-8-6 | 453 |
| 599494 | 2598 | 2617 | Exon 18 | GCTGTTTTAATTCAATCCCA | 90 | 7833 | 7852 | 3-10-7 | 454 |
| 599434 | 2598 | 2617 | Exon 18 | GCTGTTTTAATTCAATCCCA | 89 | 7833 | 7852 | 6-8-6 | 454 |
| 599495 | 2599 | 2618 | Exon 18 | AGCTGTTTTAATTCAATCCC | 88 | 7834 | 7853 | 3-10-7 | 239 |
| 599435 | 2599 | 2618 | Exon 18 | AGCTGTTTTAATTCAATCCC | 91 | 7834 | 7853 | 6-8-6 | 239 |
| 599496 | 2600 | 2619 | Exon 18 | CAGCTGTTTTAATTCAATCC | 89 | 7835 | 7854 | 3-10-7 | 455 |
| 599436 | 2600 | 2619 | Exon 18 | CAGCTGTTTTAATTCAATCC | 89 | 7835 | 7854 | 6-8-6 | 455 |
| 599497 | 2601 | 2620 | Exon 18 | GCAGCTGTTTTAATTCAATC | 89 | 7836 | 7855 | 3-10-7 | 456 |
| 599437 | 2601 | 2620 | Exon 18 | GCAGCTGTTTTAATTCAATC | 91 | 7836 | 7855 | 6-8-6 | 456 |
| 599498 | 2602 | 2621 | Exon 18 | CGCAGCTGTTTTAATTCAAT | 88 | 7837 | 7856 | 3-10-7 | 457 |
| 599438 | 2602 | 2621 | Exon 18 | CGCAGCTGTTTTAATTCAAT | 90 | 7837 | 7856 | 6-8-6 | 457 |
| 599499 | 2603 | 2622 | Exon 18 | TCGCAGCTGTTTTAATTCAA | 81 | 7838 | 7857 | 3-10-7 | 458 |
| 599439 | 2603 | 2622 | Exon 18 | TCGCAGCTGTTTTAATTCAA | 88 | 7838 | 7857 | 6-8-6 | 458 |
| 532917 | 2604 | 2623 | Exon 18 | GTCGCAGCTGTTTTAATTCA | 90 | 7839 | 7858 | 5-10-5 | 317 |
| 599500 | 2604 | 2623 | Exon 18 | GTCGCAGCTGTTTTAATTCA | 88 | 7839 | 7858 | 3-10-7 | 317 |
| 599440 | 2604 | 2623 | Exon 18 | GTCGCAGCTGTTTTAATTCA | 88 | 7839 | 7858 | 6-8-6 | 317 |
| 599501 | 2605 | 2624 | Exon 18 | TGTCGCAGCTGTTTTAATTC | 78 | 7840 | 7859 | 3-10-7 | 459 |
| 599441 | 2605 | 2624 | Exon 18 | TGTCGCAGCTGTTTTAATTC | 90 | 7840 | 7859 | 6-8-6 | 459 |
| 599502 | 2606 | 2625 | Exon 18 | TTGTCGCAGCTGTTTTAATT | 87 | 7841 | 7860 | 3-10-7 | 460 |
| 599442 | 2606 | 2625 | Exon 18 | TTGTCGCAGCTGTTTTAATT | 76 | 7841 | 7860 | 6-8-6 | 460 |
| 599503 | 2607 | 2626 | Exon 18 | GTTGTCGCAGCTGTTTTAAT | 83 | 7842 | 7861 | 3-10-7 | 461 |
| 599443 | 2607 | 2626 | Exon 18 | GTTGTCGCAGCTGTTTTAAT | 77 | 7842 | 7861 | 6-8-6 | 461 |
| 599504 | 2608 | 2627 | Exon 18 | TGTTGTCGCAGCTGTTTTAA | 89 | 7843 | 7862 | 3-10-7 | 395 |
| 599444 | 2608 | 2627 | Exon 18 | TGTTGTCGCAGCTGTTTTAA | 69 | 7843 | 7862 | 6-8-6 | 395 |
| 599505 | 2609 | 2628 | Exon 19/Repeat | TTGTTGTCGCAGCTGTTTTA | 83 | n/a | n/a | 3-10-7 | 462 |
| 599445 | 2609 | 2628 | Exon 19/Repeat | TTGTTGTCGCAGCTGTTTTA | 85 | n/a | n/a | 6-8-6 | 462 |
| 599506 | 2610 | 2629 | Exon 19/Repeat | TTTGTTGTCGCAGCTGTTTT | 89 | n/a | n/a | 3-10-7 | 463 |
| 599446 | 2610 | 2629 | Exon 19/Repeat | TTTGTTGTCGCAGCTGTTTT | 85 | n/a | n/a | 6-8-6 | 463 |
| 599507 | 2611 | 2630 | Exon 19/Repeat | TTTTGTTGTCGCAGCTGTTT | 82 | n/a | n/a | 3-10-7 | 464 |
| 599447 | 2611 | 2630 | Exon 19/Repeat | TTTTGTTGTCGCAGCTGTTT | 83 | n/a | n/a | 6-8-6 | 464 |

TABLE 137-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599508 | 2612 | 2631 | Exon 19/ Repeat | TTTTTGTTGTCGCAGCTGTT | 90 | n/a | n/a | 3-10-7 | 465 |
| 599448 | 2612 | 2631 | Exon 19/ Repeat | TTTTTGTTGTCGCAGCTGTT | 87 | n/a | n/a | 6-8-6 | 465 |

Example 119: Antisense Inhibition of Human Complement Factor B (CFB) in HepG2 Cells by MOE Gapmers Additional antisense oligonucleotides were designed targeting human Complement Factor B (CFB) nucleic acid and were tested for their effects on CFB mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 2,000 nM antisense oligonucleotide. After a treatment period of approximately 24 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The newly designed chimeric antisense oligonucleotides in the Tables below were designed as 4-8-5 MOE, 5-8-5 MOE, 5-9-5 MOE, 5-10-5 MOE, 6-7-6-MOE, 3-10-5 MOE, or 6-8-6 MOE gapmers.

The 4-8-5 MOE gapmers are 17 nucleosides in length, wherein the central gap segment comprises of eight 2'-deoxynucleosides and is flanked by wing segments on the 5' direction and the 3' direction comprising four and five nucleosides respectively. The 5-8-5 MOE gapmers are 18 nucleosides in length, wherein the central gap segment comprises of eight 2'-deoxynucleosides and is flanked by wing segments on the 5' direction and the 3' direction comprising five nucleosides each. The 5-9-5 MOE gapmers are 19 nucleosides in length, wherein the central gap segment comprises of nine 2'-deoxynucleosides and is flanked by wing segments on the 5' direction and the 3' direction comprising five nucleosides each. The 5-10-5 MOE gapmers are 20 nucleosides in length, wherein the central gap segment comprises of ten 2'-deoxynucleosides and is flanked by wing segments on the 5' direction and the 3' direction comprising five nucleosides each. The 3-10-5 MOE gapmers are 18 nucleosides in length, wherein the central gap segment comprises of ten 2'-deoxynucleosides and is flanked by wing segments on the 5' direction and the 3' direction comprising three and five nucleosides respectively. The 6-7-6 MOE gapmers are 19 nucleosides in length, wherein the central gap segment comprises of seven 2'-deoxynucleosides and is flanked by wing segments on the 5' direction and the 3' direction comprising six nucleosides each. The 6-8-6 MOE gapmers are 20 nucleosides in length, wherein the central gap segment comprises of eight 2'-deoxynucleosides and is flanked by wing segments on the 5' direction and the 3' direction comprising six nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

"Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human CFB mRNA, designated herein as SEQ ID NO: 1 (GENBANK Accession No. NM_001710.5) or the human CFB genomic sequence, designated herein as SEQ ID NO: 2 (GENBANK Accession No. NT_007592.15 truncated from nucleotides 31852000 to 31861000), or both. 'n/a' indicates that the antisense oligonucleotide does not target that particular gene sequence with 10000 complementarity.

TABLE 138

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599160 | 2560 | 2577 | Exon 18 | CCCCTTATAGAAAACCCA | 26 | 7795 | 7812 | 5-8-5 | 740 |
| 599161 | 2561 | 2578 | Exon 18 | ACCCCTTATAGAAAACCC | 20 | 7796 | 7813 | 5-8-5 | 741 |
| 599162 | 2562 | 2579 | Exon 18 | AACCCCTTATAGAAAACC | 12 | 7797 | 7814 | 5-8-5 | 742 |
| 599163 | 2563 | 2580 | Exon 18 | AAACCCCTTATAGAAAAC | 11 | 7798 | 7815 | 5-8-5 | 743 |
| 599164 | 2564 | 2581 | Exon 18 | GAAACCCCTTATAGAAAA | 11 | 7799 | 7816 | 5-8-5 | 744 |

TABLE 138-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599165 | 2566 | 2583 | Exon 18 | AGGAAACCCCTTATAGAA | 0 | 7801 | 7818 | 5-8-5 | 745 |
| 599166 | 2567 | 2584 | Exon 18 | CAGGAAACCCCTTATAGA | 12 | 7802 | 7819 | 5-8-5 | 746 |
| 599167 | 2568 | 2585 | Exon 18 | GCAGGAAACCCCTTATAG | 14 | 7803 | 7820 | 5-8-5 | 747 |
| 599168 | 2569 | 2586 | Exon 18 | AGCAGGAAACCCCTTATA | 16 | 7804 | 7821 | 5-8-5 | 748 |
| 599169 | 2570 | 2587 | Exon 18 | CAGCAGGAAACCCCTTAT | 24 | 7805 | 7822 | 5-8-5 | 749 |
| 599170 | 2571 | 2588 | Exon 18 | CCAGCAGGAAACCCCTTA | 37 | 7806 | 7823 | 5-8-5 | 750 |
| 599171 | 2572 | 2589 | Exon 18 | TCCAGCAGGAAACCCCTT | 30 | 7807 | 7824 | 5-8-5 | 751 |
| 599172 | 2573 | 2590 | Exon 18 | GTCCAGCAGGAAACCCCT | 43 | 7808 | 7825 | 5-8-5 | 752 |
| 599173 | 2574 | 2591 | Exon 18 | TGTCCAGCAGGAAACCCC | 47 | 7809 | 7826 | 5-8-5 | 753 |
| 599174 | 2575 | 2592 | Exon 18 | CTGTCCAGCAGGAAACCC | 27 | 7810 | 7827 | 5-8-5 | 754 |
| 599175 | 2576 | 2593 | Exon 18 | CCTGTCCAGCAGGAAACC | 30 | 7811 | 7828 | 5-8-5 | 755 |
| 599176 | 2577 | 2594 | Exon 18 | CCCTGTCCAGCAGGAAAC | 34 | 7812 | 7829 | 5-8-5 | 756 |
| 599177 | 2578 | 2595 | Exon 18 | CCCCTGTCCAGCAGGAAA | 41 | 7813 | 7830 | 5-8-5 | 757 |
| 599178 | 2580 | 2597 | Exon 18 | CGCCCCTGTCCAGCAGGA | 67 | 7815 | 7832 | 5-8-5 | 758 |
| 599179 | 2581 | 2598 | Exon 18 | ACGCCCCTGTCCAGCAGG | 61 | 7816 | 7833 | 5-8-5 | 759 |
| 599180 | 2582 | 2599 | Exon 18 | CACGCCCCTGTCCAGCAG | 62 | 7817 | 7834 | 5-8-5 | 760 |
| 599181 | 2583 | 2600 | Exon 18 | CCACGCCCCTGTCCAGCA | 63 | 7818 | 7835 | 5-8-5 | 761 |
| 599128 | 2584 | 2600 | Exon 18 | CCACGCCCCTGTCCAGC | 55 | 7819 | 7835 | 4-8-5 | 649 |
| 599182 | 2584 | 2601 | Exon 18 | CCCACGCCCCTGTCCAGC | 58 | 7819 | 7836 | 5-8-5 | 762 |
| 599129 | 2585 | 2601 | Exon 18 | CCCACGCCCCTGTCCAG | 41 | 7820 | 7836 | 4-8-5 | 650 |
| 599183 | 2585 | 2602 | Exon 18 | TCCCACGCCCCTGTCCAG | 43 | 7820 | 7837 | 5-8-5 | 763 |
| 599130 | 2586 | 2602 | Exon 18 | TCCCACGCCCCTGTCCA | 46 | 7821 | 7837 | 4-8-5 | 651 |
| 599184 | 2586 | 2603 | Exon 18 | ATCCCACGCCCCTGTCCA | 32 | 7821 | 7838 | 5-8-5 | 764 |
| 599131 | 2587 | 2603 | Exon 18 | ATCCCACGCCCCTGTCC | 30 | 7822 | 7838 | 4-8-5 | 652 |
| 599185 | 2587 | 2604 | Exon 18 | AATCCCACGCCCCTGTCC | 35 | 7822 | 7839 | 5-8-5 | 765 |
| 599132 | 2588 | 2604 | Exon 18 | AATCCCACGCCCCTGTC | 52 | 7823 | 7839 | 4-8-5 | 653 |
| 599186 | 2588 | 2605 | Exon 18 | CAATCCCACGCCCCTGTC | 55 | 7823 | 7840 | 5-8-5 | 766 |
| 599133 | 2589 | 2605 | Exon 18 | CAATCCCACGCCCCTGT | 66 | 7824 | 7840 | 4-8-5 | 654 |
| 599187 | 2589 | 2606 | Exon 18 | TCAATCCCACGCCCCTGT | 72 | 7824 | 7841 | 5-8-5 | 767 |
| 599134 | 2590 | 2606 | Exon 18 | TCAATCCCACGCCCCTG | 80 | 7825 | 7841 | 4-8-5 | 655 |
| 599188 | 2590 | 2607 | Exon 18 | TTCAATCCCACGCCCCTG | 92 | 7825 | 7842 | 5-8-5 | 768 |
| 599135 | 2591 | 2607 | Exon 18 | TTCAATCCCACGCCCCT | 61 | 7826 | 7842 | 4-8-5 | 656 |
| 599189 | 2591 | 2608 | Exon 18 | ATTCAATCCCACGCCCCT | 52 | 7826 | 7843 | 5-8-5 | 769 |
| 599136 | 2592 | 2608 | Exon 18 | ATTCAATCCCACGCCCC | 68 | 7827 | 7843 | 4-8-5 | 657 |
| 599190 | 2592 | 2609 | Exon 18 | AATTCAATCCCACGCCCC | 62 | 7827 | 7844 | 5-8-5 | 770 |
| 599137 | 2593 | 2609 | Exon 18 | AATTCAATCCCACGCCC | 51 | 7828 | 7844 | 4-8-5 | 658 |

TABLE 138-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599191 | 2593 | 2610 | Exon 18 | TAATTCAATCCCACGCCC | 54 | 7828 | 7845 | 5-8-5 | 771 |
| 599138 | 2594 | 2610 | Exon 18 | TAATTCAATCCCACGCC | 71 | 7829 | 7845 | 4-8-5 | 659 |
| 599192 | 2594 | 2611 | Exon 18 | TTAATTCAATCCCACGCC | 66 | 7829 | 7846 | 5-8-5 | 772 |
| 599139 | 2595 | 2611 | Exon 18 | TTAATTCAATCCCACGC | 80 | 7830 | 7846 | 4-8-5 | 660 |
| 599193 | 2595 | 2612 | Exon 18 | TTTAATTCAATCCCACGC | 74 | 7830 | 7847 | 5-8-5 | 773 |
| 599140 | 2596 | 2612 | Exon 18 | TTTAATTCAATCCCACG | 66 | 7831 | 7847 | 4-8-5 | 786 |
| 599194 | 2596 | 2613 | Exon 18 | TTTTAATTCAATCCCACG | 66 | 7831 | 7848 | 5-8-5 | 774 |
| 599141 | 2597 | 2613 | Exon 18 | TTTTAATTCAATCCCAC | 63 | 7832 | 7848 | 4-8-5 | 662 |
| 599195 | 2597 | 2614 | Exon 18 | GTTTTAATTCAATCCCAC | 86 | 7832 | 7849 | 5-8-5 | 775 |
| 599142 | 2598 | 2614 | Exon 18 | GTTTTAATTCAATCCCA | 69 | 7833 | 7849 | 4-8-5 | 663 |
| 599196 | 2598 | 2615 | Exon 18 | TGTTTTAATTCAATCCCA | 82 | 7833 | 7850 | 5-8-5 | 776 |
| 599143 | 2599 | 2615 | Exon 18 | TGTTTTAATTCAATCCC | 59 | 7834 | 7850 | 4-8-5 | 664 |
| 599197 | 2599 | 2616 | Exon 18 | CTGTTTTAATTCAATCCC | 79 | 7834 | 7851 | 5-8-5 | 777 |
| 599144 | 2600 | 2616 | Exon 18 | CTGTTTTAATTCAATCC | 52 | 7835 | 7851 | 4-8-5 | 665 |
| 599198 | 2600 | 2617 | Exon 18 | GCTGTTTTAATTCAATCC | 86 | 7835 | 7852 | 5-8-5 | 778 |
| 599145 | 2601 | 2617 | Exon 18 | GCTGTTTTAATTCAATC | 53 | 7836 | 7852 | 4-8-5 | 666 |
| 599199 | 2601 | 2618 | Exon 18 | AGCTGTTTTAATTCAATC | 72 | 7836 | 7853 | 5-8-5 | 779 |
| 599146 | 2602 | 2618 | Exon 18 | AGCTGTTTTAATTCAAT | 42 | 7837 | 7853 | 4-8-5 | 667 |
| 599200 | 2602 | 2619 | Exon 18 | CAGCTGTTTTAATTCAAT | 76 | 7837 | 7854 | 5-8-5 | 780 |
| 599147 | 2603 | 2619 | Exon 18 | CAGCTGTTTTAATTCAA | 55 | 7838 | 7854 | 4-8-5 | 668 |
| 599201 | 2603 | 2620 | Exon 18 | GCAGCTGTTTTAATTCAA | 87 | 7838 | 7855 | 5-8-5 | 781 |
| 532917 | 2604 | 2623 | Exon 18 | GTCGCAGCTGTTTTAATTCA | 93 | 7839 | 7858 | 5-10-5 | 317 |
| 599148 | 2604 | 2620 | Exon 18 | GCAGCTGTTTTAATTCA | 84 | 7839 | 7855 | 4-8-5 | 669 |
| 599202 | 2604 | 2621 | Exon 18 | CGCAGCTGTTTTAATTCA | 89 | 7839 | 7856 | 5-8-5 | 782 |
| 599149 | 2605 | 2621 | Exon 18 | CGCAGCTGTTTTAATTC | 92 | 7840 | 7856 | 4-8-5 | 670 |
| 599203 | 2605 | 2622 | Exon 18 | TCGCAGCTGTTTTAATTC | 90 | 7840 | 7857 | 5-8-5 | 783 |
| 599150 | 2606 | 2622 | Exon 18 | TCGCAGCTGTTTTAATT | 75 | 7841 | 7857 | 4-8-5 | 671 |
| 599151 | 2607 | 2623 | Exon 18 | GTCGCAGCTGTTTTAAT | 80 | 7842 | 7858 | 4-8-5 | 672 |
| 599152 | 2608 | 2624 | Exon 18 | TGTCGCAGCTGTTTTAA | 76 | 7843 | 7859 | 4-8-5 | 673 |
| 599153 | 2609 | 2625 | Exon 18 | TTGTCGCAGCTGTTTTA | 56 | 7844 | 7860 | 4-8-5 | 674 |
| 599154 | 2610 | 2626 | Exon 18 | GTTGTCGCAGCTGTTTT | 85 | 7845 | 7861 | 4-8-5 | 675 |
| 599155 | 2611 | 2627 | Exon 18 | TGTTGTCGCAGCTGTTT | 89 | 7846 | 7862 | 4-8-5 | 676 |
| 599156 | 2612 | 2628 | Exon 18/ Repeat | TTGTTGTCGCAGCTGTT | 83 | n/a | n/a | 4-8-5 | 813 |
| 599157 | 2613 | 2629 | Exon 18/ Repeat | TTTGTTGTCGCAGCTGT | 78 | n/a | n/a | 4-8-5 | 678 |

TABLE 138-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599158 | 2614 | 2630 | Exon 18/ Repeat | TTTTGTTGTCGCAGCTG | 83 | n/a | n/a | 4-8-5 | 679 |
| 599159 | 2615 | 2631 | Exon 18/ Repeat | TTTTTGTTGTCGCAGCT | 65 | n/a | n/a | 4-8-5 | 680 |
| 599204 | 2606 | 2623 | Exon 18 | GTCGCAGCTGTTTTAATT | 83 | 7841 | 7858 | 5-8-5 | 784 |

TABLE 139

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599509 | 2552 | 2570 | Exon 18 | TAGAAAACCCAAATCCTCA | 45 | 7787 | 7805 | 6-7-6 | 681 |
| 599213 | 2553 | 2570 | Exon 18 | TAGAAAACCCAAATCCTC | 89 | 7788 | 7805 | 3-10-5 | 785 |
| 599273 | 2553 | 2571 | Exon 18 | ATAGAAAACCCAAATCCTC | 85 | 7788 | 7806 | 6-7-6 | 682 |
| 599214 | 2554 | 2571 | Exon 18 | ATAGAAAACCCAAATCCT | 79 | 7789 | 7806 | 3-10-5 | 786 |
| 599274 | 2554 | 2572 | Exon 18 | TATAGAAAACCCAAATCCT | 75 | 7789 | 7807 | 6-7-6 | 683 |
| 599215 | 2555 | 2572 | Exon 18 | TATAGAAAACCCAAATCC | 81 | 7790 | 7807 | 3-10-5 | 787 |
| 599216 | 2556 | 2573 | Exon 18 | TTATAGAAAACCCAAATC | 87 | 7791 | 7808 | 3-10-5 | 788 |
| 599275 | 2556 | 2574 | Exon 18 | CTTATAGAAAACCCAAATC | 84 | 7791 | 7809 | 6-7-6 | 684 |
| 599217 | 2557 | 2574 | Exon 18 | CTTATAGAAAACCCAAAT | 84 | 7792 | 7809 | 3-10-5 | 789 |
| 599276 | 2557 | 2575 | Exon 18 | CCTTATAGAAAACCCAAAT | 68 | 7792 | 7810 | 6-7-6 | 685 |
| 599218 | 2558 | 2575 | Exon 18 | CCTTATAGAAAACCCAAA | 82 | 7793 | 7810 | 3-10-5 | 790 |
| 599277 | 2558 | 2576 | Exon 18 | CCCTTATAGAAAACCCAAA | 82 | 7793 | 7811 | 6-7-6 | 686 |
| 599219 | 2559 | 2576 | Exon 18 | CCCTTATAGAAAACCCAA | 81 | 7794 | 7811 | 3-10-5 | 791 |
| 599278 | 2559 | 2577 | Exon 18 | CCCCTTATAGAAAACCCAA | 84 | 7794 | 7812 | 6-7-6 | 687 |
| 599220 | 2560 | 2577 | Exon 18 | CCCCTTATAGAAAACCCA | 92 | 7795 | 7812 | 3-10-5 | 740 |
| 599279 | 2560 | 2578 | Exon 18 | ACCCCTTATAGAAAACCCA | 92 | 7795 | 7813 | 6-7-6 | 688 |
| 599221 | 2561 | 2578 | Exon 18 | ACCCCTTATAGAAAACCC | 93 | 7796 | 7813 | 3-10-5 | 741 |
| 599280 | 2561 | 2579 | Exon 18 | AACCCCTTATAGAAAACCC | 90 | 7796 | 7814 | 6-7-6 | 689 |
| 599222 | 2562 | 2579 | Exon 18 | AACCCCTTATAGAAAACC | 95 | 7797 | 7814 | 3-10-5 | 742 |
| 599223 | 2563 | 2580 | Exon 18 | AAACCCCTTATAGAAAAC | 93 | 7798 | 7815 | 3-10-5 | 743 |
| 599224 | 2564 | 2581 | Exon 18 | GAAACCCCTTATAGAAAA | 90 | 7799 | 7816 | 3-10-5 | 744 |
| 599225 | 2566 | 2583 | Exon 18 | AGGAAACCCCTTATAGAA | 93 | 7801 | 7818 | 3-10-5 | 745 |
| 599226 | 2567 | 2584 | Exon 18 | CAGGAAACCCCTTATAGA | 95 | 7802 | 7819 | 3-10-5 | 746 |
| 599227 | 2568 | 2585 | Exon 18 | GCAGGAAACCCCTTATAG | 94 | 7803 | 7820 | 3-10-5 | 747 |
| 599228 | 2569 | 2586 | Exon 18 | AGCAGGAAACCCCTTATA | 96 | 7804 | 7821 | 3-10-5 | 748 |
| 599229 | 2570 | 2587 | Exon 18 | CAGCAGGAAACCCCTTAT | 92 | 7805 | 7822 | 3-10-5 | 749 |

TABLE 139-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhi- bition | SEQ ID NO: 2 Start site | SEQ ID NO: 2 Stop site | Motif | SEQ ID NO: |
|---|---|---|---|---|---|---|---|---|---|
| 599230 | 2571 | 2588 | Exon 18 | CCAGCAGGAAACCCCTTA | 88 | 7806 | 7823 | 3-10-5 | 750 |
| 599231 | 2572 | 2589 | Exon 18 | TCCAGCAGGAAACCCCTT | 83 | 7807 | 7824 | 3-10-5 | 751 |
| 599232 | 2573 | 2590 | Exon 18 | GTCCAGCAGGAAACCCCT | 89 | 7808 | 7825 | 3-10-5 | 752 |
| 599233 | 2574 | 2591 | Exon 18 | TGTCCAGCAGGAAACCCC | 83 | 7809 | 7826 | 3-10-5 | 753 |
| 599234 | 2575 | 2592 | Exon 18 | CTGTCCAGCAGGAAACCC | 88 | 7810 | 7827 | 3-10-5 | 754 |
| 599235 | 2576 | 2593 | Exon 18 | CCTGTCCAGCAGGAAACC | 91 | 7811 | 7828 | 3-10-5 | 755 |
| 599236 | 2577 | 2594 | Exon 18 | CCCTGTCCAGCAGGAAAC | 90 | 7812 | 7829 | 3-10-5 | 756 |
| 599237 | 2578 | 2595 | Exon 18 | CCCCTGTCCAGCAGGAAA | 34 | 7813 | 7830 | 3-10-5 | 757 |
| 599238 | 2580 | 2597 | Exon 18 | CGCCCCTGTCCAGCAGGA | 14 | 7815 | 7832 | 3-10-5 | 758 |
| 599239 | 2581 | 2598 | Exon 18 | ACGCCCCTGTCCAGCAGG | 10 | 7816 | 7833 | 3-10-5 | 759 |
| 599240 | 2582 | 2599 | Exon 18 | CACGCCCCTGTCCAGCAG | 26 | 7817 | 7834 | 3-10-5 | 760 |
| 599241 | 2583 | 2600 | Exon 18 | CCACGCCCCTGTCCAGCA | 11 | 7818 | 7835 | 3-10-5 | 761 |
| 599242 | 2584 | 2601 | Exon 18 | CCCACGCCCCTGTCCAGC | 24 | 7819 | 7836 | 3-10-5 | 762 |
| 599243 | 2585 | 2602 | Exon 18 | TCCCACGCCCCTGTCCAG | 23 | 7820 | 7837 | 3-10-5 | 763 |
| 599244 | 2586 | 2603 | Exon 18 | ATCCCACGCCCCTGTCCA | 29 | 7821 | 7838 | 3-10-5 | 764 |
| 599245 | 2587 | 2604 | Exon 18 | AATCCCACGCCCCTGTCC | 11 | 7822 | 7839 | 3-10-5 | 765 |
| 599246 | 2588 | 2605 | Exon 18 | CAATCCCACGCCCCTGTC | 0 | 7823 | 7840 | 3-10-5 | 766 |
| 599247 | 2589 | 2606 | Exon 18 | TCAATCCCACGCCCCTGT | 21 | 7824 | 7841 | 3-10-5 | 767 |
| 599248 | 2590 | 2607 | Exon 18 | TTCAATCCCACGCCCCTG | 0 | 7825 | 7842 | 3-10-5 | 768 |
| 599249 | 2591 | 2608 | Exon 18 | ATTCAATCCCACGCCCCT | 9 | 7826 | 7843 | 3-10-5 | 769 |
| 599250 | 2592 | 2609 | Exon 18 | AATTCAATCCCACGCCCC | 4 | 7827 | 7844 | 3-10-5 | 770 |
| 599251 | 2593 | 2610 | Exon 18 | TAATTCAATCCCACGCCC | 12 | 7828 | 7845 | 3-10-5 | 771 |
| 599252 | 2594 | 2611 | Exon 18 | TTAATTCAATCCCACGCC | 2 | 7829 | 7846 | 3-10-5 | 772 |
| 599253 | 2595 | 2612 | Exon 18 | TTTAATTCAATCCCACGC | 28 | 7830 | 7847 | 3-10-5 | 773 |
| 599254 | 2596 | 2613 | Exon 18 | TTTTAATTCAATCCCACG | 27 | 7831 | 7848 | 3-10-5 | 774 |
| 599255 | 2597 | 2614 | Exon 18 | GTTTTAATTCAATCCCAC | 38 | 7832 | 7849 | 3-10-5 | 775 |
| 599256 | 2598 | 2615 | Exon 18 | TGTTTTAATTCAATCCCA | 36 | 7833 | 7850 | 3-10-5 | 776 |
| 599257 | 2599 | 2616 | Exon 18 | CTGTTTTAATTCAATCCC | 48 | 7834 | 7851 | 3-10-5 | 777 |
| 599258 | 2600 | 2617 | Exon 18 | GCTGTTTTAATTCAATCC | 19 | 7835 | 7852 | 3-10-5 | 778 |
| 599259 | 2601 | 2618 | Exon 18 | AGCTGTTTTAATTCAATC | 36 | 7836 | 7853 | 3-10-5 | 779 |
| 599260 | 2602 | 2619 | Exon 18 | CAGCTGTTTTAATTCAAT | 58 | 7837 | 7854 | 3-10-5 | 780 |
| 599261 | 2603 | 2620 | Exon 18 | GCAGCTGTTTTAATTCAA | 35 | 7838 | 7855 | 3-10-5 | 781 |
| 532917 | 2604 | 2623 | Exon 18 | GTCGCAGCTGTTTTAATTCA | 96 | 7839 | 7858 | 5-10-5 | 317 |
| 599262 | 2604 | 2621 | Exon 18 | CGCAGCTGTTTTAATTCA | 52 | 7839 | 7856 | 3-10-5 | 782 |
| 599263 | 2605 | 2622 | Exon 18 | TCGCAGCTGTTTTAATTC | 66 | 7840 | 7857 | 3-10-5 | 783 |
| 599264 | 2606 | 2623 | Exon 18 | GTCGCAGCTGTTTTAATT | 48 | 7841 | 7858 | 3-10-5 | 784 |

TABLE 139-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599265 | 2607 | 2624 | Exon 18 | TGTCGCAGCTGTTTTAAT | 46 | 7842 | 7859 | 3-10-5 | 792 |
| 599205 | 2607 | 2624 | Exon 18 | TGTCGCAGCTGTTTTAAT | 83 | 7842 | 7859 | 5-8-5 | 792 |
| 599266 | 2608 | 2625 | Exon 18 | TTGTCGCAGCTGTTTTAA | 76 | 7843 | 7860 | 3-10-5 | 793 |
| 599206 | 2608 | 2625 | Exon 18 | TTGTCGCAGCTGTTTTAA | 90 | 7843 | 7860 | 5-8-5 | 793 |
| 599267 | 2609 | 2626 | Exon 18 | GTTGTCGCAGCTGTTTTA | 53 | 7844 | 7861 | 3-10-5 | 794 |
| 599207 | 2609 | 2626 | Exon 18 | GTTGTCGCAGCTGTTTTA | 82 | 7844 | 7861 | 5-8-5 | 794 |
| 599268 | 2610 | 2627 | Exon 18 | TGTTGTCGCAGCTGTTTT | 58 | 7845 | 7862 | 3-10-5 | 795 |
| 599208 | 2610 | 2627 | Exon 18 | TGTTGTCGCAGCTGTTTT | 70 | 7845 | 7862 | 5-8-5 | 795 |
| 599269 | 2611 | 2628 | Exon 18/ Repeat | TTGTTGTCGCAGCTGTTT | 38 | n/a | n/a | 3-10-5 | 796 |
| 599209 | 2611 | 2628 | Exon 18/ Repeat | TTGTTGTCGCAGCTGTTT | 50 | n/a | n/a | 5-8-5 | 796 |
| 599270 | 2612 | 2629 | Exon 18/ Repeat | TTTGTTGTCGCAGCTGTT | 46 | n/a | n/a | 3-10-5 | 797 |
| 599210 | 2612 | 2629 | Exon 18/ Repeat | TTTGTTGTCGCAGCTGTT | 76 | n/a | n/a | 5-8-5 | 797 |
| 599271 | 2613 | 2630 | Exon 18/ Repeat | TTTTGTTGTCGCAGCTGT | 64 | n/a | n/a | 3-10-5 | 798 |
| 599211 | 2613 | 2630 | Exon 18/ Repeat | TTTTGTTGTCGCAGCTGT | 78 | n/a | n/a | 5-8-5 | 798 |
| 599272 | 2614 | 2631 | Exon 18/ Repeat | TTTTTGTTGTCGCAGCTG | 89 | n/a | n/a | 3-10-5 | 799 |
| 599212 | 2614 | 2631 | Exon 18/ Repeat | TTTTTGTTGTCGCAGCTG | 84 | n/a | n/a | 5-8-5 | 799 |

TABLE 140

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599511 | 2552 | 2571 | Exon 18 | ATAGAAAACCCAAATCCTCA | 38 | 7787 | 7806 | 6-8-6 | 410 |
| 599389 | 2553 | 2572 | Exon 18 | TATAGAAAACCCAAATCCTC | 80 | 7788 | 7807 | 6-8-6 | 411 |
| 599390 | 2554 | 2573 | Exon 18 | TTATAGAAAACCCAAATCCT | 92 | 7789 | 7808 | 6-8-6 | 412 |
| 599391 | 2555 | 2574 | Exon 18 | CTTATAGAAAACCCAAATCC | 90 | 7790 | 7809 | 6-8-6 | 413 |
| 599392 | 2556 | 2575 | Exon 18 | CCTTATAGAAAACCCAAATC | 87 | 7791 | 7810 | 6-8-6 | 414 |
| 599393 | 2557 | 2576 | Exon 18 | CCCTTATAGAAAACCCAAAT | 87 | 7792 | 7811 | 6-8-6 | 415 |
| 599394 | 2558 | 2577 | Exon 18 | CCCCTTATAGAAAACCCAAA | 74 | 7793 | 7812 | 6-8-6 | 416 |
| 599395 | 2559 | 2578 | Exon 18 | ACCCCTTATAGAAAACCCAA | 78 | 7794 | 7813 | 6-8-6 | 417 |
| 599396 | 2560 | 2579 | Exon 18 | AACCCCTTATAGAAAACCCA | 77 | 7795 | 7814 | 6-8-6 | 418 |

TABLE 140-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599397 | 2561 | 2580 | Exon 18 | AAACCCCTTATAGAAAACCC | 89 | 7796 | 7815 | 6-8-6 | 419 |
| 599398 | 2562 | 2581 | Exon 18 | GAAACCCCTTATAGAAAACC | 90 | 7797 | 7816 | 6-8-6 | 420 |
| 599399 | 2563 | 2582 | Exon 18 | GGAAACCCCTTATAGAAAAC | 91 | 7798 | 7817 | 6-8-6 | 421 |
| 599400 | 2564 | 2583 | Exon 18 | AGGAAACCCCTTATAGAAAA | 88 | 7799 | 7818 | 6-8-6 | 422 |
| 599401 | 2565 | 2584 | Exon 18 | CAGGAAACCCCTTATAGAAA | 85 | 7800 | 7819 | 6-8-6 | 423 |
| 599402 | 2566 | 2585 | Exon 18 | GCAGGAAACCCCTTATAGAA | 77 | 7801 | 7820 | 6-8-6 | 424 |
| 599403 | 2567 | 2586 | Exon 18 | AGCAGGAAACCCCTTATAGA | 85 | 7802 | 7821 | 6-8-6 | 425 |
| 599404 | 2568 | 2587 | Exon 18 | CAGCAGGAAACCCCTTATAG | 90 | 7803 | 7822 | 6-8-6 | 426 |
| 599405 | 2569 | 2588 | Exon 18 | CCAGCAGGAAACCCCTTATA | 89 | 7804 | 7823 | 6-8-6 | 427 |
| 599406 | 2570 | 2589 | Exon 18 | TCCAGCAGGAAACCCCTTAT | 72 | 7805 | 7824 | 6-8-6 | 428 |
| 599407 | 2571 | 2590 | Exon 18 | GTCCAGCAGGAAACCCCTTA | 87 | 7806 | 7825 | 6-8-6 | 237 |
| 599408 | 2572 | 2591 | Exon 18 | TGTCCAGCAGGAAACCCCTT | 87 | 7807 | 7826 | 6-8-6 | 429 |
| 599409 | 2573 | 2592 | Exon 18 | CTGTCCAGCAGGAAACCCCT | 83 | 7808 | 7827 | 6-8-6 | 430 |
| 599410 | 2574 | 2593 | Exon 18 | CCTGTCCAGCAGGAAACCCC | 88 | 7809 | 7828 | 6-8-6 | 431 |
| 599411 | 2575 | 2594 | Exon 18 | CCCTGTCCAGCAGGAAACCC | 45 | 7810 | 7829 | 6-8-6 | 432 |
| 599412 | 2576 | 2595 | Exon 18 | CCCCTGTCCAGCAGGAAACC | 66 | 7811 | 7830 | 6-8-6 | 433 |
| 599413 | 2577 | 2596 | Exon 18 | GCCCCTGTCCAGCAGGAAAC | 92 | 7812 | 7831 | 6-8-6 | 238 |
| 599414 | 2578 | 2597 | Exon 18 | CGCCCCTGTCCAGCAGGAAA | 92 | 7813 | 7832 | 6-8-6 | 434 |
| 599415 | 2579 | 2598 | Exon 18 | ACGCCCCTGTCCAGCAGGAA | 87 | 7814 | 7833 | 6-8-6 | 435 |
| 599416 | 2580 | 2599 | Exon 18 | CACGCCCCTGTCCAGCAGGA | 91 | 7815 | 7834 | 6-8-6 | 436 |
| 599417 | 2581 | 2600 | Exon 18 | CCACGCCCCTGTCCAGCAGG | 84 | 7816 | 7835 | 6-8-6 | 437 |
| 599357 | 2582 | 2600 | Exon 18 | CCACGCCCCTGTCCAGCAG | 88 | 7817 | 7835 | 5-9-5 | 708 |
| 599418 | 2582 | 2601 | Exon 18 | CCCACGCCCCTGTCCAGCAG | 85 | 7817 | 7836 | 6-8-6 | 438 |
| 599358 | 2583 | 2601 | Exon 18 | CCCACGCCCCTGTCCAGCA | 86 | 7818 | 7836 | 5-9-5 | 709 |
| 599419 | 2583 | 2602 | Exon 18 | TCCCACGCCCCTGTCCAGCA | 91 | 7818 | 7837 | 6-8-6 | 833 |
| 599359 | 2584 | 2602 | Exon 18 | TCCCACGCCCCTGTCCAGC | 85 | 7819 | 7837 | 5-9-5 | 834 |
| 599420 | 2584 | 2603 | Exon 18 | ATCCCACGCCCCTGTCCAGC | 91 | 7819 | 7838 | 6-8-6 | 440 |
| 599360 | 2585 | 2603 | Exon 18 | ATCCCACGCCCCTGTCCAG | 89 | 7820 | 7838 | 5-9-5 | 711 |
| 599421 | 2585 | 2604 | Exon 18 | AATCCCACGCCCCTGTCCAG | 87 | 7820 | 7839 | 6-8-6 | 441 |
| 599361 | 2586 | 2604 | Exon 18 | AATCCCACGCCCCTGTCCA | 89 | 7821 | 7839 | 5-9-5 | 712 |
| 599422 | 2586 | 2605 | Exon 18 | CAATCCCACGCCCCTGTCCA | 90 | 7821 | 7840 | 6-8-6 | 442 |
| 599362 | 2587 | 2605 | Exon 18 | CAATCCCACGCCCCTGTCC | 94 | 7822 | 7840 | 5-9-5 | 713 |
| 599423 | 2587 | 2606 | Exon 18 | TCAATCCCACGCCCCTGTCC | 85 | 7822 | 7841 | 6-8-6 | 841 |
| 599363 | 2588 | 2606 | Exon 18 | TCAATCCCACGCCCCTGTC | 88 | 7823 | 7841 | 5-9-5 | 714 |
| 599424 | 2588 | 2607 | Exon 18 | TTCAATCCCACGCCCCTGTC | 88 | 7823 | 7842 | 6-8-6 | 444 |
| 599364 | 2589 | 2607 | Exon 18 | TTCAATCCCACGCCCCTGT | 88 | 7824 | 7842 | 5-9-5 | 715 |

TABLE 140-continued

Inhibition of CFB mRNA by MOE gapmers targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 599425 | 2589 | 2608 | Exon 18 | ATTCAATCCCACGCCCTGT | 68 | 7824 | 7843 | 6-8-6 | 445 |
| 599365 | 2590 | 2608 | Exon 18 | ATTCAATCCCACGCCCTG | 48 | 7825 | 7843 | 5-9-5 | 716 |
| 599426 | 2590 | 2609 | Exon 18 | AATTCAATCCCACGCCCTG | 55 | 7825 | 7844 | 6-8-6 | 446 |
| 599366 | 2591 | 2609 | Exon 18 | AATTCAATCCCACGCCCT | 28 | 7826 | 7844 | 5-9-5 | 717 |
| 599427 | 2591 | 2610 | Exon 18 | TAATTCAATCCCACGCCCT | 13 | 7826 | 7845 | 6-8-6 | 849 |
| 599367 | 2592 | 2610 | Exon 18 | TAATTCAATCCCACGCCC | 21 | 7827 | 7845 | 5-9-5 | 718 |
| 599428 | 2592 | 2611 | Exon 18 | TTAATTCAATCCCACGCCC | 39 | 7827 | 7846 | 6-8-6 | 448 |
| 599368 | 2593 | 2611 | Exon 18 | TTAATTCAATCCCACGCC | 20 | 7828 | 7846 | 5-9-5 | 719 |
| 599429 | 2593 | 2612 | Exon 18 | TTTAATTCAATCCCACGCC | 18 | 7828 | 7847 | 6-8-6 | 449 |
| 599369 | 2594 | 2612 | Exon 18 | TTTAATTCAATCCCACGC | 78 | 7829 | 7847 | 5-9-5 | 720 |
| 599430 | 2594 | 2613 | Exon 18 | TTTTAATTCAATCCCACGC | 24 | 7829 | 7848 | 6-8-6 | 450 |
| 599370 | 2595 | 2613 | Exon 18 | TTTTAATTCAATCCCACG | 25 | 7830 | 7848 | 5-9-5 | 721 |
| 599431 | 2595 | 2614 | Exon 18 | GTTTTAATTCAATCCCACG | 30 | 7830 | 7849 | 6-8-6 | 451 |
| 599371 | 2596 | 2614 | Exon 18 | GTTTTAATTCAATCCCACG | 84 | 7831 | 7849 | 5-9-5 | 722 |
| 599432 | 2596 | 2615 | Exon 18 | TGTTTTAATTCAATCCCACG | 29 | 7831 | 7850 | 6-8-6 | 452 |
| 599372 | 2597 | 2615 | Exon 18 | TGTTTTAATTCAATCCCAC | 83 | 7832 | 7850 | 5-9-5 | 723 |
| 599373 | 2598 | 2616 | Exon 18 | CTGTTTTAATTCAATCCCA | 81 | 7833 | 7851 | 5-9-5 | 724 |
| 599374 | 2599 | 2617 | Exon 18 | GCTGTTTTAATTCAATCCC | 26 | 7834 | 7852 | 5-9-5 | 725 |
| 599375 | 2600 | 2618 | Exon 18 | AGCTGTTTTAATTCAATCC | 26 | 7835 | 7853 | 5-9-5 | 726 |
| 599376 | 2601 | 2619 | Exon 18 | CAGCTGTTTTAATTCAATC | 62 | 7836 | 7854 | 5-9-5 | 727 |
| 599377 | 2602 | 2620 | Exon 18 | GCAGCTGTTTTAATTCAAT | 21 | 7837 | 7855 | 5-9-5 | 728 |
| 599378 | 2603 | 2621 | Exon 18 | CGCAGCTGTTTTAATTCAA | 90 | 7838 | 7856 | 5-9-5 | 729 |
| 532917 | 2604 | 2623 | Exon 18 | GTCGCAGCTGTTTTAATTCA | 95 | 7839 | 7858 | 5-10-5 | 867 |
| 599379 | 2604 | 2622 | Exon 18 | TCGCAGCTGTTTTAATTCA | 88 | 7839 | 7857 | 5-9-5 | 730 |
| 599380 | 2605 | 2623 | Exon 18 | GTCGCAGCTGTTTTAATTC | 37 | 7840 | 7858 | 5-9-5 | 869 |
| 599381 | 2606 | 2624 | Exon 18 | TGTCGCAGCTGTTTTAATT | 33 | 7841 | 7859 | 5-9-5 | 732 |
| 599382 | 2607 | 2625 | Exon 18 | TTGTCGCAGCTGTTTTAAT | 81 | 7842 | 7860 | 5-9-5 | 733 |
| 599383 | 2608 | 2626 | Exon 18 | GTTGTCGCAGCTGTTTTAA | 54 | 7843 | 7861 | 5-9-5 | 734 |
| 599384 | 2609 | 2627 | Exon 18 | TGTTGTCGCAGCTGTTTTA | 85 | 7844 | 7862 | 5-9-5 | 873 |
| 599385 | 2610 | 2628 | Exon 18/ Repeat | TTGTTGTCGCAGCTGTTTT | 59 | n/a | n/a | 5-9-5 | 736 |
| 599386 | 2611 | 2629 | Exon 18/ Repeat | TTTGTTGTCGCAGCTGTTT | 81 | n/a | n/a | 5-9-5 | 737 |
| 599387 | 2612 | 2630 | Exon 18/ Repeat | TTTTGTTGTCGCAGCTGTT | 80 | n/a | n/a | 5-9-5 | 738 |
| 599388 | 2613 | 2631 | Exon 18/ Repeat | TTTTTGTTGTCGCAGCTGT | 84 | n/a | n/a | 5-9-5 | 739 |

Example 120: Antisense Inhibition of Human Complement Factor B (CFB) in HepG2 Cells by MOE Gapmers Additional antisense oligonucleotides were designed targeting human Complement Factor B (CFB) nucleic acid and were tested for their effects on CFB mRNA in vitro. Cultured HepG2 cells at a density of 20,000 cells per well were transfected using electroporation with 1,000 nM antisense oligonucleotide. After a treatment period of approximately 24 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The newly designed chimeric antisense oligonucleotides in the Tables below were designed deoxy, MOE and (S)-cEt oligonucleotides. The deoxy, MOE and (S)-cEt oligonucleotides are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; 'd' indicates deoxyribose; and 'e' indicates a MOE modification.

"Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human CFB mRNA, designated herein as SEQ ID NO: 1 (GENBANK Accession No. NM_001710.5) or the human CFB genomic sequence, designated herein as SEQ ID NO: 2 (GENBANK Accession No. NT_007592.15 truncated from nucleotides 31852000 to 31861000), or both. 'n/a' indicates that the antisense oligonucleotide does not target that particular gene sequence with 10000 complementarity.

TABLE 141

Inhibition of CFB mRNA by deoxy, MOE and (S)-cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599513 | 2551 | 2566 | Exon 18 | AAACCCAAATCCTCAT | 11 | 7786 | 7801 | ekkeekkddddddddk | 557 |
| 599514 | 2553 | 2568 | Exon 18 | GAAAACCCAAATCCTC | 13 | 7788 | 7803 | ekkeekkddddddddk | 801 |
| 599515 | 2555 | 2570 | Exon 18 | TAGAAAACCCAAATCC | 54 | 7790 | 7805 | ekkeekkddddddddk | 559 |
| 599516 | 2559 | 2574 | Exon 18 | CTTATAGAAAACCCAA | 16 | 7794 | 7809 | ekkeekkddddddddk | 561 |
| 599517 | 2560 | 2575 | Exon 18 | CCTTATAGAAAACCCA | 29 | 7795 | 7810 | ekkeekkddddddddk | 562 |
| 599518 | 2561 | 2576 | Exon 18 | CCCTTATAGAAAACCC | 55 | 7796 | 7811 | ekkeekkddddddddk | 563 |
| 599519 | 2562 | 2577 | Exon 18 | CCCCTTATAGAAAACC | 31 | 7797 | 7812 | ekkeekkddddddddk | 564 |
| 599520 | 2563 | 2578 | Exon 18 | ACCCCTTATAGAAAAC | 14 | 7798 | 7813 | ekkeekkddddddddk | 565 |
| 599521 | 2564 | 2579 | Exon 18 | AACCCCTTATAGAAAA | 9 | 7799 | 7814 | ekkeekkddddddddk | 566 |
| 599522 | 2565 | 2580 | Exon 18 | AAACCCCTTATAGAAA | 8 | 7800 | 7815 | ekkeekkddddddddk | 567 |
| 599523 | 2566 | 2581 | Exon 18 | GAAACCCCTTATAGAA | 6 | 7801 | 7816 | ekkeekkddddddddk | 568 |
| 599524 | 2567 | 2582 | Exon 18 | GGAAACCCCTTATAGA | 14 | 7802 | 7817 | ekkeekkddddddddk | 569 |
| 599525 | 2568 | 2583 | Exon 18 | AGGAAACCCCTTATAG | 6 | 7803 | 7818 | ekkeekkddddddddk | 570 |
| 599526 | 2569 | 2584 | Exon 18 | CAGGAAACCCCTTATA | 16 | 7804 | 7819 | ekkeekkddddddddk | 571 |
| 599527 | 2570 | 2585 | Exon 18 | GCAGGAAACCCCTTAT | 0 | 7805 | 7820 | ekkeekkddddddddk | 572 |
| 599528 | 2571 | 2586 | Exon 18 | AGCAGGAAACCCCTTA | 6 | 7806 | 7821 | ekkeekkddddddddk | 573 |
| 599529 | 2572 | 2587 | Exon 18 | CAGCAGGAAACCCCTT | 6 | 7807 | 7822 | ekkeekkddddddddk | 574 |
| 599530 | 2574 | 2589 | Exon 18 | TCCAGCAGGAAACCCC | 29 | 7809 | 7824 | ekkeekkddddddddk | 576 |
| 599531 | 2575 | 2590 | Exon 18 | GTCCAGCAGGAAACCC | 64 | 7810 | 7825 | ekkeekkddddddddk | 577 |
| 599532 | 2576 | 2591 | Exon 18 | TGTCCAGCAGGAAACC | 43 | 7811 | 7826 | ekkeekkddddddddk | 578 |
| 599533 | 2577 | 2592 | Exon 18 | CTGTCCAGCAGGAAAC | 25 | 7812 | 7827 | ekkeekkddddddddk | 820 |
| 599534 | 2578 | 2593 | Exon 18 | CCTGTCCAGCAGGAAA | 12 | 7813 | 7828 | ekkeekkddddddddk | 580 |
| 599535 | 2580 | 2595 | Exon 18 | CCCCTGTCCAGCAGGA | 16 | 7815 | 7830 | ekkeekkddddddddk | 582 |

TABLE 141-continued

Inhibition of CFB mRNA by deoxy, MOE and (S)-cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599536 | 2582 | 2597 | Exon 18 | CGCCCCTGTCCAGCAG | 27 | 7817 | 7832 | ekkeekkddddddddk | 584 |
| 599537 | 2583 | 2598 | Exon 18 | ACGCCCCTGTCCAGCA | 35 | 7818 | 7833 | ekkeekkddddddddk | 585 |
| 599538 | 2584 | 2599 | Exon 18 | CACGCCCCTGTCCAGC | 26 | 7819 | 7834 | ekkeekkddddddddk | 586 |
| 599539 | 2585 | 2600 | Exon 18 | CCACGCCCCTGTCCAG | 33 | 7820 | 7835 | ekkeekkddddddddk | 587 |
| 599540 | 2586 | 2601 | Exon 18 | CCCACGCCCCTGTCCA | 27 | 7821 | 7836 | ekkeekkddddddddk | 588 |
| 599541 | 2587 | 2602 | Exon 18 | TCCCACGCCCCTGTCC | 52 | 7822 | 7837 | ekkeekkddddddddk | 589 |
| 599542 | 2588 | 2603 | Exon 18 | ATCCCACGCCCCTGTC | 16 | 7823 | 7838 | ekkeekkddddddddk | 590 |
| 599543 | 2589 | 2604 | Exon 18 | AATCCCACGCCCCTGT | 19 | 7824 | 7839 | ekkeekkddddddddk | 591 |
| 599544 | 2590 | 2605 | Exon 18 | CAATCCCACGCCCCTG | 33 | 7825 | 7840 | ekkeekkddddddddk | 831 |
| 599545 | 2591 | 2606 | Exon 18 | TCAATCCCACGCCCCT | 24 | 7826 | 7841 | ekkeekkddddddddk | 593 |
| 599546 | 2592 | 2607 | Exon 18 | TTCAATCCCACGCCCC | 54 | 7827 | 7842 | ekkeekkddddddddk | 594 |
| 599547 | 2593 | 2608 | Exon 18 | ATTCAATCCCACGCCC | 87 | 7828 | 7843 | ekkeekkddddddddk | 595 |
| 599548 | 2594 | 2609 | Exon 18 | AATTCAATCCCACGCC | 79 | 7829 | 7844 | ekkeekkddddddddk | 596 |
| 599549 | 2595 | 2610 | Exon 18 | TAATTCAATCCCACGC | 62 | 7830 | 7845 | ekkeekkddddddddk | 597 |
| 599550 | 2596 | 2611 | Exon 18 | TTAATTCAATCCCACG | 52 | 7831 | 7846 | ekkeekkddddddddk | 598 |
| 599551 | 2597 | 2612 | Exon 18 | TTTAATTCAATCCCAC | 27 | 7832 | 7847 | ekkeekkddddddddk | 599 |
| 599577 | 2597 | 2613 | Exon 18 | TTTTAATTCAATCCCAC | 90 | 7832 | 7848 | eeekkddddddddkeee | 662 |
| 599552 | 2598 | 2613 | Exon 18 | TTTTAATTCAATCCCA | 92 | 7833 | 7848 | ekkeekkddddddddk | 600 |
| 599578 | 2598 | 2614 | Exon 18 | GTTTTAATTCAATCCCA | 88 | 7833 | 7849 | eeekkddddddddkeee | 663 |
| 599553 | 2599 | 2614 | Exon 18 | GTTTTAATTCAATCCC | 91 | 7834 | 7849 | ekkeekkddddddddk | 601 |
| 599579 | 2599 | 2615 | Exon 18 | TGTTTTAATTCAATCCC | 79 | 7834 | 7850 | eeekkddddddddkeee | 664 |
| 599554 | 2600 | 2615 | Exon 18 | TGTTTTAATTCAATCC | 90 | 7835 | 7850 | ekkeekkddddddddk | 602 |
| 599580 | 2600 | 2616 | Exon 18 | CTGTTTTAATTCAATCC | 79 | 7835 | 7851 | eeekkddddddddkeee | 665 |
| 599555 | 2601 | 2616 | Exon 18 | CTGTTTTAATTCAATC | 79 | 7836 | 7851 | ekkeekkddddddddk | 846 |
| 599581 | 2601 | 2617 | Exon 18 | GCTGTTTTAATTCAATC | 90 | 7836 | 7852 | eeekkddddddddkeee | 666 |
| 599556 | 2602 | 2617 | Exon 18 | GCTGTTTTAATTCAAT | 47 | 7837 | 7852 | ekkeekkddddddddk | 604 |
| 599582 | 2602 | 2618 | Exon 18 | AGCTGTTTTAATTCAAT | 89 | 7837 | 7853 | eeekkddddddddkeee | 849 |
| 599557 | 2603 | 2618 | Exon 18 | AGCTGTTTTAATTCAA | 67 | 7838 | 7853 | ekkeekkddddddddk | 850 |
| 599583 | 2603 | 2619 | Exon 18 | CAGCTGTTTTAATTCAA | 49 | 7838 | 7854 | eeekkddddddddkeee | 668 |
| 532917 | 2604 | 2623 | Exon 18 | GTCGCAGCTGTTTTAATTCA | 78 | 7839 | 7858 | eeeeeddddddddddeeeee | 317 |
| 599558 | 2604 | 2619 | Exon 18 | CAGCTGTTTTAATTCA | 80 | 7839 | 7854 | ekkeekkddddddddk | 606 |
| 599584 | 2604 | 2620 | Exon 18 | GCAGCTGTTTTAATTCA | 66 | 7839 | 7855 | eeekkddddddddkeee | 669 |
| 599559 | 2605 | 2620 | Exon 18 | GCAGCTGTTTTAATTC | 38 | 7840 | 7855 | ekkeekkddddddddk | 607 |
| 599585 | 2605 | 2621 | Exon 18 | CGCAGCTGTTTTAATTC | 80 | 7840 | 7856 | eeekkddddddddkeee | 670 |
| 599560 | 2606 | 2621 | Exon 18 | CGCAGCTGTTTTAATT | 16 | 7841 | 7856 | ekkeekkddddddddk | 608 |
| 599586 | 2606 | 2622 | Exon 18 | TCGCAGCTGTTTTAATT | 78 | 7841 | 7857 | eeekkddddddddkeee | 671 |

TABLE 141-continued

Inhibition of CFB mRNA by deoxy, MOE and (S)-cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599561 | 2607 | 2622 | Exon 18 | TCGCAGCTGTTTTAAT | 58 | 7842 | 7857 | ekkeekkddddddddk | 609 |
| 599587 | 2607 | 2623 | Exon 18 | GTCGCAGCTGTTTTAAT | 81 | 7842 | 7858 | eeekkddddddddkeee | 672 |
| 588860 | 2608 | 2623 | Exon 18 | GTCGCAGCTGTTTTAA | 92 | 7843 | 7858 | eekddddddddddke | 610 |
| 599562 | 2608 | 2623 | Exon 18 | GTCGCAGCTGTTTTAA | 78 | 7843 | 7858 | ekkeekkddddddddk | 610 |
| 599588 | 2608 | 2624 | Exon 18 | TGTCGCAGCTGTTTTAA | 81 | 7843 | 7859 | eeekkddddddddkeee | 673 |
| 599563 | 2609 | 2624 | Exon 18 | TGTCGCAGCTGTTTTA | 86 | 7844 | 7859 | ekkeekkddddddddk | 611 |
| 599589 | 2609 | 2625 | Exon 18 | TTGTCGCAGCTGTTTTA | 75 | 7844 | 7860 | eeekkddddddddkeee | 674 |
| 599564 | 2610 | 2625 | Exon 18 | TTGTCGCAGCTGTTTT | 75 | 7845 | 7860 | ekkeekkddddddddk | 612 |
| 599590 | 2610 | 2626 | Exon 18 | GTTGTCGCAGCTGTTTT | 88 | 7845 | 7861 | eeekkddddddddkeee | 675 |
| 599565 | 2611 | 2626 | Exon 18 | GTTGTCGCAGCTGTTT | 65 | 7846 | 7861 | ekkeekkddddddddk | 613 |
| 599591 | 2611 | 2627 | Exon 18 | TGTTGTCGCAGCTGTTT | 94 | 7846 | 7862 | eeekkddddddddkeee | 676 |
| 599566 | 2612 | 2627 | Exon 18 | TGTTGTCGCAGCTGTT | 72 | 7847 | 7862 | ekkeekkddddddddk | 614 |
| 599592 | 2612 | 2628 | Exon 18/Repeat | TTGTTGTCGCAGCTGTT | 90 | n/a | n/a | eeekkddddddddkeee | 677 |
| 599567 | 2613 | 2628 | Exon 18/Repeat | TTGTTGTCGCAGCTGT | 82 | n/a | n/a | ekkeekkddddddddk | 615 |
| 599593 | 2613 | 2629 | Exon 18/Repeat | TTTGTTGTCGCAGCTGT | 95 | n/a | n/a | eeekkddddddddkeee | 678 |
| 599568 | 2614 | 2629 | Exon 18/Repeat | TTTGTTGTCGCAGCTG | 92 | n/a | n/a | ekkeekkddddddddk | 616 |
| 599594 | 2614 | 2630 | Exon 18/Repeat | TTTTGTTGTCGCAGCTG | 86 | n/a | n/a | eeekkddddddddkeee | 679 |
| 599569 | 2615 | 2630 | Exon 18/Repeat | TTTTGTTGTCGCAGCT | 89 | n/a | n/a | ekkeekkddddddddk | 617 |
| 599595 | 2615 | 2631 | Exon 18/Repeat | TTTTTGTTGTCGCAGCT | 76 | n/a | n/a | eeekkddddddddkeee | 680 |
| 599570 | 2616 | 2631 | Exon 18/Repeat | TTTTTGTTGTCGCAGC | 95 | n/a | n/a | ekkeekkddddddddk | 618 |

Example 121: Antisense Inhibition of Human Complement Factor B (CFB) in HepG2 Cells by MOE Gapmers Additional antisense oligonucleotides were designed targeting human Complement Factor B (CFB) nucleic acid and were tested for their effects on CFB mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 500 nM antisense oligonucleotide. After a treatment period of approximately 24 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The newly designed chimeric antisense oligonucleotides in the Tables below were designed as deoxy, MOE and (S)-cEt oligonucleotides, or as 5-8-5 MOE, 5-9-5 MOE, 5-10-5 MOE, 6-7-6-MOE, 3-10-5 MOE, or 6-8-6 MOE gapmers.

The deoxy, MOE and (S)-cEt oligonucleotides are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; 'd' indicates deoxyribose; and 'e' indicates a MOE modification.

The 5-8-5 MOE gapmers are 18 nucleosides in length, wherein the central gap segment comprises of eight 2'-deoxynucleosides and is flanked by wing segments on the 5' direction and the 3' direction comprising five nucleosides each. The 5-9-5 MOE gapmers are 19 nucleosides in length, wherein the central gap segment comprises of nine 2'-deoxynucleosides and is flanked by wing segments on the 5' direction and the 3' direction comprising five nucleosides each. The 5-10-5 MOE gapmers are 20 nucleosides in length, wherein the central gap segment comprises of ten 2'-deoxynucleosides and is flanked by wing segments on the 5' direction and the 3' direction comprising five nucleosides each. The 3-10-5 MOE gapmers are 18 nucleosides in length, wherein the central gap segment comprises of ten 2'-deoxynucleosides and is flanked by wing segments on the 5' direction and the 3' direction comprising three and five nucleosides respectively. The 6-7-6 MOE gapmers are 19 nucleosides in length, wherein the central gap segment comprises of seven 2'-deoxynucleosides and is flanked by wing segments on the 5' direction and the 3' direction comprising six nucleosides each. The 6-8-6 MOE gapmers are 20 nucleosides in length, wherein the central gap segment comprises of eight 2'-deoxynucleosides and is flanked by wing segments on the 5' direction and the 3' direction comprising six nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

"Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human CFB mRNA, designated herein as SEQ ID NO: 1 (GENBANK Accession No. NM_001710.5) or the human CFB genomic sequence, designated herein as SEQ ID NO: 2 (GENBANK Accession No. NT_007592.15 truncated from nucleotides 31852000 to 31861000), or both. 'n/a' indicates that the antisense oligonucleotide does not target that particular gene sequence with 100% complementarity.

TABLE 142

Inhibition of CFB mRNA by deoxy, MOE and (S)-cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601152 | 2551 | 2566 | Exon 18 | AAACCCAAATCCTCAT | 22 | 7786 | 7801 | eekkddddddddddkee | 557 |
| 601218 | 2551 | 2566 | Exon 18 | AAACCCAAATCCTCAT | 21 | 7786 | 7801 | edkkddddddddddeee | 557 |
| 601153 | 2552 | 2567 | Exon 18 | AAAACCCAAATCCTCA | 27 | 7787 | 7802 | eekkddddddddddkee | 800 |
| 601219 | 2552 | 2567 | Exon 18 | AAAACCCAAATCCTCA | 19 | 7787 | 7802 | edkkddddddddddeee | 800 |
| 601154 | 2553 | 2568 | Exon 18 | GAAAACCCAAATCCTC | 23 | 7788 | 7803 | eekkddddddddddkee | 558 |
| 601220 | 2553 | 2568 | Exon 18 | GAAAACCCAAATCCTC | 24 | 7788 | 7803 | edkkddddddddddeee | 558 |
| 601155 | 2554 | 2569 | Exon 18 | AGAAAACCCAAATCCT | 20 | 7789 | 7804 | eekkddddddddddkee | 801 |
| 601221 | 2554 | 2569 | Exon 18 | AGAAAACCCAAATCCT | 0 | 7789 | 7804 | edkkddddddddddeee | 801 |
| 601156 | 2555 | 2570 | Exon 18 | TAGAAAACCCAAATCC | 11 | 7790 | 7805 | eekkddddddddddkee | 559 |
| 601222 | 2555 | 2570 | Exon 18 | TAGAAAACCCAAATCC | 23 | 7790 | 7805 | edkkddddddddddeee | 559 |
| 601157 | 2556 | 2571 | Exon 18 | ATAGAAAACCCAAATC | 9 | 7791 | 7806 | eekkddddddddddkee | 560 |
| 601223 | 2556 | 2571 | Exon 18 | ATAGAAAACCCAAATC | 0 | 7791 | 7806 | edkkddddddddddeee | 560 |
| 601158 | 2557 | 2572 | Exon 18 | TATAGAAAACCCAAAT | 0 | 7792 | 7807 | eekkddddddddddkee | 802 |
| 601224 | 2557 | 2572 | Exon 18 | TATAGAAAACCCAAAT | 0 | 7792 | 7807 | edkkddddddddddeee | 802 |
| 601159 | 2558 | 2573 | Exon 18 | TTATAGAAAACCCAAA | 2 | 7793 | 7808 | eekkddddddddddkee | 803 |
| 601225 | 2558 | 2573 | Exon 18 | TTATAGAAAACCCAAA | 0 | 7793 | 7808 | edkkddddddddddeee | 803 |
| 601160 | 2559 | 2574 | Exon 18 | CTTATAGAAAACCCAA | 0 | 7794 | 7809 | eekkddddddddddkee | 561 |
| 601226 | 2559 | 2574 | Exon 18 | CTTATAGAAAACCCAA | 0 | 7794 | 7809 | edkkddddddddddeee | 561 |
| 601161 | 2560 | 2575 | Exon 18 | CCTTATAGAAAACCCA | 1 | 7795 | 7810 | eekkddddddddddkee | 562 |
| 601227 | 2560 | 2575 | Exon 18 | CCTTATAGAAAACCCA | 14 | 7795 | 7810 | edkkddddddddddeee | 562 |
| 601162 | 2561 | 2576 | Exon 18 | CCCTTATAGAAAACCC | 9 | 7796 | 7811 | eekkddddddddddkee | 563 |
| 601228 | 2561 | 2576 | Exon 18 | CCCTTATAGAAAACCC | 9 | 7796 | 7811 | edkkddddddddddeee | 563 |
| 601163 | 2562 | 2577 | Exon 18 | CCCCTTATAGAAAACC | 0 | 7797 | 7812 | eekkddddddddddkee | 564 |
| 601164 | 2563 | 2578 | Exon 18 | ACCCCTTATAGAAAAC | 3 | 7798 | 7813 | eekkddddddddddkee | 565 |

TABLE 142-continued

Inhibition of CFB mRNA by deoxy, MOE and (S)-cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601165 | 2564 | 2579 | Exon 18 | AACCCCTTATAGAAAA | 0 | 7799 | 7814 | eekkddddddddddkee | 566 |
| 601166 | 2565 | 2580 | Exon 18 | AAACCCCTTATAGAAA | 0 | 7800 | 7815 | eekkddddddddddkee | 567 |
| 601167 | 2566 | 2581 | Exon 18 | GAAACCCCTTATAGAA | 0 | 7801 | 7816 | eekkddddddddddkee | 568 |
| 601168 | 2567 | 2582 | Exon 18 | GGAAACCCCTTATAGA | 0 | 7802 | 7817 | eekkddddddddddkee | 569 |
| 601169 | 2568 | 2583 | Exon 18 | AGGAAACCCCTTATAG | 0 | 7803 | 7818 | eekkddddddddddkee | 570 |
| 601170 | 2569 | 2584 | Exon 18 | CAGGAAACCCCTTATA | 10 | 7804 | 7819 | eekkddddddddddkee | 571 |
| 601171 | 2570 | 2585 | Exon 18 | GCAGGAAACCCCTTAT | 9 | 7805 | 7820 | eekkddddddddddkee | 572 |
| 601172 | 2571 | 2586 | Exon 18 | AGCAGGAAACCCCTTA | 15 | 7806 | 7821 | eekkddddddddddkee | 573 |
| 601173 | 2572 | 2587 | Exon 18 | CAGCAGGAAACCCCTT | 29 | 7807 | 7822 | eekkddddddddddkee | 574 |
| 601174 | 2573 | 2588 | Exon 18 | CCAGCAGGAAACCCCT | 25 | 7808 | 7823 | eekkddddddddddkee | 575 |
| 601175 | 2574 | 2589 | Exon 18 | TCCAGCAGGAAACCCC | 15 | 7809 | 7824 | eekkddddddddddkee | 576 |
| 601176 | 2575 | 2590 | Exon 18 | GTCCAGCAGGAAACCC | 18 | 7810 | 7825 | eekkddddddddddkee | 577 |
| 601177 | 2576 | 2591 | Exon 18 | TGTCCAGCAGGAAACC | 10 | 7811 | 7826 | eekkddddddddddkee | 578 |
| 601178 | 2577 | 2592 | Exon 18 | CTGTCCAGCAGGAAAC | 11 | 7812 | 7827 | eekkddddddddddkee | 579 |
| 601179 | 2578 | 2593 | Exon 18 | CCTGTCCAGCAGGAAA | 19 | 7813 | 7828 | eekkddddddddddkee | 580 |
| 601180 | 2579 | 2594 | Exon 18 | CCCTGTCCAGCAGGAA | 7 | 7814 | 7829 | eekkddddddddddkee | 581 |
| 601181 | 2580 | 2595 | Exon 18 | CCCCTGTCCAGCAGGA | 3 | 7815 | 7830 | eekkddddddddddkee | 582 |
| 601182 | 2581 | 2596 | Exon 18 | GCCCCTGTCCAGCAGG | 0 | 7816 | 7831 | eekkddddddddddkee | 583 |
| 601183 | 2582 | 2597 | Exon 18 | CGCCCCTGTCCAGCAG | 4 | 7817 | 7832 | eekkddddddddddkee | 584 |
| 601184 | 2583 | 2598 | Exon 18 | ACGCCCCTGTCCAGCA | 14 | 7818 | 7833 | eekkddddddddddkee | 585 |
| 601185 | 2584 | 2599 | Exon 18 | CACGCCCCTGTCCAGC | 26 | 7819 | 7834 | eekkddddddddddkee | 586 |
| 601186 | 2585 | 2600 | Exon 18 | CCACGCCCCTGTCCAG | 8 | 7820 | 7835 | eekkddddddddddkee | 587 |
| 601187 | 2586 | 2601 | Exon 18 | CCCACGCCCCTGTCCA | 18 | 7821 | 7836 | eekkddddddddddkee | 588 |
| 601188 | 2587 | 2602 | Exon 18 | TCCCACGCCCCTGTCC | 20 | 7822 | 7837 | eekkddddddddddkee | 589 |
| 601189 | 2588 | 2603 | Exon 18 | ATCCCACGCCCCTGTC | 12 | 7823 | 7838 | eekkddddddddddkee | 590 |
| 601190 | 2589 | 2604 | Exon 18 | AATCCCACGCCCCTGT | 33 | 7824 | 7839 | eekkddddddddddkee | 591 |
| 601191 | 2590 | 2605 | Exon 18 | CAATCCCACGCCCCTG | 52 | 7825 | 7840 | eekkddddddddddkee | 592 |
| 601192 | 2591 | 2606 | Exon 18 | TCAATCCCACGCCCCT | 46 | 7826 | 7841 | eekkddddddddddkee | 593 |
| 601193 | 2592 | 2607 | Exon 18 | TTCAATCCCACGCCCC | 30 | 7827 | 7842 | eekkddddddddddkee | 594 |
| 601194 | 2593 | 2608 | Exon 18 | ATTCAATCCCACGCCC | 41 | 7828 | 7843 | eekkddddddddddkee | 595 |
| 601195 | 2594 | 2609 | Exon 18 | AATTCAATCCCACGCC | 40 | 7829 | 7844 | eekkddddddddddkee | 596 |
| 601196 | 2595 | 2610 | Exon 18 | TAATTCAATCCCACGC | 71 | 7830 | 7845 | eekkddddddddddkee | 597 |
| 601197 | 2596 | 2611 | Exon 18 | TTAATTCAATCCCACG | 42 | 7831 | 7846 | eekkddddddddddkee | 598 |
| 601198 | 2597 | 2612 | Exon 18 | TTTAATTCAATCCCAC | 63 | 7832 | 7847 | eekkddddddddddkee | 599 |
| 601199 | 2598 | 2613 | Exon 18 | TTTTAATTCAATCCCA | 51 | 7833 | 7848 | eekkddddddddddkee | 600 |
| 601200 | 2599 | 2614 | Exon 18 | GTTTTAATTCAATCCC | 65 | 7834 | 7849 | eekkddddddddddkee | 601 |

TABLE 142-continued

Inhibition of CFB mRNA by deoxy, MOE and (S)-cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601201 | 2600 | 2615 | Exon 18 | TGTTTTAATTCAATCC | 49 | 7835 | 7850 | eekkddddddddddkee | 602 |
| 601202 | 2601 | 2616 | Exon 18 | CTGTTTTAATTCAATC | 33 | 7836 | 7851 | eekkddddddddddkee | 603 |
| 601203 | 2602 | 2617 | Exon 18 | GCTGTTTTAATTCAAT | 63 | 7837 | 7852 | eekkddddddddddkee | 604 |
| 601204 | 2603 | 2618 | Exon 18 | AGCTGTTTTAATTCAA | 69 | 7838 | 7853 | eekkddddddddddkee | 605 |
| 532917 | 2604 | 2623 | Exon 18 | GTCGCAGCTGTTTTAATTCA | 73 | 7839 | 7858 | eeeeeddddddddddeeeee | 317 |
| 601205 | 2604 | 2619 | Exon 18 | CAGCTGTTTTAATTCA | 51 | 7839 | 7854 | eekkddddddddddkee | 606 |
| 601206 | 2605 | 2620 | Exon 18 | GCAGCTGTTTTAATTC | 43 | 7840 | 7855 | eekkddddddddddkee | 607 |
| 601207 | 2606 | 2621 | Exon 18 | CGCAGCTGTTTTAATT | 52 | 7841 | 7856 | eekkddddddddddkee | 608 |
| 601208 | 2607 | 2622 | Exon 18 | TCGCAGCTGTTTTAAT | 61 | 7842 | 7857 | eekkddddddddddkee | 609 |
| 588860 | 2608 | 2623 | Exon 18 | GTCGCAGCTGTTTTAA | 75 | 7843 | 7858 | eekddddddddddke | 610 |
| 601209 | 2608 | 2623 | Exon 18 | GTCGCAGCTGTTTTAA | 73 | 7843 | 7858 | eekkddddddddddkee | 610 |
| 601210 | 2609 | 2624 | Exon 18 | TGTCGCAGCTGTTTTA | 80 | 7844 | 7859 | eekkddddddddddkee | 611 |
| 601211 | 2610 | 2625 | Exon 18 | TTGTCGCAGCTGTTTT | 64 | 7845 | 7860 | eekkddddddddddkee | 612 |
| 601212 | 2611 | 2626 | Exon 18 | GTTGTCGCAGCTGTTT | 86 | 7846 | 7861 | eekkddddddddddkee | 613 |
| 601213 | 2612 | 2627 | Exon 18 | TGTTGTCGCAGCTGTT | 87 | 7847 | 7862 | eekkddddddddddkee | 614 |
| 601214 | 2613 | 2628 | Exon 18/ Repeat | TTGTTGTCGCAGCTGT | 84 | n/a | n/a | eekkddddddddddkee | 615 |
| 601215 | 2614 | 2629 | Exon 18/ Repeat | TTTGTTGTCGCAGCTG | 78 | n/a | n/a | eekkddddddddddkee | 616 |
| 601216 | 2615 | 2630 | Exon 18/ Repeat | TTTTGTTGTCGCAGCT | 73 | n/a | n/a | eekkddddddddddkee | 617 |
| 601217 | 2616 | 2631 | Exon 18/ Repeat | TTTTTGTTGTCGCAGC | 66 | n/a | n/a | eekkddddddddddkee | 618 |

TABLE 143

Inhibition of CFB mRNA by deoxy, MOE and (S)-cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601284 | 2551 | 2566 | Exon 18 | AAACCCAAATCCTCAT | 8 | 7786 | 7801 | ekkddddddddddkeee | 557 |
| 601285 | 2552 | 2567 | Exon 18 | AAAACCCAAATCCTCA | 15 | 7787 | 7802 | ekkddddddddddkeee | 800 |
| 601286 | 2553 | 2568 | Exon 18 | GAAAACCCAAATCCTC | 21 | 7788 | 7803 | ekkddddddddddkeee | 558 |
| 601287 | 2554 | 2569 | Exon 18 | AGAAAACCCAAATCCT | 9 | 7789 | 7804 | ekkddddddddddkeee | 801 |
| 601288 | 2555 | 2570 | Exon 18 | TAGAAAACCCAAATCC | 0 | 7790 | 7805 | ekkddddddddddkeee | 559 |
| 601289 | 2556 | 2571 | Exon 18 | ATAGAAAACCCAAATC | 40 | 7791 | 7806 | ekkddddddddddkeee | 560 |
| 601290 | 2557 | 2572 | Exon 18 | TATAGAAAACCCAAAT | 16 | 7792 | 7807 | ekkddddddddddkeee | 802 |
| 601291 | 2558 | 2573 | Exon 18 | TTATAGAAAACCCAAA | 15 | 7793 | 7808 | ekkddddddddddkeee | 803 |

TABLE 143-continued

Inhibition of CFB mRNA by deoxy, MOE and (S)-cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601292 | 2559 | 2574 | Exon 18 | CTTATAGAAAACCCAA | 5 | 7794 | 7809 | ekkddddddddddkeee | 561 |
| 601293 | 2560 | 2575 | Exon 18 | CCTTATAGAAAACCCA | 15 | 7795 | 7810 | ekkddddddddddkeee | 562 |
| 601294 | 2561 | 2576 | Exon 18 | CCCTTATAGAAAACCC | 3 | 7796 | 7811 | ekkddddddddddkeee | 563 |
| 601229 | 2562 | 2577 | Exon 18 | CCCCTTATAGAAAACC | 15 | 7797 | 7812 | edkddddddddddeee | 564 |
| 601295 | 2562 | 2577 | Exon 18 | CCCCTTATAGAAAACC | 5 | 7797 | 7812 | ekkddddddddddkeee | 564 |
| 601230 | 2563 | 2578 | Exon 18 | ACCCCTTATAGAAAAC | 14 | 7798 | 7813 | edkkddddddddddeee | 565 |
| 601296 | 2563 | 2578 | Exon 18 | ACCCCTTATAGAAAAC | 0 | 7798 | 7813 | ekkddddddddddkeee | 565 |
| 601231 | 2564 | 2579 | Exon 18 | AACCCCTTATAGAAAA | 14 | 7799 | 7814 | edkkddddddddddeee | 566 |
| 601297 | 2564 | 2579 | Exon 18 | AACCCCTTATAGAAAA | 14 | 7799 | 7814 | ekkddddddddddkeee | 566 |
| 601232 | 2565 | 2580 | Exon 18 | AAACCCCTTATAGAAA | 15 | 7800 | 7815 | edkddddddddddeee | 567 |
| 601298 | 2565 | 2580 | Exon 18 | AAACCCCTTATAGAAA | 7 | 7800 | 7815 | ekkddddddddddkeee | 567 |
| 601233 | 2566 | 2581 | Exon 18 | GAAACCCCTTATAGAA | 0 | 7801 | 7816 | edkddddddddddeee | 568 |
| 601299 | 2566 | 2581 | Exon 18 | GAAACCCCTTATAGAA | 0 | 7801 | 7816 | ekkddddddddddkeee | 568 |
| 601234 | 2567 | 2582 | Exon 18 | GGAAACCCCTTATAGA | 0 | 7802 | 7817 | edkddddddddddeee | 569 |
| 601300 | 2567 | 2582 | Exon 18 | GGAAACCCCTTATAGA | 9 | 7802 | 7817 | ekkddddddddddkeee | 569 |
| 601235 | 2568 | 2583 | Exon 18 | AGGAAACCCCTTATAG | 3 | 7803 | 7818 | edkddddddddddeee | 570 |
| 601301 | 2568 | 2583 | Exon 18 | AGGAAACCCCTTATAG | 14 | 7803 | 7818 | ekkddddddddddkeee | 570 |
| 601236 | 2569 | 2584 | Exon 18 | CAGGAAACCCCTTATA | 0 | 7804 | 7819 | edkkddddddddddeee | 571 |
| 601302 | 2569 | 2584 | Exon 18 | CAGGAAACCCCTTATA | 0 | 7804 | 7819 | ekkddddddddddkeee | 571 |
| 601237 | 2570 | 2585 | Exon 18 | GCAGGAAACCCCTTAT | 16 | 7805 | 7820 | edkkddddddddddeee | 572 |
| 601303 | 2570 | 2585 | Exon 18 | GCAGGAAACCCCTTAT | 16 | 7805 | 7820 | ekkddddddddddkeee | 572 |
| 601238 | 2571 | 2586 | Exon 18 | AGCAGGAAACCCCTTA | 11 | 7806 | 7821 | edkkddddddddddeee | 573 |
| 601304 | 2571 | 2586 | Exon 18 | AGCAGGAAACCCCTTA | 10 | 7806 | 7821 | ekkddddddddddkeee | 573 |
| 601239 | 2572 | 2587 | Exon 18 | CAGCAGGAAACCCCTT | 21 | 7807 | 7822 | edkkddddddddddeee | 574 |
| 601305 | 2572 | 2587 | Exon 18 | CAGCAGGAAACCCCTT | 7 | 7807 | 7822 | ekkddddddddddkeee | 574 |
| 601240 | 2573 | 2588 | Exon 18 | CCAGCAGGAAACCCCT | 6 | 7808 | 7823 | edkkddddddddddeee | 575 |
| 601241 | 2574 | 2589 | Exon 18 | TCCAGCAGGAAACCCC | 10 | 7809 | 7824 | edkkddddddddddeee | 576 |
| 601242 | 2575 | 2590 | Exon 18 | GTCCAGCAGGAAACCC | 19 | 7810 | 7825 | edkkddddddddddeee | 577 |
| 601243 | 2576 | 2591 | Exon 18 | TGTCCAGCAGGAAACC | 10 | 7811 | 7826 | edkkddddddddddeee | 578 |
| 601244 | 2577 | 2592 | Exon 18 | CTGTCCAGCAGGAAAC | 28 | 7812 | 7827 | edkkddddddddddeee | 579 |
| 601245 | 2578 | 2593 | Exon 18 | CCTGTCCAGCAGGAAA | 5 | 7813 | 7828 | edkkddddddddddeee | 580 |
| 601246 | 2579 | 2594 | Exon 18 | CCCTGTCCAGCAGGAA | 18 | 7814 | 7829 | edkkddddddddddeee | 581 |
| 601247 | 2580 | 2595 | Exon 18 | CCCCTGTCCAGCAGGA | 4 | 7815 | 7830 | edkkddddddddddeee | 582 |
| 601248 | 2581 | 2596 | Exon 18 | GCCCCTGTCCAGCAGG | 6 | 7816 | 7831 | edkkddddddddddeee | 583 |
| 601249 | 2582 | 2597 | Exon 18 | CGCCCCTGTCCAGCAG | 18 | 7817 | 7832 | edkkddddddddddeee | 584 |
| 601250 | 2583 | 2598 | Exon 18 | ACGCCCCTGTCCAGCA | 26 | 7818 | 7833 | edkkddddddddddeee | 585 |

TABLE 143-continued

Inhibition of CFB mRNA by deoxy, MOE and (S)-cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601251 | 2584 | 2599 | Exon 18 | CACGCCCCTGTCCAGC | 27 | 7819 | 7834 | edkkddddddddeee | 586 |
| 601252 | 2585 | 2600 | Exon 18 | CCACGCCCCTGTCCAG | 21 | 7820 | 7835 | edkkddddddddeee | 587 |
| 601253 | 2586 | 2601 | Exon 18 | CCCACGCCCCTGTCCA | 0 | 7821 | 7836 | edkkddddddddeee | 588 |
| 601254 | 2587 | 2602 | Exon 18 | TCCCACGCCCCTGTCC | 31 | 7822 | 7837 | edkkddddddddeee | 589 |
| 601255 | 2588 | 2603 | Exon 18 | ATCCCACGCCCCTGTC | 3 | 7823 | 7838 | edkkddddddddeee | 590 |
| 601256 | 2589 | 2604 | Exon 18 | AATCCCACGCCCCTGT | 21 | 7824 | 7839 | edkkddddddddeee | 591 |
| 601257 | 2590 | 2605 | Exon 18 | CAATCCCACGCCCCTG | 47 | 7825 | 7840 | edkkddddddddeee | 592 |
| 601258 | 2591 | 2606 | Exon 18 | TCAATCCCACGCCCCT | 48 | 7826 | 7841 | edkkddddddddeee | 593 |
| 601259 | 2592 | 2607 | Exon 18 | TTCAATCCCACGCCCC | 38 | 7827 | 7842 | edkkddddddddeee | 594 |
| 601260 | 2593 | 2608 | Exon 18 | ATTCAATCCCACGCCC | 33 | 7828 | 7843 | edkkddddddddeee | 595 |
| 601261 | 2594 | 2609 | Exon 18 | AATTCAATCCCACGCC | 17 | 7829 | 7844 | edkkddddddddeee | 596 |
| 601262 | 2595 | 2610 | Exon 18 | TAATTCAATCCCACGC | 40 | 7830 | 7845 | edkkddddddddeee | 597 |
| 601263 | 2596 | 2611 | Exon 18 | TTAATTCAATCCCACG | 31 | 7831 | 7846 | edkkddddddddeee | 598 |
| 601264 | 2597 | 2612 | Exon 18 | TTTAATTCAATCCCAC | 72 | 7832 | 7847 | edkkddddddddeee | 599 |
| 601265 | 2598 | 2613 | Exon 18 | TTTTAATTCAATCCCA | 48 | 7833 | 7848 | edkkddddddddeee | 600 |
| 601266 | 2599 | 2614 | Exon 18 | GTTTTAATTCAATCCC | 64 | 7834 | 7849 | edkkddddddddeee | 601 |
| 601267 | 2600 | 2615 | Exon 18 | TGTTTTAATTCAATCC | 43 | 7835 | 7850 | edkkddddddddeee | 602 |
| 601268 | 2601 | 2616 | Exon 18 | CTGTTTTAATTCAATC | 44 | 7836 | 7851 | edkkddddddddeee | 603 |
| 601269 | 2602 | 2617 | Exon 18 | GCTGTTTTAATTCAAT | 66 | 7837 | 7852 | edkkddddddddeee | 604 |
| 601270 | 2603 | 2618 | Exon 18 | AGCTGTTTTAATTCAA | 47 | 7838 | 7853 | edkkddddddddeee | 605 |
| 532917 | 2604 | 2623 | Exon 18 | GTCGCAGCTGTTTTAATTCA | 3 | 7839 | 7858 | eeeeeddddddddddeeeee | 317 |
| 601271 | 2604 | 2619 | Exon 18 | CAGCTGTTTTAATTCA | 26 | 7839 | 7854 | edkkddddddddeee | 606 |
| 601272 | 2605 | 2620 | Exon 18 | GCAGCTGTTTTAATTC | 33 | 7840 | 7855 | edkkddddddddeee | 607 |
| 601273 | 2606 | 2621 | Exon 18 | CGCAGCTGTTTTAATT | 34 | 7841 | 7856 | edkkddddddddeee | 608 |
| 601274 | 2607 | 2622 | Exon 18 | TCGCAGCTGTTTTAAT | 39 | 7842 | 7857 | edkkddddddddeee | 609 |
| 588860 | 2608 | 2623 | Exon 18 | GTCGCAGCTGTTTTAA | 72 | 7843 | 7858 | eekddddddddddke | 610 |
| 601275 | 2608 | 2623 | Exon 18 | GTCGCAGCTGTTTTAA | 65 | 7843 | 7858 | edkkddddddddeee | 610 |
| 601276 | 2609 | 2624 | Exon 18 | TGTCGCAGCTGTTTTA | 65 | 7844 | 7859 | edkkddddddddeee | 611 |
| 601277 | 2610 | 2625 | Exon 18 | TTGTCGCAGCTGTTTT | 51 | 7845 | 7860 | edkkddddddddeee | 612 |
| 601278 | 2611 | 2626 | Exon 18 | GTTGTCGCAGCTGTTT | 78 | 7846 | 7861 | edkkddddddddeee | 613 |
| 601279 | 2612 | 2627 | Exon 18 | TGTTGTCGCAGCTGTT | 79 | 7847 | 7862 | edkkddddddddeee | 614 |
| 601280 | 2613 | 2628 | Exon 18/Repeat | TTGTTGTCGCAGCTGT | 70 | n/a | n/a | edkkddddddddeee | 615 |
| 601281 | 2614 | 2629 | Exon 18/Repeat | TTTGTTGTCGCAGCTG | 78 | n/a | n/a | edkkddddddddeee | 616 |
| 601282 | 2615 | 2630 | Exon 18/Repeat | TTTTGTTGTCGCAGCT | 68 | n/a | n/a | edkkddddddddeee | 617 |

TABLE 143-continued

Inhibition of CFB mRNA by deoxy, MOE and (S)-cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601283 | 2616 | 2631 | Exon 18/Repeat | TTTTTGTTGTCGCAGC | 61 | n/a | n/a | edkkddddddddeee | 618 |

TABLE 144

Inhibition of CFB mRNA by deoxy, MOE and (S)-cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601306 | 2573 | 2588 | Exon 18 | CCAGCAGGAAACCCCT | 22 | 7808 | 7823 | ekkddddddddkeee | 575 |
| 601307 | 2574 | 2589 | Exon 18 | TCCAGCAGGAAACCCC | 22 | 7809 | 7824 | ekkddddddddkeee | 576 |
| 601308 | 2575 | 2590 | Exon 18 | GTCCAGCAGGAAACCC | 33 | 7810 | 7825 | ekkddddddddkeee | 577 |
| 601309 | 2576 | 2591 | Exon 18 | TGTCCAGCAGGAAACC | 33 | 7811 | 7826 | ekkddddddddkeee | 578 |
| 601310 | 2577 | 2592 | Exon 18 | CTGTCCAGCAGGAAAC | 28 | 7812 | 7827 | ekkddddddddkeee | 579 |
| 601311 | 2578 | 2593 | Exon 18 | CCTGTCCAGCAGGAAA | 33 | 7813 | 7828 | ekkddddddddkeee | 580 |
| 601312 | 2579 | 2594 | Exon 18 | CCCTGTCCAGCAGGAA | 13 | 7814 | 7829 | ekkddddddddkeee | 581 |
| 601313 | 2580 | 2595 | Exon 18 | CCCCTGTCCAGCAGGA | 32 | 7815 | 7830 | ekkddddddddkeee | 582 |
| 601314 | 2581 | 2596 | Exon 18 | GCCCCTGTCCAGCAGG | 0 | 7816 | 7831 | ekkddddddddkeee | 583 |
| 601315 | 2582 | 2597 | Exon 18 | CGCCCCTGTCCAGCAG | 36 | 7817 | 7832 | ekkddddddddkeee | 584 |
| 601316 | 2583 | 2598 | Exon 18 | ACGCCCCTGTCCAGCA | 39 | 7818 | 7833 | ekkddddddddkeee | 585 |
| 601317 | 2584 | 2599 | Exon 18 | CACGCCCCTGTCCAGC | 33 | 7819 | 7834 | ekkddddddddkeee | 586 |
| 601356 | 2584 | 2599 | Exon 18 | CACGCCCCTGTCCAGC | 27 | 7819 | 7834 | kdkddddddddeeee | 586 |
| 601318 | 2585 | 2600 | Exon 18 | CCACGCCCCTGTCCAG | 35 | 7820 | 7835 | ekkddddddddkeee | 587 |
| 601357 | 2585 | 2600 | Exon 18 | CCACGCCCCTGTCCAG | 26 | 7820 | 7835 | kdkddddddddeeee | 587 |
| 601319 | 2586 | 2601 | Exon 18 | CCCACGCCCCTGTCCA | 33 | 7821 | 7836 | ekkddddddddkeee | 588 |
| 601358 | 2586 | 2601 | Exon 18 | CCCACGCCCCTGTCCA | 26 | 7821 | 7836 | kdkddddddddeeee | 588 |
| 601320 | 2587 | 2602 | Exon 18 | TCCCACGCCCCTGTCC | 25 | 7822 | 7837 | ekkddddddddkeee | 589 |
| 601359 | 2587 | 2602 | Exon 18 | TCCCACGCCCCTGTCC | 23 | 7822 | 7837 | kdkddddddddeeee | 589 |
| 601321 | 2588 | 2603 | Exon 18 | ATCCCACGCCCCTGTC | 50 | 7823 | 7838 | ekkddddddddkeee | 590 |
| 601360 | 2588 | 2603 | Exon 18 | ATCCCACGCCCCTGTC | 33 | 7823 | 7838 | kdkddddddddeeee | 590 |
| 601322 | 2589 | 2604 | Exon 18 | AATCCCACGCCCCTGT | 52 | 7824 | 7839 | ekkddddddddkeee | 591 |
| 601361 | 2589 | 2604 | Exon 18 | AATCCCACGCCCCTGT | 48 | 7824 | 7839 | kdkddddddddeeee | 591 |
| 601323 | 2590 | 2605 | Exon 18 | CAATCCCACGCCCCTG | 67 | 7825 | 7840 | ekkddddddddkeee | 592 |
| 601362 | 2590 | 2605 | Exon 18 | CAATCCCACGCCCCTG | 51 | 7825 | 7840 | kdkddddddddeeee | 592 |
| 601324 | 2591 | 2606 | Exon 18 | TCAATCCCACGCCCCT | 42 | 7826 | 7841 | ekkddddddddkeee | 593 |
| 601363 | 2591 | 2606 | Exon 18 | TCAATCCCACGCCCCT | 42 | 7826 | 7841 | kdkddddddddeeee | 593 |
| 601325 | 2592 | 2607 | Exon 18 | TTCAATCCCACGCCCC | 52 | 7827 | 7842 | ekkddddddddkeee | 594 |

TABLE 144-continued

Inhibition of CFB mRNA by deoxy, MOE and (S)-cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601364 | 2592 | 2607 | Exon 18 | TTCAATCCCACGCCCC | 48 | 7827 | 7842 | kdkddddddddeeee | 594 |
| 601326 | 2593 | 2608 | Exon 18 | ATTCAATCCCACGCCC | 27 | 7828 | 7843 | ekkddddddddkeee | 595 |
| 601365 | 2593 | 2608 | Exon 18 | ATTCAATCCCACGCCC | 36 | 7828 | 7843 | kdkddddddddeeee | 595 |
| 601327 | 2594 | 2609 | Exon 18 | AATTCAATCCCACGCC | 66 | 7829 | 7844 | ekkddddddddkeee | 596 |
| 601366 | 2594 | 2609 | Exon 18 | AATTCAATCCCACGCC | 49 | 7829 | 7844 | kdkddddddddeeee | 596 |
| 601328 | 2595 | 2610 | Exon 18 | TAATTCAATCCCACGC | 55 | 7830 | 7845 | ekkddddddddkeee | 597 |
| 601367 | 2595 | 2610 | Exon 18 | TAATTCAATCCCACGC | 57 | 7830 | 7845 | kdkddddddddeeee | 597 |
| 601329 | 2596 | 2611 | Exon 18 | TTAATTCAATCCCACG | 69 | 7831 | 7846 | ekkddddddddkeee | 598 |
| 601368 | 2596 | 2611 | Exon 18 | TTAATTCAATCCCACG | 68 | 7831 | 7846 | kdkddddddddeeee | 598 |
| 601330 | 2597 | 2612 | Exon 18 | TTTAATTCAATCCCAC | 58 | 7832 | 7847 | ekkddddddddkeee | 599 |
| 601369 | 2597 | 2612 | Exon 18 | TTTAATTCAATCCCAC | 65 | 7832 | 7847 | kdkddddddddeeee | 599 |
| 601331 | 2598 | 2613 | Exon 18 | TTTTAATTCAATCCCA | 45 | 7833 | 7848 | ekkddddddddkeee | 600 |
| 601370 | 2598 | 2613 | Exon 18 | TTTTAATTCAATCCCA | 42 | 7833 | 7848 | kdkddddddddeeee | 600 |
| 601332 | 2599 | 2614 | Exon 18 | GTTTTAATTCAATCCC | 84 | 7834 | 7849 | ekkddddddddkeee | 601 |
| 601371 | 2599 | 2614 | Exon 18 | GTTTTAATTCAATCCC | 79 | 7834 | 7849 | kdkddddddddeeee | 601 |
| 601333 | 2600 | 2615 | Exon 18 | TGTTTTAATTCAATCC | 61 | 7835 | 7850 | ekkddddddddkeee | 602 |
| 601372 | 2600 | 2615 | Exon 18 | TGTTTTAATTCAATCC | 71 | 7835 | 7850 | kdkddddddddeeee | 602 |
| 601334 | 2601 | 2616 | Exon 18 | CTGTTTTAATTCAATC | 61 | 7836 | 7851 | ekkddddddddkeee | 603 |
| 601373 | 2601 | 2616 | Exon 18 | CTGTTTTAATTCAATC | 57 | 7836 | 7851 | kdkddddddddeeee | 603 |
| 601335 | 2602 | 2617 | Exon 18 | GCTGTTTTAATTCAAT | 73 | 7837 | 7852 | ekkddddddddkeee | 604 |
| 601374 | 2602 | 2617 | Exon 18 | GCTGTTTTAATTCAAT | 66 | 7837 | 7852 | kdkddddddddeeee | 604 |
| 601336 | 2603 | 2618 | Exon 18 | AGCTGTTTTAATTCAA | 64 | 7838 | 7853 | ekkddddddddkeee | 605 |
| 601375 | 2603 | 2618 | Exon 18 | AGCTGTTTTAATTCAA | 61 | 7838 | 7853 | kdkddddddddeeee | 605 |
| 532917 | 2604 | 2623 | Exon 18 | GTCGCAGCTGTTTTAATTCA | 66 | 7839 | 7858 | eeeeddddddddddeeeee | 317 |
| 601337 | 2604 | 2619 | Exon 18 | CAGCTGTTTTAATTCA | 53 | 7839 | 7854 | ekkddddddddkeee | 606 |
| 601376 | 2604 | 2619 | Exon 18 | CAGCTGTTTTAATTCA | 39 | 7839 | 7854 | kdkddddddddeeee | 606 |
| 601338 | 2605 | 2620 | Exon 18 | GCAGCTGTTTTAATTC | 67 | 7840 | 7855 | ekkddddddddkeee | 607 |
| 601377 | 2605 | 2620 | Exon 18 | GCAGCTGTTTTAATTC | 67 | 7840 | 7855 | kdkddddddddeeee | 607 |
| 601339 | 2606 | 2621 | Exon 18 | CGCAGCTGTTTTAATT | 63 | 7841 | 7856 | ekkddddddddkeee | 608 |
| 601378 | 2606 | 2621 | Exon 18 | CGCAGCTGTTTTAATT | 60 | 7841 | 7856 | kdkddddddddeeee | 608 |
| 601340 | 2607 | 2622 | Exon 18 | TCGCAGCTGTTTTAAT | 40 | 7842 | 7857 | ekkddddddddkeee | 609 |
| 601379 | 2607 | 2622 | Exon 18 | TCGCAGCTGTTTTAAT | 36 | 7842 | 7857 | kdkddddddddeeee | 609 |
| 588860 | 2608 | 2623 | Exon 18 | GTCGCAGCTGTTTTAA | 84 | 7843 | 7858 | eekddddddddddke | 610 |
| 601341 | 2608 | 2623 | Exon 18 | GTCGCAGCTGTTTTAA | 74 | 7843 | 7858 | ekkddddddddkeee | 610 |
| 601380 | 2608 | 2623 | Exon 18 | GTCGCAGCTGTTTTAA | 78 | 7843 | 7858 | kdkddddddddeeee | 610 |

TABLE 144-continued

Inhibition of CFB mRNA by deoxy, MOE and (S)-cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601342 | 2609 | 2624 | Exon 18 | TGTCGCAGCTGTTTTA | 68 | 7844 | 7859 | ekkddddddddkeee | 611 |
| 601381 | 2609 | 2624 | Exon 18 | TGTCGCAGCTGTTTTA | 66 | 7844 | 7859 | kdkddddddddeeee | 611 |
| 601343 | 2610 | 2625 | Exon 18 | TTGTCGCAGCTGTTTT | 71 | 7845 | 7860 | ekkddddddddkeee | 612 |
| 601382 | 2610 | 2625 | Exon 18 | TTGTCGCAGCTGTTTT | 84 | 7845 | 7860 | kdkddddddddeeee | 612 |
| 601344 | 2611 | 2626 | Exon 18 | GTTGTCGCAGCTGTTT | 87 | 7846 | 7861 | ekkddddddddkeee | 613 |
| 601383 | 2611 | 2626 | Exon 18 | GTTGTCGCAGCTGTTT | 85 | 7846 | 7861 | kdkddddddddeeee | 613 |
| 601345 | 2612 | 2627 | Exon 18 | TGTTGTCGCAGCTGTT | 82 | 7847 | 7862 | ekkddddddddkeee | 614 |
| 601384 | 2612 | 2627 | Exon 18 | TGTTGTCGCAGCTGTT | 79 | 7847 | 7862 | kdkddddddddeeee | 614 |
| 601346 | 2613 | 2628 | Exon 18/ Repeat | TTGTTGTCGCAGCTGT | 73 | n/a | n/a | ekkddddddddkeee | 615 |
| 601385 | 2613 | 2628 | Exon 18/ Repeat | TTGTTGTCGCAGCTGT | 84 | n/a | n/a | kdkddddddddeeee | 615 |
| 601347 | 2614 | 2629 | Exon 18/ Repeat | TTTGTTGTCGCAGCTG | 70 | n/a | n/a | ekkddddddddkeee | 616 |
| 601386 | 2614 | 2629 | Exon 18/ Repeat | TTTGTTGTCGCAGCTG | 71 | n/a | n/a | kdkddddddddeeee | 616 |
| 601348 | 2615 | 2630 | Exon 18/ Repeat | TTTTGTTGTCGCAGCT | 71 | n/a | n/a | ekkddddddddkeee | 617 |
| 601387 | 2615 | 2630 | Exon 18/ Repeat | TTTTGTTGTCGCAGCT | 76 | n/a | n/a | kdkddddddddeeee | 617 |
| 601349 | 2616 | 2631 | Exon 18/ Repeat | TTTTTGTTGTCGCAGC | 71 | n/a | n/a | ekkddddddddkeee | 618 |
| 601388 | 2616 | 2631 | Exon 18/ Repeat | TTTTTGTTGTCGCAGC | 67 | n/a | n/a | kdkddddddddeeee | 618 |

TABLE 145

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599357 | 2582 | 2600 | Exon 18 | CCACGCCCCTGTCCAGCAG | 26 | 7817 | 7835 | 5-9-5 | 708 |
| 599358 | 2583 | 2601 | Exon 18 | CCCACGCCCCTGTCCAGCA | 22 | 7818 | 7836 | 5-9-5 | 709 |
| 599359 | 2584 | 2602 | Exon 18 | TCCCACGCCCCTGTCCAGC | 13 | 7819 | 7837 | 5-9-5 | 710 |
| 599360 | 2585 | 2603 | Exon 18 | ATCCCACGCCCCTGTCCAG | 7 | 7820 | 7838 | 5-9-5 | 711 |
| 599361 | 2586 | 2604 | Exon 18 | AATCCCACGCCCCTGTCCA | 11 | 7821 | 7839 | 5-9-5 | 712 |
| 599362 | 2587 | 2605 | Exon 18 | CAATCCCACGCCCCTGTCC | 14 | 7822 | 7840 | 5-9-5 | 713 |
| 599363 | 2588 | 2606 | Exon 18 | TCAATCCCACGCCCCTGTC | 17 | 7823 | 7841 | 5-9-5 | 714 |
| 599364 | 2589 | 2607 | Exon 18 | TTCAATCCCACGCCCCTGT | 20 | 7824 | 7842 | 5-9-5 | 715 |
| 599365 | 2590 | 2608 | Exon 18 | ATTCAATCCCACGCCCCTG | 22 | 7825 | 7843 | 5-9-5 | 716 |
| 599366 | 2591 | 2609 | Exon 18 | AATTCAATCCCACGCCCCT | 13 | 7826 | 7844 | 5-9-5 | 717 |

TABLE 145-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599367 | 2592 | 2610 | Exon 18 | TAATTCAATCCCACGCCCC | 11 | 7827 | 7845 | 5-9-5 | 718 |
| 599368 | 2593 | 2611 | Exon 18 | TTAATTCAATCCCACGCCC | 10 | 7828 | 7846 | 5-9-5 | 719 |
| 599369 | 2594 | 2612 | Exon 18 | TTTAATTCAATCCCACGCC | 19 | 7829 | 7847 | 5-9-5 | 720 |
| 599370 | 2595 | 2613 | Exon 18 | TTTTAATTCAATCCCACGC | 23 | 7830 | 7848 | 5-9-5 | 721 |
| 599371 | 2596 | 2614 | Exon 18 | GTTTTAATTCAATCCCACG | 4 | 7831 | 7849 | 5-9-5 | 722 |
| 599372 | 2597 | 2615 | Exon 18 | TGTTTTAATTCAATCCCAC | 16 | 7832 | 7850 | 5-9-5 | 723 |
| 599373 | 2598 | 2616 | Exon 18 | CTGTTTTAATTCAATCCCA | 3 | 7833 | 7851 | 5-9-5 | 724 |
| 599374 | 2599 | 2617 | Exon 18 | GCTGTTTTAATTCAATCCC | 10 | 7834 | 7852 | 5-9-5 | 725 |
| 599375 | 2600 | 2618 | Exon 18 | AGCTGTTTTAATTCAATCC | 17 | 7835 | 7853 | 5-9-5 | 726 |
| 599376 | 2601 | 2619 | Exon 18 | CAGCTGTTTTAATTCAATC | 18 | 7836 | 7854 | 5-9-5 | 727 |
| 599377 | 2602 | 2620 | Exon 18 | GCAGCTGTTTTAATTCAAT | 22 | 7837 | 7855 | 5-9-5 | 728 |
| 599378 | 2603 | 2621 | Exon 18 | CGCAGCTGTTTTAATTCAA | 11 | 7838 | 7856 | 5-9-5 | 729 |
| 599511 | 2552 | 2571 | Exon 18 | ATAGAAAACCCAAATCCTCA | 7 | 7787 | 7806 | 6-8-6 | 410 |
| 599389 | 2553 | 2572 | Exon 18 | TATAGAAAACCCAAATCCTC | 22 | 7788 | 7807 | 6-8-6 | 411 |
| 599390 | 2554 | 2573 | Exon 18 | TTATAGAAAACCCAAATCCT | 21 | 7789 | 7808 | 6-8-6 | 412 |
| 599391 | 2555 | 2574 | Exon 18 | CTTATAGAAAACCCAAATCC | 27 | 7790 | 7809 | 6-8-6 | 413 |
| 599392 | 2556 | 2575 | Exon 18 | CCTTATAGAAAACCCAAATC | 30 | 7791 | 7810 | 6-8-6 | 414 |
| 599393 | 2557 | 2576 | Exon 18 | CCCTTATAGAAAACCCAAAT | 30 | 7792 | 7811 | 6-8-6 | 415 |
| 599394 | 2558 | 2577 | Exon 18 | CCCCTTATAGAAAACCCAAA | 28 | 7793 | 7812 | 6-8-6 | 416 |
| 599395 | 2559 | 2578 | Exon 18 | ACCCCTTATAGAAAACCCAA | 23 | 7794 | 7813 | 6-8-6 | 417 |
| 599396 | 2560 | 2579 | Exon 18 | AACCCCTTATAGAAAACCCA | 53 | 7795 | 7814 | 6-8-6 | 418 |
| 599397 | 2561 | 2580 | Exon 18 | AAACCCCTTATAGAAAACCC | 33 | 7796 | 7815 | 6-8-6 | 419 |
| 599398 | 2562 | 2581 | Exon 18 | GAAACCCCTTATAGAAAACC | 58 | 7797 | 7816 | 6-8-6 | 420 |
| 599399 | 2563 | 2582 | Exon 18 | GGAAACCCCTTATAGAAAAC | 23 | 7798 | 7817 | 6-8-6 | 421 |
| 599400 | 2564 | 2583 | Exon 18 | AGGAAACCCCTTATAGAAAA | 54 | 7799 | 7818 | 6-8-6 | 422 |
| 599401 | 2565 | 2584 | Exon 18 | CAGGAAACCCCTTATAGAAA | 30 | 7800 | 7819 | 6-8-6 | 423 |
| 599402 | 2566 | 2585 | Exon 18 | GCAGGAAACCCCTTATAGAA | 25 | 7801 | 7820 | 6-8-6 | 424 |
| 599403 | 2567 | 2586 | Exon 18 | AGCAGGAAACCCCTTATAGA | 17 | 7802 | 7821 | 6-8-6 | 425 |
| 599404 | 2568 | 2587 | Exon 18 | CAGCAGGAAACCCCTTATAG | 20 | 7803 | 7822 | 6-8-6 | 426 |
| 599405 | 2569 | 2588 | Exon 18 | CCAGCAGGAAACCCCTTATA | 12 | 7804 | 7823 | 6-8-6 | 427 |
| 599406 | 2570 | 2589 | Exon 18 | TCCAGCAGGAAACCCCTTAT | 51 | 7805 | 7824 | 6-8-6 | 428 |
| 599407 | 2571 | 2590 | Exon 18 | GTCCAGCAGGAAACCCCTTA | 39 | 7806 | 7825 | 6-8-6 | 237 |
| 599408 | 2572 | 2591 | Exon 18 | TGTCCAGCAGGAAACCCCTT | 53 | 7807 | 7826 | 6-8-6 | 429 |
| 599409 | 2573 | 2592 | Exon 18 | CTGTCCAGCAGGAAACCCCT | 65 | 7808 | 7827 | 6-8-6 | 430 |
| 599410 | 2574 | 2593 | Exon 18 | CCTGTCCAGCAGGAAACCCC | 56 | 7809 | 7828 | 6-8-6 | 431 |
| 599411 | 2575 | 2594 | Exon 18 | CCCTGTCCAGCAGGAAACCC | 60 | 7810 | 7829 | 6-8-6 | 432 |

TABLE 145-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599412 | 2576 | 2595 | Exon 18 | CCCCTGTCCAGCAGGAAACC | 61 | 7811 | 7830 | 6-8-6 | 433 |
| 599413 | 2577 | 2596 | Exon 18 | GCCCCTGTCCAGCAGGAAAC | 40 | 7812 | 7831 | 6-8-6 | 238 |
| 599414 | 2578 | 2597 | Exon 18 | CGCCCCTGTCCAGCAGGAAA | 41 | 7813 | 7832 | 6-8-6 | 434 |
| 599415 | 2579 | 2598 | Exon 18 | ACGCCCCTGTCCAGCAGGAA | 37 | 7814 | 7833 | 6-8-6 | 435 |
| 599416 | 2580 | 2599 | Exon 18 | CACGCCCCTGTCCAGCAGGA | 54 | 7815 | 7834 | 6-8-6 | 436 |
| 599417 | 2581 | 2600 | Exon 18 | CCACGCCCCTGTCCAGCAGG | 36 | 7816 | 7835 | 6-8-6 | 437 |
| 599418 | 2582 | 2601 | Exon 18 | CCCACGCCCCTGTCCAGCAG | 53 | 7817 | 7836 | 6-8-6 | 438 |
| 599419 | 2583 | 2602 | Exon 18 | TCCCACGCCCCTGTCCAGCA | 54 | 7818 | 7837 | 6-8-6 | 439 |
| 599420 | 2584 | 2603 | Exon 18 | ATCCCACGCCCCTGTCCAGC | 50 | 7819 | 7838 | 6-8-6 | 440 |
| 599421 | 2585 | 2604 | Exon 18 | AATCCCACGCCCCTGTCCAG | 48 | 7820 | 7839 | 6-8-6 | 441 |
| 599422 | 2586 | 2605 | Exon 18 | CAATCCCACGCCCCTGTCCA | 55 | 7821 | 7840 | 6-8-6 | 442 |
| 599423 | 2587 | 2606 | Exon 18 | TCAATCCCACGCCCCTGTCC | 75 | 7822 | 7841 | 6-8-6 | 443 |
| 599424 | 2588 | 2607 | Exon 18 | TTCAATCCCACGCCCCTGTC | 69 | 7823 | 7842 | 6-8-6 | 444 |
| 599425 | 2589 | 2608 | Exon 18 | ATTCAATCCCACGCCCCTGT | 77 | 7824 | 7843 | 6-8-6 | 445 |
| 599426 | 2590 | 2609 | Exon 18 | AATTCAATCCCACGCCCCTG | 60 | 7825 | 7844 | 6-8-6 | 446 |
| 599427 | 2591 | 2610 | Exon 18 | TAATTCAATCCCACGCCCCT | 72 | 7826 | 7845 | 6-8-6 | 447 |
| 599428 | 2592 | 2611 | Exon 18 | TTAATTCAATCCCACGCCCC | 81 | 7827 | 7846 | 6-8-6 | 448 |
| 599429 | 2593 | 2612 | Exon 18 | TTTAATTCAATCCCACGCCC | 68 | 7828 | 7847 | 6-8-6 | 449 |
| 599430 | 2594 | 2613 | Exon 18 | TTTTAATTCAATCCCACGCC | 58 | 7829 | 7848 | 6-8-6 | 450 |
| 599431 | 2595 | 2614 | Exon 18 | GTTTTAATTCAATCCCACGC | 70 | 7830 | 7849 | 6-8-6 | 451 |
| 599432 | 2596 | 2615 | Exon 18 | TGTTTTAATTCAATCCCACG | 85 | 7831 | 7850 | 6-8-6 | 452 |
| 532917 | 2604 | 2623 | Exon 18 | GTCGCAGCTGTTTTAATTCA | 85 | 7839 | 7858 | 5-10-5 | 317 |
| 599379 | 2604 | 2622 | Exon 18 | TCGCAGCTGTTTTAATTCA | 73 | 7839 | 7857 | 5-9-5 | 730 |
| 599380 | 2605 | 2623 | Exon 18 | GTCGCAGCTGTTTTAATTC | 77 | 7840 | 7858 | 5-9-5 | 731 |
| 599381 | 2606 | 2624 | Exon 18 | TGTCGCAGCTGTTTTAATT | 69 | 7841 | 7859 | 5-9-5 | 732 |
| 599382 | 2607 | 2625 | Exon 18 | TTGTCGCAGCTGTTTTAAT | 58 | 7842 | 7860 | 5-9-5 | 733 |
| 599383 | 2608 | 2626 | Exon 18 | GTTGTCGCAGCTGTTTTAA | 52 | 7843 | 7861 | 5-9-5 | 734 |
| 599384 | 2609 | 2627 | Exon 18 | TGTTGTCGCAGCTGTTTTA | 63 | 7844 | 7862 | 5-9-5 | 735 |
| 599385 | 2610 | 2628 | Exon 18/ Repeat | TTGTTGTCGCAGCTGTTTT | 53 | n/a | n/a | 5-9-5 | 736 |
| 599386 | 2611 | 2629 | Exon 18/ Repeat | TTTGTTGTCGCAGCTGTTT | 63 | n/a | n/a | 5-9-5 | 737 |
| 599387 | 2612 | 2630 | Exon 18/ Repeat | TTTTGTTGTCGCAGCTGTT | 64 | n/a | n/a | 5-9-5 | 438 |
| 599388 | 2613 | 2631 | Exon 18/ Repeat | TTTTTGTTGTCGCAGCTGT | 66 | n/a | n/a | 5-9-5 | 739 |

TABLE 146

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599213 | 2553 | 2570 | Exon 18 | TAGAAAACCCAAATCCTC | 0 | 7788 | 7805 | 3-10-5 | 785 |
| 599214 | 2554 | 2571 | Exon 18 | ATAGAAAACCCAAATCCT | 0 | 7789 | 7806 | 3-10-5 | 786 |
| 599215 | 2555 | 2572 | Exon 18 | TATAGAAAACCCAAATCC | 36 | 7790 | 7807 | 3-10-5 | 787 |
| 599216 | 2556 | 2573 | Exon 18 | TTATAGAAAACCCAAATC | 8 | 7791 | 7808 | 3-10-5 | 788 |
| 599217 | 2557 | 2574 | Exon 18 | CTTATAGAAAACCCAAAT | 5 | 7792 | 7809 | 3-10-5 | 789 |
| 599218 | 2558 | 2575 | Exon 18 | CCTTATAGAAAACCCAAA | 0 | 7793 | 7810 | 3-10-5 | 790 |
| 599219 | 2559 | 2576 | Exon 18 | CCCTTATAGAAAACCCAA | 8 | 7794 | 7811 | 3-10-5 | 791 |
| 599220 | 2560 | 2577 | Exon 18 | CCCCTTATAGAAAACCCA | 0 | 7795 | 7812 | 3-10-5 | 740 |
| 599221 | 2561 | 2578 | Exon 18 | ACCCCTTATAGAAAACCC | 54 | 7796 | 7813 | 3-10-5 | 741 |
| 599222 | 2562 | 2579 | Exon 18 | AACCCCTTATAGAAAACC | 3 | 7797 | 7814 | 3-10-5 | 742 |
| 599223 | 2563 | 2580 | Exon 18 | AAACCCCTTATAGAAAAC | 0 | 7798 | 7815 | 3-10-5 | 743 |
| 599224 | 2564 | 2581 | Exon 18 | GAAACCCCTTATAGAAAA | 0 | 7799 | 7816 | 3-10-5 | 744 |
| 599225 | 2566 | 2583 | Exon 18 | AGGAAACCCCTTATAGAA | 60 | 7801 | 7818 | 3-10-5 | 745 |
| 599226 | 2567 | 2584 | Exon 18 | CAGGAAACCCCTTATAGA | 0 | 7802 | 7819 | 3-10-5 | 746 |
| 599227 | 2568 | 2585 | Exon 18 | GCAGGAAACCCCTTATAG | 37 | 7803 | 7820 | 3-10-5 | 747 |
| 599228 | 2569 | 2586 | Exon 18 | AGCAGGAAACCCCTTATA | 0 | 7804 | 7821 | 3-10-5 | 748 |
| 599229 | 2570 | 2587 | Exon 18 | CAGCAGGAAACCCCTTAT | 39 | 7805 | 7822 | 3-10-5 | 749 |
| 599230 | 2571 | 2588 | Exon 18 | CCAGCAGGAAACCCCTTA | 10 | 7806 | 7823 | 3-10-5 | 750 |
| 599231 | 2572 | 2589 | Exon 18 | TCCAGCAGGAAACCCCTT | 16 | 7807 | 7824 | 3-10-5 | 751 |
| 599232 | 2573 | 2590 | Exon 18 | GTCCAGCAGGAAACCCCT | 9 | 7808 | 7825 | 3-10-5 | 752 |
| 599233 | 2574 | 2591 | Exon 18 | TGTCCAGCAGGAAACCCC | 44 | 7809 | 7826 | 3-10-5 | 753 |
| 599234 | 2575 | 2592 | Exon 18 | CTGTCCAGCAGGAAACCC | 14 | 7810 | 7827 | 3-10-5 | 754 |
| 599235 | 2576 | 2593 | Exon 18 | CCTGTCCAGCAGGAAACC | 0 | 7811 | 7828 | 3-10-5 | 755 |
| 599236 | 2577 | 2594 | Exon 18 | CCCTGTCCAGCAGGAAAC | 43 | 7812 | 7829 | 3-10-5 | 756 |
| 599237 | 2578 | 2595 | Exon 18 | CCCCTGTCCAGCAGGAAA | 0 | 7813 | 7830 | 3-10-5 | 757 |
| 599238 | 2580 | 2597 | Exon 18 | CGCCCTGTCCAGCAGGA | 9 | 7815 | 7832 | 3-10-5 | 758 |
| 599239 | 2581 | 2598 | Exon 18 | ACGCCCTGTCCAGCAGG | 36 | 7816 | 7833 | 3-10-5 | 759 |
| 599240 | 2582 | 2599 | Exon 18 | CACGCCCTGTCCAGCAG | 11 | 7817 | 7834 | 3-10-5 | 760 |
| 599241 | 2583 | 2600 | Exon 18 | CCACGCCCTGTCCAGCA | 51 | 7818 | 7835 | 3-10-5 | 761 |
| 599242 | 2584 | 2601 | Exon 18 | CCCACGCCCTGTCCAGC | 7 | 7819 | 7836 | 3-10-5 | 762 |
| 599243 | 2585 | 2602 | Exon 18 | TCCCACGCCCTGTCCAG | 47 | 7820 | 7837 | 3-10-5 | 763 |
| 599244 | 2586 | 2603 | Exon 18 | ATCCCACGCCCTGTCCA | 37 | 7821 | 7838 | 3-10-5 | 764 |
| 599245 | 2587 | 2604 | Exon 18 | AATCCCACGCCCTGTCC | 35 | 7822 | 7839 | 3-10-5 | 765 |
| 599246 | 2588 | 2605 | Exon 18 | CAATCCCACGCCCTGTC | 21 | 7823 | 7840 | 3-10-5 | 766 |
| 599247 | 2589 | 2606 | Exon 18 | TCAATCCCACGCCCTGT | 61 | 7824 | 7841 | 3-10-5 | 767 |
| 599248 | 2590 | 2607 | Exon 18 | TTCAATCCCACGCCCTG | 51 | 7825 | 7842 | 3-10-5 | 768 |

TABLE 146-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599249 | 2591 | 2608 | Exon 18 | ATTCAATCCCACGCCCT | 58 | 7826 | 7843 | 3-10-5 | 769 |
| 599250 | 2592 | 2609 | Exon 18 | AATTCAATCCCACGCCC | 49 | 7827 | 7844 | 3-10-5 | 770 |
| 599251 | 2593 | 2610 | Exon 18 | TAATTCAATCCCACGCC | 46 | 7828 | 7845 | 3-10-5 | 771 |
| 599252 | 2594 | 2611 | Exon 18 | TTAATTCAATCCCACGCC | 32 | 7829 | 7846 | 3-10-5 | 772 |
| 599253 | 2595 | 2612 | Exon 18 | TTTAATTCAATCCCACGC | 23 | 7830 | 7847 | 3-10-5 | 773 |
| 599254 | 2596 | 2613 | Exon 18 | TTTTAATTCAATCCCACG | 0 | 7831 | 7848 | 3-10-5 | 774 |
| 599255 | 2597 | 2614 | Exon 18 | GTTTTAATTCAATCCCAC | 61 | 7832 | 7849 | 3-10-5 | 775 |
| 599256 | 2598 | 2615 | Exon 18 | TGTTTTAATTCAATCCCA | 64 | 7833 | 7850 | 3-10-5 | 776 |
| 599257 | 2599 | 2616 | Exon 18 | CTGTTTTAATTCAATCCC | 66 | 7834 | 7851 | 3-10-5 | 777 |
| 599258 | 2600 | 2617 | Exon 18 | GCTGTTTTAATTCAATCC | 59 | 7835 | 7852 | 3-10-5 | 778 |
| 599259 | 2601 | 2618 | Exon 18 | AGCTGTTTTAATTCAATC | 40 | 7836 | 7853 | 3-10-5 | 779 |
| 599260 | 2602 | 2619 | Exon 18 | CAGCTGTTTTAATTCAAT | 38 | 7837 | 7854 | 3-10-5 | 780 |
| 599261 | 2603 | 2620 | Exon 18 | GCAGCTGTTTTAATTCAA | 54 | 7838 | 7855 | 3-10-5 | 781 |
| 599509 | 2552 | 2570 | Exon 18 | TAGAAAACCCAAATCCTCA | 54 | 7787 | 7805 | 6-7-6 | 681 |
| 599273 | 2553 | 2571 | Exon 18 | ATAGAAAACCCAAATCCTC | 0 | 7788 | 7806 | 6-7-6 | 682 |
| 599274 | 2554 | 2572 | Exon 18 | TATAGAAAACCCAAATCCT | 57 | 7789 | 7807 | 6-7-6 | 683 |
| 599275 | 2556 | 2574 | Exon 18 | CTTATAGAAAACCCAAATC | 0 | 7791 | 7809 | 6-7-6 | 684 |
| 599276 | 2557 | 2575 | Exon 18 | CCTTATAGAAAACCCAAAT | 44 | 7792 | 7810 | 6-7-6 | 685 |
| 599277 | 2558 | 2576 | Exon 18 | CCCTTATAGAAAACCCAAA | 0 | 7793 | 7811 | 6-7-6 | 686 |
| 599278 | 2559 | 2577 | Exon 18 | CCCCTTATAGAAAACCCAA | 0 | 7794 | 7812 | 6-7-6 | 687 |
| 599279 | 2560 | 2578 | Exon 18 | ACCCCTTATAGAAAACCCA | 20 | 7795 | 7813 | 6-7-6 | 688 |
| 599280 | 2561 | 2579 | Exon 18 | AACCCCTTATAGAAAACCC | 70 | 7796 | 7814 | 6-7-6 | 689 |
| 532917 | 2604 | 2623 | Exon 18 | GTCGCAGCTGTTTTAATTCA | 85 | 7839 | 7858 | 5-10-5 | 317 |
| 599262 | 2604 | 2621 | Exon 18 | CGCAGCTGTTTTAATTCA | 49 | 7839 | 7856 | 3-10-5 | 782 |
| 599263 | 2605 | 2622 | Exon 18 | TCGCAGCTGTTTTAATTC | 49 | 7840 | 7857 | 3-10-5 | 783 |
| 599264 | 2606 | 2623 | Exon 18 | GTCGCAGCTGTTTTAATT | 62 | 7841 | 7858 | 3-10-5 | 784 |
| 599265 | 2607 | 2624 | Exon 18 | TGTCGCAGCTGTTTTAAT | 63 | 7842 | 7859 | 3-10-5 | 792 |
| 599266 | 2608 | 2625 | Exon 18 | TTGTCGCAGCTGTTTTAA | 41 | 7843 | 7860 | 3-10-5 | 793 |
| 599267 | 2609 | 2626 | Exon 18 | GTTGTCGCAGCTGTTTTA | 52 | 7844 | 7861 | 3-10-5 | 794 |
| 599268 | 2610 | 2627 | Exon 18 | TGTTGTCGCAGCTGTTTT | 51 | 7845 | 7862 | 3-10-5 | 795 |
| 599269 | 2611 | 2628 | Exon 18/Repeat | TTGTTGTCGCAGCTGTTT | 58 | n/a | n/a | 3-10-5 | 796 |
| 599270 | 2612 | 2629 | Exon 18/Repeat | TTTGTTGTCGCAGCTGTT | 69 | n/a | n/a | 3-10-5 | 797 |
| 599271 | 2613 | 2630 | Exon 18/Repeat | TTTTGTTGTCGCAGCTGT | 69 | n/a | n/a | 3-10-5 | 798 |
| 599272 | 2614 | 2631 | Exon 18/Repeat | TTTTTGTTGTCGCAGCTG | 72 | n/a | n/a | 3-10-5 | 799 |

TABLE 146-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599205 | 2607 | 2624 | Exon 18 | TGTCGCAGCTGTTTTAAT | 54 | 7842 | 7859 | 5-8-5 | 792 |
| 599206 | 2608 | 2625 | Exon 18 | TTGTCGCAGCTGTTTTAA | 62 | 7843 | 7860 | 5-8-5 | 793 |
| 599207 | 2609 | 2626 | Exon 18 | GTTGTCGCAGCTGTTTTA | 62 | 7844 | 7861 | 5-8-5 | 794 |
| 599208 | 2610 | 2627 | Exon 18 | TGTTGTCGCAGCTGTTTT | 66 | 7845 | 7862 | 5-8-5 | 795 |
| 599209 | 2611 | 2628 | Exon 18/ Repeat | TTGTTGTCGCAGCTGTTT | 60 | n/a | n/a | 5-8-5 | 796 |
| 599210 | 2612 | 2629 | Exon 18/ Repeat | TTTGTTGTCGCAGCTGTT | 62 | n/a | n/a | 5-8-5 | 797 |
| 599211 | 2613 | 2630 | Exon 18/ Repeat | TTTTGTTGTCGCAGCTGT | 65 | n/a | n/a | 5-8-5 | 798 |
| 599212 | 2614 | 2631 | Exon 18/ Repeat | TTTTTGTTGTCGCAGCTG | 67 | n/a | n/a | 5-8-5 | 799 |

TABLE 147

Inhibition of CFB mRNA by 5-10-5 MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | SEQ ID NO: |
|---|---|---|---|---|---|---|---|---|
| 588570 | 150 | 169 | Exon 1 | TGGTCACATTCCCTTCCCCT | 72 | 1871 | 1890 | 396 |
| 588571 | 152 | 171 | Exon 1 | CCTGGTCACATTCCCTTCCC | 80 | 1873 | 1892 | 397 |
| 532614 | 154 | 173 | Exon 1 | GACCTGGTCACATTCCCTTC | 65 | 1875 | 1894 | 12 |
| 588572 | 156 | 175 | Exon 1 | TAGACCTGGTCACATTCCCT | 74 | 1877 | 1896 | 398 |
| 588573 | 158 | 177 | Exon 1 | CCTAGACCTGGTCACATTCC | 72 | 1879 | 1898 | 399 |
| 588566 | 2189 | 2208 | Exon 15 | CCTTCCGAGTCAGCTTTTTC | 66 | 6977 | 6996 | 400 |
| 588567 | 2191 | 2210 | Exon 15 | CTCCTTCCGAGTCAGCTTTT | 66 | 6979 | 6998 | 401 |
| 532770 | 2193 | 2212 | Exon 15 | ACCTCCTTCCGAGTCAGCTT | 64 | 6981 | 7000 | 198 |
| 588568 | 2195 | 2214 | Exon 15 | AGACCTCCTTCCGAGTCAGC | 78 | 6983 | 7002 | 402 |
| 588569 | 2197 | 2216 | Exon 15 | GTAGACCTCCTTCCGAGTCA | 74 | 6985 | 7004 | 403 |
| 588574 | 2453 | 2472 | Exon 18 | TTTGCCGCTTCTGGTTTTTG | 71 | 7688 | 7707 | 404 |
| 588575 | 2455 | 2474 | Exon 18 | CTTTTGCCGCTTCTGGTTTT | 72 | 7690 | 7709 | 405 |
| 532800 | 2457 | 2476 | Exon 18 | TGCTTTTGCCGCTTCTGGTT | 71 | 7692 | 7711 | 228 |
| 588576 | 2459 | 2478 | Exon 18 | CCTGCTTTTGCCGCTTCTGG | 59 | 7694 | 7713 | 406 |
| 588577 | 2461 | 2480 | Exon 18 | TACCTGCTTTTGCCGCTTCT | 76 | 7696 | 7715 | 407 |
| 516350 | 2550 | 2569 | Exon 18 | AGAAAACCCAAATCCTCATC | 58 | 7785 | 7804 | 408 |
| 588509 | 2551 | 2570 | Exon 18 | TAGAAAACCCAAATCCTCAT | 6 | 7786 | 7805 | 409 |
| 588510 | 2552 | 2571 | Exon 18 | ATAGAAAACCCAAATCCTCA | 10 | 7787 | 7806 | 410 |
| 588511 | 2553 | 2572 | Exon 18 | TATAGAAAACCCAAATCCTC | 9 | 7788 | 7807 | 411 |
| 588512 | 2554 | 2573 | Exon 18 | TTATAGAAAACCCAAATCCT | 80 | 7789 | 7808 | 412 |

TABLE 147-continued

Inhibition of CFB mRNA by 5-10-5 MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | SEQ ID NO: |
|---|---|---|---|---|---|---|---|---|
| 588513 | 2555 | 2574 | Exon 18 | CTTATAGAAAACCCAAATCC | 70 | 7790 | 7809 | 413 |
| 588514 | 2556 | 2575 | Exon 18 | CCTTATAGAAAACCCAAATC | 71 | 7791 | 7810 | 414 |
| 588515 | 2557 | 2576 | Exon 18 | CCCTTATAGAAAACCCAAAT | 78 | 7792 | 7811 | 415 |
| 588516 | 2558 | 2577 | Exon 18 | CCCCTTATAGAAAACCCAAA | 72 | 7793 | 7812 | 416 |
| 588517 | 2559 | 2578 | Exon 18 | ACCCCTTATAGAAAACCCAA | 80 | 7794 | 7813 | 417 |
| 588518 | 2560 | 2579 | Exon 18 | AACCCCTTATAGAAAACCCA | 80 | 7795 | 7814 | 418 |
| 588519 | 2561 | 2580 | Exon 18 | AAACCCCTTATAGAAAACCC | 62 | 7796 | 7815 | 419 |
| 588520 | 2562 | 2581 | Exon 18 | GAAACCCCTTATAGAAAACC | 59 | 7797 | 7816 | 420 |
| 588521 | 2563 | 2582 | Exon 18 | GGAAACCCCTTATAGAAAAC | 40 | 7798 | 7817 | 421 |
| 588522 | 2564 | 2583 | Exon 18 | AGGAAACCCCTTATAGAAAA | 66 | 7799 | 7818 | 422 |
| 588523 | 2565 | 2584 | Exon 18 | CAGGAAACCCCTTATAGAAA | 63 | 7800 | 7819 | 423 |
| 588524 | 2566 | 2585 | Exon 18 | GCAGGAAACCCCTTATAGAA | 70 | 7801 | 7820 | 424 |
| 588525 | 2567 | 2586 | Exon 18 | AGCAGGAAACCCCTTATAGA | 67 | 7802 | 7821 | 425 |
| 588526 | 2568 | 2587 | Exon 18 | CAGCAGGAAACCCCTTATAG | 0 | 7803 | 7822 | 426 |
| 588527 | 2569 | 2588 | Exon 18 | CCAGCAGGAAACCCCTTATA | 11 | 7804 | 7823 | 427 |
| 588528 | 2570 | 2589 | Exon 18 | TCCAGCAGGAAACCCCTTAT | 15 | 7805 | 7824 | 428 |
| 532809 | 2571 | 2590 | Exon 18 | GTCCAGCAGGAAACCCCTTA | 75 | 7806 | 7825 | 237 |
| 588529 | 2572 | 2591 | Exon 18 | TGTCCAGCAGGAAACCCCTT | 16 | 7807 | 7826 | 429 |
| 588530 | 2573 | 2592 | Exon 18 | CTGTCCAGCAGGAAACCCCT | 16 | 7808 | 7827 | 430 |
| 588531 | 2574 | 2593 | Exon 18 | CCTGTCCAGCAGGAAACCCC | 19 | 7809 | 7828 | 431 |
| 588532 | 2575 | 2594 | Exon 18 | CCCTGTCCAGCAGGAAACCC | 15 | 7810 | 7829 | 432 |
| 588533 | 2576 | 2595 | Exon 18 | CCCCTGTCCAGCAGGAAACC | 29 | 7811 | 7830 | 433 |
| 532810 | 2577 | 2596 | Exon 18 | GCCCCTGTCCAGCAGGAAAC | 74 | 7812 | 7831 | 238 |
| 588534 | 2578 | 2597 | Exon 18 | CGCCCCTGTCCAGCAGGAAA | 21 | 7813 | 7832 | 434 |
| 588535 | 2579 | 2598 | Exon 18 | ACGCCCCTGTCCAGCAGGAA | 16 | 7814 | 7833 | 435 |
| 588536 | 2580 | 2599 | Exon 18 | CACGCCCCTGTCCAGCAGGA | 0 | 7815 | 7834 | 436 |
| 588537 | 2581 | 2600 | Exon 18 | CCACGCCCCTGTCCAGCAGG | 8 | 7816 | 7835 | 437 |
| 588538 | 2582 | 2601 | Exon 18 | CCCACGCCCCTGTCCAGCAG | 10 | 7817 | 7836 | 438 |
| 588539 | 2583 | 2602 | Exon 18 | TCCCACGCCCCTGTCCAGCA | 23 | 7818 | 7837 | 439 |
| 588540 | 2584 | 2603 | Exon 18 | ATCCCACGCCCCTGTCCAGC | 16 | 7819 | 7838 | 440 |
| 588541 | 2585 | 2604 | Exon 18 | AATCCCACGCCCCTGTCCAG | 16 | 7820 | 7839 | 441 |
| 588542 | 2586 | 2605 | Exon 18 | CAATCCCACGCCCCTGTCCA | 12 | 7821 | 7840 | 442 |
| 588543 | 2587 | 2606 | Exon 18 | TCAATCCCACGCCCCTGTCC | 26 | 7822 | 7841 | 443 |
| 588544 | 2588 | 2607 | Exon 18 | TTCAATCCCACGCCCCTGTC | 26 | 7823 | 7842 | 444 |
| 588545 | 2589 | 2608 | Exon 18 | ATTCAATCCCACGCCCCTGT | 31 | 7824 | 7843 | 445 |
| 588546 | 2590 | 2609 | Exon 18 | AATTCAATCCCACGCCCCTG | 22 | 7825 | 7844 | 446 |

TABLE 147-continued

Inhibition of CFB mRNA by 5-10-5 MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | SEQ ID NO: |
|---|---|---|---|---|---|---|---|---|
| 588547 | 2591 | 2610 | Exon 18 | TAATTCAATCCCACGCCCCT | 12 | 7826 | 7845 | 447 |
| 588548 | 2592 | 2611 | Exon 18 | TTAATTCAATCCCACGCCCC | 20 | 7827 | 7846 | 448 |
| 588549 | 2593 | 2612 | Exon 18 | TTTAATTCAATCCCACGCCC | 26 | 7828 | 7847 | 449 |
| 588550 | 2594 | 2613 | Exon 18 | TTTTAATTCAATCCCACGCC | 32 | 7829 | 7848 | 450 |
| 588551 | 2595 | 2614 | Exon 18 | GTTTTAATTCAATCCCACGC | 48 | 7830 | 7849 | 451 |
| 588552 | 2596 | 2615 | Exon 18 | TGTTTTAATTCAATCCCACG | 57 | 7831 | 7850 | 452 |
| 588553 | 2597 | 2616 | Exon 18 | CTGTTTTAATTCAATCCCAC | 49 | 7832 | 7851 | 453 |
| 588554 | 2598 | 2617 | Exon 18 | GCTGTTTTAATTCAATCCCA | 64 | 7833 | 7852 | 454 |
| 532811 | 2599 | 2618 | Exon 18 | AGCTGTTTTAATTCAATCCC | 78 | 7834 | 7853 | 239 |
| 588555 | 2600 | 2619 | Exon 18 | CAGCTGTTTTAATTCAATCC | 48 | 7835 | 7854 | 455 |
| 588556 | 2601 | 2620 | Exon 18 | GCAGCTGTTTTAATTCAATC | 55 | 7836 | 7855 | 456 |
| 588557 | 2602 | 2621 | Exon 18 | CGCAGCTGTTTTAATTCAAT | 51 | 7837 | 7856 | 457 |
| 588558 | 2603 | 2622 | Exon 18 | TCGCAGCTGTTTTAATTCAA | 51 | 7838 | 7857 | 458 |
| 532917 | 2604 | 2623 | Exon 18 | GTCGCAGCTGTTTTAATTCA | 82 | 7839 | 7858 | 317 |
| 588559 | 2605 | 2624 | Exon 18 | TGTCGCAGCTGTTTTAATTC | 58 | 7840 | 7859 | 459 |
| 588560 | 2606 | 2625 | Exon 18 | TTGTCGCAGCTGTTTTAATT | 72 | 7841 | 7860 | 460 |
| 588561 | 2607 | 2626 | Exon 18 | GTTGTCGCAGCTGTTTTAAT | 75 | 7842 | 7861 | 461 |
| 532952 | 2608 | 2627 | Exon 18 | TGTTGTCGCAGCTGTTTTAA | 39 | 7843 | 7862 | 395 |
| 588562 | 2609 | 2628 | Exon 18/Repeat | TTGTTGTCGCAGCTGTTTTA | 53 | n/a | n/a | 462 |
| 588563 | 2610 | 2629 | Exon 18/Repeat | TTTGTTGTCGCAGCTGTTTT | 62 | n/a | n/a | 463 |
| 588564 | 2611 | 2630 | Exon 18/Repeat | TTTTGTTGTCGCAGCTGTTT | 63 | n/a | n/a | 464 |
| 588565 | 2612 | 2631 | Exon 18/Repeat | TTTTTGTTGTCGCAGCTGTT | 64 | n/a | n/a | 465 |

Example 122: Dose-Dependent Antisense Inhibition of Human CFB in HepG2 Cells by 5-10-5 MOE Gapmers Gapmers from studies described above exhibiting in vitro inhibition of CFB mRNA were selected and tested at various doses in HepG2 cells. Cells were plated at a density of 20,000 cells per well and transfected using electroporation with 0.313 µM, 0.625 µM, 1.25 µM, 2.50 µM, 5.00 µM, or 10.00 µM concentrations of antisense oligonucleotide, as specified in the Table below. After a treatment period of approximately 16 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The half maximal inhibitory concentration ($IC_{50}$) of each oligonucleotide is also presented. CFB mRNA levels were reduced in a dose-dependent manner in antisense oligonucleotide treated cells.

TABLE 148

| ISIS No | 0.313 µM | 0.625 µM | 1.25 µM | 2.50 µM | 5.00 µM | 10.00 µM | $IC_{50}$ (µM) |
|---|---|---|---|---|---|---|---|
| 532614 | 7 | 13 | 43 | 72 | 65 | 71 | 2.2 |
| 532635 | 12 | 0 | 3 | 28 | 0 | 0 | >10 |
| 532692 | 26 | 0 | 12 | 52 | 55 | 74 | 3.7 |
| 532770 | 21 | 18 | 32 | 73 | 64 | 88 | 1.8 |
| 532775 | 8 | 0 | 26 | 35 | 47 | 59 | 6.2 |
| 532800 | 0 | 5 | 30 | 65 | 50 | 75 | 3.1 |
| 532809 | 12 | 30 | 28 | 40 | 46 | 66 | 4.6 |
| 532810 | 28 | 44 | 32 | 69 | 84 | 95 | 1.2 |
| 532811 | 66 | 83 | 90 | 94 | 97 | 99 | <0.3 |

TABLE 148-continued

| ISIS No | 0.313 µM | 0.625 µM | 1.25 µM | 2.50 µM | 5.00 µM | 10.00 µM | IC$_{50}$ (µM) |
|---|---|---|---|---|---|---|---|
| 532917 | 64 | 85 | 88 | 96 | 97 | 99 | <0.3 |
| 532952 | 50 | 53 | 68 | 80 | 91 | 94 | 0.4 |

Example 123: Dose-Dependent Antisense Inhibition of Human CFB in HepG2 Cells

Gapmers from studies described above exhibiting in vitro inhibition of CFB mRNA were selected and tested at various doses in HepG2 cells. The antisense oligonucleotides were tested in a number of experiments with similar culture conditions. The results for each experiment are presented in separate tables shown below. Cells were plated at a density of 20,000 cells per well and transfected using electroporation with 0.08 µM, 0.25 µM, 0.74 µM, 2.22 µM, 6.67 µM, and 20.00 µM concentrations of antisense oligonucleotide, as specified in the Table below. After a treatment period of approximately 16 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The half maximal inhibitory concentration (IC$_{50}$) of each oligonucleotide is also presented. CFB mRNA levels were reduced in a dose-dependent manner in antisense oligonucleotide treated cells.

TABLE 149

| ISIS No | 0.08 µM | 0.25 µM | 0.74 µM | 2.22 µM | 6.67 µM | 20.00 µM | IC$_{50}$ (µM) |
|---|---|---|---|---|---|---|---|
| 532811 | 19 | 53 | 81 | 87 | 96 | 97 | 0.2 |
| 588834 | 7 | 42 | 64 | 92 | 98 | 98 | 0.5 |
| 588835 | 11 | 30 | 66 | 89 | 97 | 97 | 0.5 |
| 588836 | 14 | 40 | 61 | 91 | 97 | 97 | 0.5 |
| 588837 | 6 | 39 | 67 | 89 | 96 | 97 | 0.5 |
| 588838 | 0 | 27 | 41 | 81 | 87 | 97 | 1.0 |
| 588842 | 17 | 51 | 68 | 86 | 93 | 95 | 0.3 |
| 588843 | 21 | 38 | 72 | 90 | 95 | 96 | 0.4 |
| 588870 | 9 | 31 | 56 | 88 | 95 | 97 | 0.6 |
| 588871 | 14 | 25 | 47 | 79 | 93 | 97 | 0.7 |
| 588872 | 18 | 28 | 59 | 84 | 92 | 97 | 0.6 |

TABLE 150

| ISIS No | 0.08 µM | 0.25 µM | 0.74 µM | 2.22 µM | 6.67 µM | 20.00 µM | IC$_{50}$ (µM) |
|---|---|---|---|---|---|---|---|
| 532811 | 31 | 70 | 89 | 94 | 97 | 97 | 0.1 |
| 588844 | 31 | 60 | 77 | 91 | 95 | 96 | 0.1 |
| 588846 | 32 | 52 | 78 | 89 | 95 | 97 | 0.2 |
| 588847 | 22 | 52 | 77 | 91 | 95 | 97 | 0.2 |
| 588848 | 20 | 40 | 73 | 91 | 96 | 98 | 0.3 |
| 588851 | 40 | 52 | 82 | 94 | 97 | 97 | 0.1 |
| 588854 | 17 | 55 | 59 | 84 | 94 | 96 | 0.4 |
| 588855 | 10 | 32 | 56 | 82 | 93 | 96 | 0.6 |
| 588856 | 13 | 46 | 75 | 90 | 96 | 97 | 0.3 |
| 588857 | 11 | 52 | 73 | 94 | 96 | 97 | 0.3 |
| 588858 | 19 | 48 | 75 | 94 | 97 | 98 | 0.3 |

TABLE 151

| ISIS No | 0.08 µM | 0.25 µM | 0.74 µM | 2.22 µM | 6.67 µM | 20.00 µM | IC$_{50}$ (µM) |
|---|---|---|---|---|---|---|---|
| 532811 | 42 | 66 | 88 | 96 | 97 | 98 | 0.1 |
| 588859 | 18 | 46 | 66 | 90 | 96 | 97 | 0.4 |
| 588860 | 55 | 80 | 94 | 97 | 97 | 97 | <0.1 |
| 588861 | 24 | 61 | 86 | 93 | 96 | 97 | 0.2 |
| 588862 | 25 | 64 | 85 | 94 | 96 | 98 | 0.1 |
| 588863 | 50 | 73 | 89 | 96 | 96 | 98 | <0.1 |
| 588864 | 52 | 80 | 92 | 96 | 98 | 98 | <0.1 |
| 588865 | 46 | 72 | 91 | 96 | 96 | 99 | <0.1 |
| 588866 | 47 | 76 | 88 | 96 | 97 | 98 | <0.1 |
| 588867 | 43 | 69 | 83 | 92 | 96 | 99 | 0.1 |
| 588868 | 43 | 56 | 65 | 84 | 93 | 97 | 0.1 |

TABLE 152

| ISIS No | 0.08 µM | 0.25 µM | 0.74 µM | 2.22 µM | 6.67 µM | 20.00 µM | IC$_{50}$ (µM) |
|---|---|---|---|---|---|---|---|
| 532810 | 0 | 14 | 38 | 72 | 89 | 96 | 1.2 |
| 532811 | 18 | 54 | 79 | 93 | 96 | 97 | 0.3 |
| 532952 | 19 | 34 | 73 | 87 | 94 | 96 | 0.4 |
| 588534 | 17 | 13 | 44 | 77 | 93 | 97 | 0.9 |
| 588544 | 12 | 43 | 69 | 86 | 89 | 93 | 0.4 |
| 588545 | 17 | 55 | 67 | 86 | 91 | 93 | 0.3 |
| 588546 | 10 | 32 | 67 | 85 | 91 | 93 | 0.6 |
| 588552 | 27 | 54 | 76 | 90 | 94 | 97 | 0.2 |
| 588553 | 32 | 68 | 87 | 93 | 95 | 97 | 0.1 |
| 588560 | 16 | 54 | 76 | 90 | 94 | 96 | 0.3 |
| 588561 | 18 | 45 | 68 | 85 | 93 | 96 | 0.4 |

TABLE 153

| ISIS No | 0.08 µM | 0.25 µM | 0.74 µM | 2.22 µM | 6.67 µM | 20.00 µM | IC$_{50}$ (µM) |
|---|---|---|---|---|---|---|---|
| 532811 | 22 | 60 | 82 | 94 | 97 | 98 | 0.2 |
| 588536 | 2 | 38 | 65 | 90 | 96 | 97 | 0.6 |
| 588537 | 12 | 38 | 63 | 87 | 94 | 97 | 0.5 |
| 588547 | 19 | 35 | 61 | 86 | 93 | 97 | 0.5 |
| 588548 | 19 | 36 | 75 | 88 | 95 | 96 | 0.4 |
| 588554 | 0 | 76 | 92 | 95 | 97 | 97 | <0.1 |
| 588555 | 31 | 61 | 89 | 96 | 97 | 98 | 0.1 |
| 588556 | 33 | 56 | 82 | 95 | 94 | 97 | 0.1 |
| 588562 | 12 | 39 | 71 | 87 | 94 | 97 | 0.4 |
| 588563 | 25 | 48 | 72 | 86 | 94 | 96 | 0.3 |
| 588564 | 15 | 33 | 63 | 89 | 91 | 97 | 0.5 |

TABLE 154

| ISIS No | 0.08 µM | 0.25 µM | 0.74 µM | 2.22 µM | 6.67 µM | 20.00 µM | IC$_{50}$ (µM) |
|---|---|---|---|---|---|---|---|
| 532811 | 39 | 68 | 86 | 96 | 98 | 98 | 0.1 |
| 588538 | 0 | 40 | 82 | 94 | 97 | 98 | 0.3 |
| 588539 | 34 | 65 | 88 | 95 | 98 | 98 | 0.1 |
| 588540 | 30 | 51 | 81 | 91 | 97 | 98 | 0.2 |
| 588549 | 31 | 57 | 82 | 95 | 96 | 98 | 0.1 |
| 588550 | 34 | 65 | 88 | 96 | 98 | 98 | 0.1 |
| 588551 | 47 | 66 | 87 | 96 | 98 | 99 | <0.1 |
| 588557 | 40 | 84 | 95 | 98 | 98 | 98 | <0.1 |
| 588558 | 45 | 73 | 93 | 97 | 98 | 99 | <0.1 |
| 588559 | 51 | 69 | 83 | 96 | 98 | 99 | <0.1 |
| 588565 | 19 | 56 | 81 | 92 | 96 | 98 | 0.2 |

Example 124: Dose-Dependent Antisense Inhibition of Human CFB in HepG2 Cells

Gapmers from studies described above exhibiting in vitro inhibition of CFB mRNA were selected and tested at various doses in HepG2 cells. The antisense oligonucleotides were tested in a number of experiments with similar culture conditions. The results for each experiment are presented in separate tables shown below. Cells were plated at a density of 20,000 cells per well and transfected using electroporation with 0.06 μM, 0.25 μM, 1.00 μM, and 4.00 μM concentrations of antisense oligonucleotide, as specified in the Table below. After a treatment period of approximately 16 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The half maximal inhibitory concentration ($IC_{50}$) of each oligonucleotide is also presented. CFB mRNA levels were reduced in a dose-dependent manner in antisense oligonucleotide treated cells.

TABLE 155

| ISIS No | 0.06 μM | 0.25 μM | 1.00 μM | 4.00 μM | $IC_{50}$ (μM) |
|---|---|---|---|---|---|
| 532917 | 31 | 58 | 87 | 92 | 0.2 |
| 588860 | 18 | 50 | 79 | 93 | 0.3 |
| 599001 | 16 | 28 | 69 | 90 | 0.5 |
| 599024 | 14 | 32 | 74 | 90 | 0.4 |
| 599025 | 0 | 31 | 56 | 92 | 0.7 |
| 599032 | 28 | 44 | 62 | 88 | 0.3 |
| 599033 | 28 | 46 | 80 | 92 | 0.2 |
| 599077 | 8 | 20 | 59 | 80 | 0.8 |
| 599080 | 9 | 33 | 48 | 76 | 0.9 |
| 599086 | 7 | 22 | 53 | 83 | 0.8 |
| 599087 | 21 | 31 | 74 | 87 | 0.4 |
| 599088 | 13 | 37 | 69 | 82 | 0.5 |
| 599089 | 3 | 36 | 55 | 79 | 0.7 |
| 599093 | 25 | 59 | 79 | 88 | 0.2 |
| 599094 | 19 | 29 | 75 | 89 | 0.4 |
| 599095 | 29 | 43 | 67 | 87 | 0.3 |
| 599096 | 23 | 51 | 70 | 88 | 0.3 |
| 599149 | 20 | 53 | 82 | 92 | 0.3 |
| 599188 | 0 | 21 | 62 | 85 | 0.8 |

TABLE 156

| ISIS No | 0.06 μM | 0.25 μM | 1.00 μM | 4.00 μM | $IC_{50}$ (μM) |
|---|---|---|---|---|---|
| 532917 | 0 | 42 | 81 | 91 | 0.4 |
| 588860 | 17 | 49 | 74 | 92 | 0.3 |
| 599155 | 29 | 52 | 67 | 87 | 0.3 |
| 599198 | 3 | 25 | 64 | 89 | 0.6 |
| 599201 | 13 | 26 | 67 | 91 | 0.5 |
| 599202 | 0 | 44 | 72 | 87 | 0.5 |
| 599203 | 22 | 41 | 75 | 88 | 0.3 |
| 599314 | 12 | 34 | 71 | 84 | 0.5 |
| 599316 | 7 | 37 | 66 | 88 | 0.5 |
| 599317 | 8 | 1 | 54 | 83 | 1.0 |
| 599321 | 8 | 33 | 70 | 85 | 0.5 |
| 599322 | 24 | 38 | 66 | 87 | 0.4 |
| 599327 | 22 | 32 | 66 | 89 | 0.4 |
| 599328 | 0 | 31 | 59 | 88 | 0.7 |
| 599330 | 5 | 43 | 67 | 84 | 0.5 |
| 599374 | 23 | 42 | 80 | 91 | 0.3 |
| 599378 | 21 | 57 | 80 | 93 | 0.2 |
| 599380 | 23 | 56 | 82 | 93 | 0.2 |
| 599432 | 17 | 37 | 73 | 93 | 0.4 |

TABLE 157

| ISIS No | 0.06 μM | 0.25 μM | 1.00 μM | 4.00 μM | $IC_{50}$ (μM) |
|---|---|---|---|---|---|
| 532917 | 23 | 65 | 76 | 93 | 0.2 |
| 588860 | 17 | 60 | 76 | 90 | 0.3 |
| 601282 | 48 | 68 | 81 | 88 | 0.1 |
| 601269 | 18 | 59 | 80 | 94 | 0.2 |
| 601276 | 34 | 64 | 81 | 91 | 0.1 |
| 601275 | 14 | 39 | 78 | 90 | 0.4 |
| 601344 | 52 | 84 | 92 | 94 | <0.06 |
| 601383 | 53 | 81 | 86 | 94 | <0.06 |
| 601382 | 41 | 76 | 88 | 94 | 0.1 |
| 601385 | 52 | 74 | 89 | 91 | <0.06 |
| 601332 | 41 | 69 | 86 | 94 | 0.1 |
| 601345 | 36 | 75 | 86 | 95 | 0.1 |
| 601371 | 34 | 72 | 91 | 93 | 0.1 |
| 601384 | 50 | 78 | 91 | 95 | <0.06 |
| 601380 | 28 | 57 | 83 | 92 | 0.2 |
| 601387 | 48 | 61 | 82 | 88 | 0.1 |
| 601341 | 28 | 65 | 83 | 91 | 0.2 |
| 601346 | 31 | 69 | 82 | 93 | 0.1 |
| 601335 | 24 | 56 | 85 | 92 | 0.2 |

TABLE 158

| ISIS No | 0.06 μM | 0.25 μM | 1.00 μM | 4.00 μM | $IC_{50}$ (μM) |
|---|---|---|---|---|---|
| 532917 | 31 | 66 | 86 | 93 | 0.1 |
| 588860 | 28 | 62 | 85 | 94 | 0.2 |
| 599208 | 24 | 50 | 71 | 89 | 0.3 |
| 599261 | 31 | 49 | 81 | 94 | 0.2 |
| 599267 | 41 | 48 | 80 | 88 | 0.2 |
| 599268 | 28 | 56 | 75 | 92 | 0.2 |
| 599313 | 14 | 24 | 71 | 92 | 0.5 |
| 599441 | 24 | 57 | 80 | 87 | 0.2 |
| 599494 | 13 | 55 | 86 | 94 | 0.3 |
| 599552 | 30 | 69 | 93 | 95 | 0.1 |
| 599553 | 34 | 71 | 93 | 96 | 0.1 |
| 599554 | 30 | 74 | 93 | 96 | 0.1 |
| 599568 | 40 | 77 | 90 | 97 | 0.1 |
| 599570 | 61 | 82 | 93 | 96 | <0.06 |
| 599577 | 18 | 62 | 81 | 93 | 0.2 |
| 599581 | 27 | 60 | 80 | 94 | 0.2 |
| 599591 | 49 | 74 | 93 | 96 | <0.06 |
| 599592 | 46 | 76 | 90 | 94 | 0.1 |
| 599593 | 44 | 72 | 91 | 95 | 0.1 |

TABLE 159

| ISIS No | 0.06 μM | 0.25 μM | 1.00 μM | 4.00 μM | $IC_{50}$ (μM) |
|---|---|---|---|---|---|
| 532917 | 25 | 56 | 84 | 92 | 0.2 |
| 588860 | 11 | 51 | 80 | 92 | 0.3 |
| 599547 | 23 | 60 | 82 | 90 | 0.2 |
| 599569 | 42 | 73 | 85 | 88 | 0.1 |
| 599578 | 29 | 49 | 82 | 89 | 0.2 |
| 599582 | 21 | 56 | 78 | 91 | 0.2 |
| 599590 | 24 | 62 | 80 | 90 | 0.2 |
| 601209 | 21 | 49 | 85 | 88 | 0.3 |
| 601210 | 34 | 64 | 86 | 92 | 0.1 |
| 601212 | 46 | 68 | 88 | 90 | 0.1 |
| 601213 | 54 | 80 | 90 | 92 | <0.06 |
| 601214 | 38 | 77 | 88 | 95 | 0.1 |
| 601215 | 42 | 64 | 85 | 92 | 0.1 |
| 601216 | 45 | 57 | 76 | 89 | 0.1 |
| 601264 | 29 | 58 | 86 | 95 | 0.2 |
| 601278 | 51 | 82 | 83 | 93 | <0.06 |
| 601279 | 44 | 80 | 92 | 96 | 0.1 |
| 601280 | 44 | 73 | 87 | 94 | 0.1 |
| 601281 | 51 | 80 | 91 | 94 | <0.06 |

Example 125: Dose-Dependent Antisense Inhibition of Human CFB in HepG2 Cells

Gapmers from studies described above exhibiting in vitro inhibition of CFB mRNA were selected and tested at various doses in HepG2 cells. Additionally, a deoxy, MOE and (S)-cEt oligonucleotide, ISIS 594430, was designed with the same sequence (CTCCTTCCGAGTCAGC, SEQ ID NO: 549) and target region (target start site 2195 of SEQ ID NO: 1 and target start site 6983 of SED ID NO: 2) as ISIS 588870, another deoxy, MOE, and (S)-cEt oligonucleotide. ISIS 594430 is a 3-10-3 (S)-cEt gapmer.

Cells were plated at a density of 20,000 cells per well and transfected using electroporation with 0.01 µM, 0.04 µM, 0.12 µM, 0.37 µM, 1.11 µM, 3.33 µM, and 10.00 µM concentrations of antisense oligonucleotide, as specified in the Table below. After a treatment period of approximately 16 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The half maximal inhibitory concentration ($IC_{50}$) of each oligonucleotide is also presented. CFB mRNA levels were reduced in a dose-dependent manner in antisense oligonucleotide treated cells.

TABLE 160

| ISIS No | 0.01 µM | 0.04 µM | 0.12 µM | 0.37 µM | 1.11 µM | 3.33 µM | 10.00 µM | $IC_{50}$ (µM) |
|---|---|---|---|---|---|---|---|---|
| 588536 | 0 | 0 | 0 | 5 | 45 | 73 | 94 | 1.4 |
| 588548 | 0 | 0 | 0 | 19 | 52 | 78 | 90 | 1.2 |
| 588553 | 0 | 0 | 9 | 42 | 76 | 85 | 94 | 0.6 |
| 588555 | 0 | 52 | 23 | 58 | 78 | 83 | 95 | 0.3 |
| 588847 | 4 | 1 | 18 | 45 | 67 | 84 | 96 | 0.5 |
| 588848 | 0 | 3 | 13 | 38 | 67 | 83 | 95 | 0.6 |
| 594430 | 0 | 0 | 10 | 34 | 50 | 55 | 84 | 1.4 |

Example 126: Tolerability of MOE Gapmers Targeting Human CFB in CD1 Mice

CD1® mice (Charles River, Mass.) are a multipurpose mice model, frequently utilized for safety and efficacy testing. The mice were treated with ISIS antisense oligonucleotides selected from studies described above and evaluated for changes in the levels of various plasma chemistry markers.

Study 1 (with 5-10-5 MOE Gapmers)

Groups of seven-week old male CD1 mice were injected subcutaneously once a week for 6 weeks with 100 mg/kg of ISIS oligonucleotide. A group of male CD1 mice was injected subcutaneously once a week for 6 weeks with PBS. One group of mice was injected with subcutaneously once a week for 6 weeks with 100 mg/kg of control oligonucleotide ISIS 141923 (CCTTCCCTGAAGGTTCCTCC, designated herein as SEQ ID NO: 809, 5-10-5 MOE gapmer with no known murine target). Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, and BUN were measured using an automated clinical chemistry analyzer (Hitachi Olympus AU400e, Melville, N.Y.). The results are presented in the Table below. ISIS oligonucleotides that caused changes in the levels of any of the liver or kidney function markers outside the expected range for antisense oligonucleotides were excluded in further studies.

TABLE 161

Plasma chemistry markers in CD1 mice plasma on day 40

|  | ALT (IU/L) | AST (IU/L) | BUN (mg/dL) |
|---|---|---|---|
| PBS | 25 | 46 | 20 |
| ISIS 532614 | 513 | 407 | 22 |
| ISIS 532692 | 131 | 130 | 24 |
| ISIS 532770 | 36 | 53 | 25 |
| ISIS 532775 | 193 | 158 | 23 |
| ISIS 532800 | 127 | 110 | 25 |
| ISIS 532809 | 36 | 42 | 22 |
| ISIS 532810 | 229 | 286 | 26 |
| ISIS 532811 | 197 | 183 | 21 |
| ISIS 532917 | 207 | 204 | 27 |
| ISIS 532952 | 246 | 207 | 25 |
| ISIS 141923 | 39 | 67 | 23 |

Weights

Body weights of the mice were measured on day 40 before sacrificing the mice. Weights of organs, liver, kidney, and spleen were also measured after the mice were sacrificed. The results are presented in the Table below. ISIS oligonucleotides that caused changes in the weights outside the expected range for antisense oligonucleotides were excluded in further studies.

TABLE 162

Weights (g) of CD1 mice on day 40

|  | Body | Kidney | Liver | Spleen |
|---|---|---|---|---|
| PBS | 44 | 0.8 | 2.0 | 0.1 |
| ISIS 532614 | 43 | 0.7 | 4.3 | 0.2 |
| ISIS 532692 | 42 | 0.7 | 2.6 | 0.2 |
| ISIS 532770 | 42 | 0.6 | 2.3 | 0.2 |
| ISIS 532775 | 42 | 0.7 | 2.5 | 0.2 |
| ISIS 532800 | 43 | 0.6 | 2.8 | 0.3 |
| ISIS 532809 | 42 | 0.6 | 2.2 | 0.1 |
| ISIS 532810 | 43 | 0.6 | 2.3 | 0.2 |
| ISIS 532811 | 41 | 0.7 | 2.4 | 0.2 |
| ISIS 532917 | 42 | 0.7 | 3.0 | 0.2 |
| ISIS 532952 | 44 | 0.8 | 2.5 | 0.3 |
| ISIS 141923 | 41 | 0.6 | 2.0 | 0.1 |

Study 2 (with 5-10-5 MOE Gapmers)

Groups of six- to eight-week old male CD1 mice were injected subcutaneously once a week for 6 weeks with 100 mg/kg of ISIS oligonucleotide. Two groups of male CD1 mice were injected subcutaneously once a week for 6 weeks with PBS. One group of mice was injected with subcutaneously once a week for 6 weeks with 100 mg/kg of control oligonucleotide ISIS 141923. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, albumin, and BUN were measured using an automated clinical chemistry analyzer (Hitachi Olympus AU400e, Melville, N.Y.). The results are presented in the Table below. ISIS oligonucleotides that caused changes in the levels of any of the liver or kidney function markers outside the expected range for antisense oligonucleotides were excluded in further studies.

TABLE 163

Plasma chemistry markers in CD1 mice plasma on day 45

|  | ALT (IU/L) | AST (IU/L) | Albumin (g/dL) | BUN (mg/dL) |
|---|---|---|---|---|
| PBS | 39 | 53 | 2.9 | 29 |
| PBS | 50 | 97 | 2.9 | 30 |
| ISIS 141923 | 163 | 174 | 4.1 | 25 |
| ISIS 532810 | 321 | 297 | 2.5 | 26 |
| ISIS 532952 | 182 | 199 | 2.7 | 27 |
| ISIS 588534 | 276 | 248 | 2.6 | 29 |
| ISIS 588536 | 48 | 60 | 2.9 | 31 |
| ISIS 588537 | 72 | 79 | 4.0 | 25 |
| ISIS 588538 | 63 | 67 | 4.5 | 29 |
| ISIS 588539 | 238 | 177 | 3.9 | 28 |
| ISIS 588545 | 496 | 256 | 4.4 | 24 |
| ISIS 588547 | 323 | 210 | 4.4 | 25 |
| ISIS 588548 | 61 | 63 | 4.2 | 27 |
| ISIS 588549 | 127 | 132 | 4.1 | 23 |
| ISIS 588551 | 302 | 282 | 4.2 | 22 |
| ISIS 588552 | 76 | 98 | 4.0 | 30 |
| ISIS 588558 | 1066 | 521 | 3.9 | 27 |
| ISIS 588559 | 76 | 94 | 4.1 | 26 |
| ISIS 588561 | 502 | 500 | 4.4 | 26 |
| ISIS 588563 | 50 | 99 | 4.4 | 28 |

Weights

Body weights of the mice were measured on day 42. Weights of organs, liver, kidney, and spleen were also measured after the mice were sacrificed on day 45. The results are presented in the Table below. ISIS oligonucleotides that caused changes in the weights outside the expected range for antisense oligonucleotides were excluded in further studies.

TABLE 164

Weights (g) of CD1 mice on day 40

|  | Body | Kidney | Liver | Spleen |
|---|---|---|---|---|
| PBS | 44 | 0.7 | 2.4 | 0.1 |
| PBS | 43 | 0.7 | 2.4 | 0.2 |
| ISIS 141923 | 43 | 0.6 | 2.4 | 0.2 |
| ISIS 532810 | 41 | 0.6 | 1.9 | 0.1 |
| ISIS 532952 | 43 | 0.6 | 2.4 | 0.2 |
| ISIS 588534 | 44 | 0.7 | 2.8 | 0.2 |
| ISIS 588536 | 43 | 0.7 | 2.7 | 0.2 |
| ISIS 588537 | 43 | 0.7 | 2.4 | 0.2 |
| ISIS 588538 | 44 | 0.7 | 2.8 | 0.2 |
| ISIS 588539 | 44 | 0.6 | 2.7 | 0.2 |
| ISIS 588545 | 44 | 0.8 | 3.3 | 0.3 |
| ISIS 588547 | 42 | 0.6 | 3.3 | 0.3 |
| ISIS 588548 | 43 | 0.6 | 2.8 | 0.2 |
| ISIS 588549 | 42 | 0.6 | 2.8 | 0.3 |
| ISIS 588551 | 39 | 0.6 | 2.2 | 0.2 |
| ISIS 588552 | 41 | 0.6 | 2.2 | 0.2 |
| ISIS 588558 | 44 | 0.7 | 3.3 | 0.3 |
| ISIS 588559 | 43 | 0.6 | 2.7 | 0.3 |
| ISIS 588561 | 40 | 0.7 | 2.4 | 0.3 |
| ISIS 588563 | 41 | 0.7 | 2.4 | 0.2 |

Study 3 (with 5-10-5 MOE Gapmers)

Groups of six- to eight-week old male CD1 mice were injected subcutaneously once a week for 6 weeks with 100 mg/kg of ISIS oligonucleotide. Two groups of male CD1 mice were injected subcutaneously once a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, albumin, and BUN were measured using an automated clinical chemistry analyzer (Hitachi Olympus AU400e, Melville, N.Y.). The results are presented in the Table below. ISIS oligonucleotides that caused changes in the levels of any of the liver or kidney function markers outside the expected range for antisense oligonucleotides were excluded in further studies.

TABLE 165

Plasma chemistry markers in CD1 mice plasma on day 42

|  | ALT (IU/L) | AST (IU/L) | Albumin (g/dL) | BUN (mg/dL) |
|---|---|---|---|---|
| PBS | 37 | 108 | 3.1 | 30 |
| PBS | 45 | 51 | 3.0 | 27 |
| ISIS 588544 | 209 | 168 | 2.9 | 26 |
| ISIS 588546 | 526 | 279 | 3.0 | 22 |
| ISIS 588550 | 82 | 136 | 2.7 | 25 |
| ISIS 588553 | 79 | 105 | 3.0 | 24 |
| ISIS 588554 | 112 | 220 | 3.2 | 19 |
| ISIS 588555 | 95 | 162 | 2.8 | 25 |
| ISIS 588556 | 345 | 236 | 3.0 | 26 |
| ISIS 588557 | 393 | 420 | 2.8 | 24 |
| ISIS 588560 | 109 | 148 | 2.7 | 27 |
| ISIS 588562 | 279 | 284 | 2.8 | 22 |
| ISIS 588564 | 152 | 188 | 3.0 | 23 |
| ISIS 588565 | 247 | 271 | 2.8 | 28 |

Weights

Body weights of the mice were measured on day 42. Weights of organs, liver, kidney, and spleen were also measured after the mice were sacrificed on day 42. The results are presented in the Table below. ISIS oligonucleotides that caused changes in the weights outside the expected range for antisense oligonucleotides were excluded in further studies.

TABLE 166

Weights (g) of CD1 mice on day 40

|  | Body | Kidney | Liver | Spleen |
|---|---|---|---|---|
| PBS | 42 | 0.7 | 2.4 | 0.1 |
| PBS | 41 | 0.7 | 2.4 | 0.2 |
| ISIS 588544 | 44 | 0.6 | 1.9 | 0.1 |
| ISIS 588546 | 43 | 0.6 | 2.4 | 0.2 |
| ISIS 588550 | 41 | 0.7 | 2.8 | 0.2 |
| ISIS 588553 | 44 | 0.7 | 2.7 | 0.2 |
| ISIS 588554 | 40 | 0.7 | 2.4 | 0.2 |
| ISIS 588555 | 44 | 0.7 | 2.8 | 0.2 |
| ISIS 588556 | 39 | 0.6 | 2.7 | 0.2 |
| ISIS 588557 | 41 | 0.8 | 3.3 | 0.3 |
| ISIS 588560 | 38 | 0.6 | 3.2 | 0.3 |
| ISIS 588562 | 41 | 0.6 | 2.8 | 0.2 |
| ISIS 588564 | 40 | 0.6 | 2.8 | 0.3 |
| ISIS 588565 | 39 | 0.6 | 2.2 | 0.2 |

Study 4 (with (S) cEt Gapmers and Deoxy, MOE and (S)-cEt Oligonucleotides)

Groups of ten-week old male CD1 mice were injected subcutaneously once a week for 6 weeks with 50 mg/kg of ISIS oligonucleotide from the studies described above. In addition, two oligonucleotides, ISIS 594431 and ISIS 594432, were designed as 3-10-3 (S)-cEt gapmers and were also tested in this study. ISIS 594431 (ACCTCCTT-CCGAGTCA, SEQ ID NO: 550) targets the same region as ISIS 588871, a deoxy, MOE and (S)-cEt gapmer (target start site 2197 of SEQ ID NO: 1 and target start site 6985 of SEQ ID NO: 2). ISIS 594432 (TGGTCACATTCCCTTC, SEQ ID NO: 542) targets the same region as ISIS 588872 a deoxy, MOE and (S)-cEt gapmer (target start site 154 of SEQ ID NO: 1 and target start site 1875 of SEQ ID NO: 2).

Two groups of male CD1 mice were injected subcutaneously once a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, albumin, creatinine, and BUN were measured using an automated clinical chemistry analyzer (Hitachi Olympus AU400e, Melville, N.Y.). The results are presented in the Table below. ISIS oligonucleotides that caused changes in the levels of any of the liver or kidney function markers outside the expected range for antisense oligonucleotides were excluded in further studies.

TABLE 167

Plasma chemistry markers in CD1 mice plasma on day 42

| | Chemistry | ALT (IU/L) | AST (IU/L) | Albumin (g/dL) | Creatinine (mg/dL) | BUN (mg/dL) |
|---|---|---|---|---|---|---|
| PBS | — | 71 | 77 | 2.7 | 0.2 | 29 |
| PBS | — | 30 | 36 | 2.7 | 0.2 | 26 |
| ISIS 588834 | Deoxy, MOE and (S)-cEt | 436 | 510 | 2.8 | 0.2 | 25 |
| ISIS 588835 | Deoxy, MOE and (S)-cEt | 70 | 98 | 3.0 | 0.2 | 27 |
| ISIS 588836 | Deoxy, MOE and (S)-cEt | 442 | 312 | 2.7 | 0.2 | 27 |
| ISIS 588846 | Deoxy, MOE and (S)-cEt | 50 | 75 | 2.5 | 0.1 | 28 |
| ISIS 588847 | Deoxy, MOE and (S)-cEt | 44 | 71 | 2.6 | 0.1 | 24 |
| ISIS 588848 | Deoxy, MOE and (S)-cEt | 47 | 70 | 2.4 | 0.1 | 27 |
| ISIS 588857 | Deoxy, MOE and (S)-cEt | 1287 | 655 | 2.7 | 0.2 | 26 |
| ISIS 588858 | Deoxy, MOE and (S)-cEt | 1169 | 676 | 2.5 | 0.2 | 26 |
| ISIS 588859 | Deoxy, MOE and (S)-cEt | 1036 | 1300 | 3.2 | 0.2 | 25 |
| ISIS 588861 | Deoxy, MOE and (S)-cEt | 749 | 466 | 3.1 | 0.1 | 24 |
| ISIS 588862 | Deoxy, MOE and (S)-cEt | 1564 | 1283 | 2.9 | 0.2 | 22 |
| ISIS 588863 | Deoxy, MOE and (S)-cEt | 477 | 362 | 2.8 | 0.1 | 23 |
| ISIS 588864 | Deoxy, MOE and (S)-cEt | 118 | 165 | 2.9 | 0.2 | 27 |
| ISIS 588866 | Deoxy, MOE and (S)-cEt | 843 | 784 | 3.2 | 0.2 | 25 |
| ISIS 594430 | 3-10-3 (S)-cEt | 89 | 99 | 2.4 | 0.1 | 28 |
| ISIS 594431 | 3-10-3 (S)-cEt | 590 | 433 | 3.0 | 0.2 | 24 |
| ISIS 594432 | 3-10-3 (S)-cEt | 2595 | 2865 | 2.4 | 0.1 | 25 |

Weights

Body weights of the mice were measured on day 39. Weights of organs, liver, kidney, and spleen were also measured after the mice were sacrificed on day 42. The results are presented in the Table below. ISIS oligonucleotides that caused changes in the weights outside the expected range for antisense oligonucleotides were excluded in further studies.

TABLE 168

Weights (g) of CD1 mice

| | Chemistry | Body | Kidney | Liver | Spleen |
|---|---|---|---|---|---|
| PBS | — | 37 | 0.6 | 2.1 | 0.1 |
| PBS | — | 45 | 0.7 | 2.5 | 0.2 |
| ISIS 588834 | Deoxy, MOE and (S)-cEt | 40 | 0.6 | 3.2 | 0.2 |
| ISIS 588835 | Deoxy, MOE and (S)-cEt | 38 | 0.7 | 2.8 | 0.3 |
| ISIS 588836 | Deoxy, MOE and (S)-cEt | 41 | 0.7 | 2.3 | 0.2 |
| ISIS 588837 | Deoxy, MOE and (S)-cEt | 38 | 0.6 | 2.4 | 0.3 |

TABLE 168-continued

Weights (g) of CD1 mice

| | Chemistry | Body | Kidney | Liver | Spleen |
|---|---|---|---|---|---|
| ISIS 588846 | Deoxy, MOE and (S)-cEt | 39 | 0.6 | 2.3 | 0.2 |
| ISIS 588847 | Deoxy, MOE and (S)-cEt | 40 | 0.7 | 2.5 | 0.2 |
| ISIS 588848 | Deoxy, MOE and (S)-cEt | 43 | 0.7 | 2.6 | 0.3 |
| ISIS 588857 | Deoxy, MOE and (S)-cEt | 39 | 0.6 | 3.3 | 0.2 |
| ISIS 588858 | Deoxy, MOE and (S)-cEt | 37 | 0.6 | 3.4 | 0.2 |
| ISIS 588859 | Deoxy, MOE and (S)-cEt | 41 | 0.7 | 2.5 | 0.3 |
| ISIS 588861 | Deoxy, MOE and (S)-cEt | 39 | 0.6 | 2.6 | 0.4 |
| ISIS 588862 | Deoxy, MOE and (S)-cEt | 34 | 0.6 | 2.5 | 0.4 |
| ISIS 588863 | Deoxy, MOE and (S)-cEt | 40 | 0.6 | 2.7 | 0.3 |
| ISIS 588864 | Deoxy, MOE and (S)-cEt | 40 | 0.7 | 2.3 | 0.2 |
| ISIS 588866 | Deoxy, MOE and (S)-cEt | 45 | 0.7 | 3.0 | 0.2 |
| ISIS 594430 | 3-10-3 (S)-cEt | 39 | 0.6 | 2.2 | 0.2 |
| ISIS 594431 | 3-10-3 (S)-cEt | 36 | 0.6 | 3.2 | 0.2 |
| ISIS 594432 | 3-10-3 (S)-cEt | 31 | 0.4 | 1.9 | 0.1 |

Study 5 (with MOE Gapmers, (S) cEt Gapmers and Deoxy, MOE and (S)-cEt Oligonucleotides)

Groups of eight- to nine-week old male CD1 mice were injected subcutaneously once a week for 6 weeks with 50 mg/kg of ISIS oligonucleotide. Two groups of male CD1 mice were injected subcutaneously once a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, albumin, creatinine, and BUN were measured using an automated clinical chemistry analyzer (Hitachi Olympus AU400e, Melville, N.Y.). The results are presented in the Table below. ISIS oligonucleotides that caused changes in the levels of any of the liver or kidney function markers outside the expected range for antisense oligonucleotides were excluded in further studies.

TABLE 169

Plasma chemistry markers in CD1 mice plasma on day 42

| | Chemistry | ALT (IU/L) | AST (IU/L) | Albumin (g/dL) | Creatinine (mg/dL) | BUN (mg/dL) |
|---|---|---|---|---|---|---|
| PBS | — | 33 | 84 | 2.9 | 0.2 | 28 |
| PBS | — | 32 | 65 | 2.5 | 0.1 | 27 |
| ISIS 532692 | 5-10-5 MOE | 363 | 281 | 3.0 | 0.2 | 30 |
| ISIS 532770 | 5-10-5 MOE | 69 | 100 | 2.9 | 0.1 | 28 |
| ISIS 532775 | 5-10-5 MOE | 371 | 333 | 2.6 | 0.1 | 29 |
| ISIS 532800 | 5-10-5 MOE | 104 | 106 | 2.7 | 0.1 | 31 |
| ISIS 532809 | 5-10-5 MOE | 69 | 127 | 2.8 | 0.1 | 26 |
| ISIS 588540 | 5-10-5 MOE | 66 | 110 | 2.8 | 0.1 | 26 |
| ISIS 588838 | 3-10-3 (S)-cEt | 391 | 330 | 2.9 | 0.1 | 25 |
| ISIS 588842 | Deoxy, MOE and (S)-cEt | 224 | 264 | 2.6 | 0.1 | 26 |
| ISIS 588843 | 3-10-3 (S)-cEt | 185 | 160 | 2.8 | 0.1 | 24 |
| ISIS 588844 | Deoxy, MOE and (S)-cEt | 304 | 204 | 2.7 | 0.1 | 25 |
| ISIS 588851 | Deoxy, MOE and (S)-cEt | 186 | 123 | 2.7 | 0.1 | 31 |
| ISIS 588854 | Deoxy, MOE and (S)-cEt | 1232 | 925 | 2.7 | 0.1 | 25 |
| ISIS 588855 | Deoxy, MOE and (S)-cEt | 425 | 321 | 2.7 | 0.1 | 28 |
| ISIS 588856 | Deoxy, MOE and (S)-cEt | 78 | 101 | 2.4 | 0.1 | 31 |
| ISIS 588865 | Deoxy, MOE and (S)-cEt | 126 | 145 | 2.5 | 0.1 | 23 |
| ISIS 588867 | Deoxy, MOE and (S)-cEt | 108 | 112 | 2.5 | 0.1 | 32 |
| ISIS 588868 | Deoxy, MOE and (S)-cEt | 61 | 124 | 2.5 | 0.1 | 28 |
| ISIS 588870 | Deoxy, MOE and (S)-cEt | 48 | 69 | 2.4 | 0.1 | 31 |
| ISIS 588871 | Deoxy, MOE and (S)-cEt | 723 | 881 | 2.5 | 0.1 | 24 |
| ISIS 588872 | Deoxy, MOE and (S)-cEt | 649 | 654 | 2.7 | 0.1 | 26 |

Weights

Body weights of the mice were measured on day 40. Weights of organs, liver, kidney, and spleen were also measured after the mice were sacrificed on day 42. The results are presented in the Table below. ISIS oligonucleotides that caused changes in the weights outside the expected range for antisense oligonucleotides were excluded in further studies.

TABLE 170

Weights (g) of CD1 mice

| | Chemistry | Body | Kidney | Liver | Spleen |
|---|---|---|---|---|---|
| PBS | — | 46 | 0.7 | 2.3 | 0.2 |
| PBS | — | 44 | 0.7 | 2.3 | 0.2 |
| ISIS 532692 | 5-10-5 MOE | 44 | 0.6 | 2.8 | 0.2 |
| ISIS 532770 | 5-10-5 MOE | 43 | 0.6 | 2.2 | 0.2 |
| ISIS 532775 | 5-10-5 MOE | 43 | 0.6 | 2.8 | 0.2 |
| ISIS 532800 | 5-10-5 MOE | 47 | 0.7 | 2.9 | 0.2 |
| ISIS 532809 | 5-10-5 MOE | 44 | 0.7 | 2.6 | 0.2 |
| ISIS 588540 | 5-10-5 MOE | 44 | 0.7 | 2.5 | 0.2 |
| ISIS 588838 | 3-10-3 (S)-cEt | 45 | 0.7 | 3.1 | 0.2 |
| ISIS 588842 | Deoxy, MOE and (S)-cEt | 41 | 0.6 | 2.6 | 0.2 |
| ISIS 588843 | 3-10-3 (S)-cEt | 43 | 0.7 | 2.9 | 0.2 |
| ISIS 588844 | Deoxy, MOE and (S)-cEt | 43 | 0.7 | 2.8 | 0.2 |
| ISIS 588851 | Deoxy, MOE and (S)-cEt | 46 | 0.6 | 2.6 | 0.2 |
| ISIS 588854 | Deoxy, MOE and (S)-cEt | 45 | 0.7 | 4.1 | 0.2 |
| ISIS 588855 | Deoxy, MOE and (S)-cEt | 44 | 0.7 | 2.9 | 0.3 |
| ISIS 588856 | Deoxy, MOE and (S)-cEt | 44 | 0.7 | 3.2 | 0.2 |
| ISIS 588865 | Deoxy, MOE and (S)-cEt | 45 | 0.7 | 2.6 | 0.3 |

TABLE 170-continued

Weights (g) of CD1 mice

| | Chemistry | Body | Kidney | Liver | Spleen |
|---|---|---|---|---|---|
| ISIS 588867 | Deoxy, MOE and (S)-cEt | 46 | 0.7 | 3.2 | 0.3 |
| ISIS 588868 | Deoxy, MOE and (S)-cEt | 42 | 0.7 | 2.9 | 0.3 |
| ISIS 588870 | Deoxy, MOE and (S)-cEt | 43 | 0.6 | 2.2 | 0.2 |
| ISIS 588871 | Deoxy, MOE and (S)-cEt | 41 | 0.7 | 3.1 | 0.2 |
| ISIS 588872 | Deoxy, MOE and (S)-cEt | 39 | 0.6 | 3.2 | 0.3 |

Study 6 (with deoxy, MOE and (S)-cEt Oligonucleotides)

Groups of eight- to nine-week old male CD1 mice were injected subcutaneously once a week for 6 weeks with 50 mg/kg of deoxy, MOE, and (S)-cEt oligonucleotides. Two groups of male CD1 mice were injected subcutaneously once a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, albumin, creatinine, bilirubin, and BUN were measured using an automated clinical chemistry analyzer (Hitachi Olympus AU400e, Melville, N.Y.). The results are presented in the Table below. ISIS oligonucleotides that caused changes in the levels of any of the liver or kidney function markers outside the expected range for antisense oligonucleotides were excluded in further studies.

TABLE 171

Plasma chemistry markers in CD1 mice plasma on day 45

| | ALT (IU/L) | AST (IU/L) | Albumin (g/dL) | Creatinine (mg/dL) | Bilirubin (mg/dL) | BUN (mg/dL) |
|---|---|---|---|---|---|---|
| PBS | 39 | 78 | 3.4 | 0.2 | 0.2 | 31 |
| PBS | 37 | 59 | 2.9 | 0.1 | 0.2 | 27 |
| ISIS 599552 | 167 | 208 | 3.0 | 0.1 | 0.2 | 32 |
| ISIS 599553 | 43 | 86 | 2.9 | 0.1 | 0.2 | 28 |
| ISIS 599554 | 57 | 101 | 2.2 | 0.2 | 0.2 | 31 |
| ISIS 599569 | 469 | 530 | 3.5 | 0.2 | 0.3 | 27 |

TABLE 171-continued

Plasma chemistry markers in CD1 mice plasma on day 45

|  | ALT (IU/L) | AST (IU/L) | Albumin (g/dL) | Creatinine (mg/dL) | Bilirubin (mg/dL) | BUN (mg/dL) |
|---|---|---|---|---|---|---|
| ISIS 599577 | 37 | 84 | 2.9 | 0.1 | 0.1 | 31 |
| ISIS 599578 | 45 | 104 | 2.8 | 0.1 | 0.2 | 30 |
| ISIS 599581 | 54 | 88 | 3.1 | 0.1 | 0.2 | 31 |
| ISIS 599590 | 1741 | 1466 | 3.1 | 0.1 | 0.3 | 25 |
| ISIS 599591 | 2230 | 1183 | 3.2 | 0.1 | 0.3 | 27 |
| ISIS 601209 | 68 | 104 | 2.9 | 0.1 | 0.2 | 30 |
| ISIS 601212 | 1795 | 968 | 3.2 | 0.1 | 0.3 | 22 |
| ISIS 601215 | 424 | 385 | 3.1 | 0.1 | 0.4 | 25 |
| ISIS 601216 | 90 | 125 | 2.9 | 0.1 | 0.2 | 29 |
| ISIS 601276 | 946 | 366 | 2.9 | 0.1 | 0.5 | 31 |
| ISIS 601282 | 831 | 540 | 3.3 | 0.2 | 0.2 | 32 |

Weights

Body weights of the mice were measured on day 40. Weights of organs, liver, kidney, and spleen were also measured after the mice were sacrificed on day 45. The results are presented in the Table below. ISIS oligonucleotides that caused changes in the weights outside the expected range for antisense oligonucleotides were excluded in further studies.

TABLE 172

Weights (g) of CD1 mice

|  | Body | Kidney | Liver | Spleen |
|---|---|---|---|---|
| PBS | 40 | 0.7 | 2.1 | 0.2 |
| PBS | 42 | 0.8 | 2.3 | 0.2 |
| ISIS 599552 | 38 | 0.6 | 2.3 | 0.2 |
| ISIS 599553 | 39 | 0.7 | 2.2 | 0.2 |
| ISIS 599554 | 39 | 0.7 | 2.4 | 0.2 |
| ISIS 599569 | 39 | 0.7 | 2.2 | 0.2 |
| ISIS 599577 | 41 | 0.7 | 2.5 | 0.2 |
| ISIS 599578 | 37 | 0.6 | 2.0 | 0.2 |
| ISIS 599581 | 40 | 0.6 | 2.5 | 0.2 |
| ISIS 599590 | 34 | 0.6 | 3.5 | 0.2 |
| ISIS 599591 | 38 | 0.8 | 2.7 | 0.2 |
| ISIS 601209 | 42 | 0.7 | 2.6 | 0.3 |
| ISIS 601212 | 38 | 0.6 | 2.9 | 0.2 |
| ISIS 601215 | 36 | 0.7 | 2.6 | 0.2 |

TABLE 172-continued

Weights (g) of CD1 mice

|  | Body | Kidney | Liver | Spleen |
|---|---|---|---|---|
| ISIS 601216 | 42 | 0.6 | 2.7 | 0.2 |
| ISIS 601276 | 42 | 0.7 | 3.2 | 0.2 |
| ISIS 601282 | 38 | 0.7 | 3.2 | 0.2 |

Study 7 (with MOE Gapmers and Deoxy, MOE and (S)-cEt Oligonucleotides)

Groups of eight- to nine-week old male CD1 mice were injected subcutaneously once a week for 6 weeks with 100 mg/kg of ISIS oligonucleotides. One group of male CD1 mice was injected subcutaneously once a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, albumin, creatinine, and BUN were measured using an automated clinical chemistry analyzer (Hitachi Olympus AU400e, Melville, N.Y.). The results are presented in the Table below. ISIS oligonucleotides that caused changes in the levels of any of the liver or kidney function markers outside the expected range for antisense oligonucleotides were excluded in further studies.

TABLE 173

Plasma chemistry markers in CD1 mice plasma on day 45

|  | Chemistry | ALT (IU/L) | AST (IU/L) | Albumin (g/dL) | Creatinine (mg/dL) | BUN (mg/dL) |
|---|---|---|---|---|---|---|
| PBS | — | 120 | 102 | 2.7 | 0.2 | 26 |
| ISIS 588842 | Deoxy, MOE and (S)-cEt | 177 | 164 | 2.7 | 0.1 | 23 |
| ISIS 588843 | Deoxy, MOE and (S)-cEt | 98 | 194 | 2.7 | 0.1 | 24 |
| ISIS 588851 | Deoxy, MOE and (S)-cEt | 91 | 142 | 2.6 | 0.1 | 23 |
| ISIS 588856 | Deoxy, MOE and (S)-cEt | 78 | 110 | 2.7 | 0.1 | 23 |
| ISIS 599024 | 3-10-4 MOE | 91 | 108 | 2.7 | 0.1 | 23 |
| ISIS 599087 | 5-7-5 MOE | 198 | 183 | 2.6 | 0.2 | 28 |
| ISIS 599093 | 5-7-5 MOE | 3285 | 2518 | 2.6 | 0.2 | 24 |
| ISIS 599149 | 4-8-5 MOE | 30 | 64 | 2.9 | 0.2 | 25 |
| ISIS 599155 | 4-8-5 MOE | 145 | 189 | 2.6 | 0.2 | 25 |
| ISIS 599202 | 5-8-5 MOE | 150 | 128 | 2.8 | 0.2 | 23 |
| ISIS 599203 | 5-8-5 MOE | 111 | 127 | 2.8 | 0.2 | 24 |
| ISIS 599208 | 5-8-5 MOE | 146 | 178 | 2.9 | 0.2 | 22 |
| ISIS 599261 | 3-10-5 MOE | 144 | 165 | 2.8 | 0.2 | 26 |

TABLE 173-continued

Plasma chemistry markers in CD1 mice plasma on day 45

| | Chemistry | ALT (IU/L) | AST (IU/L) | Albumin (g/dL) | Creatinine (mg/dL) | BUN (mg/dL) |
|---|---|---|---|---|---|---|
| ISIS 599267 | 3-10-5 MOE | 96 | 132 | 2.6 | 0.2 | 27 |
| ISIS 599268 | 3-10-5 MOE | 87 | 115 | 2.6 | 0.1 | 23 |
| ISIS 599322 | 6-7-6 MOE | 115 | 138 | 2.7 | 0.1 | 22 |
| ISIS 599374 | 5-9-5 MOE | 375 | 271 | 2.6 | 0.1 | 21 |
| ISIS 599378 | 5-9-5 MOE | 77 | 99 | 2.7 | 0.1 | 23 |
| ISIS 599441 | 6-8-6 MOE | 150 | 250 | 2.9 | 0.1 | 23 |

Weights

Body weights of the mice were measured on day 44. Weights of organs, liver, kidney, and spleen were also measured after the mice were sacrificed on day 49. The results are presented in the Table below. ISIS oligonucleotides that caused changes in the weights outside the expected range for antisense oligonucleotides were excluded in further studies.

TABLE 174

Weights (g) of CD1 mice

| | Chemistry | Body | Kidney | Liver | Spleen |
|---|---|---|---|---|---|
| PBS | — | 39 | 0.6 | 1.9 | 0.1 |
| ISIS 588842 | Deoxy, MOE and (S)-cEt | 38 | 0.5 | 2.1 | 0.1 |
| ISIS 588843 | Deoxy, MOE and (S)-cEt | 41 | 0.6 | 2.4 | 0.2 |
| ISIS 588851 | Deoxy, MOE and (S)-cEt | 42 | 0.6 | 2.2 | 0.2 |
| ISIS 588856 | Deoxy, MOE and (S)-cEt | 42 | 0.7 | 2.6 | 0.2 |
| ISIS 599024 | 3-10-4 MOE | 41 | 0.6 | 4.0 | 0.2 |
| ISIS 599087 | 5-7-5 MOE | 44 | 0.8 | 2.6 | 0.3 |
| ISIS 599093 | 5-7-5 MOE | 39 | 0.6 | 2.3 | 0.2 |
| ISIS 599149 | 4-8-5 MOE | 42 | 0.7 | 2.8 | 0.2 |
| ISIS 599155 | 4-8-5 MOE | 41 | 0.7 | 2.1 | 0.2 |
| ISIS 599202 | 5-8-5 MOE | 43 | 0.6 | 2.6 | 0.2 |
| ISIS 599203 | 5-8-5 MOE | 42 | 0.6 | 2.6 | 0.2 |
| ISIS 599208 | 5-8-5 MOE | 40 | 0.6 | 2.1 | 0.2 |
| ISIS 599261 | 3-10-5 MOE | 39 | 0.7 | 3.4 | 0.3 |
| ISIS 599267 | 3-10-5 MOE | 42 | 0.8 | 2.5 | 0.3 |
| ISIS 599268 | 3-10-5 MOE | 41 | 0.7 | 2.1 | 0.2 |
| ISIS 599322 | 6-7-6 MOE | 43 | 0.6 | 2.2 | 0.2 |
| ISIS 599374 | 5-9-5 MOE | 37 | 0.6 | 2.2 | 0.2 |
| ISIS 599378 | 5-9-5 MOE | 43 | 0.7 | 2.7 | 0.2 |
| ISIS 599441 | 6-8-6 MOE | 42 | 0.6 | 2.5 | 0.3 |

Study 8 (with MOE Gapmers, Deoxy, MOE and (S)-cEt Oligonucleotides, and (S)-cEt Gapmers)

Groups of eight- to nine-week old male CD1 mice were injected subcutaneously once a week for 6 weeks with 100 mg/kg of MOE gapmers, or 50 mg/kg of deoxy, MOE and (S)-cEt oligonucleotides or (S)-cEt gapmers. One group of male CD s mice was injected subcutaneously once a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, albumin, creatinine, and BUN were measured using an automated clinical chemistry analyzer (Hitachi Olympus AU400e, Melville, N.Y.). The results are presented in the Table below.

TABLE 175

Plasma chemistry markers in CD1 mice plasma on day 43

| | Chemistry | Dose (mg/kg/wk) | ALT (IU/L) | AST (IU/L) | Albumin (g/dL) | Creatinine (mg/dL) | BUN (mg/dL) |
|---|---|---|---|---|---|---|---|
| PBS | — | — | 37 | 57 | 2.5 | 0.08 | 26 |
| ISIS 532770 | 5-10-5 MOE | 100 | 57 | 73 | 2.5 | 0.07 | 24 |
| ISIS 532800 | 5-10-5 MOE | 100 | 74 | 126 | 2.8 | 0.10 | 26 |
| ISIS 532809 | 5-10-5 MOE | 100 | 83 | 73 | 2.5 | 0.07 | 23 |
| ISIS 588540 | 5-10-5 MOE | 100 | 106 | 102 | 2.7 | 0.09 | 27 |
| ISIS 588544 | 5-10-5 MOE | 100 | 66 | 62 | 2.6 | 0.10 | 24 |
| ISIS 588548 | 5-10-5 MOE | 100 | 48 | 67 | 2.6 | 0.08 | 23 |
| ISIS 588550 | 5-10-5 MOE | 100 | 65 | 106 | 2.5 | 0.10 | 25 |
| ISIS 588553 | 5-10-5 MOE | 100 | 78 | 90 | 2.6 | 0.09 | 25 |
| ISIS 588555 | 5-10-5 MOE | 100 | 94 | 89 | 2.5 | 0.08 | 23 |
| ISIS 588848 | Deoxy, MOE and (S)-cEt | 50 | 38 | 54 | 2.3 | 0.07 | 25 |
| ISIS 594430 | 3-10-3 (S)-cEt | 50 | 63 | 72 | 2.5 | 0.10 | 27 |

Weights

Body weights of the mice were measured on day 36. Weights of organs, liver, kidney, and spleen were also measured after the mice were sacrificed on day 43. The results for the organ weights were expressed as a ratio to the body weights and normalized to the PBS control ratio.

TABLE 176

Organ Weights/Body weight (BW) of CD1 mice

| | Chemistry | Dose (mg/kg/wk) | Kidney/ BW | Liver/ BW | Spleen/ BW |
|---|---|---|---|---|---|
| PBS | — | — | 1.0 | 1.0 | 1.0 |
| ISIS 532770 | 5-10-5 MOE | 100 | 1.4 | 1.1 | 1.0 |
| ISIS 532800 | 5-10-5 MOE | 100 | 1.5 | 1.1 | 0.9 |
| ISIS 532809 | 5-10-5 MOE | 100 | 1.3 | 1.2 | 0.9 |
| ISIS 588540 | 5-10-5 MOE | 100 | 1.3 | 1.2 | 1.0 |

TABLE 176-continued

Organ Weights/Body weight (BW) of CD1 mice

| | Chemistry | Dose (mg/kg/wk) | Kidney/ BW | Liver/ BW | Spleen/ BW |
|---|---|---|---|---|---|
| ISIS 588544 | 5-10-5 MOE | 100 | 1.6 | 1.1 | 1.0 |
| ISIS 588548 | 5-10-5 MOE | 100 | 1.7 | 1.2 | 1.0 |
| ISIS 588550 | 5-10-5 MOE | 100 | 1.5 | 1.2 | 1.0 |
| ISIS 588553 | 5-10-5 MOE | 100 | 1.5 | 1.0 | 0.8 |
| ISIS 588555 | 5-10-5 MOE | 100 | 1.8 | 1.2 | 1.0 |
| ISIS 588848 | Deoxy, MOE and (S)-cEt | 50 | 1.3 | 1.0 | 0.9 |
| ISIS 594430 | 3-10-3 (S)-cEt | 50 | 1.4 | 1.1 | 0.9 |

Cytokine Assays

Blood obtained from all mice groups were sent to Antech Diagnostics for measurements of the various cytokine levels, such as IL-6, MDC, MIP1β, IP-10, MCP1, MIP-1α, and RANTES. The results are presented in Table 54.

TABLE 177

Cytokine levels (pg/mL) in CD1 mice plasma

| | Chemistry | IL-6 | MDC | MIP1β | IP-10 | MCP1 | MIP-1α | RANTES |
|---|---|---|---|---|---|---|---|---|
| PBS | — | 70 | 16 | 23 | 20 | 17 | 6 | 2 |
| ISIS 532770 | 5-10-5 MOE | 101 | 18 | 146 | 116 | 101 | 24 | 6 |
| ISIS 532800 | 5-10-5 MOE | 78 | 17 | 83 | 53 | 105 | 1 | 3 |
| ISIS 532809 | 5-10-5 MOE | 66 | 19 | 60 | 32 | 55 | 20 | 4 |
| ISIS 588540 | 5-10-5 MOE | 51 | 18 | 126 | 70 | 75 | 4 | 3 |
| ISIS 588544 | 5-10-5 MOE | 157 | 14 | 94 | 34 | 102 | 1 | 3 |
| ISIS 588548 | 5-10-5 MOE | 164 | 12 | 90 | 66 | 84 | 10 | 4 |
| ISIS 588550 | 5-10-5 MOE | 58 | 21 | 222 | 124 | 157 | 3 | 5 |
| ISIS 588553 | 5-10-5 MOE | 62 | 14 | 183 | 60 | 103 | 9 | 4 |
| ISIS 588555 | 5-10-5 MOE | 70 | 19 | 172 | 171 | 178 | 16 | 9 |
| ISIS 588848 | Deoxy, MOE and (S)-cEt | 59 | 13 | 61 | 27 | 63 | 12 | 4 |
| ISIS 594430 | 3-10-3 (S)-cEt | 48 | 14 | 56 | 38 | 85 | 10 | 3 |

Hematology Assays

Blood obtained from all mice groups were sent to Antech Diagnostics for measurements of hematocrit (HCT), as well as of the various blood cells, such as WBC, RBC, and platelets, and total hemoglobin (Hb) content. The results are presented in Table 55.

TABLE 178

Hematology markers in CD1 mice plasma

| | Chemistry | HCT (%) | Hb (g/dL) | WBC ($10^3/\mu L$) | RBC ($10^6/\mu L$) | Platelets ($10^3/\mu L$) |
|---|---|---|---|---|---|---|
| PBS | — | 46 | 15 | 7 | 9 | 960 |
| ISIS 532770 | 5-10-5 MOE | 45 | 14 | 5 | 9 | 879 |
| ISIS 532800 | 5-10-5 MOE | 45 | 14 | 5 | 9 | 690 |
| ISIS 532809 | 5-10-5 MOE | 46 | 14 | 6 | 9 | 1005 |
| ISIS 588540 | 5-10-5 MOE | 49 | 15 | 6 | 10 | 790 |
| ISIS 588544 | 5-10-5 MOE | 36 | 11 | 7 | 7 | 899 |
| ISIS 588548 | 5-10-5 MOE | 46 | 14 | 6 | 9 | 883 |
| ISIS 588550 | 5-10-5 MOE | 42 | 13 | 8 | 8 | 721 |
| ISIS 588553 | 5-10-5 MOE | 45 | 14 | 6 | 9 | 719 |
| ISIS 588555 | 5-10-5 MOE | 43 | 13 | 8 | 9 | 838 |
| ISIS 588848 | Deoxy, MOE and (S)-cEt | 40 | 15 | 8 | 10 | 840 |
| ISIS 594430 | 3-10-3 (S)-cEt | 45 | 14 | 8 | 9 | 993 |

Example 127: Tolerability of Antisense Oligonucleotides Targeting Human CFB in Sprague-Dawley Rats Sprague-Dawley rats are a multipurpose model used for safety and efficacy evaluations. The rats were treated with ISIS antisense oligonucleotides from the studies described in the Examples above and evaluated for changes in the levels of various plasma chemistry markers.

Study 1 (with 5-10-5 MOE Gapmers)

Male Sprague-Dawley rats, seven- to eight-week old, were maintained on a 12-hour light/dark cycle and fed ad libitum with Purina normal rat chow, diet 5001. Groups of 4 Sprague-Dawley rats each were injected subcutaneously once a week for 6 weeks with 100 mg/kg of 5-10-5 MOE gapmers. One control group of 6 rats was injected subcutaneously once a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured and the results are presented in the Table below expressed in IU/L. ISIS oligonucleotides that caused changes in the levels of any markers of liver function outside the expected range for antisense oligonucleotides were excluded in further studies.

TABLE 179

Liver function markers in Sprague-Dawley rats

|  | ALT (IU/L) | AST (IU/L) |
|---|---|---|
| PBS | 66 | 134 |
| ISIS 588544 | 101 | 329 |
| ISIS 588550 | 69 | 157 |
| ISIS 588553 | 88 | 304 |
| ISIS 588554 | 202 | 243 |
| ISIS 588555 | 94 | 113 |
| ISIS 588556 | 102 | 117 |
| ISIS 588560 | 206 | 317 |
| ISIS 588564 | 292 | 594 |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, N.Y.). Results are presented in the Table below, expressed in mg/dL. ISIS oligonucleotides that caused changes in the levels of any of the kidney function markers outside the expected range for antisense oligonucleotides were excluded in further studies.

TABLE 180

Kidney function markers (mg/dL) in Sprague-Dawley rats

|  | BUN | Creatinine |
|---|---|---|
| PBS | 18 | 3.5 |
| ISIS 588544 | 21 | 3.1 |
| ISIS 588550 | 21 | 3.0 |
| ISIS 588553 | 22 | 2.8 |
| ISIS 588554 | 23 | 3.0 |
| ISIS 588555 | 22 | 3.5 |
| ISIS 588556 | 21 | 3.2 |
| ISIS 588560 | 26 | 2.4 |
| ISIS 588564 | 24 | 2.7 |

Weights

Body weight measurements were taken on day 39. Liver, heart, spleen and kidney weights were measured at the end of the study on day 42, and are presented in the Table below. ISIS oligonucleotides that caused any changes in organ weights outside the expected range for antisense oligonucleotides were excluded from further studies.

TABLE 181

Weights (g)

|  | Body | Liver | Spleen | Kidney |
|---|---|---|---|---|
| PBS | 422 | 16 | 1.2 | 3.9 |
| ISIS 588544 | 353 | 15 | 1.7 | 2.9 |
| ISIS 588550 | 321 | 14 | 2.1 | 3.2 |
| ISIS 588553 | 313 | 15 | 2.3 | 3.2 |
| ISIS 588554 | 265 | 11 | 1.6 | 2.7 |
| ISIS 588555 | 345 | 14 | 1.4 | 3.3 |
| ISIS 588556 | 328 | 13 | 1.7 | 3.1 |
| ISIS 588560 | 270 | 13 | 2.4 | 3.0 |
| ISIS 588564 | 253 | 12 | 2.9 | 3.0 |

Study 2 (with Deoxy, MOE and (S)-cEt Oligonucleotides)

Male Sprague-Dawley rats, nine- to ten-week old, were maintained on a 12-hour light/dark cycle and fed ad libitum with Purina normal rat chow, diet 5001. Groups of 4 Sprague-Dawley rats each were injected subcutaneously once a week for 6 weeks with 100 mg/kg of deoxy, MOE, and (S)-cEt oligonucleotides. Two control groups of 3 rats each were injected subcutaneously once a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured on day 42 using an automated clinical chemistry analyzer (Hitachi Olympus AU400e, Melville, N.Y.). Plasma levels of ALT (alanine transaminase) and AST (aspartate transaminase), and albumin were measured and the results are presented in the Table below. ISIS oligonucleotides that caused changes in the levels of any markers of liver function outside the expected range for antisense oligonucleotides were excluded in further studies.

TABLE 182

Liver function markers in Sprague-Dawley rats

|  | ALT (IU/L) | AST (IU/L) | Albumin (g/dL) |
|---|---|---|---|
| PBS | 55 | 150 | 3.4 |
| PBS | 64 | 91 | 3.5 |
| ISIS 588554 | 52 | 92 | 3.2 |
| ISIS 588835 | 971 | 844 | 4.1 |
| ISIS 588842 | 317 | 359 | 3.8 |
| ISIS 588843 | 327 | 753 | 2.9 |
| ISIS 588846 | 70 | 111 | 3.2 |
| ISIS 588847 | 65 | 100 | 3.0 |

TABLE 182-continued

Liver function markers in Sprague-Dawley rats

|  | ALT (IU/L) | AST (IU/L) | Albumin (g/dL) |
|---|---|---|---|
| ISIS 588864 | 91 | 109 | 3.0 |
| ISIS 594430 | 85 | 106 | 3.7 |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, N.Y.). Results are presented in the Table below, expressed in mg/dL. ISIS oligonucleotides that caused changes in the levels of any of the kidney function markers outside the expected range for antisense oligonucleotides were excluded in further studies.

TABLE 183

Kidney function markers (mg/dL) in Sprague-Dawley rats

|  | BUN | Creatinine |
|---|---|---|
| PBS | 17 | 0.4 |
| PBS | 21 | 0.4 |
| ISIS 588554 | 20 | 0.4 |
| ISIS 588835 | 23 | 0.5 |
| ISIS 588842 | 22 | 0.4 |
| ISIS 588843 | 51 | 0.4 |
| ISIS 588846 | 25 | 0.5 |
| ISIS 588847 | 23 | 0.5 |
| ISIS 588864 | 23 | 0.4 |
| ISIS 594430 | 22 | 0.5 |

Weights

Body weight measurements were taken on day 39. Liver, heart, spleen and kidney weights were measured at the end of the study on day 42, and are presented in the Table below. ISIS oligonucleotides that caused any changes in organ weights outside the expected range for antisense oligonucleotides were excluded from further studies.

TABLE 184

Weights (g)

|  | Body | Liver | Spleen | Kidney |
|---|---|---|---|---|
| PBS | 466 | 16 | 0.9 | 3.8 |
| PBS | 485 | 16 | 0.9 | 3.6 |
| ISIS 588554 | 393 | 15 | 2.3 | 2.6 |
| ISIS 588835 | 387 | 16 | 1.0 | 3.3 |
| ISIS 588842 | 414 | 22 | 1.5 | 3.7 |
| ISIS 588843 | 427 | 20 | 2.5 | 4.2 |
| ISIS 588846 | 366 | 16 | 2.1 | 3.3 |
| ISIS 588847 | 402 | 15 | 1.6 | 3.1 |
| ISIS 588864 | 364 | 15 | 2.1 | 3.8 |
| ISIS 594430 | 420 | 16 | 1.2 | 3.6 |

Study 3 (with MOE Gapmers)

Male Sprague-Dawley rats, nine- to ten-week old, were maintained on a 12-hour light/dark cycle and fed ad libitum with Purina normal rat chow, diet 5001. Groups of 4 Sprague-Dawley rats each were injected subcutaneously once a week for 6 weeks with 100 mg/kg of MOE gapmers. One control group of 6 rats was injected subcutaneously once a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured on day 43 using an automated clinical chemistry analyzer (Hitachi Olympus AU400e, Melville, N.Y.). Plasma levels of ALT (alanine transaminase) and AST (aspartate transaminase) were measured and the results are presented in the Table below expressed in IU/L. ISIS oligonucleotides that caused changes in the levels of any markers of liver function outside the expected range for antisense oligonucleotides were excluded in further studies.

TABLE 185

Liver function markers in Sprague-Dawley rats

|  | Chemistry | ALT (IU/L) | AST (IU/L) | Albumin (g/dL) |
|---|---|---|---|---|
| PBS | — | 52 | 110 | 3.7 |
| ISIS 588563 | 5-10-5 MOE | 175 | 291 | 2.9 |
| ISIS 599024 | 3-10-4 MOE | 139 | 173 | 1.4 |
| ISIS 599093 | 5-7-5 MOE | 116 | 238 | 2.6 |
| ISIS 599149 | 4-8-5 MOE | 232 | 190 | 3.4 |
| ISIS 599155 | 4-8-5 MOE | 108 | 215 | 2.5 |
| ISIS 599202 | 5-8-5 MOE | 65 | 86 | 3.5 |
| ISIS 599203 | 5-8-5 MOE | 71 | 97 | 3.1 |
| ISIS 599208 | 5-8-5 MOE | 257 | 467 | 1.9 |
| ISIS 599261 | 3-10-5 MOE | 387 | 475 | 1.5 |
| ISIS 599267 | 3-10-5 MOE | 201 | 337 | 2.7 |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, N.Y.). Results are presented in the Table below, expressed in mg/dL. ISIS oligonucleotides that caused changes in the levels of any of the kidney function markers outside the expected range for antisense oligonucleotides were excluded in further studies.

TABLE 186

Kidney function markers (mg/dL) in Sprague-Dawley rats

|  | Chemistry | BUN | Creatinine |
|---|---|---|---|
| PBS | — | 16 | 0.3 |
| ISIS 588563 | 5-10-5 MOE | 26 | 0.4 |
| ISIS 599024 | 3-10-4 MOE | 135 | 1.2 |
| ISIS 599093 | 5-7-5 MOE | 29 | 0.4 |
| ISIS 599149 | 4-8-5 MOE | 23 | 0.4 |
| ISIS 599155 | 4-8-5 MOE | 29 | 0.4 |
| ISIS 599202 | 5-8-5 MOE | 19 | 0.4 |
| ISIS 599203 | 5-8-5 MOE | 22 | 0.4 |
| ISIS 599208 | 5-8-5 MOE | 26 | 0.3 |
| ISIS 599261 | 3-10-5 MOE | 228 | 1.6 |
| ISIS 599267 | 3-10-5 MOE | 24 | 0.4 |

Weights

Body weight measurements were taken on day 39. Liver, heart, spleen and kidney weights were measured at the end of the study on day 42, and are presented in the Table below. ISIS oligonucleotides that caused any changes in organ weights outside the expected range for antisense oligonucleotides were excluded from further studies.

TABLE 187

Weights (g)

|  | Chemistry | Body | Liver | Spleen | Kidney |
|---|---|---|---|---|---|
| PBS | — | 471 | 16 | 1.0 | 4.1 |
| ISIS 588563 | 5-10-5 MOE | 311 | 16 | 3.4 | 4.1 |
| ISIS 599024 | 3-10-4 MOE | 297 | 11 | 1.0 | 3.5 |
| ISIS 599093 | 5-7-5 MOE | 332 | 18 | 4.1 | 5.0 |

TABLE 187-continued

| | Weights (g) | | | | |
|---|---|---|---|---|---|
| | Chemistry | Body | Liver | Spleen | Kidney |
| ISIS 599149 | 4-8-5 MOE | 388 | 16 | 2.3 | 3.7 |
| ISIS 599155 | 4-8-5 MOE | 290 | 15 | 2.9 | 4.5 |
| ISIS 599202 | 5-8-5 MOE | 359 | 13 | 1.3 | 3.2 |
| ISIS 599203 | 5-8-5 MOE | 334 | 14 | 1.8 | 3.3 |
| ISIS 599208 | 5-8-5 MOE | 353 | 29 | 4.7 | 4.6 |
| ISIS 599261 | 3-10-5 MOE | 277 | 10 | 0.9 | 3.2 |
| ISIS 599267 | 3-10-5 MOE | 344 | 21 | 3.9 | 4.7 |

Study 4 (with MOE Gapmers)

Male Sprague-Dawley rats, nine- to ten-week old, were maintained on a 12-hour light/dark cycle and fed ad libitum with Purina normal rat chow, diet 5001. Groups of 4 Sprague-Dawley rats each were injected subcutaneously once a week for 6 weeks with 100 mg/kg of MOE gapmers. One control group of 6 rats was injected subcutaneously once a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured on day 42 using an automated clinical chemistry analyzer (Hitachi Olympus AU400e, Melville, N.Y.). Plasma levels of ALT (alanine transaminase) and AST (aspartate transaminase) were measured and the results are presented in the Table below expressed in IU/L. ISIS oligonucleotides that caused changes in the levels of any markers of liver function outside the expected range for antisense oligonucleotides were excluded in further studies.

TABLE 188

| Liver function markers in Sprague-Dawley rats | | | | |
|---|---|---|---|---|
| | Chemistry | ALT (IU/L) | AST (IU/L) | Albumin (g/dL) |
| PBS | — | 48 | 77 | 3.9 |
| ISIS 532800 | 5-10-5 MOE | 72 | 111 | 3.4 |
| ISIS 532809 | 5-10-5 MOE | 59 | 89 | 3.8 |
| ISIS 588540 | 5-10-5 MOE | 146 | 259 | 3.8 |
| ISIS 599268 | 3-10-5 MOE | 175 | 206 | 2.7 |
| ISIS 599322 | 6-7-6 MOE | 523 | 567 | 3.3 |
| ISIS 599374 | 5-9-5 MOE | 114 | 176 | 3.0 |
| ISIS 599378 | 5-9-5 MOE | 124 | 116 | 3.2 |
| ISIS 599380 | 5-9-5 MOE | 148 | 210 | 3.4 |
| ISIS 599441 | 6-8-6 MOE | 51 | 91 | 2.6 |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, N.Y.). Results are presented in the Table below, expressed in mg/dL. ISIS oligonucleotides that caused changes in the levels of any of the kidney function markers outside the expected range for antisense oligonucleotides were excluded in further studies.

TABLE 189

| Kidney function markers (mg/dL) in Sprague-Dawley rats | | | |
|---|---|---|---|
| | Chemistry | BUN | Creatinine |
| PBS | — | 15 | 0.4 |
| ISIS 532800 | 5-10-5 MOE | 26 | 0.5 |
| ISIS 532809 | 5-10-5 MOE | 18 | 0.5 |

TABLE 189-continued

| Kidney function markers (mg/dL) in Sprague-Dawley rats | | | |
|---|---|---|---|
| | Chemistry | BUN | Creatinine |
| ISIS 588540 | 5-10-5 MOE | 22 | 0.5 |
| ISIS 599268 | 3-10-5 MOE | 28 | 0.5 |
| ISIS 599322 | 6-7-6 MOE | 24 | 0.5 |
| ISIS 599374 | 5-9-5 MOE | 29 | 0.5 |
| ISIS 599378 | 5-9-5 MOE | 22 | 0.4 |
| ISIS 599380 | 5-9-5 MOE | 26 | 0.5 |
| ISIS 599441 | 6-8-6 MOE | 24 | 0.4 |

Weights

Body weight measurements were taken on day 39. Liver, heart, spleen and kidney weights were measured at the end of the study on day 42, and are presented in the Table below. ISIS oligonucleotides that caused any changes in organ weights outside the expected range for antisense oligonucleotides were excluded from further studies.

TABLE 190

| | Weights (g) | | | | |
|---|---|---|---|---|---|
| | Chemistry | Body | Liver | Spleen | Kidney |
| PBS | — | 502 | 16 | 0.9 | 3.7 |
| ISIS 532800 | 5-10-5 MOE | 376 | 16 | 2.0 | 3.4 |
| ISIS 532809 | 5-10-5 MOE | 430 | 16 | 1.4 | 3.4 |
| ISIS 588540 | 5-10-5 MOE | 391 | 16 | 1.8 | 3.5 |
| ISIS 599268 | 3-10-5 MOE | 332 | 16 | 3.6 | 3.6 |
| ISIS 599322 | 6-7-6 MOE | 348 | 13 | 2.1 | 3.4 |
| ISIS 599374 | 5-9-5 MOE | 302 | 12 | 2.0 | 3.3 |
| ISIS 599378 | 5-9-5 MOE | 332 | 11 | 1.1 | 2.8 |
| ISIS 599380 | 5-9-5 MOE | 350 | 11 | 1.5 | 3.3 |
| ISIS 599441 | 6-8-6 MOE | 368 | 16 | 2.5 | 3.3 |

Study 5 (with MOE Gapmers and Deoxy, MOE and (S)-cEt Oligonucleotides)

Male Sprague-Dawley rats, nine- to ten-week old, were maintained on a 12-hour light/dark cycle and fed ad libitum with Purina normal rat chow, diet 5001. Groups of 4 Sprague-Dawley rats each were injected subcutaneously once a week for 6 weeks with 100 mg/kg of MOE gapmer or with 50 mg/kg of deoxy, MOE and (S)-cEt oligonucleotides. One control group of 4 rats was injected subcutaneously once a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured on day 42 using an automated clinical chemistry analyzer (Hitachi Olympus AU400e, Melville, N.Y.). Plasma levels of ALT (alanine transaminase) and AST (aspartate transaminase) were measured and the results are presented in the Table below expressed in IU/L. ISIS oligonucleotides that caused changes in the levels of any markers of liver function outside the expected range for antisense oligonucleotides were excluded in further studies.

TABLE 191

| Liver function markers in Sprague-Dawley rats | | | | |
|---|---|---|---|---|
| | Chemistry | ALT (IU/L) | AST (IU/L) | Albumin (g/dL) |
| PBS | — | 49 | 74 | 3.3 |
| ISIS 532770 | 5-10-5 MOE | 95 | 132 | 3.3 |
| ISIS 588851 | Deoxy, MOE, and (S)-cEt | 47 | 72 | 3.1 |
| ISIS 588856 | Deoxy, MOE, and (S)-cEt | 56 | 75 | 3.0 |

TABLE 191-continued

Liver function markers in Sprague-Dawley rats

| Chemistry | | ALT (IU/L) | AST (IU/L) | Albumin (g/dL) |
|---|---|---|---|---|
| ISIS 588865 | Deoxy, MOE, and (S)-cEt | 62 | 84 | 2.9 |
| ISIS 588867 | Deoxy, MOE, and (S)-cEt | 73 | 214 | 2.9 |
| ISIS 588868 | Deoxy, MOE, and (S)-cEt | 59 | 83 | 3.1 |
| ISIS 588870 | Deoxy, MOE, and (S)-cEt | 144 | 144 | 3.4 |

Kidney Function

To evaluate the effect of ISIS oligonucleotides on kidney function, plasma and urine levels of blood urea nitrogen (BUN) and creatinine were measured using an automated clinical chemistry analyzer (Hitachi Olympus AU400e, Melville, N.Y.). Results are presented in the Tables below, expressed in mg/dL. ISIS oligonucleotides that caused changes in the levels of any of the kidney function markers outside the expected range for antisense oligonucleotides were excluded in further studies.

TABLE 192

Kidney function markers (mg/dL) in the plasma of Sprague-Dawley rats

| Chemistry | | BUN | Creatinine |
|---|---|---|---|
| PBS | — | 18 | 0.3 |
| ISIS 532770 | 5-10-5 MOE | 20 | 0.4 |
| ISIS 588851 | Deoxy, MOE, and (S)-cEt | 20 | 0.4 |
| ISIS 588856 | Deoxy, MOE, and (S)-cEt | 22 | 0.4 |
| ISIS 588865 | Deoxy, MOE, and (S)-cEt | 24 | 0.5 |
| ISIS 588867 | Deoxy, MOE, and (S)-cEt | 22 | 0.4 |
| ISIS 588868 | Deoxy, MOE, and (S)-cEt | 19 | 0.4 |
| ISIS 588870 | Deoxy, MOE, and (S)-cEt | 20 | 0.5 |

TABLE 193

Kidney function markers (mg/dL) in the urine of Sprague-Dawley rats

| Chemistry | | Total protein | Creatinine |
|---|---|---|---|
| PBS | — | 80 | 92 |
| ISIS 532770 | 5-10-5 MOE | 466 | 69 |
| ISIS 588851 | Deoxy, MOE, and (S)-cEt | 273 | 64 |
| ISIS 588856 | Deoxy, MOE, and (S)-cEt | 259 | 68 |
| ISIS 588865 | Deoxy, MOE, and (S)-cEt | 277 | 67 |
| ISIS 588867 | Deoxy, MOE, and (S)-cEt | 337 | 68 |
| ISIS 588868 | Deoxy, MOE, and (S)-cEt | 326 | 75 |
| ISIS 588870 | Deoxy, MOE, and (S)-cEt | 388 | 82 |

Weights

Body weight measurements were taken on day 39. Liver, heart, spleen and kidney weights were measured at the end of the study on day 42, and are presented in the Table below. ISIS oligonucleotides that caused any changes in organ weights outside the expected range for antisense oligonucleotides were excluded from further studies.

TABLE 194

Weights (g)

| Chemistry | | Body | Liver | Spleen | Kidney |
|---|---|---|---|---|---|
| PBS | — | 489 | 16 | 0.9 | 3.5 |
| ISIS 532770 | 5-10-5 MOE | 372 | 15 | 1.7 | 3.1 |
| ISIS 588851 | Deoxy, MOE, and (S)-cEt | 285 | 14 | 1.4 | 3.2 |
| ISIS 588856 | Deoxy, MOE, and (S)-cEt | 415 | 15 | 1.1 | 3.3 |
| ISIS 588865 | Deoxy, MOE, and (S)-cEt | 362 | 14 | 2.0 | 3.3 |
| ISIS 588867 | Deoxy, MOE, and (S)-cEt | 406 | 15 | 2.4 | 3.4 |
| ISIS 588868 | Deoxy, MOE, and (S)-cEt | 399 | 15 | 1.5 | 3.4 |
| ISIS 588870 | Deoxy, MOE, and (S)-cEt | 446 | 14 | 1.4 | 3.3 |

Study 6 (with MOE Gapmers, Deoxy, MOE and (S)-cEt Oligonucleotides, and (S)-cEt Gapmers)

Male rats were maintained on a 12-hour light/dark cycle and fed ad libitum with Purina normal rat chow, diet 5001. Groups of 4 rats each were injected subcutaneously once a week for 6 weeks with 100 mg/kg of MOE gapmers or with 50 mg/kg of deoxy, MOE and (S)-cEt oligonucleotide or (S)-cEt gapmer.

One control group of 4 rats was injected subcutaneously once a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured on day 42 using an automated clinical chemistry analyzer (Hitachi Olympus AU400e, Melville, N.Y.). Plasma levels of ALT (alanine transaminase) and AST (aspartate transaminase) were measured and the results are presented in the Table below expressed in IU/L.

TABLE 195

Liver function markers

| Chemistry | | Dose (mg/kg/wk) | ALT (IU/L) | AST (IU/L) | Albumin (g/dL) |
|---|---|---|---|---|---|
| PBS | — | — | 54 | 73 | 4.3 |
| ISIS 532770 | 5-10-5 MOE | 100 | 57 | 114 | 4.4 |
| ISIS 532800 | 5-10-5 MOE | 100 | 176 | 180 | 4.3 |
| ISIS 532809 | 5-10-5 MOE | 100 | 71 | 132 | 4.1 |
| ISIS 588540 | 5-10-5 MOE | 100 | 89 | 202 | 4.4 |
| ISIS 588544 | 5-10-5 MOE | 100 | 75 | 152 | 3.9 |
| ISIS 588548 | 5-10-5 MOE | 100 | 50 | 71 | 4.1 |
| ISIS 588550 | 5-10-5 MOE | 100 | 80 | 133 | 3.6 |
| ISIS 588553 | 5-10-5 MOE | 100 | 59 | 112 | 3.9 |
| ISIS 588555 | 5-10-5 MOE | 100 | 97 | 142 | 3.8 |
| ISIS 588848 | Deoxy, MOE and (S)-cEt | 50 | 53 | 82 | 3.9 |
| ISIS 594430 | 3-10-3 (S)-cEt | 50 | 198 | 172 | 4.4 |

Kidney Function

To evaluate the effect of ISIS oligonucleotides on kidney function, urine levels of total protein and creatinine were measured using an automated clinical chemistry analyzer (Hitachi Olympus AU400e, Melville, N.Y.). Results are presented in the Table below. ISIS oligonucleotides that caused changes in the levels of any of the kidney function markers outside the expected range for antisense oligonucleotides were excluded in further studies.

TABLE 196

Total protein/creatinine ratio in the urine of rats

|  | Chemistry | Dose (mg/kg/wk) | P/C ratio |
|---|---|---|---|
| PBS | — | — | 1.1 |
| ISIS 532770 | 5-10-5 MOE | 100 | 8.3 |
| ISIS 532800 | 5-10-5 MOE | 100 | 6.5 |
| ISIS 532809 | 5-10-5 MOE | 100 | 6.1 |
| ISIS 588540 | 5-10-5 MOE | 100 | 10.1 |
| ISIS 588544 | 5-10-5 MOE | 100 | 7.9 |
| ISIS 588548 | 5-10-5 MOE | 100 | 6.6 |
| ISIS 588550 | 5-10-5 MOE | 100 | 7.6 |
| ISIS 588553 | 5-10-5 MOE | 100 | 7.0 |
| ISIS 588555 | 5-10-5 MOE | 100 | 6.2 |
| ISIS 588848 | Deoxy, MOE and (S)-cEt | 50 | 5.2 |
| ISIS 594430 | 3-10-3 (S)-cEt | 50 | 5.3 |

Weights

Body weight measurements were taken on day 39. Liver, heart, spleen and kidney weights were measured at the end of the study on day 42, and are presented in the Table below. The results for the organ weights were expressed as a ratio to the body weights and normalized to the PBS control ratio.

TABLE 197

Organ weights/Body weight (BW) ratios

|  | Chemistry | Dose (mg/kg/wk) | Spleen/BW | Liver/BW | Kidney/BW |
|---|---|---|---|---|---|
| PBS | — | — | 1.0 | 1.0 | 1.0 |
| ISIS 532770 | 5-10-5 MOE | 100 | 2.0 | 1.2 | 1.0 |
| ISIS 532800 | 5-10-5 MOE | 100 | 2.8 | 1.3 | 1.0 |
| ISIS 532809 | 5-10-5 MOE | 100 | 2.2 | 1.1 | 1.0 |
| ISIS 588540 | 5-10-5 MOE | 100 | 2.2 | 1.4 | 1.0 |
| ISIS 588544 | 5-10-5 MOE | 100 | 2.5 | 1.3 | 1.1 |
| ISIS 588548 | 5-10-5 MOE | 100 | 2.1 | 1.3 | 1.1 |
| ISIS 588550 | 5-10-5 MOE | 100 | 3.9 | 1.4 | 1.1 |
| ISIS 588553 | 5-10-5 MOE | 100 | 4.1 | 1.4 | 1.4 |
| ISIS 588555 | 5-10-5 MOE | 100 | 1.8 | 1.3 | 1.0 |
| ISIS 588848 | Deoxy, MOE and (S)-cEt | 50 | 3.1 | 1.3 | 1.1 |
| ISIS 594430 | 3-10-3 (S)-cEt | 50 | 1.7 | 1.0 | 1.1 |

Example 128: Efficacy of Antisense Oligonucleotides Against CFB mRNA in hCFB Mice Selected compounds were tested for efficacy in human CFB transgenic mice, founder line 46 The human CFB gene is located on chromosome 6: position 31913721-31919861. A Fosmid (ABC14-50933200C$_{23}$) containing the CFB sequence was selected to make transgenic mice expressing the human CFB gene. Cla I (31926612) and Age 1 (31926815) restriction enzymes were used to generate a 22,127 bp fragment containing the CFB gene for pronuclear injection. DNA was confirmed by restriction enzyme analysis using Pvu I. The 22,127 bp DNA fragment was injected into C57BL/6NTac embryos. 6 positive founders were bred. Founder #6 expressed the liver human CFB mRNA and was crossbreed to the 3' generation. Progeny from 3$^{rd}$ generation mice were used to evaluate human CFB ASOs for human CFB mRNA reduction.

Treatment

Groups of 3 mice each were injected subcutaneously twice a week for the first week with 50 mg/kg of ISIS oligonucleotides, followed by once a week dosing with 50 mg/kg of ISIS oligonucleotides for an additional three weeks. One control group of 4 mice was injected subcutaneously twice a week for 2 weeks for the first week with PBS for the first week for an additional three weeks. Forty eight hours after the last dose, mice were euthanized and organs and plasma were harvested for further analysis.

RNA Analysis

At the end of the dosing period, RNA was extracted from the liver and kidney for real-time PCR analysis of CFB mRNA levels. Human CFB mRNA levels were measured using the human primer probe set RTS3459. CFB mRNA levels were normalized to RIBOGREEN®, and also to the housekeeping gene, Cyclophilin. Results were calculated as percent inhibition of CFB mRNA expression compared to the control. All the antisense oligonucleotides effected inhibition of human CFB mRNA levels in the liver.

TABLE 198

Percent reduction of CFB mRNA levels in hCFB mice

| ISIS No | Normalized to RIBOGREEN | Normalized to Cyclophilin |
|---|---|---|
| 532770 | 86 | 87 |
| 532800 | 88 | 87 |
| 532809 | 69 | 69 |
| 588540 | 95 | 94 |
| 588544 | 91 | 91 |
| 588548 | 78 | 77 |
| 588550 | 89 | 88 |
| 588553 | 94 | 94 |
| 588555 | 94 | 94 |
| 588848 | 83 | 82 |
| 594430 | 78 | 76 |

Example 129: In Vivo Antisense Inhibition of Murine CFB

Several antisense oligonucleotides were designed that were targeted to murine CFB mRNA (GENBANK Accession No. NM_008198.2, incorporated herein as SEQ ID NO: 5). The target start sites and sequences of each oligonucleotide are described in the table below. The chimeric antisense oligonucleotides in the table below were designed as 5-10-5 MOE gapmers. The gapmers are 20 nucleosides in length, wherein the central gap segment is comprised of 10 2'-deoxynucleosides and is flanked on both sides (in the 5' and 3' directions) by wings comprising 5 nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

TABLE 199

Gapmers targeting murine CFB

| ISIS No | Sequence | Target Start Site on SEQ ID NO: 5 | SEQ ID NO |
|---|---|---|---|
| 516269 | GCATAAGAGGGTACCAGCTG | 2593 | 804 |
| 516272 | GTCCTTTAGCCAGGGCAGCA | 2642 | 805 |
| 516323 | TCCACCCATGTTGTGCAAGC | 1568 | 806 |
| 516330 | CCACACCATGCCACAGAGAC | 1826 | 807 |
| 516341 | TTCCGAGTCAGGCTCTTCCC | 2308 | 808 |

Treatment

Groups of four C57BL/6 mice each were injected with 50 mg/kg of ISIS 516269, ISIS 516272, ISIS 516323, ISIS 516330, or ISIS 516341 administered weekly for 3 weeks. A control group of mice was injected with phosphate buffered saline (PBS) administered weekly for 3 weeks.

CFB RNA Analysis

At the end of the study, RNA was extracted from liver tissue for real-time PCR analysis of CFB, using primer probe set RTS3430 (forward sequence GGGCAAACA GCAATTTGTGA, designated herein as SEQ ID NO: 816; reverse sequence TGGCTACCCACCTTCCTTGT, designated herein as SEQ ID NO: 817; probe sequence CTGGA-TACTGTCCCAATCCCGGTATTCCX, designated herein as SEQ ID NO: 818). The mRNA levels were normalized using RIBOGREEN®. As shown in the Table below, some of the antisense oligonucleotides achieved reduction of murine CFB over the PBS control. Results are presented as percent inhibition of CFB, relative to control.

TABLE 200

Percent inhibition of murine CFB mRNA in C57BL/6 mice

| ISIS No | % |
|---|---|
| 516269 | 29 |
| 516272 | 72 |
| 516323 | 77 |
| 516330 | 62 |
| 516341 | 72 |

Protein Analysis

CFB protein levels were measured in the kidney, liver, plasma, and in the eye by western Blot using goat anti-CFB antibody (Sigma Aldrich). Results are presented as percent inhibition of CFB, relative to PBS control. 'n/a' indicates that measurements were not taken for that sample. As shown in the Table below, antisense inhibition of CFB by ISIS oligonucleotides resulted in a reduction of CFB protein in various tissues. As shown in the Table below, systemic administration of ISIS oligonucleotides was effective in reducing CFB levels in the eye.

TABLE 201

Percent inhibition of murine CFB protein in C57BL/6 mice

| ISIS No | Kidney | Liver | Plasma | Eye |
|---|---|---|---|---|
| 516269 | 20 | 58 | n/a | 70 |
| 516272 | 48 | 74 | n/a | 99 |
| 516323 | 73 | 85 | 90 | 93 |
| 516330 | 77 | 80 | n/a | n/a |
| 516341 | 80 | 88 | 68 | n/a |

Example 130: Dose-Dependent Antisense Inhibition of Murine CFB

Groups of four C57BL/6 mice each were injected with 25 mg/kg, 50 mg/kg, or 100 mg/kg of ISIS 516272, and ISIS 516323 administered weekly for 6 weeks. Another two groups of mice were injected with 100 mg/kg of ISIS 516330 or ISIS 516341 administered weekly for 6 weeks. Two control groups of mice were injected with phosphate buffered saline (PBS) administered weekly for 6 weeks.

CFB RNA Analysis

RNA was extracted from liver and kidney tissues for real-time PCR analysis of CFB, using primer probe set RTS3430. The mRNA levels were normalized using RIBOGREEN®. As shown in the Table below, the antisense oligonucleotides achieved dose-dependent reduction of murine CFB over the PBS control. Results are presented as percent inhibition of CFB, relative to control.

TABLE 202

Percent inhibition of murine CFB mRNA in C57BL/6 mice

| ISIS No | Dose (mg/kg/wk) | Liver | Kidney |
|---|---|---|---|
| 516272 | 25 | 39 | 32 |
|  | 50 | 73 | 36 |
|  | 100 | 87 | 42 |
| 516323 | 25 | 36 | 41 |
|  | 50 | 65 | 47 |
|  | 100 | 79 | 71 |
| 516330 | 100 | 85 | 45 |
| 516341 | 200 | 89 | 65 |

Protein Analysis

CFB protein levels were measured in the plasma by western Blot using goat anti-CFB antibody (Sigma Aldrich). As shown in the table below, antisense inhibition of CFB by the ISIS oligonucleotides resulted in a reduction of CFB protein. Results are presented as percent inhibition of CFB, relative to PBS control. 'n/a' indicates that measurements were not taken for that sample.

CFB protein levels were also measured in the eye by Western Blot. All treatment groups demonstrated an inhibition of CFB by 95%, with some sample measurements being below detection levels of the assay.

TABLE 203

Percent inhibition of murine CFB protein in C57BL/6 mice

| ISIS No | Dose (mg/kg/wk) | Liver |
|---|---|---|
| 516272 | 25 | 32 |
|  | 50 | 70 |
|  | 100 | 83 |
| 516323 | 25 | 43 |
|  | 50 | 80 |
|  | 100 | 90 |
| 516330 | 100 | n/a |
| 516341 | 200 | n/a |

Example 131: Effect of Antisense Inhibition of CFB in the NZB/W F1 Mouse Model

The NZB/W F1 is the oldest classical model of lupus, where the mice develop severe lupus-like phenotypes comparable to that of lupus patients (Theofilopoulos, A. N. and Dixon, F. J. Advances in Immunology, vol. 37, pp. 269-390, 1985). These lupus-like phenotypes include lymphadenopathy, splenomegaly, elevated serum antinuclear autoantibodies (ANA) including anti-dsDNA IgG, a majority of which are IgG2a and IgG3, and immune complex-mediated glomerulonephritis (GN) that becomes apparent at 5-6 months of age, leading to kidney failure and death at 10-12 months of age.

Study 1

A study was conducted to demonstrate that treatment with antisense oligonucleotides targeting CFB would improve renal pathology in the mouse model. Female NZB/W F1 mice, 17 weeks old, were purchased from Jackson Laboratories. Groups of 16 mice each received doses of 100 µg/kg/week of ISIS 516272 or ISIS 516323 for 20 weeks. Another group of 16 mice received doses of 100 µg/kg/week of control oligonucleotide ISIS 141923 for 20 weeks. Another group of 10 mice received doses of PBS for 20 weeks and served as the control group to which all the other groups were compared. Terminal endpoints were collected 48 hours after the last dose was injected.

CFB RNA Analysis

RNA was extracted from liver and kidney tissue for real-time PCR analysis of CFB, using primer probe set RTS3430. The mRNA levels were normalized using RIBOGREEN®. As shown in the Table below, some of the antisense oligonucleotides achieved reduction of murine CFB over the PBS control. Results are presented as percent inhibition of CFB, relative to control.

TABLE 204

Percent inhibition of murine CFB mRNA in NZB/W F1 mice

| ISIS No | Liver | Kidney |
|---|---|---|
| 516272 | 55 | 25 |
| 516323 | 63 | 43 |
| 141923 | 0 | 0 |

Proteinuria

Proteinuria is expected in 60% of animals in this mouse model. The cumulative incidence of severe proteinuria was measured by calculating the total protein to creatinine ratio using a clinical analyzer. The results are presented in the table below and demonstrate that treatment with antisense oligonucleotides targeting CFB achieved reduction of proteinuria in the mice compared to the PBS control and the control oligonucleotide treated mice.

TABLE 205

Percent cumulative incidence of severe proteinuria in NZB/W F1 mice

| | % |
|---|---|
| PBS | 40 |
| ISIS 516272 | 6 |
| ISIS 516323 | 0 |
| ISIS 141923 | 25 |

Survival

Survival of the mice was monitored by keeping count of the mice at the start of treatment and then again at week 20. The results are presented in the table below and demonstrate that treatment with antisense oligonucleotides targeting CFB increased survival in the mice compared to the PBS control and the control oligonucleotide treated mice.

TABLE 206

Number of surviving mice and % survival

| | Week 1 | Week 20 | % survival at week 20 |
|---|---|---|---|
| PBS | 10 | 6 | 60 |
| ISIS 516272 | 16 | 15 | 94 |
| ISIS 516323 | 16 | 16 | 100 |
| ISIS 141923 | 16 | 12 | 75 |

Glomerular Deposition

The amount of C3 deposition, as well as IgG deposition, in the glomeruli of the kidneys was measured by immunohistochemistry with an anti-C3 antibody. The results are presented in the table below and demonstrate that treatment with antisense oligonucleotides targeting CFB achieved reduction of both C3 and IgG depositions in the kidney glomeruli compared to the PBS control and the control oligonucleotide treated mice.

TABLE 207

Percent inhibition of glomerula deposition in NZB/W F1 mice

| ISIS No | C3 | IgG |
|---|---|---|
| 516272 | 45 | 20 |
| 516323 | 48 | 2 |
| 141923 | 0 | 0 |

Study 2

Female NZB/W F1 mice, 16 weeks old, were purchased from Jackson Laboratories. A group of 10 mice received doses of 100 µg/kg/week of ISIS 516323 for 12 weeks. Another group of 10 mice received doses of 100 µg/kg/week of control oligonucleotide ISIS 141923 for 12 weeks. Another group of 10 mice received doses of PBS for 12 weeks and served as the control group to which all the other groups were compared. Terminal endpoints were collected 48 hours after the last dose was injected.

CFB RNA Analysis

RNA was extracted from liver and kidney tissue for real-time PCR analysis of CFB, using primer probe set RTS3430. As shown in the table below, treatment with ISIS 516323 achieved reduction of murine CFB over the PBS control. Results are presented as percent inhibition of CFB, relative to control.

TABLE 208

Percent inhibition of murine CFB mRNA in NZB/W F1 mice

| ISIS No | Liver | Kidney |
|---|---|---|
| 516323 | 75 | 46 |
| 141923 | 0 | 6 |

Proteinuria

The cumulative incidence of severe proteinuria was assessed by measuring urine total protein to creatinine ratio, as well as by measuring total microalbumin levels. The results are presented in the tables below and demonstrate that treatment with antisense oligonucleotides targeting CFB reduced proteinuria in the mice compared to the PBS control and the control oligonucleotide treated mice.

TABLE 209

Proteinuria in NZB/W F1 mice measured as urine microalbumin levels (mg/dl)

| ISIS No | Week 0 | Week 6 | Week 8 | Week 10 |
|---|---|---|---|---|
| 516323 | 0 | 0 | 5.4 | 0.4 |
| 141923 | 0 | 8.28 | 8.6 | 5.6 |

TABLE 210

Proteinuria in NZB/W F1 mice measured as total protein to creatinine ratio

| ISIS No | Week 0 | Week 6 | Week 8 | Week 10 |
|---|---|---|---|---|
| 516323 | 5.5 | 7.8 | 8.6 | 7.2 |
| 141923 | 6.9 | 10.0 | 13.5 | 7.2 |

Survival

Survival of the mice was monitored by keeping count of the mice at the start of treatment and then again at week 12. The results are presented in the table below and demonstrate that treatment with antisense oligonucleotides targeting CFB increased survival in the mice compared to the PBS control and the control oligonucleotide treated mice.

TABLE 211

Number of surviving mice

| | Week 1 | Week 12 |
|---|---|---|
| PBS | 10 | 9 |
| ISIS 516323 | 10 | 10 |
| ISIS 141923 | 10 | 9 |

Example 132: Effect of Antisense Inhibition of CFB in the MRL Mouse Model

The MRL/lpr lupus nephritis mouse model develops an SLE-like phenotype characterized by lymphadenopathy due to an accumulation of double negative (CD4$^-$ CD8$^-$) and B220$^+$ T-cells. These mice display an accelerated mortality rate. In addition, the mice have high concentrations of circulating immunoglobulins, which included elevated levels of autoantibodies such as ANA, anti-ssDNA, anti-dsDNA, anti-Sm, and rheumatoid factors, resulting in large amounts of immune complexes (Andrews, B. et al., J. Exp. Med. 148: 1198-1215, 1978).

Treatment

A study was conducted to investigate whether treatment with antisense oligonucleotides targeting CFB would reverse renal pathology in the mouse model. Female MRL/lpr mice, 14 weeks old, were purchased from Jackson Laboratories. A group of 10 mice received doses of 50 µg/kg/week of ISIS 516323 for 7 weeks. Another group of 10 mice received doses of 50 µg/kg/week of control oligonucleotide ISIS 141923 for 7 weeks. Another group of 10 mice received doses of PBS for 7 weeks and served as the control group to which all the other groups were compared. Terminal endpoints were collected 48 hours after the last dose was injected.

CFB RNA Analysis

RNA was extracted from liver tissue for real-time PCR analysis of CFB, using primer probe set RTS3430. As shown in the Table below, ISIS 516323 reduced CFB over the PBS control. Results are presented as percent inhibition of CFB, relative to control.

TABLE 212

Percent inhibition of murine CFB mRNA in MRL/lpr mice

| ISIS No | % |
|---|---|
| 516323 | 68 |
| 141923 | 4 |

Renal Pathology

Renal pathology was evaluated by two methods. Histological sections of the kidney were stained with Haematoxylin & Eosin. The PBS control demonstrated presence of multiglomerular crescents tubular casts, which is a symptom of glomerulosclerosis. In contrast, the sections from mice treated with ISIS 516323 showed absent crescents tubular casts with minimal bowman capsule fibrotic changes, moderate to severe segmental mesangial cell expansion and glomerular basement membrane thickening.

Accumulation of C3 in the kidney was also assessed by immunohistochemistry with anti-C3 antibodies. The whole kidney C3 immunohistochemistry intensity score was calculated by intensity scoring system, which was computed by capturing 10 glomeruli per kidney and calculation the intensity of positive C3 staining. The results are presented in the table below and demonstrate that treatment with ISIS 516323 reduced renal C3 accumulation compared to the control groups.

TABLE 213

Renal C3 accumulation in MRL/lpr mice

| | Whole kidney C3 intensity score | C3 quantification (area/total area) % of average PBS |
|---|---|---|
| PBS | 2.5 | 100 |
| ISIS 516323 | 1.6 | 68 |
| ISIS 141923 | 2.2 | 99 |

Plasma C3 Levels

Reduction of CFB inhibits activation of the alternative complement pathway, preventing C3 consumption and leading to an apparent elevation of plasma C3 levels. Plasma C3 levels from terminal bleed were measured by clinical analyzer. The results are presented in the table below and demonstrate that treatment with ISIS 516323 increased C3 levels (p<0.001) in the plasma compared to the control groups.

TABLE 214

Plasma C3 levels (mg/dL) in MRL/lpr mice

| ISIS No | C3 |
|---|---|
| 516323 | 28 |
| 141923 | 16 |

The results indicate that treatment with antisense oligonucleotides targeting CFB reverses renal pathology in the lupus mouse model.

Example 133: Effect of Antisense Inhibition of CFB in the CFH Het Mouse Model CFH heterozygous (CFH Het, CFH$^{+/-}$) mouse model express a mutant Factor H protein in combination with the full-length mouse protein (Pickering, M. C. et al., J. Exp.

Med. 2007. 204: 1249-56). Renal histology remains normal in these mice up to six months old.

Study 1

Groups of 8 CFH$^{+/-}$ mice, 6 weeks old, each received doses of 75 mg/kg/week of ISIS 516323 or ISIS 516341 for 6 weeks. Another group of 8 mice received doses of 75 mg/kg/week of control oligonucleotide ISIS 141923 for 6 weeks. Another group of 8 mice received doses of PBS for 6 weeks and served as the control group to which all the other groups were compared. Terminal endpoints were collected 48 hours after the last dose was injected.

CFB RNA Analysis

RNA was extracted from liver and kidney tissue for real-time PCR analysis of CFB, using primer probe set RTS3430. As shown in the Table below, the antisense oligonucleotides reduced CFB over the PBS control. Results are presented as percent inhibition of CFB, relative to control.

TABLE 215

Percent inhibition of murine CFB mRNA in CFH$^{+/-}$ mice

| ISIS No | Liver | Kidney |
|---|---|---|
| 516323 | 80 | 38 |
| 516341 | 90 | 44 |
| 141923 | 0 | 17 |

Plasma C3 Levels

Reduction of CFB inhibits activation of the alternative complement pathway, preventing C3 consumption and leading to an apparent elevation of plasma C3 levels. Plasma C3 levels from terminal plasma collection were measured by clinical analyzer. The results are presented in the table below and demonstrate that treatment with ISIS 516323 increased C3 to normal levels in the plasma.

TABLE 216

Plasma C3 levels (mg/dL) in CFH$^{+/-}$ mice

| ISIS No | C3 |
|---|---|
| 516323 | 15 |
| 516341 | 17 |
| 141923 | 8 |

Study 2

Groups of 5 CFH$^{+/-}$ mice each received doses of 12.5 mg/kg/week, 25 mg/kg/week, 50 mg/kg/week, 75 mg/kg/week, or 100 mg/kg/week of ISIS 516323 or ISIS 516341 for 6 weeks. Another group of 5 mice received doses of 75 µg/kg/week of control oligonucleotide ISIS 141923 for 6 weeks. Another group of 5 mice received doses of PBS for 6 weeks and served as the control group to which all the other groups were compared. Terminal endpoints were collected 48 hours after the last dose was injected.

CFB RNA Analysis

RNA was extracted from liver and kidney tissue for real-time PCR analysis of CFB, using primer probe set RTS3430. As shown in the Table below, the antisense oligonucleotides reduced CFB over the PBS control in a dose dependent manner. Results are presented as percent inhibition of CFB, relative to control.

TABLE 217

Percent inhibition of murine CFB mRNA in the liver of CFH$^{+/-}$ mice

| ISIS No | Dose (mg/kg/week) | % |
|---|---|---|
| 516323 | 12.5 | 34 |
|  | 25 | 51 |
|  | 50 | 72 |
|  | 75 | 79 |
|  | 100 | 92 |
| 516341 | 12.5 | 38 |
|  | 25 | 57 |
|  | 50 | 89 |
|  | 75 | 92 |
|  | 100 | 90 |
| 141923 | 75 | 13 |

Plasma C3 Levels

Reduction of CFB inhibits activation of the alternative complement pathway, preventing C3 consumption and leading to an apparent elevation of plasma C3 levels. Plasma C3 levels from terminal plasma collection were measured by clinical analyzer. The results are presented in the table below and demonstrate that treatment with ISIS oligonucleotides targeting CFB increased C3 levels in the plasma.

TABLE 218

Plasma C3 levels (mg/dL) in CFH$^{+/-}$ mice

| | Dose (mg/kg/week) | C3 |
|---|---|---|
| PBS | — | 10.1 |
| 516323 | 12.5 | 11.4 |
|  | 25 | 15.5 |
|  | 50 | 17.0 |
|  | 75 | 18.3 |
|  | 100 | 18.8 |
| 516341 | 12.5 | 12.1 |
|  | 25 | 16.3 |
|  | 50 | 18.6 |
|  | 75 | 22.1 |
|  | 100 | 19.1 |
| 141923 | 75 | 8.9 |

Example 134: Effect of ISIS Antisense Oligonucleotides Targeting Human CFB in Cynomolgus Monkeys Cynomolgus monkeys were treated with ISIS antisense oligonucleotides selected from studies described in the Examples above. Antisense oligonucleotide efficacy and tolerability, as well as their pharmacokinetic profile in the liver and kidney, were evaluated.

At the time this study was undertaken, the cynomolgus monkey genomic sequence was not available in the National Center for Biotechnology Information (NCBI) database; therefore cross-reactivity with the cynomolgus monkey gene sequence could not be confirmed. Instead, the sequences of the ISIS antisense oligonucleotides used in the cynomolgus monkeys was compared to a rhesus monkey sequence for homology. It is expected that ISIS oligonucleotides with homology to the rhesus monkey sequence are fully cross-reactive with the cynomolgus monkey sequence as well. The human antisense oligonucleotides tested are cross-reactive with the rhesus genomic sequence (GENBANK Accession No. NW_001116486.1 truncated from nucleotides 536000 to 545000, designated herein as SEQ ID NO: 3). The greater the complementarity between the human oligonucleotide and the rhesus monkey sequence, the more likely the human oligonucleotide can cross-react with the rhesus monkey sequence. The start and stop sites of each oligonucleotide targeted to SEQ ID NO: 3 is presented in the Table below. "Start site" indicates the 5'-most nucleotide to which the gapmer is targeted in the rhesus monkey gene sequence. 'Mismatches' indicates the number of nucleobases in the human oligonucleotide that are mismatched with the rhesus genomic sequence.

TABLE 219

Antisense oligonucleotides complementary to the rhesus CFB genomic sequence (SEQ ID NO: 3)

| ISIS No | Target Start Site | Mismatches | Chemistry | SEQ ID NO |
|---|---|---|---|---|
| 532770 | 6788 | 0 | 5-10-5 MOE | 198 |
| 532800 | 7500 | 0 | 5-10-5 MOE | 228 |
| 532809 | 7614 | 0 | 5-10-5 MOE | 237 |
| 588540 | 7627 | 1 | 5-10-5 MOE | 440 |
| 588544 | 7631 | 1 | 5-10-5 MOE | 444 |
| 588548 | 7635 | 1 | 5-10-5 MOE | 448 |
| 588550 | 7637 | 1 | 5-10-5 MOE | 450 |
| 588553 | 7640 | 1 | 5-10-5 MOE | 453 |
| 588555 | 7643 | 0 | 5-10-5 MOE | 455 |
| 588848 | 7639 | 1 | Deoxy, MOE and cEt | 598 |
| 594430 | 6790 | 0 | 3-10-3 cEt | 549 |

Treatment

Prior to the study, the monkeys were kept in quarantine for at least a 30 day period, during which the animals were observed daily for general health. The monkeys were 2-4 years old and weighed between 2 and 4 kg. Eleven groups of 4-6 randomly assigned male cynomolgus monkeys each were injected subcutaneously with ISIS oligonucleotide or PBS at four sites on the back in a clockwise rotation (i.e. left, top, right, and bottom), one site per dose. The monkeys were given four loading doses of PBS or 40 mg/kg of ISIS 532800, ISIS 532809, ISIS 588540, ISIS 588544, ISIS 588548, ISIS 588550, ISIS 588553, ISIS 588555, ISIS 588848, or ISIS 594430 for the first week (days 1, 3, 5, and 7), and were subsequently dosed once a week for 12 weeks (days 14, 21, 28, 35, 42, 49, 56, 63, 70, 77, and 84) with PBS or 40 mg/kg of ISIS oligonucleotide. ISIS 532770 was tested in a separate study with similar conditions with two male and two female cynomolgus monkeys in the group.

Hepatic Target Reduction
RNA Analysis

On day 86, liver and kidney samples were collected in duplicate (approximately 250 mg each) for CFB mRNA analysis. The samples were flash frozen in liquid nitrogen at necropsy within approximately 10 minutes of sacrifice.

RNA was extracted from liver and kidney for real-time PCR analysis of measurement of mRNA expression of CFB. Results are presented as percent change of mRNA, relative to PBS control, normalized with RIBOGREEN®. RNA levels were also normalized with the house-keeping gene, Cyclophilin A. RNA levels were measured with the primer probe sets RTS3459, described above, or RTS4445_MGB (forward sequence CGAAGAAGCTCAGTGAAATCAA, designated herein as SEQ ID NO: 819; reverse sequence TGCCTGGAGGGCCCTCTT, designated herein as SEQ ID NO: 820; probe sequence AGACCACAAGTTGAAGTC, designated herein as SEQ ID NO: 815).

As shown in the Tables below, treatment with ISIS antisense oligonucleotides resulted in reduction of CFB mRNA in comparison to the PBS control. Analysis of CFB mRNA levels revealed that several of the ISIS oligonucleotides reduced CFB levels in liver and/or kidney. Here '0' indicates that the expression levels were not inhibited. '*' indicates that the oligonucleotide was tested in a separate study with similar conditions.

TABLE 220

Percent inhibition of CFB mRNA in the cynomolgus monkey liver relative to the PBS control

| ISIS No | RTS3459/ Cyclophilin A | RTS3459/ RIBOGREEN | RTS445_MGB/ Cyclophilin A | RTS445_MGB/ RIBOGREEN |
|---|---|---|---|---|
| 532770* | 12 | 37 | 24 | 45 |
| 532800 | 54 | 45 | 56 | 46 |
| 588540 | 31 | 27 | 28 | 24 |
| 588548 | 68 | 67 | 68 | 67 |
| 588550 | 53 | 39 | 51 | 37 |
| 588553 | 74 | 59 | 74 | 59 |
| 588555 | 73 | 71 | 71 | 69 |
| 588848 | 9 | 0 | 6 | 0 |
| 594430 | 24 | 26 | 23 | 25 |

TABLE 221

Percent inhibition of CFB mRNA in the cynomolgus monkey kidney relative to the PBS control

| ISIS No | RTS3459/ Cyclophilin A | RTS3459/ RIBOGREEN | RTS445_MGB/ Cyclophilin A | RTS445_MGB/ RIBOGREEN |
|---|---|---|---|---|
| 532770* | 34 | 56 | 2 | 31 |
| 532800 | 36 | 30 | 43 | 37 |
| 588540 | 70 | 71 | 67 | 69 |
| 588548 | 83 | 84 | 82 | 83 |
| 588550 | 81 | 77 | 78 | 74 |
| 588553 | 86 | 84 | 86 | 85 |
| 588555 | 32 | 34 | 48 | 50 |

TABLE 221-continued

Percent inhibition of CFB mRNA in the cynomolgus monkey kidney relative to the PBS control

| ISIS No | RTS3459/ Cyclophilin A | RTS3459/ RIBOGREEN | RTS445_MGB/ Cyclophilin A | RTS445_MGB/ RIBOGREEN |
|---|---|---|---|---|
| 588848 | 89 | 91 | 87 | 90 |
| 594430 | 33 | 37 | 19 | 23 |

Protein Analysis

Approximately 1 mL of blood was collected from all available animals at day 85 and placed in tubes containing the potassium salt of EDTA. The blood samples were placed in wet-ice or Kryorack immediately, and centrifuged (3000 rpm for 10 min at 4° C.) to obtain plasma (approximately 0.4 mL) within 60 minutes of collection. Plasma levels of CFB were measured in the plasma by radial immunodiffusion (RTD), using a polyclonal anti-Factor B antibody. The results are presented in the Table below. ISIS 532770 was tested in a separate study and plasma protein levels were measured on day 91 or 92 in that group.

Analysis of plasma CFB revealed that several ISIS oligonucleotides reduced protein levels in a sustained manner. ISIS 532770, which was tested in a separate study, reduced CFB protein levels on day 91/92 by 50% compared to baseline values. The reduction in plasma CFB protein levels correlates well with liver CFB mRNA level reduction in the corresponding groups of animals.

TABLE 222

Plasma protein levels (% baseline values) in the cynomolgus monkey

| | Day 1 | Day 30 | Day 58 | Day 72 | Day 86 |
|---|---|---|---|---|---|
| PBS | 113 | 115 | 95 | 83 | 86 |
| ISIS 532800 | 117 | 68 | 52 | 39 | 34 |
| ISIS 532809 | 104 | 121 | 100 | 80 | 71 |
| ISIS 588540 | 108 | 72 | 61 | 40 | 38 |
| ISIS 588544 | 118 | 74 | 53 | 33 | 29 |
| ISIS 588548 | 110 | 41 | 28 | 20 | 16 |
| ISIS 588550 | 104 | 64 | 54 | 38 | 37 |
| ISIS 588553 | 97 | 42 | 35 | 18 | 16 |
| ISIS 588555 | 107 | 35 | 37 | 18 | 18 |
| ISIS 588848 | 116 | 95 | 92 | 69 | 71 |
| ISIS 594430 | 104 | 64 | 59 | 45 | 46 |

Tolerability Studies
Body Weight Measurements

To evaluate the effect of ISIS oligonucleotides on the overall health of the animals, body and organ weights were measured and are presented in the Table below. '*' indicates that the oligonucleotide was tested in a separate study with similar conditions and is the average of the measurements from male and female monkeys. The results indicate that effect of treatment with antisense oligonucleotides on body and organ weights was within the expected range for antisense oligonucleotides.

TABLE 223

Final body weights (g) in cynomolgus monkey

| | Day 1 | Day 14 | Day 28 | Day 42 | Day 56 | Day 70 | Day 84 |
|---|---|---|---|---|---|---|---|
| PBS | 2887 | 2953 | 3028 | 3094 | 3125 | 3143 | 3193 |
| ISIS 532770* | 2963 | 2947 | 2966 | 3050 | 3097 | 3138 | 3160 |

TABLE 223-continued

Final body weights (g) in cynomolgus monkey

| | Day 1 | Day 14 | Day 28 | Day 42 | Day 56 | Day 70 | Day 84 |
|---|---|---|---|---|---|---|---|
| ISIS 532800 | 2886 | 2976 | 3072 | 3149 | 3220 | 3269 | 3265 |
| ISIS 532809 | 2755 | 2836 | 2927 | 2983 | 3019 | 3071 | 3098 |
| ISIS 588540 | 2779 | 2834 | 2907 | 2934 | 2981 | 3034 | 3057 |
| ISIS 588544 | 2837 | 2896 | 3009 | 3064 | 3132 | 3163 | 3199 |
| ISIS 588548 | 2694 | 2816 | 2882 | 2990 | 3073 | 3149 | 3161 |
| ISIS 588550 | 2855 | 2988 | 3062 | 3188 | 3219 | 3282 | 3323 |
| ISIS 588553 | 3033 | 3156 | 3256 | 3335 | 3379 | 3372 | 3442 |
| ISIS 588555 | 2757 | 2863 | 2965 | 3022 | 3075 | 3088 | 3158 |
| ISIS 588848 | 2850 | 3018 | 3032 | 3187 | 3230 | 3212 | 3291 |
| ISIS 594430 | 2884 | 2963 | 2953 | 3149 | 3187 | 3204 | 3256 |

TABLE 224

Final organ weights (g) in cynomolgus monkey

| | Spleen | Heart | Kidney | Liver |
|---|---|---|---|---|
| PBS | 2.8 | 11.6 | 11.9 | 55.8 |
| ISIS 532770* | 5.0 | 11.3 | 20.6 | 77.9 |
| ISIS 532800 | 6.2 | 11.9 | 18.6 | 94.4 |
| ISIS 588540 | 4.0 | 11.4 | 13.5 | 67.1 |
| ISIS 588548 | 4.1 | 11.7 | 17.3 | 72.0 |
| ISIS 588550 | 5.8 | 10.9 | 18.5 | 81.8 |
| ISIS 588553 | 5.0 | 12.7 | 17.2 | 85.9 |
| ISIS 588555 | 4.7 | 11.8 | 15.9 | 88.3 |
| ISIS 588848 | 5.0 | 12.7 | 14.4 | 75.7 |
| ISIS 594430 | 3.9 | 11.9 | 14.8 | 69.9 |

Liver Function

To evaluate the effect of ISIS oligonucleotides on hepatic function, blood samples were collected from all the study groups. The blood samples were collected from the cephalic, saphenous, or femoral veins, 48 hours post-dosing. The monkeys were fasted overnight prior to blood collection. Blood (1.5 mL) was collected in tubes without anticoagulant for serum separation. The tubes were kept at room temperature for a minimum of 90 minutes and then centrifuged (approximately 3,000 rpm for 10 min) to obtain serum. Levels of various liver function markers were measured using a Toshiba 200FR NEO chemistry analyzer (Toshiba Co., Japan).

Plasma levels of ALT and AST were measured and the results are presented in the Table below, expressed in IU/L. Bilirubin, a liver function marker, was similarly measured and is presented in the Table below expressed in mg/dL. '*' indicates that the oligonucleotide was tested in a separate study with similar conditions and is the average of the measurements from male and female monkeys. The results indicate that most of the antisense oligonucleotides had no effect on liver function outside the expected range for antisense oligonucleotides.

TABLE 225

Liver chemistry marker levels in cynomolgus monkey plasma on day 86

|  | ALT (IU/L) | AST (IU/L) | Bilirubin (mg/dL) |
|---|---|---|---|
| PBS | 71 | 57 | 0.3 |
| ISIS 532770* | 59 | 58 | 0.1 |
| ISIS 532800 | 65 | 86 | 0.1 |
| ISIS 532809 | 35 | 58 | 0.1 |
| ISIS 588540 | 70 | 88 | 0.2 |
| ISIS 588544 | 55 | 97 | 0.2 |
| ISIS 588548 | 61 | 85 | 0.2 |
| ISIS 588550 | 94 | 84 | 0.2 |
| ISIS 588553 | 44 | 65 | 0.2 |
| ISIS 588555 | 63 | 84 | 0.2 |
| ISIS 588848 | 69 | 65 | 0.2 |
| ISIS 594430 | 86 | 53 | 0.2 |

Kidney Function

To evaluate the effect of ISIS oligonucleotides on kidney function, blood samples were collected from all the study groups. The blood samples were collected from the cephalic, saphenous, or femoral veins, 48 hours post-dosing. The monkeys were fasted overnight prior to blood collection. Blood was collected in tubes without anticoagulant for serum separation. The tubes were kept at room temperature for a minimum of 90 minutes and then centrifuged (approximately 3,000 rpm for 10 min) to obtain serum. Levels of BUN and creatinine were measured using a Toshiba 200FR NEO chemistry analyzer (Toshiba Co., Japan). Results are presented in the Table below, expressed in mg/dL. '*' indicates that the oligonucleotide was tested in a separate study with similar conditions and is the average of the measurements from male and female monkeys.

For urinalysis, fresh urine from all the animals was collected in the morning using a clean cage pan on wet ice. Food was removed overnight the day before urine collection but water was supplied. Urine samples (approximately 1 mL) were analyzed for protein to creatinine (P/C) ratio using a Toshiba 200FR NEO automated chemistry analyzer (Toshiba Co., Japan). 'n.d.' indicates that the urine protein level was under the detection limit of the analyzer.

The plasma and urine chemistry data indicate that most of the ISIS oligonucleotides did not have any effect on the kidney function outside the expected range for antisense oligonucleotides.

TABLE 226

Renal chemistry marker levels (mg/dL) in cynomolgus monkey plasma on day 86

|  | BUN | Creatinine | Total protein |
|---|---|---|---|
| PBS | 28 | 0.9 | 8.0 |
| ISIS 532770* | 20 | 0.9 | 6.9 |
| ISIS 532800 | 25 | 0.9 | 7.5 |
| ISIS 532809 | 23 | 0.8 | 7.4 |
| ISIS 588540 | 30 | 0.8 | 7.5 |
| ISIS 588544 | 26 | 0.9 | 7.4 |
| ISIS 588548 | 25 | 0.9 | 7.6 |
| ISIS 588550 | 24 | 0.9 | 7.2 |
| ISIS 588553 | 25 | 0.8 | 7.2 |
| ISIS 588555 | 25 | 0.8 | 7.6 |
| ISIS 588848 | 24 | 0.9 | 7.5 |
| ISIS 594430 | 25 | 0.8 | 7.2 |

TABLE 227

Renal chemistry marker levels in cynomolgus monkey urine on day 44 and day 86

|  | Day 44 | Day 86 |
|---|---|---|
| PBS | 0.03 | n.d. |
| ISIS 532800 | 0.01 | n.d. |
| ISIS 532809 | 0.01 | n.d. |
| ISIS 588540 | 0.03 | n.d. |
| ISIS 588544 | 0.01 | 0.09 |
| ISIS 588548 | 0.01 | 0.01 |
| ISIS 588550 | 0.04 | 0.01 |
| ISIS 588553 | 0.05 | n.d. |
| ISIS 588555 | 0.03 | 0.03 |
| ISIS 588848 | 0.09 | n.d. |
| ISIS 594430 | 0.03 | n.d. |

Hematology

To evaluate any effect of ISIS oligonucleotides in cynomolgus monkeys on hematologic parameters, blood samples of approximately 0.5 mL of blood was collected from each of the available study animals in tubes containing $K_2$-EDTA. Samples were analyzed for red blood cell (RBC) count, white blood cells (WBC) count, individual white blood cell counts, such as that of monocytes, neutrophils, lymphocytes, as well as for platelet count, hemoglobin content and hematocrit, using an ADVIA120 hematology analyzer (Bayer, USA). The data is presented in the Tables below. '*' indicates that the oligonucleotide was tested in a separate study with similar conditions and is the average of the measurements from male and female monkeys.

The data indicate the oligonucleotides did not cause any changes in hematologic parameters outside the expected range for antisense oligonucleotides at this dose.

TABLE 228

Blood cell counts in cynomolgus monkeys

|  | RBC ($\times 10^6/\mu L$) | Platelets ($\times 10^3/\mu L$) | WBC ($\times 10^3/\mu L$) | Neutrophils (% WBC) | Lymphocytes (% total) | Monocytes (% total) |
|---|---|---|---|---|---|---|
| PBS | 5.8 | 347 | 9.4 | 42.7 | 53.1 | 3.0 |
| ISIS 532770* | 5.4 | 386 | 10.8 | 22.3 | 71.7 | 3.3 |
| ISIS 532800 | 5.6 | 360 | 13.1 | 29.5 | 61.1 | 6.5 |
| ISIS 532809 | 5.2 | 400 | 11.5 | 56.6 | 38.2 | 2.5 |
| ISIS 588540 | 5.5 | 367 | 11.7 | 50.9 | 42.7 | 2.1 |
| ISIS 588544 | 5.2 | 373 | 14.3 | 56.6 | 37.6 | 4.3 |
| ISIS 588548 | 5.1 | 373 | 9.7 | 40.4 | 54.3 | 3.9 |
| ISIS 588550 | 6.1 | 343 | 9.9 | 32.1 | 61.7 | 4.6 |
| ISIS 588553 | 5.2 | 424 | 9.3 | 41.7 | 53.2 | 3.6 |
| ISIS 588555 | 5.1 | 411 | 9.6 | 45.1 | 49.7 | 3.5 |

TABLE 228-continued

Blood cell counts in cynomolgus monkeys

| | RBC (×10⁶/μL) | Platelets (×10³/μL) | WBC (×10³/μL) | Neutrophils (% WBC) | Lymphocytes (% total) | Monocytes (% total) |
|---|---|---|---|---|---|---|
| ISIS 588848 | 5.7 | 370 | 10.0 | 39.8 | 55.8 | 3.1 |
| ISIS 594430 | 5.7 | 477 | 10.6 | 47.3 | 47.8 | 3.6 |

TABLE 229

Hematologic parameters in cynomolgus monkeys

| | Hemoglobin (g/dL) | HCT (%) |
|---|---|---|
| PBS | 14.1 | 46.6 |
| ISIS 532770* | 12.4 | 40.9 |
| ISIS 532800 | 12.3 | 40.5 |
| ISIS 532809 | 12.2 | 40.4 |
| ISIS 588540 | 12.5 | 41.5 |
| ISIS 588544 | 11.9 | 38.1 |
| ISIS 588548 | 12.3 | 39.6 |
| ISIS 588550 | 13.4 | 45.0 |
| ISIS 588553 | 12.6 | 39.8 |
| ISIS 588555 | 11.6 | 38.1 |
| ISIS 588848 | 13.2 | 42.7 |
| ISIS 594430 | 13.4 | 43.1 |

Measurement of Oligonucleotide Concentration

The concentration of the full-length oligonucleotide was measured in the kidney and liver tissues. The method used is a modification of previously published methods (Leeds et al., 1996; Geary et al., 1999) which consist of a phenol-chloroform (liquid-liquid) extraction followed by a solid phase extraction. Tissue sample concentrations were calculated using calibration curves, with a lower limit of quantitation (LLOQ) of approximately 1.14 μg/g. The results are presented in the Table below, expressed as μg/g liver or kidney tissue.

TABLE 230

Antisense oligonucleotide distribution

| | Kidney (μg/g) | Liver (μg/g) | Kidney/Liver ratio |
|---|---|---|---|
| ISIS 532800 | 3881 | 1633 | 2.4 |
| ISIS 588540 | 3074 | 1410 | 2.2 |
| ISIS 588548 | 3703 | 1233 | 3.0 |
| ISIS 588550 | 4242 | 860 | 4.9 |
| ISIS 588553 | 3096 | 736 | 4.2 |
| ISIS 588555 | 4147 | 1860 | 2.2 |
| ISIS 588848 | 2235 | 738 | 3.0 |
| ISIS 594430 | 1548 | 752 | 2.1 |

Example 135: 6 Week Efficacy Study of Unconjugated and 5'-THA-GalNAc₃ Conjugated Antisense Oligonucleotides Targeted to Human CFB in Transgenic Mice Two antisense oligonucleotides having the same nucleobase sequence: unconjugated antisense oligonucleotide ISIS 588540 and 5'-THA-GalNAc₃-conjugated antisense oligonucleotide ISIS 696844, were tested in human CFB transgenic mice (hCFB-Tg mice).

The mice were administered subcutaneously with ISIS 696844 at doses of 0.1, 1.25, 0.5, 2.0, 6.0, or 12.0 mg/kg/week or with ISIS 588540 at doses of 2, 6, 12, 25, or 50 mg/kg/week for 6 weeks. A control group of mice were administered subcutaneously with PBS for 6 weeks. Mice were sacrificed 48 hours after the last dose. Hepatic mRNA levels were analyzed by qRT-PCR.

Study 1

The results are presented in the Table below and demonstrate that the 5'-THA-GalNAc₃-conjugated antisense oligonucleotide targeting CFB is more potent than the unconjugated antisense oligonucleotide with the same sequence.

TABLE 231

Efficacy of antisense oligonucleotides targeting CFB

| | $ED_{50}$ (mg/kg) | $ED_{75}$ (mg/kg) |
|---|---|---|
| ISIS 588540 | 4.52 | 9.26 |
| ISIS 696844 | 0.52 | 1.12 |

Study 2

Liver mRNA levels were measured with two different primer probe sets targeting different regions of the mRNA and normalized to either RIBOGREEN® (RGB) or Cyclophilin. The primer probe sets were RTS3459, described above, and RTS3460 (forward sequence CGAAGCAGCT-CAATGAAATCAA, designated herein as SEQ ID NO: 813; reverse sequence TGCCTGGAGGGCCTTCTT, designated herein as SEQ ID NO: 814; probe sequence AGAC-CACAAGTTGAAGTC, designated herein as SEQ ID NO: 815). The results are presented in the Table below and demonstrate that the 5'-THA-GalNAc₃-conjugated antisense oligonucleotide targeting CFB is more potent than the unconjugated antisense oligonucleotide with the same sequence, irrespective of the primer probe set used.

TABLE 231

Efficacy of antisense oligonucleotides targeting CFB

| | $ED_{50}$ RTS3459 (RGB) | $ED_{50}$ RTS3460 (RGB) | $ED_{50}$ RTS3459 (Cyclophilin) | $ED_{50}$ RTS3460 (Cyclophilin) | $ED_{75}$ RTS3459 (RGB) | $ED_{75}$ RTS3460 (RGB) | $ED_{75}$ RTS3459 (Cyclophilin) | $ED_{75}$ RTS3460 (Cyclophilin) |
|---|---|---|---|---|---|---|---|---|
| ISIS 588540 | 4.5 | 4.1 | 5.2 | 5.4 | 9.3 | 10.0 | 10.0 | 9.3 |
| ISIS 696844 | 0.5 | 0.5 | 0.6 | 0.5 | 1.1 | 1.3 | 1.2 | 0.9 |

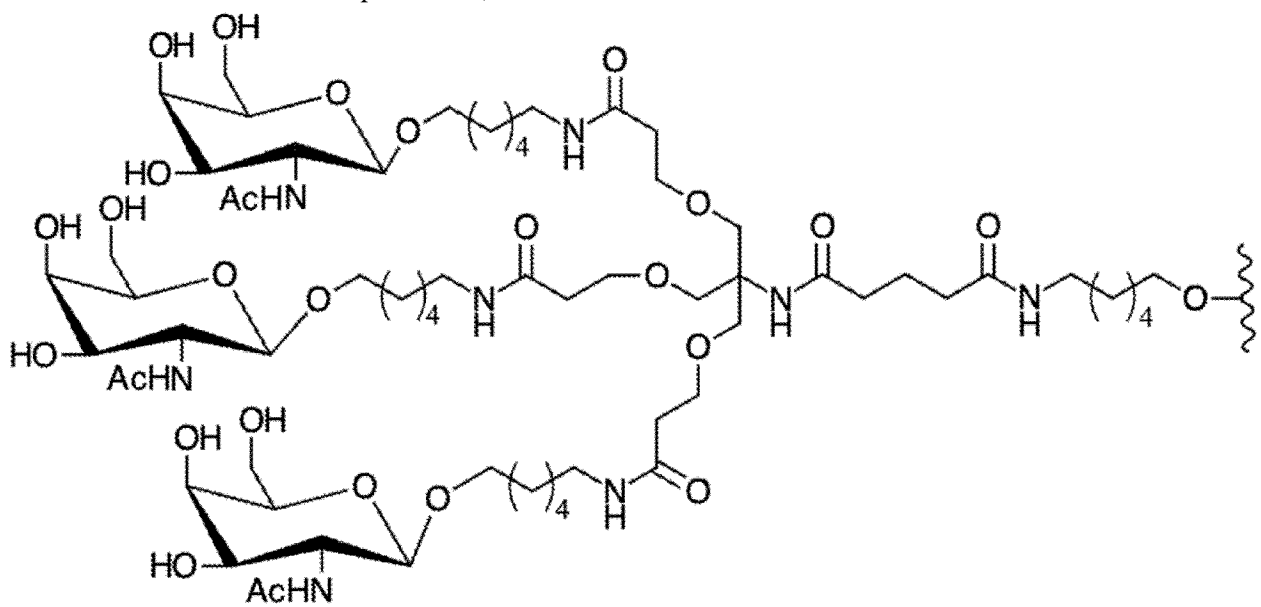

What is claimed:

1. A modified single-stranded oligonucleotide covalently attached to a conjugate group, wherein the modified single-stranded oligonucleotide consists of 10 to 30 linked nucleosides and has a nucleobase sequence comprising at least 8 contiguous nucleobases of the nucleobase sequence of SEQ ID NO: 455, and wherein the conjugate group covalently attached to the modified single-stranded oligonucleotide comprises:

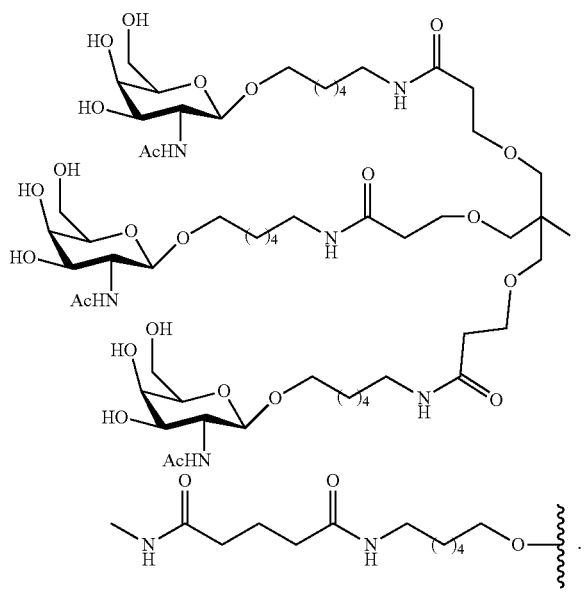

2. The modified single-stranded oligonucleotide covalently attached to a conjugate group of claim 1, wherein the modified single-stranded oligonucleotide has:
   a gap segment consisting of linked deoxynucleosides;
   a 5' wing segment consisting of linked nucleosides; and
   a 3' wing segment consisting of linked nucleosides;
   wherein the gap segment is positioned between the 5' wing segment and the 3' wing segment and wherein each nucleoside of each wing segment comprises a modified sugar.

3. The modified single-stranded oligonucleotide covalently attached to a conjugate group of claim 1, wherein the modified single-stranded oligonucleotide is at least 85% complementary to SEQ ID NO: 1.

4. The modified single-stranded oligonucleotide covalently attached to a conjugate group of claim 1, wherein the modified single-stranded oligonucleotide comprises at least one modified internucleoside linkage, at least one modified sugar, or at least one modified nucleobase.

5. The modified single-stranded oligonucleotide covalently attached to a conjugate group of claim 4, wherein the modified single-stranded oligonucleotide comprises at least one modified internucleoside linkage.

6. The modified single-stranded oligonucleotide covalently attached to a conjugate group of claim 5, wherein the modified internucleoside linkage is a phosphorothioate internucleoside linkage.

7. The modified single-stranded oligonucleotide covalently attached to a conjugate group of claim 6, wherein the modified single-stranded oligonucleotide comprises at least 1 phosphodiester internucleoside linkage.

8. The modified single-stranded oligonucleotide covalently attached to a conjugate group of claim 7, wherein each internucleoside linkage of the modified single-stranded oligonucleotide is selected from a phosphodiester internucleoside linkage and a phosphorothioate internucleoside linkage.

9. The modified single-stranded oligonucleotide covalently attached to a conjugate group of claim 4, wherein each internucleoside linkage of the modified single-stranded oligonucleotide comprises a phosphorothioate internucleoside linkage.

10. The modified single-stranded oligonucleotide covalently attached to a conjugate group of claim 4, wherein the modified sugar is a bicyclic sugar.

11. The modified single-stranded oligonucleotide covalently attached to a conjugate group of claim 10, wherein the bicyclic sugar is selected from the group consisting of: 4'-($CH_2$)—O-2' (LNA); 4'-($CH_2$)$_2$—O-2' (ENA); and 4'-CH($CH_3$)—O-2' (cEt).

12. The modified single-stranded oligonucleotide covalently attached to a conjugate group of claim 4, wherein the modified sugar is 2'-O-methoxyethyl.

13. The modified single-stranded oligonucleotide covalently attached to a conjugate group of claim 4, wherein the modified nucleobase is 5-methylcytosine.

14. A modified double-stranded oligonucleotide comprising the modified single-stranded oligonucleotide covalently attached to a conjugate group of claim 1, and a second single stranded oligonucleotide hybridized to said modified single stranded oligonucleotide.

15. The modified single-stranded oligonucleotide covalently attached to a conjugate group of claim 1, wherein the conjugate group is linked to the modified oligonucleotide at the 5' end of the modified oligonucleotide.

16. The modified single-stranded oligonucleotide covalently attached to a conjugate group of claim 1, wherein the conjugate group is linked to the modified oligonucleotide at the 3' end of the modified oligonucleotide.

17. A method of treating a disease associated with dysregulation of the complement alternative pathway in a subject comprising administering to the subject the modified single-stranded oligonucleotide covalently attached to a conjugate group of claim 1, or a pharmaceutically acceptable salt thereof, thereby treating the disease.

18. The method of claim 17, wherein the disease is macular degeneration, age related macular degeneration (AMD), wet AMD, dry AMD, or Geographic Atrophy.

19. The method of claim 17, wherein the disease is a kidney disease.

20. The method of claim 19, wherein the kidney disease is lupus nephritis, systemic lupus erythematosus (SLE), dense deposit disease (DDD), C3 glomerulonephritis (C3GN), CFHR5 nephropathy, IgA nephropathy, or atypical hemolytic uremic syndrome (aHUS).

21. A modified single-stranded oligonucleotide covalently attached to a conjugate group, wherein the modified single-stranded oligonucleotide consists of 20 to 30 linked nucleosides and has a nucleobase sequence comprising the nucleobase sequence of SEQ ID NO: 455, and wherein the conjugate group covalently attached to the modified single-stranded oligonucleotide comprises:

22. The modified single-stranded oligonucleotide covalently attached to a conjugate group of claim 21, wherein the modified single-stranded oligonucleotide consists of the nucleobase sequence of SEQ ID NO: 455.

23. The modified single-stranded oligonucleotide covalently attached to a conjugate group of claim 21, wherein the modified single-stranded oligonucleotide consists of 20 linked nucleosides and has a nucleobase sequence consisting of the nucleobase sequence of SEQ ID NO: 455, and wherein the modified single-stranded oligonucleotide has:
a gap segment consisting of ten linked deoxynucleosides;
a 5' wing segment consisting of five linked nucleosides; and
a 3' wing segment consisting of five linked nucleosides;
wherein the gap segment is positioned between the 5' wing segment and the 3' wing segment, wherein each nucleoside of each wing segment comprises a 2'-O-methoxyethyl sugar;
wherein each internucleoside linkage of the modified single-stranded oligonucleotide is a phosphorothioate linkage, and wherein each cytosine is 5-methylcytosine.

24. The modified single-stranded oligonucleotide covalently attached to a conjugate group of claim 23, wherein the modified single-stranded oligonucleotide has a nucleobase sequence consisting of the nucleobase sequence of SEQ ID NO: 455.

25. A method of treating a disease associated with dysregulation of the complement alternative pathway in a subject comprising administering to the subject the modified single-stranded oligonucleotide covalently attached to a conjugate group of claim 23, or a pharmaceutically acceptable salt thereof, thereby treating the disease.

26. The method of claim 25, wherein the disease is macular degeneration, age related macular degeneration (AMD), wet AMD, dry AMD, or Geographic Atrophy.

27. The method of claim 26, wherein the disease is a kidney disease.

28. The method of claim 27, wherein the kidney disease is lupus nephritis, systemic lupus erythematosus (SLE), dense deposit disease (DDD), C3 glomerulonephritis (C3GN), CFHR5 nephropathy, IgA nephropathy, or atypical hemolytic uremic syndrome (aHUS).

* * * * *

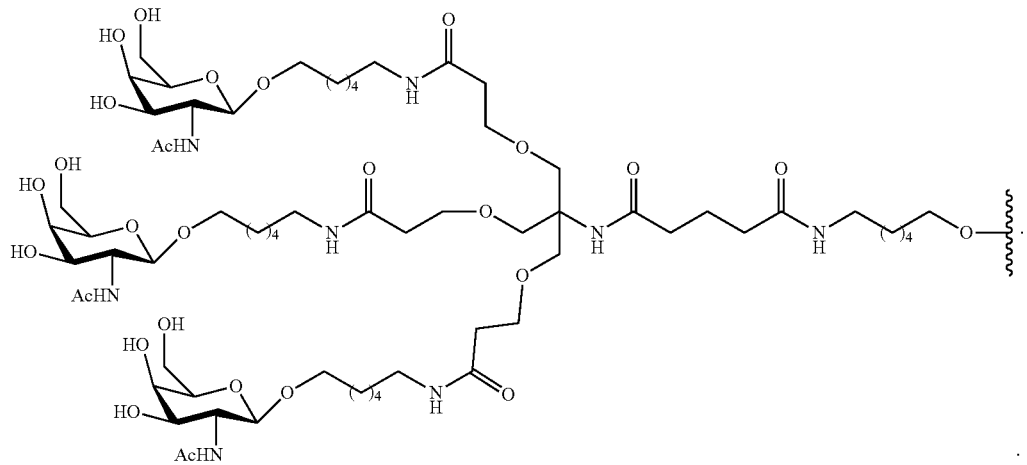

UNITED STATES PATENT AND TRADEMARK OFFICE
CERTIFICATE OF CORRECTION

PATENT NO. : 11,732,265 B2
APPLICATION NO. : 17/314537
DATED : August 22, 2023
INVENTOR(S) : Thazha P. Prakash et al.

It is certified that error appears in the above-identified patent and that said Letters Patent is hereby corrected as shown below:

On the Title Page

Item (60) (Related U.S. Application Data section), the following text:
"(60) Continuation of application No. 16/357,018, filed on Mar. 18, 2019, now abandoned, which is a division of application No. 15/307,526, filed as application No. PCT/US2015/028916 on May, 12015, now Pat. No. 10,280.423."
Should read:
"(60) Continuation of application No. 16/357,018, filed on Mar. 18, 2019, now abandoned, which is a division of application No. 15/307,526, filed on Oct. 28, 2016, now Pat. No. 10,280,423, which is a 371 of PCT/US2015/028916, filed on May 1, 2015."

Signed and Sealed this
Second Day of January, 2024

Katherine Kelly Vidal
*Director of the United States Patent and Trademark Office*

CERTIFICATE OF CORRECTION (continued)
U.S. Pat. No. 11,732,265 B2

In the Claims

In Column 927, Lines 34-57 (i.e., Claim 1), the chemical structure is listed in the following broken form:

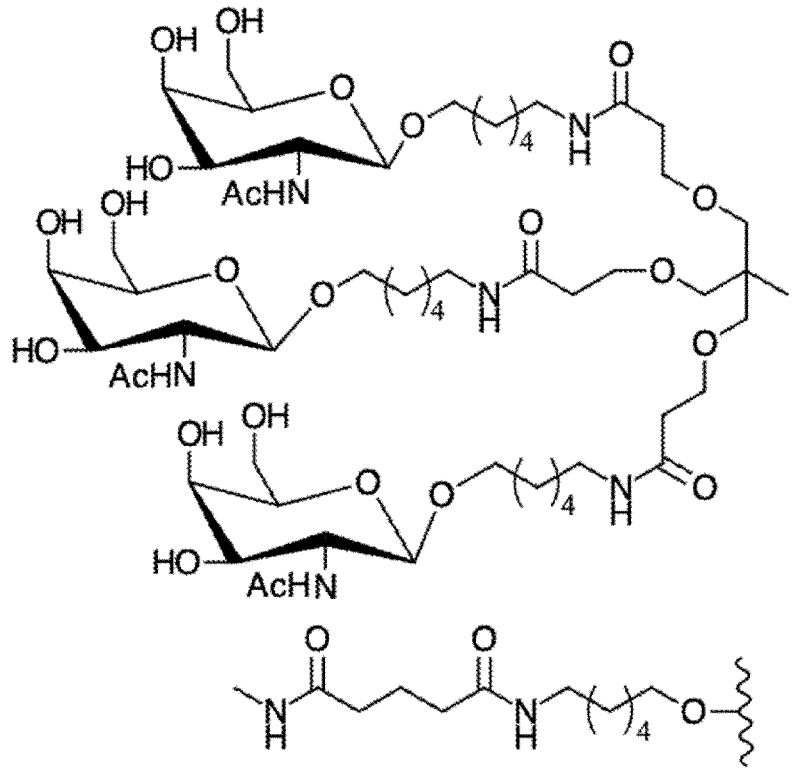

But should be listed in its complete form, as follows:

SEQUENCE LISTING

<160> NUMBER OF SEQ ID NOS: 854

<210> SEQ ID NO 1
<211> LENGTH: 2646
<212> TYPE: DNA
<213> ORGANISM: Homo sapiens

<400> SEQUENCE: 1

| | | | | | |
|---|---|---|---|---|---|
| gacttctgca | gtttctgttt | ccttgactgg | cagctcagcg | ggccctccc | gcttggatgt | 60 |
| tccgggaaag | tgatgtgggt | aggacaggcg | gggcgagccg | caggtgccag | aacacagatt | 120 |
| gtataaaagg | ctgggggctg | gtggggagca | ggggaaggga | atgtgaccag | gtctaggtct | 180 |
| ggagtttcag | cttggacact | gagccaagca | gacaagcaaa | gcaagccagg | acacaccatc | 240 |
| ctgccccagg | cccagcttct | ctcctgcctt | ccaacgccat | ggggagcaat | ctcagccccc | 300 |
| aactctgcct | gatgcccttt | atcttgggcc | tcttgtctgg | aggtgtgacc | accactccat | 360 |
| ggtctttggc | ccggccccag | ggatcctgct | ctctggaggg | gtagagatc | aaaggcggct | 420 |
| ccttccgact | tctccaagag | ggccaggcac | tggagtacgt | gtgtccttct | ggcttctacc | 480 |
| cgtaccctgt | gcagacacgt | acctgcagat | ctacggggtc | ctggagcacc | ctgaagactc | 540 |
| aagaccaaaa | gactgtcagg | aaggcagagt | gcagagcaat | ccactgtcca | agaccacacg | 600 |
| acttcgagaa | cggggaatac | tggccccggt | ctccctacta | caatgtgagt | gatgagatct | 660 |
| ctttccactg | ctatgacggt | tacactctcc | ggggctctgc | caatcgcacc | tgccaagtga | 720 |
| atggccgatg | gagtgggcag | acagcgatct | gtgacaacgg | agcggggtac | tgctccaacc | 780 |
| cgggcatccc | cattggcaca | aggaaggtgg | gcagccagta | ccgccttgaa | gacagcgtca | 840 |
| cctaccactg | cagccggggg | cttaccctgc | gtggctccca | gcggcgaacg | tgtcaggaag | 900 |
| gtggctcttg | gagcgggacg | gagccttcct | gccaagactc | cttcatgtac | gacaccctc | 960 |
| aagaggtggc | cgaagctttc | ctgtcttccc | tgacagagac | catagaagga | gtcgatgctg | 1020 |
| aggatgggca | cggcccaggg | gaacaacaga | agcggaagat | cgtcctggac | ccttcaggct | 1080 |
| ccatgaacat | ctacctggtg | ctagatggat | cagacacgca | tggggccagc | aacttcacag | 1140 |
| gagccaaaaa | gtgtctagtc | aacttaattg | agaaggtggc | aagttatggt | gtgaagccaa | 1200 |
| gatatggtct | agtgacatat | gccacatacc | ccaaaatttg | ggtcaaagtg | tctgaagcag | 1260 |
| acagcagtaa | tgcagactgg | gtcacgaagc | agctcaatga | aatcaattat | gaagaccaca | 1320 |
| agttgaagtc | agggactaac | accaagaagg | ccctccaggc | agtgtacagc | atgatgagct | 1380 |
| ggccagatga | cgtccctcct | gaaggctgga | accgcacccg | ccatgtcatc | atcctcatga | 1440 |
| ctgatggatt | gcacaacatg | ggcgggaccc | caattactgt | cattgatgag | atccgggact | 1500 |
| tgctatacat | tggcaaggat | cgcaaaaacc | caagggagga | ttatctggat | gtctatgtgt | 1560 |
| ttgggggtcgg | gccttttggtg | aaccaagtga | acatcaatgc | tttggcttcc | aagaaagaca | 1620 |
| atgagcaaca | tgtgttcaaa | gtcaaggata | tggaaaacct | ggaagatgtt | ttctaccaaa | 1680 |
| tgatcgatga | aagccagtct | ctgagtctct | gtggcatggt | ttggaacac | aggaagggta | 1740 |
| ccgattacca | caagcaacca | tggcaggcca | agatctcagt | cattcgccct | tcaaagggac | 1800 |
| acgagagctg | tatgggggct | gtggtgtctg | agtactttgt | gctgacagca | gcacattgtt | 1860 |
| tcactgtgga | tgacaaggaa | cactcaatca | ggtcagcgt | aggaggggag | aagcgggacc | 1920 |
| tggagatag | agtagtccta | tttcacccca | actacaacat | taatgggaaa | aagaagcag | 1980 |
| gaattcctga | attttatgac | tatgacgttg | ccctgatcaa | gctcaagaat | aagctgaaat | 2040 |
| atggccagac | tatcaggccc | atttgtctcc | cctgcaccga | gggaacaact | cgagctttga | 2100 |

-continued

| | |
|---|---|
| ggcttcctcc aactaccact tgccagcaac aaaaggaaga gctgctccct gcacaggata | 2160 |
| tcaaagctct gtttgtgtct gaggaggaga aaaagctgac tcggaaggag gtctacatca | 2220 |
| agaatgggga taagaaaggc agctgtgaga gagatgctca atatgcccca ggctatgaca | 2280 |
| aagtcaagga catctcagag gtggtcaccc ctcggttcct ttgtactgga ggagtgagtc | 2340 |
| cctatgctga ccccaatact tgcagaggtg attctggcgg cccccttgata gttcacaaga | 2400 |
| gaagtcgttt cattcaagtt ggtgtaatca gctggggagt agtggatgtc tgcaaaaacc | 2460 |
| agaagcggca aaagcaggta cctgctcacg cccgagactt tcacatcaac ctctttcaag | 2520 |
| tgctgccctg gctgaaggag aaactccaag atgaggattt gggttttcta aagggggttt | 2580 |
| cctgctggac aggggcgtgg gattgaatta aacagctgc gacaacaaaa aaaaaaaaa | 2640 |
| aaaaaa | 2646 |

<210> SEQ ID NO 2
<211> LENGTH: 9001
<212> TYPE: DNA
<213> ORGANISM: Homo sapiens

<400> SEQUENCE: 2

| | |
|---|---|
| ggaggtgagg gtctcaggtt ggggatgctg ggatcccct gtgacagctc ccagaatgtc | 60 |
| tctcttcctt ctccaggtct ggctgctttc tctctctgac gcgggtcacc cctcctccca | 120 |
| agcctcacaa acctgctagg tgtccctggg tctgcttatt ctttttttgt tgttattgag | 180 |
| atggagtctt gctctgtctc ccaggctgga gtgcagtggc acgacctcag ctcactgcaa | 240 |
| cttctgcctc ctgggttcaa gcgattctcc tacttcagcc tcccgagtag ctgagattac | 300 |
| aggtgcccac caccacacca gctaattttt gtattttag tagagacggg atttcgccat | 360 |
| gttggccagg atggtcttga actcctgacc tcaagtgatc tgcctgcctc aacctcccaa | 420 |
| agtgctgaga ttacaggcgt gagccactgc acccacccgg gtctgcttat tctacccttc | 480 |
| tctctggttc cacccctgct gcagtggaca agctgtgccg aggttgtctc ccaagaaaaa | 540 |
| accatgttcc caacttgac agatgtcagg gaggtggtga cagaccagtt cctatgcagt | 600 |
| gggacccagg aggatgagag tccctgcaag ggtgagtccc tcaccatgcc tggattccca | 660 |
| aggggaaggc cacctgtgtc tctgtggcca gcatgcatgc cagaacacca gtccactgcc | 720 |
| ctagatgaca ctgtctcctg tcacccttg ctggcaggaa atctgggggg agcagttttc | 780 |
| cttgagcgga gattcaggtt ttttcaggtg agaaggtaga agcttgcagg acccaggggt | 840 |
| tacaggatct cagccttgtt ggggggatga gggaggcctt tgagggatct agggaggttg | 900 |
| gggcttacag ttggggctgt ggcagcctcc cagccagttc tctccttttc tccaggtggg | 960 |
| tctggtgagc tggggtcttt acaacccctg ccttggctct gctgacaaaa actcccgcaa | 1020 |
| aagggcccct cgtagcaagg tcccgccgcc acgagacttt cacatcaatc tcttccgcat | 1080 |
| gcagccctgg ctgaggcagc acctggggga tgtcctgaat tttttacccc tctagccatg | 1140 |
| gccactgagc cctctgctgc cctgccagaa tctgccgccc ctccatcttc tacctctgaa | 1200 |
| tggccaccct tagaccctgt gatccatcct ctctcctagc tgagtaaatc cgggtctcta | 1260 |
| ggatgccaga ggcagcgcac acaagctggg aaatcctcag ggctcctacc agcaggactg | 1320 |
| cctcgctgcc ccacctcccg ctccttggcc tgtccccaga ttccttccct ggttgacttg | 1380 |
| actcatgctt gtttcacttt cacatggaat ttcccagtta tgaaattaat aaaaatcaat | 1440 |
| ggtttccaca tctctcagtg cctctatctg gaggccaggt agggctggcc ttgggggagg | 1500 |

```
gggaggccag aatgactcca agagctacag gaaggcaggt cagagacccc actggacaaa    1560
cagtggctgg actctgcacc ataacacaca atcaacaggg gagtgagctg gatccttatt    1620
tctggtccct aagtgggtgg tttgggctta ctggggagga gctaaggccg agaggaggt    1680 actgaagggg agagtcctgg acctttggca gcaaagggtg ggacttctgc agtttctgtt    1740
tccttgactg gcagctcagc ggggccctcc cgcttggatg ttccgggaaa gtgatgtggg    1800
taggacaggc ggggcgagcc gcaggtgcca gaacacagat tgtataaaag gctggggct    1860 ggtggggagc aggggaaggg aatgtgacca ggtctaggtc tggagtttca gcttggacac    1920
tgagccaagc agacaagcaa agcaagccag gacacaccat cctgcccag gcccagcttc    1980 tctcctgcct tccaacgcca tggggagcaa tctcagcccc caactctgcc tgatgccctt    2040
tatcttgggc ctcttgtctg gaggtaagcg agggtaacct tcccttcctg ctgtctccag    2100
catccctcct tggcctttg gggccaggct tcatcagcct ttctcttcag gtgtgaccac    2160
cactccatgg tctttggccc ggccccaggg atcctgctct ctggagggg tagagatcaa    2220 aggcggctcc ttccgacttc tccaagaggg ccaggcactg gagtacgtgt gtccttctgg    2280
cttctacccg tacccgtgc agacacgtac ctgcagatct acggggtcct ggagcaccct    2340
gaagactcaa gaccaaaaga ctgtcaggaa ggcagagtgc agaggtttga gggcaatgag    2400
tgtgggcagt ggcctaaggc agaaacaggg caggcggcag caaggtcagg actaggatga    2460
gactaggcag ggtgacaagg tgggctgacc gggagtagga gcagttttag ggtggcaggc    2520
ggaaaggggg caagaaaaag cggagttaac ccttactaag catttaccct gggcttccag    2580
gcagccctgg aagtcaagag aacactcaga aatgggagg gagaagcagt ggaaatccat    2640
atgggttgag gagtaggtaa gatgctgctt ctgcgggact gggaatgcgc tgtttctcag    2700
tgacatggtc tccgagacca ggagggatac acctaaggca gcctttccct cttgatgact    2760
tctacttgtc ccccttctc aaagcaatcc actgtccaag accacgcgac ttcgagaacg    2820
gggaatactg gccccggtct ccctactaca atgtgagtga tgagatctct ttccactgct    2880
atgacggtta cactctccgg ggctctgcca atcgcacctg ccaagtgaat ggccgatgga    2940
gtgggcagac agcgatctgt gacaacggag gtgagaagca tccccctcccc ctacattgct    3000 gtctccctga cggcgcccag cccgaggagt gggcactcgg ctccggacac tgtaactctt    3060
gctctctacc ttgctcacgg ggcctcaggc ttcagtgctt acctcgatgt tcatacctc    3120 tgcagcgggg tactgctcca acccgggcat ccccattggc acaaggaagg tgggcagcca    3180
gtaccgcctt gaagacagcg tcacctacca ctgcagccgg gggcttaccc tgcgtggctc    3240
ccagcggcga acgtgtcagg aaggtggctc ttggagcggg acggagcctt cctgccaagg    3300
tgacctttga cctgtacccc caggtcagat cctggtcttc catcctactg tcttctctcc    3360
ccacctcaac cctgctcttt cctcactttg tttaaacctc cctgtacaac tatctcactt    3420
ctgagccttt tataccctgg aaacccatga tcccccgtct ctttggtcac tgtatccctg    3480
acactcccag acatttgacc tcatttctga ctctcccaga ctccttcatg tacgacaccc    3540
ctcaagaggt ggccgaagct ttcctgtctt ccctgacaga gaccatagaa ggagtcgatg    3600
ctgaggatgg gcacggccca ggtttgaaga cagagaaggg aggcagggca gggaactggg    3660
ggaaaatgga gaagggacag aactgttaat gctggagcct gagccactct cctggcaccc    3720
aggggaacaa cagaagcgga agatcgtcct ggacccttca ggctccatga acatctacct    3780
ggtgctagat ggatcagaca gcattgggc cagcaacttc acaggagcca aaaagtgtct    3840
agtcaactta attgagaagg tggaatcctc ctatccctga actcggggga atggaatctc    3900
```

```
gctgatcttc caggactagc tccctgatca ttccagcccc tctgaacaac agggccccag   3960
gaaaatctcc aggtcctatt ctgtcctcct tcccttttac ttgaagcagt ttcttgactg   4020
gtaattcctc catgaacctc agcccttgag cctcttactg agagcctccc tgtcccagca   4080
aagtcgctga aatctcccaa tcacagtatt ctattttcaa tgccatggcg ccttgttctc   4140
ctcacccaca ggtggcaagt tatggtgtga agccaagata tggtctagtg acatatgcca   4200 catacccccaa aatttgggtc aaagtgtctg aagcagacag cagtaatgca gactgggtca   4260
cgaagcagct caatgaaatc aattatgaag gtcagaggtt agggaatggt gggaggttca   4320 cttttggggtc aggaggttca gggtggaggg ggtcatgaga ctaccttgag ggcgacaggg   4380
aggaccactt tgtagtcaaa agttgaacag caggatcgtt gggcaatgga ggttagtggg   4440
aacctgttgg gggctggaag ggccactttg tggtcaaagg gaagtccgtg taatgatgat   4500
taacttaaaa agttgaaaga tgtgggattt cagttgcaga ttggtctctg gggttaaaag   4560
atggcttgga agaccaggtg aagtgatggt ctcttccctc tccacagacc acaagttgaa   4620
gtcagggact aacaccaaga aggccctcca ggcagtgtac agcatgatga gctggccaga   4680
tgacgtccct cctgaaggct ggaaccgcac ccgccatgtc atcatcctca tgactgatgg   4740
tcagaaggga cctctctcct gtcccagcct ccccaccttc tcagaccagc atgtgggccct   4800 taagtccact tgtaacacta tacccatggt tggggccctg aatgtgactc atagctggct   4860
gttcatctct cctgtgaccc ttcataagga attcttccta agccctgtga tcaactatct   4920
ctaacccttc tcaacttgc tcaccctgcc atgtgtatcc ctgcctttag ccagtttatc   4980
ttccttatct cctaccctca tggtcctgtc tcttctgcag gattgcacaa catgggcggg   5040
gacccaatta ctgtcattga tgagatccgg gacttgctat acattggcaa ggatcgcaaa   5100
aacccaaggg aggattatct gggtgagtaa cctgcctagg acccagcacc ccacttcctc   5160
agggcttgga ccctcatcct tccttttat ccctcagatg tctatgtgtt tggggtcggg   5220
cctttggtga accaagtgaa catcaatgct ttggcttcca agaaagacaa tgagcaacat   5280
gtgttcaaag tcaaggatat ggaaaaacctg gaagatgttt tctaccaaat gatcggtagg   5340
gagatacaag ggaataaaga acacaactct cctcaggttc ccctgaagta attcattctt   5400
cctctacacc tgaagctcta gttgcctgga aagccttctt cattcctcct tctctacctc   5460
agtgtcacta ttcttgtttc ctggcactgt tcacttaacc ttagaatcac agagctctga   5520
gcacttcaga gatctttcta tagtcctaca tttgacacgt ggaaacagaa gccaaaggag   5580
gtcaagggac agcaagttag caacaagggt gggcttgaaa acagccaggc ctctgacagc   5640
ttgatcccaa gttctttccc ttttcagtcc accatagcag ttttctccta acacgaggaa   5700
acaaataccc gtggtcttc cctttctcct tttgggcctt tgctccccat agactcctac   5760
ccaaaaggct gctgccattt gggaatgaag tgttccgagt tttcagcaca ttctccttct   5820
ctgccagatg aaagccagtc tctgagtctc tgtggcatgg tttgggaaca caggaagggt   5880
accgattacc acaagcaacc atggcaggcc aagatctcag tcattgtaag cacagaatcc   5940
cagtagtggg gacttggggg aggtgaggtc aaggtgaaat gggagtaggg gaaggaaaaa   6000
atggccataa gagatggtgg tttgtgaaag ttgagctttc cctctctact gttgtgtccc   6060 cagcgcccctt caaagggaca cgagagctgt atggggctg tggtgtctga gtactttgtg   6120
ctgacagcag cacattgttt cactgtggat gacaaggaac actcaatcaa ggtcagcgta   6180
ggtaaggatg caactgaagg tcctgggctg cacctatgct ctccaggcaa cacctcccac   6240
```

```
tttctacaga tcctacactc cacccatcct caatgcagcc ccattccttg caccccagac    6300
cagtcaggga tggggaaga cgtgaagtta ggaatgacac ggggccagag gcaggaagct    6360
gcccacaaag aggtggtacc tactctccta cttcaggagg ggagaagcgg gacctggaga    6420
tagaagtagt cctatttcac cccaactaca acattaatgg gaaaaaagaa gcaggaattc    6480
ctgaatttta tgactatgac gttgccctga tcaagctcaa gaataagctg aaatatggcc    6540
agactatcag gtgagagcgt ccagatccct gaggaaaggc tgggaaaggc tggaggactg    6600
gggtgaggag caggcctggt ttgctgttct ccttgtcctt tataggccca tttgtctccc    6660
ctgcaccgag ggaacaactc gagctttgag gcttcctcca actaccactt gccagcaaca    6720
aagtaagaca tacttggcaa gaggataagg atgagatccc aagagacaag tggggcatga    6780
gagggaggtg caataggaag agatgatgcc tgcccagaa cctagctcta gaagggctta    6840
ggggacatct actgagtgac aaaggcaatg ggagatgac agtggtggga gcagctgaag    6900
tgacgcagtc tattcgtcca gaggaagagc tgctccctgc acaggatatc aaagctctgt    6960
ttgtgtctga ggaggagaaa aagctgactc ggaaggaggt ctacatcaag aatggggata    7020
aggtgagaaa cggcatcct aaggaggcac tctaggcccc aatccttcct aagccacttc     7080
tgttcattac ttctccatgc ttcccactc ccctacagaa aggcagctgt gagagagatg     7140
ctcaatatgc cccaggctat gacaaagtca aggacatctc agaggtggtc acccctcggt    7200 tccttttgtac tggaggagtg agtccctatg ctgaccccaa tacttgcaga ggtgagagaa    7260
tgctctttgg ttgtgctaca agtgcccaag gcccaacagt cctttctct acagcttctc     7320 ctctccttgc aggtgattct ggcggcccct tgatagttca aagagaagt cgtttcattc     7380 aagtgagtcc tccctttcct atctggggag atgccaagtg gtcagcatgg gccccaaagc    7440
aggaaagctc aatgcatgtg gctagtaatt cgaggtaggc agagcctgcc tcaccttagg    7500
accgcatgtc ttgcctgcgt gtgtcaagaa cgaggctgag ctgggtccct agtctgattc     7560
ctttaggtca gctaagacac aagcaggaac agccatgctt ccaggattag gaattctact    7620
gaatgatcca tggcaccca ctgcctctgc aggttggtgt aatcagctgg ggagtagtgg     7680
atgtctgcaa aaaccagaag cggcaaaagc aggtacctgc tcacgcccga gactttcaca    7740
tcaacctctt tcaagtgctg ccctggctga aggagaaact ccaagatgag gatttgggtt    7800
ttctataagg ggtttcctgc tggacagggg cgtgggattg aattaaaaca gctgcgacaa    7860
cacctgtgtt ccagatcctt ttggggcaag ggagtgggga acaggcactg gccatgttgt    7920
tacactgaga tcaaacctga cagccgtttt taaaggttta accccaatcc caagtgctga    7980
aaaaccagag gctgagggag atgtgtaagc ttccacctca gtgttttact gagaccagca    8040
ttggggcata tgaggcacaa ggaatccagc tctgttccct agaagccatc cacaaggttt    8100
tccttgtaga cgtcatcact gtagacaatc tgggtcctct tgtcccggtg caaccctta    8160 gggctgttct ggacagctag ggagggagga gaggaacagt taaggtctaa aggagatcat    8220
agaacagacc ctgaggctga ctcctgacca cctcactcct ggccactggc ccctggaagc    8280
ccagtttcca cgctgccctc tggtggccag gatggcctgt cttccttagc tcctttgtgc    8340
caacccatgg ccaagaaaag tataagtgga cattttgatg aatgttttgt tcttagaaaa    8400
atcccaaatg tcattgttga gacacgtgaa tgatattaac ccactactta cagtcagtat    8460
gtcagaagct aaaaactaga aaacctctgt agccctttt tgacatgctg gtcaattcta    8520
gttcctttct tttgcctgaa gggccactgt agctgagccc ttctttctgc tcactccttt    8580
cccaggaaaa tctactttca gggaaaatgg attattcaca ctaagaaatg ctactagctc    8640
```

-continued

| | |
|---|---|
| caccagaact cattcagggt gtagctttgg ccctcaccat tctctctcaa gcctctagct | 8700 |
| gtttcttccc cttcctcttt cctccctcca ccagacatgt tactctcttc accccatcca | 8760 |
| atggttccat ccccaccacc cttgagctac agagaatctc tctcacccac tccatcctg | 8820 |
| tgatctctgt gcctcaacac tgctggctac tccctctttc tcaaagtgtg tgtccttttg | 8880 |
| cttcagtggc ccaggcccct gcggtgctgc tcccagccct ccgacccctc ctcctgtctc | 8940 |
| ctttgctaac gttaggctca cgttagcct aacatgtcag acagctggg gacatgtggg | 9000 |
| g | 9001 |

<210> SEQ ID NO 3
<211> LENGTH: 9001
<212> TYPE: DNA
<213> ORGANISM: Macaca mulatta

<400> SEQUENCE: 3

| | |
|---|---|
| gatggaatct tgctctgtct cccacactgg agtgcagtgg cacgatcttg gctcactgcg | 60 |
| acttctgcct cccagattta agtgattctc ctacctcggc ctcccaagta gctgggatta | 120 |
| taggtgcttg ccaccacatg cagctaattt ttgtattttt agtagagaca ggattccgcc | 180 |
| atgttggcca ggatggtctt gaactcctga cctcaagtga ttcgcccacc tcagcctccc | 240 |
| aaactgctgg gattacaggc gtgagccatt gcacccagtc aggtctgctt attcttccct | 300 |
| tctctctggt tccacccta cggcagtgga caagctgtgc cgaggtcgtc tcccaagaaa | 360 |
| aaaccatgtt ccccaacttg acagatgtca gggaggtggt gacagaccag tttctatgca | 420 |
| gtgggaccca ggaggatgag agtccctgca agggtgagtc cctcaccatg cctggattcc | 480 |
| caaaggggaa ggccacctgt gtctctgtgg ccagggtgca tgccagaaca ccagtccact | 540 |
| gccctgtatg acgctgtctc ctgtcaccct ttgctggcag agaatctggg ggagcagtt | 600 |
| ttccttgagc ggagattcag gttttttcag gtgagaaggt ggaagcttgc aggacccagg | 660 |
| ggttacagga tgtcagcctt gttggggga tgagggaggc ctttgaggga tctagggagg | 720 |
| ttggggctta cagctggagc tgtggcagcc tcccagccag ttctctcctt ttctccaggt | 780 |
| gggtctggtg agctggggtc tttacaaccc ctgccttggc tctgctgaca aaaactcccg | 840 |
| caaaagggcc cctcgtagca aggtcccgcc gccacgagac tttcacatca atctcttccg | 900 |
| catgcagccc tggctgaggc agcacctggg ggatgtcctg aattttttac ccctttagtc | 960 |
| atggccactg agccctctgc tgtcctgtta gaatccgccc ccctccatc ttctacctct | 1020 |
| gaatgcccac ccttagactc tgtgacccat gctgtctcct agttgagtaa atctgggtct | 1080 |
| ctaggatgcc aggggcagcg cacacaagct gggaaatcct cagggctcct accagcggga | 1140 |
| ctgcctcgct gccccacctc ccgctccttg gcctgtcccc aaattcctcc cctggttgac | 1200 |
| ttgactcatg ctcatttcac tttcatatgg aatttcccag ttatgaaatt aataaaaatc | 1260 |
| agtggtttcc acatctgtct gtgactctat ctggaggcca ggtagggctg gcctgggggg | 1320 |
| aaggggaggc cagaatgact ccaagagcca caggaaggca ggtcagagac cccactggac | 1380 |
| aaacagtggc tggactctgt accataacac acaagcaaca ggggagtgag ctggatcctt | 1440 |
| atttctggtc cctaagtggg tggtctggc ttgctgggga ggagctgagg ccagaaggag | 1500 |
| gtactgaagg ggagagtcct ggaccttggg cagcaaaggg tgggacttct gcagtttctg | 1560 |
| cttccttgac tggcagctca gcggggcct cccgcttgga tgttccggga aagtgatgag | 1620 |
| ggtaggacag gcggggcaag ctgcaggtgc cagaacacga attgcataaa aggccgggag | 1680 |

```
ctggtgggggg gcaggggaag ggaatgtgac caggtctagg tctggagtttt cagcttggac   1740
actgagctaa gtagacaagc aaaacaagcc aggacacgcc atcctgcccc aggcccagct     1800
tctctcctgc cttctaacgc catggggagc agtctcagcc cccagctcta cctgatgccc    1860
ttcatcttgg gcctcttatc tggaggtaag tgagggtaac cttcccttcc tgctgtcccc    1920
agcatccctc cttggccttt tggggccagg cttcatcagc ctttctcttc aggtgtgacc    1980
accactccat tgtcttcggc ccagcctcaa ggatcctgct ctctggaggg ggtagagatc    2040
aaaggtggct ccttccgact tctccaagag ggccaggcac tggaatacgt gtgtccttct   2100
ggcttctacc cgtaccctgt gcagacacgt acctgcagat ccacggggtc ctggagcacc   2160
ctgcagactc aagatcgaaa aactgtcaag aaggcagagt gcagaggttt gagggcaatg   2220
agtgtgggca gtggcctaag ggagaaacag ggcagatggc agcaaggtca ggactaggat   2280
gagactaggc agggtgacaa ggtgggctga ccaggagtag gagcagtttt agggttgtag   2340
agggaaagga agggaaaaaa aaaggggagt taacctttag taagcattta ccctgggctt   2400
ccacgcagcc ctggaagtca agagaacact cagcaatggg gagggaggag cagcggaaac   2460
ccctatgggt tgaagggtag gtaagatgca gcttctgcag gactgggaat gctctgtttc   2520
tcagtgacct ggtctctgag accaggaggg aaacacctaa ggcagccttt ccctcttaat   2580
gacttctact tctcccctct tctcaaagca atccgctgtc cacgaccaca ggacttcgag   2640
aacgggaat accggccccg gtctccctac tacaatgtga gtgatgagat ctctttccac   2700
tgctatgacg gttacactct ccggggctct gccaatcgca cctgccaagt gaatggccgg   2760
tggagtgggc agacagcgat ctgtgacaac ggaggtgaga agcatcctct cccccccacat  2820
tgctgtctcc ctgacagcgc ctagcctgag gagtgggcat ttgccccgg acactgtaac   2880
tcttgctctc taccttgccc tcggggcctc aggcttcagc gcttacctcc atgtctcatg   2940
cctctgcagc ggggtactgc tccaacccag gcatccccat tggcacaagg aaggtgggca   3000
gccggtaccg ccttgaagac agcgtcacct accactgcag ccgggggctt accctgcgtg   3060
gctcccagcg gcgaacatgt caggaaggtg gctcttggag cgggacggag ccttcctgcc   3120
aaggtgaccc ttgacctgta cccccaggtc agatcctgat cttgcatcct actgtcttct   3180
ctccccacct caaccctgct cttttcctcac ttcttttaaa ccttcctcta gaactgtctc   3240
acttctgagc cttttctacc ctggaaaccc acaatcccct gtctctttgg tcactgtgtc   3300
cctgacactc ccagacattt gacctcattt ctgactctcc cagactcctt catgtacgac   3360
accectcaag aggtggccga agctttcctg tcttccctga cggagaccat agaaggagtc   3420
gatgccgagg atgggcacag cccaggtttg aaggcagaga ggggaggcaa ggcagggaac   3480
tgggggaaaa tggagaaggg acaagataat cgttcatgct ggagcctgag tcactctcct   3540
ggcacccagg ggaacaacag aagcggagga tcatcctaga cccttcaggc tccatgaaca   3600
tctacctggt gctagatgga tcagacagca ttggggccgg caacttcaca ggagccaaaa   3660
agtgtctagt caacttaatt gagaaggtgg agtcctccta tccctgaact tgggggaatg   3720
gaatcttgct gatcttccag gactagctcc ctgatcattc cagcccctct gaaccgcagg   3780
gccccaggaa agtctccagg tcctattctg tcctccttcc cttgtacttg attcctccat   3840
gaacctgtgc ttgagcctct tcctaagagc ctccctgtcc cagcaacgtt gctgaagtct   3900
cccaatcaca gtattctact ttcaatgcca tggcgccttg ttctcctcac ccacaggtgg   3960
caagttatgg tgtgaagcca agatatgctc tagtgacata tgccacatac cccagaaattt  4020
gggtcaaagt gtctgaccaa gagagcagca atgcagactg ggtcacgaag aagctcagtg   4080
```

```
aaatcaatta tgaaggtcag aggttaggga atggtgggag gttcactttg gggtcaggag    4140
gttcaggagt gttgtgtgga gggggtcatg agactacctt gagggcaaca gggggaccac    4200
tttgtagtca aaggttgaac agcaggatca ttgggcaatg gaggttagtg ggaacctgct    4260
gagggctgga agggccactt tgtggtcaaa gggaagtcca tatgatgatt aacttaaaaa    4320
gttgaagatg tgagatttca gttgcagatt ggtctctggg gttaaaagat ggcttggaag    4380
accaggtgag gcgatgctct cttccctccc cacagaccac aagttgaagt cagggactaa    4440
caccaagagg gccctccagg cagtgtacag catgatgagt tggccagagg acatccctcc    4500
tgaaggctgg aaccgcaccc gccatgtcat catcctcatg accgatggtc agaagggacc    4560
tctctcctgt cccagcctcc ccaccttctc agaccagcat gtggccctta agtccacttg    4620
taacactata cccatggttg gggccctgaa tgtgactcgt aactggctgt tcatctctcc    4680
tgtgacccct cataaagaat tattcctaaa gccctgtgat caactacctc taacccttcc    4740
tcaacttact caccctgcca cgtgtatcac tgcctctagc caatttatct tatctcctac    4800
cctcatggtc ccgtctcttc tgcaggattg cacaacatgg gcggggaccc aattactgtc    4860
attgatgaga tccgggactt gttatacatc ggcaaggatc gtaaaaaccc gagggaggat    4920
tatctgggtg agtaacctgc ctaggaccca gcaccctact tcctcagggc ttggaccgtc    4980
atccttcctt tttctccctc agatgtctat gtgtttgggg ttggacctt ggtgaccaa     5040 gtgaacatca atgctttggc ttccaagaaa gacaatgagc aacatgtgtt caaagtcaag    5100
gatatgaaaa acctgaaga cgttttcttc caaatgattg gtaggcagac acaagggaat    5160
caagaacgca actctcctca gcttcccctg aaataattca ttcttcctct accctgaag    5220 ctctagttgc ctggaaagcc ttcttcattc ctccttctct acctcagtat cactattctt    5280
gtttcctggc actgtttgct tcttaacctt agaatcacag agctctaggc acttcagaga    5340
tctttctatt gtcctacatt tgacacatgt ggaaacaaag gccaaggag gtcaaggggc     5400 agcaagctag caacagggct gggcttgaaa acagccaggc ctctgatagc ttgatcccaa    5460
gttctttccc ttttcactcc accacagcag ttttctccta acacgaggaa acaaatacct    5520
gtggcctttc cctttctcct tttgggcctc tgccccccac agacttctac ccaaaggctg    5580
ctgccgtttg ggaatgaagt gttccaagtt ttcagcacat tctccttctc tgccagatga    5640
aagccagtct ctgagtctct gtggcatggt ttgggaacac agcaagggta ccgattacca    5700
caagcaacca tggcaggcca agatctcagt cactgtaagc acagaatccc agtagtgagg    5760
acttggggga ggtgaggtca aggtgaaatg ggagtagggg aagggcaaaa tggccgtaag    5820
agatggtggt ttgtgaaagt tgagttttcc ctttctactg ttctgttccc agcgcccttc    5880
gaagggacat gagagctgta tggggctgt ggtgtctgag tactttgtgc tgacagcagc    5940
acattgtttt actgtggacg acaaggaaca ctcaatcaag gtcagcgtgg gtaaggatgc    6000
aactgaaggt cccgggctgc acctacgccc tccaggcaac acctcccact ttctacagat    6060
cccacactcc actcatctgc aatgcagccc catcccttgc accccagacc agtcagggat    6120
ggggaagact tgaagttagg aatgacatgg ggccagaggc aagaagctgc ccacaaagag    6180
gtggtaccta ttctcctact tcaagggaag aagcgggacc tggagataga aaaagtccta    6240
tttcaccccg actacaacat tagcgagaaa aaagaagcag gaattcctga attttatgac    6300
tatgacgttg ccctgatcaa gctcaagaat aagttgaatt atgacccgac tatcaggtga    6360
gagcatccag atccctgagg aaaggctggg aaaggctgga ggactgggt gaggagcagg     6420
```

```
cctagtttgc tgttctttct ccatccttta taggcccatt tgtctcccct gcaccgaggg    6480
aacaactcga gctttgaggc ttcctccaac taccacttgc cagcaacaga gtaagacata    6540 ctaggggga ggataaggat gagatcccga gacaagtgag gcatgagagg gagatgcaat     6600
aggaagagac gatgcctggc ccagaaccta gcactaggaa gggcttaggg gacatctgct    6660
gagtgacaaa gtcaatagg agatgacagt ggtgggagca gctgaagtga tgcagtctat    6720
ttgtccagag gaagagctgc tccctgcaca ggatatcaaa gctctgtttg tgtctgagga    6780
ggagaagaag ctgactcgga aggaggtcta catcaagaat ggggataagg tgagaaatgg    6840
gcatcctaag gaggcactct aggccctaat ccttcctaag ccacctctgt tcattacctt    6900
tctccatgct tcccacctcc cctacagaaa ggcagctgtg agagagatgc tcaatatgcc    6960
ccaggctatg acaaagtcaa ggacatctcg gaggtggtca cccctcggtt cctttgtact    7020
ggaggagtga gtccctatgc tgaccccaat acttgcagag gtgagagaac gctctctggt    7080
tgtgctccaa gtgcccgagg gccaagagtc cttttcccta cagcttctcc tctccttgca    7140
ggtgattctg gcggcccctt gatagttcac aagagaagtc gtttcattca agtgagtcct    7200
ccctttccta tctggggaga tgccaagtgg tcagcatggg ccccaaagca ggaaagcaca    7260
atgcatgtgg ctagtaattc gaggtgggca gagcctgcct cactttagga ctgcatgtct    7320
ggcctgtgtg tgtcaagaat gaggctgagc tgggtcccta gcctgattcc tttaggtcag    7380
ctaagacaca atcaggaaca gtcatgcttc caggattagg aattctatga atgatccatg    7440 gcacccact gcctctgcag gttggtgtca tcagctgggg agtagtggat gtctgcaaaa    7500
accagaagcg gcaaaagcag gtacctgctc acgcccgaga cttcacgtc aacctcttcc     7560 aagtgctgcc ctggctgaag gagaaactcc aagatgagga tttgggtttt ctctaagggg    7620
tttcctgctg gacaggggcg cgggattgaa ttaaaacagc tgcgacaaca cttgtgttcc    7680
agatcctttt gggcaaggg agtggggaac gggcactggc catgttgtta cactgagatc     7740
aaacctgaca cccatttta aaggcttaac cccaatccca agtgctgaaa accagaggc     7800 tgagggagat atgtaagctt ccacctcagt gttttactga gaccagcatt ggggcatttg    7860
aggcacaagg aatccagctc tgttccctag aagccatcca caaggttttc cttgtagacg    7920
tcatcactgt agacaatctg ggtcctcttg tcccggtggc aacccttagg gctgttctgg    7980
acagctaggg agggaggaga ggaacagtta aggtctaaag gagatcatag atcagaccct    8040
gaggctgact cctgaccacc tcagtcctgg ctgctggccc ctggaaaccc agtttccacg    8100
ctgccctctg gtggccagga tggcctgtct tccttagctc ctttgtgcca acccatggcc    8160
aaggagagtg taagtggaca ttttgatgaa tgttttgttc ttagaaaaat cccaaatgtc    8220
attgttgaga tatatgaatg atattaaccc actacttata gtcagtatgt cagaagctaa    8280
aaactagaaa acctctgtag ccctttattg acatgctggt caactctagt tcctttcttt    8340
tgcctgaaag gccactgttg ctctgagtcc ttctttctgc tcactccttt cccaggaaaa    8400
tctactttca ggtaaatggg ttactcatac taaggaatgc tactagctcc accagaactc    8460
atccagcatg tagctttggc cctcaccatt ctctctcaag cctctagctg tttcttcccc    8520 ttcctcttttt cctccctcca ccagacatgt tactctcttc accccatcca aagattccat    8580
ccccaccacc cttgacctag agagaatctc tcccacccac ttctcatcct gtgatctctg    8640
taccttgaca ctgctggcta ctccctcttt ctcaaagcat gtgtcctttc gcttcagtgg    8700
cccaggcccc tctggtgctg ctcccagccc tctgaccct cctcctgtct cctttgctaa     8760
cgttaggctc aacgttagcc taacgtgtca ggagagctgg agacacgtgg ggcgtaaggt    8820
```

```
ggacagtcct gtttcctaac atagtccctg agtattcctc aagtctagtc ctgggtcgtt    8880 tttttctcc gaaatcagtc tccctcatga tcggggagcc accctgtgat gcagatgact    8940
taatctatgt tttcattcct tacctcacac ctgagttcca gaccctaat ttcaaatact    9000 t                                                                    9001

<210> SEQ ID NO 4
<211> LENGTH: 4086
<212> TYPE: DNA
<213> ORGANISM: Macaca mulatta

<400> SEQUENCE: 4
atagatatat tagcatcagg gagacagggc aaaggttcca cccttcagct cagtccccag      60
tccctgctta ttatttccct aacagaagac catccccctt gccactccct gggttttctt     120
ctctggcagc aatgaagcag ctgctgagcc agctctggtt ttcgggaagt cagatgacct     180 tttcctccc gcggctctct gcctctcgct gtccctaggg aggacaccat ggacccactg     240
atggttcttt tttgcctgct gttcctgtac ccaggtccgg cagactcggc tacctcctgc     300
cctcagaacg tgaatatctc tggtggcacc ttcaccctca gccatggctg ggcccctggg     360
agccttctca tctactcctg tccccagggc ctgtacccat ccccagcgtc acggctgtgc     420
aagagcagcg acagtggca gaccccaaga gccaccggt ctctgactaa ggcggtctgc     480
aaacctggcc actgccccaa cccggcatt tcgctgggcg cggtgcggac aggctcccgc     540
tttggtcatg gggacaaggt ccgctatcgc tgctcctcga atcttgtgct cacggggtct     600
gcggagcggg agtgccaggg caacggggtc tggagtggaa cggagcccat ctgccgccag     660
ccctactctt atgacttccc tgaggacgtg gcccctgccc tgggcacctc cttctcccac     720
atgcttgggg ccaccaatcc cacccagagg acaaaggatc atgaaaatgg aactgggact     780
aacacctatg cagcctaaa cagtgtctat ctcatgatga acaatcaaat gcaactcctt     840
ggcatgaaaa cgatggcctg caggaaatc cgacatgcca tcatccttct gacagatgga     900
aagtccaata tgggtggctc tcccaaaaca gctgttgacc aaatcagaga gatcttgaat     960
atcaaccaga gaggaatga ctatctggac atctatgcca tcgggtggg caagctggat    1020 gtggactgga gagaactgaa tgagctgggg tccaagaagg atggcgagag gcatgccttc    1080
attctgcagg acacaaaggc tctgcaccag gtctttgaac atatgctgga tgtctccaag    1140
ctcacagaca ccatctgcgg ggtggggaac atgtcagcaa cgcctctga ccaagagagg    1200 acaccctggc atgtcactat taagcccaag agccaagaga cctgccgggg agccctcatc    1260
tccgaccaat gggtcctgac agcggctcac tgcttccgcg atggcaacga ccactcccta    1320
tggagggtca atgtgggaga ccccaaatcc cagtgggca aagaattcct tattgagaag    1380
gcagtgattt ccccaggatt tgatgtcttt gccaaaaaga accagggaat cctggagttc    1440
tatggtgatg acatcgccct gctgaagctg gcccagaaag taaagatgtc cacccatgcc    1500
aggcccatct gccttccctg caccatggag gccatctgg ctctgcggag acctcaaggc    1560
agcacctgta gggaccatga gaatgaactg ctgaacaaac agagtgttcc tgctcatttt    1620
gtcgccttga tgggagcaa actgaacatt aaccttaaga tggagtgga gtggacaagc    1680 tgtgccgagg tcgtctccca agaaaaaacc atgttcccca acttgacaga tgtcagggag    1740
gtggtgacag accagtttct atgcagtggg acccaggagg atgagagtcc ctgcaagggt    1800
gtgaccacca ctccattgtc ttcggcccag cctcaaggat cctgctctct ggagggggta    1860
```

| | | | | |
|---|---|---|---|---|
| gagatcaaag | gtggctcctt | ccgacttctc | caagagggcc | aggcactgga | atacgtgtgt | 1920 |
| ccttctggct | tctacccgta | ccctgtgcag | acacgtacct | gcagatccac | ggggtcctgg | 1980 |
| agcaccctgc | agactcaaga | tcgaaaaact | gtcaagaagg | cagagtgcag | agcaatccgc | 2040 |
| tgtccacgac | cacaggactt | cgagaacggg | gaataccggc | cccggtctcc | ctactacaat | 2100 |
| gtgagtgatg | agatctcttt | ccactgctat | gacggttaca | ctctccgggg | ctctgccaat | 2160 |
| cgcacctgcc | aagtgaatgg | ccggtggagt | gggcagacag | cgatctgtga | caacggagcg | 2220 |
| gggtactgct | ccaacccagg | catccccatt | ggcacaagga | aggtgggcag | ccggtaccgc | 2280 |
| cttgaagaca | gcgtcaccta | ccactgcagc | cgggggctta | ccctgcgtgg | ctcccagcgg | 2340 |
| cgaacatgtc | aggaaggtgg | ctcttggagc | gggacggagc | cttcctgcca | agactccttc | 2400 |
| atgtacgaca | cccctcaaga | ggtggccgaa | gctttcctgt | cttccctgac | ggagaccata | 2460 |
| gaaggagtcg | atgccgagga | tgggcacagc | ccaggggaac | aacagaagcg | gaggatcatc | 2520 |
| ctagaccctt | caggctccat | gaacatctac | ctggtgctag | atggatcaga | cagcattggg | 2580 |
| gccggcaact | tcacaggagc | caaaaagtgt | ctagtcaact | taattgagaa | ggtggcaagt | 2640 |
| tatggtgtga | agccaagata | tgctctagtg | acatatgcca | catccccag | aatttgggtc | 2700 |
| aaagtgtctg | accaagagag | cagcaatgca | gactgggtca | cgaagaagct | cagtgaaatc | 2760 |
| aattatgaag | accacaagtt | gaagtcaggg | actaacacca | agagggccct | ccaggcagtg | 2820 |
| tacagcatga | tgagttggcc | agaggacatc | cctcctgaag | gctggaaccg | cacccgccat | 2880 |
| gtcatcatcc | tcatgaccga | tggattgcac | aacatgggcg | gggacccaat | tactgtcatt | 2940 |
| gatgagatcc | gggacttgtt | atacatcggc | aaggatcgta | aaaacccgag | ggaggattat | 3000 |
| ctggatgtct | atgtgtttgg | ggttggacct | ttggtggacc | aagtgaacat | caatgctttg | 3060 |
| gcttccaaga | aagacaatga | gcaacatgtg | ttcaaagtca | aggatatgga | aaacctggaa | 3120 |
| gacgttttct | tccaaatgat | tgatgaaagc | cagtctctga | gtctctgtgg | catggttttgg | 3180 |
| gaacacagca | agggtaccga | ttaccacaag | caaccatggc | aggccaagat | ctcagtcact | 3240 |
| cgcccttcga | agggacatga | gagctgtatg | ggggctgtgg | tgtctgagta | ctttgtgctg | 3300 |
| acagcagcac | attgttttac | tgtggacgac | aaggaacact | caatcaaggt | cagcgtggga | 3360 |
| gggaagaagc | gggacctgga | gatagaaaaa | gtcctatttc | accccgacta | caacattagc | 3420 |
| gagaaaaaag | aagcaggaat | tcctgaattt | tatgactatg | acgttgccct | gatcaagctc | 3480 |
| aagaataagt | tgaattatga | cccgactatc | aggcccattt | gtctcccctg | caccgaggga | 3540 |
| acaactcgag | ctttgaggct | tcctccaact | accacttgcc | agcaacagaa | ggaagagctg | 3600 |
| ctccctgcac | aggatatcaa | agctctgttt | gtgtctgagg | aggagaagaa | gctgactcgg | 3660 |
| aaggaggtct | acatcaagaa | tgggggataag | aaaggcagct | gtgagagaga | tgctcaatat | 3720 |
| gccccaggct | atgacaaagt | caaggacatc | tcggaggtgg | tcaccccctcg | gttccttttgt | 3780 |
| actggaggag | tgagtcccta | tgctgacccc | aatacttgca | gaggtgattc | tggcggcccc | 3840 |
| ttgatagttc | acaagagaag | tcgtttcatt | caagttggtg | tcatcagctg | gggagtagtg | 3900 |
| gatgtctgca | aaaaccagaa | gcggcaaaag | caggtacctg | ctcacgcccg | agactttcac | 3960 |
| gtcaacctct | tccaagtgct | gccctggctg | aaggagaaac | tccaagatga | ggatttgggt | 4020 |
| tttctctaag | gggtttcctg | ctggacaggg | gcgcgggatt | gaattaaaac | agctgcgaca | 4080 |
| acactt | | | | | 4086 |

<210> SEQ ID NO 5
<211> LENGTH: 2767

<212> TYPE: DNA
<213> ORGANISM: Mus musculus

<400> SEQUENCE: 5

| | | | | | |
|---|---|---|---|---|---|
| gctccatcac | acagtccatg | gaaagactga | tcttttaaat | tgggggtagt | ggaggtggtg | 60 |
| gtctgtgctt | gttaggaggg | gtctgggggc | taagagggag | ctttgaaagg | gaagttctgg | 120 |
| cccttggtca | gtcaagggtg | gggctcacat | agtttctgtt | tcctcagttg | gcagttcagc | 180 |
| tggggccctc | cttcatgaat | gttccgggaa | gcagtggctg | cgtgcgcagg | gtaggctggc | 240 |
| caggctgcag | atgccagagc | agattgcata | aaaggttagg | ggacagtggg | aaggggtgt | 300 |
| agccagatcc | agcatttggg | tttcagtttg | gacaggaggt | caaataggca | cccagagtga | 360 |
| cctggagagg | gctttgggcc | actggactct | ctggtgcttt | ccatgacaat | ggagagcccc | 420 |
| cagctctgcc | tcgtcctctt | ggtcttaggc | ttctcctctg | gaggtgtgag | cgcaactcca | 480 |
| gtgcttgagg | cccggcccca | gtctcctgc | tctctggagg | gagtagagat | caaaggcggc | 540 |
| tcctttcaac | ttctccaagg | cggtcaggcc | ctggagtacc | tatgtccctc | tggcttctac | 600 |
| ccatacccg | tgcagactcg | aacctgcaga | tccacaggct | cctggagcga | cctgcagacc | 660 |
| cgagaccaaa | agattgtcca | gaaggcggaa | tgcagagcaa | tacgctgccc | acgaccgcag | 720 |
| gactttgaaa | atggggaatt | ctggccccgg | tcccccttct | acaacctgag | tgaccagatt | 780 |
| tcttttcaat | gctatgatgg | ttacgttctc | cggggtctctg | ctaatcgcac | ctgccaagag | 840 |
| aatggccggt | gggatgggca | aacagcaatt | tgtgatgatg | gagctggata | ctgtcccaat | 900 |
| cccggtattc | ctattgggac | aaggaaggtg | ggtagccaat | accgccttga | agacattgtt | 960 |
| acttaccact | gcagccgggg | acttgtcctg | cgtggctccc | agaagcgaaa | gtgtcaagaa | 1020 |
| ggtggctcat | ggagtgggac | agagccttcc | tgccaagatt | ccttcatgta | tgacagccct | 1080 |
| caagaagtgg | ccgaagcatt | cctatcctcc | ctgacagaga | ccatcgaagg | agccgatgct | 1140 |
| gaggatgggc | acagcccagg | agaacagcag | aagaggaaga | ttgtcctaga | ccctcgggc | 1200 |
| tccatgaata | tctacctggt | gctagatgga | tcagacagca | tcggaagcag | caacttcaca | 1260 |
| ggggctaagc | ggtgcctcac | caacttgatt | gagaaggtgg | cgagttacgg | ggtgaggcca | 1320 |
| cgatatggtc | tcctgacata | tgctacagtc | cccaaagtgt | tggtcagagt | gtctgatgag | 1380 |
| aggagtagcg | atgccgactg | ggtcacagag | aagctcaacc | aaatcagtta | tgaagaccac | 1440 |
| aagctgaagt | cagggaccaa | caccaagagg | gctctccagg | ctgtgtatag | catgatgagc | 1500 |
| tgggcagggg | atgccccgcc | tgaaggctgg | aatagaaccc | gccatgtcat | catcattatg | 1560 |
| actgatggct | tgcacaacat | gggtggaaac | cctgtcactg | tcattcagga | catccgagcc | 1620 |
| ttgctggaca | tcggcaggga | tcccaaaaat | cccagggagg | attacctgga | tgtgtatgtg | 1680 |
| tttggggtcg | ggcctctggt | ggactccgtg | aacatcaatg | ccttagcttc | caaaaaggac | 1740 |
| aatgagcatc | atgtgtttaa | agtcaaggat | atggaagacc | tggagaatgt | tttctaccaa | 1800 |
| atgattgatg | aaaccaaatc | tctgagtctc | tgtggcatgg | tgtgggagca | taaaaaaggc | 1860 |
| aacgattatc | ataagcaacc | atggcaagcc | aagatctcag | tcactcgccc | tctgaaagga | 1920 |
| catgagacct | gtatgggggc | cgtggtgtct | gagtacttcg | tgctgacagc | agcgcactgc | 1980 |
| ttcatggtgg | atgatcagaa | acattccatc | aaggtcagcg | tggggggtca | gaggcggac | 2040 |
| ctggagattg | aagaggtcct | gttccaccc | aaatacaata | ttaatgggaa | aaaggcagaa | 2100 |
| gggatccctg | agttctatga | ttatgatgtg | gccctagtca | agctcaagaa | caagctcaag | 2160 |
| tatggccaga | ctctcaggcc | catctgtctc | ccctgcacgg | agggaaccac | acgagccttg | 2220 |

| | | |
|---|---|---|
| aggcttcctc agacagccac ctgcaagcag cacaaggaac agttgctccc tgtgaaggat | 2280 | |
| gtcaaagctc tgtttgtatc tgagcaaggg aagagcctga ctcggaagga ggtgtacatc | 2340 | |
| aagaatgggg acaagaaagc cagttgtgag agagatgcta caaaggccca aggctatgag | 2400 | |
| aaggtcaaag atgcctctga ggtggtcact ccacggttcc tctgcacagg aggggtggat | 2460 | |
| ccctatgctg accccaacac atgcaaagga gattccgggg gccctctcat tgttcacaag | 2520 | |
| agaagccgct tcattcaagt tggtgtgatt agctggggag tagtagatgt ctgcagagac | 2580 | |
| cagaggcggc aacagctggt accctcttat gcccgggact tccacatcaa cctcttccag | 2640 | |
| gtgctgccct ggctaaagga caagctcaaa gatgaggatt tgggttttct ataaagagct | 2700 | |
| tcctgcaggg agagtgtgag gacagattaa agcagttaca ataacaaaaa aaaaaaaaaa | 2760 | |
| aaaaaaa | 2767 | |

<210> SEQ ID NO 6
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 6
gctgagctgc cagtcaagga    20

<210> SEQ ID NO 7
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 7
ggccccgctg agctgccagt    20

<210> SEQ ID NO 8
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 8
cggaacatcc aagcgggagg    20

<210> SEQ ID NO 9
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 9
ctttcccgga acatccaagc    20

<210> SEQ ID NO 10
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 10
atctgtgttc tggcacctgc    20

<210> SEQ ID NO 11
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 11
gtcacattcc cttcccctgc                                              20

<210> SEQ ID NO 12
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 12
gacctggtca cattcccttc                                              20

<210> SEQ ID NO 13
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 13
gacctagacc tggtcacatt                                              20

<210> SEQ ID NO 14
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 14
actccagacc tagacctggt                                              20

<210> SEQ ID NO 15
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 15
gctgaaactc cagacctaga                                              20

<210> SEQ ID NO 16
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 16
gtccaagctg aaactccaga                                              20

<210> SEQ ID NO 17
<211> LENGTH: 20
<212> TYPE: DNA
<213> ORGANISM: Artificial sequence
<220> FEATURE:

<223> OTHER INFORMATION: Synthetic Oligonucleotide

<400> SEQUENCE: 17
ctcagtgtcc aagctgaaac                                         20

<210> SEQ ID NO 18
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 18
aggagagaag ctgggcctgg                                         20

<210> SEQ ID NO 19
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 19
gaaggcagga gagaagctgg                                         20

<210> SEQ ID NO 20
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 20
gtggtggtca cacctccaga                                         20

<210> SEQ ID NO 21
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 21
ccctccagag agcaggatcc                                         20

<210> SEQ ID NO 22
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 22
tctaccccct ccagagagca                                         20

<210> SEQ ID NO 23
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 23
ttgatctcta ccccctccag                                         20

```
<210> SEQ ID NO 24
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 24
tggagaagtc ggaaggagcc                                              20

<210> SEQ ID NO 25
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 25
ccctcttgga gaagtcggaa                                              20

<210> SEQ ID NO 26
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 26
gcctggccct cttggagaag                                              20

<210> SEQ ID NO 27
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 27
tccagtgcct ggccctcttg                                              20

<210> SEQ ID NO 28
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 28
agaagccaga aggacacacg                                              20

<210> SEQ ID NO 29
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 29
acgggtagaa gccagaagga                                              20

<210> SEQ ID NO 30
<211> LENGTH: 20
<212> TYPE: DNA
<213> ORGANISM: Artificial sequence
<220> FEATURE:
<223> OTHER INFORMATION: Synthetic Oligonucleotide
```

-continued

<400> SEQUENCE: 30
cgtgtctgca cagggtacgg                                            20

<210> SEQ ID NO 31
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 31
agggtgctcc aggaccccgt                                            20

<210> SEQ ID NO 32
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 32
ttgctctgca ctctgccttc                                            20

<210> SEQ ID NO 33
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 33
tattccccgt tctcgaagtc                                            20

<210> SEQ ID NO 34
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 34
cattgtagta gggagaccgg                                            20

<210> SEQ ID NO 35
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 35
cactcacatt gtagtaggga                                            20

<210> SEQ ID NO 36
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 36
tctcatcact cacattgtag                                            20

<210> SEQ ID NO 37
<211> LENGTH: 20

```
<212> TYPE: DNA
<213> ORGANISM: Artificial sequence
<220> FEATURE:
<223> OTHER INFORMATION: Synthetic Oligonucleotide

<400> SEQUENCE: 37
aagagatctc atcactcaca                                               20

<210> SEQ ID NO 38
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 38
agtggaaaga gatctcatca                                               20

<210> SEQ ID NO 39
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 39
catagcagtg gaaagagatc                                               20

<210> SEQ ID NO 40
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 40
aaccgtcata gcagtggaaa                                               20

<210> SEQ ID NO 41
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 41
gagtgtaacc gtcatagcag                                               20

<210> SEQ ID NO 42
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 42
cccggagagt gtaaccgtca                                               20

<210> SEQ ID NO 43
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 43
```

```
cagagccccg gagagtgtaa                                                    20

<210> SEQ ID NO 44
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 44
gattggcaga gccccggaga                                                    20

<210> SEQ ID NO 45
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 45
aggtgcgatt ggcagagccc                                                    20

<210> SEQ ID NO 46
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 46
cttggcaggt gcgattggca                                                    20

<210> SEQ ID NO 47
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 47
cattcacttg gcaggtgcga                                                    20

<210> SEQ ID NO 48
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 48
atcgctgtct gcccactcca                                                    20

<210> SEQ ID NO 49
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 49
tcacagatcg ctgtctgccc                                                    20

<210> SEQ ID NO 50
<211> LENGTH: 20
<212> TYPE: DNA
<213> ORGANISM: Artificial sequence
```

```
<220> FEATURE:
<223> OTHER INFORMATION: Synthetic Oligonucleotide

<400> SEQUENCE: 50
ccgttgtcac agatcgctgt                                              20

<210> SEQ ID NO 51
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 51
cccgctccgt tgtcacagat                                              20

<210> SEQ ID NO 52
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 52
cagtaccccg ctccgttgtc                                              20

<210> SEQ ID NO 53
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 53
ttggagcagt accccgctcc                                              20

<210> SEQ ID NO 54
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 54
accttccttg tgccaatggg                                              20

<210> SEQ ID NO 55
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 55
ctgcccacct tccttgtgcc                                              20

<210> SEQ ID NO 56
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 56
cgctgtcttc aaggcggtac                                              20
```

```
<210> SEQ ID NO 57
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 57
gctgcagtgg taggtgacgc                                                  20

<210> SEQ ID NO 58
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 58
cccccggctg cagtggtagg                                                  20

<210> SEQ ID NO 59
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 59
ggtaagcccc cggctgcagt                                                  20

<210> SEQ ID NO 60
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 60
acgcagggta agccccggc                                                   20

<210> SEQ ID NO 61
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 61
ggagccacgc agggtaagcc                                                  20

<210> SEQ ID NO 62
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 62
gccgctggga gccacgcagg                                                  20

<210> SEQ ID NO 63
<211> LENGTH: 20
<212> TYPE: DNA
<213> ORGANISM: Artificial sequence
<220> FEATURE:
<223> OTHER INFORMATION: Synthetic Oligonucleotide
```

```
<400> SEQUENCE: 63
caagagccac cttcctgaca                                              20

<210> SEQ ID NO 64
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 64
ccgctccaag agccaccttc                                              20

<210> SEQ ID NO 65
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 65
tccgtcccgc tccaagagcc                                              20

<210> SEQ ID NO 66
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 66
gaaggctccg tcccgctcca                                              20

<210> SEQ ID NO 67
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 67
tggcaggaag gctccgtccc                                              20

<210> SEQ ID NO 68
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 68
gagtcttggc aggaaggctc                                              20

<210> SEQ ID NO 69
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 69
atgaaggagt cttggcagga                                              20

<210> SEQ ID NO 70
```

```
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 70
cttcggccac ctcttgaggg                                               20

<210> SEQ ID NO 71
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 71
ggaaagcttc ggccacctct                                               20

<210> SEQ ID NO 72
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 72
aagacaggaa agcttcggcc                                               20

<210> SEQ ID NO 73
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 73
tcagggaaga caggaaagct                                               20

<210> SEQ ID NO 74
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 74
tcgactcctt ctatggtctc                                               20

<210> SEQ ID NO 75
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 75
cttctgttgt tcccctgggc                                               20

<210> SEQ ID NO 76
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 76
```
ttcatggagc ctgaagggtc 20

<210> SEQ ID NO 77
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 77
tagatgttca tggagcctga 20

<210> SEQ ID NO 78
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 78
accaggtaga tgttcatgga 20

<210> SEQ ID NO 79
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 79
tctagcacca ggtagatgtt 20

<210> SEQ ID NO 80
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 80
gatccatcta gcaccaggta 20

<210> SEQ ID NO 81
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 81
ctgtctgatc catctagcac 20

<210> SEQ ID NO 82
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 82
ccaatgctgt ctgatccatc 20

<210> SEQ ID NO 83
<211> LENGTH: 20
<212> TYPE: DNA

-continued

```
<213> ORGANISM: Artificial sequence
<220> FEATURE:
<223> OTHER INFORMATION: Synthetic Oligonucleotide

<400> SEQUENCE: 83
tttggctcct gtgaagttgc                                                  20

<210> SEQ ID NO 84
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 84 acacttttg gctcctgtga                                                   20

<210> SEQ ID NO 85
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 85
gactagacac ttttggctc                                                   20

<210> SEQ ID NO 86
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 86
taagttgact agacactttt                                                  20

<210> SEQ ID NO 87
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 87
ctcaattaag ttgactagac                                                  20

<210> SEQ ID NO 88
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 88
caccttctca attaagttga                                                  20

<210> SEQ ID NO 89
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 89
acttgccacc ttctcaatta                                                  20
```

<210> SEQ ID NO 90
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 90
accataactt gccaccttct                                               20

<210> SEQ ID NO 91
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 91
cttcacacca taacttgcca                                               20

<210> SEQ ID NO 92
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 92
tcttggcttc acaccataac                                               20

<210> SEQ ID NO 93
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 93
atgtggcata tgtcactaga                                               20

<210> SEQ ID NO 94
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 94
cagacacttt gacccaaatt                                               20

<210> SEQ ID NO 95
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 95
ggtcttcata attgatttca                                               20

<210> SEQ ID NO 96
<211> LENGTH: 20
<212> TYPE: DNA
<213> ORGANISM: Artificial sequence
<220> FEATURE:

<223> OTHER INFORMATION: Synthetic Oligonucleotide

<400> SEQUENCE: 96
acttgtggtc ttcataattg                                           20

<210> SEQ ID NO 97
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 97
acttcaactt gtggtcttca                                           20

<210> SEQ ID NO 98
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 98
tccctgactt caacttgtgg                                           20

<210> SEQ ID NO 99
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 99
tgttagtccc tgacttcaac                                           20

<210> SEQ ID NO 100
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 100
tcttggtgtt agtccctgac                                           20

<210> SEQ ID NO 101
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 101
tgtacactgc ctggagggcc                                           20

<210> SEQ ID NO 102
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 102
tcatgctgta cactgcctgg                                           20

```
<210> SEQ ID NO 103
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 103
gttccagcct tcaggaggga                                                      20

<210> SEQ ID NO 104
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 104
ggtgcggttc cagccttcag                                                      20

<210> SEQ ID NO 105
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 105
atggcgggtg cggttccagc                                                      20

<210> SEQ ID NO 106
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 106
gatgacatgg cgggtgcggt                                                      20

<210> SEQ ID NO 107
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 107
gaggatgatg acatggcggg                                                      20

<210> SEQ ID NO 108
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 108
cccatgttgt gcaatccatc                                                      20

<210> SEQ ID NO 109
<211> LENGTH: 20
<212> TYPE: DNA
<213> ORGANISM: Artificial sequence
<220> FEATURE:
<223> OTHER INFORMATION: Synthetic Oligonucleotide
```

<400> SEQUENCE: 109
tccccgccca tgttgtgcaa                                           20

<210> SEQ ID NO 110
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 110
attgggtccc cgcccatgtt                                           20

<210> SEQ ID NO 111
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 111
acagtaattg ggtccccgcc                                           20

<210> SEQ ID NO 112
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 112
tcaatgacag taattgggtc                                           20

<210> SEQ ID NO 113
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 113
atctcatcaa tgacagtaat                                           20

<210> SEQ ID NO 114
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 114
tcccggatct catcaatgac                                           20

<210> SEQ ID NO 115
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 115
acatccagat aatcctccct                                           20

<210> SEQ ID NO 116
<211> LENGTH: 20

```
<212> TYPE: DNA
<213> ORGANISM: Artificial sequence
<220> FEATURE:
<223> OTHER INFORMATION: Synthetic Oligonucleotide

<400> SEQUENCE: 116
acatagacat ccagataatc                                               20

<210> SEQ ID NO 117
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 117
ccaaacacat agacatccag                                               20

<210> SEQ ID NO 118
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 118
agcattgatg ttcacttggt                                               20

<210> SEQ ID NO 119
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 119
agccaaagca ttgatgttca                                               20

<210> SEQ ID NO 120
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 120
cttggaagcc aaagcattga                                               20

<210> SEQ ID NO 121
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 121
gtctttcttg gaagccaaag                                               20

<210> SEQ ID NO 122
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 122
```

```
ctcattgtct ttcttggaag                                              20

<210> SEQ ID NO 123
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 123
atgttgctca ttgtctttct                                              20

<210> SEQ ID NO 124
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 124
gaacacatgt tgctcattgt                                              20

<210> SEQ ID NO 125
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 125
gactttgaac acatgttgct                                              20

<210> SEQ ID NO 126
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 126
atccttgact ttgaacacat                                              20

<210> SEQ ID NO 127
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 127
ttccatatcc ttgactttga                                              20

<210> SEQ ID NO 128
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 128
caggttttcc atatccttga                                              20

<210> SEQ ID NO 129
<211> LENGTH: 20
<212> TYPE: DNA
<213> ORGANISM: Artificial sequence
```

```
<220> FEATURE:
<223> OTHER INFORMATION: Synthetic Oligonucleotide

<400> SEQUENCE: 129
ctcagagact ggctttcatc                                                  20

<210> SEQ ID NO 130
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 130
cagagactca gagactggct                                                  20

<210> SEQ ID NO 131
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 131
atgccacaga gactcagaga                                                  20

<210> SEQ ID NO 132
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 132
caaaccatgc cacagagact                                                  20

<210> SEQ ID NO 133
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 133
tgttcccaaa ccatgccaca                                                  20

<210> SEQ ID NO 134
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 134
ttgtggtaat cggtaccctt                                                  20

<210> SEQ ID NO 135
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 135
ggttgcttgt ggtaatcggt                                                  20
```

```
<210> SEQ ID NO 136
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 136
tgccatggtt gcttgtggta                                               20

<210> SEQ ID NO 137
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 137
ttggcctgcc atggttgctt                                               20

<210> SEQ ID NO 138
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 138
gagatcttgg cctgccatgg                                               20

<210> SEQ ID NO 139
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 139
acagccccca tacagctctc                                               20

<210> SEQ ID NO 140
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 140
gacaccacag cccccataca                                               20

<210> SEQ ID NO 141
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 141
tactcagaca ccacagcccc                                               20

<210> SEQ ID NO 142
<211> LENGTH: 20
<212> TYPE: DNA
<213> ORGANISM: Artificial sequence
<220> FEATURE:
<223> OTHER INFORMATION: Synthetic Oligonucleotide
```

```
<400> SEQUENCE: 142
acaaagtact cagacaccac                                                   20

<210> SEQ ID NO 143
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 143
gtcagcacaa agtactcaga                                                   20

<210> SEQ ID NO 144
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 144
ttgattgagt gttccttgtc                                                   20

<210> SEQ ID NO 145
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 145
ctgaccttga ttgagtgttc                                                   20

<210> SEQ ID NO 146
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 146
tatctccagg tcccgcttct                                                   20

<210> SEQ ID NO 147
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 147
gaattcctgc ttcttttttc                                                   20

<210> SEQ ID NO 148
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 148
attcaggaat tcctgcttct                                                   20

<210> SEQ ID NO 149
```

```
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 149
cataaaattc aggaattcct                                             20

<210> SEQ ID NO 150
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 150
catagtcata aaattcagga                                             20

<210> SEQ ID NO 151
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 151
tgagcttgat cagggcaacg                                             20

<210> SEQ ID NO 152
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 152
tattcttgag cttgatcagg                                             20

<210> SEQ ID NO 153
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 153
gacaaatggg cctgatagtc                                             20

<210> SEQ ID NO 154
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 154
gttgttccct cggtgcaggg                                             20

<210> SEQ ID NO 155
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 155
```

```
gctcgagttg ttccctcggt                                              20

<210> SEQ ID NO 156
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 156
ctcaaagctc gagttgttcc                                              20

<210> SEQ ID NO 157
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 157
ggaagcctca aagctcgagt                                              20

<210> SEQ ID NO 158
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 158
gttggaggaa gcctcaaagc                                              20

<210> SEQ ID NO 159
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 159
gtggtagttg gaggaagcct                                              20

<210> SEQ ID NO 160
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 160
tggcaagtgg tagttggagg                                              20

<210> SEQ ID NO 161
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 161
tgttgctggc aagtggtagt                                              20

<210> SEQ ID NO 162
<211> LENGTH: 20
<212> TYPE: DNA
```

```
<213> ORGANISM: Artificial sequence
<220> FEATURE:
<223> OTHER INFORMATION: Synthetic Oligonucleotide

<400> SEQUENCE: 162
tccagctcac tccctgttg                                              20

<210> SEQ ID NO 163
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 163
taaggatcca gctcactccc                                             20

<210> SEQ ID NO 164
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 164
cagaaataag gatccagctc                                             20

<210> SEQ ID NO 165
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 165
agggaccaga ataaggatc                                              20

<210> SEQ ID NO 166
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 166
ccacttaggg accagaaata                                             20

<210> SEQ ID NO 167
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 167
tccaggactc tcccttcag                                              20

<210> SEQ ID NO 168
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 168
aagtcccacc ctttgctgcc                                             20
```

<210> SEQ ID NO 169
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 169
ctgcagaagt cccacccttt                                        20

<210> SEQ ID NO 170
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 170
cagaaactgc agaagtccca                                        20

<210> SEQ ID NO 171
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 171
aacctctgca ctctgccttc                                        20

<210> SEQ ID NO 172
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 172
ccctcaaacc tctgcactct                                        20

<210> SEQ ID NO 173
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 173
tcattgccct caaacctctg                                        20

<210> SEQ ID NO 174
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 174
ccacactcat tgccctcaaa                                        20

<210> SEQ ID NO 175
<211> LENGTH: 20
<212> TYPE: DNA
<213> ORGANISM: Artificial sequence
<220> FEATURE:

<223> OTHER INFORMATION: Synthetic Oligonucleotide

<400> SEQUENCE: 175
cactgcccac actcattgcc                                                  20

<210> SEQ ID NO 176
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 176
ttaggccact gcccacactc                                                  20

<210> SEQ ID NO 177
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 177
ctagtcctga ccttgctgcc                                                  20

<210> SEQ ID NO 178
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 178
ctcatcctag tcctgacctt                                                  20

<210> SEQ ID NO 179
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 179
cctagtctca tcctagtcct                                                  20

<210> SEQ ID NO 180
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 180
accctgccta gtctcatcct                                                  20

<210> SEQ ID NO 181
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 181
cttgtcaccc tgcctagtct                                                  20

<210> SEQ ID NO 182
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 182
gcccaccttg tcaccctgcc                                          20

<210> SEQ ID NO 183
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 183
cctaaaactg ctcctactcc                                          20

<210> SEQ ID NO 184
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 184
gagtcagaaa tgaggtcaaa                                          20

<210> SEQ ID NO 185
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 185
ccctactccc atttcacctt                                          20

<210> SEQ ID NO 186
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 186
tgttgtgcaa tcctgcagaa                                          20

<210> SEQ ID NO 187
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 187
aaaggctgat gaagcctggc                                          20

<210> SEQ ID NO 188
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 188
cctttgacca caaagtggcc                                                 20

<210> SEQ ID NO 189
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 189
aggtaccacc tctttgtggg                                                 20

<210> SEQ ID NO 190
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 190
tggtggtcac acctgaagag                                                 20

<210> SEQ ID NO 191
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 191
gcagggagca gctcttcctt                                                 20

<210> SEQ ID NO 192
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 192
tcctgtgcag ggagcagctc                                                 20

<210> SEQ ID NO 193
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 193
ttgatatcct gtgcagggag                                                 20

<210> SEQ ID NO 194
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 194
agagctttga tatcctgtgc                                                 20

<210> SEQ ID NO 195
<211> LENGTH: 20

```
<212> TYPE: DNA
<213> ORGANISM: Artificial sequence
<220> FEATURE:
<223> OTHER INFORMATION: Synthetic Oligonucleotide

<400> SEQUENCE: 195
acaaacagag ctttgatatc                                              20

<210> SEQ ID NO 196
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 196
tcagacacaa acagagcttt                                              20

<210> SEQ ID NO 197
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 197
tcctcctcag acacaaacag                                              20

<210> SEQ ID NO 198
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 198
acctccttcc gagtcagctt                                              20

<210> SEQ ID NO 199
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 199
atgtagacct ccttccgagt                                              20

<210> SEQ ID NO 200
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 200
ttcttgatgt agacctcctt                                              20

<210> SEQ ID NO 201
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 201
``` tcccccattct tgatgtagac                                              20

<210> SEQ ID NO 202
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 202
ttcttatccc cattcttgat                                               20

<210> SEQ ID NO 203
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 203
ctgcctttct tatccccatt                                               20

<210> SEQ ID NO 204
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 204
tcacagctgc ctttcttatc                                               20

<210> SEQ ID NO 205
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 205
tctctctcac agctgccttt                                               20

<210> SEQ ID NO 206
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 206
tgagcatctc tctcacagct                                               20

<210> SEQ ID NO 207
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 207
gcatattgag catctctctc                                               20

<210> SEQ ID NO 208
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 208
tgactttgtc atagcctggg                                          20

<210> SEQ ID NO 209
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 209
tgtccttgac tttgtcatag                                          20

<210> SEQ ID NO 210
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 210
cagtacaaag gaaccgaggg                                          20

<210> SEQ ID NO 211
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 211
ctcctccagt acaaaggaac                                          20

<210> SEQ ID NO 212
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 212
gactcactcc tccagtacaa                                          20

<210> SEQ ID NO 213
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 213
catagggact cactcctcca                                          20

<210> SEQ ID NO 214
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 214
ggtcagcata gggactcact                                          20

<210> SEQ ID NO 215
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 215
tcacctctgc aagtattggg                                              20

<210> SEQ ID NO 216
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 216
ccagaatcac ctctgcaagt                                              20

<210> SEQ ID NO 217
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 217
gggccgccag aatcacctct                                              20

<210> SEQ ID NO 218
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 218
ctcttgtgaa ctatcaaggg                                              20

<210> SEQ ID NO 219
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 219
cgacttctct tgtgaactat                                              20

<210> SEQ ID NO 220
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 220
atgaaacgac ttctcttgtg                                              20

<210> SEQ ID NO 221
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 221
acttgaatga aacgacttct                                           20

<210> SEQ ID NO 222
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 222
acaccaactt gaatgaaacg                                           20

<210> SEQ ID NO 223
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 223
tccactactc cccagctgat                                           20

<210> SEQ ID NO 224
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 224
cagacatcca ctactcccca                                           20

<210> SEQ ID NO 225
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 225
tttttgcaga catccactac                                           20

<210> SEQ ID NO 226
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 226
ttctggtttt tgcagacatc                                           20

<210> SEQ ID NO 227
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 227
tgccgcttct ggttttgca                                            20

<210> SEQ ID NO 228

```
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 228
tgcttttgcc gcttctggtt                                          20

<210> SEQ ID NO 229
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 229
ggtacctgct tttgccgctt                                          20

<210> SEQ ID NO 230
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 230
tgagcaggta cctgcttttg                                          20

<210> SEQ ID NO 231
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 231
ttcagccagg gcagcacttg                                          20

<210> SEQ ID NO 232
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 232
ttctccttca gccagggcag                                          20

<210> SEQ ID NO 233
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 233
tggagtttct ccttcagcca                                          20

<210> SEQ ID NO 234
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 234
```
tcatcttgga gtttctcctt                                            20

<210> SEQ ID NO 235
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 235
aaatcctcat cttggagttt                                            20

<210> SEQ ID NO 236
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 236
aaacccaaat cctcatcttg                                            20

<210> SEQ ID NO 237
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 237
gtccagcagg aaacccctta                                            20

<210> SEQ ID NO 238
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 238
gcccctgtcc agcaggaaac                                            20

<210> SEQ ID NO 239
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 239
agctgtttta attcaatccc                                            20

<210> SEQ ID NO 240
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 240
aacttgccac ctgtgggtga                                            20

<210> SEQ ID NO 241
<211> LENGTH: 20
<212> TYPE: DNA

```
<213> ORGANISM: Artificial sequence
<220> FEATURE:
<223> OTHER INFORMATION: Synthetic Oligonucleotide

<400> SEQUENCE: 241
tcaccttatc cccattcttg                                               20

<210> SEQ ID NO 242
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 242
tcaactttca caaaccacca                                               20

<210> SEQ ID NO 243
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 243
ccgccagaat cacctgcaag                                               20

<210> SEQ ID NO 244
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 244
aggaggaatg aagaaggctt                                               20

<210> SEQ ID NO 245
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 245
gcctttcctc agggatctgg                                               20

<210> SEQ ID NO 246
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 246
aaatgtctgg gagtgtcagg                                               20

<210> SEQ ID NO 247
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 247
gcctagagtg cctccttagg                                               20
```

<210> SEQ ID NO 248
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 248
ggcatctccc cagataggaa                                              20

<210> SEQ ID NO 249
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 249
agggagctag tcctggaaga                                              20

<210> SEQ ID NO 250
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 250
acacctgaag agaaaggctg                                              20

<210> SEQ ID NO 251
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 251
ccctttgacc acaaagtggc                                              20

<210> SEQ ID NO 252
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 252
gccctcaagg tagtctcatg                                              20

<210> SEQ ID NO 253
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 253
aagggaagga ggacagaata                                              20

<210> SEQ ID NO 254
<211> LENGTH: 20
<212> TYPE: DNA
<213> ORGANISM: Artificial sequence
<220> FEATURE:

<223> OTHER INFORMATION: Synthetic Oligonucleotide

<400> SEQUENCE: 254
aaaggccaag gagggatgct                                               20

<210> SEQ ID NO 255
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 255
agaggtccct tctgaccatc                                               20

<210> SEQ ID NO 256
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 256
gctgggacag gagagaggtc                                               20

<210> SEQ ID NO 257
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 257
tcaaatgtct gggagtgtca                                               20

<210> SEQ ID NO 258
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 258
agaaggagaa tgtgctgaaa                                               20

<210> SEQ ID NO 259
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 259
tgctgaccac ttggcatctc                                               20

<210> SEQ ID NO 260
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 260
caactttcac aaaccaccat                                               20

<210> SEQ ID NO 261
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 261
agctctgtga ttctaaggtt                                              20

<210> SEQ ID NO 262
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 262
ccacctgtgg gtgaggagaa                                              20

<210> SEQ ID NO 263
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 263
gaggactcac ttgaatgaaa                                              20

<210> SEQ ID NO 264
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 264
tggaatgatc agggagctag                                              20

<210> SEQ ID NO 265
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 265
gtcccttctc cattttcccc                                              20

<210> SEQ ID NO 266
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 266 tcaactttt aagttaatca                                              20

<210> SEQ ID NO 267
<211> LENGTH: 20
<212> TYPE: DNA
<213> ORGANISM: Artificial sequence
<220> FEATURE:
<223> OTHER INFORMATION: Synthetic Oligonucleotide

```
<400> SEQUENCE: 267
gggtgaggag aacaaggcgc                                               20

<210> SEQ ID NO 268
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 268
cttccaagcc atctttttaac                                              20

<210> SEQ ID NO 269
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 269
aggactcact tgaatgaaac                                               20

<210> SEQ ID NO 270
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 270
ttccaggcaa ctagagcttc                                               20

<210> SEQ ID NO 271
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 271
cagagtccag ccactgtttg                                               20

<210> SEQ ID NO 272
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 272
ccaacctgca gaggcagtgg                                               20

<210> SEQ ID NO 273
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 273
tgcaaggaga ggagaagctg                                               20

<210> SEQ ID NO 274
<211> LENGTH: 20
```

```
<212> TYPE: DNA
<213> ORGANISM: Artificial sequence
<220> FEATURE:
<223> OTHER INFORMATION: Synthetic Oligonucleotide

<400> SEQUENCE: 274
ctaggcaggt tactcaccca                                              20

<210> SEQ ID NO 275
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 275
caccataact tgccacctgt                                              20

<210> SEQ ID NO 276
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 276
taggtaccac ctctttgtgg                                              20

<210> SEQ ID NO 277
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 277
cttgacctca cctcccccaa                                              20

<210> SEQ ID NO 278
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 278
ccacctcttt gtgggcagct                                              20

<210> SEQ ID NO 279
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 279
ttcacaaacc accatctctt                                              20

<210> SEQ ID NO 280
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 280
```
ttctcacctc cgttgtcaca                                              20

<210> SEQ ID NO 281
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 281
gaaagtggga ggtgttgcct                                              20

<210> SEQ ID NO 282
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 282
acagcaggaa gggaaggtta                                              20

<210> SEQ ID NO 283
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 283
catgctgacc acttggcatc                                              20

<210> SEQ ID NO 284
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 284
ggtcaccttg gcaggaaggc                                              20

<210> SEQ ID NO 285
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 285
gtatagtgtt acaagtggac                                              20

<210> SEQ ID NO 286
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 286
ggacttccct ttgaccacaa                                              20

<210> SEQ ID NO 287
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 287
tcaccttgac ctcacctccc                                              20

<210> SEQ ID NO 288
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 288
tagagtgcct ccttaggatg                                              20

<210> SEQ ID NO 289
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 289
tgacttcaac ttgtggtctg                                              20

<210> SEQ ID NO 290
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 290
cagagaagga gaatgtgctg                                              20

<210> SEQ ID NO 291
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 291
agggagcagc tcttcctctg                                              20

<210> SEQ ID NO 292
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 292
tgttcccctg ggtgccagga                                              20

<210> SEQ ID NO 293
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 293
ggcctggctg ttttcaagcc                                              20

<210> SEQ ID NO 294
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 294
gactggcttt catctggcag                                                   20

<210> SEQ ID NO 295
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 295
gaaggctttc caggcaacta                                                   20

<210> SEQ ID NO 296
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 296
tcacttgaat gaaacgactt                                                   20

<210> SEQ ID NO 297
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 297
ggccccaaaa ggccaaggag                                                   20

<210> SEQ ID NO 298
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 298
aatcacctgc aaggagagga                                                   20

<210> SEQ ID NO 299
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 299
gaccttcagt tgcatcctta                                                   20

<210> SEQ ID NO 300
<211> LENGTH: 20
<212> TYPE: DNA
<213> ORGANISM: Artificial sequence
<220> FEATURE:
<223> OTHER INFORMATION: Synthetic Oligonucleotide

```
<400> SEQUENCE: 300
tgatgaagcc tggccccaaa                                              20

<210> SEQ ID NO 301
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 301
tagaaagtgg gaggtgttgc                                              20

<210> SEQ ID NO 302
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 302
cccatccctg actggtctgg                                              20

<210> SEQ ID NO 303
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 303
ccatgggtat agtgttacaa                                              20

<210> SEQ ID NO 304
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 304
gtgttctctt gacttccagg                                              20

<210> SEQ ID NO 305
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 305
ggcctgctcc tcaccccagt                                              20

<210> SEQ ID NO 306
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 306
gaggcctggc tgttttcaag                                              20

<210> SEQ ID NO 307
```

```
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 307
gactctcccc ttcagtacct                                                   20

<210> SEQ ID NO 308
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 308
catgggtata gtgttacaag                                                   20

<210> SEQ ID NO 309
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 309
gaaggagaat gtgctgaaaa                                                   20

<210> SEQ ID NO 310
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 310
tcacctggtc ttccaagcca                                                   20

<210> SEQ ID NO 311
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 311
ctccccagat aggaaaggga                                                   20

<210> SEQ ID NO 312
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 312
ggactcactt gaatgaaacg                                                   20

<210> SEQ ID NO 313
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 313
```
ggccgccaga atcacctgca                                               20

<210> SEQ ID NO 314
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 314
ctcacttgaa tgaaacgact                                               20

<210> SEQ ID NO 315
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 315
ctttcccagc ctttcctcag                                               20

<210> SEQ ID NO 316
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 316
agaaagtggg aggtgttgcc                                               20

<210> SEQ ID NO 317
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 317
gtcgcagctg ttttaattca                                               20

<210> SEQ ID NO 318
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 318
ccaggactct ccccttcagt                                               20

<210> SEQ ID NO 319
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 319
agggaaggag gacagaatag                                               20

<210> SEQ ID NO 320
<211> LENGTH: 20
<212> TYPE: DNA

```
<213> ORGANISM: Artificial sequence
<220> FEATURE:
<223> OTHER INFORMATION: Synthetic Oligonucleotide

<400> SEQUENCE: 320
gaaatgaggt caaatgtctg                                               20

<210> SEQ ID NO 321
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 321
ggagagtcag aaatgaggtc                                               20

<210> SEQ ID NO 322
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 322
gtagaaagtg ggaggtgttg                                               20

<210> SEQ ID NO 323
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 323
tagaaagatc tctgaagtgc                                               20

<210> SEQ ID NO 324
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 324
ctgctcctca ccccagtcct                                               20

<210> SEQ ID NO 325
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 325
ctactgggat tctgtgctta                                               20

<210> SEQ ID NO 326
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 326
cccaaaaggc caaggaggga                                               20
```

-continued

<210> SEQ ID NO 327
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 327
tgaccacttg gcatctcccc                                           20

<210> SEQ ID NO 328
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 328
cctgcaagga gaggagaagc                                           20

<210> SEQ ID NO 329
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 329
ctctcacctc tgcaagtatt                                           20

<210> SEQ ID NO 330
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 330
ccccaaaagg ccaaggaggg                                           20

<210> SEQ ID NO 331
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 331
gtcttccaag ccatcttta                                            20

<210> SEQ ID NO 332
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 332
gttacaagtg gacttaaggg                                           20

<210> SEQ ID NO 333
<211> LENGTH: 20
<212> TYPE: DNA
<213> ORGANISM: Artificial sequence
<220> FEATURE:

<223> OTHER INFORMATION: Synthetic Oligonucleotide

<400> SEQUENCE: 333
cccatgttgt gcaatcctgc                                               20

<210> SEQ ID NO 334
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 334
gaggtgggaa gcatggagaa                                               20

<210> SEQ ID NO 335
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 335
tgctcccacc actgtcatct                                               20

<210> SEQ ID NO 336
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 336
aggcaggtta ctcacccaga                                               20

<210> SEQ ID NO 337
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 337
tactgggatt ctgtgcttac                                               20

<210> SEQ ID NO 338
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 338
gcctttccca gcctttcctc                                               20

<210> SEQ ID NO 339
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 339
gtgcaatcct gcagaagaga                                               20

```
<210> SEQ ID NO 340
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 340
acaggagaga ggtcccttct                                               20

<210> SEQ ID NO 341
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 341
cccaaaagga gaagggaaa                                                20

<210> SEQ ID NO 342
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 342
aagcccaggg taaatgctta                                               20

<210> SEQ ID NO 343
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 343
gatgaagcct ggccccaaaa                                               20

<210> SEQ ID NO 344
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 344
tggcagagaa ggagaatgtg                                               20

<210> SEQ ID NO 345
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 345
ttcccagcct ttcctcaggg                                               20

<210> SEQ ID NO 346
<211> LENGTH: 20
<212> TYPE: DNA
<213> ORGANISM: Artificial sequence
<220> FEATURE:
<223> OTHER INFORMATION: Synthetic Oligonucleotide
```

<400> SEQUENCE: 346
ggcagagaag gagaatgtgc                                              20

<210> SEQ ID NO 347
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 347
acagtgccag gaaacaagaa                                              20

<210> SEQ ID NO 348
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 348
taggcaggtt actcacccag                                              20

<210> SEQ ID NO 349
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 349
ttctcttgac ttccagggct                                              20

<210> SEQ ID NO 350
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 350
cctgctcctc accccagtcc                                              20

<210> SEQ ID NO 351
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 351
tcccactaac ctccattgcc                                              20

<210> SEQ ID NO 352
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 352
ttccctttga ccacaaagtg                                              20

<210> SEQ ID NO 353
<211> LENGTH: 20

```
<212> TYPE: DNA
<213> ORGANISM: Artificial sequence
<220> FEATURE:
<223> OTHER INFORMATION: Synthetic Oligonucleotide

<400> SEQUENCE: 353
ctgggtccta ggcaggttac                                              20

<210> SEQ ID NO 354
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 354
tccaggcaac tagagcttca                                              20

<210> SEQ ID NO 355
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 355
gcccatgttg tgcaatcctg                                              20

<210> SEQ ID NO 356
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 356
ggttcccact aacctccatt                                              20

<210> SEQ ID NO 357
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 357
aggtagagag caagagttac                                              20

<210> SEQ ID NO 358
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 358
ccactaacct ccattgccca                                              20

<210> SEQ ID NO 359
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 359
```
tcacaaacca ccatctctta                                              20

<210> SEQ ID NO 360
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 360
tactcaccca gataatcctc                                              20

<210> SEQ ID NO 361
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 361
tgctcctcac cccagtcctc                                              20

<210> SEQ ID NO 362
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 362
tctcacagct gcctttctgt                                              20

<210> SEQ ID NO 363
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 363
gaaagggagg actcacttga                                              20

<210> SEQ ID NO 364
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 364 ccatcttttta accccagaga                                             20

<210> SEQ ID NO 365
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 365
tcctcacccc agtcctccag                                              20

<210> SEQ ID NO 366
<211> LENGTH: 20
<212> TYPE: DNA
<213> ORGANISM: Artificial sequence

```
<220> FEATURE:
<223> OTHER INFORMATION: Synthetic Oligonucleotide

<400> SEQUENCE: 366
ctggcagaga aggagaatgt                                                      20

<210> SEQ ID NO 367
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 367
tctccccaga taggaaaggg                                                      20

<210> SEQ ID NO 368
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 368
acttcagctg ctcccaccac                                                      20

<210> SEQ ID NO 369
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 369
gacagcagga agggaaggtt                                                      20

<210> SEQ ID NO 370
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 370
ggagacaaat gggcctataa                                                      20

<210> SEQ ID NO 371
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 371
ctgctcccac cactgtcatc                                                      20

<210> SEQ ID NO 372
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 372
aggaatgaag aaggctttcc                                                      20
```

```
<210> SEQ ID NO 373
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 373
gggatctcat ccttatcctc                                               20

<210> SEQ ID NO 374
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 374
gtgctgggtc ctaggcaggt                                               20

<210> SEQ ID NO 375
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 375
caaaaggcca aggagggatg                                               20

<210> SEQ ID NO 376
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 376
ccatgctgac cacttggcat                                               20

<210> SEQ ID NO 377
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 377
ggaggctggg acaggagaga                                               20

<210> SEQ ID NO 378
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 378
ggagcagctc ttcctctgga                                               20

<210> SEQ ID NO 379
<211> LENGTH: 20
<212> TYPE: DNA
<213> ORGANISM: Artificial sequence
<220> FEATURE:
<223> OTHER INFORMATION: Synthetic Oligonucleotide
```

```
<400> SEQUENCE: 379
tctcacctcc gttgtcacag                                              20

<210> SEQ ID NO 380
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 380
cagtcctcca gcctttccca                                              20

<210> SEQ ID NO 381
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 381
agtcctccag cctttcccag                                              20

<210> SEQ ID NO 382
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 382
tgaaggagtc tgggagagtc                                              20

<210> SEQ ID NO 383
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 383
cagaatcacc tgcaaggaga                                              20

<210> SEQ ID NO 384
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 384
taggaaaggg aggactcact                                              20

<210> SEQ ID NO 385
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 385
accttggcag gaaggctccg                                              20

<210> SEQ ID NO 386
```

```
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 386
gagacaaatg ggcctataaa                                          20

<210> SEQ ID NO 387
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 387
ctgaagagaa aggctgatga                                          20

<210> SEQ ID NO 388
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 388
aatgatcagg gagctagtcc                                          20

<210> SEQ ID NO 389
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 389
cttagctgac ctaaaggaat                                          20

<210> SEQ ID NO 390
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 390
tgggtatagt gttacaagtg                                          20

<210> SEQ ID NO 391
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 391
tgaagagaaa ggctgatgaa                                          20

<210> SEQ ID NO 392
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 392
```
gtgttacaag tggacttaag                                               20

<210> SEQ ID NO 393
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 393
acctgtgggt gaggagaaca                                               20

<210> SEQ ID NO 394
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 394
tcacccagat aatcctccct                                               20

<210> SEQ ID NO 395
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 395
tgttgtcgca gctgttttaa                                               20

<210> SEQ ID NO 396
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 396
tggtcacatt cccttcccct                                               20

<210> SEQ ID NO 397
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 397
cctggtcaca ttcccttccc                                               20

<210> SEQ ID NO 398
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 398
tagacctggt cacattccct                                               20

<210> SEQ ID NO 399
<211> LENGTH: 20
<212> TYPE: DNA

<213> ORGANISM: Artificial sequence
<220> FEATURE:
<223> OTHER INFORMATION: Synthetic Oligonucleotide

<400> SEQUENCE: 399
cctagacctg gtcacattcc                                               20

<210> SEQ ID NO 400
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 400
ccttccgagt cagcttttc                                                20

<210> SEQ ID NO 401
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 401
ctccttccga gtcagctttt                                               20

<210> SEQ ID NO 402
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 402
agacctcctt ccgagtcagc                                               20

<210> SEQ ID NO 403
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 403
gtagacctcc ttccgagtca                                               20

<210> SEQ ID NO 404
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 404
tttgccgctt ctggtttttg                                               20

<210> SEQ ID NO 405
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 405
cttttgccgc ttctggtttt                                               20

<210> SEQ ID NO 406
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 406
cctgcttttg ccgcttctgg                                      20

<210> SEQ ID NO 407
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 407
tacctgcttt tgccgcttct                                      20

<210> SEQ ID NO 408
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 408
agaaaaccca aatcctcatc                                      20

<210> SEQ ID NO 409
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 409
tagaaaaccc aaatcctcat                                      20

<210> SEQ ID NO 410
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 410
atagaaaacc caaatcctca                                      20

<210> SEQ ID NO 411
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 411
tatagaaaac ccaaatcctc                                      20

<210> SEQ ID NO 412
<211> LENGTH: 20
<212> TYPE: DNA
<213> ORGANISM: Artificial sequence
<220> FEATURE:

<223> OTHER INFORMATION: Synthetic Oligonucleotide

<400> SEQUENCE: 412
ttatagaaaa cccaaatcct                                          20

<210> SEQ ID NO 413
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 413
cttatagaaa acccaaatcc                                          20

<210> SEQ ID NO 414
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 414
ccttatagaa aacccaaatc                                          20

<210> SEQ ID NO 415
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 415
cccttataga aaacccaaat                                          20

<210> SEQ ID NO 416
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 416
ccccttatag aaaacccaaa                                          20

<210> SEQ ID NO 417
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 417
accccttata gaaaacccaa                                          20

<210> SEQ ID NO 418
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 418
aaccccttat agaaaaccca                                          20

-continued

<210> SEQ ID NO 419
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 419
aaacccctta tagaaaaccc 20

<210> SEQ ID NO 420
<211> LENGTH: 20
<212> TYPE: DNA
<213> ORGANISM: Artificial sequence
<220> FEATURE:
<223> OTHER INFORMATION: Synthetic Oligonucleotide
<400> SEQUENCE: 420
gaaacccctt atagaaaacc 20

<210> SEQ ID NO 421
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 421
ggaaacccct tatagaaaac 20

<210> SEQ ID NO 422
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 422
aggaaacccc ttatagaaaa 20

<210> SEQ ID NO 423
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 423
caggaaaccc cttatagaaa 20

<210> SEQ ID NO 424
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 424
gcaggaaacc ccttatagaa 20

<210> SEQ ID NO 425
<211> LENGTH: 20
<212> TYPE: DNA
<213> ORGANISM: Artificial sequence
<220> FEATURE:
<223> OTHER INFORMATION: Synthetic Oligonucleotide
```
<400> SEQUENCE: 425
agcaggaaac cccttataga                                               20

<210> SEQ ID NO 426
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 426
cagcaggaaa cccttatag                                                20

<210> SEQ ID NO 427
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 427
ccagcaggaa acccttata                                                20

<210> SEQ ID NO 428
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 428
tccagcagga aacccttat                                                20

<210> SEQ ID NO 429
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 429
tgtccagcag gaaaccctt                                                20

<210> SEQ ID NO 430
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 430
ctgtccagca ggaaacccct                                               20

<210> SEQ ID NO 431
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 431
cctgtccagc aggaaacccc                                               20

<210> SEQ ID NO 432
<211> LENGTH: 20
```

```
<212> TYPE: DNA
<213> ORGANISM: Artificial sequence
<220> FEATURE:
<223> OTHER INFORMATION: Synthetic Oligonucleotide

<400> SEQUENCE: 432
ccctgtccag caggaaaccc                                                 20

<210> SEQ ID NO 433
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 433
cccctgtcca gcaggaaacc                                                 20

<210> SEQ ID NO 434
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 434 cgccctgtc cagcaggaaa                                                  20

<210> SEQ ID NO 435
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 435 acgccctgt ccagcaggaa                                                  20

<210> SEQ ID NO 436
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 436 cacgccctg tccagcagga                                                  20

<210> SEQ ID NO 437
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 437 ccacgccct gtccagcagg                                                  20

<210> SEQ ID NO 438
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 438
```
cccacgcccc tgtccagcag                                          20

<210> SEQ ID NO 439
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 439
tcccacgccc ctgtccagca                                          20

<210> SEQ ID NO 440
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 440
atcccacgcc cctgtccagc                                          20

<210> SEQ ID NO 441
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 441
aatcccacgc ccctgtccag                                          20

<210> SEQ ID NO 442
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 442
caatcccacg cccctgtcca                                          20

<210> SEQ ID NO 443
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 443
tcaatcccac gcccctgtcc                                          20

<210> SEQ ID NO 444
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 444
ttcaatccca cgcccctgtc                                          20

<210> SEQ ID NO 445
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 445
attcaatccc acgcccctgt                                            20

<210> SEQ ID NO 446
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 446
aattcaatcc cacgcccctg                                            20

<210> SEQ ID NO 447
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 447
taattcaatc ccacgcccct                                            20

<210> SEQ ID NO 448
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 448
ttaattcaat cccacgcccc                                            20

<210> SEQ ID NO 449
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 449
tttaattcaa tcccacgccc                                            20

<210> SEQ ID NO 450
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 450
ttttaattca atcccacgcc                                            20

<210> SEQ ID NO 451
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 451
gttttaattc aatcccacgc                                            20

<210> SEQ ID NO 452
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 452
tgttttaatt caatcccacg                                               20

<210> SEQ ID NO 453
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 453
ctgttttaat tcaatcccac                                               20

<210> SEQ ID NO 454
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 454
gctgttttaa ttcaatccca                                               20

<210> SEQ ID NO 455
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 455
cagctgtttt aattcaatcc                                               20

<210> SEQ ID NO 456
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 456
gcagctgttt taattcaatc                                               20

<210> SEQ ID NO 457
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 457
cgcagctgtt ttaattcaat                                               20

<210> SEQ ID NO 458
<211> LENGTH: 20
<212> TYPE: DNA
<213> ORGANISM: Artificial sequence
<220> FEATURE:
<223> OTHER INFORMATION: Synthetic Oligonucleotide

```
<400> SEQUENCE: 458
tcgcagctgt tttaattcaa                                               20

<210> SEQ ID NO 459
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 459
tgtcgcagct gttttaattc                                               20

<210> SEQ ID NO 460
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 460
ttgtcgcagc tgttttaatt                                               20

<210> SEQ ID NO 461
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 461
gttgtcgcag ctgttttaat                                               20

<210> SEQ ID NO 462
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 462
ttgttgtcgc agctgtttta                                               20

<210> SEQ ID NO 463
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 463
tttgttgtcg cagctgtttt                                               20

<210> SEQ ID NO 464
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 464
ttttgttgtc gcagctgttt                                               20

<210> SEQ ID NO 465
```

```
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 465
tttttgttgt cgcagctgtt                                                 20

<210> SEQ ID NO 466
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 466
ggatccagct cactcccctg                                                 20

<210> SEQ ID NO 467
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 467
aaataaggat ccagctcact                                                 20

<210> SEQ ID NO 468
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 468
gaccagaaat aaggatccag                                                 20

<210> SEQ ID NO 469
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 469
cttagggacc agaaataagg                                                 20

<210> SEQ ID NO 470
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 470
cacccactta gggaccagaa                                                 20

<210> SEQ ID NO 471
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 471
```
accacccact tagggaccag                                                        20

<210> SEQ ID NO 472
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 472
aggtccagga ctctcccctt                                                        20

<210> SEQ ID NO 473
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 473
aaggtccagg actctcccct                                                        20

<210> SEQ ID NO 474
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 474
aaactgcaga agtcccaccc                                                        20

<210> SEQ ID NO 475
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 475
ggagggcccc gctgagctgc                                                        20

<210> SEQ ID NO 476
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 476
tcccggaaca tccaagcggg                                                        20

<210> SEQ ID NO 477
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 477
catcactttc ccggaacatc                                                        20

<210> SEQ ID NO 478
<211> LENGTH: 20
<212> TYPE: DNA

```
<213> ORGANISM: Artificial sequence
<220> FEATURE:
<223> OTHER INFORMATION: Synthetic Oligonucleotide

<400> SEQUENCE: 478
ctggtcacat tcccttcccc                                              20

<210> SEQ ID NO 479
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 479
ctagacctgg tcacattccc                                              20

<210> SEQ ID NO 480
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 480
ggagtggtgg tcacacctcc                                              20

<210> SEQ ID NO 481
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 481 acccccctcca gagagcagga                                             20

<210> SEQ ID NO 482
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 482
atctctaccc cctccagaga                                              20

<210> SEQ ID NO 483
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 483
ggtacgggta gaagccagaa                                              20

<210> SEQ ID NO 484
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 484
ggagagtgta accgtcatag                                              20
```

<210> SEQ ID NO 485
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 485
tgcgattggc agagccccgg                                            20

<210> SEQ ID NO 486
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 486
ggcaggtgcg attggcagag                                            20

<210> SEQ ID NO 487
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 487
ggccattcac ttggcaggtg                                            20

<210> SEQ ID NO 488
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 488
ttgtcacaga tcgctgtctg                                            20

<210> SEQ ID NO 489
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 489
aaggagtctt ggcaggaagg                                            20

<210> SEQ ID NO 490
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 490
gtacatgaag gagtcttggc                                            20

<210> SEQ ID NO 491
<211> LENGTH: 20
<212> TYPE: DNA
<213> ORGANISM: Artificial sequence
<220> FEATURE:

<223> OTHER INFORMATION: Synthetic Oligonucleotide

<400> SEQUENCE: 491
aagcttcggc cacctcttga                                       20

<210> SEQ ID NO 492
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 492
ccatctagca ccaggtagat                                       20

<210> SEQ ID NO 493
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 493
ggccccaatg ctgtctgatc                                       20

<210> SEQ ID NO 494
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 494
aattaagttg actagacact                                       20

<210> SEQ ID NO 495
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 495
tgccaccttc tcaattaagt                                       20

<210> SEQ ID NO 496
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 496
taacttgcca ccttctcaat                                       20

<210> SEQ ID NO 497
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 497
cataacttgc caccttctca                                       20

```
<210> SEQ ID NO 498
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 498
acaccataac ttgccacctt                                              20

<210> SEQ ID NO 499
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 499
tcacaccata acttgccacc                                              20

<210> SEQ ID NO 500
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 500
tagtccctga cttcaacttg                                              20

<210> SEQ ID NO 501
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 501
tggtgttagt ccctgacttc                                              20

<210> SEQ ID NO 502
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 502
gcggttccag ccttcaggag                                              20

<210> SEQ ID NO 503
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 503
tcatgaggat gatgacatgg                                              20

<210> SEQ ID NO 504
<211> LENGTH: 20
<212> TYPE: DNA
<213> ORGANISM: Artificial sequence
<220> FEATURE:
<223> OTHER INFORMATION: Synthetic Oligonucleotide
```

-continued

<400> SEQUENCE: 504
ccgcccatgt tgtgcaatcc                                              20

<210> SEQ ID NO 505
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 505
gtaattgggt ccccgcccat                                              20

<210> SEQ ID NO 506
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 506
aagtcccgga tctcatcaat                                              20

<210> SEQ ID NO 507
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 507
aacacataga catccagata                                              20

<210> SEQ ID NO 508
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 508
caaagcattg atgttcactt                                              20

<210> SEQ ID NO 509
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 509
tttgaacaca tgttgctcat                                              20

<210> SEQ ID NO 510
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 510
cttccaggtt ttccatatcc                                              20

<210> SEQ ID NO 511
<211> LENGTH: 20

```
<212> TYPE: DNA
<213> ORGANISM: Artificial sequence
<220> FEATURE:
<223> OTHER INFORMATION: Synthetic Oligonucleotide

<400> SEQUENCE: 511
tcttccaggt tttccatatc                                              20

<210> SEQ ID NO 512
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 512
agactcagag actggctttc                                              20

<210> SEQ ID NO 513
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 513
gcctgccatg gttgcttgtg                                              20

<210> SEQ ID NO 514
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 514
tgactgagat cttggcctgc                                              20

<210> SEQ ID NO 515
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 515
ttctatctcc aggtcccgct                                              20

<210> SEQ ID NO 516
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 516
agtcataaaa ttcaggaatt                                              20

<210> SEQ ID NO 517
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 517
```
cgagttgttc cctcggtgca                                              20

<210> SEQ ID NO 518
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 518
agcctcaaag ctcgagttgt                                              20

<210> SEQ ID NO 519
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 519
ggaggaagcc tcaaagctcg                                              20

<210> SEQ ID NO 520
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 520
gtagttggag gaagcctcaa                                              20

<210> SEQ ID NO 521
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 521
caagtggtag ttggaggaag                                              20

<210> SEQ ID NO 522
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 522
tcctcagaca caaacagagc                                              20

<210> SEQ ID NO 523
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 523
ttctcctcct cagacacaaa                                              20

<210> SEQ ID NO 524
<211> LENGTH: 20
<212> TYPE: DNA
<213> ORGANISM: Artificial sequence

```
<220> FEATURE:
<223> OTHER INFORMATION: Synthetic Oligonucleotide

<400> SEQUENCE: 524
tagacctcct tccgagtcag                                              20

<210> SEQ ID NO 525
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 525
ttgatgtaga cctccttccg                                              20

<210> SEQ ID NO 526
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 526
ctttcttatc cccattcttg                                              20

<210> SEQ ID NO 527
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 527
gcctttctta tccccattct                                              20

<210> SEQ ID NO 528
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 528
agctgccttt cttatcccca                                              20

<210> SEQ ID NO 529
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 529
cagctgcctt tcttatcccc                                              20

<210> SEQ ID NO 530
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 530
acagctgcct ttcttatccc                                              20
```

<210> SEQ ID NO 531
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 531
gcatctctct cacagctgcc                                              20

<210> SEQ ID NO 532
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 532
agatgtcctt gactttgtca                                              20

<210> SEQ ID NO 533
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 533
cagcataggg actcactcct                                              20

<210> SEQ ID NO 534
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 534
ccgccagaat cacctctgca                                              20

<210> SEQ ID NO 535
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 535
tgaatgaaac gacttctctt                                              20

<210> SEQ ID NO 536
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 536
acatccacta ctccccagct                                              20

<210> SEQ ID NO 537
<211> LENGTH: 20
<212> TYPE: DNA
<213> ORGANISM: Artificial sequence
<220> FEATURE:
<223> OTHER INFORMATION: Synthetic Oligonucleotide -continued

<400> SEQUENCE: 537
cgcttctggt ttttgcagac                                           20

<210> SEQ ID NO 538
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 538
ttttgccgct tctggttttt                                           20

<210> SEQ ID NO 539
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 539
gcaggtacct gcttttgccg                                           20

<210> SEQ ID NO 540
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 540
tcttggagtt tctccttcag                                           20

<210> SEQ ID NO 541
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 541
ggaacatcca agcggg                                               16

<210> SEQ ID NO 542
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 542
tggtcacatt cccttc                                               16

<210> SEQ ID NO 543
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 543
cctggtcaca ttccct                                               16

<210> SEQ ID NO 544

```
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 544
gacctggtca cattcc                                                       16

<210> SEQ ID NO 545
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 545
taacttgcca ccttct                                                       16

<210> SEQ ID NO 546
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 546
cataacttgc cacctt                                                       16

<210> SEQ ID NO 547
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 547
accataactt gccacc                                                       16

<210> SEQ ID NO 548
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 548
ccttccgagt cagctt                                                       16

<210> SEQ ID NO 549
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 549
ctccttccga gtcagc                                                       16

<210> SEQ ID NO 550
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 550
```
acctccttcc gagtca 16

<210> SEQ ID NO 551
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 551
ctttcttatc cccatt 16

<210> SEQ ID NO 552
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 552
gcctttctta tccca 16

<210> SEQ ID NO 553
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 553
ctgcctttct tatccc 16

<210> SEQ ID NO 554
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 554
tttgccgctt ctggtt 16

<210> SEQ ID NO 555
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 555
cttttgccgc ttctgg 16

<210> SEQ ID NO 556
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 556
tgcttttgcc gcttct 16

<210> SEQ ID NO 557
<211> LENGTH: 16
<212> TYPE: DNA

```
<213> ORGANISM: Artificial sequence
<220> FEATURE:
<223> OTHER INFORMATION: Synthetic Oligonucleotide

<400> SEQUENCE: 557
aaacccaaat cctcat                                                      16

<210> SEQ ID NO 558
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 558
gaaaacccaa atcctc                                                      16

<210> SEQ ID NO 559
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 559 tagaaaccc aaatcc                                                       16

<210> SEQ ID NO 560
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 560
atagaaaacc caaatc                                                      16

<210> SEQ ID NO 561
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 561
cttatagaaa acccaa                                                      16

<210> SEQ ID NO 562
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 562
ccttatagaa aaccca                                                      16

<210> SEQ ID NO 563
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 563
cccttataga aaaccc                                                      16
```

<210> SEQ ID NO 564
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 564 cccttatag aaaacc                                                    16

<210> SEQ ID NO 565
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 565 acccttata gaaaac                                                    16

<210> SEQ ID NO 566
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 566
aaccccttat agaaaa                                                   16

<210> SEQ ID NO 567
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 567 aaaccccta tagaaa                                                    16

<210> SEQ ID NO 568
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 568 gaaaccccttt atagaa                                                  16

<210> SEQ ID NO 569
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 569 ggaaaccct tataga                                                    16

<210> SEQ ID NO 570
<211> LENGTH: 16
<212> TYPE: DNA
<213> ORGANISM: Artificial sequence
<220> FEATURE:

<223> OTHER INFORMATION: Synthetic Oligonucleotide

<400> SEQUENCE: 570
aggaaacccc ttatag                                                        16

<210> SEQ ID NO 571
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 571
caggaaaccc cttata                                                        16

<210> SEQ ID NO 572
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 572
gcaggaaacc ccttat                                                        16

<210> SEQ ID NO 573
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 573
agcaggaaac cccta                                                         16

<210> SEQ ID NO 574
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 574
cagcaggaaa cccctt                                                        16

<210> SEQ ID NO 575
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 575
ccagcaggaa acccct                                                        16

<210> SEQ ID NO 576
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 576
tccagcagga aacccc                                                        16

```
<210> SEQ ID NO 577
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 577
gtccagcagg aaaccc                                                   16

<210> SEQ ID NO 578
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 578
tgtccagcag gaaacc                                                   16

<210> SEQ ID NO 579
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 579
ctgtccagca ggaaac                                                   16

<210> SEQ ID NO 580
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 580
cctgtccagc aggaaa                                                   16

<210> SEQ ID NO 581
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 581
ccctgtccag caggaa                                                   16

<210> SEQ ID NO 582
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 582
cccctgtcca gcagga                                                   16

<210> SEQ ID NO 583
<211> LENGTH: 16
<212> TYPE: DNA
<213> ORGANISM: Artificial sequence
<220> FEATURE:
<223> OTHER INFORMATION: Synthetic Oligonucleotide
```

```
<400> SEQUENCE: 583
gcccctgtcc agcagg                                                      16

<210> SEQ ID NO 584
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 584
cgcccctgtc cagcag                                                      16

<210> SEQ ID NO 585
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 585
acgcccctgt ccagca                                                      16

<210> SEQ ID NO 586
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 586
cacgcccctg tccagc                                                      16

<210> SEQ ID NO 587
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 587
ccacgcccct gtccag                                                      16

<210> SEQ ID NO 588
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 588
cccacgcccc tgtcca                                                      16

<210> SEQ ID NO 589
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 589
tcccacgccc ctgtcc                                                      16

<210> SEQ ID NO 590
<211> LENGTH: 16
```

<210> SEQ ID NO 590
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 590
atcccacgcc cctgtc                                          16

<210> SEQ ID NO 591
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 591
aatcccacgc ccctgt                                          16

<210> SEQ ID NO 592
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 592
caatcccacg cccctg                                          16

<210> SEQ ID NO 593
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 593
tcaatcccac gcccct                                          16

<210> SEQ ID NO 594
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 594
ttcaatccca cgcccc                                          16

<210> SEQ ID NO 595
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 595
attcaatccc acgccc                                          16

<210> SEQ ID NO 596
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 596
aattcaatcc cacgcc                                                    16

<210> SEQ ID NO 597
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 597
taattcaatc ccacgc                                                    16

<210> SEQ ID NO 598
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 598
ttaattcaat cccacg                                                    16

<210> SEQ ID NO 599
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 599
tttaattcaa tcccac                                                    16

<210> SEQ ID NO 600
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 600
ttttaattca atccca                                                    16

<210> SEQ ID NO 601
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 601
gttttaattc aatccc                                                    16

<210> SEQ ID NO 602
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 602
tgttttaatt caatcc                                                    16

<210> SEQ ID NO 603
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 603
ctgttttaat tcaatc                                                    16

<210> SEQ ID NO 604
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 604
gctgttttaa ttcaat                                                    16

<210> SEQ ID NO 605
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 605
agctgtttta attcaa                                                    16

<210> SEQ ID NO 606
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 606
cagctgtttt aattca                                                    16

<210> SEQ ID NO 607
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 607
gcagctgttt taattc                                                    16

<210> SEQ ID NO 608
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 608
cgcagctgtt ttaatt                                                    16

<210> SEQ ID NO 609
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 609
tcgcagctgt tttaat                                                    16

```
<210> SEQ ID NO 610
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 610
gtcgcagctg ttttaa                                                  16

<210> SEQ ID NO 611
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 611
tgtcgcagct gtttta                                                  16

<210> SEQ ID NO 612
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 612
ttgtcgcagc tgtttt                                                  16

<210> SEQ ID NO 613
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 613
gttgtcgcag ctgttt                                                  16

<210> SEQ ID NO 614
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 614
tgttgtcgca gctgtt                                                  16

<210> SEQ ID NO 615
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 615
ttgttgtcgc agctgt                                                  16

<210> SEQ ID NO 616
<211> LENGTH: 16
<212> TYPE: DNA
<213> ORGANISM: Artificial sequence
<220> FEATURE:
<223> OTHER INFORMATION: Synthetic Oligonucleotide
```

```
<400> SEQUENCE: 616
tttgttgtcg cagctg                                                    16

<210> SEQ ID NO 617
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 617
ttttgttgtc gcagct                                                    16

<210> SEQ ID NO 618
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 618
tttttgttgt cgcagc                                                    16

<210> SEQ ID NO 619
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 619
gaaaacccaa atcctca                                                   17

<210> SEQ ID NO 620
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 620
agaaaaccca aatcctc                                                   17

<210> SEQ ID NO 621
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 621
tagaaaaccc aaatcct                                                   17

<210> SEQ ID NO 622
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 622
atagaaaacc caaatcc                                                   17

<210> SEQ ID NO 623
```

-continued

```
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 623
ttatagaaaa cccaaat                                                    17

<210> SEQ ID NO 624
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 624
cttatagaaa acccaaa                                                    17

<210> SEQ ID NO 625
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 625
ccttatagaa aacccaa                                                    17

<210> SEQ ID NO 626
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 626
cccttataga aaaccca                                                    17

<210> SEQ ID NO 627
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 627 cccctttatag aaaaccc                                                   17

<210> SEQ ID NO 628
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 628
accccttata gaaaacc                                                    17

<210> SEQ ID NO 629
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 629
```
aaccccttat agaaaac    17

<210> SEQ ID NO 630
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 630
aaacccctta tagaaaa    17

<210> SEQ ID NO 631
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 631
gaaacccctt atagaaa    17

<210> SEQ ID NO 632
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 632
ggaaacccct tatagaa    17

<210> SEQ ID NO 633
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 633
aggaaacccc ttataga    17

<210> SEQ ID NO 634
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 634
caggaaaccc cttatag    17

<210> SEQ ID NO 635
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 635
gcaggaaacc ccttata    17

<210> SEQ ID NO 636
<211> LENGTH: 17
<212> TYPE: DNA

```
<213> ORGANISM: Artificial sequence
<220> FEATURE:
<223> OTHER INFORMATION: Synthetic Oligonucleotide

<400> SEQUENCE: 636
agcaggaaac cccttat                                                    17

<210> SEQ ID NO 637
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 637
cagcaggaaa cccctta                                                    17

<210> SEQ ID NO 638
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 638
ccagcaggaa acccctt                                                    17

<210> SEQ ID NO 639
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 639
tccagcagga aacccct                                                    17

<210> SEQ ID NO 640
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 640
gtccagcagg aaacccc                                                    17

<210> SEQ ID NO 641
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 641
tgtccagcag gaaaccc                                                    17

<210> SEQ ID NO 642
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 642
ctgtccagca ggaaacc                                                    17
```

<210> SEQ ID NO 643
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 643
cctgtccagc aggaaac                                                  17

<210> SEQ ID NO 644
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 644
ccctgtccag caggaaa                                                  17

<210> SEQ ID NO 645
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 645 gccctgtcc agcagga                                                   17

<210> SEQ ID NO 646
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 646 cgccctgtc cagcagg                                                   17

<210> SEQ ID NO 647
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 647
acgcccctgt ccagcag                                                  17

<210> SEQ ID NO 648
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 648
cacgcccctg tccagca                                                  17

<210> SEQ ID NO 649
<211> LENGTH: 17
<212> TYPE: DNA
<213> ORGANISM: Artificial sequence
<220> FEATURE:

<223> OTHER INFORMATION: Synthetic Oligonucleotide

<400> SEQUENCE: 649
ccacgcccct gtccagc                                                    17

<210> SEQ ID NO 650
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 650
cccacgcccc tgtccag                                                    17

<210> SEQ ID NO 651
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 651
tcccacgccc ctgtcca                                                    17

<210> SEQ ID NO 652
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 652
atcccacgcc cctgtcc                                                    17

<210> SEQ ID NO 653
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 653
aatcccacgc ccctgtc                                                    17

<210> SEQ ID NO 654
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 654
caatcccacg cccctgt                                                    17

<210> SEQ ID NO 655
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 655
tcaatcccac gcccctg                                                    17

```
<210> SEQ ID NO 656
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 656
ttcaatccca cgcccct                                                    17

<210> SEQ ID NO 657
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 657
attcaatccc acgcccc                                                    17

<210> SEQ ID NO 658
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 658
aattcaatcc cacgccc                                                    17

<210> SEQ ID NO 659
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 659
taattcaatc ccacgcc                                                    17

<210> SEQ ID NO 660
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 660
ttaattcaat cccacgc                                                    17

<210> SEQ ID NO 661
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 661
tttaattcaa tcccacg                                                    17

<210> SEQ ID NO 662
<211> LENGTH: 17
<212> TYPE: DNA
<213> ORGANISM: Artificial sequence
<220> FEATURE:
<223> OTHER INFORMATION: Synthetic Oligonucleotide
```

```
<400> SEQUENCE: 662
ttttaattca atcccac                                                    17

<210> SEQ ID NO 663
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 663
gttttaattc aatccca                                                    17

<210> SEQ ID NO 664
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 664
tgttttaatt caatccc                                                    17

<210> SEQ ID NO 665
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 665
ctgttttaat tcaatcc                                                    17

<210> SEQ ID NO 666
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 666
gctgttttaa ttcaatc                                                    17

<210> SEQ ID NO 667
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 667
agctgtttta attcaat                                                    17

<210> SEQ ID NO 668
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 668
cagctgtttt aattcaa                                                    17

<210> SEQ ID NO 669
<211> LENGTH: 17
```

```
<212> TYPE: DNA
<213> ORGANISM: Artificial sequence
<220> FEATURE:
<223> OTHER INFORMATION: Synthetic Oligonucleotide

<400> SEQUENCE: 669
gcagctgttt taattca                                              17

<210> SEQ ID NO 670
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 670
cgcagctgtt ttaattc                                              17

<210> SEQ ID NO 671
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 671
tcgcagctgt tttaatt                                              17

<210> SEQ ID NO 672
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 672
gtcgcagctg ttttaat                                              17

<210> SEQ ID NO 673
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 673
tgtcgcagct gttttaa                                              17

<210> SEQ ID NO 674
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 674
ttgtcgcagc tgtttta                                              17

<210> SEQ ID NO 675
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 675
```

```
gttgtcgcag ctgtttt                                                          17

<210> SEQ ID NO 676
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 676
tgttgtcgca gctgttt                                                          17

<210> SEQ ID NO 677
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 677
ttgttgtcgc agctgtt                                                          17

<210> SEQ ID NO 678
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 678
tttgttgtcg cagctgt                                                          17

<210> SEQ ID NO 679
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 679
ttttgttgtc gcagctg                                                          17

<210> SEQ ID NO 680
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 680
tttttgttgt cgcagct                                                          17

<210> SEQ ID NO 681
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 681 tagaaaccc aaatcctca                                                         19

<210> SEQ ID NO 682
<211> LENGTH: 19
<212> TYPE: DNA
<213> ORGANISM: Artificial sequence
```

```
<220> FEATURE:
<223> OTHER INFORMATION: Synthetic Oligonucleotide

<400> SEQUENCE: 682
atagaaaacc caaatcctc                                                19

<210> SEQ ID NO 683
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 683
tatagaaaac ccaaatcct                                                19

<210> SEQ ID NO 684
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 684
cttatagaaa acccaaatc                                                19

<210> SEQ ID NO 685
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 685
ccttatagaa aacccaaat                                                19

<210> SEQ ID NO 686
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 686
cccttataga aaacccaaa                                                19

<210> SEQ ID NO 687
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 687 cccctttatag aaaacccaa                                               19

<210> SEQ ID NO 688
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 688 acccccttata gaaaaccca                                               19
```

<210> SEQ ID NO 689
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 689 aacccctttat agaaaaccc                          19

<210> SEQ ID NO 690
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 690
aaacccctta tagaaaacc                           19

<210> SEQ ID NO 691
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 691
gaaacccctt atagaaaac                           19

<210> SEQ ID NO 692
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 692
ggaaacccct tatagaaaa                           19

<210> SEQ ID NO 693
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 693
aggaaacccc ttatagaaa                           19

<210> SEQ ID NO 694
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 694
caggaaaccc cttatagaa                           19

<210> SEQ ID NO 695
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 695
gcaggaaacc ccttataga                                                19

<210> SEQ ID NO 696
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 696
agcaggaaac cccttatag                                                19

<210> SEQ ID NO 697
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 697
cagcaggaaa ccccttata                                                19

<210> SEQ ID NO 698
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 698
ccagcaggaa accccttat                                                19

<210> SEQ ID NO 699
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 699
tccagcagga aacccctta                                                19

<210> SEQ ID NO 700
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 700
gtccagcagg aaacccctt                                                19

<210> SEQ ID NO 701
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 701
tgtccagcag gaaacccct                                                19

<210> SEQ ID NO 702

```
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 702
cctgtccagc aggaaaccc                                             19

<210> SEQ ID NO 703
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 703
ccctgtccag caggaaacc                                             19

<210> SEQ ID NO 704
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 704
cccctgtcca gcaggaaac                                             19

<210> SEQ ID NO 705
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 705 gccctgtcc agcaggaaa                                              19

<210> SEQ ID NO 706
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 706
acgcccctgt ccagcagga                                             19

<210> SEQ ID NO 707
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 707
cacgcccctg tccagcagg                                             19

<210> SEQ ID NO 708
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 708
``` ccacgccccct gtccagcag                                          19

<210> SEQ ID NO 709
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 709
cccacgcccc tgtccagca                                           19

<210> SEQ ID NO 710
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 710
tcccacgccc ctgtccagc                                           19

<210> SEQ ID NO 711
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 711
atcccacgcc cctgtccag                                           19

<210> SEQ ID NO 712
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 712
aatcccacgc ccctgtcca                                           19

<210> SEQ ID NO 713
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 713
caatcccacg ccctgtcc                                            19

<210> SEQ ID NO 714
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 714
tcaatcccac gccctgtc                                            19

<210> SEQ ID NO 715
<211> LENGTH: 19
<212> TYPE: DNA

```
<213> ORGANISM: Artificial sequence
<220> FEATURE:
<223> OTHER INFORMATION: Synthetic Oligonucleotide

<400> SEQUENCE: 715
ttcaatccca cgcccctgt                                               19

<210> SEQ ID NO 716
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 716
attcaatccc acgcccctg                                               19

<210> SEQ ID NO 717
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 717
aattcaatcc cacgcccct                                               19

<210> SEQ ID NO 718
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 718
taattcaatc ccacgcccc                                               19

<210> SEQ ID NO 719
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 719
ttaattcaat cccacgccc                                               19

<210> SEQ ID NO 720
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 720
tttaattcaa tcccacgcc                                               19

<210> SEQ ID NO 721
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 721
ttttaattca atcccacgc                                               19
```

<210> SEQ ID NO 722
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 722
gttttaattc aatcccacg                                               19

<210> SEQ ID NO 723
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 723
tgttttaatt caatcccac                                               19

<210> SEQ ID NO 724
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 724
ctgttttaat tcaatccca                                               19

<210> SEQ ID NO 725
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 725
gctgttttaa ttcaatccc                                               19

<210> SEQ ID NO 726
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 726
agctgtttta attcaatcc                                               19

<210> SEQ ID NO 727
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 727
cagctgtttt aattcaatc                                               19

<210> SEQ ID NO 728
<211> LENGTH: 19
<212> TYPE: DNA
<213> ORGANISM: Artificial sequence
<220> FEATURE:

<223> OTHER INFORMATION: Synthetic Oligonucleotide

<400> SEQUENCE: 728
gcagctgttt taattcaat					19

<210> SEQ ID NO 729
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 729
cgcagctgtt ttaattcaa					19

<210> SEQ ID NO 730
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 730
tcgcagctgt tttaattca					19

<210> SEQ ID NO 731
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 731
gtcgcagctg ttttaattc					19

<210> SEQ ID NO 732
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 732
tgtcgcagct gttttaatt					19

<210> SEQ ID NO 733
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 733
ttgtcgcagc tgttttaat					19

<210> SEQ ID NO 734
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 734
gttgtcgcag ctgttttaa					19

```
<210> SEQ ID NO 735
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 735
tgttgtcgca gctgtttta                                                  19

<210> SEQ ID NO 736
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 736
ttgttgtcgc agctgtttt                                                  19

<210> SEQ ID NO 737
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 737
tttgttgtcg cagctgttt                                                  19

<210> SEQ ID NO 738
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 738
ttttgttgtc gcagctgtt                                                  19

<210> SEQ ID NO 739
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 739
tttttgttgt cgcagctgt                                                  19

<210> SEQ ID NO 740
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 740 cccc ttatag aaaaccca                                                  18

<210> SEQ ID NO 741
<211> LENGTH: 18
<212> TYPE: DNA
<213> ORGANISM: Artificial sequence
<220> FEATURE:
<223> OTHER INFORMATION: Synthetic Oligonucleotide
```

```
<400> SEQUENCE: 741
accccttata gaaaaccc                                              18

<210> SEQ ID NO 742
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 742
aaccccttat agaaaacc                                              18

<210> SEQ ID NO 743
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 743
aaacccctta tagaaaac                                              18

<210> SEQ ID NO 744
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 744
gaaacccctt atagaaaa                                              18

<210> SEQ ID NO 745
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 745
aggaaacccc ttatagaa                                              18

<210> SEQ ID NO 746
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 746
caggaaaccc cttataga                                              18

<210> SEQ ID NO 747
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 747
gcaggaaacc ccttatag                                              18

<210> SEQ ID NO 748
<211> LENGTH: 18
```

```
<212> TYPE: DNA
<213> ORGANISM: Artificial sequence
<220> FEATURE:
<223> OTHER INFORMATION: Synthetic Oligonucleotide

<400> SEQUENCE: 748
agcaggaaac cccttata                                                   18

<210> SEQ ID NO 749
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 749
cagcaggaaa cccctttat                                                  18

<210> SEQ ID NO 750
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 750
ccagcaggaa acccctta                                                   18

<210> SEQ ID NO 751
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 751
tccagcagga aaccccctt                                                   18

<210> SEQ ID NO 752
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 752
gtccagcagg aaacccct                                                   18

<210> SEQ ID NO 753
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 753
tgtccagcag gaaacccc                                                   18

<210> SEQ ID NO 754
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 754
```
ctgtccagca ggaaaccc                                              18

<210> SEQ ID NO 755
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 755
cctgtccagc aggaaacc                                              18

<210> SEQ ID NO 756
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 756
ccctgtccag caggaaac                                              18

<210> SEQ ID NO 757
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 757
cccctgtcca gcaggaaa                                              18

<210> SEQ ID NO 758
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 758
cgcccctgtc cagcagga                                              18

<210> SEQ ID NO 759
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 759
acgcccctgt ccagcagg                                              18

<210> SEQ ID NO 760
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 760
cacgcccctg tccagcag                                              18

<210> SEQ ID NO 761
<211> LENGTH: 18
<212> TYPE: DNA
<213> ORGANISM: Artificial sequence

```
<220> FEATURE:
<223> OTHER INFORMATION: Synthetic Oligonucleotide

<400> SEQUENCE: 761
ccacgcccct gtccagca                                                    18

<210> SEQ ID NO 762
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 762
cccacgcccc tgtccagc                                                    18

<210> SEQ ID NO 763
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 763
tcccacgccc ctgtccag                                                    18

<210> SEQ ID NO 764
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 764
atcccacgcc cctgtcca                                                    18

<210> SEQ ID NO 765
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 765
aatcccacgc ccctgtcc                                                    18

<210> SEQ ID NO 766
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 766
caatcccacg cccctgtc                                                    18

<210> SEQ ID NO 767
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 767
tcaatcccac gccctgt                                                     18
```

```
<210> SEQ ID NO 768
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 768
ttcaatccca cgcccctg                                               18

<210> SEQ ID NO 769
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 769
attcaatccc acgccct                                                18

<210> SEQ ID NO 770
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 770
aattcaatcc cacgcccc                                               18

<210> SEQ ID NO 771
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 771
taattcaatc ccacgccc                                               18

<210> SEQ ID NO 772
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 772
ttaattcaat cccacgcc                                               18

<210> SEQ ID NO 773
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 773
tttaattcaa tcccacgc                                               18

<210> SEQ ID NO 774
<211> LENGTH: 18
<212> TYPE: DNA
<213> ORGANISM: Artificial sequence
<220> FEATURE:
<223> OTHER INFORMATION: Synthetic Oligonucleotide
```

<400> SEQUENCE: 774
ttttaattca atcccacg                                                  18

<210> SEQ ID NO 775
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 775
gttttaattc aatcccac                                                  18

<210> SEQ ID NO 776
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 776
tgttttaatt caatccca                                                  18

<210> SEQ ID NO 777
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 777
ctgttttaat tcaatccc                                                  18

<210> SEQ ID NO 778
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 778
gctgttttaa ttcaatcc                                                  18

<210> SEQ ID NO 779
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 779
agctgtttta attcaatc                                                  18

<210> SEQ ID NO 780
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 780
cagctgtttt aattcaat                                                  18

<210> SEQ ID NO 781

```
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 781
gcagctgttt taattcaa                                                       18

<210> SEQ ID NO 782
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 782
cgcagctgtt ttaattca                                                       18

<210> SEQ ID NO 783
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 783
tcgcagctgt tttaattc                                                       18

<210> SEQ ID NO 784
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 784
gtcgcagctg ttttaatt                                                       18

<210> SEQ ID NO 785
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 785
tagaaaaccc aaatcctc                                                       18

<210> SEQ ID NO 786
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 786
atagaaaacc caaatcct                                                       18

<210> SEQ ID NO 787
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 787
```
tatagaaaac ccaaatcc                                                18

<210> SEQ ID NO 788
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 788
ttatagaaaa cccaaatc                                                18

<210> SEQ ID NO 789
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 789
cttatagaaa acccaaat                                                18

<210> SEQ ID NO 790
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 790
ccttatagaa aacccaaa                                                18

<210> SEQ ID NO 791
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 791
cccttataga aaacccaa                                                18

<210> SEQ ID NO 792
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 792
tgtcgcagct gttttaat                                                18

<210> SEQ ID NO 793
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 793
ttgtcgcagc tgttttaa                                                18

<210> SEQ ID NO 794
<211> LENGTH: 18
<212> TYPE: DNA

```
<213> ORGANISM: Artificial sequence
<220> FEATURE:
<223> OTHER INFORMATION: Synthetic Oligonucleotide

<400> SEQUENCE: 794
gttgtcgcag ctgtttta                                                  18

<210> SEQ ID NO 795
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 795
tgttgtcgca gctgtttt                                                  18

<210> SEQ ID NO 796
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 796
ttgttgtcgc agctgttt                                                  18

<210> SEQ ID NO 797
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 797
tttgttgtcg cagctgtt                                                  18

<210> SEQ ID NO 798
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 798
ttttgttgtc gcagctgt                                                  18

<210> SEQ ID NO 799
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 799
tttttgttgt cgcagctg                                                  18

<210> SEQ ID NO 800
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 800
aaaacccaaa tcctca                                                    16
```

<210> SEQ ID NO 801
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 801 agaaaccca aatcct                                                        16

<210> SEQ ID NO 802
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 802
tatagaaaac ccaaat                                                       16

<210> SEQ ID NO 803
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 803
ttatagaaaa cccaaa                                                       16

<210> SEQ ID NO 804
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 804
gcataagagg gtaccagctg                                                   20

<210> SEQ ID NO 805
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 805
gtcctttagc cagggcagca                                                   20

<210> SEQ ID NO 806
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 806
tccacccatg ttgtgcaagc                                                   20

<210> SEQ ID NO 807
<211> LENGTH: 20
<212> TYPE: DNA
<213> ORGANISM: Artificial sequence
<220> FEATURE:

<223> OTHER INFORMATION: Synthetic Oligonucleotide

<400> SEQUENCE: 807
ccacaccatg ccacagagac    20

<210> SEQ ID NO 808
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 808
ttccgagtca ggctcttccc    20

<210> SEQ ID NO 809
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 809
ccttccctga aggttcctcc    20

<210> SEQ ID NO 810
<211> LENGTH: 21
<212> TYPE: DNA
<213> ORGANISM: Artificial sequence
<220> FEATURE:
<223> OTHER INFORMATION: Primer

<400> SEQUENCE: 810
agtctctgtg gcatggtttg g    21

<210> SEQ ID NO 811
<211> LENGTH: 21
<212> TYPE: DNA
<213> ORGANISM: Artificial sequence
<220> FEATURE:
<223> OTHER INFORMATION: primer

<400> SEQUENCE: 811
gggcgaatga ctgagatctt g    21

<210> SEQ ID NO 812
<211> LENGTH: 27
<212> TYPE: DNA
<213> ORGANISM: Artificial sequence
<220> FEATURE:
<223> OTHER INFORMATION: Probe

<400> SEQUENCE: 812
taccgattac cacaagcaac catggca    27

<210> SEQ ID NO 813
<211> LENGTH: 22
<212> TYPE: DNA
<213> ORGANISM: Artificial sequence
<220> FEATURE:
<223> OTHER INFORMATION: Primer

<400> SEQUENCE: 813
cgaagcagct caatgaaatc aa    22

```
<210> SEQ ID NO 814
<211> LENGTH: 18
<212> TYPE: DNA
<213> ORGANISM: Artificial sequence
<220> FEATURE:
<223> OTHER INFORMATION: Primer

<400> SEQUENCE: 814
tgcctggagg gccttctt                                                 18

<210> SEQ ID NO 815
<211> LENGTH: 18
<212> TYPE: DNA
<213> ORGANISM: Artificial sequence
<220> FEATURE:
<223> OTHER INFORMATION: Probe

<400> SEQUENCE: 815
agaccacaag ttgaagtc                                                 18

<210> SEQ ID NO 816
<211> LENGTH: 20
<212> TYPE: DNA
<213> ORGANISM: Artificial sequence
<220> FEATURE:
<223> OTHER INFORMATION: Primer

<400> SEQUENCE: 816
gggcaaacag caatttgtga                                               20

<210> SEQ ID NO 817
<211> LENGTH: 20
<212> TYPE: DNA
<213> ORGANISM: Artificial sequence
<220> FEATURE:
<223> OTHER INFORMATION: Primer

<400> SEQUENCE: 817
tggctaccca ccttccttgt                                               20

<210> SEQ ID NO 818
<211> LENGTH: 28
<212> TYPE: DNA
<213> ORGANISM: Artificial sequence
<220> FEATURE:
<223> OTHER INFORMATION: Probe

<400> SEQUENCE: 818
ctggatactg tcccaatccc ggtattcc                                      28

<210> SEQ ID NO 819
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 819
cgaagaagct cagtgaaatc aa                                            22

<210> SEQ ID NO 820
<211> LENGTH: 18
<212> TYPE: DNA
<213> ORGANISM: Artificial sequence
<220> FEATURE:
<223> OTHER INFORMATION: Synthetic Oligonucleotide
```

```
<400> SEQUENCE: 820
tgcctggagg gccctctt                                               18

<210> SEQ ID NO 821
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 821
agcttcttgt ccagctttat                                             20

<210> SEQ ID NO 822
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 822
agcttcttgt ccagctttat a                                           21

<210> SEQ ID NO 823
<211> LENGTH: 14
<212> TYPE: DNA
<213> ORGANISM: Artificial sequence
<220> FEATURE:
<223> OTHER INFORMATION: Synthetic Oligonucleotide

<400> SEQUENCE: 823
tcagtcatga cttc                                                   14

<210> SEQ ID NO 824
<211> LENGTH: 15
<212> TYPE: DNA
<213> ORGANISM: Artificial sequence
<220> FEATURE:
<223> OTHER INFORMATION: Synthetic Oligonucleotide

<400> SEQUENCE: 824
tcagtcatga cttca                                                  15

<210> SEQ ID NO 825
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 825
gctgattaga gagaggtccc                                             20

<210> SEQ ID NO 826
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 826
tcccatttca ggagacctgg                                             20

<210> SEQ ID NO 827
<211> LENGTH: 15
```

```
<212> TYPE: DNA
<213> ORGANISM: Artificial sequence
<220> FEATURE:
<223> OTHER INFORMATION: Synthetic Oligonucleotide

<400> SEQUENCE: 827
atcagtcatg acttc                                                        15

<210> SEQ ID NO 828
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 828
cggtgcaagg cttaggaatt                                                   20

<210> SEQ ID NO 829
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 829
gcttcagtca tgacttcctt                                                   20

<210> SEQ ID NO 830
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 830
gcttcagtca tgacttcctt a                                                 21

<210> SEQ ID NO 831
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 831
agcttcagtc atgacttcct t                                                 21

<210> SEQ ID NO 832
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 832
tggtaatcca ctttcagagg                                                   20

<210> SEQ ID NO 833
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 833
```
tggtaatcca ctttcagagg a						21

<210> SEQ ID NO 834
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 834
tgcttcagtc atgacttcct t						21

<210> SEQ ID NO 835
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 835
cactgatttt tgcccaggat						20

<210> SEQ ID NO 836
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 836
cactgatttt tgcccaggat a						21

<210> SEQ ID NO 837
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 837
aagcttcttg tccagcttta t						21

<210> SEQ ID NO 838
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 838
acccaattca gaaggaagga						20

<210> SEQ ID NO 839
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 839
acccaattca gaaggaagga a						21

<210> SEQ ID NO 840
<211> LENGTH: 21
<212> TYPE: DNA
<213> ORGANISM: Artificial sequence

```
<220> FEATURE:
<223> OTHER INFORMATION: Synthetic Oligonucleotide

<400> SEQUENCE: 840
aacccaattc agaaggaagg a                                              21

<210> SEQ ID NO 841
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 841
atggtaatcc actttcagag g                                              21

<210> SEQ ID NO 842
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 842
tcttggttac atgaaatccc                                                20

<210> SEQ ID NO 843
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 843
tcttggttac atgaaatccc a                                              21

<210> SEQ ID NO 844
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 844
attcactttc ataatgctgg                                                20

<210> SEQ ID NO 845
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 845
attcactttc ataatgctgg a                                              21

<210> SEQ ID NO 846
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 846
atcttggtta catgaaatcc c                                              21
```

<210> SEQ ID NO 847
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 847
tgctccgttg gtgcttgttc                                                   20

<210> SEQ ID NO 848
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 848
atgcatggtg atgcttctga                                                   20

<210> SEQ ID NO 849
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 849
cagctttatt agggacagca                                                   20

<210> SEQ ID NO 850
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 850
cagctttatt agggacagca a                                                 21

<210> SEQ ID NO 851
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 851
acagctttat tagggacagc a                                                 21

<210> SEQ ID NO 852
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 852
ttcagtcatg acttcc                                                       16

<210> SEQ ID NO 853
<211> LENGTH: 20
<212> TYPE: DNA
<213> ORGANISM: Artificial sequence
<220> FEATURE:
<223> OTHER INFORMATION: Synthetic Oligonucleotide

```
<220> FEATURE:
<221> NAME/KEY: misc_feature
<222> LOCATION: (1)..(5)
<223> OTHER INFORMATION: Bases at these positions are RNA
<220> FEATURE:
<221> NAME/KEY: misc_feature
<222> LOCATION: (16)..(20)
<223> OTHER INFORMATION: Bases at these positions are RNA

<400> SEQUENCE: 853
gcuucagtca tgactuccuu                                             20

<210> SEQ ID NO 854
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 854
tgctccgttg gtgcttgttc a                                           21
```